US012558428B2

(12) United States Patent
Eastman et al.

(10) Patent No.: US 12,558,428 B2
(45) Date of Patent: Feb. 24, 2026

(54) HETEROBIFUNCTIONAL COMPOUNDS AND THEIR USE IN TREATING DISEASE

(71) Applicant: Halda Therapeutics OpCo, Inc., New Haven, CT (US)

(72) Inventors: Kyle J. Eastman, Killingworth, CT (US); Katherine J. Kayser-Bricker, Branford, CT (US); James John Mousseau, Salem, CT (US); Matthew Alexander Perry, Uncasville, CT (US); David E. Puleo, Fairfield, CT (US); Samuel W. Gerritz, Guilford, CT (US)

(73) Assignee: Halda Therapeutics OpCo, Inc., New Haven, CT (US)

( * ) Notice: Subject to any disclaimer, the term of this patent is extended or adjusted under 35 U.S.C. 154(b) by 0 days.

(21) Appl. No.: 19/073,111

(22) Filed: Mar. 7, 2025

(65) Prior Publication Data

US 2025/0281623 A1 Sep. 11, 2025

Related U.S. Application Data

(60) Provisional application No. 63/761,647, filed on Feb. 21, 2025, provisional application No. 63/562,801, filed on Mar. 8, 2024.

(51) Int. Cl.
*A61K 47/55* (2017.01)
*A61K 47/54* (2017.01)
*A61P 35/00* (2006.01)
*C07D 495/14* (2006.01)

(52) U.S. Cl.
CPC ............ *A61K 47/55* (2017.08); *A61K 47/545* (2017.08); *A61P 35/00* (2018.01); *C07D 495/14* (2013.01)

(58) Field of Classification Search
CPC ....... A61K 47/55; A61K 47/545; A61P 35/00; C07D 495/14
See application file for complete search history.

(56) References Cited

U.S. PATENT DOCUMENTS 4,133,814 A 1/1979 Jones et al.
7,344,699 B2 3/2008 Lappin et al.
7,390,784 B2 6/2008 Briesewitz et al.
9,597,343 B2 3/2017 Chimmanamada et al.
10,772,962 B2 9/2020 Qian et al.
10,836,749 B1 11/2020 Fan et al.
11,572,371 B2 2/2023 Fan et al.
2006/0116364 A1 6/2006 Hamaoka et al.
2014/0357661 A1 12/2014 Bradbury et al.
2016/0175284 A1 6/2016 Labadie et al.
2016/0175289 A1 6/2016 Labadie et al.
2016/0272639 A1 9/2016 Crew et al.
2016/0367526 A1 12/2016 Govek et al.
2017/0065719 A1 3/2017 Qian et al.
2017/0129855 A1 5/2017 Liang et al.
2017/0281784 A1 10/2017 Wang et al.
2017/0327469 A1 11/2017 Crew et al.
2018/0015087 A1 1/2018 Liu et al.
2018/0021316 A1 1/2018 Scott et al.
2018/0099940 A1 4/2018 Crew et al.
2018/0111931 A1 4/2018 Barlaam et al.
2018/0155322 A1 6/2018 Crew et al.
2018/0215731 A1 8/2018 Crew et al.
2018/0228907 A1 8/2018 Crew et al.
2018/0291019 A1 10/2018 Guan et al.
2018/0346461 A1 12/2018 Crew et al.
2019/0119243 A1 4/2019 Strum
2019/0375732 A1 12/2019 Hung et al.
2020/0095205 A1 3/2020 Crew et al.
2020/0155521 A1 5/2020 Schwartz et al.
2020/0155689 A1 5/2020 Crew et al.
2020/0255450 A1 8/2020 Fan et al.
2021/0085700 A1 3/2021 Chimmanamada et al.
2021/0087169 A1 3/2021 Fan et al.
2021/0187108 A1 6/2021 Qian et al.
2021/0196710 A1 7/2021 Snyder et al.
2021/0220475 A1 7/2021 Crew et al.
2021/0284654 A1 9/2021 Yamazaki et al.
2022/0079931 A1 3/2022 Wang et al.
2022/0259154 A1 8/2022 Berlin et al.
2023/0135173 A1 5/2023 Fan et al.
2023/0183209 A1 6/2023 Crew et al.
2023/0203030 A1 6/2023 Crew et al.
2023/0263893 A1 8/2023 Qian et al.
2023/0331681 A1 10/2023 Berlin et al.
2023/0406837 A1 12/2023 London et al.
2024/0059686 A1 2/2024 Crew et al.
(Continued)

FOREIGN PATENT DOCUMENTS

AU 2020259946 B2 5/2023
CN 108379591 A 8/2018
(Continued)

OTHER PUBLICATIONS

H.P. Eikesdal et al., Olaparib monotherapy as primary treatment in unselected triple negative breast cancer Annals of Oncology, vol. 32, Issue 2, 2021 (Year: 2021).*
Abdel-Magid, A. F. "Combination of Cyclin-Dependent Kinase 4 Inhibitors and Androgen Receptor Inhibitors as Cancer Therapy," ACS Medicinal Chemistry Letters, 2022, 13(9), 1408-1410.
Barchéchath, S. et al. "Rational Design of Multitargeted Tyrosine Kinase Inhibitors: A Novel Approach," Chem. Biol. Drug Des., 2009, 73, 380-387.
Beckers, T. et al. "Chimerically designed HDAC- and tyrosine kinase inhibitors. A series of erlotinib hybrids as dual-selective inhibitors of EGFR, HER2 and histone deacetylases," Med. Chem. Commun., 2012, 3, 829-835.
(Continued)

*Primary Examiner* — Adam C Milligan
*Assistant Examiner* — Ernesto Valle, Jr.
(74) *Attorney, Agent, or Firm* — Morgan, Lewis & Bockius LLP

(57) ABSTRACT

The invention provides heterobifunctional compounds, pharmaceutical compositions, and their use in treating disease, such as cancer.

30 Claims, No Drawings

(56) References Cited

U.S. PATENT DOCUMENTS

| | | | |
|---|---|---|---|
| 2024/0059711 | A1 | 2/2024 | Wang et al. |
| 2024/0066032 | A1 | 2/2024 | Chirnomas et al. |
| 2024/0076295 | A1 | 3/2024 | Crew et al. |
| 2024/0131023 | A1 | 4/2024 | Snyder et al. |
| 2024/0139326 | A1 | 5/2024 | London et al. |
| 2024/0180900 | A1 | 6/2024 | Peck et al. |
| 2024/0238424 | A1 | 7/2024 | Gerritz et al. |
| 2024/0299366 | A1 | 9/2024 | Crew et al. |
| 2024/0325547 | A1 | 10/2024 | Berlin et al. |
| 2024/0408093 | A1 | 12/2024 | Gerritz et al. |
| 2025/0009737 | A1 | 1/2025 | Zhang et al. |
| 2025/0082763 | A1 | 3/2025 | Li et al. |
| 2025/0082764 | A1 | 3/2025 | Li et al. |
| 2025/0136611 | A1 | 5/2025 | Eastman et al. |
| 2025/0136619 | A1 | 5/2025 | Gerritz et al. |

FOREIGN PATENT DOCUMENTS

| | | | | |
|---|---|---|---|---|
| CN | 112574278 | A | 3/2021 | |
| CN | 113582974 | A | 11/2021 | |
| CN | 113896669 | A | 1/2022 | |
| CN | 114105977 | A | 3/2022 | |
| CN | 114181277 | A | 3/2022 | |
| CN | 116354933 | A | 6/2023 | |
| EP | 3699167 | A1 | 8/2020 | |
| EP | 3957633 | A1 | 2/2022 | |
| EP | 4166550 | A1 | 4/2023 | |
| WO | WO-2001077093 | A1 | 10/2001 | |
| WO | WO-2004022561 | A1 | 3/2004 | |
| WO | WO-2009063054 | A1 | 5/2009 | |
| WO | WO-2011156518 | A2 | 12/2011 | |
| WO | WO-2015160845 | A2 | 10/2015 | |
| WO | WO-2015160845 | A3 | 12/2015 | |
| WO | WO-2016073903 | A1 | 5/2016 | |
| WO | WO-2016118666 | A1 | 7/2016 | |
| WO | WO-2016149668 | A1 | 9/2016 | |
| WO | WO-2017059139 | A1 | 4/2017 | |
| WO | WO-2017136688 | A1 | 8/2017 | |
| WO | WO-2017140669 | A1 | 8/2017 | |
| WO | WO-2017201069 | A1 | 11/2017 | |
| WO | WO-2017204445 | A2 | 11/2017 | |
| WO | WO-2018033556 | A1 | 2/2018 | |
| WO | WO-2018071606 | A1 | 4/2018 | |
| WO | WO-2018119441 | A1 | 6/2018 | |
| WO | WO-2018144649 | A1 | 8/2018 | |
| WO | WO-2018178060 | A1 | 10/2018 | |
| WO | WO-2018191199 | A1 | 10/2018 | |
| WO | WO-2019020559 | A1 | 1/2019 | |
| WO | WO-2019023553 | A1 | 1/2019 | |
| WO | WO-2019040274 | A1 | 2/2019 | |
| WO | WO-2019052519 | A1 | 3/2019 | |
| WO | WO-2019079701 | A1 | 4/2019 | |
| WO | WO-2019114770 | A1 | 6/2019 | |
| WO | WO-2019144132 | A1 | 7/2019 | |
| WO | WO-2019173224 | A1 | 9/2019 | |
| WO | WO-2019195609 | A2 | 10/2019 | |
| WO | WO-2019199816 | A1 | 10/2019 | |
| WO | WO-2019215488 | A1 | 11/2019 | |
| WO | WO-2019222272 | A1 | 11/2019 | |
| WO | WO-2020049150 | A1 | 3/2020 | |
| WO | WO-2020049153 | A1 | 3/2020 | |
| WO | WO-2020081450 | A1 | 4/2020 | |
| WO | WO-2020206137 | A1 | 10/2020 | |
| WO | WO-2020211822 | A1 | 10/2020 | |
| WO | WO-2020214952 | A1 * | 10/2020 | ........... C07D 495/14 |
| WO | WO-2020225375 | A1 | 11/2020 | |
| WO | WO-2020232119 | A1 | 11/2020 | |
| WO | WO-2021026153 | A1 | 2/2021 | |
| WO | WO-2021063967 | A1 | 4/2021 | |
| WO | WO-2021091575 | A1 | 5/2021 | |
| WO | WO-2021097046 | A1 | 5/2021 | |
| WO | WO-2021113557 | A1 | 6/2021 | |
| WO | WO-2021116074 | A1 | 6/2021 | |
| WO | WO-2021127039 | A1 | 6/2021 | |
| WO | WO-2021127042 | A1 | 6/2021 | |
| WO | WO-2021127043 | A1 | 6/2021 | |
| WO | WO-2021127046 | A1 | 6/2021 | |
| WO | WO-2021127443 | A1 | 6/2021 | |
| WO | WO-2021170793 | A1 | 9/2021 | |
| WO | WO-2021178846 | A1 | 9/2021 | |
| WO | WO-2021214253 | A1 | 10/2021 | |
| WO | WO-2021214254 | A1 | 10/2021 | |
| WO | WO-2021231927 | A1 | 11/2021 | |
| WO | WO-2021249534 | A1 | 12/2021 | |
| WO | WO-2022011205 | A1 | 1/2022 | |
| WO | WO-2022025640 | A1 | 2/2022 | |
| WO | WO-2022048527 | A1 | 3/2022 | |
| WO | WO-2022087125 | A1 | 4/2022 | |
| WO | WO-2022106711 | A1 | 5/2022 | |
| WO | WO-2022109395 | A2 | 5/2022 | |
| WO | WO-2022125969 | A1 | 6/2022 | |
| WO | WO-2022133446 | A1 | 6/2022 | |
| WO | WO-2022166980 | A1 | 8/2022 | |
| WO | WO-2022187392 | A1 | 9/2022 | |
| WO | WO-2022187588 | A1 | 9/2022 | |
| WO | WO-2022218956 | A1 | 10/2022 | |
| WO | WO-2022218958 | A1 | 10/2022 | |
| WO | WO-2022235585 | A1 | 11/2022 | |
| WO | WO-2022235698 | A1 | 11/2022 | |
| WO | WO-2022251588 | A1 | 12/2022 | |
| WO | WO-2023287938 | A1 | 1/2023 | |
| WO | WO-2023023531 | A1 | 2/2023 | |
| WO | WO-2023059581 | A1 | 4/2023 | |
| WO | WO-2023059582 | A1 | 4/2023 | |
| WO | WO-2023059583 | A1 | 4/2023 | |
| WO | WO-2023059605 | A1 | 4/2023 | |
| WO | WO-2023059609 | A1 | 4/2023 | |
| WO | WO-2023175477 | A1 | 9/2023 | |
| WO | WO-2023180388 | A1 | 9/2023 | |
| WO | WO-2023187086 | A1 | 10/2023 | |
| WO | WO-2023212599 | A2 | 11/2023 | |
| WO | WO-2023215311 | A1 | 11/2023 | |
| WO | WO-2024006781 | A1 | 1/2024 | |
| WO | WO-2024033513 | A1 | 2/2024 | |
| WO | WO-2024054602 | A1 | 3/2024 | |
| WO | WO-2024054603 | A1 | 3/2024 | |
| WO | WO-2024054604 | A1 | 3/2024 | |
| WO | WO-2024054952 | A1 | 3/2024 | |
| WO | WO-2024054953 | A1 | 3/2024 | |
| WO | WO-2024054954 | A1 | 3/2024 | |
| WO | WO-2024054955 | A1 | 3/2024 | |
| WO | WO-2024054956 | A1 | 3/2024 | |
| WO | WO-2024083716 | A1 | 4/2024 | |
| WO | WO-2024097775 | A1 | 5/2024 | |
| WO | WO-2024102784 | A1 | 5/2024 | |
| WO | WO-2024105147 | A1 | 5/2024 | |
| WO | WO-2024138077 | A1 | 6/2024 | |
| WO | WO-2024146617 | A1 | 7/2024 | |
| WO | WO-2024197429 | A1 | 10/2024 | |
| WO | WO-2024211684 | A1 | 10/2024 | |
| WO | WO-2025011623 | A1 | 1/2025 | |
| WO | WO-2025040147 | A1 | 2/2025 | |
| WO | WO-2025081082 | A1 | 4/2025 | |
| WO | WO-2025081091 | A1 | 4/2025 | |
| WO | WO-2025085738 | A1 | 4/2025 | |

OTHER PUBLICATIONS

Duan, Y. et al. "Targeting Brd4 for cancer therapy: inhibitors and degraders," Med. Chem. Commun., 2018, 9, 1779-1802.

Filippakopoulos, P. et al. "Selective Inhibition of BET Bromodomains," Nature, 2010, 468 (7327), 1067-1073.

Gourisankar, S. et al. "Rewiring Cancer Drivers to Activate Apoptosis," bioRxiv reprints, Dec. 7, 2022, retrieved from https://doi.org/10.1101/2022.12.04.517548, 36 pages.

Guo, J. et al. "BCL6 confers KRAS-mutant non-small-cell lung cancer resistance to BET inhibitors," J. Clin. Invest., 2021, 131(1), e133090.

Han, X. et al. "Discovery of ARD-69 as a highly potent proteolysis targeting chimera (PROTAC) degrader of androgen receptor (AR) for the treatment of prostate cancer," Journal of Medicinal Chemistry, 2019, 62(2), 941-964.

(56) References Cited

OTHER PUBLICATIONS

Hu, J. et al. "Discovery of ERD-308 as a highly potent proteolysis targeting chimera (PROTAC) degrader of estrogen receptor (ER)," Journal of Medicinal Chemistry, 2019, 62(3), 1420-1442.
International Search Report for International Application No. PCT/US2022/031280 dated Aug. 31, 2022 (11 pages).
International Search Report for International Application No. PCT/US2022/045603 dated Jan. 10, 2023 (8 pages).
International Search Report for International Application No. PCT/US2022/045604 dated Dec. 19, 2022 (6 pages).
International Search Report for International Application No. PCT/US2022/045606 dated Jan. 10, 2023 (7 pages).
International Search Report for International Application No. PCT/US2022/045631 dated Jan. 9, 2023 (6 pages).
International Search Report for International Application No. PCT/US2022/045637 dated Jan. 10, 2023 (7 pages).
International Search Report for International Application No. PCT/US2023/032248 dated Oct. 31, 2023 (10 pages).
International Search Report for International Application No. PCT/US2023/032252 dated Dec. 1, 2023 (8 pages).
International Search Report for International Application No. PCT/US2023/032254 dated Dec. 6, 2023 (7 pages).
International Search Report for International Application No. PCT/US2023/073694 dated Nov. 28, 2023 (8 pages).
International Search Report for International Application No. PCT/US2023/073695 dated Nov. 15, 2023 (7 pages).
International Search Report for International Application No. PCT/US2023/073696 dated Nov. 16, 2023 (9 pages).
International Search Report for International Application No. PCT/US2023/073697 dated Dec. 5, 2023 (8 pages).
International Search Report for International Application No. PCT/US2023/073698 dated Dec. 7, 2023 (7 pages).
International Search Report for International Application No. PCT/US2024/023239 dated Jun. 27, 2024 (6 pages).
International Search Report for International Application No. PCT/US2024/051958 dated Jan. 17, 2025 (7 pages).
Kerres, N. et al. "Chemically Induced Degradation of the Oncogenic Transcription Factor BCL6," Cell Reports, 2017, 20, 2860-2875.
Mu, X. et al. "Protein targeting chimeric molecules specific for dual bromodomain 4 (BRD4) and Polo-like kinase 1 (PLK1) proteins in acute myeloid leukemia cells," Biochemical and Biophysical Research Communications, 2020, 521, 833-839.
Ogitani, Y. et al. "Bystander killing effect of DS-8201a, a novel anti-human epidermal growth factor receptor 2 antibody-drug conjugate, in tumors with human epidermal growth factor receptor 2 heterogeneity," Cancer Sci., 2016, 107, 1039-1046.
Powell, C. E. et al. "Selective degradation of GSPT1 by cereblon modulators identified via a focused combinatorial library," ACS Chemical Biology, 2020, 15(10), 2722-2730.
Reddi, R. N. et al. "Tunable Methacrylamides for Covalent Ligand Directed Release Chemistry," JACS, 2021, 143, 4979-4992.
Sheppard, G. S. et al. "Discovery of N-Ethyl-4-[2-(4-fluoro-2,6-dimethyl-phenoxy)-5-(1-hydroxy-1-methyl-ethyl)phenyl]-6-methyl-7-oxo-1H-pyrrolo[2,3-c]pyridine-2-carboxamide (ABBV-744), a BET Bromodomain Inhibitor with Selectivity for the Second Bromodomain," J. Med. Chem., 2020, 63, 5585-5623.
Skidmore, L. et al. "ARX788, a Site-specific Anti-HER2 Antibody-Drug Conjugate, Demonstrates Potent and Selective Activity in HER2-low and T-DM1-resistant Breast and Gastric Cancers," Mol. Cancer Ther., 2020, 19, 1833-1843.
Stazi, G. et al. "Histone deacetylases as an epigenetic pillar for the development of hybrid inhibitors in cancer," Current Opinion in Chemical Biology, 2019, 50, 89-100.
Tang, P. et al. "Targeting Bromodomain and Extraterminal Proteins for Drug Discovery: From Current Progress to Technological Development," J. Med. Chem., 2021, 64, 2419-2435.
Tinworth, C. P. et al. "PROTAC-mediated degradation of Bruton's Tyrosine Kinase is inhibited by covalent binding," ACS Chemical Biology, 2019, 14(3), 342-347.
Trabucco, S. E. et al. "Inhibition of Bromodomain Proteins for the Treatment of Human Diffuse Large B-cell Lymphoma," Clinical Cancer Research, 2014, 21(1), 113-122.
Written Opinion for International Application No. PCT/US2022/031280 dated Aug. 31, 2022 (9 pages).
Written Opinion for International Application No. PCT/US2022/045603 dated Jan. 10, 2023 (11 pages).
Written Opinion for International Application No. PCT/US2022/045604 dated Dec. 19, 2022 (7 pages).
Written Opinion for International Application No. PCT/US2022/045606 dated Jan. 10, 2023 (8 pages).
Written Opinion for International Application No. PCT/US2022/045631 dated Jan. 9, 2023 (8 pages).
Written Opinion for International Application No. PCT/US2022/045637 dated Jan. 10, 2023 (6 pages).
Written Opinion for International Application No. PCT/US2023/032248 dated Oct. 31, 2023 (6 pages).
Written Opinion for International Application No. PCT/US2023/032252 dated Dec. 1, 2023 (9 pages).
Written Opinion for International Application No. PCT/US2023/032254 dated Dec. 6, 2023 (6 pages).
Written Opinion for International Application No. PCT/US2023/073694 dated Nov. 28, 2023 (10 pages).
Written Opinion for International Application No. PCT/US2023/073695 dated Nov. 15, 2023 (10 pages).
Written Opinion for International Application No. PCT/US2023/073696 dated Nov. 16, 2023 (10 pages).
Written Opinion for International Application No. PCT/US2023/073697 dated Dec. 5, 2023 (10 pages).
Written Opinion for International Application No. PCT/US2023/073698 dated Dec. 7, 2023 (9 pages).
Written Opinion for International Application No. PCT/US2024/023239 dated Jun. 27, 2024 (10 pages).
Written Opinion for International Application No. PCT/US2024/051958 dated Jan. 17, 2025 (6 pages).
Yu, X. et al. "Exploring Degradation of Mutant and Wild-Type Epidermal Growth Factor Receptors Induced by Proteolysis-Targeting Chimeras," J. Med. Chem., 2022, 65, 8416-8443.
Zhang, Q. et al. "Light-mediated multi-target protein degradation using arylazopyrazole photoswitchable PROTACs (AP-PROTACs)," Chemical Communications, 2022, 58(78), 10933-10936.
Ha, S. et al. "A Comprehensive Overview of Small-Molecule Androgen Receptor Degraders: Recent Progress and Future Perspectives," J. Med. Chem., 2022, vol. 65, p. 16128-16154.
Kargbo, Robert B. "Targeted Degradation of Androgen Receptor for the Potential Treatment of Prostate Cancer," ACS Med. Chem. Lett., 2022, vol. 13, p. 1558-1560.
Zhang, S. et al. "Design, Synthesis, and Biological Evaluation of Androgen Receptor (AR) Antagonist-Heat Shock Protein 90 (Hsp90) Inhibitor Conjugates for Targeted Therapy of Castration-Resistant Prostate Cancer," J. Med. Chem., 2023, vol. 66, p. 4784-4801.
Choudhary, D., et al., "Target protein degradation by protacs: A budding cancer treatment strategy," Pharmacology & Therapeutics, 2023, vol. 250, Article 108525.
Liu, Z., et al., "An overview of PROTACs: a promising drug discovery paradigm," Molecular Biomedicine, 2022, vol. 3, Article 46.
Noblejas-Lopez, M. d. M., et al., "TACkling Cancer by Targeting Selective Protein Degradation," Pharmaceutics, 2023, vol. 15, Article 2442.
Raina, K., et al., "PROTAC-induced BET protein degradation as a therapy for castration-resistant prostate cancer," Proc. Natl. Acad. Sci. USA, 2016, vol. 113, No. 26, p. 7124-7129.
Ma, Z., et al., "RIPTACs: A groundbreaking approach to drug discovery," Drug Discovery Today, 2023, vol. 28, No. 11, Article 103774.
Gerry and Schreiber, "Unifying principles of bifunctional, proximity-inducing small molecules", Nat. Chem. Biol. 2020;16(4):369-378.
Meanwell, N.A., "Synopsis of Some Recent Tactical Application of Bioisosteres in Drug Design." J. Med. Chem. 2011, vol. 54, p. 2529-2591.

(56) References Cited

OTHER PUBLICATIONS

Zhang, S. and Roeder, R. G., "Resistance of estrogen receptor function to BET bromodomain inhibition is mediated by transcriptional coactivator cooperativity," Nat. Struct. Mol. Biol. 2025;32:98-112.

Faivre, E. J. et al., "Selective inhibition of the BD2 bromodomain of BET proteins in prostate cancer," Nature 2020;578:306-310.

Eischer, N. et al., "Emerging roles of BET proteins in transcription and co-transcriptional RNA processing," WIREs RNA 2023;14(1):e1734.

Zhang, B. et al., "BRCA1 deficiency sensitizes breast cancer cells to bromodomain and extra- terminal domain (BET) inhibition," Oncogene 2018;37:6341-6356.

Winter, G. E. et al., "BET Bromodomain Proteins Function as Master Transcription Elongation Factors Independent of CDK9 Recruitment," Molecular Cell 2017;67:5-18.

Donati, B. et al., "BRD4 and Cancer: going beyond transcriptional regulation," Mol. Cancer 2018;17:164.

Shorstova, T. et al., "Achieving clinical success with BET inhibitors as anti-cancer agents," Br. J. Cancer 2021; 124:1478-1490.

Zheng, Z. et al., "Super-enhancer-controlled positive feedback loop BRD4/ERα-RET-ERα promotes ERα-positive breast cancer," Nucleic Acids Research 2022;50(18):10230-10248.

Nagarajan, S. et al., "Bromodomain Protein BRD4 Is Required for Estrogen Receptor-Dependent Enhancer Activation and Gene Transcription" Cell Reports 2014;8:460-469.

Bowry, A. et al. "BET Inhibition Induces HEXIM1- and RAD51-Dependent Conflicts between Transcription and Replication" Cell Reports 2018;25:2061-2069.

Marcotte, R. et al. "Functional Genomic Landscape of Human Breast Cancer Drivers, Vulnerabilities, and Resistance" Cell 2016;164:293-309.

Wang, C. et al., "Estrogen induces c-myc gene expression via an upstream enhancer activated by the estrogen receptor and the AP-1 transcription factor," Mol. Endocrinol. 2011;25(9):1527-38.

Murakami, S. et al., "Distinct Roles for BET Family Members in Estrogen Receptor α Enhancer Function and Gene Regulation in Breast Cancer Cells," Mol. Cancer Res. 2019;17(12):2356-2368.

Lin, X. et al., "HEXIM1 as a Robust Pharmacodynamic Marker for Monitoring Target Engagement of BET Family Bromodomain Inhibitors in Tumors and Surrogate Tissues," Mol. Cancer Ther. 2017;16(2):388-396.

Shao, H. et al., "HEXIM1 controls P-TEFb processing and regulates drug sensitivity in triple-negative breast cancer," Mol. Biol. Cell. 2020;31:1867-1878.

Feng, Q. et al., "An epigenomic approach to therapy for tamoxifen-resistant breast cancer," Cell Res. 2014;24:809-819.

Udden, S. N. et al., "Targeting ESR1 mutation-induced transcriptional addiction in breast cancer with BET inhibition," JCI Insight. 2022;7(17):e151851.

Bauer, K. et al., "Degradation of BRD4—a promising treatment approach not only for hematologic but also for solid cancer," Am. J. Cancer Res. 2021;11(2):530-545.

Devaraj, S. G. T. et al., "HEXIM1 induction is mechanistically involved in mediating anti-AML activity of BET protein bromodomain antagonist," Leukemia 2016;30:504-508.

Yeh, T. et al., "Identification of CCR2 and CD180 as Robust Pharmacodynamic Tumor and Blood Biomarkers for Clinical Use with BRD4/BET Inhibitors," Clin. Cancer Res. 2017;23(4):1025-1035.

Sengupta, S. et al., "Inhibition of BET proteins impairs estrogen-mediated growth and transcription in breast cancers by pausing RNA polymerase advancement," Breast Cancer Res. Treat. 2015;150:265-278.

Ogba, N. et al., "HEXIM1 regulates 17beta-estradiol/estrogen receptor-alpha-mediated expression of cyclin D1 in mammary cells via modulation of P-TEFb," Cancer Res. 2008;68(17):7015-7024.

Wang, Y.-C. et al. "Different mechanisms for resistance to trastuzumab versus lapatinib in HER2-positive breast cancers—role of estrogen receptor and HER2 reactivation," Breast Cancer Res. 2011;13(6):R121.

Chung, G. G. et al., "Quantitative analysis of estrogen receptor heterogeneity in breast cancer," Lab. Invest. 2007;87:662-669.

Rich, R. L. et al., "Kinetic analysis of estrogen receptor/ligand interactions," Proc. Natl. Acad. Sci. U. S. A. 2002;99(13):8562-8567.

Miller, M. M. et al., "Development of an In vitro Assay Measuring Uterine-Specific Estrogenic Responses for Use in Chemical Safety Assessment," Toxicological Sciences 2016;154(1):162-173.

Welsh, A. W. et al., "Standardization of estrogen receptor measurement in breast cancer suggests false-negative results are a function of threshold intensity rather than percentage of positive cells," J. Clin. Oncol. 2011;29(22):2978-2984.

Guglielmi, G. et al., "Pharmacological insights on novel oral selective estrogen receptor degraders in breast cancer," Eur. J. Pharmacology, 2024;969:176424.

Luo, G. et al., "Development of novel tetrahydroisoquinoline-hydroxamate conjugates as potent dual SERDs/HDAC inhibitors for the treatment of breast cancer," Eur. J. Med. Chem. 2021;226:113870.

Bardia, A. et al. "AMEERA-5: a randomized, double-blind phase 3 study of amcenestrant plus palbociclib versus letrozole plus palbociclib for previously untreated ER+/HER2-advanced breast cancer," Ther. Adv. Med. Oncol. 2022;14:1-12.

Bardia, A. et al., "AMEERA-1 phase 1/2 study of amcenestrant, SAR439859, in postmenopausal women with ER-positive/HER2-negative advanced breast cancer," Nat. Commun. 2022;13:4116.

Campone, M. et al., "AMEERA-4: a randomized, preoperative window-of-opportunity study of amcenestrant versus letrozole in early breast cancer," Breast Cancer Res. 2023;25:141.

Chen, Y.-C. et al., "Latest generation estrogen receptor degraders for the treatment of hormone receptor-positive breast cancer," Expert Opin. Investigational Drugs, 2021;31(6):515-529.

Scott, J. S. et al., "Discovery of AZD9833, a Potent and Orally Bioavailable Selective Estrogen Receptor Degrader and Antagonist," J. Med. Chem. 2020;63:14530-14559.

Besret, L. et al., "Translational strategy using multiple nuclear imaging biomarkers to evaluate target engagement and early therapeutic efficacy of SAR439859, a novel selective estrogen receptor degrader," EJNMMI Res. 2020;10:70.

Shomali, M. et al., "SAR439859, a Novel Selective Estrogen Receptor Degrader (SERD), Demonstrates Effective and Broad Antitumor Activity in Wild-Type and Mutant ER-Positive Breast Cancer Models," Mol. Cancer Ther. 2021;20:250-262.

Rej, R. K. et al., "Targeting the Estrogen Receptor for the Treatment of Breast Cancer: Recent Advances and Challenges" J. Med. Chem. 2023;66(13):8339-8381.

El-Ahmad, Y. et al., "Discovery of 6-(2,4-Dichlorophenyl)-5-[4-[(3S)-1-(3-fluoropropyl)pyrrolidin-3-yl]oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," J. Med. Chem. 2020;63:512-528.

Lawson, M. et al., "The Next-Generation Oral Selective Estrogen Receptor Degrader Camizestrant (AZD9833) Suppresses ER+ Breast Cancer Growth and Overcomes Endocrine and CDK4/6 Inhibitor Resistance," Cancer Res. 2023;83:3989-4004.

Turner, N. et al., "Design of SERENA-6, a phase III switching trial of camizestrant in ESR1-mutant breast cancer during first-line treatment," Future Oncol. 2023;19(8):559-573.

Liang, J. et al., "GDC-9545 (Giredestrant): A Potent and Orally Bioavailable Selective Estrogen Receptor Antagonist and Degrader with an Exceptional Preclinical Profile for ER+ Breast Cancer," J. Med. Chem. 2021;64:11841-11856.

Tatton, M. R. et al. "First Multikilogram Synthesis of the Next-Generation Oral Selective ER Degrader Camizestrant," Org. Process Res. Dev. 2024;28:2334-2342.

Hamilton, E. et al., "A phase I dose escalation and expansion trial of the next-generation oral SERD camizestrant in women with ER-positive, HER2-negative advanced breast cancer: SERENA-1 monotherapy results," Ann. Oncology, 2024;35(8):707-717.

Zhou, F. et al., "SCR-6852, an oral and highly brain-penetrating estrogen receptor degrader (SERD), effectively shrinks tumors both in intracranial and subcutaneous ER + breast cancer models," Breast Cancer Res. 2023;25:96.

(56) References Cited

OTHER PUBLICATIONS

Joseph, J. D. et al., "The selective estrogen receptor downregulator GDC-0810 is efficacious in diverse models of ER+ breast cancer," eLife 2016;5:e15828.
Chen, Z. et al., "Discovery of ERD-3111 as a Potent and Orally Efficacious Estrogen Receptor PROTAC Degrader with Strong Antitumor Activity," J. Med. Chem. 2023;66:12559-12585.
Will, M. et al. "Therapeutic resistance to anti-oestrogen therapy in breast cancer," Nat. Rev. Cancer 2023;23:673-685.
De Savi, C. et al., "Optimization of a Novel Binding Motif to (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic Acid (AZD9496), a Potent and Orally Bioavailable Selective Estrogen Receptor Downregulator and Antagonist," J. Med. Chem. 2015;58:8128-8140.
Nagasawa, J. et al., "Identification of an Orally Bioavailable Chromene-Based Selective Estrogen Receptor Degrader (SERD) That Demonstrates Robust Activity in a Model of Tamoxifen-Resistant Breast Cancer," J. Med. Chem. 2018;61:7917-7928.
Von Angerer, E. and Strohmeier, J. "2-Phenylindoles. Effect of N-Benzylation on Estrogen Receptor Affinity, Estrogenic Properties, and Mammary Tumor Inhibiting Activity" J. Med. Chem. 1987;30(1):131-136.
Collier, A. et al., "Exploratory biomarker analysis of acelERA Breast Cancer (BC): Phase II study of giredestrant vs. physician's choice of endocrine therapy (PCET) for previously treated, estrogen receptor-positive, HER2-negative advanced BC (ER+, HER2-aBC)," Poster presented on Jun. 3, 2023 at the American Society of Clinical Oncology Annual Meeting.
Grese, T. A. et al., "Structure-Activity Relationships of Selective Estrogen Receptor Modulators: Modifications to the 2-Arylbenzothiophene Core of Raloxifene," J. Med. Chem. 1997;40:146-167.
Yu, D. et al., "Hydrogen Peroxide-Inducible PROTACs for Targeted Protein Degradation in Cancer Cells," ChemBioChem 2023;24(17):e202300422.
International Search Report and Written Opinion for International Application No. PCT/US2025/018835, dated Jun. 12, 2025 (14 pages).
Welsh, A. W. et al., "Quantitative Analysis of Estrogen Receptor Expression Shows SP1 Antibody Is More Sensitive Than 1D5," Appl. Immunohistochem. Mol. Morphol. 2013;21(2):139-147.

* cited by examiner

HETEROBIFUNCTIONAL COMPOUNDS AND THEIR USE IN TREATING DISEASE

CROSS REFERENCE TO RELATED APPLICATIONS

This application claims the benefit of and priority to U.S. Provisional Patent Application Ser. No. 63/761,647, filed Feb. 21, 2025, and U.S. Provisional Patent Application Ser. No. 63/562,801, filed Mar. 8, 2024; the contents of each of which are hereby incorporated by reference in their entirety.

FIELD OF THE INVENTION

The invention provides heterobifunctional compounds, pharmaceutical compositions, and their use in treating disease, such as cancer.

BACKGROUND

Cancer continues to be a significant health problem despite the substantial research efforts and scientific advances reported in the literature for treating this disease. Solid tumors, including prostate cancer, breast cancer, and lung cancer remain highly prevalent among the world population. The incidence of prostate cancer increases with age, and with increasing longevity of human subjects, there continues to be a corresponding rise in the number of patients suffering from prostate cancer. Breast cancer is one of the most common cancers among women and is a leading cause of death for women between ages 50-55. Lung cancer is a leading cause of death among cancer patients, where over 85% of lung cancers are non-small cell lung cancer (NSCLC). Many lung cancers are attributed to tobacco smoking. Current treatment options for these cancers are not effective for all patients and/or can have substantial adverse side effects.

New therapies are needed to address this unmet need in cancer therapy. In particular, new therapies are needed that achieve an anti-cancer effect through a different mechanism than commonly available therapies. Exemplary mechanisms for common anti-cancer therapies include (a) alkylation of DNA, which limits ability of the cell to reproduce, (b) topoisomerase inhibition, in which the therapeutic agent inhibits the activity of one or more topoisomerases, thereby limiting separation of strands of DNA, and (c) mitotic inhibition, where the therapeutic agent reduces ability of the cell to divide. New therapies that achieve an anti-cancer effect through a different mechanism present an opportunity to treat cancers more effectively and/or to treat cancers that have become resistant to currently available medicines.

The present invention addresses the foregoing needs and provides other related advantages.

SUMMARY

The invention provides heterobifunctional compounds, pharmaceutical compositions, and their use in treating disease, such as cancer. In particular, one aspect of the invention provides a collection of heterobifunctional compounds, such as a compound represented by Formula I:

(I)

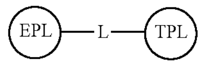

or a pharmaceutically acceptable salt thereof, where the variables are as defined in the detailed description. Further description of additional collections of heterobifunctional compounds are described in the detailed description. The compounds may be part of a pharmaceutical composition comprising a pharmaceutically acceptable carrier.

Another aspect of the invention provides a collection of heterobifunctional compounds, such as a compound represented by Formula II:

(II)

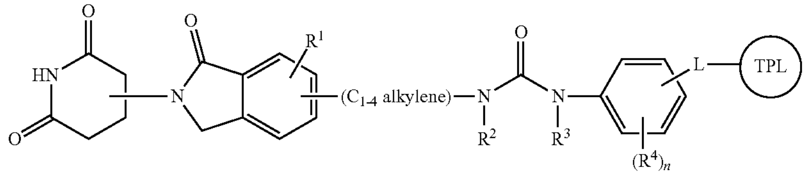

or a pharmaceutically acceptable salt thereof, where the variables are as defined in the detailed description. Further description of additional collections of heterobifunctional compounds are described in the detailed description. The compounds may be part of a pharmaceutical composition comprising a pharmaceutically acceptable carrier.

Another aspect of the invention provides a method of treating cancer. The method comprises administering to a patient in need thereof a therapeutically effective amount of a compound described herein, such as a compound of Formula I or II, to treat the cancer.

Another aspect of the invention provides a method of causing death of a cancer cell. The method comprises contacting a cancer cell with an effective amount of a compound described herein, such as a compound of Formula I or II, to cause death of the cancer cell.

DETAILED DESCRIPTION

The invention provides heterobifunctional compounds, pharmaceutical compositions, and their use in treating disease, such as cancer. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "alkyl" applies to "alkyl" as well as the "alkyl" portions of "—O-alkyl" etc. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e., carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

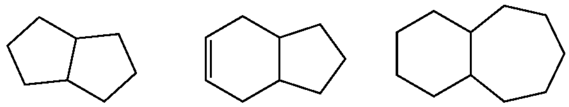
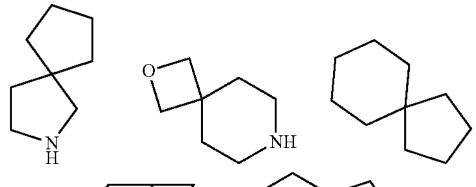
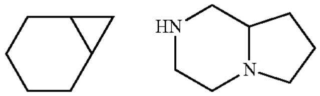

Exemplary bridged bicyclics include:

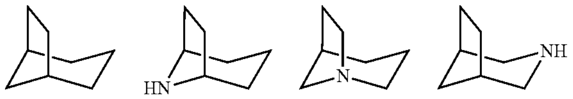
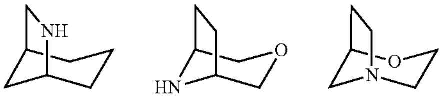
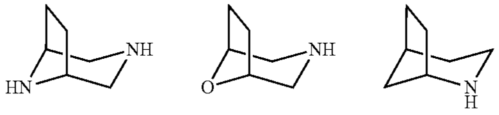
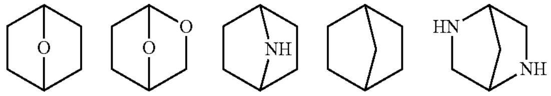
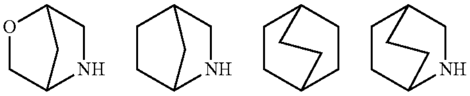
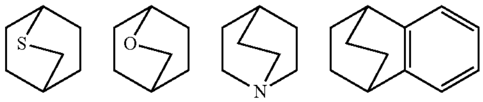
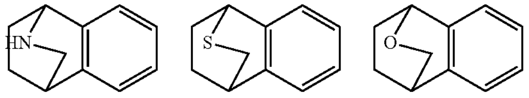
.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "—($C_0$ alkylene)-" refers to a bond. Accordingly, the term "—($C_{0-3}$ alkylene)-" encompasses a bond (i.e., $C_0$) and a —($C_{1-3}$ alkylene)- group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "haloaryl" refers to an aryl group that is substituted with at least one halogen. Exemplary haloaryl groups include chlorophenyl (e.g., 3-chlorophenyl, 4-chlorophenyl), fluorophenyl, and the like. The term "phenylene" refers to a bivalent phenyl group.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted. The term "haloheteroaryl" refers to a heteroaryl group that is substituted with at least one halogen. Exemplary haloheteroaryl groups include chloropyridine, fluoropyridine, chloropyrazole, fluoropyrazole, and the like. The term "heteroarylene" refers to a bivalent heteroaryl group. Similarly, the terms "pyrazolylene", "imidazolylene", and "pyrrolylene", respectively refer to bivalent pyrazolyl, imidazolyl, and pyrrolyl groups. Similarly, the terms "pyridinylene" and "pyrimidinylene", respectively refer to bivalent pyridinyl and pyrimidinyl groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "heterocyclylene" refers to a bivalent heterocyclyl group.

As used herein, the term "heterocycloakyl" refers to a saturated heterocyclyl. The term "heterocycloakyl" refers to a bivalent heterocycloakyl group.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}$R°; —$(CH_2)_{0-4}$OR°; —O$(CH_2)_{0-4}$R°, —O—$(CH_2)_{0-4}$C(O)OR°; —$(CH_2)_{0-4}$CH(OR°)$_2$; —$(CH_2)_{0-4}$SR°; —$(CH_2)_{0-4}$Ph, which may be substituted with R°; —$(CH_2)_{0-4}$O$(CH_2)_{0-1}$Ph which may be substituted with R°; —CH═CHPh, which may be substituted with R°; —$(CH_2)_{0-4}$O$(CH_2)_{0-1}$-pyridyl which may be substituted with R°; —$NO_2$; —CN; —$N_3$; —$(CH_2)_{0-4}$N(R°)$_2$; —$(CH_2)_{0-4}$N(R°)C(O)R°; —N(R°)C(S)R°; —$(CH_2)_{0-4}$N(R°)C(O)NR°$_2$; —N(R°)C(S)NR°$_2$; —$(CH_2)_{0-4}$N(R°)C(O)OR°; —N(R°)N(R°)C(O)R°; —N(R°)N(R°)C(O)NR°$_2$, —N(R°)N(R°)C(O)OR°; —$(CH_2)_{0-4}$C(O)R°; —C(S)R°; —$(CH_2)_{0-4}$C(O)OR°; —$(CH_2)_{0-4}$C(O)SR°; —$(CH_2)_{0-4}$C(O)OSiR°$_3$; —$(CH_2)_{0-4}$OC(O)R°; —OC(O)$(CH_2)_{0-4}$SR—, SC(S)SR°; —$(CH_2)_{0-4}$SC(O)R°; —$(CH_2)_{0-4}$C(O)NR°$_2$; —C(S)NR°$_2$; —C(S)SR°; —SC(S)SR°, —$(CH_2)_{0-4}$OC(O)NR°$_2$; —C(O)N(OR°)R°; —C(O)C(O)R°; —C(O)$CH_2$C(O)R°; —C(NOR°)R°; —$(CH_2)_{0-4}$SSR°; —$(CH_2)_{0-4}$S(O)$_2$R°; —$(CH_2)_{0-4}$S(O)$_2$OR°; —$(CH_2)_{0-4}$OS(O)$_2$R°; —S(O)$_2$NR°$_2$; —S(O)(NR°)R°; —S(O)$_2$N═C(NR°$_2$)$_2$; —$(CH_2)_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —($C_{1-4}$ straight or branched alkylene)O—N(R°)$_2$; or —($C_{1-4}$ straight or branched alkylene)C(O)O—N(R°)$_2$.

Each R° is independently hydrogen, $C_{1-6}$ aliphatic, —$CH_2$Ph, —O$(CH_2)_{0-1}$Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R° selected from ═O and ═S; or each R° is optionally substituted with a monovalent substituent independently selected from halogen, —$(CH_2)_{0-2}$R●, -(haloR●), —$(CH_2)_{0-2}$OH, —$(CH_2)_{0-2}$OR●, —$(CH_2)_{0-2}$CH(OR●)$_2$; —O(haloR●), —CN, —$N_3$, —$(CH_2)_{0-2}$C(O)R●, —$(CH_2)_{0-2}$C(O)OH, —$(CH_2)_{0-2}$C(O)OR●, —$(CH_2)_{0-2}$SR●, —$(CH_2)_{0-2}$SH, —$(CH_2)_{0-2}$$NH_2$, —$(CH_2)_{0-2}$NHR●, —$(CH_2)_{0-2}$NR●$_2$, —$NO_2$, —SiR●$_3$, —OSiR●$_3$, —C(O)SR●, —($C_{1-4}$ straight or branched alkylene)C(O)OR●, or —SSR●.

Each R● is independently selected from $C_{1-4}$ aliphatic, —$CH_2$Ph, —O$(CH_2)_{0-1}$Ph, or a 5-6-membered saturated, partially unsaturated, or aryl ring having 0-4 heteroatoms independently selected from nitrogen, oxygen, or sulfur, and wherein each R● is unsubstituted or where preceded by halo is substituted only with one or more halogens; or wherein an optional substituent on a saturated carbon is a divalent substituent independently selected from ═O, ═S, ═NNR●$_2$, ═NNHC(O)R●, ═NNHC(O)OR●, ═NNHS(O)$_2$R●, ═NR●, ═NOR●, —O(C(R●$_2$))$_{2-3}$O—, or —S(C(R●2))$_{2-3}$S—, or a divalent substituent bound to vicinal substitutable carbons of an "optionally substituted" group is —O(CR●$_2$)$_{2-3}$O—, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —R●, -(haloR●), —OH, —OR●, —O(haloR●), —CN, —C(O)OH, —C(O)OR●, —$NH_2$, —NHR●, —NR●$_2$, or —$NO_2$, wherein each R● is independently selected from $C_{1-4}$ aliphatic, —$CH_2$Ph, —O$(CH_2)_{0-1}$Ph, or a 5-6-membered saturated, partially unsaturated, or aryl ring having 0-4 heteroatoms independently selected from nitrogen, oxygen, or sulfur, and wherein each R● is unsubstituted or where preceded by halo is substituted only with one or more halogens.

An optional substituent on a substitutable nitrogen is independently —R†, —NR†$_2$, —C(O)R†, —C(O)OR†, —C(O)C(O)R†, —C(O)$CH_2$C(O)R†, —S(O)$_2$R†, —S(O)$_2$NR†$_2$, —C(S)NR†$_2$, —C(NH)NR†$_2$, or —N(R†)S(O)$_2$R†; wherein each RT is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R† is $C_{1-6}$ aliphatic, RT is optionally substituted with halogen, —R●, -(haloR●), —OH, —OR●, —O(haloR●), —CN, —C(O)OH, —C(O)OR●, —$NH_2$, —NHR●, —NR●$_2$, or —$NO_2$, wherein each R● is independently selected from $C_{1-4}$ aliphatic, —$CH_2$Ph, —O$(CH_2)_{0-1}$Ph, or a 5-6-membered saturated, partially unsaturated, or aryl ring having 0-4 heteroatoms independently selected from nitrogen, oxygen, or sulfur, and wherein each R● is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. In certain embodiments, the compound is in the form of a single stereoisomer. In certain embodiments, a stereogenic center in a single stereoisomer compound has the R configuration. In certain embodiments, a stereogenic center in a single stereoisomer compound has the S configuration. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, the compound depicted by a chemical structure herein has the natural distribution of isotopes (i.e., it is not isotopically enriched).

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the *IUPAC* 1974 Recommendations. Further, to the extent a compound described herein may exist as an atropisomer (e.g., substituted biaryls), all forms of such atropisomer are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples and tables herein is assumed to have the sufficient number of hydrogen atom(s) to satisfy the valences.

The terms "a" and "an" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The term "haloalkyl" refers to an alkyl group that is substituted with at least one halogen. Exemplary haloalkyl groups include $—CH_2F$, $—CHF_2$, $—CF_3$, $—CH_2CF_3$, $—CF_2CF_3$, and the like. The term "chloroalkyl" refers to an alkyl group that is substituted with at least one chloro. The term "bromoalkyl" refers to an alkyl group that is substituted with at least one bromo. The term "haloalkylene" refers to a bivalent haloalkyl group.

The term "hydroxyalkyl" refers to an alkyl group that is substituted with at least one hydroxyl. Exemplary hydroxyalkyl groups include $—CH_2CH_2OH$, $—C(H)(OH)CH_3$, $—CH_2C(H)(OH)CH_2CH_2OH$, and the like.

The term "heteroalkyl" refers to an alkyl group in which one or more carbon atoms has been replaced by a heteroatom (e.g., N, O, or S). Exemplary heteroalkyl groups include $—OCH_3$, $—CH_2OCH_3$, $—CH_2CH_2N(CH_3)_2$, and $—CH_2CH_2OH$. The heteroalkyl group may contain, for example, from 2-4, 2-6, or 2-8 atoms selected from the group consisting of carbon and a heteroatom (e.g., N, O, or S). The phrase 3-8 membered heteroalkyl refers to a heteroalkyl group having from 3 to 8 atoms selected from the group consisting of carbon and a heteroatom. The term "heteroalkylene" refers to a bivalent heteroalkyl group.

The terms "alkenyl" and "alkynyl" are art-recognized and refer to unsaturated aliphatic groups analogous in length and possible substitution to the alkyls described above, but that contain at least one double or triple bond respectively. The term "haloalkenyl" refers to an alkenyl group that is substituted with at least one halogen. The term "fluoroalkenyl" refers to an alkenyl group that is substituted with at least one fluoro. The term "nitroalkenyl" refers to an alkenyl group that is substituted with at least one nitro.

The term "carbocyclylene" refers to a bivalent cycloaliphatic group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. The term "haloalkoxyl" refers to an alkoxyl group that is substituted with at least one halogen. Exemplary haloalkoxyl groups include $—OCH_2F$, $—OCHF_2$, $—OCF_3$, $—OCH_2CF_3$, $—OCF_2CF_3$, and the like.

The term "oxo" is art-recognized and refers to a "$=O$" substituent. For example, a cyclopentane susbsituted with an oxo group is cyclopentanone.

The term "amino" is art-recognized and refers to both unsubstituted and substituted amines, e.g., a moiety that may be represented by the general formulas:

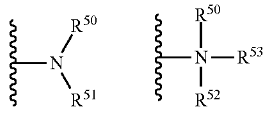

wherein $R^{50}$, $R^{51}$, $R^{52}$ and $R^{53}$ each independently represent a hydrogen, an alkyl, an alkenyl, $—(CH_2)_m—R^{61}$, or $R^{50}$ and $R^{51}$, taken together with the N atom to which they are attached complete a heterocycle having from 4 to 8 atoms in the ring structure; $R^{61}$ represents an aryl, a 3-7 membered cycloalkyl, a 4-7 membered cycloalkenyl, 5-10 membered heteroaryl, or 3-10 membered heterocyclyl; and m is zero or an integer in the range of 1 to 8.

The term "amido" is art-recognized and refers to both unsubstituted and substituted amides, e.g., a moiety that may be represented by the general formulas:

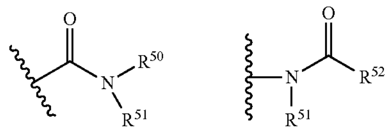

wherein $R^{50}$ and $R^{51}$ each independently represent a hydrogen, an alkyl, an alkenyl, $—(CH_2)_m—R^{61}$, or $R^{50}$ and $R^{51}$, taken together with the N atom to which they are attached complete a heterocycle having from 4 to 8 atoms in the ring structure; $R^{61}$ represents an aryl, a 3-7 membered cycloalkyl, a 4-7 membered cycloalkenyl, 5-10 membered heteroaryl, or 3-10 membered heterocyclyl; and m is zero or an integer in the range of 1 to 8; and $R^{52}$ is an alkyl, an alkenyl, or $—(CH_2)_m—R^{61}$.

The symbol "  " indicates a point of attachment.

When any substituent or variable occurs more than one time in any constituent or the compound of the invention, its definition on each occurrence is independent of its definition at every other occurrence, unless otherwise indicated.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required to achieve 50% inhibition of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Heterobifunctional Compounds

The invention provides heterobifunctional compounds. The compounds are generally represented by the following formula:

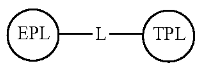

or a pharmaceutically acceptable salt thereof, wherein EPL is a moiety that binds to an effector protein selected from BRD4, CDK1, CDK2, CDK9, or GSPT1; L is a linker; and TPL is a moiety that binds to estrogen receptor.

The compounds may be used in the pharmaceutical compositions and therapeutic methods described herein. Exemplary compounds are described in the following sections, along with exemplary procedures for making the compounds.

Part A: Compounds of Formula I

One aspect of the invention provides a compound represented by Formula I:

(I)

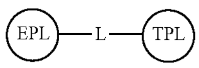

or a pharmaceutically acceptable salt thereof, wherein:

EPL is a moiety that binds to an effector protein selected from BRD4, CDK1, CDK2, or CDK9;

L is a linker; and

TPL is a moiety that binds to an estrogen receptor.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I.

The compound may be further characterized according to, for example, the identity of L and/or TPL. Exemplary further embodiments for L and TPL are provided in Parts C and D below.

As generally defined above, EPL is a moiety that binds to an effector protein selected from BRD4, CDK1, CDK2, and CDK9. In certain embodiments, the EPL is a moiety that binds to BRD4. In certain embodiments, the EPL is a moiety that binds to CDK1. In certain embodiments, the EPL is a moiety that binds to CDK2. In certain embodiments, the EPL is a moiety that binds to CDK9.

A. Moiety for BRD4

In certain embodiments, the EPL is a moiety that binds to bromodomain-containing protein 4 (BRD4). Exemplary compounds that bind to BRD4 are reported in the literature, including:

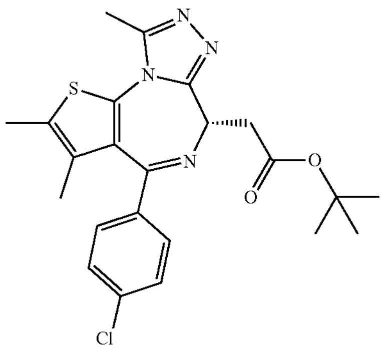

, as described by Bradner, J. E., et al. in WO 2011/143669;

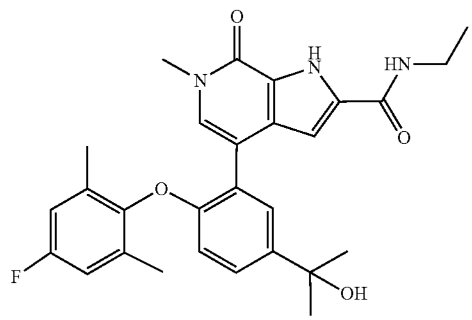

, as described by Fidanze, S. D., et al. in WO 2017/177955.

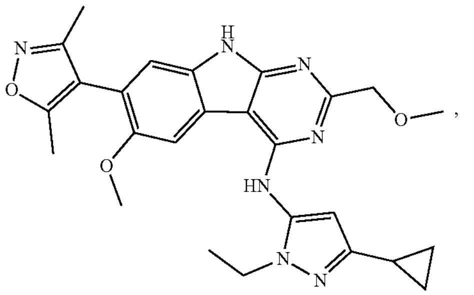 [SMILES: CCn1nc(C2CC2)cc1Nc1nc(COC)nc2[nH]c3cc(-c4c(C)noc4C)c(OC)cc3c12]

as described by Wang, S., et al. in WO 2016/138332;

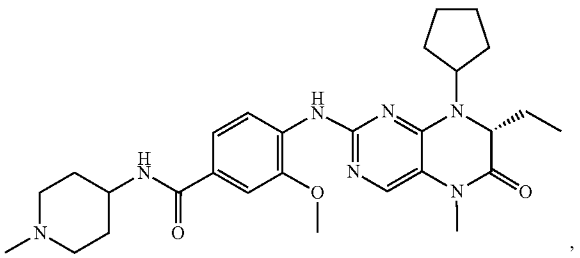 [SMILES: CC[C@@H]1C(=O)N(C)c2cnc(Nc3ccc(C(=O)NC4CCN(C)CC4)cc3OC)nc2N1C1CCCC1]

as described by Chen, L., et al. in *ACS Med Chem Lett* 2015, vol. 6(7), page 764;

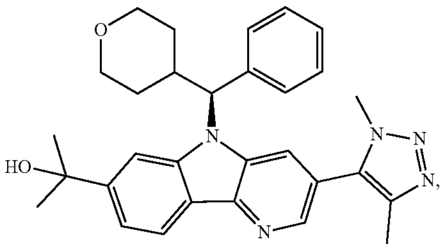 [SMILES: Cc1nnn(C)c1-c1cnc2c3ccc(C(C)(C)O)cc3n([C@H](c3ccccc3)C3CCOCC3)c2c1]

described by Norris, D. J., et al. in WO 2015/100282.

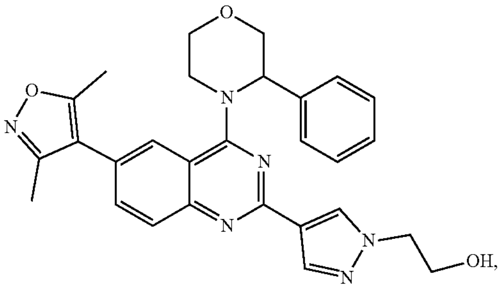 [SMILES: Cc1noc(C)c1-c1ccc2nc(-c3cnn(CCO)c3)nc(N3CCOCC3c3ccccc3)c2c1]

as described by Yang, S. M., et al. in *Bioorg Med Chem Lett* 2018, vol. 28(21), page 3483;

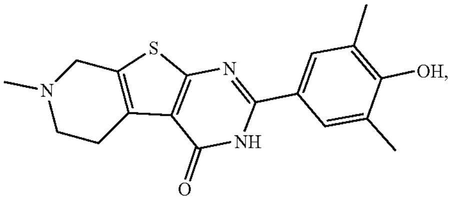 [SMILES: Cc1cc(-c2nc3sc4c(c3c(=O)[nH]2)CCN(C)C4)cc(C)c1O]

as described by Ouyang, L., et al. in *J Med Chem* 2017, vol. 60(24), page 9990;

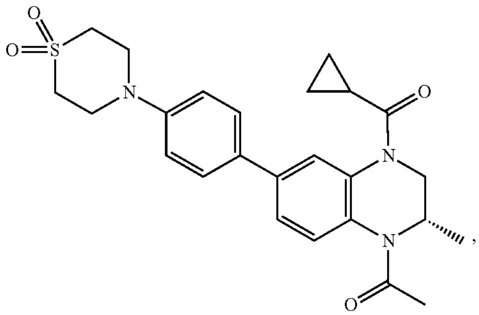 [SMILES: CC(=O)N1c2ccc(-c3ccc(N4CCS(=O)(=O)CC4)cc3)cc2N(C(=O)C2CC2)C[C@@H]1C]

as described by Millan, D. S., et al. in *ACS Med Chem Lett* 2017, vol. 8(8), page 847;

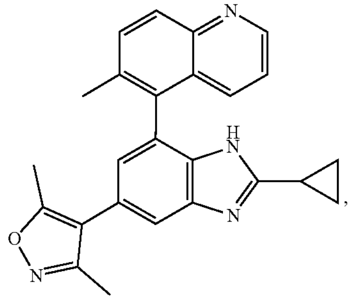 [SMILES: Cc1ccc2ncccc2c1-c1cc(-c2c(C)noc2C)cc2nc(C3CC3)[nH]c12]

as described by Aktoudianakis, E, et al. in WO 2014/182929;

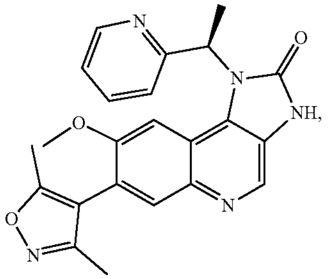 [SMILES: COc1cc2c(cc1-c1c(C)noc1C)ncc1[nH]c(=O)n([C@H](C)c3ccccn3)c12]

as described by Chekler, E. L. P., et al. in WO 2017/037567;

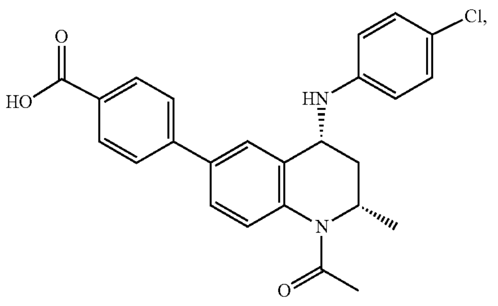 [SMILES: CC(=O)N1c2ccc(-c3ccc(C(=O)O)cc3)cc2[C@H](Nc2ccc(Cl)cc2)C[C@@H]1C]

as described by Demont, E. H., et al. in WO 2011/054848;

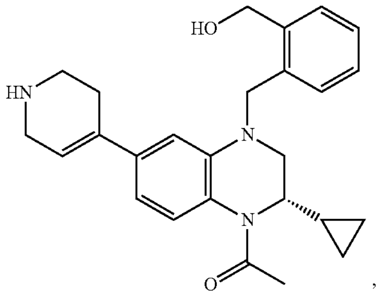 [SMILES: CC(=O)N1c2ccc(C3=CCNCC3)cc2N(Cc2ccccc2CO)C[C@@H]1C1CC1]

as described in Law, R. P., et al., et al. in *J Med Chem* 2018, vol. 61(10), page 4317;

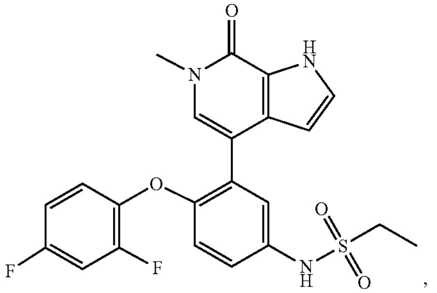 [SMILES: CCS(=O)(=O)Nc1ccc(Oc2ccc(F)cc2F)c(-c2cn(C)c(=O)c3[nH]ccc23)c1]

as described by Hu, Y., et al., et al. in WO 2018/086605;

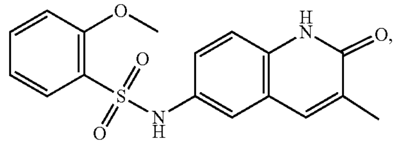 [SMILES: COc1ccccc1S(=O)(=O)Nc1ccc2[nH]c(=O)c(C)cc2c1]

as described by Fish, P. V., et al. in WO 2013/027168;

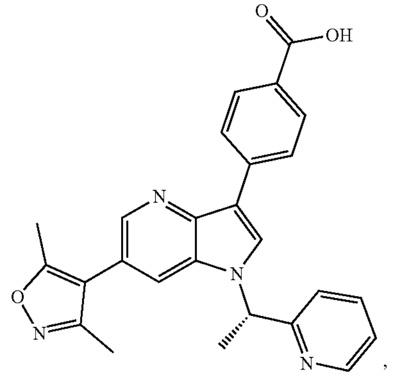 [SMILES: Cc1noc(C)c1-c1cnc2c(-c3ccc(C(=O)O)cc3)cn([C@@H](C)c3ccccn3)c2c1]

as described by Ozer, H. G., et al. in *Cancer Discov* 2018, vol. 8(4), page 458;

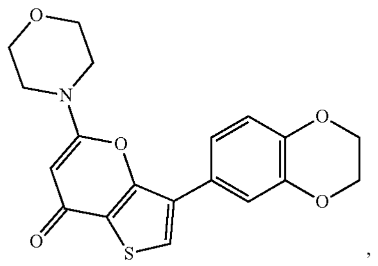 [SMILES: O=c1cc(N2CCOCC2)oc2c(-c3ccc4c(c3)OCCO4)csc12]

as described by Andrews, F. H., et al. in *Proc Natl Acad Sci USA* (*PNAS*) 2017, vol. 114(7), page E1072;

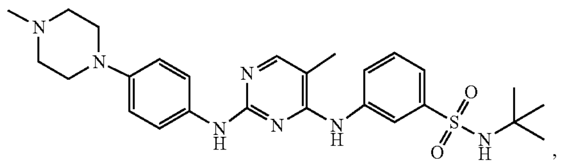 [SMILES: Cc1cnc(Nc2ccc(N3CCN(C)CC3)cc2)nc1Nc1cccc(S(=O)(=O)NC(C)(C)C)c1]

as described by Embe, et al. in *ACS Chem Biol* 2014, vol. 9(5), page 1160;

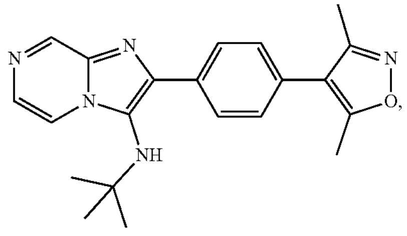 [SMILES: Cc1noc(C)c1-c1ccc(-c2nc3cnccn3c2NC(C)(C)C)cc1]

as described by Marineau, J. J., et al. in WO 2015/013635;

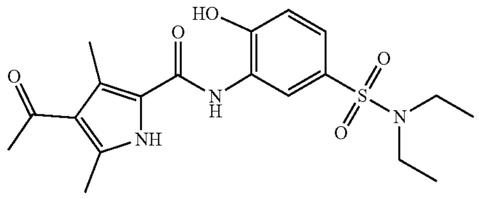
, as described by Huegle, M., et al. in *J Med Chem* 2016, vol. 59(4), page 1518;

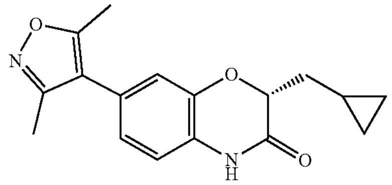
, as described by Xue, X. Q., et al. in *Eur J Med Chem* 2018, vol. 152, page 542;

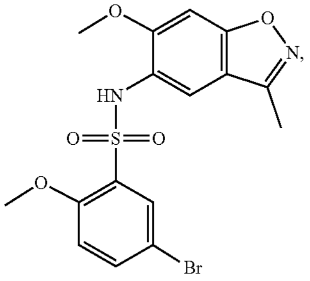 [SMILES: COc1cc2onc(C)c2cc1NS(=O)(=O)c1cc(Br)ccc1OC]

as described by Zhang, M., et al. in *J Med Chem* 2018, vol. 61(7), page 3037;

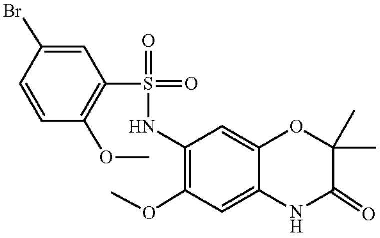
, as described by Xiang. Q., et al. in *ACS Med Chem Lett* 2018, vol. 9(3), page 262;

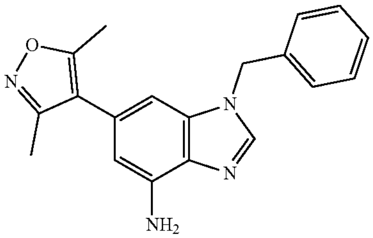
, as described by Kharenko, O. A., et al. in *J Med Chem* 2018, vol. 61(18), page 8202.

In certain embodiments, the EPL is a radical of one of the above compounds, which is attached to L through a modifiable oxygen, nitrogen, or carbon atom.

In certain embodiments, the EPL has the following formula:

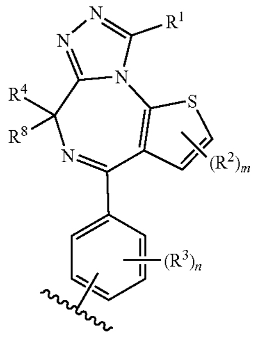

wherein:

$R^1$ is $C_{1-4}$ alkyl or $C_{3-4}$ cycloalkyl;

$R^2$ represents independently for each occurrence $C_{1-4}$ alkyl or $C_{3-4}$ cycloalkyl;

$R^3$ represents independently for each occurrence hydrogen, halo, $C_{1-4}$ alkyl, $C_{1-4}$ haloalkyl, or $C_{1-4}$ alkoxyl;

$R^4$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^5$)($R^6$), —($C_{1-6}$ alkylene)-N($R^5$)C(O)$R^7$, —($C_{1-6}$ alkylene)-$CO_2R^7$, —($C_{1-6}$ alkylene)-OC(O)$R^7$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^4$ and $R^8$ taken together with the carbon atom to which they are attached form a $C_{3-5}$ saturated carbocyclic ring;

$R^5$ and $R^6$ are independently hydrogen, $C_{1-6}$ alkyl, or $C_{3-6}$ cycloalkyl; or $R^5$ and $R^6$ are taken together with the nitrogen atom to which they are attached to form a 3-7 membered ring containing 1 nitrogen atom;

$R^7$ is $C_{1-6}$ alkyl, —($C_{1-6}$ alkylene)-($C_{3-6}$ cycloalkyl), or $C_{3-6}$ cycloalkyl;

$R^8$ is hydrogen or $C_{1-4}$ alkyl; and m and n are independently 0, 1, or 2.

In certain embodiments, $R^3$ represents independently for each occurrence hydrogen, fluoro, chloro, methoxy, or methyl. In certain embodiments, $R^3$ represents independently for each occurrence hydrogen or halo. In certain embodiments, $R^3$ represents independently for each occurrence hydrogen, fluoro, or chloro. In certain embodiments, $R^3$ represents independently for each occurrence hydrogen or fluoro.

In certain embodiments, $R^3$ is hydrogen. In certain embodiments, $R^3$ represents independently for each occurrence halo. In certain embodiments, $R^3$ represents independently for each occurrence fluoro or chloro. In certain embodiments, $R^3$ is fluoro. In certain embodiments, $R^3$ is chloro. In certain embodiments, $R^3$ represents independently for each occurrence $C_{1-4}$ alkyl. In certain embodiments, $R^3$ is methyl. In certain embodiments, $R^3$ represents independently for each occurrence $C_{1-4}$ haloalkyl. In certain embodiments, $R^3$ represents independently for each occurrence $C_{1-4}$ alkoxyl. In certain embodiments, $R^3$ is methoxy.

In certain embodiments, n is 0. In certain embodiments, n is 1. In certain embodiments, n is 2.

In certain embodiments, $R^1$ is $C_{1-4}$ alkyl, $R^2$ represents independently for each occurrence $C_{1-4}$ alkyl, and m is 2. In certain embodiments, $R^1$ and $R^2$ are methyl, and m is 2.

In certain embodiments, each of variables $R^1$, $R^2$, $R^4$, $R^5$, $R^6$, $R^7$, $R^8$, and m is as defined in the embodiments below, both singly, and in combination.

In certain embodiments, the EPL has the following formula:

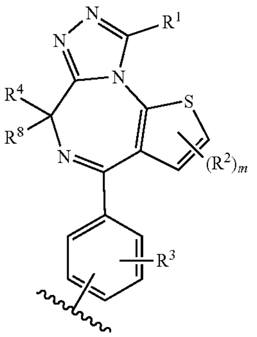

wherein:

$R^1$ is $C_{1-4}$ alkyl or $C_{3-4}$ cycloalkyl;

$R^2$ represents independently for each occurrence $C_{1-4}$ alkyl or $C_{3-4}$ cycloalkyl;

$R^3$ is hydrogen, halo, $C_{1-4}$ alkyl, $C_{1-4}$ haloalkyl, or $C_{1-4}$ alkoxyl;

$R^4$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^5$)($R^6$), —($C_{1-6}$ alkylene)-N($R^5$)C(O)$R^7$, —($C_{1-6}$ alkylene)-$CO_2R^7$, —($C_{1-6}$ alkylene)-OC(O)$R^7$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^4$ and $R^8$ taken together with the carbon atom to which they are attached form a $C_{3-5}$ saturated carbocyclic ring;

$R^5$ and $R^6$ are independently hydrogen, $C_{1-6}$ alkyl, or $C_{3-6}$ cycloalkyl; or $R^5$ and $R^6$ are taken together with the nitrogen atom to which they are attached to form a 3-7 membered ring containing 1 nitrogen atom;

$R^7$ is $C_{1-6}$ alkyl, —($C_{1-6}$ alkylene)-($C_{3-6}$ cycloalkyl), or $C_{3-6}$ cycloalkyl;

$R^8$ is hydrogen or $C_{1-4}$ alkyl; and m is 0, 1, or 2.

In certain embodiments, $R^1$ is $C_{1-4}$ alkyl. In certain embodiments, $R^1$ is methyl. In certain embodiments, $R^1$ is $C_{3-4}$ cycloalkyl.

In certain embodiments, $R^2$ represents independently for each occurrence $C_{1-4}$ alkyl. In certain embodiments, $R^2$ is methyl. In certain embodiments, $R^2$ represents independently for each occurrence $C_{3-4}$ cycloalkyl.

In certain embodiments, $R^3$ is hydrogen or halo. In certain embodiments, $R^3$ is hydrogen or fluoro. In certain embodiments, $R^3$ is hydrogen. In certain embodiments, $R^3$ is halo. In certain embodiments, $R^3$ is fluoro. In certain embodiments, $R^3$ is $C_{1-4}$ alkyl. In certain embodiments, $R^3$ is $C_{1-4}$ haloalkyl. In certain embodiments, $R^3$ is $C_{1-4}$ alkoxyl.

In certain embodiments, $R^4$ is —$CH_2$-(oxazolyl), methyl, or —$CH_2$-(thiazolyl). In certain embodiments, $R^4$ is —$CH_2$-(oxazol-2-yl), methyl, or —$CH_2$-(thiazol-2-yl). In certain embodiments, $R^4$ is —$CH_2$-(oxazolyl) or methyl. In certain embodiments, $R^4$ is —$CH_2$-(oxazol-2-yl) or methyl.

In certain embodiments, $R^4$ is —($C_{0-6}$ alkylene)-(5-6 membered heteroaryl containing 1, 2, or 3 heteroatoms independently selected from nitrogen, oxygen, and sulfur). In certain embodiments, $R^4$ is —$CH_2$-(5-6 membered heteroaryl containing 1, 2, or 3 heteroatoms independently selected from nitrogen, oxygen, and sulfur). In certain embodiments, $R^4$ is —$CH_2$-(5-membered heteroaryl containing 1, 2, or 3 heteroatoms independently selected from nitrogen, oxygen, and sulfur). In certain embodiments, $R^4$ is —$CH_2$-(oxazolyl) or —$CH_2$-(thiazolyl). In certain embodiments, $R^4$ is —$CH_2$-(oxazol-2-yl) or —$CH_2$-(thiazol-2-yl). In certain embodiments, $R^4$ is —$CH_2$-(oxazolyl). In certain embodiments, $R^4$ is —$CH_2$-(oxazol-2-yl). In certain embodiments, $R^4$ is —$CH_2$-(thiazolyl). In certain embodiments, $R^4$ is —$CH_2$-(thiazol-2-yl).

In certain embodiments, $R^4$ is —($C_{1-6}$ alkylene)-C(O)N($R^5$)($R^6$). In certain embodiments, $R^4$ is —($C_{1-6}$ alkylene)-N($R^5$)C(O)$R^7$. In certain embodiments, $R^4$ is —($C_{1-6}$ alkylene)-$CO_2R^7$. In certain embodiments, $R^4$ is —($C_{1-6}$ alkylene)-OC(O)$R^7$. In certain embodiments, $R^4$ is —($C_{1-6}$ alkylene)-cyano. In certain embodiments, $R^4$ is —($C_{1-6}$ alkylene)-O—($C_{1-6}$ alkyl). In certain embodiments, $R^4$ is $C_{1-6}$ alkyl. In certain embodiments, $R^4$ is methyl. In certain embodiments, $R^4$ is $C_{3-6}$ cycloalkyl. In certain embodiments, $R^4$ is hydrogen. In certain embodiments, $R^4$ and $R^8$ taken together with the carbon atom to which they are attached form a $C_{3-5}$ saturated carbocyclic ring. In certain embodiments, $R^4$ is methyl.

In certain embodiments, $R^5$ and $R^6$ are independently hydrogen, $C_{1-6}$ alkyl, or $C_{3-6}$ cycloalkyl. In certain embodiments, $R^5$ is hydrogen. In certain embodiments, $R^5$ is $C_{1-6}$ alkyl. In certain embodiments, $R^5$ is $C_{3-6}$ cycloalkyl. In certain embodiments, $R^6$ is hydrogen. In certain embodiments, $R^6$ is $C_{1-6}$ alkyl. In certain embodiments, $R^6$ is $C_{3-6}$ cycloalkyl. In certain embodiments, $R^5$ and $R^6$ are taken together with the nitrogen atom to which they are attached to form a 3-7 membered ring containing 1 nitrogen atom.

In certain embodiments, $R^7$ is $C_{1-6}$ alkyl. In certain embodiments, $R^7$ is —($C_{1-6}$ alkylene)-($C_{3-6}$ cycloalkyl). In certain embodiments, $R^7$ is $C_{3-6}$ cycloalkyl.

In certain embodiments, $R^8$ is hydrogen. In certain embodiments, $R^8$ is $C_{1-4}$ alkyl.

In certain embodiments, m is 0. In certain embodiments, m is 1. In certain embodiments, m is 2.

In certain embodiments, $R^1$ is $C_{1-4}$ alkyl, $R^1$ and $R^3$ are independently $C_1$-$C_6$ alkyl, and m is 2. In certain embodiments, $R^1$ is $C_{1-4}$ alkyl, $R^2$ represents independently for each occurrence $C_{1-4}$ alkyl, and m is 2. In certain embodiments, $R^1$ and $R^2$ are methyl, and m is 2.

In certain embodiments, the EPL is

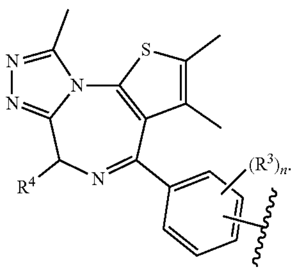

In certain embodiments, the EPL is

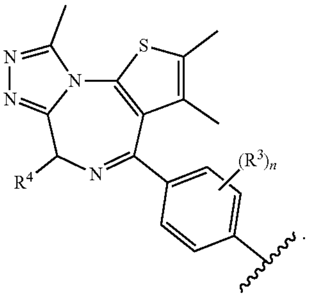

In certain embodiments, the EPL is

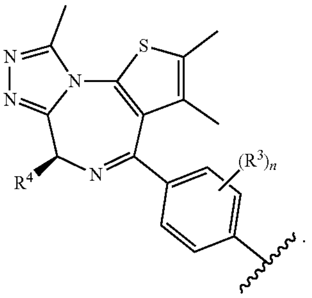

In certain embodiments, the EPL is

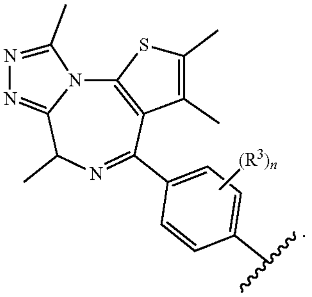

In certain embodiments, the EPL is

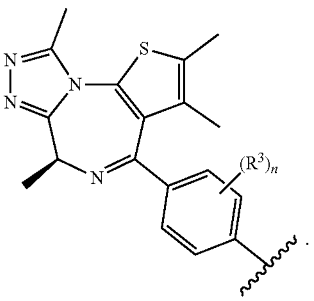

In certain embodiments, the EPL is

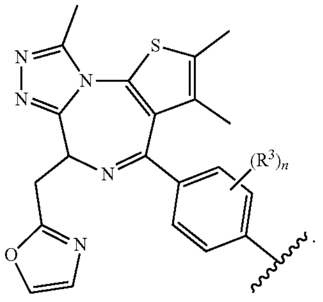

In certain embodiments, the EPL is

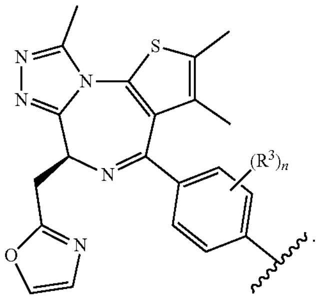

In certain embodiments, the EPL is

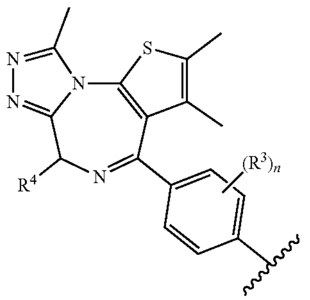

or

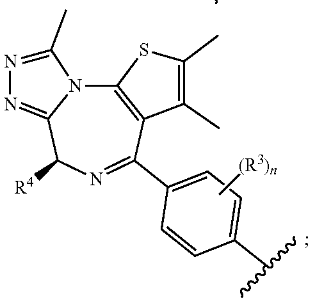

wherein $R^3$ is independently for each occurrence hydrogen, fluoro, chloro, methoxy, or methyl; and $R^4$ is methyl, —$CH_2$-(oxazolyl), or —$CH_2$-(thiazolyl).

In certain embodiments, the EPL is
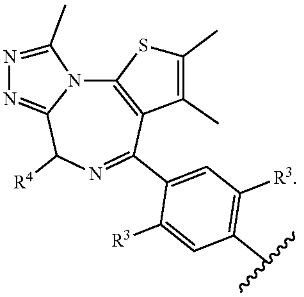
In certain embodiments, the EPL is
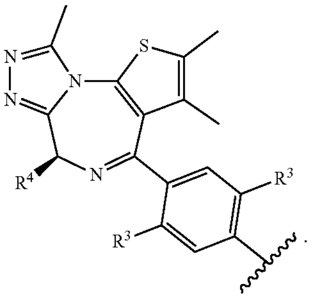
In certain embodiments, the EPL is
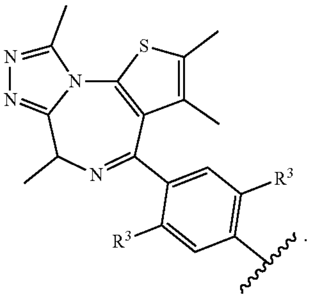
In certain embodiments, the EPL is
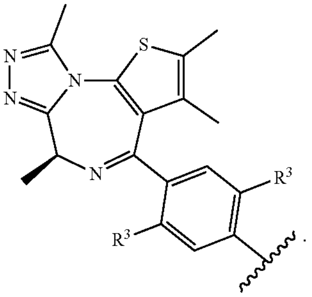
In certain embodiments, the EPL is
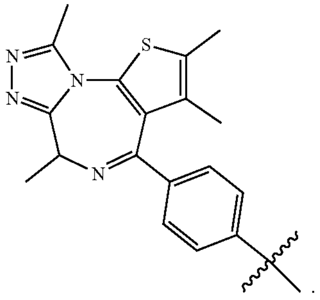 [SMILES: *c1ccc(C2=NC(C)c3nnc(C)n3-c3sc(C)c(C)c32)cc1]
In certain embodiments, the EPL is
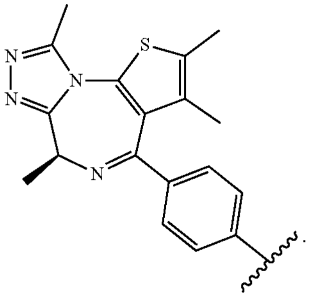 [SMILES: *c1ccc(C2=N[C@@H](C)c3nnc(C)n3-c3sc(C)c(C)c32)cc1]
In certain embodiments, the EPL is
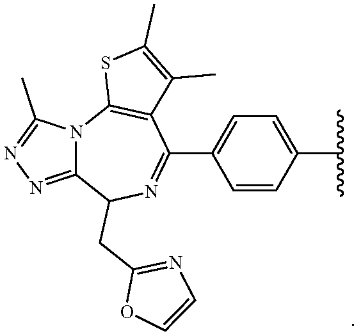 [SMILES: *c1ccc(C2=NC(Cc3ncco3)c3nnc(C)n3-c3sc(C)c(C)c32)cc1]
In certain embodiments, the EPL is
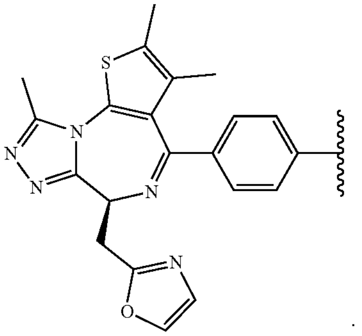 [SMILES: *c1ccc(C2=N[C@@H](Cc3ncco3)c3nnc(C)n3-c3sc(C)c(C)c32)cc1]

In certain embodiments, the EPL has the following formula that is substituted by one occurrence of $R^{II-1}$:

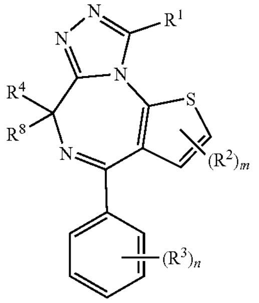

wherein:

$R^{II-1}$ is a bond to L;

$R^1$ is $C_{1-4}$ alkyl or $C_{3-4}$ cycloalkyl;

$R^2$ represents independently for each occurrence $C_{1-4}$ alkyl or $C_{3-4}$ cycloalkyl;

$R^3$ represents independently for each occurrence hydrogen, halo, $C_{1-4}$ alkyl, $C_{1-4}$ haloalkyl, or $C_{1-4}$ alkoxyl;

$R^4$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^5$)($R^6$), —($C_{1-6}$ alkylene)-N($R^5$)C(O)$R^7$, —($C_{1-6}$ alkylene)-$CO_2R^7$, —($C_{1-6}$ alkylene)-OC(O)$R^7$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^4$ and $R^8$ taken together with the carbon atom to which they are attached form a $C_{3-5}$ saturated carbocyclic ring;

$R^5$ and $R^6$ are independently hydrogen, $C_{1-6}$ alkyl, or $C_{3-6}$ cycloalkyl; or $R^5$ and $R^6$ are taken together with the nitrogen atom to which they are attached to form a 3-7 membered ring containing 1 nitrogen atom;

$R^7$ is $C_{1-6}$ alkyl, —($C_{1-6}$ alkylene)-($C_{3-6}$ cycloalkyl), or $C_{3-6}$ cycloalkyl;

$R^8$ is hydrogen or $C_{1-4}$ alkyl; and m and n are independently 0, 1, or 2.

In certain embodiments, the EPL has the following formula that is substituted by one occurrence of $R^{II-1}$:

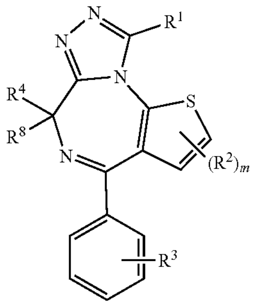

wherein:

$R^{II-1}$ is a bond to L;

$R^1$ is $C_{1-4}$ alkyl or $C_{3-4}$ cycloalkyl;

$R^2$ represents independently for each occurrence $C_{1-4}$ alkyl or $C_{3-4}$ cycloalkyl;

$R^3$ is hydrogen, halo, $C_{1-4}$ alkyl, $C_{1-4}$ haloalkyl, or $C_{1-4}$ alkoxyl;

$R^4$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^5$)($R^6$), —($C_{1-6}$ alkylene)-N($R^5$)C(O)$R^7$, —($C_{1-6}$ alkylene)-$CO_2R^7$, —($C_{1-6}$ alkylene)-OC(O)$R^7$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^4$ and $R^8$ taken together with the carbon atom to which they are attached form a $C_{3-5}$ saturated carbocyclic ring;

$R^5$ and $R^6$ are independently hydrogen, $C_{1-6}$ alkyl, or $C_{3-6}$ cycloalkyl; or $R^5$ and $R^6$ are taken together with the nitrogen atom to which they are attached to form a 3-7 membered ring containing 1 nitrogen atom;

$R^7$ is $C_{1-6}$ alkyl, —($C_{1-6}$ alkylene)-($C_{3-6}$ cycloalkyl), or $C_{3-6}$ cycloalkyl;

$R^8$ is hydrogen or $C_{1-4}$ alkyl; and m is 0, 1, or 2.

In certain embodiments, the EPL has the following formula:

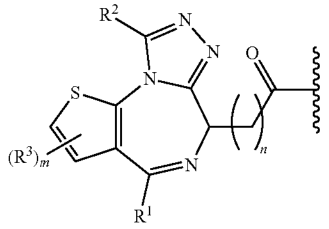

wherein:

$R^1$ is phenyl or 6-membered heteroaryl containing 1 or 2 heteroatoms independently selected from nitrogen, oxygen, and sulfur; wherein the phenyl and heteroaryl are optionally substituted with 1, 2, or 3 substituents independently selected from halo, $C_1$-$C_6$ alkyl, $C_1$-$C_6$ haloalkyl, hydroxyl, or $C_1$-$C_6$ alkoxy;

$R^2$ and $R^3$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

m is 0, 1, or 2; and n is 0, 1, 2, 3, or 4.

In certain embodiments, $R^1$ is phenyl optionally substituted with 1, 2, or 3 substituents independently selected from halo, $C_1$-$C_6$ alkyl, $C_1$-$C_6$ haloalkyl, hydroxyl, or $C_1$-$C_6$ alkoxy. In certain embodiments, $R^1$ is 6-membered heteroaryl containing 1 or 2 heteroatoms independently selected from nitrogen, oxygen, and sulfur; wherein the heteroaryl is optionally substituted with 1, 2, or 3 substituents independently selected from halo, $C_1$-$C_6$ alkyl, $C_1$-$C_6$ haloalkyl, hydroxyl, or $C_1$-$C_6$ alkoxy. In certain embodiments, $R^1$ is phenyl. In certain embodiments, $R^1$ is 6-membered heteroaryl containing 1 or 2 heteroatoms independently selected from nitrogen, oxygen, and sulfur.

In certain embodiments, $R^2$ is halo. In certain embodiments, $R^2$ is $C_1$-$C_6$ alkyl. In certain embodiments, $R^2$ is $C_1$-$C_6$ haloalkyl. In certain embodiments, $R^2$ is $C_3$-$C_6$ cycloalkyl. In certain embodiments, $R^2$ is hydroxyl. In certain embodiments, $R^2$ is $C_1$-$C_6$ alkoxy. In certain embodiments, $R^2$ is cyano.

In certain embodiments, $R^3$ is halo. In certain embodiments, $R^3$ is $C_1$-$C_6$ alkyl. In certain embodiments, $R^3$ is $C_1$-$C_6$ haloalkyl. In certain embodiments, $R^3$ is $C_3$-$C_6$ cycloalkyl. In certain embodiments, $R^3$ is hydroxyl. In certain embodiments, $R^3$ is $C_1$-$C_6$ alkoxy. In certain embodiments, $R^3$ is cyano.

In certain embodiments, m is 0. In certain embodiments, m is 1. In certain embodiments, m is 2. In certain embodiments, n is 0. In certain embodiments, n is 1. In certain embodiments, n is 2. In certain embodiments, n is 3. In certain embodiments, n is 4.

In certain embodiments, $R^2$ and $R^3$ are independently $C_1$-$C_6$ alkyl, and m is 2.

In certain embodiments, the EPL is

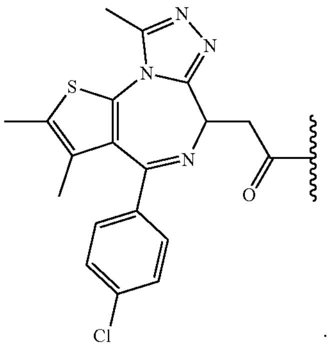

.

In certain embodiments, the EPL is

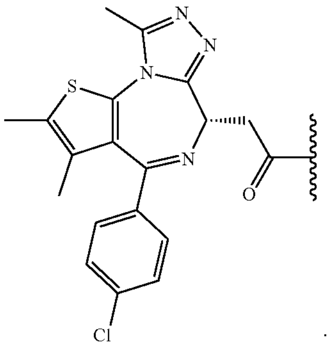 [SMILES: *C(=O)C[C@@H]1N=C(c2ccc(Cl)cc2)c2c(sc(C)c2C)-n2c(C)nnc21]

.

In certain embodiments, the EPL has the following formula that is substituted by one occurrence of $R^{II-1}$:

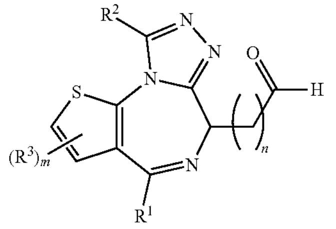

wherein:

$R^{II-1}$ is a bond to L;

$R^1$ is phenyl or 6-membered heteroaryl containing 1 or 2 heteroatoms independently selected from nitrogen, oxygen, and sulfur; wherein the phenyl and heteroaryl are optionally substituted with 1, 2, or 3 substituents independently selected from halo, $C_1$-$C_6$ alkyl, $C_1$-$C_6$ haloalkyl, hydroxyl, or $C_1$-$C_6$ alkoxy;

$R^2$ and $R^3$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

m is 0, 1, or 2; and n is 0, 1, 2, 3, or 4.

In certain embodiments, the EPL has the following formula:

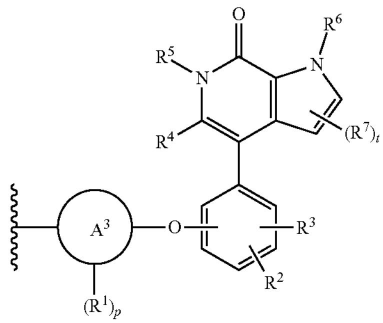

wherein:

$R^1$ represents independently for each occurrence halo, $C_{1-4}$ alkyl, or $C_{1-4}$ haloalkyl;

$R^2$ is hydrogen, halo, $C_{1-4}$ alkyl, or $C_{1-4}$ haloalkyl;

$R^3$ is —$N(R^8)SO_2R^9$, —$SO_2N(R^8)_2$, —$SO_2R^9$, —($C_{1-6}$ alkylene)-$SO_2R^9$, $C_{1-6}$ hydroxyalkyl, or a 4-7 membered saturated carbocyclic ring in which one $CH_2$ is replaced with $SO_2$;

$R^4$ is hydrogen, halo, or $C_{1-4}$ alkyl;

$R^5$ is $C_{1-4}$ alkyl or $C_{3-4}$ cycloalkyl;

$R^6$ is hydrogen, $C_{1-4}$ alkyl, or $C_{3-4}$ cycloalkyl;

$R^7$ represents independently for each occurrence $C_{1-4}$ alkyl or $C_{3-4}$ cycloalkyl;

$R^8$ represents independently for each occurrence hydrogen or $C_{1-4}$ alkyl; or two occurrences of $R^8$ are taken together with the nitrogen atom to which they are attached to form a 3-7 membered heterocyclic ring containing 1 or 2 heteroatoms independently selected from nitrogen and oxygen; or $R^8$ and $R^9$ are taken together with their intervening atoms to a form a 5-7 membered ring containing 1, 2, or 3 heteroatoms independently selected from nitrogen, oxygen, and sulfur;

$R^9$ is $C_{1-6}$ alkyl, $C_{1-6}$ haloalkyl, —($C_{1-6}$ alkylene)-($C_{3-6}$ cycloalkyl), or $C_{3-6}$ cycloalkyl;

$A^3$ is phenylene, a 3-10 membered saturated monocyclic, bicyclic or spirocyclic carbocyclylene, or $C_{1-6}$ alkylene; and p and t are independently 0, 1, or 2.

In certain embodiments, $R^1$ represents independently for each occurrence halo. In certain embodiments, $R^1$ represents independently for each occurrence $C_{1-4}$ alkyl. In certain embodiments, $R^1$ represents independently for each occurrence $C_{1-4}$ haloalkyl.

In certain embodiments, $R^2$ is hydrogen. In certain embodiments, $R^2$ is halo. In certain embodiments, $R^2$ is $C_{1-4}$ alkyl. In certain embodiments, $R^2$ is $C_{1-4}$ haloalkyl.

In certain embodiments, $R^3$ is —$N(R^8)SO_2R^9$. In certain embodiments, $R^3$ is —$SO_2N(R^8)_2$. In certain embodiments, $R^3$ is —$SO_2R^9$. In certain embodiments, $R^3$ is —($C_{1-6}$ alkylene)-$SO_2R^9$. In certain embodiments, $R^3$ is $C_{1-6}$ hydroxyalkyl. In certain embodiments, $R^3$ is a 4-7 membered saturated carbocyclic ring in which one $CH_2$ is replaced with $SO_2$.

In certain embodiments, $R^4$ is hydrogen. In certain embodiments, $R^4$ is halo. In certain embodiments, $R^4$ is $C_{1-4}$ alkyl. In certain embodiments, $R^5$ is $C_{1-4}$ alkyl. In certain embodiments, $R^5$ is $C_{3-4}$ cycloalkyl. In certain embodiments, $R^6$ is hydrogen. In certain embodiments, $R^6$ is $C_{1-4}$ alkyl. In certain embodiments, $R^6$ is $C_{3-4}$ cycloalkyl. In certain embodiments, $R^7$ represents independently for each occurrence $C_{1-4}$ alkyl. In certain embodiments, $R^7$ represents independently for each occurrence $C_{3-4}$ cycloalkyl.

In certain embodiments, $R^8$ represents independently for each occurrence hydrogen. In certain embodiments, $R^8$ represents independently for each occurrence $C_{1-4}$ alkyl. In certain embodiments, two occurrences of $R^8$ are taken together with the nitrogen atom to which they are attached to form a 3-7 membered heterocyclic ring containing 1 or 2 heteroatoms independently selected from nitrogen and oxygen; or $R^8$ and $R^9$ are taken together with their intervening atoms to a form a 5-7 membered ring containing 1, 2, or 3 heteroatoms independently selected from nitrogen, oxygen, and sulfur.

In certain embodiments, $R^9$ is $C_{1-6}$ alkyl. In certain embodiments, $R^9$ is $C_{1-6}$ haloalkyl. In certain embodiments, $R^9$ is —($C_{1-6}$ alkylene)-($C_{3-6}$ cycloalkyl). In certain embodiments, $R^9$ is $C_{3-6}$ cycloalkyl.

In certain embodiments, $A^3$ is phenylene. In certain embodiments, $A^3$ is a 3-10 membered saturated monocyclic, bicyclic or spirocyclic carbocyclylene. In certain embodiments, $A^3$ is $C_{1-6}$ alkylene.

In certain embodiments, p is 0. In certain embodiments, p is 1. In certain embodiments, p is 2. In certain embodiments, t is 0. In certain embodiments, t is 1. In certain embodiments, t is 2.

In certain embodiments, the EPL has the following formula:

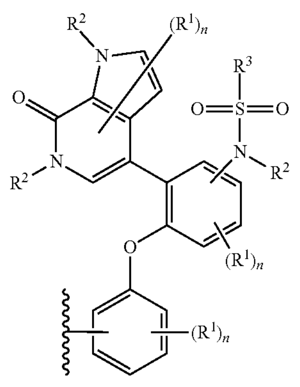

wherein:

$R^1$ represents independently for each occurrence halo, $C_1$-$C_6$ alkyl, $C_1$-$C_6$ haloalkyl, $C_3$-$C_6$ cycloalkyl, or hydroxyl;

$R^2$ represents independently for each occurrence hydrogen, $C_1$-$C_6$ alkyl, or $C_3$-$C_6$ cycloalkyl;

$R^3$ is $C_1$-$C_6$ alkyl or $C_3$-$C_6$ cycloalkyl; and n represents independently for each occurrence 0, 1, 2, or 3.

In certain embodiments, $R^1$ represents independently for each occurrence halo. In certain embodiments, $R^1$ represents independently for each occurrence $C_1$-$C_6$ alkyl. In certain embodiments, $R^1$ represents independently for each occurrence $C_1$-$C_6$ haloalkyl. In certain embodiments, $R^1$ represents independently for each occurrence $C_3$-$C_6$ cycloalkyl. In certain embodiments, $R^1$ represents independently for each occurrence hydroxyl.

In certain embodiments, $R^2$ represents independently for each occurrence hydrogen. In certain embodiments, $R^2$ represents independently for each occurrence $C_1$-$C_6$ alkyl. In certain embodiments, $R^2$ represents independently for each occurrence $C_3$-$C_6$ cycloalkyl.

In certain embodiments, $R^3$ is $C_1$-$C_6$ alkyl. In certain embodiments, $R^3$ is $C_3$-$C_6$ cycloalkyl. In certain embodiments, n is 0. In certain embodiments, n is 1. In certain embodiments, n is 2. In certain embodiments, n is 3.

In certain embodiments, the EPL is

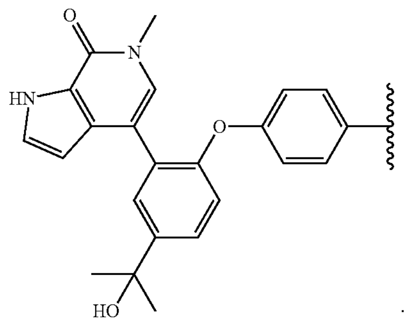 [SMILES: *c1ccc(Oc2ccc(C(C)(C)O)cc2-c2cn(C)c(=O)c3[nH]ccc23)cc1]

In certain embodiments, the EPL is

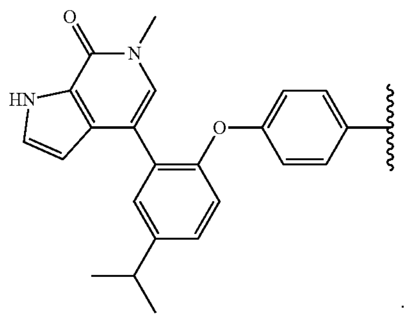 [SMILES: *c1ccc(Oc2ccc(C(C)C)cc2-c2cn(C)c(=O)c3[nH]ccc23)cc1]

In certain embodiments, the EPL has the following formula that is substituted by one occurrence of $R^{II-1}$:

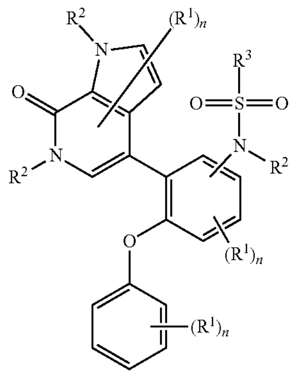

wherein:

$R^{II-1}$ is a bond to L;

$R^1$ represents independently for each occurrence halo, $C_1$-$C_6$ alkyl, $C_1$-$C_6$ haloalkyl, $C_3$-$C_6$ cycloalkyl, or hydroxyl;

$R^2$ represents independently for each occurrence hydrogen, $C_1$-$C_6$ alkyl, or $C_3$-$C_6$ cycloalkyl;

$R^3$ is $C_1$-$C_6$ alkyl or $C_3$-$C_6$ cycloalkyl; and n represents independently for each occurrence 0, 1, 2, or 3.

B. Moiety for CDK1

In certain embodiments, the EPL is a moiety that binds to Cyclin-Dependent Kinase 1 (CDK1). Exemplary compounds that bind to CDK1 are reported in the literature, including:

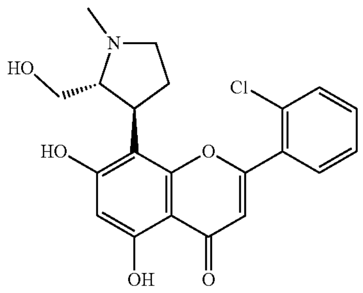

, as described by Sivakumar, M., et al. in WO2007/148158;

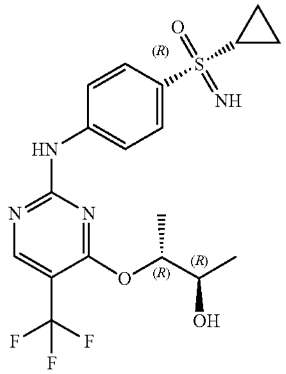

, as described by Lucking, U., et al. in WO2005/037800;

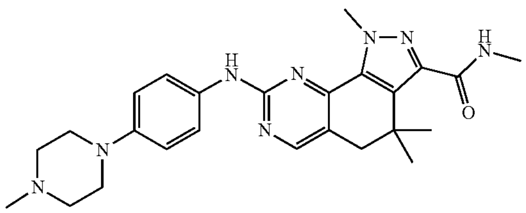

, as described by D'Alessio, R., et al. in WO2004/104007;

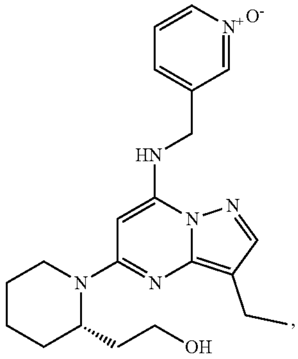

, as described by Guzi, T. J., et al. in WO2005/077954;

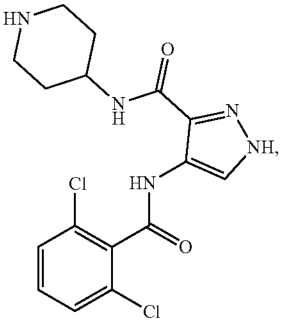 [SMILES: O=C(NC1CCNCC1)c1n[nH]cc1NC(=O)c1c(Cl)cccc1Cl]

as described by Wyatt, P. G., et al. in WO2005/012256;

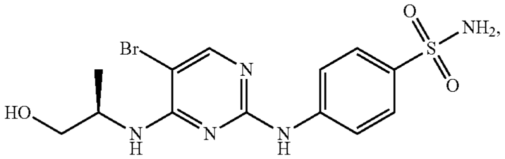 [SMILES: C[C@H](CO)Nc1nc(Nc2ccc(S(N)(=O)=O)cc2)ncc1Br]

as described by Brumby, T., et al. in WO2002/096888;

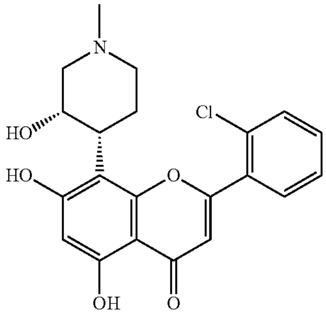

, as described by Dumont, J. A., et al. in WO2000/044362;

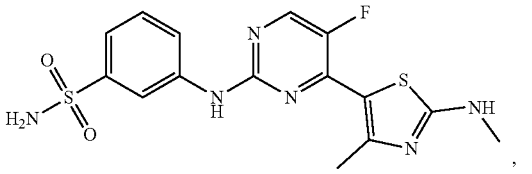 [SMILES: CNc1nc(C)c(-c2nc(Nc3cccc(S(N)(=O)=O)c3)ncc2F)s1]

as described by Wang, S., et al. in WO2013/156780;

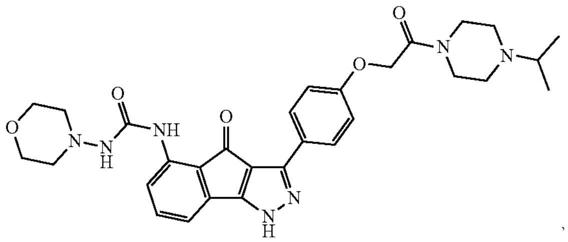 [SMILES: CC(C)N1CCN(C(=O)COc2ccc(-c3n[nH]c4c3C(=O)c3c(NC(=O)NN5CCOCC5)cccc3-4)cc2)CC1]

as described by Wang, Z., et al. in WO2004/092139;

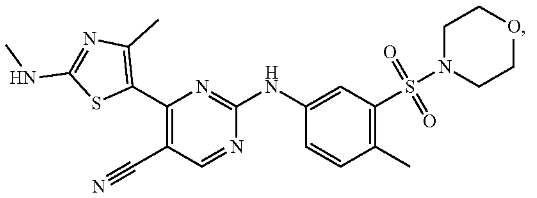 [SMILES: CNc1nc(C)c(-c2nc(Nc3ccc(C)c(S(=O)(=O)N4CCOCC4)c3)ncc2C#N)s1]

as described by Wang, S., et al. in WO2009/118567;

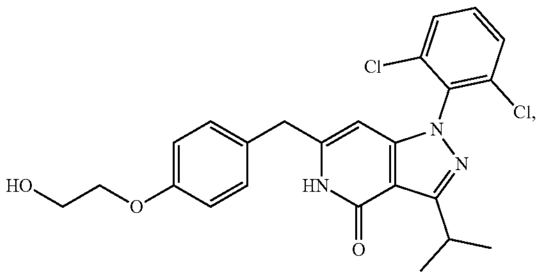 [SMILES: CC(C)c1nn(-c2c(Cl)cccc2Cl)c2cc(Cc3ccc(OCCO)cc3)[nH]c(=O)c12]

as described by Caligiuri, M., et al. in Chem Biol (London) 2005, 12(10): 1103.

In certain embodiments, the EPL is a radical of one of the above compounds, which is attached to L through a modifiable oxygen, nitrogen, or carbon atom.

In certain embodiments, the EPL has the following formula:

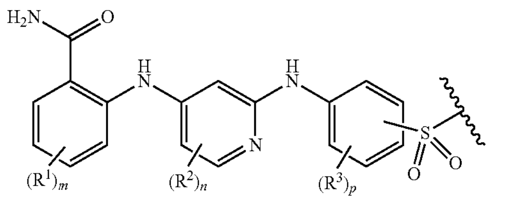

wherein:

$R^1$, $R^2$ and $R^3$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

m and p each represent independently 0, 1, or 2; and n is 0, 1 or 2.

In certain embodiments the EPL is

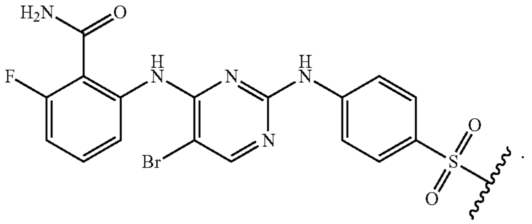 [SMILES: *S(=O)(=O)c1ccc(Nc2ncc(Br)c(Nc3cccc(F)c3C(N)=O)n2)cc1]

In certain embodiments, the EPL has the following formula:

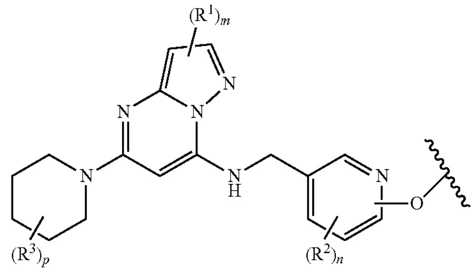

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

In certain embodiments, the EPL has the following formula:

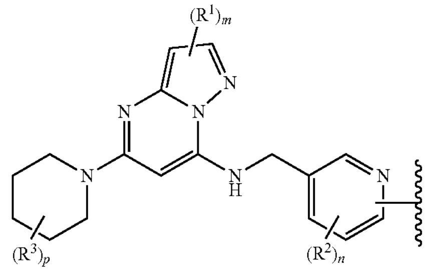

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

In certain embodiments, the EPL has the following formula:

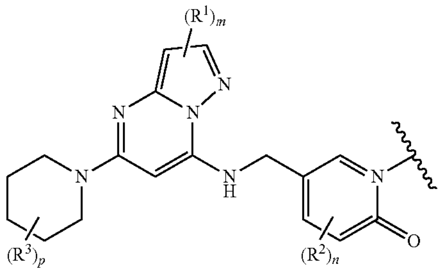

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

C. Moiety for CDK2

In certain embodiments, the EPL is a moiety that binds to Cyclin-Dependent Kinase 2 (CDK2). Exemplary compounds that bind to CDK2 are reported in the literature, including:

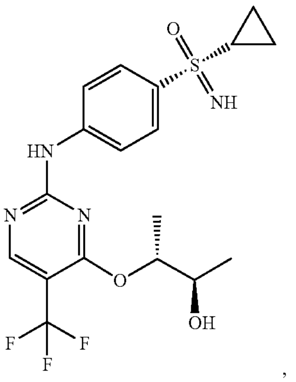 [SMILES: C[C@@H](O)[C@@H](C)Oc1nc(Nc2ccc([S@](=N)(=O)C3CC3)cc2)ncc1C(F)(F)F]

, as described by Lucking, U., et al. in WO2005/037800;

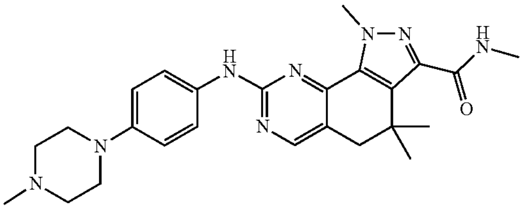

, as described by D'Alessio, R., et al. in WO2004/104007;

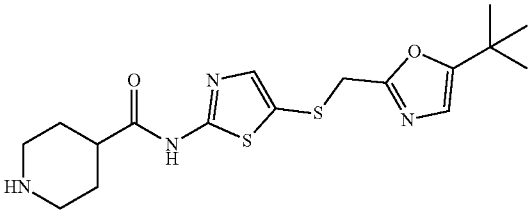

, as described by Misra, R. N., et al. in WO2001/044242;

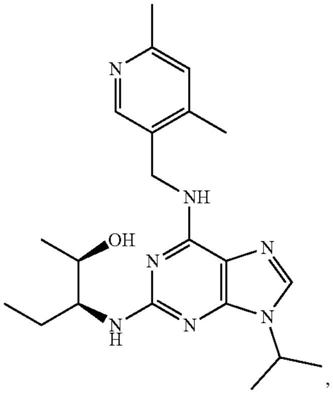 [SMILES: CC[C@H](Nc1nc(NCc2cnc(C)cc2C)c2ncn(C(C)C)c2n1)[C@@H](C)O]

, as described by Sheldrake, P. W., et al. in WO2008/122767;

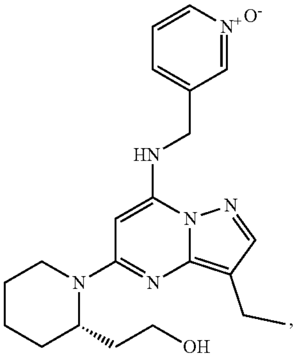

as described by Guzi, T. J., et al. in WO2005/077954;

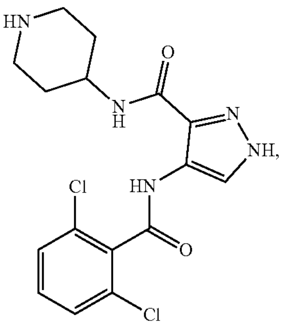 [SMILES: O=C(NC1CCNCC1)c1n[nH]cc1NC(=O)c1c(Cl)cccc1Cl]

as described by Wyatt, P. G., et al. in WO2005/012256;

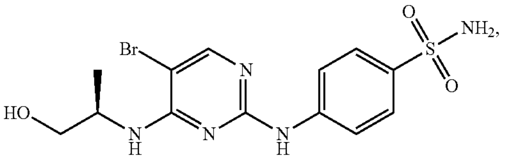 [SMILES: C[C@H](CO)Nc1nc(Nc2ccc(S(N)(=O)=O)cc2)ncc1Br]

described by Brumby, T., et al. in WO2002/096888;

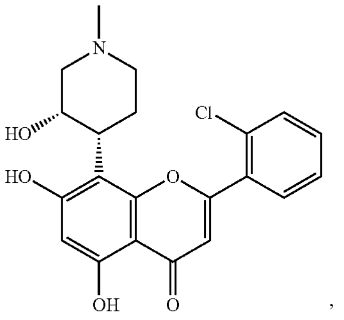 [SMILES: CN1CC[C@H](c2c(O)cc(O)c3c(=O)cc(-c4ccccc4Cl)oc23)[C@H](O)C1]

as described by Dumont, J. A., et al. in WO2000/044362;

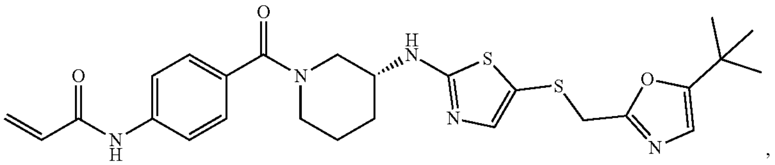 [SMILES: C=CC(=O)Nc1ccc(C(=O)N2CCC[C@@H](Nc3ncc(SCc4ncc(C(C)(C)C)o4)s3)C2)cc1]

as described by Hao, M., et al. in WO2017/044858.

In certain embodiments, the EPL is a radical of one of the above compounds, which is attached to L through a modifiable oxygen, nitrogen, or carbon atom.

In certain embodiments, the EPL has the following formula:

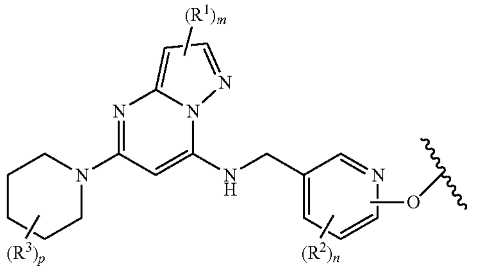

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

In certain embodiments, the EPL has the following formula:

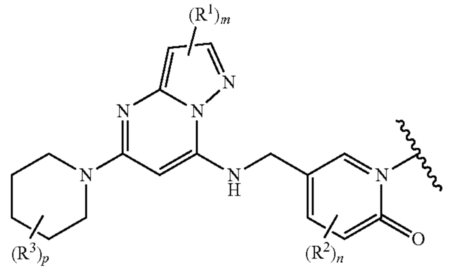

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

In certain embodiments, the EPL has the following formula:

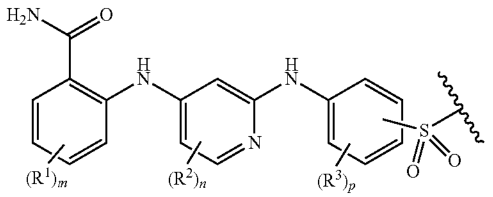

wherein:

$R^1$, $R^2$ and $R^3$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

m and p each represent independently 0, 1, or 2; and n is 0, 1 or 2.

In certain embodiments the EPL is

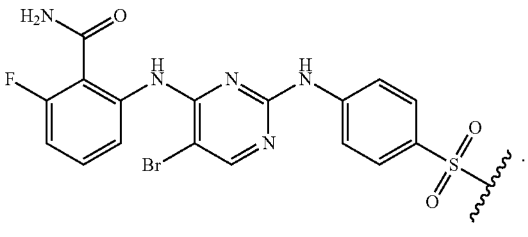 [SMILES: *S(=O)(=O)c1ccc(Nc2ncc(Br)c(Nc3cccc(F)c3C(N)=O)n2)cc1]

D. Moiety for CDK9

In certain embodiments, the EPL is a moiety that binds to Cyclin-Dependent Kinase 9 (CDK9). Exemplary compounds that bind to CDK9 are reported in the literature, including:

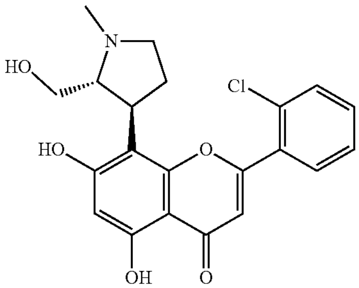
, as described by Sivakumar, M., et al. in WO2007/148158;

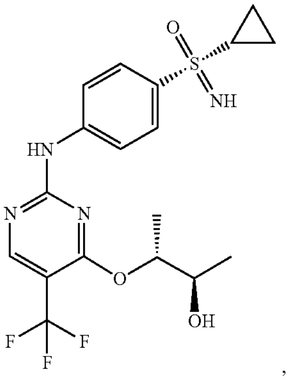 [SMILES: C[C@@H](O)[C@@H](C)Oc1nc(Nc2ccc([S@](=N)(=O)C3CC3)cc2)ncc1C(F)(F)F]
, as described by Lucking, U., et al. in WO2005/037800;

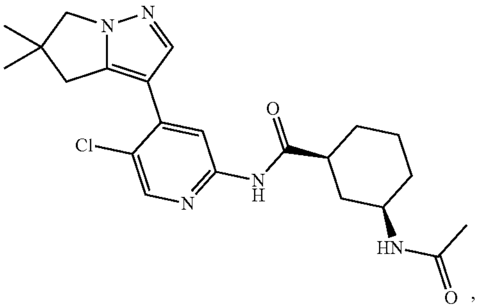 [SMILES: CC(=O)N[C@@H]1CCC[C@H](C(=O)Nc2cc(-c3cnn4c3CC(C)(C)C4)c(Cl)cn2)C1]
, as described by Pike, K. G., et al. in WO2017001354;

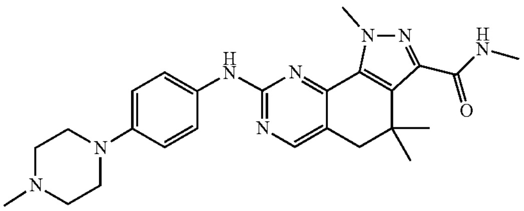
, as described by D'Alessio, R., et al. in WO2004/104007;

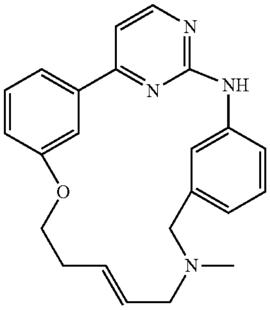
, as described by Blanchard, S., et al. in WO2007/058628;

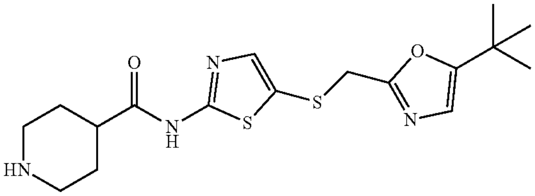
, as described by Misra, R. N., et al. in WO2001/044242;

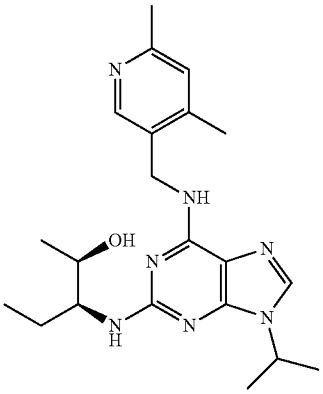
, as described by Sheldrake, P. W. et al. in WO2008/122767;

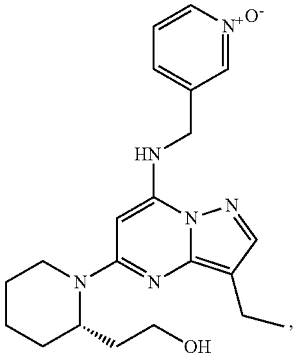
, as described by Guzi, T. J., et al. in WO2005/077954;

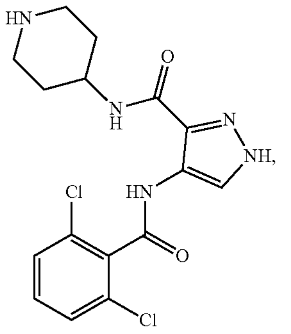 [SMILES: O=C(NC1CCNCC1)c1n[nH]cc1NC(=O)c1c(Cl)cccc1Cl]

as described by Wyatt, P. G., et al. in WO2005/012256;

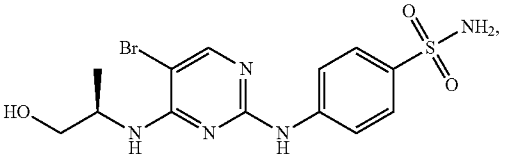 [SMILES: C[C@H](CO)Nc1nc(Nc2ccc(S(N)(=O)=O)cc2)ncc1Br]

as described by Brumby, T., et al. in WO2002/096888;

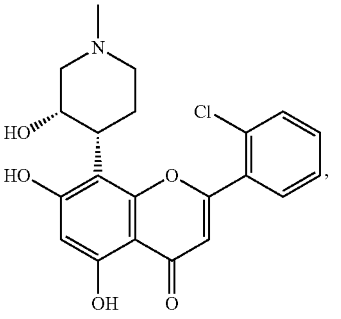 [SMILES: CN1CC[C@H](c2c(O)cc(O)c3c(=O)cc(-c4ccccc4Cl)oc23)[C@H](O)C1 ; ","]

as described by Dumont, J. A., et al. in WO2000/044362;

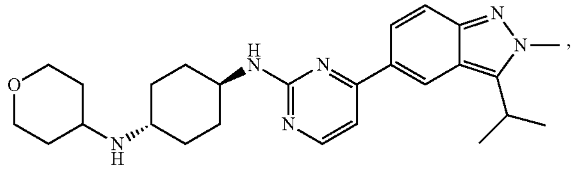

as described by Gao, Q., et al. in CN105111191.

In certain embodiments, the EPL is a radical of one of the above compounds, which is attached to L through a modifiable oxygen, nitrogen, or carbon atom.

In certain embodiments, the EPL has the following formula:

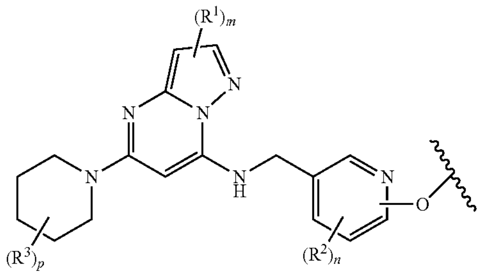

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

In certain embodiments, the EPL has the following formula:

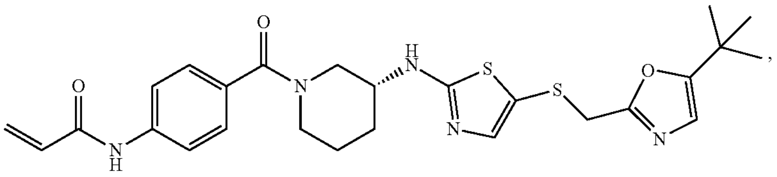 [SMILES: C=CC(=O)Nc1ccc(C(=O)N2CCC[C@@H](Nc3ncc(SCc4ncc(C(C)(C)C)o4)s3)C2)cc1 ; ","]

as described by Hao, M., et al. in WO2017/044858;

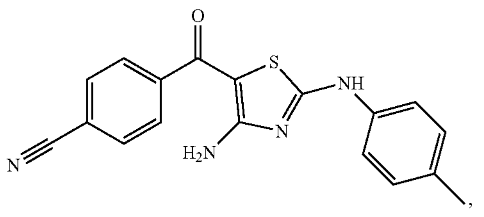 [SMILES: Cc1ccc(Nc2nc(N)c(C(=O)c3ccc(C#N)cc3)s2)cc1 ; ","]

as described by Smith, C. D., et al. in WO2018/089902;

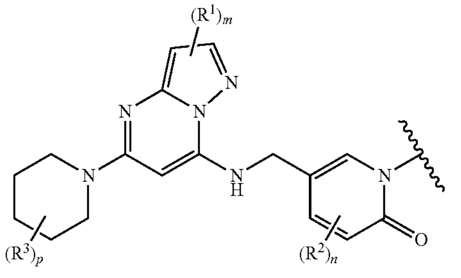

wherein:

$R^1$ and $R^2$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

$R^3$ represents independently for each occurrence $C_1$-$C_6$ alkyl, $C_1$-$C_6$ haloalkyl, $C_3$-$C_6$ cycloalkyl, hydroxyl, $C_1$-$C_6$ alkoxy, $C_1$-$C_6$ hydroxyalkyl, or —($C_1$-$C_6$ alkylene)-($C_1$-$C_6$ alkoxy), m is 0, 1, or 2; and n and p each represent independently 0, 1, 2, or 3.

In certain embodiments, the EPL has the following formula:

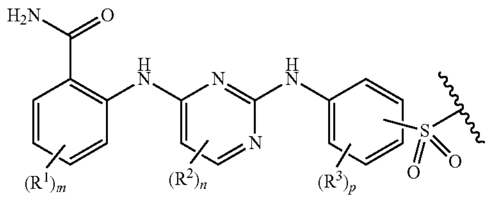

wherein:

$R^1$, $R^2$ and $R^3$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

m and p each represent independently 0, 1, or 2; and n is 0, 1 or 2.

In certain embodiments, the EPL is

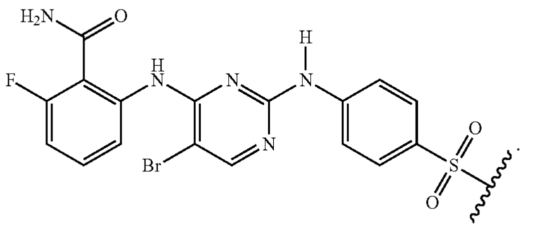 [SMILES: *S(=O)(=O)c1ccc(Nc2ncc(Br)c(Nc3cccc(F)c3C(N)=O)n2)cc1 ; "."]

In certain embodiments, the EPL is selected from those depicted in the compounds in Tables 1, 3, 4, and 5, below. In certain embodiments, the EPL is selected from those depicted in the compounds in Tables 3 and 4, below. In certain embodiments, the EPL is selected from those depicted in the compounds in Table 1, below. In certain embodiments, the EPL is selected from those depicted in the compounds in Table 3, below. In certain embodiments, the EPL is selected from those depicted in the compounds in Table 4, below. In certain embodiments, the EPL is selected from those depicted in the compounds in Table 5, below.

The description above regarding the identity of the EPL, and in Parts C and D below regarding the identity of the TPL and linker, describe multiple embodiments relating to compounds of Formula I. The patent application specifically contemplates all combinations of the embodiments.

Part B: Compounds of Formula II

Another aspect of the invention provides a compound represented by the formula:

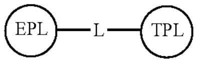

or a pharmaceutically acceptable salt thereof, wherein EPL is a moiety that binds to an effector protein selected from Eukaryotic Peptide Chain Release Factor GTP-Binding Subunit ERF3A (GSPT1); L is a linker; and TPL is a moiety that binds to estrogen receptor.

Exemplary moieties that bind GSPT1 are reported in the literature, including:

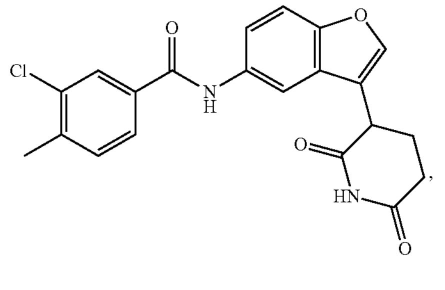 [SMILES: Cc1ccc(C(=O)Nc2ccc3occ(C4CCC(=O)NC4=O)c3c2)cc1Cl ; ","]

as described in Luo, Y. et al., in WO2021047627.

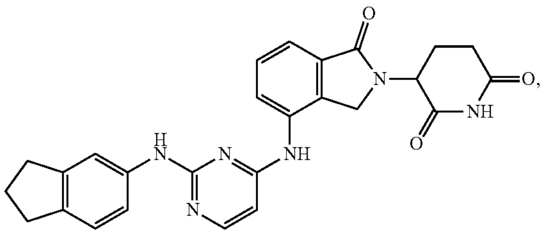 [SMILES: O=C1CCC(N2Cc3c(Nc4ccnc(Nc5ccc6c(c5)CCC6)n4)cccc3C2=O)C(=O)N1]

as described in Gray, N. et al., in WO2020006264.

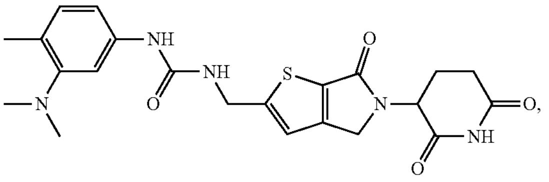 [SMILES: Cc1ccc(NC(=O)NCc2cc3c(s2)C(=O)N(C2CCC(=O)NC2=O)C3)cc1N(C)C]

as described in Chan, K. et al., in US2020369679.

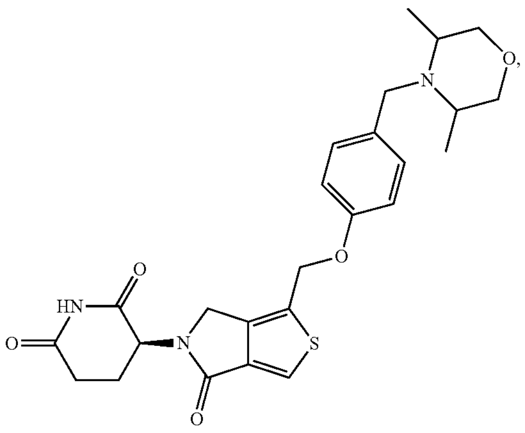 [SMILES: CC1COCC(C)N1Cc1ccc(OCc2scc3c2CN([C@H]2CCC(=O)NC2=O)C3=O)cc1]

as described in Chan, K. et al., in WO2019241271.

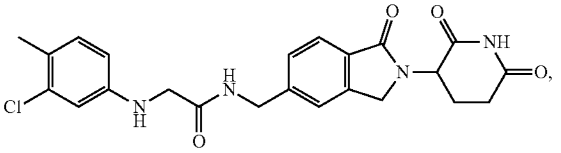 [SMILES: Cc1ccc(NCC(=O)NCc2ccc3c(c2)CN(C2CCC(=O)NC2=O)C3=O)cc1Cl]

as described in Chan, K. et al., in WO2019241274.

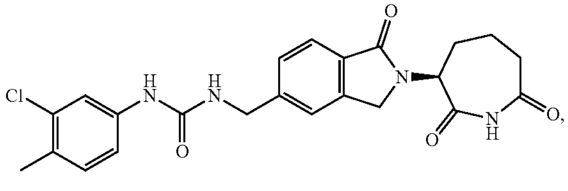 [SMILES: Cc1ccc(NC(=O)NCc2ccc3c(c2)CN([C@H]2CCCC(=O)NC2=O)C3=O)cc1Cl]

as described in Chan, K. et al., in WO2019241274.

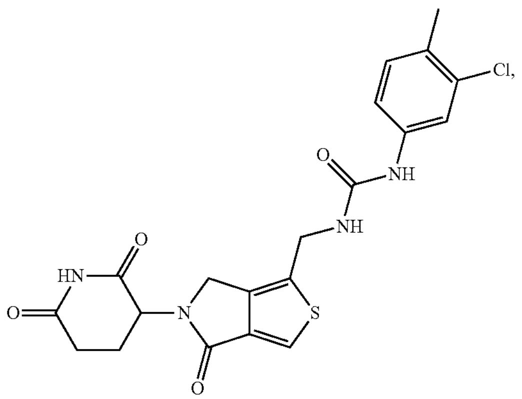 [SMILES: Cc1ccc(NC(=O)NCc2scc3c2CN(C2CCC(=O)NC2=O)C3=O)cc1Cl]

as described in Chan, K. et al., in US2018298027.

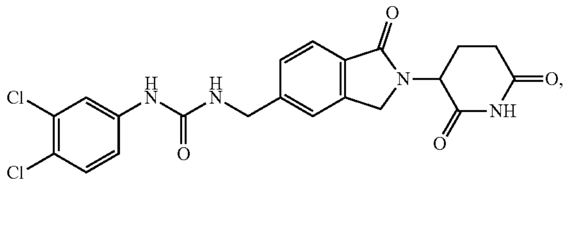 [SMILES: O=C1CCC(N2Cc3cc(CNC(=O)Nc4ccc(Cl)c(Cl)c4)ccc3C2=O)C(=O)N1]

as described in Muller, G. et al., in US2009142297.

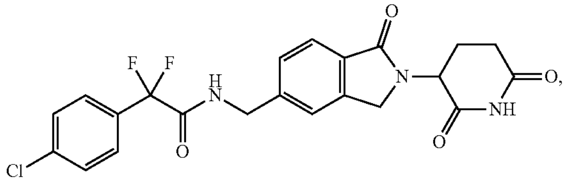 [SMILES: O=C1CCC(N2Cc3cc(CNC(=O)C(F)(F)c4ccc(Cl)cc4)ccc3C2=O)C(=O)N1]

as described in Hansen, J. et al., in WO2016007848.

In certain embodiments, the EPL is a radical of one of the above compounds, which is attached to L through a modifiable oxygen, nitrogen, or carbon atom.

In certain embodiments, the EPL has the following formula:

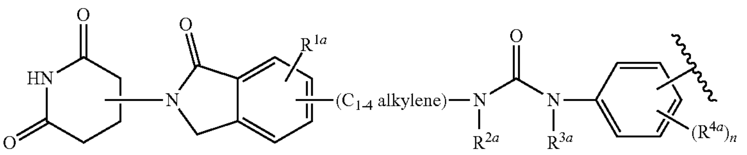

wherein:

$R^{1a}$ is hydrogen, halo, or $C_{1-4}$ alkyl;

$R^{2a}$ and $R^{3a}$ are independently hydrogen or $C_{1-4}$ alkyl;

$R^{4a}$ represents independently for each occurrence halo, $C_{1-4}$ alkyl, $C_{1-4}$ haloalkyl, hydroxyl, or $C_{1-4}$ alkoxyl; and n is 0, 1, 2, or 3.

In certain embodiments, the EPL is one of the following:

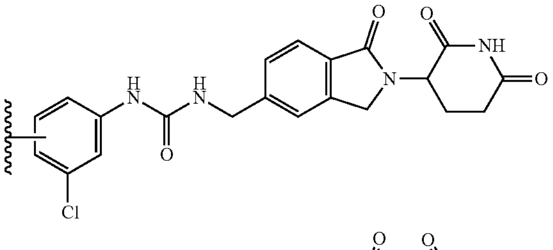

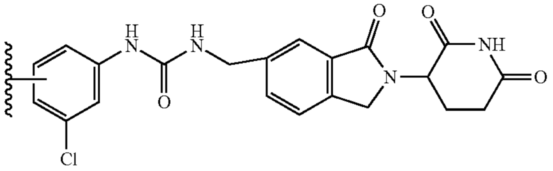

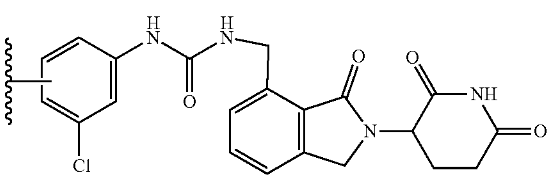

-continued

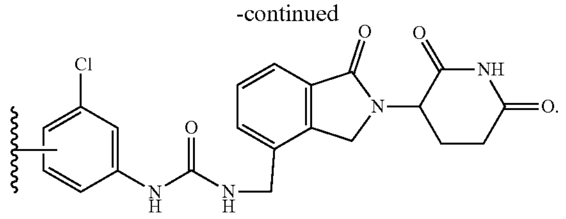

In certain embodiments, the EPL is

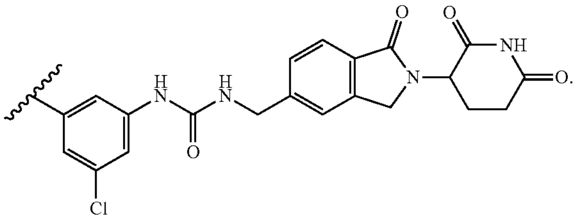 [SMILES: *c1cc(Cl)cc(NC(=O)NCc2ccc3c(c2)CN(C2CCC(=O)NC2=O)C3=O)c1]

In certain embodiments, EPL is selected from those depicted in the compounds in Table 2, below.

Another aspect of the invention provides a compound represented by Formula II:

(II)

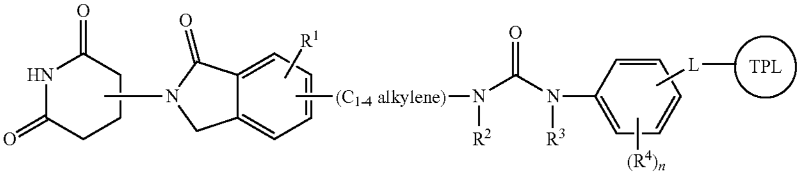

or a pharmaceutically acceptable salt thereof, wherein:

$R^1$ is hydrogen, halo, or $C_{1-4}$ alkyl;

$R^2$ and $R^3$ are independently hydrogen or $C_{1-4}$ alkyl;

$R^4$ represents independently for each occurrence halo, $C_{1-4}$ alkyl, $C_{1-4}$haloalkyl, hydroxyl, or $C_{1-4}$ alkoxyl;

n is 0, 1, 2, or 3;

L is a linker; and

TPL is represented by:

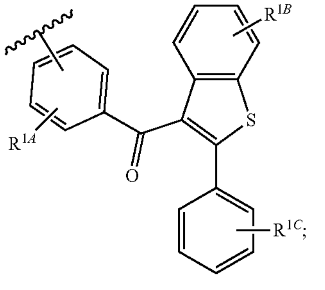

$R^{1A}$ is hydrogen, halo, or $C_{1-4}$ alkyl; and $R^{1B}$ and $R^{1C}$ are independently hydroxyl, halo, $C_{1-4}$ alkyl, or $C_{1-4}$ alkoxyl.

As generally defined above for Formula II, $R^1$ is hydrogen, halo, or $C_{1-4}$ alkyl. In certain embodiments, $R^1$ is hydrogen. In certain embodiments, $R^1$ is halo. In certain embodiments, $R^1$ is $C_{1-4}$ alkyl. In certain embodiments, $R^1$, $R^2$, and $R^3$ are hydrogen.

As generally defined above for Formula II, $R^{1B}$ and $R^{1C}$ are independently hydroxyl, halo, $C_{1-4}$ alkyl, or $C_{1-4}$ alkoxyl. In certain embodiments, $R^{1B}$ is hydroxyl. In certain embodiments, $R^{1B}$ is halo. In certain embodiments, $R^{1B}$ is $C_{1-4}$ alkyl. In certain embodiments, $R^{1B}$ is $C_{1-4}$ alkoxyl. In certain embodiments, $R^{1C}$ is hydroxyl. In certain embodiments, $R^{1C}$ is halo. In certain embodiments, $R^{1C}$ is $C_{1-4}$ alkyl. In certain embodiments, $R^{1C}$ is $C_{1-4}$ alkoxyl.

In certain embodiments, the compound is represented by one of the following:

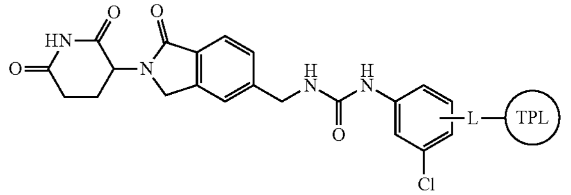

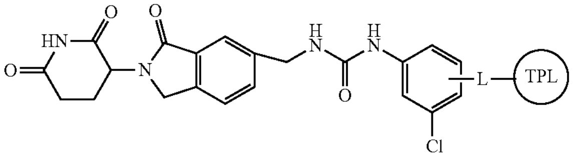

-continued

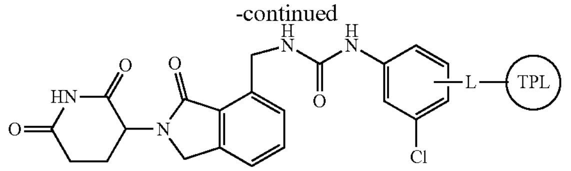

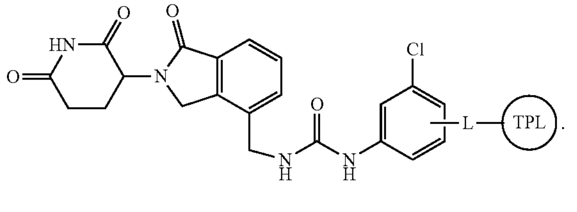

In certain embodiments, $R^{1A}$ is hydrogen. In certain embodiments, $R^{1B}$ and $R^{1C}$ are hydroxyl. In certain embodiments, $R^{1B}$ is halo, and $R^{1C}$ is hydroxyl.

Part C: Exemplary Further Description of the TPL Component of Compounds of Formula I and Formula II Compounds of Formula I and II may be further characterized according to, for example, the identity of the TPL component. As generally described above, the TPL is a moiety that binds to an estrogen receptor. Exemplary moieties for the TPL component are described in more detail below.

In certain embodiments, the TPL is a moiety that is an activator, inhibitor, and/or bind to the estrogen receptor (ER). Compounds that activate, inhibit, and/or bind to the ER are reported in the literature, which include:

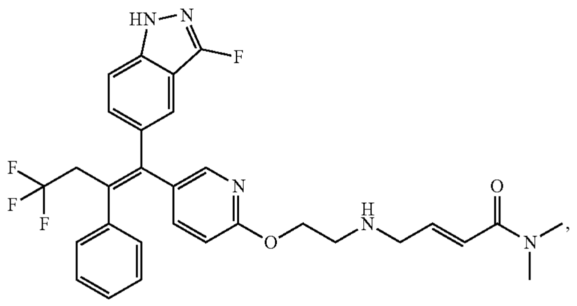 [SMILES: CN(C)C(=O)/C=C/CNCCOc1ccc(/C(=C(/CC(F)(F)F)c2ccccc2)c2ccc3[nH]nc(F)c3c2)cn1]
as described in Bock, M. et al., in US20160347717.
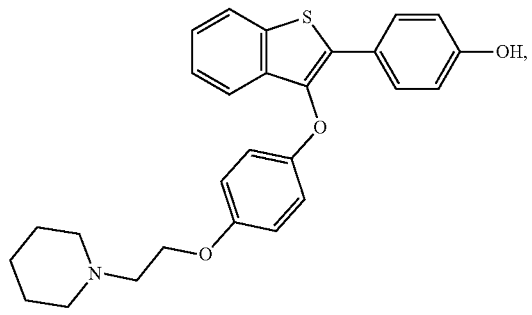 [SMILES: Oc1ccc(-c2sc3ccccc3c2Oc2ccc(OCCN3CCCCC3)cc2)cc1]
as described in Palkowitz, A., in U.S. Pat. No. 5,488,058.
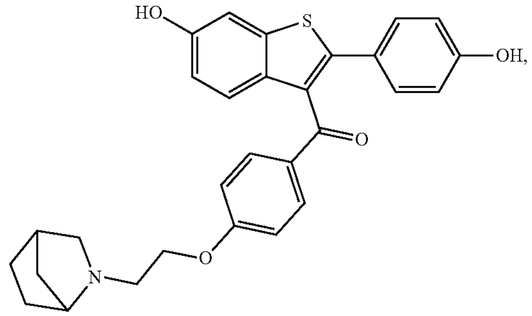 [SMILES: O=C(c1ccc(OCCN2CC3CCC2C3)cc1)c1c(-c2ccc(O)cc2)sc2cc(O)ccc12]
as described in Cameron, K. et al., in WO1995010513.
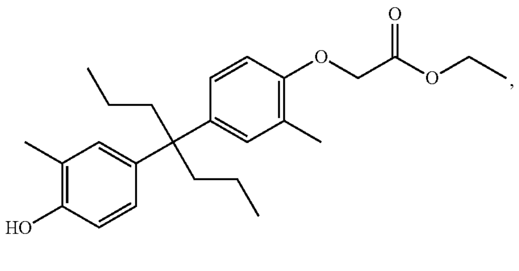 [SMILES: CCCC(CCC)(c1ccc(O)c(C)c1)c1ccc(OCC(=O)OCC)c(C)c1]
as described in Nanjyo, S. et al., in Bioorg Med Chem 2019, 27(10): 1952.
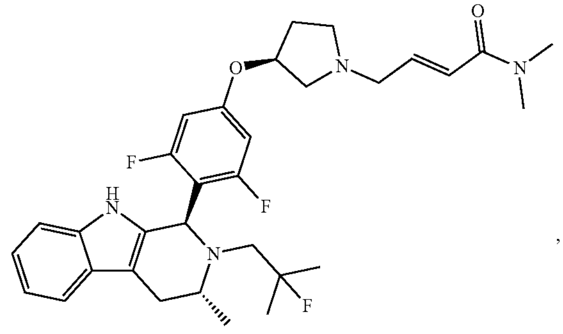 [SMILES: C[C@@H]1Cc2c([nH]c3ccccc23)[C@@H](c2c(F)cc(O[C@H]3CCN(C/C=C/C(=O)N(C)C)C3)cc2F)N1CC(C)(C)F]
,
as described in Yang, F. et al., in WO2019223715.
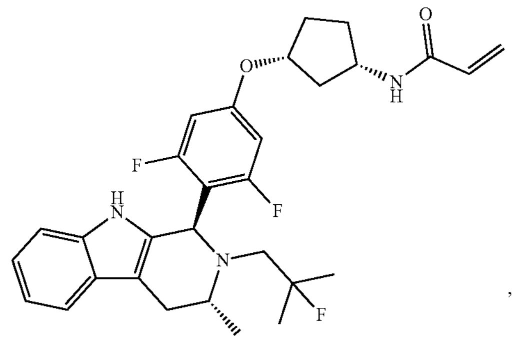 [SMILES: C=CC(=O)N[C@H]1CC[C@@H](Oc2cc(F)c([C@@H]3c4[nH]c5ccccc5c4C[C@@H](C)N3CC(C)(C)F)c(F)c2)C1]
,
as described in Yang, F. et al., in WO2019223715.
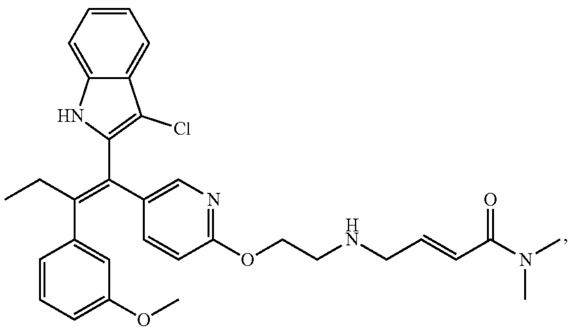 [SMILES: CC/C(=C(/c1ccc(OCCNC/C=C/C(=O)N(C)C)nc1)c1[nH]c2ccccc2c1Cl)c1cccc(OC)c1]
as described in Duan, S. et al., in WO2020125640.
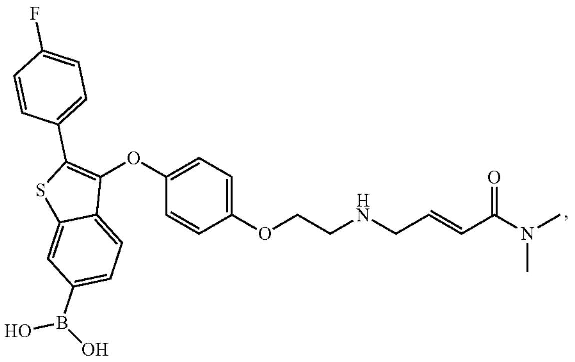 [SMILES: CN(C)C(=O)/C=C/CNCCOc1ccc(Oc2c(-c3ccc(F)cc3)sc3cc(B(O)O)ccc23)cc1]

as described in Wang, G. et al., in WO2020055973.
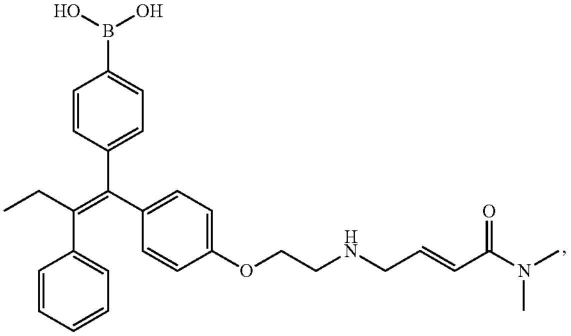 [SMILES: CC/C(=C(/c1ccc(OCCNC/C=C/C(=O)N(C)C)cc1)c1ccc(B(O)O)cc1)c1ccccc1]
as described in Wang, G. et al., in WO2020055973.
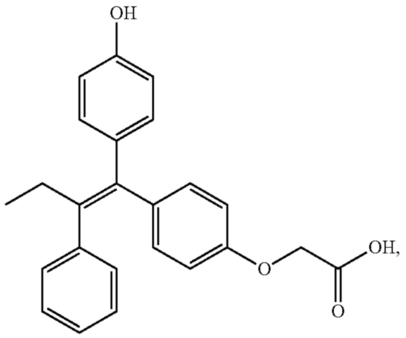 [SMILES: CC/C(=C(\c1ccc(O)cc1)c1ccc(OCC(=O)O)cc1)c1ccccc1]
as described in Ruenitz, P., in 219th Am Chem Soc (ACS) Natl Meet 2000-03-26/2000-03-30 San Francisco, United States Abst MEDI 330.
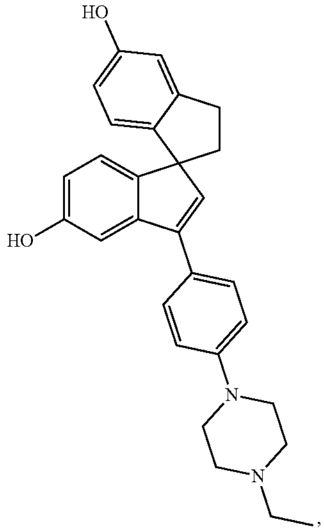 [SMILES: CCN1CCN(c2ccc(C3=CC4(CCc5cc(O)ccc54)c4ccc(O)cc43)cc2)CC1]
as described in Watanabe, N. et al., in Bioorg Med Chem Lett 2003, 13(24): 4317.
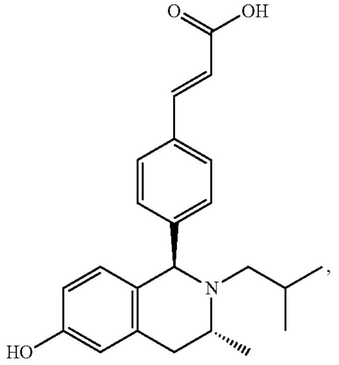 [SMILES: CC(C)CN1[C@H](c2ccc(/C=C/C(=O)O)cc2)c2ccc(O)cc2C[C@H]1C]
as described in Scott, J. et al., in ACS Med Chem Lett 2016, 7(1): 94.
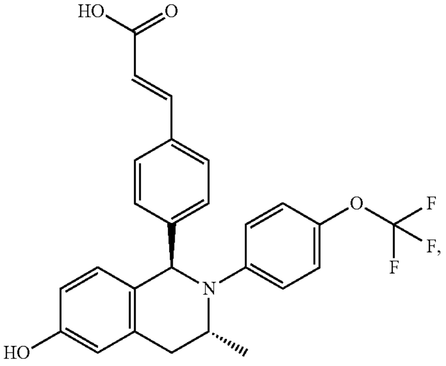 [SMILES: C[C@@H]1Cc2cc(O)ccc2[C@@H](c2ccc(/C=C/C(=O)O)cc2)N1c1ccc(OC(F)(F)F)cc1]
as described in Scott, J. et al., in ACS Med Chem Lett 2016, 7(1): 94.
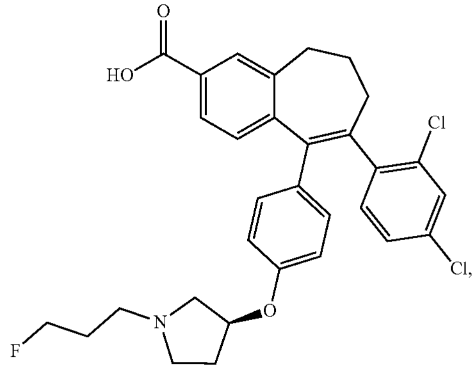 [SMILES: O=C(O)c1ccc2c(c1)CCCC(c1ccc(Cl)cc1Cl)=C2c1ccc(O[C@H]2CCN(CCCF)C2)cc1]
as described in Bouaboula, M. et al., in US2020392081.
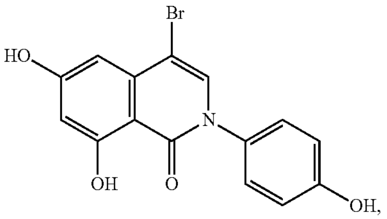 [SMILES: O=c1c2c(O)cc(O)cc2c(Br)cn1-c1ccc(O)cc1]

as described in Dalton, J. et al., in WO2008091555.

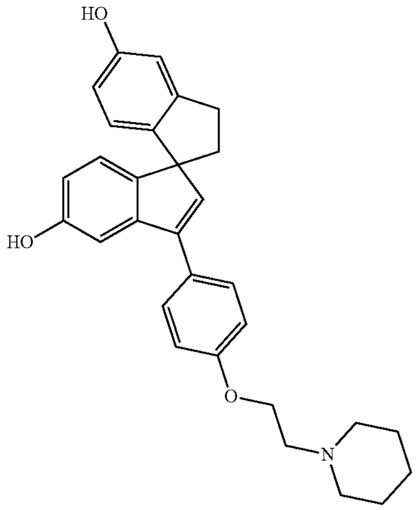

, as described in Watanabe, N. et al., in J Med Chem 2003, 46(19): 3961.

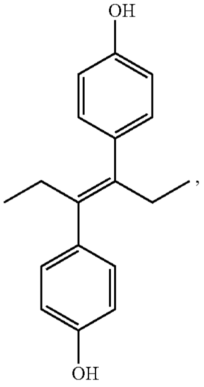 [SMILES: CC/C(=C(/CC)c1ccc(O)cc1)c1ccc(O)cc1]

as described in Nanjyo, S. et al., in Bioorg Med Chem 2019, 27(10): 1952.

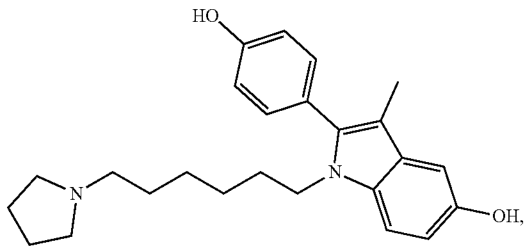 [SMILES: Cc1c(-c2ccc(O)cc2)n(CCCCCCN2CCCC2)c2ccc(O)cc12]

as described in Miller, C. et al., in J Med Chem 2001, 44(11): 1654.

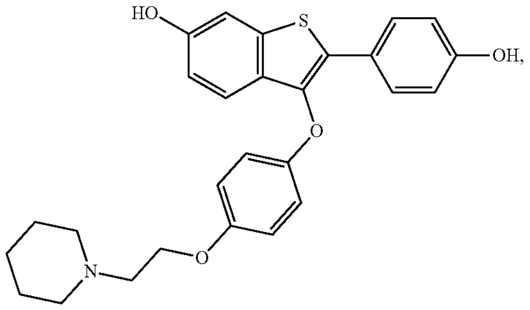 [SMILES: Oc1ccc(-c2sc3cc(O)ccc3c2Oc2ccc(OCCN3CCCCC3)cc2)cc1]

as described in Cameron, K. et al., in WO1995010513.

In certain embodiments, the TPL is a moiety that binds to the estrogen receptor (ER). Exemplary compounds that bind to ER are reported in the literature, such as raloxifene, H3B-6545, and AZD9496. A radical of such compounds reported in the literature that bind ER are amenable for use in the present invention.

In certain embodiments, the TPL is a radical of one of the above compounds, which is attached to L through a modifiable oxygen, nitrogen, or carbon atom.

In certain embodiments, the TPL is

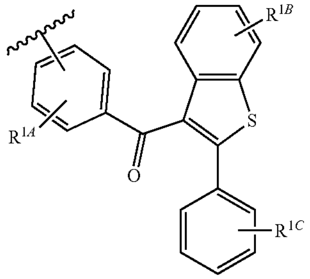

wherein:

$R^{1A}$ is hydrogen, halo, or $C_{1-4}$ alkyl; and $R^{1B}$ and $R^{1C}$ are independently hydroxyl, halo, $C_{1-4}$ alkyl, or $C_{1-4}$ alkoxyl.

In certain embodiments, $R^{1A}$ is hydrogen. In certain embodiments, $R^{1A}$ is halo. In certain embodiments, $R^{1A}$ is $C_{1-4}$ alkyl.

In certain embodiments, the TPL is

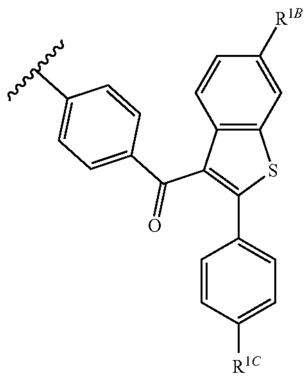

wherein $R^{1B}$ and $R^{1C}$ are independently hydroxyl, halo, $C_{1-4}$ alkyl, or $C_{1-4}$ alkoxyl.

In certain embodiments, $R^{1B}$ is hydroxyl. In certain embodiments, $R^{1B}$ is halo. In certain embodiments, $R^{1B}$ is $C_{1-4}$ alkyl. In certain embodiments, $R^{1B}$ is $C_{1-4}$ alkoxyl. In certain embodiments, $R^{1C}$ is hydroxyl. In certain embodiments, $R^{1C}$ is halo. In certain embodiments, $R^{1C}$ is $C_{1-4}$ alkyl. In certain embodiments, $R^{1C}$ is $C_{1-4}$ alkoxyl. In certain embodiments, $R^{1B}$ and $R^{1C}$ are hydroxyl. In certain embodiments, $R^{1B}$ is halo, and $R^{1C}$ is hydroxyl. In certain embodiments, $R^{1B}$ and $R^{1C}$ are methoxy.

In certain embodiments, the TPL is

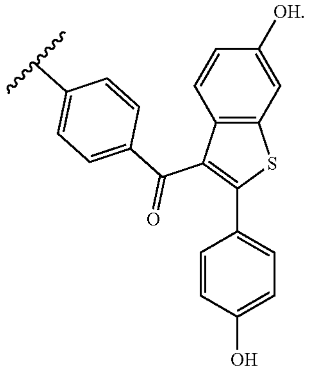 [SMILES: *c1ccc(C(=O)c2c(-c3ccc(O)cc3)sc3cc(O)ccc23)cc1]

In certain embodiments, the TPL is

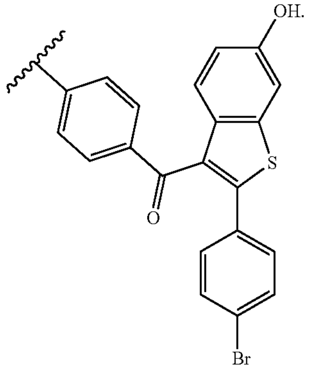 [SMILES: *c1ccc(C(=O)c2c(-c3ccc(Br)cc3)sc3cc(O)ccc23)cc1]

In certain embodiments, the TPL is

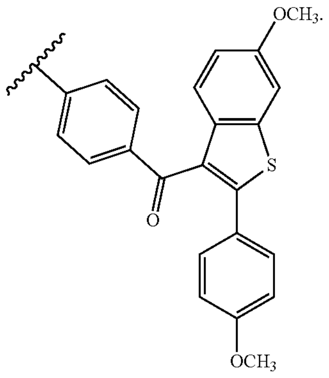 [SMILES: *c1ccc(C(=O)c2c(-c3ccc(OC)cc3)sc3cc(OC)ccc23)cc1]

In certain embodiments, the TPL has the following formula that is substituted by one occurrence of $R^{II-1A}$:

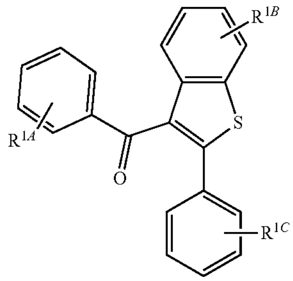

wherein:

$R^{II-1A}$ is a bond to L;

$R^{1A}$ is hydrogen, halo, or $C_{1-4}$ alkyl; and $R^{1B}$ and $R^{1C}$ are independently hydroxyl, halo, $C_{1-4}$ alkyl, or $C_{1-4}$ alkoxyl.

In certain embodiments, the TPL is

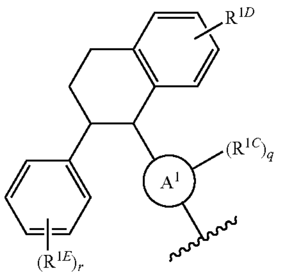

wherein:

$A^1$ is phenylene or 6-membered heteroarylene containing 1 or 2 heteroatoms that are nitrogen;

$R^{1C}$ and $R^{1E}$ are each independently for each occurrence hydrogen, halo, $C_{1-4}$ alkoxyl, $C_{1-4}$ alkyl, or $C_{1-4}$ haloalkyl;

$R^{1D}$ is hydroxyl, $-CO_2H$, or $-B(OH)_2$; and q and r are independently 0, 1, 2, or 3.

In certain embodiments, $A^1$ is phenylene. In certain embodiments, $A^1$ is para-phenylene. In certain embodiments, $A^1$ is a 6-membered heteroarylene containing 1 or 2 heteroatoms that are nitrogen. In certain embodiments, $A^1$ is pyridinylene, pyrimidinylene, or pyridazinylene. In certain embodiments, $A^1$ is

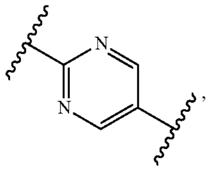
,
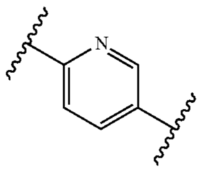
, or

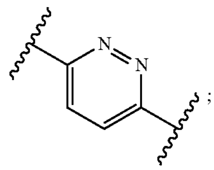
;

wherein the attachment point adjacent to a nitrogen atom of $A^1$ is connected to L.

In certain embodiments, $A^1$ is para-phenylene, and $R^{1D}$ is hydroxyl.

In certain embodiments, $R^{1D}$ is hydroxyl. In certain embodiments, $R^{1D}$ is $—CO_2H$. In certain embodiments, $R^{1D}$ is $—B(OH)_2$.
In certain embodiments, the TPL is
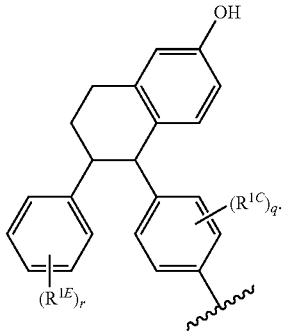
In certain embodiments, the TPL is
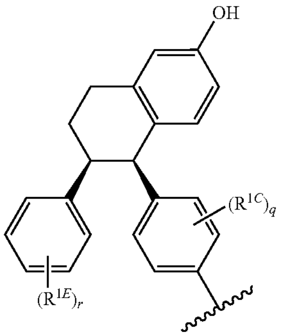
or
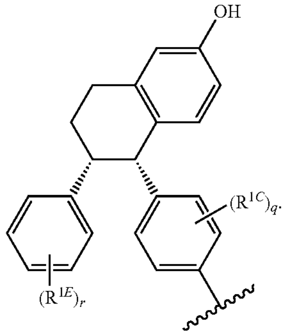
In certain embodiments, the TPL is
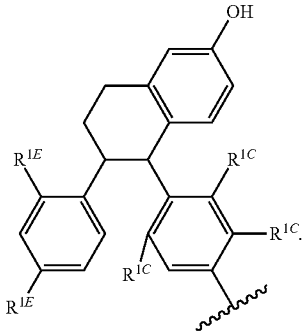
In certain embodiments the TPL is
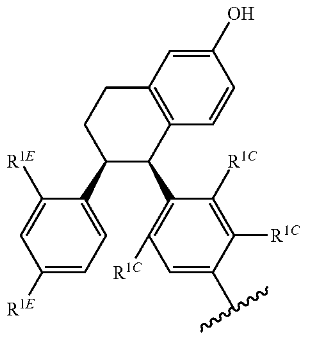
or
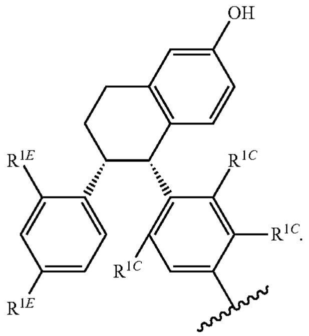
In certain embodiments, the TPL is one of the following:
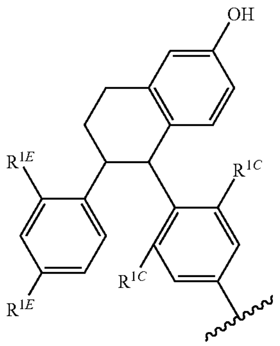
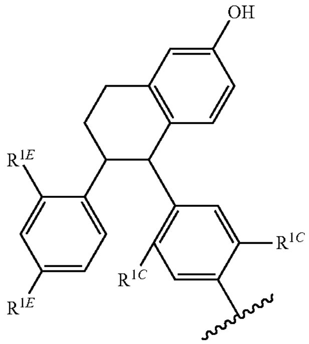

-continued
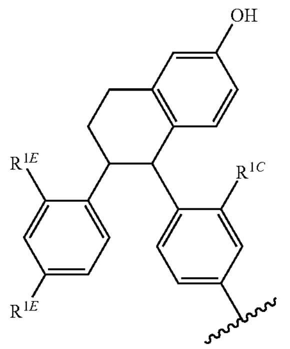
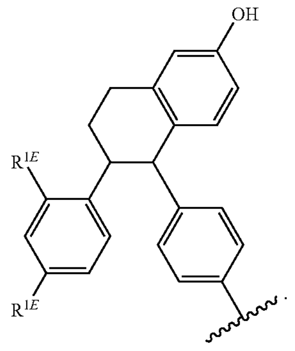
In certain embodiments, the TPL is one of the following:
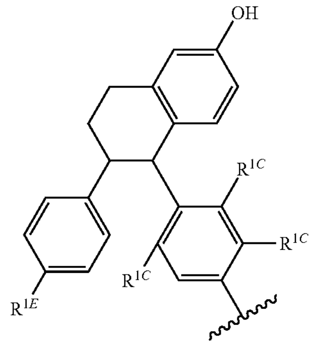
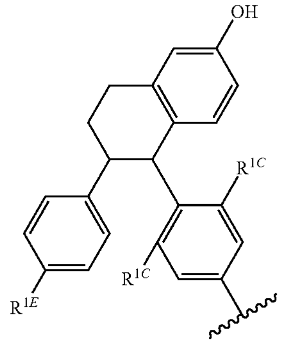
-continued
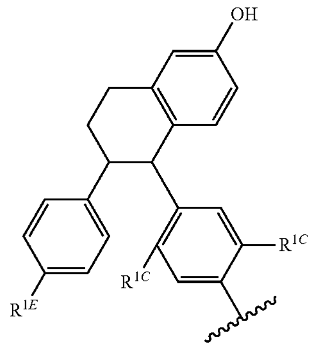
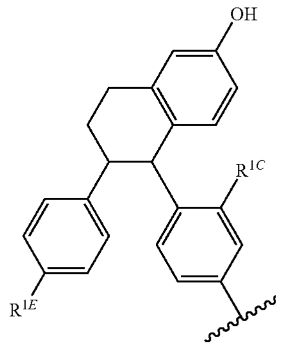
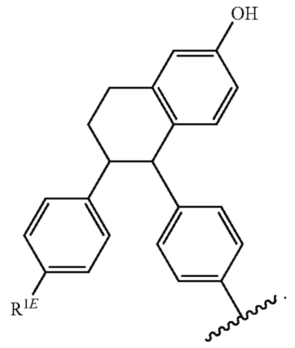
In certain embodiments, the TPL is one of the following:
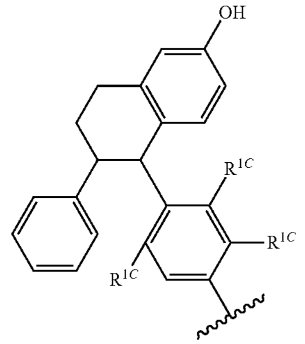

-continued

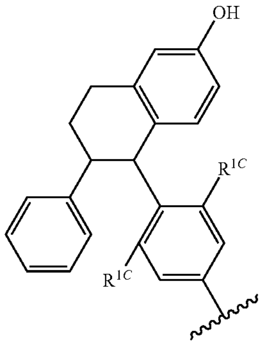

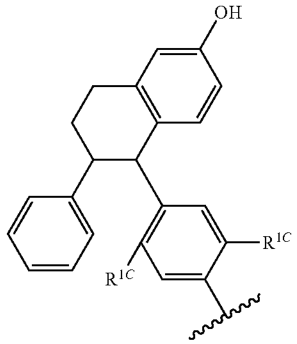

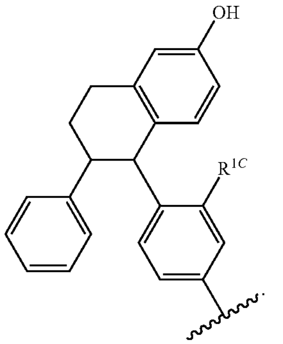

In certain embodiments, $R^{1C}$ and $R^{1E}$ are each independently for each occurrence hydrogen or halo. In certain embodiments, $R^{1C}$ and $R^{1E}$ are each independently for each occurrence hydrogen, fluoro, chloro, methoxy, methyl, or trifluoromethyl. In certain embodiments, $R^{1C}$ and $R^{1E}$ are each independently for each occurrence hydrogen, fluoro, chloro, methoxy, or methyl.

In certain embodiments, $R^{1C}$ is independently for each occurrence halo, $C_{1-4}$ alkoxyl, or $C_{1-4}$ alkyl. In certain embodiments, $R^{1C}$ is independently for each occurrence hydrogen or halo. In certain embodiments, $R^{1C}$ is independently for each occurrence hydrogen or $C_{1-4}$ alkoxyl. In certain embodiments, $R^{1C}$ is independently for each occurrence hydrogen or $C_{1-4}$ alkyl. In certain embodiments, $R^{1C}$ is independently for each occurrence halo or $C_{1-4}$ alkoxyl. In certain embodiments, $R^{1C}$ is independently for each occurrence halo or $C_{1-4}$ alkyl.

In certain embodiments, $R^{1C}$ is independently for each occurrence halo. In certain embodiments, $R^{1C}$ is independently for each occurrence $C_{1-4}$ alkoxyl. In certain embodiments, $R^{1C}$ is independently for each occurrence $C_{1-4}$ alkyl. In certain embodiments, $R^{1C}$ is independently for each occurrence $C_{1-4}$ haloalkyl. In certain embodiments, $R^{1C}$ is $-CF_3$. In certain embodiments, $R^{1C}$ is independently for each occurrence hydrogen, fluoro, chloro, methoxy, or methyl.

In certain embodiments, $R^{1E}$ is independently for each occurrence halo, $C_{1-4}$ alkoxyl, or $C_{1-4}$ alkyl. In certain embodiments, $R^{1E}$ is independently for each occurrence hydrogen or halo. In certain embodiments, $R^{1E}$ is independently for each occurrence hydrogen or $C_{1-4}$ alkyl. In certain embodiments, $R^{1E}$ is independently for each occurrence halo or $C_{1-4}$ alkyl.

In certain embodiments, $R^{1E}$ is independently for each occurrence halo. In certain embodiments, $R^{1E}$ is independently for each occurrence $C_{1-4}$ alkoxyl. In certain embodiments, $R^{1E}$ is independently for each occurrence $C_{1-4}$ alkyl. In certain embodiments, $R^{1E}$ is independently for each occurrence $C_{1-4}$ haloalkyl. In certain embodiments, $R^{1E}$ is $-CF_3$. In certain embodiments, $R^{1E}$ is independently for each occurrence hydrogen, fluoro, chloro, methoxy, or methyl.

In certain embodiments, the TPL is one of the following:

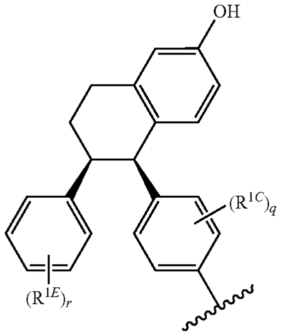

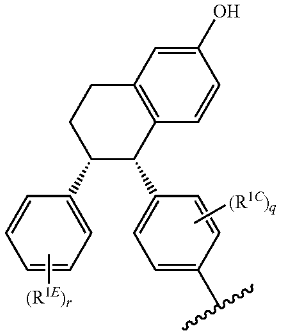

wherein $R^{1C}$ and $R^{1E}$ are each independently for each occurrence hydrogen, fluoro, chloro, methoxy, or methyl; and q and r are independently 0, 1, or 2.

In certain embodiments, q and r are 0. In certain embodiments, q and r are independently 0 or 1. In certain embodiments, q and r are independently 1 or 2. In certain embodiments, q and r are independently 0, 1, or 2. In certain embodiments, q is 0. In certain embodiments, q is 1. In certain embodiments, q is 2. In certain embodiments, q is 3. In certain embodiments, q is 0 or 1. In certain embodiments, q is 1 or 2. In certain embodiments, q is 0, 1, or 2. In certain embodiments, r is 0. In certain embodiments, r is 1. In certain embodiments, r is 2. In certain embodiments, r is 3. In certain embodiments, r is 0 or 1. In certain embodiments, r is 1 or 2. In certain embodiments, r is 0, 1, or 2.

In certain embodiments, the TPL is one of the following:

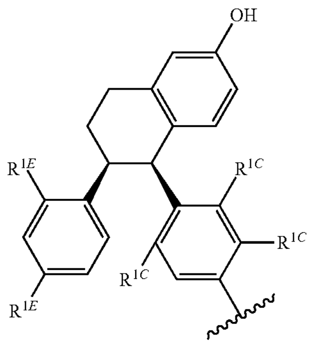

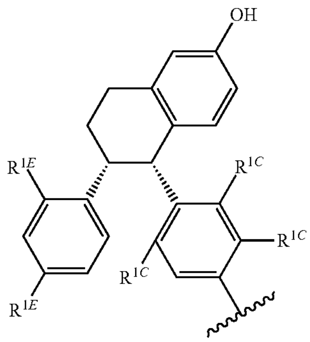

wherein $R^{1C}$ and $R^{1E}$ are each independently for each occurrence hydrogen, fluoro, chloro, methoxy, or methyl.

In certain embodiments, $R^{1C}$ and $R^{1E}$ are each independently for each occurrence fluoro, chloro, methoxy, or methyl. In certain embodiments, $R^{1C}$ and $R^{1E}$ are each independently for each occurrence hydrogen, fluoro, or methoxy. In certain embodiments, $R^{1C}$ and $R^{1E}$ are each independently for each occurrence hydrogen or fluoro. In certain embodiments, $R^{1C}$ and $R^{1E}$ are hydrogen. In certain embodiments, $R^{1C}$ and $R^{1E}$ are fluoro.

In certain embodiments, $R^{1C}$ is independently for each occurrence fluoro, chloro, methoxy, or methyl. In certain embodiments, $R^{1C}$ is independently for each occurrence hydrogen, fluoro, chloro, or methoxy. In certain embodiments, $R^{1C}$ is independently for each occurrence hydrogen, fluoro, or methoxy. In certain embodiments, $R^{1C}$ is independently for each occurrence hydrogen or fluoro. In certain embodiments, $R^{1C}$ is independently for each occurrence hydrogen or methoxy. In certain embodiments, $R^{1C}$ is independently for each occurrence hydrogen or methyl. In certain embodiments, $R^{1C}$ is independently for each occurrence fluoro or methoxy. In certain embodiments, $R^{1C}$ is independently for each occurrence fluoro or methyl. In certain embodiments, $R^{1C}$ is methoxy.

In certain embodiments, $R^{1E}$ is independently for each occurrence fluoro, chloro, methoxy, or methyl. In certain embodiments, $R^{1E}$ is independently for each occurrence hydrogen, fluoro, or methoxy. In certain embodiments, $R^{1E}$ is independently for each occurrence hydrogen or fluoro. In certain embodiments, $R^{1C}$ is independently for each occurrence hydrogen or methyl. In certain embodiments, $R^{1C}$ is independently for each occurrence fluoro or methyl. In certain embodiments, $R^{1C}$ is methoxy.

In certain embodiments, the TPL is

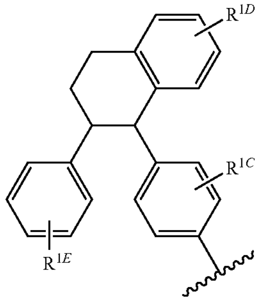

wherein:

$R^{1C}$ and $R^{1E}$ are independently hydrogen, halo, or $C_{1-4}$ alkyl; and $R^{1D}$ is hydroxyl.

In certain embodiments, $R^{1C}$ and $R^{1E}$ are independently hydrogen or halo. In certain embodiments, $R^{1C}$ and $R^{1E}$ are independently hydrogen or fluoro. In certain embodiments, $R^{1C}$ and $R^{1E}$ are hydrogen. In certain embodiments, $R^{1C}$ and $R^{1E}$ are fluoro.

In certain embodiments, $R^{1C}$ is hydrogen or halo. In certain embodiments, $R^{1C}$ is hydrogen or fluoro. In certain embodiments, $R^{1C}$ is hydrogen. In certain embodiments, $R^{1C}$ is halo. In certain embodiments, $R^{1C}$ is fluoro. In certain embodiments, $R^{1C}$ is chloro. In certain embodiments, $R^{1C}$ is $C_{1-4}$ alkyl. In certain embodiments, $R^{1C}$ is methyl.

In certain embodiments, $R^{1E}$ is hydrogen or halo. In certain embodiments, $R^{1E}$ is hydrogen or fluoro. In certain embodiments, $R^{1E}$ is hydrogen. In certain embodiments, $R^{1E}$ is halo. In certain embodiments, $R^{1E}$ is fluoro. In certain embodiments, $R^{1E}$ is chloro. In certain embodiments, $R^{1E}$ is $C_{1-4}$ alkyl. In certain embodiments, $R^{1E}$ is methyl.

In certain embodiments, the TPL is

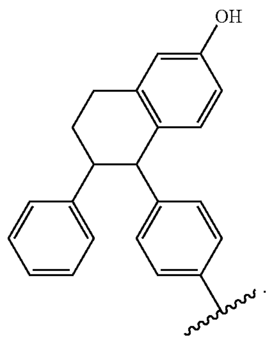 [SMILES: *c1ccc(C2c3ccc(O)cc3CCC2c2ccccc2)cc1]

In certain embodiments, the TPL is

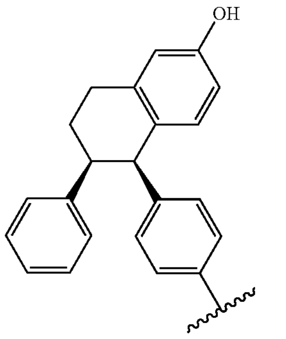

or

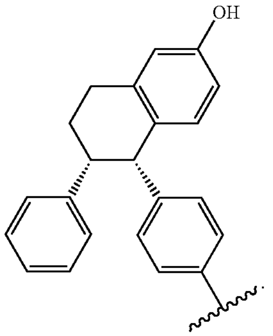

In certain embodiments, the TPL is

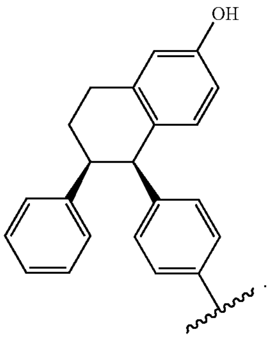 [SMILES: *c1ccc([C@@H]2c3ccc(O)cc3CC[C@@H]2c2ccccc2)cc1]

In certain embodiments, the TPL is

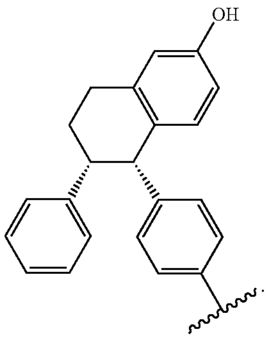 [SMILES: *c1ccc([C@H]2c3ccc(O)cc3CC[C@H]2c2ccccc2)cc1]

In certain embodiments, the TPL has the following formula that is substituted by one occurrence of $R^{II-1A}$:

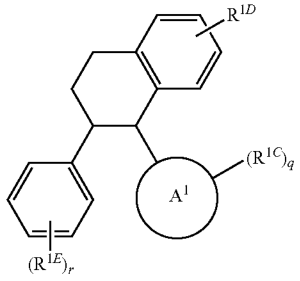

wherein:

$R^{II-1A}$ is a bond to L;

$A^1$ is phenyl or 6-membered heteroaryl containing 1 or 2 heteroatoms that are nitrogen;

$R^{1C}$ and $R^{1E}$ are each independently for each occurrence hydrogen, halo, $C_{1-4}$ alkoxyl, $C_{1-4}$ alkyl, or $C_{1-4}$ haloalkyl;

$R^{1D}$ is hydroxyl, —$CO_2H$, or —$B(OH)_2$; and q and r are independently 0, 1, 2, or 3.

In certain embodiments, each of the variables is independently as described and defined in embodiments above.

In certain embodiments, the TPL has the following formula that is substituted by one occurrence of $R^{II-1A}$:

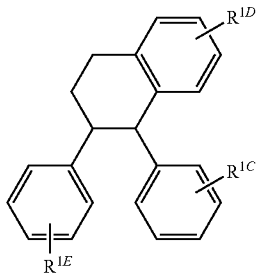

wherein:

$R^{II-1A}$ is a bond to L;

$R^{1C}$ and $R^{1E}$ are independently hydrogen, halo, or $C_{1-4}$ alkyl; and $R^{1D}$ is hydroxyl.

In certain embodiments, each of the variables is independently as described and defined in embodiments above.

In certain embodiments, the TPL is

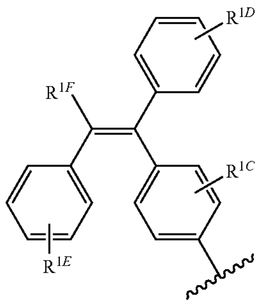

wherein:

$R^{1C}$ and $R^{1E}$ are independently hydrogen, halo, or $C_{1-4}$ alkyl;

$R^{1D}$ is hydroxyl; and $R^{1F}$ is hydrogen or $C_{1-4}$ alkyl.

In certain embodiments, $R^{1C}$ is hydrogen. In certain embodiments, $R^{1C}$ is halo. In certain embodiments, $R^{1C}$ is $C_{1-4}$ alkyl. In certain embodiments, $R^{1E}$ is hydrogen. In certain embodiments, $R^{1E}$ is halo. In certain embodiments, $R^{1E}$ is $C_{1-4}$ alkyl. In certain embodiments, $R^{1F}$ is hydrogen. In certain embodiments, $R^{1F}$ is $C_{1-4}$ alkyl.

In certain embodiments, the TPL is

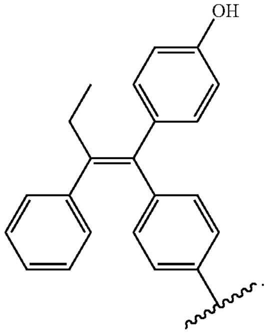 [SMILES: *c1ccc(/C(=C(/CC)c2ccccc2)c2ccc(O)cc2)cc1]

In certain embodiments, the TPL has the following formula that is substituted by one occurrence of $R^{II-1A}$:

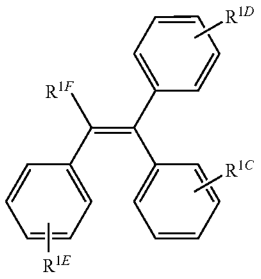

wherein:

$R^{II-1A}$ is a bond to L;

$R^{1C}$ and $R^{1E}$ are independently hydrogen, halo, or $C_{1-4}$ alkyl;

$R^{1D}$ is hydroxyl; and $R^{1F}$ is hydrogen or $C_{1-4}$ alkyl.

In certain embodiments, the TPL is

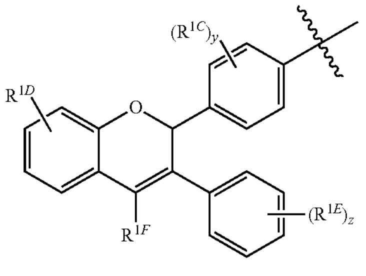

wherein:

$R^{1C}$ represents independently for each occurrence hydrogen, halo, hydroxyl, or $C_{1-4}$ alkyl;

$R^{1D}$ is hydroxyl;

$R^{1E}$ represents independently for each occurrence halo, hydroxyl, or $C_{1-4}$ alkyl;

$R^{1F}$ is hydrogen or $C_{1-4}$ alkyl;

y is 1 or 2; and z is 1, 2, or 3.

In certain embodiments, $R^{1C}$ is hydrogen. In certain embodiments, $R^{1C}$ is halo. In certain embodiments, $R^{1C}$ is hydroxyl. In certain embodiments, $R^{1C}$ is $C_{1-4}$ alkyl. In certain embodiments, $R^{1E}$ is halo. In certain embodiments, $R^{1E}$ is fluoro. In certain embodiments, $R^{1E}$ is hydroxyl. In certain embodiments, $R^{1E}$ is $C_{1-4}$ alkyl. In certain embodiments, $R^{1F}$ is hydrogen. In certain embodiments, $R^{1F}$ is $C_{1-4}$ alkyl. In certain embodiments, $R^{1F}$ is $—CH_3$. In certain embodiments, y is 1. In certain embodiments, y is 2. In certain embodiments, z is 1. In certain embodiments, z is 2. In certain embodiments, z is 3.

In certain embodiments, the TPL is

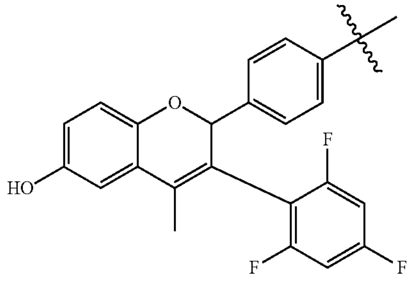

or

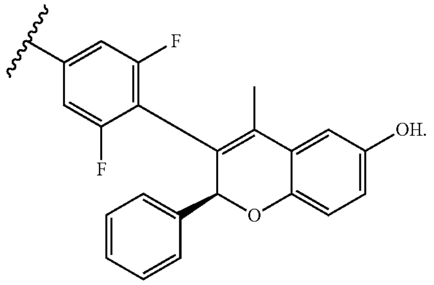

In certain embodiments, the TPL is

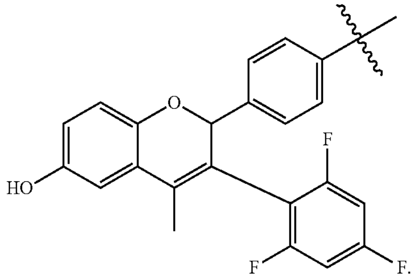 [SMILES: *c1ccc(C2Oc3ccc(O)cc3C(C)=C2c2c(F)cc(F)cc2F)cc1]

In certain embodiments, the TPL is

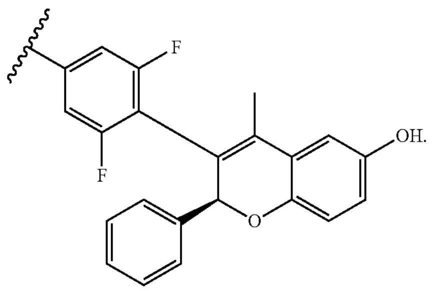 [SMILES: *c1cc(F)c(C2=C(C)c3cc(O)ccc3O[C@H]2c2ccccc2)c(F)c1]

In certain embodiments, the TPL is

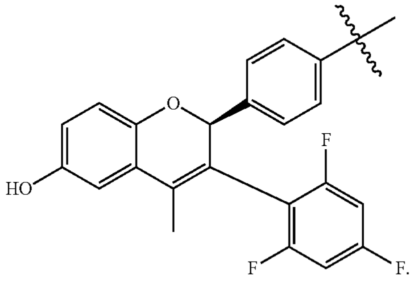 [SMILES: *c1ccc([C@@H]2Oc3ccc(O)cc3C(C)=C2c2c(F)cc(F)cc2F)cc1]

In certain embodiments the TPL is

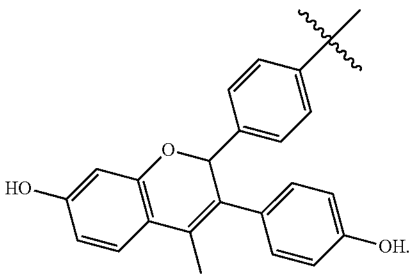 [SMILES: *c1ccc(C2Oc3cc(O)ccc3C(C)=C2c2ccc(O)cc2)cc1]

In certain embodiments, the TPL is

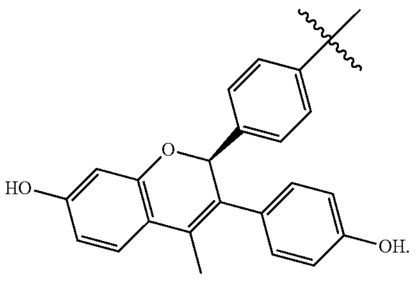 [SMILES: *c1ccc([C@@H]2Oc3cc(O)ccc3C(C)=C2c2ccc(O)cc2)cc1]

In certain embodiments, the TPL has the following formula that is substituted by one occurrence of $R^{II-1A}$:

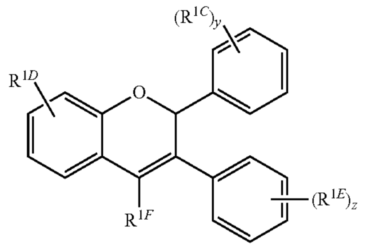

wherein:

$R^{II-1A}$ is a bond to L;

$R^{1C}$ represents independently for each occurrence hydrogen, halo, hydroxyl, or $C_{1-4}$ alkyl;

$R^{1D}$ is hydroxyl;

$R^{1E}$ represents independently for each occurrence halo, hydroxyl, or $C_{1-4}$ alkyl;

$R^{1F}$ is hydrogen or $C_{1-4}$ alkyl;

y is 1 or 2; and z is 1, 2, or 3.

In certain embodiments, the TPL is

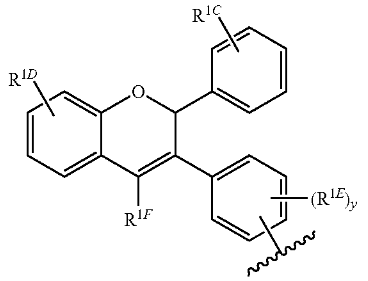

wherein:

$R^{1C}$ is hydrogen, hydroxyl, or $C_{1-4}$ alkyl;

$R^{1D}$ is hydroxyl;

$R^{1E}$ represents independently for each occurrence halo, hydroxyl, or $C_{1-4}$ alkyl;

$R^{1F}$ is hydrogen or $C_{1-4}$ alkyl; and y is 1, 2, or 3.

In certain embodiments, $R^{1C}$ is hydrogen. In certain embodiments, $R^{1C}$ is hydroxyl. In certain embodiments, $R^{1C}$ is $C_{1-4}$ alkyl. In certain embodiments, $R^{1E}$ is halo. In certain embodiments, $R^{1E}$ is fluoro. In certain embodiments, $R^{1E}$ is hydroxyl. In certain embodiments, $R^{1E}$ is $C_{1-4}$ alkyl. In certain embodiments, $R^{1F}$ is hydrogen. In certain embodiments, $R^{1F}$ is $C_{1-4}$ alkyl. In certain embodiments, $R^{1F}$ is —$CH_3$. In certain embodiments, y is 1. In certain embodiments, y is 2. In certain embodiments, y is 3.

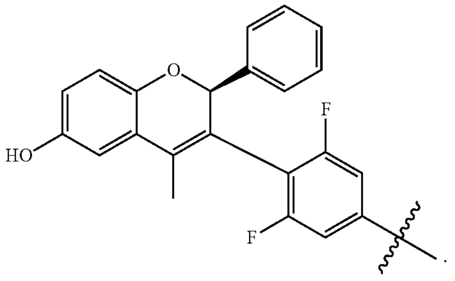 [SMILES: *c1cc(F)c(C2=C(C)c3cc(O)ccc3O[C@H]2c2ccccc2)c(F)c1]

In certain embodiments, the TPL is F

In certain embodiments, the TPL has the following formula that is substituted by one occurrence of $R^{II\text{-}1A}$:

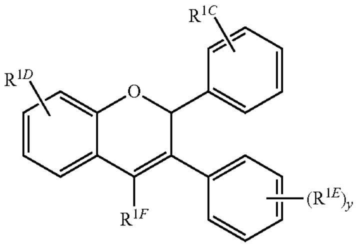

wherein:

$R^{II\text{-}1A}$ is a bond to L;

$R^{1C}$ is hydrogen, hydroxyl, or $C_{1\text{-}4}$ alkyl;

$R^{1D}$ is hydroxyl;

$R^{1E}$ represents independently for each occurrence halo, hydroxyl, or $C_{1\text{-}4}$ alkyl;

$R^{1F}$ is hydrogen or $C_{1\text{-}4}$ alkyl; and y is 1, 2, or 3.

In certain embodiments, the TPL is

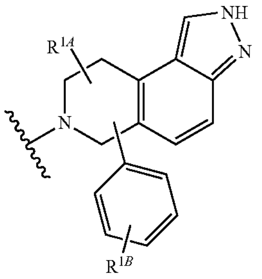

wherein:

$R^{1A}$ is hydrogen or $C_{1\text{-}4}$ alkyl; and $R^{1B}$ is —C(O)$CH_3$, hydrogen, hydroxyl, or $C_{1\text{-}4}$ alkyl.

In certain embodiments, $R^{1A}$ is hydrogen. In certain embodiments, $R^{1A}$ is $C_{1\text{-}4}$ alkyl. In certain embodiments, $R^{1B}$ is —C(O)$CH_3$. In certain embodiments, $R^{1B}$ is hydrogen. In certain embodiments, $R^{1B}$ is hydroxyl. In certain embodiments, $R^{1B}$ is $C_{1\text{-}4}$ alkyl.

In certain embodiments, the TPL is

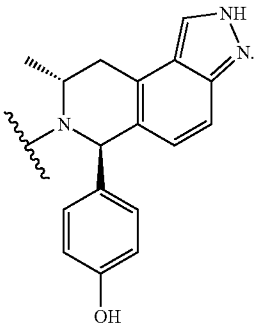 [SMILES: *N1[C@H](c2ccc(O)cc2)c2ccc3n[nH]cc3c2C[C@H]1C]

In certain embodiments, the TPL has the following formula that is substituted by one occurrence of $R^{II\text{-}1A}$:

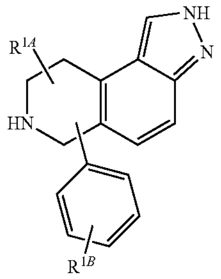

wherein:

$R^{III\text{-}1A}$ is a bond to L;

$R^{1A}$ is hydrogen or $C_{1\text{-}4}$ alkyl; and $R^{1B}$ is —C(O)$CH_3$, hydrogen, hydroxyl, or $C_{1\text{-}4}$ alkyl.

In certain embodiments, the TPL is

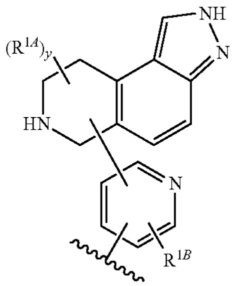

or

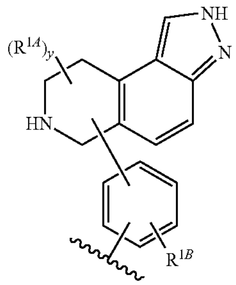

wherein:

$R^{1A}$ represents independently for each occurrence hydrogen, $C_{1\text{-}4}$ haloalkyl, $C_{1\text{-}4}$ alkyl, or halo;

$R^{1B}$ is hydrogen, halo, or $C_{1\text{-}4}$ alkyl; and y is 1, 2, or 3.

In certain embodiments, the TPL is

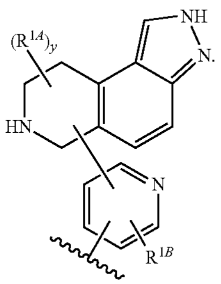

In certain embodiments, the TPL is

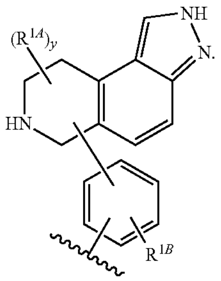

In certain embodiments, $R^{1A}$ is hydrogen. In certain embodiments, $R^{1A}$ is $C_{1-4}$ haloalkyl. In certain embodiments, $R^{1A}$ is $C_{1-4}$ alkyl. In certain embodiments, $R^{1A}$ is halo. In certain embodiments, $R^{1B}$ is hydrogen. In certain embodiments, $R^{1B}$ is halo. In certain embodiments, $R^{1B}$ is $C_{1-4}$ alkyl. In certain embodiments, y is 1. In certain embodiments, y is 2. In certain embodiments, y is 3.

In certain embodiments, the TPL is

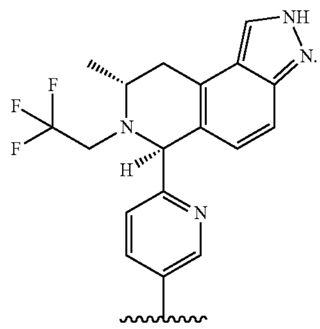 [SMILES: *c1ccc([C@@H]2c3ccc4n[nH]cc4c3C[C@@H](C)N2CC(F)(F)F)nc1]

In certain embodiments, the TPL is

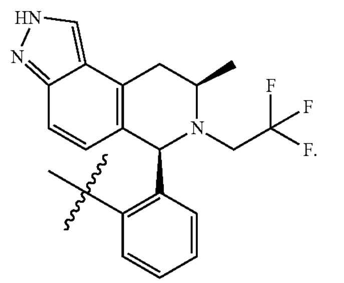 [SMILES: *c1ccccc1[C@H]1c2ccc3n[nH]cc3c2C[C@@H](C)N1CC(F)(F)F]

In certain embodiments, the TPL has the following formula that is substituted by one occurrence of $R^{II-1A}$:

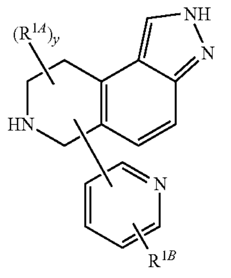

or

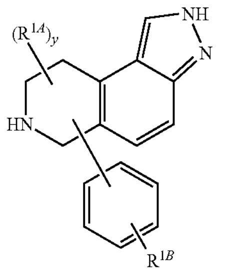

wherein:

$R^{III-1A}$ is a bond to L;

$R^{1A}$ represents independently for each occurrence hydrogen, $C_{1-4}$ haloalkyl, $C_{1-4}$ alkyl, or halo;

$R^{1B}$ is hydrogen, halo, or $C_{1-4}$ alkyl; and y is 1, 2, or 3.

In certain embodiments, the TPL is

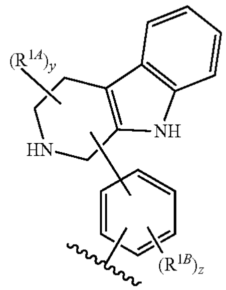

wherein:

$R^{1A}$ represents independently for each occurrence hydrogen, $C_{1-4}$ haloalkyl, $C_{1-4}$ alkyl, or halo;

$R^{1B}$ represents independently for each occurrence hydrogen, halo, or $C_{1-4}$ alkyl;

y is 1, 2, or 3; and z is 1 or 2.

In certain embodiments, $R^{1A}$ is hydrogen. In certain embodiments, $R^{1A}$ is $C_{1-4}$ haloalkyl. In certain embodiments, $R^{1A}$ is $C_{1-4}$ alkyl. In certain embodiments, $R^{1A}$ is halo. In certain embodiments, $R^{1B}$ is hydrogen. In certain embodiments, $R^{1B}$ is halo. In certain embodiments, $R^{1B}$ is $C_{1-4}$ alkyl. In certain embodiments, y is 1. In certain embodiments, y is 2. In certain embodiments, y is 3. In certain embodiments, z is 1. In certain embodiments, z is 2.

In certain embodiments, the TPL is

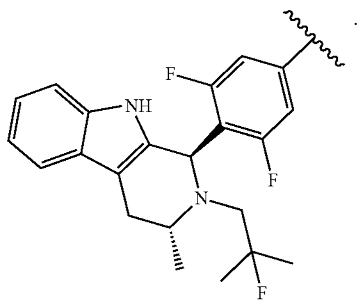 [SMILES: *c1cc(F)c([C@@H]2c3[nH]c4ccccc4c3C[C@@H](C)N2CC(C)(C)F)c(F)c1]

In certain embodiments, the TPL has the following formula that is substituted by one occurrence of $R^{II-1A}$:

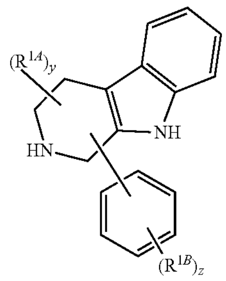

wherein:

$R^{III-1A}$ is a bond to L;

$R^{1A}$ represents independently for each occurrence hydrogen, $C_{1-4}$ haloalkyl, $C_{1-4}$ alkyl, or halo;

$R^{1B}$ represents independently for each occurrence hydrogen, halo, or $C_{1-4}$ alkyl;

y is 1, 2, or 3; and z is 1 or 2.

In certain embodiments, the TPL is

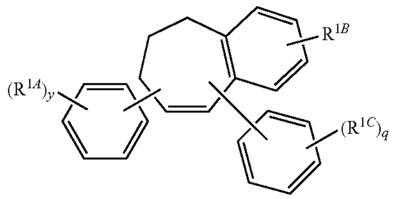

wherein:

$R^{1A}$ and $R^{1C}$ each represents independently for each occurrence hydrogen, halo, $C_{1-4}$ alkyl, or $C_{1-4}$ alkoxy;

$R^{1B}$ is —C(O)OH, hydrogen, halo, hydroxyl, —$B(OH)_2$, or $C_{1-4}$ alkyl;

q is 1 or 2; and y is 1, 2, or 3.

In certain embodiments, $R^{1A}$ represents independently for each occurrence hydrogen, fluoro, chloro, methyl, or methoxy. In certain embodiments, $R^{1A}$ represents independently for each occurrence hydrogen, halo, or $C_{1-4}$ alkoxy. In certain embodiments, $R^{1A}$ represents independently for each occurrence hydrogen or halo. In certain embodiments, $R^{1A}$ represents independently for each occurrence $C_{1-4}$ alkoxy. In certain embodiments, $R^{1B}$ is —C(O)OH, —OH, or —$B(OH)_2$. In certain embodiments, $R^{1C}$ represents independently for each occurrence hydrogen, fluoro, chloro, methyl, or methoxy. In certain embodiments, $R^{1C}$ represents independently for each occurrence hydrogen, halo, or $C_{1-4}$ alkoxy. In certain embodiments, $R^{1C}$ represents independently for each occurrence hydrogen or halo.

In certain embodiments, the TPL is

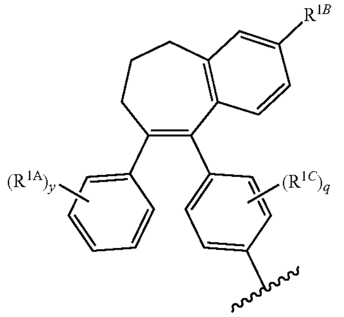

wherein:

$R^{1A}$ and $R^{1C}$ each represents independently for each occurrence hydrogen, fluoro, chloro, methyl, or methoxy;

$R^{1B}$ is —C(O)OH, —OH, or —$B(OH)_2$;

q is 1 or 2; and y is 1, 2, or 3.

In certain embodiments, q is 1. In certain embodiments, q is 2.

In certain embodiments, the TPL is

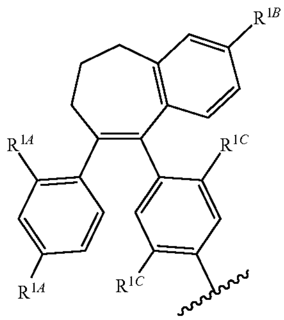

wherein:

$R^{1A}$ and $R^{1C}$ each represents independently for each occurrence hydrogen, fluoro, chloro, methyl, or methoxy; and $R^{1B}$ is —C(O)OH, —OH, or —$B(OH)_2$.

In certain embodiments, $R^{1A}$ represents independently for each occurrence hydrogen, fluoro, or chloro, and $R^{1C}$ represents independently for each occurrence hydrogen, fluoro, or methoxy. In certain embodiments, $R^{1A}$ represents independently for each occurrence hydrogen, fluoro, or chloro, and $R^{1C}$ is hydrogen or fluoro. In certain embodiments, $R^{1A}$ is methoxy. In certain embodiments, $R^{1B}$ is —$B(OH)_2$. In certain embodiments, $R^{1C}$ represents independently for each occurrence hydrogen, fluoro, or methoxy. In certain embodiments, $R^{1C}$ is hydrogen or fluoro. In certain embodiments, $R^{1C}$ is fluoro or chloro. In certain embodiments, $R^{1C}$ is hydrogen. In certain embodiments, $R^{1C}$ is fluoro. In certain embodiments, $R^{1C}$ is chloro. In certain embodiments, $R^{1C}$ is methoxy. In certain embodiments, $R^{1C}$ is methyl.

In certain embodiments the TPL is

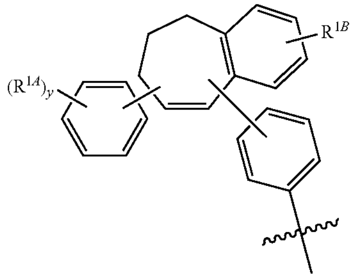

wherein:

$R^{1A}$ represents independently for each occurrence hydrogen, halo, or $C_{1-4}$ alkyl;

$R^{1B}$ is —C(O)OH, hydrogen, halo, hydroxyl, or $C_{1-4}$ alkyl; and y is 1, 2, or 3.

In certain embodiments, $R^{1A}$ represents independently for each occurrence hydrogen, fluoro, chloro, or methyl. In certain embodiments, $R^{1A}$ represents independently for each occurrence hydrogen or halo. In certain embodiments, $R^{1A}$ represents independently for each occurrence hydrogen, fluoro, or chloro. In certain embodiments, $R^{1A}$ is hydrogen, fluoro, or chloro. In certain embodiments, $R^{1A}$ is hydrogen or chloro.

In certain embodiments, $R^{1A}$ is hydrogen. In certain embodiments, $R^{1A}$ is halo. In certain embodiments, $R^{1A}$ is fluoro. In certain embodiments, $R^{1A}$ is chloro. In certain embodiments, $R^{1A}$ is $C_{1-4}$ alkyl. In certain embodiments, $R^{1A}$ is methyl.

In certain embodiments, $R^{1B}$ is —C(O)OH or —OH. In certain embodiments, RB is —C(O)OH. In certain embodiments, $R^{1B}$ is hydrogen. In certain embodiments, $R^{1B}$ is halo. In certain embodiments, $R^{1B}$ is hydroxyl. In certain embodiments, $R^{1B}$ is $C_{1-4}$ alkyl. In certain embodiments, y is 1. In certain embodiments, y is 2. In certain embodiments, y is 3.

In certain embodiments, the TPL is

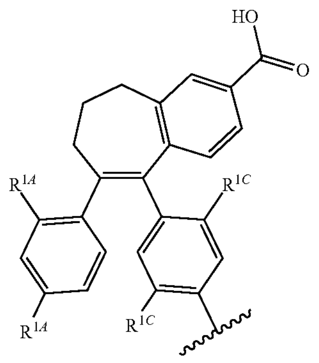

wherein $R^{1A}$ and $R^{1C}$ each represents independently for each occurrence hydrogen, fluoro, chloro, methyl, or methoxy.

In certain embodiments, $R^{1A}$ represents independently for each occurrence hydrogen, fluoro, or chloro, and $R^{1C}$ represents independently for each occurrence hydrogen, fluoro, or methoxy. In certain embodiments, $R^{1A}$ represents independently for each occurrence hydrogen, fluoro, or chloro, and $R^{1C}$ is hydrogen or fluoro.

In certain embodiments, $R^{1A}$ represents independently for each occurrence hydrogen, fluoro, or chloro. In certain embodiments, $R^{1A}$ is hydrogen, fluoro, or chloro. In certain embodiments, $R^{1A}$ is hydrogen or chloro. In certain embodiments, $R^{1A}$ is hydrogen. In certain embodiments, $R^{1A}$ is fluoro. In certain embodiments, $R^{1A}$ is chloro.

In certain embodiments, $R^{1C}$ represents independently for each occurrence hydrogen, fluoro, or methoxy. In certain embodiments, $R^{1C}$ is hydrogen or fluoro. In certain embodiments, $R^{1C}$ is hydrogen. In certain embodiments, $R^{1C}$ is fluoro.

In certain embodiments, the TPL is

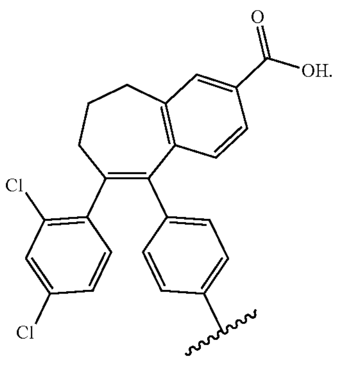 [SMILES: *c1ccc(C2=C(c3ccc(Cl)cc3Cl)CCCc3cc(C(=O)O)ccc32)cc1]

In certain embodiments, the TPL is

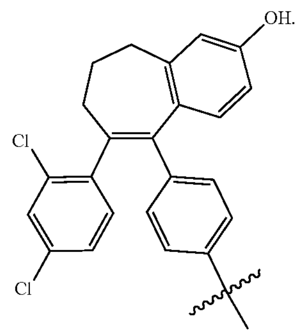 [SMILES: *c1ccc(C2=C(c3ccc(Cl)cc3Cl)CCCc3cc(O)ccc32)cc1]

In certain embodiments, the TPL has the following formula that is substituted by one occurrence of $R^{II-1A}$:

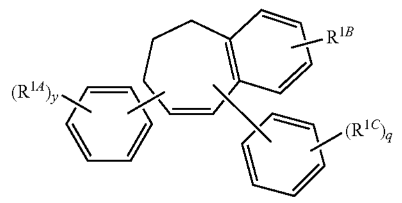

wherein:

$R^{III-1A}$ is a bond to L;

$R^{1A}$ and $R^{1C}$ each represents independently for each occurrence hydrogen, halo, $C_{1-4}$ alkyl, or $C_{1-4}$ alkoxy;

$R^{1B}$ is —C(O)OH, hydrogen, halo, hydroxyl, —$B(OH)_2$, or $C_{1-4}$ alkyl;

q is 1 or 2; and y is 1, 2, or 3.

In certain embodiments, the TPL has the following formula that is substituted by one occurrence of $R^{II-1A}$:

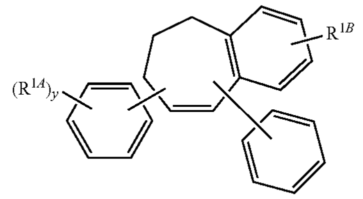

wherein:

$R^{III-1A}$ is a bond to L;

$R^{1A}$ represents independently for each occurrence hydrogen, halo, or $C_{1-4}$ alkyl;

$R^{1B}$ is —C(O)OH, hydrogen, halo, hydroxyl, or $C_{1-4}$ alkyl; and y is 1, 2, or 3.

In certain embodiments, the TPL is

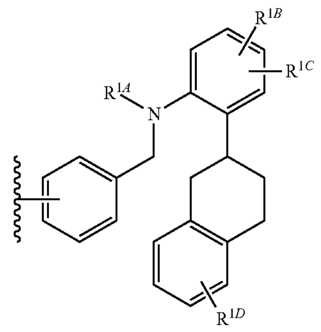

wherein:

$R^{1A}$ is $C_{1-4}$ alkyl;

$R^{1B}$ is $C_{1-4}$ alkoxyl;

$R^{1C}$ is hydrogen, halo, or $C_{1-4}$ alkyl; and $R^{1D}$ is hydroxyl.

In certain embodiments, $R^{1C}$ is hydrogen. In certain embodiments, $R^{1C}$ is halo. In certain embodiments, $R^{1C}$ is $C_{1-4}$ alkyl.

In certain embodiments, the TPL is

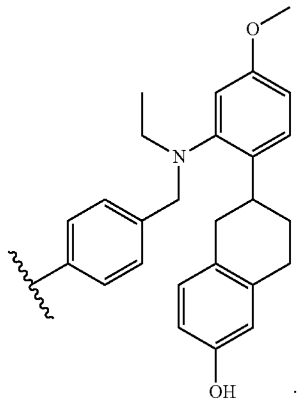 [SMILES: *c1ccc(CN(CC)c2cc(OC)ccc2C2CCc3cc(O)ccc3C2)cc1]

In certain embodiments, the TPL has the following formula that is substituted by one occurrence of $R^{II-1A}$:

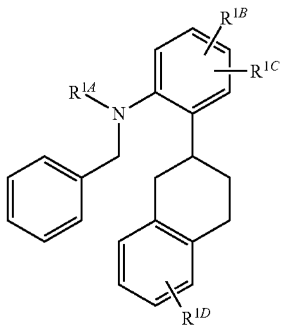

wherein:

$R^{III-1A}$ is a bond to L;

$R^{1A}$ is $C_{1-4}$ alkyl;

$R^{1B}$ is $C_{1-4}$ alkoxyl;

$R^{1C}$ is hydrogen, halo, or $C_{1-4}$ alkyl; and $R^{1D}$ is hydroxyl.

In certain embodiments, the TPL is selected from those depicted in the compounds in Tables 1, 2, 3, 4, and 5, below. In certain embodiments, the TPL is selected from those depicted in the compounds in Table 1, below. In certain embodiments, the TPL is selected from those depicted in the compounds in Table 2, below. In certain embodiments, the TPL is selected from those depicted in the compounds in Table 3, below. In certain embodiments, the TPL is selected from those depicted in the compounds in Table 4, below. In certain embodiments, the TPL is selected from those depicted in the compounds in Table 5, below.

Additional Features

Compounds of Formula I and/or II may be further characterized according to the molecular weight of the TPL. In certain embodiments, the TPL has a molecular weight of less than 1500 Da, 1200 Da, 1000 Da, 800 Da, 600 Da, 400 Da, 300 Da, 200 Da, 150 Da, or 100 Da. Compounds of Formula II may be further characterized according to the molecular weight of the EPL. In certain embodiments, the EPL has a molecular weight of less than 1500 Da, 1200 Da, 1000 Da, 800 Da, 600 Da, 400 Da, 300 Da, 200 Da, 150 Da, or 100 Da.

Part D: Exemplary Further Description of the Linker (L) Component of Compounds of Formula I and II Compounds of Formula I and II may be further characterized according to, for example, the identity of the linker (L) component. A variety of linkers are known to one of skill in the art and may be used in the heterobifunctional compounds described herein. For example, in certain embodiments, L comprises one or more optionally substituted groups selected from amino acids, polyether chains, aliphatic groups, and any combinations thereof. In certain embodiments, L consists of one or more optionally substituted groups selected from amino acids, polyether chains, aliphatic groups, and any combinations thereof. In certain embodiments, L consists of one or more groups selected from amino acids, polyether chains, aliphatic groups, and any combinations thereof.

In some embodiments, L is symmetrical. In some embodiments, L is asymmetric. In certain embodiments, L is a bond.

In certain embodiments, L is a covalent bond or a bivalent $C_{1-30}$ saturated or unsaturated, straight or branched, hydrocarbon chain, wherein 1-15 methylene units of L are optionally and independently replaced by cyclopropylene, —N(H)—, —N($C_{1-4}$ alkyl)-, —N($C_{3-5}$ cycloalkyl)-, —O—, —C(O)—, —OC(O)—, —C(O)O—, —S—, —S(O)—, —$S(O)_2$—, —$S(O)_2$N(H)—, —$S(O)_2$N($C_{1-4}$ alkyl)-, —$S(O)_2$N($C_{3-5}$ cycloalkyl)-, —N(H)C(O)—, —N($C_{1-4}$ alkyl)C(O)—, —N($C_{3-5}$ cycloalkyl)C(O)—, —C(O)N(H)—, —C(O)N($C_{1-4}$ alkyl)-, —C(O)N($C_{3-5}$ cycloalkyl)-, phenylene, an 8-10 membered bicyclic arylene, a 4-7 membered saturated or partially unsaturated carbocyclylene, an 8-10 membered bicyclic saturated or partially unsaturated carbocyclylene, a 3-7 membered saturated or partially unsaturated heterocyclylene having 1-2 heteroatoms independently selected from nitrogen, oxygen, and sulfur, an 8-10 membered bicyclic saturated or partially unsaturated heterocyclylene having 1-2 heteroatoms independently selected from nitrogen, oxygen, and sulfur, a 5-6 membered heteroarylene having 1-4 heteroatoms independently selected from nitrogen, oxygen, and sulfur, or an 8-10 membered bicyclic heteroarylene having 1-5 heteroatoms independently selected from nitrogen, oxygen, or sulfur.

In certain embodiments, L is a bivalent, saturated or unsaturated, straight or branched $C_{1-60}$ hydrocarbon chain, wherein 0-20 methylene units of the hydrocarbon are independently replaced with —O—, —S—, —N(R)—, —OC(O)—, —C(O)O—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—, optionally substituted 3-10 membered carbocyclyl, or optionally substituted 3-10 membered heterocyclyl containing 1, 2, 3, or 4 heteroatoms independently selected from nitrogen, oxygen, and sulfur, wherein R represents independently for each occurrence hydrogen, $C_{1-6}$ alkyl, or $C_{3-6}$ cycloalkyl.

In certain embodiments, L is a bivalent, saturated or unsaturated, straight or branched $C_{1-60}$ hydrocarbon chain, wherein 0-20 methylene units of the hydrocarbon are independently replaced with —O—, —S—, —N(H)—, —N($C_{1-6}$ alkyl)-, —OC(O)—, —C(O)O—, —S(O)—, —$S(O)_2$—, —N(H)$S(O)_2$—, —N($C_{1-6}$ alkyl)$S(O)_2$—, —$S(O)_2$N(H)—, —$S(O)_2$N($C_{1-6}$ alkyl)-, —N(H)C(O)—, —N($C_{1-6}$ alkyl)C(O)—, —C(O)N(H)—, —C(O)N($C_{1-6}$ alkyl)-, —OC(O)N(H)—, —OC(O)N($C_{1-6}$ alkyl)-, —N(H)C(O)O—, —N($C_{1-6}$ alkyl)C(O)O—, optionally substituted 3-10 membered carbocyclyl, or optionally substituted 3-10 membered heterocyclyl containing 1, 2, 3, or 4 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl)C(O)—, —C(O)N(H)—, —C(O)N($C_{1-6}$ alkyl)-, 3-10 membered carbocyclyl, or 3-10 membered heterocyclyl containing 1, 2, or 3 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl)C(O)—, —C(O)N(H)—, or —C(O)N($C_{1-6}$ alkyl)-.

In certain embodiments, L is a bivalent, saturated or unsaturated, straight or branched $C_{1-60}$ hydrocarbon chain, wherein 0-20 methylene units of the hydrocarbon are independently replaced with —O—, —S—, —N(H)—, —N($C_{1-6}$ alkyl)-, —OC(O)—, —C(O)O—, —S(O)—, —$S(O)_2$—, —N(H)$S(O)_2$—, —N($C_{1-6}$ alkyl)$S(O)_2$—, —$S(O)_2$N(H)—, —$S(O)_2$N($C_{1-6}$ alkyl)-, —N(H)C(O)—, —N($C_{1-6}$ alkyl)C(O)—, —C(O)N(H)—, —C(O)N($C_{1-6}$ alkyl)-, —OC(O)N(H)—, —OC(O)N($C_{1-6}$ alkyl)-, —N(H)C(O)O—, —N($C_{1-6}$ alkyl)C(O)O—, optionally substituted 3-10 membered carbocyclyl, optionally substituted 8-11 membered spirocyclic heterocyclyl containing 1, 2, 3, or 4 heteroatoms independently selected from nitrogen, oxygen, and sulfur, or optionally substituted 3-10 membered heterocyclyl containing 1, 2, 3, or 4 heteroatoms independently selected from nitrogen, oxygen, and sulfur.

In certain embodiments, L is a bivalent, saturated, straight or branched $C_{3-30}$ hydrocarbon chain, wherein 0-15 methylene units of the hydrocarbon are independently replaced with —O—, —N(H)—, —N($C_{1-6}$ alkyl)-, —OC(O)—, —C(O)O—, —N(H)C(O)—, —N($C_{1-6}$ alkyl)C(O)—, —C(O)N(H)—, —C(O)N($C_{1-6}$ alkyl)-, 3-10 membered carbocyclyl, optionally substituted 8-11 membered spirocyclic heterocyclyl containing 1, 2, 3, or 4 heteroatoms independently selected from nitrogen, oxygen, and sulfur, or 3-10 membered heterocyclyl containing 1, 2, or 3 heteroatoms independently selected from nitrogen, oxygen, and sulfur.

In yet other embodiments, L comprises a polyethylene glycol chain ranging in size from about 1 to about 12 ethylene glycol units, from about 1 to about 10 ethylene glycol units, from about 2 to about 6 ethylene glycol units, from about 2 to about 5 ethylene glycol units, or from about 2 to about 4 ethylene glycol units. In yet other embodiments, L is a diradical of a polyethylene glycol chain ranging in size from about 1 to about 12 ethylene glycol units, from about 1 to about 10 ethylene glycol units, from about 2 to about 6 ethylene glycol units, from about 2 to about 5 ethylene glycol units, or from about 2 to about 4 ethylene glycol units.

In certain embodiments, L is a heteroalkylene having from 4 to 30 atoms selected from carbon, oxygen, nitrogen, and sulfur. In certain embodiments, L is a heteroalkylene having from 4 to 20 atoms selected from carbon, oxygen, nitrogen, and sulfur. In certain embodiments, L is a heteroalkylene having from 4 to 10 atoms selected from carbon, oxygen, nitrogen, and sulfur. In certain embodiments, L is a heteroalkylene having from 4 to 30 atoms selected from carbon, oxygen, and nitrogen. In certain embodiments, L is a heteroalkylene having from 4 to 20 atoms selected from carbon, oxygen, and nitrogen. In certain embodiments, L is a heteroalkylene having from 4 to 10 atoms selected from carbon, oxygen, and nitrogen. In certain embodiments, L is a heteroalkylene having from 4 to 30 atoms selected from carbon and oxygen. In certain embodiments, L is a heteroalkylene having from 4 to 20 atoms selected from carbon and oxygen. In certain embodiments, L is a heteroalkylene having from 4 to 10 atoms selected from carbon and oxygen.

In additional embodiments, the L is an optionally substituted (poly)ethyleneglycol having between 1 and about 100 ethylene glycol units, between about 1 and about 50 ethylene glycol units, between 1 and about 25 ethylene glycol units, between about 1 and about 10 ethylene glycol units, between 1 and about 8 ethylene glycol units, between 1 and about 6 ethylene glycol units, between 2 and about 4 ethylene glycol units, or optionally substituted alkyl groups interspersed with optionally substituted, O, N, S, P or Si atoms. In certain embodiments, L is substituted with an aryl, phenyl, benzyl, alkyl, alkylene, or heterocycle group.

In certain embodiments, L is a bivalent, saturated or unsaturated, straight or branched $C_{1-45}$ hydrocarbon chain, wherein 0-10 methylene units of the hydrocarbon are independently replaced with —O—, —S—, —N(R)—, —OC(O)—, —C(O)O—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—, optionally substituted carbocyclyl, or optionally substituted heterocyclyl, wherein R represents independently for each occurrence hydrogen, $C_{1-6}$ alkyl, or $C_{3-6}$ cycloalkyl.

In certain embodiments, L is a bivalent, saturated or unsaturated, straight or branched $C_{1-45}$ hydrocarbon chain, wherein 0-10 methylene units of the hydrocarbon are independently replaced with —O—, —S—, —N(R)—, —OC(O)—, —C(O)O—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—, optionally substituted 3-10 membered carbocyclyl, or optionally substituted 3-10 membered heterocyclyl containing 1, 2, 3, or 4 heteroatoms selected from nitrogen, oxygen, and sulfur, wherein R represents independently for each occurrence hydrogen, $C_{1-6}$ alkyl, or $C_{3-6}$ cycloalkyl.

In certain embodiments, L has the formula —N(R)-(optionally substituted 3-20 membered heteroalkylene)$_p$-$CH_2$—C(O)—, wherein R is hydrogen or optionally substituted $C_1$-$C_6$ alkyl, and p is 0 or 1.

In certain embodiments, L has the formula —N(R)-(3-20 membered heteroalkylene)$_p$-$CH_2$—C(O)—; wherein the 3-20 membered heteroalkylene is optionally substituted with 1, 2, 3, or 4 substituents independently selected from halogen, $C_1$-$C_6$ haloalkyl, $C_3$-$C_6$ cycloalkyl, hydroxyl, and cyano; R is hydrogen or optionally substituted $C_1$-$C_6$ alkyl; and p is 0 or 1.

In certain embodiments, L has the formula —N(R)-(3-20 membered heteroalkylene)$_p$-$CH_2$—C(O)—; wherein the 3-20 membered heteroalkylene is optionally substituted with 1, 2, or 3 substituents independently selected from halogen and $C_1$-$C_6$ haloalkyl; R is hydrogen or $C_1$-$C_6$ alkyl; and p is 0 or 1.

In certain embodiments, L is —N(H)—($C_{2-9}$ alkylene)-O—($C_{1-6}$ alkylene)-C(O)—*, —N(H)—($C_{10-20}$ alkylene)-O—($C_{1-6}$ alkylene)-C(O)—*, —N(H)—[($C_{2-4}$ alkylene)-O-]$_{2-6}$—($C_{1-6}$ alkylene)-C(O)—*, —N(H)—[($C_{2-4}$ alkylene)-O-]$_{7-15}$—($C_{1-6}$ alkylene)-C(O)—*, —N(H)—($C_{1-6}$ alkylene)-C(O)—*, —N(H)—($C_{7-15}$ alkylene)-C(O)—*, —N(H)—[($C_{2-4}$ alkylene)-O-]$_{2-6}$—($C_{1-6}$ alkylene)-*, —N(H)—[($C_{2-4}$ alkylene)-O-]$_{7-15}$—($C_{1-6}$ alkylene)-*, —N(H)—($C_{2-9}$ alkylene)-O—($C_{1-6}$ alkylene)-C(O)N($C_{1-6}$ alkyl)-($C_{1-6}$ alkylene)-*, —N(H)—($C_{2-9}$ alkylene)-O—($C_{1-6}$ alkylene)-C(O)N(H)—($C_{1-6}$ alkylene)-*, —N(H)—[($C_{2-4}$ alkylene)-O-]$_{2-6}$—($C_{1-6}$ alkylene)-N(H)—($C_{1-6}$ alkylene)-*, —N(H)—[($C_{2-4}$ alkylene)-O-]$_{7-15}$-($C_{1-6}$ alkylene)-N(H)—($C_{1-6}$ alkylene)-*, —N(H)—[($C_{2-4}$ alkylene)-O-]$_{2-6}$—($C_{1-6}$ alkylene)-N($C_{1-6}$ alkyl)-($C_{1-6}$ alkylene)-*, or —N(H)—[($C_{2-4}$ alkylene)-O-]$_{7-15}$—($C_{1-6}$ alkylene)-N($C_{1-6}$ alkyl)-($C_{1-6}$ alkylene)-*, where *** is a point of attachment to TPL.

In certain embodiments, L is —N(H)—($C_{2-9}$ alkylene)-O—($C_{1-6}$ alkylene)-C(O)—*, —N(H)—($C_{10-20}$ alkylene)-O—($C_{1-6}$ alkylene)-C(O)—*, —N(H)—[$CH_2CH_2$—O-]$_{2-6}$—($C_{1-6}$ alkylene)-C(O)—*, —N(H)—[$CH_2CH_2$—O-]$_{7-15}$—($C_{1-6}$ alkylene)-C(O)—*, —N(H)—($C_{1-6}$ alkylene)-C(O)—*, —N(H)—($C_{7-15}$ alkylene)-C(O)—*, —N(H)—[$CH_2CH_2$—O-]$_{2-6}$—($C_{1-6}$ alkylene)-*, —N(H)—[$CH_2CH_2$—O-]$_{7-15}$—($C_{1-6}$ alkylene)-*, —N(H)—($C_{2-9}$ alkylene)-O—($C_{1-6}$ alkylene)-C(O)N($C_{1-6}$ alkyl)-($C_{1-6}$ alkylene)-*, —N(H)—($C_{2-9}$ alkylene)-O—($C_{1-6}$ alkylene)-C(O)N(H)—($C_{1-6}$ alkylene)-*, —N(H)—[$CH_2CH_2$—O-]$_{2-6}$—($C_{1-6}$ alkylene)-N(H)—($C_{1-6}$ alkylene)-*, —N(H)—[$CH_2CH_2$—O-]$_{7-15}$—($C_{1-6}$ alkylene)-N(H)—($C_{1-6}$ alkylene)-*, —N(H)—[$CH_2CH_2$—O-]$_{2-6}$—($C_{1-6}$ alkylene)-N($C_{1-6}$ alkyl)-($C_{1-6}$ alkylene)-*, or —N(H)—[$CH_2CH_2$—O-]$_{7-15}$—($C_{1-6}$ alkylene)-N($C_{1-6}$ alkyl)-($C_{1-6}$ alkylene)-*, where *** is a point of attachment to TPL.

In certain embodiments, L is —N(H)—[($C_{2-4}$ alkylene)-O-]$_{2-6}$—($C_{1-6}$ alkylene)-C(O)—*, —N(H)—[($C_{2-4}$ alkylene)-O-]$_{7-15}$—($C_{1-6}$ alkylene)-C(O)—*, —N(H)—($C_{1-6}$ alkylene)-N($C_{1-6}$ alkyl)C(O)—($C_{1-6}$ alkylene)*, —N(H)—($C_{1-6}$ alkylene)-N(H)C(O)—($C_{1-6}$ alkylene)*, —N(H)—($C_{2-6}$ alkylene)-*, —N(H)—($C_{7-15}$ alkylene)-*, —N($C_{1-6}$ alkyl)-($C_{2-6}$ alkylene)-*, —N($C_{1-6}$ alkyl)-($C_{7-15}$ alkylene)-*, —N(H)—[($C_{2-4}$ alkylene)-O-]$_{2-6}$—($C_{1-6}$ alkylene)-*, —N(H)—[($C_{2-4}$ alkylene)-O-]$_{7-15}$—($C_{1-6}$ alkylene)-*, —N(H)—($C_{1-6}$ alkylene)-(3-6 membered heterocycloalkylene)-($C_{1-6}$ alkylene)-N($C_{1-6}$ alkyl)-($C_{1-6}$ alkylene)-*, —N(H)—($C_{1-6}$ alkylene)-(3-6 membered heterocycloalkylene)-($C_{1-6}$ alkylene)-N(H)—($C_{1-6}$ alkylene)-*, —N(H)—($C_{2-6}$ alkylene)-N(H)—($C_{1-6}$ alkylene)-*, or —N(H)—($C_{2-6}$ alkylene)-N($C_{1-6}$ alkyl)-($C_{1-6}$ alkylene)-*, where *** is a point of attachment to TPL.

In certain embodiments, L is —N(H)—[$CH_2CH_2$—O-]$_{2-6}$—($C_{1-6}$ alkylene)-C(O)—*, —N(H)—[$CH_2CH_2$—O-]$_{7-15}$—($C_{1-6}$ alkylene)-C(O)—*, —N(H)—($C_{1-6}$ alkylene)-N($C_{1-6}$ alkyl)C(O)—($C_{1-6}$ alkylene)*, —N(H)—($C_{1-6}$ alkylene)-N(H)C(O)—($C_{1-6}$ alkylene)*, —N(H)—($C_{2-6}$ alkylene)-*, —N(H)—($C_{7-15}$ alkylene)-*, —N($C_{1-6}$ alkyl)-($C_{2-6}$ alkylene)-*, —N($C_{1-6}$ alkyl)-($C_{7-15}$ alkylene)-*, —N(H)—[$CH_2CH_2$—O-]$_{2-6}$—($C_{1-6}$ alkylene)-*, —N(H)—[$CH_2CH_2$—O-]$_{7-15}$—($C_{1-6}$ alkylene)-*, —N(H)—($C_{1-6}$ alkylene)-(3-6 membered heterocycloalkylene)-($C_{1-6}$ alkylene)-N($C_{1-6}$ alkyl)-($C_{1-6}$ alkylene)-*, —N(H)—($C_{1-6}$ alkylene)-(3-6 membered heterocycloalkylene)-($C_{1-6}$ alkylene)-N(H)—($C_{1-6}$ alkylene)-*, —N(H)—($C_{2-6}$ alkylene)-N(H)—($C_{1-6}$ alkylene)-*, or —N(H)—($C_{2-6}$ alkylene)-N($C_{1-6}$ alkyl)-($C_{1-6}$ alkylene)-*, where *** is a point of attachment to TPL.

In certain embodiments, L is —[($C_{2-4}$ alkylene)-O-]$_{2-6}$—($C_{1-6}$ alkylene)-*, —[($C_{2-4}$ alkylene)-O-]$_{7-15}$—($C_{1-6}$ alkylene)-*, —[($C_{2-4}$ alkylene)-O-]$_{2-6}$—($C_{1-6}$ alkylene)-N($C_{1-6}$ alkyl)($C_{1-6}$ alkylene)-*, —[($C_{2-4}$ alkylene)-O-]$_{7-15}$—($C_{1-6}$ alkylene)-N($C_{1-6}$ alkyl)($C_{1-6}$ alkylene)-*, —[($C_{2-4}$ alkylene)-O-]$_{2-6}$—($C_{1-6}$ alkylene)-N(H)($C_{1-6}$ alkylene)-*, —[($C_{2-4}$ alkylene)-O-]$_{7-15}$—($C_{1-6}$ alkylene)-N(H)($C_{1-6}$ alkylene)-*, —($C_{1-9}$ alkylene)-C(O)N(H)—($C_{1-6}$ alkylene)-*, —($C_{1-9}$ alkylene)-N(H)C(O)—($C_{1-6}$ alkylene)-*, —($C_{1-9}$ alkylene)-C(O)N(H)—[($C_{2-4}$ alkylene)-O-]$_{2-6}$—($C_{1-6}$ alkylene)-*, —($C_{1-9}$ alkylene)-N(H)C(O)—[($C_{2-4}$ alkylene)-O-]$_{2-6}$—($C_{1-6}$ alkylene)-*, —($C_{1-9}$ alkylene)-C(O)N(H)—[($C_{2-4}$ alkylene)-O-]$_{7-15}$—($C_{1-6}$ alkylene)-*, —($C_{1-9}$ alkylene)-N(H)C(O)—[($C_{2-4}$ alkylene)-O-]$_{7-15}$—($C_{1-6}$ alkylene)-*, —($C_{1-9}$ alkylene)-C(O)N(H)—[($C_{2-4}$ alkylene)-O-]$_{2-6}$—($C_{1-6}$ alkylene)-N($C_{1-6}$ alkyl)-($C_{1-6}$ alkylene)-*, —($C_{1-9}$ alkylene)-N(H)C(O)—[($C_{2-4}$ alkylene)-O-]$_{2-6}$—($C_{1-6}$ alkylene)-N($C_{1-6}$ alkyl)-($C_{1-6}$ alkylene)-*, —($C_{1-9}$ alkylene)-C(O)N(H)—[($C_{2-4}$ alkylene)-O-]$_{7-15}$-($C_{1-6}$ alkylene)-N($C_{1-6}$ alkyl)-($C_{1-6}$ alkylene)-*, or —($C_{1-9}$ alkylene)-N(H)C(O)—[($C_{2-4}$ alkylene)-O-]$_{7-15}$—($C_{1-6}$ alkylene)-N($C_{1-6}$ alkyl)-($C_{1-6}$ alkylene)-*, where *** is a point of attachment to TPL.

In certain embodiments, L is —[$CH_2CH_2$—O-]$_{2-6}$—($C_{1-6}$ alkylene)-*, —[$CH_2CH_2$—O-]$_{7-15}$-($C_{1-6}$ alkylene)-*, —[$CH_2CH_2$—O-]$_{2-6}$—($C_{1-6}$ alkylene)-N($C_{1-6}$ alkyl)($C_{1-6}$ alkylene)-*, —[$CH_2CH_2$—O-]$_{7-15}$—($C_{1-6}$ alkylene)-N($C_{1-6}$ alkyl)($C_{1-6}$ alkylene)-*, —[$CH_2CH_2$—O-]$_{2-6}$—($C_{1-6}$ alkylene)-N(H)($C_{1-6}$ alkylene)-*, —[$CH_2CH_2$—O-]$_{7-15}$—($C_{1-6}$ alkylene)-N(H)($C_{1-6}$ alkylene)-*, —($C_{1-9}$ alkylene)-C(O)N(H)—($C_{1-6}$ alkylene)-*, —($C_{1-9}$ alkylene)-N(H)C(O)—($C_{1-6}$ alkylene)-*, —($C_{1-9}$ alkylene)-C(O)N(H)—[$CH_2CH_2$—O-]$_{2-6}$—($C_{1-6}$ alkylene)-*, —($C_{1-9}$ alkylene)-N(H)C(O)—[$CH_2CH_2$—O-]$_{2-6}$—($C_{1-6}$ alkylene)-*, —($C_{1-9}$ alkylene)-C(O)N(H)—[$CH_2CH_2$—O-]$_{7-15}$—($C_{1-6}$ alkylene)-*, —($C_{1-9}$ alkylene)-N(H)C(O)—[$CH_2CH_2$—O-]$_{7-15}$—($C_{1-6}$ alkylene)-*, —($C_{1-9}$ alkylene)-C(O)N(H)—[$CH_2CH_2$—O-]$_{2-6}$—($C_{1-6}$ alkylene)-N($C_{1-6}$ alkyl)-($C_{1-6}$ alkylene)-*, —($C_{1-9}$ alkylene)-N(H)C(O)—[$CH_2CH_2$—O-]$_{2-6}$—($C_{1-6}$ alkylene)-N($C_{1-6}$ alkyl)-($C_{1-6}$ alkylene)-*, —($C_{1-9}$ alkylene)-C(O)N(H)—[$CH_2CH_2$—O-]$_{7-15}$—($C_{1-6}$ alkylene)-N($C_{1-6}$ alkyl)-($C_{1-6}$ alkylene)-*, or —($C_{1-9}$ alkylene)-N(H)C(O)—[($CH_2CH_2$—O-]$_{7-15}$—($C_{1-6}$ alkylene)-N($C_{1-6}$ alkyl)-($C_{1-6}$ alkylene)-*, where *** is a point of attachment to TPL.

In certain embodiments, L is —N(H)—[($C_{2-4}$ alkylene)-O-]$_{2-6}$—($C_{1-6}$ alkylene)-N(H)—*, —N(H)—[($C_{2-4}$ alkylene)-O-]$_{7-15}$—($C_{1-6}$ alkylene)-N(H)—*, —N($C_{1-6}$ alkyl)-[($C_{2-4}$ alkylene)-O-]$_{2-6}$—($C_{1-6}$ alkylene)-N(H)—*, —N($C_{1-6}$ alkyl)-[($C_{2-4}$alkylene)-O-]$_{7-15}$—($C_{1-6}$ alkylene)-N(H)—*, —N($C_{1-6}$ alkyl)-[($C_{2-4}$ alkylene)-O-]$_{2-6}$—($C_{1-6}$ alkylene)-N($C_{1-6}$ alkyl)-*, or —N($C_{1-6}$ alkyl)-[($C_{2-4}$ alkylene)-O-]$_{7-15}$—($C_{1-6}$ alkylene)-N($C_{1-6}$ alkyl)-*, where *** is a point of attachment to TPL.

In certain embodiments, L is —N(H)—[$CH_2CH_2$—O-]$_{2-6}$—($C_{1-6}$ alkylene)-N(H)—*, —N(H)—[$CH_2CH_2$—O-]$_{7-15}$—($C_{1-6}$ alkylene)-N(H)—*, —N($C_{1-6}$ alkyl)-[$CH_2CH_2$—O-]$_{2-6}$—($C_{1-6}$ alkylene)-N(H)—*, —N($C_{1-6}$ alkyl)-[$CH_2CH_2$—O-]$_{7-15}$—($C_{1-6}$ alkylene)-N(H)—*, —N($C_{1-6}$ alkyl)-[$CH_2CH_2$—O-]$_{2-6}$—($C_{1-6}$ alkylene)-N($C_{1-6}$ alkyl)-*, or —N($C_{1-6}$ alkyl)-[$CH_2CH_2$—O-]$_{7-15}$—($C_{1-6}$ alkylene)-N($C_{1-6}$ alkyl)-*, where *** is a point of attachment to TPL.

In some embodiments, L is one of the following:

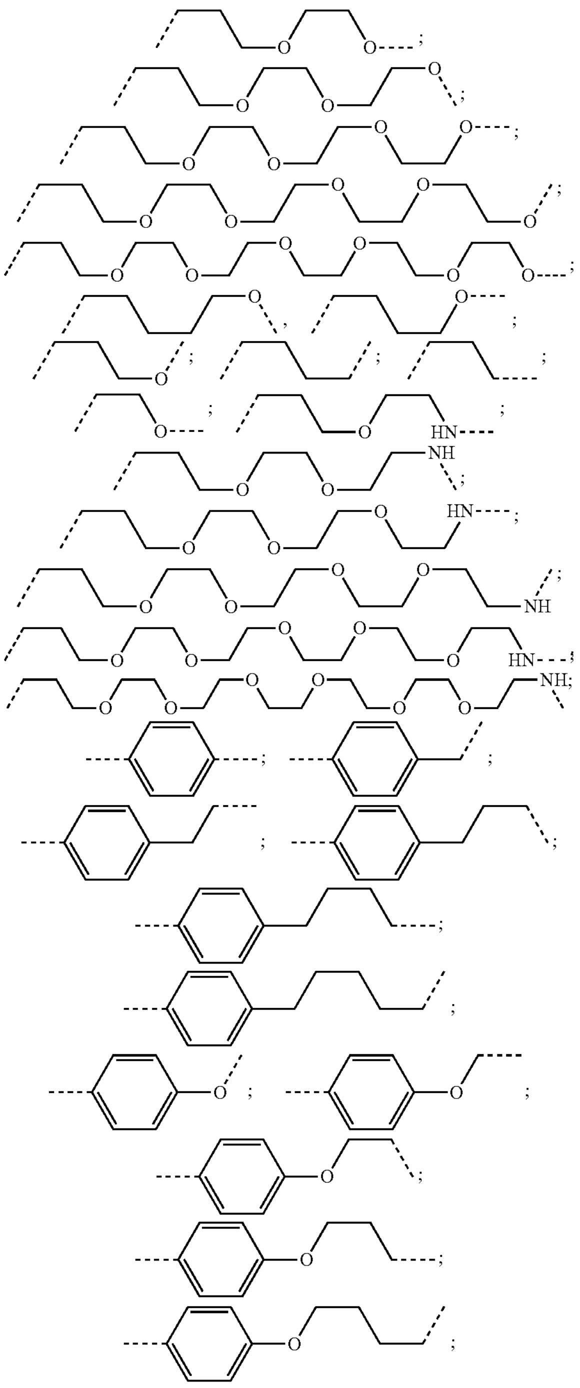

-continued

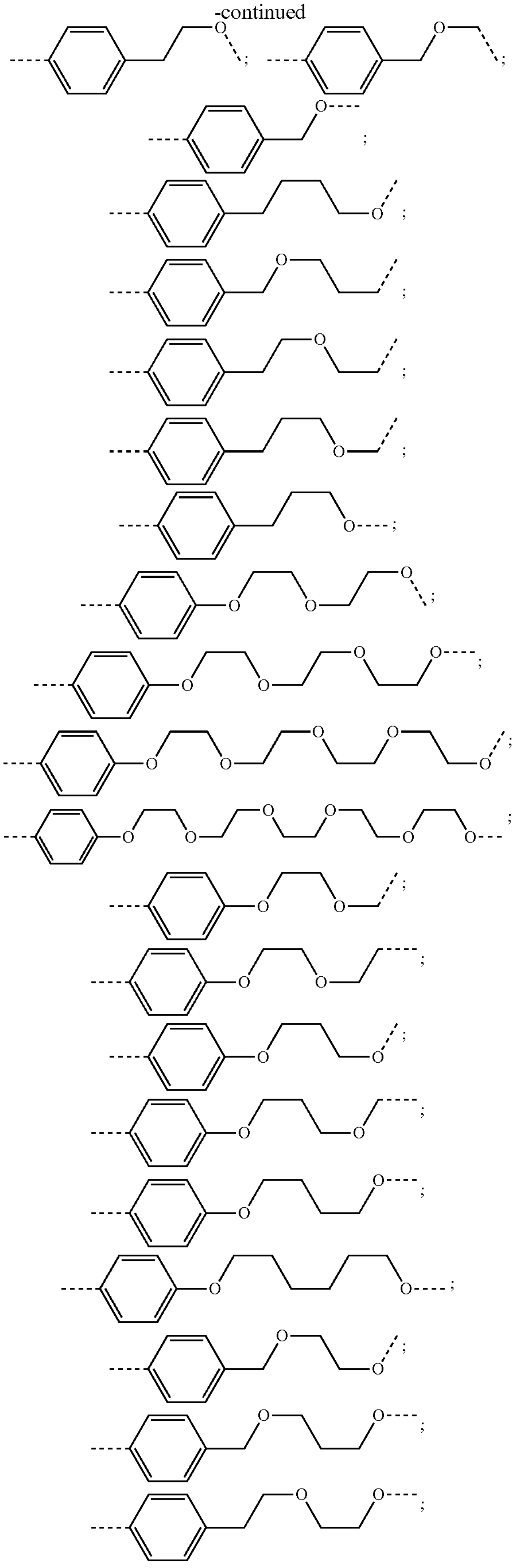

-continued
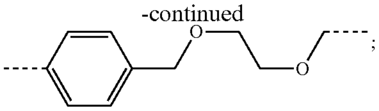
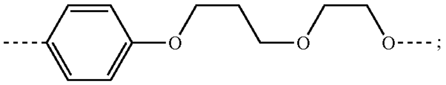
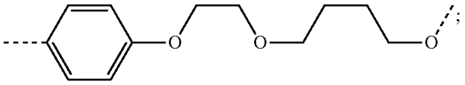
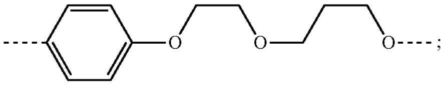
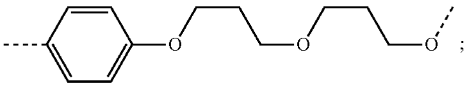
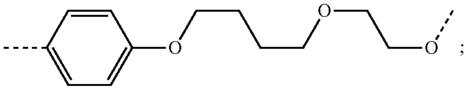
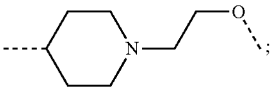
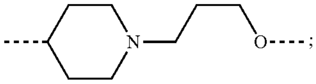
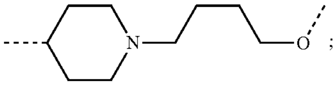
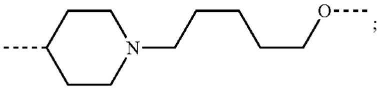
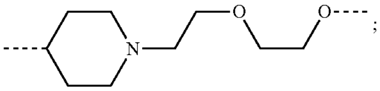
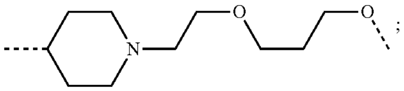
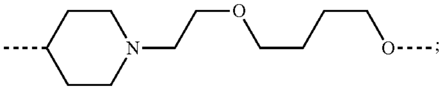
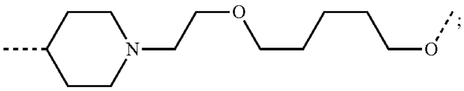
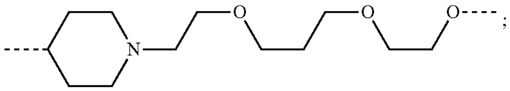
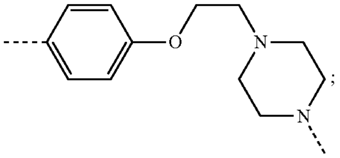
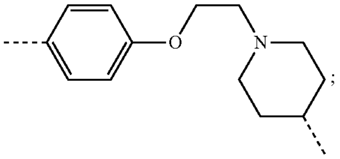
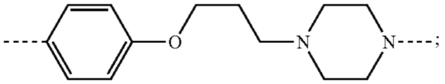
-continued
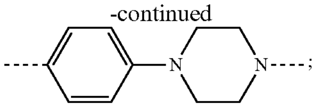
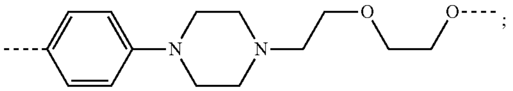
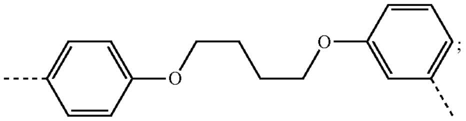
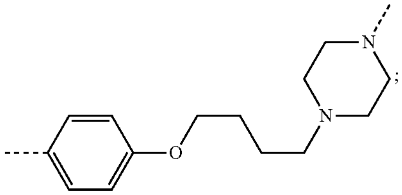
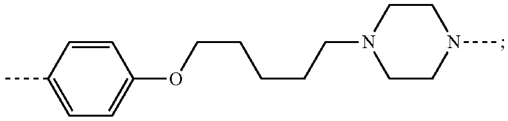
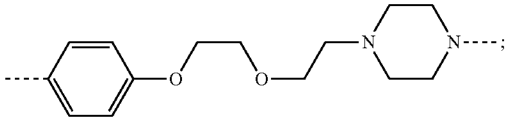
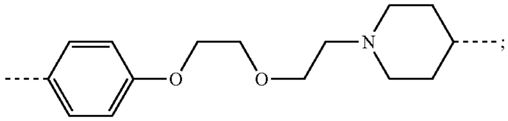
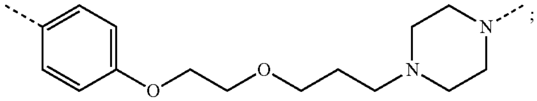
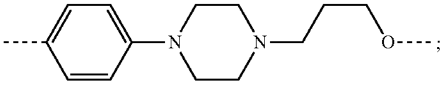
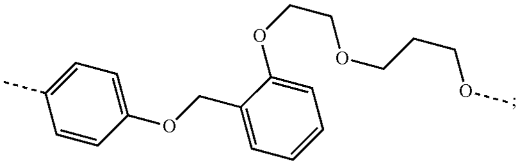
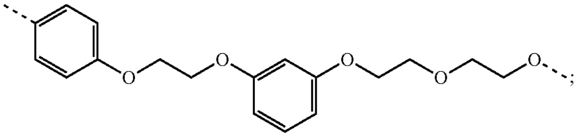
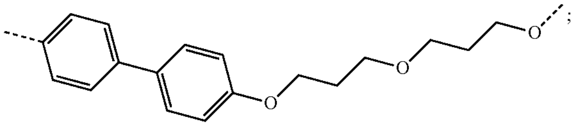
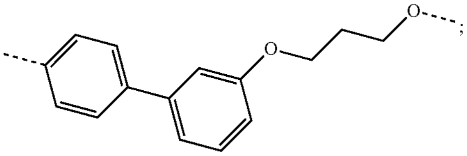
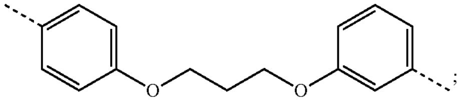

-continued
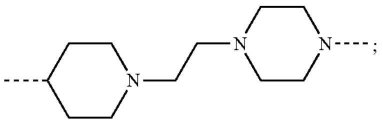
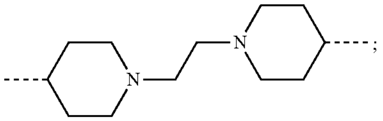
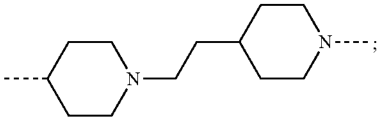
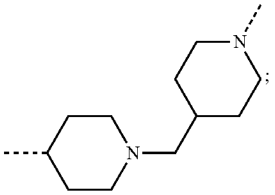
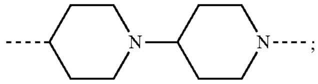
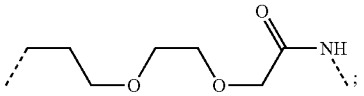
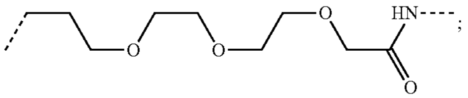
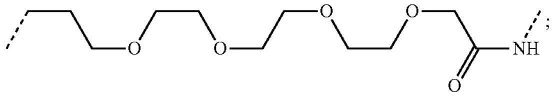
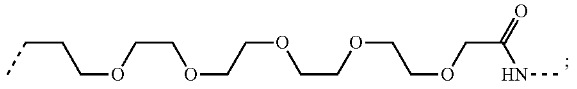
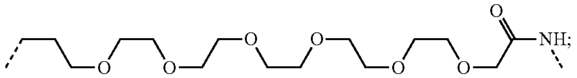
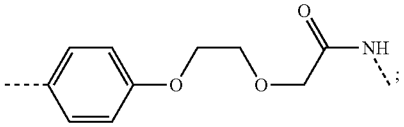
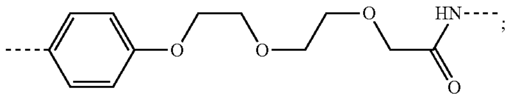
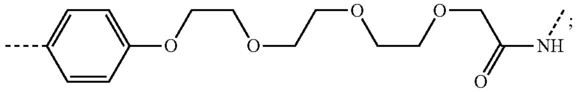
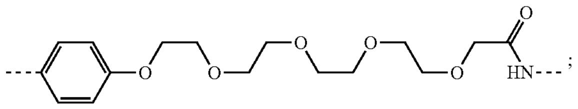
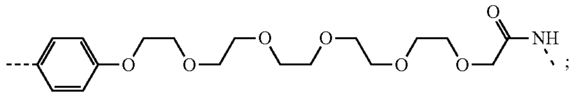
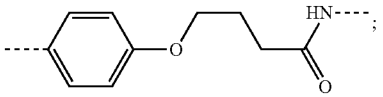
-continued
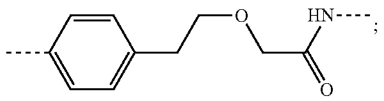
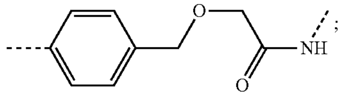
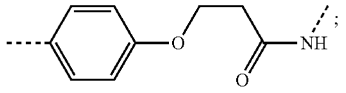
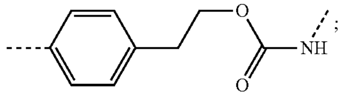
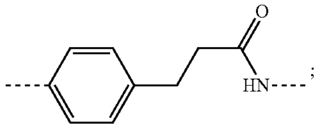
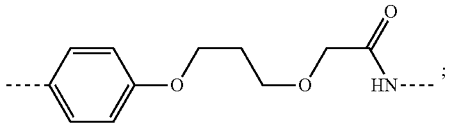
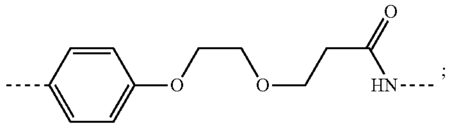
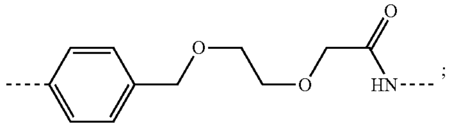
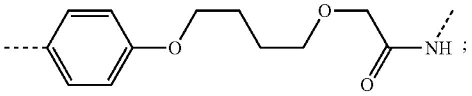
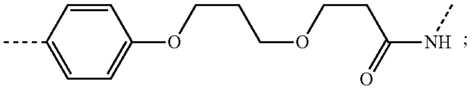
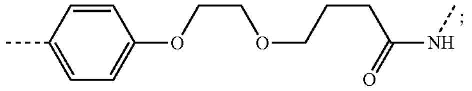
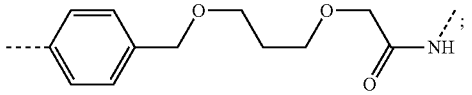
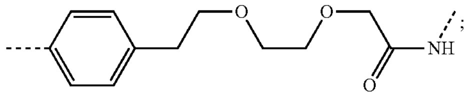
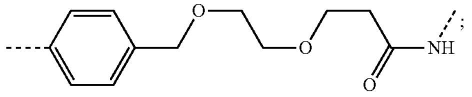
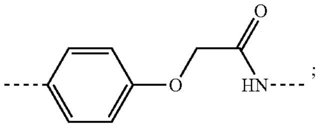
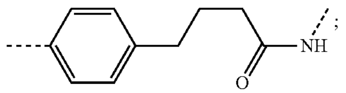

-continued
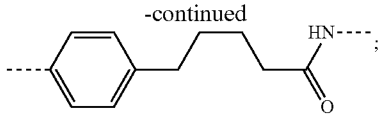
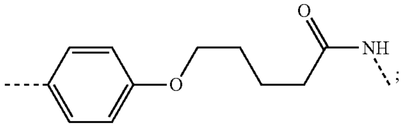
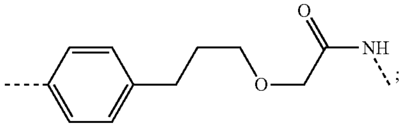
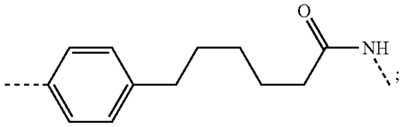
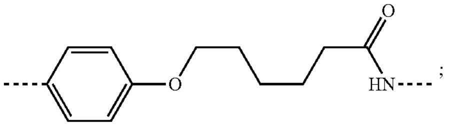
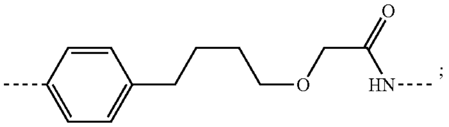
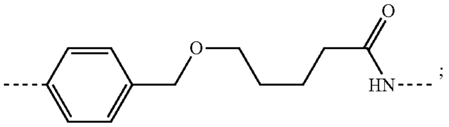
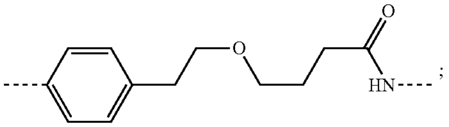
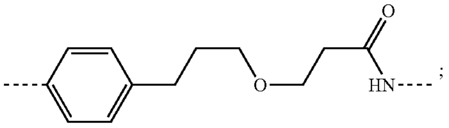
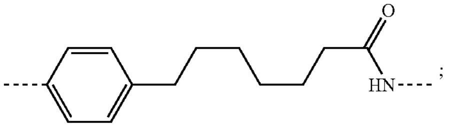
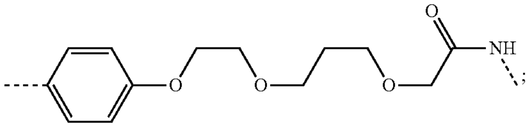
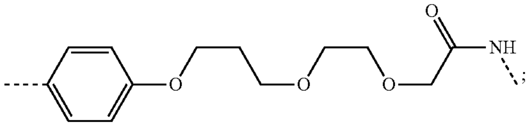
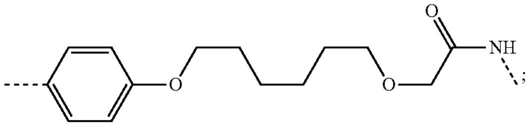
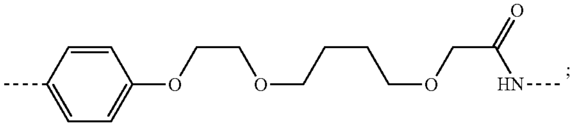
-continued
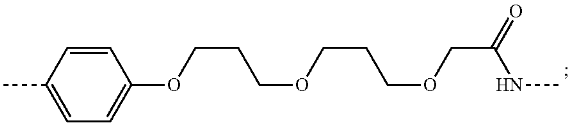
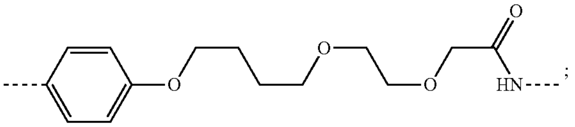
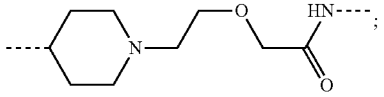
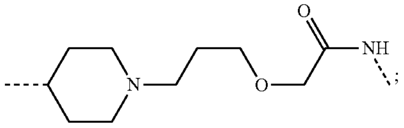
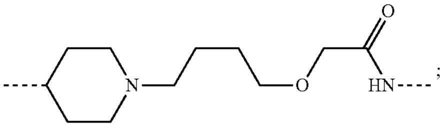
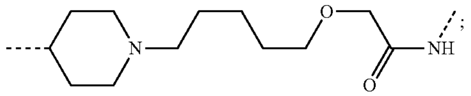
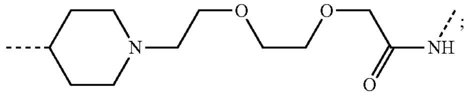
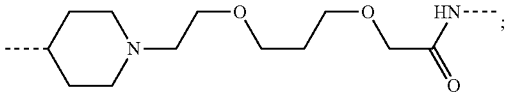
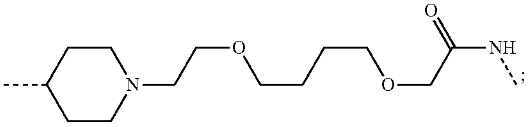
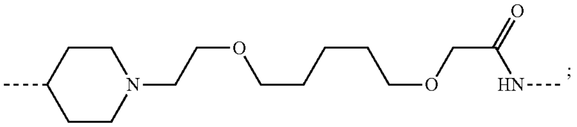
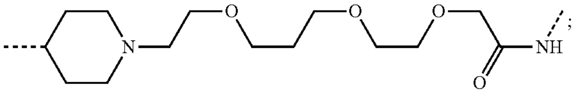
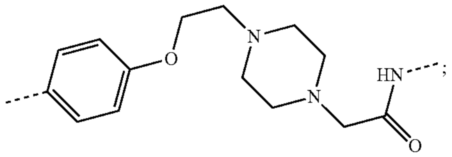
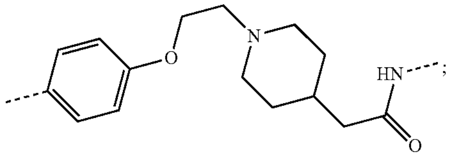
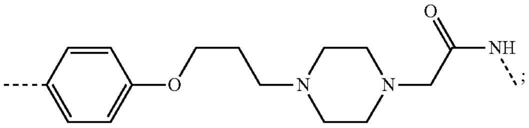

-continued
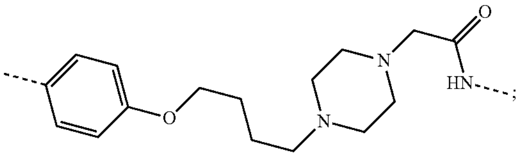
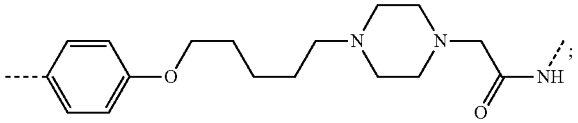
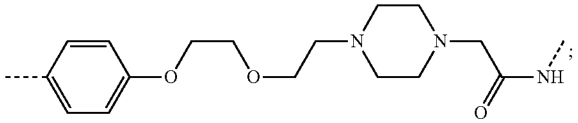
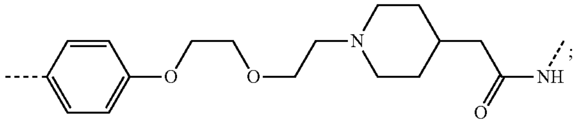
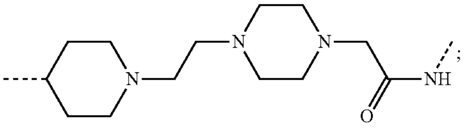
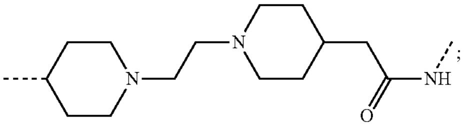
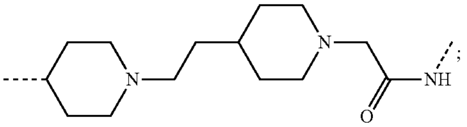
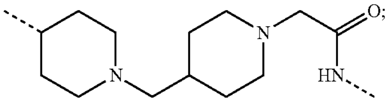
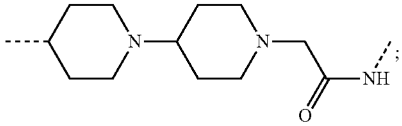
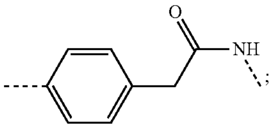
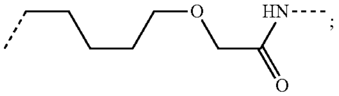
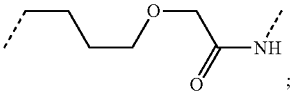
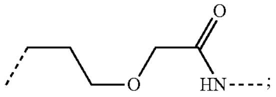
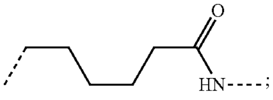
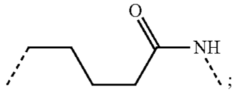
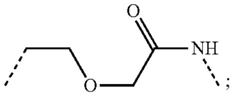
-continued
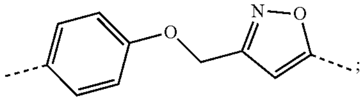
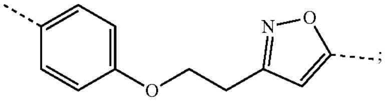
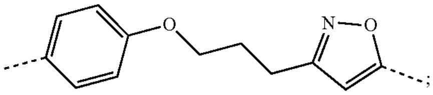
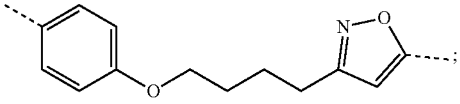
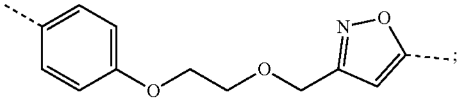
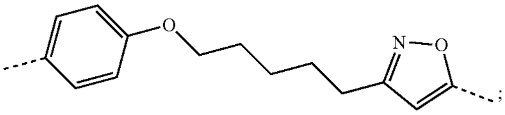
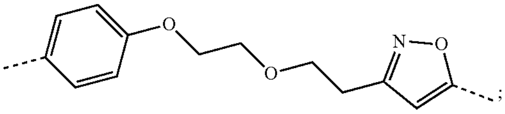
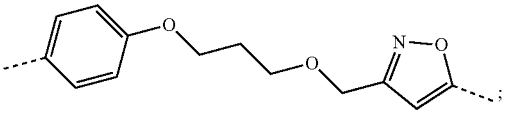
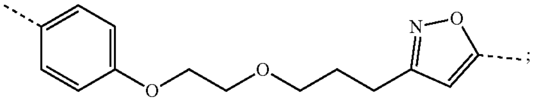
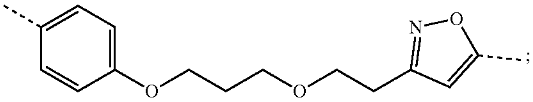
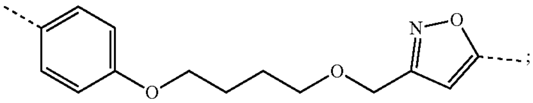
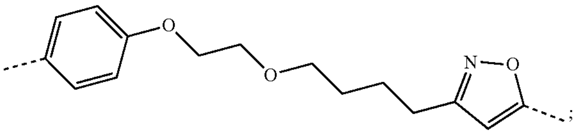
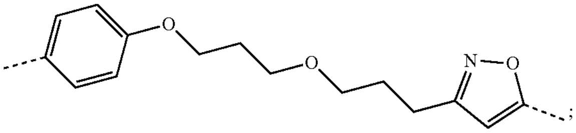
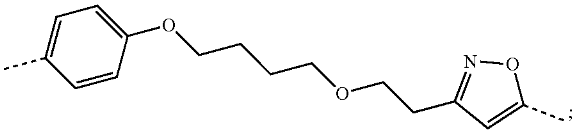
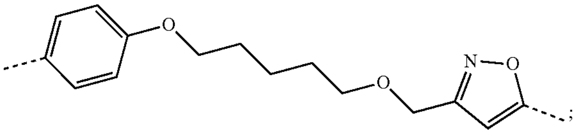

-continued
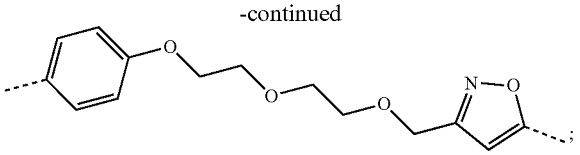
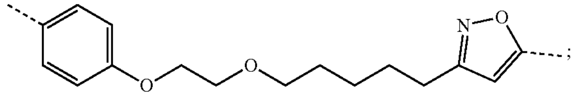
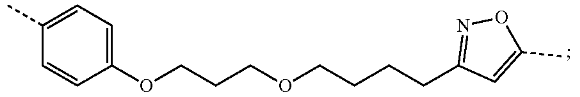
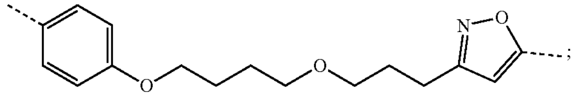
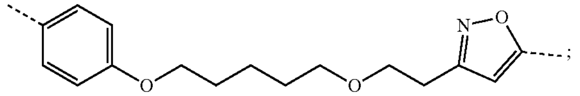
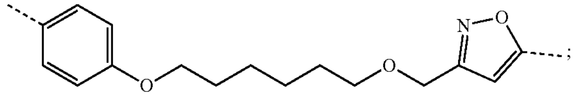
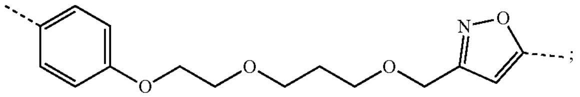
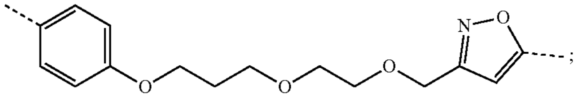
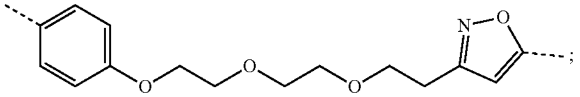
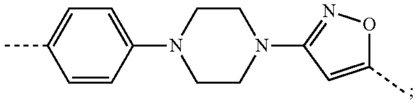
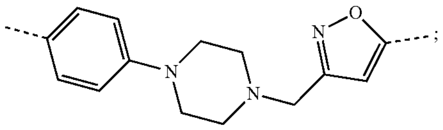
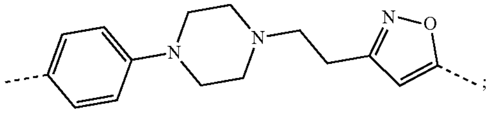
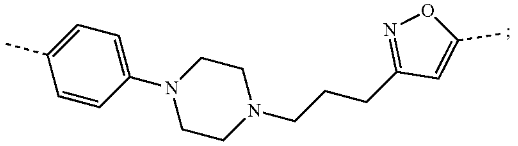
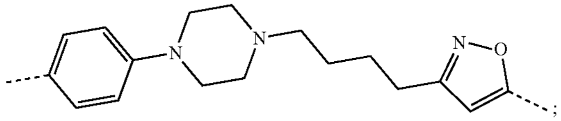
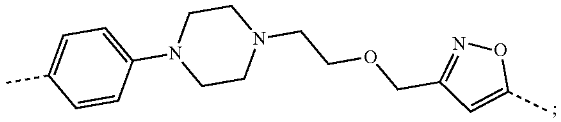
-continued
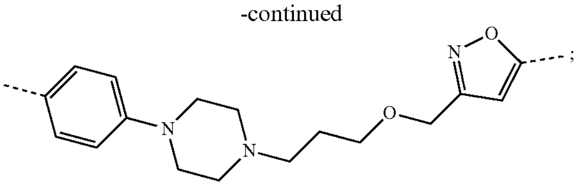
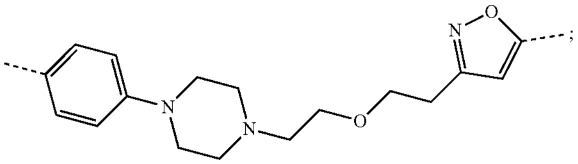
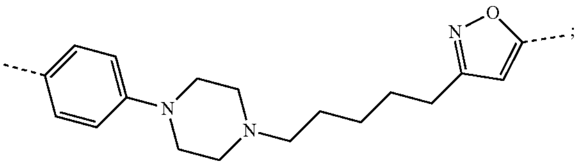
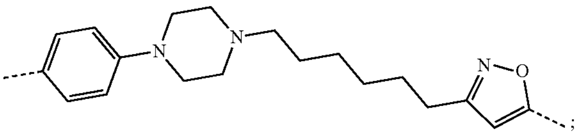
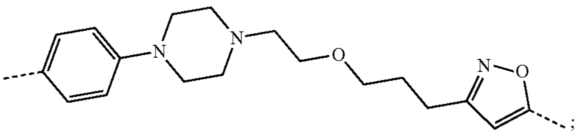
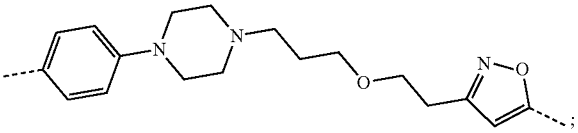
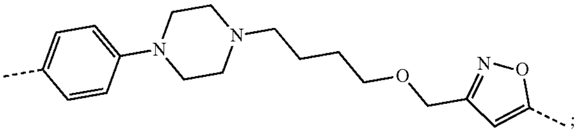
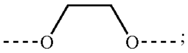
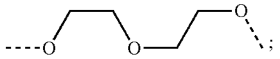
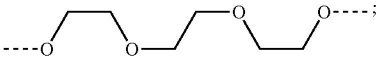
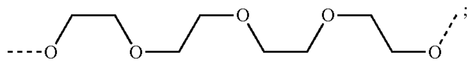
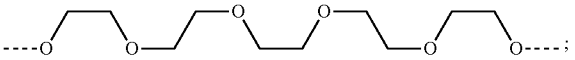
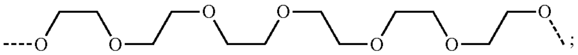
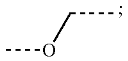
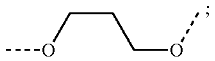
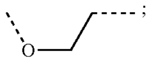
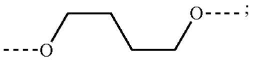
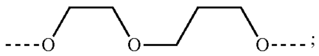
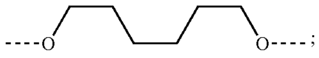
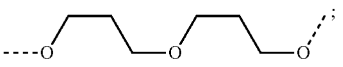
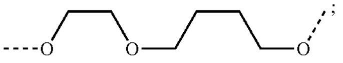

-continued
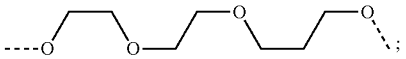
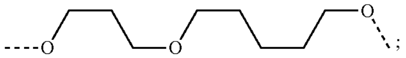
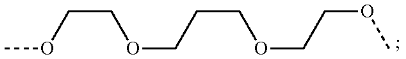
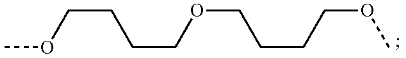
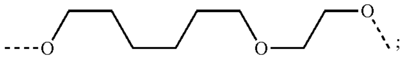
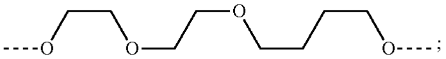
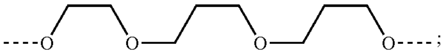
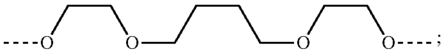
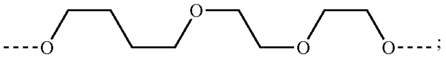
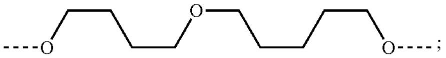
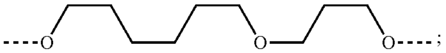
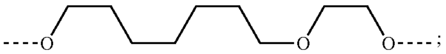
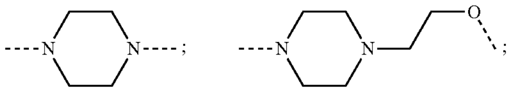
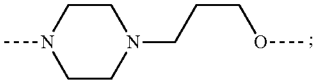
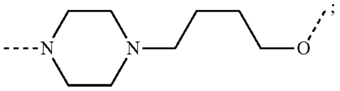
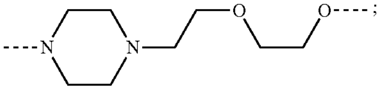
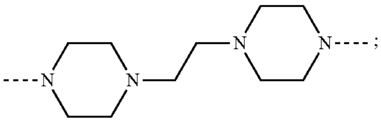
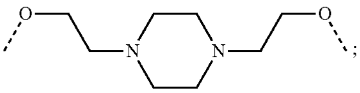
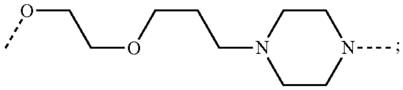
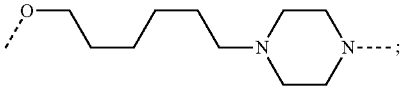
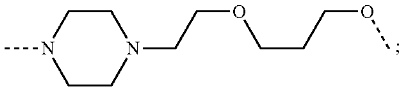
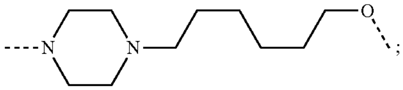
-continued
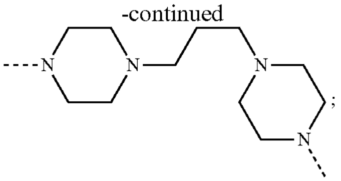
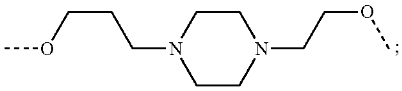
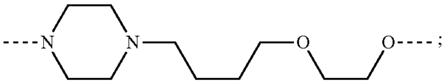
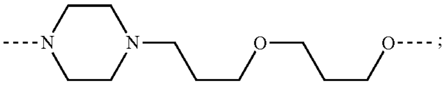
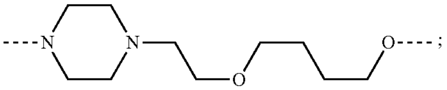
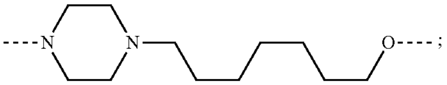
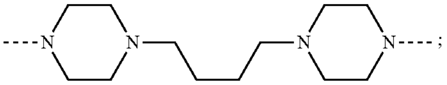
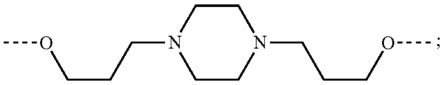
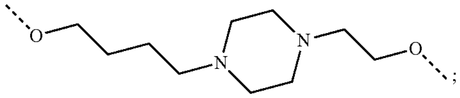
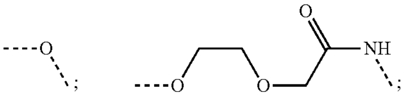
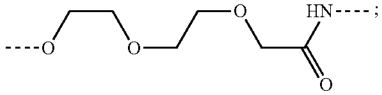
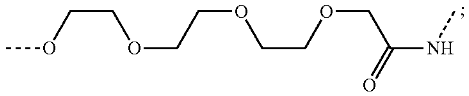
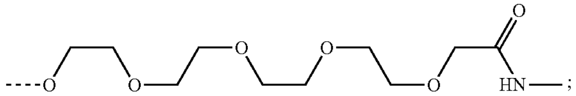
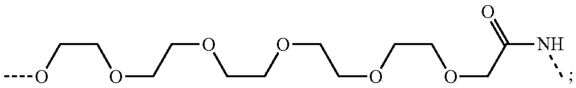
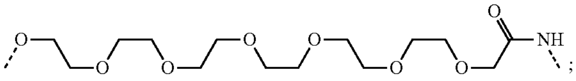
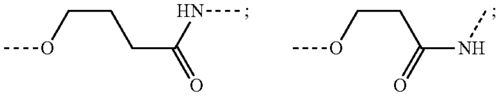
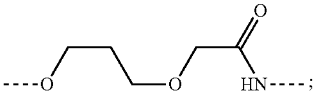
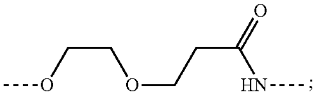

-continued
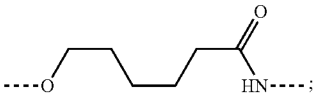
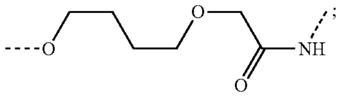
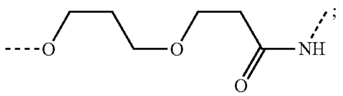
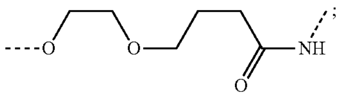
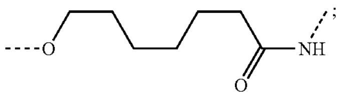
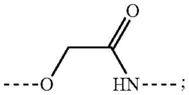
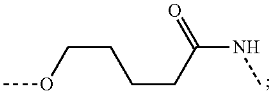
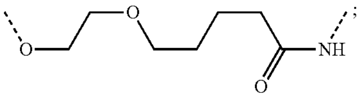
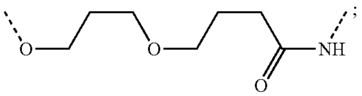
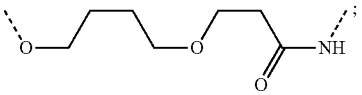
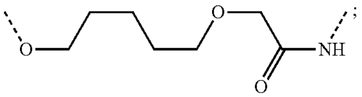
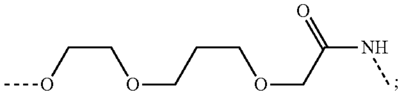
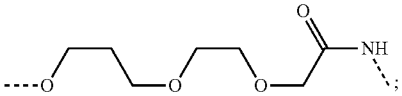
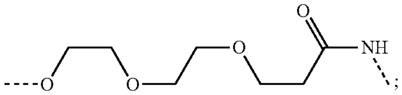
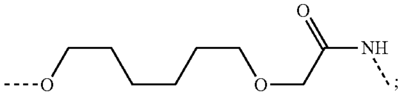
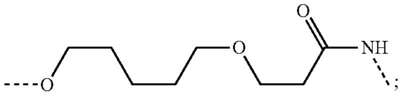
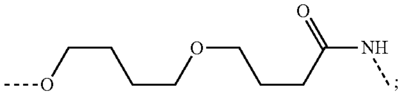
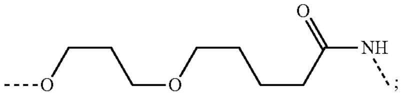
-continued
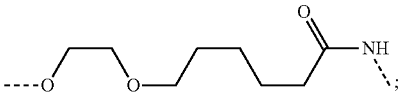
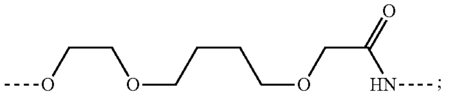
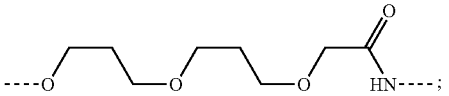
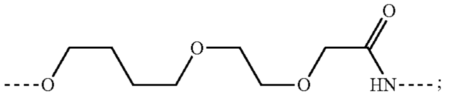
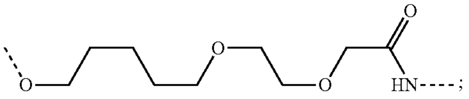
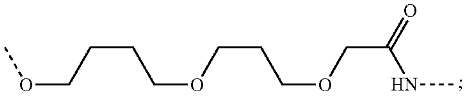
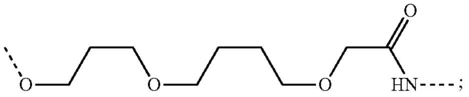
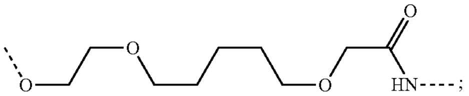
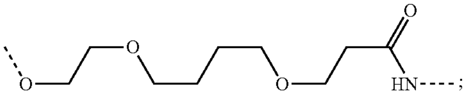
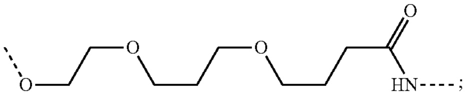
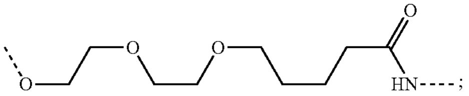
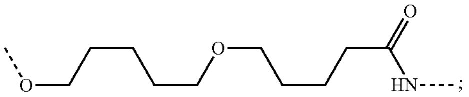
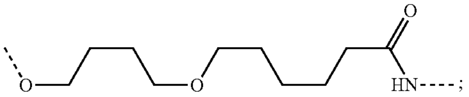
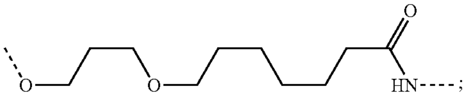
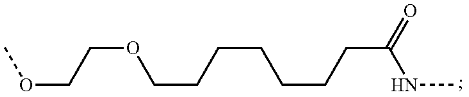
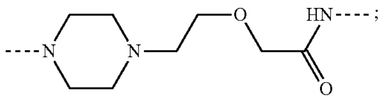
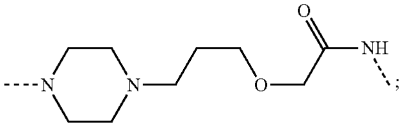

-continued
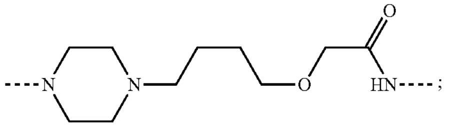
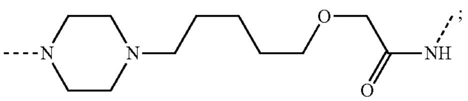
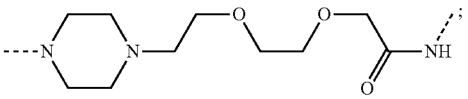
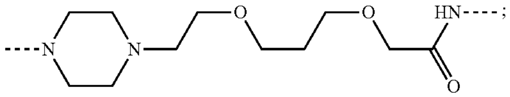
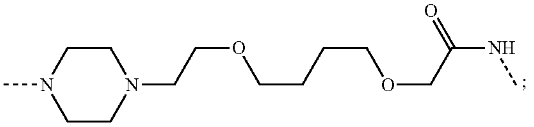
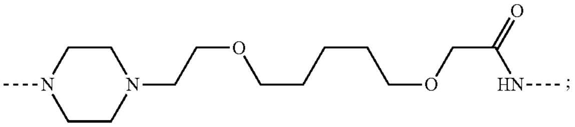
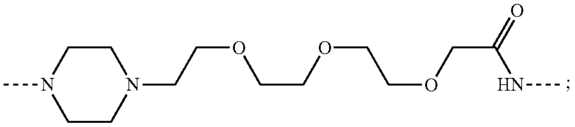
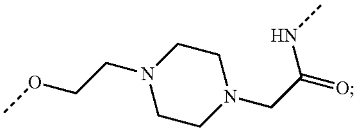
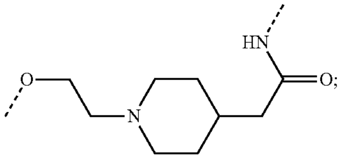
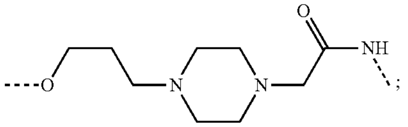
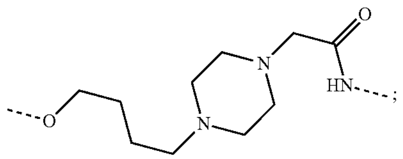
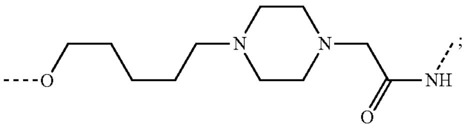
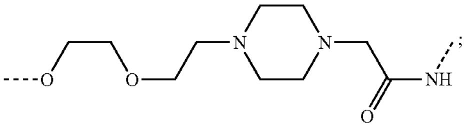
-continued
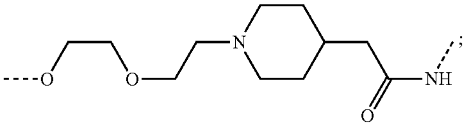
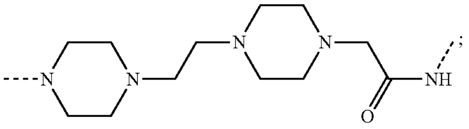
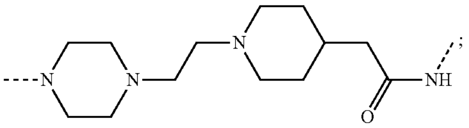
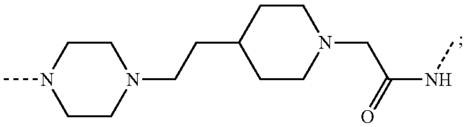
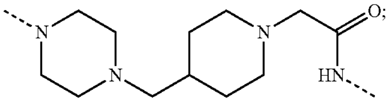
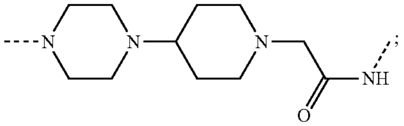
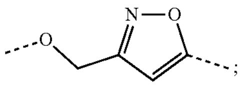
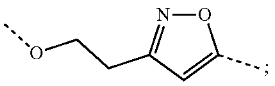
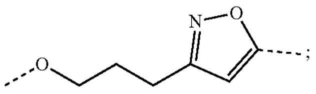
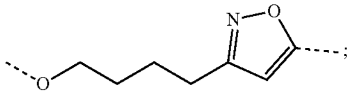
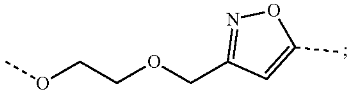
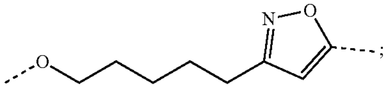
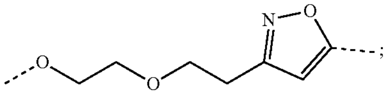
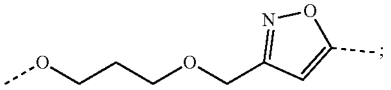
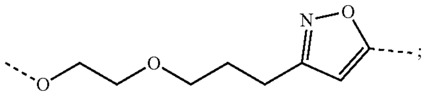
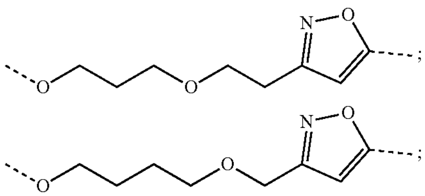

-continued

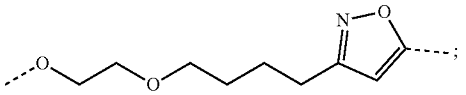

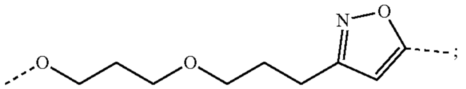

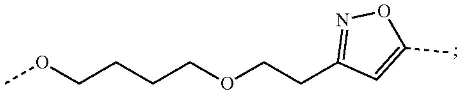

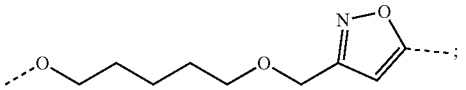

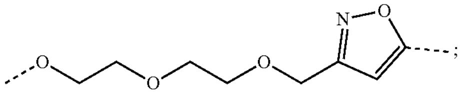

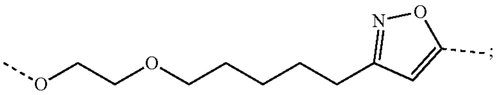

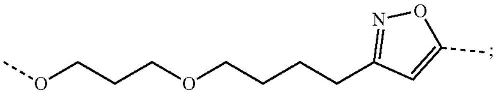

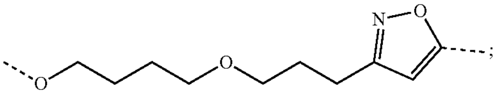

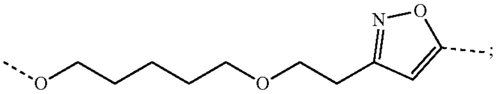

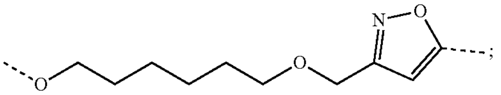

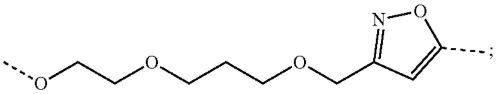

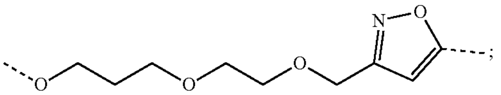

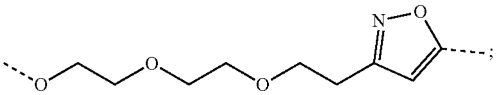

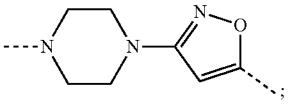

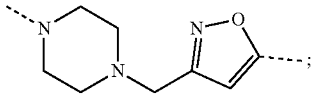

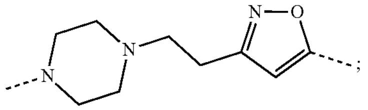

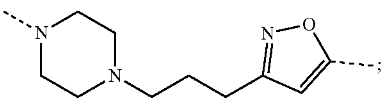

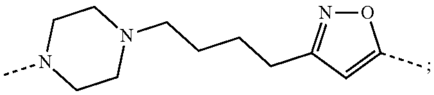

-continued

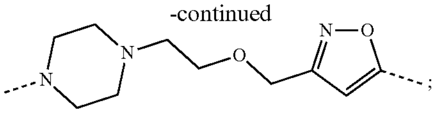

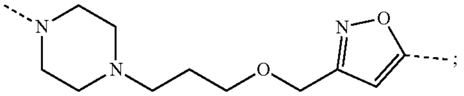

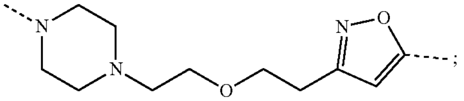

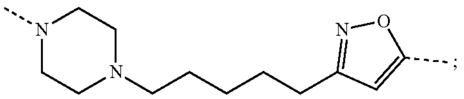

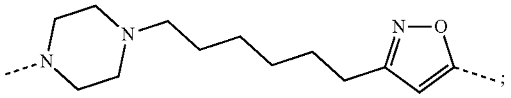

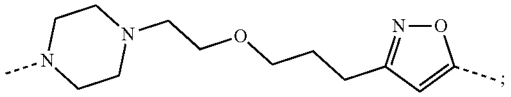

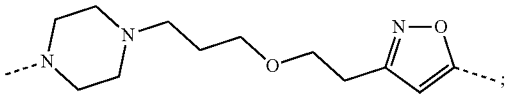

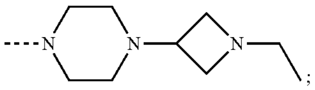

and

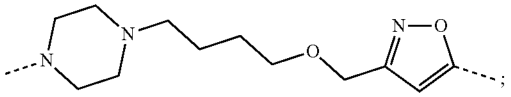

wherein a dashed bond indicates a point of attachment.

In certain embodiments, L has the formula —($C_{0-12}$ alkylene)-(optionally substituted 3-40 membered heteroalkylene)-($C_{0-12}$ alkylene)-. In certain embodiments, L is $C_{4-14}$ alkylene. In certain embodiments, L is —$(CH_2)_{6-10}$—.

In certain embodiments, L is —$CH_2CH_2(OCH_2CH_2)$—*, —$CH_2CH_2(OCH_2CH_2)_2$—*, —$CH_2CH_2(OCH_2CH_2)_3$—*, —$CH_2CH_2(OCH_2CH_2)_4$—*, —$CH_2CH_2(OCH_2CH_2)_5$—***, —$CH_2CH_2(OCH_2CH_2)_6$—* **, —$CH_2CH_2(OCH_2CH_2)_7$—* **, —$CH_2CH_2(OCH_2CH_2)_8$—* , —$CH_2CH_2(OCH_2CH_2)_9$—*, —$CH_2CH_2(OCH_2CH_2)_{10}$—*, —$CH_2CH_2(OCH_2CH_2)_{11}$—*, —$CH_2CH_2(OCH_2CH_2)_{12}$—*, —$CH_2CH_2(OCH_2CH_2)_{13}$—*, —$CH_2CH_2(OCH_2CH_2)_{14}$—*, —$CH_2CH_2(OCH_2CH_2)_{15}$—*, or —$CH_2CH_2(OCH_2CH_2)_{16-20}$—*, where * is a point of attachment to TPL.

In certain embodiments, L is —($C_{2-20}$ alkylene)-$(OCH_2CH_2)_{2-4}$—($C_{0-4}$ alkylene)-***, —($C_{2-20}$ alkylene)-$(OCH_2CH_2)_{5-7}$—($C_{0-4}$ alkylene)-* , —($C_{2-20}$ alkylene)-$(OCH_2CH_2)_{8-10}$—($C_{0-4}$ alkylene)-*, —($C_{2-20}$ alkylene)-$(OCH_2CH_2)_{11-13}$—($C_{0-4}$ alkylene)-*, —($C_{2-20}$ alkylene)-$(OCH_2CH_2)_{14-16}$—($C_{0-4}$ alkylene)-*, —($C_{2-20}$ alkylene)-$(OCH_2CH_2)_{17-20}$—($C_{0-4}$ alkylene)-*, —($C_{1-20}$ alkylene)-$(OCH_2CH_2)_{1-10}$—($C_{0-4}$ alkylene)-C(O)—*, or —($C_{1-20}$ alkylene)-$(OCH_2CH_2)_{11-20}$—($C_{0-4}$ alkylene)-C(O)—*, where * is a point of attachment to TPL.

In certain embodiments, L is —$O(CH_2CH_2O)_{2-4}$—($C_{0-4}$ alkylene)-*, —$O(CH_2CH_2O)_{5-7}$—($C_{0-4}$alkylene)-*, —$O(CH_2CH_2O)_{8-10}$—($C_{0-4}$alkylene)-*, —$O(CH_2CH_2O)_{11-13}$—($C_{0-4}$ alkylene)-* —$O(CH_2CH_2O)_{14-16}$—($C_{0-4}$alkylene)-*, —$O(CH_2CH_2O)_{16-20}$—($C_{0-4}$alkylene)-*, —$O(CH_2CH_2O)_{2-10}$—($C_{0-4}$ alkylene)C(O)—*, or —$O(CH_2CH_2O)_{11-20}$—($C_{0-4}$ alkylene)C(O)—*, where *** is a point of attachment to TPL.

In certain embodiments, L is —($C_{0-20}$ alkylene)-$(OCH_2CH_2)_{1-10}$—(N($C_{1-4}$ alkyl))-*, —($C_{0-20}$ alkylene)-$(OCH_2CH_2)_{11-20}$—(N($C_{1-4}$ alkyl))-*, —($C_{0-20}$ alkylene)-$(CH_2CH_2O)_{1-10}$—($C_{2-10}$ alkylene)-(N($C_{1-4}$ alkyl))—($C_{0-10}$ alkylene)-*, or —($C_{0-20}$ alkylene)-$(CH_2CH_2O)_{11-20}$—($C_{2-10}$ alkylene)-(N($C_{1-4}$ alkyl))—($C_{0-10}$ alkylene)-*, where *** is a point of attachment to TPL.

In certain embodiments, L is —($C_{2-10}$ alkylene)-$(OCH_2CH_2)_{2-4}$—O-(3-6 membered saturated heterocyclylene containing 1 or 2 heteroatoms independently selected from nitrogen and oxygen)-($C_{1-5}$ alkylene)-*, —($C_{2-10}$ alkylene)-(3-6 membered saturated heterocyclylene containing 1 or 2 heteroatoms independently selected from nitrogen and oxygen)-($C_{1-5}$ alkylene)-*, —($C_{2-10}$ alkylene)-N(H)—($C_{1-5}$ alkylene)-*, —($C_{2-10}$ alkylene)-N($C_{1-6}$ alkyl)-($C_{1-5}$ alkylene)-*, —N(H)—($C_{1-5}$ alkylene)-*, —$(CH_2CH_2O)_{1-4}$—($C_{1-4}$ alkylene)-*, —$(CH_2CH_2O)_{1-4}$—($C_{1-4}$ alkylene)-N($C_{1-6}$ alkyl)-($C_{1-6}$ alkylene)-*, —N(H)—($C_{2-6}$ alkylene)-(3-6 membered saturated heterocyclylene containing 1 or 2 heteroatoms independently selected from nitrogen and oxygen)-($C_{1-5}$ alkylene)-*, —N(H)—($C_{2-6}$ alkylene)-$(OCH_2CH_2)_{1-4}$—O-(3-6 membered saturated heterocyclylene containing 1 or 2 heteroatoms independently selected from nitrogen and oxygen)-($C_{1-5}$ alkylene)-*, —N(H)—[—$CH_2CH_2$O-$]_{2-6}$—($C_{1-6}$ alkylene)-N($C_{1-6}$ alkyl)-($C_{1-6}$ alkylene)-*, —($C_{1-6}$ alkylene)-(3-6 membered saturated heterocyclylene containing 1 or 2 heteroatoms independently selected from nitrogen and oxygen)-($C_{1-6}$ alkylene)-*, —N(H)—($C_{2-10}$ alkylene)-*, —($C_{1-6}$ alkylene)-(3-6 membered saturated heterocyclylene containing 1 or 2 heteroatoms independently selected from nitrogen and oxygen)-($C_{1-6}$ alkylene)-N($C_{1-6}$ alkyl)-($C_{1-6}$ alkylene)-*, —N(H)—[$CH_2CH_2$—O-$]_{2-6}$—($C_{1-6}$ alkylene)-N($C_{1-6}$ alkyl)-($C_{1-6}$ alkylene)-*, —N(H)—[$CH_2CH_2$—O-$]_{2-10}$—($C_{1-6}$ alkylene)-*, —N(H)—[$CH_2CH_2$—O-$]_{2-6}$—($C_{1-6}$ alkylene)-N($C_{1-6}$ alkyl) C(O)—($C_{1-6}$ alkylene)-*, —[$CH_2CH_2$—O-$]_{1-6}$—($C_{1-6}$ alkylene)-N($C_{1-6}$ alkyl)-*, —[$CH_2CH_2$—O-$]_{1-6}$—($C_{1-6}$ alkylene)-N(H)—*, or —($C_{2-10}$ alkylene)-$(OCH_2CH_2)_{2-6}$—($C_{3-6}$ cycloalkylene)-*, where * is a point of attachment to TPL.

In certain embodiments, L is -(5-6 membered monocyclic heterocyclyl containing 1 or 2 nitrogen atoms)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-*, -(4-6 membered monocyclic heterocyclyl containing 1 nitrogen atom, wherein the heterocyclyl is substituted with 0 or 1 occurrences of hydroxyl)-($C_{0-6}$ alkylene)-(4-6 membered monocyclic heterocyclyl containing 1 nitrogen atom)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-($C_{0-6}$ alkylene)-O—*, —($C_{0-6}$ alkylene)-(7-11 membered spirocyclic heterocyclyl containing 1-2 nitrogen atoms)-($C_{0-6}$ alkylene)-O—*, —($C_{0-6}$ alkylene)-(7-11 membered spirocyclic heterocyclyl containing 1-2 heteroatoms selected from nitrogen)-*, —O-(7-11 membered spirocyclic heterocyclyl containing 1-2 nitrogen atoms)-($C_{0-6}$ alkylene)-O—*, —O-(7-11 membered spirocyclic heterocyclyl containing 1-2 nitrogen atoms)-*, —($C_{2-3}$ alkynylene)-(7-11 membered spirocyclic heterocyclyl containing 1-2 nitrogen atoms)-($C_{0-6}$ alkylene)-O—*, —($C_{2-3}$ alkynylene)-(7-11 membered spirocyclic heterocyclyl containing 1-2 nitrogen atoms)-*, —O—($C_{0-6}$ alkylene)-(5-6 membered monocyclic heterocyclyl containing 1 nitrogen atom)-*, —O—($C_{0-6}$ alkylene)-(5-6 membered monocyclic heterocyclyl containing 1 nitrogen atom)-($C_{1-6}$ alkylene)-O—*, or —O—($C_{1-6}$ alkylene)-O—($C_{1-6}$ alkylene)-(4-6 membered monocyclic heterocyclyl containing 1 nitrogen atom)-($C_{0-6}$ alkylene)-O—*, where * is a point of attachment to TPL. In certain embodiments, L is -(5-6 membered monocyclic heterocyclyl containing 1 or 2 nitrogen atoms)-*, where * is a point of attachment to TPL. In certain embodiments, L is -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-*, where * is a point of attachment to TPL. In certain embodiments, L is -(4-6 membered monocyclic heterocyclyl containing 1 nitrogen atom, wherein the heterocyclyl is substituted with 0 or 1 occurrences of hydroxyl)-($C_{0-6}$ alkylene)-(4-6 membered monocyclic heterocyclyl containing 1 nitrogen atom)-*, where * is a point of attachment to TPL. In certain embodiments, L is -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-($C_{0-6}$ alkylene)-O—*, where * is a point of attachment to TPL. In certain embodiments, L is —($C_{0-6}$ alkylene)-(7-11 membered spirocyclic heterocyclyl containing 1-2 nitrogen atoms)-($C_{0-6}$ alkylene)-O—*, where * is a point of attachment to TPL. In certain embodiments, L is —($C_{0-6}$ alkylene)-(7-11 membered spirocyclic heterocyclyl containing 1-2 heteroatoms selected from nitrogen)-*, where * is a point of attachment to TPL. In certain embodiments, L is —O-(7-11 membered spirocyclic heterocyclyl containing 1-2 nitrogen atoms)-($C_{0-6}$ alkylene)-O—*, where * is a point of attachment to TPL. In certain embodiments, L is —O-(7-11 membered spirocyclic heterocyclyl containing 1-2 nitrogen atoms)-*, where * is a point of attachment to TPL. In certain embodiments, L is —($C_{2-3}$ alkynylene)-(7-11 membered spirocyclic heterocyclyl containing 1-2 nitrogen atoms)-($C_{0-6}$ alkylene)-O—*, where * is a point of attachment to TPL. In certain embodiments, L is —($C_{2-3}$ alkynylene)-(7-11 membered spirocyclic heterocyclyl containing 1-2 nitrogen atoms)-*, where * is a point of attachment to TPL. In certain embodiments, L is —O—($C_{0-6}$ alkylene)-(5-6 membered monocyclic heterocyclyl containing 1 nitrogen atom)-*, where * is a point of attachment to TPL. In certain embodiments, L is —O—($C_{0-6}$ alkylene)-(5-6 membered monocyclic heterocyclyl containing 1 nitrogen atom)-($C_{1-6}$ alkylene)-O—*, where *is a point of attachment to TPL. In certain embodiments, L is —O—($C_{1-6}$ alkylene)-O—($C_{1-6}$ alkylene)-(4-6 membered monocyclic heterocyclyl containing 1 nitrogen atom)-($C_{0-6}$ alkylene)-O—*, where * is a point of attachment to TPL.

In certain embodiments, L is —O—($C_{1-6}$ alkylene)-O—($C_{1-6}$ alkylene)-O-(4-6 membered monocyclic heterocyclyl containing 1 nitrogen atom)-($C_{0-6}$ alkylene)-*, —O—($C_{1-6}$ alkylene)-O—($C_{1-6}$ alkylene)-O—*, —O—($C_{1-6}$ alkylene)-O—($C_{1-6}$ alkylene)-O—($C_{1-6}$ alkylene)-*, —O—($C_{1-6}$ alkylene)-O—($C_{1-6}$ alkylene)-O—($C_{1-6}$ alkylene)-O—*, —N(H)—[—($C_{1-6}$ alkylene)-O—$]_{1-6}$—($C_{1-6}$ alkylene)-N($C_{1-4}$ alkyl)-($C_{1-6}$ alkylene)-O—*, —N(H)—($C_{1-10}$ alkylene)-O—*, —N(H)—($C_{1-6}$ alkylene)-O—($C_{1-6}$ alkylene)-O—*, —O—($C_{1-6}$ alkylene)-O—($C_{1-6}$ alkylene)-(4 membered monocyclic heterocyclyl containing 1 nitrogen atom, wherein the heterocyclyl is substituted with 0 or 1 occurrences of fluoro)-($C_{0-6}$ alkylene)-*, or —O—($C_{1-6}$ alkylene)-O—($C_{1-6}$ alkylene)-(4 membered monocyclic heterocyclyl containing 1 nitrogen atom)-N(H)—*, where * is a point of attachment to TPL. In certain embodiments, L is —O—($C_{1-6}$ alkylene)-O—($C_{1-6}$ alkylene)-O-(4-6 membered monocyclic heterocyclyl containing 1 nitrogen atom)-($C_{0-6}$ alkylene)-*, where * is a point of attachment to TPL. In certain embodiments, L is —O—($C_{1-6}$ alkylene)-O—($C_{1-6}$ alkylene)-O—*, where * is a point of attachment to TPL. In certain embodiments, L is —O—($C_{1-6}$ alkylene)-O—($C_{1-6}$ alkylene)-O—($C_{1-6}$ alkylene)-*, where * is a point of attachment to TPL. In certain embodiments, L is —O—($C_{1-6}$ alkylene)-O—($C_{1-6}$ alkylene)-O—($C_{1-6}$ alkylene)-O—*, where *is a point of attachment to TPL. In certain embodiments, L is —N(H)—[—($C_{1-6}$ alkylene)-O-]$_{1-6}$—($C_{1-6}$ alkylene)-N($C_{1-4}$ alkyl)-($C_{1-6}$ alkylene)-O—*, where * is a point of attachment to TPL. In certain embodiments, L is-N(H)—($C_{1-10}$ alkylene)-O—*, where * is a point of attachment to TPL. In certain embodiments, L is —N(H)—($C_{1-6}$ alkylene)-O—($C_{1-6}$ alkylene)-O—*, where * is a point of attachment to TPL. In certain embodiments, L is —O—($C_{1-6}$ alkylene)-O—($C_{1-6}$ alkylene)-(4 membered monocyclic heterocyclyl containing 1 nitrogen atom, wherein the heterocyclyl is substituted with 0 or 1 occurrences of fluoro)-($C_{0-6}$ alkylene)-*, where * is a point of attachment to TPL. In certain embodiments, L is —O—($C_{1-6}$ alkylene)-O—($C_{1-6}$ alkylene)-(4 membered monocyclic heterocyclyl containing 1 nitrogen atom)-N(H)—*, where * is a point of attachment to TPL.

In certain embodiments, L is —O—($C_{1-6}$ alkylene)-O—($C_{1-6}$ alkylene)-O—($C_{1-6}$ alkylene)-(4 membered monocyclic heterocyclyl containing 1 nitrogen atom)-N(H)—*, —($C_{1-10}$ alkylene)-N($C_{1-4}$ alkyl)-($C_{1-6}$ alkylene)-O—*, or —($C_{1-15}$ alkylene)-[—O—($C_{1-6}$ alkylene)-]$_{1-8}$-N($C_{1-4}$ alkyl)-($C_{1-6}$ alkylene)-O—*, where * is a point of attachment to TPL. In certain embodiments, L is —O—($C_{1-6}$ alkylene)-O—($C_{1-6}$ alkylene)-O—($C_{1-6}$ alkylene)-(4 membered monocyclic heterocyclyl containing 1 nitrogen atom)-N(H)—*, where * is a point of attachment to TPL. In certain embodiments, L is —($C_{1-10}$ alkylene)-N($C_{1-4}$ alkyl)-($C_{1-6}$ alkylene)-O—*, where * is a point of attachment to TPL. In certain embodiments, L is —($C_{1-15}$ alkylene)-[—O—($C_{1-6}$ alkylene)-]$_{1-8}$-N($C_{1-4}$ alkyl)-($C_{1-6}$ alkylene)-O—*, where * is a point of attachment to TPL.

In certain embodiments, L is.

(i) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-***

(ii) -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*, or (iii) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic ring containing 0, 1, or 2 nitrogen atoms, wherein the ring is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein *** is the point of attachment to TPL.

In certain embodiments, L is.

(i) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*, or (ii) -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*;

wherein *** is the point of attachment to TPL.

In certain embodiments, L is -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to TPL. In certain embodiments, L is -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to TPL. In certain embodiments, L is -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic ring containing 0, 1, or 2 nitrogen atoms, wherein the ring is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to TPL. In certain embodiments, L is -(azetidinylene)-$CH_2$-(piperazinylene or piperidinylene)-$CH_2$-(azetidinylene)-.

In certain embodiments, L is one of the following, where *** is a point of attachment to TPL:

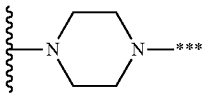

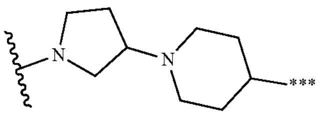

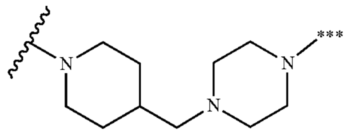

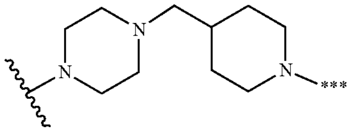

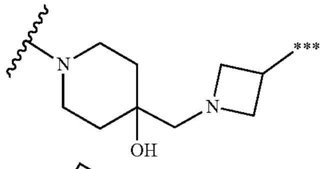

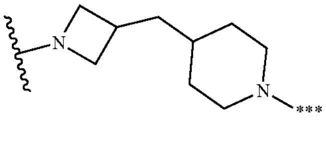

-continued
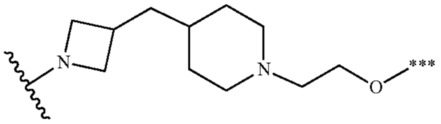
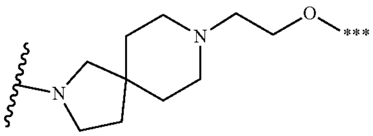
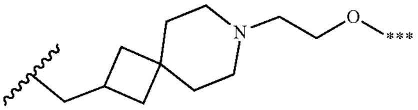
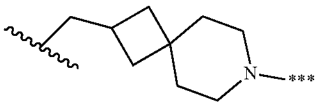
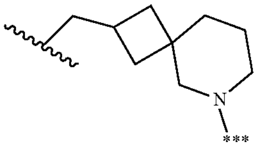
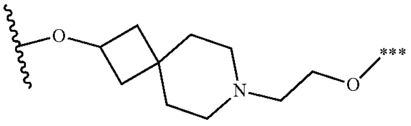
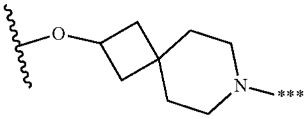
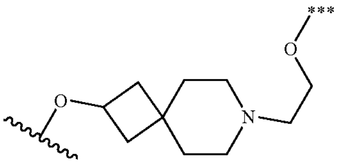
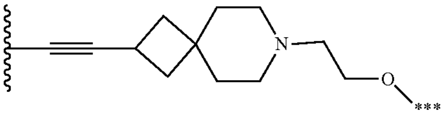
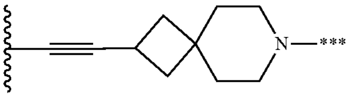
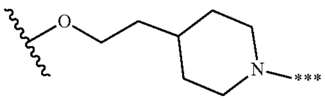
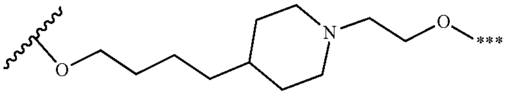
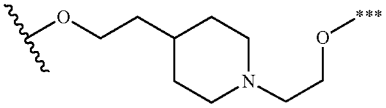
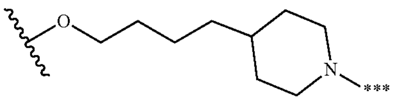
-continued
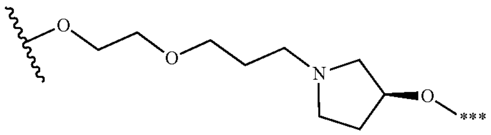
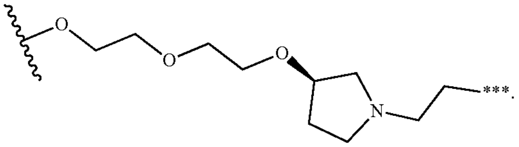
In certain embodiments, L is one of the following, where *** is a point of attachment to TPL:
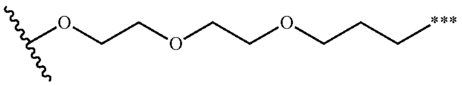
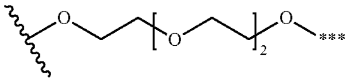
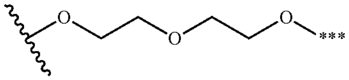
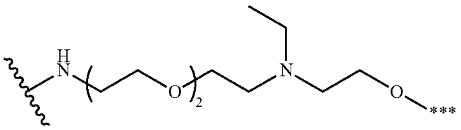
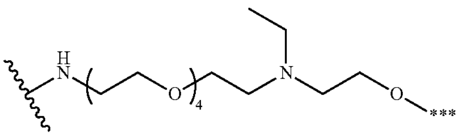
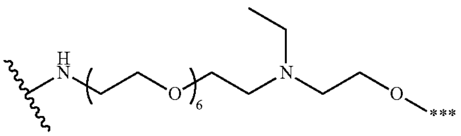
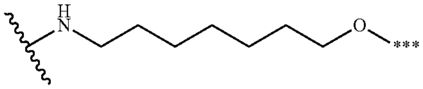
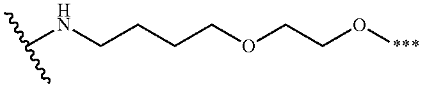
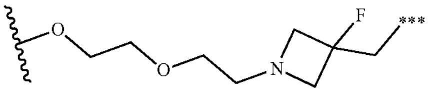
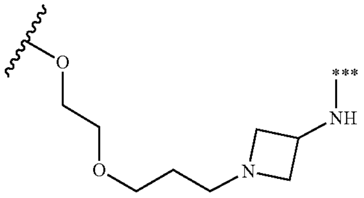
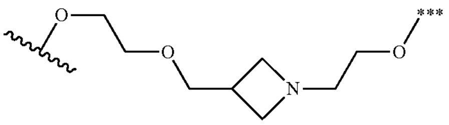

-continued

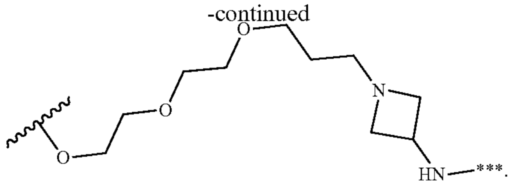

In certain embodiments, L is one of the following, where *** is a point of attachment to TPL:

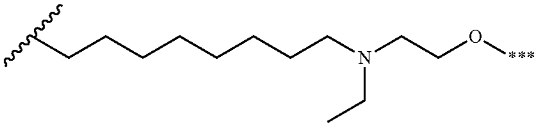

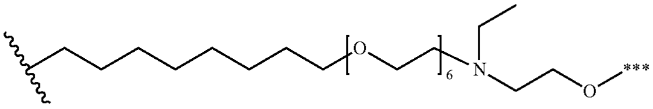

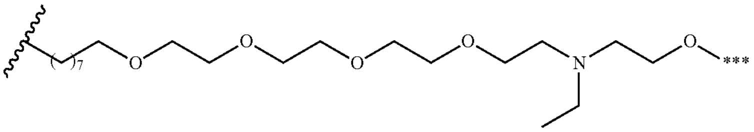

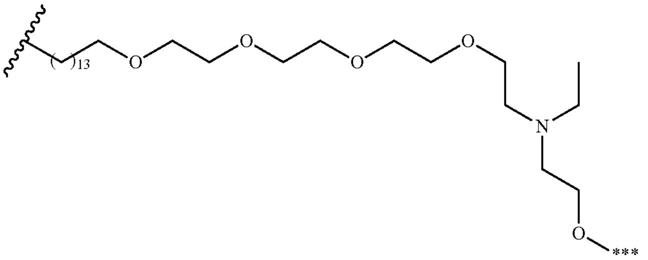

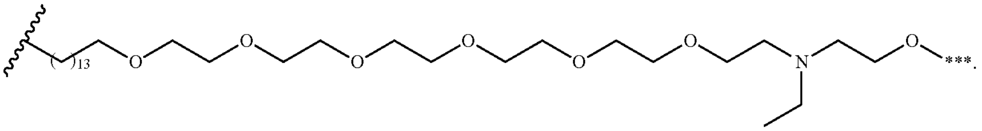

In certain embodiments, L is one of the following:

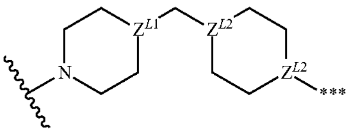

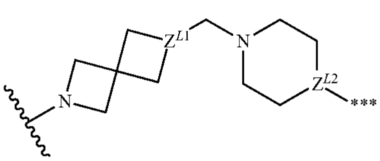

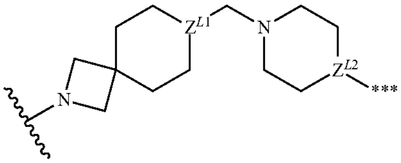

-continued

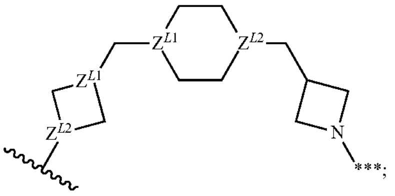

wherein: $Z^{L1}$ is C(OH), C(H), C(F), or N;

$Z^{L2}$ is independently for each occurrence N or C(H); and

** is the point of attachment to TPL.

In certain embodiments, L is one of the following:

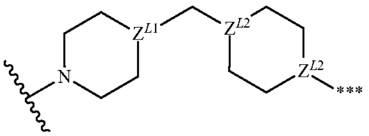

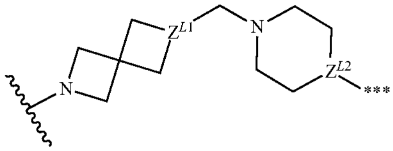

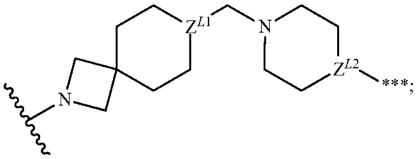

wherein: $Z^{L1}$ is C(OH), C(H), C(F), or N;

$Z^{L2}$ is independently for each occurrence N or C(H); and

** is the point of attachment to TPL.

In certain embodiments, L is

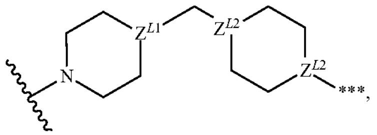

wherein *** is the point of attachment to TPL. In certain embodiments, L is

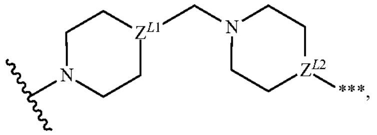

wherein *** is the point of attachment to TPL. In certain embodiments, L is

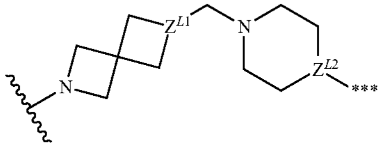

or

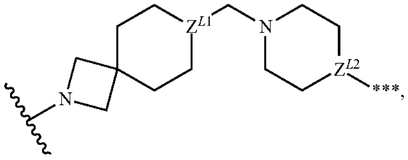

wherein *** is the point of attachment to TPL. In certain embodiments, L is

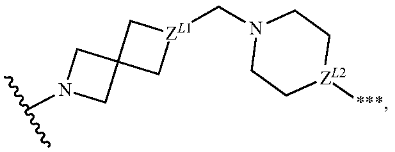

wherein *** is the point of attachment to TPL. In certain embodiments, L is

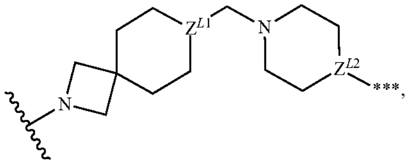

wherein *** is the point of attachment to TPL. In certain embodiments, L is

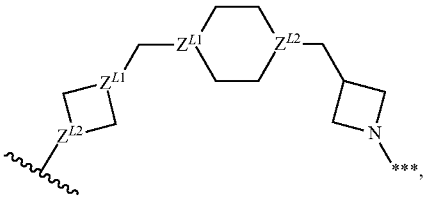

wherein *** is the point of attachment to TPL.

In certain embodiments, $Z^{L1}$ is C(OH) or C(H), and $Z^{L2}$ is N or C(H). In certain embodiments, $Z^{L1}$ is C(OH), and $Z^{L2}$ is N. In certain embodiments, $Z^{L1}$ is C(OH), C(H), or C(F). In certain embodiments, $Z^{L1}$ is C(OH) or C(H). In certain embodiments, $Z^{L1}$ is C(OH). In certain embodiments, $Z^{L1}$ is C(H). In certain embodiments, $Z^{L1}$ is C(F). In certain embodiments, $Z^{L1}$ is N. In certain embodiments, $Z^{L2}$ is independently for each occurrence N or C(H). In certain embodiments, $Z^{L2}$ is N or C(H). In certain embodiments, $Z^{L2}$ is N. In certain embodiments, $Z^{L2}$ is C(H).

In certain embodiments, L is one of the following, wherein *** is the point of attachment to TPL:

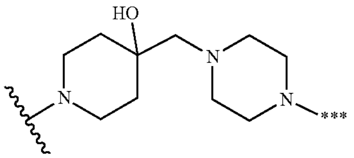

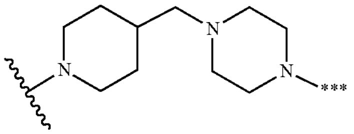

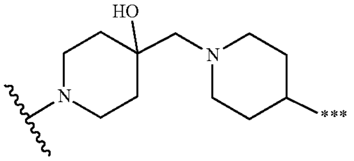

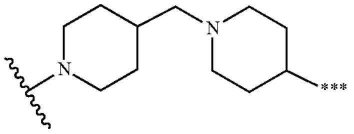

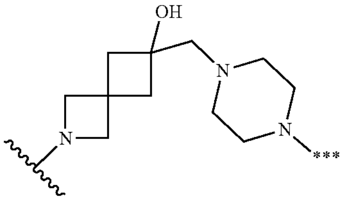

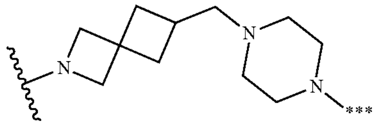

-continued
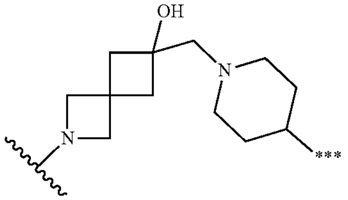
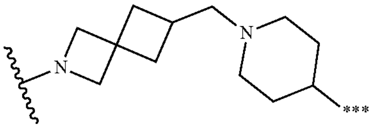
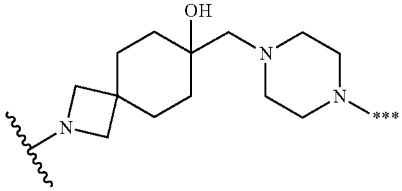
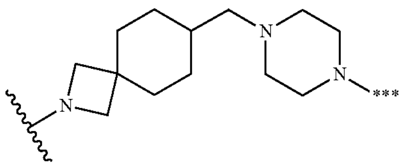
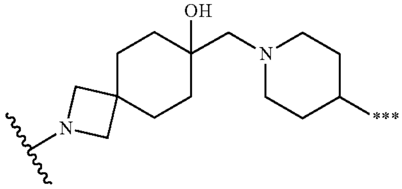
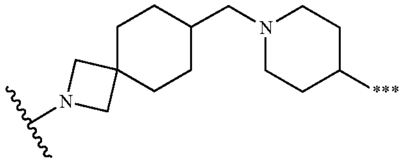
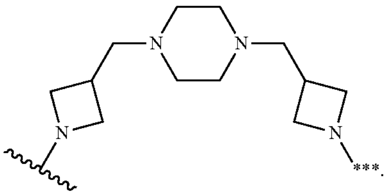.
In certain embodiments, L is
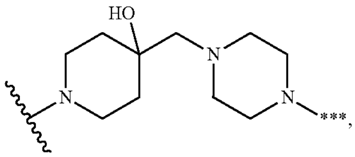,
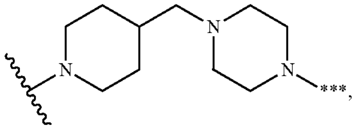,
-continued
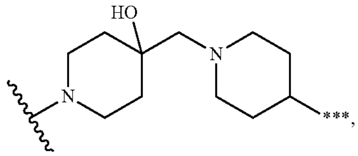, or
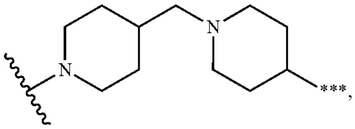,
wherein *** is the point of attachment to TPL. In certain embodiments, L is
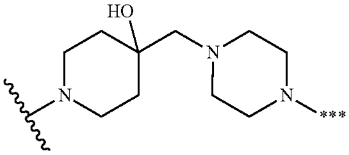
or
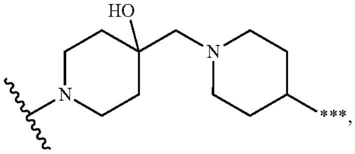,
wherein * is the point of attachment to TPL. In certain embodiments, L is one of the following, wherein * is the point of attachment to TPL:
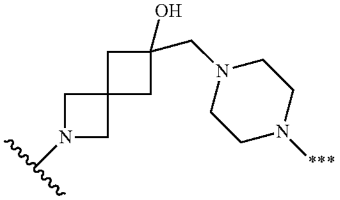
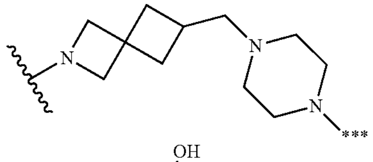
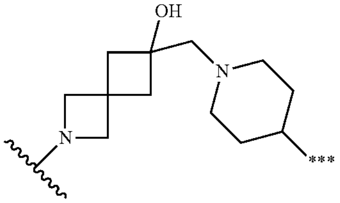
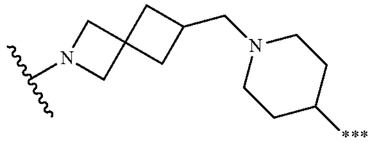

-continued

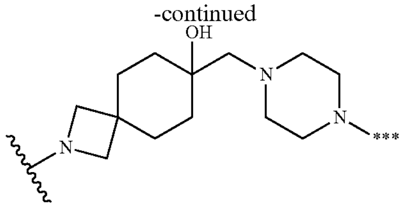

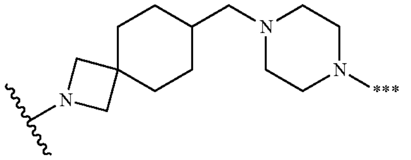

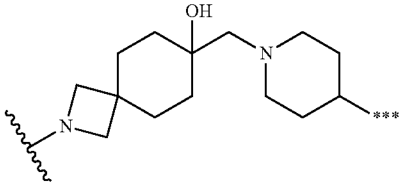

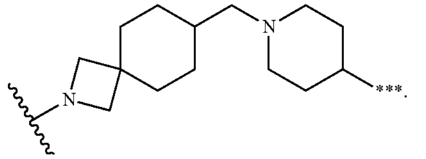

In certain embodiments, L is

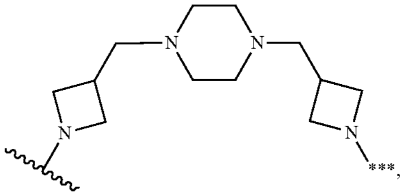

wherein *** is the point of attachment to TPL.

In certain embodiments, L is selected from those depicted in the compounds in Table 1, 3, 4, and 5, below. In certain embodiments, L is selected from those depicted in the compounds in Table 1, below. In certain embodiments, L is selected from those depicted in the compounds in Table 2, below. In certain embodiments, L is selected from those depicted in the compounds in Table 3, below. In certain embodiments, L is selected from those depicted in the compounds in Table 4, below. In certain embodiments, L is selected from those depicted in the compounds in Table 5, below.

Part E: Exemplary More Specific Embodiments

Embodiments described above may be combined to provide more specific embodiments defining compounds. All combinations and permutations are contemplated.

For example, in certain embodiments, the compound of Formula I is a compound of Formula I-A or I-B, or a pharmaceutically acceptable salt thereof. In certain embodiments, the compound is a compound of Formula I-A or I-B. In certain embodiments, the compound of each of Formula I-A and I-B is as defined and described in the following embodiments.

In certain embodiments, the compound of Formula I is represented by Formula I-A:

(I-A)

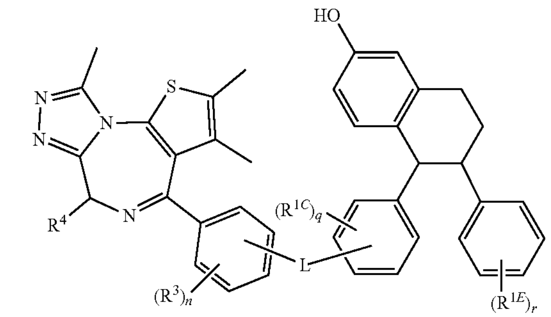

or a pharmaceutically acceptable salt thereof, wherein:

$R^3$, $R^{1C}$, and $R^{1E}$ are each independently for each occurrence hydrogen, fluoro, chloro, methoxy, or methyl;

$R^4$ is methyl, —$CH_2$-(oxazolyl), or —$CH_2$-(thiazolyl);

L is one of the following, wherein *** is the point of attachment to the phenyl ring bearing $R^{1C}$:

(i) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*, or (ii) -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; and n, q, and r are independently 0, 1, or 2.

In certain embodiments, the compound is a compound of Formula I-A.

In certain embodiments, $R^3$ represents independently for each occurrence hydrogen, fluoro, or chloro. In certain embodiments, $R^3$ represents independently for each occurrence hydrogen or fluoro. In certain embodiments, $R^3$ represents independently for each occurrence fluoro or chloro. In certain embodiments, $R^3$ is hydrogen. In certain embodiments, $R^3$ is fluoro. In certain embodiments, $R^3$ is chloro. In certain embodiments, $R^3$ is methyl. In certain embodiments, $R^3$ is methoxy.

In certain embodiments, $R^4$ is methyl. In certain embodiments, $R^4$ is —$CH_2$-(oxazolyl) or —$CH_2$-(thiazolyl). In certain embodiments, $R^4$ is —$CH_2$-(oxazol-2-yl) or —$CH_2$-(thiazol-2-yl). In certain embodiments, $R^4$ is —$CH_2$-(oxazolyl). In certain embodiments, $R^4$ is —$CH_2$-(oxazol-2-yl). In certain embodiments, $R^4$ is —$CH_2$-(thiazolyl). In certain embodiments, $R^4$ is —$CH_2$-(thiazol-2-yl).

In certain embodiments, L is -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to the phenyl ring bearing $R^{1C}$ In certain embodiments, L is -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to the phenyl ring bearing $R^{1C}$ In certain embodiments, L is one of the following:

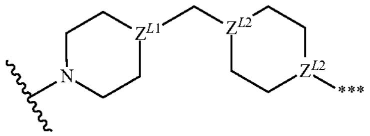

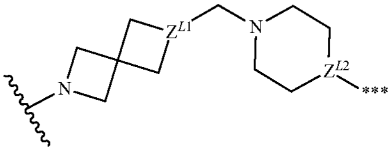

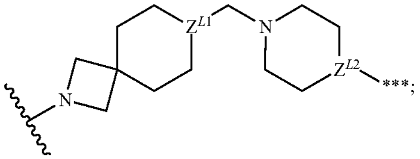

wherein: $Z^{L1}$ is C(OH), C(H), C(F), or N;

$Z^{L2}$ is independently for each occurrence N or C(H); and

** is the point of attachment to the phenyl ring bearing $R^{1C}$.

In certain embodiments, L is

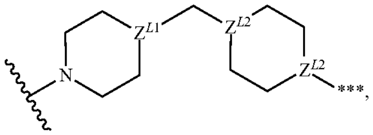

wherein *** is the point of attachment to the phenyl ring bearing $R^{1C}$. In certain embodiments, L is

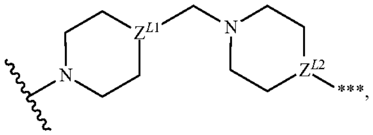

wherein *** is the point of attachment to the phenyl ring bearing $R^{1C}$. In certain embodiments, L is

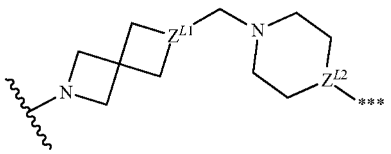

or

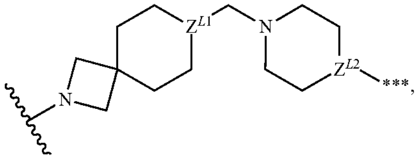

wherein *** is the point of attachment to the phenyl ring bearing $R^{1C}$. In certain embodiments, L is

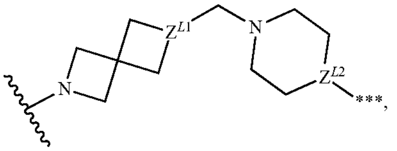

wherein *** is the point of attachment to the phenyl ring bearing $R^{1C}$. In certain embodiments, L is

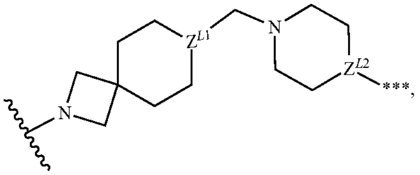

wherein *** is the point of attachment to the phenyl ring bearing $R^{1C}$.

In certain embodiments, $Z^{L1}$ is C(OH) or C(H), and $Z^{L2}$ is N or C(H). In certain embodiments, $Z^{L1}$ is C(OH), and $Z^{L2}$ is N. In certain embodiments, $Z^{L1}$ is C(OH), C(H), or C(F). In certain embodiments, $Z^{L1}$ is C(OH) or C(H). In certain embodiments, $Z^{L1}$ is C(OH). In certain embodiments, $Z^{L1}$ is C(H). In certain embodiments, $Z^{L1}$ is C(F). In certain embodiments, $Z^{L1}$ is N. In certain embodiments, $Z^{L2}$ is independently for each occurrence N or C(H). In certain embodiments, $Z^{L2}$ is N or C(H). In certain embodiments, $Z^{L2}$ is N. In certain embodiments, $Z^{L2}$ is C(H).

In certain embodiments, L is one of the following, wherein *** is the point of attachment to the phenyl ring bearing $R^{1C}$:

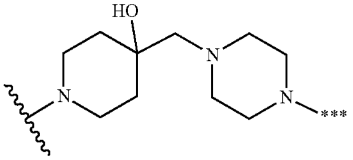

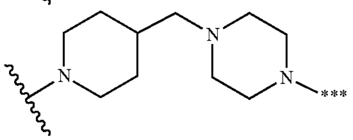

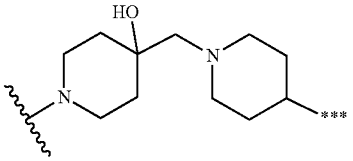

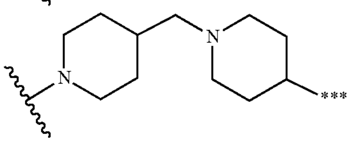

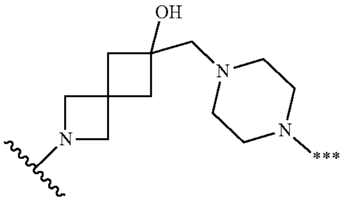

-continued
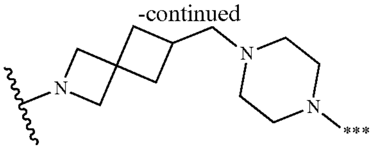
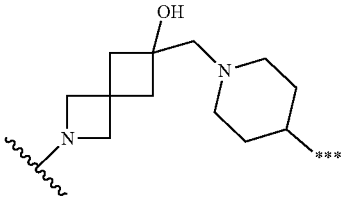
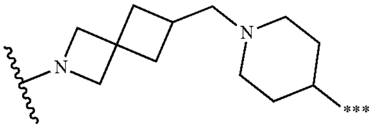
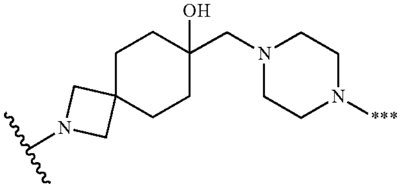
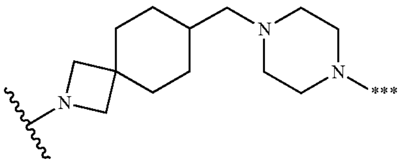
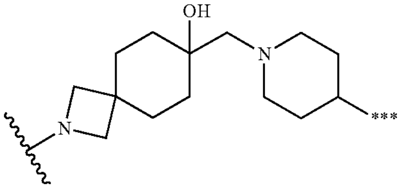
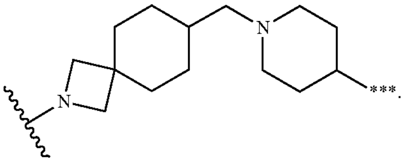
In certain embodiments, L is
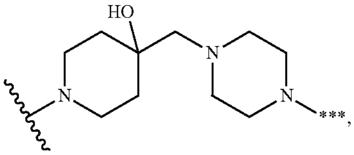
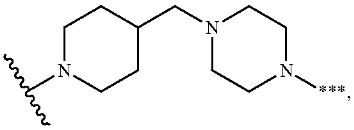
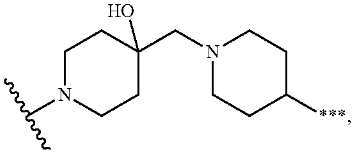
or
-continued
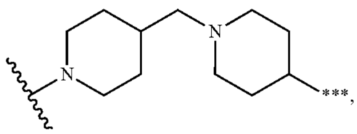
wherein *** is the point of attachment to the phenyl ring bearing $R^{1C}$. In certain embodiments, L is
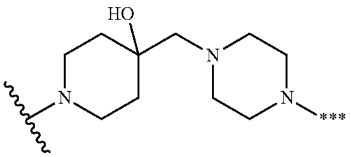
or
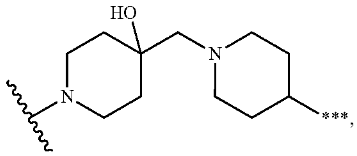
wherein * is the point of attachment to the phenyl ring bearing $R^{1C}$. In certain embodiments, L is one of the following, wherein * is the point of attachment to the phenyl ring bearing $R^{1C}$:
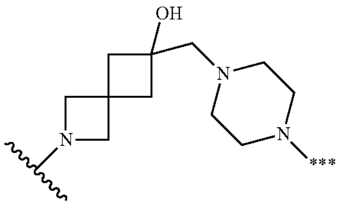
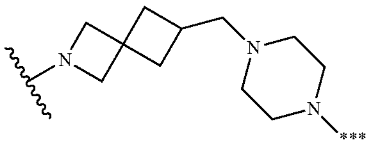
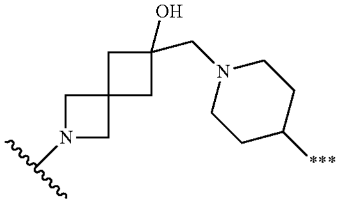
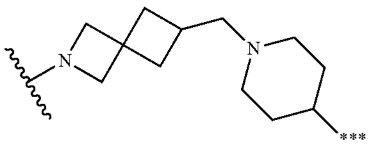
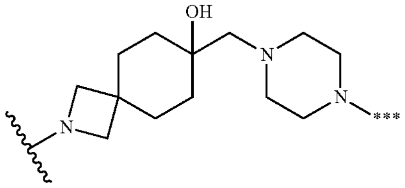

-continued

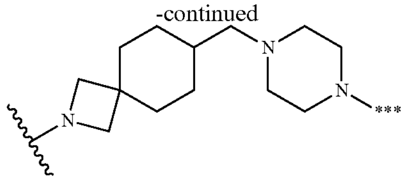

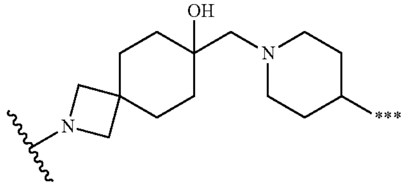

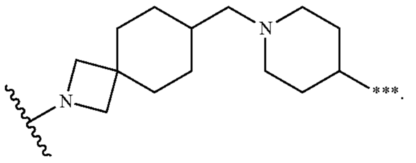

In certain embodiments, $R^{1C}$ and $R^{1E}$ are each independently for each occurrence fluoro, chloro, methoxy, or methyl. In certain embodiments, $R^{1C}$ and $R^{1E}$ are each independently for each occurrence hydrogen, fluoro, or methoxy. In certain embodiments, $R^{1C}$ and $R^{1E}$ are each independently for each occurrence hydrogen or fluoro. In certain embodiments, $R^{1C}$ and $R^{1E}$ are hydrogen. In certain embodiments, $R^{1C}$ and $R^{1E}$ are fluoro.

In certain embodiments, $R^{1C}$ is independently for each occurrence fluoro, chloro, methoxy, or methyl. In certain embodiments, $R^{1C}$ is independently for each occurrence hydrogen, fluoro, chloro, or methoxy. In certain embodiments, $R^{1C}$ is independently for each occurrence hydrogen, fluoro, or methoxy. In certain embodiments, $R^{1C}$ is independently for each occurrence hydrogen or fluoro. In certain embodiments, $R^{1C}$ is hydrogen or fluoro. In certain embodiments, $R^{1C}$ is independently for each occurrence hydrogen or methoxy. In certain embodiments, $R^{1C}$ is independently for each occurrence hydrogen or methyl. In certain embodiments, $R^{1C}$ is independently for each occurrence fluoro or methoxy. In certain embodiments, $R^{1C}$ is independently for each occurrence fluoro or methyl. In certain embodiments, $R^{1C}$ is hydrogen. In certain embodiments, $R^{1C}$ is fluoro. In certain embodiments, $R^{1C}$ is chloro. In certain embodiments, $R^{1C}$ is methyl. In certain embodiments, $R^{1C}$ is methoxy.

In certain embodiments, $R^{1E}$ is independently for each occurrence fluoro, chloro, methoxy, or methyl. In certain embodiments, $R^{1E}$ is independently for each occurrence hydrogen, fluoro, or methoxy. In certain embodiments, $R^{1E}$ is independently for each occurrence hydrogen or fluoro. In certain embodiments, $R^{1E}$ is hydrogen or fluoro. In certain embodiments, $R^{1C}$ is independently for each occurrence hydrogen or methyl. In certain embodiments, $R^{1C}$ is independently for each occurrence fluoro or methyl. In certain embodiments, $R^{1E}$ is hydrogen. In certain embodiments, $R^{1E}$ is fluoro. In certain embodiments, $R^{1E}$ is chloro. In certain embodiments, $R^{1E}$ is methyl. In certain embodiments, $R^{1C}$ is methoxy.

In certain embodiments, n is 0. In certain embodiments, n is 1. In certain embodiments, n is 2.

In certain embodiments, q and r are 0. In certain embodiments, q and r are independently 0 or 1. In certain embodiments, q and r are independently 1 or 2. In certain embodiments, q and r are independently 0, 1, or 2. In certain embodiments, q is 0. In certain embodiments, q is 1. In certain embodiments, q is 2. In certain embodiments, q is 3. In certain embodiments, q is 0 or 1. In certain embodiments, q is 1 or 2. In certain embodiments, q is 0, 1, or 2. In certain embodiments, r is 0. In certain embodiments, r is 1. In certain embodiments, r is 2. In certain embodiments, r is 3. In certain embodiments, r is 0 or 1. In certain embodiments, r is 1 or 2. In certain embodiments, r is 0, 1, or 2.

In certain embodiments:

$R^3$ represents independently for each occurrence hydrogen, fluoro, or chloro;

$R^4$ is methyl or —$CH_2$-(oxazolyl);

$R^{1C}$ and $R^{1E}$ are each independently for each occurrence hydrogen, fluoro, or methoxy; and L is one of the following, wherein *** is the point of attachment to the phenyl ring bearing $R^{1C}$.

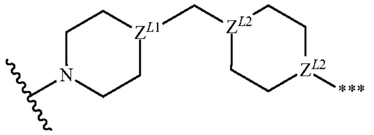

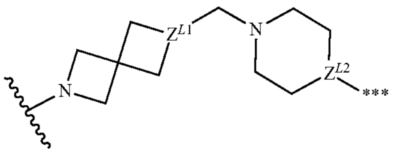

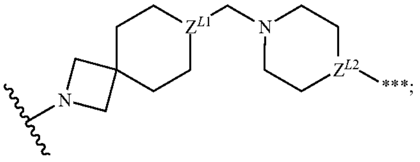

wherein: $Z^{L1}$ is C(OH), C(H), C(F), or N;

$Z^{L2}$ is independently for each occurrence N or C(H); and

** is the point of attachment to the phenyl ring bearing $R^{1C}$

In certain embodiments:

$R^3$ represents independently for each occurrence hydrogen or fluoro;

$R^4$ is methyl;

$R^{1C}$ and $R^{1E}$ are each independently for each occurrence hydrogen, fluoro, or methoxy; and L is

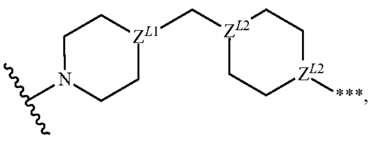

wherein *** is the point of attachment to the phenyl ring bearing $R^{1C}$, $Z^{L1}$ is C(OH), C(H), C(F), or N, and $Z^{L2}$ is independently for each occurrence N or C(H).

In certain embodiments, L is

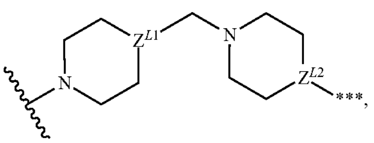

wherein *** is the point of attachment to the phenyl ring bearing $R^{1C}$, $Z^{L1}$ is C(OH), C(H), C(F), or N, and $Z^{L2}$ is N or C(H). In certain embodiments, L is

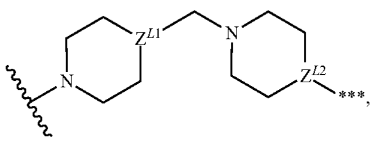

wherein *** is the point of attachment to the phenyl ring bearing $R^{1C}$, $Z^{L1}$ is C(OH) or C(H), and $Z^{L2}$ is N or C(H).

In certain embodiments, $R^4$ is methyl, and L is

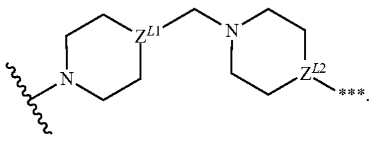

In certain embodiments, $R^3$ represents independently for each occurrence hydrogen, fluoro, or chloro, and $R^{1C}$ and $R^{1E}$ are each independently for each occurrence hydrogen, fluoro, or methoxy. In certain embodiments, $R^3$ represents independently for each occurrence hydrogen and fluoro, and $R^{1C}$ and $R^{1E}$ are each independently for each occurrence hydrogen, fluoro, or methoxy.

The description above describes multiple embodiments relating to compounds of Formula I-A. The patent application specifically contemplates all combinations of the embodiments.

In certain embodiments, the compound of Formula I or I-A is represented by Formula I-A-1 or I-A-2, or a pharmaceutically acceptable salt thereof.

(I-A-1)

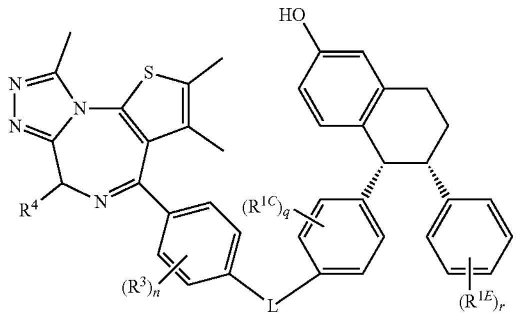

(I-A-2)

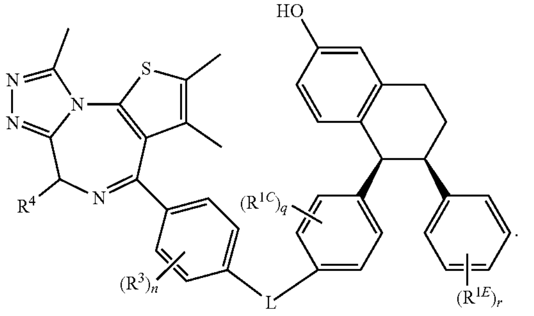

In certain embodiments, the compound is a compound of Formula I-A-1, or a pharmaceutically acceptable salt thereof. In certain embodiments, the compound is a compound of Formula I-A-2, or a pharmaceutically acceptable salt thereof. In certain embodiments, the compound is a compound of Formula I-A-1 or I-A-2. In certain embodiments, the compound is a compound of Formula I-A-1. In certain embodiments, the compound is a compound of Formula I-A-2.

In certain embodiments, each of variables $R^3$, $R^4$, L, $R^{1C}$, $R^{1E}$, n, q, and r in Formula I-A-1 and I-A-2 is as defined and described in embodiments above for compounds of Formula I-A, both singly and in combination. The description above describes multiple embodiments relating to compounds of Formula I-A-1 and I-A-2. The patent application specifically contemplates all combinations of the embodiments.

In certain embodiments, the compound of Formula I or I-A is represented by Formula I-A-3* or I-A-4*, or a pharmaceutically acceptable salt thereof:

(I-A-3*)

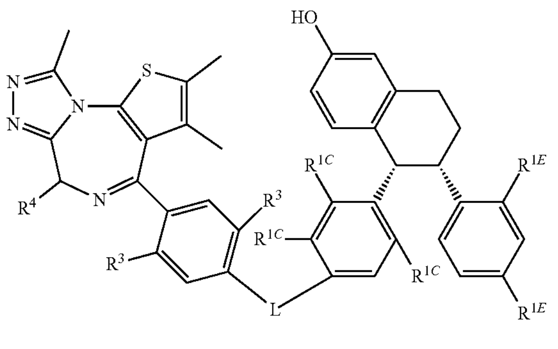

(I-A-4*)

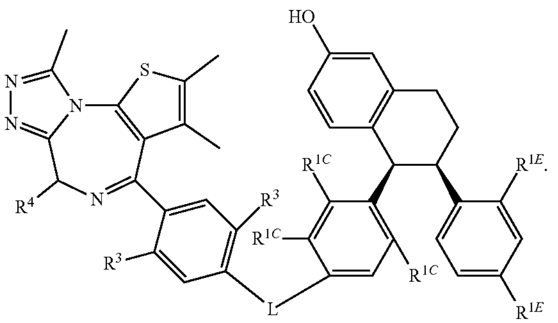

In certain embodiments, the compound is a compound of Formula I-A-3*, or a pharmaceutically acceptable salt thereof. In certain embodiments, the compound is a compound of Formula I-A-4*, or a pharmaceutically acceptable salt thereof. In certain embodiments, the compound is a compound of Formula I-A-3* or I-A-4*. In certain embodiments, the compound is a compound of Formula I-A-3*. In certain embodiments, the compound is a compound of Formula I-A-4*.

In certain embodiments, the compound of Formula I or I-A is represented by Formula I-A-3 or I-A-4, or a pharmaceutically acceptable salt thereof:

(I-A-3)

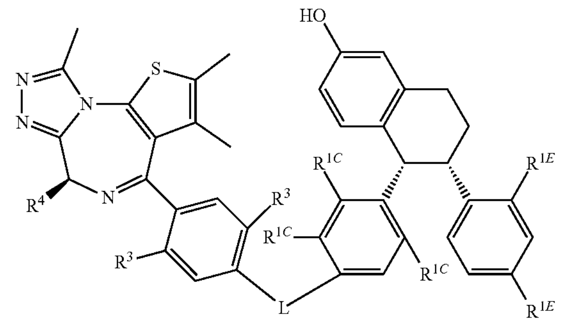

(I-A-4)

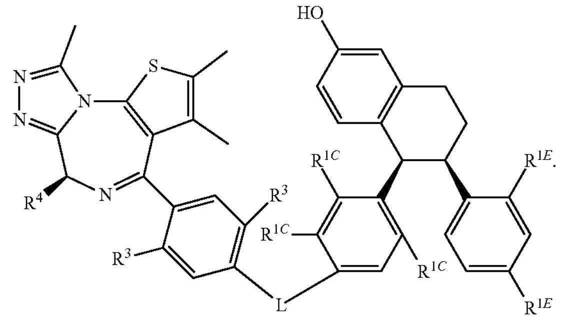

In certain embodiments, the compound is a compound of Formula I-A-3, or a pharmaceutically acceptable salt thereof:

(I-A-3)

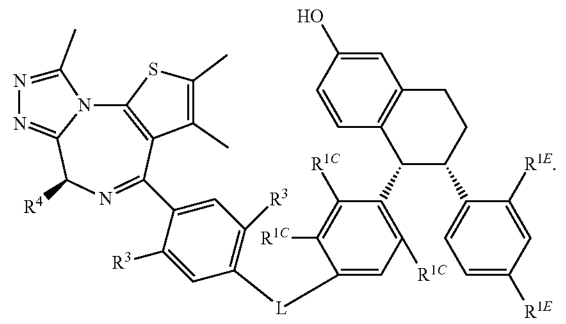

In certain embodiments, the compound is a compound of Formula I-A-4, or a pharmaceutically acceptable salt thereof:

(I-A-4)

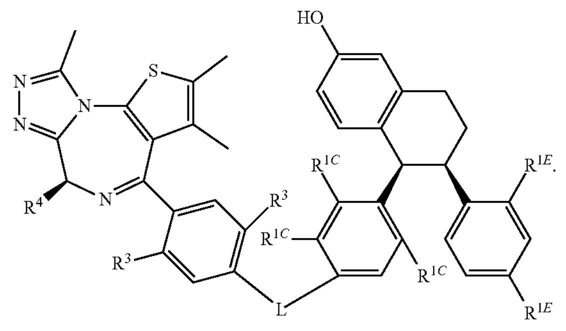

In certain embodiments, the compound is a compound of Formula I-A-3 or I-A-4. In certain embodiments, the compound is a compound of Formula I-A-3. In certain embodiments, the compound is a compound of Formula I-A-4.

In certain embodiments, the compound of Formula I or I-A is represented by Formula I-A-3 or I-A-4, or a pharmaceutically acceptable salt thereof:

(I-A-3**)

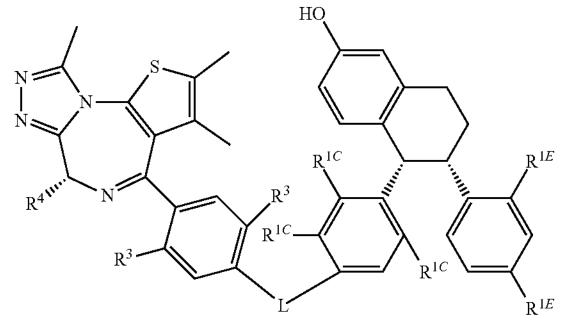

(I-A-4**)

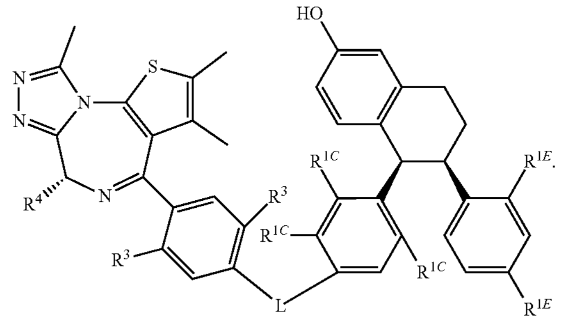

In certain embodiments, the compound is a compound of Formula I-A-3**, or a pharmaceutically acceptable salt thereof:

(I-A-3**)

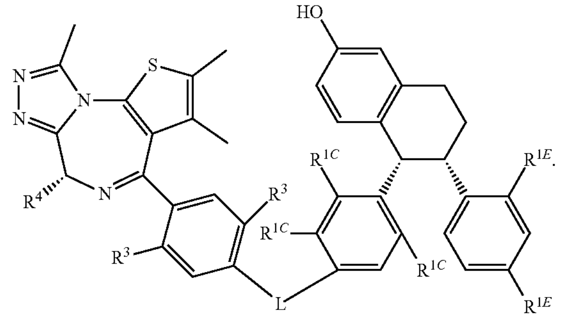

In certain embodiments, the compound is a compound of Formula I-A-4**, or a pharmaceutically acceptable salt thereof:

(I-A-4**)

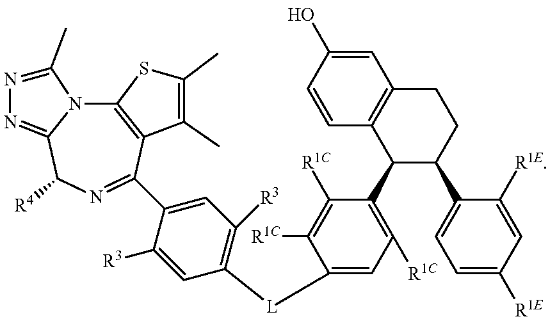

In certain embodiments, the compound is a compound of Formula I-A-3 or I-A-4. In certain embodiments, the compound is a compound of Formula I-A-3. In certain embodiments, the compound is a compound of Formula I-A-4.

In certain embodiments, each of variables $R^3$, $R^4$, L, $R^{1C}$, and $R^{1E}$ in Formula I-A-3*, I-A-4*, I-A-3, I-A-4, I-A-3 and I-A-4 is as defined and described in embodiments above for compounds of Formula I-A, both singly and in combination. The description above describes multiple embodiments relating to compounds of Formula I-A-3*, I-A-4*, I-A-3, I-A-4, I-A-3 and I-A-4. The patent application specifically contemplates all combinations of the embodiments.

In certain embodiments, the compound of Formula I or I-A is represented by Formula I-A-5, or a pharmaceutically acceptable salt thereof.

(I-A-5)

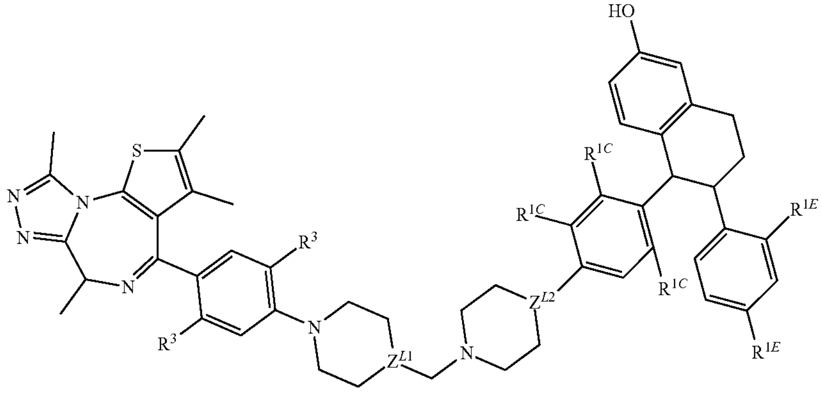

wherein $Z^{L1}$ is C(OH) or C(H), and $Z^{L2}$ is N or C(H).

In certain embodiments, the compound is a compound of Formula I-A-5. In certain embodiments, $Z^{L1}$ is C(OH). In certain embodiments, $Z^{L1}$ is C(H). In certain embodiments, $Z^{L2}$ is N. In certain embodiments, $Z^{L2}$ is C(H). In certain embodiments, $Z^{L1}$ is C(OH), and $Z^{L2}$ is N.

In certain embodiments, each of variables $R^3$, $R^{1C}$, and $R^{1E}$ in Formula I-A-5 is as defined and described in embodiments above for compounds of Formula I-A, both singly and in combination. The description above describes multiple embodiments relating to compounds of Formula I-A-5. The patent application specifically contemplates all combinations of the embodiments.

In certain embodiments, the compound of Formula I or I-A is represented by Formula I-A-6 or I-A-7, or a pharmaceutically acceptable salt thereof.

(I-A-6)

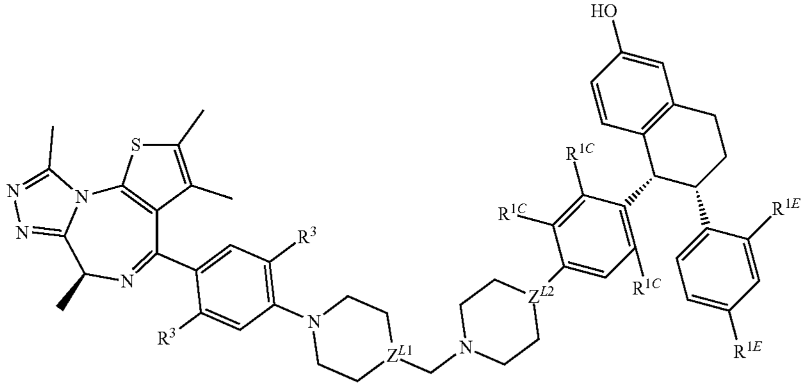

-continued (I-A-7)

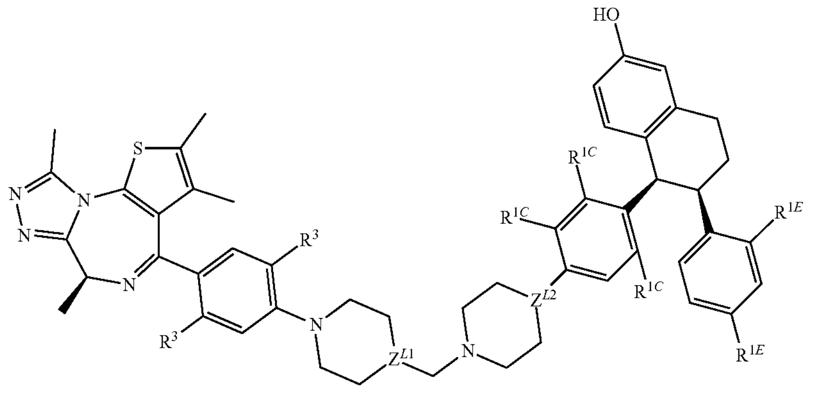

wherein $Z^{L1}$ is C(OH) or C(H), and $Z^{L2}$ is N or C(H).

In certain embodiments, the compound is a compound of Formula I-A-6, or a pharmaceutically acceptable salt thereof:

(I-A-6)

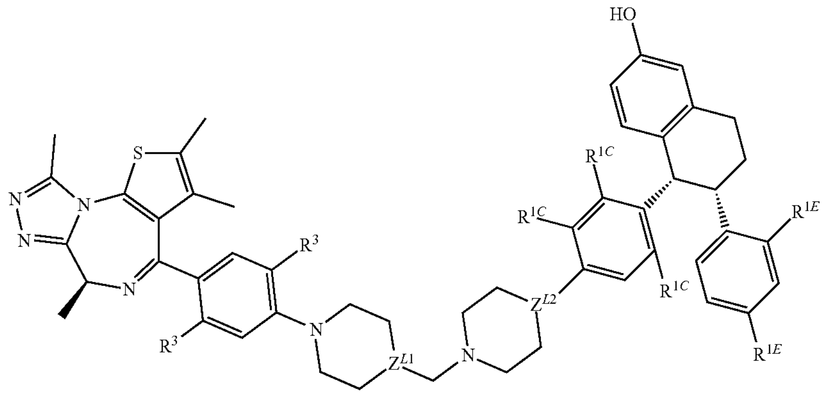

wherein $Z^{L1}$ is C(OH) or C(H), and $Z^{L2}$ is N or C(H).

In certain embodiments, the compound is a compound of Formula I-A-7, or a pharmaceutically acceptable salt thereof:

(I-A-7)

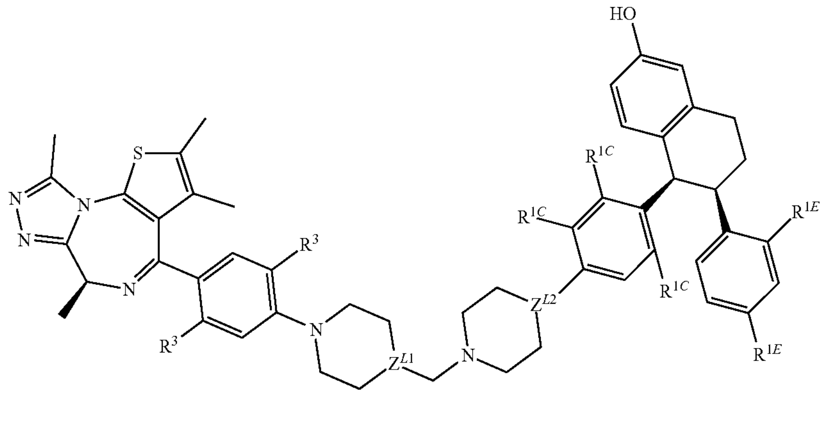

wherein $Z^{L1}$ is C(OH) or C(H), and $Z^{L2}$ is N or C(H).

In certain embodiments, the compound is a compound of Formula I-A-6 or I-A-7. In certain embodiments, the compound is a compound of Formula I-A-6. In certain embodiments, the compound is a compound of Formula I-A-7.

In certain embodiments, $Z^{L1}$ is C(OH). In certain embodiments, $Z^{L1}$ is C(H). In certain embodiments, $Z^{L2}$ is N. In certain embodiments, $Z^{L2}$ is C(H). In certain embodiments, $Z^{L1}$ is C(OH), and $Z^{L2}$ is N.

In certain embodiments, $R^3$ represents independently for each occurrence hydrogen, fluoro, or chloro, and $R^{1C}$ and $R^{1E}$ are each independently for each occurrence hydrogen, fluoro, or methoxy. In certain embodiments, $R^3$ represents independently for each occurrence hydrogen and fluoro, and $R^{1C}$ and $R^{1E}$ are each independently for each occurrence hydrogen, fluoro, or methoxy.

In certain embodiments, each of variables $R^3$, $R^{1C}$, and $R^{1E}$ in Formula I-A-6 and I-A-7 is as defined and described in embodiments above for compounds of Formula I-A, both singly and in combination. The description above describes multiple embodiments relating to compounds of Formula I-A-6 and I-A-7. The patent application specifically contemplates all combinations of the embodiments.

In certain embodiments, the compound of Formula I is represented by Formula I-B:

(I-B)

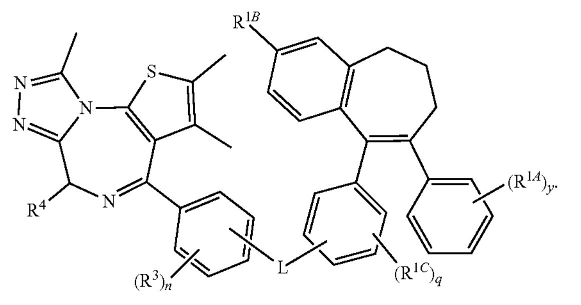

or a pharmaceutically acceptable salt thereof, wherein:

$R^3$ represents independently for each occurrence hydrogen, fluoro, chloro, methoxy, or methyl;

$R^4$ is methyl, —$CH_2$-(oxazolyl), or —$CH_2$-(thiazolyl);

n is 0, 1, or 2;

L is one of the following, wherein *** is the point of attachment to the phenyl ring bearing $R^{1C}$:

(i) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*, (ii) -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*, or (iii) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic ring containing 0, 1, or 2 nitrogen atoms, wherein the ring is substituted with 0 or 1 occurrence of hydroxyl or fluoro)-($C_{1-4}$ alkylene)-(4-6 membered saturated monocyclic heterocyclyl containing 1 or 2 nitrogen atoms)-***;

$R^{1A}$ and $R^{1C}$ each represents independently for each occurrence hydrogen, fluoro, chloro, methoxy, or methyl;

$R^{1B}$ is —C(O)OH, —OH, or —$B(OH)_2$;

q is 1 or 2; and y is 1, 2, or 3.

In certain embodiments, the compound is a compound of Formula I-B.

In certain embodiments, $R^3$ represents independently for each occurrence hydrogen, fluoro, or chloro. In certain embodiments, $R^3$ represents independently for each occurrence hydrogen or fluoro. In certain embodiments, $R^3$ represents independently for each occurrence fluoro or chloro. In certain embodiments, $R^3$ is hydrogen. In certain embodiments, $R^3$ is fluoro. In certain embodiments, $R^3$ is chloro. In certain embodiments, $R^3$ is methyl. In certain embodiments, $R^3$ is methoxy.

In certain embodiments, $R^4$ is methyl. In certain embodiments, $R^4$ is —$CH_2$-(oxazolyl) or —$CH_2$-(thiazolyl). In certain embodiments, $R^4$ is —$CH_2$-(oxazol-2-yl) or —$CH_2$-(thiazol-2-yl). In certain embodiments, $R^4$ is —$CH_2$-(oxazolyl). In certain embodiments, $R^4$ is —$CH_2$-(oxazol-2-yl). In certain embodiments, $R^4$ is —$CH_2$-(thiazolyl). In certain embodiments, $R^4$ is —$CH_2$-(thiazol-2-yl).

In certain embodiments, n is 0. In certain embodiments, n is 1. In certain embodiments, n is 2.

In certain embodiments, L is.

(i) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*, or (ii) -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*;

wherein *** is the point of attachment to the phenyl ring bearing $R^{1C}$

In certain embodiments, L is -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to the phenyl ring bearing $R^{1C}$ In certain embodiments, L is -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to the phenyl ring bearing $R^{1C}$. In certain embodiments, L is -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic ring containing 0, 1, or 2 nitrogen atoms, wherein the ring is substituted with 0 or 1 occurrence of hydroxyl or fluoro)-($C_{1-4}$ alkylene)-(4-6 membered saturated monocyclic heterocyclyl containing 1 or 2 nitrogen atoms)-*; wherein * is the point of attachment to the phenyl ring bearing $R^{1C}$. In certain embodiments, L is -(azetidinylene)-$CH_2$-(piperazinylene or piperidinylene)-$CH_2$-(azetidinylene)-.

In certain embodiments, L is one of the following:

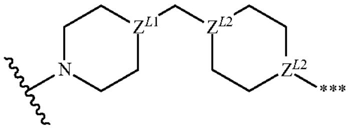

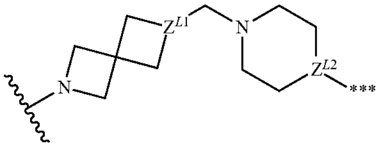

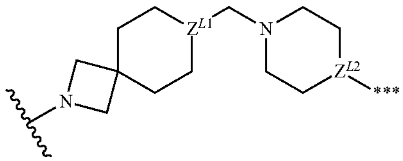

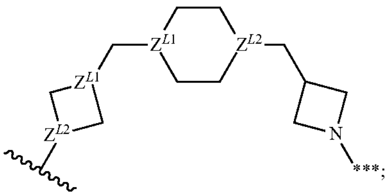

wherein: $Z^{L1}$ is C(OH), C(H), C(F), or N;

$Z^{L2}$ is independently for each occurrence N or C(H); and

** is the point of attachment to the phenyl ring bearing $R^{1C}$

In certain embodiments, L is one of the following:

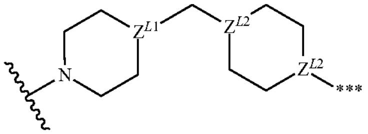

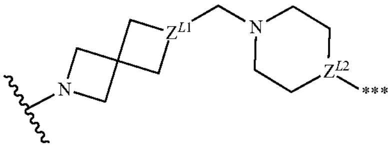

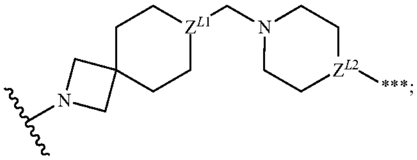

wherein: $Z^{L1}$ is C(OH), C(H), C(F), or N;

$Z^{L2}$ is independently for each occurrence N or C(H); and

** is the point of attachment to the phenyl ring bearing $R^{1C}$.

In certain embodiments, L is

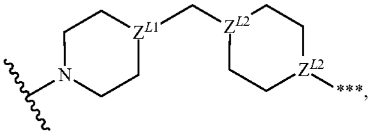

wherein *** is the point of attachment to the phenyl ring bearing $R^{1C}$. In certain embodiments, L is

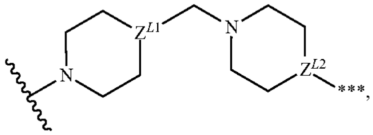

wherein *** is the point of attachment to the phenyl ring bearing $R^{1C}$. In certain embodiments, L is

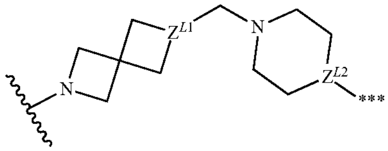

or

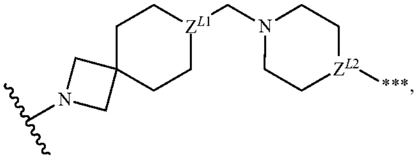

wherein *** is the point of attachment to the phenyl ring bearing $R^{1C}$. In certain embodiments, L is

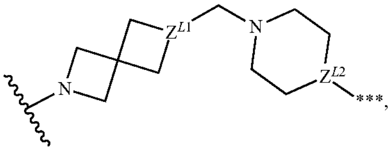

wherein *** is the point of attachment to the phenyl ring bearing $R^{1C}$. In certain embodiments, L is

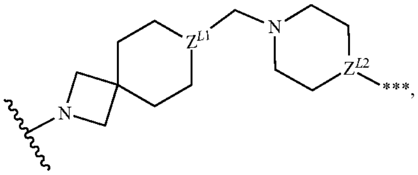

wherein *** is the point of attachment to the phenyl ring bearing $R^{1C}$. In certain embodiments, L is

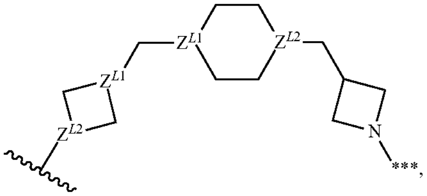

wherein *** is the point of attachment to the phenyl ring bearing $R^{1C}$.

In certain embodiments, $Z^{L1}$ is C(OH) or C(H), and $Z^{L2}$ is N or C(H). In certain embodiments, $Z^{L1}$ is C(OH), and $Z^{L2}$ is N. In certain embodiments, $Z^{L1}$ is C(OH), C(H), or C(F). In certain embodiments, $Z^{L1}$ is C(OH) or C(H). In certain embodiments, $Z^{L1}$ is C(OH). In certain embodiments, $Z^{L1}$ is C(H). In certain embodiments, $Z^{L1}$ is C(F). In certain embodiments, $Z^{L1}$ is N. In certain embodiments, $Z^{L2}$ is independently for each occurrence N or C(H). In certain embodiments, $Z^{L2}$ is N or C(H). In certain embodiments, $Z^{L2}$ is N. In certain embodiments, $Z^{L2}$ is C(H).

In certain embodiments, L is one of the following, wherein *** is the point of attachment to the phenyl ring bearing $R^{1C}$:

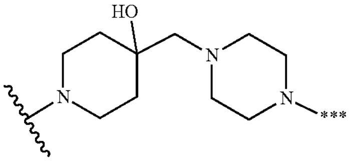

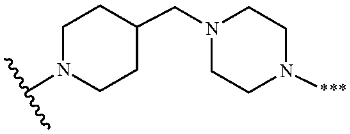

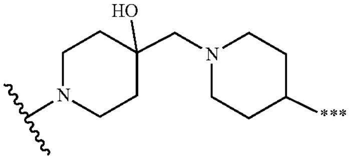

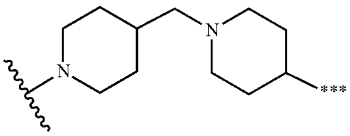

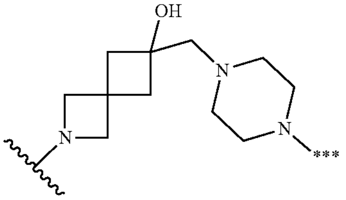

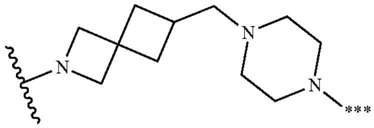

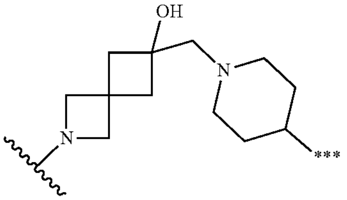

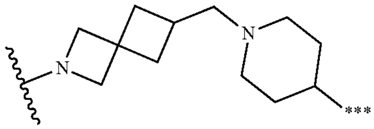

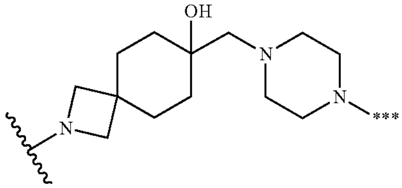

-continued

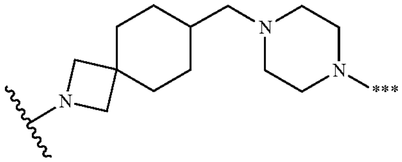

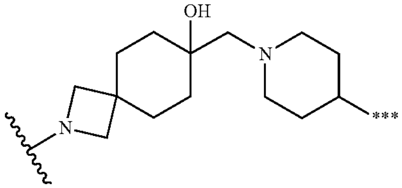

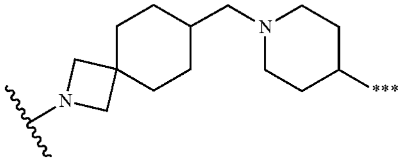

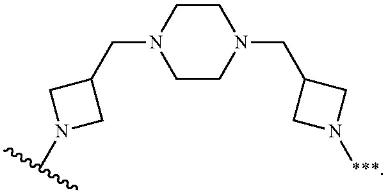

In certain embodiments, L is one of the following, wherein *** is the point of attachment to the phenyl ring bearing $R^{1C}$:

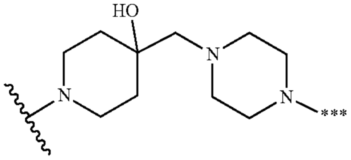

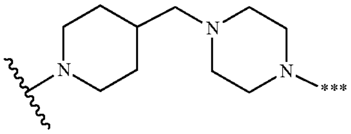

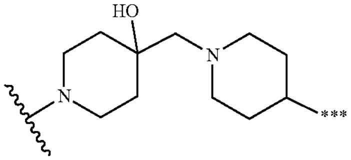

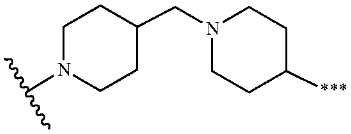

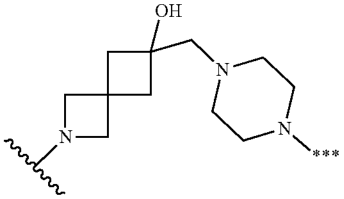

-continued
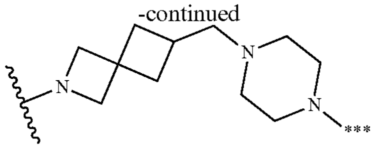
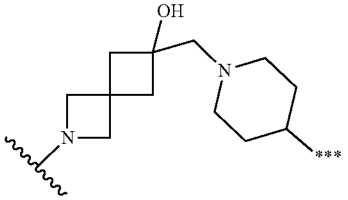
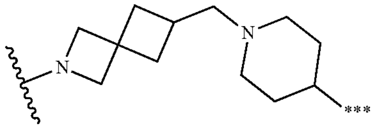
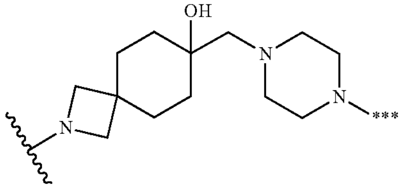
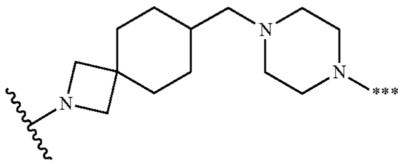
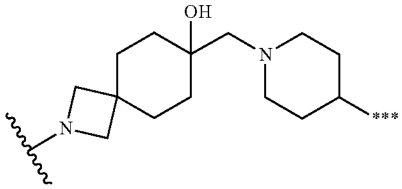
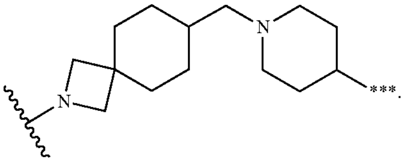
In certain embodiments, L is
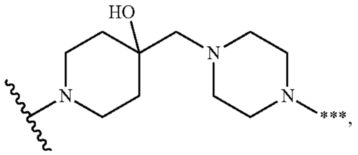
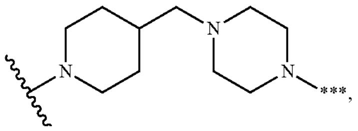
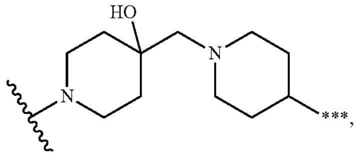
or
-continued
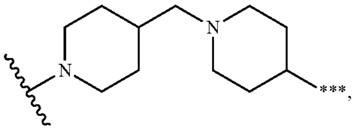
wherein *** is the point of attachment to the phenyl ring bearing $R^{1C}$. In certain embodiments, L is
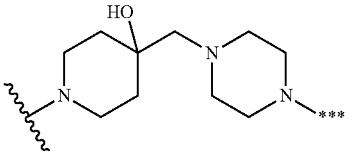
or
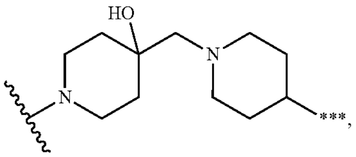
wherein * is the point of attachment to the phenyl ring bearing $R^{1C}$ In certain embodiments, L is one of the following, wherein * is the point of attachment to the phenyl ring bearing $R^{1C}$:
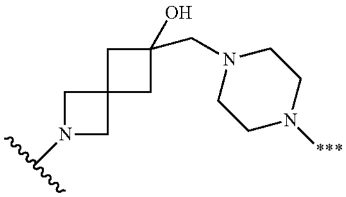
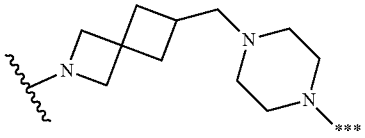
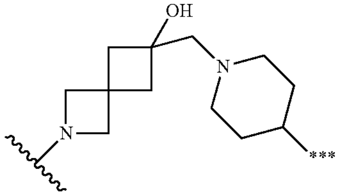
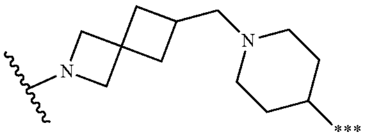
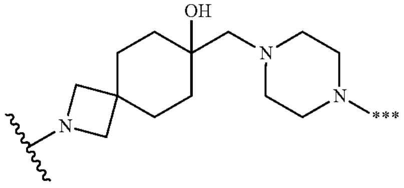

-continued

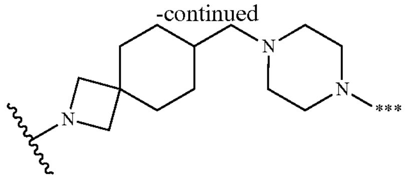

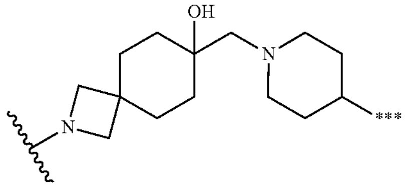

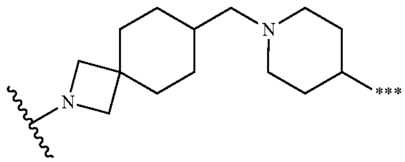

In certain embodiments, L is

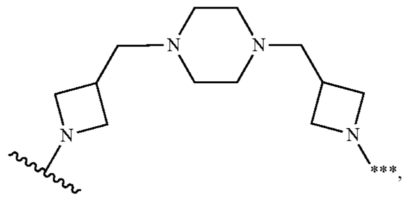

wherein *** is the point of attachment to the phenyl ring bearing $R^{1C}$.

In certain embodiments, $R^{1A}$ represents independently for each occurrence hydrogen, fluoro, or chloro, and $R^{1C}$ represents independently for each occurrence hydrogen, fluoro, or methoxy. In certain embodiments, $R^{1A}$ represents independently for each occurrence hydrogen, fluoro, or chloro. In certain embodiments, $R^{1A}$ is hydrogen, fluoro, or chloro. In certain embodiments, $R^{1A}$ is hydrogen or chloro. In certain embodiments, $R^{1A}$ is hydrogen. In certain embodiments, $R^{1A}$ is fluoro. In certain embodiments, $R^{1A}$ is chloro. In certain embodiments, $R^{1A}$ is methyl. In certain embodiments, $R^{1A}$ is methoxy.

In certain embodiments, $R^{1B}$ is —C(O)OH or —OH. In certain embodiments, RB is —C(O)OH. In certain embodiments, $R^{1B}$ is hydroxyl. In certain embodiments, $R^{1B}$ is —$B(OH)_2$. In certain embodiments, $R^{1C}$ represents independently for each occurrence hydrogen, fluoro, or methoxy. In certain embodiments, $R^{1C}$ is hydrogen or fluoro. In certain embodiments, $R^{1C}$ is fluoro or chloro. In certain embodiments, $R^{1C}$ is hydrogen. In certain embodiments, $R^{1C}$ is fluoro. In certain embodiments, $R^{1C}$ is chloro. In certain embodiments, $R^{1C}$ is methoxy. In certain embodiments, $R^{1C}$ is methyl.

In certain embodiments, q is 1. In certain embodiments, q is 2. In certain embodiments, y is 1. In certain embodiments, y is 2. In certain embodiments, y is 3.

The description above describes multiple embodiments relating to compounds of Formula I-B. The patent application specifically contemplates all combinations of the embodiments.

In certain embodiments, the compound of Formula I or Formula I-B is represented by Formula I-B-1, or a pharmaceutically acceptable salt thereof.

(I-B-1)

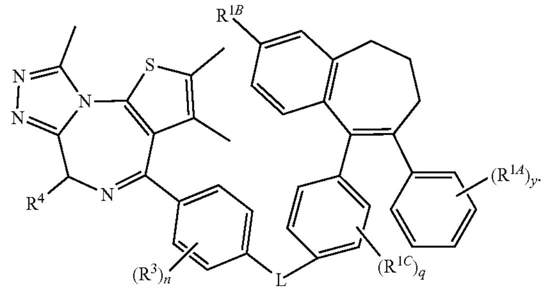

In certain embodiments, the compound is a compound of Formula I-B-1. In certain embodiments, each of variables $R^3$, $R^4$, L, $R^{1A}$, $R^{1B}$, $R^{1C}$, n, q, and y in Formula I-B-1 is as defined and described in embodiments above for compounds of Formula I-B, both singly and in combination. The description above describes multiple embodiments relating to compounds of Formula I-B-1. The patent application specifically contemplates all combinations of the embodiments.

In certain embodiments, the compound of Formula I or Formula I-B is represented by Formula I-B-2, or a pharmaceutically acceptable salt thereof.

(I-B-2)

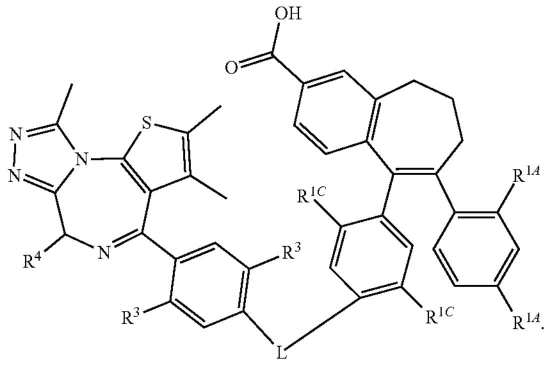

In certain embodiments, the compound of Formula I or Formula I-B is represented by Formula I-B-3, or a pharmaceutically acceptable salt thereof:

(I-B-3)

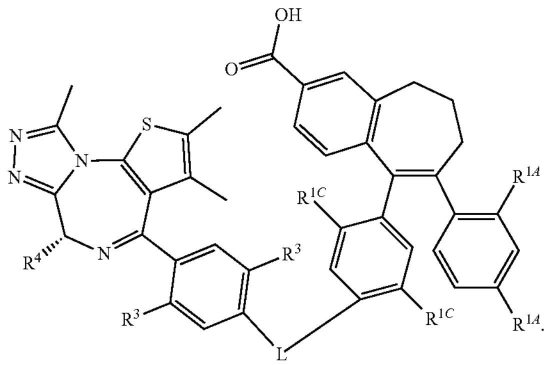

In certain embodiments, the compound of Formula I or Formula I-B is represented by Formula I-B-4, or a pharmaceutically acceptable salt thereof:

(I-B-4)

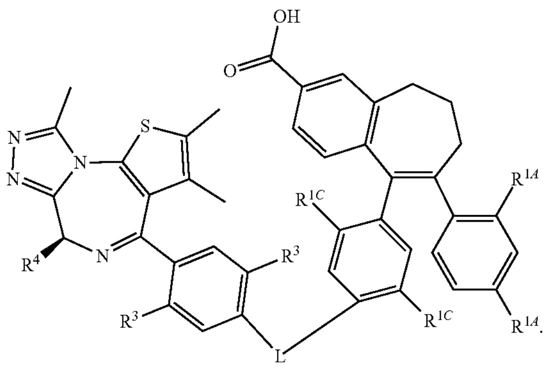

In certain embodiments, the compound is a compound of Formula I-B-2. In certain embodiments, the compound is a compound of Formula I-B-3. In certain embodiments, the compound is a compound of Formula I-B-4.

In certain embodiments, each of variables $R^3$, $R^4$, L, $R^{1A}$, and $R^{1C}$ in Formula I-B-2, I-B-3, and I-B-4 is as defined and described in embodiments above for compounds of Formula I-B, both singly and in combination. The description above describes multiple embodiments relating to compounds of Formula I-B-2, I-B-3, and I-B-4. The patent application specifically contemplates all combinations of the embodiments.

Another aspect of the invention provides a compound of Formula I-1:

(I-1)

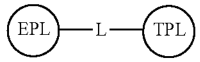

or a pharmaceutically acceptable salt thereof, wherein:

EPL has the following formula:

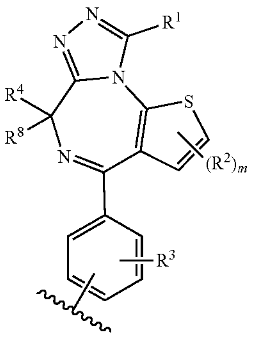

wherein:

$R^1$ is $C_{1-4}$ alkyl or $C_{3-4}$ cycloalkyl;

$R^2$ represents independently for each occurrence $C_{1-4}$ alkyl or $C_{3-4}$ cycloalkyl;

$R^3$ is hydrogen, halo, $C_{1-4}$ alkyl, $C_{1-4}$ haloalkyl, or $C_{1-4}$ alkoxyl;

$R^4$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^5$)($R^6$), —($C_{1-6}$ alkylene)-N($R^5$)C(O)$R^7$, —($C_{1-6}$ alkylene)-$CO_2R^7$, —($C_{1-6}$ alkylene)-OC(O)$R^7$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^4$ and $R^8$ taken together with the carbon atom to which they are attached form a $C_{3-5}$ saturated carbocyclic ring;

$R^5$ and $R^6$ are independently hydrogen, $C_{1-6}$ alkyl, or $C_{3-6}$ cycloalkyl; or $R^5$ and $R^6$ are taken together with the nitrogen atom to which they are attached to form a 3-7 membered ring containing 1 nitrogen atom;

$R^7$ is $C_{1-6}$ alkyl, —($C_{1-6}$ alkylene)-($C_{3-6}$ cycloalkyl), or $C_{3-6}$ cycloalkyl;

$R^8$ is hydrogen or $C_{1-4}$ alkyl; and m is 0, 1, or 2;

TPL is

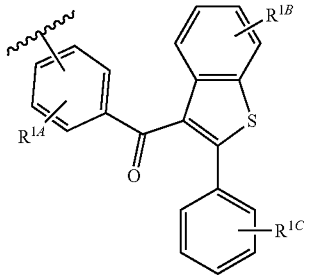

wherein:

$R^{1A}$ is hydrogen, halo, or $C_{1-4}$ alkyl; and $R^{1B}$ and $R^{1C}$ are independently hydroxyl, halo, $C_{1-4}$ alkyl, or $C_{1-4}$ alkoxyl; and L is one of the following:

(i) -(5-6 membered monocyclic heterocyclyl containing 1 or 2 nitrogen atoms)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-*, -(4-6 membered monocyclic heterocyclyl containing 1 nitrogen atom, wherein the heterocyclyl is substituted with 0 or 1 occurrences of hydroxyl)-($C_{0-6}$ alkylene)-(4-6 membered monocyclic heterocyclyl containing 1 nitrogen atom)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-($C_{0-6}$ alkylene)-O—*, —($C_{0-6}$ alkylene)-(7-11 membered spirocyclic heterocyclyl containing 1-2 nitrogen atoms)-($C_{0-6}$ alkylene)-O—*, —($C_{0-6}$ alkylene)-(7-11 membered spirocyclic heterocyclyl containing 1-2 heteroatoms selected from nitrogen)-*, —O-(7-11 membered spirocyclic heterocyclyl containing 1-2 nitrogen atoms)-($C_{0-6}$ alkylene)-O—*, —O-(7-11 membered spirocyclic heterocyclyl containing 1-2 nitrogen atoms)-*, —($C_{2-3}$ alkynylene)-(7-11 membered spirocyclic heterocyclyl containing 1-2 nitrogen atoms)-($C_{0-6}$ alkylene)-O—*, —($C_{2-3}$ alkynylene)-(7-11 membered spirocyclic heterocyclyl containing 1-2 nitrogen atoms)-*, —O—($C_{0-6}$ alkylene)-(5-6 membered monocyclic heterocyclyl containing 1 nitrogen atom)-*, —O—($C_{0-6}$ alkylene)-(5-6 membered monocyclic heterocyclyl containing 1 nitrogen atom)-($C_{1-6}$ alkylene)-O—*, or —O—($C_{1-6}$ alkylene)-O—($C_{1-6}$ alkylene)-(4-6 membered monocyclic heterocyclyl containing 1 nitrogen atom)-($C_{0-6}$ alkylene)-O—*, where * is a point of attachment to TPL;

(ii) —O—($C_{1-6}$ alkylene)-O—($C_{1-6}$ alkylene)-O-(4-6 membered monocyclic heterocyclyl containing 1 nitrogen atom)-($C_{0-6}$ alkylene)-*, —O—($C_{1-6}$ alkylene)-O—($C_{1-6}$ alkylene)-O—*, —O—($C_{1-6}$ alkylene)-O—($C_{1-6}$ alkylene)-O—($C_{1-6}$ alkylene)-*, —O—($C_{1-6}$ alkylene)-O—($C_{1-6}$ alkylene)-O—($C_{1-6}$ alkylene)-O—*, —N(H)—[—($C_{1-6}$ alkylene)-O-]$_{1-6}$—($C_{1-6}$ alkylene)-N($C_{1-4}$ alkyl)-($C_{1-6}$ alkylene)-O—*, —N(H)—($C_{1-10}$ alkylene)-O—*, —N(H)—($C_{1-6}$ alkylene)-O—($C_{1-6}$ alkylene)-O—*, —O—($C_{1-6}$ alkylene)-O—($C_{1-6}$ alkylene)-(4 membered monocyclic heterocyclyl containing 1 nitrogen atom, wherein the heterocyclyl is substituted with 0 or 1 occurrences of fluoro)-($C_{0-6}$ alkylene)-*, or —O—($C_{1-6}$ alkylene)-O—($C_{1-6}$ alkylene)-(4 membered monocyclic heterocyclyl containing 1 nitrogen atom)-N(H)—*, where * is a point of attachment to TPL; or (iii) —O—($C_{1-6}$ alkylene)-O—($C_{1-6}$ alkylene)-O—($C_{1-6}$ alkylene)-(4 membered monocyclic heterocyclyl containing 1 nitrogen atom)-N(H)—*, —($C_{1-10}$ alkylene)-N($C_{1-4}$ alkyl)-($C_{1-6}$ alkylene)-O—*, or —($C_{1-15}$ alkylene)-[—O—($C_{1-6}$ alkylene)-]$_{1-8}$-N($C_{1-4}$ alkyl)-($C_{1-6}$ alkylene)-O—*, where * is a point of attachment to TPL.

In certain embodiments, L is one of the following, where *** is a point of attachment to TPL:

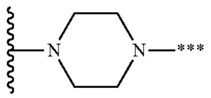
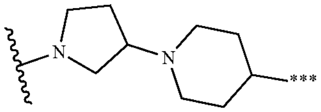
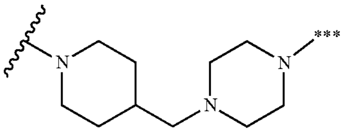
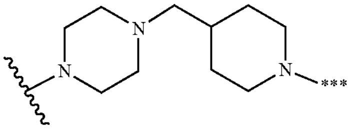
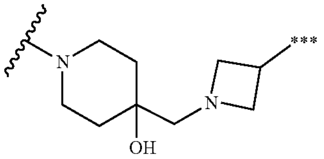
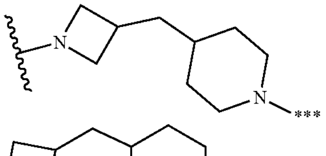
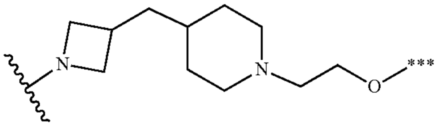

-continued

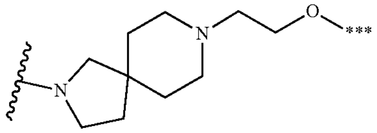
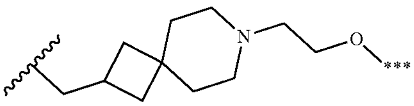
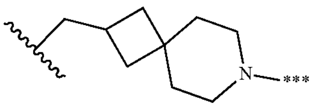
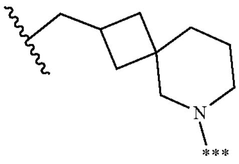
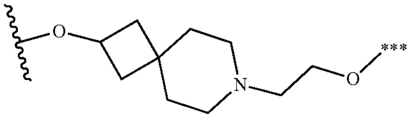
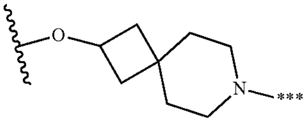
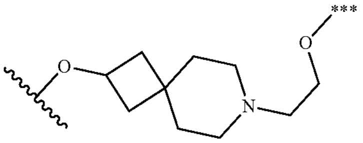
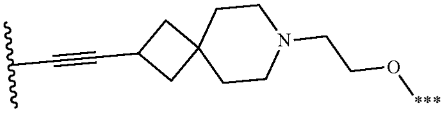
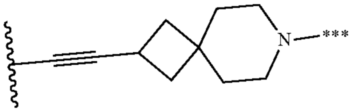
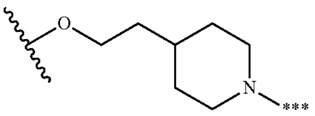
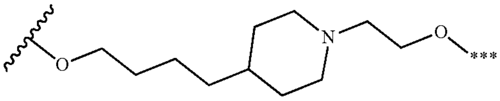
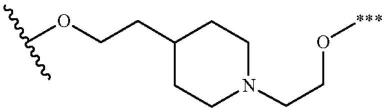
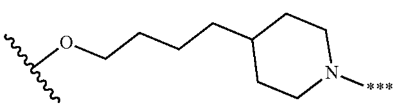
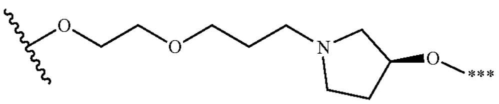

-continued
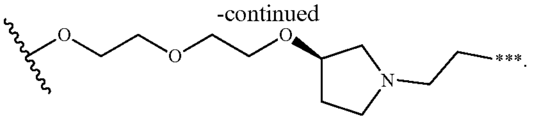
In certain embodiments, L is one of the following, where *** is a point of attachment to TPL:
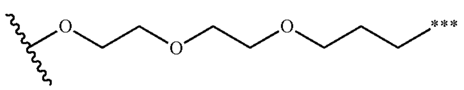
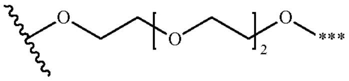
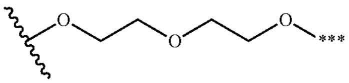
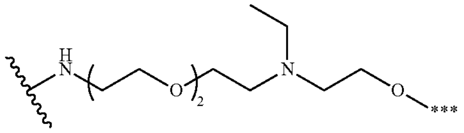
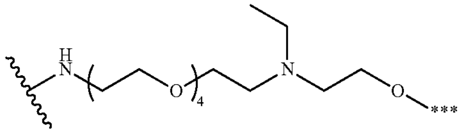
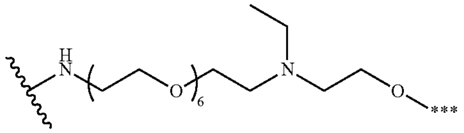
-continued
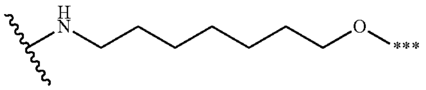
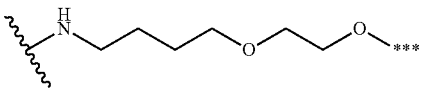
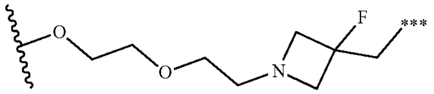
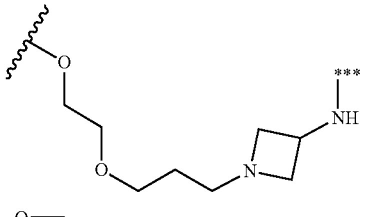
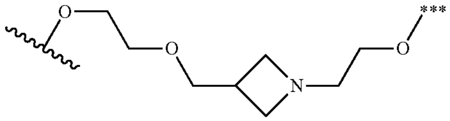
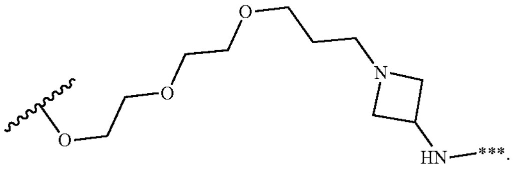
In certain embodiments, L is one of the following, where *** is a point of attachment to TPL:
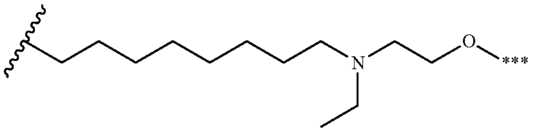
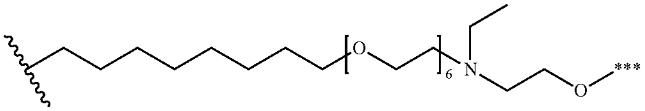
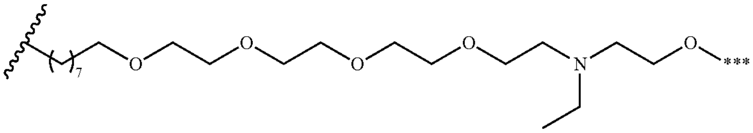
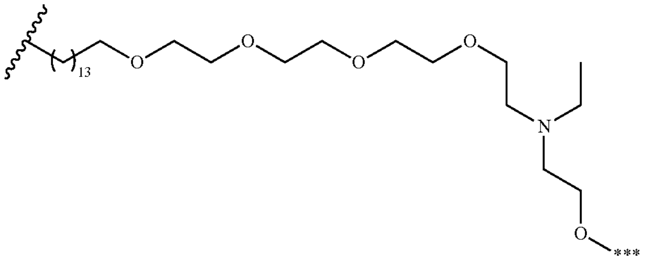

-continued

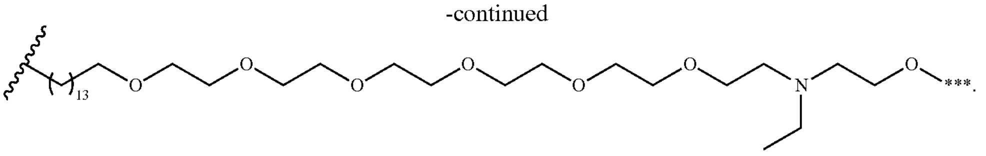

Another aspect of the invention provides a compound of Formula I-2:

(I-2)

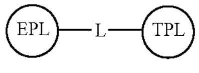

or a pharmaceutically acceptable salt thereof, wherein:

EPL has the following formula:

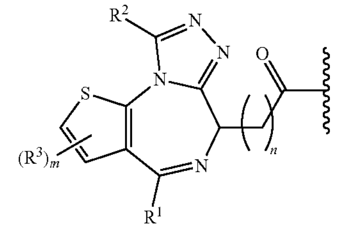

wherein:

$R^1$ is phenyl or 6-membered heteroaryl containing 1 or 2 heteroatoms independently selected from nitrogen, oxygen, and sulfur; wherein the phenyl and heteroaryl are optionally substituted with 1, 2, or 3 substituents independently selected from halo, $C_1$-$C_6$ alkyl, $C_1$-$C_6$ haloalkyl, hydroxyl, or $C_1$-$C_6$ alkoxy;

$R^2$ and $R^3$ each represent independently for each occurrence halo, $C_1$-$C_6$ alkyl, $C_1$-$C_6$ haloalkyl, $C_3$-$C_6$ cycloalkyl, hydroxyl, $C_1$-$C_6$ alkoxy, or cyano;

m is 0, 1, or 2; and n is 0, 1, 2, 3, or 4;

TPL is

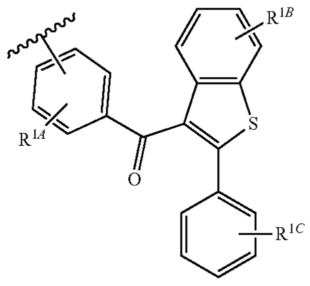

wherein:

$R^{1A}$ is hydrogen, halo, or $C_{1-4}$ alkyl; and $R^{1B}$ and $R^{1C}$ are independently hydroxyl, halo, $C_{1-4}$ alkyl, or $C_{1-4}$ alkoxyl; and L is one of the following:

(i) -(5-6 membered monocyclic heterocyclyl containing 1 or 2 nitrogen atoms)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-*, -(4-6 membered monocyclic heterocyclyl containing 1 nitrogen atom, wherein the heterocyclyl is substituted with 0 or 1 occurrences of hydroxyl)-($C_{0-6}$ alkylene)-(4-6 membered monocyclic heterocyclyl containing 1 nitrogen atom)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-($C_{0-6}$ alkylene)-O—*, —($C_{0-6}$ alkylene)-(7-11 membered spirocyclic heterocyclyl containing 1-2 nitrogen atoms)-($C_{0-6}$ alkylene)-O—*, —($C_{0-6}$ alkylene)-(7-11 membered spirocyclic heterocyclyl containing 1-2 heteroatoms selected from nitrogen)-*, —O-(7-11 membered spirocyclic heterocyclyl containing 1-2 nitrogen atoms)-($C_{0-6}$ alkylene)-O—*, —O-(7-11 membered spirocyclic heterocyclyl containing 1-2 nitrogen atoms)-*, —($C_{2-3}$ alkynylene)-(7-11 membered spirocyclic heterocyclyl containing 1-2 nitrogen atoms)-($C_{0-6}$ alkylene)-O—*, —($C_{2-3}$ alkynylene)-(7-11 membered spirocyclic heterocyclyl containing 1-2 nitrogen atoms)-*, —O—($C_{0-6}$ alkylene)-(5-6 membered monocyclic heterocyclyl containing 1 nitrogen atom)-*, —O—($C_{0-6}$ alkylene)-(5-6 membered monocyclic heterocyclyl containing 1 nitrogen atom)-($C_{1-6}$ alkylene)-O—*, or —O—($C_{1-6}$ alkylene)-O—($C_{1-6}$ alkylene)-(4-6 membered monocyclic heterocyclyl containing 1 nitrogen atom)-($C_{0-6}$ alkylene)-O—*, where * is a point of attachment to TPL;

(ii) —O—($C_{1-6}$ alkylene)-O—($C_{1-6}$ alkylene)-O-(4-6 membered monocyclic heterocyclyl containing 1 nitrogen atom)-($C_{0-6}$ alkylene)-*, —O—($C_{1-6}$ alkylene)-O—($C_{1-6}$ alkylene)-O—*, —O—($C_{1-6}$ alkylene)-O—($C_{1-6}$ alkylene)-O—($C_{1-6}$ alkylene)-*, —O—($C_{1-6}$ alkylene)-O—($C_{1-6}$ alkylene)-O—($C_{1-6}$ alkylene)-O—*, —N(H)—[—($C_{1-6}$ alkylene)-O-]$_{1-6}$—($C_{1-6}$ alkylene)-N($C_{1-4}$ alkyl)-($C_{1-6}$ alkylene)-O—*, —N(H)—($C_{1-10}$ alkylene)-O—*, —N(H)—($C_{1-6}$ alkylene)-O—($C_{1-6}$ alkylene)-O—*, —O—($C_{1-6}$ alkylene)-O—($C_{1-6}$ alkylene)-(4 membered monocyclic heterocyclyl containing 1 nitrogen atom, wherein the heterocyclyl is substituted with 0 or 1 occurrences of fluoro)-($C_{0-6}$ alkylene)-*, or —O—($C_{1-6}$ alkylene)-O—($C_{1-6}$ alkylene)-(4 membered monocyclic heterocyclyl containing 1 nitrogen atom)-N(H)—*, where * is a point of attachment to TPL; or (iii) —O—($C_{1-6}$ alkylene)-O—($C_{1-6}$ alkylene)-O—($C_{1-6}$ alkylene)-(4 membered monocyclic heterocyclyl containing 1 nitrogen atom)-N(H)—*, —($C_{1-10}$ alkylene)-N($C_{1-4}$ alkyl)-($C_{1-6}$ alkylene)-O—*, or —($C_{1-15}$ alkylene)-[—O—($C_{1-6}$ alkylene)-]$_{1-8}$-N($C_{1-4}$ alkyl)-($C_{1-6}$ alkylene)-O—*, where * is a point of attachment to TPL.

In certain embodiments, L is one of the following, where *** is a point of attachment to TPL:

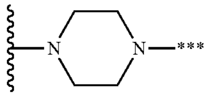
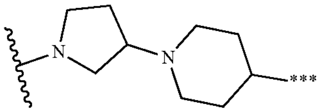
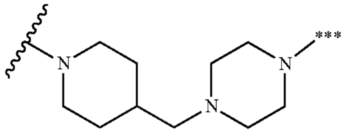
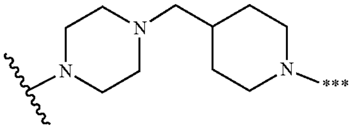
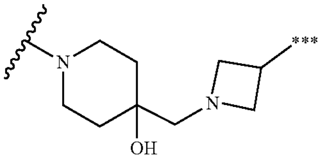
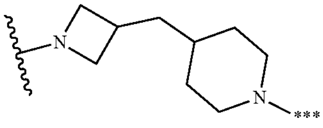
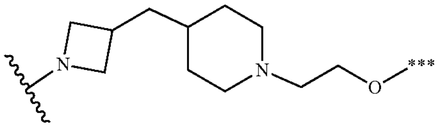
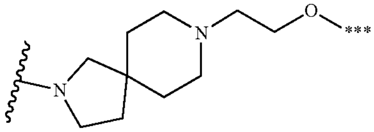
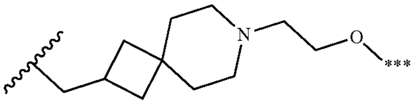
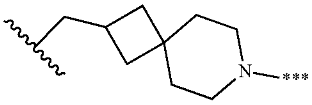
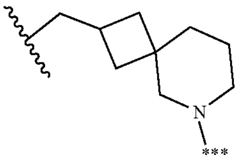
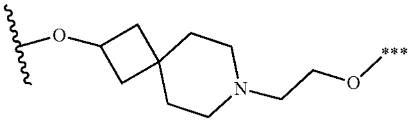
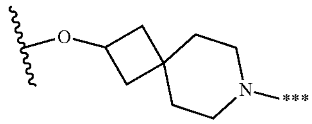
-continued
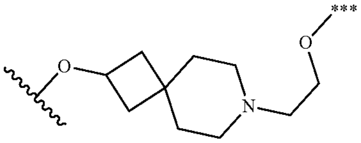
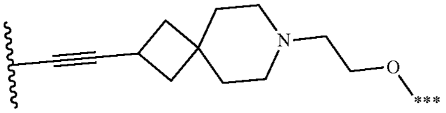
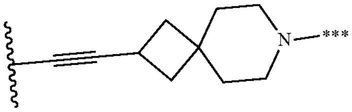
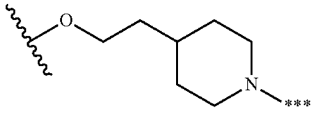
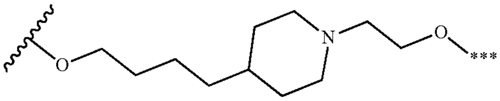
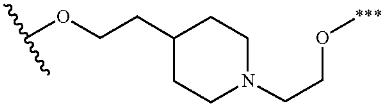
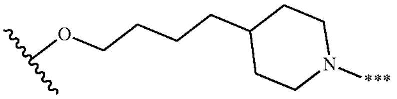
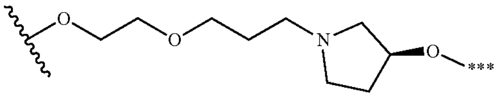
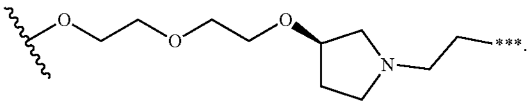
In certain embodiments, L is one of the following, where *** is a point of attachment to TPL:
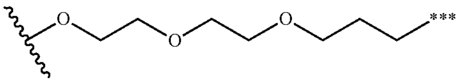
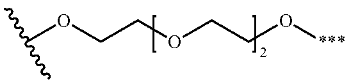
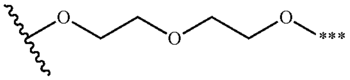
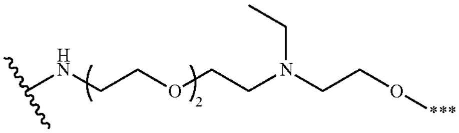
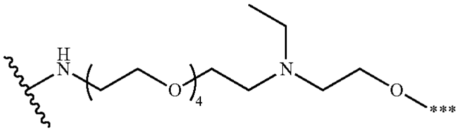

-continued
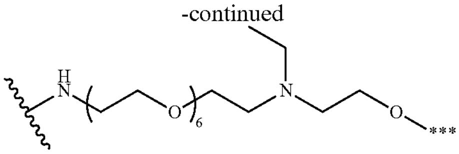
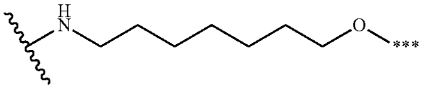
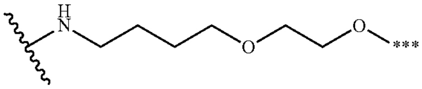
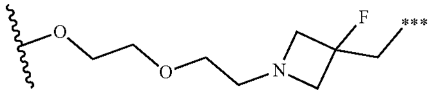
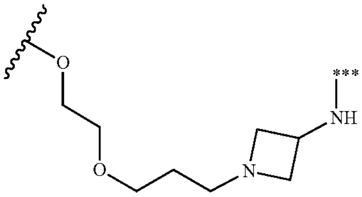
-continued
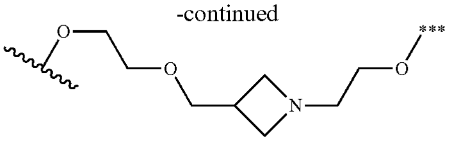
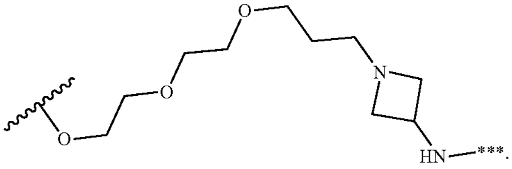
In certain embodiments, L is one of the following, where *** is a point of attachment to TPL:
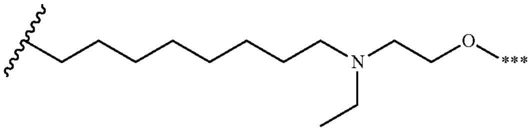
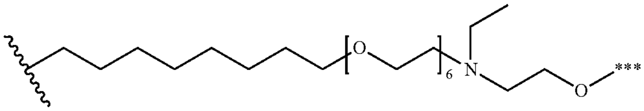
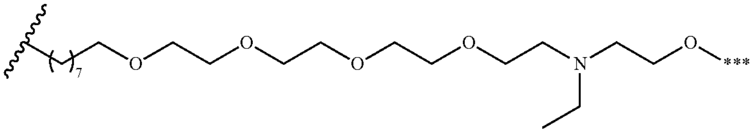
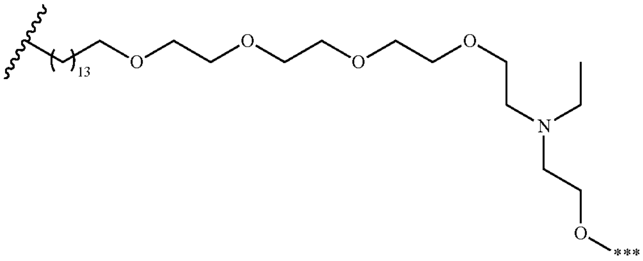
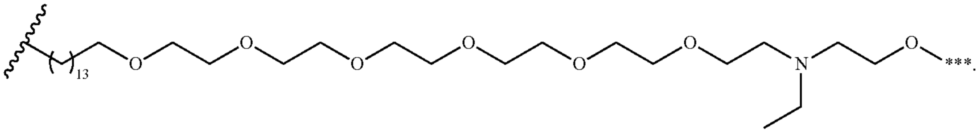

Another aspect of the invention provides a compound of Formula I-3:

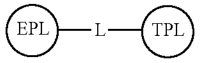

(I-3)

or a pharmaceutically acceptable salt thereof, wherein:

EPL has the following formula:

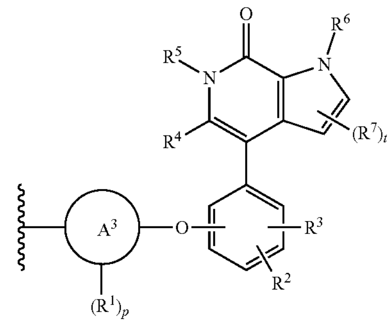

wherein:

$R^1$ represents independently for each occurrence halo, $C_{1-4}$ alkyl, or $C_{1-4}$ haloalkyl;

$R^2$ is hydrogen, halo, $C_{1-4}$ alkyl, or $C_{1-4}$ haloalkyl;

$R^3$ is —$N(R^8)SO_2R^9$, —$SO_2N(R^8)_2$, —$SO_2R^9$, —($C_{1-6}$ alkylene)-$SO_2R^9$, $C_{1-6}$ hydroxyalkyl, or a 4-7 membered saturated carbocyclic ring in which one $CH_2$ is replaced with $SO_2$;

$R^4$ is hydrogen, halo, or $C_{1-4}$ alkyl;

$R^5$ is $C_{1-4}$ alkyl or $C_{3-4}$ cycloalkyl;

$R^6$ is hydrogen, $C_{1-4}$ alkyl, or $C_{3-4}$ cycloalkyl;

$R^7$ represents independently for each occurrence $C_{1-4}$ alkyl or $C_{3-4}$ cycloalkyl;

$R^8$ represents independently for each occurrence hydrogen or $C_{1-4}$ alkyl; or two occurrences of $R^8$ are taken together with the nitrogen atom to which they are attached to form a 3-7 membered heterocyclic ring containing 1 or 2 heteroatoms independently selected from nitrogen and oxygen; or $R^8$ and $R^9$ are taken together with their intervening atoms to a form a 5-7 membered ring containing 1, 2, or 3 heteroatoms independently selected from nitrogen, oxygen, and sulfur;

$R^9$ is $C_{1-6}$ alkyl, $C_{1-6}$ haloalkyl, —($C_{1-6}$ alkylene)-($C_{3-6}$ cycloalkyl), or $C_{3-6}$ cycloalkyl;

$A^3$ is phenylene, a 3-10 membered saturated monocyclic, bicyclic or spirocyclic carbocyclylene, or $C_{1-6}$ alkylene; and p and t are independently 0, 1, or 2;

TPL is

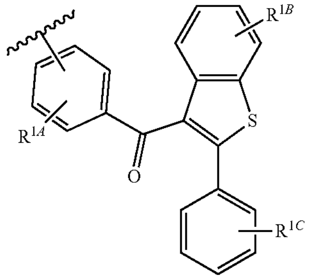

wherein:

$R^{1A}$ is hydrogen, halo, or $C_{1-4}$ alkyl; and $R^{1B}$ and $R^{1C}$ are independently hydroxyl, halo, $C_{1-4}$ alkyl, or $C_{1-4}$ alkoxyl; and L is one of the following:

(i) -(5-6 membered monocyclic heterocyclyl containing 1 or 2 nitrogen atoms)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-*, -(4-6 membered monocyclic heterocyclyl containing 1 nitrogen atom, wherein the heterocyclyl is substituted with 0 or 1 occurrences of hydroxyl)-($C_{0-6}$ alkylene)-(4-6 membered monocyclic heterocyclyl containing 1 nitrogen atom)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-($C_{0-6}$ alkylene)-O—*, —($C_{0-6}$ alkylene)-(7-11 membered spirocyclic heterocyclyl containing 1-2 nitrogen atoms)-($C_{0-6}$ alkylene)-O—*, —($C_{0-6}$ alkylene)-(7-11 membered spirocyclic heterocyclyl containing 1-2 heteroatoms selected from nitrogen)-*, —O-(7-11 membered spirocyclic heterocyclyl containing 1-2 nitrogen atoms)-($C_{0-6}$ alkylene)-O—*, —O-(7-11 membered spirocyclic heterocyclyl containing 1-2 nitrogen atoms)-*, —($C_{2-3}$ alkynylene)-(7-11 membered spirocyclic heterocyclyl containing 1-2 nitrogen atoms)-($C_{0-6}$ alkylene)-O—*, —($C_{2-3}$ alkynylene)-(7-11 membered spirocyclic heterocyclyl containing 1-2 nitrogen atoms)-*, —O—($C_{0-6}$ alkylene)-(5-6 membered monocyclic heterocyclyl containing 1 nitrogen atom)-*, —O—($C_{0-6}$ alkylene)-(5-6 membered monocyclic heterocyclyl containing 1 nitrogen atom)-($C_{1-6}$ alkylene)-O—*, or —O—($C_{1-6}$ alkylene)-O—($C_{1-6}$ alkylene)-(4-6 membered monocyclic heterocyclyl containing 1 nitrogen atom)-($C_{0-6}$ alkylene)-O—*, where * is a point of attachment to TPL;

(ii) —O—($C_{1-6}$ alkylene)-O—($C_{1-6}$ alkylene)-O-(4-6 membered monocyclic heterocyclyl containing 1 nitrogen atom)-($C_{0-6}$ alkylene)-*, —O—($C_{1-6}$ alkylene)-O—($C_{1-6}$ alkylene)-O—*, —O—($C_{1-6}$ alkylene)-O—($C_{1-6}$ alkylene)-O—($C_{1-6}$ alkylene)-*, —O—($C_{1-6}$ alkylene)-O—($C_{1-6}$ alkylene)-O—($C_{1-6}$ alkylene)-O—*, —N(H)—[—($C_{1-6}$ alkylene)-O-]$_{1-6}$—($C_{1-6}$ alkylene)-N($C_{1-4}$ alkyl)-($C_{1-6}$ alkylene)-O—*, —N(H)—($C_{1-10}$ alkylene)-O—*, —N(H)—($C_{1-6}$ alkylene)-O—($C_{1-6}$ alkylene)-O—*, —O—($C_{1-6}$ alkylene)-O—($C_{1-6}$ alkylene)-(4 membered monocyclic heterocyclyl containing 1 nitrogen atom, wherein the heterocyclyl is substituted with 0 or 1 occurrences of fluoro)-($C_{0-6}$ alkylene)-*, or —O—($C_{1-6}$ alkylene)-O—($C_{1-6}$ alkylene)-(4 membered monocyclic heterocyclyl containing 1 nitrogen atom)-N(H)—*, where * is a point of attachment to TPL; or (iii) —O—($C_{1-6}$ alkylene)-O—($C_{1-6}$ alkylene)-O—($C_{1-6}$ alkylene)-(4 membered monocyclic heterocyclyl containing 1 nitrogen atom)-N(H)—*, —($C_{1-10}$ alkylene)-N($C_{1-4}$ alkyl)-($C_{1-6}$ alkylene)-O—*, or —($C_{1-15}$ alkylene)-[—O—($C_{1-6}$ alkylene)-]$_{1-8}$—N($C_{1-4}$ alkyl)-($C_{1-6}$ alkylene)-O—*, where * is a point of attachment to TPL.

In certain embodiments, L is one of the following, where *** is a point of attachment to TPL:

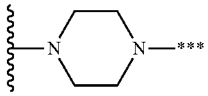

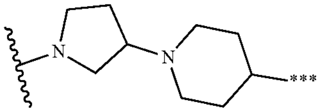

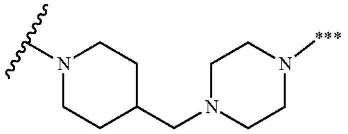

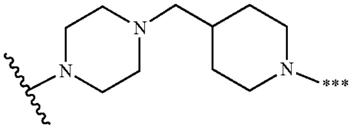

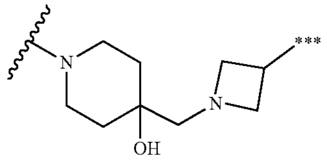

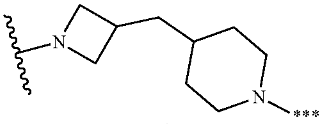

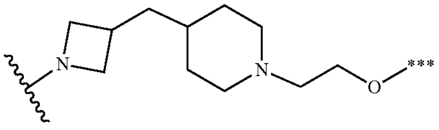

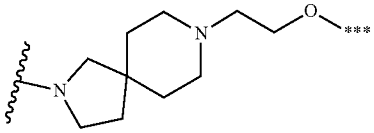

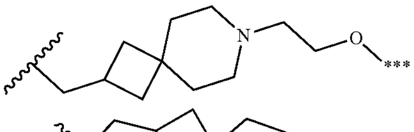

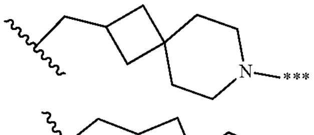

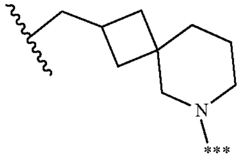

-continued

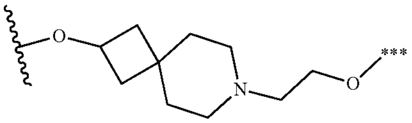

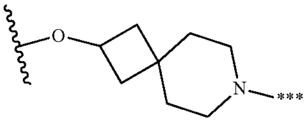

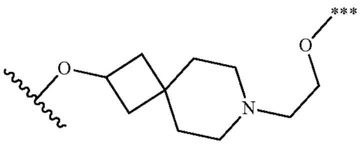

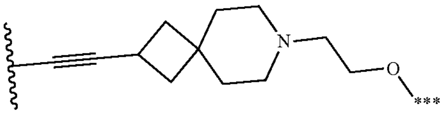

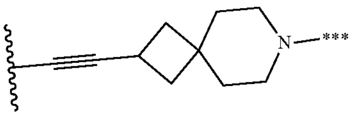

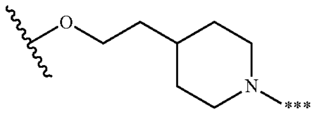

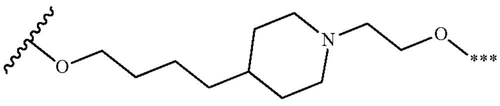

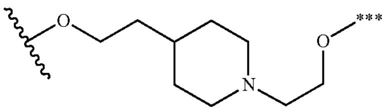

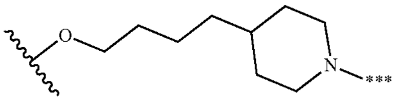

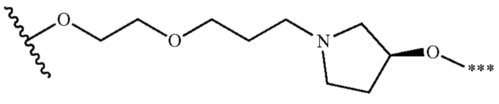

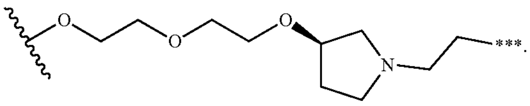

In certain embodiments, L is one of the following, where *** is a point of attachment to TPL:

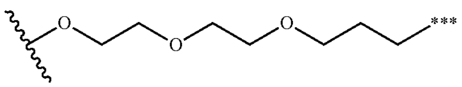

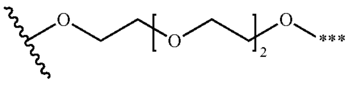

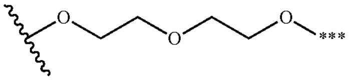

-continued
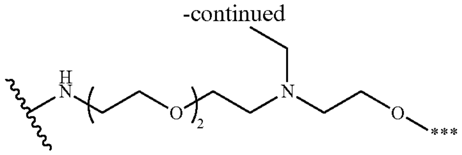
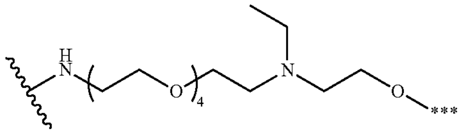
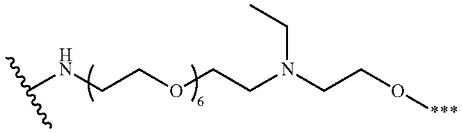
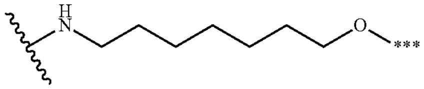
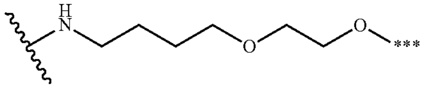
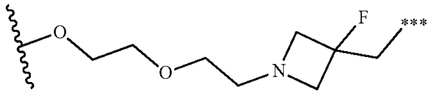
-continued
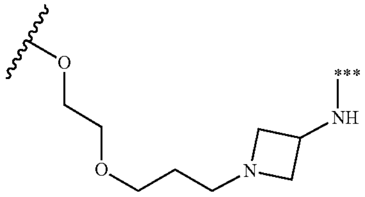
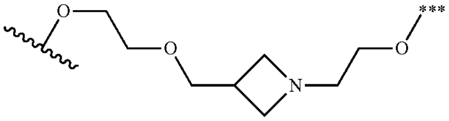
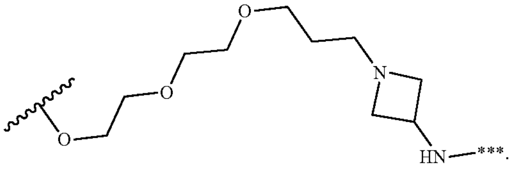
In certain embodiments, L is one of the following, where *** is a point of attachment to TPL:
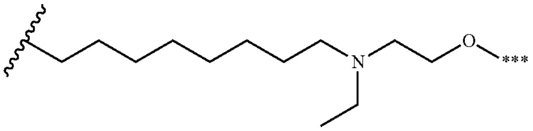
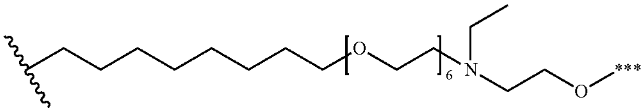
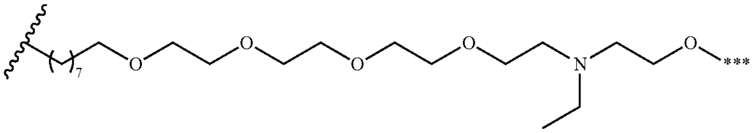
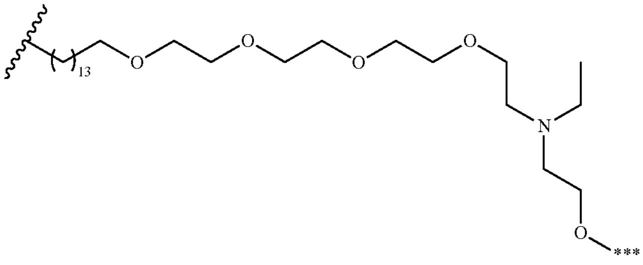
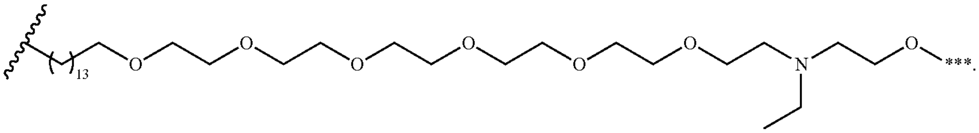

Another aspect of the invention provides a compound of Formula I-4:

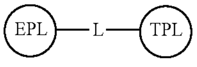

(I-4)

or a pharmaceutically acceptable salt thereof, wherein:

EPL has the following formula:

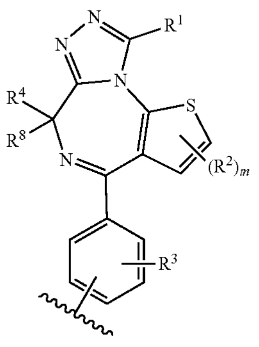

wherein:

$R^1$ is $C_{1-4}$ alkyl or $C_{3-4}$ cycloalkyl;

$R^2$ represents independently for each occurrence $C_{1-4}$ alkyl or $C_{3-4}$ cycloalkyl;

$R^3$ is hydrogen, halo, $C_{1-4}$ alkyl, $C_{1-4}$ haloalkyl, or $C_{1-4}$ alkoxyl;

$R^4$ is —($C_{0-6}$ alkylene)-(5-6 membered heteroaryl containing 1, 2, or 3 heteroatoms independently selected from nitrogen, oxygen, and sulfur), —($C_{1-6}$ alkylene)-C(O)N($R^5$)($R^6$) —($C_{1-6}$ alkylene)-N($R^5$)C(O)$R^7$, —($C_{1-6}$ alkylene)-$CO_2R^7$, —($C_{1-6}$ alkylene)-OC(O)$R^7$, —($C_{1-6}$ alkylene)-cyano, —($C_{1-6}$ alkylene)-O—($C_{1-6}$ alkyl), $C_{1-6}$ alkyl, $C_{3-6}$ cycloalkyl, or hydrogen; or $R^4$ and $R^8$ taken together with the carbon atom to which they are attached form a $C_{3-5}$ saturated carbocyclic ring;

$R^5$ and $R^6$ are independently hydrogen, $C_{1-6}$ alkyl, or $C_{3-6}$ cycloalkyl; or $R^5$ and $R^6$ are taken together with the nitrogen atom to which they are attached to form a 3-7 membered ring containing 1 nitrogen atom;

$R^7$ is $C_{1-6}$ alkyl, —($C_{1-6}$ alkylene)-($C_{3-6}$ cycloalkyl), or $C_{3-6}$ cycloalkyl;

$R^8$ is hydrogen or $C_{1-4}$ alkyl; and m is 0, 1, or 2;

TPL is

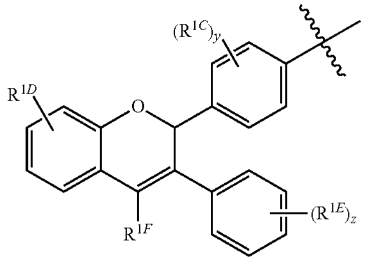

wherein:

$R^{1C}$ represents independently for each occurrence hydrogen, halo, hydroxyl, or $C_{1-4}$ alkyl;

$R^{1D}$ is hydroxyl;

$R^{1E}$ represents independently for each occurrence halo, hydroxyl, or $C_{1-4}$ alkyl;

$R^{1F}$ is hydrogen or $C_{1-4}$ alkyl;

y is 1 or 2; and z is 1, 2, or 3; and

L is one of the following:

(i) -(5-6 membered monocyclic heterocyclyl containing 1 or 2 nitrogen atoms)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-*, -(4-6 membered monocyclic heterocyclyl containing 1 nitrogen atom, wherein the heterocyclyl is substituted with 0 or 1 occurrences of hydroxyl)-($C_{0-6}$ alkylene)-(4-6 membered monocyclic heterocyclyl containing 1 nitrogen atom)-*, -(4-6 membered monocyclic heterocyclyl containing 1 or 2 nitrogen atoms)-($C_{0-6}$ alkylene)-(5-6 membered monocyclic heterocyclyl containing 1 or 2 nitrogen atoms)-($C_{0-6}$ alkylene)-O—*, —($C_{0-6}$ alkylene)-(7-11 membered spirocyclic heterocyclyl containing 1-2 nitrogen atoms)-($C_{0-6}$ alkylene)-O—*, —($C_{0-6}$ alkylene)-(7-11 membered spirocyclic heterocyclyl containing 1-2 heteroatoms selected from nitrogen)-*, —O-(7-11 membered spirocyclic heterocyclyl containing 1-2 nitrogen atoms)-($C_{0-6}$ alkylene)-O—*, —O-(7-11 membered spirocyclic heterocyclyl containing 1-2 nitrogen atoms)-*, —($C_{2-3}$ alkynylene)-(7-11 membered spirocyclic heterocyclyl containing 1-2 nitrogen atoms)-($C_{0-6}$ alkylene)-O—*, —($C_{2-3}$ alkynylene)-(7-11 membered spirocyclic heterocyclyl containing 1-2 nitrogen atoms)-*, —O—($C_{0-6}$ alkylene)-(5-6 membered monocyclic heterocyclyl containing 1 nitrogen atom)-*, —O—($C_{0-6}$ alkylene)-(5-6 membered monocyclic heterocyclyl containing 1 nitrogen atom)-($C_{1-6}$ alkylene)-O—*, or —O—($C_{1-6}$ alkylene)-O—($C_{1-6}$ alkylene)-(4-6 membered monocyclic heterocyclyl containing 1 nitrogen atom)-($C_{0-6}$ alkylene)-O—*, where * is a point of attachment to TPL;

(ii) —O—($C_{1-6}$ alkylene)-O—($C_{1-6}$ alkylene)-O-(4-6 membered monocyclic heterocyclyl containing 1 nitrogen atom)-($C_{0-6}$ alkylene)-*, —O—($C_{1-6}$ alkylene)-O—($C_{1-6}$ alkylene)-O—*, —O—($C_{1-6}$ alkylene)-O—($C_{1-6}$ alkylene)-O—($C_{1-6}$ alkylene)-*, —O—($C_{1-6}$ alkylene)-O—($C_{1-6}$ alkylene)-O—($C_{1-6}$ alkylene)-O—*, —N(H)—[—($C_{1-6}$ alkylene)-O-]$_{1-6}$—($C_{1-6}$ alkylene)-N($C_{1-4}$ alkyl)-($C_{1-6}$ alkylene)-O—*, —N(H)—($C_{1-10}$ alkylene)-O—*, —N(H)—($C_{1-6}$ alkylene)-O—($C_{1-6}$ alkylene)-O—*, —O—($C_{1-6}$ alkylene)-O—($C_{1-6}$ alkylene)-(4 membered monocyclic heterocyclyl containing 1 nitrogen atom, wherein the heterocyclyl is substituted with 0 or 1 occurrences of fluoro)-($C_{0-6}$ alkylene)-*, or —O—($C_{1-6}$ alkylene)-O—($C_{1-6}$ alkylene)-(4 membered monocyclic heterocyclyl containing 1 nitrogen atom)-N(H)—*, where * is a point of attachment to TPL; or (iii) —O—($C_{1-6}$ alkylene)-O—($C_{1-6}$ alkylene)-O—($C_{1-6}$ alkylene)-(4 membered monocyclic heterocyclyl containing 1 nitrogen atom)-N(H)—*, —($C_{1-10}$ alkylene)-N($C_{1-4}$ alkyl)-($C_{1-6}$ alkylene)-O—*, or —($C_{1-15}$ alkylene)-[—O—($C_{1-6}$ alkylene)-]$_{1-8}$-N($C_{1-4}$ alkyl)-($C_{1-6}$ alkylene)-O—*, where * is a point of attachment to TPL.

In certain embodiments, L is one of the following, where *** is a point of attachment

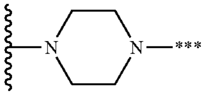
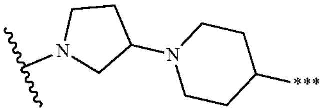
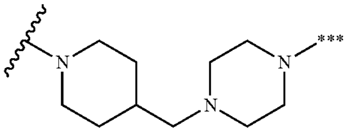
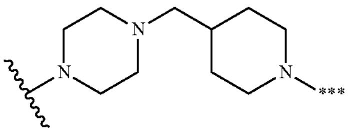
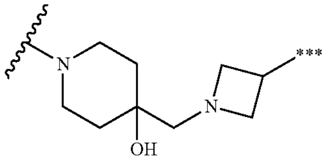
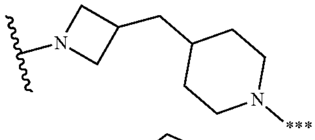
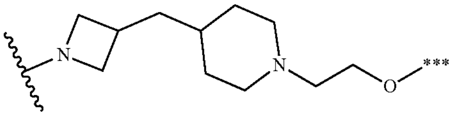
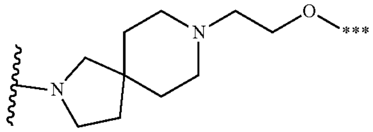
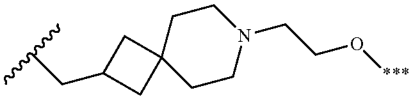
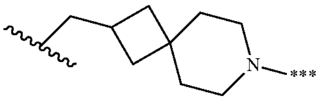
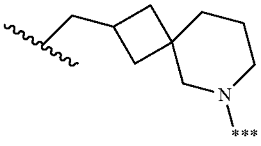
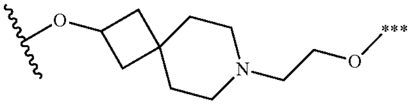
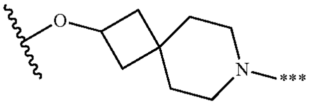
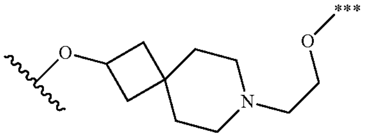
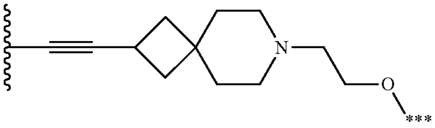
-continued
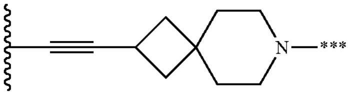
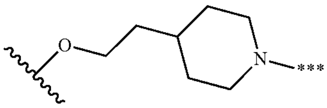
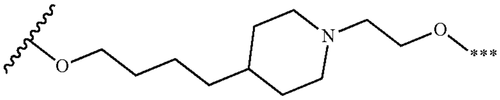
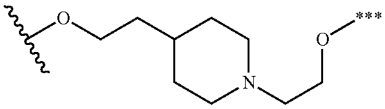
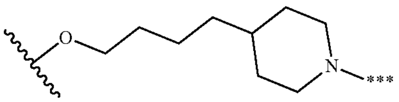
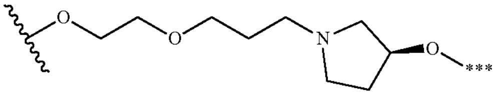
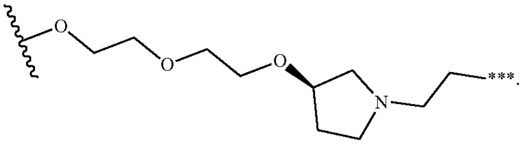
In certain embodiments, L is one of the following, where *** is a point of attachment to TPL:
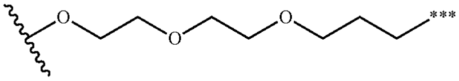
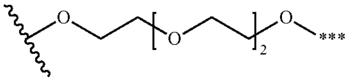
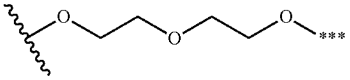
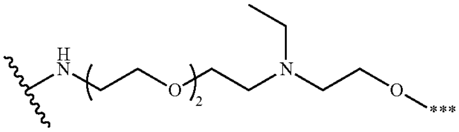
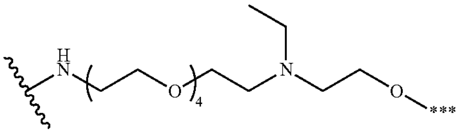
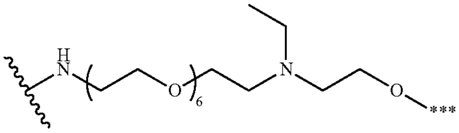
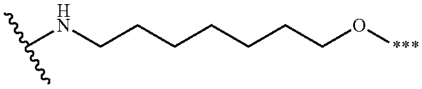
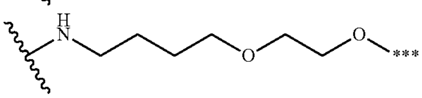

-continued

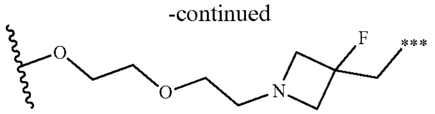

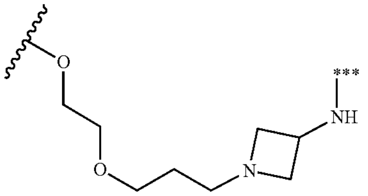

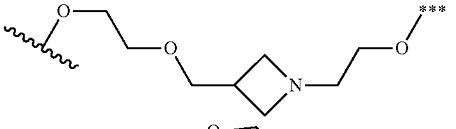

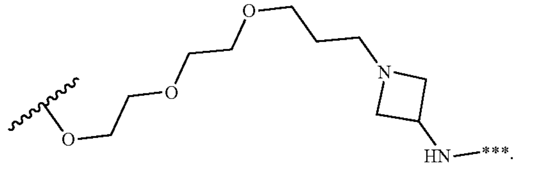

In certain embodiments, L is one of the following, where *** is a point of attachment to TPL:

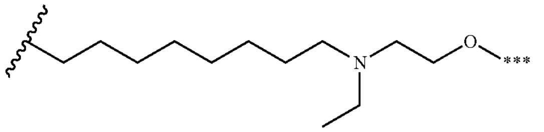

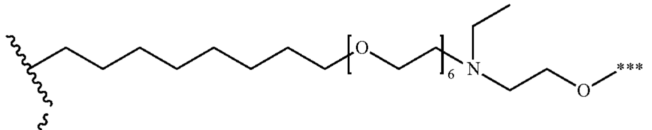

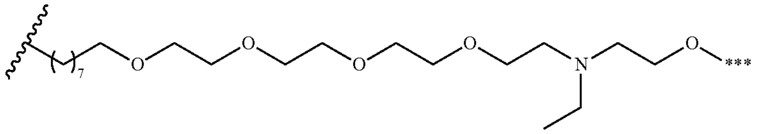

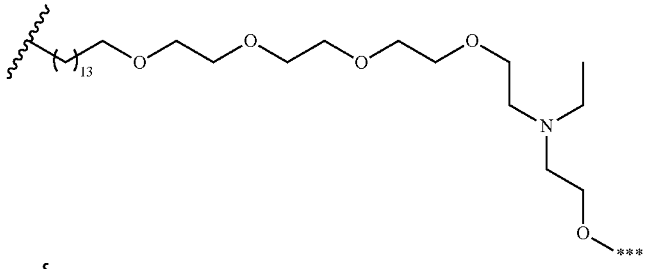

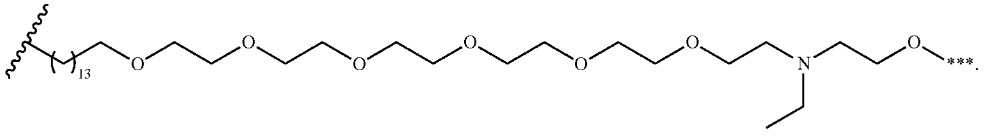

Part F: Exemplary Specific Compounds

Another aspect of the invention provides specific compounds of Formula I or II. In certain embodiments, the compound is a compound described in one of the embodiments below, a stereoisomer thereof, or a pharmaceutically acceptable salt of either of the foregoing. In certain embodiments, the compound is a compound described in one of the embodiments below, or a stereoisomer thereof.

In certain embodiments, the compound is a compound in Table 1, 2, 3, 4, or 5, or a pharmaceutically acceptable salt thereof. In certain embodiments, the compound is a compound in Table 1, 2, 3, 4, or 5. In certain embodiments, the compound is a compound in Table 1, 3, 4, or 5, or a pharmaceutically acceptable salt thereof. In certain embodiments, the compound is a compound in Table 1, 3, 4, or 5. In certain embodiments, the compound is a compound in Table 3, 4, or 5, or a pharmaceutically acceptable salt thereof. In certain embodiments, the compound is a compound in Table 3, 4, or 5.

In certain embodiments, the compound is a compound in Table 1 or 3, or a pharmaceutically acceptable salt thereof, wherein the compound is a compound of Formula I-A, or a pharmaceutically acceptable salt thereof. In certain embodiments, the compound is a compound in Table 1 or 3, wherein the compound is a compound of Formula I-A. In certain embodiments, the compound is a compound in Table 1 or 3, or a pharmaceutically acceptable salt thereof, wherein the compound is a compound of Formula I-A-1, I-A-2, I-A-3, I-A-4, I-A-3*, I-A-4*, I-A-3, I-A-4, I-A-5, I-A-6, or I-A-7, or a pharmaceutically acceptable salt thereof. In certain embodiments, the compound is a compound in Table 1 or 3, wherein the compound is a compound of Formula I-A-1, I-A-2, I-A-3, I-A-4, I-A-3*, I-A-4*, I-A-3, I-A-4, I-A-5, I-A-6, or I-A-7. In certain embodiments, the compound is a compound in Table 1 or 4, or a pharmaceutically acceptable salt thereof, wherein the compound is a compound of Formula I-B or I-B-1, or a pharmaceutically acceptable salt thereof. In certain embodiments, the compound is a compound in Table 1 or 4, wherein the compound is a compound of Formula I-B or I-B-1.

In certain embodiments, the compound is one of compounds III-244, III-245, III-250, III-251, III-275, III-276, III-307, III-308, III-311, III-312, III-321, III-322, III-327, III-328, or III-333 through III-346, or a pharmaceutically acceptable salt thereof. In certain embodiments, the compound is one of compounds III-244, III-245, III-250, III-251, III-275, III-276, III-307, III-308, III-311, III-312, III-321, III-322, III-327, III-328, or III-333 through III-346. In certain embodiments, the compound is one of compounds III-245, III-251, III-276, III-307, III-311, III-321, III-328, III-334, III-336, III-338, III-339, III-341, III-344, or III-346, or a pharmaceutically acceptable salt thereof. In certain embodiments, the compound is one of compounds III-245, III-251, III-276, III-307, III-311, III-321, III-328, III-334, III-336, III-338, III-339, III-341, III-344, or III-346.

In certain embodiments, the compound is a compound in Table 1, or a pharmaceutically acceptable salt thereof. In certain embodiments, the compound is a compound in Table 1.

TABLE 1

| Compound No. | Structure |
|---|---|
| I-1 | 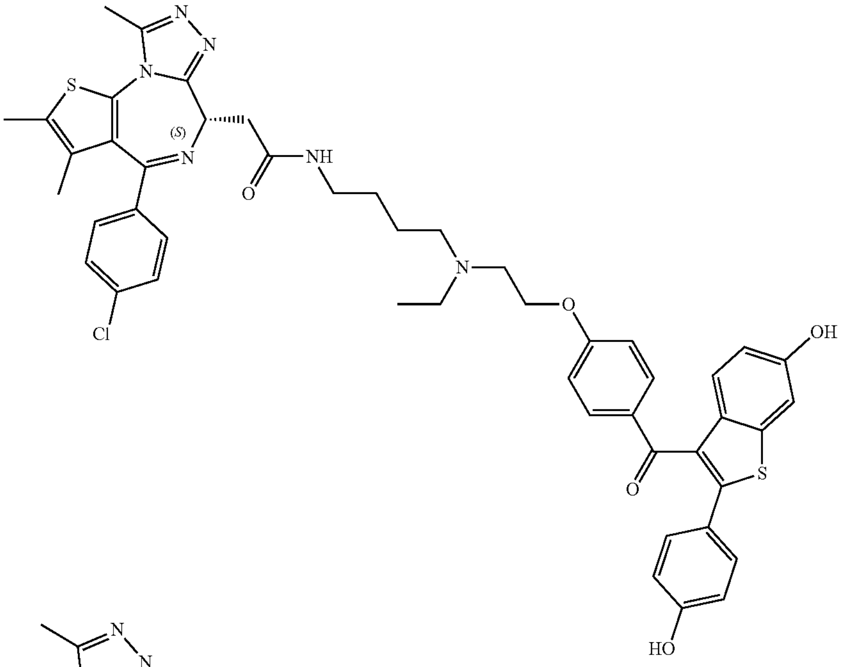 |
| I-2 | 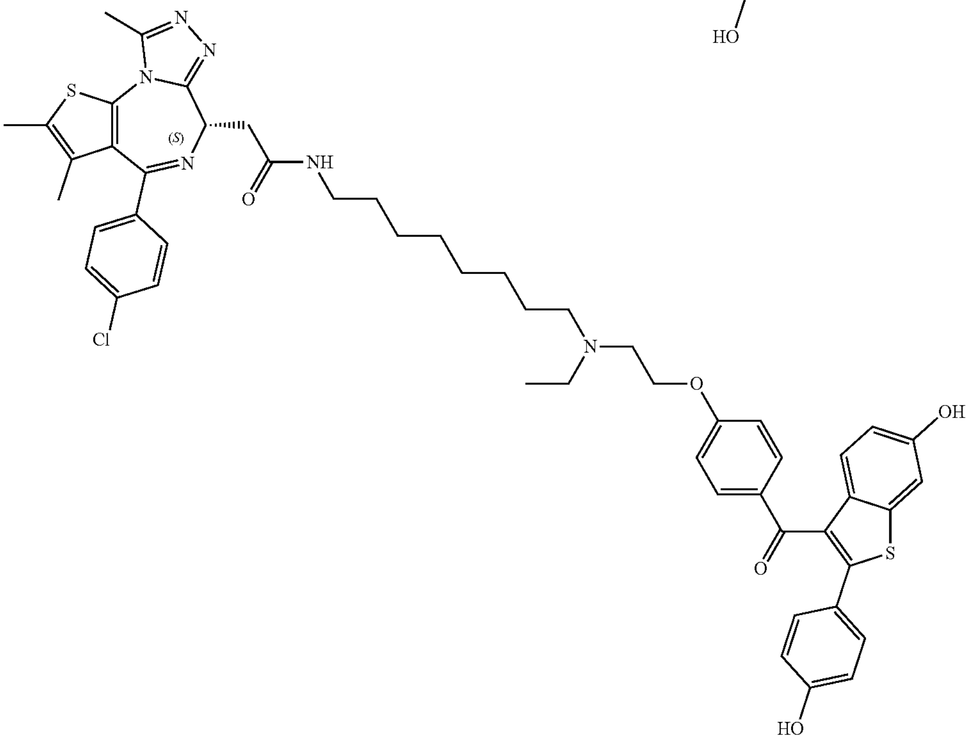 |

TABLE 1-continued
| Compound No. | Structure |
|---|---|
| I-3 | 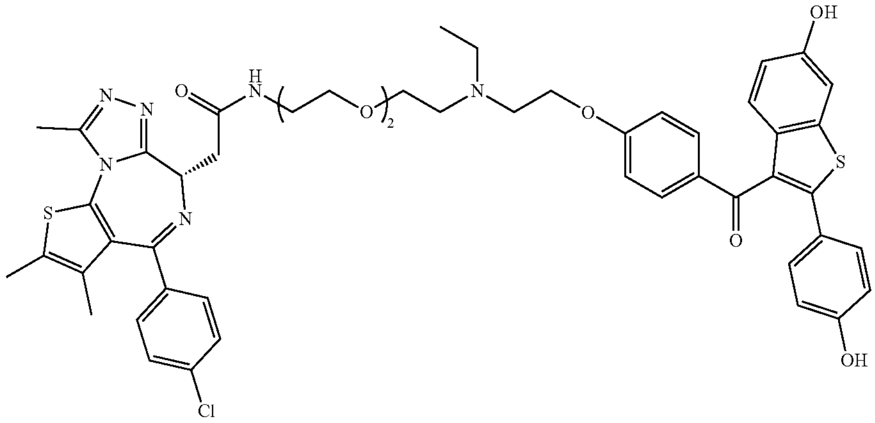 |
| I-4 | 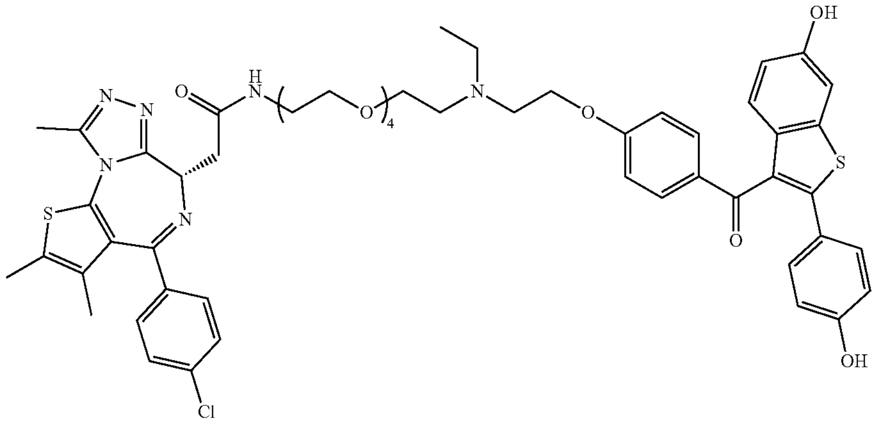 |
| I-5 | 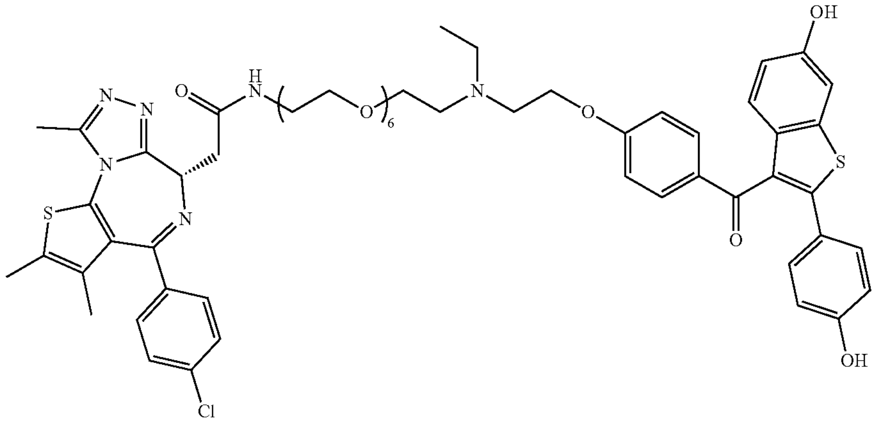 |

TABLE 1-continued
| Compound No. | Structure |
|---|---|
| I-6 | 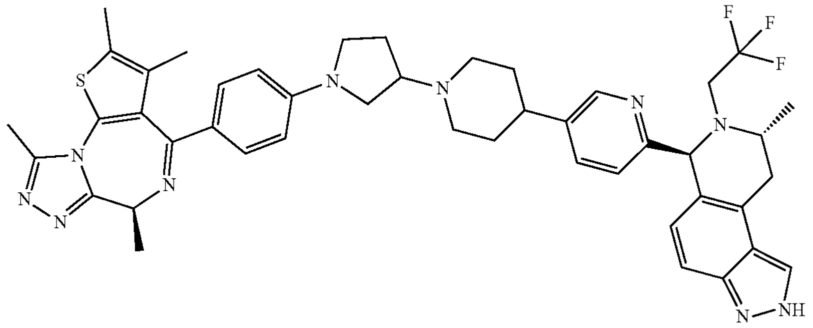 |
| I-7 | 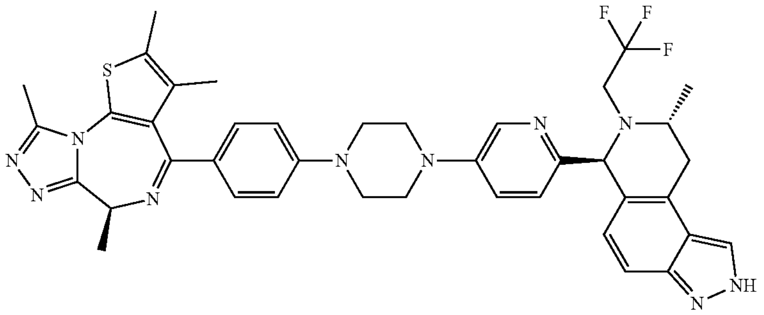 [SMILES: Cc1sc2c(c1C)C(c1ccc(N3CCN(c4ccc([C@@H]5c6ccc7n[nH]cc7c6C[C@@H](C)N5CC(F)(F)F)nc4)CC3)cc1)=N[C@@H](C)c1nnc(C)n1-2] |
| I-8 | 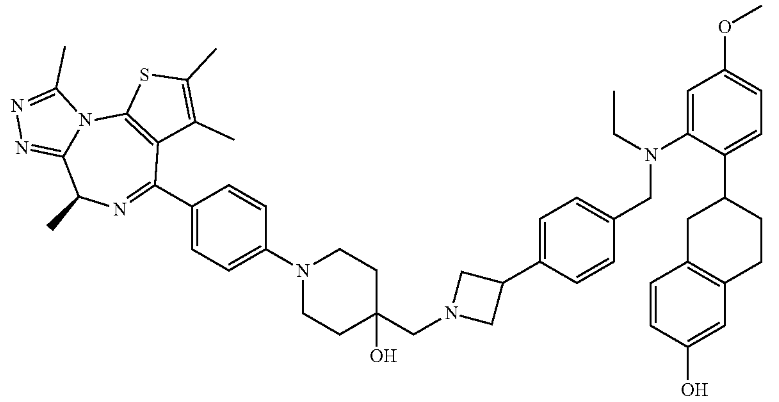 [SMILES: CCN(Cc1ccc(C2CN(CC3(O)CCN(c4ccc(C5=N[C@@H](C)c6nnc(C)n6-c6sc(C)c(C)c65)cc4)CC3)C2)cc1)c1cc(OC)ccc1C1CCc2cc(O)ccc2C1] |
| I-9 | 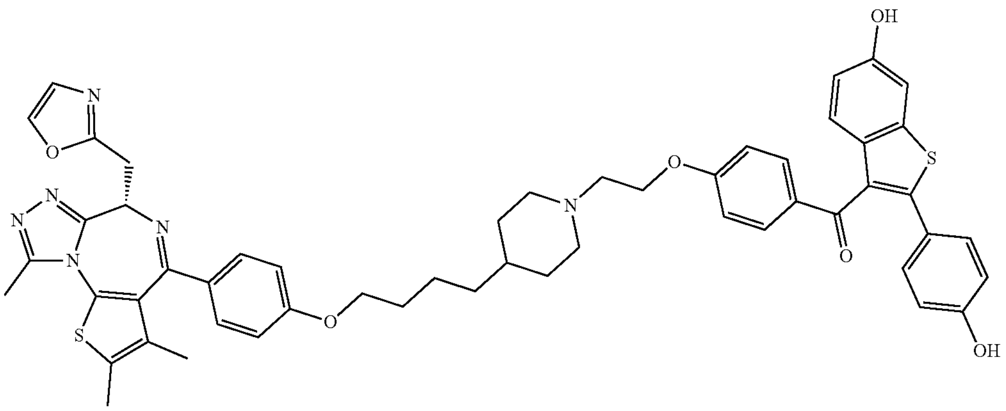 [SMILES: Cc1sc2c(c1C)C(c1ccc(OCCCCC3CCN(CCOc4ccc(C(=O)c5c(-c6ccc(O)cc6)sc6cc(O)ccc56)cc4)CC3)cc1)=N[C@@H](Cc1ncco1)c1nnc(C)n1-2] |

TABLE 1-continued
| Compound No. | Structure |
|---|---|
| I-10 | 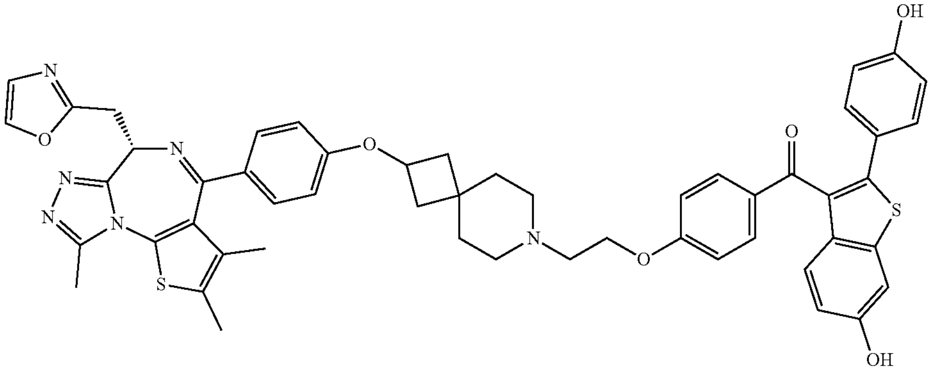 [SMILES: Cc1sc2c(c1C)C(c1ccc(OC3CC4(CCN(CCOc5ccc(C(=O)c6c(-c7ccc(O)cc7)sc7cc(O)ccc67)cc5)CC4)C3)cc1)=N[C@@H](Cc1ncco1)c1nnc(C)n1-2] |
| I-11 | 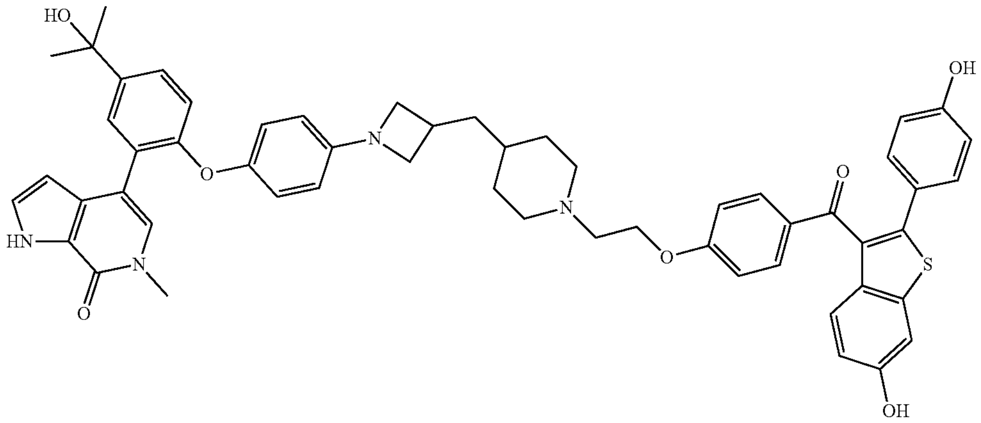 [SMILES: Cn1cc(-c2cc(C(C)(C)O)ccc2Oc2ccc(N3CC(CC4CCN(CCOc5ccc(C(=O)c6c(-c7ccc(O)cc7)sc7cc(O)ccc67)cc5)CC4)C3)cc2)c2cc[nH]c2c1=O] |
| I-12 | 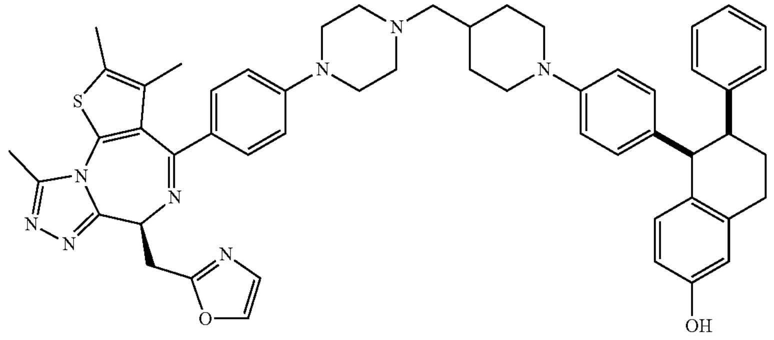 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@@H](Cc1ncco1)c1nnc(C)n1-2] |
| I-13 | 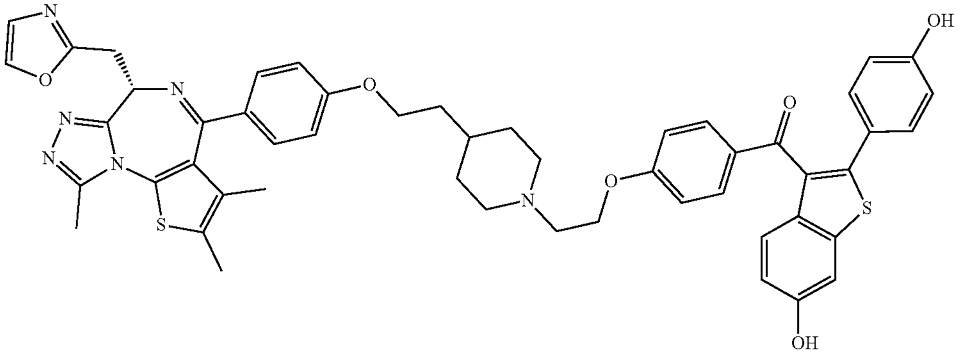 [SMILES: Cc1sc2c(c1C)C(c1ccc(OCCC3CCN(CCOc4ccc(C(=O)c5c(-c6ccc(O)cc6)sc6cc(O)ccc56)cc4)CC3)cc1)=N[C@@H](Cc1ncco1)c1nnc(C)n1-2] |

TABLE 1-continued
| Compound No. | Structure |
|---|---|
| I-14 | 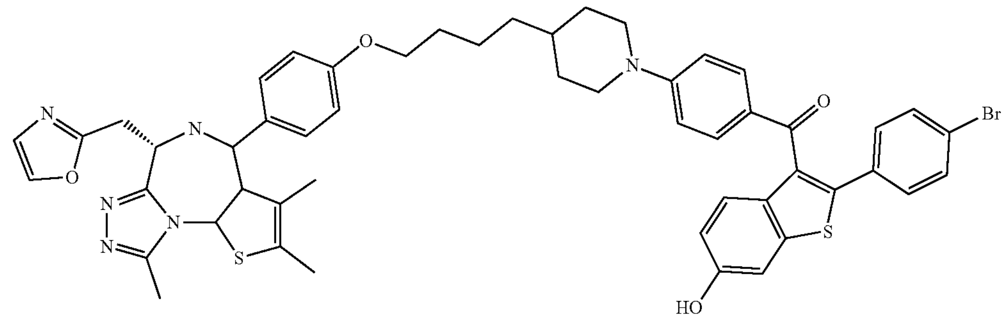 [SMILES: CC1=C(C)C2C(c3ccc(OCCCCC4CCN(c5ccc(C(=O)c6c(-c7ccc(Br)cc7)sc7cc(O)ccc67)cc5)CC4)cc3)N[C@@H](Cc3ncco3)c3nnc(C)n3C2S1] |
| I-15 | 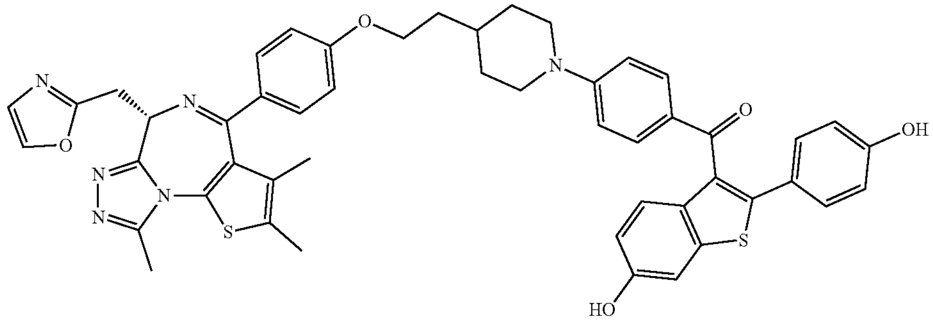 [SMILES: Cc1sc2c(c1C)C(c1ccc(OCCC3CCN(c4ccc(C(=O)c5c(-c6ccc(O)cc6)sc6cc(O)ccc56)cc4)CC3)cc1)=N[C@@H](Cc1ncco1)c1nnc(C)n1-2] |
| I-16 | 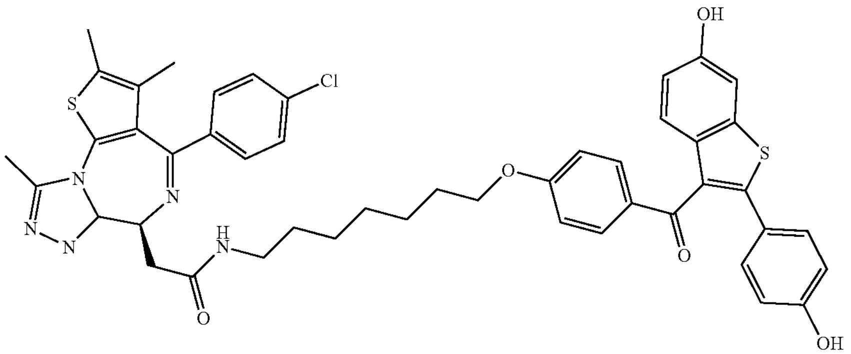 [SMILES: CC1=NNC2[C@H](CC(=O)NCCCCCCCOc3ccc(C(=O)c4c(-c5ccc(O)cc5)sc5cc(O)ccc45)cc3)N=C(c3ccc(Cl)cc3)c3c(sc(C)c3C)N12] |
| I-17 | 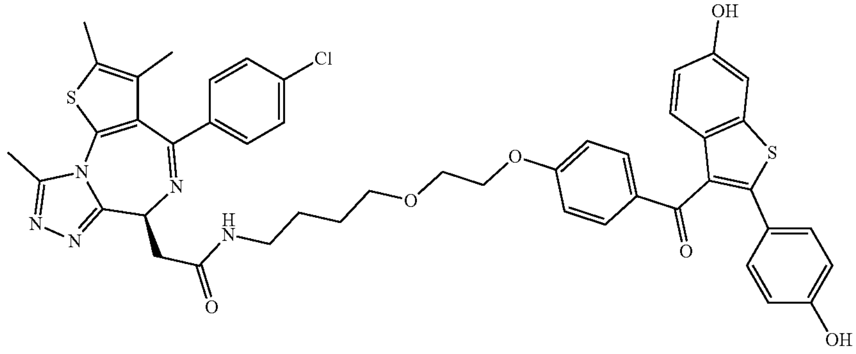 [SMILES: Cc1sc2c(c1C)C(c1ccc(Cl)cc1)=N[C@@H](CC(=O)NCCCCOCCOc1ccc(C(=O)c3c(-c4ccc(O)cc4)sc4cc(O)ccc34)cc1)c1nnc(C)n1-2] |

TABLE 1-continued
| Compound No. | Structure |
|---|---|
| I-18 | 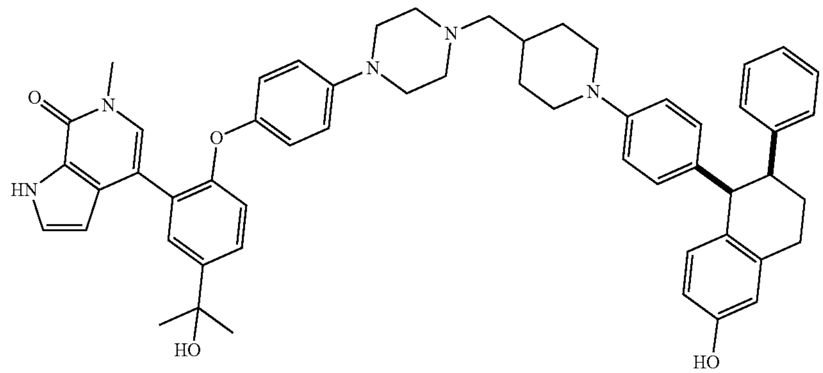 |
| I-19 | 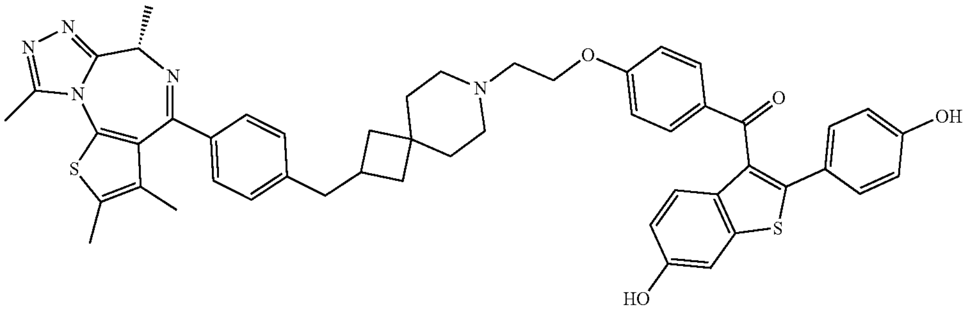 [SMILES: Cc1sc2c(c1C)C(c1ccc(CC3CC4(CCN(CCOc5ccc(C(=O)c6c(-c7ccc(O)cc7)sc7cc(O)ccc67)cc5)CC4)C3)cc1)=N[C@@H](C)c1nnc(C)n1-2] |
| I-20 | 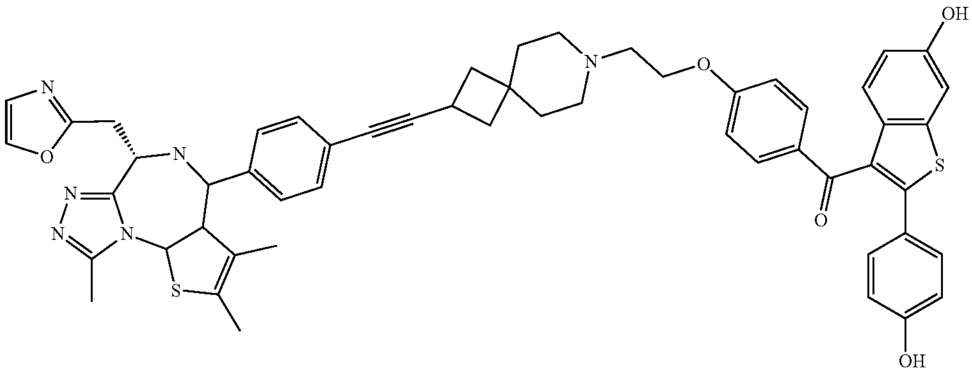 [SMILES: CC1=C(C)C2C(c3ccc(C#CC4CC5(CCN(CCOc6ccc(C(=O)c7c(-c8ccc(O)cc8)sc8cc(O)ccc78)cc6)CC5)C4)cc3)N[C@@H](Cc3ncco3)c3nnc(C)n3C2S1] |
| I-21 | 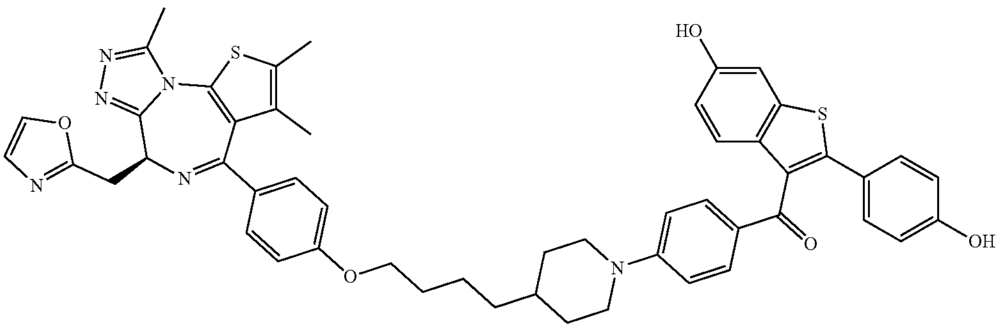 [SMILES: Cc1sc2c(c1C)C(c1ccc(OCCCCC3CCN(c4ccc(C(=O)c5c(-c6ccc(O)cc6)sc6cc(O)ccc56)cc4)CC3)cc1)=N[C@@H](Cc1ncco1)c1nnc(C)n1-2] |

TABLE 1-continued
| Compound No. | Structure |
|---|---|
| I-22 | 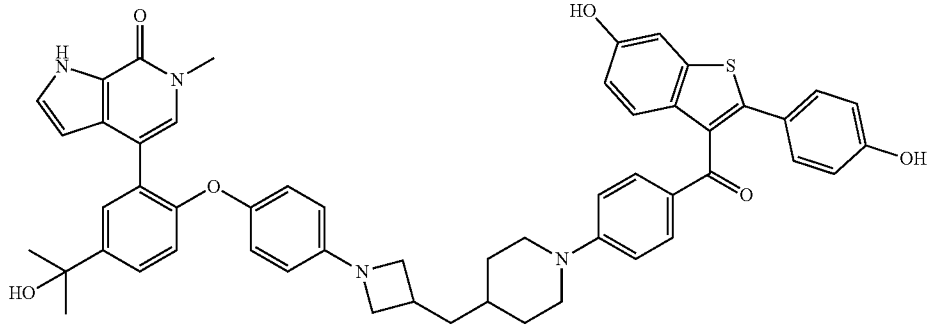 [SMILES: Cn1cc(-c2cc(C(C)(C)O)ccc2Oc2ccc(N3CC(CC4CCN(c5ccc(C(=O)c6c(-c7ccc(O)cc7)sc7cc(O)ccc67)cc5)CC4)C3)cc2)c2cc[nH]c2c1=O] |
| I-23 | 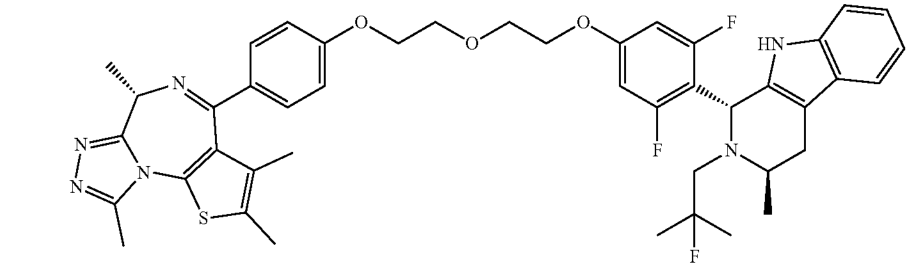 [SMILES: Cc1sc2c(c1C)C(c1ccc(OCCOCCOc3cc(F)c([C@@H]4c5[nH]c6ccccc6c5C[C@@H](C)N4CC(C)(C)F)c(F)c3)cc1)=N[C@@H](C)c1nnc(C)n1-2] |
| I-24 | 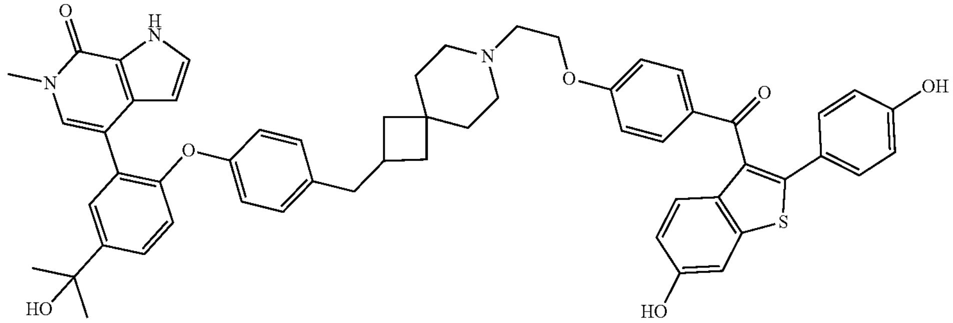 [SMILES: Cn1cc(-c2cc(C(C)(C)O)ccc2Oc2ccc(CC3CC4(CCN(CCOc5ccc(C(=O)c6c(-c7ccc(O)cc7)sc7cc(O)ccc67)cc5)CC4)C3)cc2)c2cc[nH]c2c1=O] |
| I-25 | 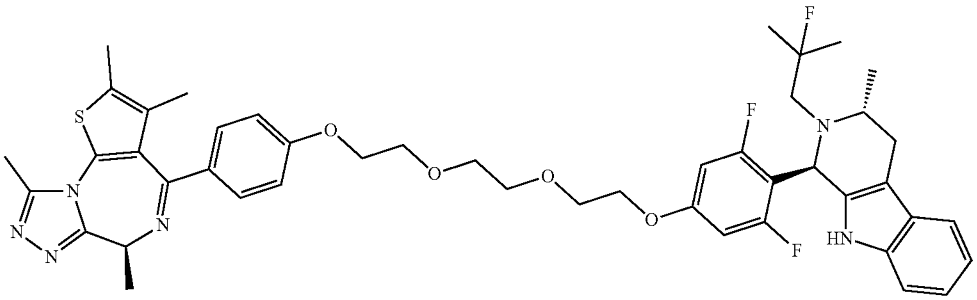 [SMILES: Cc1sc2c(c1C)C(c1ccc(OCCOCCOCCOc3cc(F)c([C@@H]4c5[nH]c6ccccc6c5C[C@@H](C)N4CC(C)(C)F)c(F)c3)cc1)=N[C@@H](C)c1nnc(C)n1-2] |
| I-26 | 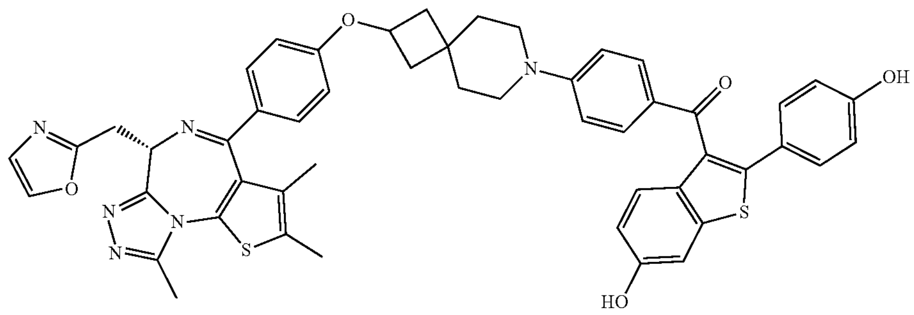 [SMILES: Cc1sc2c(c1C)C(c1ccc(OC3CC4(CCN(c5ccc(C(=O)c6c(-c7ccc(O)cc7)sc7cc(O)ccc67)cc5)CC4)C3)cc1)=N[C@@H](Cc1ncco1)c1nnc(C)n1-2] |

TABLE 1-continued
| Compound No. | Structure |
| --- | --- |
| I-27 | 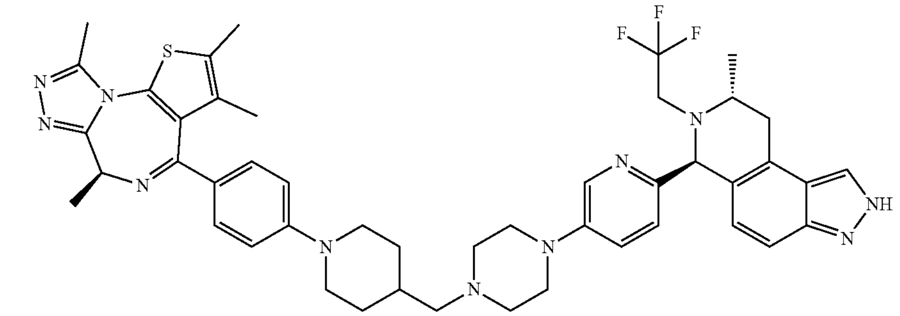 [SMILES: Cc1sc2c(c1C)C(c1ccc(N3CCC(CN4CCN(c5ccc([C@@H]6c7ccc8n[nH]cc8c7C[C@@H](C)N6CC(F)(F)F)nc5)CC4)CC3)cc1)=N[C@@H](C)c1nnc(C)n1-2] |
| I-28 | 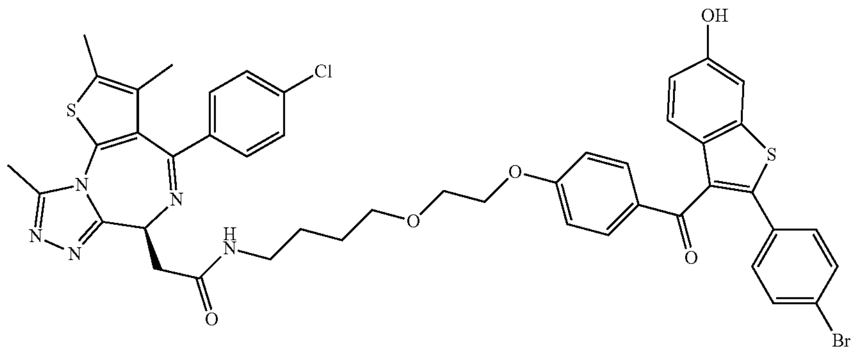 [SMILES: Cc1sc2c(c1C)C(c1ccc(Cl)cc1)=N[C@@H](CC(=O)NCCCCOCCOc1ccc(C(=O)c3c(-c4ccc(Br)cc4)sc4cc(O)ccc34)cc1)c1nnc(C)n1-2] |
| I-29 | 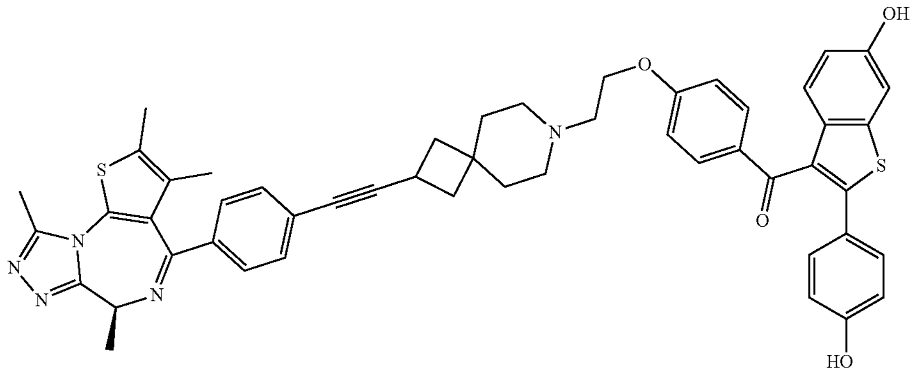 [SMILES: Cc1sc2c(c1C)C(c1ccc(C#CC3CC4(CCN(CCOc5ccc(C(=O)c6c(-c7ccc(O)cc7)sc7cc(O)ccc67)cc5)CC4)C3)cc1)=N[C@@H](C)c1nnc(C)n1-2] |
| I-30 | 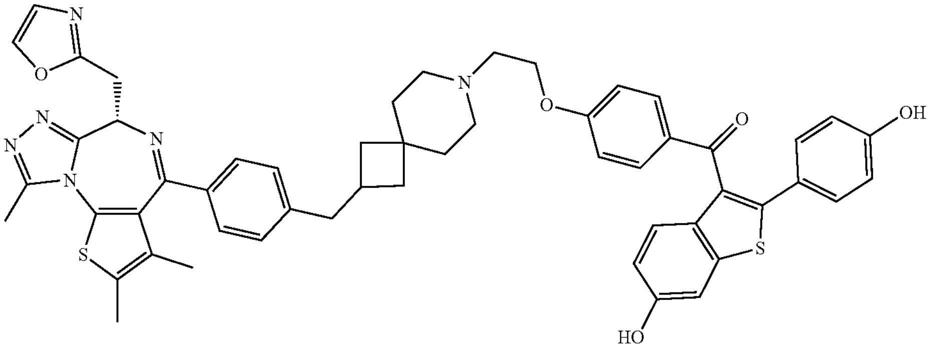 [SMILES: Cc1sc2c(c1C)C(c1ccc(CC3CC4(CCN(CCOc5ccc(C(=O)c6c(-c7ccc(O)cc7)sc7cc(O)ccc67)cc5)CC4)C3)cc1)=N[C@@H](Cc1ncco1)c1nnc(C)n1-2] |

TABLE 1-continued
| Compound No. | Structure |
|---|---|
| I-31 | 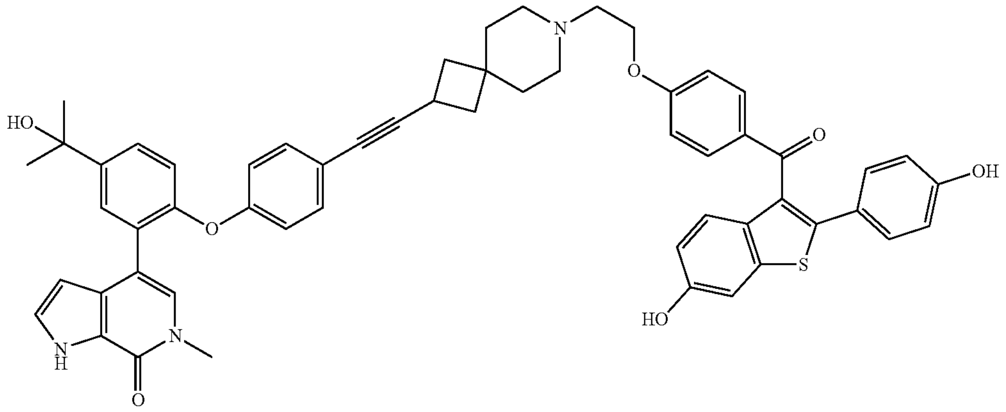 [SMILES: Cn1cc(-c2cc(C(C)(C)O)ccc2Oc2ccc(C#CC3CC4(CCN(CCOc5ccc(C(=O)c6c(-c7ccc(O)cc7)sc7cc(O)ccc67)cc5)CC4)C3)cc2)c2cc[nH]c2c1=O] |
| I-32 | 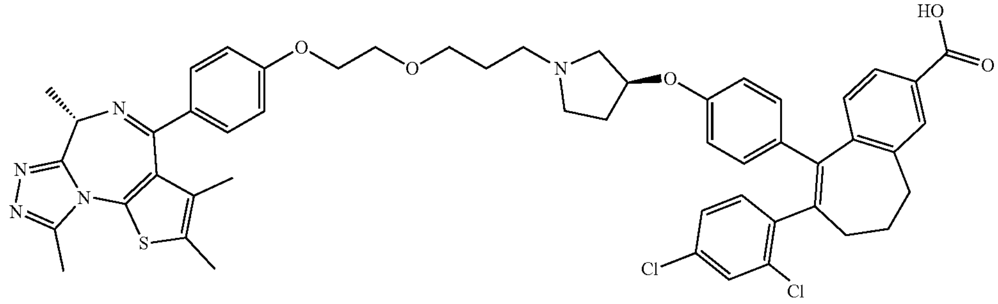 [SMILES: Cc1sc2c(c1C)C(c1ccc(OCCOCCCN3CC[C@H](Oc4ccc(C5=C(c6ccc(Cl)cc6Cl)CCCc6cc(C(=O)O)ccc65)cc4)C3)cc1)=N[C@@H](C)c1nnc(C)n1-2] |
| I-33 | 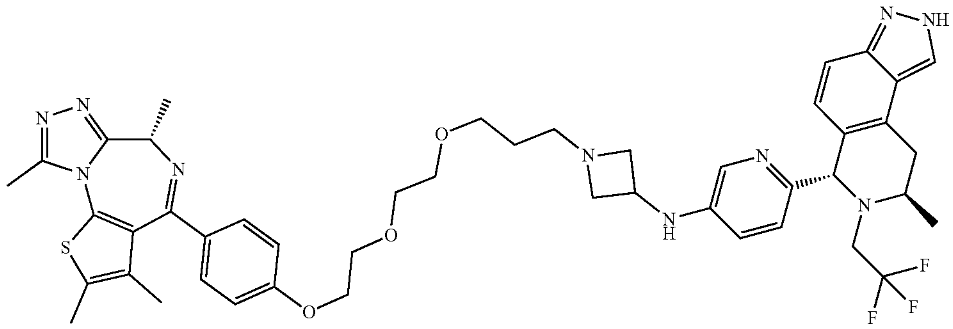 |
| I-34a | 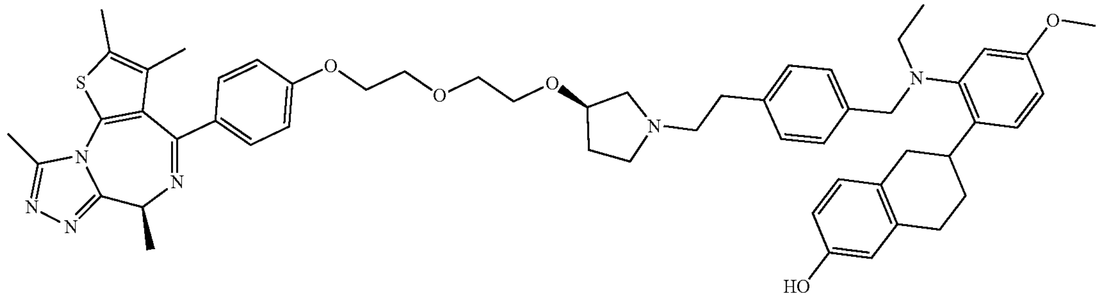 |

TABLE 1-continued
| Compound No. | Structure |
|---|---|
| | Stereoisomer I |
| I-34b | 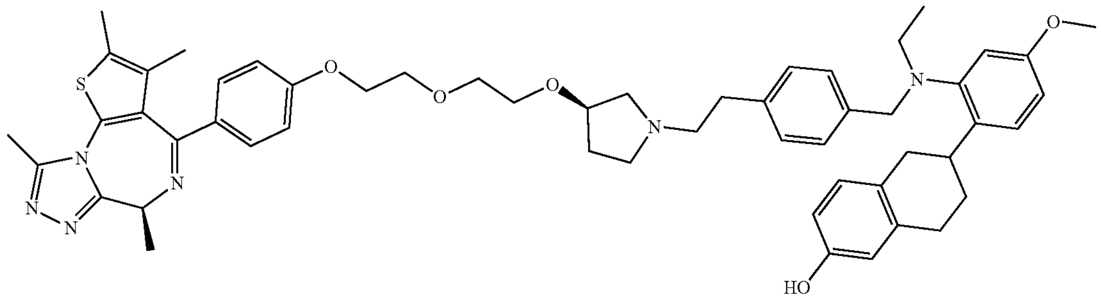 |
| | Stereoisomer II |
| I-35 | 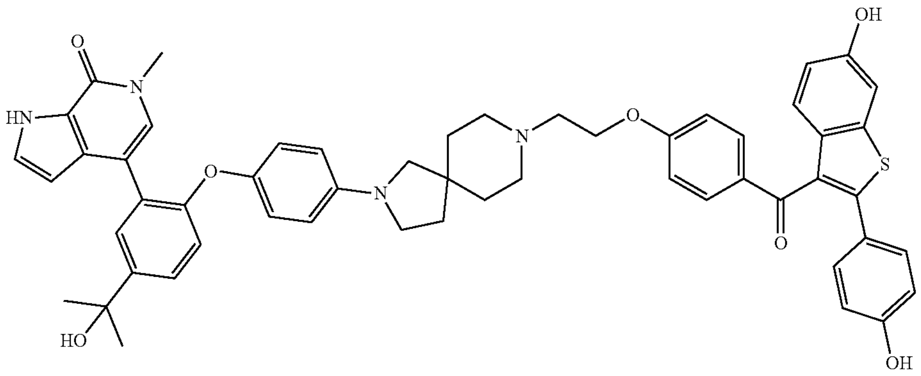 [SMILES: Cn1cc(-c2cc(C(C)(C)O)ccc2Oc2ccc(N3CCC4(CCN(CCOc5ccc(C(=O)c6c(-c7ccc(O)cc7)sc7cc(O)ccc67)cc5)CC4)C3)cc2)c2cc[nH]c2c1=O] |
| I-36 | 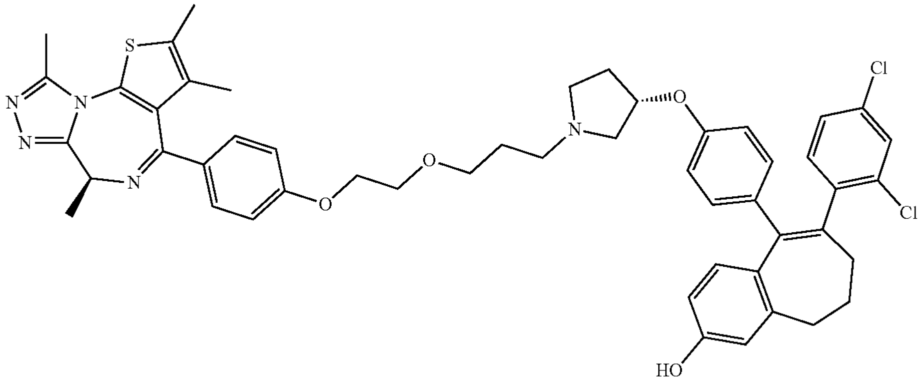 [SMILES: Cc1sc2c(c1C)C(c1ccc(OCCOCCCN3CC[C@H](Oc4ccc(C5=C(c6ccc(Cl)cc6Cl)CCCc6cc(O)ccc65)cc4)C3)cc1)=N[C@@H](C)c1nnc(C)n1-2] |
| I-37a | 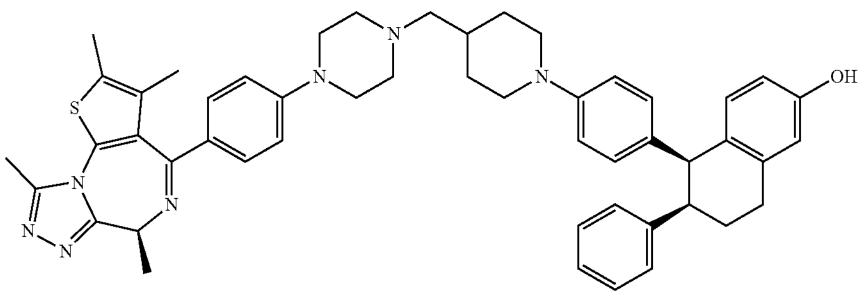 [SMILES: Cc1sc2c(c1C)C(c1ccc(N3CCN(CC4CCN(c5ccc([C@H]6c7ccc(O)cc7CC[C@H]6c6ccccc6)cc5)CC4)CC3)cc1)=N[C@@H](C)c1nnc(C)n1-2] |

TABLE 1-continued
| Compound No. | Structure |
|---|---|
| I-37b | 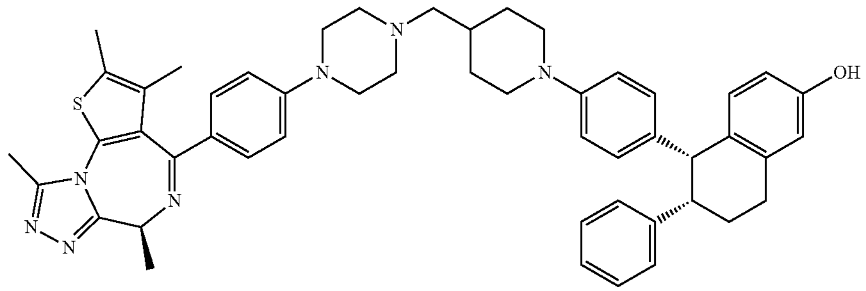 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@@H](C)c1nnc(C)n1-2] |
| I-38 | 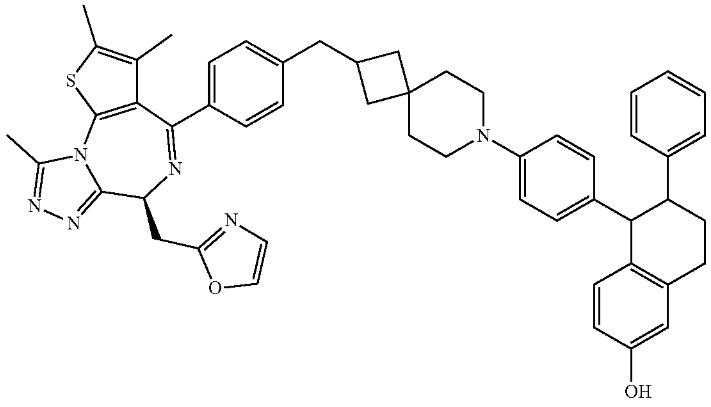 [SMILES: Cc1sc2c(c1C)C(c1ccc(CC3CC4(CCN(c5ccc(C6c7ccc(O)cc7CCC6c6ccccc6)cc5)CC4)C3)cc1)=N[C@@H](Cc1ncco1)c1nnc(C)n1-2] |
| I-39 | 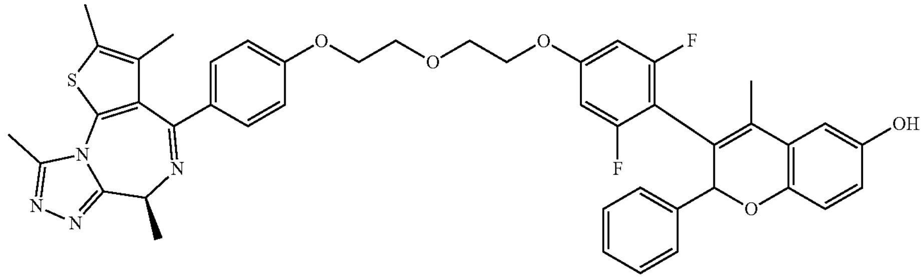 [SMILES: CC1=C(c2c(F)cc(OCCOCCOc3ccc(C4=N[C@@H](C)c5nnc(C)n5-c5sc(C)c(C)c54)cc3)cc2F)C(c2ccccc2)Oc2ccc(O)cc21]<br>Mixture of Stereoisomer I and Stereoisomer II |
| I-40 | 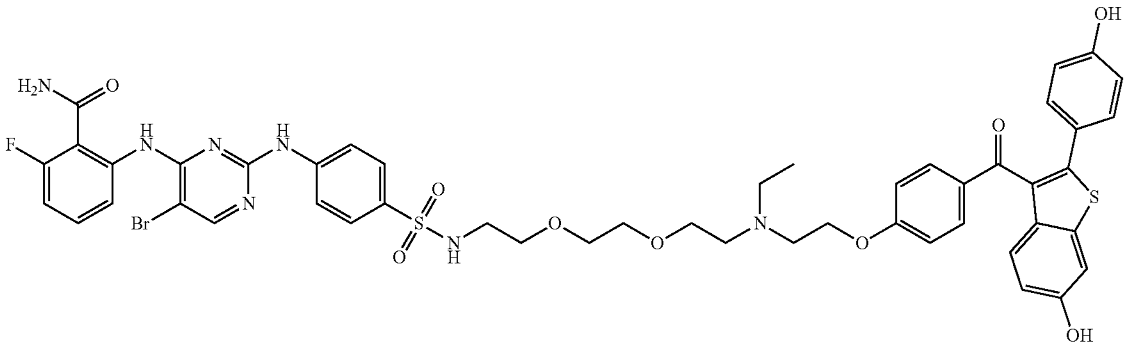 [SMILES: CCN(CCOCCOCCNS(=O)(=O)c1ccc(Nc2ncc(Br)c(Nc3cccc(F)c3C(N)=O)n2)cc1)CCOc1ccc(C(=O)c2c(-c3ccc(O)cc3)sc3cc(O)ccc23)cc1] |

TABLE 1-continued
| Compound No. | Structure |
|---|---|
| I-41 | 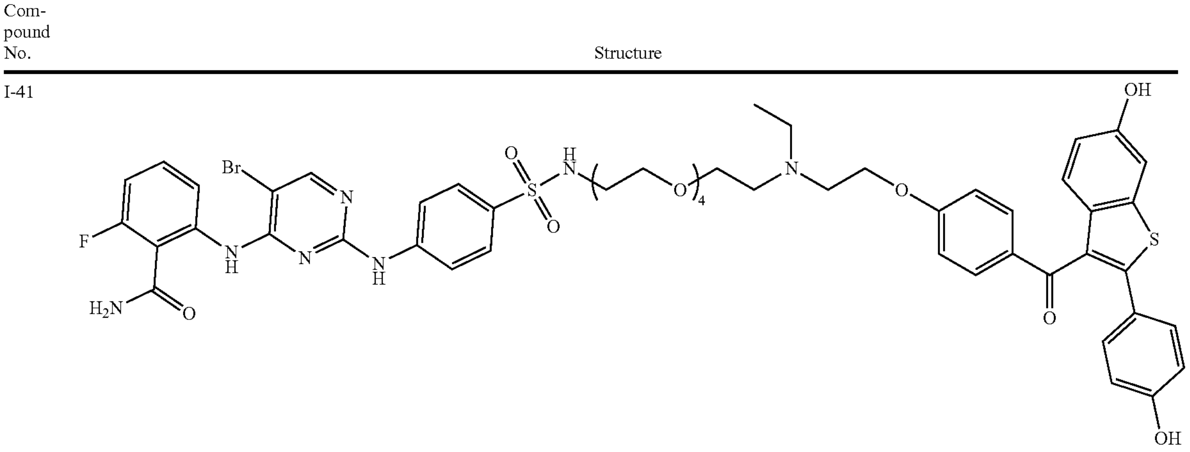 |
| I-42 | 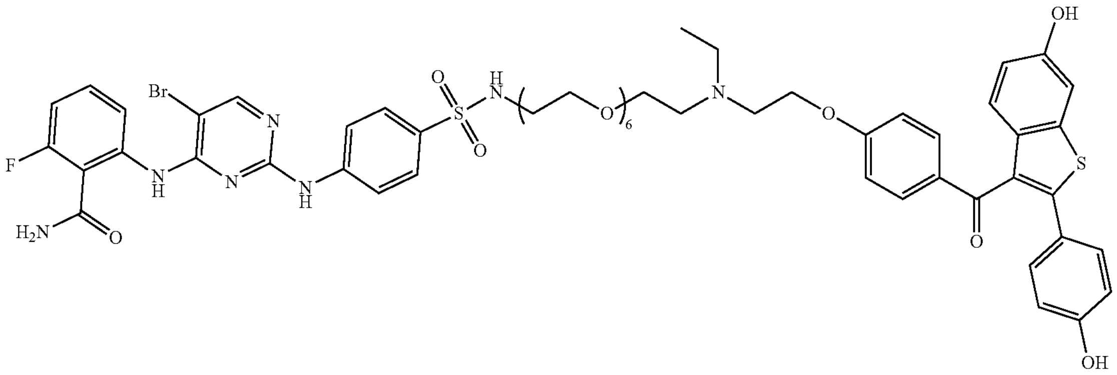 |
| I-43 | 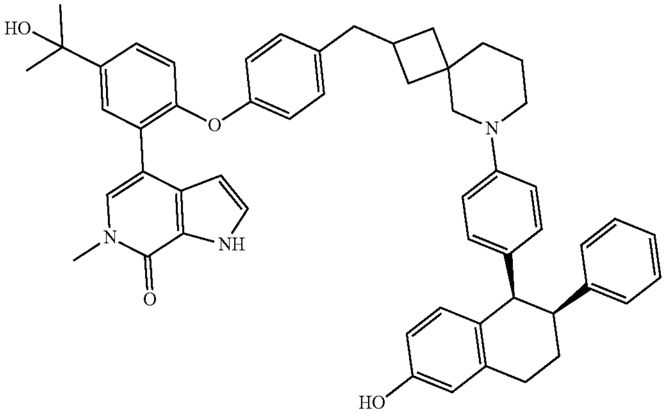 [SMILES: Cn1cc(-c2cc(C(C)(C)O)ccc2Oc2ccc(CC3CC4(CCCN(c5ccc([C@@H]6c7ccc(O)cc7CC[C@@H]6c6ccccc6)cc5)C4)C3)cc2)c2cc[nH]c2c1=O] |
| I-44 | 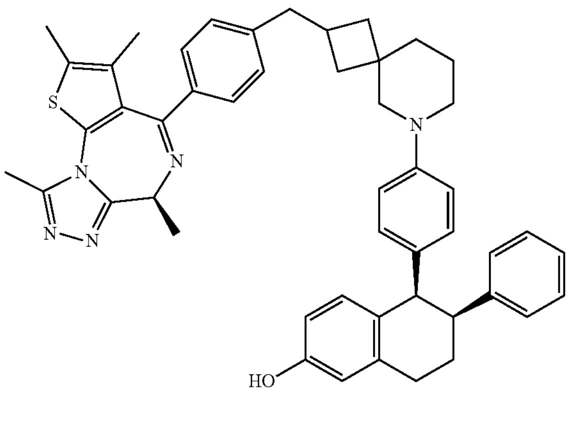 [SMILES: Cc1sc2c(c1C)C(c1ccc(CC3CC4(CCCN(c5ccc([C@@H]6c7ccc(O)cc7CC[C@@H]6c6ccccc6)cc5)C4)C3)cc1)=N[C@@H](C)c1nnc(C)n1-2] |

TABLE 1-continued
| Compound No. | Structure |
| --- | --- |
| I-45 | 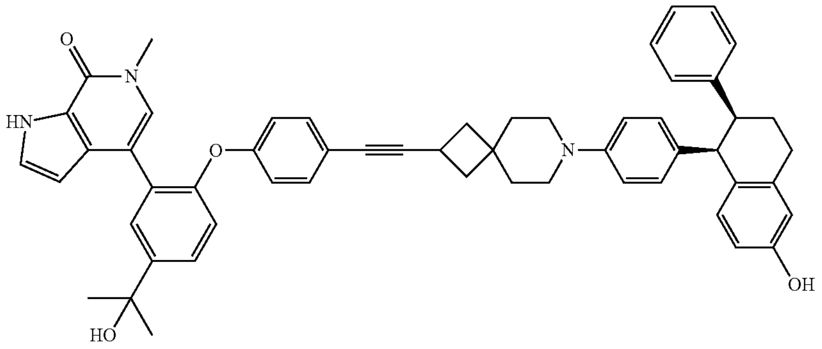 [SMILES: Cn1cc(-c2cc(C(C)(C)O)ccc2Oc2ccc(C#CC3CC4(CCN(c5ccc([C@@H]6c7ccc(O)cc7CC[C@@H]6c6ccccc6)cc5)CC4)C3)cc2)c2cc[nH]c2c1=O] |
| I-46 | 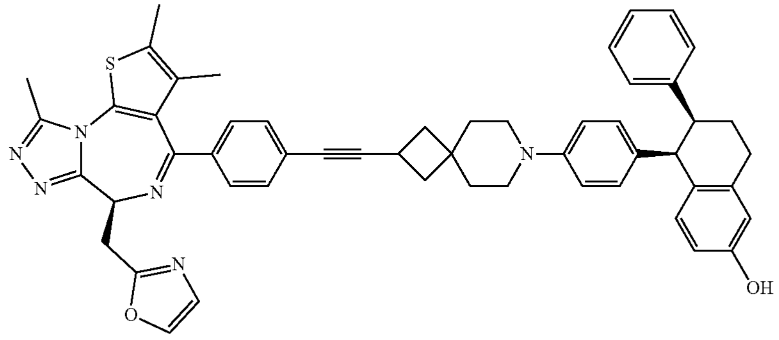 [SMILES: Cc1sc2c(c1C)C(c1ccc(C#CC3CC4(CCN(c5ccc([C@@H]6c7ccc(O)cc7CC[C@@H]6c6ccccc6)cc5)CC4)C3)cc1)=N[C@@H](Cc1ncco1)c1nnc(C)n1-2] |
| I-47 | 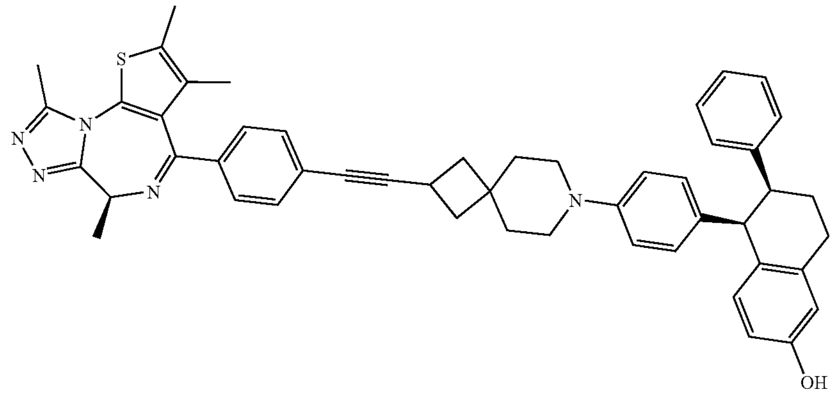 [SMILES: Cc1sc2c(c1C)C(c1ccc(C#CC3CC4(CCN(c5ccc([C@@H]6c7ccc(O)cc7CC[C@@H]6c6ccccc6)cc5)CC4)C3)cc1)=N[C@@H](C)c1nnc(C)n1-2] |
| I-48 | 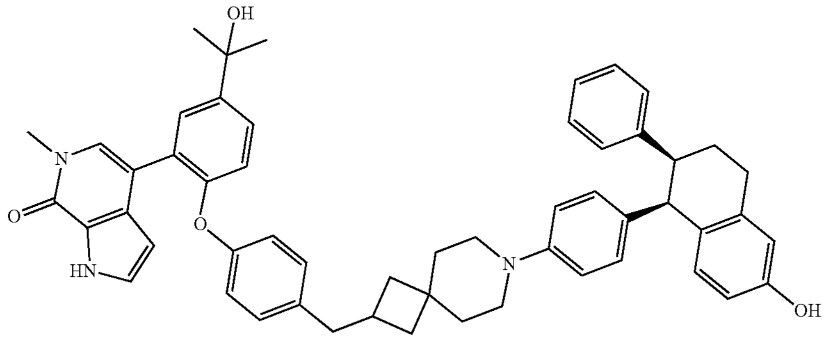 [SMILES: Cn1cc(-c2cc(C(C)(C)O)ccc2Oc2ccc(CC3CC4(CCN(c5ccc([C@@H]6c7ccc(O)cc7CC[C@@H]6c6ccccc6)cc5)CC4)C3)cc2)c2cc[nH]c2c1=O] |

TABLE 1-continued
| Compound No. | Structure |
| --- | --- |
| I-49 | 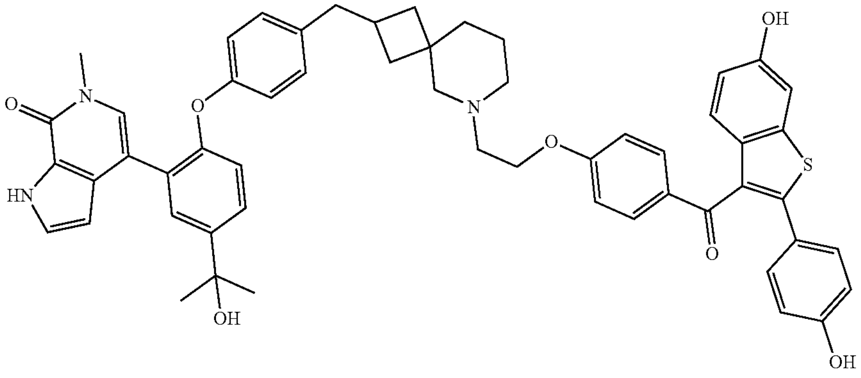 [SMILES: Cn1cc(-c2cc(C(C)(C)O)ccc2Oc2ccc(CC3CC4(CCCN(CCOc5ccc(C(=O)c6c(-c7ccc(O)cc7)sc7cc(O)ccc67)cc5)C4)C3)cc2)c2cc[nH]c2c1=O] |
| I-50 | 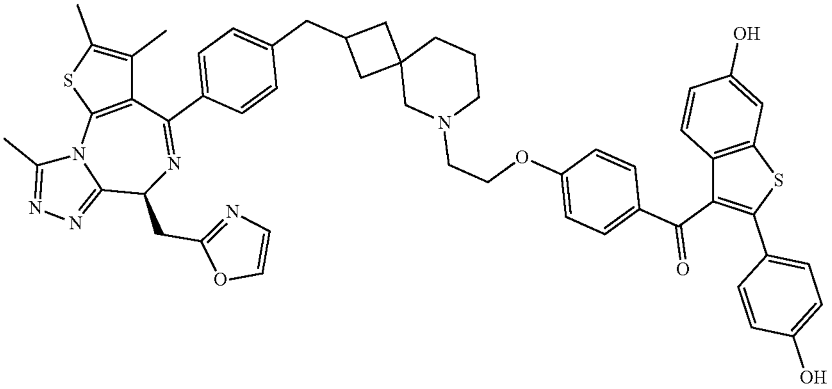 [SMILES: Cc1sc2c(c1C)C(c1ccc(CC3CC4(CCCN(CCOc5ccc(C(=O)c6c(-c7ccc(O)cc7)sc7cc(O)ccc67)cc5)C4)C3)cc1)=N[C@@H](Cc1ncco1)c1nnc(C)n1-2] |
| I-51 | 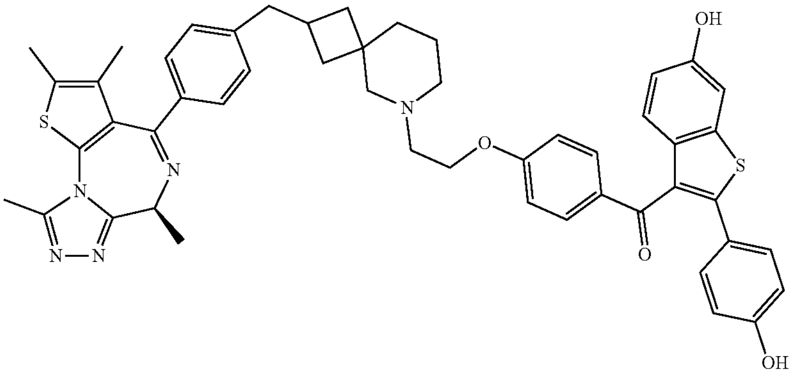 [SMILES: Cc1sc2c(c1C)C(c1ccc(CC3CC4(CCCN(CCOc5ccc(C(=O)c6c(-c7ccc(O)cc7)sc7cc(O)ccc67)cc5)C4)C3)cc1)=N[C@@H](C)c1nnc(C)n1-2] |
| I-52 | 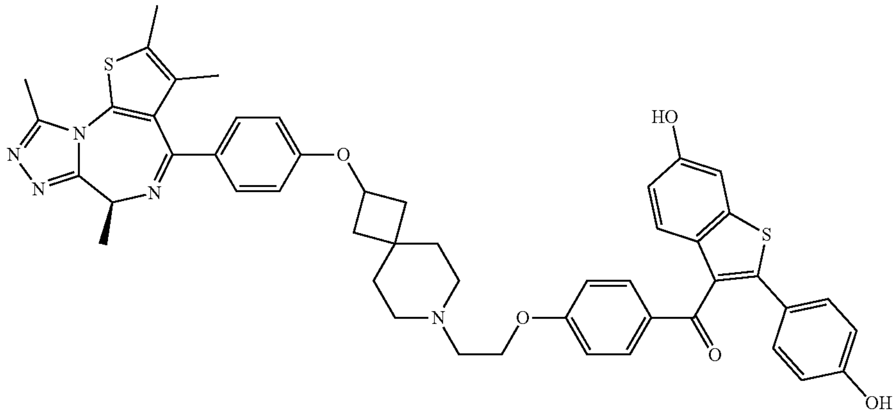 [SMILES: Cc1sc2c(c1C)C(c1ccc(OC3CC4(CCN(CCOc5ccc(C(=O)c6c(-c7ccc(O)cc7)sc7cc(O)ccc67)cc5)CC4)C3)cc1)=N[C@@H](C)c1nnc(C)n1-2] |

TABLE 1-continued
| Compound No. | Structure |
|---|---|
| I-53 | 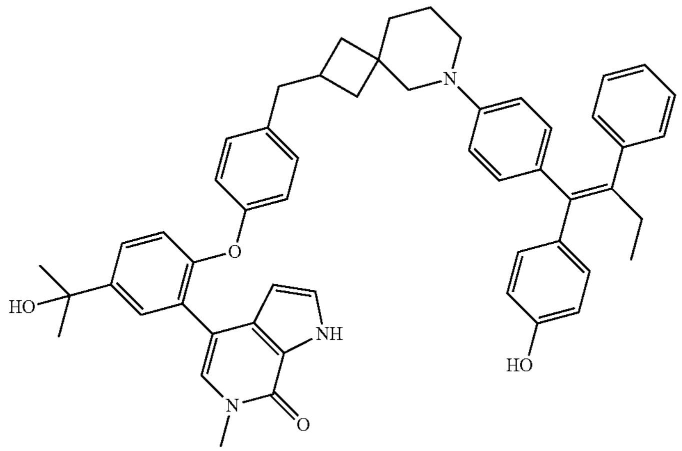 [SMILES: CC/C(=C(\c1ccc(O)cc1)c1ccc(N2CCCC3(CC(Cc4ccc(Oc5ccc(C(C)(C)O)cc5-c5cn(C)c(=O)c6[nH]ccc56)cc4)C3)C2)cc1)c1ccccc1] |
| I-54 | 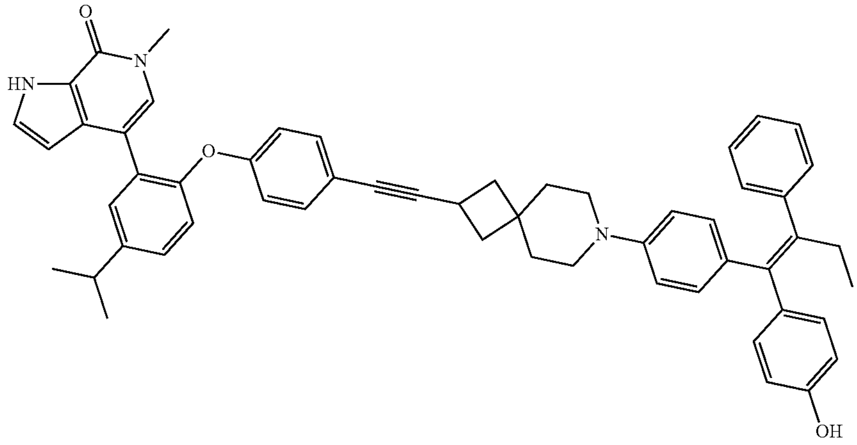 [SMILES: CC/C(=C(\c1ccc(O)cc1)c1ccc(N2CCC3(CC2)CC(C#Cc2ccc(Oc4ccc(C(C)C)cc4-c4cn(C)c(=O)c5[nH]ccc45)cc2)C3)cc1)c1ccccc1] |
| I-55 | 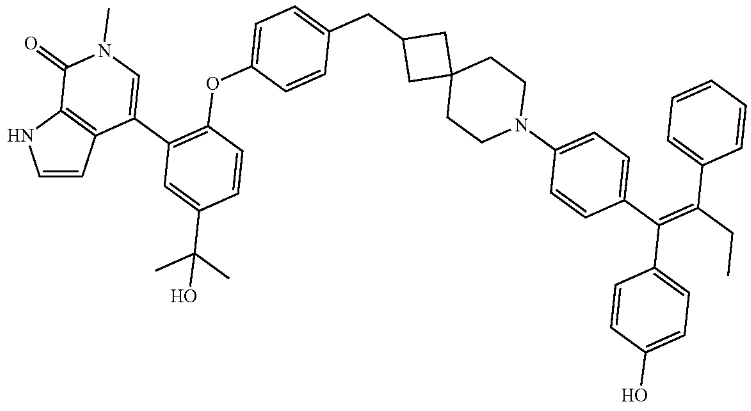 [SMILES: CC/C(=C(\c1ccc(O)cc1)c1ccc(N2CCC3(CC2)CC(Cc2ccc(Oc4ccc(C(C)(C)O)cc4-c4cn(C)c(=O)c5[nH]ccc45)cc2)C3)cc1)c1ccccc1] |

TABLE 1-continued
| Compound No. | Structure |
| --- | --- |
| I-56 | 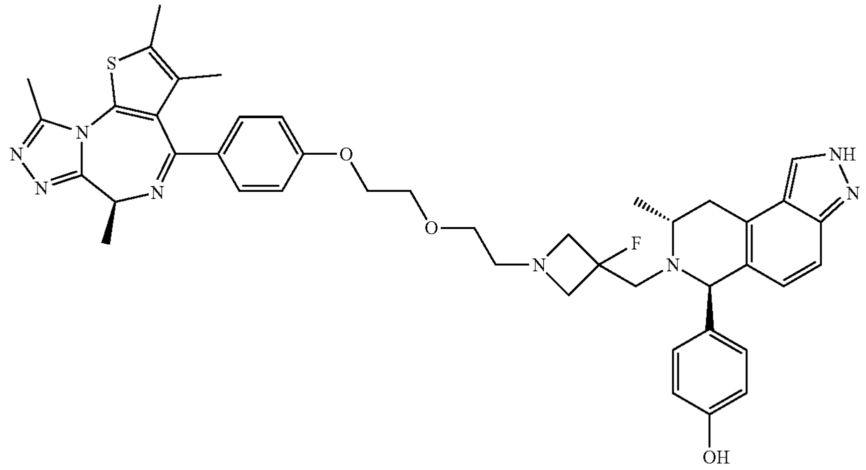 [SMILES: Cc1sc2c(c1C)C(c1ccc(OCCOCCN3CC(F)(CN4[C@H](c5ccc(O)cc5)c5ccc6n[nH]cc6c5C[C@H]4C)C3)cc1)=N[C@@H](C)c1nnc(C)n1-2] |
| I-57 | 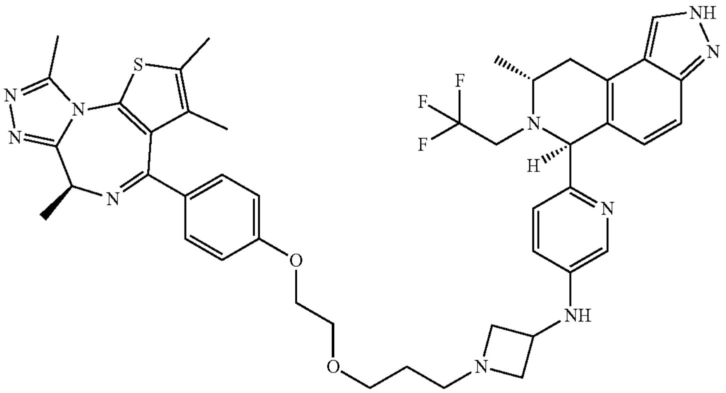 [SMILES: Cc1sc2c(c1C)C(c1ccc(OCCOCCCN3CC(Nc4ccc([C@@H]5c6ccc7n[nH]cc7c6C[C@@H](C)N5CC(F)(F)F)nc4)C3)cc1)=N[C@@H](C)c1nnc(C)n1-2] |
| I-58 | 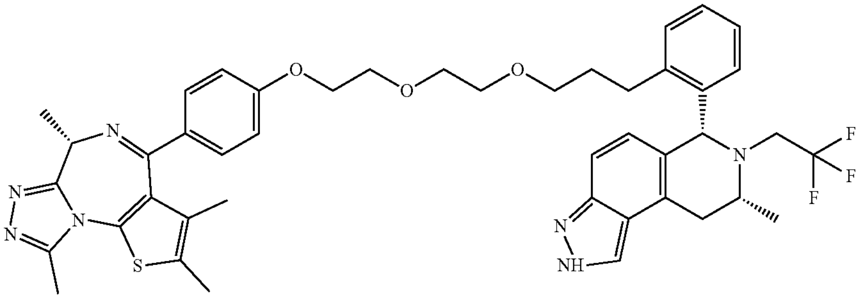 [SMILES: Cc1sc2c(c1C)C(c1ccc(OCCOCCOCCCc3ccccc3[C@H]3c4ccc5n[nH]cc5c4C[C@@H](C)N3CC(F)(F)F)cc1)=N[C@@H](C)c1nnc(C)n1-2] |
| I-59 | 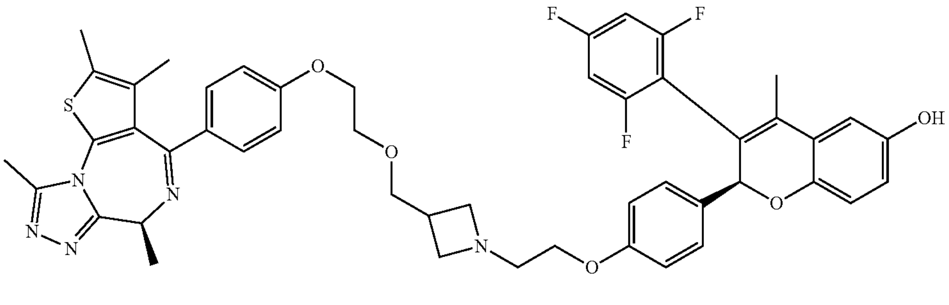 [SMILES: CC1=C(c2c(F)cc(F)cc2F)[C@H](c2ccc(OCCN3CC(COCCOc4ccc(C5=N[C@@H](C)c6nnc(C)n6-c6sc(C)c(C)c65)cc4)C3)cc2)Oc2ccc(O)cc21] |

TABLE 1-continued
| Compound No. | Structure |
| --- | --- |
| I-60 | 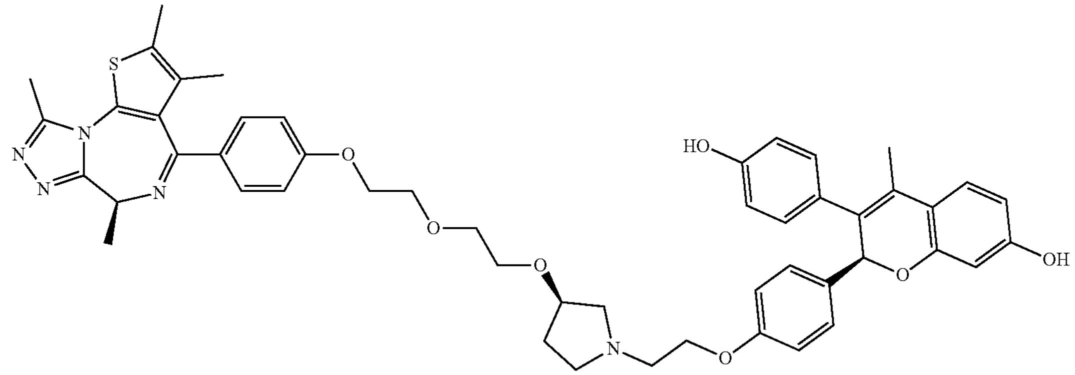 [SMILES: CC1=C(c2ccc(O)cc2)[C@H](c2ccc(OCCN3CC[C@@H](OCCOCCOc4ccc(C5=N[C@@H](C)c6nnc(C)n6-c6sc(C)c(C)c65)cc4)C3)cc2)Oc2cc(O)ccc21] |
| I-61 | 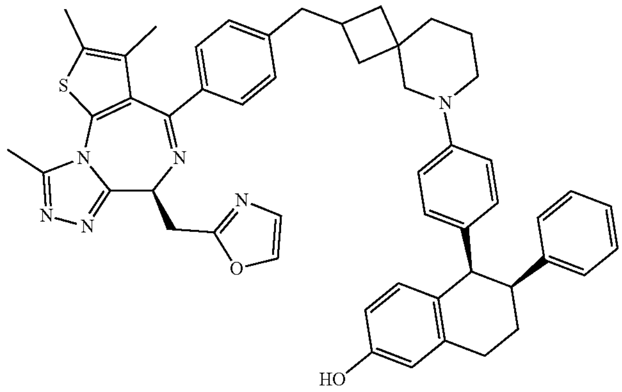 [SMILES: Cc1sc2c(c1C)C(c1ccc(CC3CC4(CCCN(c5ccc([C@@H]6c7ccc(O)cc7CC[C@@H]6c6ccccc6)cc5)C4)C3)cc1)=N[C@@H](Cc1ncco1)c1nnc(C)n1-2] |
| I-62 | 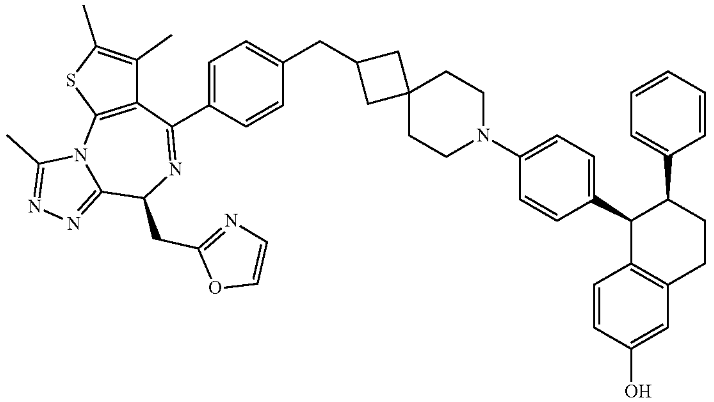 [SMILES: Cc1sc2c(c1C)C(c1ccc(CC3CC4(CCN(c5ccc([C@@H]6c7ccc(O)cc7CC[C@@H]6c6ccccc6)cc5)CC4)C3)cc1)=N[C@@H](Cc1ncco1)c1nnc(C)n1-2] |
| I-63 | 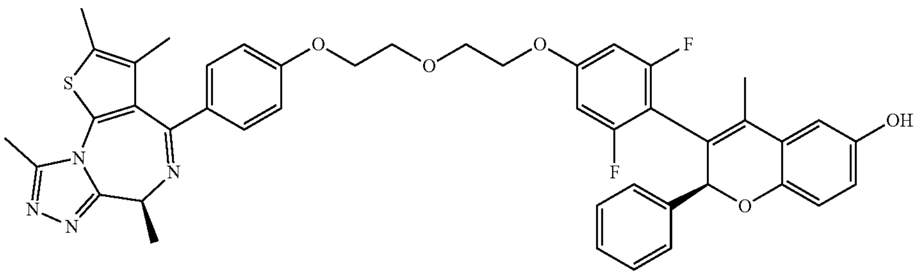 [SMILES: CC1=C(c2c(F)cc(OCCOCCOc3ccc(C4=N[C@@H](C)c5nnc(C)n5-c5sc(C)c(C)c54)cc3)cc2F)[C@H](c2ccccc2)Oc2ccc(O)cc21] |

TABLE 1-continued
| Compound No. | Structure |
|---|---|
| I-64 | 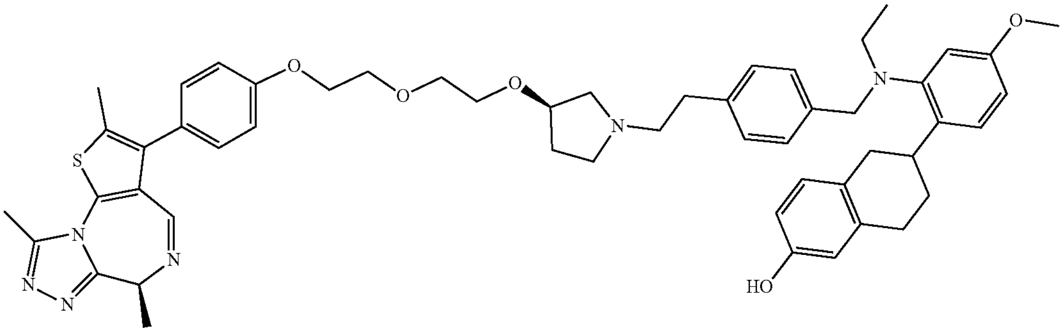 |
| I-65 | 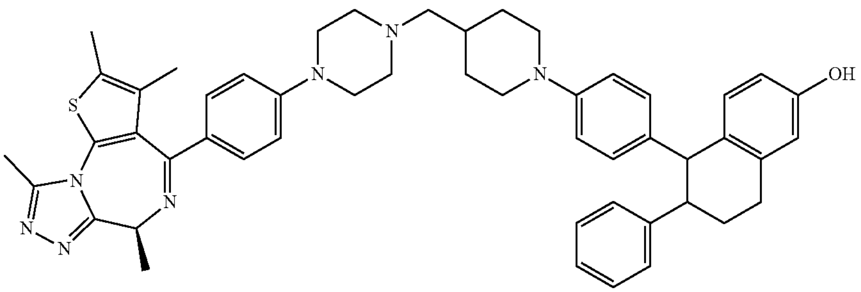 [SMILES: Cc1sc2c(c1C)C(c1ccc(N3CCN(CC4CCN(c5ccc(C6c7ccc(O)cc7CCC6c6ccccc6)cc5)CC4)CC3)cc1)=N[C@@H](C)c1nnc(C)n1-2] |
| I-66 | 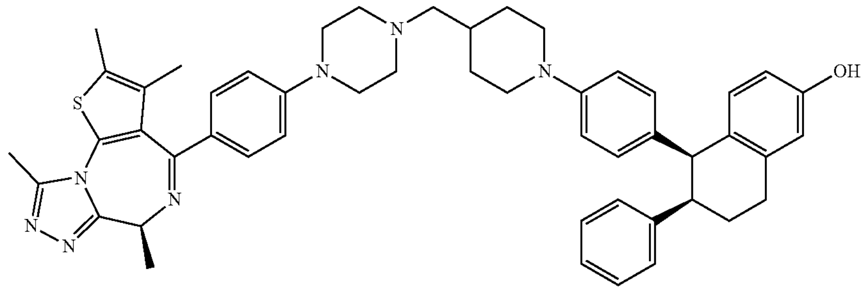 [SMILES: Cc1sc2c(c1C)C(c1ccc(N3CCN(CC4CCN(c5ccc([C@H]6c7ccc(O)cc7CC[C@H]6c6ccccc6)cc5)CC4)CC3)cc1)=N[C@@H](C)c1nnc(C)n1-2] |
| I-67 | 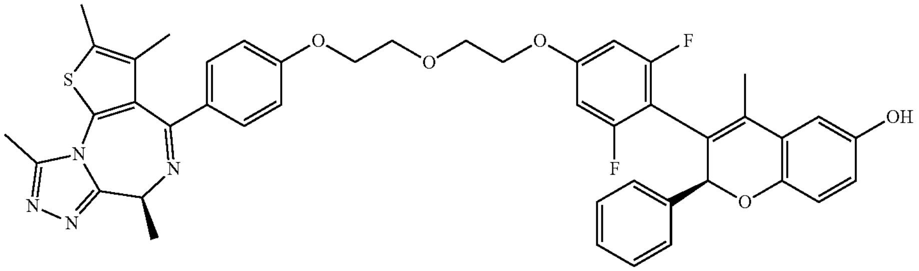 [SMILES: CC1=C(c2c(F)cc(OCCOCCOc3ccc(C4=N[C@@H](C)c5nnc(C)n5-c5sc(C)c(C)c54)cc3)cc2F)[C@H](c2ccccc2)Oc2ccc(O)cc21] |

In certain embodiments, the compound is a compound in Table 2, or a pharmaceutically acceptable salt thereof. In certain embodiments, the compound is a compound in Table 2.
TABLE 2
| Compound No. | Structure |
|---|---|
| II-1 | 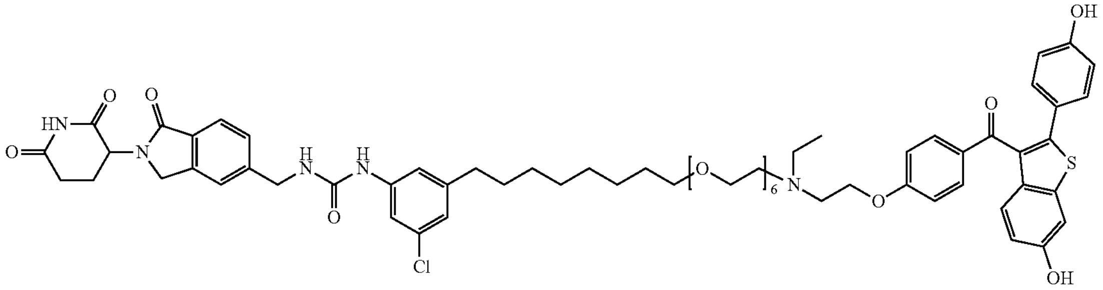 |
| II-2 | 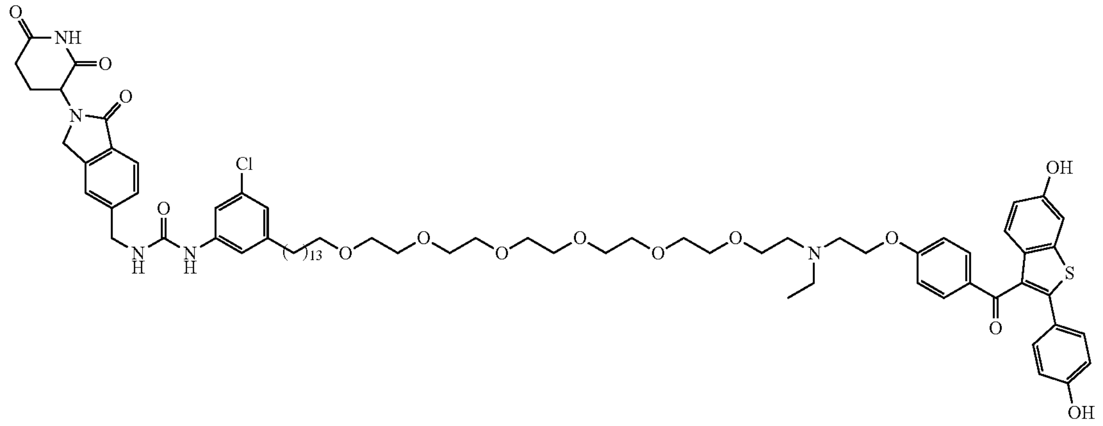 |
| II-3 | 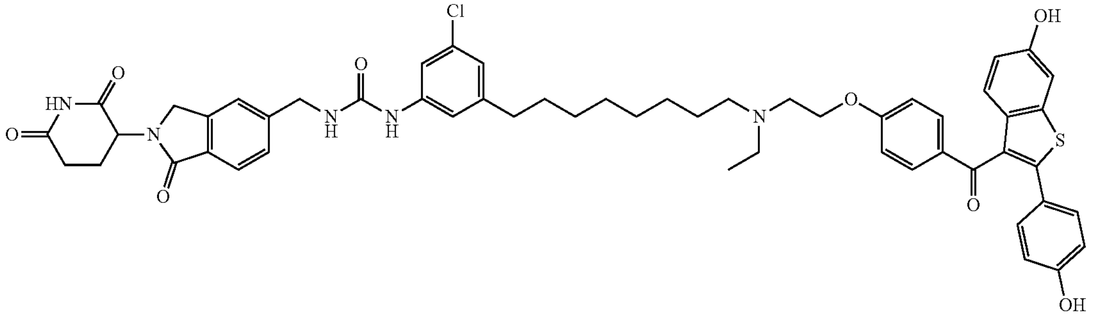 [SMILES: CCN(CCCCCCCCc1cc(Cl)cc(NC(=O)NCc2ccc3c(c2)CN(C2CCC(=O)NC2=O)C3=O)c1)CCOc1ccc(C(=O)c2c(-c3ccc(O)cc3)sc3cc(O)ccc23)cc1] |
| II-4 | 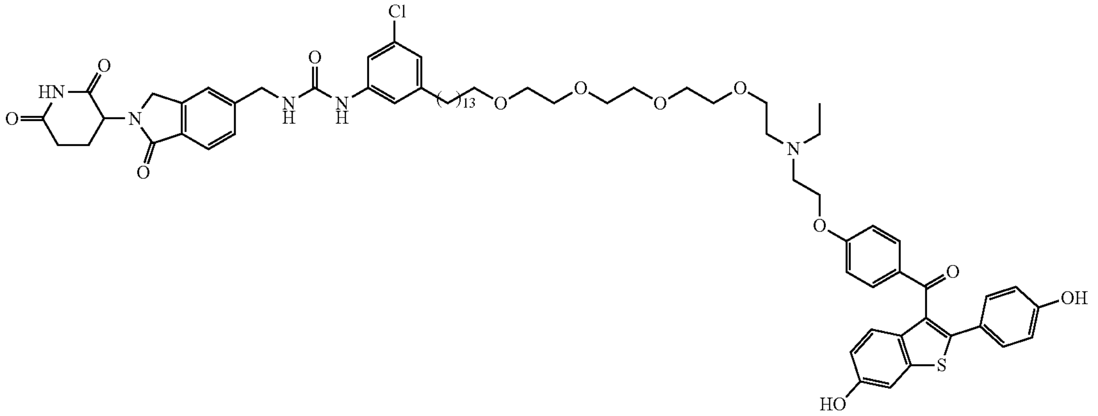 |

TABLE 2-continued
| Compound No. | Structure |
|---|---|
| II-5 | 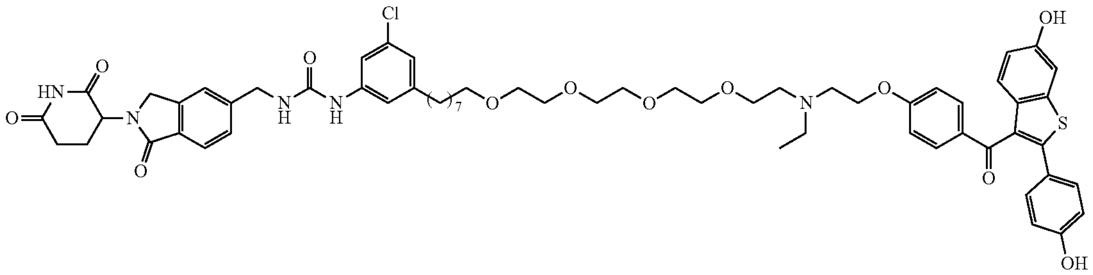 |
In certain embodiments, the compound is a compound in Table 3, or a pharmaceutically acceptable salt thereof. In certain embodiments, the compound is a compound in Table 3.
TABLE 3
| Compound No. | Compound Structure |
|---|---|
| III-1 | 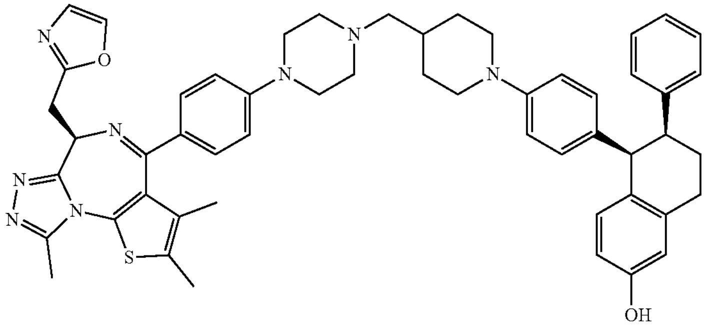 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@H](Cc1ncco1)c1nnc(C)n1-2] |
| III-2 | 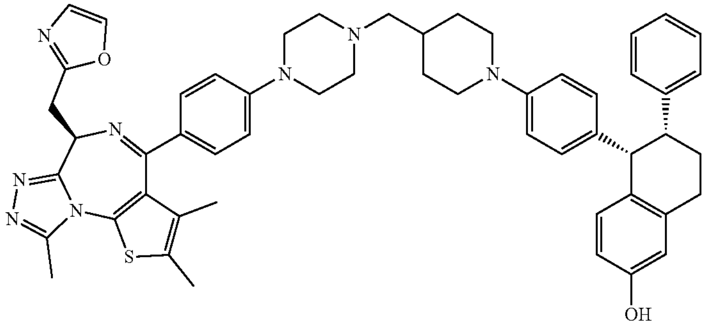 |
| III-3 | 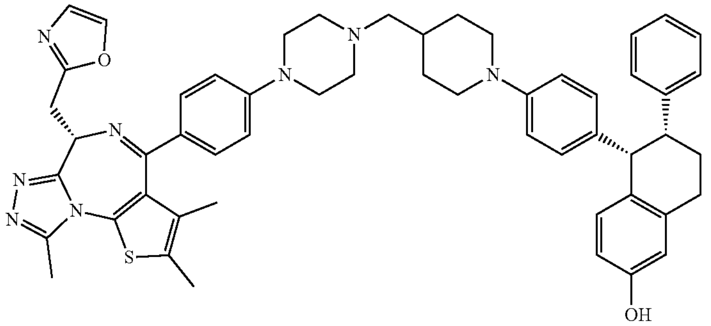 |

TABLE 3-continued
| Compound No. | Compound Structure |
|---|---|
| III-4 | 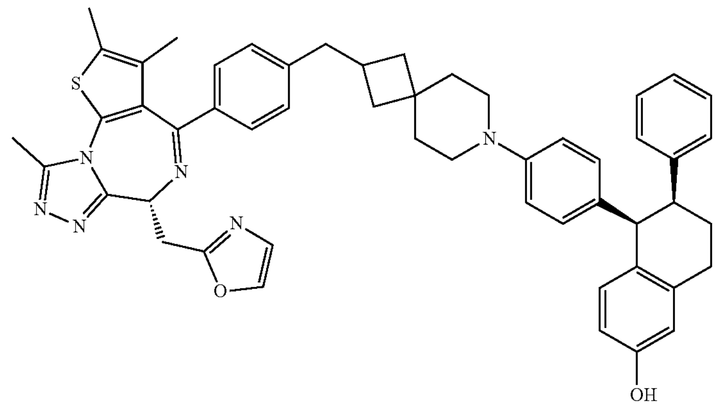 [SMILES: Cc1sc2c(c1C)C(c1ccc(CC3CC4(CCN(c5ccc([C@@H]6c7ccc(O)cc7CC[C@@H]6c6ccccc6)cc5)CC4)C3)cc1)=N[C@H](Cc1ncco1)c1nnc(C)n1-2] |
| III-5 | 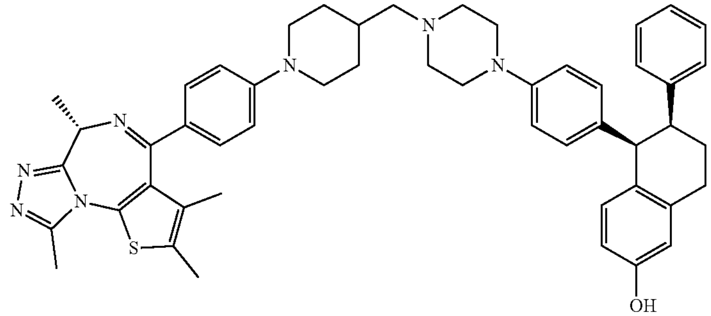 |
| III-6 | 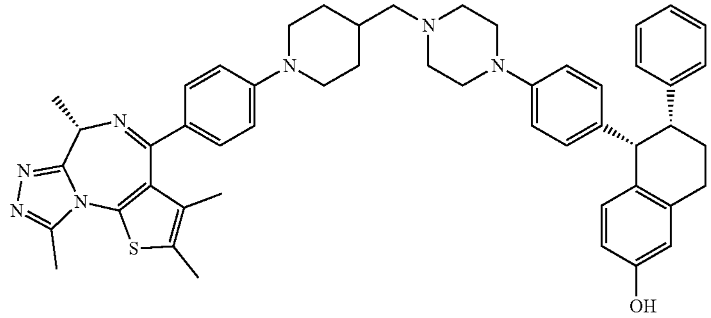 [SMILES: Cc1sc2c(c1C)C(c1ccc(N3CCC(CN4CCN(c5ccc([C@H]6c7ccc(O)cc7CC[C@H]6c6ccccc6)cc5)CC4)CC3)cc1)=N[C@@H](C)c1nnc(C)n1-2] |
| III-7 | 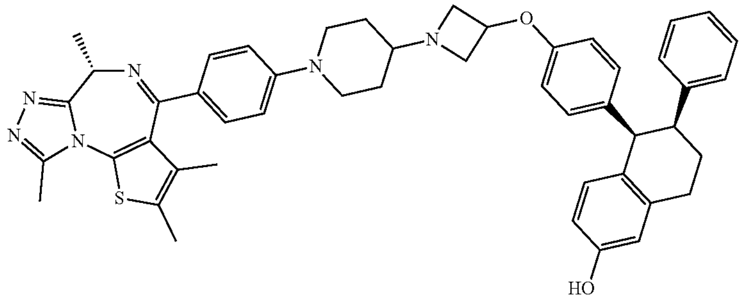 [SMILES: Cc1sc2c(c1C)C(c1ccc(N3CCC(N4CC(Oc5ccc([C@@H]6c7ccc(O)cc7CC[C@@H]6c6ccccc6)cc5)C4)CC3)cc1)=N[C@@H](C)c1nnc(C)n1-2] |

TABLE 3-continued
| Compound No. | Compound Structure |
|---|---|
| III-8 | 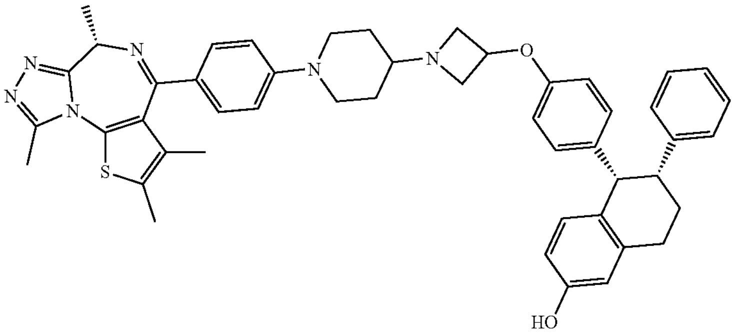 [SMILES: Cc1sc2c(c1C)C(c1ccc(N3CCC(N4CC(Oc5ccc([C@H]6c7ccc(O)cc7CC[C@H]6c6ccccc6)cc5)C4)CC3)cc1)=N[C@@H](C)c1nnc(C)n1-2] |
| III-9 | 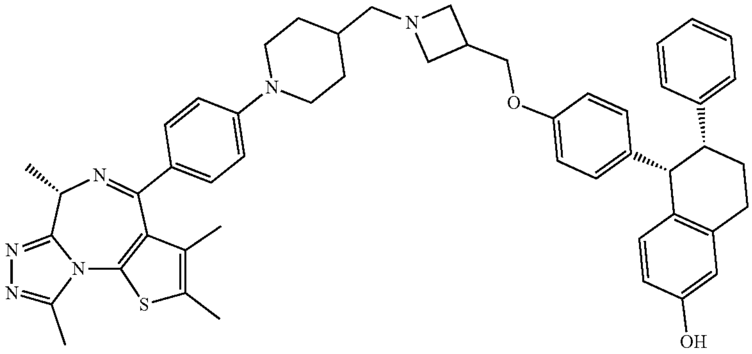 [SMILES: Cc1sc2c(c1C)C(c1ccc(N3CCC(CN4CC(COc5ccc([C@H]6c7ccc(O)cc7CC[C@H]6c6ccccc6)cc5)C4)CC3)cc1)=N[C@@H](C)c1nnc(C)n1-2] |
| III-10 | 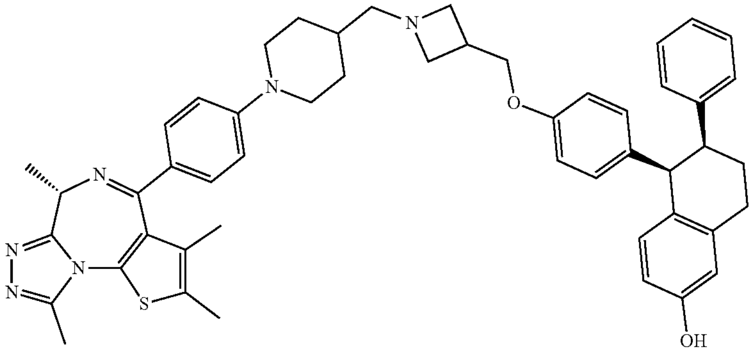 [SMILES: Cc1sc2c(c1C)C(c1ccc(N3CCC(CN4CC(COc5ccc([C@@H]6c7ccc(O)cc7CC[C@@H]6c6ccccc6)cc5)C4)CC3)cc1)=N[C@@H](C)c1nnc(C)n1-2] |
| III-11 | 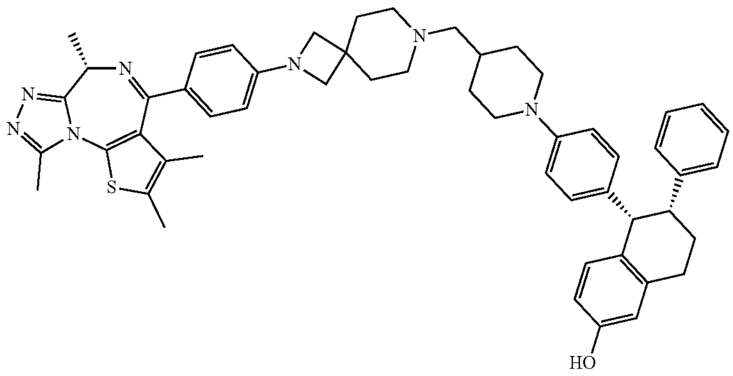 [SMILES: Cc1sc2c(c1C)C(c1ccc(N3CC4(CCN(CC5CCN(c6ccc([C@H]7c8ccc(O)cc8CC[C@H]7c7ccccc7)cc6)CC5)CC4)C3)cc1)=N[C@@H](C)c1nnc(C)n1-2] |

TABLE 3-continued
| Compound No. | Compound Structure |
| --- | --- |
| III-12 | 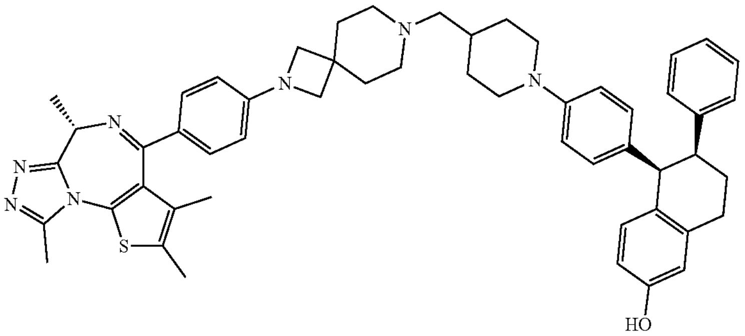 [SMILES: Cc1sc2c(c1C)C(c1ccc(N3CC4(CCN(CC5CCN(c6ccc([C@@H]7c8ccc(O)cc8CC[C@@H]7c7ccccc7)cc6)CC5)CC4)C3)cc1)=N[C@@H](C)c1nnc(C)n1-2] |
| III-13 | 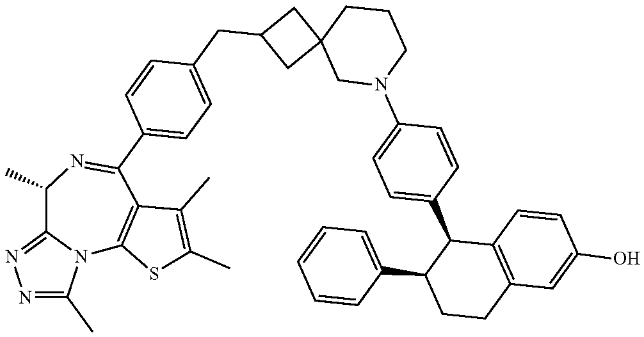 [SMILES: Cc1sc2c(c1C)C(c1ccc(CC3CC4(CCCN(c5ccc([C@H]6c7ccc(O)cc7CC[C@H]6c6ccccc6)cc5)C4)C3)cc1)=N[C@@H](C)c1nnc(C)n1-2] |
| III-14 | 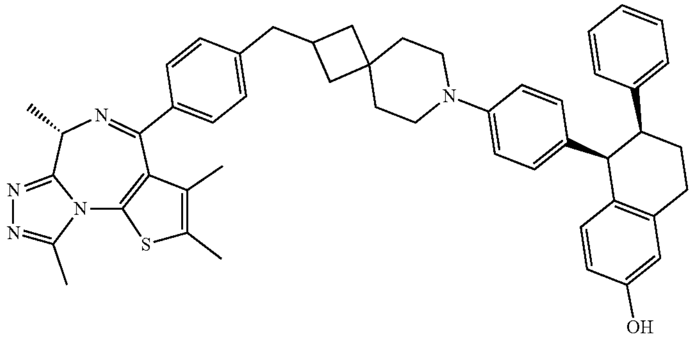 [SMILES: Cc1sc2c(c1C)C(c1ccc(CC3CC4(CCN(c5ccc([C@@H]6c7ccc(O)cc7CC[C@@H]6c6ccccc6)cc5)CC4)C3)cc1)=N[C@@H](C)c1nnc(C)n1-2] |
| III-15 | 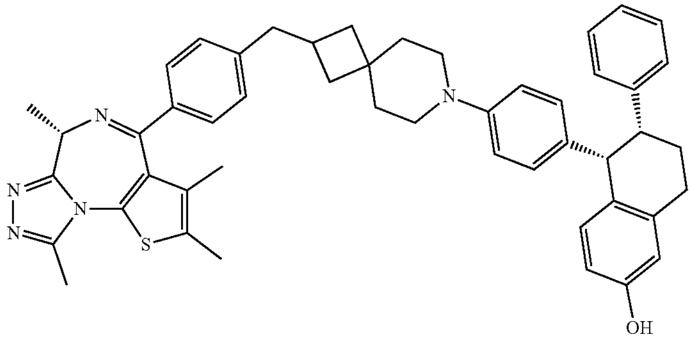 [SMILES: Cc1sc2c(c1C)C(c1ccc(CC3CC4(CCN(c5ccc([C@H]6c7ccc(O)cc7CC[C@H]6c6ccccc6)cc5)CC4)C3)cc1)=N[C@@H](C)c1nnc(C)n1-2] |

TABLE 3-continued
| Compound No. | Compound Structure |
|---|---|
| III-16 | 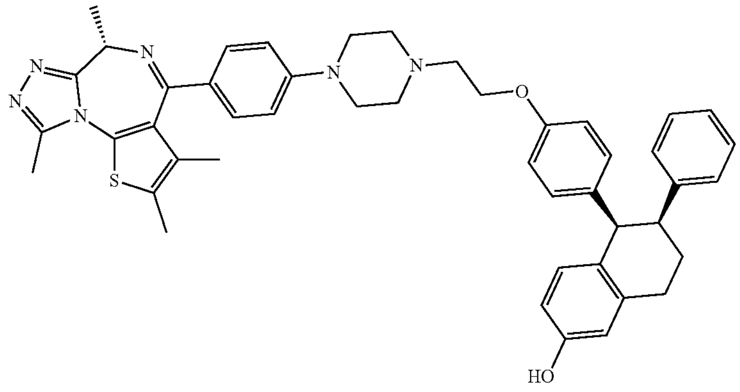 [SMILES: Cc1sc2c(c1C)C(c1ccc(N3CCN(CCOc4ccc([C@@H]5c6ccc(O)cc6CC[C@@H]5c5ccccc5)cc4)CC3)cc1)=N[C@@H](C)c1nnc(C)n1-2] |
| III-17 | 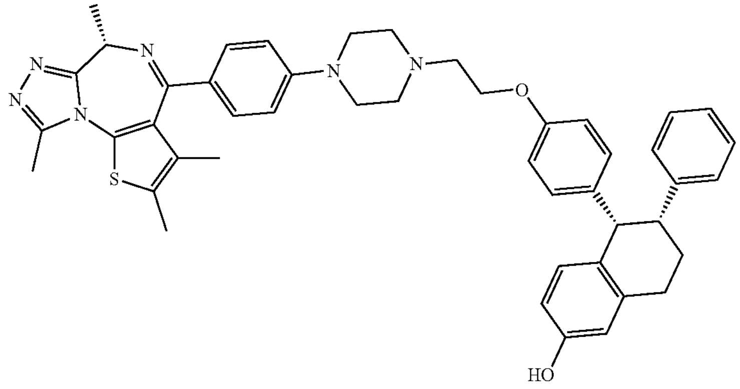 [SMILES: Cc1sc2c(c1C)C(c1ccc(N3CCN(CCOc4ccc([C@H]5c6ccc(O)cc6CC[C@H]5c5ccccc5)cc4)CC3)cc1)=N[C@@H](C)c1nnc(C)n1-2] |
| III-18 | 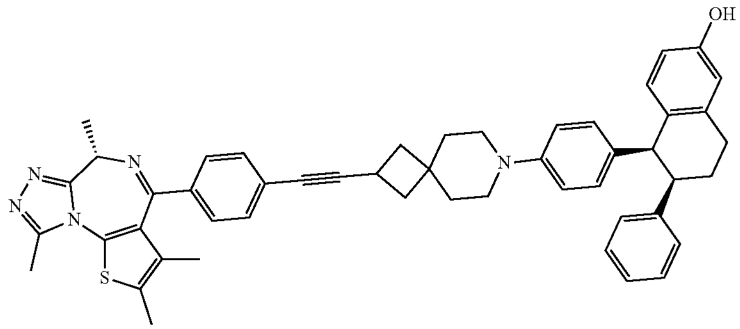 [SMILES: Cc1sc2c(c1C)C(c1ccc(C#CC3CC4(CCN(c5ccc([C@H]6c7ccc(O)cc7CC[C@H]6c6ccccc6)cc5)CC4)C3)cc1)=N[C@@H](C)c1nnc(C)n1-2] |
| III-19 | 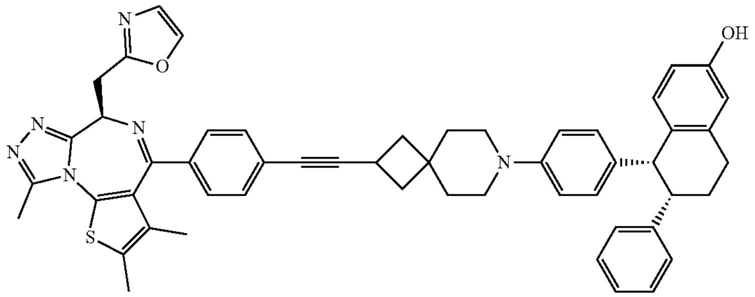 [SMILES: Cc1sc2c(c1C)C(c1ccc(C#CC3CC4(CCN(c5ccc([C@@H]6c7ccc(O)cc7CC[C@@H]6c6ccccc6)cc5)CC4)C3)cc1)=N[C@H](Cc1ncco1)c1nnc(C)n1-2] |

TABLE 3-continued
| Compound No. | Compound Structure |
|---|---|
| III-20 | 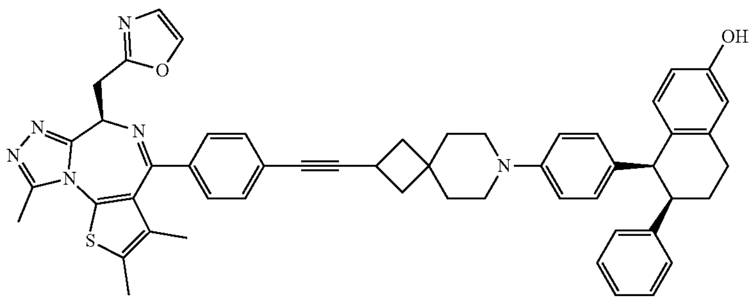 [SMILES: Cc1sc2c(c1C)C(c1ccc(C#CC3CC4(CCN(c5ccc([C@H]6c7ccc(O)cc7CC[C@H]6c6ccccc6)cc5)CC4)C3)cc1)=N[C@H](Cc1ncco1)c1nnc(C)n1-2] |
| III-21 | 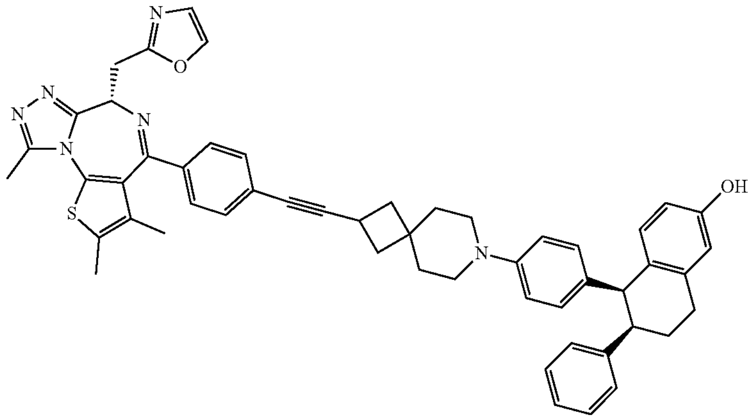 [SMILES: Cc1sc2c(c1C)C(c1ccc(C#CC3CC4(CCN(c5ccc([C@H]6c7ccc(O)cc7CC[C@H]6c6ccccc6)cc5)CC4)C3)cc1)=N[C@@H](Cc1ncco1)c1nnc(C)n1-2] |
| III-22 | 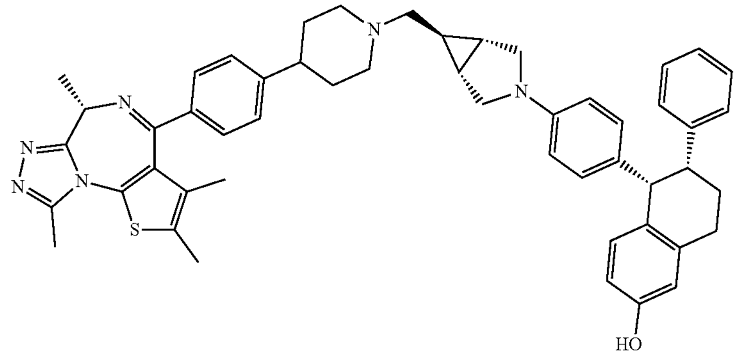 [SMILES: Cc1sc2c(c1C)C(c1ccc(C3CCN(C[C@@H]4[C@H]5CN(c6ccc([C@H]7c8ccc(O)cc8CC[C@H]7c7ccccc7)cc6)C[C@@H]45)CC3)cc1)=N[C@@H](C)c1nnc(C)n1-2] |
| III-23 | 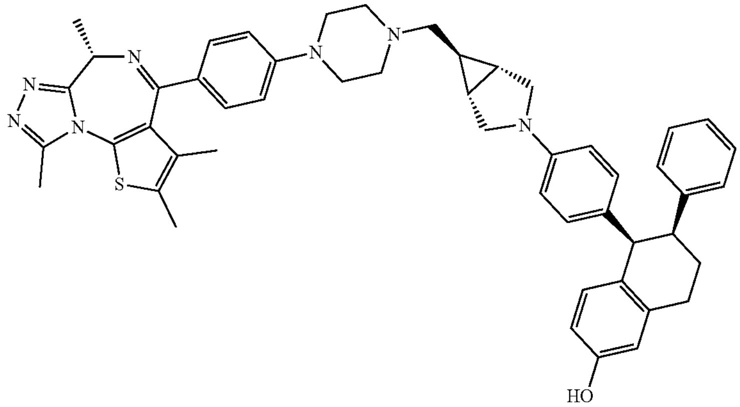 [SMILES: Cc1sc2c(c1C)C(c1ccc(N3CCN(C[C@@H]4[C@H]5CN(c6ccc([C@@H]7c8ccc(O)cc8CC[C@@H]7c7ccccc7)cc6)C[C@@H]45)CC3)cc1)=N[C@@H](C)c1nnc(C)n1-2] |

TABLE 3-continued
| Compound No. | Compound Structure |
| --- | --- |
| III-24 | 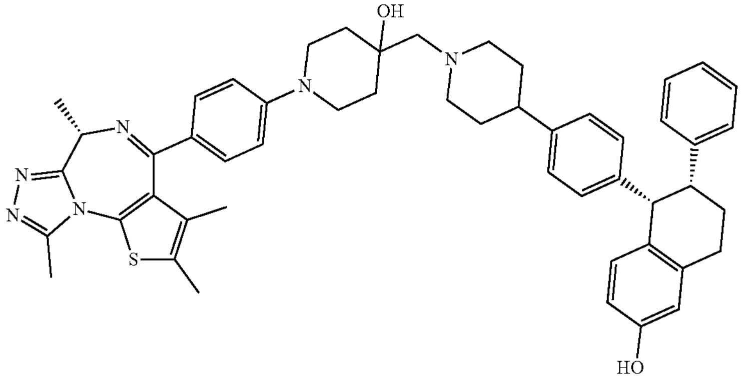 [SMILES: Cc1sc2c(c1C)C(c1ccc(N3CCC(O)(CN4CCC(c5ccc([C@H]6c7ccc(O)cc7CC[C@H]6c6ccccc6)cc5)CC4)CC3)cc1)=N[C@@H](C)c1nnc(C)n1-2] |
| III-25 | 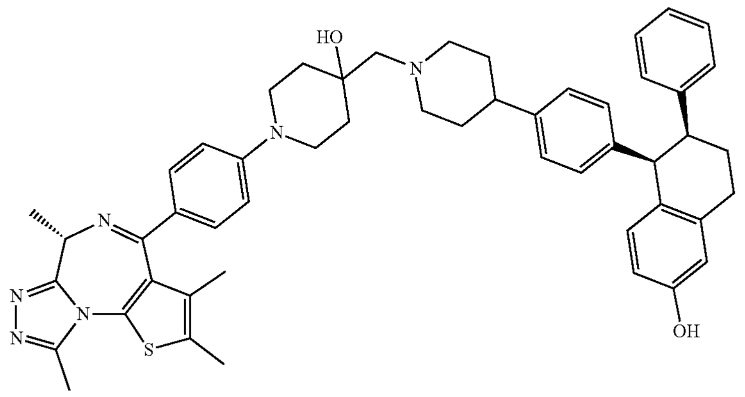 [SMILES: Cc1sc2c(c1C)C(c1ccc(N3CCC(O)(CN4CCC(c5ccc([C@@H]6c7ccc(O)cc7CC[C@@H]6c6ccccc6)cc5)CC4)CC3)cc1)=N[C@@H](C)c1nnc(C)n1-2] |
| III-26 | 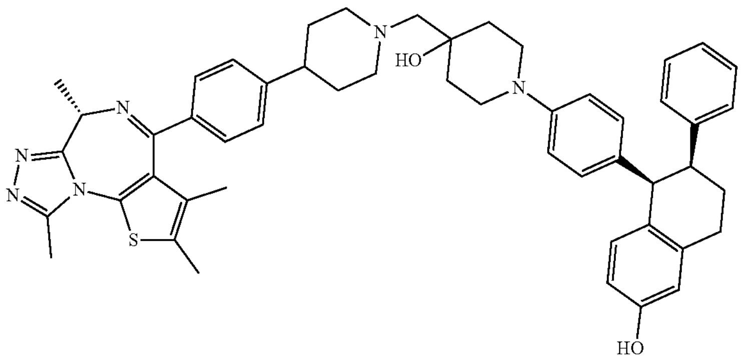 [SMILES: Cc1sc2c(c1C)C(c1ccc(C3CCN(CC4(O)CCN(c5ccc([C@@H]6c7ccc(O)cc7CC[C@@H]6c6ccccc6)cc5)CC4)CC3)cc1)=N[C@@H](C)c1nnc(C)n1-2] |
| III-27 | 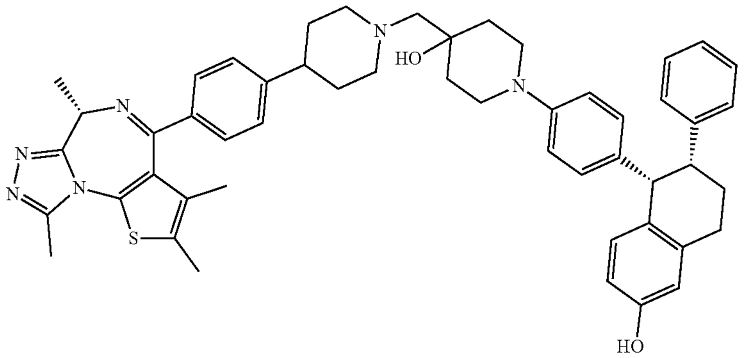 [SMILES: Cc1sc2c(c1C)C(c1ccc(C3CCN(CC4(O)CCN(c5ccc([C@H]6c7ccc(O)cc7CC[C@H]6c6ccccc6)cc5)CC4)CC3)cc1)=N[C@@H](C)c1nnc(C)n1-2] |

TABLE 3-continued
| Compound No. | Compound Structure |
|---|---|
| III-28 | 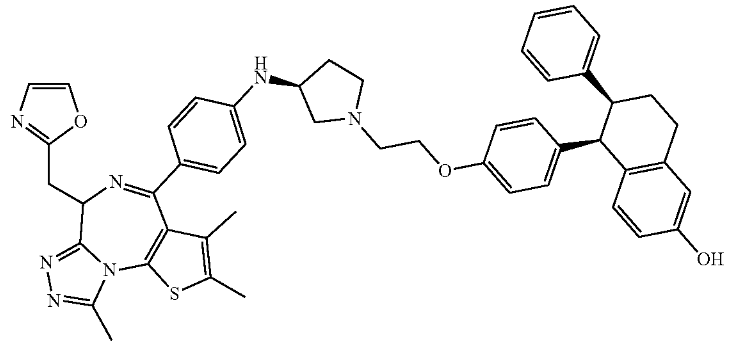 [SMILES: Cc1sc2c(c1C)C(c1ccc(N[C@H]3CCN(CCOc4ccc([C@@H]5c6ccc(O)cc6CC[C@@H]5c5ccccc5)cc4)C3)cc1)=NC(Cc1ncco1)c1nnc(C)n1-2] |
| III-29 | 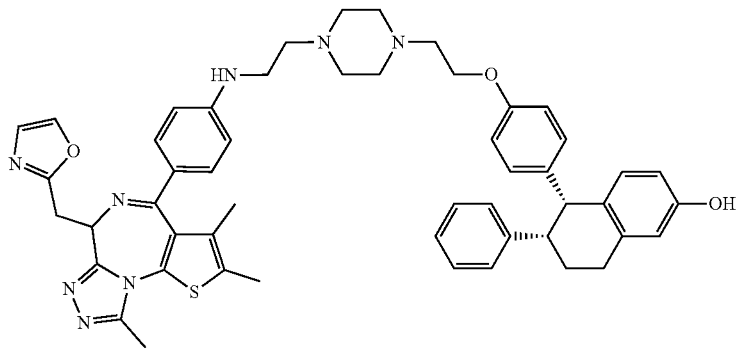 [SMILES: Cc1sc2c(c1C)C(c1ccc(NCCN3CCN(CCOc4ccc([C@@H]5c6ccc(O)cc6CC[C@@H]5c5ccccc5)cc4)CC3)cc1)=NC(Cc1ncco1)c1nnc(C)n1-2] |
| III-30 | 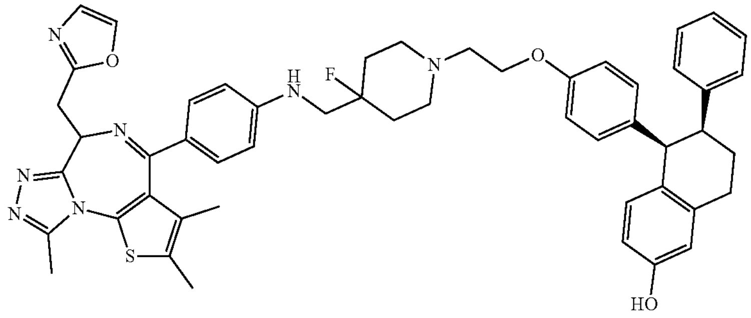 [SMILES: Cc1sc2c(c1C)C(c1ccc(NCC3(F)CCN(CCOc4ccc([C@@H]5c6ccc(O)cc6CC[C@@H]5c5ccccc5)cc4)CC3)cc1)=NC(Cc1ncco1)c1nnc(C)n1-2] |
| III-31 | 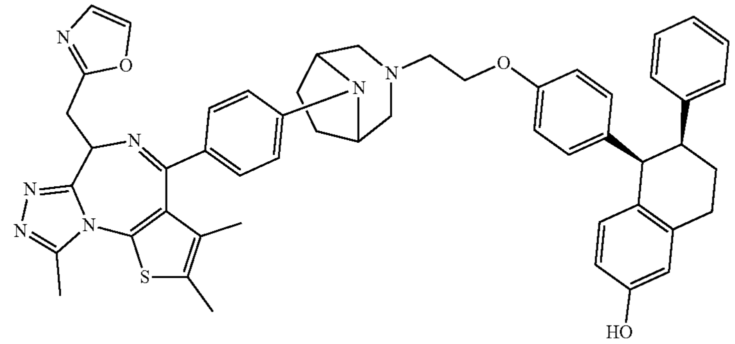 [SMILES: Cc1sc2c(c1C)C(c1ccc(N3C4CCC3CN(CCOc3ccc([C@@H]5c6ccc(O)cc6CC[C@@H]5c5ccccc5)cc3)C4)cc1)=NC(Cc1ncco1)c1nnc(C)n1-2] |

TABLE 3-continued
| Compound No. | Compound Structure |
|---|---|
| III-32 | 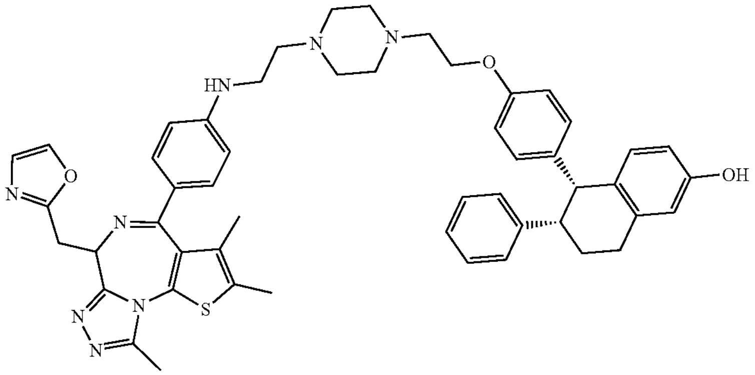 [SMILES: Cc1sc2c(c1C)C(c1ccc(NCCN3CCN(CCOc4ccc([C@@H]5c6ccc(O)cc6CC[C@@H]5c5ccccc5)cc4)CC3)cc1)=NC(Cc1ncco1)c1nnc(C)n1-2] |
| III-33 | 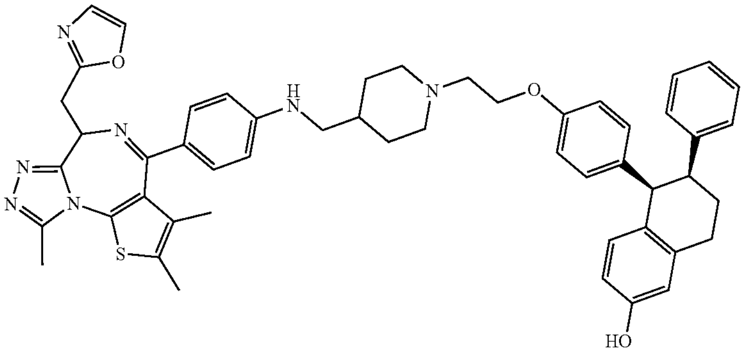 [SMILES: Cc1sc2c(c1C)C(c1ccc(NCC3CCN(CCOc4ccc([C@@H]5c6ccc(O)cc6CC[C@@H]5c5ccccc5)cc4)CC3)cc1)=NC(Cc1ncco1)c1nnc(C)n1-2] |
| III-34 | 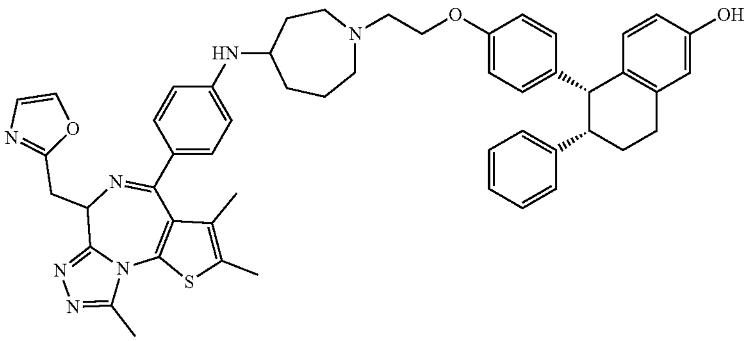 [SMILES: Cc1sc2c(c1C)C(c1ccc(NC3CCCN(CCOc4ccc([C@@H]5c6ccc(O)cc6CC[C@@H]5c5ccccc5)cc4)CC3)cc1)=NC(Cc1ncco1)c1nnc(C)n1-2] |
| III-35 | 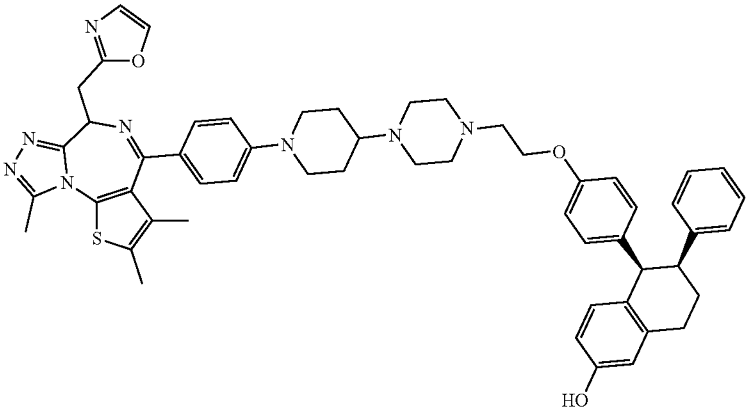 |

TABLE 3-continued
| Compound No. | Compound Structure |
|---|---|
| III-36 | 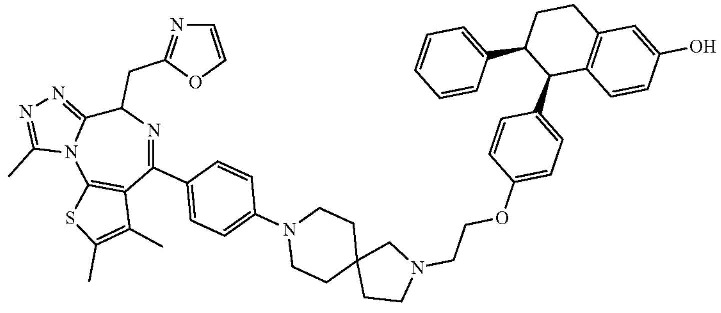 [SMILES: Cc1sc2c(c1C)C(c1ccc(N3CCC4(CCN(CCOc5ccc([C@@H]6c7ccc(O)cc7CC[C@@H]6c6ccccc6)cc5)C4)CC3)cc1)=NC(Cc1ncco1)c1nnc(C)n1-2] |
| III-37 | 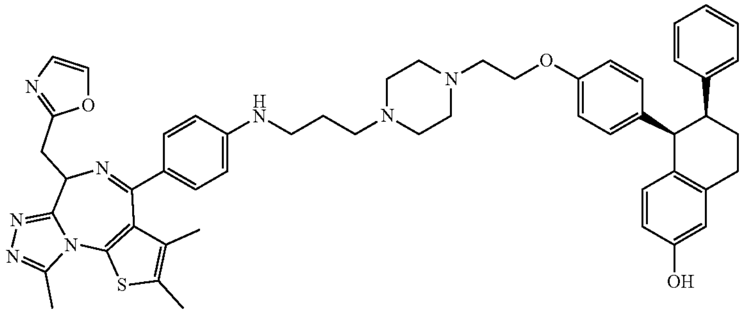 [SMILES: Cc1sc2c(c1C)C(c1ccc(NCCCN3CCN(CCOc4ccc([C@@H]5c6ccc(O)cc6CC[C@@H]5c5ccccc5)cc4)CC3)cc1)=NC(Cc1ncco1)c1nnc(C)n1-2] |
| III-38 | 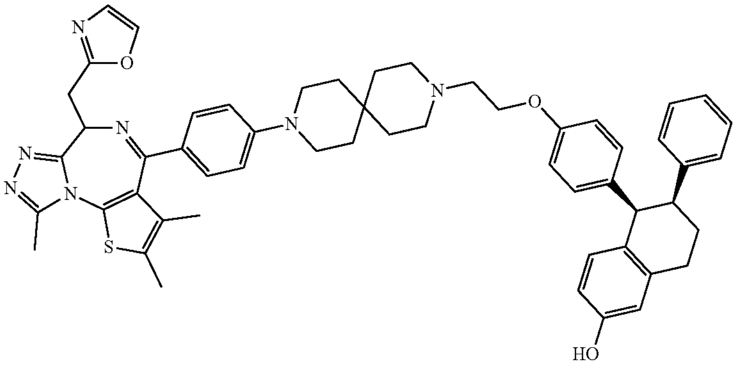 [SMILES: Cc1sc2c(c1C)C(c1ccc(N3CCC4(CCN(CCOc5ccc([C@@H]6c7ccc(O)cc7CC[C@@H]6c6ccccc6)cc5)CC4)CC3)cc1)=NC(Cc1ncco1)c1nnc(C)n1-2] |
| III-39 | 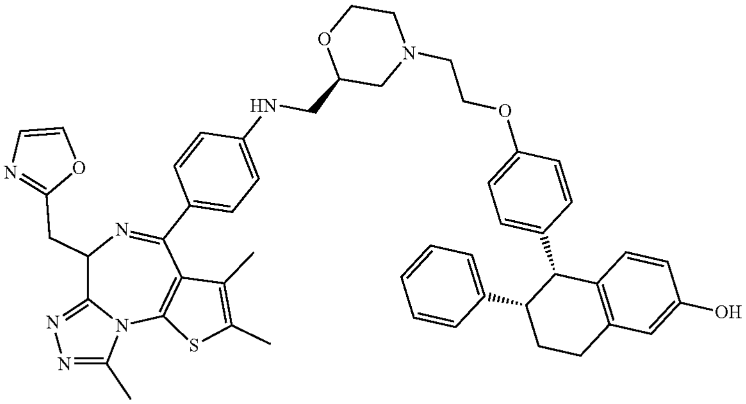 [SMILES: Cc1sc2c(c1C)C(c1ccc(NC[C@@H]3CN(CCOc4ccc([C@@H]5c6ccc(O)cc6CC[C@@H]5c5ccccc5)cc4)CCO3)cc1)=NC(Cc1ncco1)c1nnc(C)n1-2] |

TABLE 3-continued
| Compound No. | Compound Structure |
|---|---|
| III-40 | 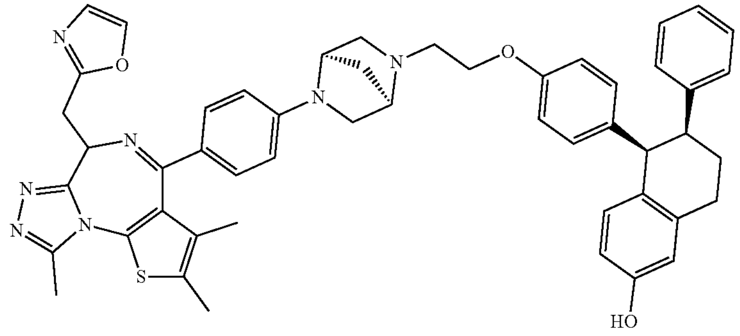 [SMILES: Cc1sc2c(c1C)C(c1ccc(N3C[C@H]4C[C@@H]3CN4CCOc3ccc([C@@H]4c5ccc(O)cc5CC[C@@H]4c4ccccc4)cc3)cc1)=NC(Cc1ncco1)c1nnc(C)n1-2] |
| III-41 | 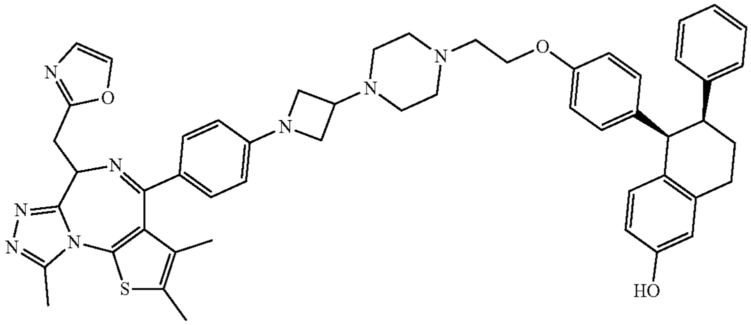 [SMILES: Cc1sc2c(c1C)C(c1ccc(N3CC(N4CCN(CCOc5ccc([C@@H]6c7ccc(O)cc7CC[C@@H]6c6ccccc6)cc5)CC4)C3)cc1)=NC(Cc1ncco1)c1nnc(C)n1-2] |
| III-42 | 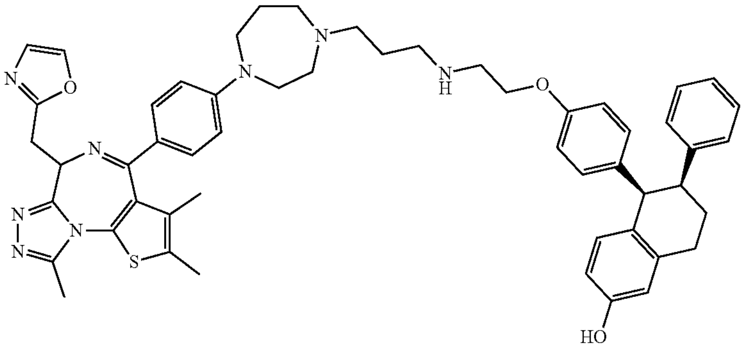 [SMILES: Cc1sc2c(c1C)C(c1ccc(N3CCCN(CCCNCCOc4ccc([C@@H]5c6ccc(O)cc6CC[C@@H]5c5ccccc5)cc4)CC3)cc1)=NC(Cc1ncco1)c1nnc(C)n1-2] |
| III-43 | 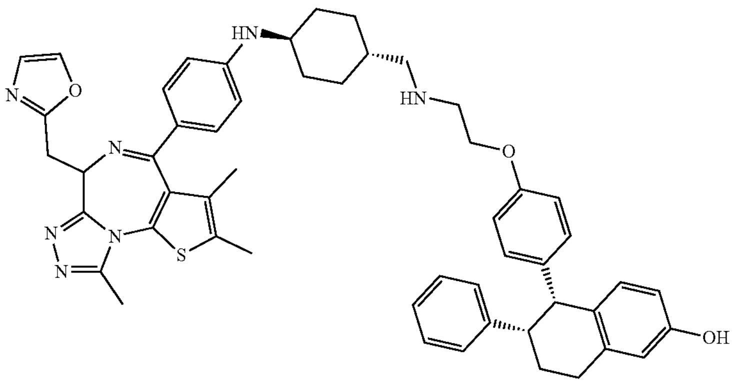 [SMILES: Cc1sc2c(c1C)C(c1ccc(N[C@H]3CC[C@H](CNCCOc4ccc([C@@H]5c6ccc(O)cc6CC[C@@H]5c5ccccc5)cc4)CC3)cc1)=NC(Cc1ncco1)c1nnc(C)n1-2] |

TABLE 3-continued
| Compound No. | Compound Structure |
|---|---|
| III-44 | 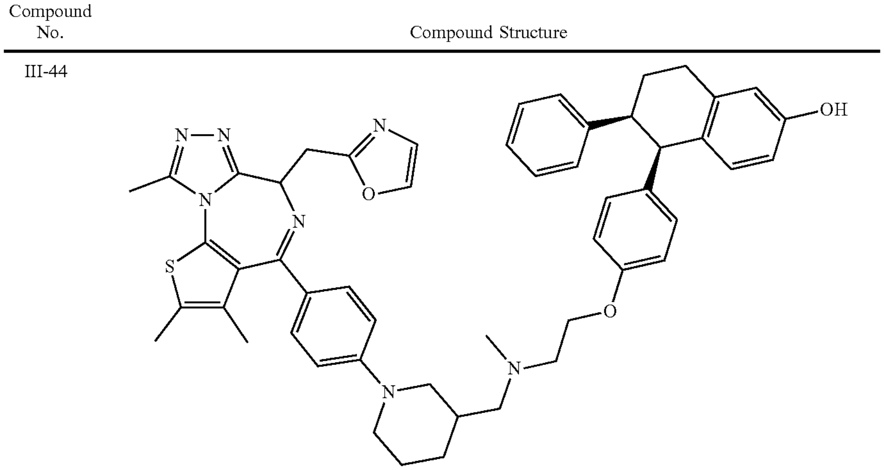 |
| III-45 | 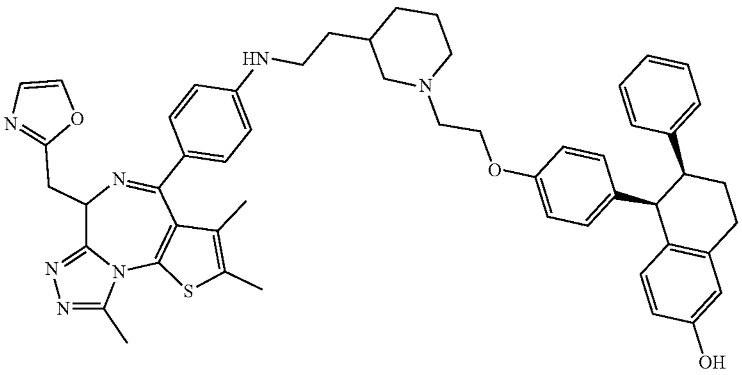 [SMILES: Cc1sc2c(c1C)C(c1ccc(NCCC3CCCN(CCOc4ccc([C@@H]5c6ccc(O)cc6CC[C@@H]5c5ccccc5)cc4)C3)cc1)=NC(Cc1ncco1)c1nnc(C)n1-2] |
| III-46 | 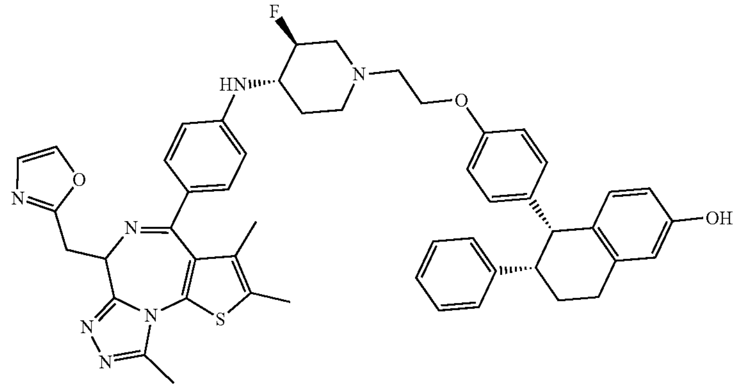 [SMILES: Cc1sc2c(c1C)C(c1ccc(N[C@H]3CCN(CCOc4ccc([C@@H]5c6ccc(O)cc6CC[C@@H]5c5ccccc5)cc4)C[C@@H]3F)cc1)=NC(Cc1ncco1)c1nnc(C)n1-2] |
| III-47 | 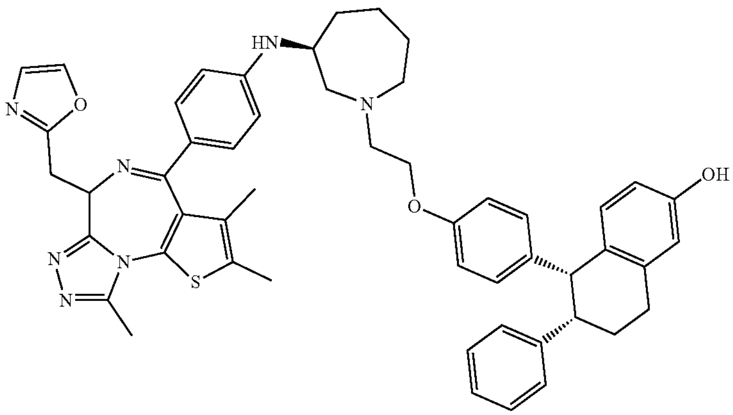 [SMILES: Cc1sc2c(c1C)C(c1ccc(N[C@H]3CCCCN(CCOc4ccc([C@@H]5c6ccc(O)cc6CC[C@@H]5c5ccccc5)cc4)C3)cc1)=NC(Cc1ncco1)c1nnc(C)n1-2] |

TABLE 3-continued
| Compound No. | Compound Structure |
|---|---|
| III-48 | 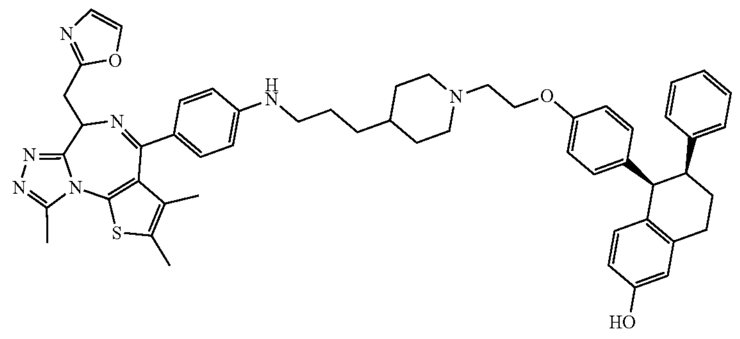 [SMILES: Cc1sc2c(c1C)C(c1ccc(NCCCC3CCN(CCOc4ccc([C@@H]5c6ccc(O)cc6CC[C@@H]5c5ccccc5)cc4)CC3)cc1)=NC(Cc1ncco1)c1nnc(C)n1-2] |
| III-49 | 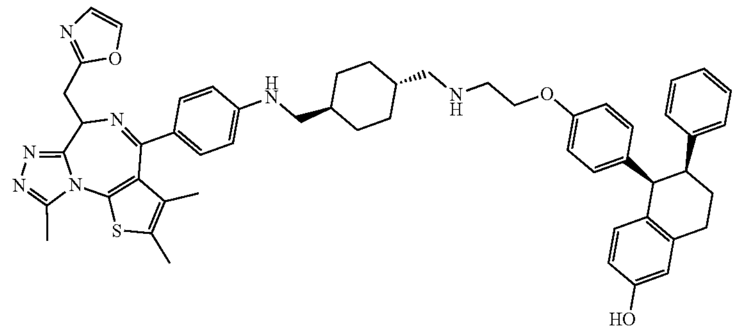 [SMILES: Cc1sc2c(c1C)C(c1ccc(NC[C@H]3CC[C@H](CNCCOc4ccc([C@@H]5c6ccc(O)cc6CC[C@@H]5c5ccccc5)cc4)CC3)cc1)=NC(Cc1ncco1)c1nnc(C)n1-2] |
| III-50 | 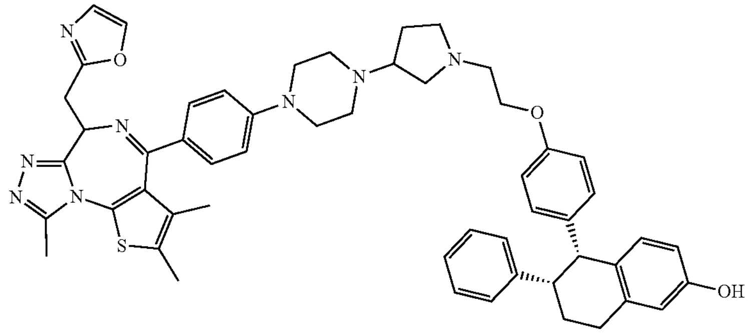 [SMILES: Cc1sc2c(c1C)C(c1ccc(N3CCN(C4CCN(CCOc5ccc([C@@H]6c7ccc(O)cc7CC[C@@H]6c6ccccc6)cc5)C4)CC3)cc1)=NC(Cc1ncco1)c1nnc(C)n1-2] |
| III-51 | 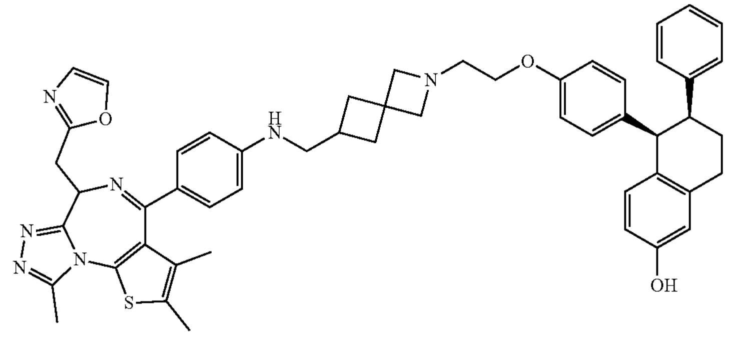 [SMILES: Cc1sc2c(c1C)C(c1ccc(NCC3CC4(C3)CN(CCOc3ccc([C@@H]5c6ccc(O)cc6CC[C@@H]5c5ccccc5)cc3)C4)cc1)=NC(Cc1ncco1)c1nnc(C)n1-2] |

TABLE 3-continued
| Compound No. | Compound Structure |
| --- | --- |
| III-52 | 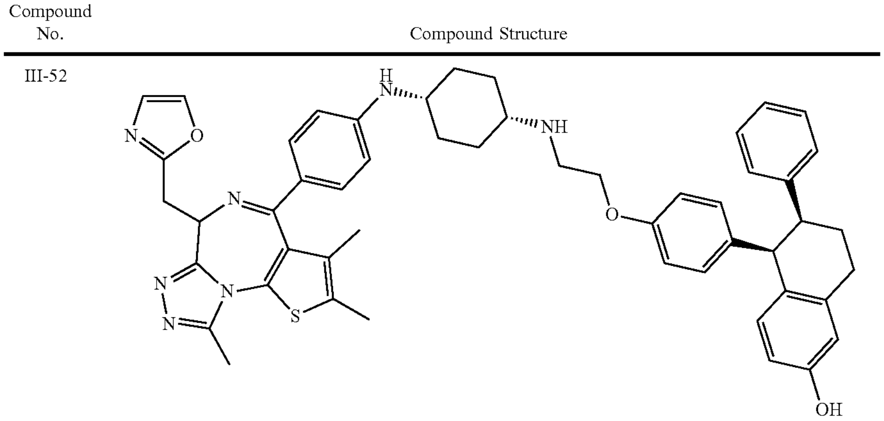 |
| III-53 | 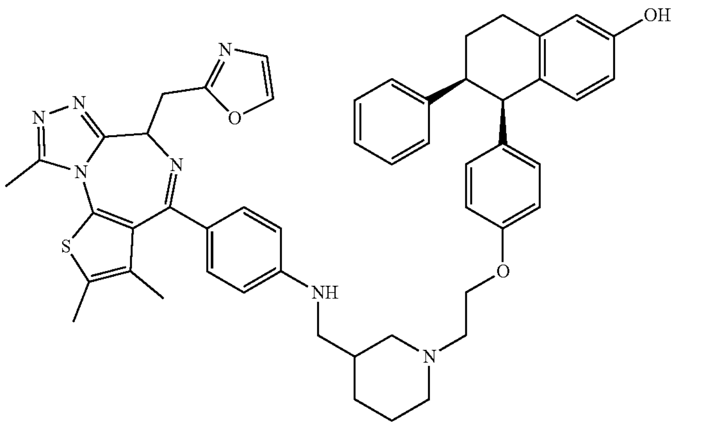 [SMILES: Cc1sc2c(c1C)C(c1ccc(NCC3CCCN(CCOc4ccc([C@@H]5c6ccc(O)cc6CC[C@@H]5c5ccccc5)cc4)C3)cc1)=NC(Cc1ncco1)c1nnc(C)n1-2] |
| III-54 | 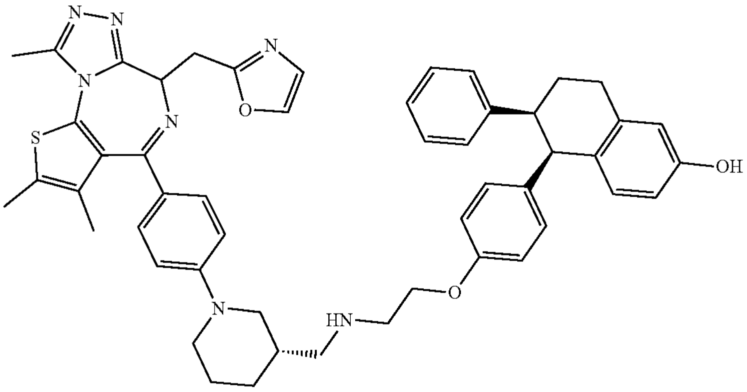 [SMILES: Cc1sc2c(c1C)C(c1ccc(N3CCC[C@@H](CNCCOc4ccc([C@@H]5c6ccc(O)cc6CC[C@@H]5c5ccccc5)cc4)C3)cc1)=NC(Cc1ncco1)c1nnc(C)n1-2] |
| III-55 | 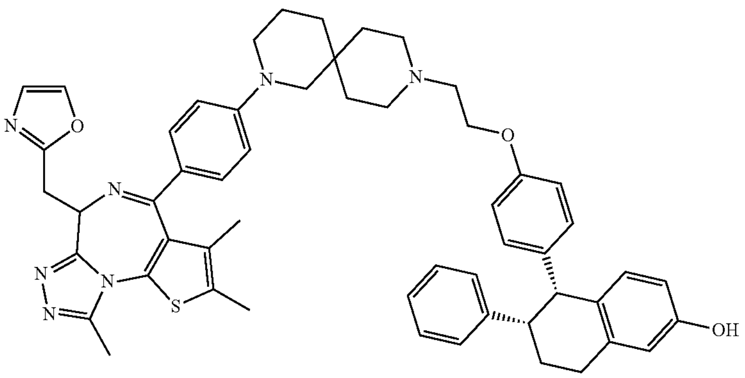 [SMILES: Cc1sc2c(c1C)C(c1ccc(N3CCCC4(CCN(CCOc5ccc([C@@H]6c7ccc(O)cc7CC[C@@H]6c6ccccc6)cc5)CC4)C3)cc1)=NC(Cc1ncco1)c1nnc(C)n1-2] |

TABLE 3-continued
| Compound No. | Compound Structure |
|---|---|
| III-56 | 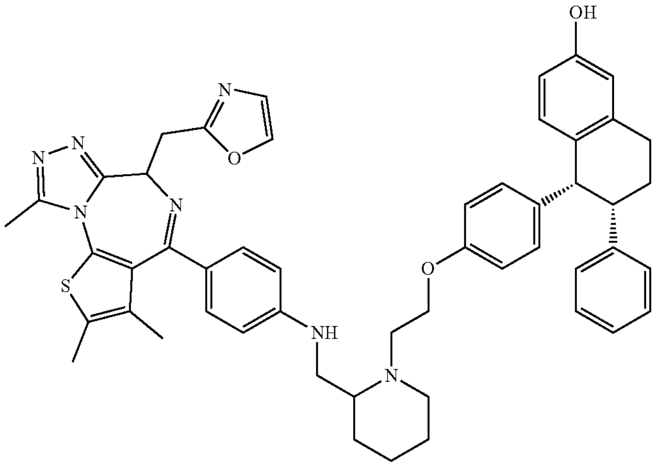 [SMILES: Cc1sc2c(c1C)C(c1ccc(NCC3CCCCN3CCOc3ccc([C@@H]4c5ccc(O)cc5CC[C@@H]4c4ccccc4)cc3)cc1)=NC(Cc1ncco1)c1nnc(C)n1-2] |
| III-57 | 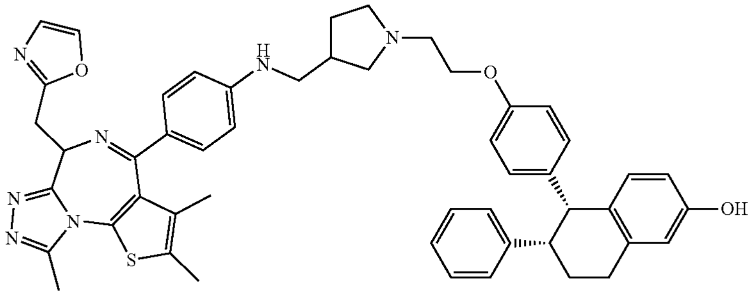 [SMILES: Cc1sc2c(c1C)C(c1ccc(NCC3CCN(CCOc4ccc([C@@H]5c6ccc(O)cc6CC[C@@H]5c5ccccc5)cc4)C3)cc1)=NC(Cc1ncco1)c1nnc(C)n1-2] |
| III-58 | 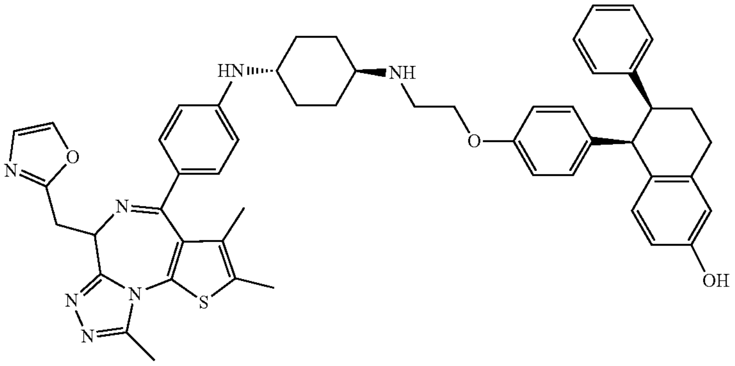 [SMILES: Cc1sc2c(c1C)C(c1ccc(N[C@H]3CC[C@H](NCCOc4ccc([C@@H]5c6ccc(O)cc6CC[C@@H]5c5ccccc5)cc4)CC3)cc1)=NC(Cc1ncco1)c1nnc(C)n1-2] |
| III-59 | 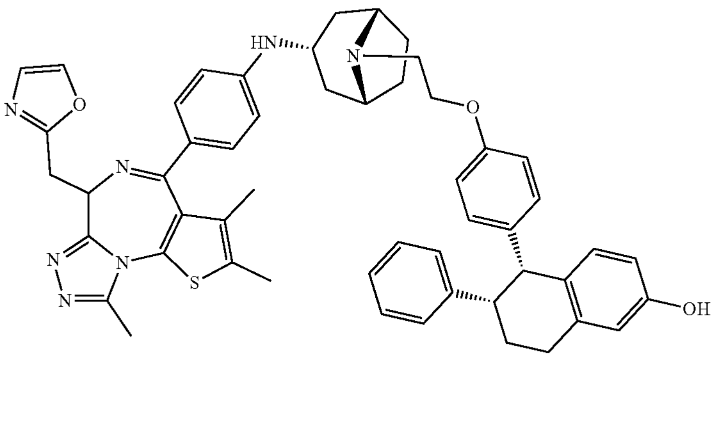 [SMILES: Cc1sc2c(c1C)C(c1ccc(N[C@H]3C[C@H]4CC[C@@H](C3)N4CCOc3ccc([C@@H]4c5ccc(O)cc5CC[C@@H]4c4ccccc4)cc3)cc1)=NC(Cc1ncco1)c1nnc(C)n1-2] |

TABLE 3-continued
| Compound No. | Compound Structure |
|---|---|
| III-60 | 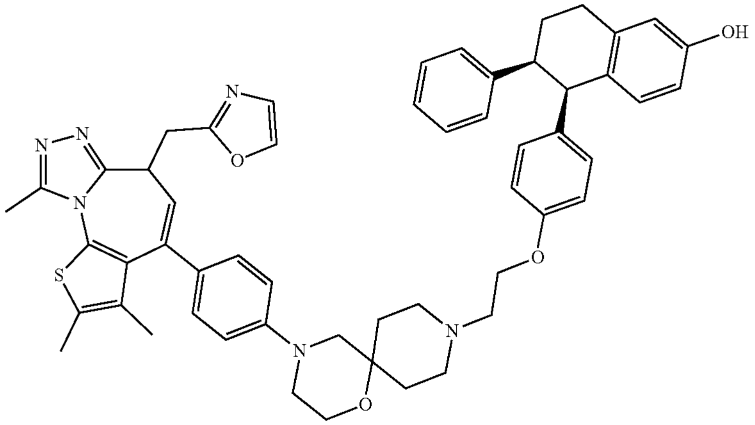 [SMILES: Cc1sc2c(c1C)C(c1ccc(N3CCOC4(CCN(CCOc5ccc([C@@H]6c7ccc(O)cc7CC[C@@H]6c6ccccc6)cc5)CC4)C3)cc1)=CC(Cc1ncco1)c1nnc(C)n1-2] |
| III-61 | 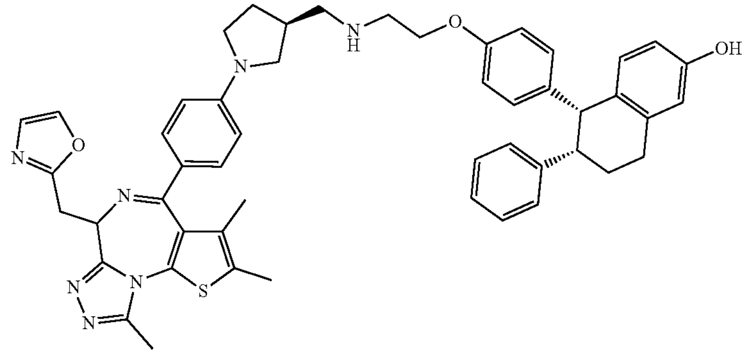 [SMILES: Cc1sc2c(c1C)C(c1ccc(N3CC[C@@H](CNCCOc4ccc([C@@H]5c6ccc(O)cc6CC[C@@H]5c5ccccc5)cc4)C3)cc1)=NC(Cc1ncco1)c1nnc(C)n1-2] |
| III-62 | 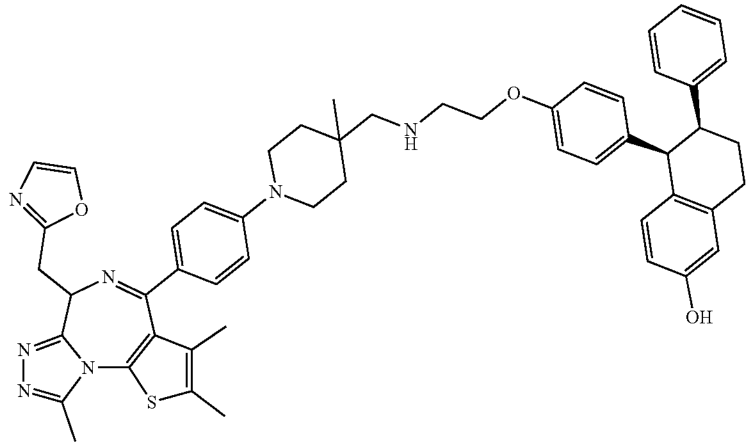 [SMILES: Cc1sc2c(c1C)C(c1ccc(N3CCC(C)(CNCCOc4ccc([C@@H]5c6ccc(O)cc6CC[C@@H]5c5ccccc5)cc4)CC3)cc1)=NC(Cc1ncco1)c1nnc(C)n1-2] |

TABLE 3-continued
| Compound No. | Compound Structure |
| --- | --- |
| III-63 | 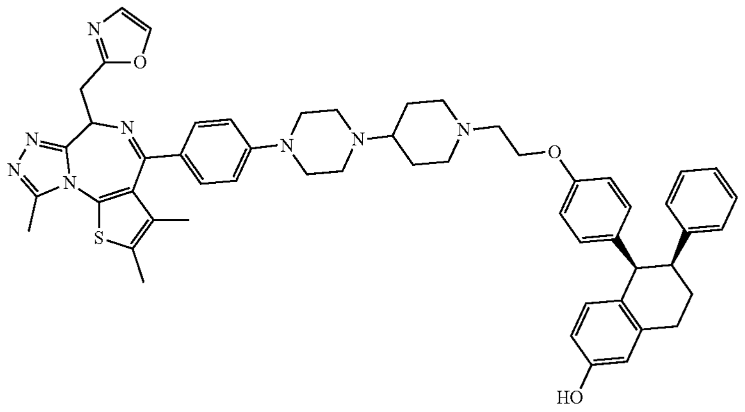 [SMILES: Cc1sc2c(c1C)C(c1ccc(N3CCN(C4CCN(CCOc5ccc([C@@H]6c7ccc(O)cc7CC[C@@H]6c6ccccc6)cc5)CC4)CC3)cc1)=NC(Cc1ncco1)c1nnc(C)n1-2] |
| III-64 | 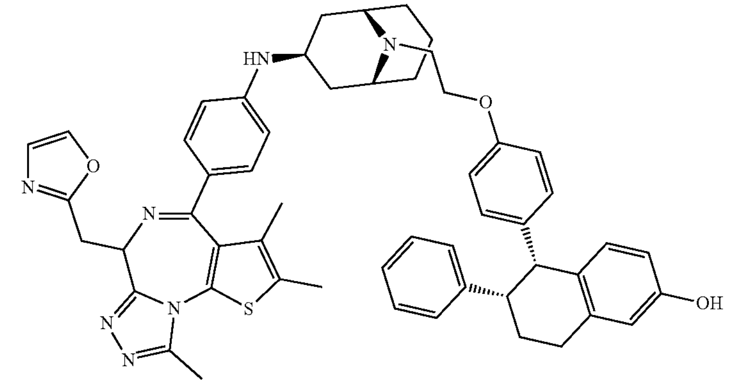 [SMILES: Cc1sc2c(c1C)C(c1ccc(N[C@@H]3C[C@H]4CCC[C@@H](C3)N4CCOc3ccc([C@@H]4c5ccc(O)cc5CC[C@@H]4c4ccccc4)cc3)cc1)=NC(Cc1ncco1)c1nnc(C)n1-2] |
| III-65 | 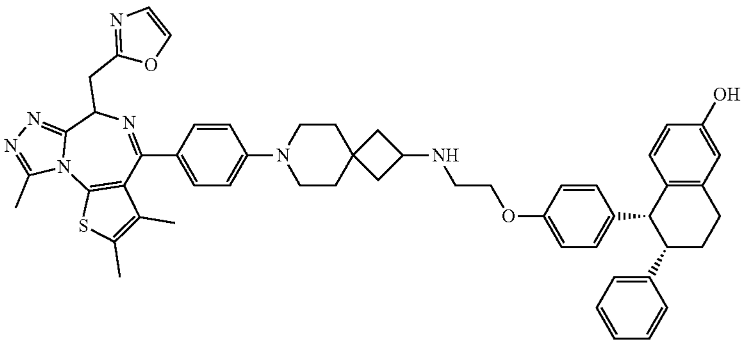 [SMILES: Cc1sc2c(c1C)C(c1ccc(N3CCC4(CC3)CC(NCCOc3ccc([C@@H]5c6ccc(O)cc6CC[C@@H]5c5ccccc5)cc3)C4)cc1)=NC(Cc1ncco1)c1nnc(C)n1-2] |
| III-66 | 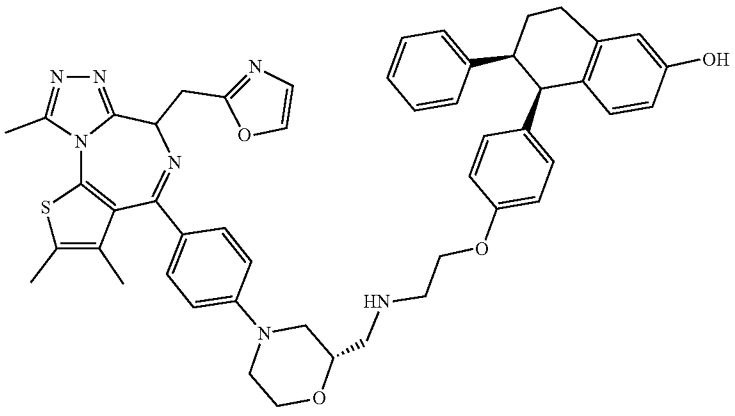 [SMILES: Cc1sc2c(c1C)C(c1ccc(N3CCO[C@@H](CNCCOc4ccc([C@@H]5c6ccc(O)cc6CC[C@@H]5c5ccccc5)cc4)C3)cc1)=NC(Cc1ncco1)c1nnc(C)n1-2] |

TABLE 3-continued
| Compound No. | Compound Structure |
|---|---|
| III-67 | 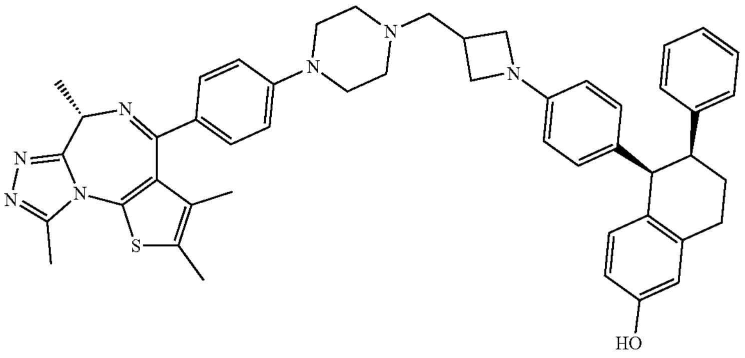 [SMILES: Cc1sc2c(c1C)C(c1ccc(N3CCN(CC4CN(c5ccc([C@@H]6c7ccc(O)cc7CC[C@@H]6c6ccccc6)cc5)C4)CC3)cc1)=N[C@@H](C)c1nnc(C)n1-2] |
| III-68 | 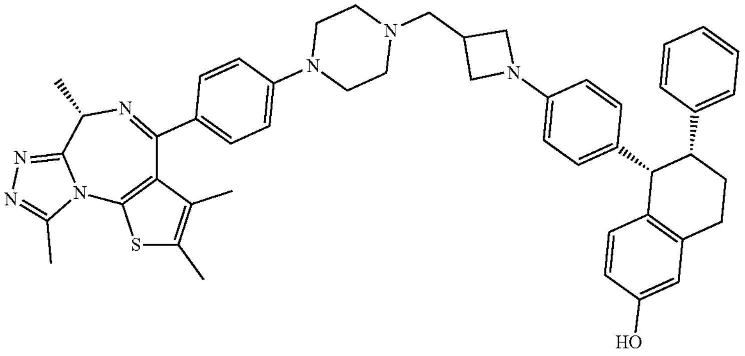 [SMILES: Cc1sc2c(c1C)C(c1ccc(N3CCN(CC4CN(c5ccc([C@H]6c7ccc(O)cc7CC[C@H]6c6ccccc6)cc5)C4)CC3)cc1)=N[C@@H](C)c1nnc(C)n1-2] |
| III-69 | 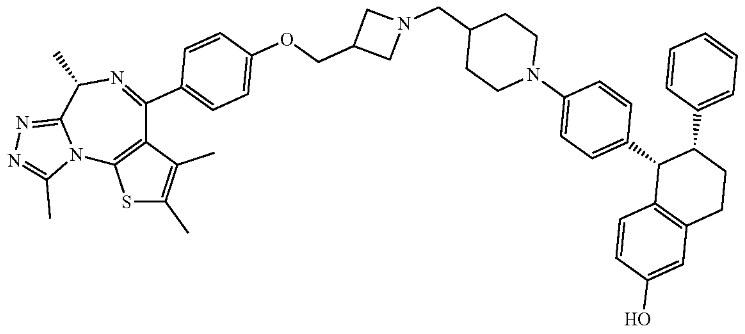 [SMILES: Cc1sc2c(c1C)C(c1ccc(OCC3CN(CC4CCN(c5ccc([C@H]6c7ccc(O)cc7CC[C@H]6c6ccccc6)cc5)CC4)C3)cc1)=N[C@@H](C)c1nnc(C)n1-2] |
| III-70 | 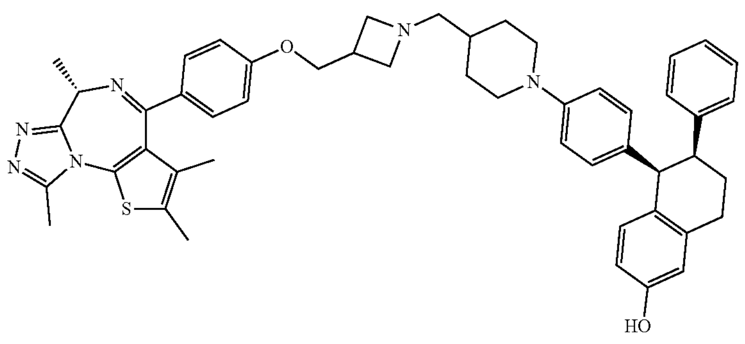 [SMILES: Cc1sc2c(c1C)C(c1ccc(OCC3CN(CC4CCN(c5ccc([C@@H]6c7ccc(O)cc7CC[C@@H]6c6ccccc6)cc5)CC4)C3)cc1)=N[C@@H](C)c1nnc(C)n1-2] |

TABLE 3-continued
| Compound No. | Compound Structure |
|---|---|
| III-71 | 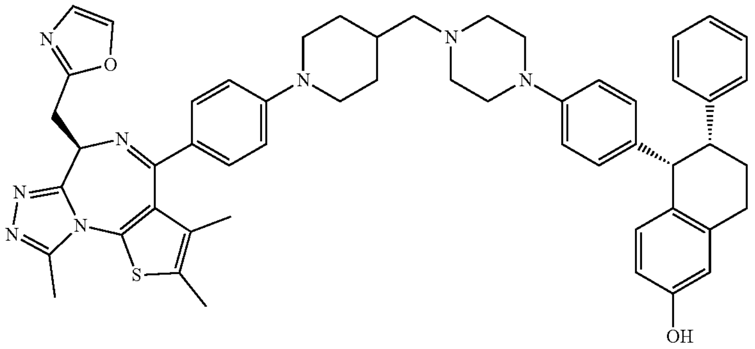 [SMILES: Cc1sc2c(c1C)C(c1ccc(N3CCC(CN4CCN(c5ccc([C@H]6c7ccc(O)cc7CC[C@H]6c6ccccc6)cc5)CC4)CC3)cc1)=N[C@H](Cc1ncco1)c1nnc(C)n1-2] |
| III-72 | 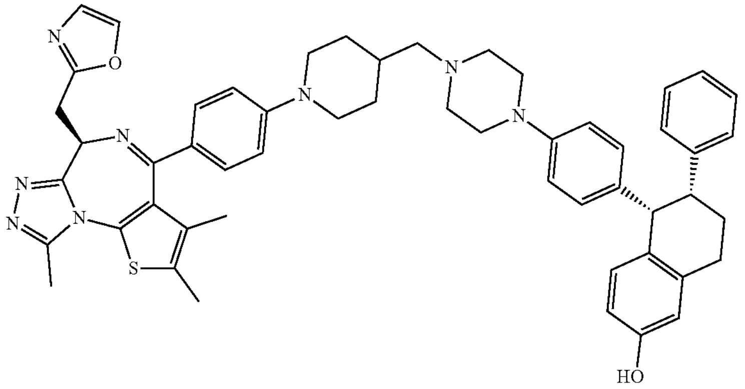 [SMILES: Cc1sc2c(c1C)C(c1ccc(N3CCC(CN4CCN(c5ccc([C@H]6c7ccc(O)cc7CC[C@H]6c6ccccc6)cc5)CC4)CC3)cc1)=N[C@H](Cc1ncco1)c1nnc(C)n1-2] |
| III-73 | 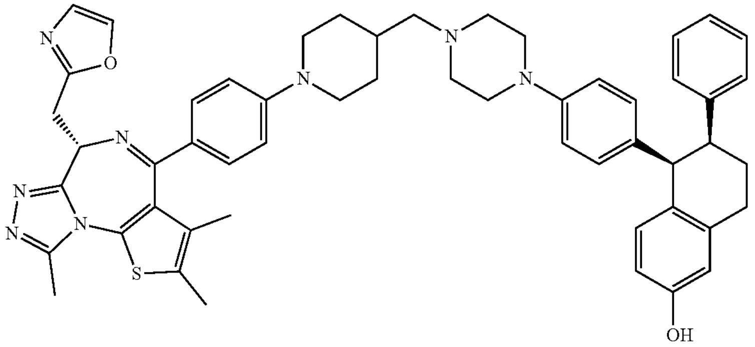 [SMILES: Cc1sc2c(c1C)C(c1ccc(N3CCC(CN4CCN(c5ccc([C@@H]6c7ccc(O)cc7CC[C@@H]6c6ccccc6)cc5)CC4)CC3)cc1)=N[C@@H](Cc1ncco1)c1nnc(C)n1-2] |
| III-74 | 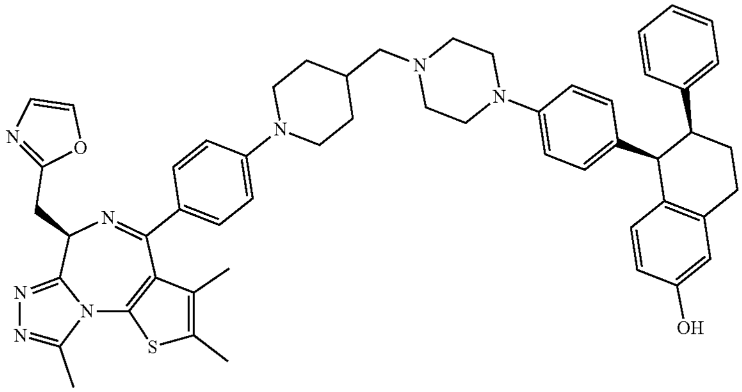 [SMILES: Cc1sc2c(c1C)C(c1ccc(N3CCC(CN4CCN(c5ccc([C@@H]6c7ccc(O)cc7CC[C@@H]6c6ccccc6)cc5)CC4)CC3)cc1)=N[C@H](Cc1ncco1)c1nnc(C)n1-2] |

TABLE 3-continued
| Compound No. | Compound Structure |
|---|---|
| III-75 | 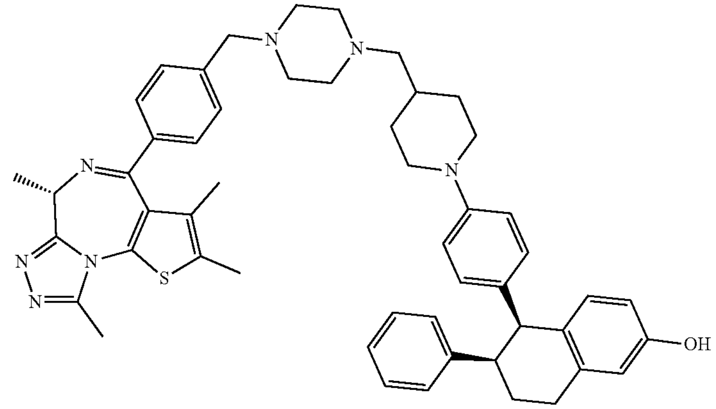 |
| III-76 | 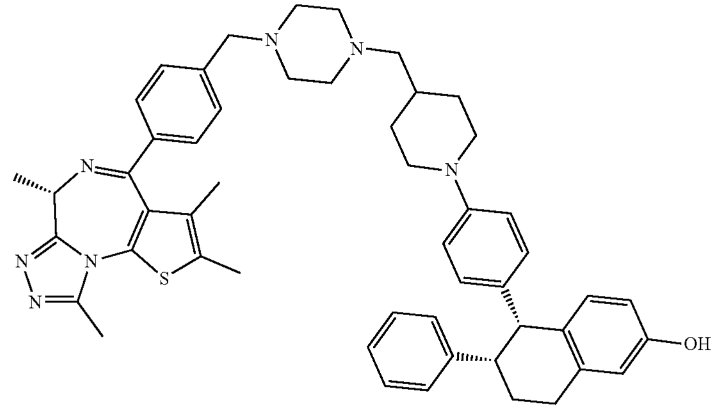 |
| III-77a | 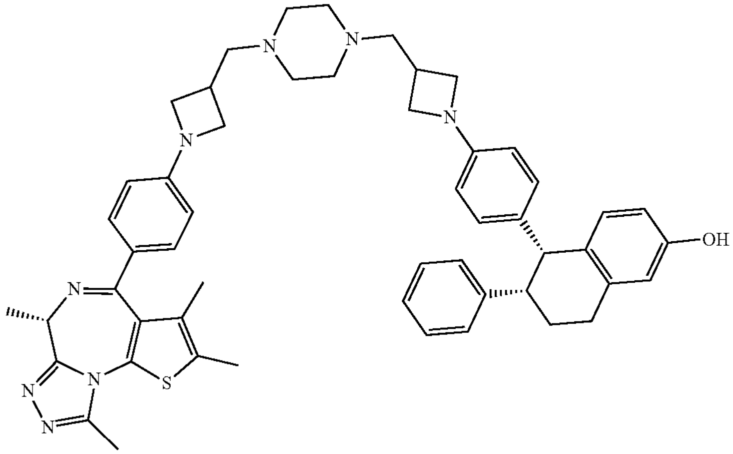 [SMILES: Cc1sc2c(c1C)C(c1ccc(N3CC(CN4CCN(CC5CN(c6ccc([C@@H]7c8ccc(O)cc8CC[C@@H]7c7ccccc7)cc6)C5)CC4)C3)cc1)=N[C@@H](C)c1nnc(C)n1-2] |

TABLE 3-continued
| Compound No. | Compound Structure |
|---|---|
| III-77b | 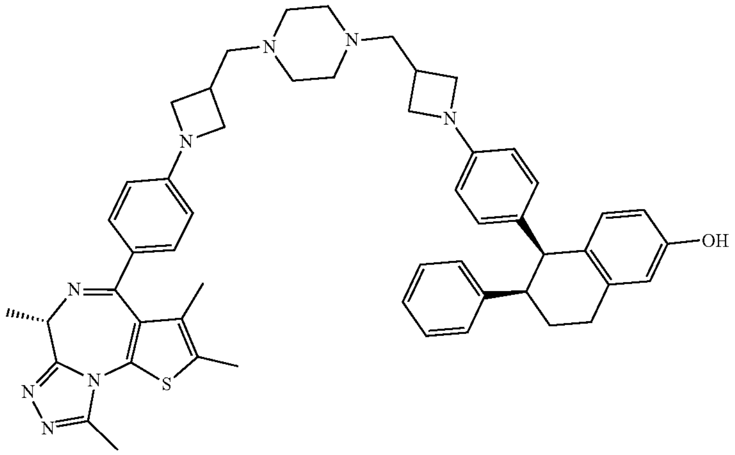 [SMILES: Cc1sc2c(c1C)C(c1ccc(N3CC(CN4CCN(CC5CN(c6ccc([C@H]7c8ccc(O)cc8CC[C@H]7c7ccccc7)cc6)C5)CC4)C3)cc1)=N[C@@H](C)c1nnc(C)n1-2] |
| III-78 | 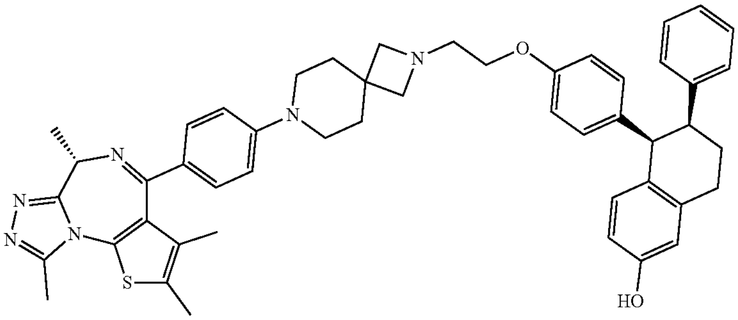 [SMILES: Cc1sc2c(c1C)C(c1ccc(N3CCC4(CC3)CN(CCOc3ccc([C@@H]5c6ccc(O)cc6CC[C@@H]5c5ccccc5)cc3)C4)cc1)=N[C@@H](C)c1nnc(C)n1-2] |
| III-79 | 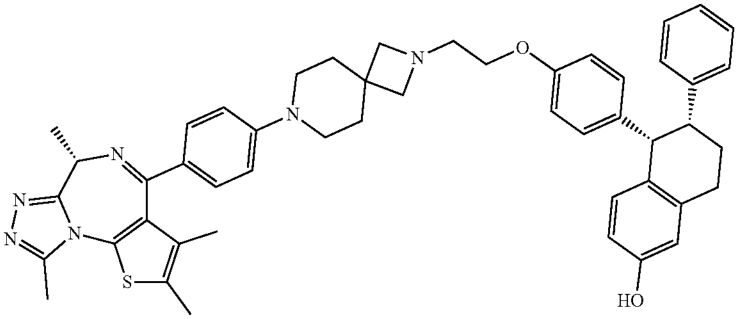 [SMILES: Cc1sc2c(c1C)C(c1ccc(N3CCC4(CC3)CN(CCOc3ccc([C@H]5c6ccc(O)cc6CC[C@H]5c5ccccc5)cc3)C4)cc1)=N[C@@H](C)c1nnc(C)n1-2] |
| III-80 | 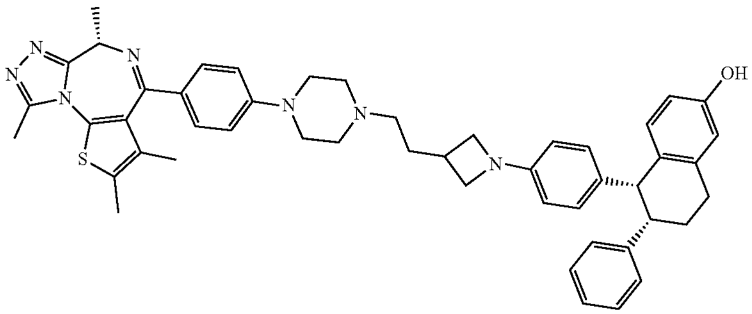 [SMILES: Cc1sc2c(c1C)C(c1ccc(N3CCN(CCC4CN(c5ccc([C@@H]6c7ccc(O)cc7CC[C@@H]6c6ccccc6)cc5)C4)CC3)cc1)=N[C@@H](C)c1nnc(C)n1-2] |

TABLE 3-continued
| Compound No. | Compound Structure |
|---|---|
| III-81 | 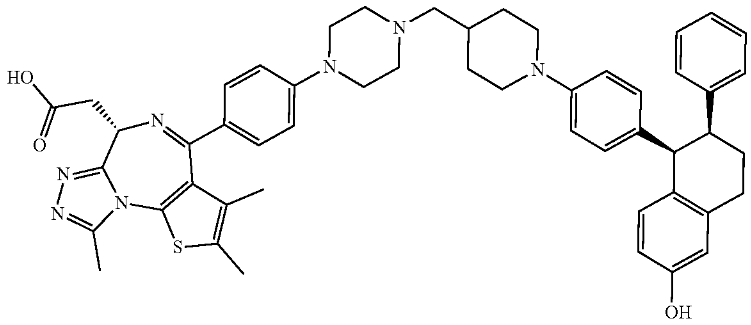 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@@H](CC(=O)O)c1nnc(C)n1-2] |
| III-82 | 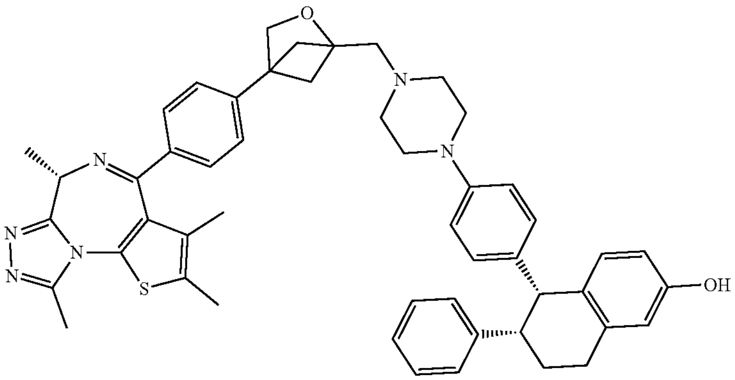 [SMILES: Cc1sc2c(c1C)C(c1ccc(C34COC(CN5CCN(c6ccc([C@@H]7c8ccc(O)cc8CC[C@@H]7c7ccccc7)cc6)CC5)(C3)C4)cc1)=N[C@@H](C)c1nnc(C)n1-2] |
| III-83 | 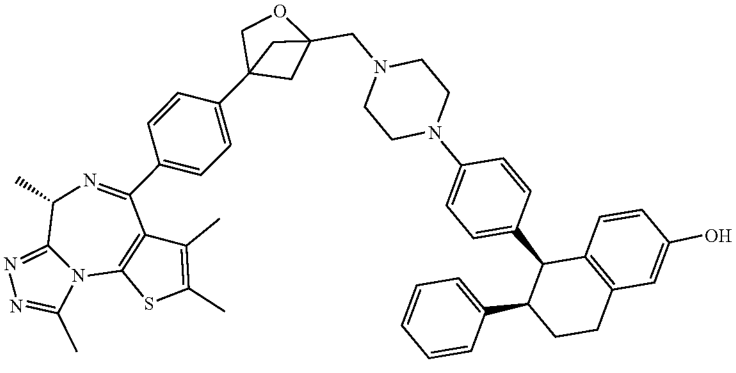 [SMILES: Cc1sc2c(c1C)C(c1ccc(C34COC(CN5CCN(c6ccc([C@H]7c8ccc(O)cc8CC[C@H]7c7ccccc7)cc6)CC5)(C3)C4)cc1)=N[C@@H](C)c1nnc(C)n1-2] |
| III-84 | 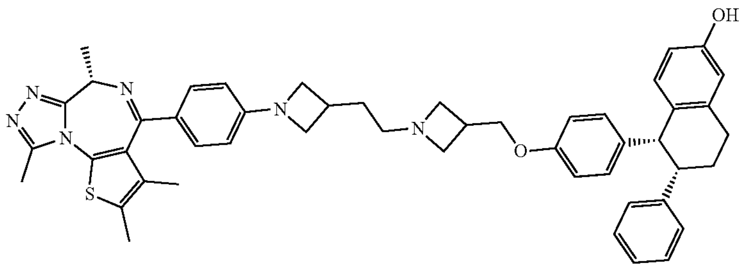 [SMILES: Cc1sc2c(c1C)C(c1ccc(N3CC(CCN4CC(COc5ccc([C@@H]6c7ccc(O)cc7CC[C@@H]6c6ccccc6)cc5)C4)C3)cc1)=N[C@@H](C)c1nnc(C)n1-2] |

TABLE 3-continued
| Compound No. | Compound Structure |
|---|---|
| III-85 | 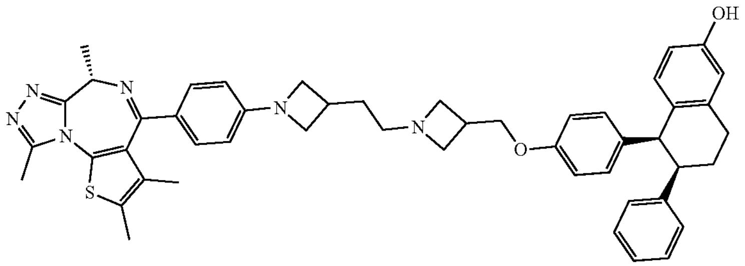 [SMILES: Cc1sc2c(c1C)C(c1ccc(N3CC(CCN4CC(COc5ccc([C@H]6c7ccc(O)cc7CC[C@H]6c6ccccc6)cc5)C4)C3)cc1)=N[C@@H](C)c1nnc(C)n1-2] |
| III-86 | 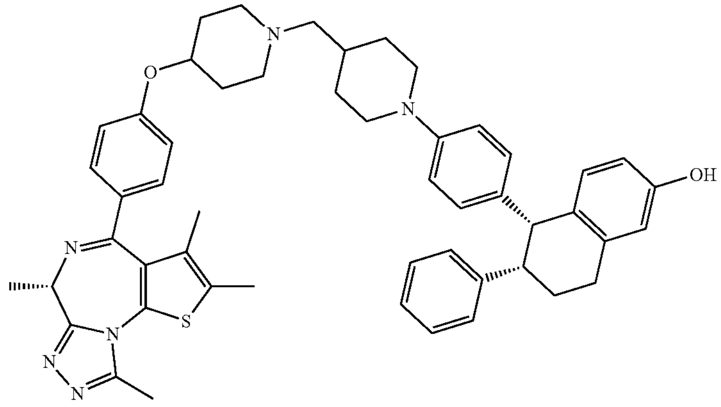 [SMILES: Cc1sc2c(c1C)C(c1ccc(OC3CCN(CC4CCN(c5ccc([C@@H]6c7ccc(O)cc7CC[C@@H]6c6ccccc6)cc5)CC4)CC3)cc1)=N[C@@H](C)c1nnc(C)n1-2] |
| III-87 | 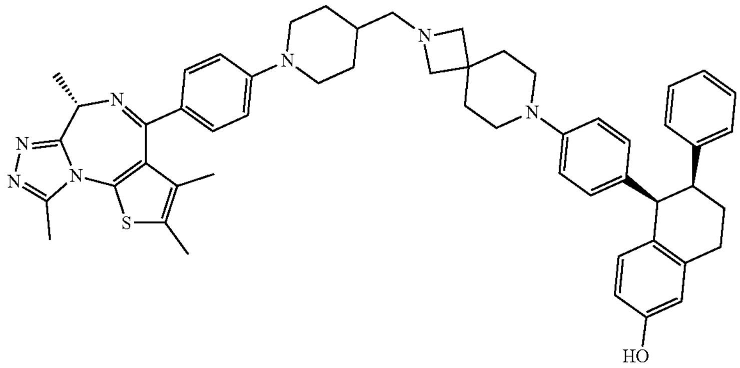 [SMILES: Cc1sc2c(c1C)C(c1ccc(N3CCC(CN4CC5(CCN(c6ccc([C@@H]7c8ccc(O)cc8CC[C@@H]7c7ccccc7)cc6)CC5)C4)CC3)cc1)=N[C@@H](C)c1nnc(C)n1-2] |
| III-88 | 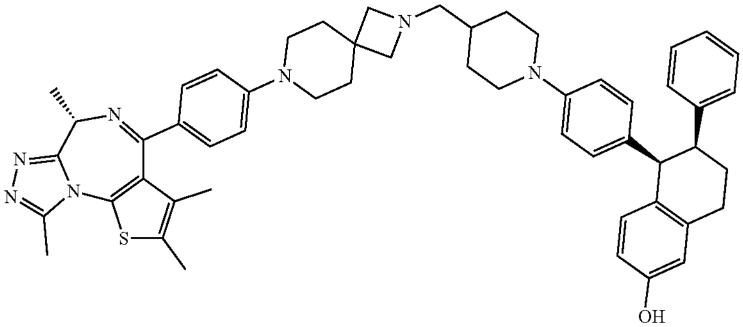 [SMILES: Cc1sc2c(c1C)C(c1ccc(N3CCC4(CC3)CN(CC3CCN(c5ccc([C@@H]6c7ccc(O)cc7CC[C@@H]6c6ccccc6)cc5)CC3)C4)cc1)=N[C@@H](C)c1nnc(C)n1-2] |

TABLE 3-continued
| Compound No. | Compound Structure |
|---|---|
| III-89 | 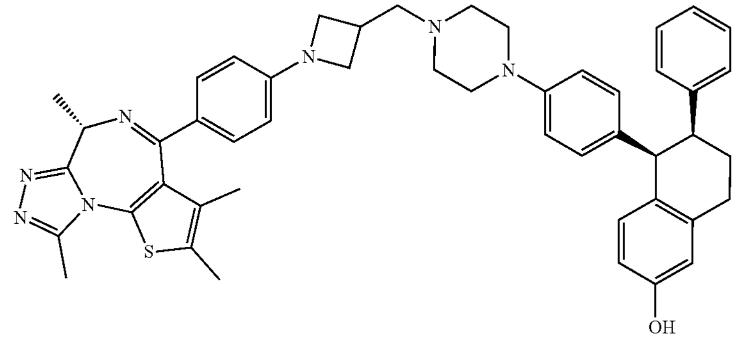 [SMILES: Cc1sc2c(c1C)C(c1ccc(N3CC(CN4CCN(c5ccc([C@@H]6c7ccc(O)cc7CC[C@@H]6c6ccccc6)cc5)CC4)C3)cc1)=N[C@@H](C)c1nnc(C)n1-2] |
| III-90 | 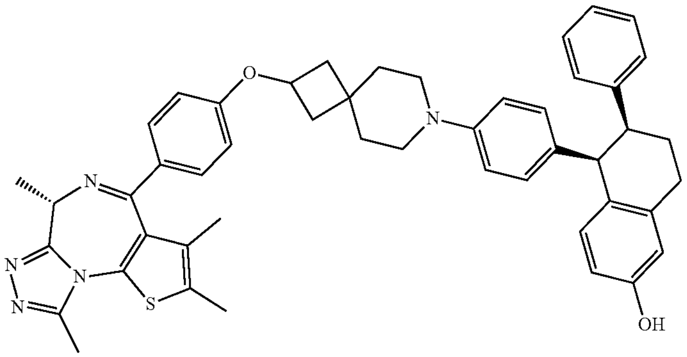 [SMILES: Cc1sc2c(c1C)C(c1ccc(OC3CC4(CCN(c5ccc([C@@H]6c7ccc(O)cc7CC[C@@H]6c6ccccc6)cc5)CC4)C3)cc1)=N[C@@H](C)c1nnc(C)n1-2] |
| III-91 | 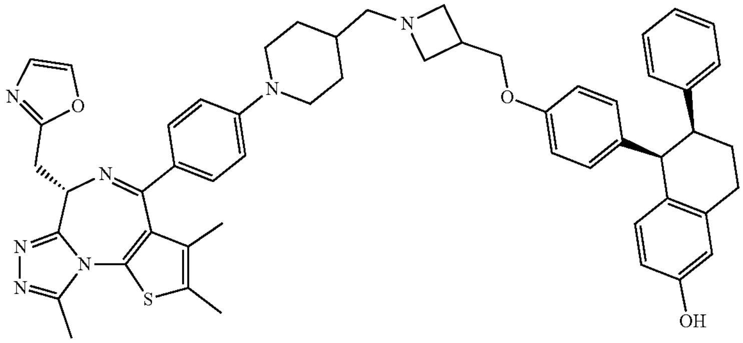 [SMILES: Cc1sc2c(c1C)C(c1ccc(N3CCC(CN4CC(COc5ccc([C@@H]6c7ccc(O)cc7CC[C@@H]6c6ccccc6)cc5)C4)CC3)cc1)=N[C@@H](Cc1ncco1)c1nnc(C)n1-2] |
| III-92 | 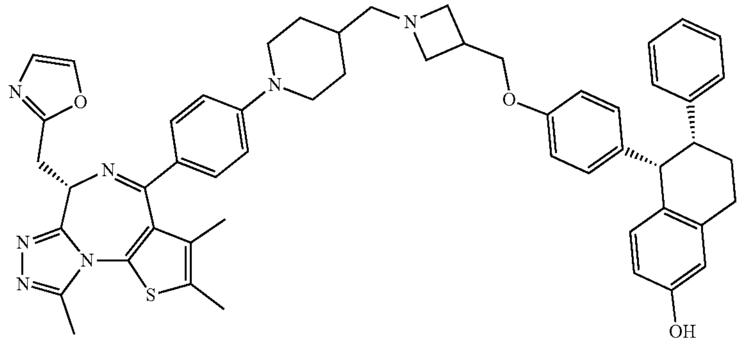 [SMILES: Cc1sc2c(c1C)C(c1ccc(N3CCC(CN4CC(COc5ccc([C@H]6c7ccc(O)cc7CC[C@H]6c6ccccc6)cc5)C4)CC3)cc1)=N[C@@H](Cc1ncco1)c1nnc(C)n1-2] |

TABLE 3-continued
| Compound No. | Compound Structure |
|---|---|
| III-93a | 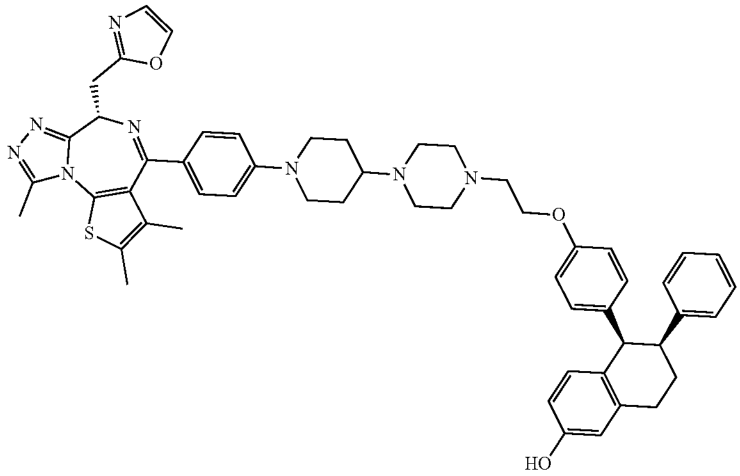 [SMILES: Cc1sc2c(c1C)C(c1ccc(N3CCC(N4CCN(CCOc5ccc([C@@H]6c7ccc(O)cc7CC[C@@H]6c6ccccc6)cc5)CC4)CC3)cc1)=N[C@@H](Cc1ncco1)c1nnc(C)n1-2] |
| III-93b | 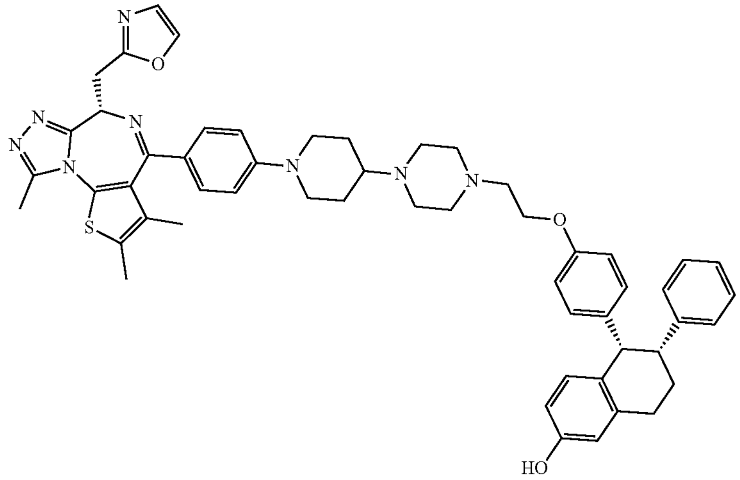 [SMILES: Cc1sc2c(c1C)C(c1ccc(N3CCC(N4CCN(CCOc5ccc([C@H]6c7ccc(O)cc7CC[C@H]6c6ccccc6)cc5)CC4)CC3)cc1)=N[C@@H](Cc1ncco1)c1nnc(C)n1-2] |
| III-94a | 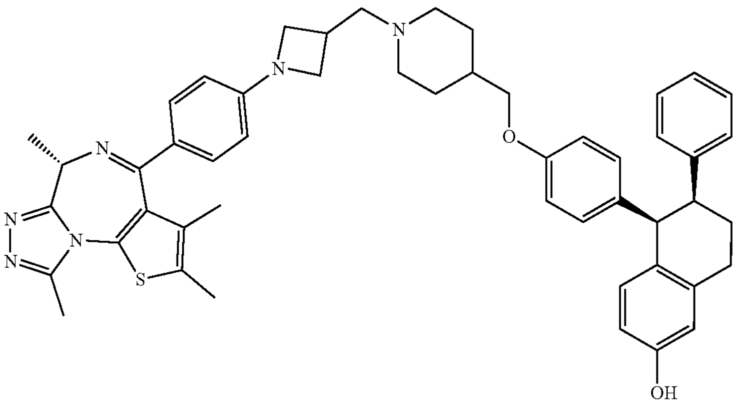 [SMILES: Cc1sc2c(c1C)C(c1ccc(N3CC(CN4CCC(COc5ccc([C@@H]6c7ccc(O)cc7CC[C@@H]6c6ccccc6)cc5)CC4)C3)cc1)=N[C@@H](C)c1nnc(C)n1-2] |

TABLE 3-continued
| Compound No. | Compound Structure |
| --- | --- |
| III-94b | 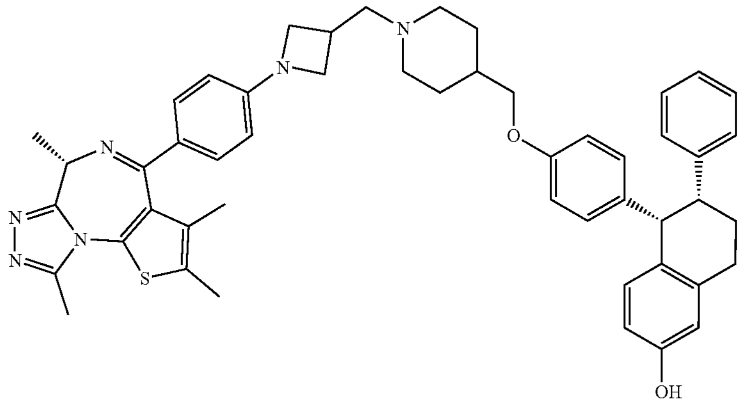 [SMILES: Cc1sc2c(c1C)C(c1ccc(N3CC(CN4CCC(COc5ccc([C@H]6c7ccc(O)cc7CC[C@H]6c6ccccc6)cc5)CC4)C3)cc1)=N[C@@H](C)c1nnc(C)n1-2] |
| III-95 | 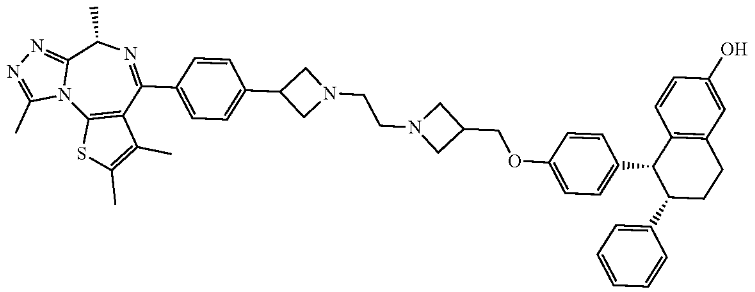 [SMILES: Cc1sc2c(c1C)C(c1ccc(C3CN(CCN4CC(COc5ccc([C@@H]6c7ccc(O)cc7CC[C@@H]6c6ccccc6)cc5)C4)C3)cc1)=N[C@@H](C)c1nnc(C)n1-2] |
| III-96 | 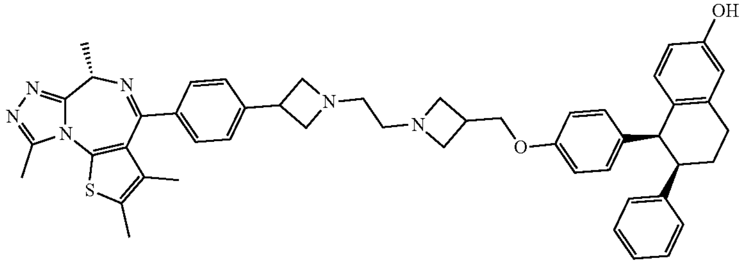 [SMILES: Cc1sc2c(c1C)C(c1ccc(C3CN(CCN4CC(COc5ccc([C@H]6c7ccc(O)cc7CC[C@H]6c6ccccc6)cc5)C4)C3)cc1)=N[C@@H](C)c1nnc(C)n1-2] |
| III-97 | 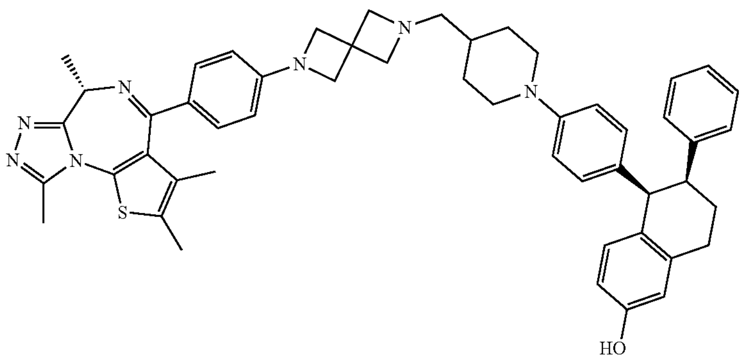 [SMILES: Cc1sc2c(c1C)C(c1ccc(N3CC4(CN(CC5CCN(c6ccc([C@@H]7c8ccc(O)cc8CC[C@@H]7c7ccccc7)cc6)CC5)C4)C3)cc1)=N[C@@H](C)c1nnc(C)n1-2] |

TABLE 3-continued
| Compound No. | Compound Structure |
|---|---|
| III-98 | 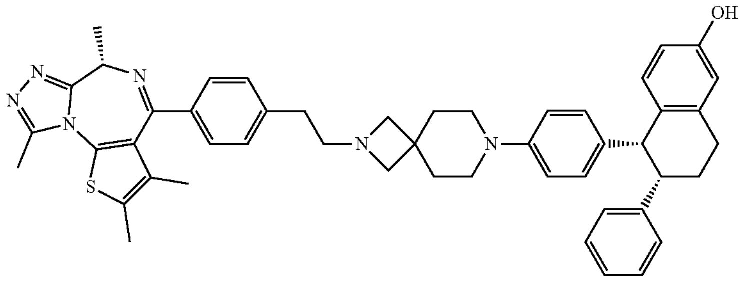 [SMILES: Cc1sc2c(c1C)C(c1ccc(CCN3CC4(CCN(c5ccc([C@@H]6c7ccc(O)cc7CC[C@@H]6c6ccccc6)cc5)CC4)C3)cc1)=N[C@@H](C)c1nnc(C)n1-2] |
| III-99 | 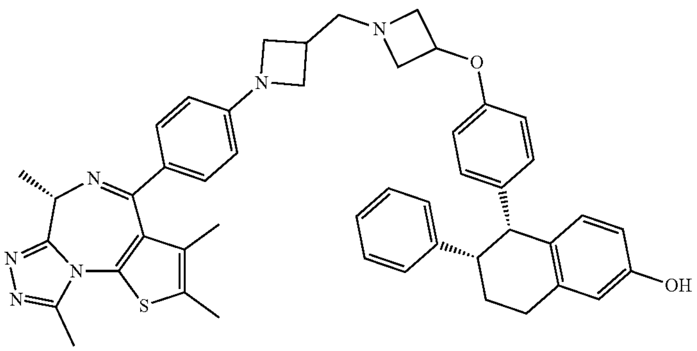 [SMILES: Cc1sc2c(c1C)C(c1ccc(N3CC(CN4CC(Oc5ccc([C@@H]6c7ccc(O)cc7CC[C@@H]6c6ccccc6)cc5)C4)C3)cc1)=N[C@@H](C)c1nnc(C)n1-2] |
| III-100 | 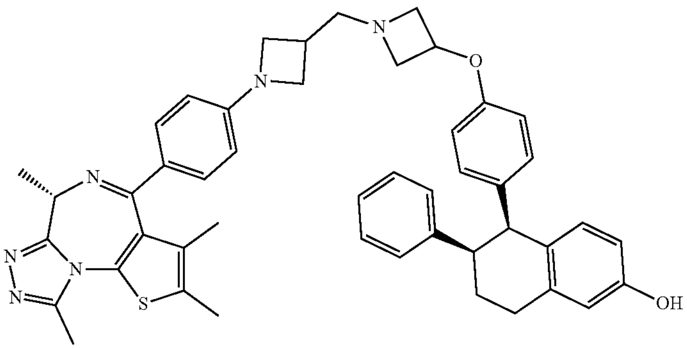 [SMILES: Cc1sc2c(c1C)C(c1ccc(N3CC(CN4CC(Oc5ccc([C@H]6c7ccc(O)cc7CC[C@H]6c6ccccc6)cc5)C4)C3)cc1)=N[C@@H](C)c1nnc(C)n1-2] |
| III-101 | 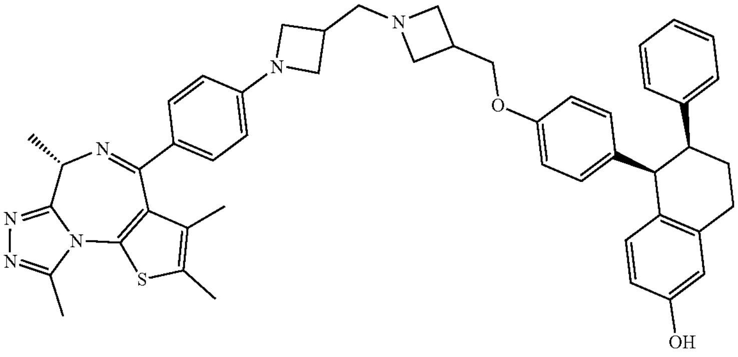 [SMILES: Cc1sc2c(c1C)C(c1ccc(N3CC(CN4CC(COc5ccc([C@@H]6c7ccc(O)cc7CC[C@@H]6c6ccccc6)cc5)C4)C3)cc1)=N[C@@H](C)c1nnc(C)n1-2] |

TABLE 3-continued
| Compound No. | Compound Structure |
|---|---|
| III-102 | 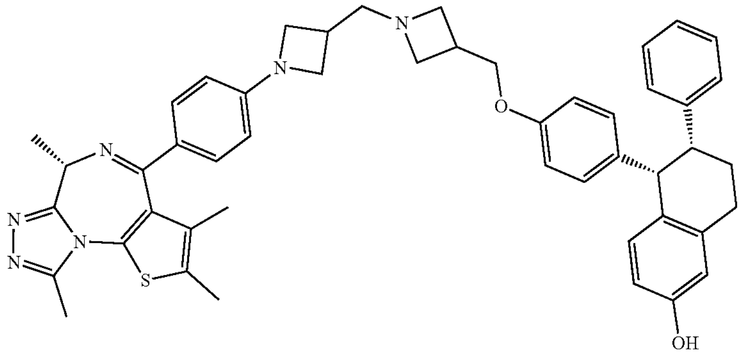 [SMILES: Cc1sc2c(c1C)C(c1ccc(N3CC(CN4CC(COc5ccc([C@H]6c7ccc(O)cc7CC[C@H]6c6ccccc6)cc5)C4)C3)cc1)=N[C@@H](C)c1nnc(C)n1-2] |
| III-103 | 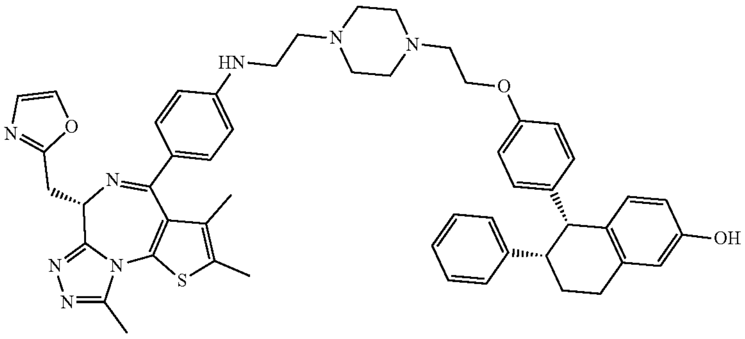 [SMILES: Cc1sc2c(c1C)C(c1ccc(NCCN3CCN(CCOc4ccc([C@@H]5c6ccc(O)cc6CC[C@@H]5c5ccccc5)cc4)CC3)cc1)=N[C@@H](Cc1ncco1)c1nnc(C)n1-2] |
| III-104 | 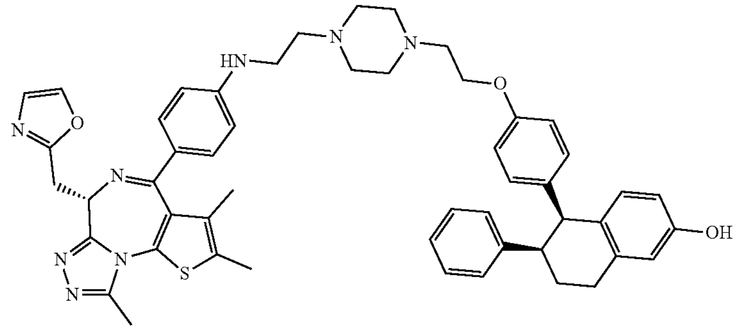 [SMILES: Cc1sc2c(c1C)C(c1ccc(NCCN3CCN(CCOc4ccc([C@H]5c6ccc(O)cc6CC[C@H]5c5ccccc5)cc4)CC3)cc1)=N[C@@H](Cc1ncco1)c1nnc(C)n1-2] |
| III-105 | 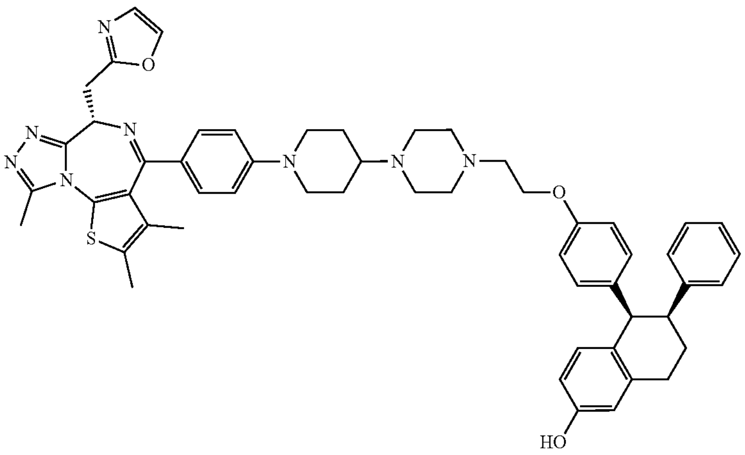 [SMILES: Cc1sc2c(c1C)C(c1ccc(N3CCC(N4CCN(CCOc5ccc([C@@H]6c7ccc(O)cc7CC[C@@H]6c6ccccc6)cc5)CC4)CC3)cc1)=N[C@@H](Cc1ncco1)c1nnc(C)n1-2] |

TABLE 3-continued
| Compound No. | Compound Structure |
|---|---|
| III-106 | 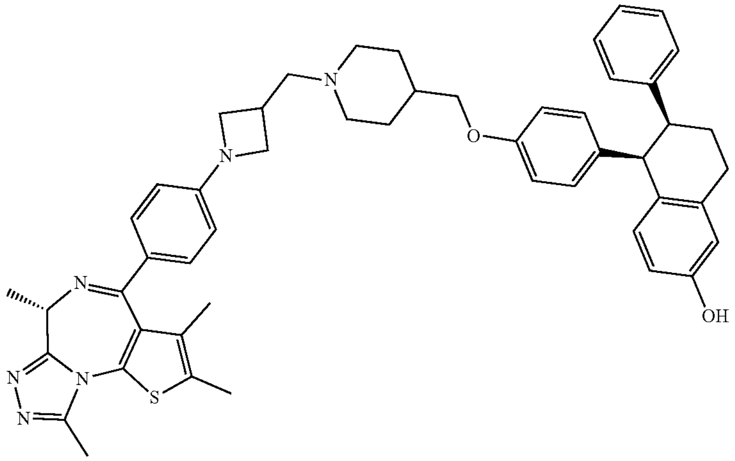 [SMILES: Cc1sc2c(c1C)C(c1ccc(N3CC(CN4CCC(COc5ccc([C@@H]6c7ccc(O)cc7CC[C@@H]6c6ccccc6)cc5)CC4)C3)cc1)=N[C@@H](C)c1nnc(C)n1-2] |
| III-107 | 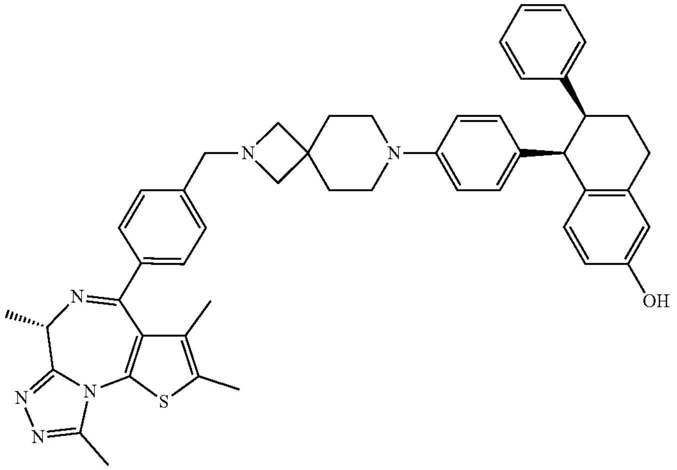 [SMILES: Cc1sc2c(c1C)C(c1ccc(CN3CC4(CCN(c5ccc([C@@H]6c7ccc(O)cc7CC[C@@H]6c6ccccc6)cc5)CC4)C3)cc1)=N[C@@H](C)c1nnc(C)n1-2] |
| III-108 | 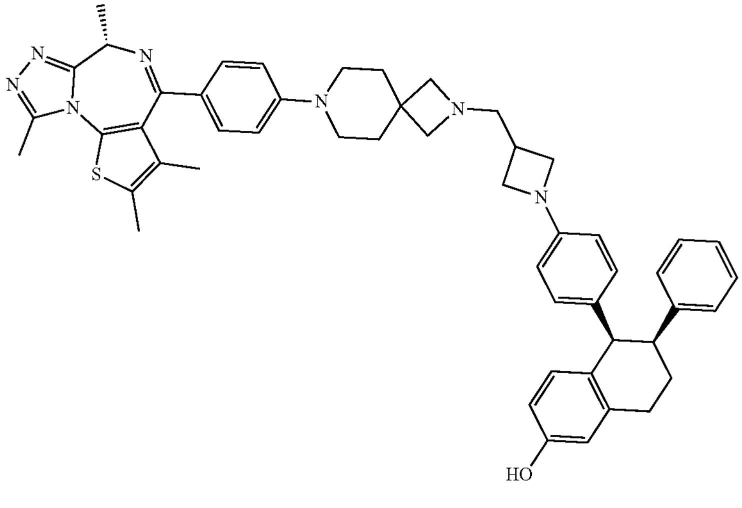 [SMILES: Cc1sc2c(c1C)C(c1ccc(N3CCC4(CC3)CN(CC3CN(c5ccc([C@@H]6c7ccc(O)cc7CC[C@@H]6c6ccccc6)cc5)C3)C4)cc1)=N[C@@H](C)c1nnc(C)n1-2] |

TABLE 3-continued
| Compound No. | Compound Structure |
|---|---|
| III-109 | 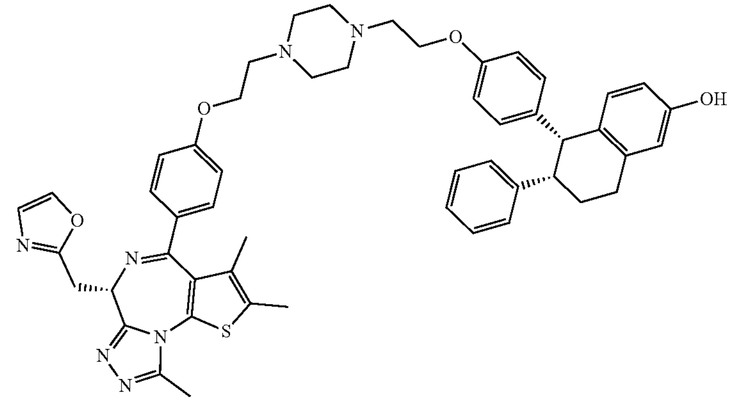 [SMILES: Cc1sc2c(c1C)C(c1ccc(OCCN3CCN(CCOc4ccc([C@@H]5c6ccc(O)cc6CC[C@@H]5c5ccccc5)cc4)CC3)cc1)=N[C@@H](Cc1ncco1)c1nnc(C)n1-2] |
| III-110 | 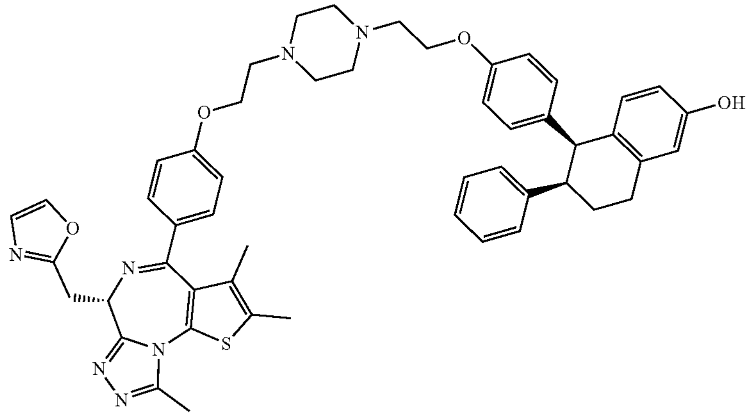 [SMILES: Cc1sc2c(c1C)C(c1ccc(OCCN3CCN(CCOc4ccc([C@H]5c6ccc(O)cc6CC[C@H]5c5ccccc5)cc4)CC3)cc1)=N[C@@H](Cc1ncco1)c1nnc(C)n1-2] |
| III-111 | 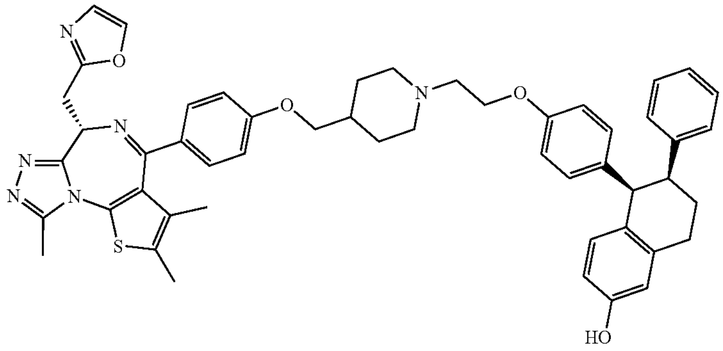 [SMILES: Cc1sc2c(c1C)C(c1ccc(OCC3CCN(CCOc4ccc([C@@H]5c6ccc(O)cc6CC[C@@H]5c5ccccc5)cc4)CC3)cc1)=N[C@@H](Cc1ncco1)c1nnc(C)n1-2] |
| III-112 | 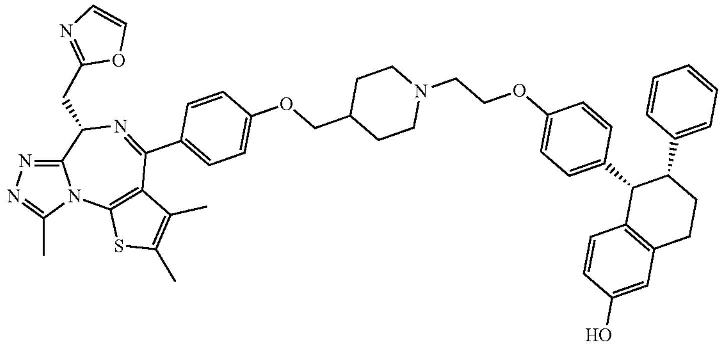 [SMILES: Cc1sc2c(c1C)C(c1ccc(OCC3CCN(CCOc4ccc([C@H]5c6ccc(O)cc6CC[C@H]5c5ccccc5)cc4)CC3)cc1)=N[C@@H](Cc1ncco1)c1nnc(C)n1-2] |

TABLE 3-continued
| Compound No. | Compound Structure |
|---|---|
| III-113 | 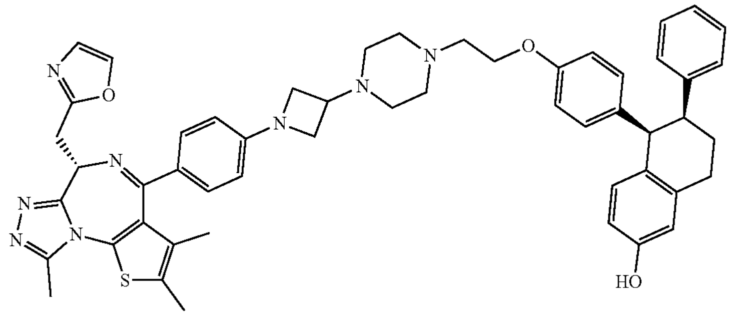 [SMILES: Cc1sc2c(c1C)C(c1ccc(N3CC(N4CCN(CCOc5ccc([C@@H]6c7ccc(O)cc7CC[C@@H]6c6ccccc6)cc5)CC4)C3)cc1)=N[C@@H](Cc1ncco1)c1nnc(C)n1-2] |
| III-114 | 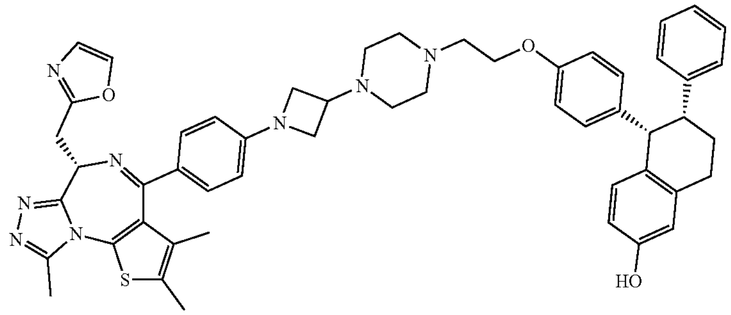 [SMILES: Cc1sc2c(c1C)C(c1ccc(N3CC(N4CCN(CCOc5ccc([C@H]6c7ccc(O)cc7CC[C@H]6c6ccccc6)cc5)CC4)C3)cc1)=N[C@@H](Cc1ncco1)c1nnc(C)n1-2] |
| III-115 | 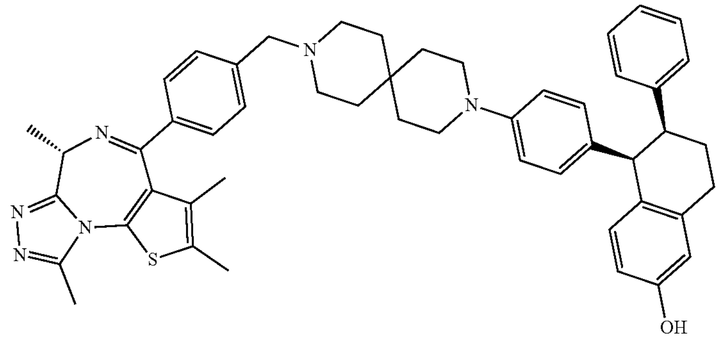 [SMILES: Cc1sc2c(c1C)C(c1ccc(CN3CCC4(CC3)CCN(c3ccc([C@@H]5c6ccc(O)cc6CC[C@@H]5c5ccccc5)cc3)CC4)cc1)=N[C@@H](C)c1nnc(C)n1-2] |
| III-116 | 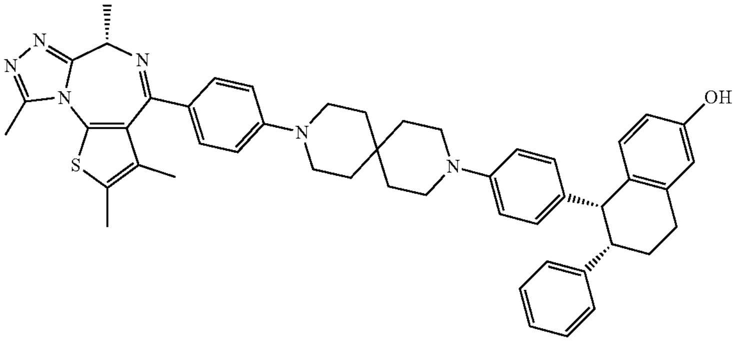 [SMILES: Cc1sc2c(c1C)C(c1ccc(N3CCC4(CC3)CCN(c3ccc([C@@H]5c6ccc(O)cc6CC[C@@H]5c5ccccc5)cc3)CC4)cc1)=N[C@@H](C)c1nnc(C)n1-2] |

TABLE 3-continued
| Compound No. | Compound Structure |
|---|---|
| III-117 | 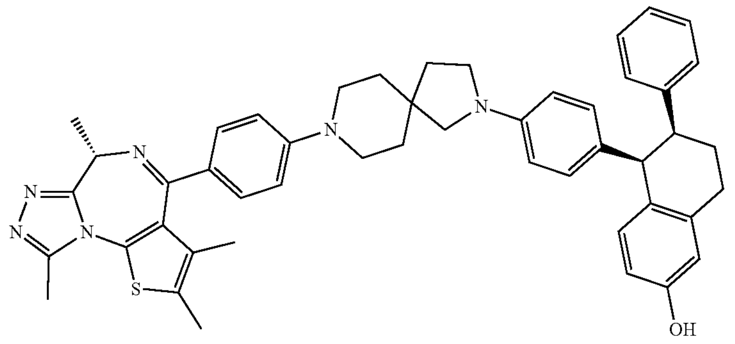 [SMILES: Cc1sc2c(c1C)C(c1ccc(N3CCC4(CC3)CCN(c3ccc([C@@H]5c6ccc(O)cc6CC[C@@H]5c5ccccc5)cc3)C4)cc1)=N[C@@H](C)c1nnc(C)n1-2] |
| III-118 | 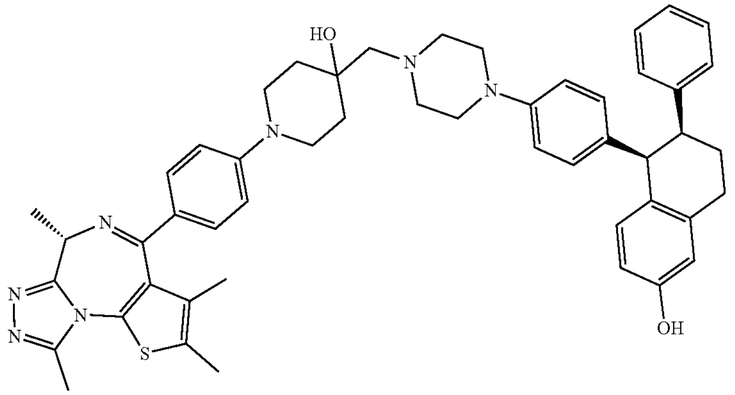 [SMILES: Cc1sc2c(c1C)C(c1ccc(N3CCC(O)(CN4CCN(c5ccc([C@@H]6c7ccc(O)cc7CC[C@@H]6c6ccccc6)cc5)CC4)CC3)cc1)=N[C@@H](C)c1nnc(C)n1-2] |
| III-119 | 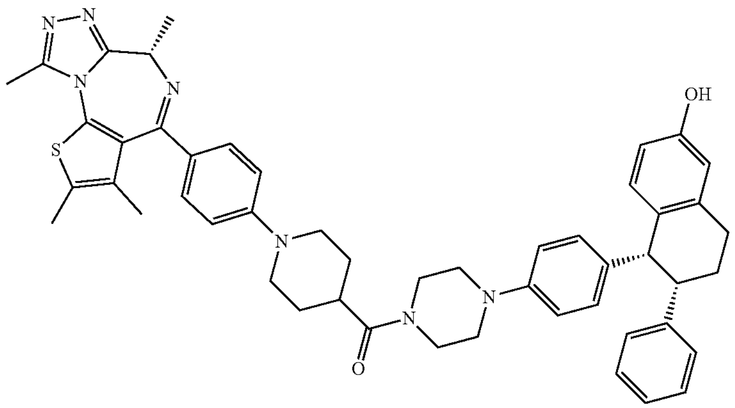 [SMILES: Cc1sc2c(c1C)C(c1ccc(N3CCC(C(=O)N4CCN(c5ccc([C@@H]6c7ccc(O)cc7CC[C@@H]6c6ccccc6)cc5)CC4)CC3)cc1)=N[C@@H](C)c1nnc(C)n1-2] |
| III-120 | 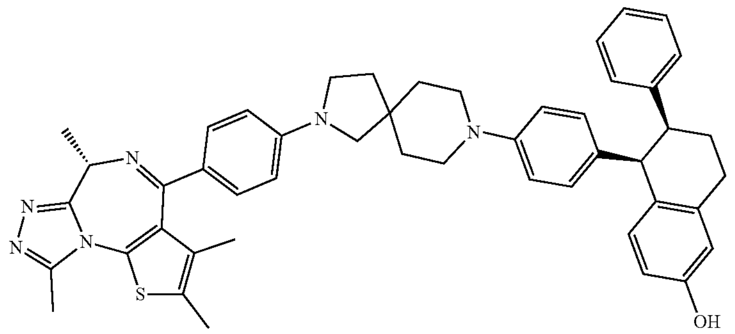 [SMILES: Cc1sc2c(c1C)C(c1ccc(N3CCC4(CCN(c5ccc([C@@H]6c7ccc(O)cc7CC[C@@H]6c6ccccc6)cc5)CC4)C3)cc1)=N[C@@H](C)c1nnc(C)n1-2] |

TABLE 3-continued
| Compound No. | Compound Structure |
|---|---|
| III-121 | 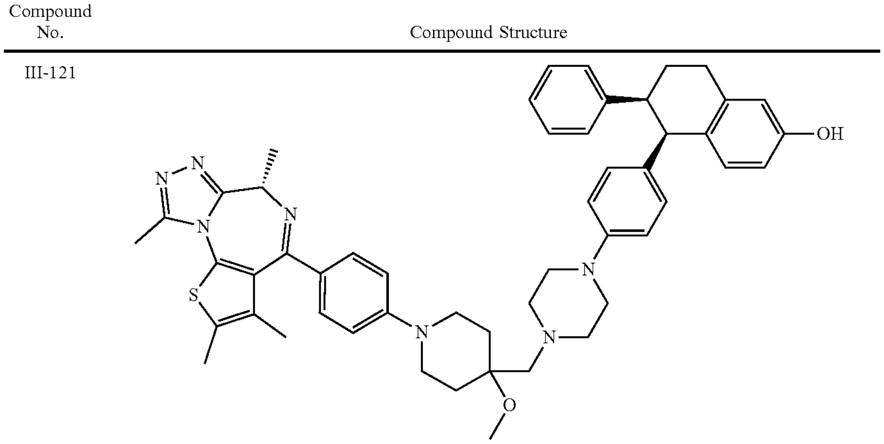 |
| III-122 | 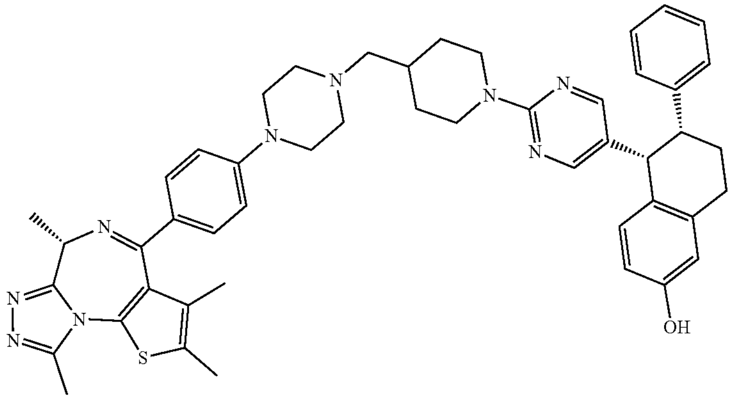 [SMILES: Cc1sc2c(c1C)C(c1ccc(N3CCN(CC4CCN(c5ncc([C@H]6c7ccc(O)cc7CC[C@H]6c6ccccc6)cn5)CC4)CC3)cc1)=N[C@@H](C)c1nnc(C)n1-2] |
| III-123 | 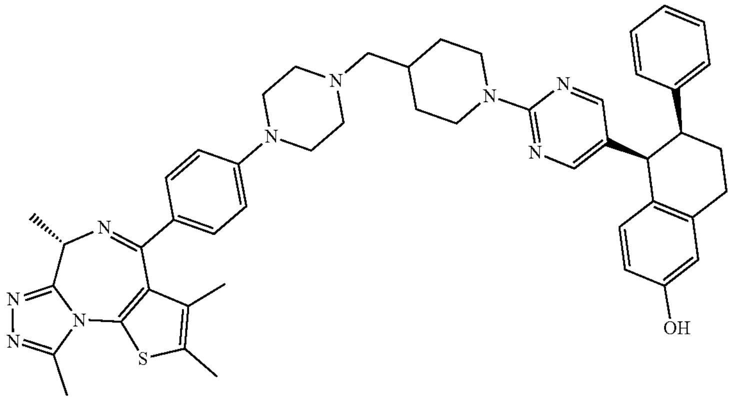 [SMILES: Cc1sc2c(c1C)C(c1ccc(N3CCN(CC4CCN(c5ncc([C@@H]6c7ccc(O)cc7CC[C@@H]6c6ccccc6)cn5)CC4)CC3)cc1)=N[C@@H](C)c1nnc(C)n1-2] |
| III-124 | 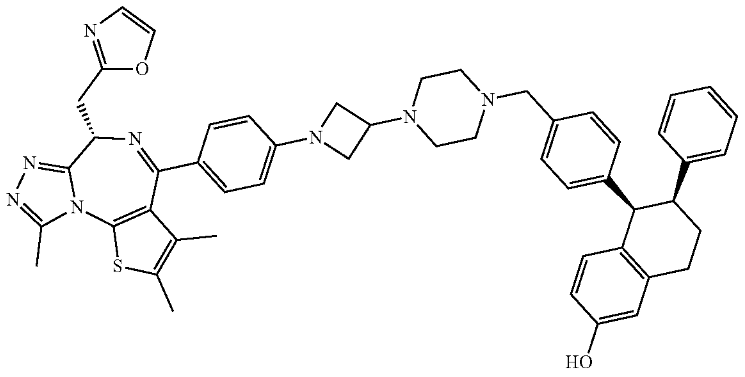 [SMILES: Cc1sc2c(c1C)C(c1ccc(N3CC(N4CCN(Cc5ccc([C@@H]6c7ccc(O)cc7CC[C@@H]6c6ccccc6)cc5)CC4)C3)cc1)=N[C@@H](Cc1ncco1)c1nnc(C)n1-2] |

TABLE 3-continued
| Compound No. | Compound Structure |
|---|---|
| III-125 | 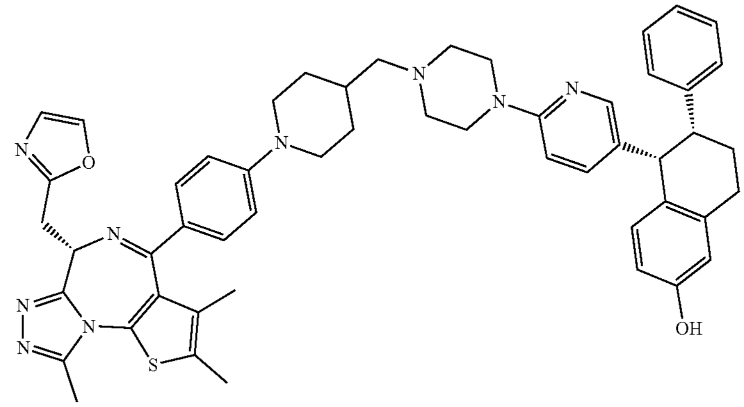 [SMILES: Cc1sc2c(c1C)C(c1ccc(N3CCC(CN4CCN(c5ccc([C@H]6c7ccc(O)cc7CC[C@H]6c6ccccc6)cn5)CC4)CC3)cc1)=N[C@@H](Cc1ncco1)c1nnc(C)n1-2] |
| III-126 | 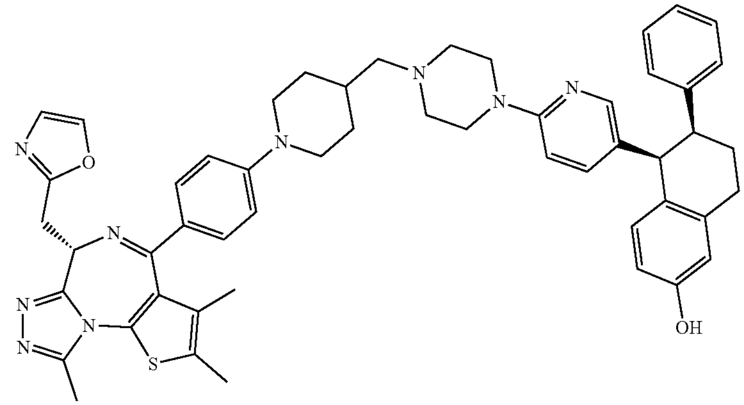 [SMILES: Cc1sc2c(c1C)C(c1ccc(N3CCC(CN4CCN(c5ccc([C@@H]6c7ccc(O)cc7CC[C@@H]6c6ccccc6)cn5)CC4)CC3)cc1)=N[C@@H](Cc1ncco1)c1nnc(C)n1-2] |
| III-127 | 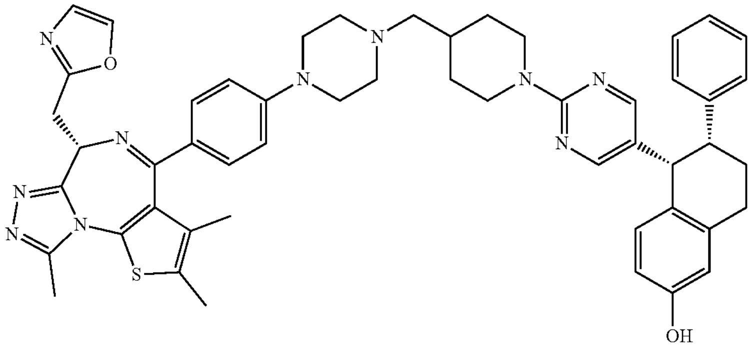 [SMILES: Cc1sc2c(c1C)C(c1ccc(N3CCN(CC4CCN(c5ncc([C@H]6c7ccc(O)cc7CC[C@H]6c6ccccc6)cn5)CC4)CC3)cc1)=N[C@@H](Cc1ncco1)c1nnc(C)n1-2] |
| III-128 | 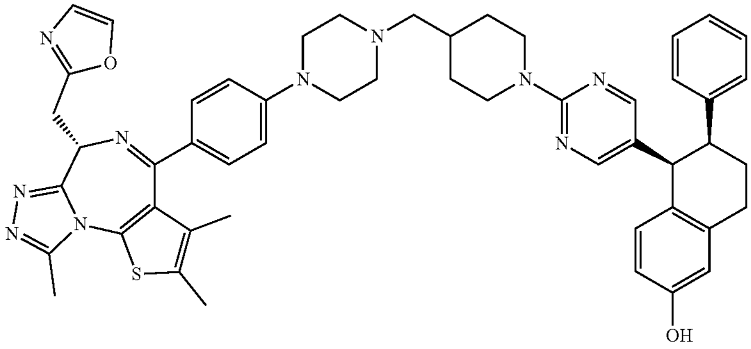 [SMILES: Cc1sc2c(c1C)C(c1ccc(N3CCN(CC4CCN(c5ncc([C@@H]6c7ccc(O)cc7CC[C@@H]6c6ccccc6)cn5)CC4)CC3)cc1)=N[C@@H](Cc1ncco1)c1nnc(C)n1-2] |

TABLE 3-continued
| Compound No. | Compound Structure |
|---|---|
| III-129 | 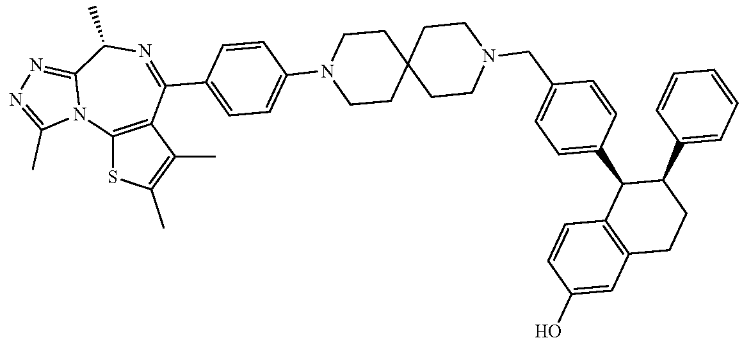 [SMILES: Cc1sc2c(c1C)C(c1ccc(N3CCC4(CCN(Cc5ccc([C@@H]6c7ccc(O)cc7CC[C@@H]6c6ccccc6)cc5)CC4)CC3)cc1)=N[C@@H](C)c1nnc(C)n1-2] |
| III-130 | 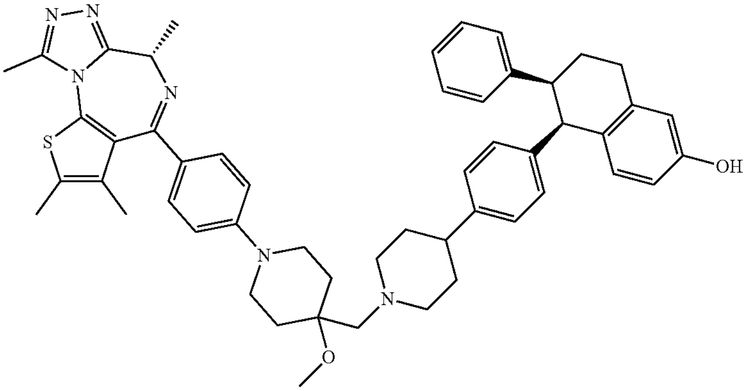 [SMILES: COC1(CN2CCC(c3ccc([C@@H]4c5ccc(O)cc5CC[C@@H]4c4ccccc4)cc3)CC2)CCN(c2ccc(C3=N[C@@H](C)c4nnc(C)n4-c4sc(C)c(C)c43)cc2)CC1] |
| III-131 | 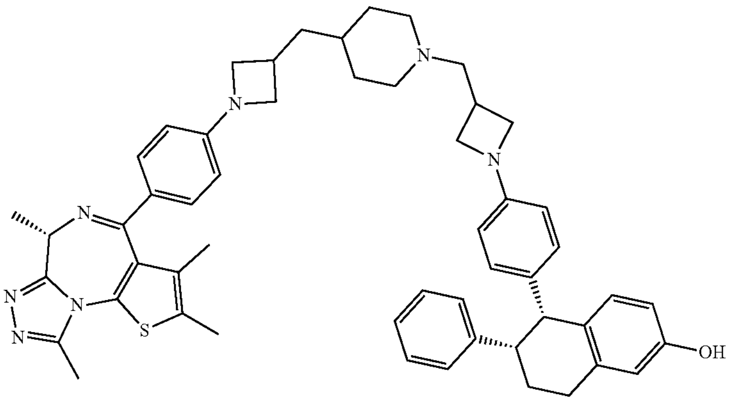 [SMILES: Cc1sc2c(c1C)C(c1ccc(N3CC(CC4CCN(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-132 | 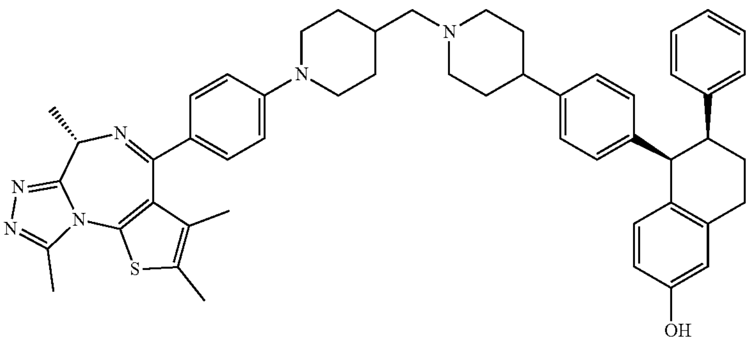 [SMILES: Cc1sc2c(c1C)C(c1ccc(N3CCC(CN4CCC(c5ccc([C@@H]6c7ccc(O)cc7CC[C@@H]6c6ccccc6)cc5)CC4)CC3)cc1)=N[C@@H](C)c1nnc(C)n1-2] |

TABLE 3-continued
| Compound No. | Compound Structure |
| --- | --- |
| III-133 | 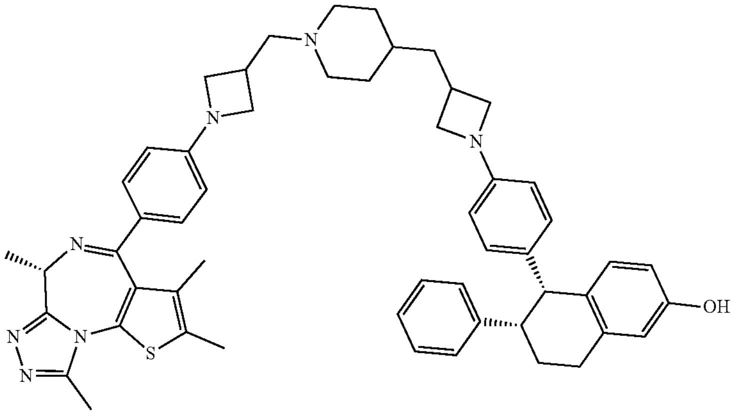 [SMILES: Cc1sc2c(c1C)C(c1ccc(N3CC(CN4CCC(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-134 | 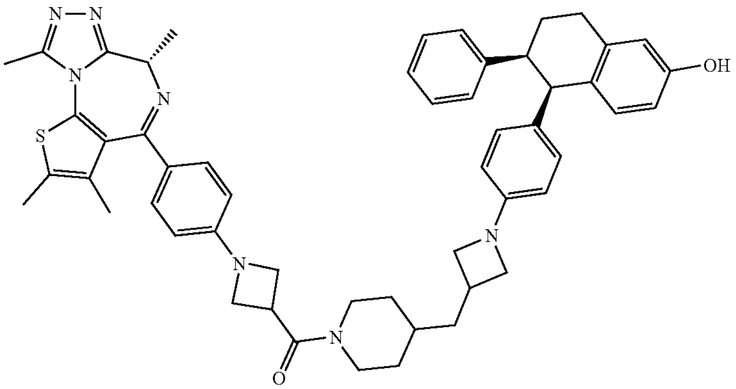 [SMILES: Cc1sc2c(c1C)C(c1ccc(N3CC(C(=O)N4CCC(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-135 | 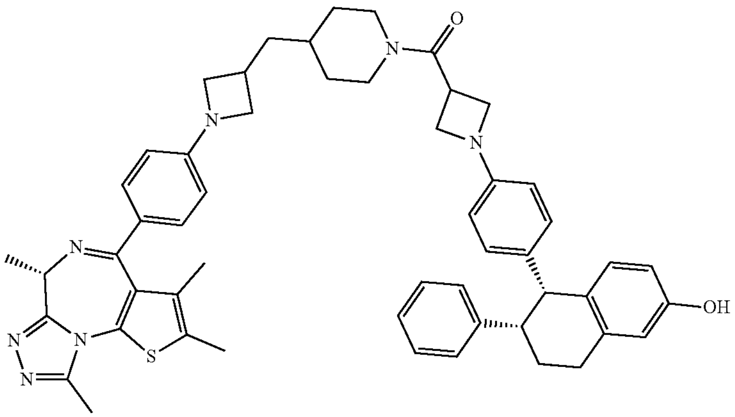 [SMILES: Cc1sc2c(c1C)C(c1ccc(N3CC(CC4CCN(C(=O)C5CN(c6ccc([C@@H]7c8ccc(O)cc8CC[C@@H]7c7ccccc7)cc6)C5)CC4)C3)cc1)=N[C@@H](C)c1nnc(C)n1-2] |

TABLE 3-continued
| Compound No. | Compound Structure |
|---|---|
| III-136 | 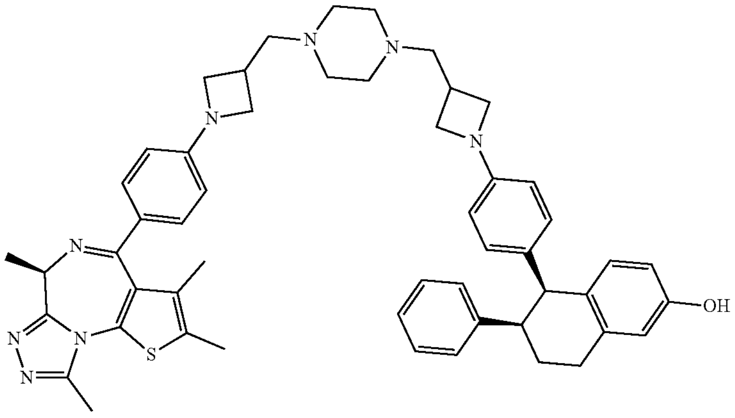 [SMILES: Cc1sc2c(c1C)C(c1ccc(N3CC(CN4CCN(CC5CN(c6ccc([C@H]7c8ccc(O)cc8CC[C@H]7c7ccccc7)cc6)C5)CC4)C3)cc1)=N[C@H](C)c1nnc(C)n1-2] |
| III-137 | 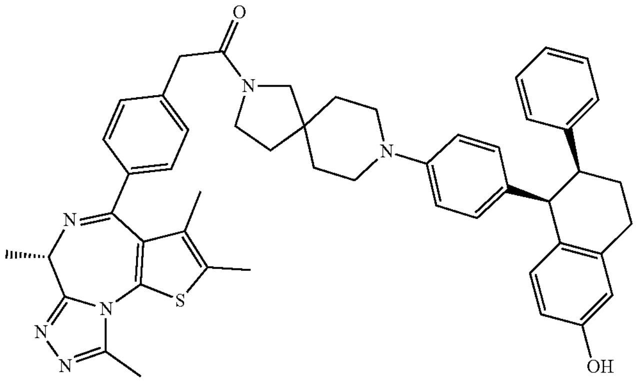 [SMILES: Cc1sc2c(c1C)C(c1ccc(CC(=O)N3CCC4(CCN(c5ccc([C@@H]6c7ccc(O)cc7CC[C@@H]6c6ccccc6)cc5)CC4)C3)cc1)=N[C@@H](C)c1nnc(C)n1-2] |
| III-138 | 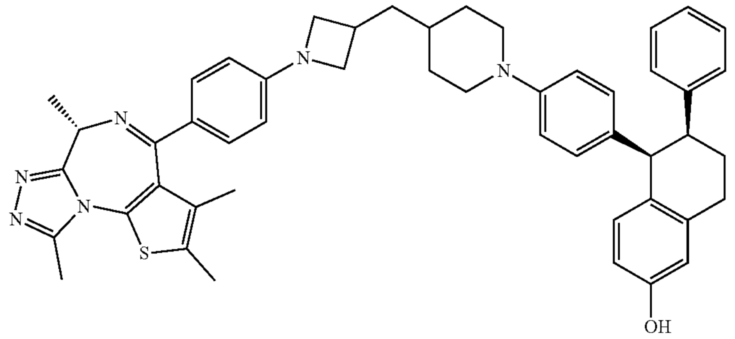 [SMILES: Cc1sc2c(c1C)C(c1ccc(N3CC(CC4CCN(c5ccc([C@@H]6c7ccc(O)cc7CC[C@@H]6c6ccccc6)cc5)CC4)C3)cc1)=N[C@@H](C)c1nnc(C)n1-2] |
| III-139 | 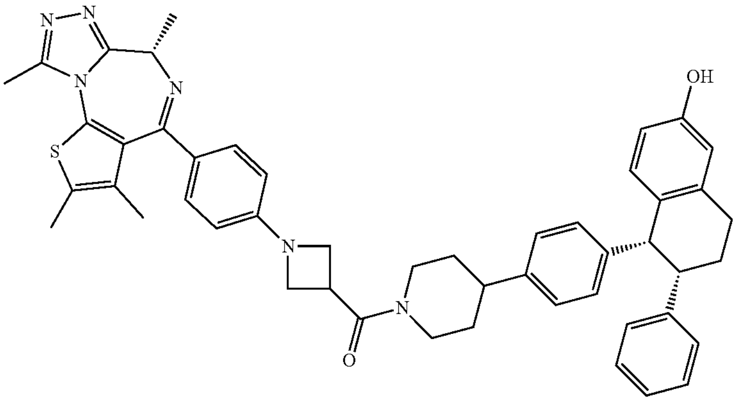 [SMILES: Cc1sc2c(c1C)C(c1ccc(N3CC(C(=O)N4CCC(c5ccc([C@@H]6c7ccc(O)cc7CC[C@@H]6c6ccccc6)cc5)CC4)C3)cc1)=N[C@@H](C)c1nnc(C)n1-2] |

TABLE 3-continued
| Compound No. | Compound Structure |
|---|---|
| III-140 | 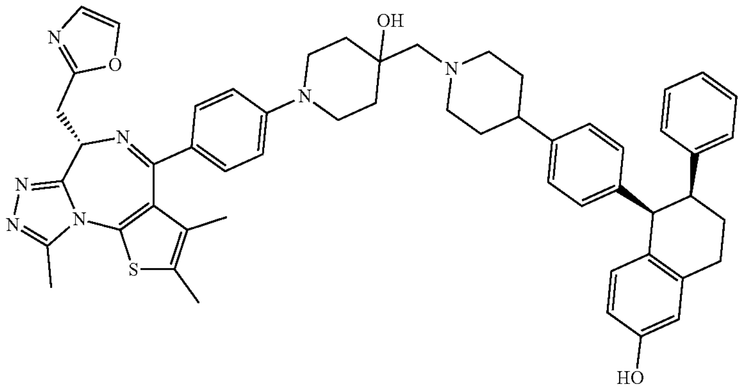 [SMILES: Cc1sc2c(c1C)C(c1ccc(N3CCC(O)(CN4CCC(c5ccc([C@@H]6c7ccc(O)cc7CC[C@@H]6c6ccccc6)cc5)CC4)CC3)cc1)=N[C@@H](Cc1ncco1)c1nnc(C)n1-2] |
| III-141 | 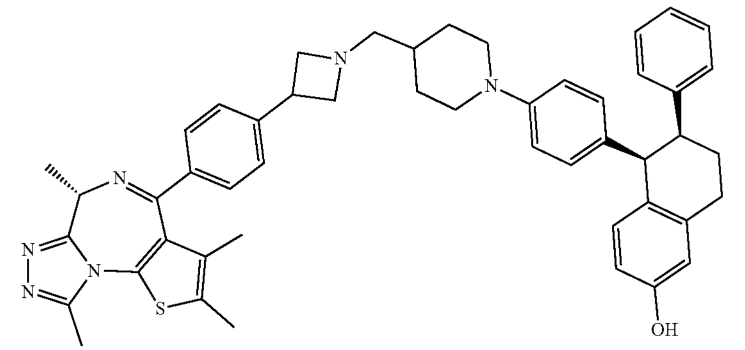 [SMILES: Cc1sc2c(c1C)C(c1ccc(C3CN(CC4CCN(c5ccc([C@@H]6c7ccc(O)cc7CC[C@@H]6c6ccccc6)cc5)CC4)C3)cc1)=N[C@@H](C)c1nnc(C)n1-2] |
| III-142 | 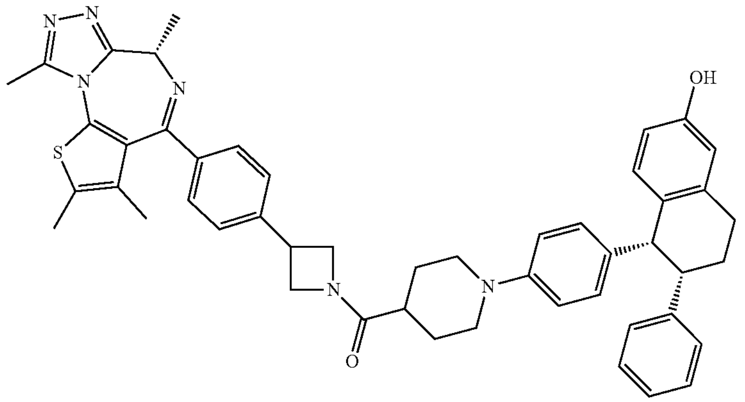 [SMILES: Cc1sc2c(c1C)C(c1ccc(C3CN(C(=O)C4CCN(c5ccc([C@@H]6c7ccc(O)cc7CC[C@@H]6c6ccccc6)cc5)CC4)C3)cc1)=N[C@@H](C)c1nnc(C)n1-2] |
| III-143 | 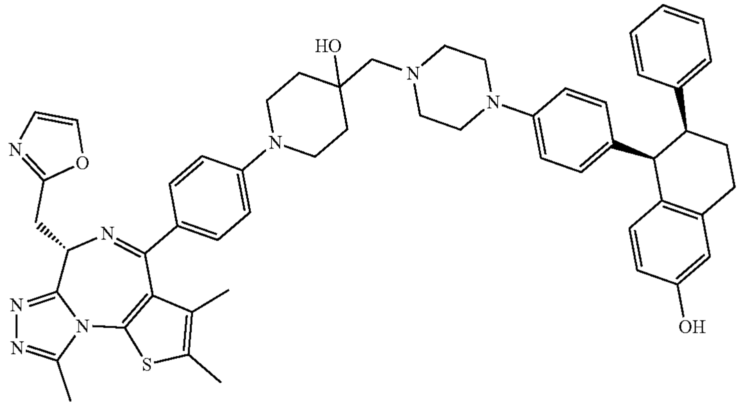 [SMILES: Cc1sc2c(c1C)C(c1ccc(N3CCC(O)(CN4CCN(c5ccc([C@@H]6c7ccc(O)cc7CC[C@@H]6c6ccccc6)cc5)CC4)CC3)cc1)=N[C@@H](Cc1ncco1)c1nnc(C)n1-2] |

TABLE 3-continued
| Compound No. | Compound Structure |
|---|---|
| III-144 | 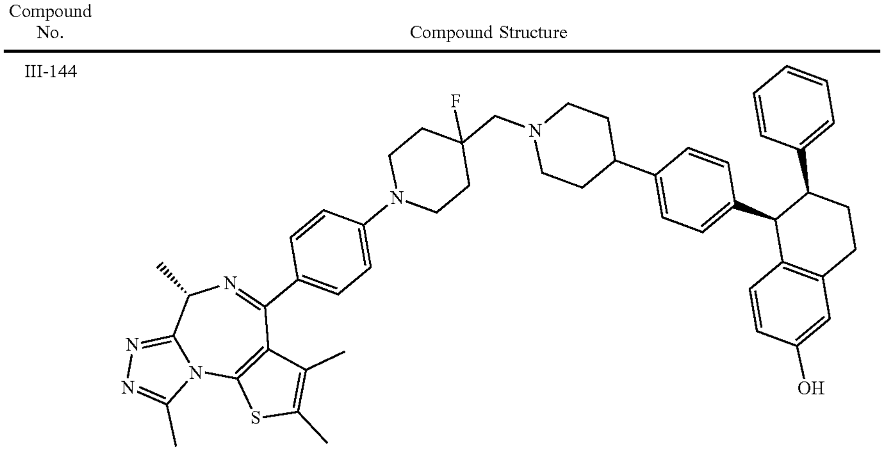 |
| III-145 | 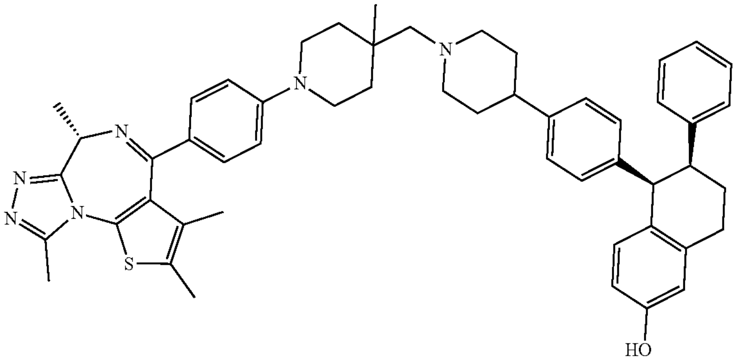 [SMILES: Cc1sc2c(c1C)C(c1ccc(N3CCC(C)(CN4CCC(c5ccc([C@@H]6c7ccc(O)cc7CC[C@@H]6c6ccccc6)cc5)CC4)CC3)cc1)=N[C@@H](C)c1nnc(C)n1-2] |
| III-146 | 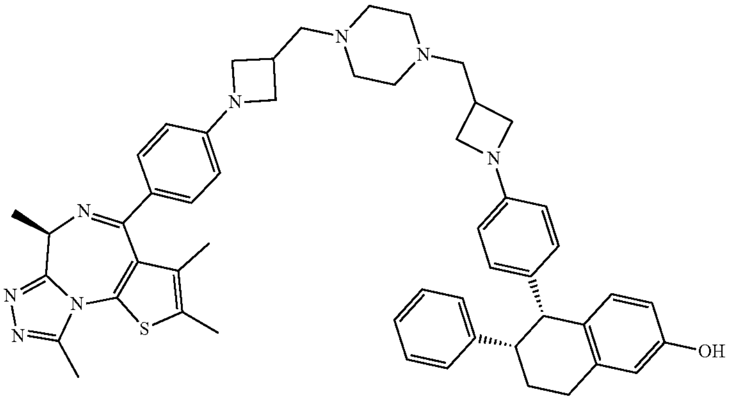 [SMILES: Cc1sc2c(c1C)C(c1ccc(N3CC(CN4CCN(CC5CN(c6ccc([C@@H]7c8ccc(O)cc8CC[C@@H]7c7ccccc7)cc6)C5)CC4)C3)cc1)=N[C@H](C)c1nnc(C)n1-2] |
| III-147 | 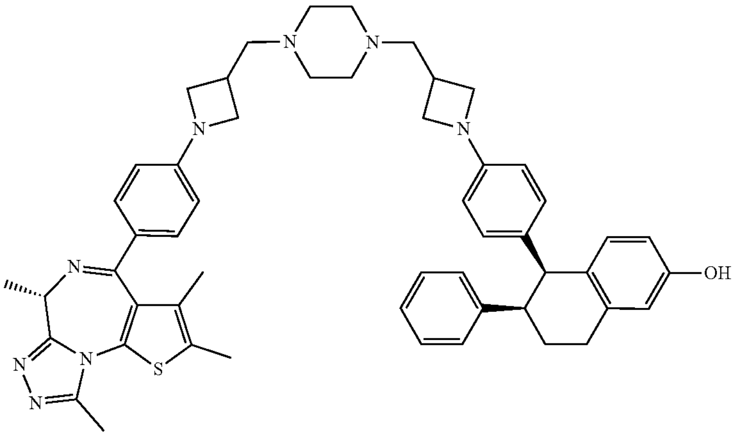 [SMILES: Cc1sc2c(c1C)C(c1ccc(N3CC(CN4CCN(CC5CN(c6ccc([C@H]7c8ccc(O)cc8CC[C@H]7c7ccccc7)cc6)C5)CC4)C3)cc1)=N[C@@H](C)c1nnc(C)n1-2] |

TABLE 3-continued
| Compound No. | Compound Structure |
|---|---|
| III-148 | 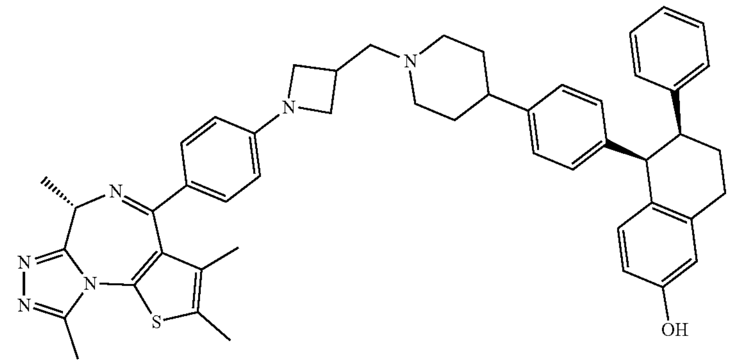 [SMILES: Cc1sc2c(c1C)C(c1ccc(N3CC(CN4CCC(c5ccc([C@@H]6c7ccc(O)cc7CC[C@@H]6c6ccccc6)cc5)CC4)C3)cc1)=N[C@@H](C)c1nnc(C)n1-2] |
| III-149 | 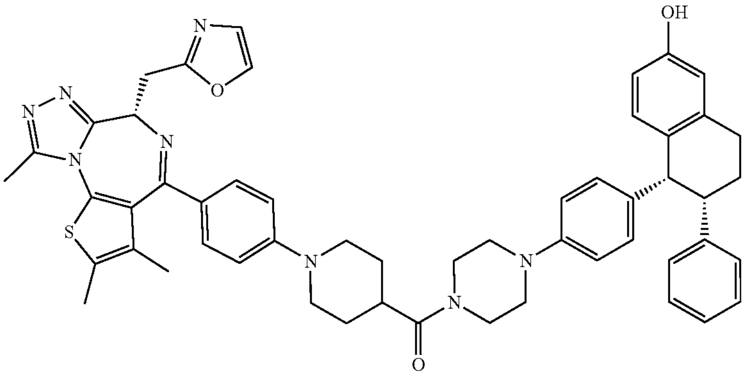 [SMILES: Cc1sc2c(c1C)C(c1ccc(N3CCC(C(=O)N4CCN(c5ccc([C@@H]6c7ccc(O)cc7CC[C@@H]6c6ccccc6)cc5)CC4)CC3)cc1)=N[C@@H](Cc1ncco1)c1nnc(C)n1-2] |
| III-150 | 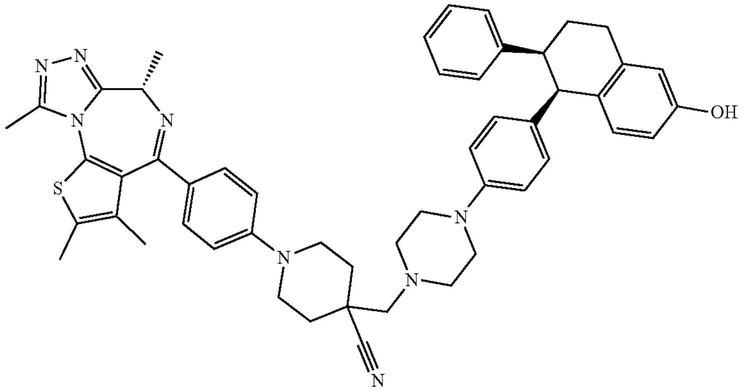 [SMILES: Cc1sc2c(c1C)C(c1ccc(N3CCC(C#N)(CN4CCN(c5ccc([C@@H]6c7ccc(O)cc7CC[C@@H]6c6ccccc6)cc5)CC4)CC3)cc1)=N[C@@H](C)c1nnc(C)n1-2] |
| III-151 | 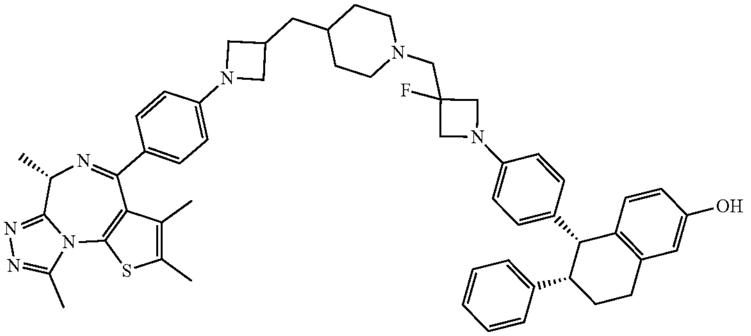 [SMILES: Cc1sc2c(c1C)C(c1ccc(N3CC(CC4CCN(CC5(F)CN(c6ccc([C@@H]7c8ccc(O)cc8CC[C@@H]7c7ccccc7)cc6)C5)CC4)C3)cc1)=N[C@@H](C)c1nnc(C)n1-2] |

TABLE 3-continued
| Compound No. | Compound Structure |
| --- | --- |
| III-152 | 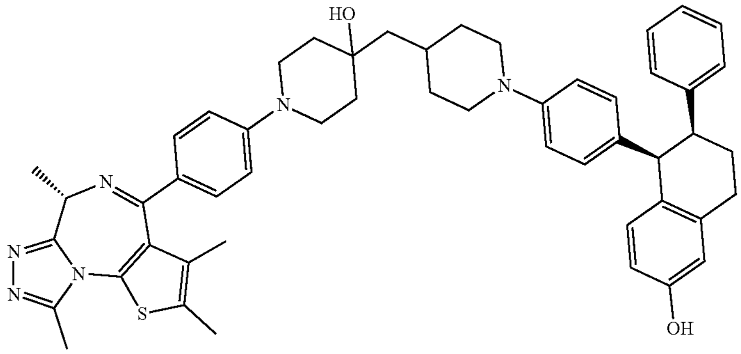 [SMILES: Cc1sc2c(c1C)C(c1ccc(N3CCC(O)(CC4CCN(c5ccc([C@@H]6c7ccc(O)cc7CC[C@@H]6c6ccccc6)cc5)CC4)CC3)cc1)=N[C@@H](C)c1nnc(C)n1-2] |
| III-153 | 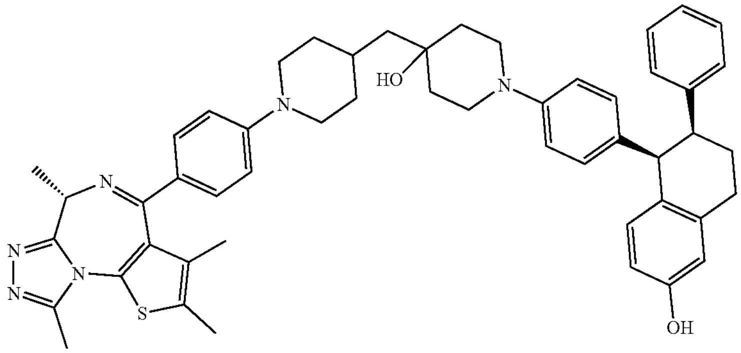 [SMILES: Cc1sc2c(c1C)C(c1ccc(N3CCC(CC4(O)CCN(c5ccc([C@@H]6c7ccc(O)cc7CC[C@@H]6c6ccccc6)cc5)CC4)CC3)cc1)=N[C@@H](C)c1nnc(C)n1-2] |
| III-154 | 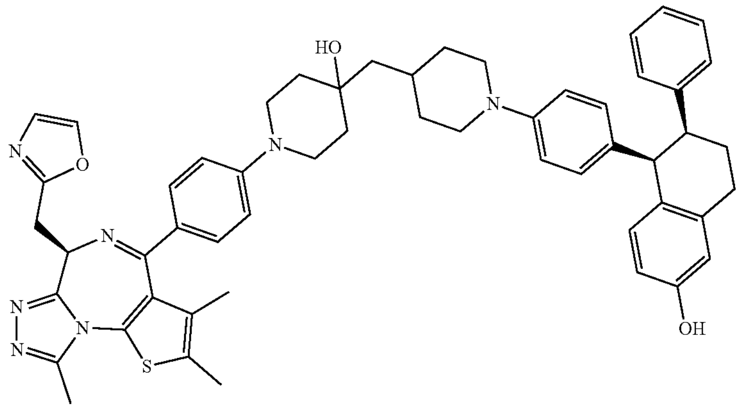 [SMILES: Cc1sc2c(c1C)C(c1ccc(N3CCC(O)(CC4CCN(c5ccc([C@@H]6c7ccc(O)cc7CC[C@@H]6c6ccccc6)cc5)CC4)CC3)cc1)=N[C@H](Cc1ncco1)c1nnc(C)n1-2] |
| III-155 | 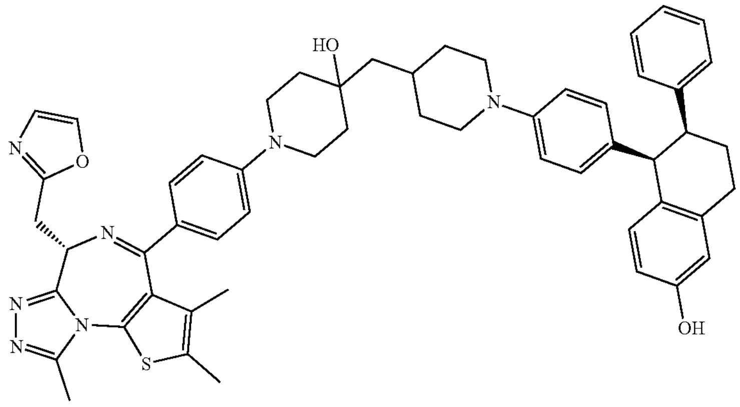 [SMILES: Cc1sc2c(c1C)C(c1ccc(N3CCC(O)(CC4CCN(c5ccc([C@@H]6c7ccc(O)cc7CC[C@@H]6c6ccccc6)cc5)CC4)CC3)cc1)=N[C@@H](Cc1ncco1)c1nnc(C)n1-2] |

TABLE 3-continued
| Compound No. | Compound Structure |
|---|---|
| III-156 | 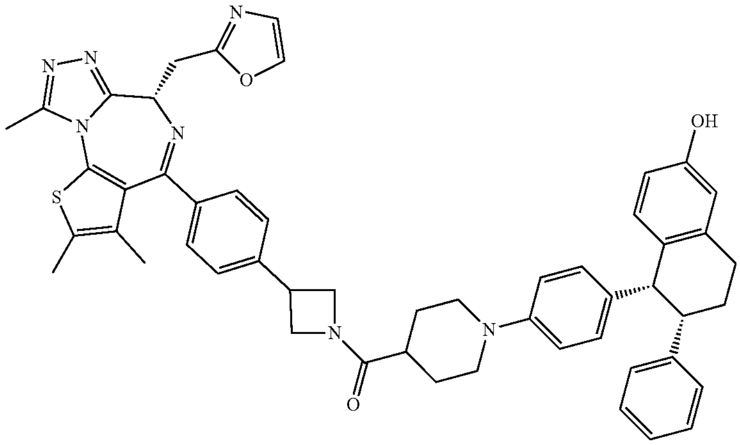 [SMILES: Cc1sc2c(c1C)C(c1ccc(C3CN(C(=O)C4CCN(c5ccc([C@@H]6c7ccc(O)cc7CC[C@@H]6c6ccccc6)cc5)CC4)C3)cc1)=N[C@@H](Cc1ncco1)c1nnc(C)n1-2] |
| III-157 | 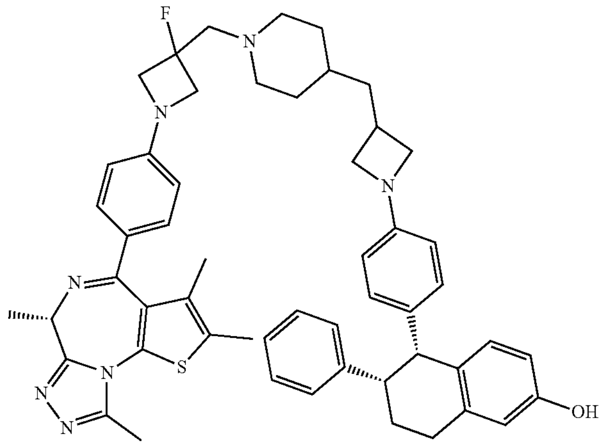 [SMILES: Cc1sc2c(c1C)C(c1ccc(N3CC(F)(CN4CCC(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-158 | 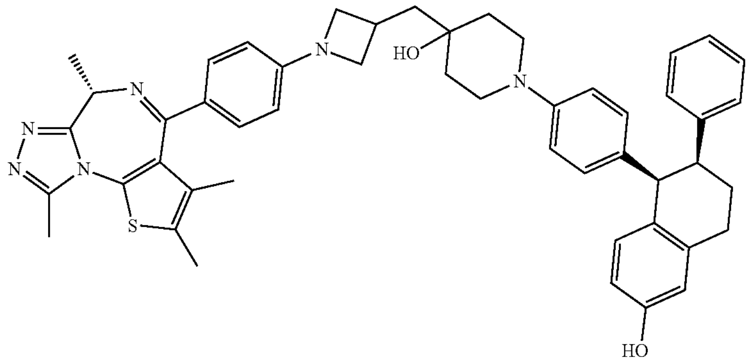 [SMILES: Cc1sc2c(c1C)C(c1ccc(N3CC(CC4(O)CCN(c5ccc([C@@H]6c7ccc(O)cc7CC[C@@H]6c6ccccc6)cc5)CC4)C3)cc1)=N[C@@H](C)c1nnc(C)n1-2] |

TABLE 3-continued
| Compound No. | Compound Structure |
|---|---|
| III-159 | 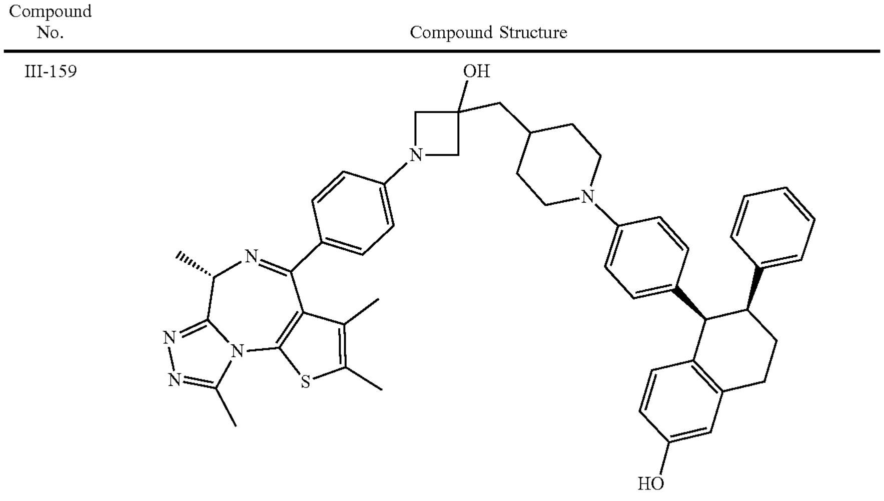 |
| III-160 | 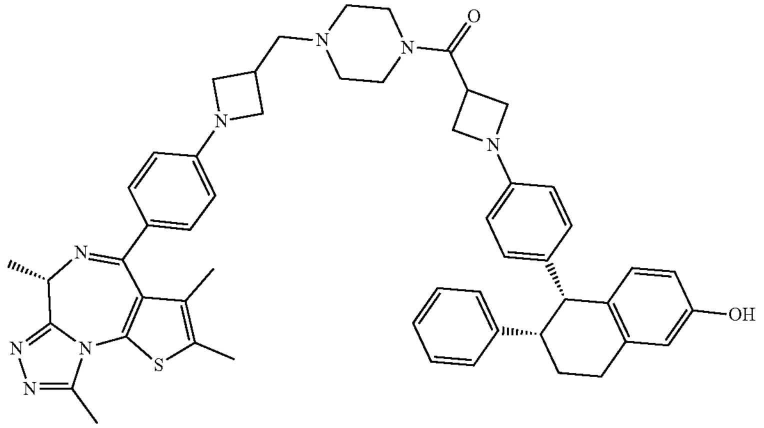 |
| III-161 | 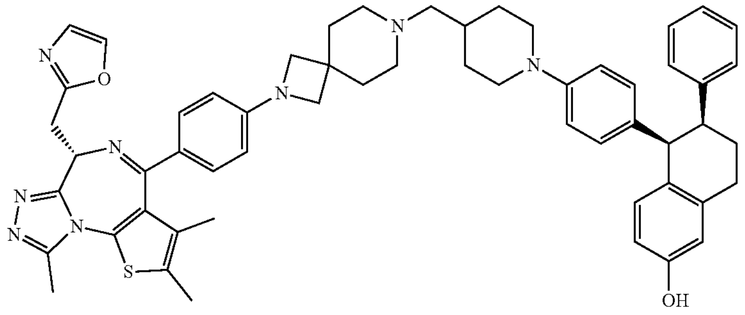 [SMILES: Cc1sc2c(c1C)C(c1ccc(N3CC4(CCN(CC5CCN(c6ccc([C@@H]7c8ccc(O)cc8CC[C@@H]7c7ccccc7)cc6)CC5)CC4)C3)cc1)=N[C@@H](Cc1ncco1)c1nnc(C)n1-2] |
| III-162 | 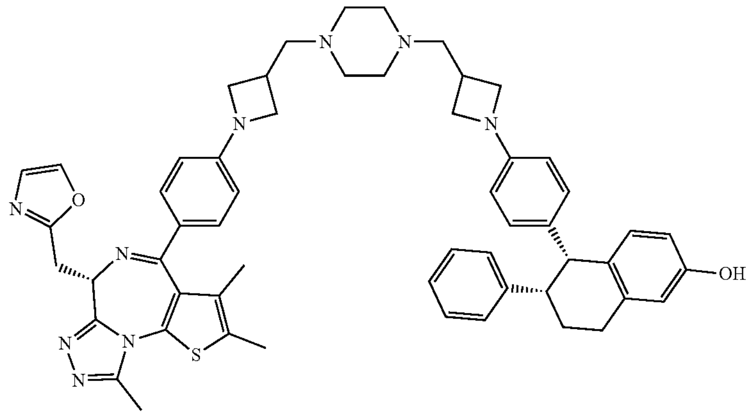 [SMILES: Cc1sc2c(c1C)C(c1ccc(N3CC(CN4CCN(CC5CN(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |

TABLE 3-continued
| Compound No. | Compound Structure |
|---|---|
| III-163 | 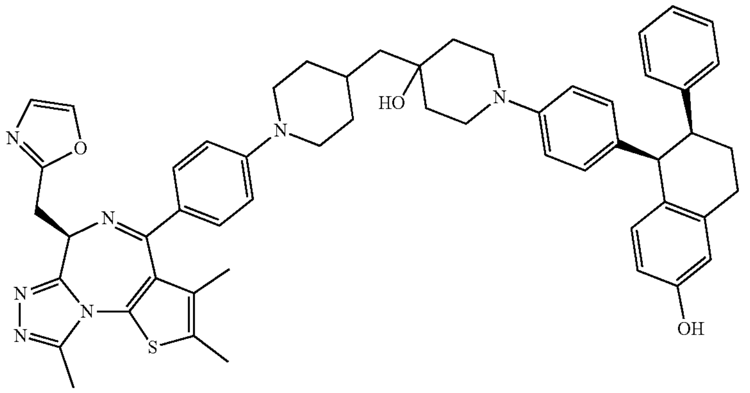 [SMILES: Cc1sc2c(c1C)C(c1ccc(N3CCC(CC4(O)CCN(c5ccc([C@@H]6c7ccc(O)cc7CC[C@@H]6c6ccccc6)cc5)CC4)CC3)cc1)=N[C@H](Cc1ncco1)c1nnc(C)n1-2] |
| III-164 | 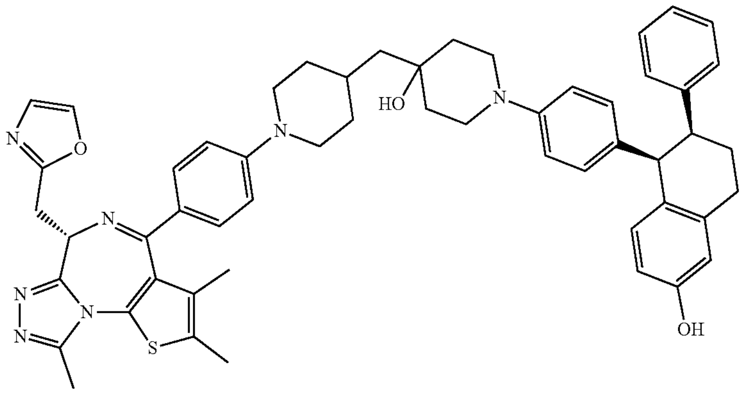 [SMILES: Cc1sc2c(c1C)C(c1ccc(N3CCC(CC4(O)CCN(c5ccc([C@@H]6c7ccc(O)cc7CC[C@@H]6c6ccccc6)cc5)CC4)CC3)cc1)=N[C@@H](Cc1ncco1)c1nnc(C)n1-2] |
| III-165 | 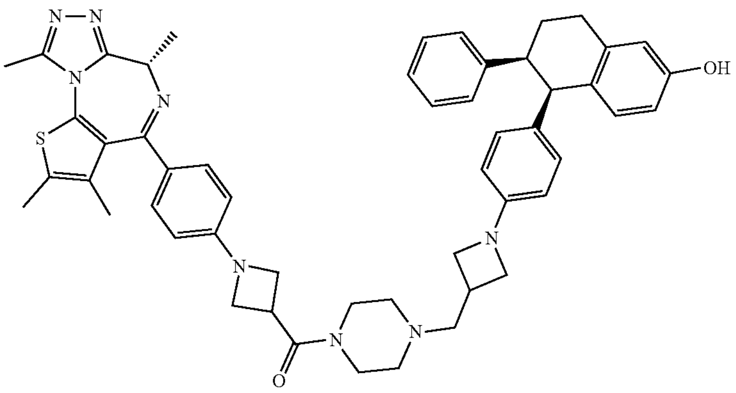 [SMILES: Cc1sc2c(c1C)C(c1ccc(N3CC(C(=O)N4CCN(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-166 | 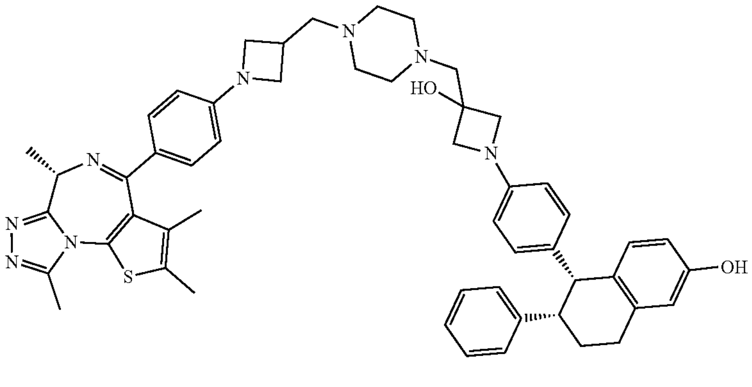 [SMILES: Cc1sc2c(c1C)C(c1ccc(N3CC(CN4CCN(CC5(O)CN(c6ccc([C@@H]7c8ccc(O)cc8CC[C@@H]7c7ccccc7)cc6)C5)CC4)C3)cc1)=N[C@@H](C)c1nnc(C)n1-2] |

TABLE 3-continued
| Compound No. | Compound Structure |
|---|---|
| III-167 | 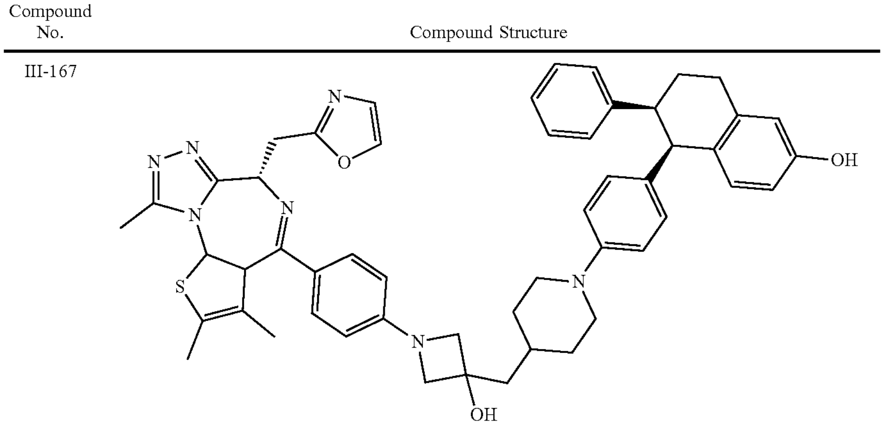 |
| III-168 | 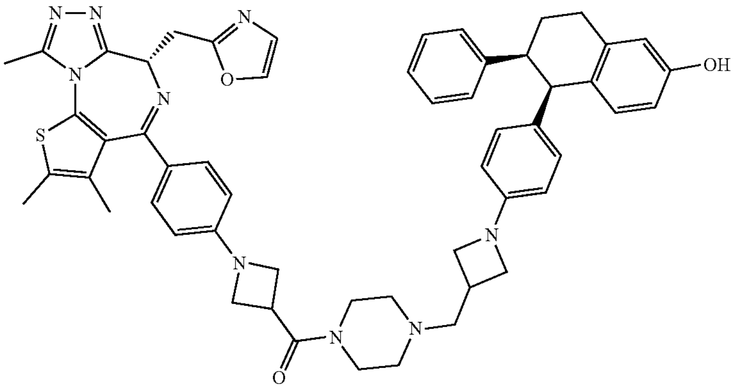 [SMILES: Cc1sc2c(c1C)C(c1ccc(N3CC(C(=O)N4CCN(CC5CN(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |
| III-169 | 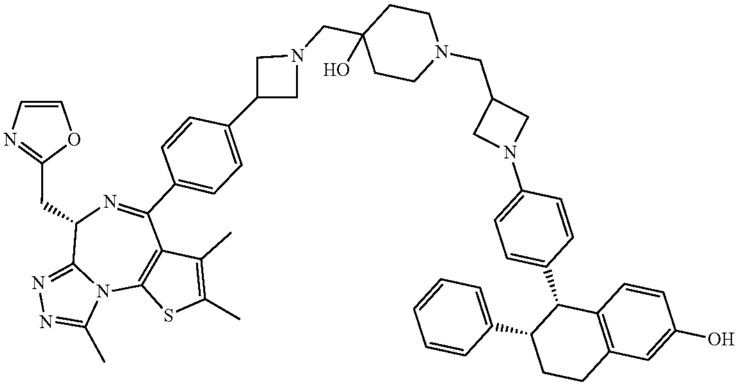 [SMILES: Cc1sc2c(c1C)C(c1ccc(C3CN(CC4(O)CCN(CC5CN(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |
| III-170 | 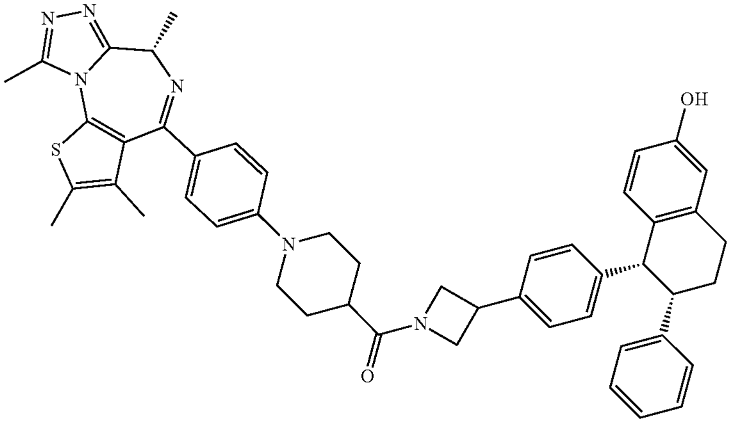 [SMILES: Cc1sc2c(c1C)C(c1ccc(N3CCC(C(=O)N4CC(c5ccc([C@@H]6c7ccc(O)cc7CC[C@@H]6c6ccccc6)cc5)C4)CC3)cc1)=N[C@@H](C)c1nnc(C)n1-2] |

TABLE 3-continued
| Compound No. | Compound Structure |
| --- | --- |
| III-171 | 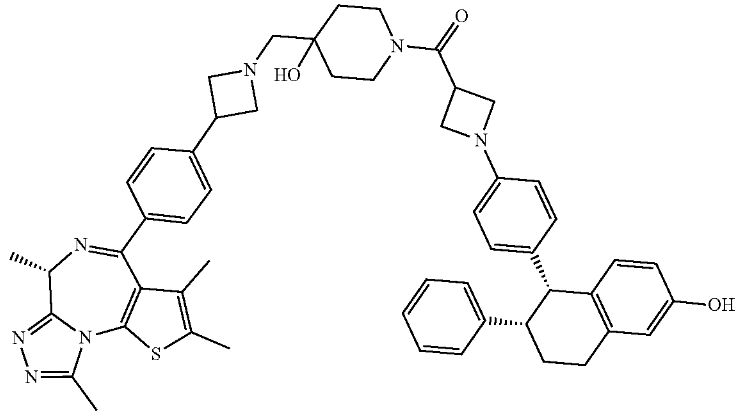 [SMILES: Cc1sc2c(c1C)C(c1ccc(C3CN(CC4(O)CCN(C(=O)C5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-172 | 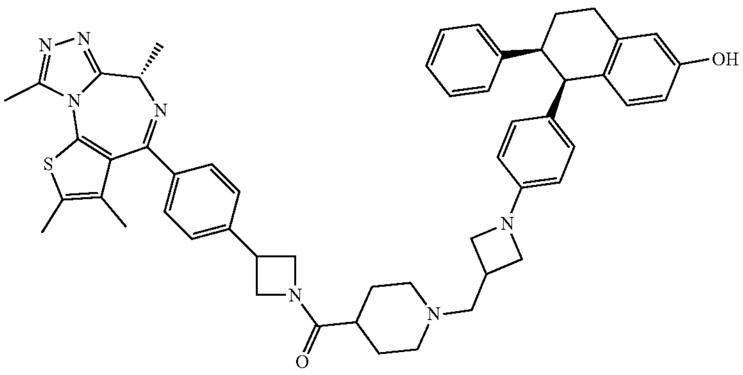 [SMILES: Cc1sc2c(c1C)C(c1ccc(C3CN(C(=O)C4CCN(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-173 | 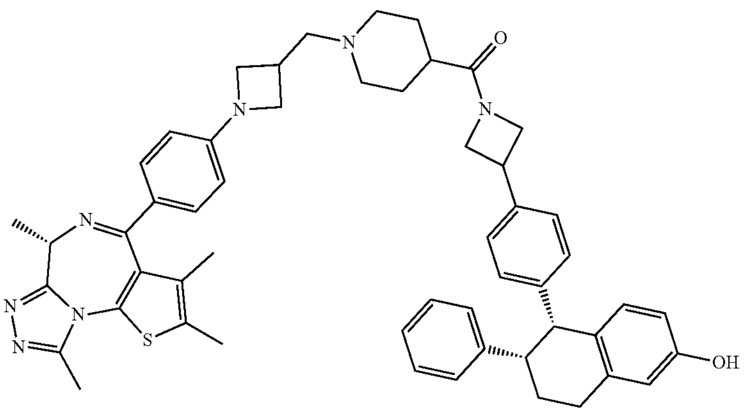 [SMILES: Cc1sc2c(c1C)C(c1ccc(N3CC(CN4CCC(C(=O)N5CC(c6ccc([C@@H]7c8ccc(O)cc8CC[C@@H]7c7ccccc7)cc6)C5)CC4)C3)cc1)=N[C@@H](C)c1nnc(C)n1-2] |

TABLE 3-continued
| Compound No. | Compound Structure |
|---|---|
| III-174 | 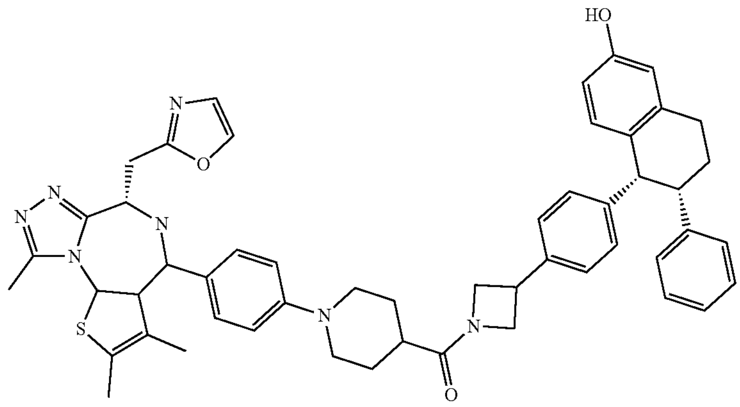 [SMILES: CC1=C(C)C2C(c3ccc(N4CCC(C(=O)N5CC(c6ccc([C@@H]7c8ccc(O)cc8CC[C@@H]7c7ccccc7)cc6)C5)CC4)cc3)N[C@@H](Cc3ncco3)c3nnc(C)n3C2S1] |
| III-175 | 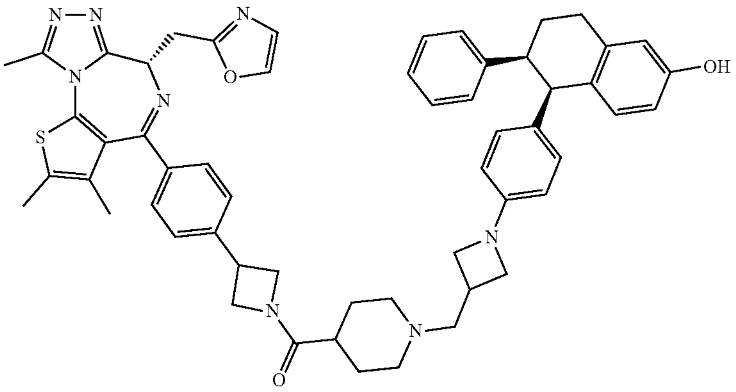 [SMILES: Cc1sc2c(c1C)C(c1ccc(C3CN(C(=O)C4CCN(CC5CN(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |
| III-176 | 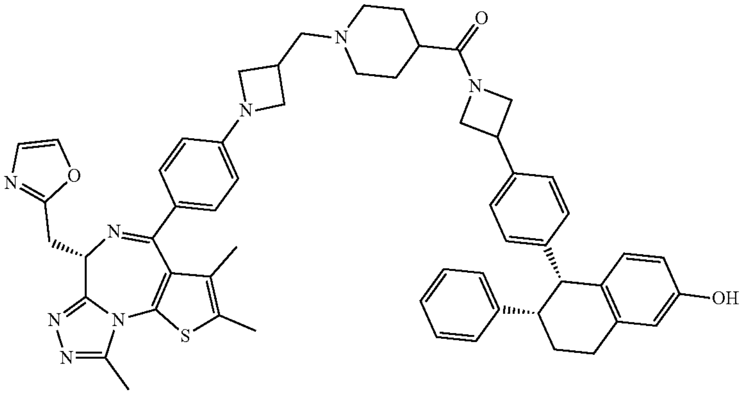 [SMILES: Cc1sc2c(c1C)C(c1ccc(N3CC(CN4CCC(C(=O)N5CC(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |

TABLE 3-continued
| Compound No. | Compound Structure |
|---|---|
| III-177 | 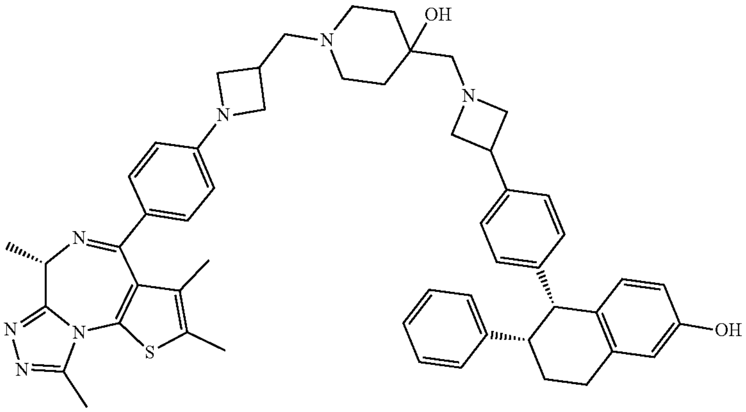 [SMILES: Cc1sc2c(c1C)C(c1ccc(N3CC(CN4CCC(O)(CN5CC(c6ccc([C@@H]7c8ccc(O)cc8CC[C@@H]7c7ccccc7)cc6)C5)CC4)C3)cc1)=N[C@@H](C)c1nnc(C)n1-2] |
| III-178 | 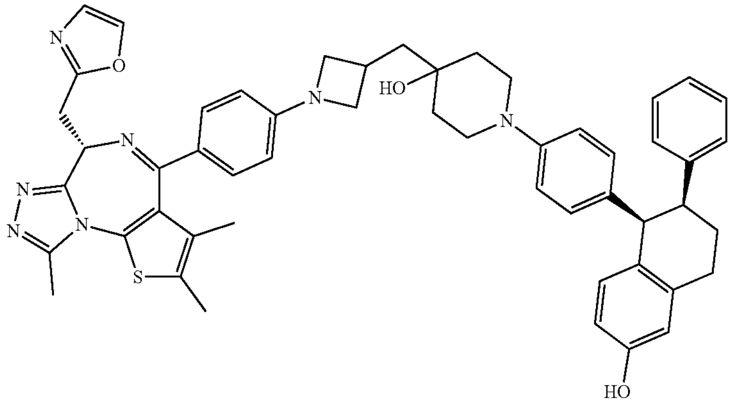 [SMILES: Cc1sc2c(c1C)C(c1ccc(N3CC(CC4(O)CCN(c5ccc([C@@H]6c7ccc(O)cc7CC[C@@H]6c6ccccc6)cc5)CC4)C3)cc1)=N[C@@H](Cc1ncco1)c1nnc(C)n1-2] |
| III-179 | 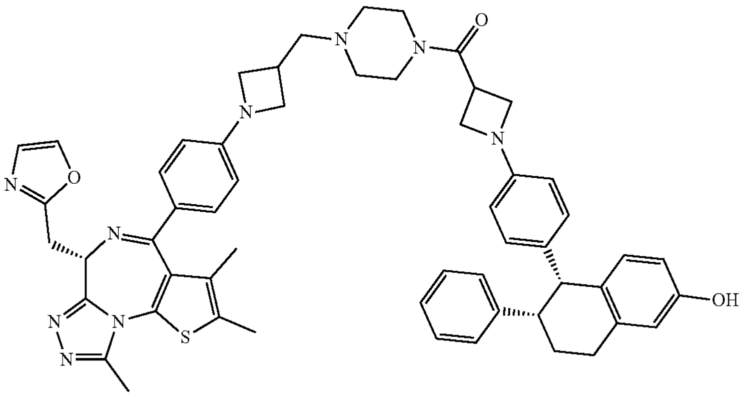 [SMILES: Cc1sc2c(c1C)C(c1ccc(N3CC(CN4CCN(C(=O)C5CN(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |

TABLE 3-continued
| Compound No. | Compound Structure |
|---|---|
| III-180 | 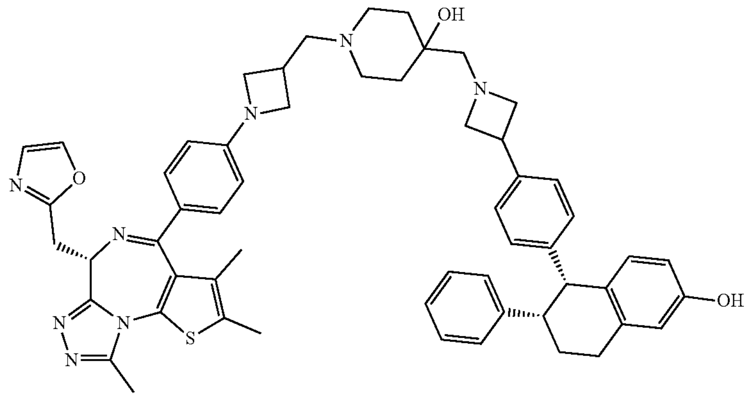 [SMILES: Cc1sc2c(c1C)C(c1ccc(N3CC(CN4CCC(O)(CN5CC(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |
| III-181 | 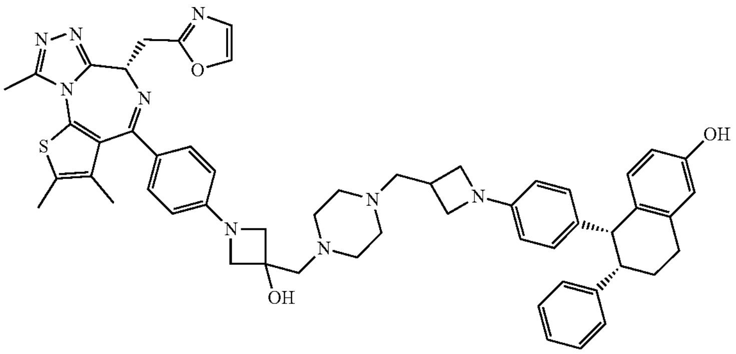 [SMILES: Cc1sc2c(c1C)C(c1ccc(N3CC(O)(CN4CCN(CC5CN(c6ccc([C@@H]7c8ccc(O)cc8CC[C@@H]7c7ccccc7)cc6)C5)CC4)C3)cc1)=N[C@@H](Cc1ncco1)c1nnc(C)n1-2] |
| III-182 | 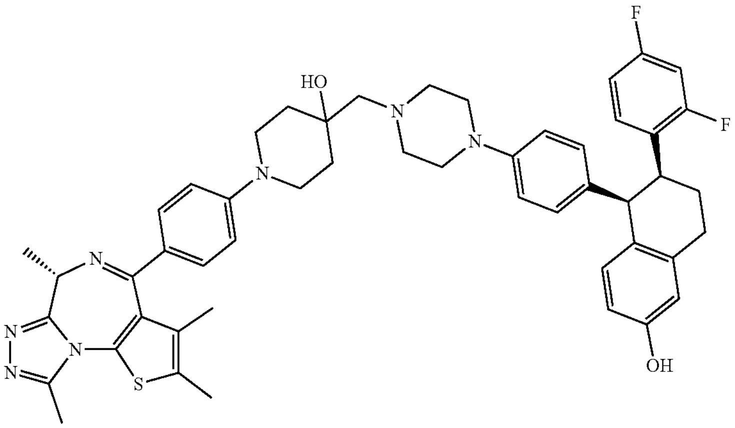 [SMILES: Cc1sc2c(c1C)C(c1ccc(N3CCC(O)(CN4CCN(c5ccc([C@@H]6c7ccc(O)cc7CC[C@@H]6c6ccc(F)cc6F)cc5)CC4)CC3)cc1)=N[C@@H](C)c1nnc(C)n1-2] |
| III-183 | 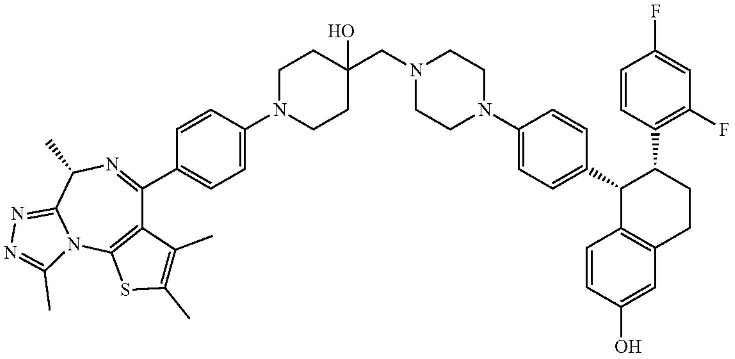 [SMILES: Cc1sc2c(c1C)C(c1ccc(N3CCC(O)(CN4CCN(c5ccc([C@H]6c7ccc(O)cc7CC[C@H]6c6ccc(F)cc6F)cc5)CC4)CC3)cc1)=N[C@@H](C)c1nnc(C)n1-2] |

TABLE 3-continued
| Compound No. | Compound Structure |
|---|---|
| III-184 | 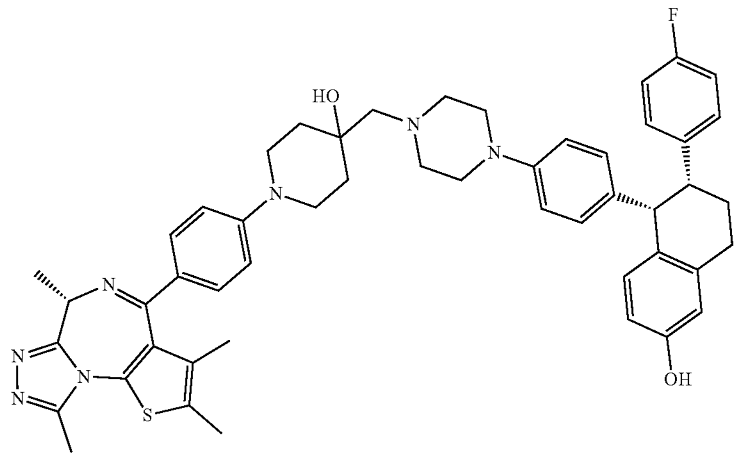 [SMILES: Cc1sc2c(c1C)C(c1ccc(N3CCC(O)(CN4CCN(c5ccc([C@H]6c7ccc(O)cc7CC[C@H]6c6ccc(F)cc6)cc5)CC4)CC3)cc1)=N[C@@H](C)c1nnc(C)n1-2] |
| III-185 | 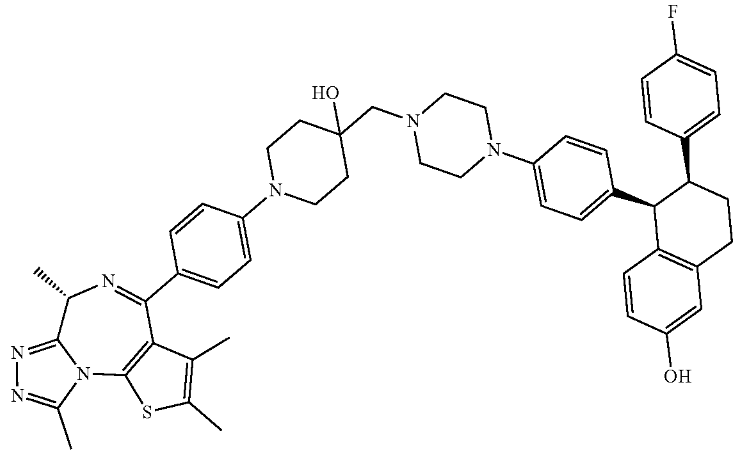 [SMILES: Cc1sc2c(c1C)C(c1ccc(N3CCC(O)(CN4CCN(c5ccc([C@@H]6c7ccc(O)cc7CC[C@@H]6c6ccc(F)cc6)cc5)CC4)CC3)cc1)=N[C@@H](C)c1nnc(C)n1-2] |
| III-186 | 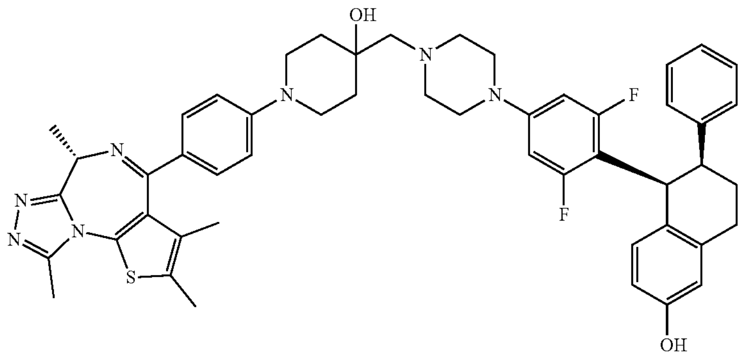 [SMILES: Cc1sc2c(c1C)C(c1ccc(N3CCC(O)(CN4CCN(c5cc(F)c([C@@H]6c7ccc(O)cc7CC[C@@H]6c6ccccc6)c(F)c5)CC4)CC3)cc1)=N[C@@H](C)c1nnc(C)n1-2] |

TABLE 3-continued
| Compound No. | Compound Structure |
|---|---|
| III-187 | 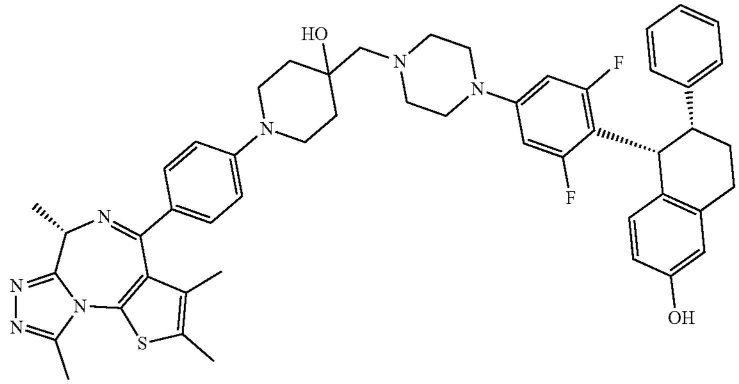 [SMILES: Cc1sc2c(c1C)C(c1ccc(N3CCC(O)(CN4CCN(c5cc(F)c([C@H]6c7ccc(O)cc7CC[C@H]6c6ccccc6)c(F)c5)CC4)CC3)cc1)=N[C@@H](C)c1nnc(C)n1-2] |
| III-188 | 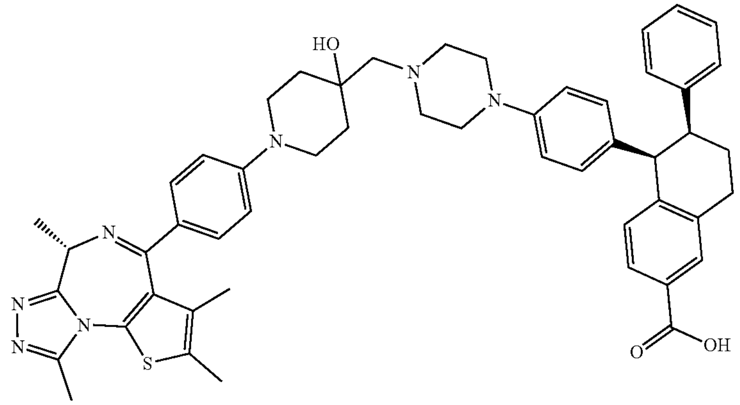 [SMILES: Cc1sc2c(c1C)C(c1ccc(N3CCC(O)(CN4CCN(c5ccc([C@@H]6c7ccc(C(=O)O)cc7CC[C@@H]6c6ccccc6)cc5)CC4)CC3)cc1)=N[C@@H](C)c1nnc(C)n1-2] |
| III-189 | 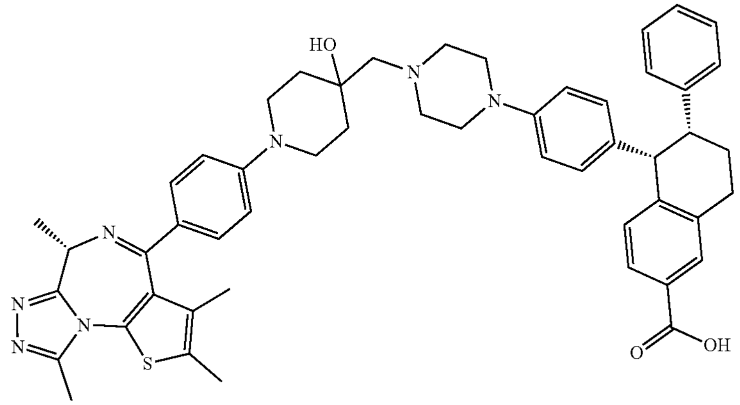 [SMILES: Cc1sc2c(c1C)C(c1ccc(N3CCC(O)(CN4CCN(c5ccc([C@H]6c7ccc(C(=O)O)cc7CC[C@H]6c6ccccc6)cc5)CC4)CC3)cc1)=N[C@@H](C)c1nnc(C)n1-2] |
| III-190 | 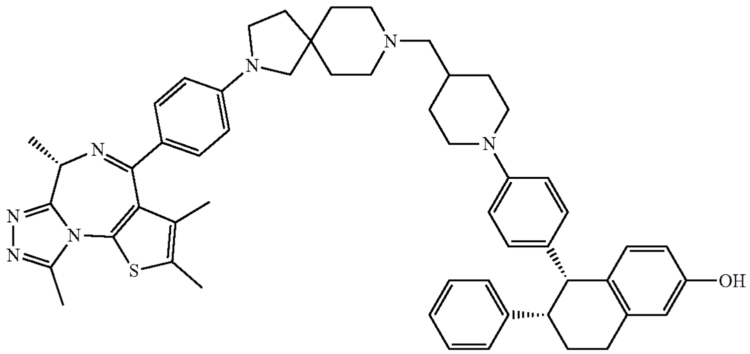 [SMILES: Cc1sc2c(c1C)C(c1ccc(N3CCC4(CCN(CC5CCN(c6ccc([C@@H]7c8ccc(O)cc8CC[C@@H]7c7ccccc7)cc6)CC5)CC4)C3)cc1)=N[C@@H](C)c1nnc(C)n1-2] |

TABLE 3-continued
| Compound No. | Compound Structure |
| --- | --- |
| III-191 | 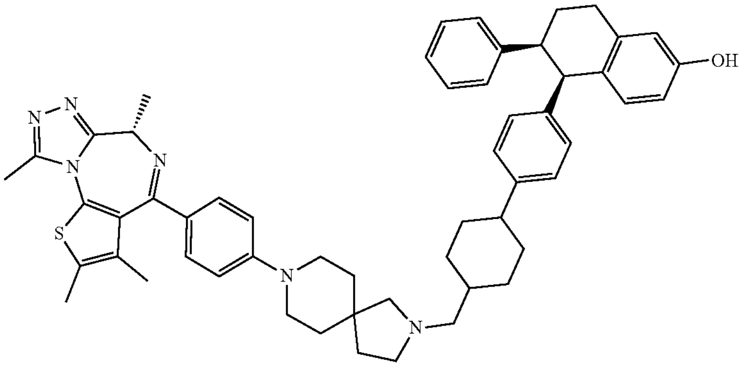 [SMILES: Cc1sc2c(c1C)C(c1ccc(N3CCC4(CCN(CC5CCC(c6ccc([C@@H]7c8ccc(O)cc8CC[C@@H]7c7ccccc7)cc6)CC5)C4)CC3)cc1)=N[C@@H](C)c1nnc(C)n1-2] |
| III-192 | 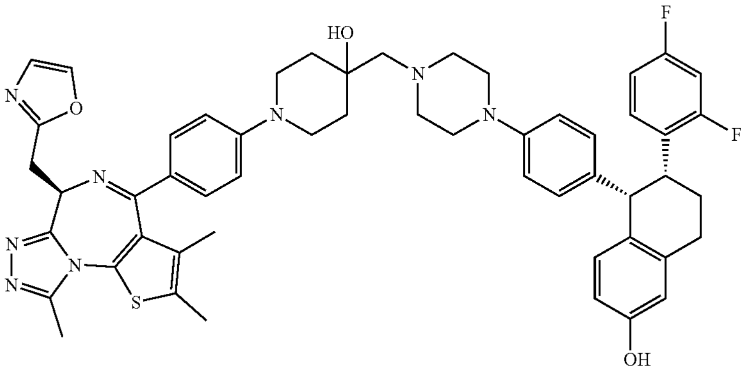 [SMILES: Cc1sc2c(c1C)C(c1ccc(N3CCC(O)(CN4CCN(c5ccc([C@H]6c7ccc(O)cc7CC[C@H]6c6ccc(F)cc6F)cc5)CC4)CC3)cc1)=N[C@H](Cc1ncco1)c1nnc(C)n1-2] |
| III-193 | 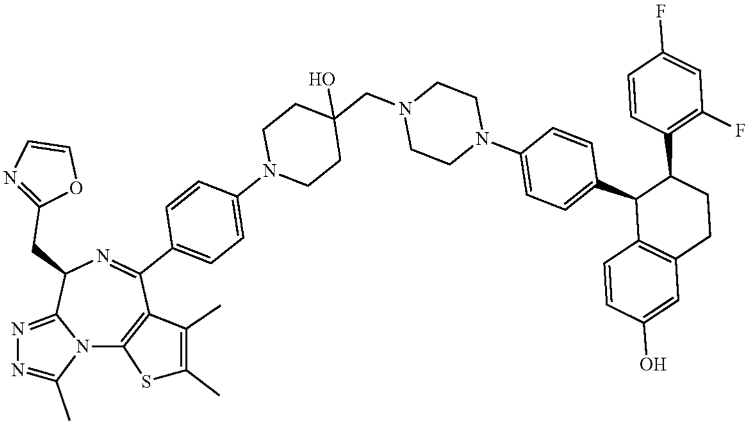 [SMILES: Cc1sc2c(c1C)C(c1ccc(N3CCC(O)(CN4CCN(c5ccc([C@@H]6c7ccc(O)cc7CC[C@@H]6c6ccc(F)cc6F)cc5)CC4)CC3)cc1)=N[C@H](Cc1ncco1)c1nnc(C)n1-2] |
| III-194 | 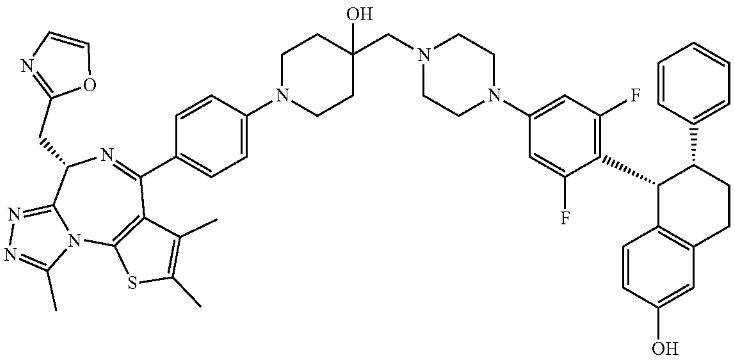 [SMILES: Cc1sc2c(c1C)C(c1ccc(N3CCC(O)(CN4CCN(c5cc(F)c([C@H]6c7ccc(O)cc7CC[C@H]6c6ccccc6)c(F)c5)CC4)CC3)cc1)=N[C@@H](Cc1ncco1)c1nnc(C)n1-2] |

TABLE 3-continued
| Compound No. | Compound Structure |
| --- | --- |
| III-195 | 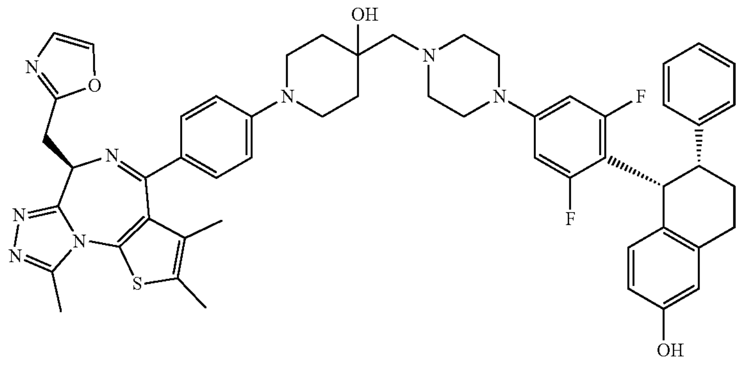 [SMILES: Cc1sc2c(c1C)C(c1ccc(N3CCC(O)(CN4CCN(c5cc(F)c([C@H]6c7ccc(O)cc7CC[C@H]6c6ccccc6)c(F)c5)CC4)CC3)cc1)=N[C@H](Cc1ncco1)c1nnc(C)n1-2] |
| III-196 | 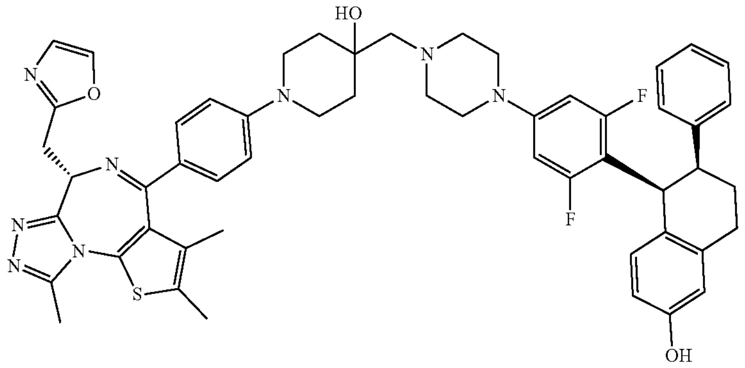 [SMILES: Cc1sc2c(c1C)C(c1ccc(N3CCC(O)(CN4CCN(c5cc(F)c([C@@H]6c7ccc(O)cc7CC[C@@H]6c6ccccc6)c(F)c5)CC4)CC3)cc1)=N[C@@H](Cc1ncco1)c1nnc(C)n1-2] |
| III-197 | 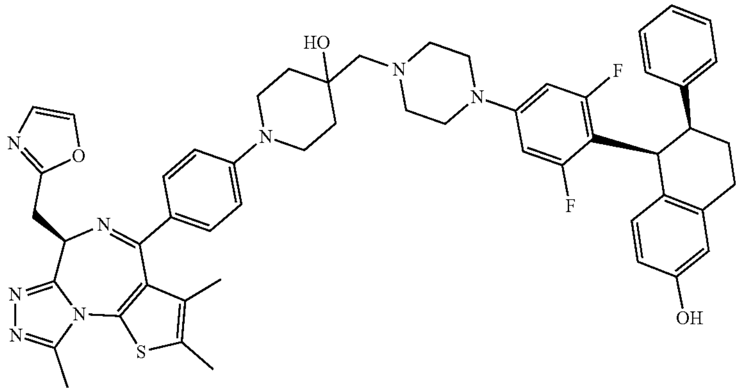 [SMILES: Cc1sc2c(c1C)C(c1ccc(N3CCC(O)(CN4CCN(c5cc(F)c([C@@H]6c7ccc(O)cc7CC[C@@H]6c6ccccc6)c(F)c5)CC4)CC3)cc1)=N[C@H](Cc1ncco1)c1nnc(C)n1-2] |
| III-198 | 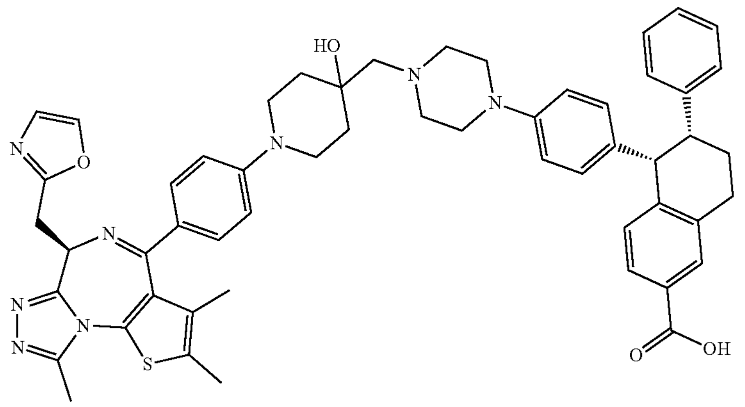 [SMILES: Cc1sc2c(c1C)C(c1ccc(N3CCC(O)(CN4CCN(c5ccc([C@H]6c7ccc(C(=O)O)cc7CC[C@H]6c6ccccc6)cc5)CC4)CC3)cc1)=N[C@H](Cc1ncco1)c1nnc(C)n1-2] |

TABLE 3-continued
| Compound No. | Compound Structure |
| --- | --- |
| III-199 | 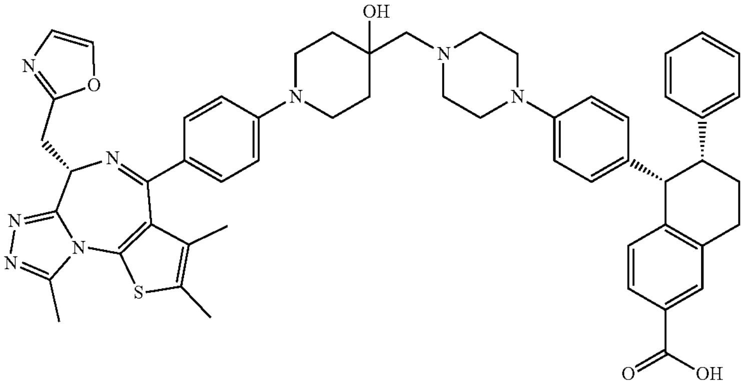 [SMILES: Cc1sc2c(c1C)C(c1ccc(N3CCC(O)(CN4CCN(c5ccc([C@H]6c7ccc(C(=O)O)cc7CC[C@H]6c6ccccc6)cc5)CC4)CC3)cc1)=N[C@@H](Cc1ncco1)c1nnc(C)n1-2] |
| III-200 | 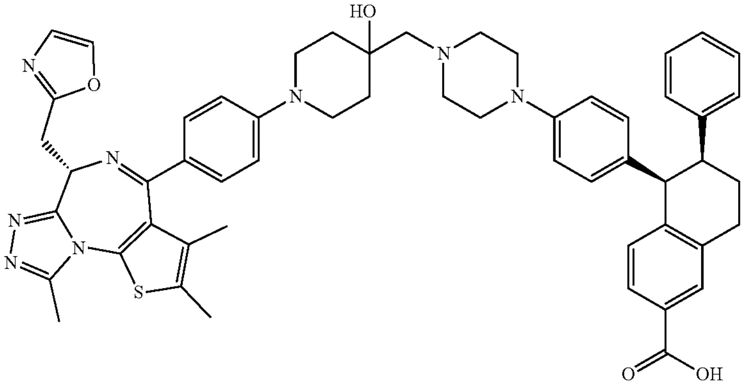 [SMILES: Cc1sc2c(c1C)C(c1ccc(N3CCC(O)(CN4CCN(c5ccc([C@@H]6c7ccc(C(=O)O)cc7CC[C@@H]6c6ccccc6)cc5)CC4)CC3)cc1)=N[C@@H](Cc1ncco1)c1nnc(C)n1-2] |
| III-201 | 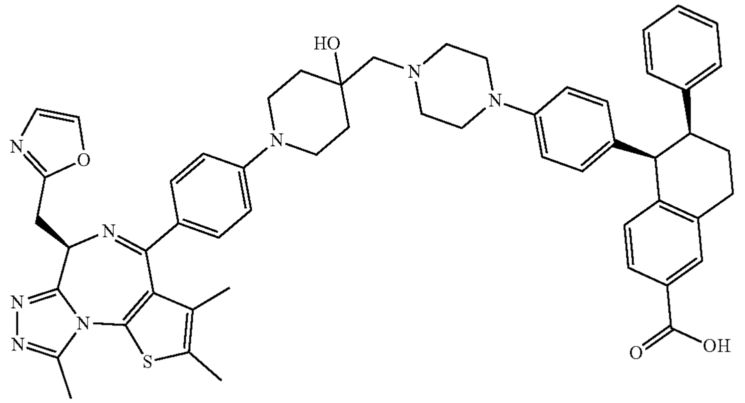 [SMILES: Cc1sc2c(c1C)C(c1ccc(N3CCC(O)(CN4CCN(c5ccc([C@@H]6c7ccc(C(=O)O)cc7CC[C@@H]6c6ccccc6)cc5)CC4)CC3)cc1)=N[C@H](Cc1ncco1)c1nnc(C)n1-2] |
| III-202 | 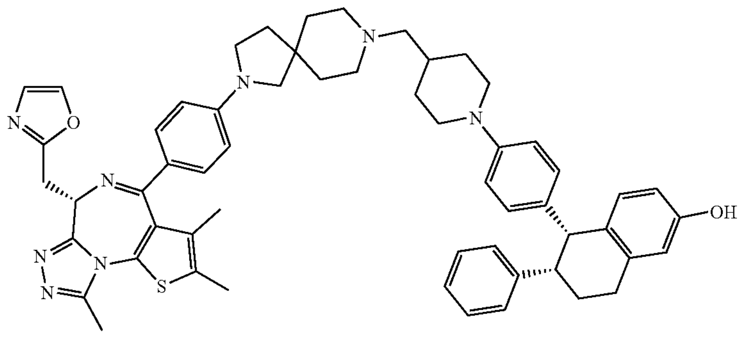 [SMILES: Cc1sc2c(c1C)C(c1ccc(N3CCC4(CCN(CC5CCN(c6ccc([C@@H]7c8ccc(O)cc8CC[C@@H]7c7ccccc7)cc6)CC5)CC4)C3)cc1)=N[C@@H](Cc1ncco1)c1nnc(C)n1-2] |

TABLE 3-continued
| Compound No. | Compound Structure |
|---|---|
| III-203 | 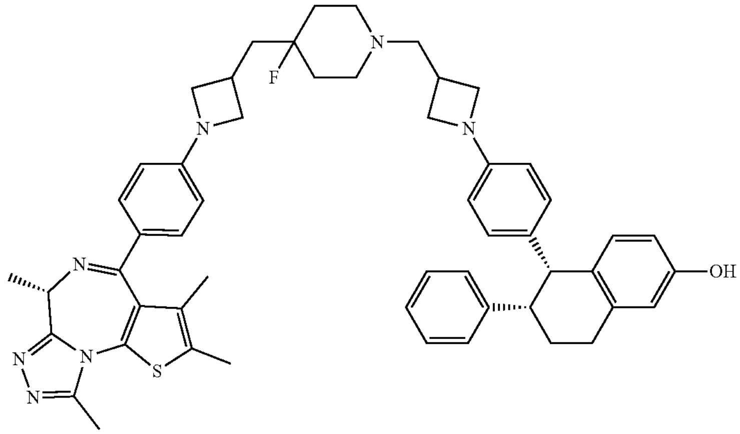 [SMILES: Cc1sc2c(c1C)C(c1ccc(N3CC(CC4(F)CCN(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-204 | 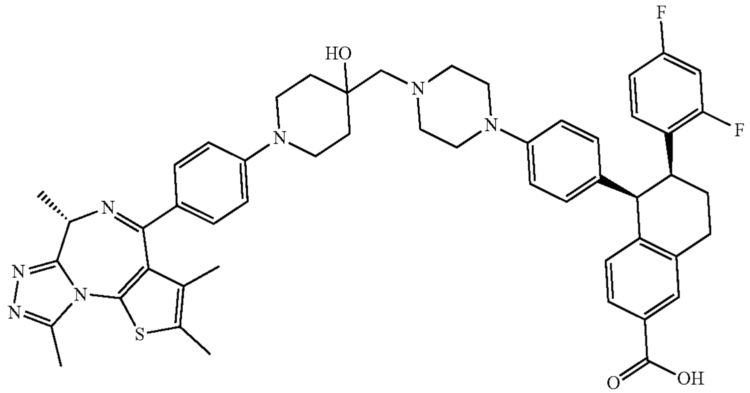 [SMILES: Cc1sc2c(c1C)C(c1ccc(N3CCC(O)(CN4CCN(c5ccc([C@@H]6c7ccc(C(=O)O)cc7CC[C@@H]6c6ccc(F)cc6F)cc5)CC4)CC3)cc1)=N[C@@H](C)c1nnc(C)n1-2] |
| III-205 | 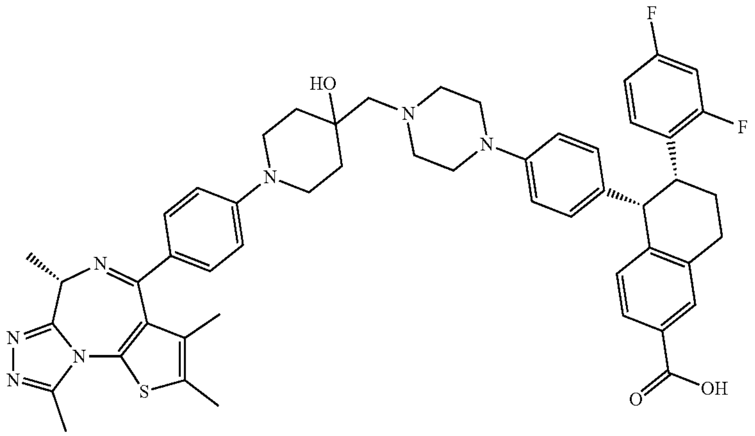 [SMILES: Cc1sc2c(c1C)C(c1ccc(N3CCC(O)(CN4CCN(c5ccc([C@H]6c7ccc(C(=O)O)cc7CC[C@H]6c6ccc(F)cc6F)cc5)CC4)CC3)cc1)=N[C@@H](C)c1nnc(C)n1-2] |

TABLE 3-continued
| Compound No. | Compound Structure |
|---|---|
| III-206 | 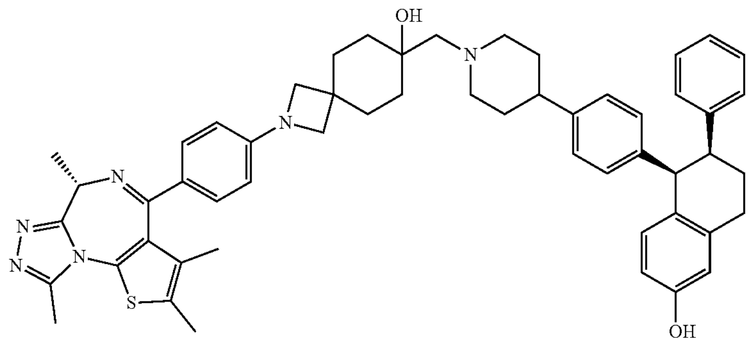 [SMILES: Cc1sc2c(c1C)C(c1ccc(N3CC4(CCC(O)(CN5CCC(c6ccc([C@@H]7c8ccc(O)cc8CC[C@@H]7c7ccccc7)cc6)CC5)CC4)C3)cc1)=N[C@@H](C)c1nnc(C)n1-2] |
| III-207 | 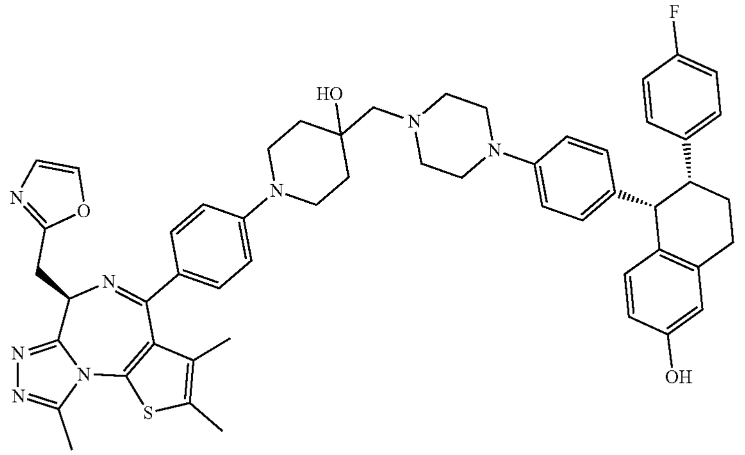 [SMILES: Cc1sc2c(c1C)C(c1ccc(N3CCC(O)(CN4CCN(c5ccc([C@H]6c7ccc(O)cc7CC[C@H]6c6ccc(F)cc6)cc5)CC4)CC3)cc1)=N[C@H](Cc1ncco1)c1nnc(C)n1-2] |
| III-208 | 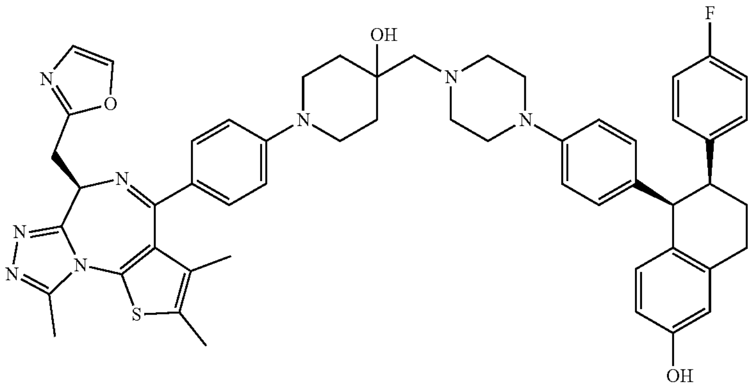 [SMILES: Cc1sc2c(c1C)C(c1ccc(N3CCC(O)(CN4CCN(c5ccc([C@@H]6c7ccc(O)cc7CC[C@@H]6c6ccc(F)cc6)cc5)CC4)CC3)cc1)=N[C@H](Cc1ncco1)c1nnc(C)n1-2] |

TABLE 3-continued
| Compound No. | Compound Structure |
|---|---|
| III-209 | 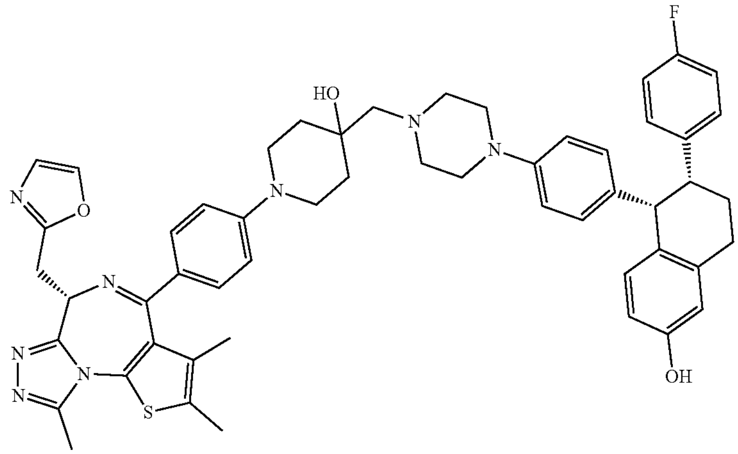 [SMILES: Cc1sc2c(c1C)C(c1ccc(N3CCC(O)(CN4CCN(c5ccc([C@H]6c7ccc(O)cc7CC[C@H]6c6ccc(F)cc6)cc5)CC4)CC3)cc1)=N[C@@H](Cc1ncco1)c1nnc(C)n1-2] |
| III-210 | 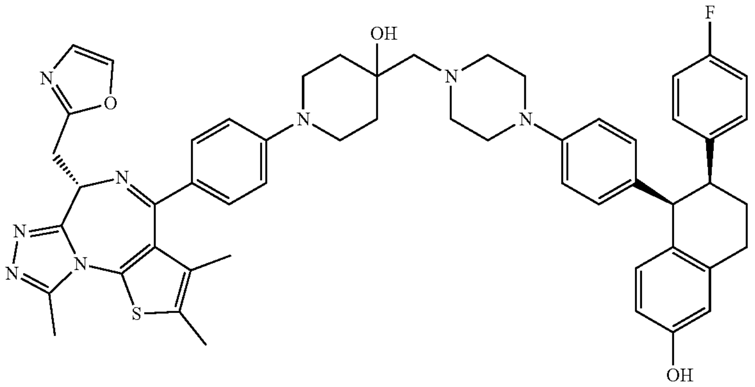 [SMILES: Cc1sc2c(c1C)C(c1ccc(N3CCC(O)(CN4CCN(c5ccc([C@@H]6c7ccc(O)cc7CC[C@@H]6c6ccc(F)cc6)cc5)CC4)CC3)cc1)=N[C@@H](Cc1ncco1)c1nnc(C)n1-2] |
| III-211 | 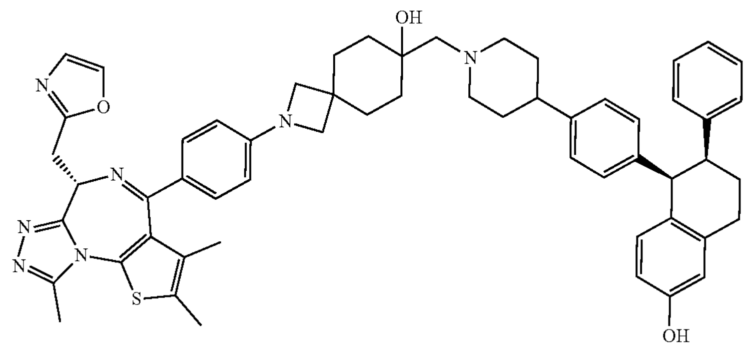 [SMILES: Cc1sc2c(c1C)C(c1ccc(N3CC4(CCC(O)(CN5CCC(c6ccc([C@@H]7c8ccc(O)cc8CC[C@@H]7c7ccccc7)cc6)CC5)CC4)C3)cc1)=N[C@@H](Cc1ncco1)c1nnc(C)n1-2] |

TABLE 3-continued
| Compound No. | Compound Structure |
|---|---|
| III-212 | 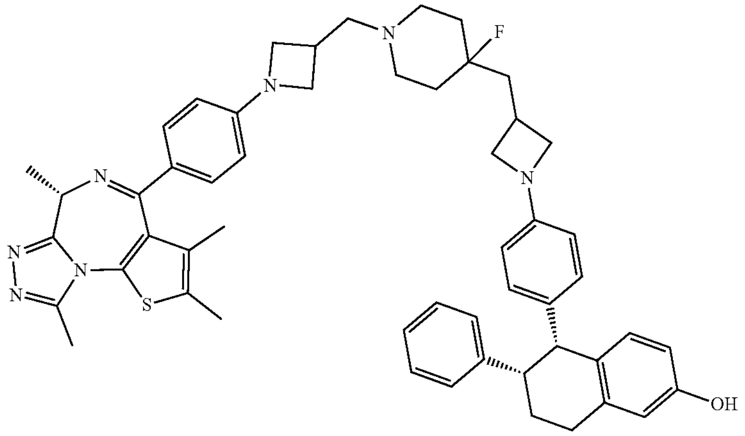 [SMILES: Cc1sc2c(c1C)C(c1ccc(N3CC(CN4CCC(F)(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-213 | 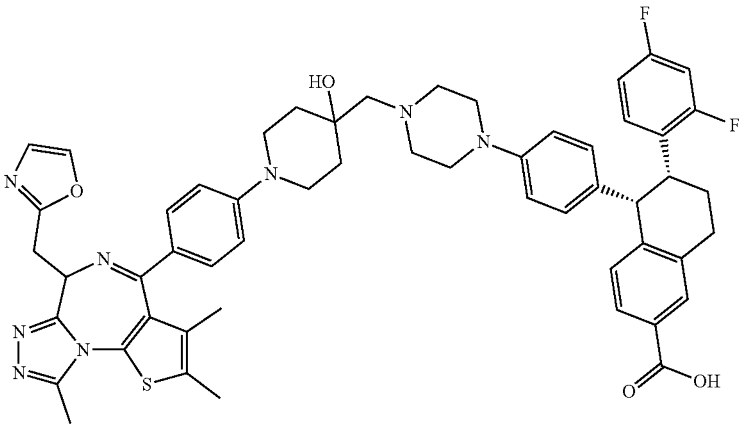 [SMILES: Cc1sc2c(c1C)C(c1ccc(N3CCC(O)(CN4CCN(c5ccc([C@H]6c7ccc(C(=O)O)cc7CC[C@H]6c6ccc(F)cc6F)cc5)CC4)CC3)cc1)=NC(Cc1ncco1)c1nnc(C)n1-2] |
| III-214 | 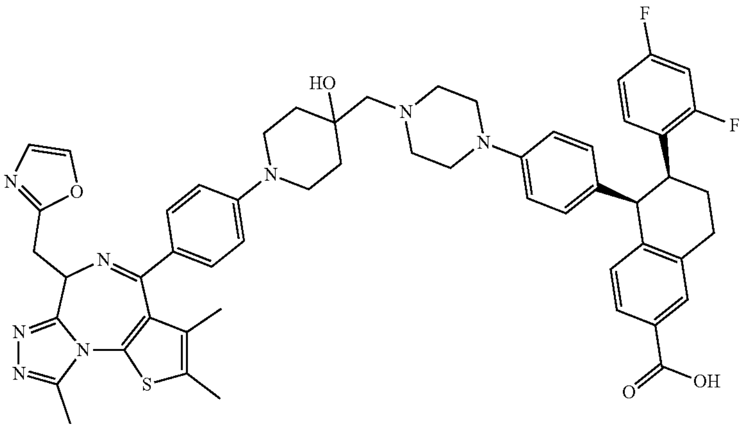 [SMILES: Cc1sc2c(c1C)C(c1ccc(N3CCC(O)(CN4CCN(c5ccc([C@@H]6c7ccc(C(=O)O)cc7CC[C@@H]6c6ccc(F)cc6F)cc5)CC4)CC3)cc1)=NC(Cc1ncco1)c1nnc(C)n1-2] |

TABLE 3-continued
| Compound No. | Compound Structure |
| --- | --- |
| III-215 | 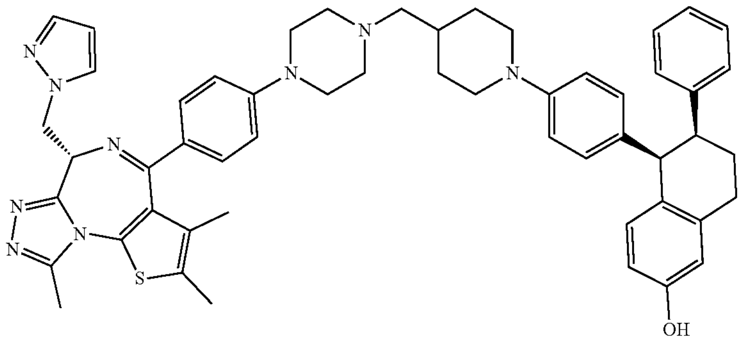 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@@H](Cn1cccn1)c1nnc(C)n1-2] |
| III-216 | 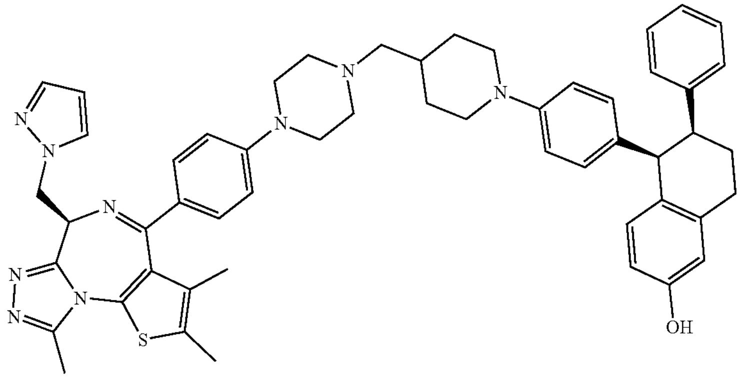 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@H](Cn1cccn1)c1nnc(C)n1-2] |
| III-217 | 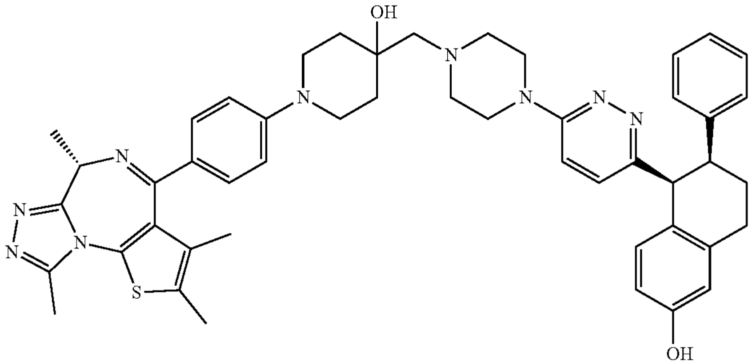 [SMILES: Cc1sc2c(c1C)C(c1ccc(N3CCC(O)(CN4CCN(c5ccc([C@@H]6c7ccc(O)cc7CC[C@@H]6c6ccccc6)nn5)CC4)CC3)cc1)=N[C@@H](C)c1nnc(C)n1-2] |
| III-218 | 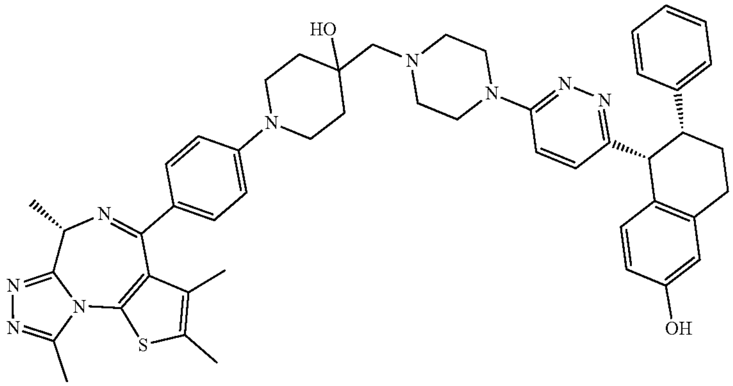 [SMILES: Cc1sc2c(c1C)C(c1ccc(N3CCC(O)(CN4CCN(c5ccc([C@H]6c7ccc(O)cc7CC[C@H]6c6ccccc6)nn5)CC4)CC3)cc1)=N[C@@H](C)c1nnc(C)n1-2] |

TABLE 3-continued
| Compound No. | Compound Structure |
|---|---|
| III-219 | 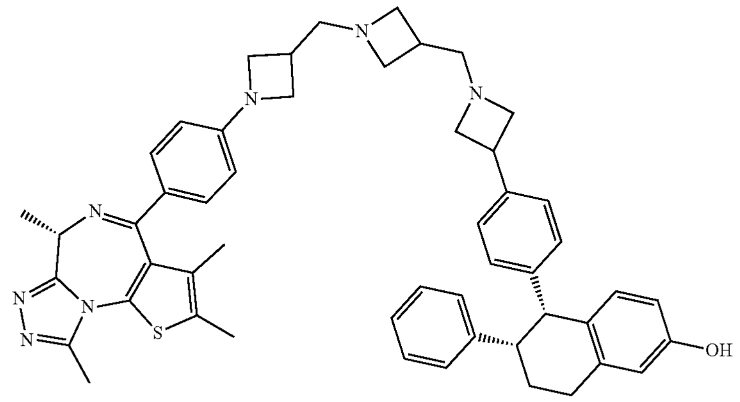 [SMILES: Cc1sc2c(c1C)C(c1ccc(N3CC(CN4CC(CN5CC(c6ccc([C@@H]7c8ccc(O)cc8CC[C@@H]7c7ccccc7)cc6)C5)C4)C3)cc1)=N[C@@H](C)c1nnc(C)n1-2] |
| III-220 | 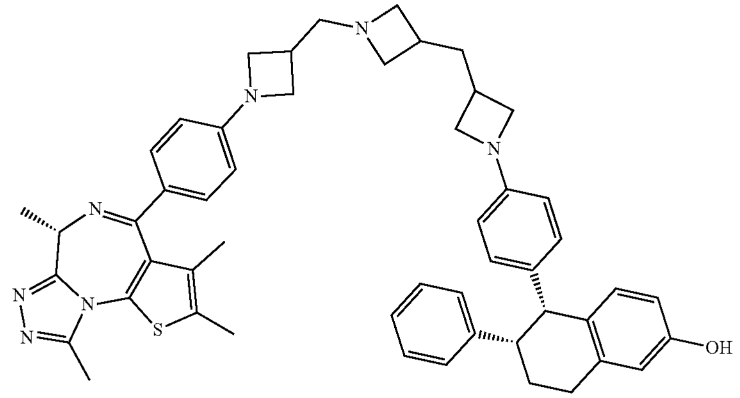 [SMILES: Cc1sc2c(c1C)C(c1ccc(N3CC(CN4CC(CC5CN(c6ccc([C@@H]7c8ccc(O)cc8CC[C@@H]7c7ccccc7)cc6)C5)C4)C3)cc1)=N[C@@H](C)c1nnc(C)n1-2] |
| III-221 | 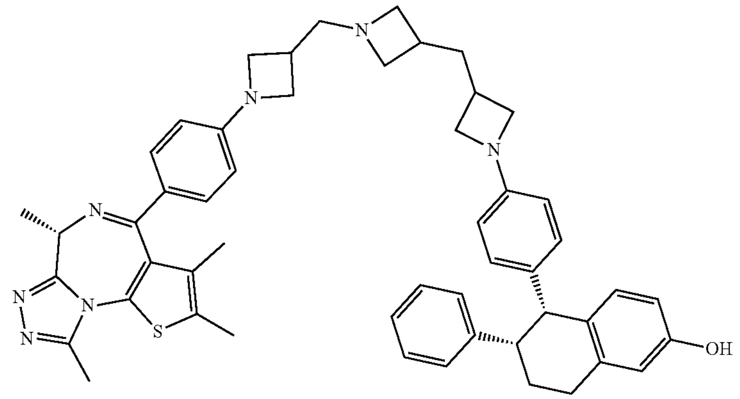 [SMILES: Cc1sc2c(c1C)C(c1ccc(N3CC(CN4CC(CC5CN(c6ccc([C@@H]7c8ccc(O)cc8CC[C@@H]7c7ccccc7)cc6)C5)C4)C3)cc1)=N[C@@H](C)c1nnc(C)n1-2] |
| III-222 | 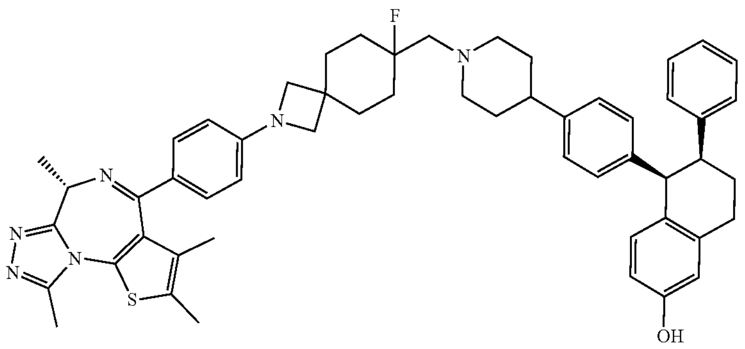 [SMILES: Cc1sc2c(c1C)C(c1ccc(N3CC4(CCC(F)(CN5CCC(c6ccc([C@@H]7c8ccc(O)cc8CC[C@@H]7c7ccccc7)cc6)CC5)CC4)C3)cc1)=N[C@@H](C)c1nnc(C)n1-2] |

TABLE 3-continued
| Compound No. | Compound Structure |
| --- | --- |
| III-223 | 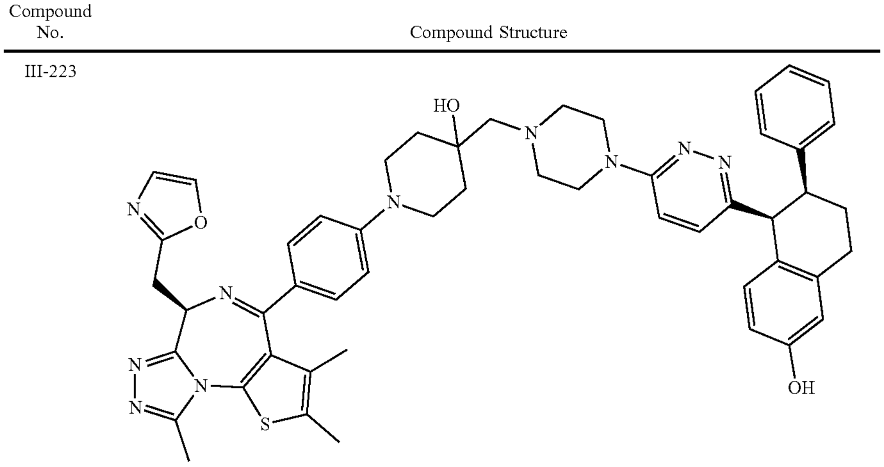 |
| III-224 | 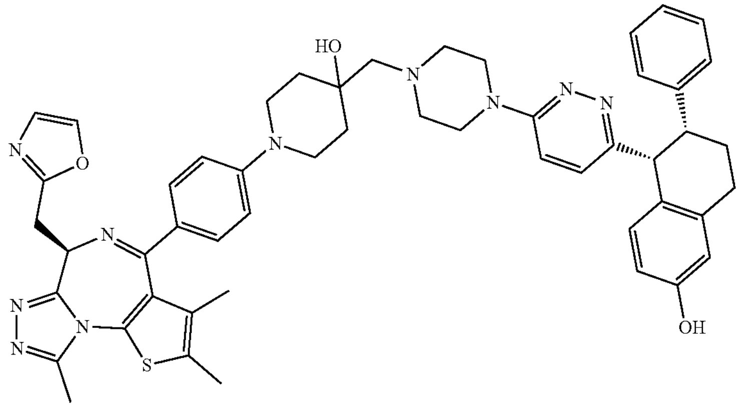 [SMILES: Cc1sc2c(c1C)C(c1ccc(N3CCC(O)(CN4CCN(c5ccc([C@H]6c7ccc(O)cc7CC[C@H]6c6ccccc6)nn5)CC4)CC3)cc1)=N[C@H](Cc1ncco1)c1nnc(C)n1-2] |
| III-225 | 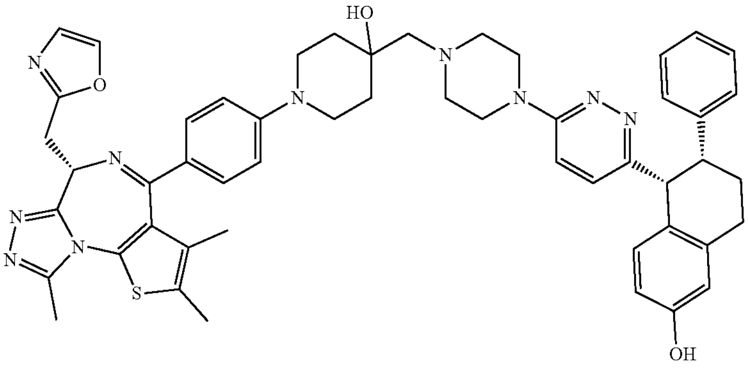 [SMILES: Cc1sc2c(c1C)C(c1ccc(N3CCC(O)(CN4CCN(c5ccc([C@H]6c7ccc(O)cc7CC[C@H]6c6ccccc6)nn5)CC4)CC3)cc1)=N[C@@H](Cc1ncco1)c1nnc(C)n1-2] |
| III-226 | 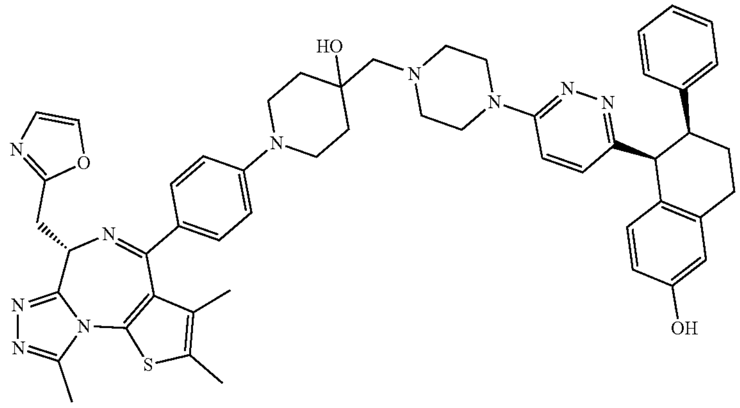 [SMILES: Cc1sc2c(c1C)C(c1ccc(N3CCC(O)(CN4CCN(c5ccc([C@@H]6c7ccc(O)cc7CC[C@@H]6c6ccccc6)nn5)CC4)CC3)cc1)=N[C@@H](Cc1ncco1)c1nnc(C)n1-2] |

TABLE 3-continued
| Compound No. | Compound Structure |
| --- | --- |
| III-227 | 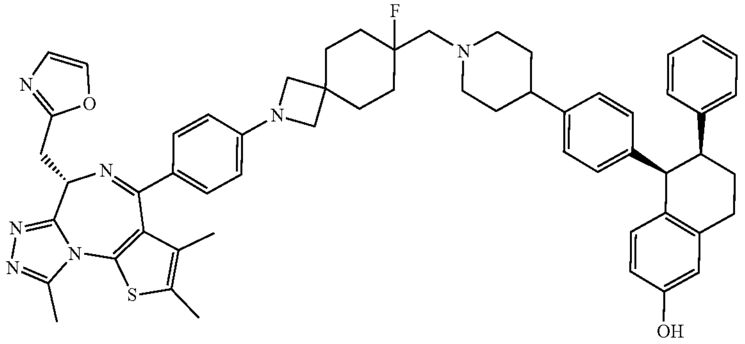 [SMILES: Cc1sc2c(c1C)C(c1ccc(N3CC4(CCC(F)(CN5CCC(c6ccc([C@@H]7c8ccc(O)cc8CC[C@@H]7c7ccccc7)cc6)CC5)CC4)C3)cc1)=N[C@@H](Cc1ncco1)c1nnc(C)n1-2] |
| III-228 | 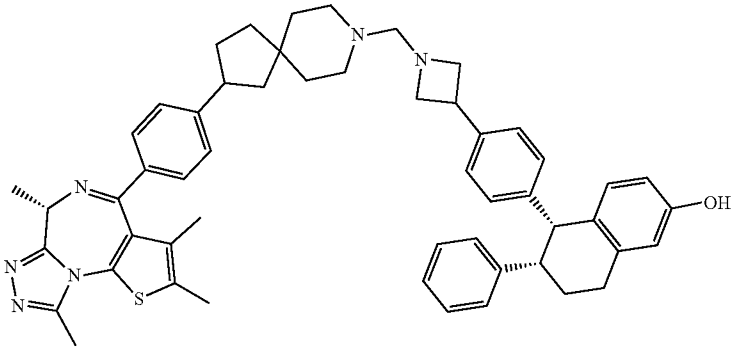 [SMILES: Cc1sc2c(c1C)C(c1ccc(C3CCC4(CCN(CN5CC(c6ccc([C@@H]7c8ccc(O)cc8CC[C@@H]7c7ccccc7)cc6)C5)CC4)C3)cc1)=N[C@@H](C)c1nnc(C)n1-2] |
| III-229 | 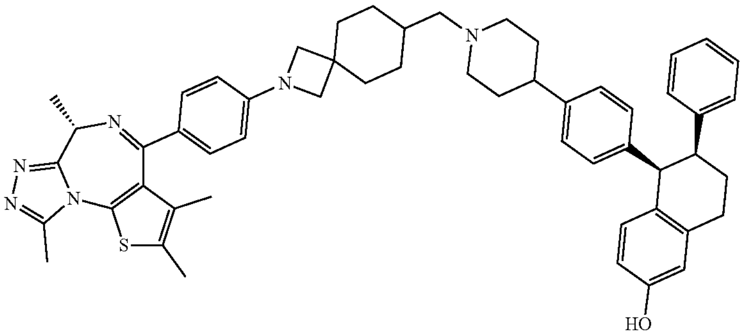 [SMILES: Cc1sc2c(c1C)C(c1ccc(N3CC4(CCC(CN5CCC(c6ccc([C@@H]7c8ccc(O)cc8CC[C@@H]7c7ccccc7)cc6)CC5)CC4)C3)cc1)=N[C@@H](C)c1nnc(C)n1-2] |
| III-230 | 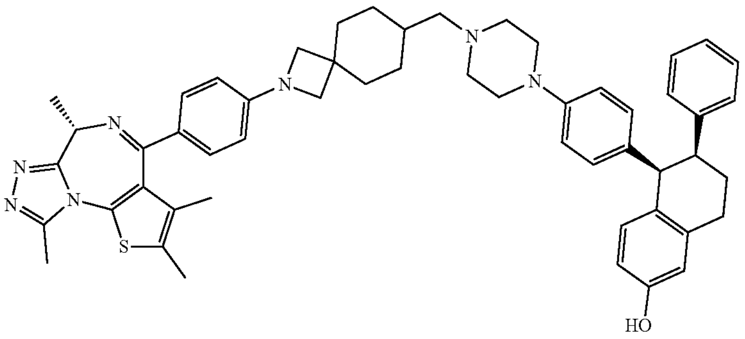 [SMILES: Cc1sc2c(c1C)C(c1ccc(N3CC4(CCC(CN5CCN(c6ccc([C@@H]7c8ccc(O)cc8CC[C@@H]7c7ccccc7)cc6)CC5)CC4)C3)cc1)=N[C@@H](C)c1nnc(C)n1-2] |

TABLE 3-continued
| Compound No. | Compound Structure |
|---|---|
| III-231 | 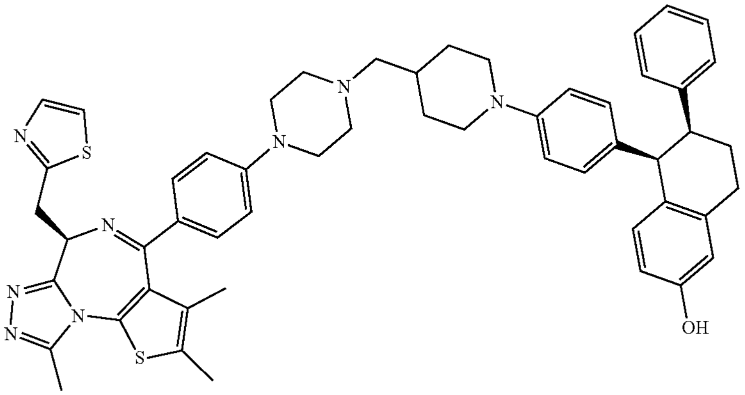 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@H](Cc1nccs1)c1nnc(C)n1-2] |
| III-232 | 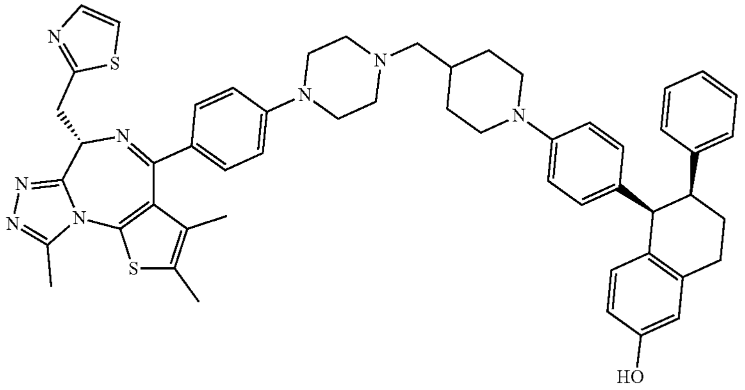 [SMILES: Cc1sc2c(c1C)C(c1ccc(N3CCN(CC4CCN(c5ccc([C@@H]6c7ccc(O)cc7CC[C@@H]6c6ccccc6)cc5)CC4)CC3)cc1)=N[C@@H](Cc1nccs1)c1nnc(C)n1-2] |
| III-233 | 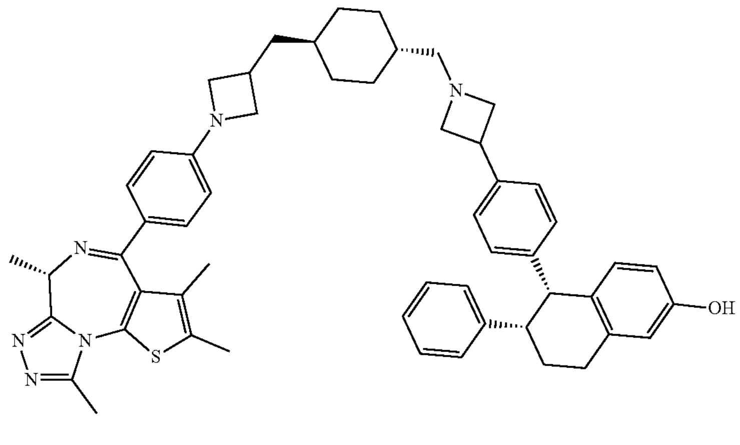 [SMILES: Cc1sc2c(c1C)C(c1ccc(N3CC(C[C@H]4CC[C@H](CN5CC(c6ccc([C@@H]7c8ccc(O)cc8CC[C@@H]7c7ccccc7)cc6)C5)CC4)C3)cc1)=N[C@@H](C)c1nnc(C)n1-2] |

TABLE 3-continued
| Compound No. | Compound Structure |
| --- | --- |
| III-234 | 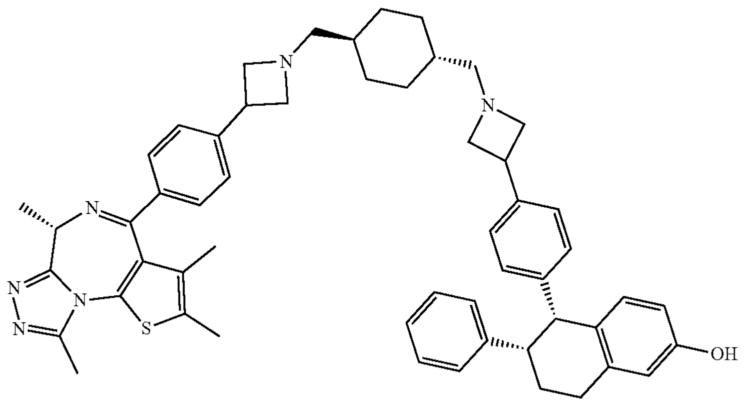 [SMILES: Cc1sc2c(c1C)C(c1ccc(C3CN(C[C@H]4CC[C@H](CN5CC(c6ccc([C@@H]7c8ccc(O)cc8CC[C@@H]7c7ccccc7)cc6)C5)CC4)C3)cc1)=N[C@@H](C)c1nnc(C)n1-2] |
| III-235 | 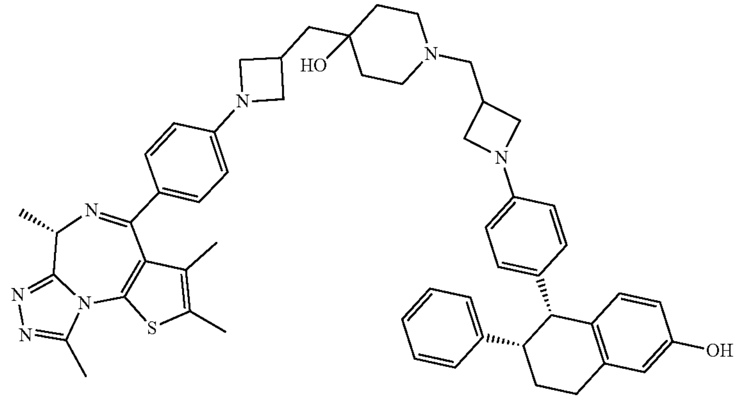 [SMILES: Cc1sc2c(c1C)C(c1ccc(N3CC(CC4(O)CCN(CC5CN(c6ccc([C@@H]7c8ccc(O)cc8CC[C@@H]7c7ccccc7)cc6)C5)CC4)C3)cc1)=N[C@@H](C)c1nnc(C)n1-2] |
| III-236 | 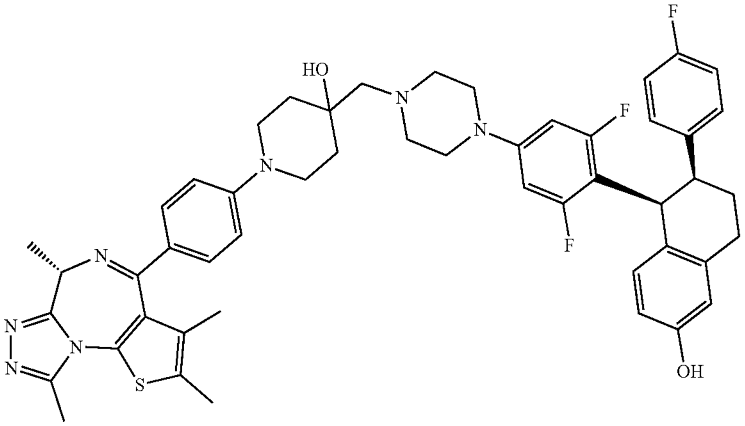 [SMILES: Cc1sc2c(c1C)C(c1ccc(N3CCC(O)(CN4CCN(c5cc(F)c([C@@H]6c7ccc(O)cc7CC[C@@H]6c6ccc(F)cc6)c(F)c5)CC4)CC3)cc1)=N[C@@H](C)c1nnc(C)n1-2] |

TABLE 3-continued
| Compound No. | Compound Structure |
|---|---|
| III-237 | 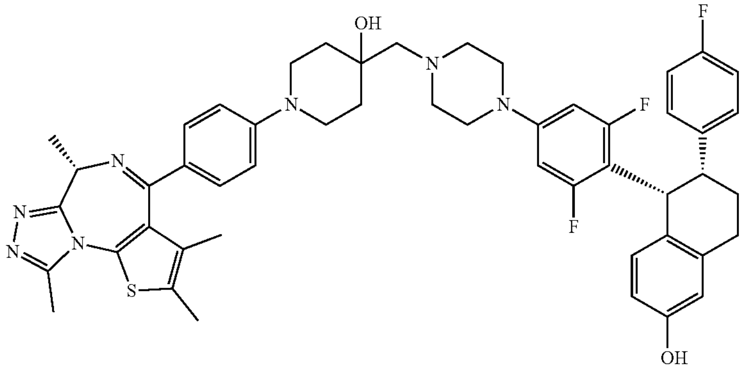 [SMILES: Cc1sc2c(c1C)C(c1ccc(N3CCC(O)(CN4CCN(c5cc(F)c([C@H]6c7ccc(O)cc7CC[C@H]6c6ccc(F)cc6)c(F)c5)CC4)CC3)cc1)=N[C@@H](C)c1nnc(C)n1-2] |
| III-238 | 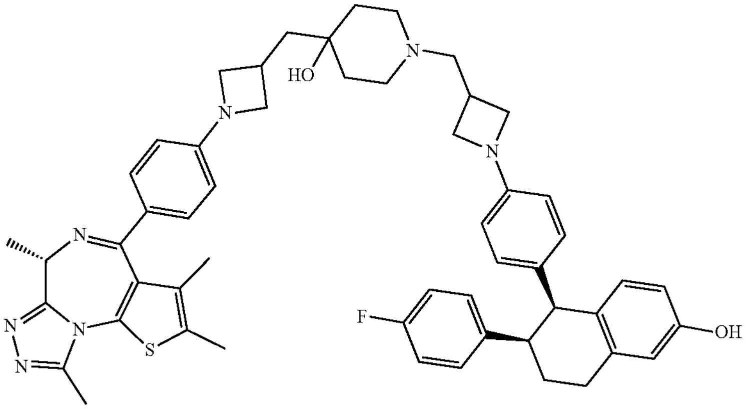 [SMILES: Cc1sc2c(c1C)C(c1ccc(N3CC(CC4(O)CCN(CC5CN(c6ccc([C@H]7c8ccc(O)cc8CC[C@H]7c7ccc(F)cc7)cc6)C5)CC4)C3)cc1)=N[C@@H](C)c1nnc(C)n1-2] |
| III-239 | 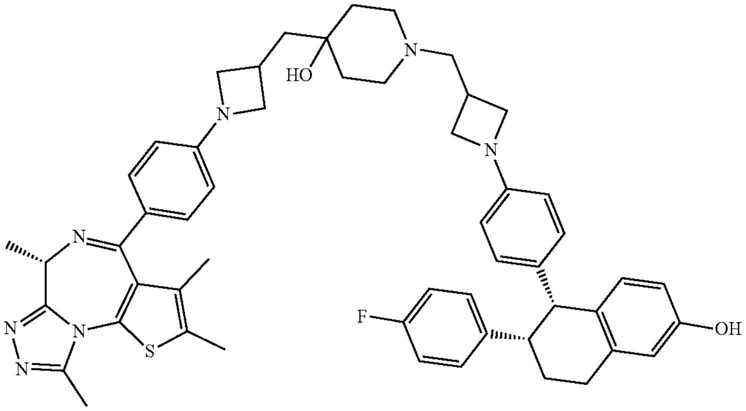 [SMILES: Cc1sc2c(c1C)C(c1ccc(N3CC(CC4(O)CCN(CC5CN(c6ccc([C@@H]7c8ccc(O)cc8CC[C@@H]7c7ccc(F)cc7)cc6)C5)CC4)C3)cc1)=N[C@@H](C)c1nnc(C)n1-2] |

TABLE 3-continued
| Compound No. | Compound Structure |
|---|---|
| III-240 | 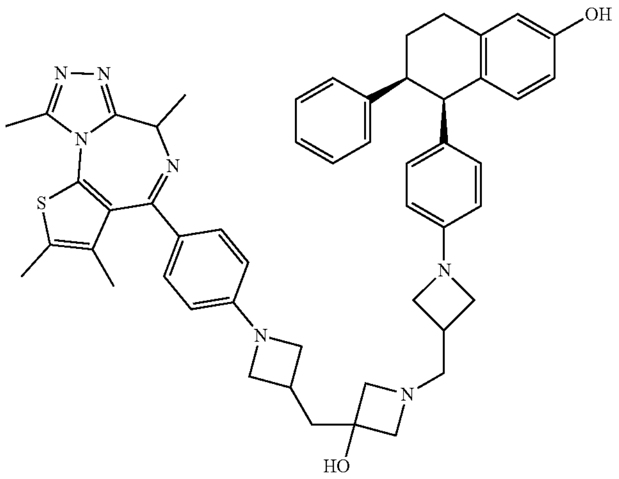 [SMILES: Cc1sc2c(c1C)C(c1ccc(N3CC(CC4(O)CN(CC5CN(c6ccc([C@@H]7c8ccc(O)cc8CC[C@@H]7c7ccccc7)cc6)C5)C4)C3)cc1)=NC(C)c1nnc(C)n1-2] |
| III-241 | 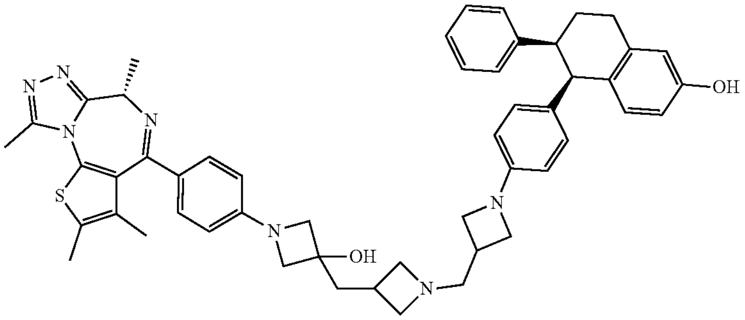 [SMILES: Cc1sc2c(c1C)C(c1ccc(N3CC(O)(CC4CN(CC5CN(c6ccc([C@@H]7c8ccc(O)cc8CC[C@@H]7c7ccccc7)cc6)C5)C4)C3)cc1)=N[C@@H](C)c1nnc(C)n1-2] |
| III-242 | 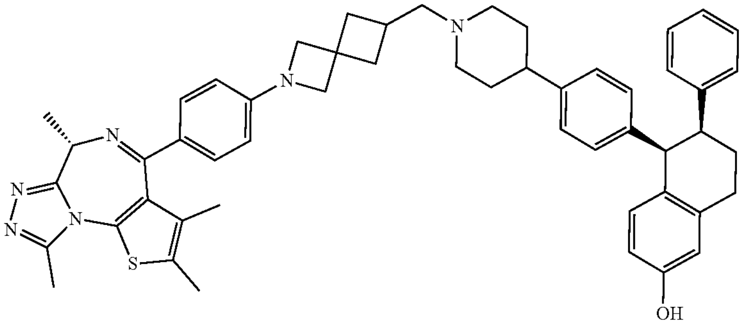 [SMILES: Cc1sc2c(c1C)C(c1ccc(N3CC4(CC(CN5CCC(c6ccc([C@@H]7c8ccc(O)cc8CC[C@@H]7c7ccccc7)cc6)CC5)C4)C3)cc1)=N[C@@H](C)c1nnc(C)n1-2] |
| III-243 | 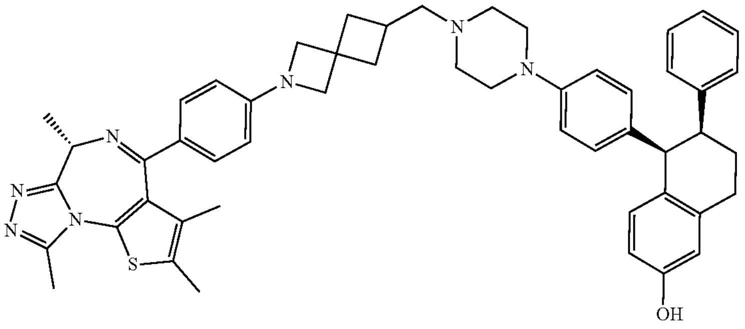 [SMILES: Cc1sc2c(c1C)C(c1ccc(N3CC4(CC(CN5CCN(c6ccc([C@@H]7c8ccc(O)cc8CC[C@@H]7c7ccccc7)cc6)CC5)C4)C3)cc1)=N[C@@H](C)c1nnc(C)n1-2] |

TABLE 3-continued
| Compound No. | Compound Structure |
|---|---|
| III-244 | 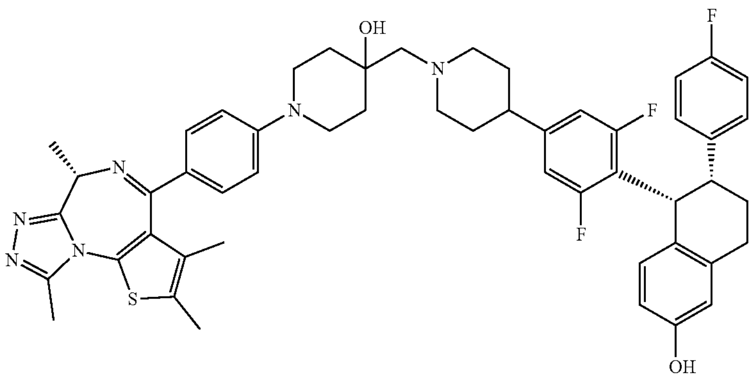 |
| III-245 | 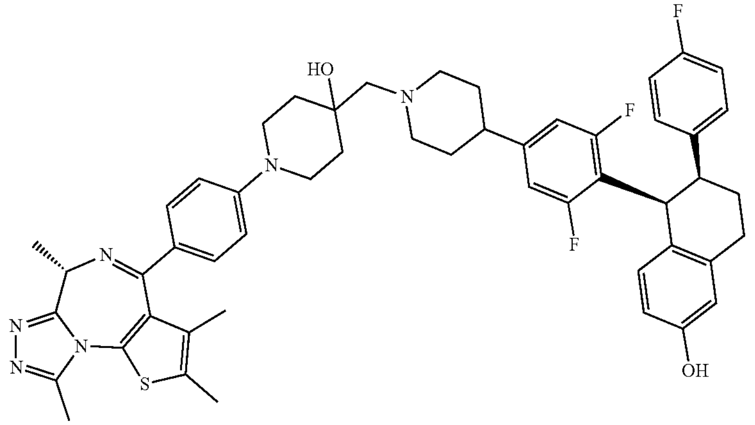 [SMILES: Cc1sc2c(c1C)C(c1ccc(N3CCC(O)(CN4CCC(c5cc(F)c([C@@H]6c7ccc(O)cc7CC[C@@H]6c6ccc(F)cc6)c(F)c5)CC4)CC3)cc1)=N[C@@H](C)c1nnc(C)n1-2] |
| III-246 | 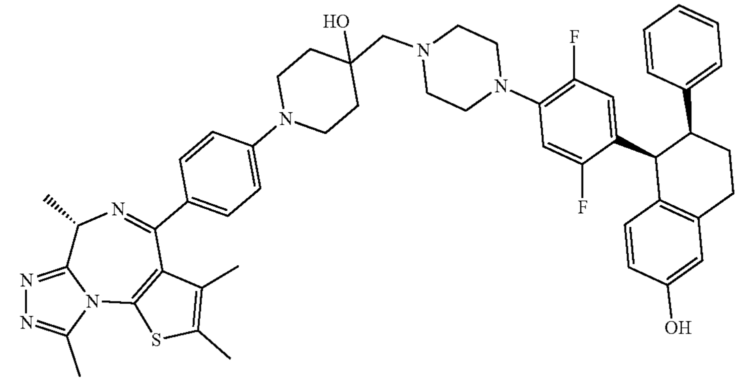 [SMILES: Cc1sc2c(c1C)C(c1ccc(N3CCC(O)(CN4CCN(c5cc(F)c([C@@H]6c7ccc(O)cc7CC[C@@H]6c6ccccc6)cc5F)CC4)CC3)cc1)=N[C@@H](C)c1nnc(C)n1-2] |
| III-247 | 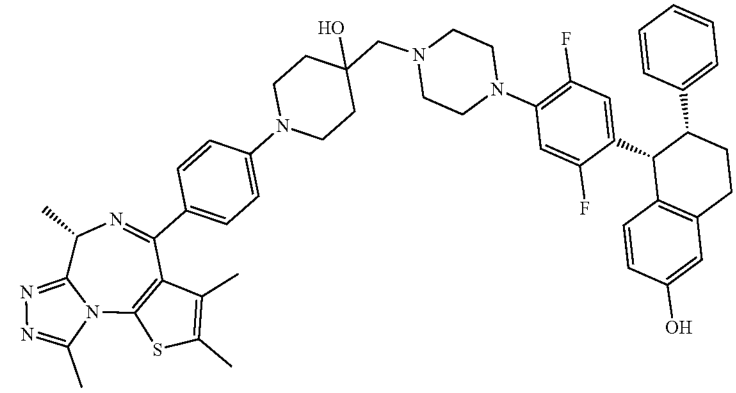 [SMILES: Cc1sc2c(c1C)C(c1ccc(N3CCC(O)(CN4CCN(c5cc(F)c([C@H]6c7ccc(O)cc7CC[C@H]6c6ccccc6)cc5F)CC4)CC3)cc1)=N[C@@H](C)c1nnc(C)n1-2] |

TABLE 3-continued
| Compound No. | Compound Structure |
|---|---|
| III-248 | 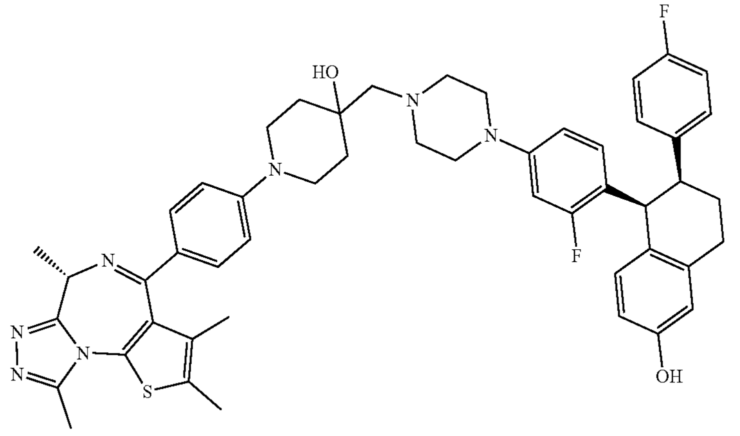 [SMILES: Cc1sc2c(c1C)C(c1ccc(N3CCC(O)(CN4CCN(c5ccc([C@@H]6c7ccc(O)cc7CC[C@@H]6c6ccc(F)cc6)c(F)c5)CC4)CC3)cc1)=N[C@@H](C)c1nnc(C)n1-2] |
| III-249 | 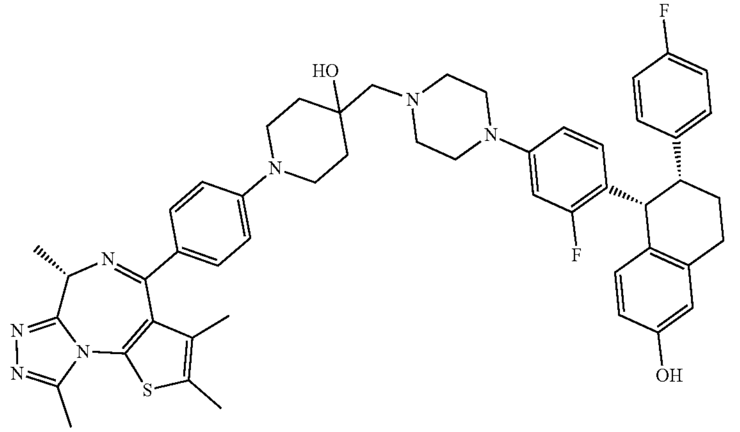 [SMILES: Cc1sc2c(c1C)C(c1ccc(N3CCC(O)(CN4CCN(c5ccc([C@H]6c7ccc(O)cc7CC[C@H]6c6ccc(F)cc6)c(F)c5)CC4)CC3)cc1)=N[C@@H](C)c1nnc(C)n1-2] |
| III-250 | 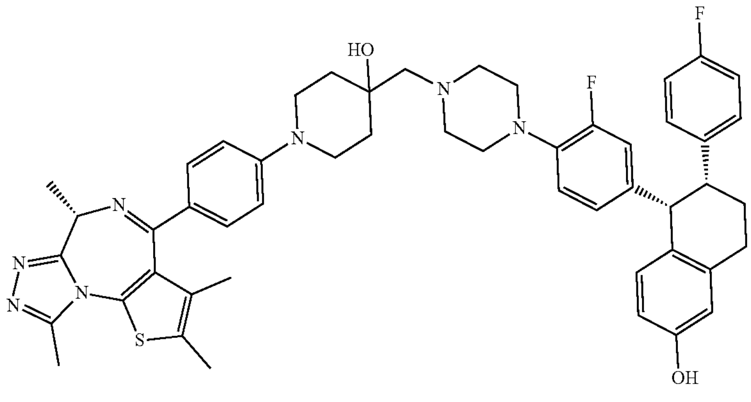 [SMILES: Cc1sc2c(c1C)C(c1ccc(N3CCC(O)(CN4CCN(c5ccc([C@H]6c7ccc(O)cc7CC[C@H]6c6ccc(F)cc6)cc5F)CC4)CC3)cc1)=N[C@@H](C)c1nnc(C)n1-2] |

TABLE 3-continued
| Compound No. | Compound Structure |
|---|---|
| III-251 | 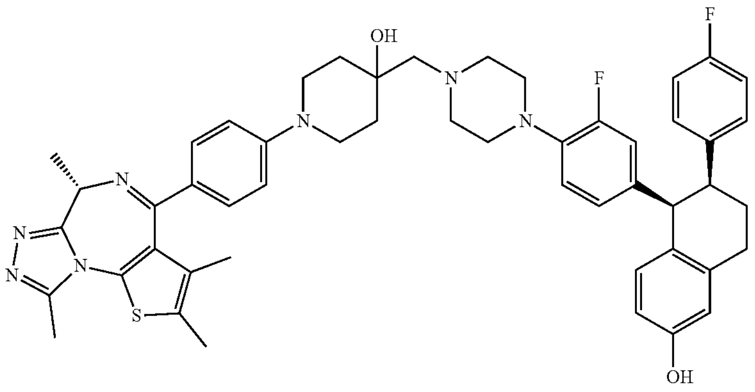 [SMILES: Cc1sc2c(c1C)C(c1ccc(N3CCC(O)(CN4CCN(c5ccc([C@@H]6c7ccc(O)cc7CC[C@@H]6c6ccc(F)cc6)cc5F)CC4)CC3)cc1)=N[C@@H](C)c1nnc(C)n1-2] |
| III-252 | 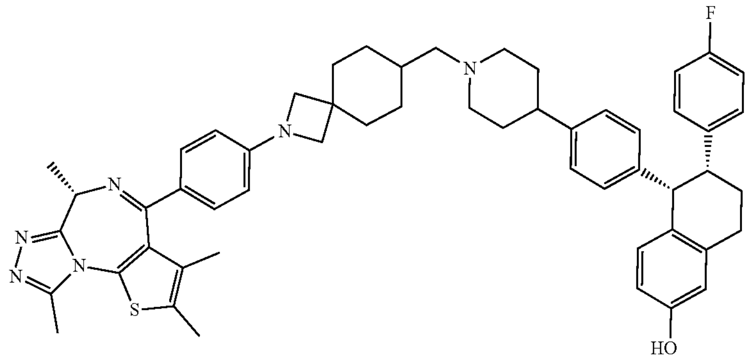 [SMILES: Cc1sc2c(c1C)C(c1ccc(N3CC4(CCC(CN5CCC(c6ccc([C@H]7c8ccc(O)cc8CC[C@H]7c7ccc(F)cc7)cc6)CC5)CC4)C3)cc1)=N[C@@H](C)c1nnc(C)n1-2] |
| III-253 | 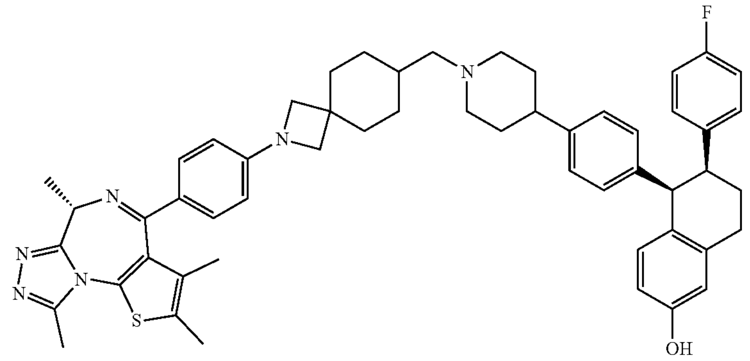 [SMILES: Cc1sc2c(c1C)C(c1ccc(N3CC4(CCC(CN5CCC(c6ccc([C@@H]7c8ccc(O)cc8CC[C@@H]7c7ccc(F)cc7)cc6)CC5)CC4)C3)cc1)=N[C@@H](C)c1nnc(C)n1-2] |
| III-254 | 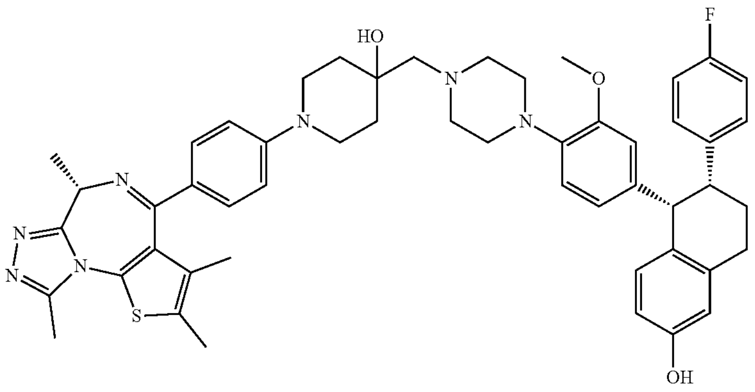 [SMILES: COc1cc([C@H]2c3ccc(O)cc3CC[C@H]2c2ccc(F)cc2)ccc1N1CCN(CC2(O)CCN(c3ccc(C4=N[C@@H](C)c5nnc(C)n5-c5sc(C)c(C)c54)cc3)CC2)CC1] |

TABLE 3-continued
| Compound No. | Compound Structure |
|---|---|
| III-255 | 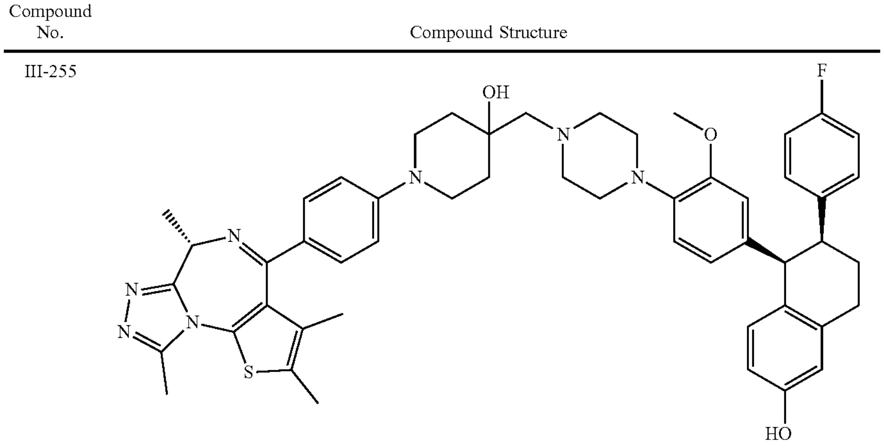 |
| III-256 | 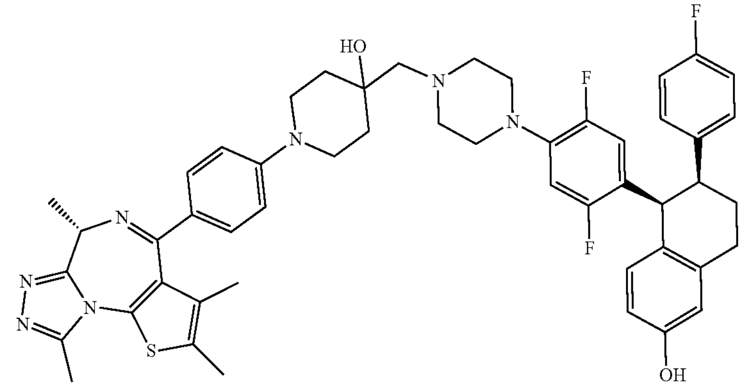 [SMILES: Cc1sc2c(c1C)C(c1ccc(N3CCC(O)(CN4CCN(c5cc(F)c([C@@H]6c7ccc(O)cc7CC[C@@H]6c6ccc(F)cc6)cc5F)CC4)CC3)cc1)=N[C@@H](C)c1nnc(C)n1-2] |
| III-257 | 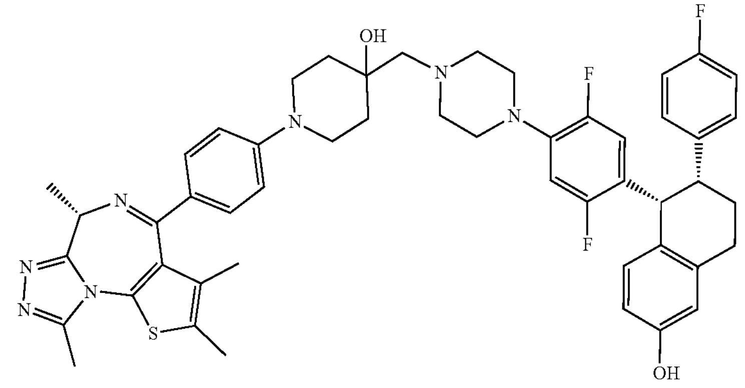 [SMILES: Cc1sc2c(c1C)C(c1ccc(N3CCC(O)(CN4CCN(c5cc(F)c([C@H]6c7ccc(O)cc7CC[C@H]6c6ccc(F)cc6)cc5F)CC4)CC3)cc1)=N[C@@H](C)c1nnc(C)n1-2] |
| III-258 | 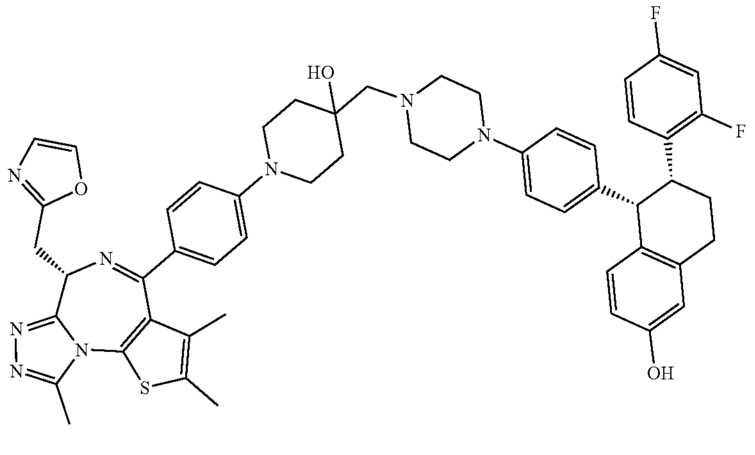 [SMILES: Cc1sc2c(c1C)C(c1ccc(N3CCC(O)(CN4CCN(c5ccc([C@H]6c7ccc(O)cc7CC[C@H]6c6ccc(F)cc6F)cc5)CC4)CC3)cc1)=N[C@@H](Cc1ncco1)c1nnc(C)n1-2] |

TABLE 3-continued
| Compound No. | Compound Structure |
|---|---|
| III-259 | 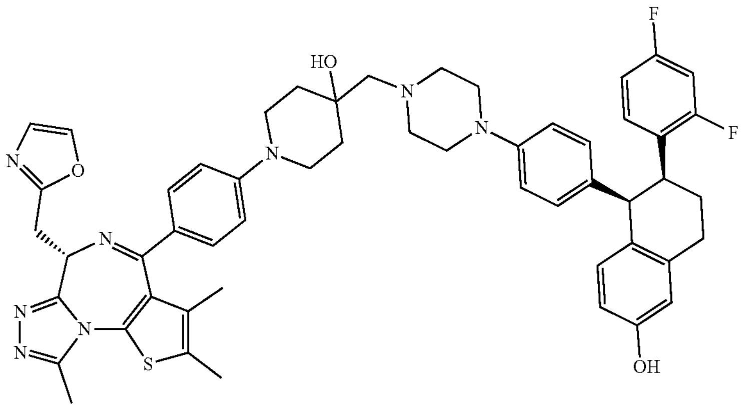 [SMILES: Cc1sc2c(c1C)C(c1ccc(N3CCC(O)(CN4CCN(c5ccc([C@@H]6c7ccc(O)cc7CC[C@@H]6c6ccc(F)cc6F)cc5)CC4)CC3)cc1)=N[C@@H](Cc1ncco1)c1nnc(C)n1-2] |
| III-260 | 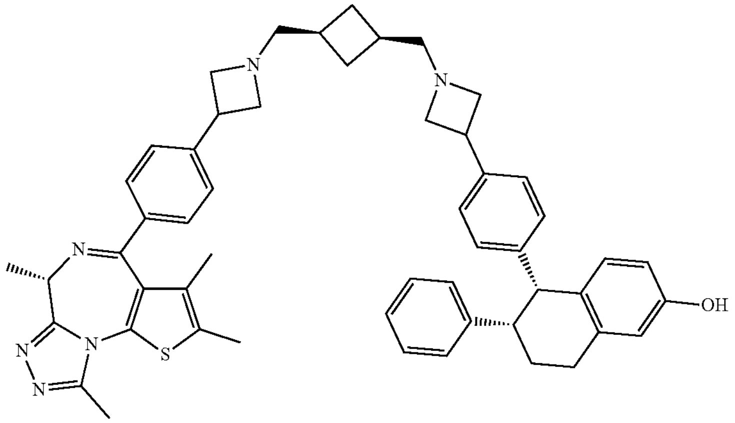 [SMILES: Cc1sc2c(c1C)C(c1ccc(C3CN(C[C@H]4C[C@@H](CN5CC(c6ccc([C@@H]7c8ccc(O)cc8CC[C@@H]7c7ccccc7)cc6)C5)C4)C3)cc1)=N[C@@H](C)c1nnc(C)n1-2] |
| III-261 | 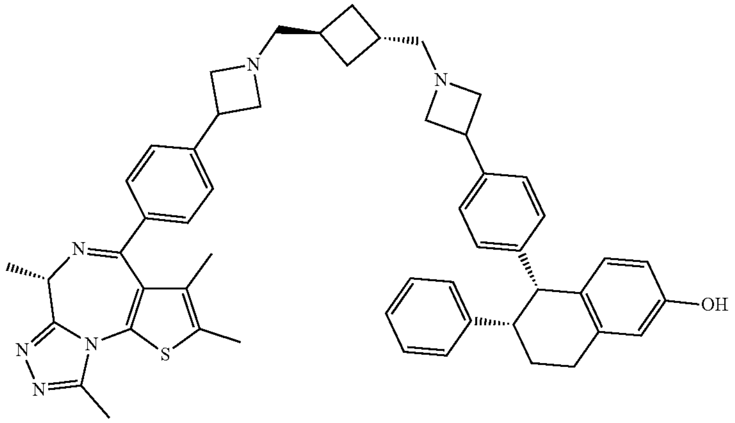 [SMILES: Cc1sc2c(c1C)C(c1ccc(C3CN(C[C@H]4C[C@H](CN5CC(c6ccc([C@@H]7c8ccc(O)cc8CC[C@@H]7c7ccccc7)cc6)C5)C4)C3)cc1)=N[C@@H](C)c1nnc(C)n1-2] |

TABLE 3-continued
| Compound No. | Compound Structure |
|---|---|
| III-262 | 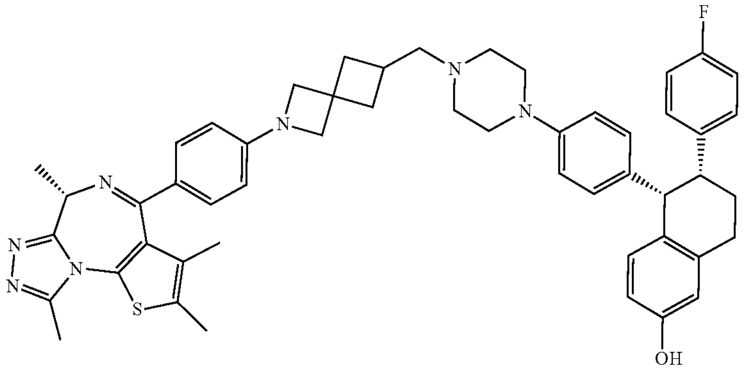 [SMILES: Cc1sc2c(c1C)C(c1ccc(N3CC4(CC(CN5CCN(c6ccc([C@H]7c8ccc(O)cc8CC[C@H]7c7ccc(F)cc7)cc6)CC5)C4)C3)cc1)=N[C@@H](C)c1nnc(C)n1-2] |
| III-263 | 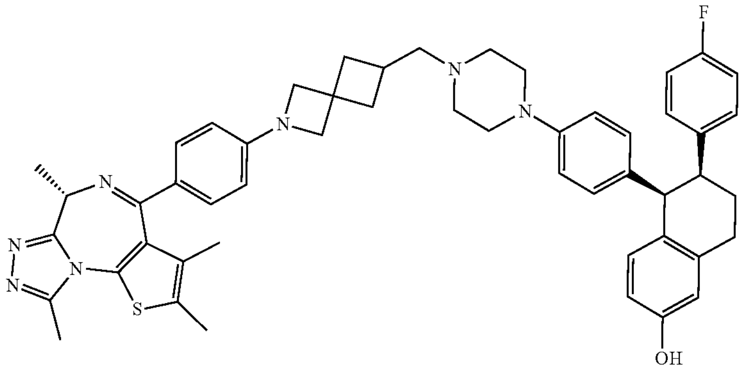 [SMILES: Cc1sc2c(c1C)C(c1ccc(N3CC4(CC(CN5CCN(c6ccc([C@@H]7c8ccc(O)cc8CC[C@@H]7c7ccc(F)cc7)cc6)CC5)C4)C3)cc1)=N[C@@H](C)c1nnc(C)n1-2] |
| III-264 | 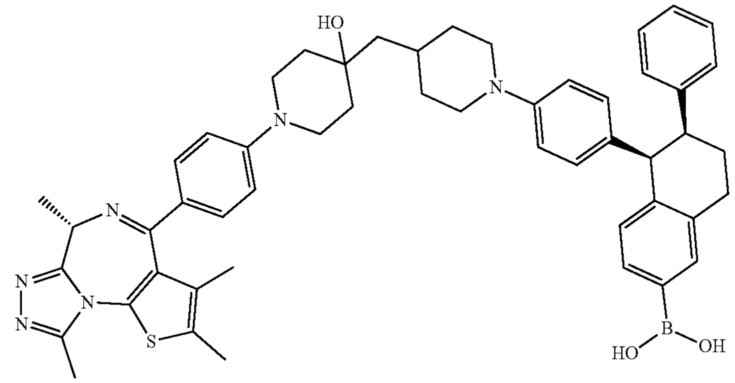 [SMILES: Cc1sc2c(c1C)C(c1ccc(N3CCC(O)(CC4CCN(c5ccc([C@@H]6c7ccc(B(O)O)cc7CC[C@@H]6c6ccccc6)cc5)CC4)CC3)cc1)=N[C@@H](C)c1nnc(C)n1-2] |
| III-265 | 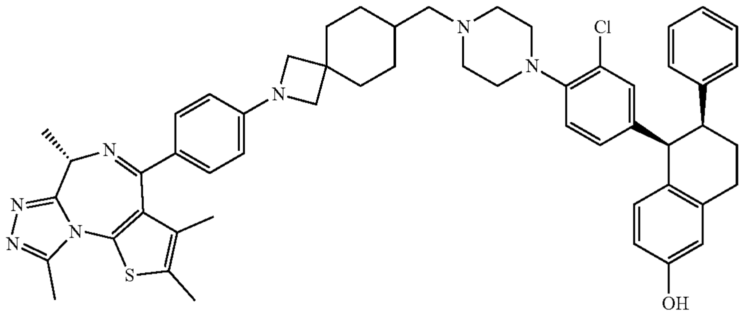 [SMILES: Cc1sc2c(c1C)C(c1ccc(N3CC4(CCC(CN5CCN(c6ccc([C@@H]7c8ccc(O)cc8CC[C@@H]7c7ccccc7)cc6Cl)CC5)CC4)C3)cc1)=N[C@@H](C)c1nnc(C)n1-2] |

TABLE 3-continued
| Compound No. | Compound Structure |
| --- | --- |
| III-266 | 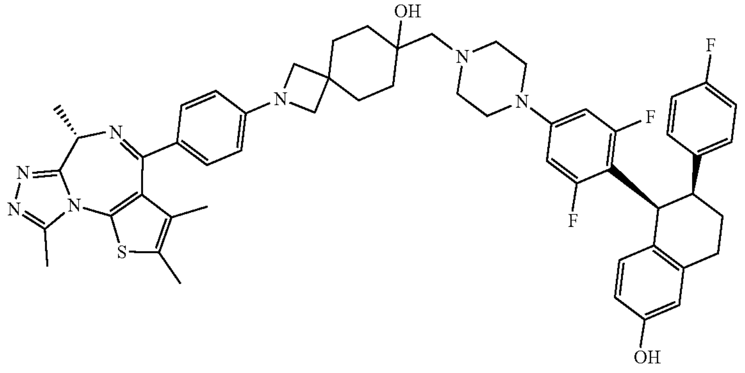 [SMILES: Cc1sc2c(c1C)C(c1ccc(N3CC4(CCC(O)(CN5CCN(c6cc(F)c([C@@H]7c8ccc(O)cc8CC[C@@H]7c7ccc(F)cc7)c(F)c6)CC5)CC4)C3)cc1)=N[C@@H](C)c1nnc(C)n1-2] |
| III-267 | 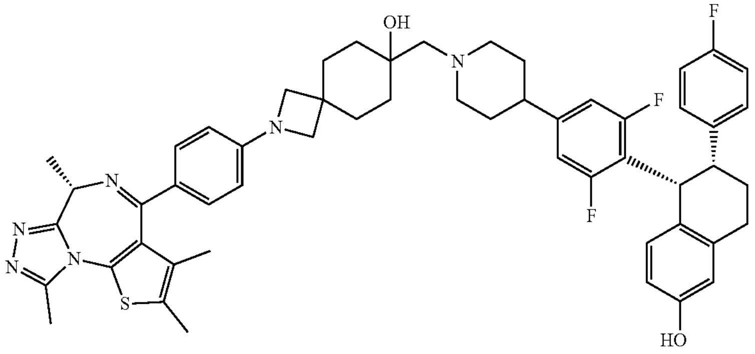 [SMILES: Cc1sc2c(c1C)C(c1ccc(N3CC4(CCC(O)(CN5CCC(c6cc(F)c([C@H]7c8ccc(O)cc8CC[C@H]7c7ccc(F)cc7)c(F)c6)CC5)CC4)C3)cc1)=N[C@@H](C)c1nnc(C)n1-2] |
| III-268 | 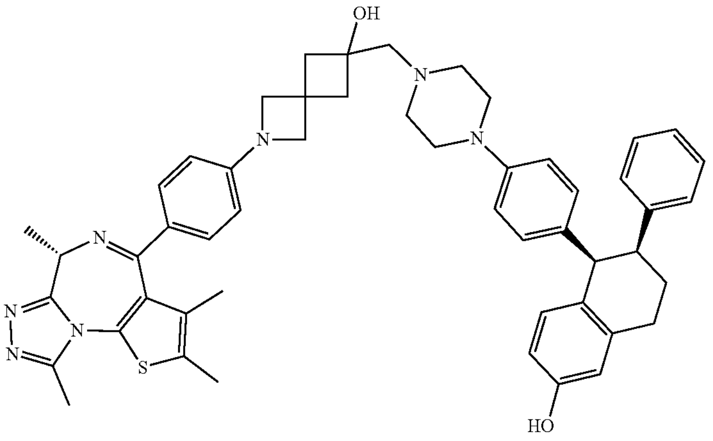 [SMILES: Cc1sc2c(c1C)C(c1ccc(N3CC4(C3)CC(O)(CN3CCN(c5ccc([C@@H]6c7ccc(O)cc7CC[C@@H]6c6ccccc6)cc5)CC3)C4)cc1)=N[C@@H](C)c1nnc(C)n1-2] |
| III-269 | 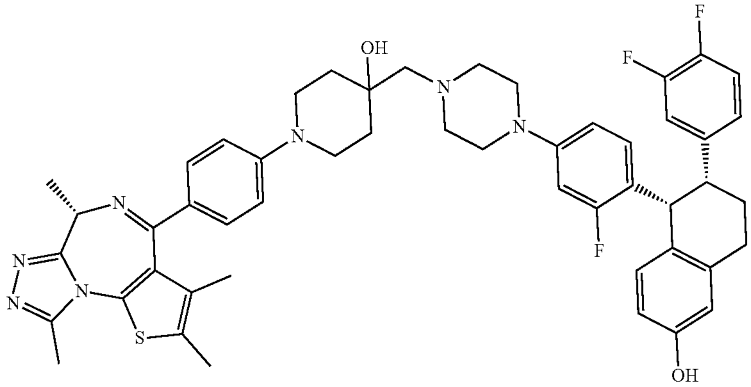 [SMILES: Cc1sc2c(c1C)C(c1ccc(N3CCC(O)(CN4CCN(c5ccc([C@H]6c7ccc(O)cc7CC[C@H]6c6ccc(F)c(F)c6)c(F)c5)CC4)CC3)cc1)=N[C@@H](C)c1nnc(C)n1-2] |

TABLE 3-continued
| Compound No. | Compound Structure |
|---|---|
| III-270 | 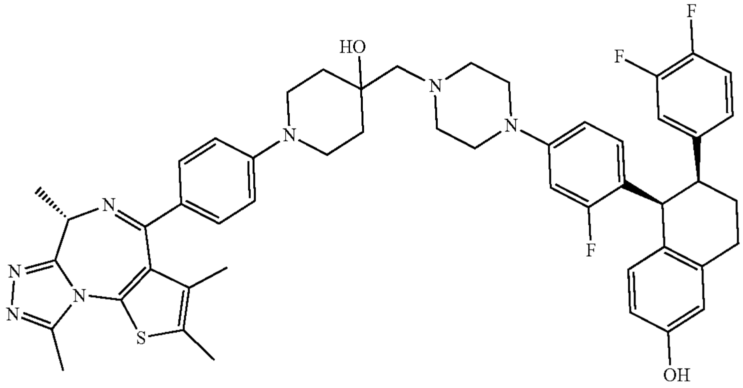 [SMILES: Cc1sc2c(c1C)C(c1ccc(N3CCC(O)(CN4CCN(c5ccc([C@@H]6c7ccc(O)cc7CC[C@@H]6c6ccc(F)c(F)c6)c(F)c5)CC4)CC3)cc1)=N[C@@H](C)c1nnc(C)n1-2] |
| III-271 | 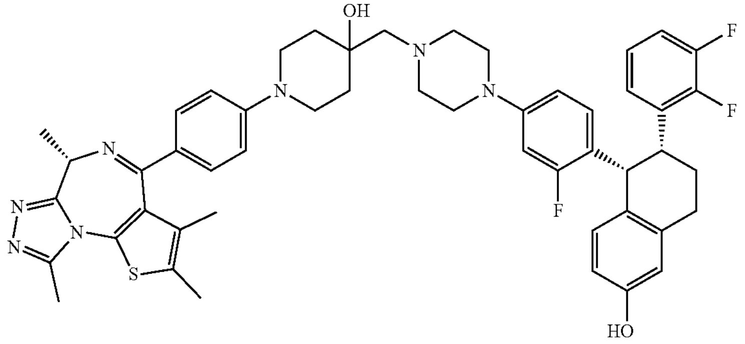 [SMILES: Cc1sc2c(c1C)C(c1ccc(N3CCC(O)(CN4CCN(c5ccc([C@H]6c7ccc(O)cc7CC[C@H]6c6cccc(F)c6F)c(F)c5)CC4)CC3)cc1)=N[C@@H](C)c1nnc(C)n1-2] |
| III-272 | 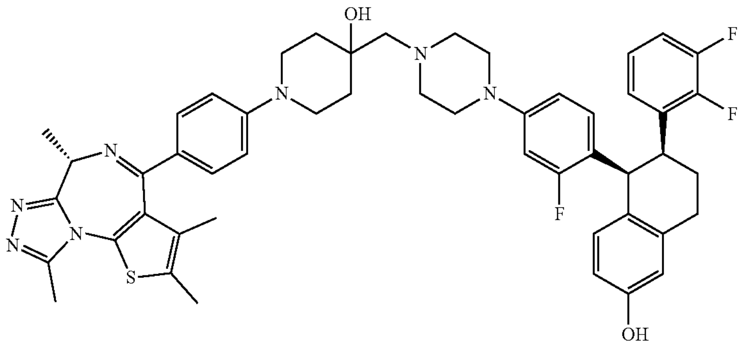 [SMILES: Cc1sc2c(c1C)C(c1ccc(N3CCC(O)(CN4CCN(c5ccc([C@@H]6c7ccc(O)cc7CC[C@@H]6c6cccc(F)c6F)c(F)c5)CC4)CC3)cc1)=N[C@@H](C)c1nnc(C)n1-2] |
| III-273 | 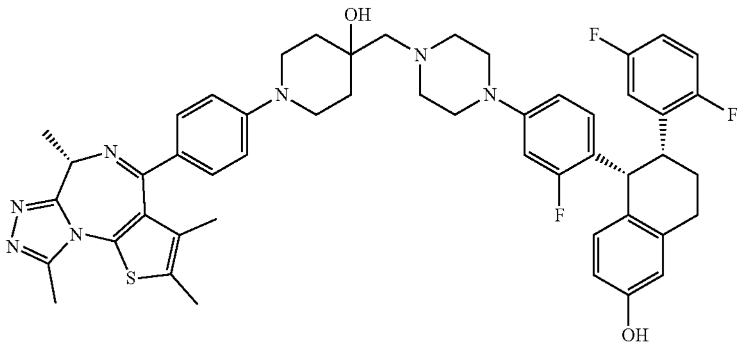 [SMILES: Cc1sc2c(c1C)C(c1ccc(N3CCC(O)(CN4CCN(c5ccc([C@H]6c7ccc(O)cc7CC[C@H]6c6cc(F)ccc6F)c(F)c5)CC4)CC3)cc1)=N[C@@H](C)c1nnc(C)n1-2] |

TABLE 3-continued
| Compound No. | Compound Structure |
| --- | --- |
| III-274 | 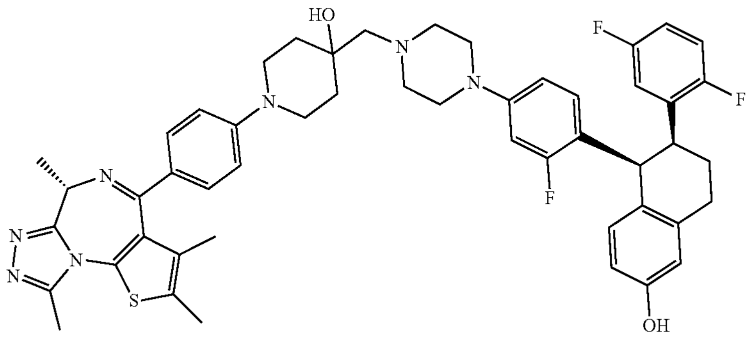 [SMILES: Cc1sc2c(c1C)C(c1ccc(N3CCC(O)(CN4CCN(c5ccc([C@@H]6c7ccc(O)cc7CC[C@@H]6c6cc(F)ccc6F)c(F)c5)CC4)CC3)cc1)=N[C@@H](C)c1nnc(C)n1-2] |
| III-275 | 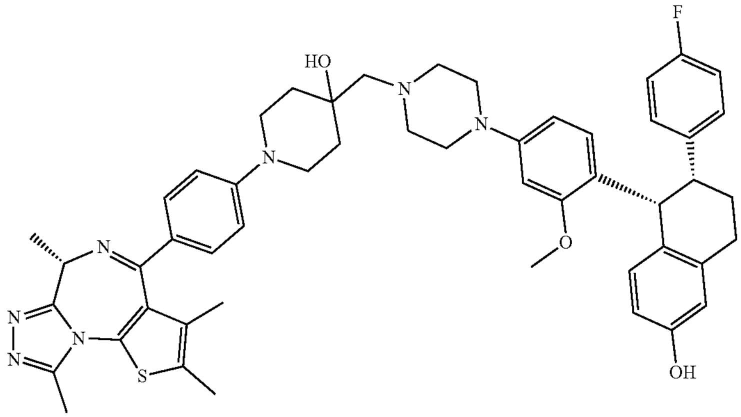 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(F)cc1] |
| III-276 | 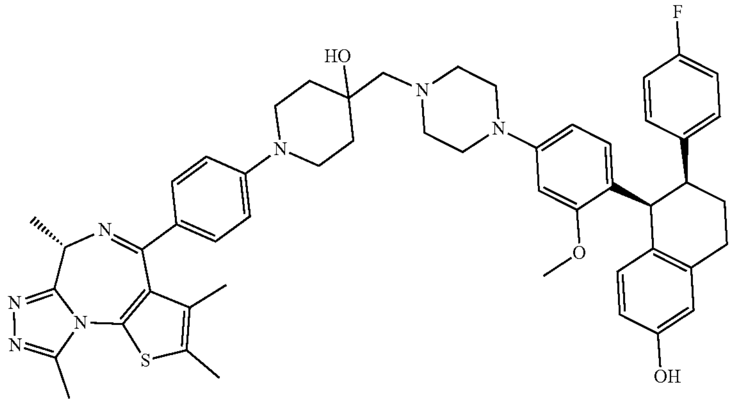 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(F)cc1] |
| III-277 | 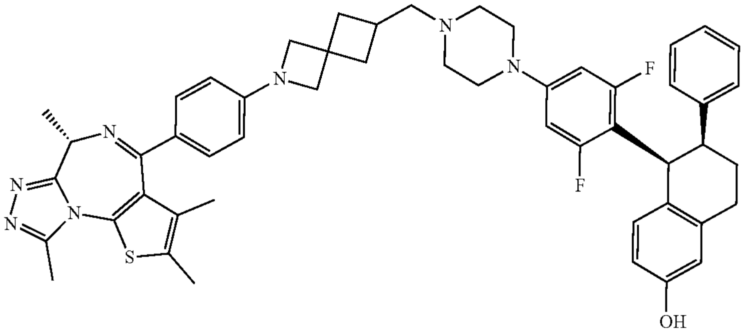 [SMILES: Cc1sc2c(c1C)C(c1ccc(N3CC4(CC(CN5CCN(c6cc(F)c([C@@H]7c8ccc(O)cc8CC[C@@H]7c7ccccc7)c(F)c6)CC5)C4)C3)cc1)=N[C@@H](C)c1nnc(C)n1-2] |

TABLE 3-continued
| Compound No. | Compound Structure |
| --- | --- |
| III-278 | 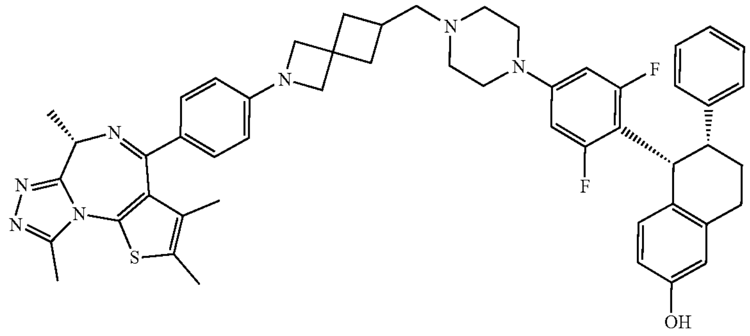 [SMILES: Cc1sc2c(c1C)C(c1ccc(N3CC4(CC(CN5CCN(c6cc(F)c([C@H]7c8ccc(O)cc8CC[C@H]7c7ccccc7)c(F)c6)CC5)C4)C3)cc1)=N[C@@H](C)c1nnc(C)n1-2] |
| III-279 | 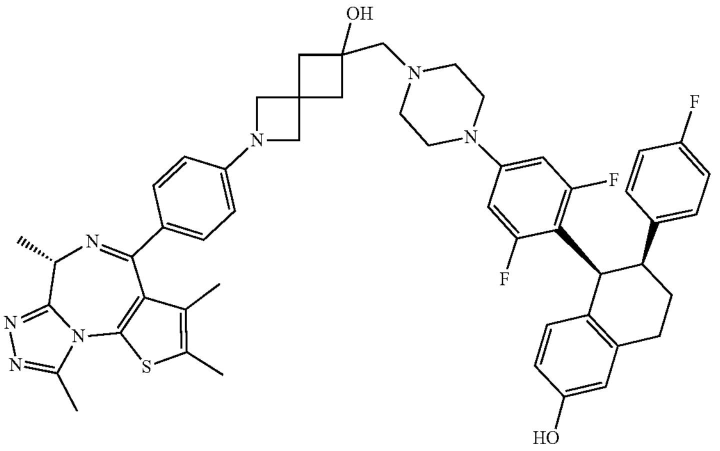 [SMILES: Cc1sc2c(c1C)C(c1ccc(N3CC4(C3)CC(O)(CN3CCN(c5cc(F)c([C@@H]6c7ccc(O)cc7CC[C@@H]6c6ccc(F)cc6)c(F)c5)CC3)C4)cc1)=N[C@@H](C)c1nnc(C)n1-2] |
| III-280 | 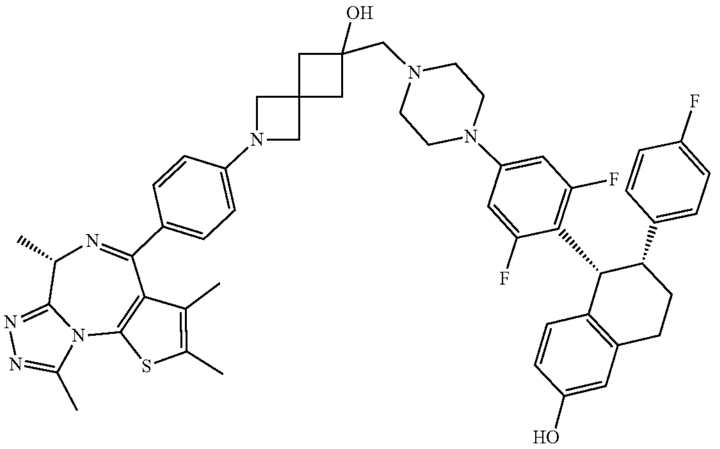 [SMILES: Cc1sc2c(c1C)C(c1ccc(N3CC4(C3)CC(O)(CN3CCN(c5cc(F)c([C@H]6c7ccc(O)cc7CC[C@H]6c6ccc(F)cc6)c(F)c5)CC3)C4)cc1)=N[C@@H](C)c1nnc(C)n1-2] |

TABLE 3-continued
| Compound No. | Compound Structure |
| --- | --- |
| III-281 | 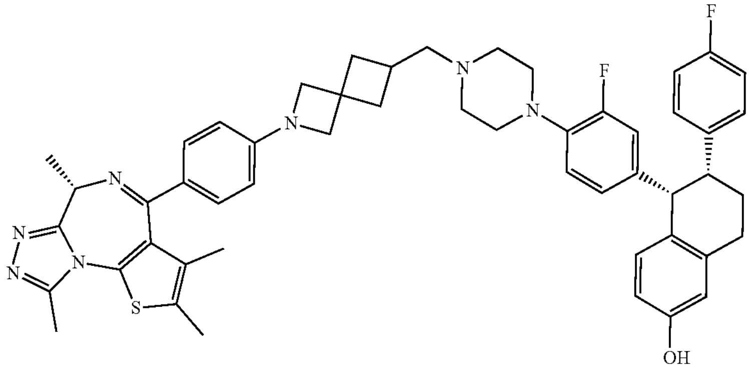 [SMILES: Cc1sc2c(c1C)C(c1ccc(N3CC4(CC(CN5CCN(c6ccc([C@H]7c8ccc(O)cc8CC[C@H]7c7ccc(F)cc7)cc6F)CC5)C4)C3)cc1)=N[C@@H](C)c1nnc(C)n1-2] |
| III-282 | 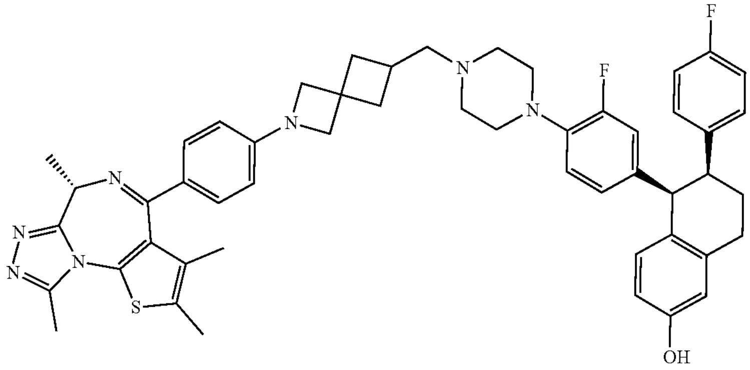 [SMILES: Cc1sc2c(c1C)C(c1ccc(N3CC4(CC(CN5CCN(c6ccc([C@@H]7c8ccc(O)cc8CC[C@@H]7c7ccc(F)cc7)cc6F)CC5)C4)C3)cc1)=N[C@@H](C)c1nnc(C)n1-2] |
| III-283 | 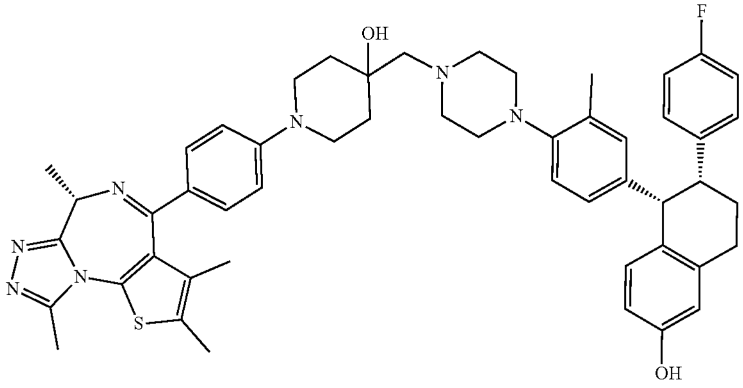 [SMILES: Cc1cc([C@H]2c3ccc(O)cc3CC[C@H]2c2ccc(F)cc2)ccc1N1CCN(CC2(O)CCN(c3ccc(C4=N[C@@H](C)c5nnc(C)n5-c5sc(C)c(C)c54)cc3)CC2)CC1] |
| III-284 | 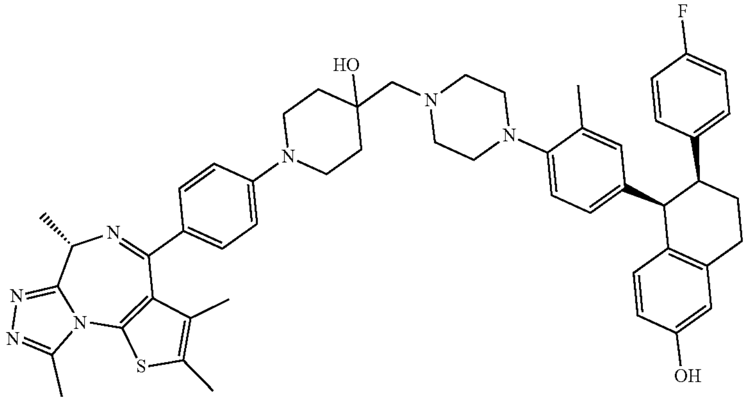 [SMILES: Cc1cc([C@@H]2c3ccc(O)cc3CC[C@@H]2c2ccc(F)cc2)ccc1N1CCN(CC2(O)CCN(c3ccc(C4=N[C@@H](C)c5nnc(C)n5-c5sc(C)c(C)c54)cc3)CC2)CC1] |

TABLE 3-continued
| Compound No. | Compound Structure |
|---|---|
| III-285 | 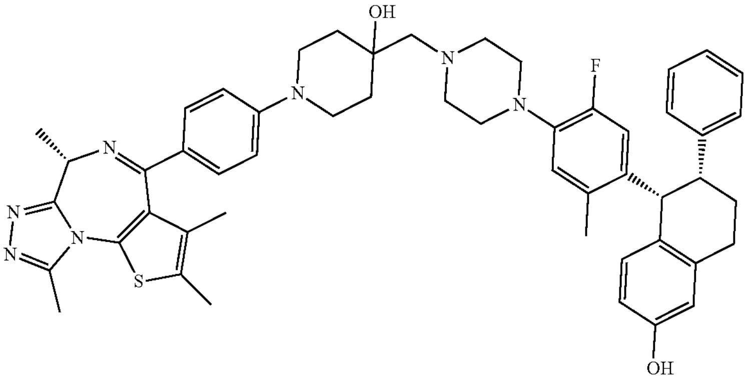 [SMILES: Cc1cc(N2CCN(CC3(O)CCN(c4ccc(C5=N[C@@H](C)c6nnc(C)n6-c6sc(C)c(C)c65)cc4)CC3)CC2)c(F)cc1[C@H]1c2ccc(O)cc2CC[C@H]1c1ccccc1] |
| III-286 | 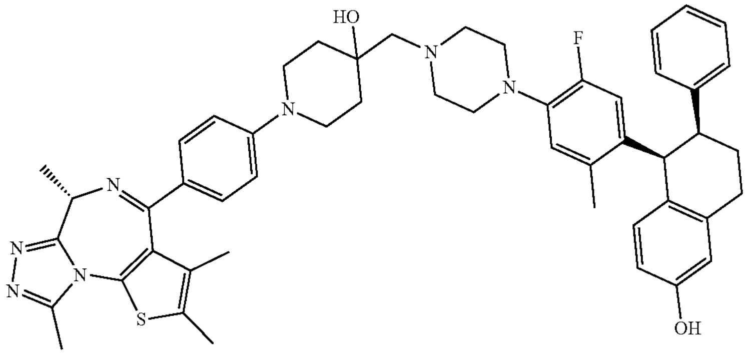 [SMILES: Cc1cc(N2CCN(CC3(O)CCN(c4ccc(C5=N[C@@H](C)c6nnc(C)n6-c6sc(C)c(C)c65)cc4)CC3)CC2)c(F)cc1[C@@H]1c2ccc(O)cc2CC[C@@H]1c1ccccc1] |
| III-287 | 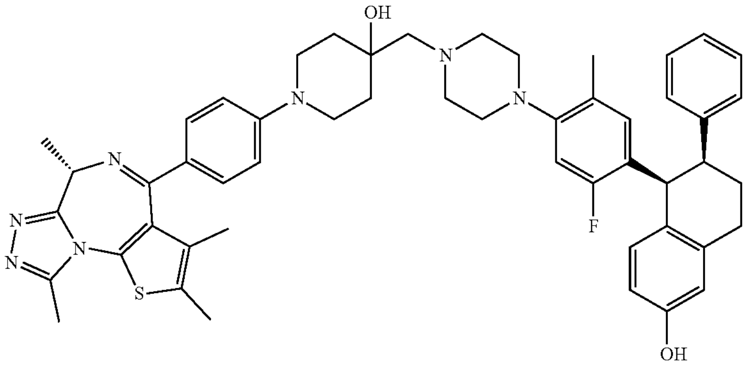 [SMILES: Cc1cc([C@@H]2c3ccc(O)cc3CC[C@@H]2c2ccccc2)c(F)cc1N1CCN(CC2(O)CCN(c3ccc(C4=N[C@@H](C)c5nnc(C)n5-c5sc(C)c(C)c54)cc3)CC2)CC1] |
| III-288 | 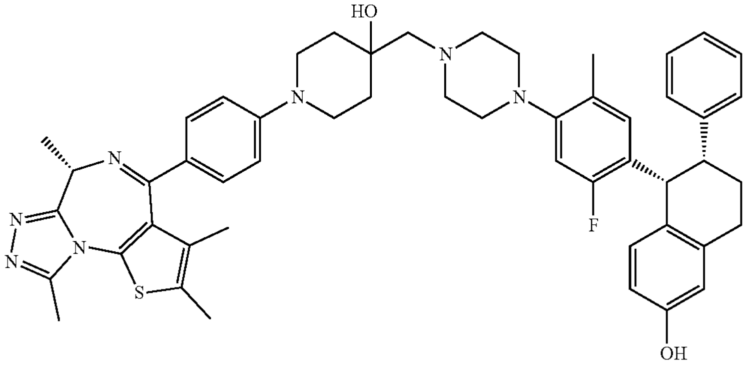 [SMILES: Cc1cc([C@H]2c3ccc(O)cc3CC[C@H]2c2ccccc2)c(F)cc1N1CCN(CC2(O)CCN(c3ccc(C4=N[C@@H](C)c5nnc(C)n5-c5sc(C)c(C)c54)cc3)CC2)CC1] |

TABLE 3-continued
| Compound No. | Compound Structure |
| --- | --- |
| III-289 | 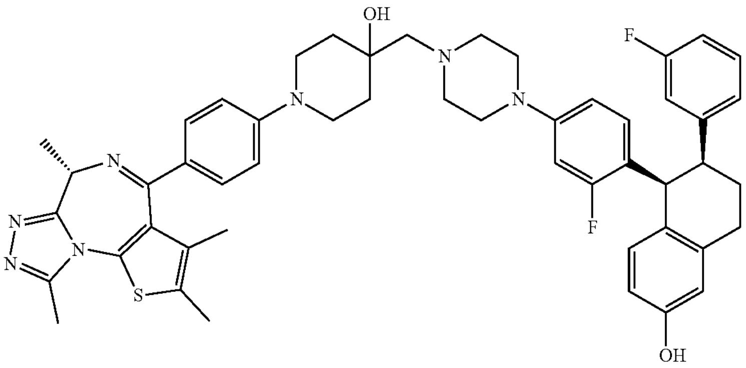 [SMILES: Cc1sc2c(c1C)C(c1ccc(N3CCC(O)(CN4CCN(c5ccc([C@@H]6c7ccc(O)cc7CC[C@@H]6c6cccc(F)c6)c(F)c5)CC4)CC3)cc1)=N[C@@H](C)c1nnc(C)n1-2] |
| III-290 | 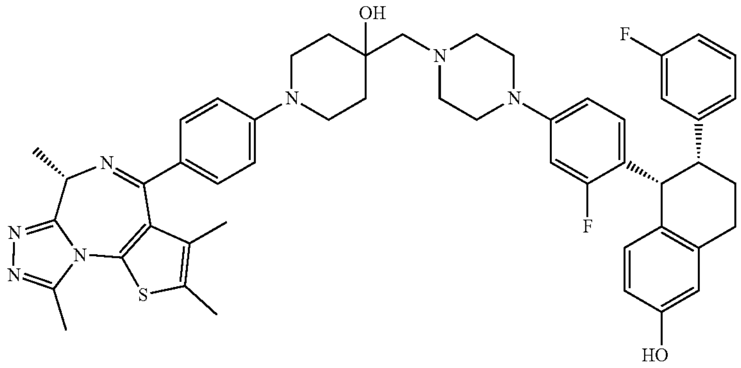 [SMILES: Cc1sc2c(c1C)C(c1ccc(N3CCC(O)(CN4CCN(c5ccc([C@H]6c7ccc(O)cc7CC[C@H]6c6cccc(F)c6)c(F)c5)CC4)CC3)cc1)=N[C@@H](C)c1nnc(C)n1-2] |
| III-291 | 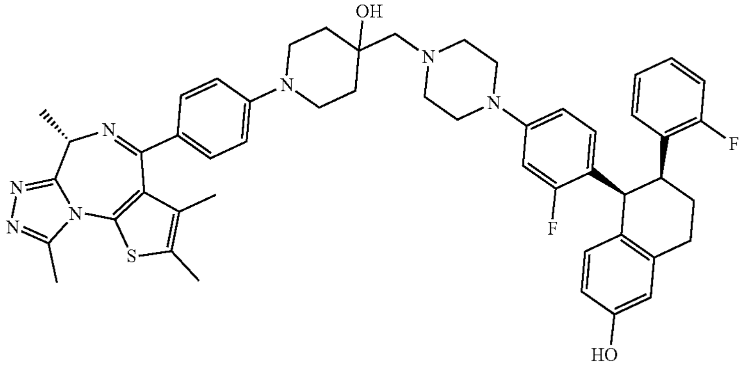 [SMILES: Cc1sc2c(c1C)C(c1ccc(N3CCC(O)(CN4CCN(c5ccc([C@@H]6c7ccc(O)cc7CC[C@@H]6c6ccccc6F)c(F)c5)CC4)CC3)cc1)=N[C@@H](C)c1nnc(C)n1-2] |
| III-292 | 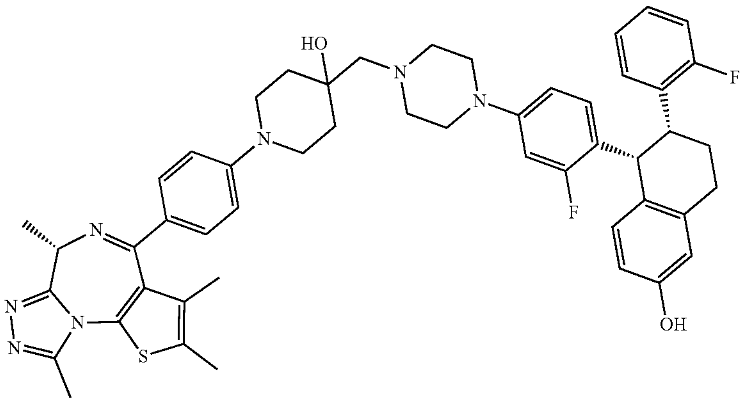 [SMILES: Cc1sc2c(c1C)C(c1ccc(N3CCC(O)(CN4CCN(c5ccc([C@H]6c7ccc(O)cc7CC[C@H]6c6ccccc6F)c(F)c5)CC4)CC3)cc1)=N[C@@H](C)c1nnc(C)n1-2] |

TABLE 3-continued
| Compound No. | Compound Structure |
|---|---|
| III-293 | 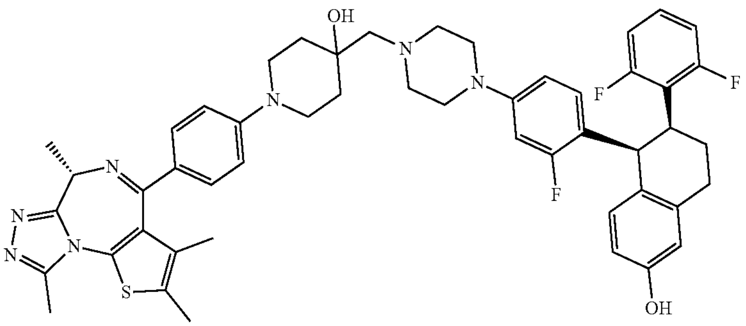 [SMILES: Cc1sc2c(c1C)C(c1ccc(N3CCC(O)(CN4CCN(c5ccc([C@@H]6c7ccc(O)cc7CC[C@@H]6c6c(F)cccc6F)c(F)c5)CC4)CC3)cc1)=N[C@@H](C)c1nnc(C)n1-2] |
| III-294 | 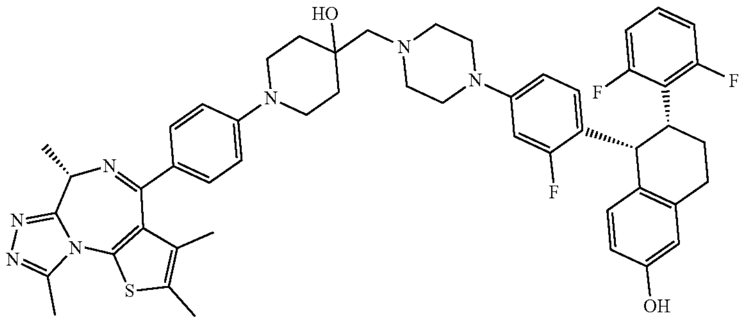 [SMILES: Cc1sc2c(c1C)C(c1ccc(N3CCC(O)(CN4CCN(c5ccc([C@H]6c7ccc(O)cc7CC[C@H]6c6c(F)cccc6F)c(F)c5)CC4)CC3)cc1)=N[C@@H](C)c1nnc(C)n1-2] |
| III-295 | 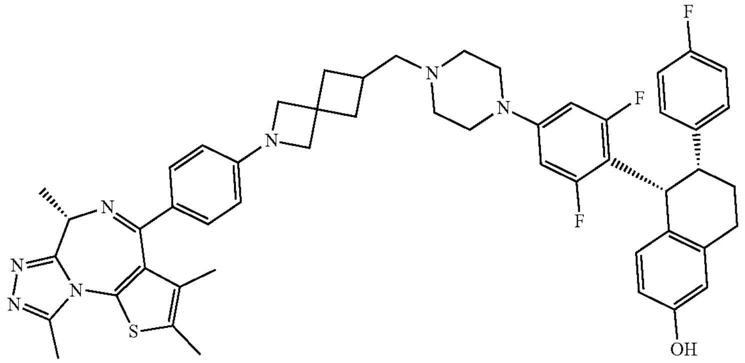 [SMILES: Cc1sc2c(c1C)C(c1ccc(N3CC4(CC(CN5CCN(c6cc(F)c([C@H]7c8ccc(O)cc8CC[C@H]7c7ccc(F)cc7)c(F)c6)CC5)C4)C3)cc1)=N[C@@H](C)c1nnc(C)n1-2] |
| III-296 | 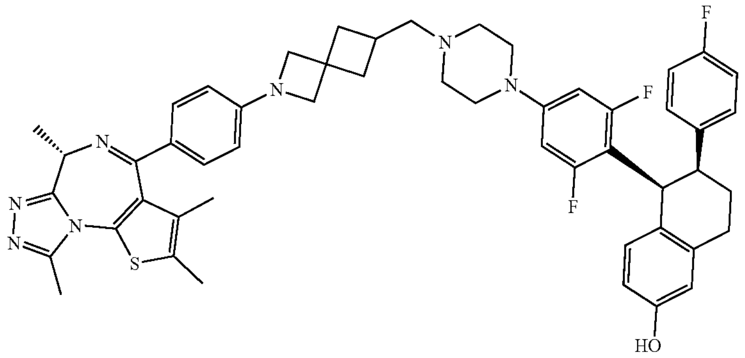 [SMILES: Cc1sc2c(c1C)C(c1ccc(N3CC4(CC(CN5CCN(c6cc(F)c([C@@H]7c8ccc(O)cc8CC[C@@H]7c7ccc(F)cc7)c(F)c6)CC5)C4)C3)cc1)=N[C@@H](C)c1nnc(C)n1-2] |

TABLE 3-continued
| Compound No. | Compound Structure |
|---|---|
| III-297 | 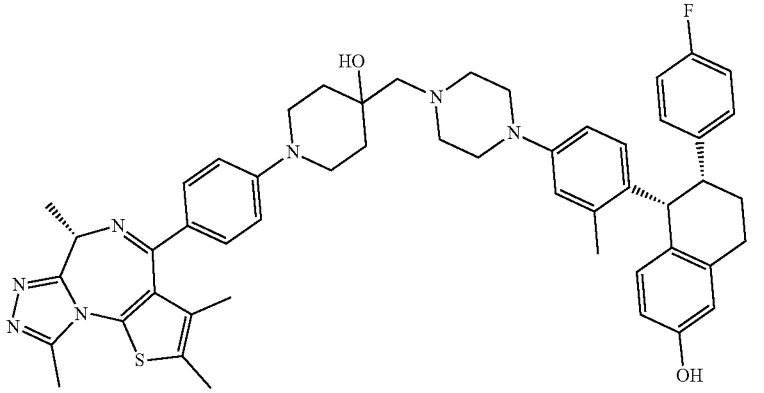 [SMILES: Cc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(F)cc1] |
| III-298 | 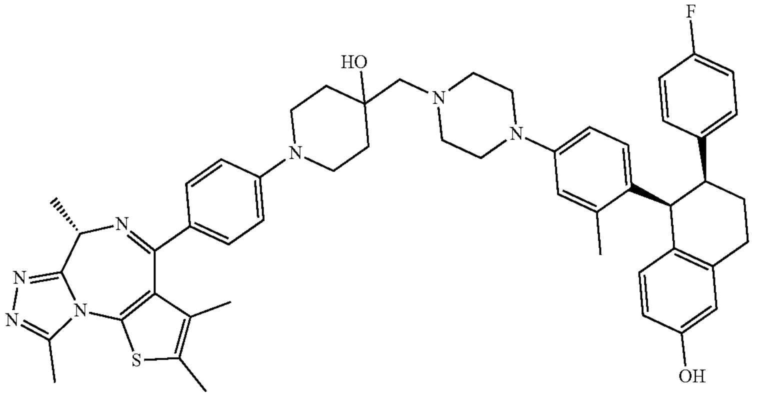 [SMILES: Cc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(F)cc1] |
| III-299 | 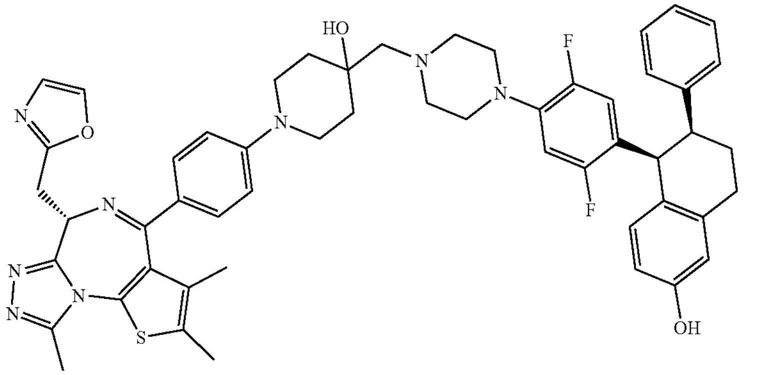 [SMILES: Cc1sc2c(c1C)C(c1ccc(N3CCC(O)(CN4CCN(c5cc(F)c([C@@H]6c7ccc(O)cc7CC[C@@H]6c6ccccc6)cc5F)CC4)CC3)cc1)=N[C@@H](Cc1ncco1)c1nnc(C)n1-2] |
| III-300 | 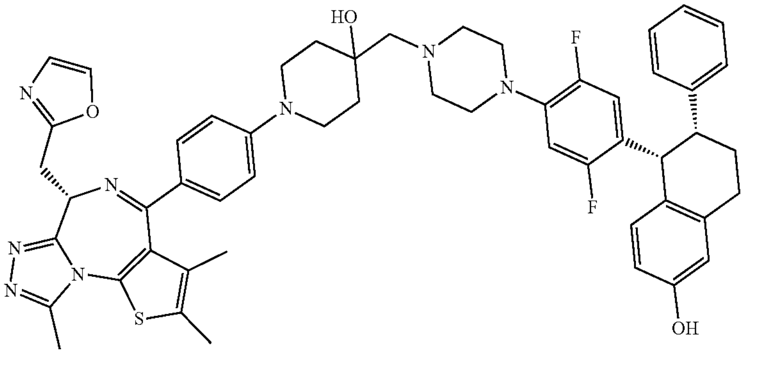 [SMILES: Cc1sc2c(c1C)C(c1ccc(N3CCC(O)(CN4CCN(c5cc(F)c([C@H]6c7ccc(O)cc7CC[C@H]6c6ccccc6)cc5F)CC4)CC3)cc1)=N[C@@H](Cc1ncco1)c1nnc(C)n1-2] |

TABLE 3-continued
| Compound No. | Compound Structure |
|---|---|
| III-301 | 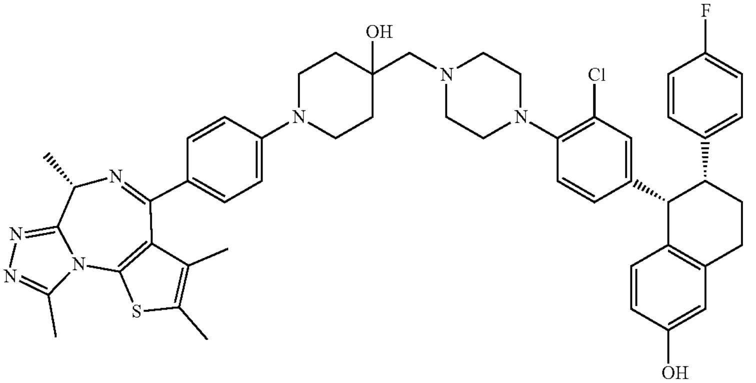 [SMILES: Cc1sc2c(c1C)C(c1ccc(N3CCC(O)(CN4CCN(c5ccc([C@H]6c7ccc(O)cc7CC[C@H]6c6ccc(F)cc6)cc5Cl)CC4)CC3)cc1)=N[C@@H](C)c1nnc(C)n1-2] |
| III-302 | 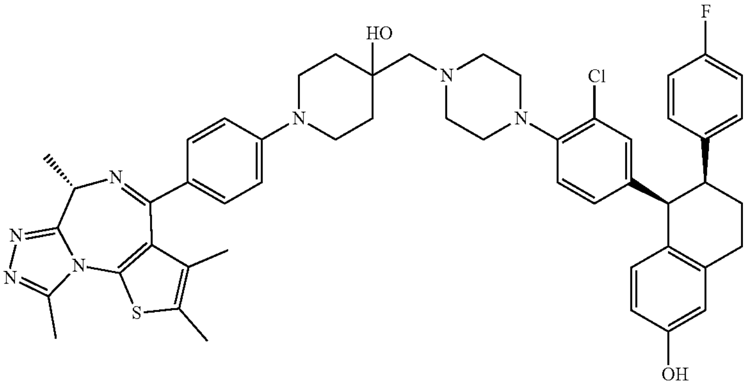 [SMILES: Cc1sc2c(c1C)C(c1ccc(N3CCC(O)(CN4CCN(c5ccc([C@@H]6c7ccc(O)cc7CC[C@@H]6c6ccc(F)cc6)cc5Cl)CC4)CC3)cc1)=N[C@@H](C)c1nnc(C)n1-2] |
| III-303 | 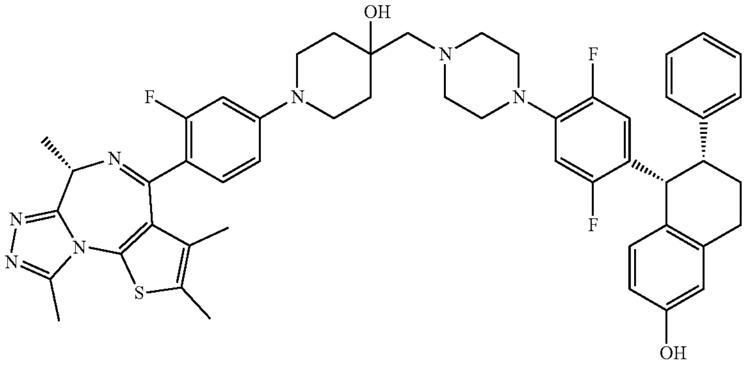 [SMILES: Cc1sc2c(c1C)C(c1ccc(N3CCC(O)(CN4CCN(c5cc(F)c([C@H]6c7ccc(O)cc7CC[C@H]6c6ccccc6)cc5F)CC4)CC3)cc1F)=N[C@@H](C)c1nnc(C)n1-2] |
| III-304 | 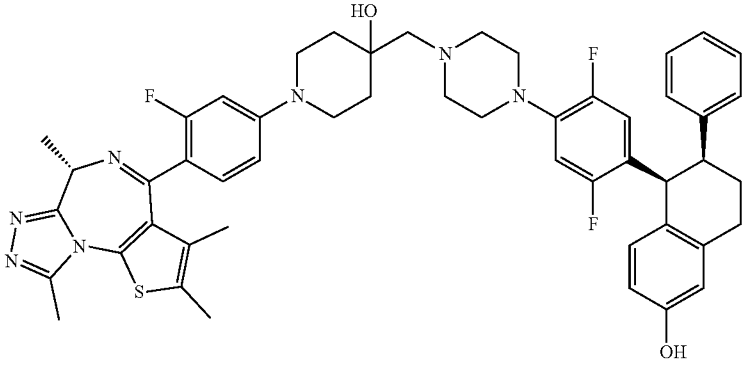 [SMILES: Cc1sc2c(c1C)C(c1ccc(N3CCC(O)(CN4CCN(c5cc(F)c([C@@H]6c7ccc(O)cc7CC[C@@H]6c6ccccc6)cc5F)CC4)CC3)cc1F)=N[C@@H](C)c1nnc(C)n1-2] |

TABLE 3-continued
| Compound No. | Compound Structure |
|---|---|
| III-305 | 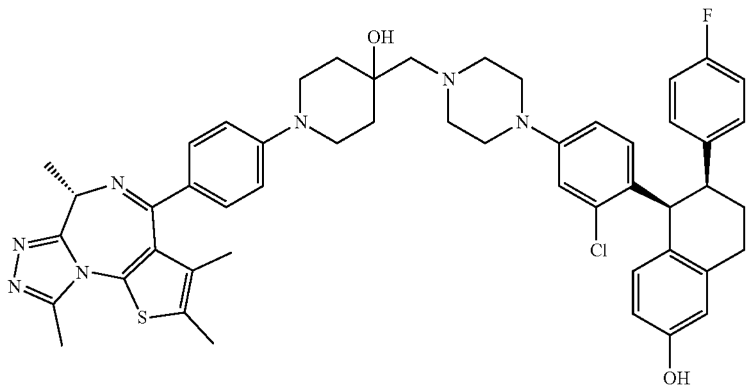 [SMILES: Cc1sc2c(c1C)C(c1ccc(N3CCC(O)(CN4CCN(c5ccc([C@@H]6c7ccc(O)cc7CC[C@@H]6c6ccc(F)cc6)c(Cl)c5)CC4)CC3)cc1)=N[C@@H](C)c1nnc(C)n1-2] |
| III-306 | 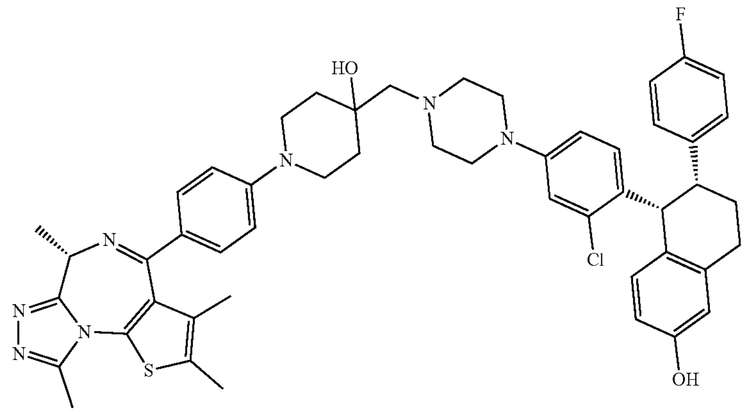 [SMILES: Cc1sc2c(c1C)C(c1ccc(N3CCC(O)(CN4CCN(c5ccc([C@H]6c7ccc(O)cc7CC[C@H]6c6ccc(F)cc6)c(Cl)c5)CC4)CC3)cc1)=N[C@@H](C)c1nnc(C)n1-2] |
| III-307 | 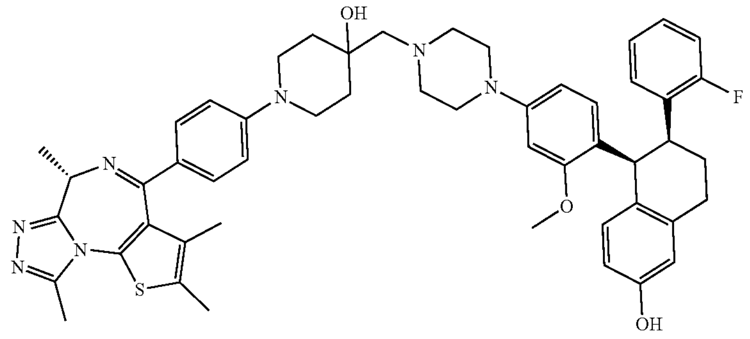 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccccc1F] |
| III-308 | 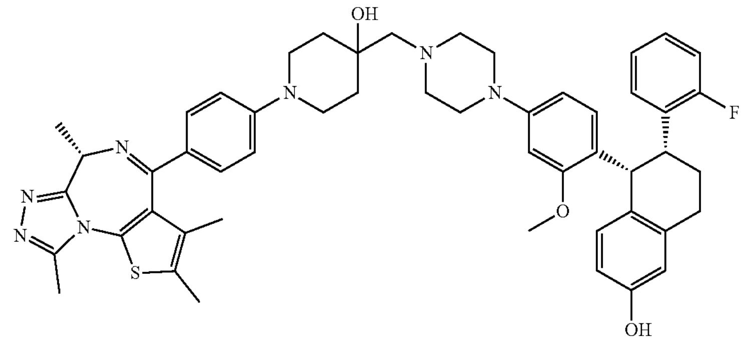 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccccc1F] |

TABLE 3-continued
| Compound No. | Compound Structure |
|---|---|
| III-309 | 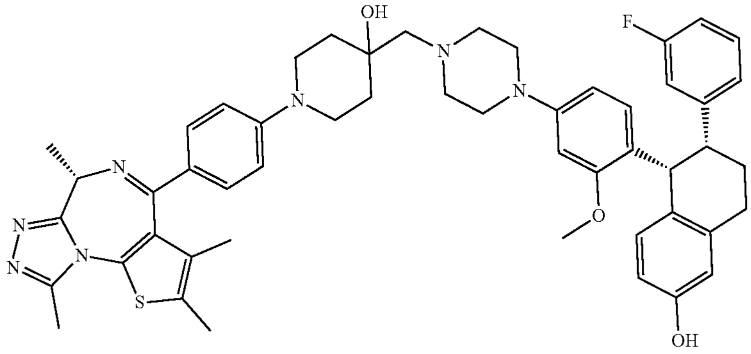 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1cccc(F)c1] |
| III-310 | 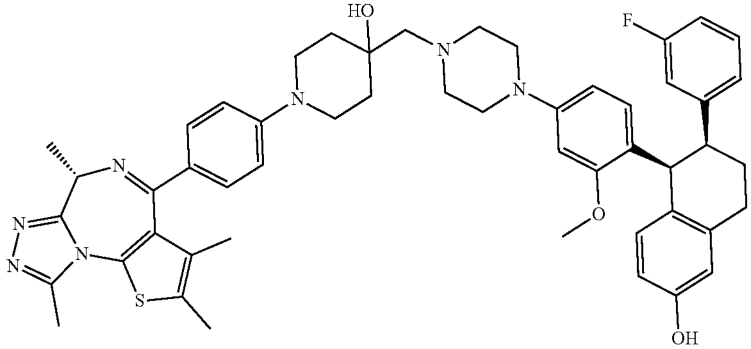 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1cccc(F)c1] |
| III-311 | 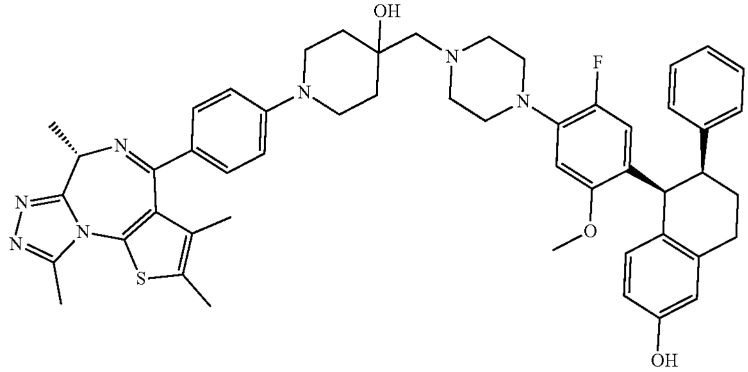 [SMILES: COc1cc(N2CCN(CC3(O)CCN(c4ccc(C5=N[C@@H](C)c6nnc(C)n6-c6sc(C)c(C)c65)cc4)CC3)CC2)c(F)cc1[C@@H]1c2ccc(O)cc2CC[C@@H]1c1ccccc1] |
| III-312 | 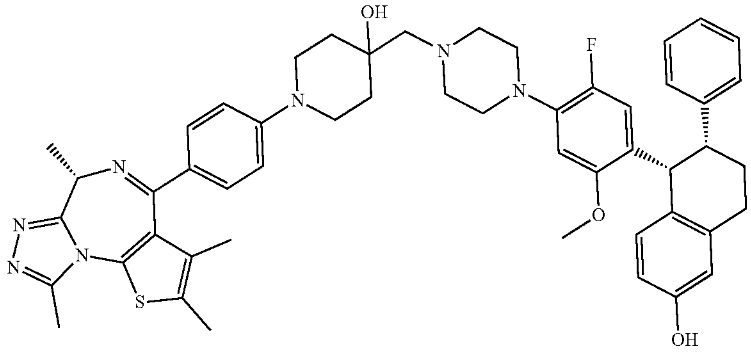 [SMILES: COc1cc(N2CCN(CC3(O)CCN(c4ccc(C5=N[C@@H](C)c6nnc(C)n6-c6sc(C)c(C)c65)cc4)CC3)CC2)c(F)cc1[C@H]1c2ccc(O)cc2CC[C@H]1c1ccccc1] |

TABLE 3-continued
| Compound No. | Compound Structure |
|---|---|
| III-313 | 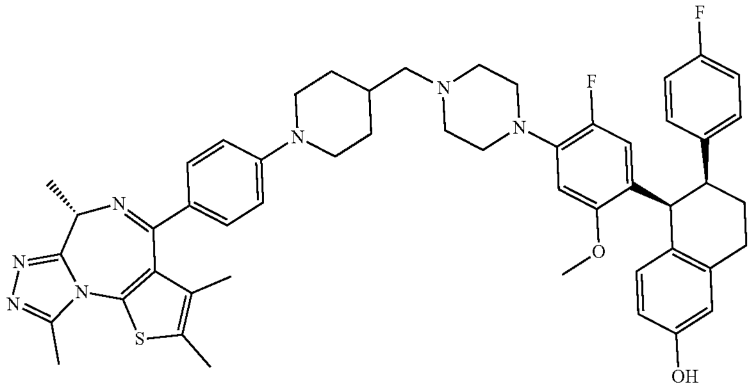 [SMILES: COc1cc(N2CCN(CC3CCN(c4ccc(C5=N[C@@H](C)c6nnc(C)n6-c6sc(C)c(C)c65)cc4)CC3)CC2)c(F)cc1[C@@H]1c2ccc(O)cc2CC[C@@H]1c1ccc(F)cc1] |
| III-314 | 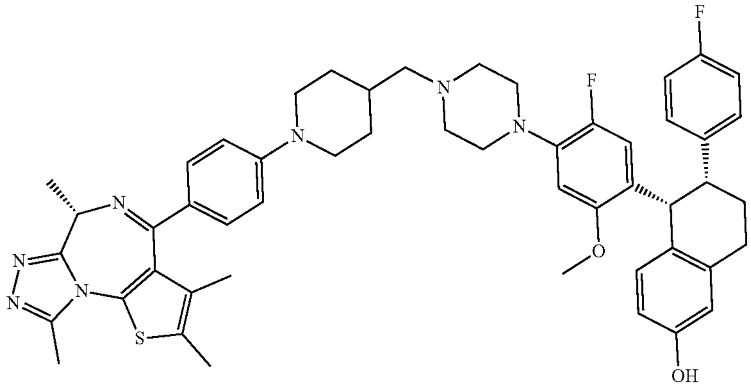 [SMILES: COc1cc(N2CCN(CC3CCN(c4ccc(C5=N[C@@H](C)c6nnc(C)n6-c6sc(C)c(C)c65)cc4)CC3)CC2)c(F)cc1[C@H]1c2ccc(O)cc2CC[C@H]1c1ccc(F)cc1] |
| III-315 | 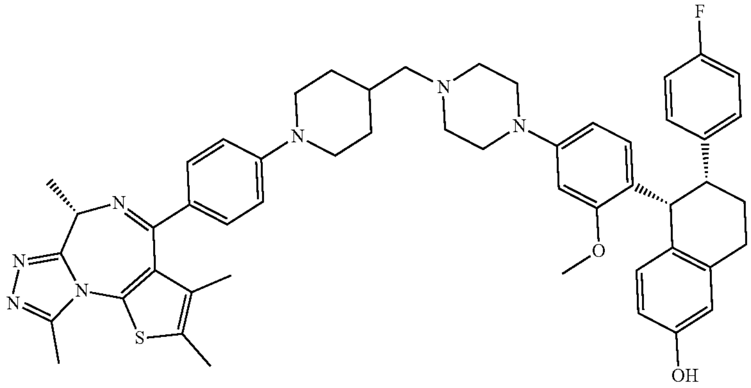 [SMILES: COc1cc(N2CCN(CC3CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(F)cc1] |
| III-316 | 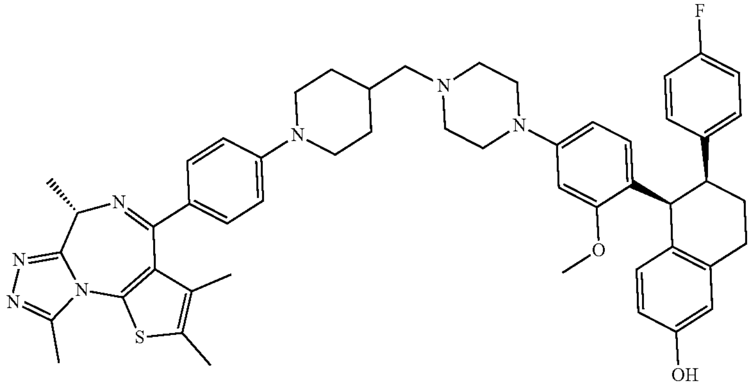 [SMILES: COc1cc(N2CCN(CC3CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(F)cc1] |

TABLE 3-continued
| Compound No. | Compound Structure |
|---|---|
| III-317 | 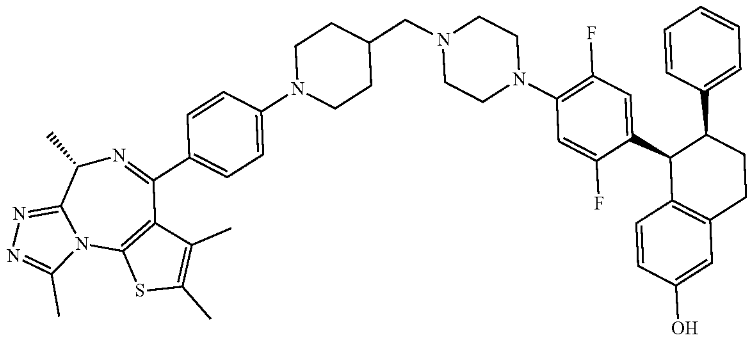 [SMILES: Cc1sc2c(c1C)C(c1ccc(N3CCC(CN4CCN(c5cc(F)c([C@@H]6c7ccc(O)cc7CC[C@@H]6c6ccccc6)cc5F)CC4)CC3)cc1)=N[C@@H](C)c1nnc(C)n1-2] |
| III-318 | 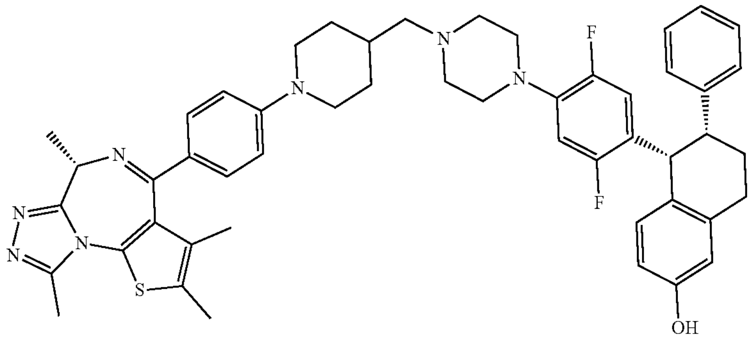 [SMILES: Cc1sc2c(c1C)C(c1ccc(N3CCC(CN4CCN(c5cc(F)c([C@H]6c7ccc(O)cc7CC[C@H]6c6ccccc6)cc5F)CC4)CC3)cc1)=N[C@@H](C)c1nnc(C)n1-2] |
| III-319 | 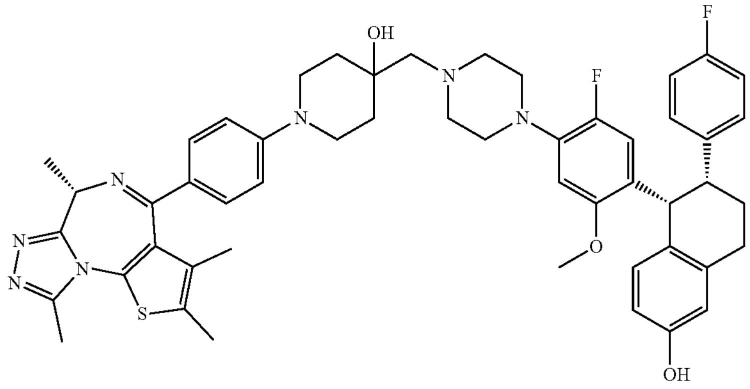 [SMILES: COc1cc(N2CCN(CC3(O)CCN(c4ccc(C5=N[C@@H](C)c6nnc(C)n6-c6sc(C)c(C)c65)cc4)CC3)CC2)c(F)cc1[C@H]1c2ccc(O)cc2CC[C@H]1c1ccc(F)cc1] |
| III-320 | 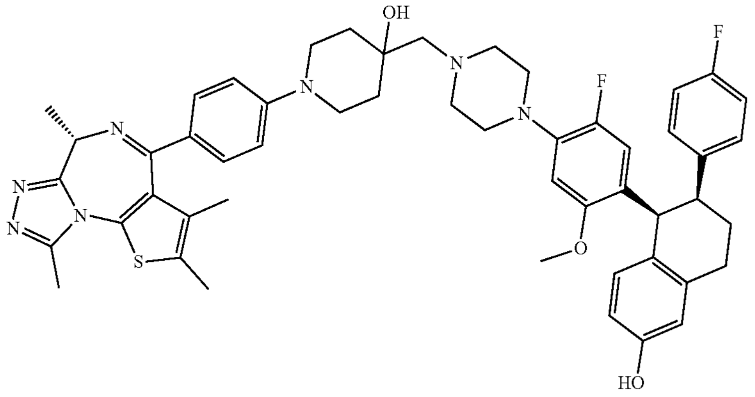 [SMILES: COc1cc(N2CCN(CC3(O)CCN(c4ccc(C5=N[C@@H](C)c6nnc(C)n6-c6sc(C)c(C)c65)cc4)CC3)CC2)c(F)cc1[C@@H]1c2ccc(O)cc2CC[C@@H]1c1ccc(F)cc1] |

TABLE 3-continued
| Compound No. | Compound Structure |
|---|---|
| III-321 | 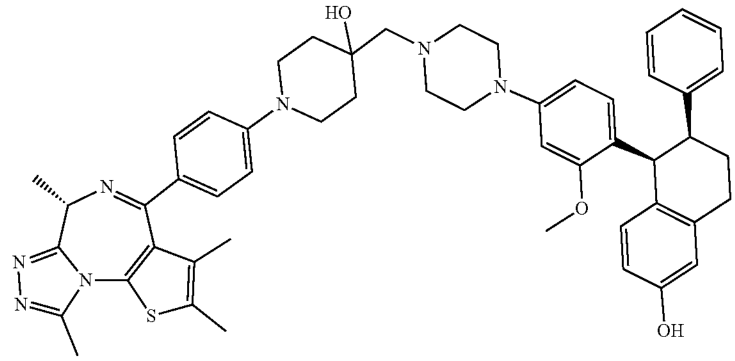 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccccc1] |
| III-322 | 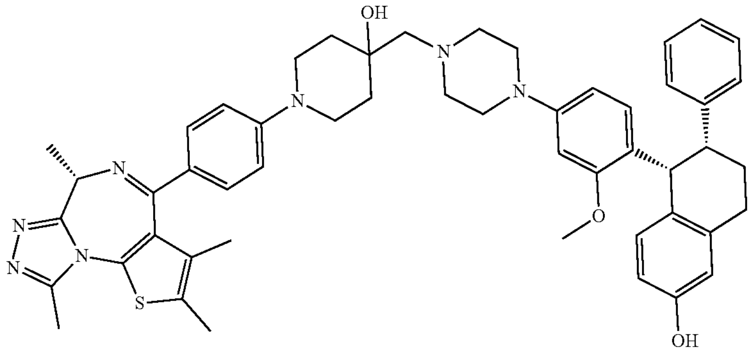 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccccc1] |
| III-323 | 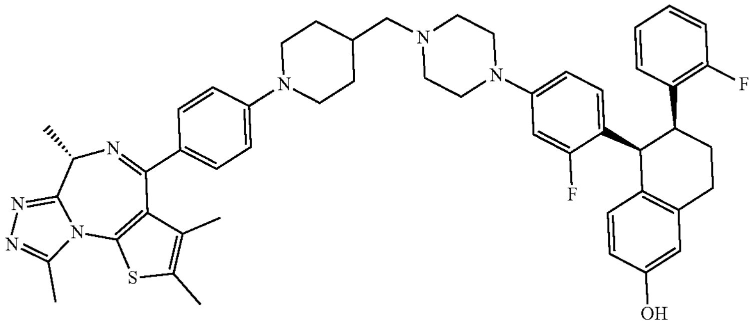 [SMILES: Cc1sc2c(c1C)C(c1ccc(N3CCC(CN4CCN(c5ccc([C@@H]6c7ccc(O)cc7CC[C@@H]6c6ccccc6F)c(F)c5)CC4)CC3)cc1)=N[C@@H](C)c1nnc(C)n1-2] |
| III-324 | 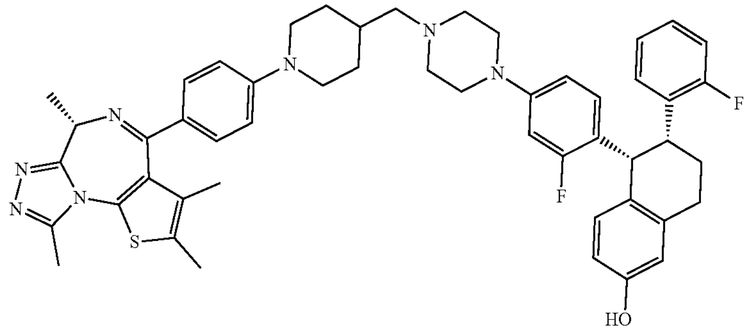 [SMILES: Cc1sc2c(c1C)C(c1ccc(N3CCC(CN4CCN(c5ccc([C@H]6c7ccc(O)cc7CC[C@H]6c6ccccc6F)c(F)c5)CC4)CC3)cc1)=N[C@@H](C)c1nnc(C)n1-2] |

TABLE 3-continued
| Compound No. | Compound Structure |
|---|---|
| III-325 | 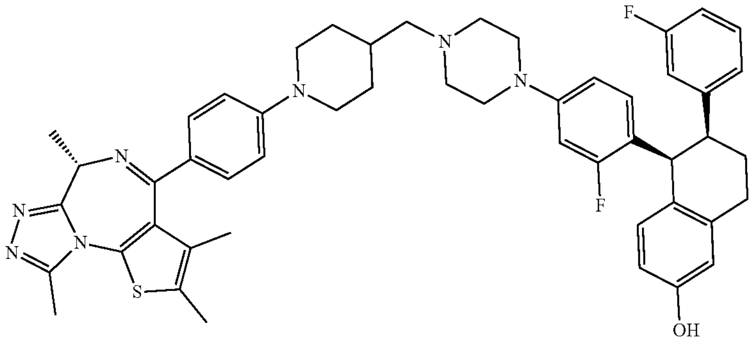 [SMILES: Cc1sc2c(c1C)C(c1ccc(N3CCC(CN4CCN(c5ccc([C@@H]6c7ccc(O)cc7CC[C@@H]6c6cccc(F)c6)c(F)c5)CC4)CC3)cc1)=N[C@@H](C)c1nnc(C)n1-2] |
| III-326 | 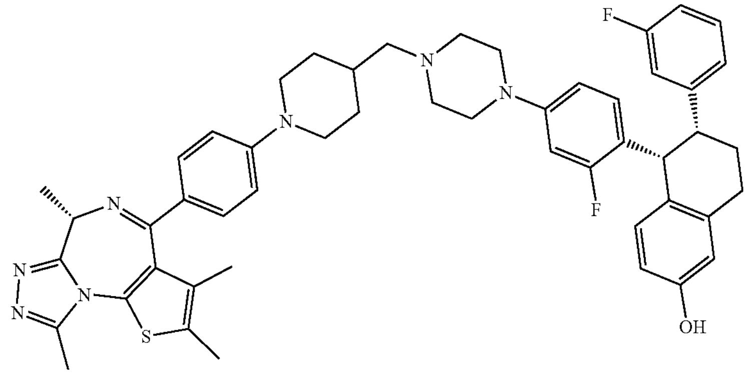 [SMILES: Cc1sc2c(c1C)C(c1ccc(N3CCC(CN4CCN(c5ccc([C@H]6c7ccc(O)cc7CC[C@H]6c6cccc(F)c6)c(F)c5)CC4)CC3)cc1)=N[C@@H](C)c1nnc(C)n1-2] |
| III-327 | 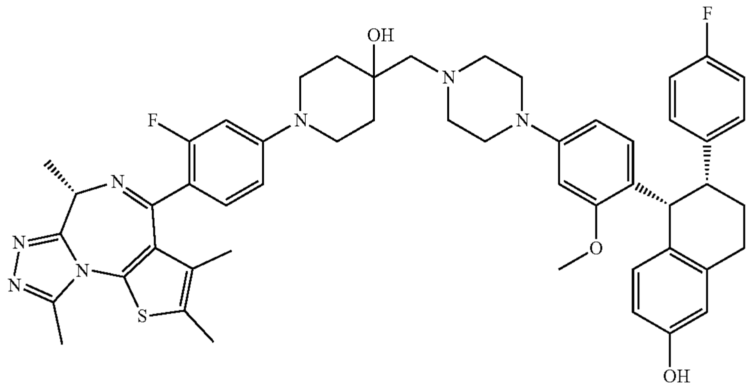 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@H]1c2ccc(O)cc2CC[C@H]1c1ccc(F)cc1] |
| III-328 | 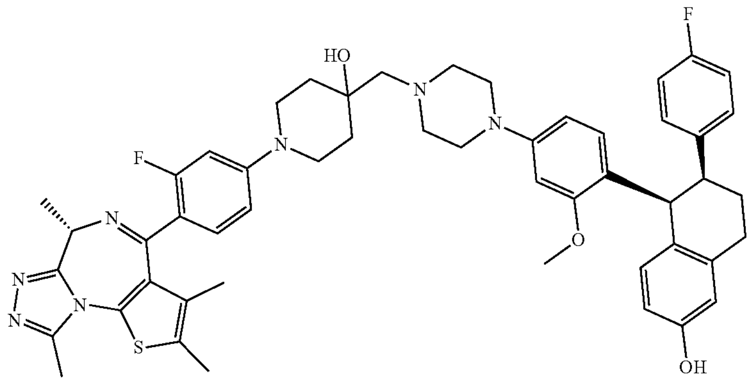 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1ccc(F)cc1] |

TABLE 3-continued
| Compound No. | Compound Structure |
|---|---|
| III-329 | 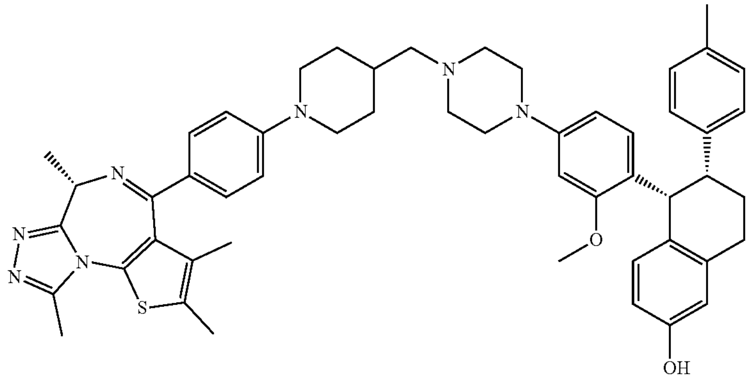 [SMILES: COc1cc(N2CCN(CC3CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(C)cc1] |
| III-330 | 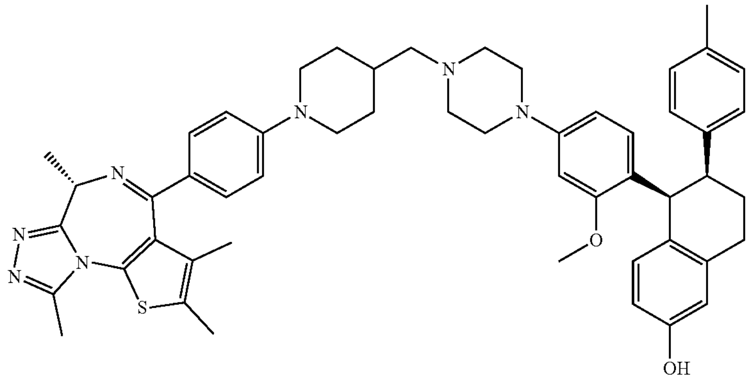 [SMILES: COc1cc(N2CCN(CC3CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(C)cc1] |
| III-331 | 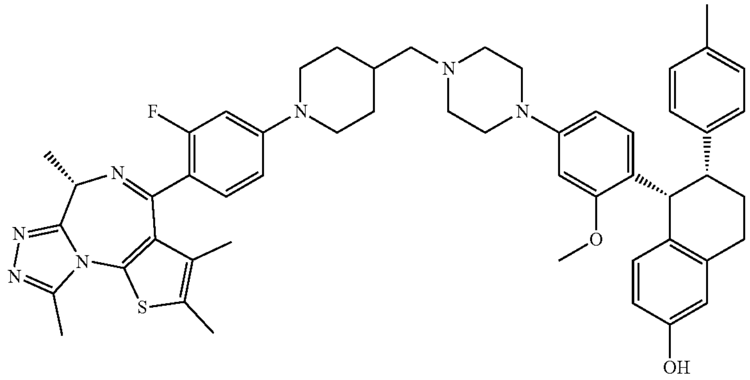 [SMILES: COc1cc(N2CCN(CC3CCN(c4ccc(C5=N[C@@H](C)c6nnc(C)n6-c6sc(C)c(C)c65)c(F)c4)CC3)CC2)ccc1[C@H]1c2ccc(O)cc2CC[C@H]1c1ccc(C)cc1] |
| III-332 | 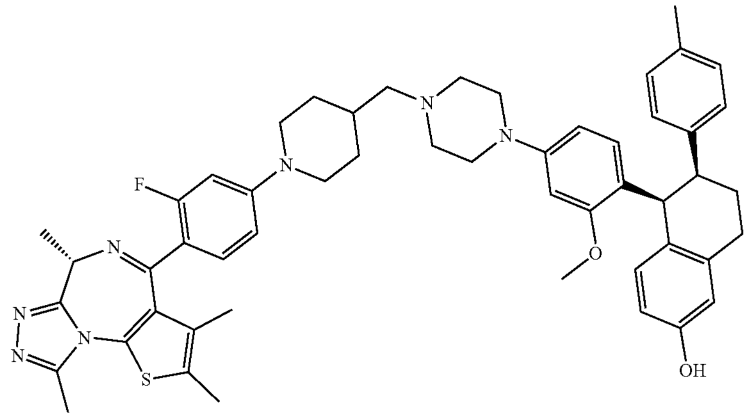 [SMILES: COc1cc(N2CCN(CC3CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1ccc(C)cc1] |

TABLE 3-continued
| Compound No. | Compound Structure |
| --- | --- |
| III-333 | 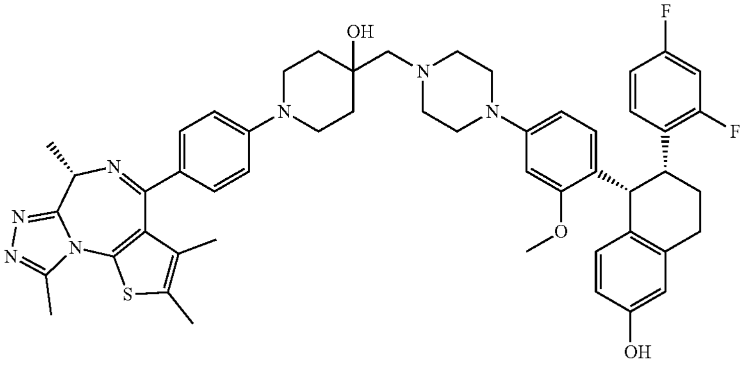 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(F)cc1F] |
| III-334 | 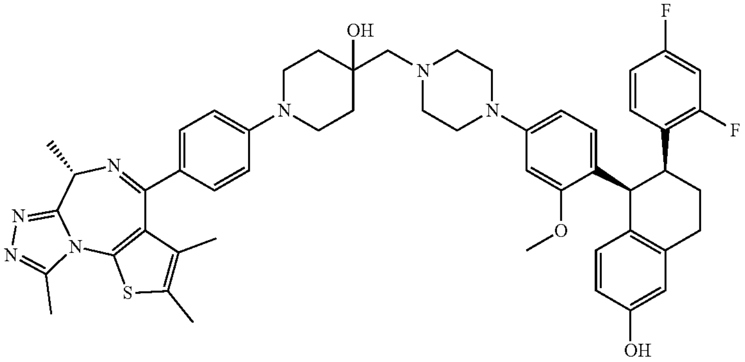 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(F)cc1F] |
| III-335 | 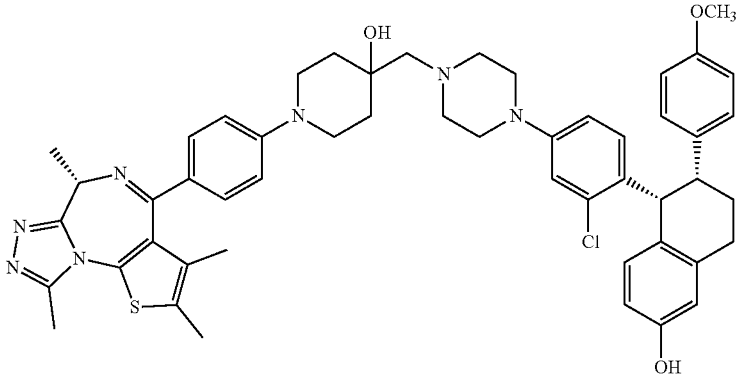 [SMILES: COc1ccc([C@@H]2CCc3cc(O)ccc3[C@@H]2c2ccc(N3CCN(CC4(O)CCN(c5ccc(C6=N[C@@H](C)c7nnc(C)n7-c7sc(C)c(C)c76)cc5)CC4)CC3)cc2Cl)cc1] |
| III-336 | 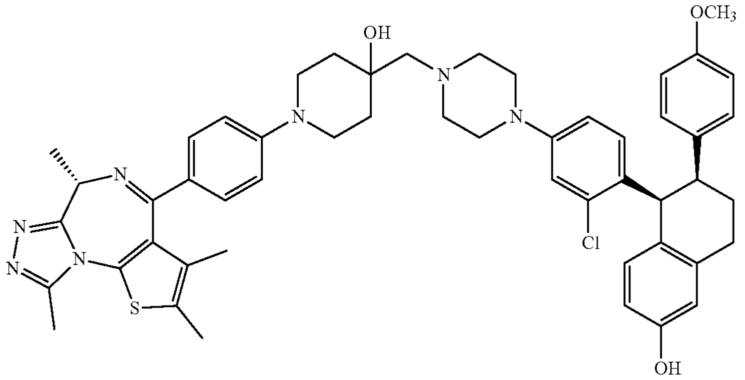 [SMILES: COc1ccc([C@H]2CCc3cc(O)ccc3[C@H]2c2ccc(N3CCN(CC4(O)CCN(c5ccc(C6=N[C@@H](C)c7nnc(C)n7-c7sc(C)c(C)c76)cc5)CC4)CC3)cc2Cl)cc1] |

TABLE 3-continued
| Compound No. | Compound Structure |
| --- | --- |
| III-337 | 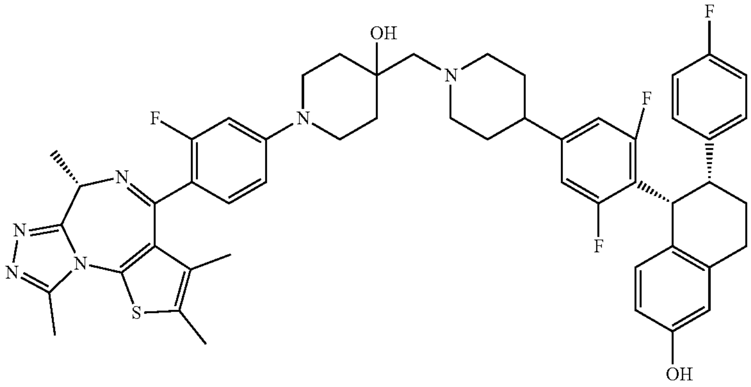 [SMILES: Cc1sc2c(c1C)C(c1ccc(N3CCC(O)(CN4CCC(c5cc(F)c([C@H]6c7ccc(O)cc7CC[C@H]6c6ccc(F)cc6)c(F)c5)CC4)CC3)cc1F)=N[C@@H](C)c1nnc(C)n1-2] |
| III-338 | 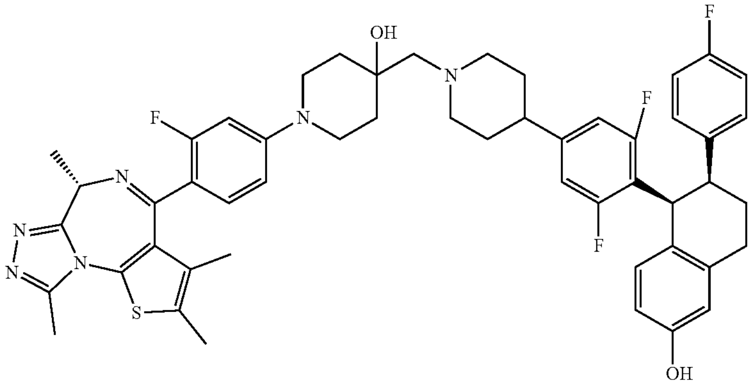 [SMILES: Cc1sc2c(c1C)C(c1ccc(N3CCC(O)(CN4CCC(c5cc(F)c([C@@H]6c7ccc(O)cc7CC[C@@H]6c6ccc(F)cc6)c(F)c5)CC4)CC3)cc1F)=N[C@@H](C)c1nnc(C)n1-2] |
| III-339 | 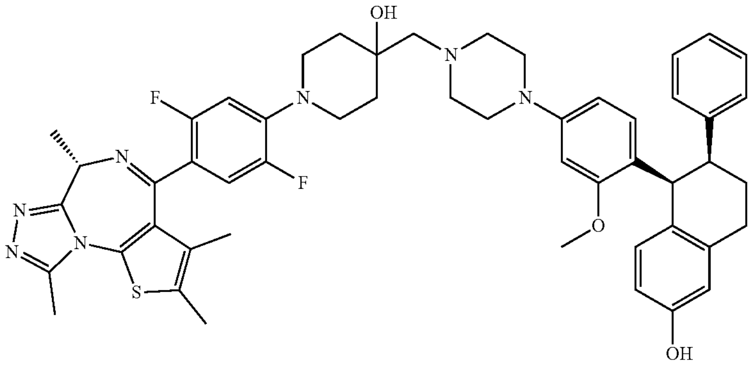 [SMILES: COc1cc(N2CCN(CC3(O)CCN(c4cc(F)c(C5=N[C@@H](C)c6nnc(C)n6-c6sc(C)c(C)c65)cc4F)CC3)CC2)ccc1[C@@H]1c2ccc(O)cc2CC[C@@H]1c1ccccc1] |
| III-340 | 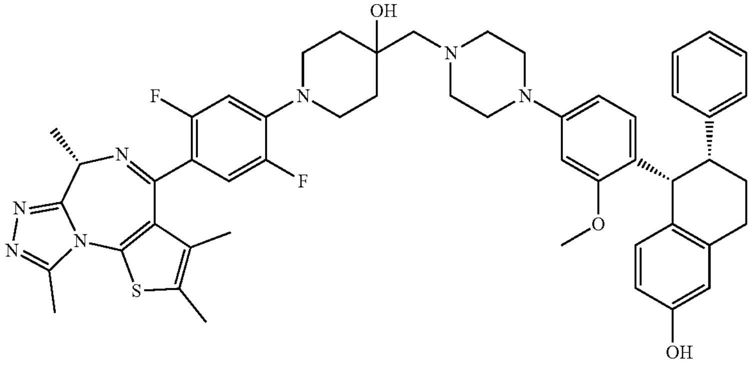 [SMILES: COc1cc(N2CCN(CC3(O)CCN(c4cc(F)c(C5=N[C@@H](C)c6nnc(C)n6-c6sc(C)c(C)c65)cc4F)CC3)CC2)ccc1[C@H]1c2ccc(O)cc2CC[C@H]1c1ccccc1] |

TABLE 3-continued
| Compound No. | Compound Structure |
| --- | --- |
| III-341 | 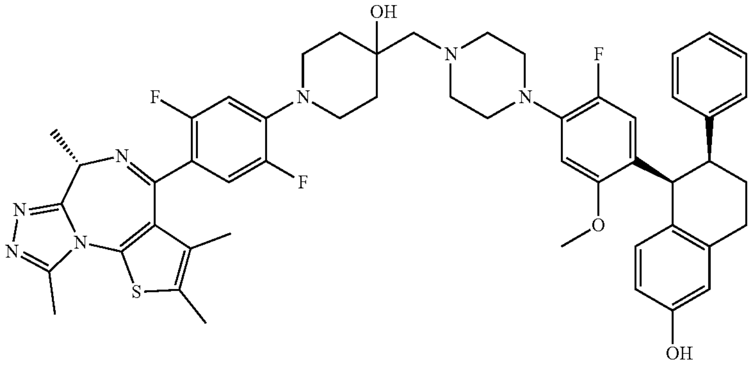 [SMILES: COc1cc(N2CCN(CC3(O)CCN(c4cc(F)c(C5=N[C@@H](C)c6nnc(C)n6-c6sc(C)c(C)c65)cc4F)CC3)CC2)c(F)cc1[C@@H]1c2ccc(O)cc2CC[C@@H]1c1ccccc1] |
| III-342 | 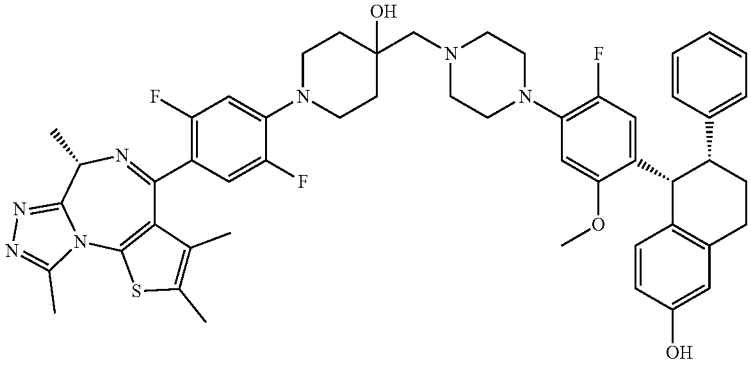 [SMILES: COc1cc(N2CCN(CC3(O)CCN(c4cc(F)c(C5=N[C@@H](C)c6nnc(C)n6-c6sc(C)c(C)c65)cc4F)CC3)CC2)c(F)cc1[C@H]1c2ccc(O)cc2CC[C@H]1c1ccccc1] |
| III-343 | 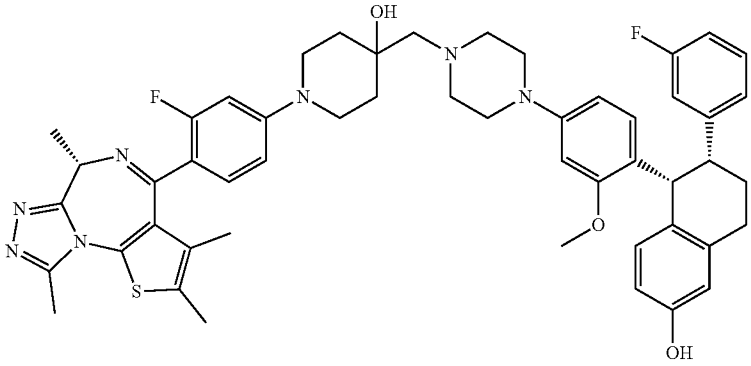 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@H]1c2ccc(O)cc2CC[C@H]1c1cccc(F)c1] |
| III-344 | 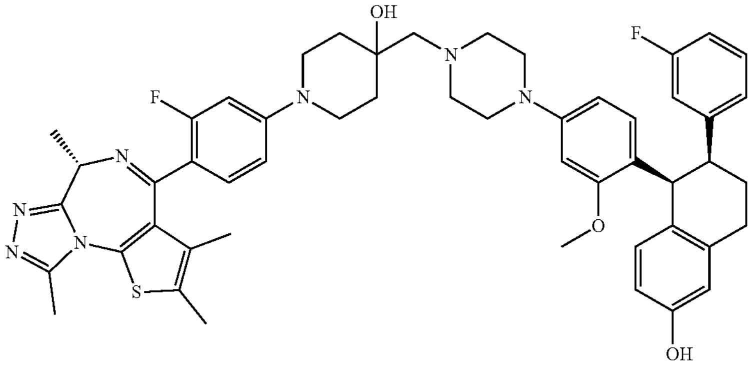 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1cccc(F)c1] |

TABLE 3-continued
| Compound No. | Compound Structure |
|---|---|
| III-345 | 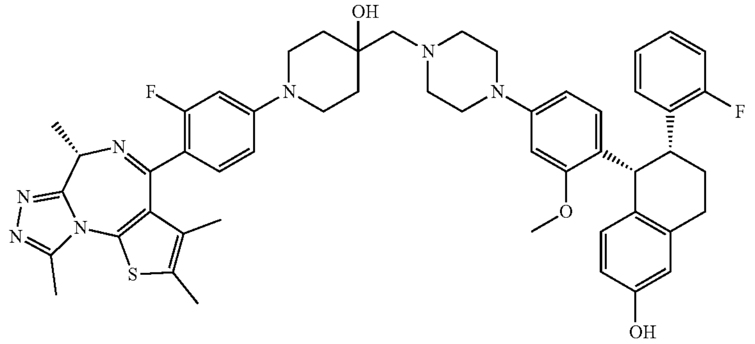 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@H]1c2ccc(O)cc2CC[C@H]1c1ccccc1F] |
| III-346 | 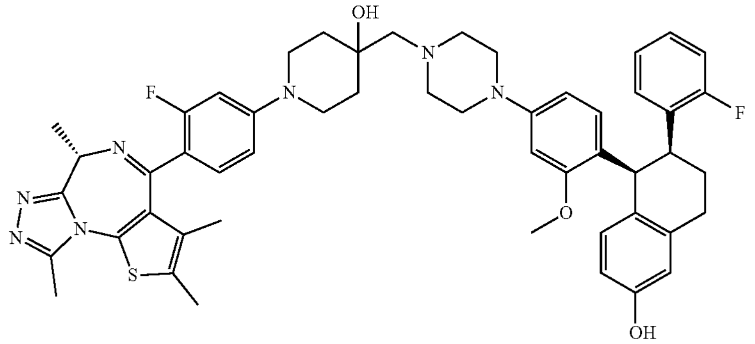 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1ccccc1F] |
| III-347 | 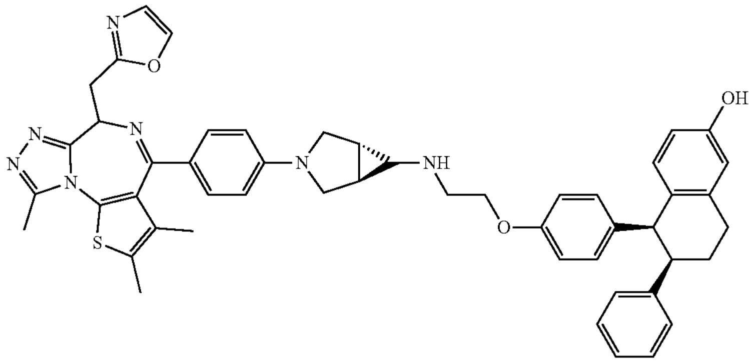 |
| III-348 | 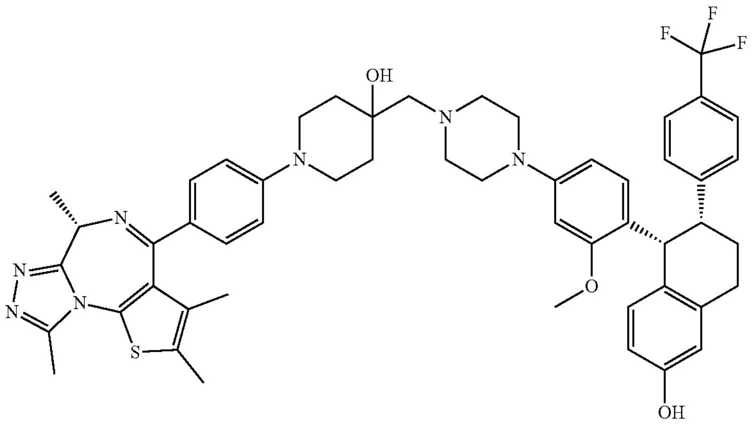 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(C(F)(F)F)cc1] |

TABLE 3-continued
| Compound No. | Compound Structure |
|---|---|
| III-349 | 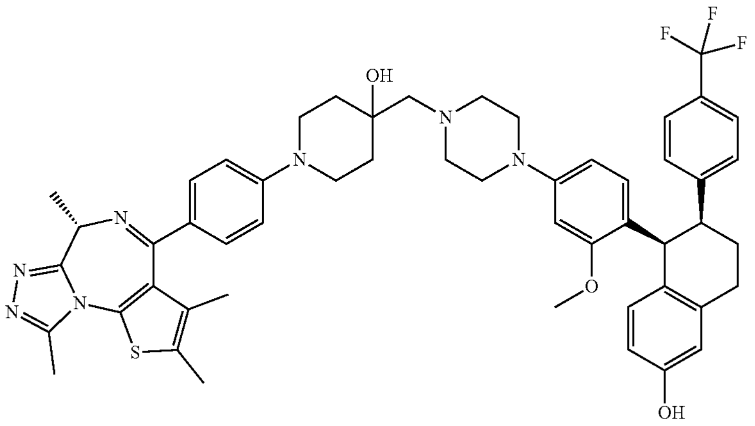 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(C(F)(F)F)cc1] |
| III-350 | 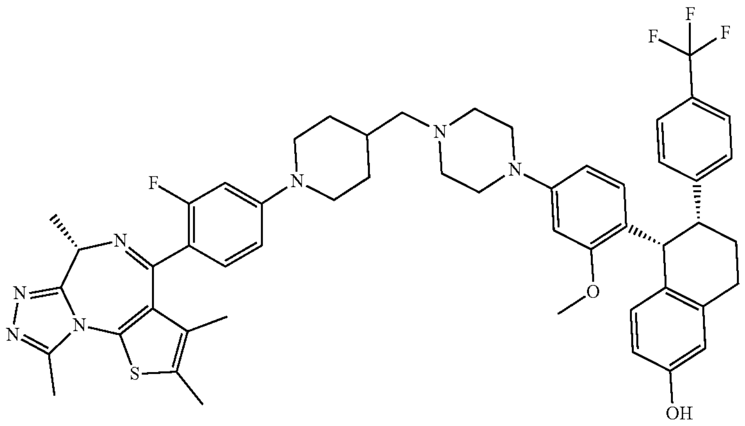 [SMILES: COc1cc(N2CCN(CC3CCN(c4ccc(C5=N[C@@H](C)c6nnc(C)n6-c6sc(C)c(C)c65)c(F)c4)CC3)CC2)ccc1[C@H]1c2ccc(O)cc2CC[C@H]1c1ccc(C(F)(F)F)cc1] |
| III-351 | 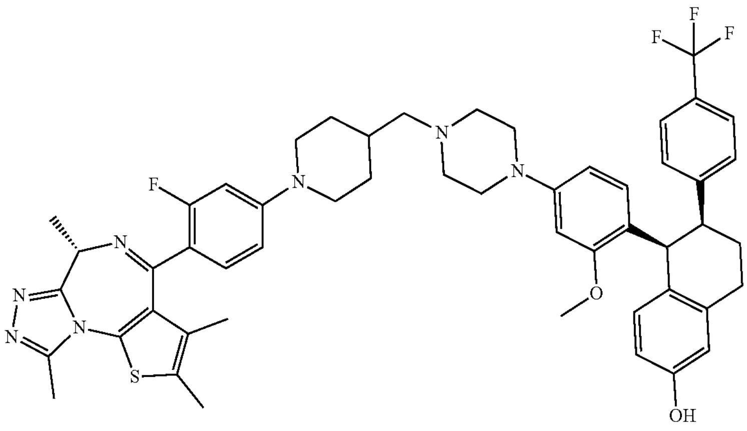 [SMILES: COc1cc(N2CCN(CC3CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1ccc(C(F)(F)F)cc1] |

TABLE 3-continued
| Compound No. | Compound Structure |
|---|---|
| III-352 | 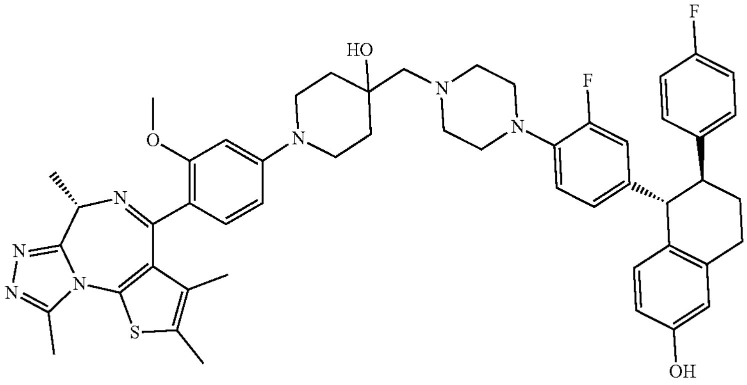 [SMILES: COc1cc(N2CCC(O)(CN3CCN(c4ccc([C@H]5c6ccc(O)cc6CC[C@@H]5c5ccc(F)cc5)cc4F)CC3)CC2)ccc1C1=N[C@@H](C)c2nnc(C)n2-c2sc(C)c(C)c21] |
| III-353 | 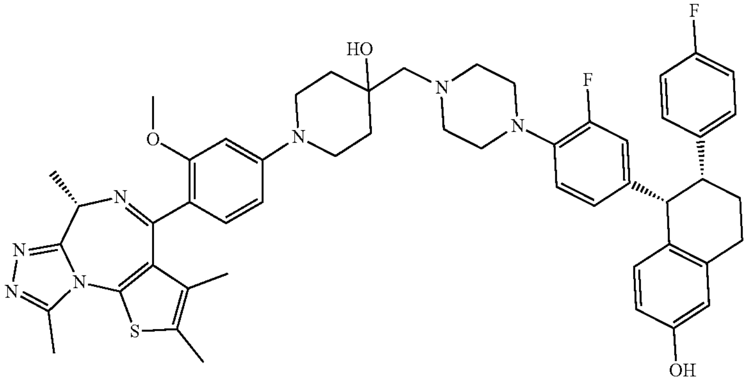 [SMILES: COc1cc(N2CCC(O)(CN3CCN(c4ccc([C@H]5c6ccc(O)cc6CC[C@H]5c5ccc(F)cc5)cc4F)CC3)CC2)ccc1C1=N[C@@H](C)c2nnc(C)n2-c2sc(C)c(C)c21] |
| III-354 | 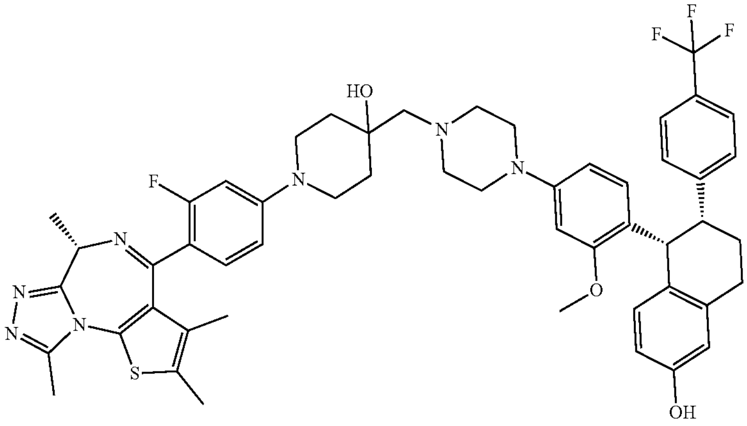 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@H]1c2ccc(O)cc2CC[C@H]1c1ccc(C(F)(F)F)cc1] |

TABLE 3-continued
| Compound No. | Compound Structure |
|---|---|
| III-355 | 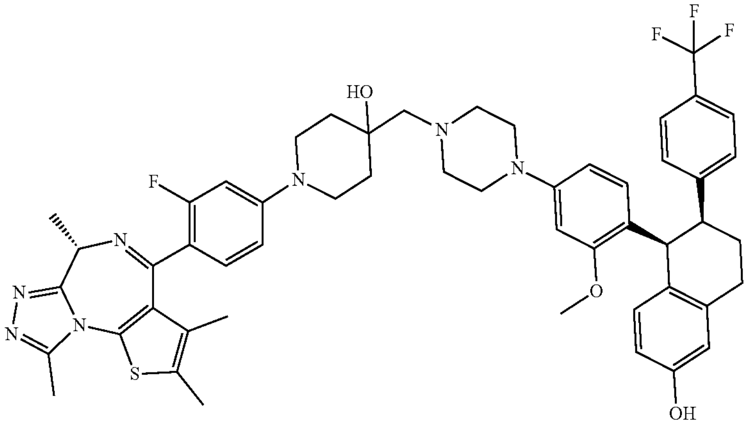 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1ccc(C(F)(F)F)cc1] |
| III-356 | 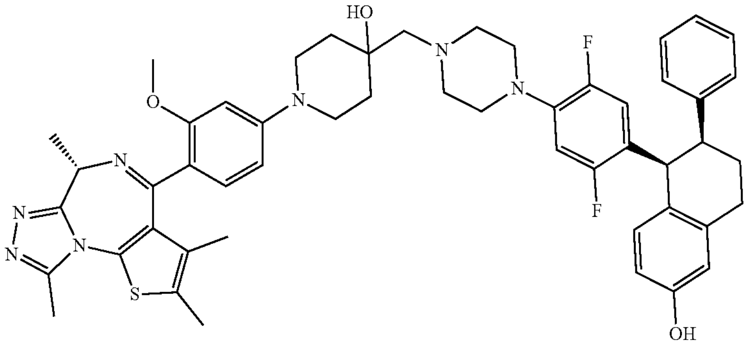 [SMILES: COc1cc(N2CCC(O)(CN3CCN(c4cc(F)c([C@@H]5c6ccc(O)cc6CC[C@@H]5c5ccccc5)cc4F)CC3)CC2)ccc1C1=N[C@@H](C)c2nnc(C)n2-c2sc(C)c(C)c21] |
| III-357 | 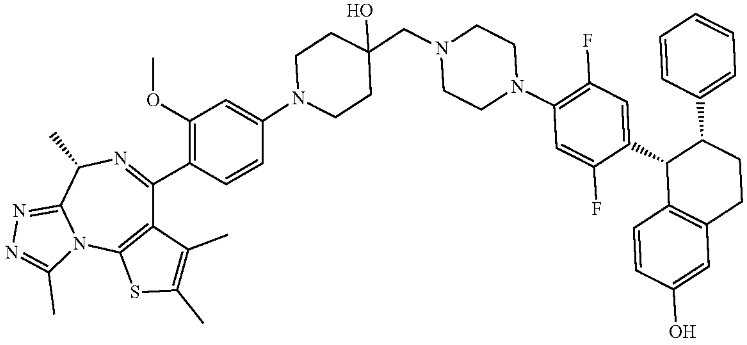 [SMILES: COc1cc(N2CCC(O)(CN3CCN(c4cc(F)c([C@H]5c6ccc(O)cc6CC[C@H]5c5ccccc5)cc4F)CC3)CC2)ccc1C1=N[C@@H](C)c2nnc(C)n2-c2sc(C)c(C)c21] |
| III-358 | 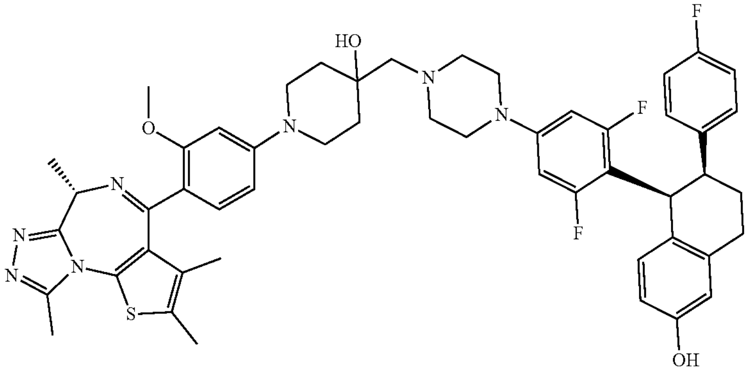 [SMILES: COc1cc(N2CCC(O)(CN3CCN(c4cc(F)c([C@@H]5c6ccc(O)cc6CC[C@@H]5c5ccc(F)cc5)c(F)c4)CC3)CC2)ccc1C1=N[C@@H](C)c2nnc(C)n2-c2sc(C)c(C)c21] |

TABLE 3-continued
| Compound No. | Compound Structure |
| --- | --- |
| III-359 | 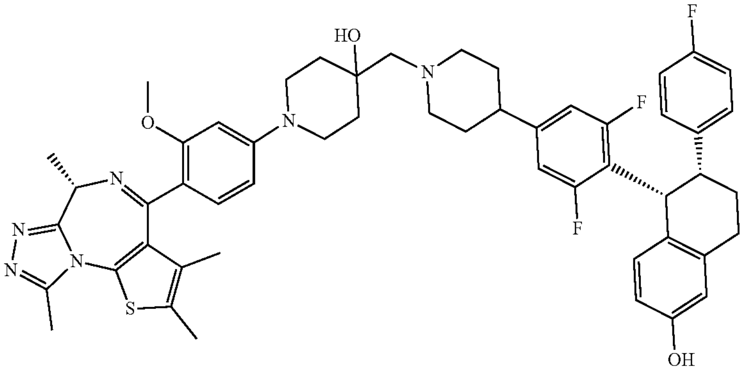 [SMILES: COc1cc(N2CCC(O)(CN3CCC(c4cc(F)c([C@H]5c6ccc(O)cc6CC[C@H]5c5ccc(F)cc5)c(F)c4)CC3)CC2)ccc1C1=N[C@@H](C)c2nnc(C)n2-c2sc(C)c(C)c21] |
In certain embodiments, the compound is a compound in Table 4, or a pharmaceutically acceptable salt thereof. In certain embodiments, the compound is a compound in Table 4.
TABLE 4
| Compound No. | Compound Structure |
| --- | --- |
| IV-1 | 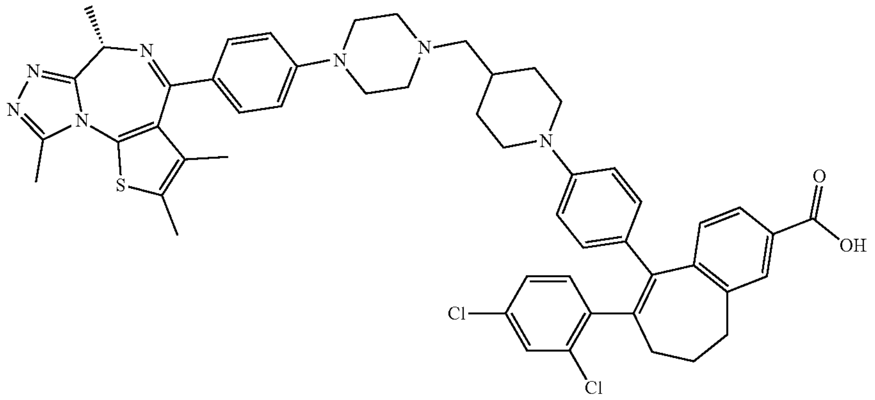 [SMILES: Cc1sc2c(c1C)C(c1ccc(N3CCN(CC4CCN(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-2 | 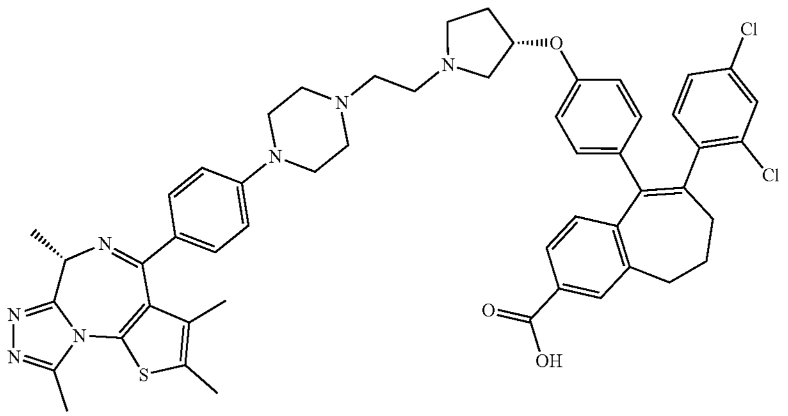 [SMILES: Cc1sc2c(c1C)C(c1ccc(N3CCN(CCN4CC[C@H](Oc5ccc(C6=C(c7ccc(Cl)cc7Cl)CCCc7cc(C(=O)O)ccc76)cc5)C4)CC3)cc1)=N[C@@H](C)c1nnc(C)n1-2] |

TABLE 4-continued
| Compound No. | Compound Structure |
|---|---|
| IV-3 | 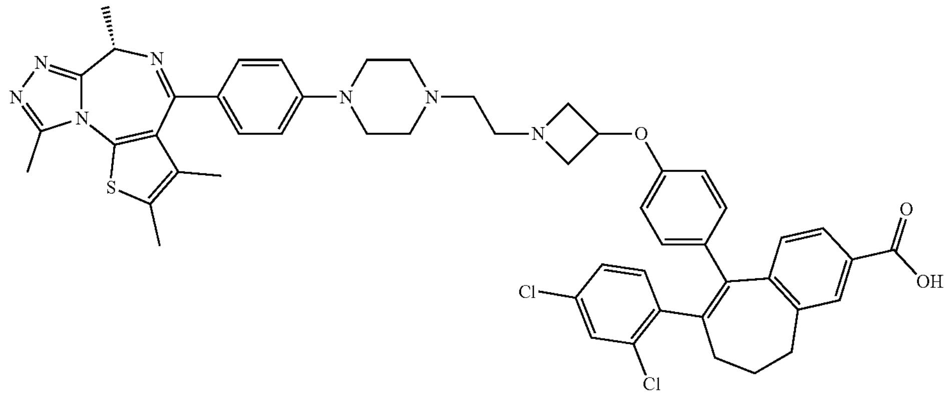 [SMILES: Cc1sc2c(c1C)C(c1ccc(N3CCN(CCN4CC(Oc5ccc(C6=C(c7ccc(Cl)cc7Cl)CCCc7cc(C(=O)O)ccc76)cc5)C4)CC3)cc1)=N[C@@H](C)c1nnc(C)n1-2] |
| IV-4 | 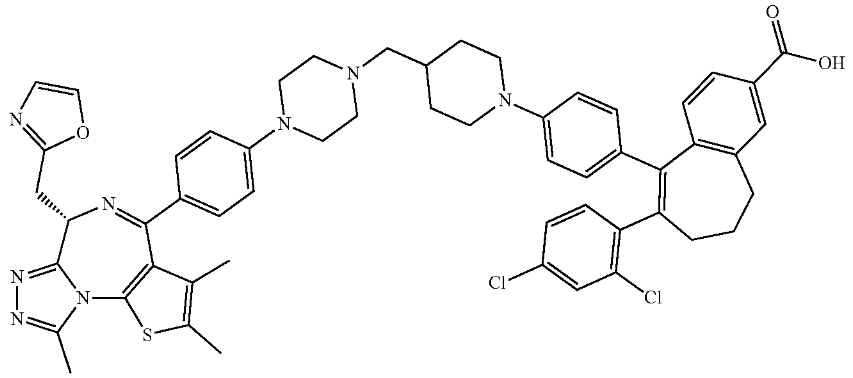 [SMILES: Cc1sc2c(c1C)C(c1ccc(N3CCN(CC4CCN(c5ccc(C6=C(c7ccc(Cl)cc7Cl)CCCc7cc(C(=O)O)ccc76)cc5)CC4)CC3)cc1)=N[C@@H](Cc1ncco1)c1nnc(C)n1-2] |
| IV-5 | 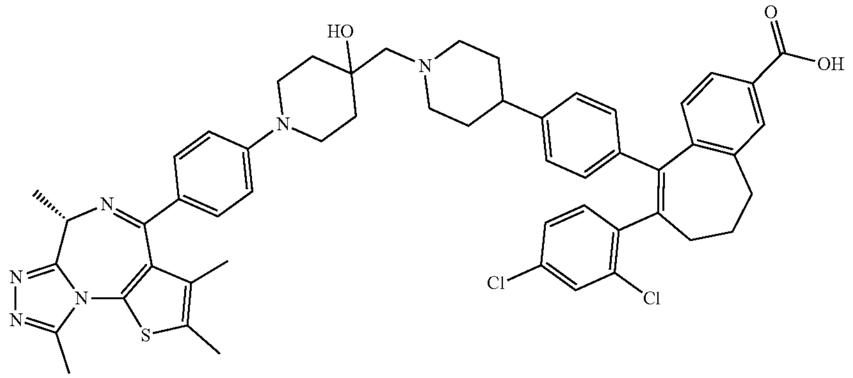 [SMILES: Cc1sc2c(c1C)C(c1ccc(N3CCC(O)(CN4CCC(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-6 | 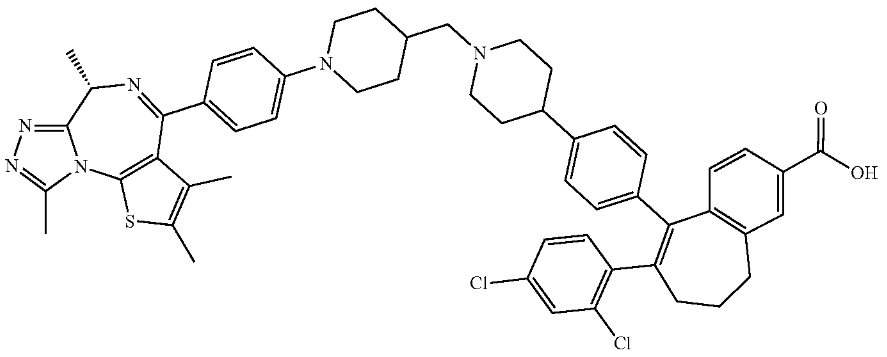 [SMILES: Cc1sc2c(c1C)C(c1ccc(N3CCC(CN4CCC(c5ccc(C6=C(c7ccc(Cl)cc7Cl)CCCc7cc(C(=O)O)ccc76)cc5)CC4)CC3)cc1)=N[C@@H](C)c1nnc(C)n1-2] |

TABLE 4-continued
| Compound No. | Compound Structure |
|---|---|
| IV-7 | 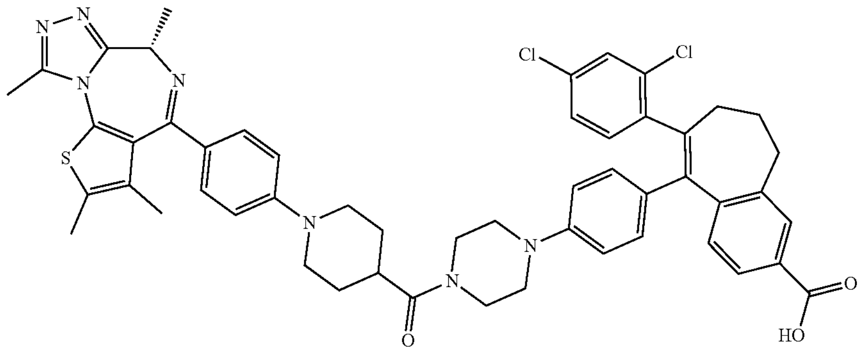 [SMILES: Cc1sc2c(c1C)C(c1ccc(N3CCC(C(=O)N4CCN(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-8 | 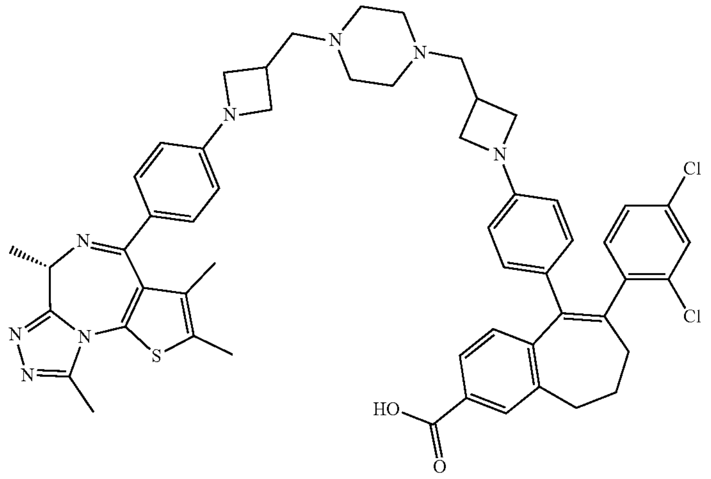 [SMILES: Cc1sc2c(c1C)C(c1ccc(N3CC(CN4CCN(CC5CN(c6ccc(C7=C(c8ccc(Cl)cc8Cl)CCCc8cc(C(=O)O)ccc87)cc6)C5)CC4)C3)cc1)=N[C@@H](C)c1nnc(C)n1-2] |
| IV-9 | 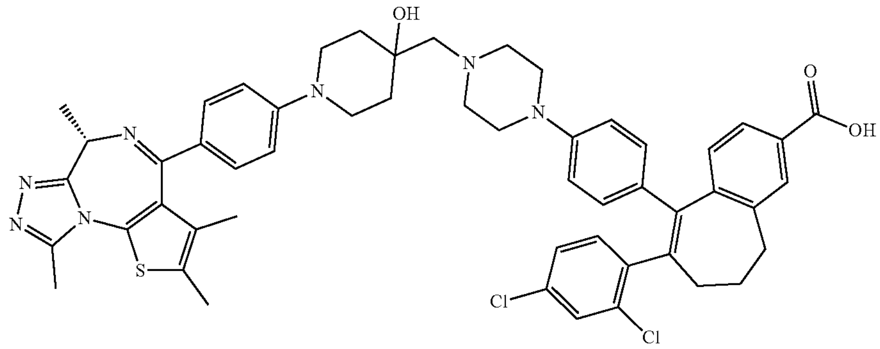 [SMILES: Cc1sc2c(c1C)C(c1ccc(N3CCC(O)(CN4CCN(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-10 | 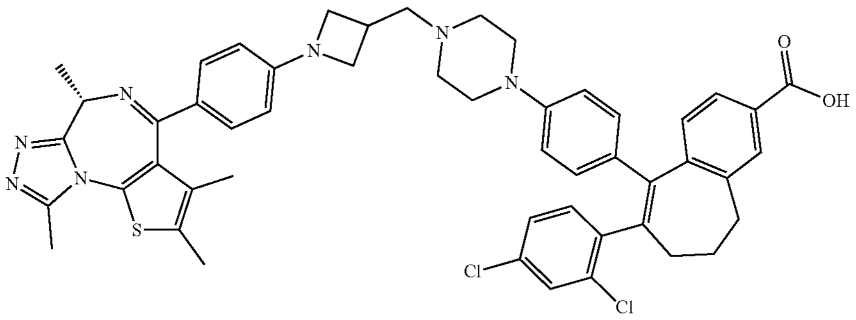 [SMILES: Cc1sc2c(c1C)C(c1ccc(N3CC(CN4CCN(c5ccc(C6=C(c7ccc(Cl)cc7Cl)CCCc7cc(C(=O)O)ccc76)cc5)CC4)C3)cc1)=N[C@@H](C)c1nnc(C)n1-2] |

TABLE 4-continued
| Compound No. | Compound Structure |
|---|---|
| IV-11 | 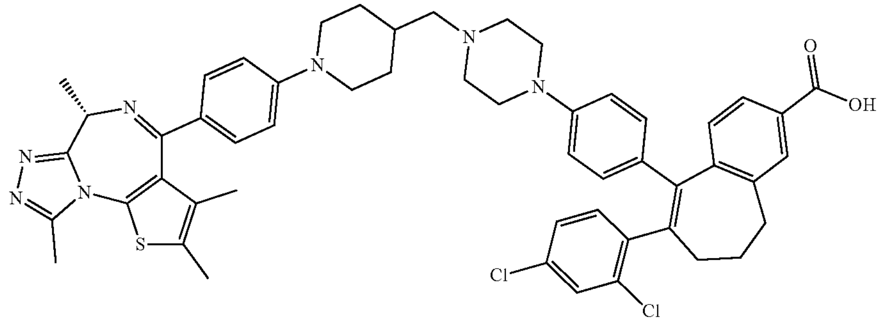 [SMILES: Cc1sc2c(c1C)C(c1ccc(N3CCC(CN4CCN(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-12 | 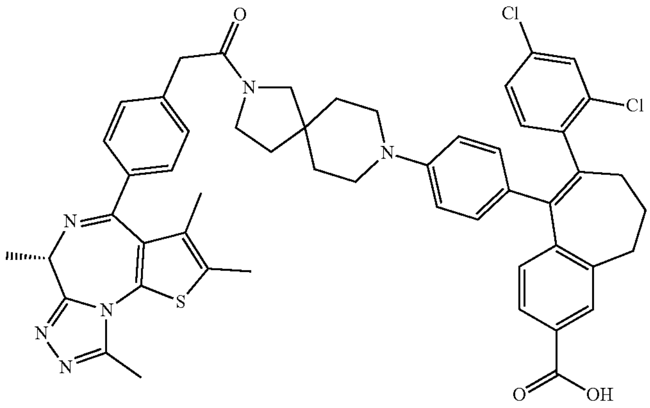 [SMILES: Cc1sc2c(c1C)C(c1ccc(CC(=O)N3CCC4(CCN(c5ccc(C6=C(c7ccc(Cl)cc7Cl)CCCc7cc(C(=O)O)ccc76)cc5)CC4)C3)cc1)=N[C@@H](C)c1nnc(C)n1-2] |
| IV-13 | 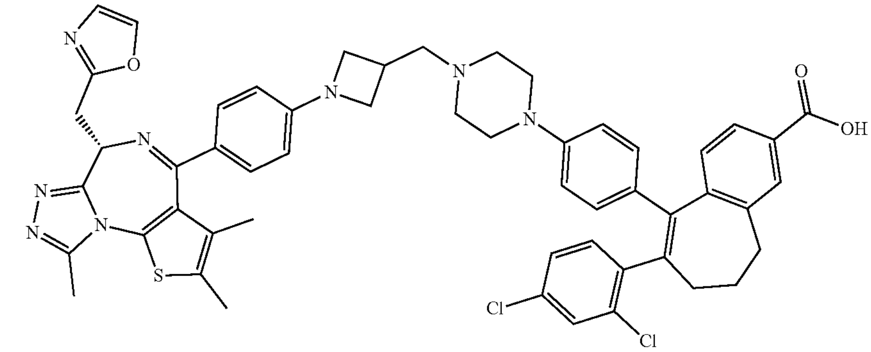 [SMILES: Cc1sc2c(c1C)C(c1ccc(N3CC(CN4CCN(c5ccc(C6=C(c7ccc(Cl)cc7Cl)CCCc7cc(C(=O)O)ccc76)cc5)CC4)C3)cc1)=N[C@@H](Cc1ncco1)c1nnc(C)n1-2] |
| IV-14 | 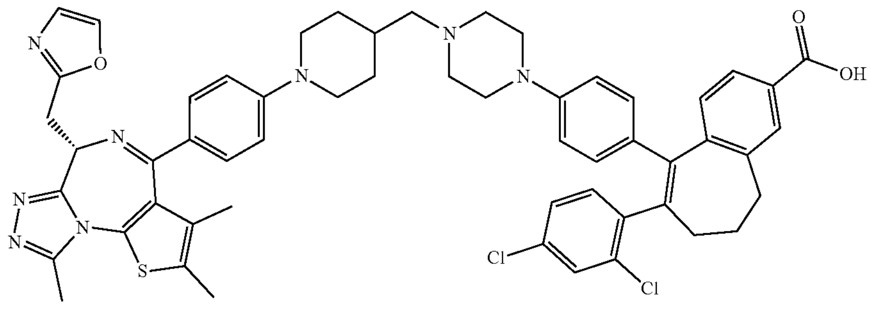 [SMILES: Cc1sc2c(c1C)C(c1ccc(N3CCC(CN4CCN(c5ccc(C6=C(c7ccc(Cl)cc7Cl)CCCc7cc(C(=O)O)ccc76)cc5)CC4)CC3)cc1)=N[C@@H](Cc1ncco1)c1nnc(C)n1-2] |

TABLE 4-continued
| Compound No. | Compound Structure |
|---|---|
| IV-15 | 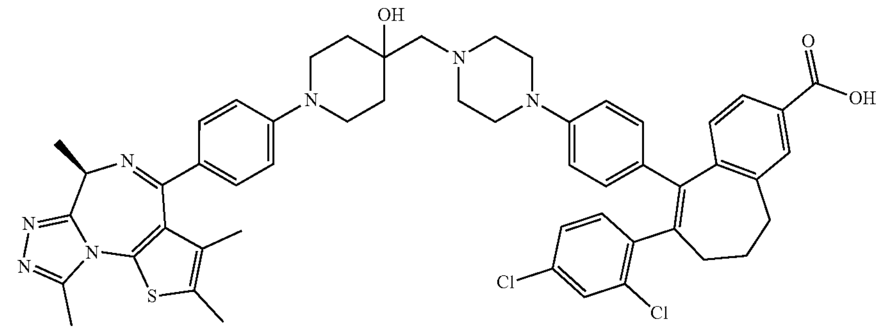 [SMILES: Cc1sc2c(c1C)C(c1ccc(N3CCC(O)(CN4CCN(c5ccc(C6=C(c7ccc(Cl)cc7Cl)CCCc7cc(C(=O)O)ccc76)cc5)CC4)CC3)cc1)=N[C@H](C)c1nnc(C)n1-2] |
| IV-16 | 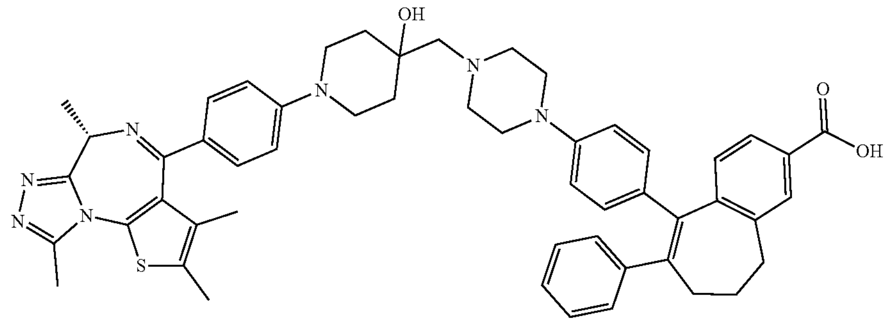 [SMILES: Cc1sc2c(c1C)C(c1ccc(N3CCC(O)(CN4CCN(c5ccc(C6=C(c7ccccc7)CCCc7cc(C(=O)O)ccc76)cc5)CC4)CC3)cc1)=N[C@@H](C)c1nnc(C)n1-2] |
| IV-17 | 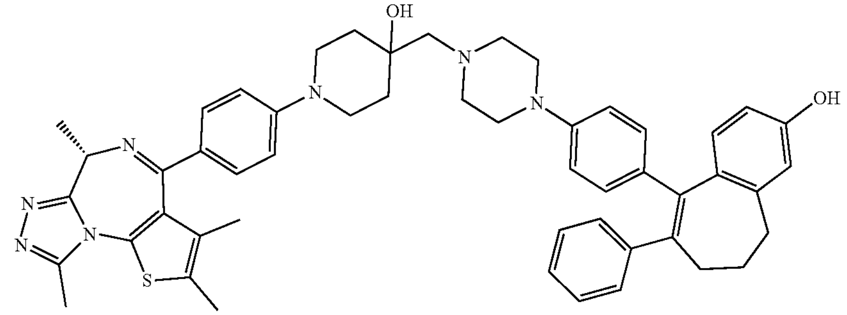 [SMILES: Cc1sc2c(c1C)C(c1ccc(N3CCC(O)(CN4CCN(c5ccc(C6=C(c7ccccc7)CCCc7cc(O)ccc76)cc5)CC4)CC3)cc1)=N[C@@H](C)c1nnc(C)n1-2] |
| IV-18 | 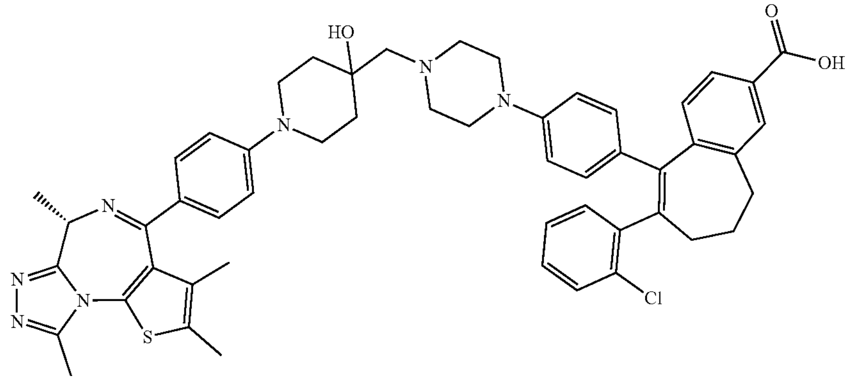 [SMILES: Cc1sc2c(c1C)C(c1ccc(N3CCC(O)(CN4CCN(c5ccc(C6=C(c7ccccc7Cl)CCCc7cc(C(=O)O)ccc76)cc5)CC4)CC3)cc1)=N[C@@H](C)c1nnc(C)n1-2] |

TABLE 4-continued
| Compound No. | Compound Structure |
|---|---|
| IV-19 | 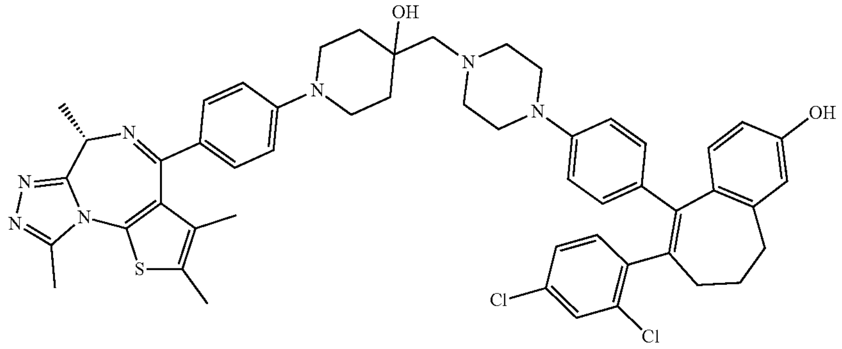 [SMILES: Cc1sc2c(c1C)C(c1ccc(N3CCC(O)(CN4CCN(c5ccc(C6=C(c7ccc(Cl)cc7Cl)CCCc7cc(O)ccc76)cc5)CC4)CC3)cc1)=N[C@@H](C)c1nnc(C)n1-2] |
| IV-20 | 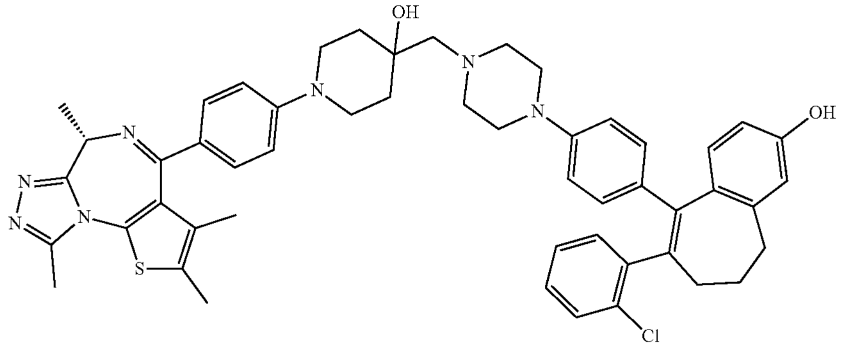 [SMILES: Cc1sc2c(c1C)C(c1ccc(N3CCC(O)(CN4CCN(c5ccc(C6=C(c7ccccc7Cl)CCCc7cc(O)ccc76)cc5)CC4)CC3)cc1)=N[C@@H](C)c1nnc(C)n1-2] |
| IV-21 | 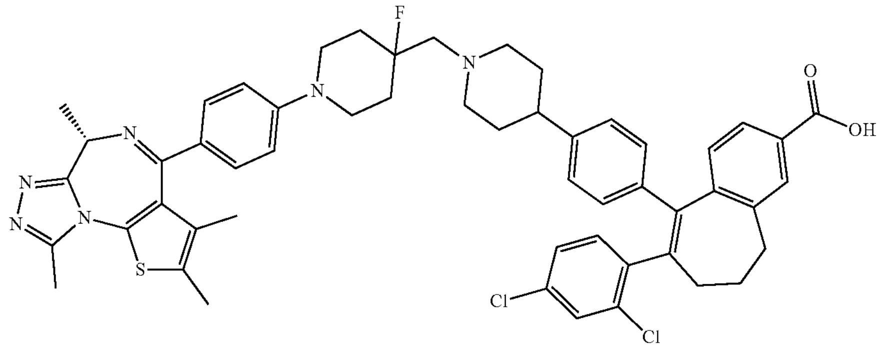 [SMILES: Cc1sc2c(c1C)C(c1ccc(N3CCC(F)(CN4CCC(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-22 | 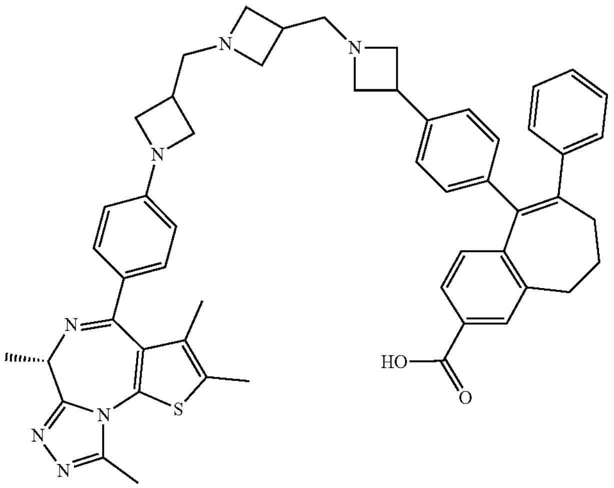 [SMILES: Cc1sc2c(c1C)C(c1ccc(N3CC(CN4CC(CN5CC(c6ccc(C7=C(c8ccccc8)CCCc8cc(C(=O)O)ccc87)cc6)C5)C4)C3)cc1)=N[C@@H](C)c1nnc(C)n1-2] |

TABLE 4-continued
| Compound No. | Compound Structure |
| --- | --- |
| IV-23 | 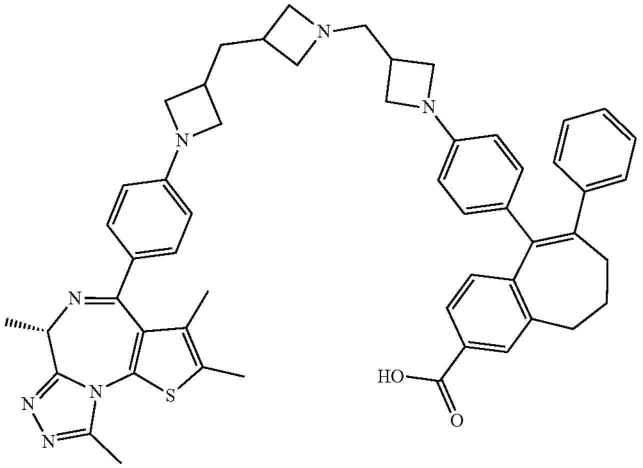 [SMILES: Cc1sc2c(c1C)C(c1ccc(N3CC(CC4CN(CC5CN(c6ccc(C7=C(c8ccccc8)CCCc8cc(C(=O)O)ccc87)cc6)C5)C4)C3)cc1)=N[C@@H](C)c1nnc(C)n1-2] |
| IV-24 | 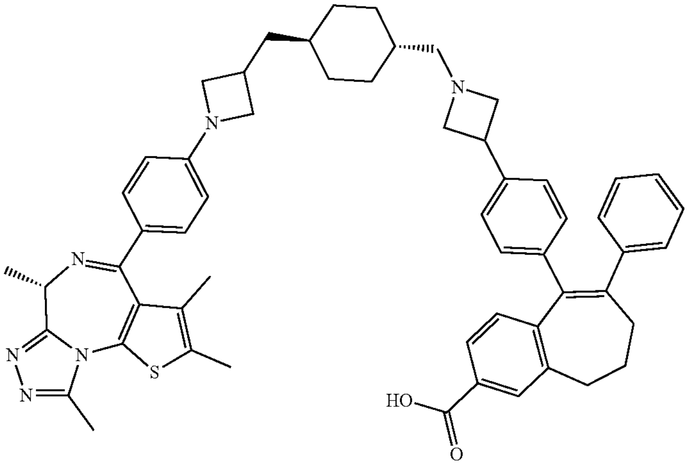 [SMILES: Cc1sc2c(c1C)C(c1ccc(N3CC(C[C@H]4CC[C@H](CN5CC(c6ccc(C7=C(c8ccccc8)CCCc8cc(C(=O)O)ccc87)cc6)C5)CC4)C3)cc1)=N[C@@H](C)c1nnc(C)n1-2] |
| IV-25 | 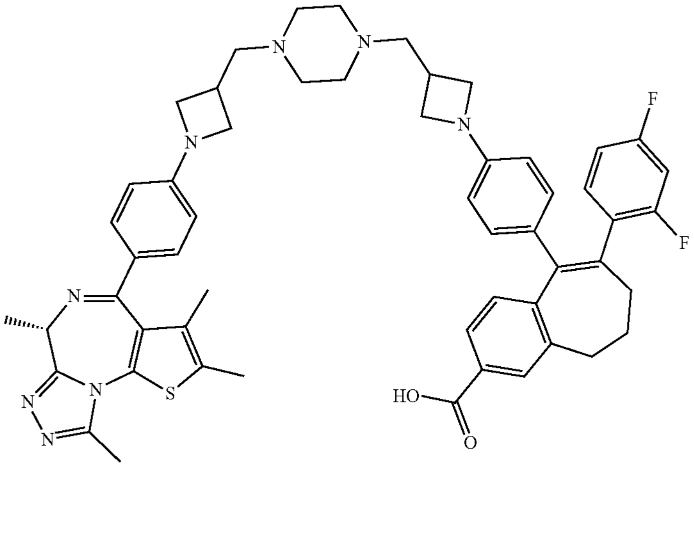 [SMILES: Cc1sc2c(c1C)C(c1ccc(N3CC(CN4CCN(CC5CN(c6ccc(C7=C(c8ccc(F)cc8F)CCCc8cc(C(=O)O)ccc87)cc6)C5)CC4)C3)cc1)=N[C@@H](C)c1nnc(C)n1-2] |

TABLE 4-continued
| Compound No. | Compound Structure |
|---|---|
| IV-26 | 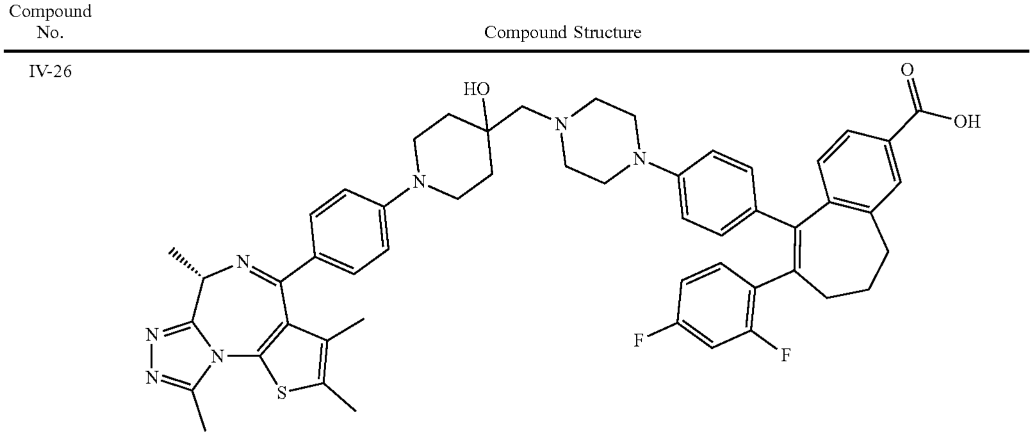 |
| IV-27 | 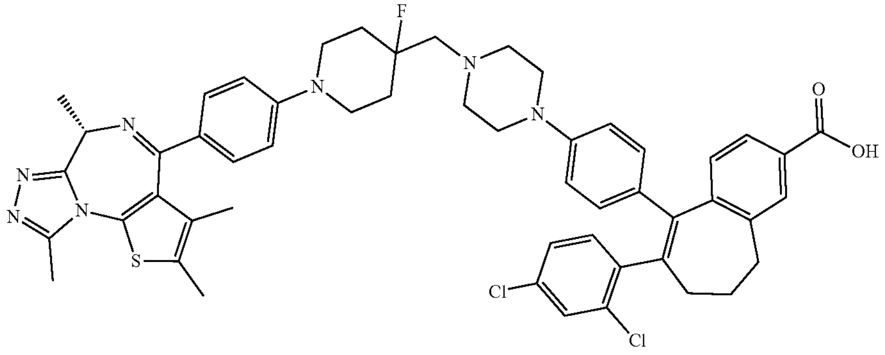 [SMILES: Cc1sc2c(c1C)C(c1ccc(N3CCC(F)(CN4CCN(c5ccc(C6=C(c7ccc(Cl)cc7Cl)CCCc7cc(C(=O)O)ccc76)cc5)CC4)CC3)cc1)=N[C@@H](C)c1nnc(C)n1-2] |
| IV-28 | 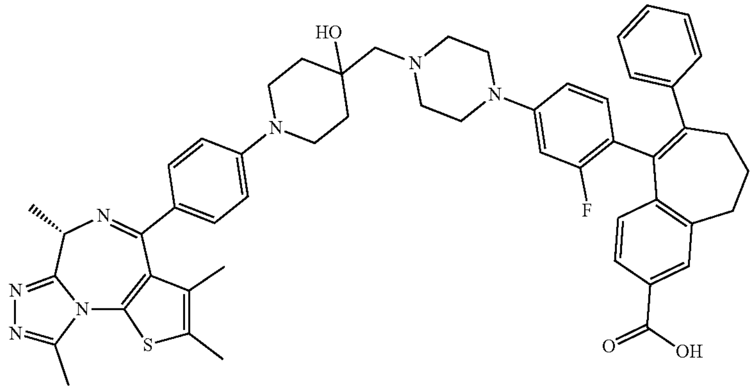 [SMILES: Cc1sc2c(c1C)C(c1ccc(N3CCC(O)(CN4CCN(c5ccc(C6=C(c7ccccc7)CCCc7cc(C(=O)O)ccc76)c(F)c5)CC4)CC3)cc1)=N[C@@H](C)c1nnc(C)n1-2] |
| IV-29 | 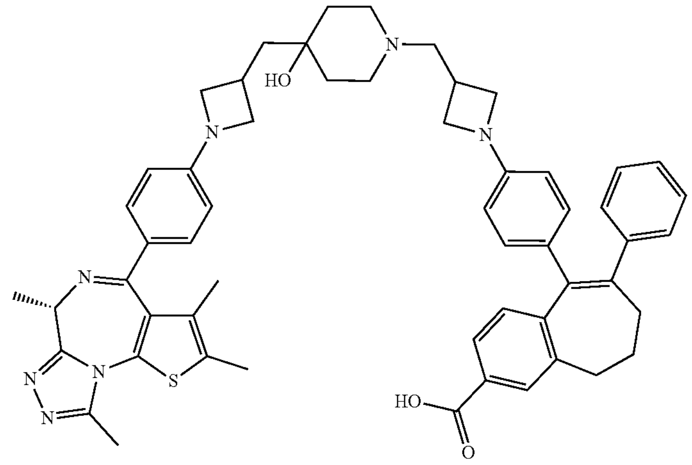 |

TABLE 4-continued
| Compound No. | Compound Structure |
|---|---|
| IV-30 | 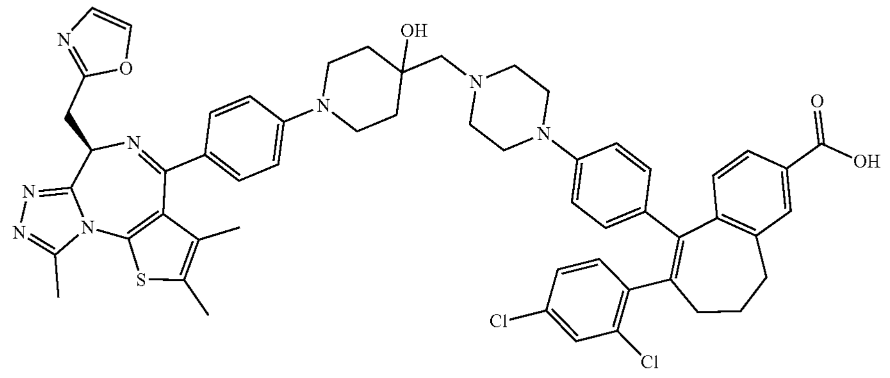 [SMILES: Cc1sc2c(c1C)C(c1ccc(N3CCC(O)(CN4CCN(c5ccc(C6=C(c7ccc(Cl)cc7Cl)CCCc7cc(C(=O)O)ccc76)cc5)CC4)CC3)cc1)=N[C@H](Cc1ncco1)c1nnc(C)n1-2] |
| IV-31 | 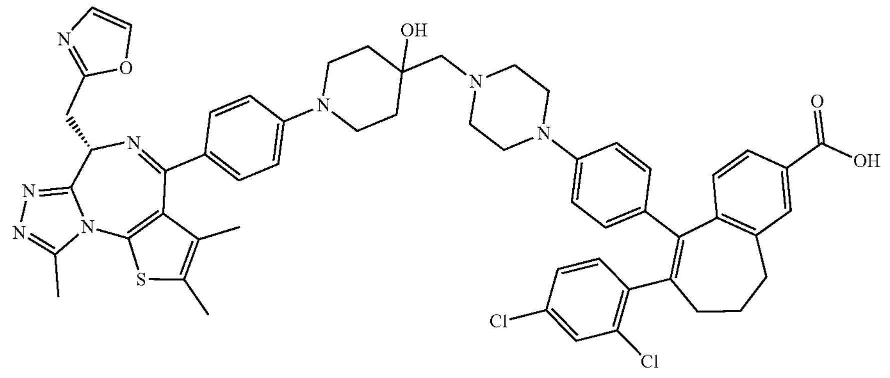 [SMILES: Cc1sc2c(c1C)C(c1ccc(N3CCC(O)(CN4CCN(c5ccc(C6=C(c7ccc(Cl)cc7Cl)CCCc7cc(C(=O)O)ccc76)cc5)CC4)CC3)cc1)=N[C@@H](Cc1ncco1)c1nnc(C)n1-2] |
| IV-32 | 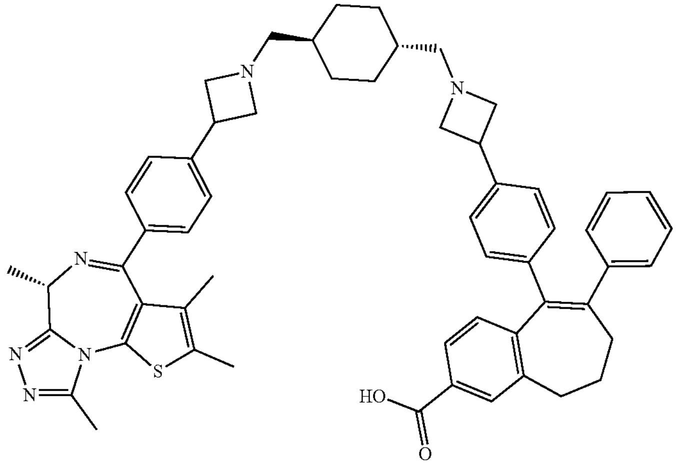 [SMILES: Cc1sc2c(c1C)C(c1ccc(C3CN(C[C@H]4CC[C@H](CN5CC(c6ccc(C7=C(c8ccccc8)CCCc8cc(C(=O)O)ccc87)cc6)C5)CC4)C3)cc1)=N[C@@H](C)c1nnc(C)n1-2] |
| IV-33 | 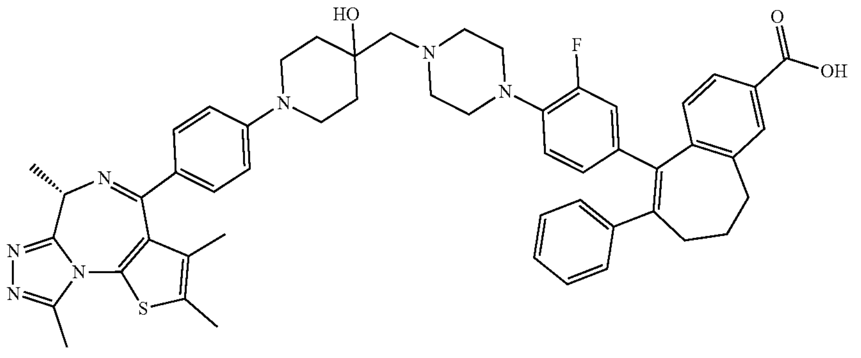 [SMILES: Cc1sc2c(c1C)C(c1ccc(N3CCC(O)(CN4CCN(c5ccc(C6=C(c7ccccc7)CCCc7cc(C(=O)O)ccc76)cc5F)CC4)CC3)cc1)=N[C@@H](C)c1nnc(C)n1-2] |

TABLE 4-continued
| Compound No. | Compound Structure |
|---|---|
| IV-34 | 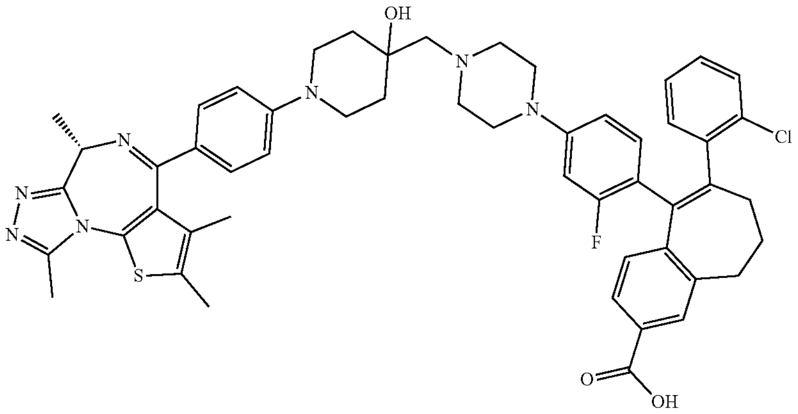 [SMILES: Cc1sc2c(c1C)C(c1ccc(N3CCC(O)(CN4CCN(c5ccc(C6=C(c7ccccc7Cl)CCCc7cc(C(=O)O)ccc76)c(F)c5)CC4)CC3)cc1)=N[C@@H](C)c1nnc(C)n1-2] |
| IV-35 | 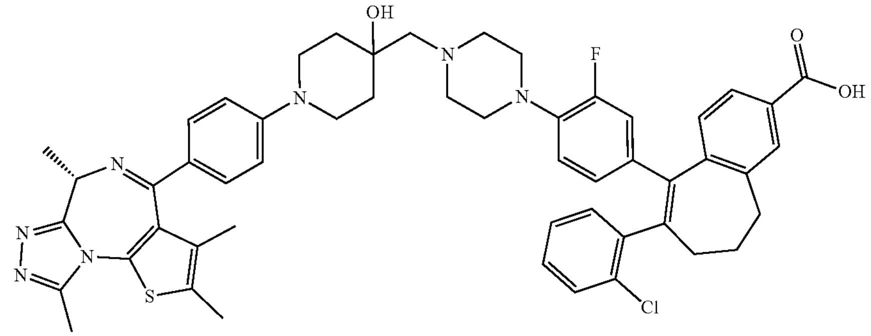 [SMILES: Cc1sc2c(c1C)C(c1ccc(N3CCC(O)(CN4CCN(c5ccc(C6=C(c7ccccc7Cl)CCCc7cc(C(=O)O)ccc76)cc5F)CC4)CC3)cc1)=N[C@@H](C)c1nnc(C)n1-2] |
| IV-36 | 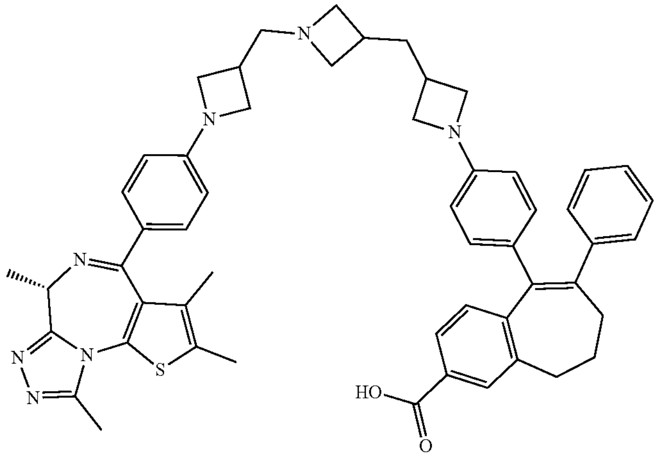 [SMILES: Cc1sc2c(c1C)C(c1ccc(N3CC(CN4CC(CC5CN(c6ccc(C7=C(c8ccccc8)CCCc8cc(C(=O)O)ccc87)cc6)C5)C4)C3)cc1)=N[C@@H](C)c1nnc(C)n1-2] |
| IV-37 | 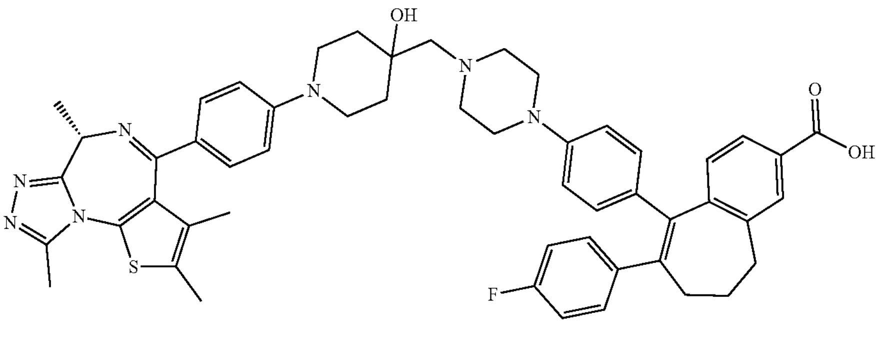 [SMILES: Cc1sc2c(c1C)C(c1ccc(N3CCC(O)(CN4CCN(c5ccc(C6=C(c7ccc(F)cc7)CCCc7cc(C(=O)O)ccc76)cc5)CC4)CC3)cc1)=N[C@@H](C)c1nnc(C)n1-2] |

TABLE 4-continued
| Compound No. | Compound Structure |
|---|---|
| IV-38 | 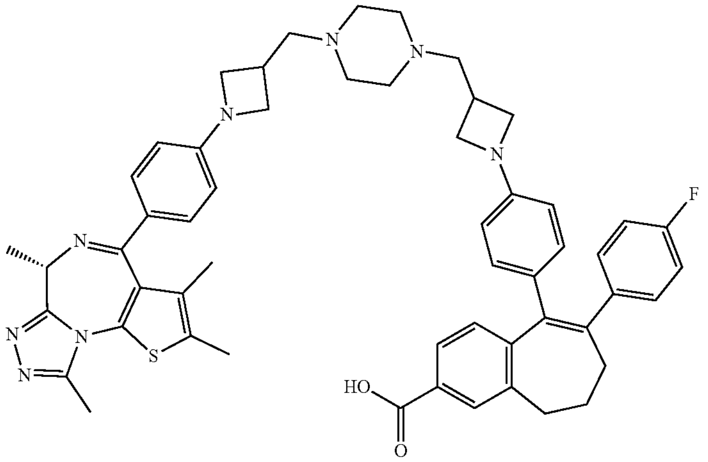 [SMILES: Cc1sc2c(c1C)C(c1ccc(N3CC(CN4CCN(CC5CN(c6ccc(C7=C(c8ccc(F)cc8)CCCc8cc(C(=O)O)ccc87)cc6)C5)CC4)C3)cc1)=N[C@@H](C)c1nnc(C)n1-2] |
| IV-39 | 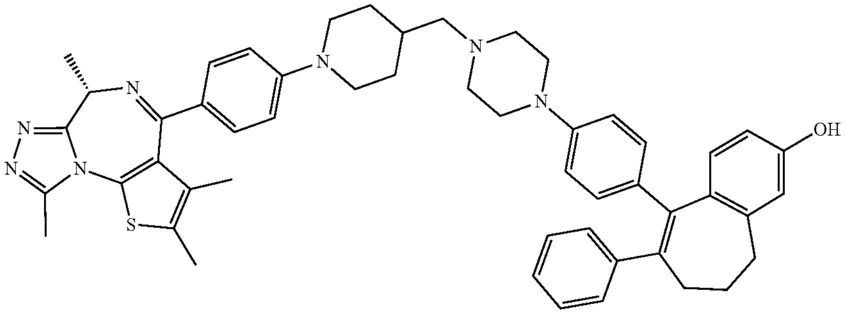 [SMILES: Cc1sc2c(c1C)C(c1ccc(N3CCC(CN4CCN(c5ccc(C6=C(c7ccccc7)CCCc7cc(O)ccc76)cc5)CC4)CC3)cc1)=N[C@@H](C)c1nnc(C)n1-2] |
| IV-40 | 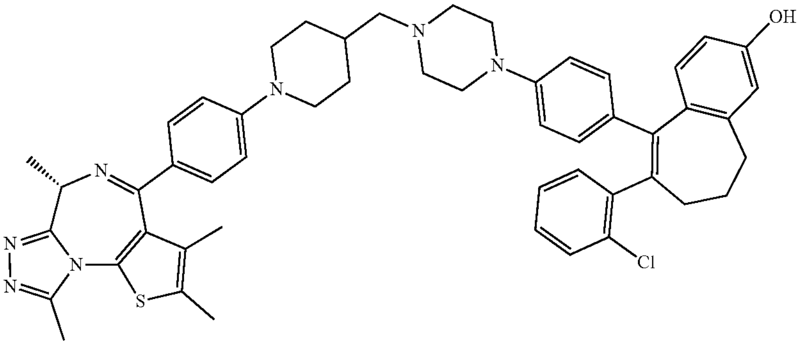 [SMILES: Cc1sc2c(c1C)C(c1ccc(N3CCC(CN4CCN(c5ccc(C6=C(c7ccccc7Cl)CCCc7cc(O)ccc76)cc5)CC4)CC3)cc1)=N[C@@H](C)c1nnc(C)n1-2] |
| IV-41 | 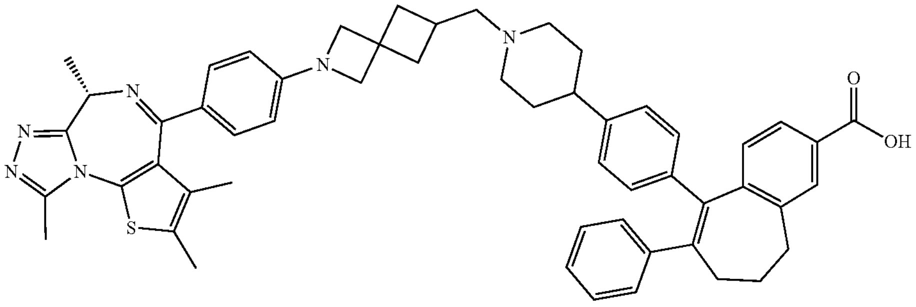 [SMILES: Cc1sc2c(c1C)C(c1ccc(N3CC4(CC(CN5CCC(c6ccc(C7=C(c8ccccc8)CCCc8cc(C(=O)O)ccc87)cc6)CC5)C4)C3)cc1)=N[C@@H](C)c1nnc(C)n1-2] |

TABLE 4-continued
| Compound No. | Compound Structure |
|---|---|
| IV-42 | 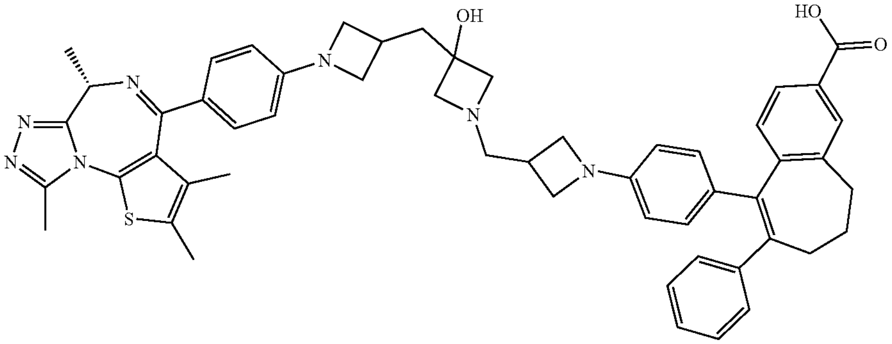 [SMILES: Cc1sc2c(c1C)C(c1ccc(N3CC(CC4(O)CN(CC5CN(c6ccc(C7=C(c8ccccc8)CCCc8cc(C(=O)O)ccc87)cc6)C5)C4)C3)cc1)=N[C@@H](C)c1nnc(C)n1-2] |
| IV-43 | 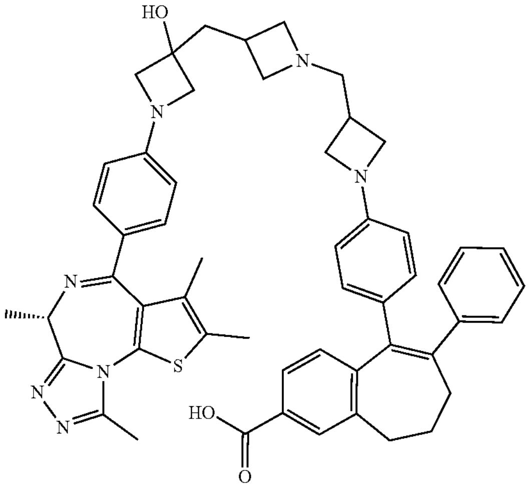 [SMILES: Cc1sc2c(c1C)C(c1ccc(N3CC(O)(CC4CN(CC5CN(c6ccc(C7=C(c8ccccc8)CCCc8cc(C(=O)O)ccc87)cc6)C5)C4)C3)cc1)=N[C@@H](C)c1nnc(C)n1-2] |
| IV-44 | 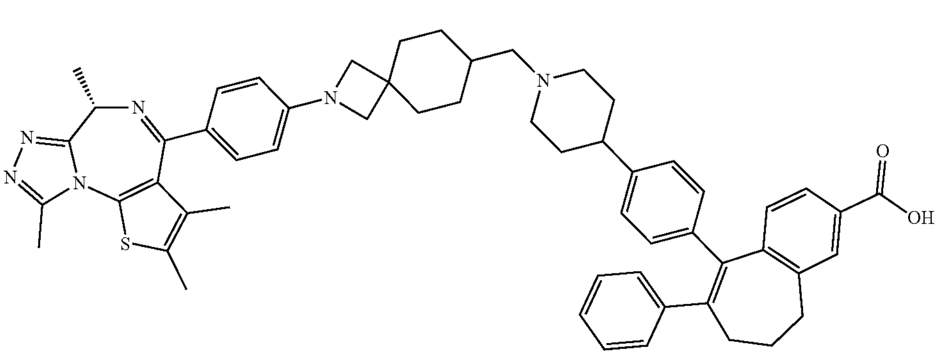 [SMILES: Cc1sc2c(c1C)C(c1ccc(N3CC4(CCC(CN5CCC(c6ccc(C7=C(c8ccccc8)CCCc8cc(C(=O)O)ccc87)cc6)CC5)CC4)C3)cc1)=N[C@@H](C)c1nnc(C)n1-2] |

TABLE 4-continued
| Compound No. | Compound Structure |
|---|---|
| IV-45 | 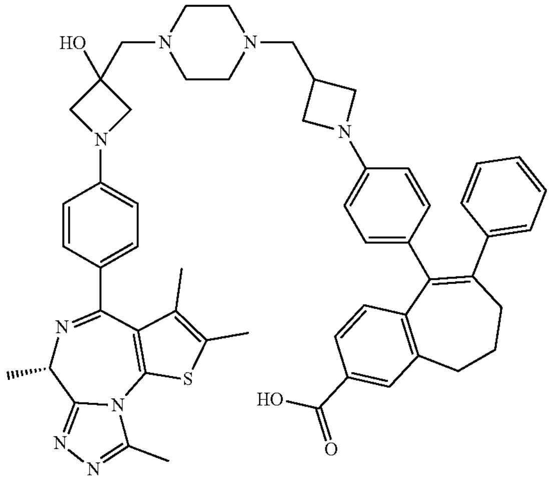 [SMILES: Cc1sc2c(c1C)C(c1ccc(N3CC(O)(CN4CCN(CC5CN(c6ccc(C7=C(c8ccccc8)CCCc8cc(C(=O)O)ccc87)cc6)C5)CC4)C3)cc1)=N[C@@H](C)c1nnc(C)n1-2] |
| IV-46 | 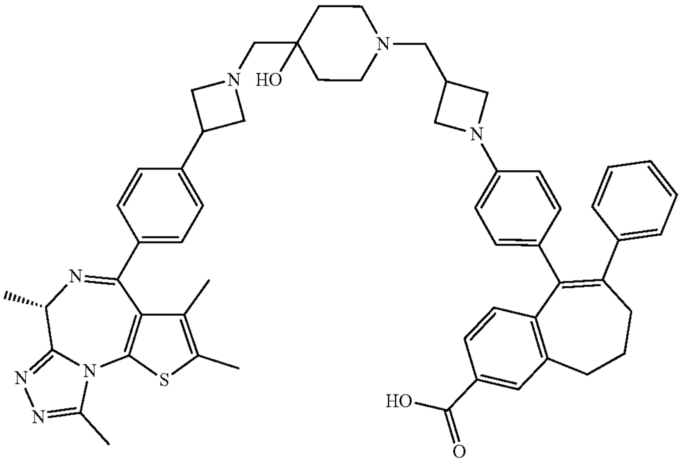 [SMILES: Cc1sc2c(c1C)C(c1ccc(C3CN(CC4(O)CCN(CC5CN(c6ccc(C7=C(c8ccccc8)CCCc8cc(C(=O)O)ccc87)cc6)C5)CC4)C3)cc1)=N[C@@H](C)c1nnc(C)n1-2] |
| IV-47 | 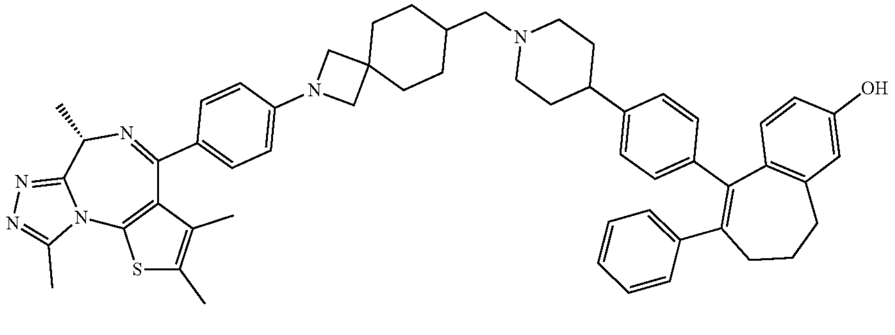 [SMILES: Cc1sc2c(c1C)C(c1ccc(N3CC4(CCC(CN5CCC(c6ccc(C7=C(c8ccccc8)CCCc8cc(O)ccc87)cc6)CC5)CC4)C3)cc1)=N[C@@H](C)c1nnc(C)n1-2] |

TABLE 4-continued
| Compound No. | Compound Structure |
|---|---|
| IV-48 | 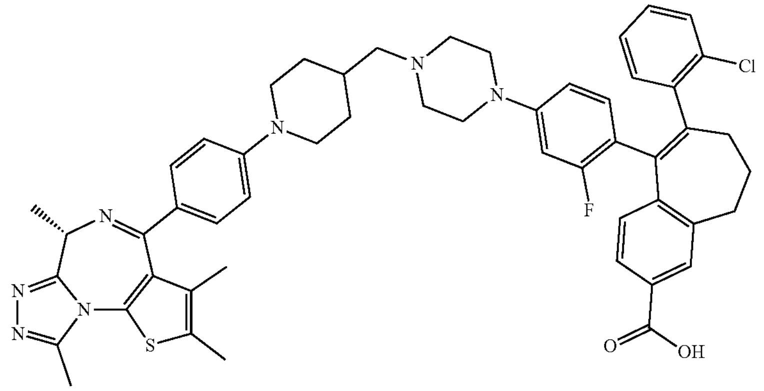 [SMILES: Cc1sc2c(c1C)C(c1ccc(N3CCC(CN4CCN(c5ccc(C6=C(c7ccccc7Cl)CCCc7cc(C(=O)O)ccc76)c(F)c5)CC4)CC3)cc1)=N[C@@H](C)c1nnc(C)n1-2] |
| IV-49 | 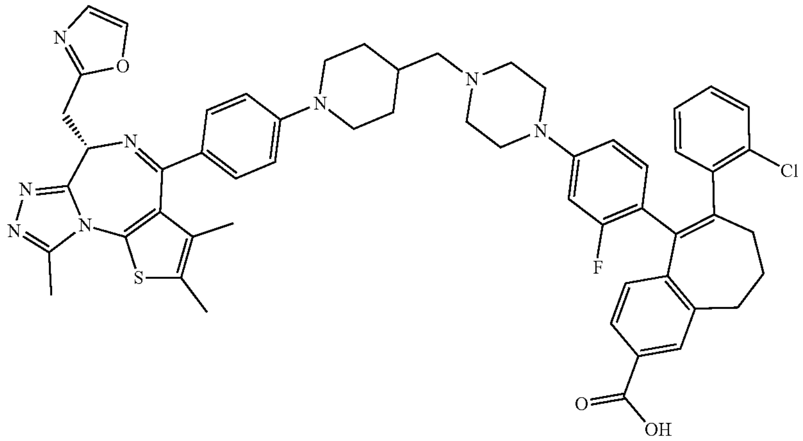 [SMILES: Cc1sc2c(c1C)C(c1ccc(N3CCC(CN4CCN(c5ccc(C6=C(c7ccccc7Cl)CCCc7cc(C(=O)O)ccc76)c(F)c5)CC4)CC3)cc1)=N[C@@H](Cc1ncco1)c1nnc(C)n1-2] |
| IV-50 | 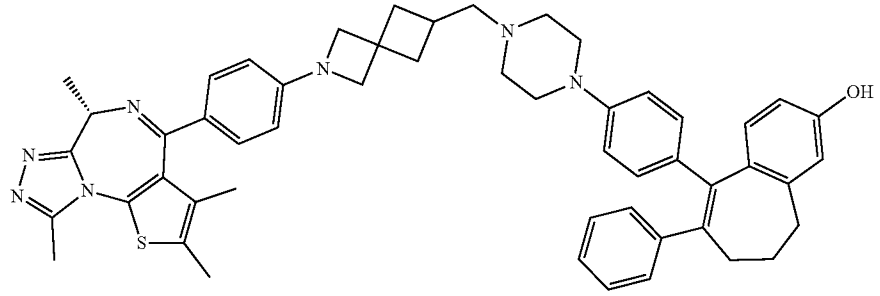 [SMILES: Cc1sc2c(c1C)C(c1ccc(N3CC4(CC(CN5CCN(c6ccc(C7=C(c8ccccc8)CCCc8cc(O)ccc87)cc6)CC5)C4)C3)cc1)=N[C@@H](C)c1nnc(C)n1-2] |
| IV-51 | 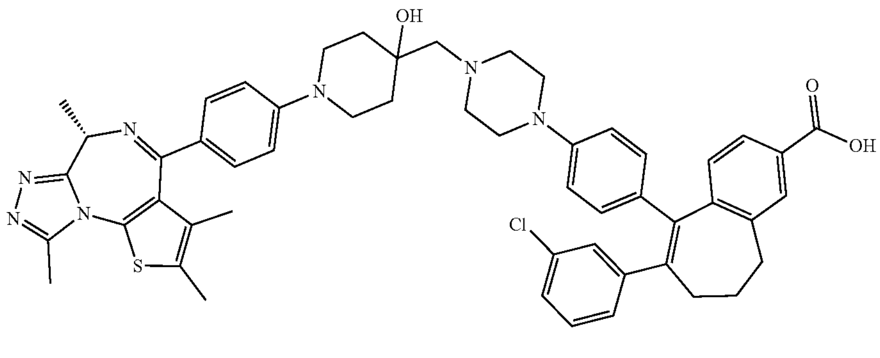 [SMILES: Cc1sc2c(c1C)C(c1ccc(N3CCC(O)(CN4CCN(c5ccc(C6=C(c7cccc(Cl)c7)CCCc7cc(C(=O)O)ccc76)cc5)CC4)CC3)cc1)=N[C@@H](C)c1nnc(C)n1-2] |

TABLE 4-continued
| Compound No. | Compound Structure |
|---|---|
| IV-52 | 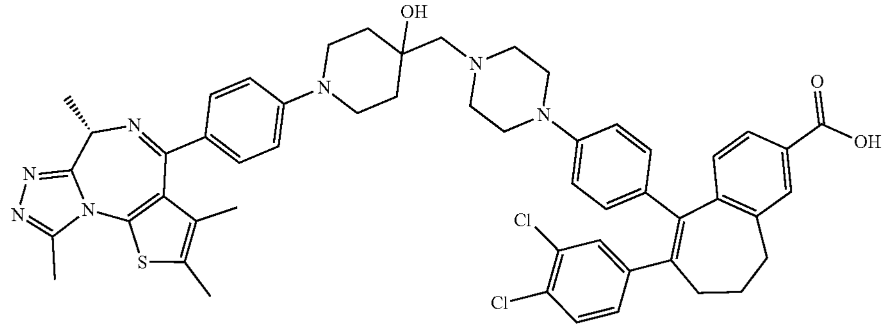 [SMILES: Cc1sc2c(c1C)C(c1ccc(N3CCC(O)(CN4CCN(c5ccc(C6=C(c7ccc(Cl)c(Cl)c7)CCCc7cc(C(=O)O)ccc76)cc5)CC4)CC3)cc1)=N[C@@H](C)c1nnc(C)n1-2] |
| IV-53 | 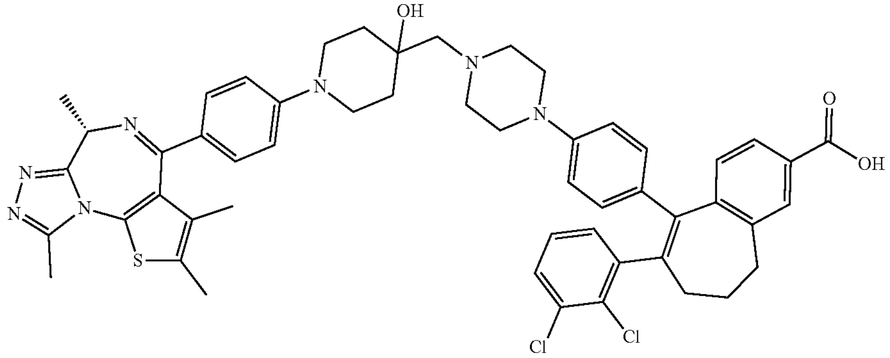 [SMILES: Cc1sc2c(c1C)C(c1ccc(N3CCC(O)(CN4CCN(c5ccc(C6=C(c7cccc(Cl)c7Cl)CCCc7cc(C(=O)O)ccc76)cc5)CC4)CC3)cc1)=N[C@@H](C)c1nnc(C)n1-2] |
| IV-54 | 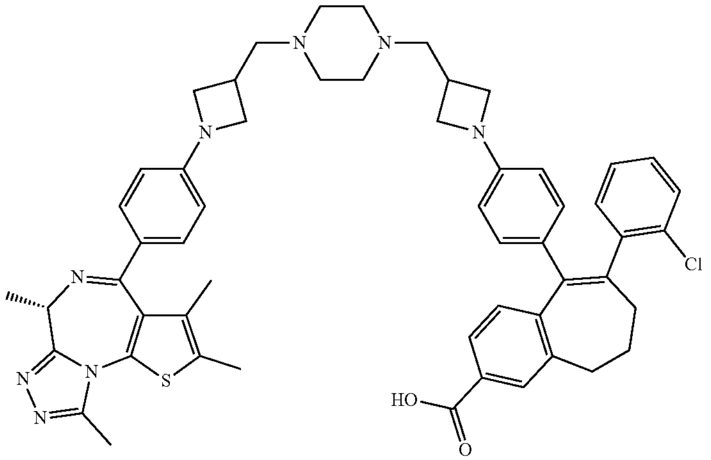 [SMILES: Cc1sc2c(c1C)C(c1ccc(N3CC(CN4CCN(CC5CN(c6ccc(C7=C(c8ccccc8Cl)CCCc8cc(C(=O)O)ccc87)cc6)C5)CC4)C3)cc1)=N[C@@H](C)c1nnc(C)n1-2] |
| IV-55 | 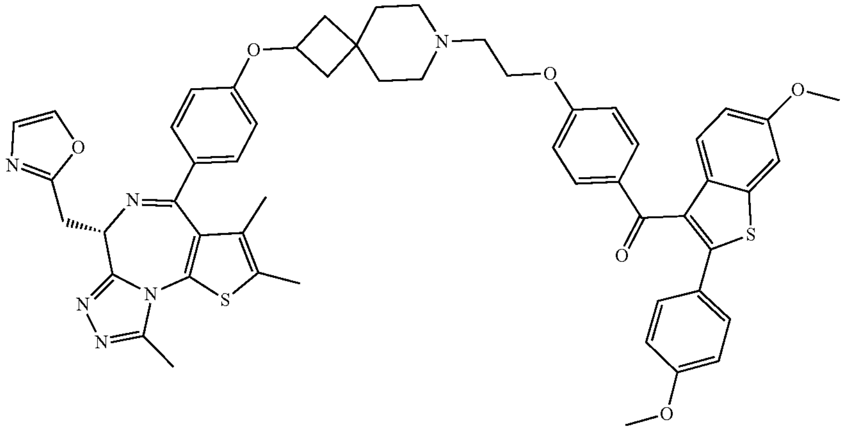 [SMILES: COc1ccc(-c2sc3cc(OC)ccc3c2C(=O)c2ccc(OCCN3CCC4(CC3)CC(Oc3ccc(C5=N[C@@H](Cc6ncco6)c6nnc(C)n6-c6sc(C)c(C)c65)cc3)C4)cc2)cc1] |

TABLE 4-continued
| Compound No. | Compound Structure |
| --- | --- |
| IV-56 | 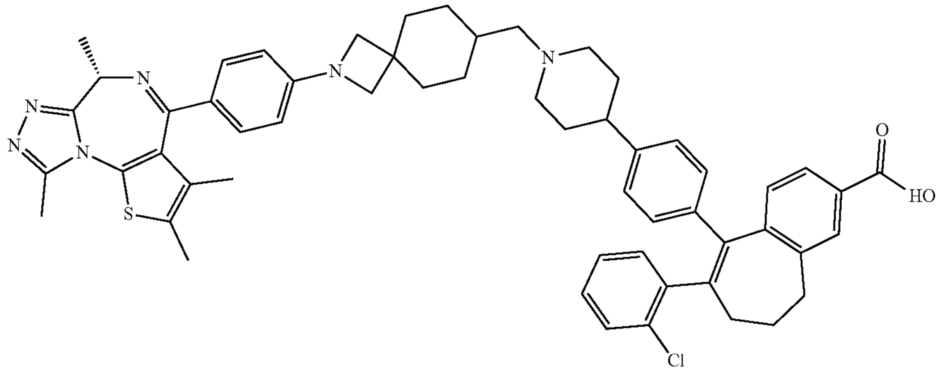 [SMILES: Cc1sc2c(c1C)C(c1ccc(N3CC4(CCC(CN5CCC(c6ccc(C7=C(c8ccccc8Cl)CCCc8cc(C(=O)O)ccc87)cc6)CC5)CC4)C3)cc1)=N[C@@H](C)c1nnc(C)n1-2] |
| IV-57 | 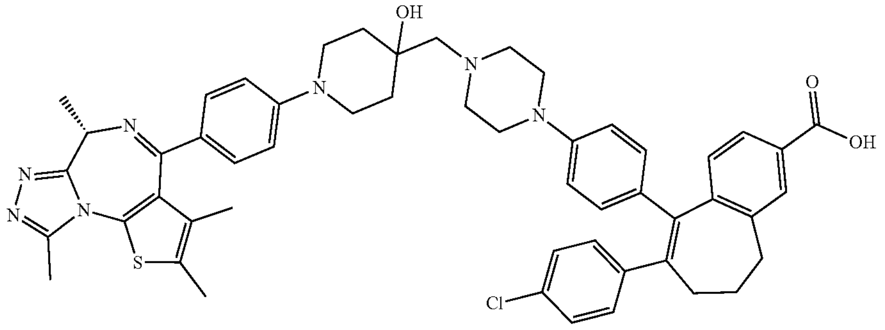 [SMILES: Cc1sc2c(c1C)C(c1ccc(N3CCC(O)(CN4CCN(c5ccc(C6=C(c7ccc(Cl)cc7)CCCc7cc(C(=O)O)ccc76)cc5)CC4)CC3)cc1)=N[C@@H](C)c1nnc(C)n1-2] |
| IV-58 | 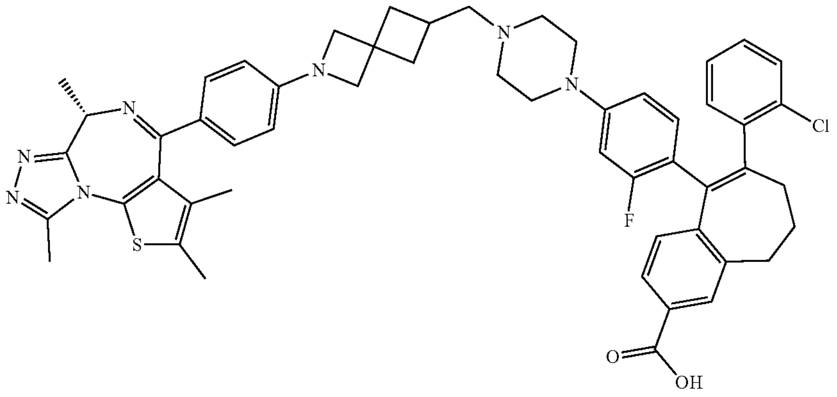 [SMILES: Cc1sc2c(c1C)C(c1ccc(N3CC4(CC(CN5CCN(c6ccc(C7=C(c8ccccc8Cl)CCCc8cc(C(=O)O)ccc87)c(F)c6)CC5)C4)C3)cc1)=N[C@@H](C)c1nnc(C)n1-2] |
| IV-59 | 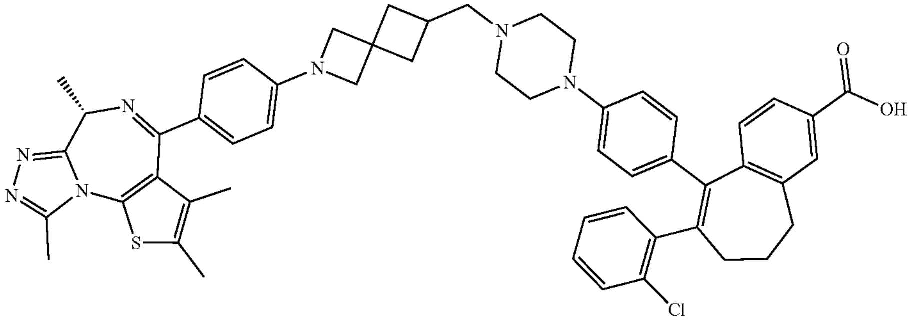 [SMILES: Cc1sc2c(c1C)C(c1ccc(N3CC4(CC(CN5CCN(c6ccc(C7=C(c8ccccc8Cl)CCCc8cc(C(=O)O)ccc87)cc6)CC5)C4)C3)cc1)=N[C@@H](C)c1nnc(C)n1-2] |

TABLE 4-continued
| Compound No. | Compound Structure |
|---|---|
| IV-60 | 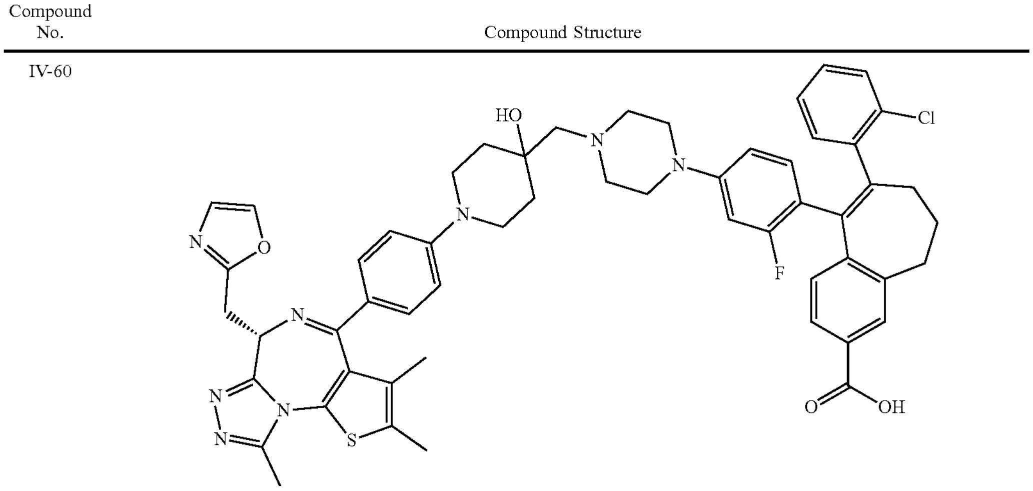 |
| IV-61 | 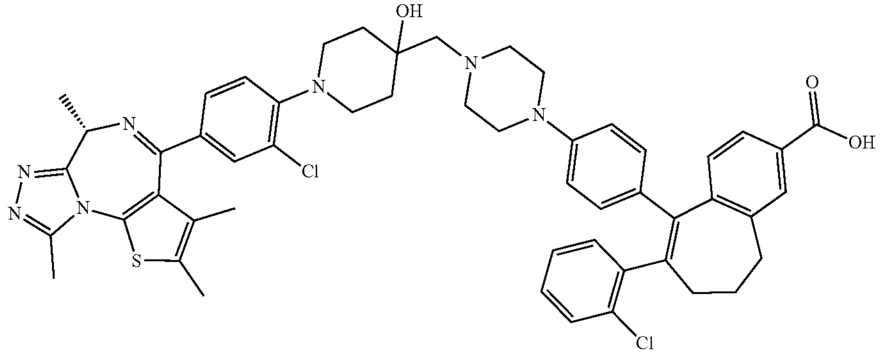 [SMILES: Cc1sc2c(c1C)C(c1ccc(N3CCC(O)(CN4CCN(c5ccc(C6=C(c7ccccc7Cl)CCCc7cc(C(=O)O)ccc76)cc5)CC4)CC3)c(Cl)c1)=N[C@@H](C)c1nnc(C)n1-2] |
| IV-62 | 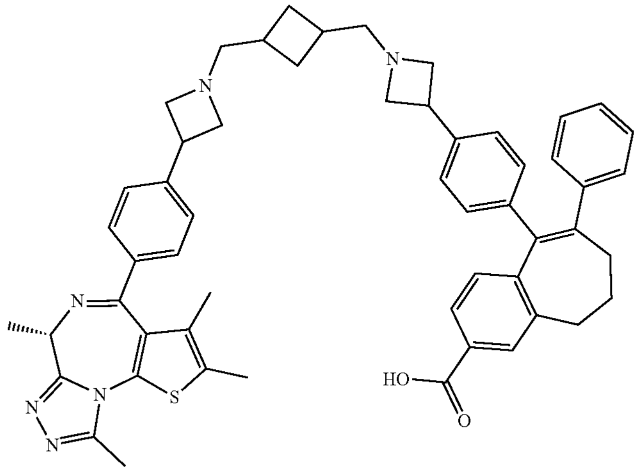 [SMILES: Cc1sc2c(c1C)C(c1ccc(C3CN(CC4CC(CN5CC(c6ccc(C7=C(c8ccccc8)CCCc8cc(C(=O)O)ccc87)cc6)C5)C4)C3)cc1)=N[C@@H](C)c1nnc(C)n1-2] |
| IV-63 | 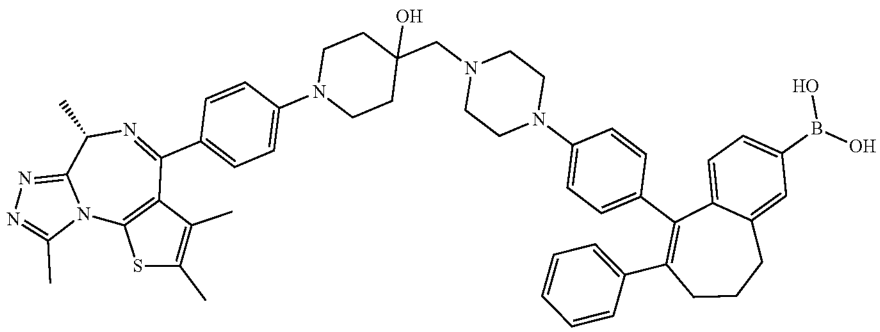 [SMILES: Cc1sc2c(c1C)C(c1ccc(N3CCC(O)(CN4CCN(c5ccc(C6=C(c7ccccc7)CCCc7cc(B(O)O)ccc76)cc5)CC4)CC3)cc1)=N[C@@H](C)c1nnc(C)n1-2] |

TABLE 4-continued
| Compound No. | Compound Structure |
|---|---|
| IV-64 | 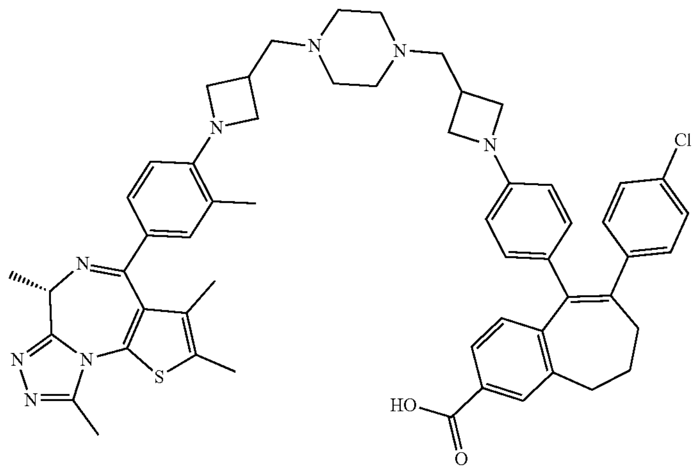 [SMILES: Cc1cc(C2=N[C@@H](C)c3nnc(C)n3-c3sc(C)c(C)c32)ccc1N1CC(CN2CCN(CC3CN(c4ccc(C5=C(c6ccc(Cl)cc6)CCCc6cc(C(=O)O)ccc65)cc4)C3)CC2)C1] |
| IV-65 | 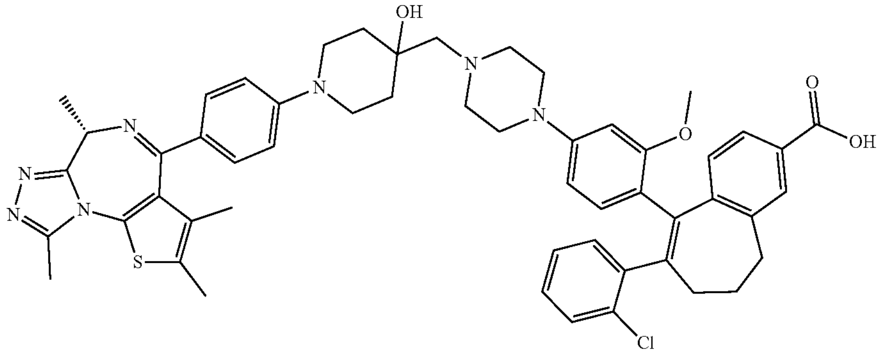 [SMILES: COc1cc(N2CCN(CC3(O)CCN(c4ccc(C5=N[C@@H](C)c6nnc(C)n6-c6sc(C)c(C)c65)cc4)CC3)CC2)ccc1C1=C(c2ccccc2Cl)CCCc2cc(C(=O)O)ccc21] |
| IV-66 | 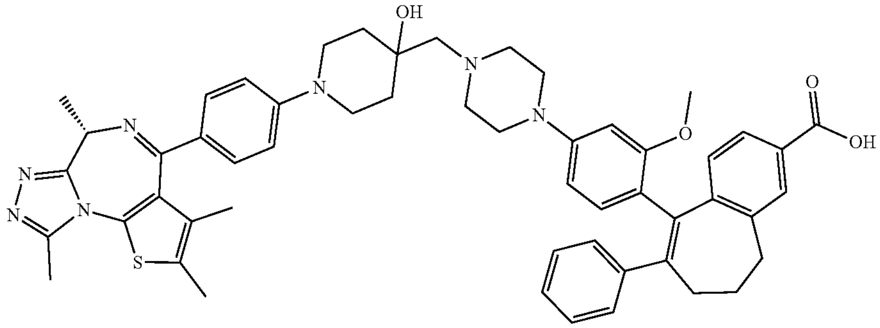 [SMILES: COc1cc(N2CCN(CC3(O)CCN(c4ccc(C5=N[C@@H](C)c6nnc(C)n6-c6sc(C)c(C)c65)cc4)CC3)CC2)ccc1C1=C(c2ccccc2)CCCc2cc(C(=O)O)ccc21] |
| IV-67 | 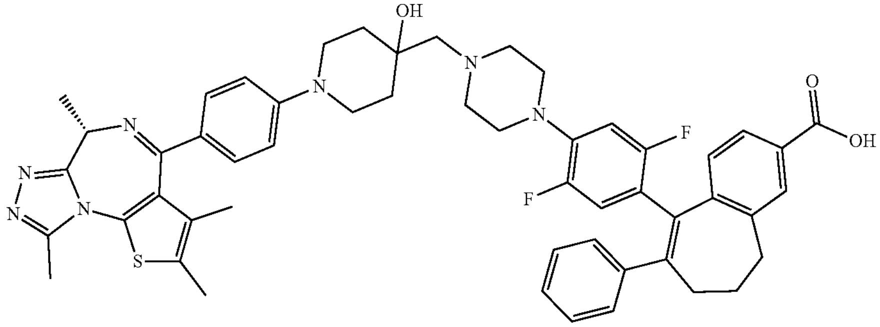 [SMILES: Cc1sc2c(c1C)C(c1ccc(N3CCC(O)(CN4CCN(c5cc(F)c(C6=C(c7ccccc7)CCCc7cc(C(=O)O)ccc76)cc5F)CC4)CC3)cc1)=N[C@@H](C)c1nnc(C)n1-2] |

TABLE 4-continued
| Compound No. | Compound Structure |
|---|---|
| IV-68 | 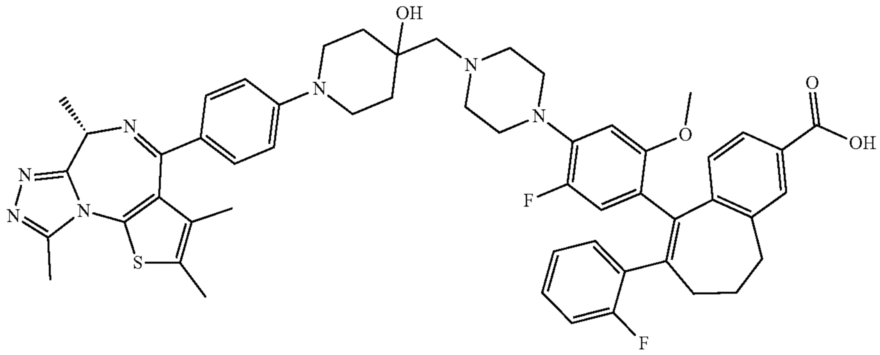 [SMILES: COc1cc(N2CCN(CC3(O)CCN(c4ccc(C5=N[C@@H](C)c6nnc(C)n6-c6sc(C)c(C)c65)cc4)CC3)CC2)c(F)cc1C1=C(c2ccccc2F)CCCc2cc(C(=O)O)ccc21] |
| IV-69 | 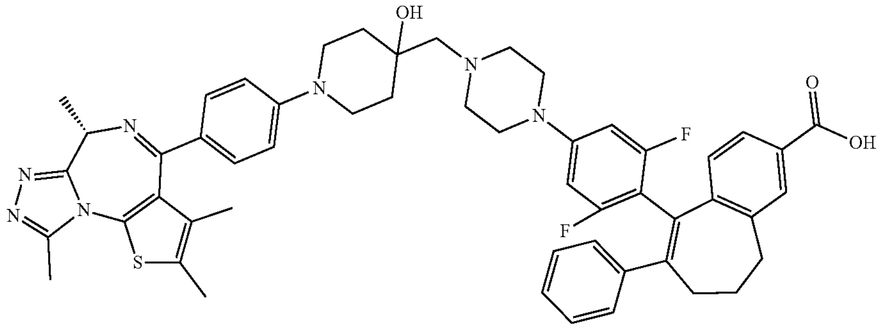 [SMILES: Cc1sc2c(c1C)C(c1ccc(N3CCC(O)(CN4CCN(c5cc(F)c(C6=C(c7ccccc7)CCCc7cc(C(=O)O)ccc76)c(F)c5)CC4)CC3)cc1)=N[C@@H](C)c1nnc(C)n1-2] |
| IV-70 | 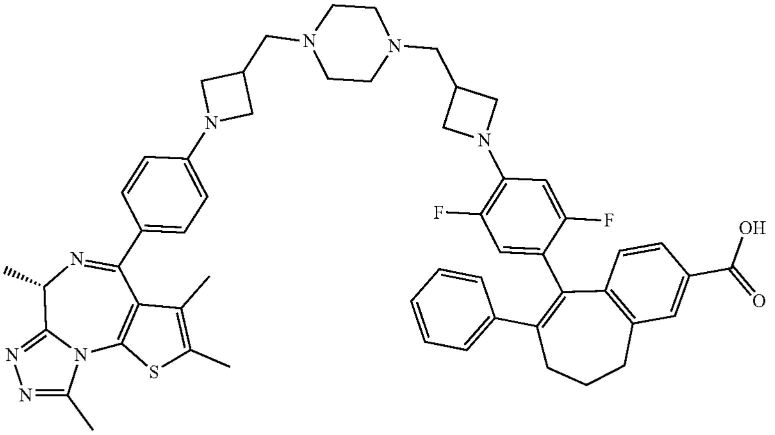 [SMILES: Cc1sc2c(c1C)C(c1ccc(N3CC(CN4CCN(CC5CN(c6cc(F)c(C7=C(c8ccccc8)CCCc8cc(C(=O)O)ccc87)cc6F)C5)CC4)C3)cc1)=N[C@@H](C)c1nnc(C)n1-2] |
| IV-71 | 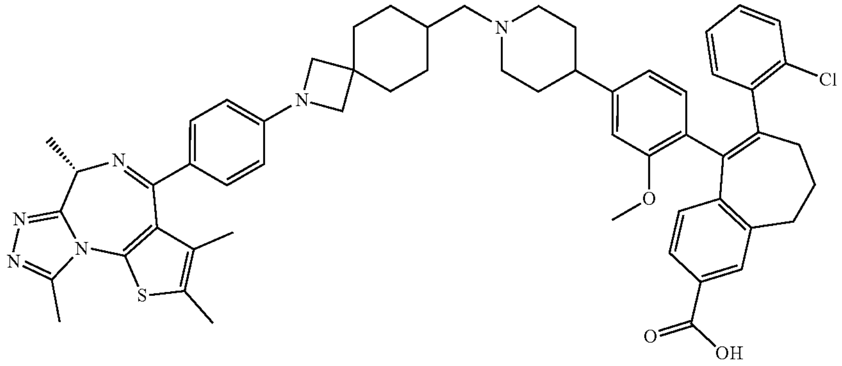 [SMILES: COc1cc(C2CCN(CC3CCC4(CC3)CN(c3ccc(C5=N[C@@H](C)c6nnc(C)n6-c6sc(C)c(C)c65)cc3)C4)CC2)ccc1C1=C(c2ccccc2Cl)CCCc2cc(C(=O)O)ccc21] |

TABLE 4-continued
| Compound No. | Compound Structure |
|---|---|
| IV-72 | 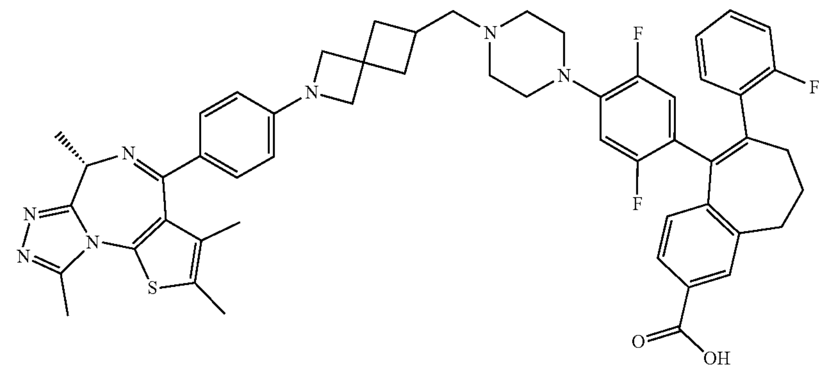 [SMILES: Cc1sc2c(c1C)C(c1ccc(N3CC4(CC(CN5CCN(c6cc(F)c(C7=C(c8ccccc8F)CCCc8cc(C(=O)O)ccc87)cc6F)CC5)C4)C3)cc1)=N[C@@H](C)c1nnc(C)n1-2] |
In certain embodiments, the compound is a compound in Table 5, or a pharmaceutically acceptable salt thereof. In certain embodiments, the compound is a compound in Table 5.
TABLE 5
| Compound No. | Compound Structure |
|---|---|
| V-1 | 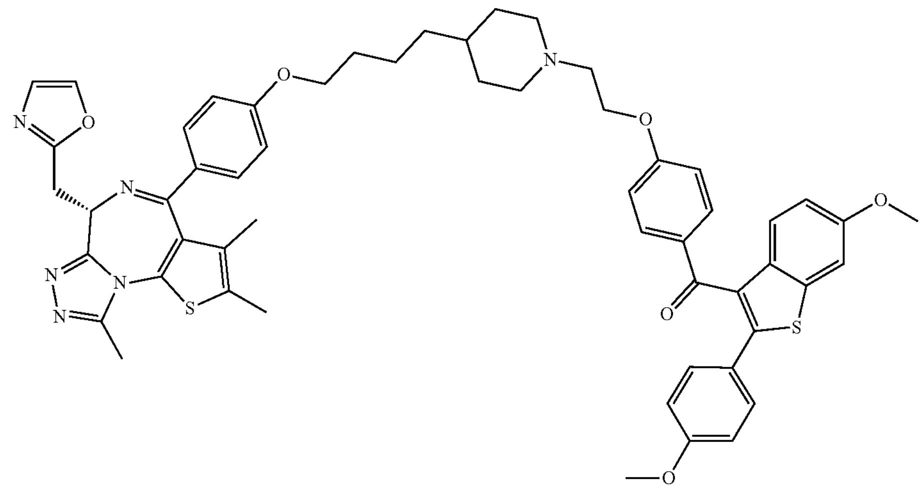 [SMILES: COc1ccc(-c2sc3cc(OC)ccc3c2C(=O)c2ccc(OCCN3CCC(CCCCOc4ccc(C5=N[C@@H](Cc6ncco6)c6nnc(C)n6-c6sc(C)c(C)c65)cc4)CC3)cc2)cc1] |
| V-2 | 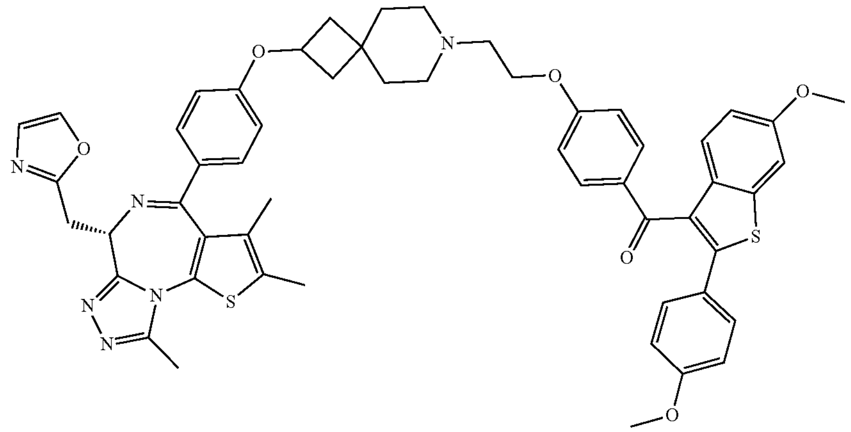 [SMILES: COc1ccc(-c2sc3cc(OC)ccc3c2C(=O)c2ccc(OCCN3CCC4(CC3)CC(Oc3ccc(C5=N[C@@H](Cc6ncco6)c6nnc(C)n6-c6sc(C)c(C)c65)cc3)C4)cc2)cc1] |

TABLE 5-continued
| Compound No. | Compound Structure |
|---|---|
| V-3 | 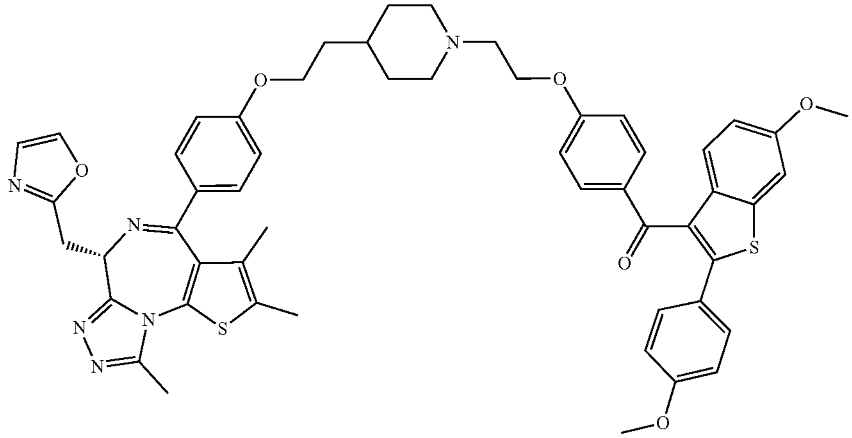 [SMILES: COc1ccc(-c2sc3cc(OC)ccc3c2C(=O)c2ccc(OCCN3CCC(CCOc4ccc(C5=N[C@@H](Cc6ncco6)c6nnc(C)n6-c6sc(C)c(C)c65)cc4)CC3)cc2)cc1] |
| V-4 | 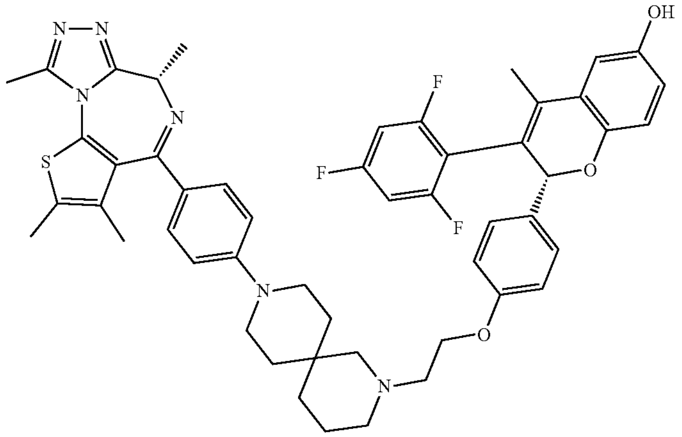 [SMILES: CC1=C(c2c(F)cc(F)cc2F)[C@@H](c2ccc(OCCN3CCCC4(CCN(c5ccc(C6=N[C@@H](C)c7nnc(C)n7-c7sc(C)c(C)c76)cc5)CC4)C3)cc2)Oc2ccc(O)cc21] |
| V-5 | 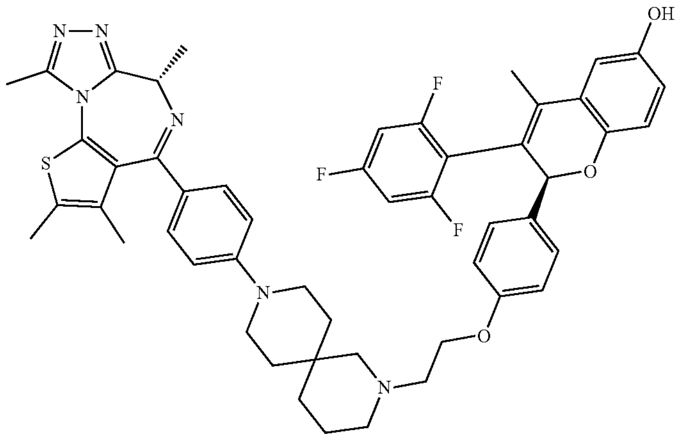 [SMILES: CC1=C(c2c(F)cc(F)cc2F)[C@H](c2ccc(OCCN3CCCC4(CCN(c5ccc(C6=N[C@@H](C)c7nnc(C)n7-c7sc(C)c(C)c76)cc5)CC4)C3)cc2)Oc2ccc(O)cc21] |

TABLE 5-continued
| Compound No. | Compound Structure |
|---|---|
| V-6 | 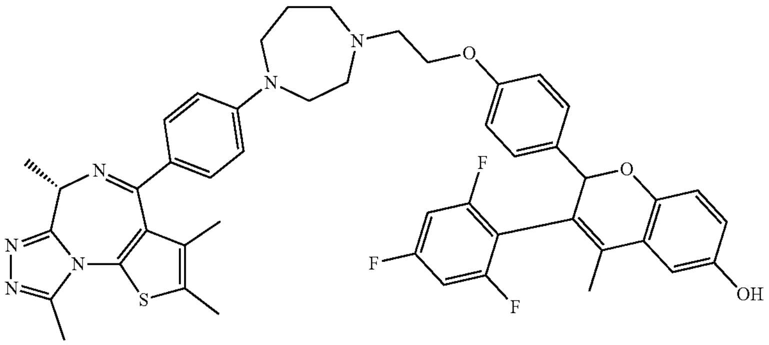 [SMILES: CC1=C(c2c(F)cc(F)cc2F)C(c2ccc(OCCN3CCCN(c4ccc(C5=N[C@@H](C)c6nnc(C)n6-c6sc(C)c(C)c65)cc4)CC3)cc2)Oc2ccc(O)cc21] |
| V-7 | 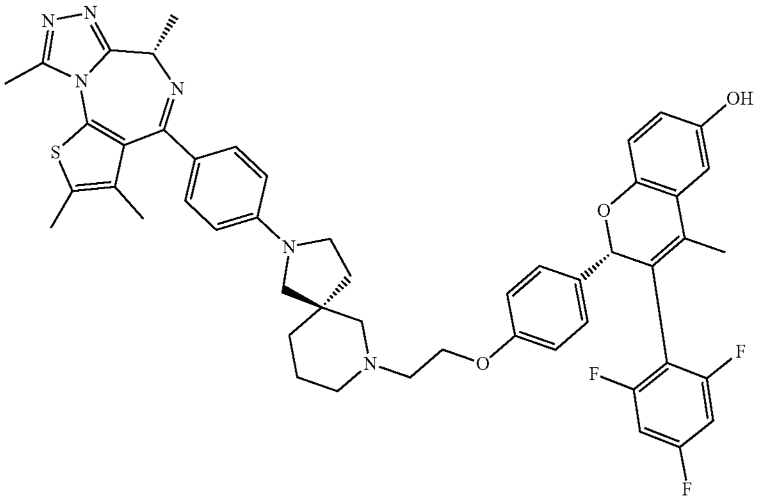 [SMILES: CC1=C(c2c(F)cc(F)cc2F)[C@H](c2ccc(OCCN3CCC[C@]4(CCN(c5ccc(C6=N[C@@H](C)c7nnc(C)n7-c7sc(C)c(C)c76)cc5)C4)C3)cc2)Oc2ccc(O)cc21] |
| V-8 | 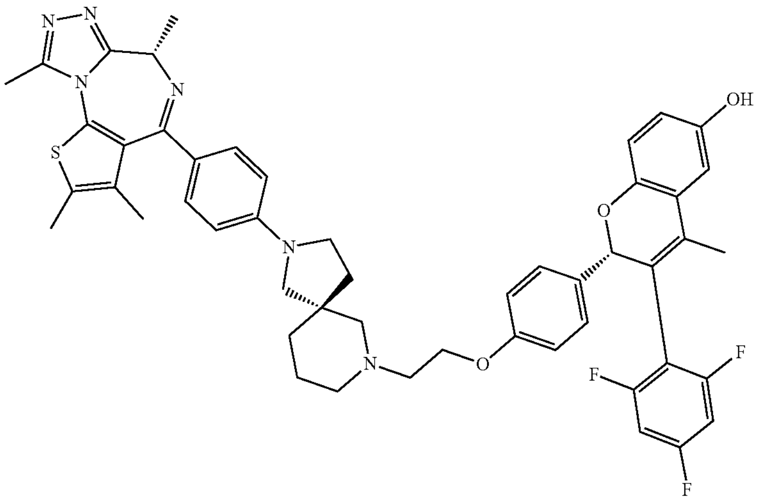 [SMILES: CC1=C(c2c(F)cc(F)cc2F)[C@H](c2ccc(OCCN3CCC[C@@]4(CCN(c5ccc(C6=N[C@@H](C)c7nnc(C)n7-c7sc(C)c(C)c76)cc5)C4)C3)cc2)Oc2ccc(O)cc21] |

TABLE 5-continued
| Compound No. | Compound Structure |
| --- | --- |
| V-9 | 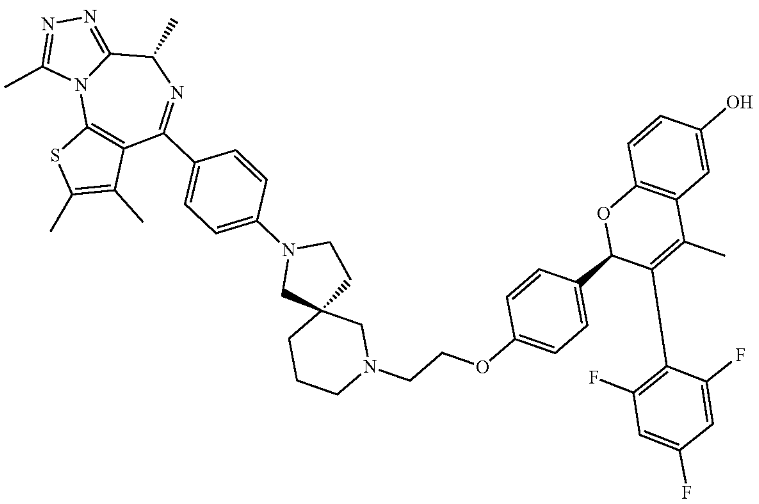 [SMILES: CC1=C(c2c(F)cc(F)cc2F)[C@@H](c2ccc(OCCN3CCC[C@]4(CCN(c5ccc(C6=N[C@@H](C)c7nnc(C)n7-c7sc(C)c(C)c76)cc5)C4)C3)cc2)Oc2ccc(O)cc21] |
| V-10 | 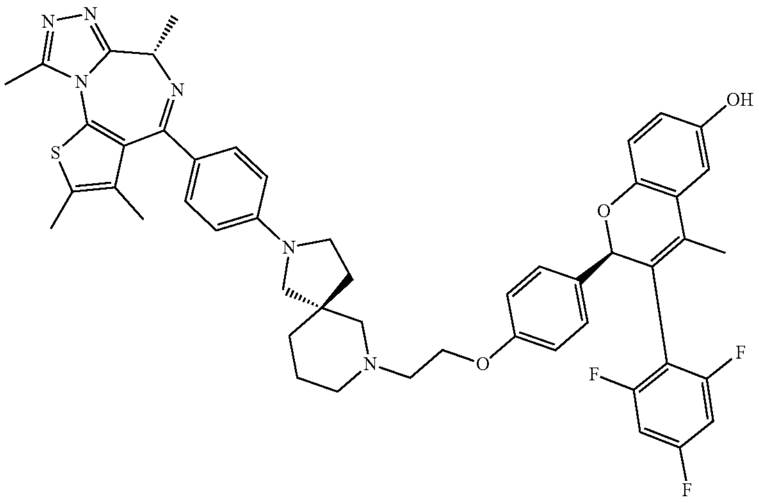 [SMILES: CC1=C(c2c(F)cc(F)cc2F)[C@@H](c2ccc(OCCN3CCC[C@@]4(CCN(c5ccc(C6=N[C@@H](C)c7nnc(C)n7-c7sc(C)c(C)c76)cc5)C4)C3)cc2)Oc2ccc(O)cc21] |
| V-11 | 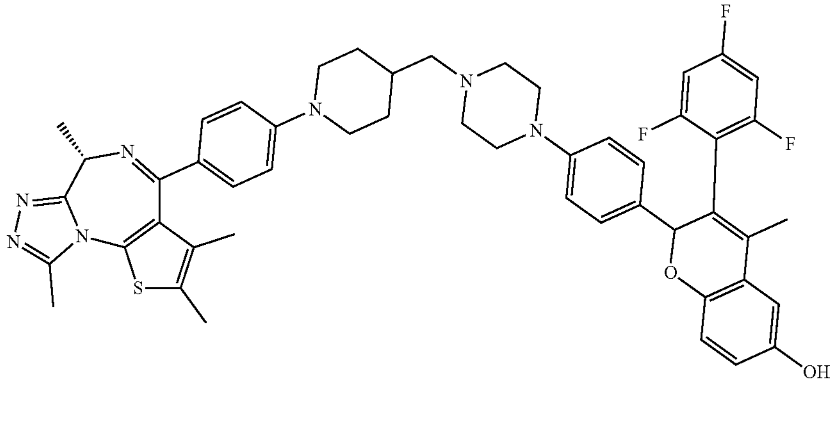 [SMILES: CC1=C(c2c(F)cc(F)cc2F)C(c2ccc(N3CCN(CC4CCN(c5ccc(C6=N[C@@H](C)c7nnc(C)n7-c7sc(C)c(C)c76)cc5)CC4)CC3)cc2)Oc2ccc(O)cc21] |

TABLE 5-continued
| Compound No. | Compound Structure |
|---|---|
| V-12 | 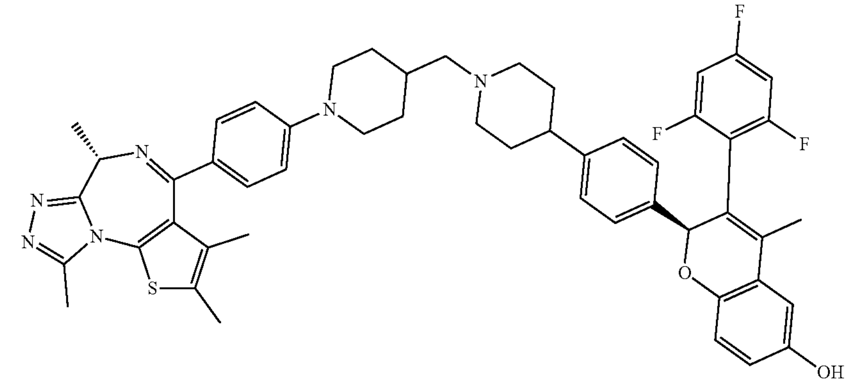 [SMILES: CC1=C(c2c(F)cc(F)cc2F)[C@H](c2ccc(C3CCN(CC4CCN(c5ccc(C6=N[C@@H](C)c7nnc(C)n7-c7sc(C)c(C)c76)cc5)CC4)CC3)cc2)Oc2ccc(O)cc21] |
| V-13 | 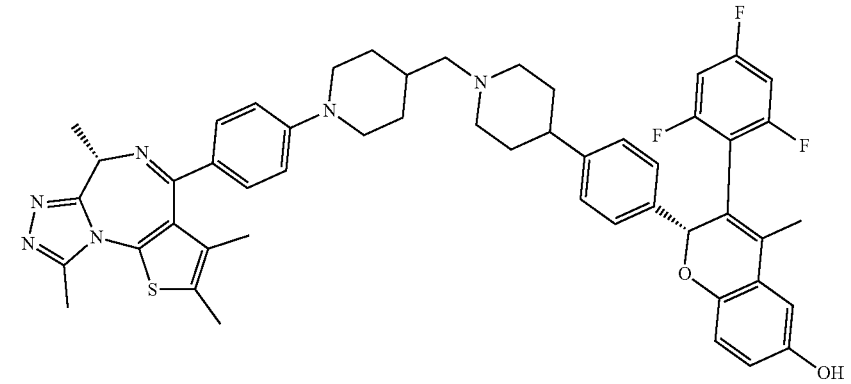 [SMILES: CC1=C(c2c(F)cc(F)cc2F)[C@@H](c2ccc(C3CCN(CC4CCN(c5ccc(C6=N[C@@H](C)c7nnc(C)n7-c7sc(C)c(C)c76)cc5)CC4)CC3)cc2)Oc2ccc(O)cc21] |
| V-14 | 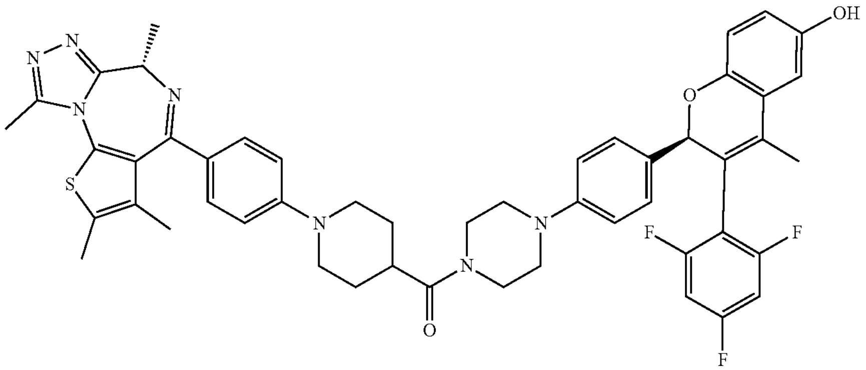 [SMILES: CC1=C(c2c(F)cc(F)cc2F)[C@@H](c2ccc(N3CCN(C(=O)C4CCN(c5ccc(C6=N[C@@H](C)c7nnc(C)n7-c7sc(C)c(C)c76)cc5)CC4)CC3)cc2)Oc2ccc(O)cc21] |
| V-15 | 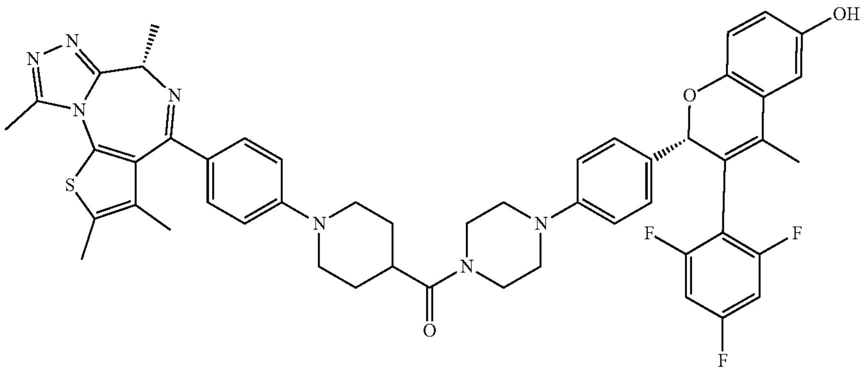 [SMILES: CC1=C(c2c(F)cc(F)cc2F)[C@H](c2ccc(N3CCN(C(=O)C4CCN(c5ccc(C6=N[C@@H](C)c7nnc(C)n7-c7sc(C)c(C)c76)cc5)CC4)CC3)cc2)Oc2ccc(O)cc21] |

TABLE 5-continued
| Compound No. | Compound Structure |
|---|---|
| V-16 | 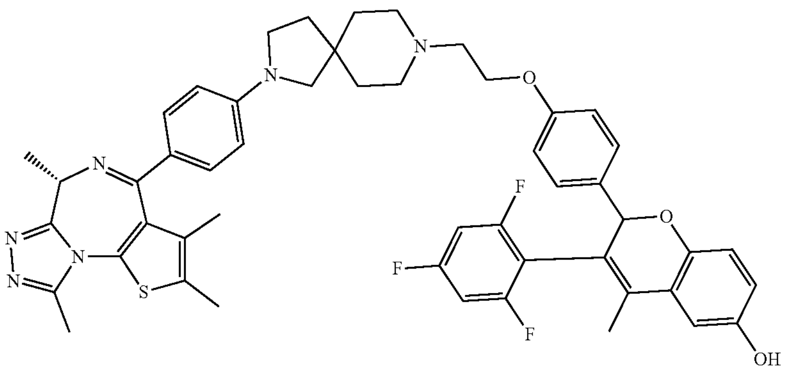 [SMILES: CC1=C(c2c(F)cc(F)cc2F)C(c2ccc(OCCN3CCC4(CC3)CCN(c3ccc(C5=N[C@@H](C)c6nnc(C)n6-c6sc(C)c(C)c65)cc3)C4)cc2)Oc2ccc(O)cc21] |
| V-17 | 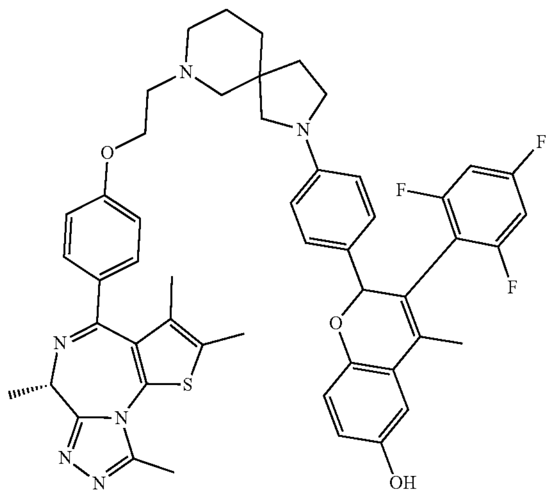 [SMILES: CC1=C(c2c(F)cc(F)cc2F)C(c2ccc(N3CCC4(CCCN(CCOc5ccc(C6=N[C@@H](C)c7nnc(C)n7-c7sc(C)c(C)c76)cc5)C4)C3)cc2)Oc2ccc(O)cc21] |
| V-18 | 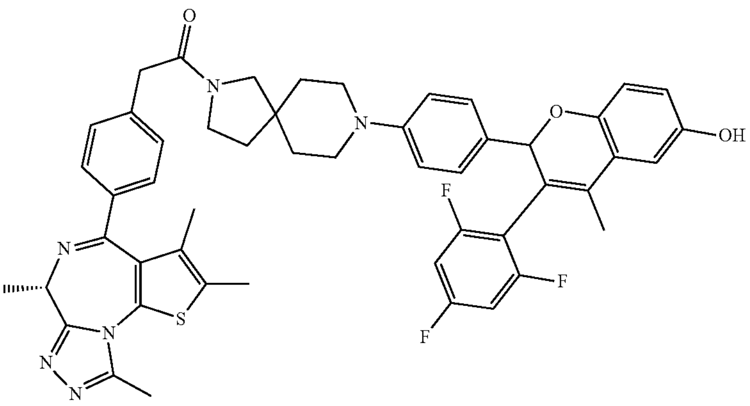 [SMILES: CC1=C(c2c(F)cc(F)cc2F)C(c2ccc(N3CCC4(CCN(C(=O)Cc5ccc(C6=N[C@@H](C)c7nnc(C)n7-c7sc(C)c(C)c76)cc5)C4)CC3)cc2)Oc2ccc(O)cc21] |

TABLE 5-continued
| Compound No. | Compound Structure |
|---|---|
| V-19 | 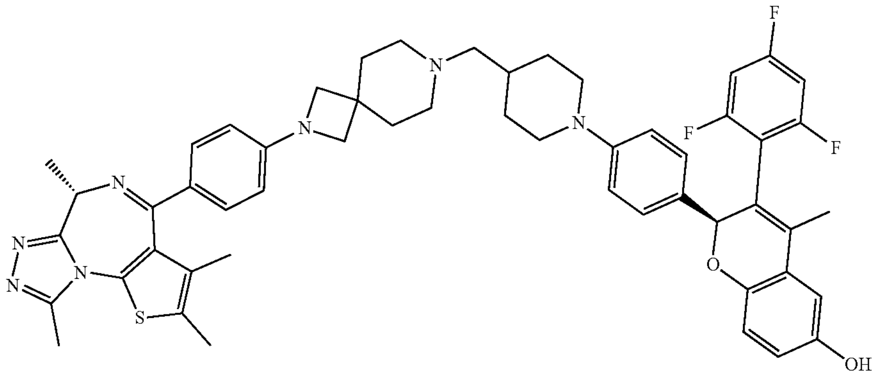 [SMILES: CC1=C(c2c(F)cc(F)cc2F)[C@H](c2ccc(N3CCC(CN4CCC5(CC4)CN(c4ccc(C6=N[C@@H](C)c7nnc(C)n7-c7sc(C)c(C)c76)cc4)C5)CC3)cc2)Oc2ccc(O)cc21] |
| V-20 | 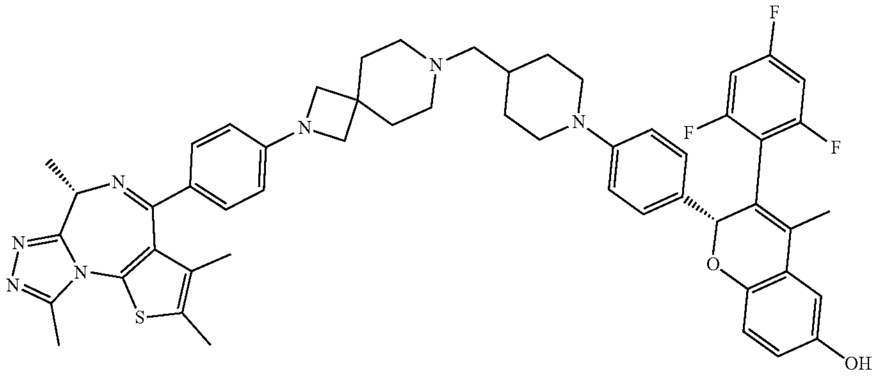 [SMILES: CC1=C(c2c(F)cc(F)cc2F)[C@@H](c2ccc(N3CCC(CN4CCC5(CC4)CN(c4ccc(C6=N[C@@H](C)c7nnc(C)n7-c7sc(C)c(C)c76)cc4)C5)CC3)cc2)Oc2ccc(O)cc21] |
| V-21 | 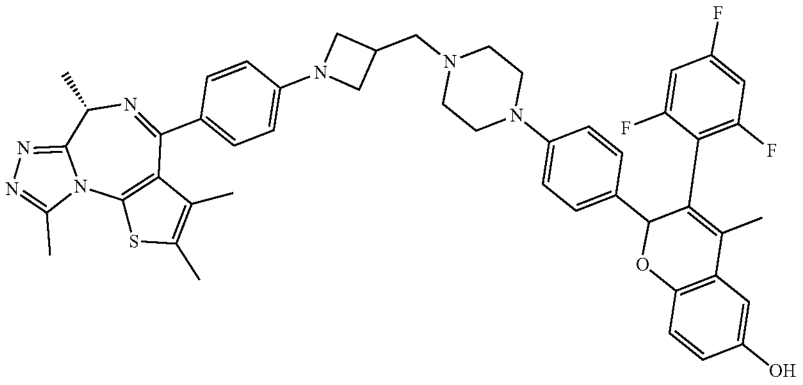 [SMILES: CC1=C(c2c(F)cc(F)cc2F)C(c2ccc(N3CCN(CC4CN(c5ccc(C6=N[C@@H](C)c7nnc(C)n7-c7sc(C)c(C)c76)cc5)C4)CC3)cc2)Oc2ccc(O)cc21] |
| V-22 | 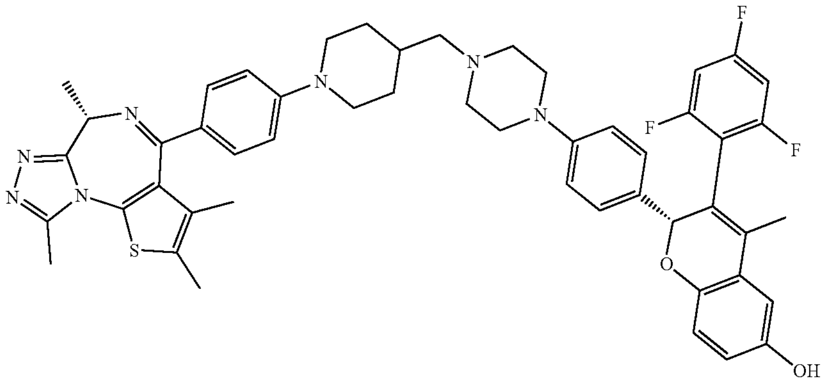 [SMILES: CC1=C(c2c(F)cc(F)cc2F)[C@@H](c2ccc(N3CCN(CC4CCN(c5ccc(C6=N[C@@H](C)c7nnc(C)n7-c7sc(C)c(C)c76)cc5)CC4)CC3)cc2)Oc2ccc(O)cc21] |

TABLE 5-continued
| Compound No. | Compound Structure |
| --- | --- |
| V-23 | 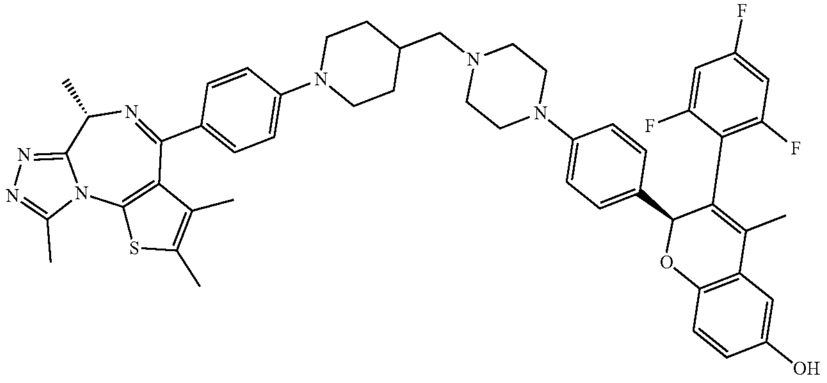 [SMILES: CC1=C(c2c(F)cc(F)cc2F)[C@H](c2ccc(N3CCN(CC4CCN(c5ccc(C6=N[C@@H](C)c7nnc(C)n7-c7sc(C)c(C)c76)cc5)CC4)CC3)cc2)Oc2ccc(O)cc21] |
| V-24 | 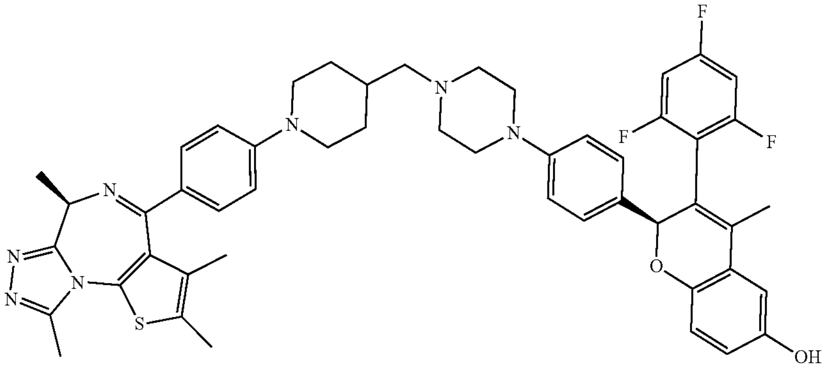 [SMILES: CC1=C(c2c(F)cc(F)cc2F)[C@H](c2ccc(N3CCN(CC4CCN(c5ccc(C6=N[C@H](C)c7nnc(C)n7-c7sc(C)c(C)c76)cc5)CC4)CC3)cc2)Oc2ccc(O)cc21] |
| V-25 | 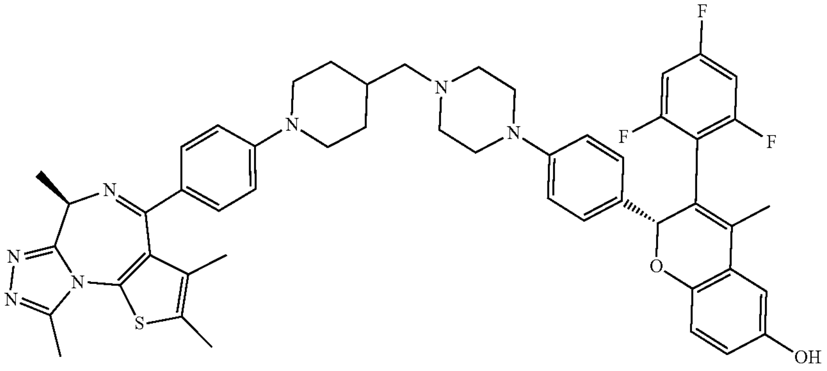 [SMILES: CC1=C(c2c(F)cc(F)cc2F)[C@@H](c2ccc(N3CCN(CC4CCN(c5ccc(C6=N[C@H](C)c7nnc(C)n7-c7sc(C)c(C)c76)cc5)CC4)CC3)cc2)Oc2ccc(O)cc21] |
| V-26 | 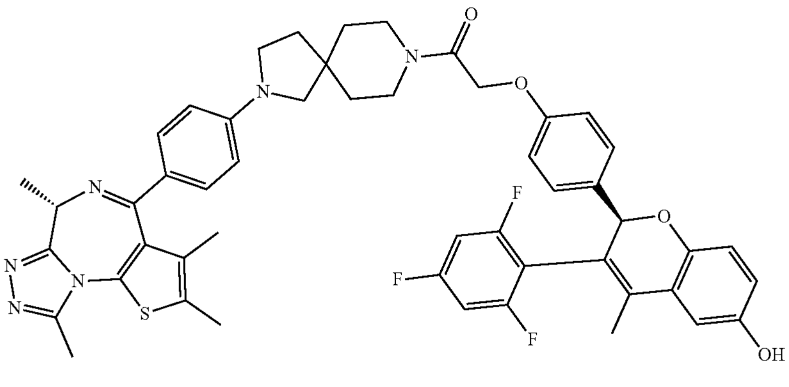 [SMILES: CC1=C(c2c(F)cc(F)cc2F)[C@@H](c2ccc(OCC(=O)N3CCC4(CC3)CCN(c3ccc(C5=N[C@@H](C)c6nnc(C)n6-c6sc(C)c(C)c65)cc3)C4)cc2)Oc2ccc(O)cc21] |

TABLE 5-continued
| Compound No. | Compound Structure |
| --- | --- |
| V-27 | 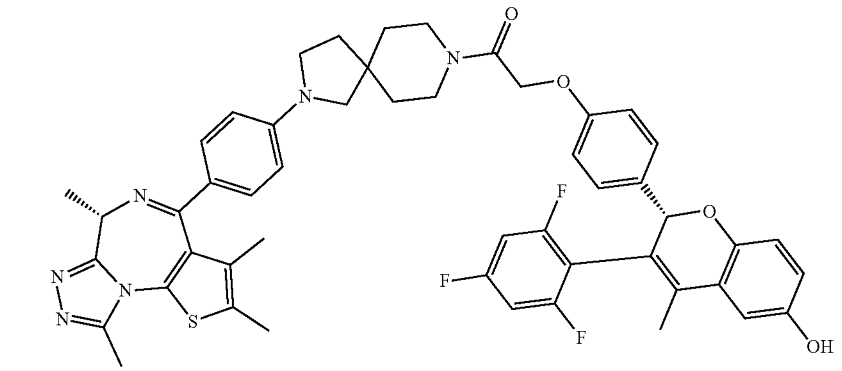 [SMILES: CC1=C(c2c(F)cc(F)cc2F)[C@H](c2ccc(OCC(=O)N3CCC4(CC3)CCN(c3ccc(C5=N[C@@H](C)c6nnc(C)n6-c6sc(C)c(C)c65)cc3)C4)cc2)Oc2ccc(O)cc21] |
| V-28 | 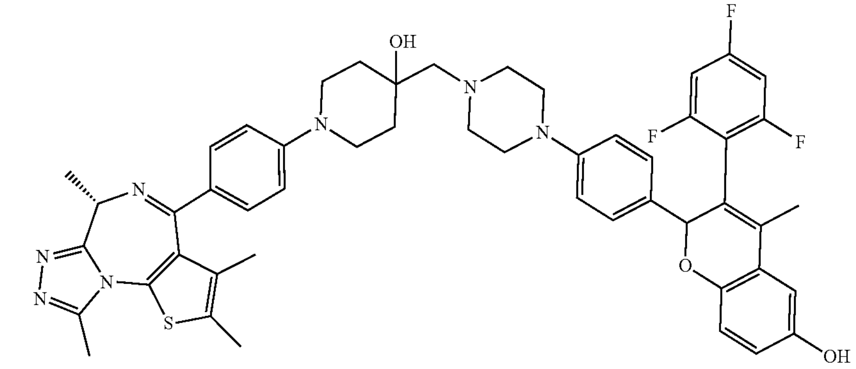 [SMILES: CC1=C(c2c(F)cc(F)cc2F)C(c2ccc(N3CCN(CC4(O)CCN(c5ccc(C6=N[C@@H](C)c7nnc(C)n7-c7sc(C)c(C)c76)cc5)CC4)CC3)cc2)Oc2ccc(O)cc21] |
| V-29 | 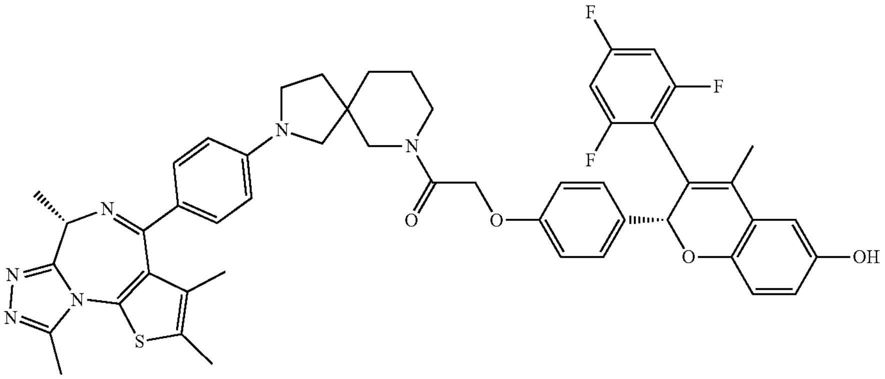 [SMILES: CC1=C(c2c(F)cc(F)cc2F)[C@@H](c2ccc(OCC(=O)N3CCCC4(CCN(c5ccc(C6=N[C@@H](C)c7nnc(C)n7-c7sc(C)c(C)c76)cc5)C4)C3)cc2)Oc2ccc(O)cc21] |
| V-30 | 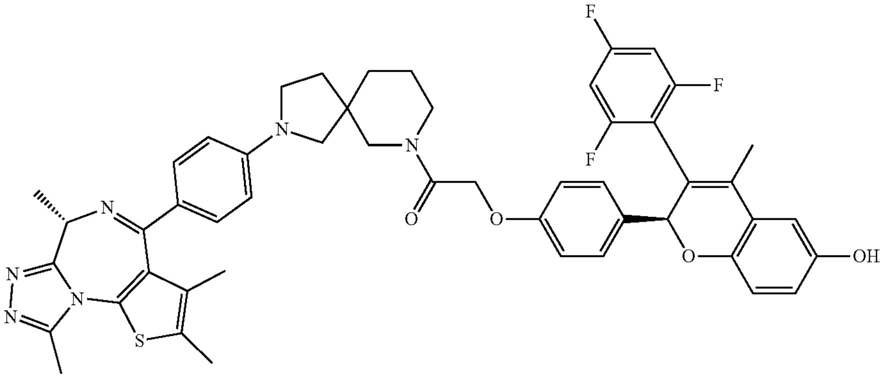 [SMILES: CC1=C(c2c(F)cc(F)cc2F)[C@H](c2ccc(OCC(=O)N3CCCC4(CCN(c5ccc(C6=N[C@@H](C)c7nnc(C)n7-c7sc(C)c(C)c76)cc5)C4)C3)cc2)Oc2ccc(O)cc21] |

TABLE 5-continued
| Compound No. | Compound Structure |
|---|---|
| V-31 | 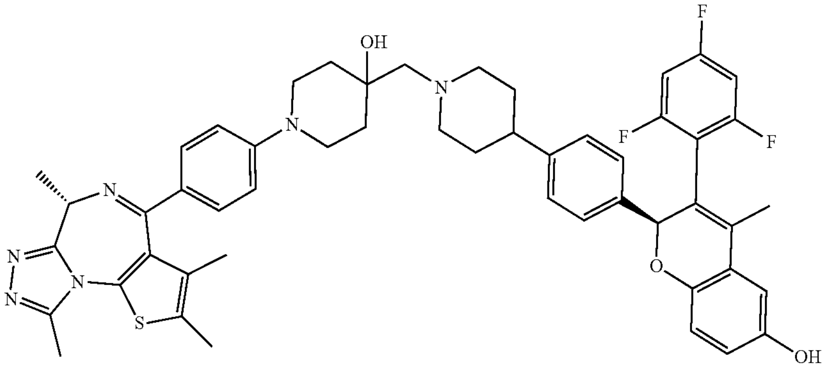 [SMILES: CC1=C(c2c(F)cc(F)cc2F)[C@H](c2ccc(C3CCN(CC4(O)CCN(c5ccc(C6=N[C@@H](C)c7nnc(C)n7-c7sc(C)c(C)c76)cc5)CC4)CC3)cc2)Oc2ccc(O)cc21] |
| V-32 | 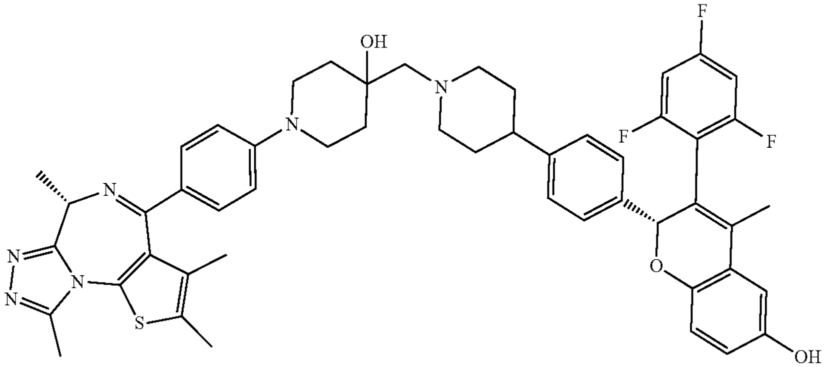 [SMILES: CC1=C(c2c(F)cc(F)cc2F)[C@@H](c2ccc(C3CCN(CC4(O)CCN(c5ccc(C6=N[C@@H](C)c7nnc(C)n7-c7sc(C)c(C)c76)cc5)CC4)CC3)cc2)Oc2ccc(O)cc21] |
| V-33 | 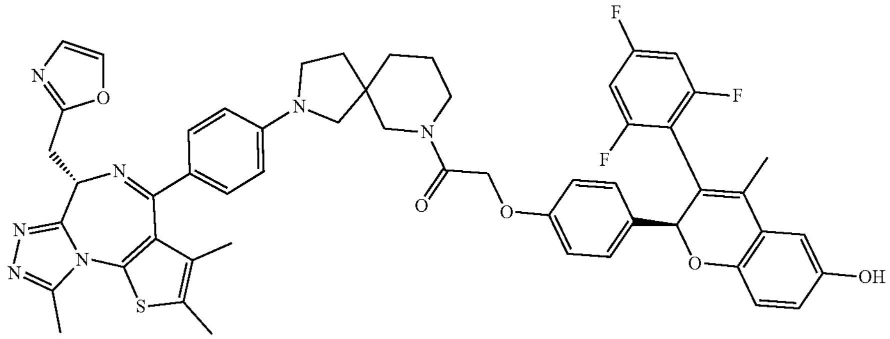 [SMILES: CC1=C(c2c(F)cc(F)cc2F)[C@H](c2ccc(OCC(=O)N3CCCC4(CCN(c5ccc(C6=N[C@@H](Cc7ncco7)c7nnc(C)n7-c7sc(C)c(C)c76)cc5)C4)C3)cc2)Oc2ccc(O)cc21] |
| V-34 | 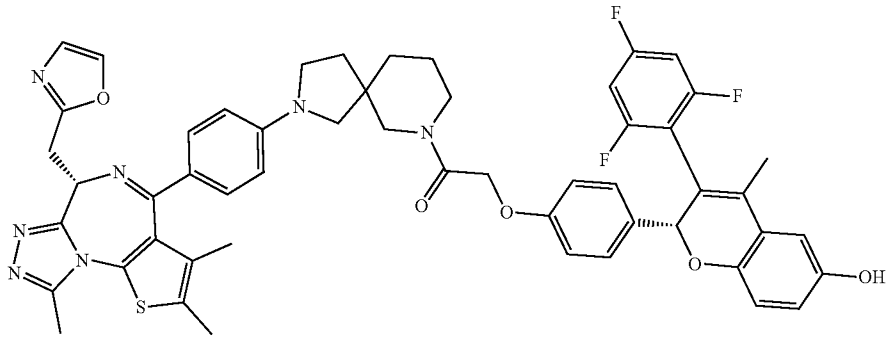 [SMILES: CC1=C(c2c(F)cc(F)cc2F)[C@@H](c2ccc(OCC(=O)N3CCCC4(CCN(c5ccc(C6=N[C@@H](Cc7ncco7)c7nnc(C)n7-c7sc(C)c(C)c76)cc5)C4)C3)cc2)Oc2ccc(O)cc21] |

TABLE 5-continued
| Compound No. | Compound Structure |
| --- | --- |
| V-35 | 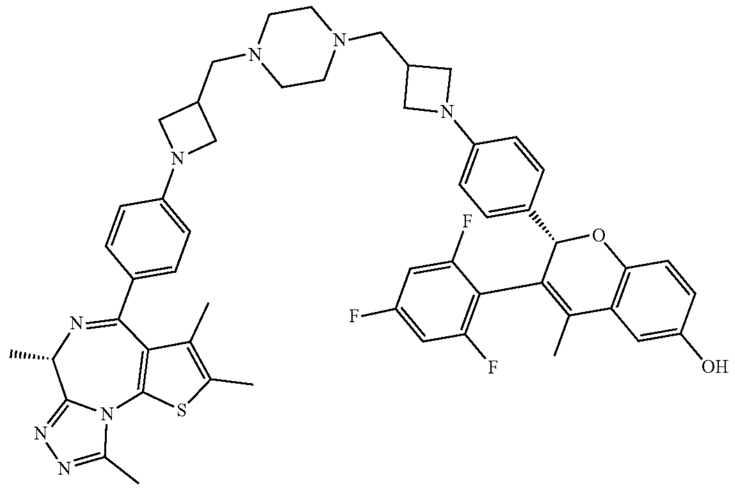 [SMILES: CC1=C(c2c(F)cc(F)cc2F)[C@H](c2ccc(N3CC(CN4CCN(CC5CN(c6ccc(C7=N[C@@H](C)c8nnc(C)n8-c8sc(C)c(C)c87)cc6)C5)CC4)C3)cc2)Oc2ccc(O)cc21] |
| V-36 | 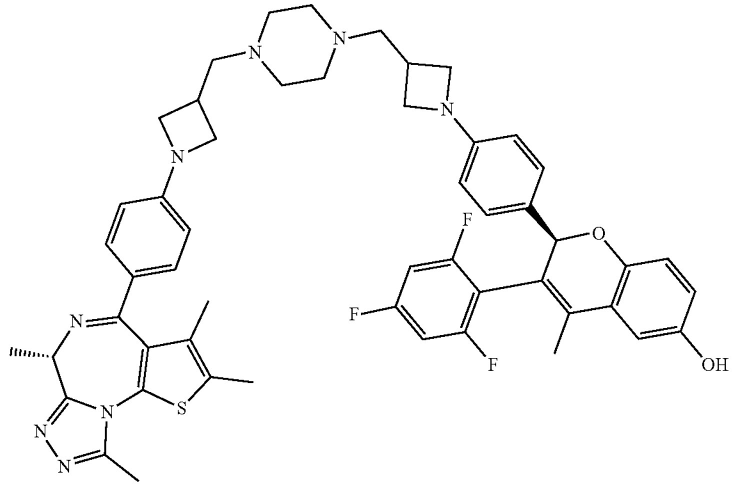 [SMILES: CC1=C(c2c(F)cc(F)cc2F)[C@@H](c2ccc(N3CC(CN4CCN(CC5CN(c6ccc(C7=N[C@@H](C)c8nnc(C)n8-c8sc(C)c(C)c87)cc6)C5)CC4)C3)cc2)Oc2ccc(O)cc21] |
| V-37 | 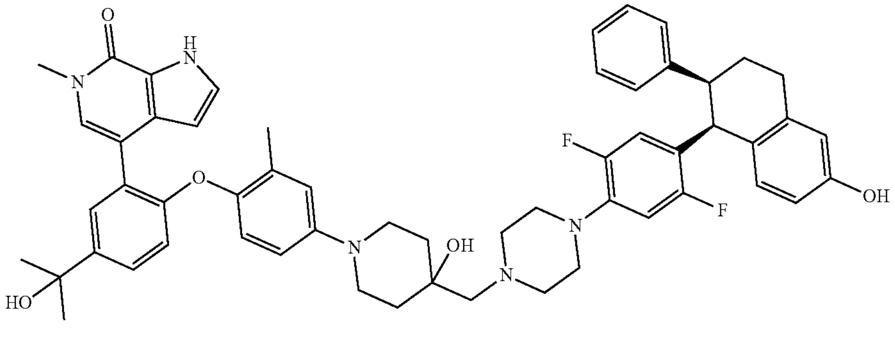 [SMILES: Cc1cc(N2CCC(O)(CN3CCN(c4cc(F)c([C@@H]5c6ccc(O)cc6CC[C@@H]5c5ccccc5)cc4F)CC3)CC2)ccc1Oc1ccc(C(C)(C)O)cc1-c1cn(C)c(=O)c2[nH]ccc12] |

TABLE 5-continued

| Compound No. | Compound Structure |
|---|---|
| V-38 | 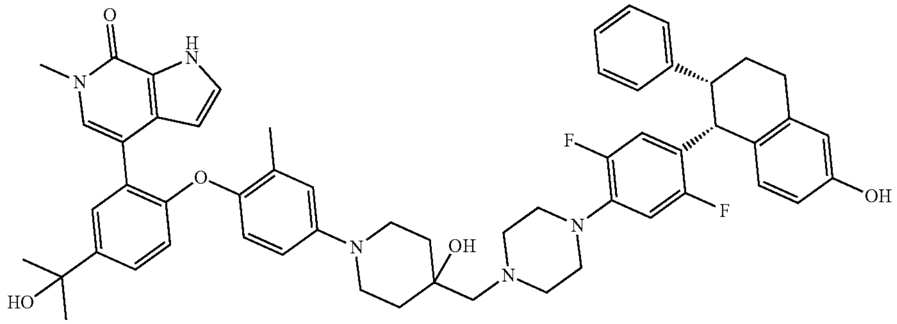 [SMILES: Cc1cc(N2CCC(O)(CN3CCN(c4cc(F)c([C@H]5c6ccc(O)cc6CC[C@H]5c5ccccc5)cc4F)CC3)CC2)ccc1Oc1ccc(C(C)(C)O)cc1-c1cn(C)c(=O)c2[nH]ccc12] |
| V-39 | 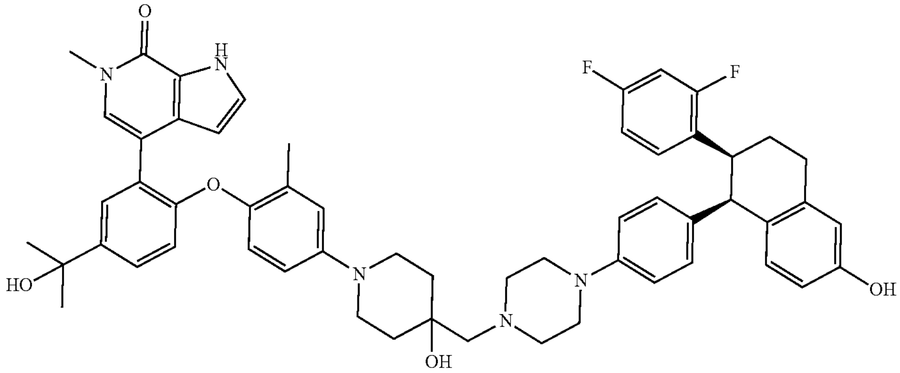 [SMILES: Cc1cc(N2CCC(O)(CN3CCN(c4ccc([C@@H]5c6ccc(O)cc6CC[C@@H]5c5ccc(F)cc5F)cc4)CC3)CC2)ccc1Oc1ccc(C(C)(C)O)cc1-c1cn(C)c(=O)c2[nH]ccc12] |
| V-40 | 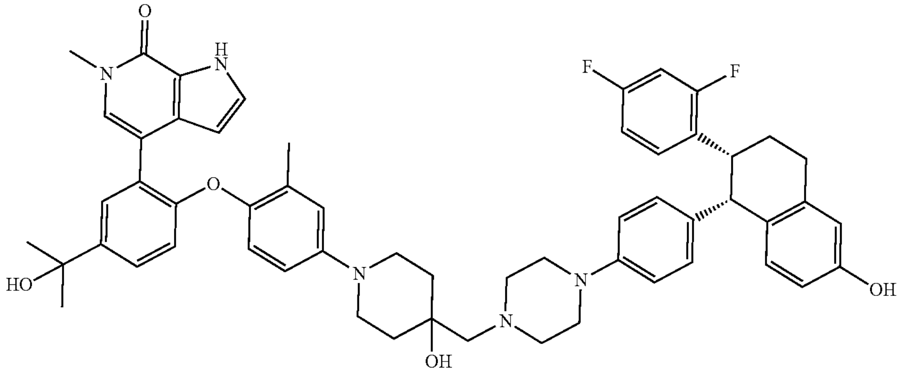 [SMILES: Cc1cc(N2CCC(O)(CN3CCN(c4ccc([C@H]5c6ccc(O)cc6CC[C@H]5c5ccc(F)cc5F)cc4)CC3)CC2)ccc1Oc1ccc(C(C)(C)O)cc1-c1cn(C)c(=O)c2[nH]ccc12] |

Synthetic Methods

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or can be prepared based on procedures described in the literature.

In the Schemes, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). Protecting group chemistry and strategy is well known in the art, for example, as described in detail in "Protecting Groups in Organic Synthesis", T. W. Greene and P. G. M. Wuts, 3rd edition, John Wiley & Sons, 1999, the entire contents of which are hereby incorporated by reference.

The synthetic route illustrated in Scheme 1 is a general method for preparing heterobifunctional compounds D. Coupling compound A (a precursor of TPL, for example, a discrete compound that is a target protein ligand) with L' (a precursor to linker L, containing functionality for coupling to the precursors of both TPL and EPL) affords intermediate B (wherein L" is a precursor to linker L that contains functionality for coupling to the EPL precursor). Coupling intermediate B with compound C (a precursor of EPL) affords heterobifunctional compound D. Alternatively, the order of coupling compounds A and C to L' may be reversed, such that L' is first coupled with compound C, before being coupled to compound A.

SCHEME 1.

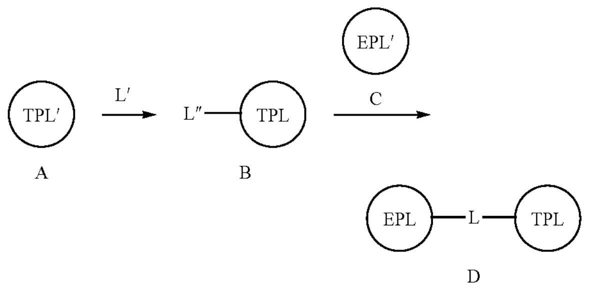

The coupling of compound A with L', and the coupling of intermediate B with compound C, can be accomplished with a wide variety of strategies. For example, amide coupling conditions can be employed when compound A (or compound C) is to be attached at a modifiable nitrogen atom and L' (or L") contains a carboxylic acid group, or vice versa (i.e. compound A contains a carboxylic acid group and L' contains a nucleophilic amine nitrogen atom). Alternatively, reductive amination conditions can be employed when compound A (or compound C) is to be attached at a modifiable nitrogen atom and L' (or L") contains an aldehyde group, or vice versa. Alternatively, nucleophilic substitution conditions can be employed when compound A (or compound C) is to be attached at a modifiable oxygen, nitrogen, or sulfur atom and L' (or L") contains a leaving group (such as an alkyl triflate, α-bromoketone, or aryl chloride), or vice versa. As yet another option, transition-metal-mediated coupling conditions can be employed when compound A (or compound C) is to be attached at a modifiable carbon, oxygen, or nitrogen atom (where the carbon atom may be activated, for example, with a bromide or sulfonate) and L' (or L") contains a suitable coupling partner (for example, an olefin for a Heck coupling, a trialkylstannane for a Stille coupling, or a boronic acid or boronate ester for a Suzuki coupling, Buchwald-Hartwig amination, or Chan-Lam coupling), or vice versa.

It is understood by one skilled in the art of organic synthesis that protecting group strategies may be employed as necessary, for example, if L' contains two of the same functional group that are to be selectively coupled to compound A and compound C. For example, L' may contain, for example, both an unprotected carboxylic acid for coupling to compound A, and a carboxylic acid group that is protected (for example, as a methyl or benzyl ester) during the coupling with compound A and subsequently deprotected (for example, via basic hydrolysis of a methyl ester or hydrogenolysis of a benzyl ester) prior to coupling with compound C.

II. Therapeutic Applications

The heterobifunctional compounds described herein, such as a compound of Formula I or II, or other compounds in Section I, provide therapeutic benefits to patients suffering from cancer. Accordingly, one aspect of the invention provides a method of treating cancer. The method comprises administering to a patient in need thereof a therapeutically effective amount of a compound described herein, such as a compound of Formula I or II, or other compounds in Section I, to treat the cancer. In certain embodiments, the particular compound of Formula I or II is a compound defined by one of the embodiments described above. In certain embodiments, the compound is a compound of Formula I, or a pharmaceutically acceptable salt thereof. In certain embodiments, the compound is a compound of Formula I. In certain embodiments, the compound is a compound of Formula I-A or I-B, or a pharmaceutically acceptable salt thereof. In certain embodiments, the compound is a compound of Formula I-A or I-B. In certain embodiments, the particular compound of Formula I, I-A, or I-B is a compound defined by one of the embodiments described above (including, for example, a compound of Formula I-A-1, I-A-2, I-A-3, I-A-4, etc.).

Cancer

In certain embodiments, the cancer is ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct and gallbladder cancers, liver cancer, pancreatic cancer, bladder cancer, urinary tract cancer, kidney cancer, eye cancer, thyroid cancer, lymphoma, or leukemia. In certain embodiments, the cancer is ovarian cancer. In certain embodiments, the cancer is endometrial cancer. In certain embodiments, the cancer is cervical cancer.

In certain embodiments, the cancer is breast cancer. In certain embodiments, the cancer is advanced breast cancer. In certain embodiments, the cancer is metastatic breast cancer. In certain embodiments, the cancer is ER+ breast cancer or ER+/HER2− breast cancer. In certain embodiments, the cancer is ER+ advanced breast cancer, ER+ metastatic breast cancer ER+/HER2− advanced breast cancer, or ER+/HER2− metastatic breast cancer. In certain embodiments, the cancer is ER+ breast cancer. In certain embodiments, the cancer is ER+ advanced breast cancer or ER+ metastatic breast cancer. In certain embodiments, the cancer is ER+/HER2− breast cancer. In certain embodiments, the cancer is ER+/HER2− advanced breast cancer or ER+/IER2− metastatic breast cancer. In certain embodiments, the cancer is sporadic breast cancer. In certain embodiments, the cancer is Cowden disease.

In certain embodiments, the cancer has a mutant estrogen receptor alpha protein. In certain embodiments, the cancer has an estrogen receptor alpha protein containing one or more of the following mutations: D538G, Y537S, and L536R.

In certain embodiments, the cancer is squamous cell cancer, lung cancer including small cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer. In certain embodiments, the cancer is at least one selected from the group consisting of ALL, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, Philadelphia chromosome positive CML, lymphoma, leukemia, multiple myeloma myeloproliferative diseases, large B cell lymphoma, or B cell Lymphoma.

In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

In certain embodiments, the cancer is a fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, or hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the cancer is bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In certain embodiments, the cancer is hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In certain embodiments, the cancer is hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In certain embodiments, the cancer is a solid tumor, such as a sarcoma, carcinoma, or lymphoma. In certain embodiments, the cancer is kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In certain embodiments, the cancer is renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In certain embodiments, the cancer is hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In certain embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

Causing Death of Cancer Cell

Another aspect of the invention provides a method of causing death of a cancer cell. The method comprises contacting a cancer cell with an effective amount of a compound described herein, such as a compound of Formula I or II, or other compounds in Section I, to cause death of the cancer cell. In certain embodiments, the compound is a compound of Formula I, or a pharmaceutically acceptable salt thereof. In certain embodiments, the compound is a compound of Formula I. In certain embodiments, the compound is a compound of Formula I-A or I-B, or a pharmaceutically acceptable salt thereof. In certain embodiments, the compound is a compound of Formula I-A or I-B. In certain embodiments, the particular compound of Formula I, I-A, or I-B is a compound defined by one of the embodiments described above (including, for example, a compound of Formula I-A-1, I-A-2, I-A-3, I-A-4, etc.).

In certain embodiments, the cancer cell is selected from ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct and gallbladder cancers, liver cancer, pancreatic cancer, bladder cancer, urinary tract cancer, kidney cancer, eye cancer, thyroid cancer, lymphoma, or leukemia cell. In certain embodiments, the cancer cell is a breast cancer cell. In certain embodiments, the cancer cell is a uterine cancer cell. In certain embodiments, the cancer cell is one or more of the cancers recited in the section above entitled "Cancer."

Diseases Mediated by the Estrogen Receptor

Another aspect of the invention provides a method of treating a disease or condition mediated by the estrogen receptor. The method comprises administering to a patient in need thereof a therapeutically effective amount of a compound described herein, such as a compound of Formula I or II, or other compounds in Section I, to treat the disease or condition. In certain embodiments, the particular compound of Formula I or II is a compound defined by one of the embodiments described above, including, for example, a compound of Formula I, I-A, I-A-1, I-A-2, I-A-3, I-A-4, etc.). In certain embodiments, the disease or condition is mediated by the estrogen receptor alpha protein. In certain embodiments, the patient has a mutant estrogen receptor alpha protein. In certain embodiments, the patient has an estrogen receptor alpha protein containing one or more of the following mutations: D538G, Y537S, and L536R. In certain embodiments, the disease or condition is endometriosis.

Combination Therapies

The compounds useful within the methods of the invention may be used in combination with one or more additional therapeutic agents useful for treating any disease contemplated herein. These additional therapeutic agents may comprise compounds that are commercially available or synthetically accessible to those skilled in the art. These additional therapeutic agents are known to treat, prevent, or reduce the symptoms, of a disease or disorder contemplated herein.

Accordingly, in certain embodiments, the method further comprises administering to the subject an additional therapeutic agent that treats the disease contemplated herein.

In certain embodiments, administering the compound of the invention to the subject allows for administering a lower dose of the additional therapeutic agent as compared to the dose of the additional therapeutic agent alone that is required to achieve similar results in treating the disease contemplated herein. For example, in certain embodiments, the compound of the invention enhances the therapeutic activity of the additional therapeutic compound, thereby allowing for a lower dose of the additional therapeutic compound to provide the same effect.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In certain embodiments, the compound of the invention and the therapeutic agent are co-administered to the subject.

In other embodiments, the compound of the invention and the therapeutic agent are coformulated and co-administered to the subject.

In certain embodiments, the compound is administered in combination with a second therapeutic agent having activity against cancer.

Accordingly, one aspect of the invention provides a method for treating cancer. The method comprises administering to a patient in need thereof a therapeutically effective amount of a compound described herein, such as a compound of Formula I or II, or other compounds in Section I, in combination with a second therapeutic agent having activity against cancer, in order to treat the cancer. In certain embodiments, the compound is a compound of Formula I, or a pharmaceutically acceptable salt thereof. In certain embodiments, the compound is a compound of Formula I. In certain embodiments, the compound is a compound of Formula I-A or I-B, or a pharmaceutically acceptable salt thereof. In certain embodiments, the compound is a compound of Formula I-A or I-B. In certain embodiments, the particular compound of Formula I, I-A, or I-B is a compound defined by one of the embodiments described above (including, for example, a compound of Formula I-A-1, I-A-2, I-A-3, I-A-4, etc.).

In certain embodiments, the method further comprises administering a third therapeutic agent having activity against cancer. In certain embodiments, the method further comprises administering a fourth therapeutic agent having activity against cancer.

In certain embodiments, the second therapeutic agent is mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

In certain embodiments, the second therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In certain embodiments, the second therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, AbbVie); and BGB-290 (BeiGene, Inc.).

In certain embodiments, the second therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In certain embodiments, the second therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In certain embodiments, the second therapeutic agent is a histone deacetylase (HDAC) inhibitor. Approved HDAC inhibitors useful in the present invention include vorinostat (Zolinza®, Merck); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In certain embodiments, the second therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In certain embodiments, the second therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); and an enzyme that breaks down kynurenine (Kynase, Kyn Therapeutics).

In certain embodiments, the second therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In certain embodiments, the second therapeutic agent is an aromatase inhibitor. Approved aromatase inhibitors which may be used in the present invention include exemestane (Aromasin®, Pfizer); anastazole (Arimidex®, AstraZeneca) and letrozole (Femara®, Novartis).

In certain embodiments, the second therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In certain embodiments, the second therapeutic agent is a folic acid inhibitor. Approved folic acid inhibitors useful in the present invention include pemetrexed (Alimta®, Eli Lilly).

In certain embodiments, the second therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In certain embodiments, the second therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In certain embodiments, the second therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In certain embodiments, the second therapeutic agent is a glutaminase inhibitor. Glutaminase inhibitors being studied which may be used in the present invention include CB-839 (Calithera Biosciences).

In certain embodiments, the second therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In certain embodiments, the second therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In certain embodiments, the second therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In certain embodiments, the second therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In certain embodiments, the second therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In certain embodiments, the second therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In certain embodiments, the second therapeutic agent is a selective estrogen receptor modulator (SERM), which interferes with the synthesis or activity of estrogens. Approved SERMs useful in the present invention include raloxifene (Evista®, Eli Lilly).

In certain embodiments, the second therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In certain embodiments, the second therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In certain embodiments, the second therapeutic agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the additional therapeutic agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1 h68/GLV-1 h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In certain embodiments, the second therapeutic agent is an immune checkpoint inhibitor selected from a PD-1 antagonist, a PD-L1 antagonist, or a CTLA-4 antagonist. In some embodiments, a compound disclosed herein or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech). Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; AstraZeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In certain embodiments, the third therapeutic agent is one of the second therapeutic agents described above. In certain embodiments, the fourth therapeutic agent is one of the second therapeutic agents described above.

Another aspect of the invention provides a compound described herein (such as a compound of Formula I, Formula II, or other compounds in Section I) for use in treating a medical disease, such a disease described herein (e.g., cancer).

Another aspect of the invention provides for the use of a compound described herein (such as a compound of Formula I, Formula II, or other compounds in Section I) in the manufacture of a medicament. In certain embodiments, the medicament is for treating a disease described herein, such as cancer.

Another aspect of the invention provides for the use of a compound described herein (such as a compound of Formula I, Formula II, or other compounds in Section I) for treating a medical disease, such a disease described herein (e.g., cancer).

III. Pharmaceutical Compositions and Dosing Considerations

As indicated above, the invention provides pharmaceutical compositions, which comprise a therapeutically effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In certain embodiments, the invention provides a pharmaceutical composition comprising a compound described herein (e.g., a compound of Formula I) and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate. Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a heterobifunctional compound described herein in a therapeutically effective amount for the treatment of a medical disorder described herein.

IV. Medical Kits

Another aspect of this invention is a kit comprising (i) a compound described herein, such as a compound of Formula I, and (ii) instructions for use, such as treating cancer.

EXAMPLES

The invention now being generally described, will be more readily understood by reference to the following examples, which are included merely for purposes of illustration of certain aspects and embodiments of the present invention, and is not intended to limit the invention.

General Methods

All reactions were carried out under an atmosphere of dry nitrogen or argon. Glassware was oven-dried prior to use. Unless otherwise indicated, common reagents or materials were obtained from commercial sources and used without further purification. N,N-Diisopropylethylamine (DIPEA) was obtained anhydrous by distillation over potassium hydroxide. Tetrahydrofuran (THF), Dichloromethane ($CH_2Cl_2$), and dimethylformamide (DMF) was dried by a PureSolv™ solvent drying system. PTLC refers to preparatory thin layer chromatographic separation. Abbreviations: HFIP (hexafluoroisopropanol), HEPES (4-(2-hydroxyethyl)-1-piperazineethanesulfonic acid. Flash column chromatography was performed using silica gel 60 (230-400 mesh). Analytical thin layer chromatography (TLC) was carried out on Merck silica gel plates with QF-254 indicator and visualized by UV or $KMnO_4$.

$^1H$ and $^{13}C$ NMR spectra were recorded on an Agilent $DD_2$ 500 (500 MHz $^1H$; 125 MHz $^{13}C$) or Agilent $DD_2$ 600 (600 MHz $^1H$; 150 MHz $^{13}C$) or Agilent $DD_2$ 400 (400 MHz $^1H$; 100 MHz $^{13}C$) spectrometer at room temperature. Chemical shifts were reported in ppm relative to the residual $CDCl_3$ (δ 7.26 ppm $^1H$; δ 77.0 ppm $^{13}C$), $CD_3OD$ (δ 3.31 ppm $^1H$; δ 49.00 ppm $^3C$), or $d_6$-DMSO (δ 2.50 ppm $^1H$; δ 39.52 ppm $^{13}C$). NMR chemical shifts were expressed in ppm relative to internal solvent peaks, and coupling constants were measured in Hz. (bs=broad signal). In most cases, only peaks of the major rotamer are reported.

Mass spectra were obtained using Agilent 1100 series LC/MSD spectrometers. Analytical HPLC analyses were carried out on 250×4.6 mm C-18 column using gradient conditions (10-100% B, flow rate=1.0 mL/min, 20 min), or as described in the LC-MS Method tables.

Unless indicated otherwise, preparative HPLC was carried out on 250×21.2 mm C-18 column using gradient conditions (10-100% B, flow rate=10.0 mL/min, 20 min). The eluents used were: solvent A ($H_2O$ with 0.1% TFA) and solvent B ($CH_3CN$ with 0.1% TFA). Final products were typically purified via reversed-phase HPLC, PTLC, or flash column chromatography. The abbreviation "TFA" refers to trifluoroacetic acid.

| LC-MS Method 01 | | | | |
|---|---|---|---|---|
| HPLC | Instrument | Agilent 1100 LC & Agilent G1956A | | |
| | Software | Agilent Chemstation Rev. B. 04.03[54] | | |
| | Column | Agilent ZORBAX 5 μm SB-Aq, 2.1*50 mm | | |
| | Mobile Phase | A: 0.0375% TFA in water (v/v)<br>B: 0.01875% TFA in Acetonitrile (v/v) | | |
| | Gradient | Time(min) | B(%) | Flow(mL/min) |
| | | 0.00 | 1 | 0.8 |
| | | 0.40 | 1 | 0.8 |
| | | 3.40 | 90 | 0.8 |
| | | 3.90 | 100 | 0.8 |
| | | 3.91 | 1 | 0.8 |
| | | 4.00 | 1 | 1.0 |
| | | 4.50 | 1 | 1.0 |
| MS | Post time(min) | 0 | | |
| | Column Temp | 50° C. | | |
| | Detector | DAD | | |
| | Ionization source | ESI | | |
| | Drying Gas | $N_2$ | | |
| | Drying Gas Flow | 10(L/min) | | |
| | Nebulizer Pressure | 40(psi) | | |
| | Drying Gas Temperature | 350° C. | | |
| | Capillary Voltage | 2500(V) | | |
| | MS Polarity | Positive | | |
| | MS Mode | Scan | | |
| | Mass Range | 100-1500 | | |

| LC-MS Method 5-95 | | | | |
|---|---|---|---|---|
| HPLC | Instrument | SHIMADZU LCMS-2020 | | |
| | Software | LabSolution Version 5.93 | | |
| | Column | Kinetex EVO C18 2.1 × 30 mm, 5 μm | | |
| | Mobile Phase | A: 0.0375% TFA in water (v/v)<br>B: 0.01875% TFA in Acetonitrile (v/v) | | |
| | Gradient | Time(min) | B(%) | Flow(mL/min) |
| | | 0.0 | 5 | 1.5 |
| | | 0.80 | 95 | 1.5 |
| | | 1.20 | 95 | 1.5 |
| | | 1.21 | 5 | 1.5 |
| | | 1.55 | 5 | 1.5 |
| MS | Column Temp | 50° C. | | |
| | Detector | PDA (220 nm&254 nm) | | |
| | Ionization source | ESI | | |
| | Drying Gas Flow | 15(L/min) | | |
| | DL Voltage | 120(v) | | |
| | Qarray DC Voltage | 20(V) | | |
| | MS Polarity | Positive | | |
| | MS Mode | Scan | | |
| | Mass range | 100-1000 | | |

| LC-MS Method 10 | | | | |
|---|---|---|---|---|
| HPLC | Instrument | Agilent 1100 LC & Agilent G1956A | | |
| | Software | Agilent Chemstation Rev. B. 04.03[54] | | |
| | Column | Agilent ZORBAX 5 μm SB-Aq, 2.1*50 mm | | |
| | Mobile Phase | A: 0.0375% TFA in water (v/v)<br>B: 0.01875% TFA in Acetonitrile (v/v) | | |
| | Gradient | Time(min) | B(%) | Flow(mL/min) |
| | | 0.00 | 10 | 0.8 |
| | | 0.40 | 10 | 0.8 |
| | | 3.40 | 100 | 0.8 |
| | | 3.90 | 100 | 0.8 |
| | | 3.91 | 10 | 0.8 |

-continued

| | | | | |
|---|---|---|---|---|
| | | 4.00 | 10 | 1.0 |
| | | 4.50 | 10 | 1.0 |
| | Post time(min) | 0 | | |
| | Column Temp | 50° C. | | |
| | Detector | DAD | | |
| MS | Ionization source | ESI | | |
| | Drying Gas | $N_2$ | | |
| | Drying Gas Flow | 10(L/min) | | |
| | Nebulizer Pressure | 40(psi) | | |
| | Drying Gas Temperature | 350° C. | | |
| | Capillary Voltage | 2500(V) | | |
| | MS Polarity | Positive | | |
| | MS Mode | Scan | | |
| | Mass Range | 100-1500 | | |

LC-MS Method 25

| | | | | |
|---|---|---|---|---|
| HPLC | Instrument | Agilent 1100 LC & Agilent G1956A | | |
| | Software | Agilent Chemstation Rev. B. 04.03[54] | | |
| | Column | Agilent ZORBAX 5 μm SB-Aq, 2.1*50 mm | | |
| | Mobile Phase | A: 0.0375% TFA in water (v/v)<br>B: 0.01875% TFA in Acetonitrile (v/v) | | |
| | Gradient | Time(min) | B(%) | Flow(mL/min) |
| | | 0.00 | 25 | 0.8 |
| | | 0.40 | 25 | 0.8 |
| | | 3.40 | 100 | 0.8 |
| | | 3.90 | 100 | 0.8 |
| | | 3.91 | 25 | 0.8 |
| | | 4.00 | 25 | 1.0 |
| | | 4.50 | 25 | 1.0 |
| | Post time(min) | 0 | | |
| | Column Temp | 50° C. | | |
| | Detector | DAD | | |
| MS | Ionization source | ESI | | |
| | Drying Gas | $N_2$ | | |
| | Drying Gas Flow | 10(L/min) | | |
| | Nebulizer Pressure | 40(psi) | | |
| | Drying Gas Temperature | 350° C. | | |
| | Capillary Voltage | 2500(V) Positive | | |
| | MS Polarity | Positive | | |
| | MS Mode | Scan | | |
| | Mass Range | 100-1500 | | |

LC-MS METHOD 40

| | | | | |
|---|---|---|---|---|
| HPLC | Instrument | Agilent 1100 LC & Agilent G1956A | | |
| | Software | Agilent Chemstation Rev. B. 04.03[16] | | |
| | Column | Agilent ZORBAX 5 μm SB-Aq, 2.1*50 mm | | |
| | Mobile Phase | A: 0.0375% TFA in water (v/v)<br>B: 0.01875% TFA in Acetonitrile (v/v) | | |
| | Gradient | Time(min) | B(%) | Flow(mL/min) |
| | | 0.00 | 40 | 0.8 |
| | | 0.40 | 40 | 0.8 |

-continued

| | | | | |
|---|---|---|---|---|
| | | 3.40 | 100 | 0.8 |
| | | 3.90 | 100 | 0.8 |
| | | 3.91 | 40 | 0.8 |
| | | 4.00 | 40 | 1.0 |
| | | 4.50 | 40 | 1.0 |
| MS | Post time(min) | 0 | | |
| | Column Temp | 50° C. | | |
| | Detector | DAD(Agilent 1100)/ELSD(Agilent 1260 Infinity) | | |
| | Ionization source | ESI | | |
| | Drying Gas | $N_2$ | | |
| | Drying Gas Flow | 10(L/min) | | |
| | Nebulizer Pressure | 2070(Torr) | | |
| | Drying Gas Temperature | 350° C. | | |
| | Capillary Voltage | 2500(V) Positive | | |

LC-MS METHOD 100

| | | | | |
|---|---|---|---|---|
| HPLC | Instrument | Agilent 1100 LC & Agilent G1956A | | |
| | Software | Agilent Chemstation Rev. B. 04.03[16] | | |
| | Column | Agilent ZORBAX 5 μm SB-Aq, 2.1*50 mm | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.00 | 0 | 0.6 |
| | | 0.40 | 0 | 0.6 |
| | | 3.40 | 80 | 0.6 |
| | | 3.90 | 100 | 0.6 |
| | | 3.91 | 0 | 0.6 |
| | | 4.00 | 0 | 1.0 |
| | | 4.50 | 0 | 1.0 |
| MS | Post time(min) | 1.20 | | |
| | Column Temp | 50° C. | | |
| | Detector | DAD | | |
| | Ionization source | ESI | | |
| | Drying Gas | N2 | | |
| | Drying Gas Flow | 10(L/min) | | |
| | Nebulizer Pressure | 2070(Torr) | | |
| | Drying Gas Temperature | 350° C. | | |
| | Capillary Voltage | 2500(V) Positive | | |
| | MS Polarity | Positive | | |
| | MS Mode | Scan | | |
| | Mass Range | 50-1500 | | |

The following abbreviations are used herein: ACN: acetonitrile; Bn: benzyl; Boc: tert-butoxycarbonyl; DCM: dichloromethane; DIEA: diisopropylethylamine; DMF: dimethylformamide; DMSO: dimethylsulfoxide; EtOH: ethanol; EA or EtOAc: ethyl acetate; equiv. or eq.: molar equivalents; FA: formic acid; h: hour or hours; HATU: 1-[bis(dimethylamino)methylene]-1H-1,2,3-triazolo[4,5-b] pyridinium 3-oxide hexafluorophosphate; HPLC: high-pressure liquid chromatography; LCMS or LC-MS: liquid chromatography-mass spectrometry; MeCN: acetonitrile; MeOH: methanol; MS: mass spectrometry; NMP: N-methylpyrrolidone; NMR: nuclear magnetic resonance; PE: petroleum ether; rt: room temperature; TEA: triethylamine; TFA: trifluoroacetic acid; THF: tetrahydrofuran; TLC: thin-layer chromatography; psi: pounds-per-square inch; and Tos or Ts: p-toluenesulfonyl.

Example 1—Synthesis of Exemplary Compounds

The compounds set forth in the table below were prepared, according to the following general approach, a related synthetic strategy, or based on procedures described herein below.

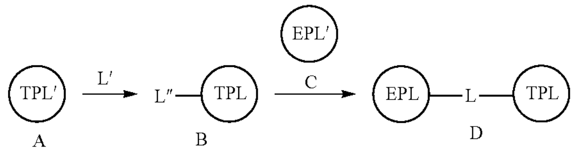

Coupling compound A (a precursor of TPL, for example, a discrete compound that is a target protein ligand) with L' (a precursor to linker L, containing functionality for coupling to the precursors of both TPL and EPL) affords intermediate B (wherein L" is a precursor to linker L that contains functionality for coupling to the EPL precursor). The coupling of compound A with L' can be accomplished using, for example, amide coupling conditions. Coupling intermediate B with compound C (a precursor of EPL) affords heterobifunctional compound D. The coupling of intermediate B with compound C can be accomplished using, for example, amide coupling conditions.

| Compound No. | Structure |
|---|---|
| I-40 | 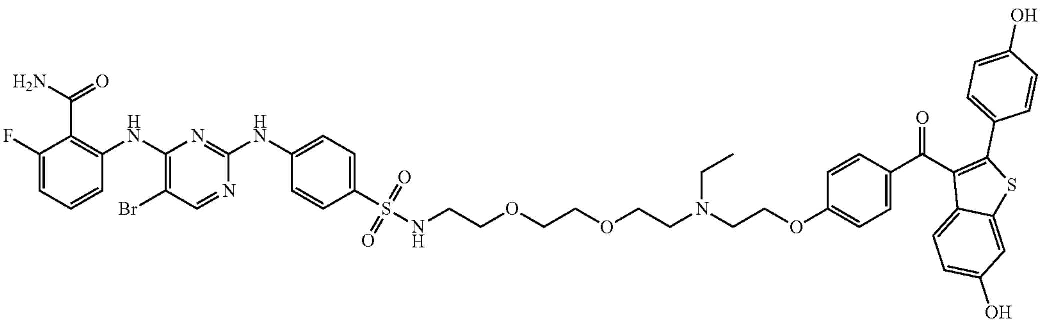 [SMILES: CCN(CCOCCOCCNS(=O)(=O)c1ccc(Nc2ncc(Br)c(Nc3cccc(F)c3C(N)=O)n2)cc1)CCOc1ccc(C(=O)c2c(-c3ccc(O)cc3)sc3cc(O)ccc23)cc1] |
| I-41 | 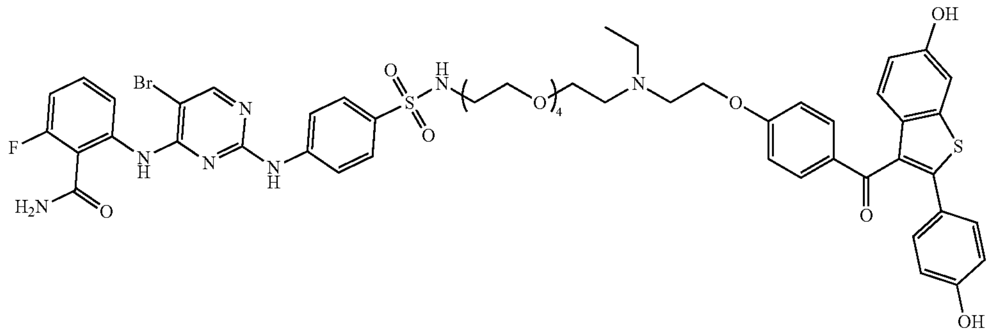 |
| I-42 | 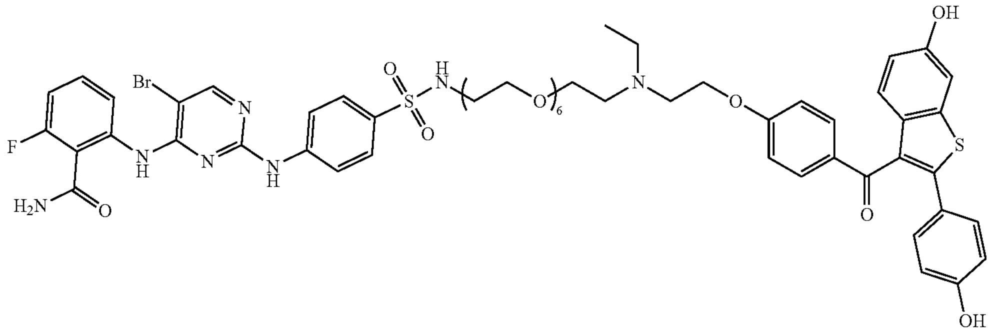 |
Physical characterization data for compounds I-40, I-41, and I-42 is provided below.
| Compound No. | Observed Mass | Retention Time (min) | LCMS Method |
|---|---|---|---|
| I-40 | 515.7, 1030.3 | 220-1.970 | 25 |
| I-41 | 559.7, 1118.3 | 220-2.013 | 25 |
| I-42 | 603.8, 1206.4 | 220-1.064 | 40 |

Example 2—Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(ethyl(2-(4-(6-hydroxy-2-(4-hydroxyphenyl) benzo[b]thiophene-3-carbonyl)phenoxy)ethyl)amino)butyl)acetamide (I-1)

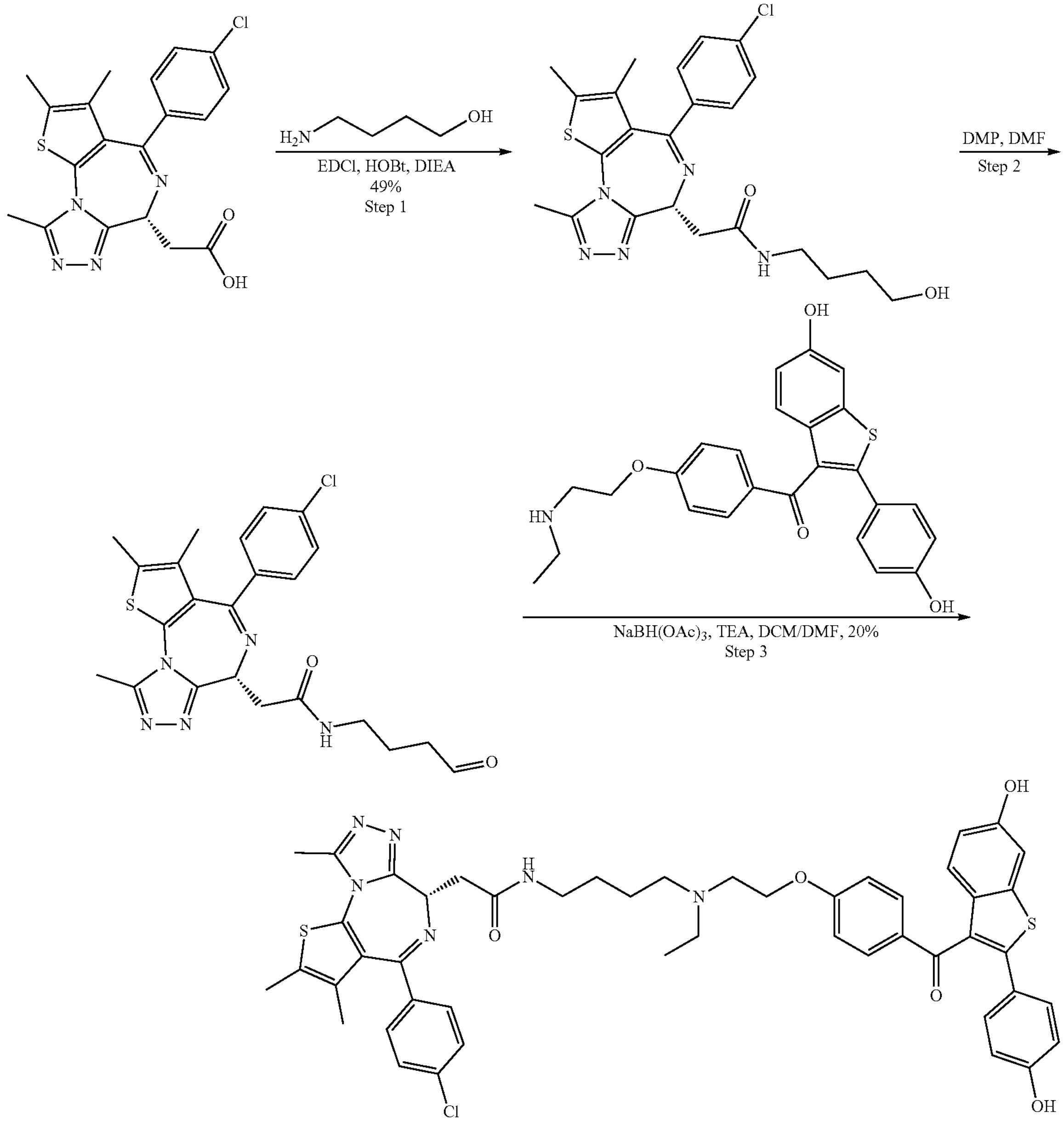

I-1

Step 1: Preparation of (S)-2-(4-(4-chlorophenyl)-2,3,9-trimethyl-6H-thieno[3,2-f][1,2,4]triazolo[4,3-a][1,4]diazepin-6-yl)-N-(4-hydroxybutyl)acetamide. To a solution of 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]acetic acid (219 mg, 546 μmol, 1.0 equiv), 4-aminobutan-1-ol (48.7 mg, 546 μmol, 50.7 μL, 1.0 equiv), EDCI (209 mg, 1.09 mmol, 2.0 equiv) and HOBt (148 mg, 1.09 mmol, 2.0 equiv) in DMF (3 mL) was added DIEA (282 mg, 2.19 mmol, 381 μL, 4.0 equiv) and the mixture was stirred at 25° C. for 16 h. The reaction mixture was diluted with water (10 mL) and extracted with DCM (20 mL×3). The combined organic layers were dried over $Na_2SO_4$, filtered and the filtrate was concentrated under reduced pressure to give a residue. The residue was purified by prep-HPLC (column: Unisil 3-100 C18 Ultra 150×50 mm×3 um; mobile phase: [water (0.225% FA)-ACN]; B %: 30%-60%, 10 min) to give (S)-2-(4-(4-chlorophenyl)-2,3,9-trimethyl-6H-thieno[3,2-f]

[1,2,4]triazolo[4,3-a][1,4]diazepin-6-yl)-N-(4-hydroxybutyl)acetamide (130 mg, 49% yield) as a white solid. LC-MS: MS ($ES^-$): RT=0.683 min, m/z=472.0 [$M+H^+$].

Step 2: Preparation of (S)-2-(4-(4-chlorophenyl)-2,3,9-trimethyl-6H-thieno[3,2-f][1,2,4]triazolo[4,3-a][1,4]diazepin-6-yl)-N-(4-oxobutyl)acetamide. To a solution of 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]-N-(4-hydroxybutyl)acetamide (50.0 mg, 106 μmol, 1.0 equiv) in DMF (1 mL) was added DMP (67.4 mg, 159 μmol, 49.2 μL, 1.5 equiv) and the mixture was stirred at 25° C. for 1 h. The mixture was filtered to give (S)-2-(4-(4-chlorophenyl)-2,3,9-trimethyl-6H-thieno[3,2-f][1,2,4]triazolo[4,3-a][1,4]diazepin-6-yl)-N-(4-oxobutyl)acetamide (50 mg) as a light yellow oil. LC-MS: MS ($ES^-$): RT=0.621 min, m/z=470.1 [$M+H^+$].

Step 3: Preparation of (S)-2-(4-(4-chlorophenyl)-2,3,9-trimethyl-6H-thieno[3,2-f][1,2,4]triazolo[4,3-a][1,4]diazepin-6-yl)-N-(4-(ethyl(2-(4-(6-hydroxy-2-(4-hydroxy phenyl)benzo[b]thiophene-3-carbonyl)phenoxy)ethyl)amino)butyl)acetamide. To a solution of [4-[2-(ethylamino)ethoxy]phenyl]-[6-hydroxy-2-(4-hydroxyphenyl) benzothiophen-3-yl]methanone (58.3 mg, 106 μmol, 1.0 equiv, TFA salt) and $NaBH(OAc)_3$ (225 mg, 1.06 mmol, 10 equiv) in DCM (1 mL) was added TEA (53.8 mg, 532 μmol, 74.0 μL, 5.0 equiv), then to the mixture solution was added a solution of (S)-2-(4-(4-chlorophenyl)-2,3,9-trimethyl-6H-thieno[3,2-f][1,2,4]triazolo[4,3-a][1,4]diazepin-6-yl)-N-(4-oxobutyl)acetamide (50.0 mg, 106 μmol, 1.0 equiv) in DMF (1 mL) and the mixture solution was stirred at 25° C. for 16 h. The reaction mixture was diluted with water (30 mL) and extracted with DCM (50 mL×3). The combined organic layers were dried over $Na_2SO_4$, filtered and the filtrate was concentrated under reduced pressure to give a residue. The residue was purified by prep-HPLC (column: Waters Xbridge 150×25 mm×5 um; mobile phase: [water (10 Mm $NH_4HCO_3$)-ACN]; B %: 36%-66%, 9 min) to give compound (S)-2-(4-(4-chlorophenyl)-2,3,9-trimethyl-6H-thieno[3,2-f][1,2,4]triazolo[4,3-a][1,4]diazepin-6-yl)-N-(4-(ethyl(2-(4-(6-hydroxy-2-(4-hydroxyphenyl) benzo[b]thiophene-3-carbonyl)phenoxy)ethyl)amino)butyl) acetamide (I-1, 18.5 mg, 20% yield) as a yellow solid. LC-MS: MS ($ES^+$): RT=1.326 min, m/z=887.3 [$M+H^+$], m/z=443.3 [$M+2H^+$]/2; LCMS method: 40. $^1$H NMR (400 MHz, DMSO-d$^6$) δ 9.76 (s, 2H), 8.17 (s, 1H), 7.63-7.61 (m, 2H), 7.45-7.42 (m, 4H), 7.33 (s, 1H), 7.32 (s, 1H), 7.17-7.15 (m, 2H), 6.89-6.87 (m, 3H), 6.68-6.65 (m, 2H), 4.51-4.50 (m, 1H), 4.03-4.00 (m, 2H), 3.32-3.30 (m, 2H), 3.21-3.18 (m, 4H), 2.73-2.67 (m, 2H), 2.58 (s, 3H), 2.50-2.44 (m, 2H), 2.37 (s, 3H), 1.42-1.41 (m, 4H), 1.09 (t, J=6.8 Hz, 3H).

Example 3—Synthesis of (S)-2-(4-(4-chlorophenyl)-2,3,9-trimethyl-6H-thieno[3,2-f][1,2,4]triazolo[4,3-a][1,4]diazepin-6-yl)-N-(8-(ethyl(2-(4-(6-hydroxy-2-(4-hydroxyphenyl) benzo[b]thiophene-3-carbonyl)phenoxy)ethyl)amino)octyl)acetamide (I-2)

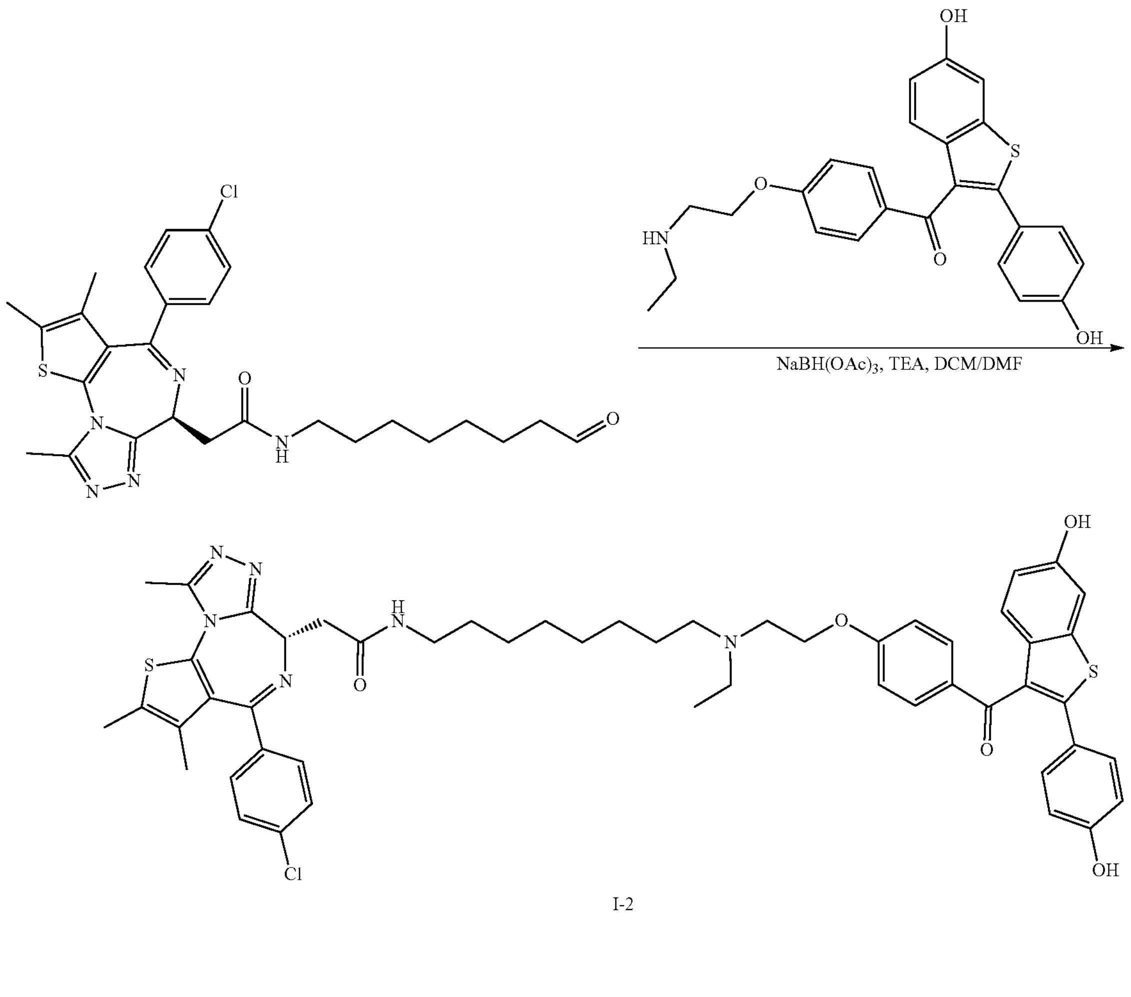

I-2

To a solution of [4-[2-(ethylamino)ethoxy]phenyl]-[6-hydroxy-2-(4-hydroxyphenyl) benzothiophen-3-yl]methanone (52.0 mg, 95.0 μmol, 1.0 equiv, TFA salt) and NaBH$(OAc)_3$ (201 mg, 950 μmol, 10 equiv) in DCM (1 mL) was added TEA (48.1 mg, 475 μmol, 66.1 μL, 5.0 equiv), then to the mixture solution was added a solution of (S)-2-(4-(4-chlorophenyl)-2,3,9-trimethyl-6H-thieno[3,2-f][1,2,4]triazolo[4,3-a][1,4]diazepin-6-yl)-N-(8-oxooctyl) acetamide (50.0 mg, 95.0 μmol, 1.0 equiv) in DMF (1 mL), the mixture solution was stirred at 25° C. for 1 h. The reaction mixture was diluted with water (30 mL), extracted with DCM (50 mL×3). The combined organic layers were dried over $Na_2SO_4$, filtered and the filtrate was concentrated under reduced pressure to give a residue. The residue was purified by prep-HPLC (column: Unisil 3-100 C18 Ultra 150×50 mm×3 um; mobile phase: [water (0.225% FA)-ACN]; B %: 28%-58%, 10 min) to give a crude product, then the crude product was purified by prep-HPLC (column: Unisil 3-100 C18 Ultra 150×50 mm×3 um; mobile phase: [water (0.225% FA)-ACN]; B %: 25%-55%, 10 min) to give 2-[(9S)-7-(4-chlorophenyl)-4,5,13-trimethyl-3-thia-1,8,11,12-tetrazatricyclo[8.3.0.$0^{2,6}$]trideca-2(6),4,7,10,12-pentaen-9-yl]-N-[8-[ethyl-[2-[4-[6-hydroxy-2-(4-hydroxyphenyl) benzothiophene-3-carbonyl]phenoxy]ethyl]amino]octyl]acetamide (I-2, 27.8 mg, 31% yield) as a yellow solid. LC-MS: MS ($ES^+$): RT=1.695 min, m/z=943.3 [$M+H^+$]; m/z=472.3 [$M+2H^+$]/2; LCMS method: 40. $^1H$ NMR (400 MHz, DMSO-$d_6$) δ 8.29 (s, 1H), 8.16-8.15 (m, 1H), 7.66-7.64 (m, 2H), 7.45-4.42 (m, 4H), 7.34-7.33 (m, 1H), 7.23 (s, 1H), 7.17-7.15 (m, 2H), 7.00-6.88 (m, 3H), 6.68-6.66 (m, 2H), 4.52-4.48 (m, 1H), 4.03-4.00 (m, 2H), 3.24-3.16 (m, 2H), 3.14-3.12 (m, 4H), 2.73-2.71 (m, 2H), 2.58 (s, 3H), 2.50-2.39 (m, 5H), 1.61 (s, 3H), 1.41-1.33 (m, 4H), 1.23-1.21 (m, 8H), 1.93-0.90 (t, J=6.8 Hz, 3H).

Example 4—Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(ethyl(2-(4-(6-hydroxy-2-(4-hydroxy phenyl)benzo[b]thiophene-3-carbonyl)phenoxy)ethyl)amino)ethoxy)ethoxy)ethyl) acetamide (I-3)

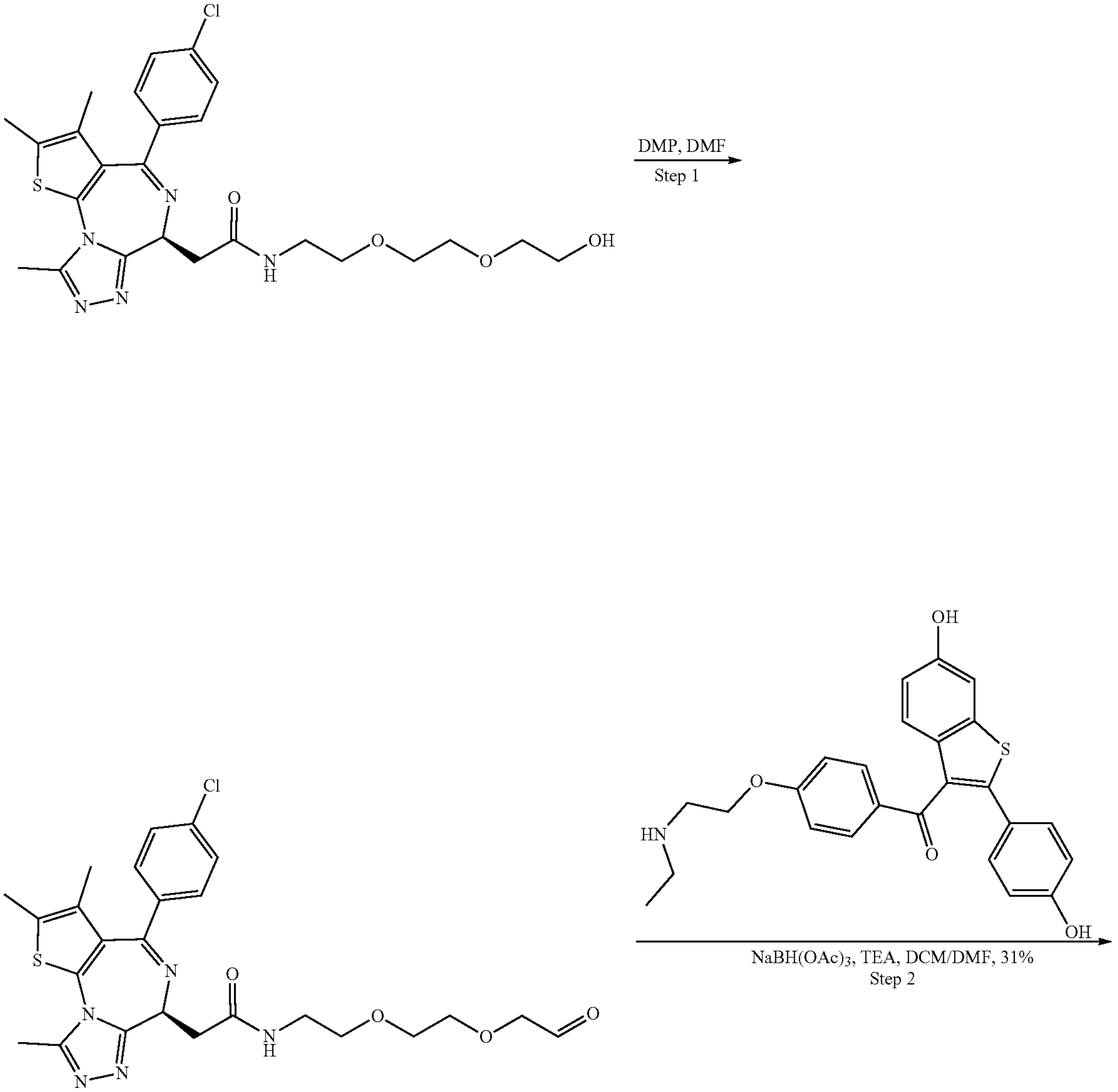

-continued

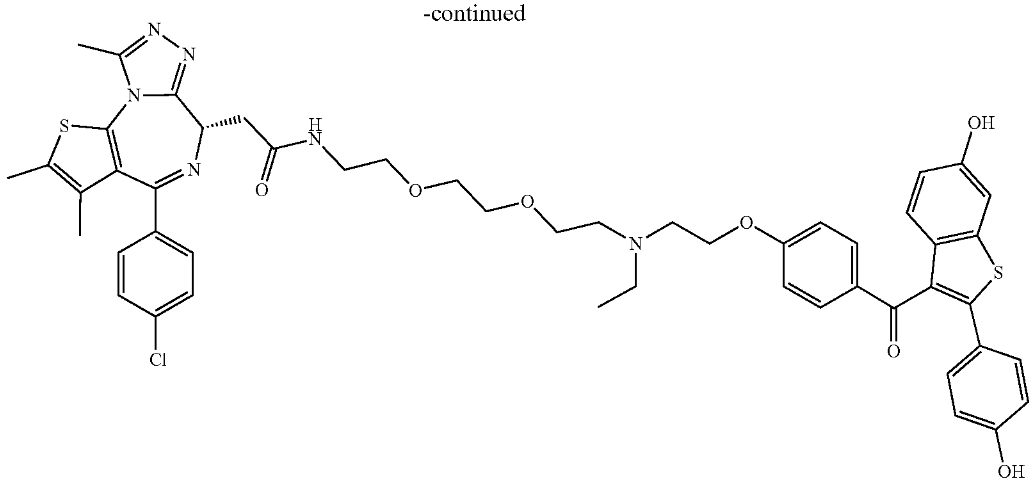

I-3

Step 1: Preparation of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-oxoethoxy)ethoxy)ethyl)acetamide. To a solution of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-oxoethoxy)ethoxy)ethyl)acetamide (55.0 mg, 103 μmol, 1.0 equiv) in DMF (1.5 mL) was added DMP (110 mg, 258 μmol, 80.0 μL, 2.5 equiv). The mixture was stirred at 25° C. for 0.5 h. The reaction mixture was concentrated to give (S)-2-(4-(4-chlorophenyl)-2,3,9-trimethyl-6H-thieno[3,2-f][1,2,4]triazolo[4,3-a][1,4]diazepin-6-yl)-N-(2-(2-(2-oxoethoxy)ethoxy)ethyl)acetamide (54 mg) as a yellow oil. LC-MS: MS ($ES^+$): RT=0.851 min, m/z=530.3 [$M+H^+$].

Step 2: Preparation of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(ethyl(2-(4-(6-hydroxy-2-(4-hydroxy phenyl)benzo[b]thiophene-3-carbonyl)phenoxy)ethyl) amino)ethoxy)ethoxy)ethyl) acetamide. To a solution of [4-[2-(ethylamino)ethoxy]phenyl]-[6-hydroxy-2-(4-hydroxy-phenyl)benzothiophen-3-yl]methanone (50.0 mg, 91.3 μmol, 1.0 equiv, TFA salt) in DCM (3 mL) was added TEA (92.4 mg, 913 μmol, 127 μL, 10 equiv) and NaBH$(OAc)_3$ (194 mg, 913 μmol, 10 equiv), then (S)-2-(4-(4-chlorophenyl)-2,3,9-trimethyl-6H-thieno[3,2-f][1,2,4]triazolo[4,3-a][1,4]diazepin-6-yl)-N-(2-(2-(2-oxoethoxy)ethoxy)ethyl)acetamide (48.4 mg, 91.3 μmol, 1.0 equiv) was added and the mixture was stirred at 20° C. for 0.5 h. The reaction mixture was concentrated under reduced pressure to remove solvent. The residue was purified by prep-HPLC (column: Waters Xbridge 150×25 mm×5 um; mobile phase: [water (10 mM $NH_4HCO_3$)-ACN]; B %: 44%-74%, 9 min)) to give compound (S)-2-(4-(4-chloro phenyl)-2,3,9-trimethyl-6H-thieno[3,2-f][1,2,4]triazolo[4,3-a][1,4]diazepin-6-yl)-N-(2-(2-(2-(ethyl(2-(4-(6-hydroxy-2-(4-hydroxy phenyl)benzo[b]thiophene-3-carbonyl)phenoxy)ethyl) amino) ethoxy)ethoxy)ethyl) acetamide (I-3, 20 mg, 23% yield) as a yellow solid. LC-MS: MS ($ES^+$): RT=2.064 min, m/z=947.2 [$M+H^+$]; m/z=474.3 [$M+2H^+$]/2 LCMS Method: 25. $^1H$ NMR (400 MHz, $CD_3OD$) δ 7.64 (d, J=8.8 Hz, 2H), 7.33-7.43 (m, 5H), 7.27 (d, J=2.1 Hz, 1H), 7.18 (d, J=8.6 Hz, 2H), 6.87 (dd, J=8.8, 2.2 Hz, 1H), 6.76 (d, J=8.9 Hz, 2H), 6.63 (d, J=8.5 Hz, 2H), 4.62 (dd, J=9.1, 5.1 Hz, 1H), 4.07 (t, J=5.7 Hz, 2H), 3.58-3.64 (m, 7H), 3.38-3.49 (m, 5H), 2.94 (t, J=5.5 Hz, 2H), 2.79 (t, J=5.6 Hz, 2H), 2.64-2.73 (m, 5H), 2.44 (s, 3H), 1.68 (s, 3H), 1.06 (t, J=7.1 Hz, 3H).

Example 5—Synthesis of (S)-2-(4-(4-chlorophenyl)-2,3,9-trimethyl-6H-thieno[3,2-f][1,2,4]triazolo [4,3-a][1,4]diazepin-6-yl)-N-(3-ethyl-1-(4-(6-hydroxy-2-(4-hydroxyphenyl) benzo[b]thiophene-3-carbonyl)phenoxy)-6,9,12,15-tetraoxa-3-azaheptadecan-17-yl) acetamide (I-4)

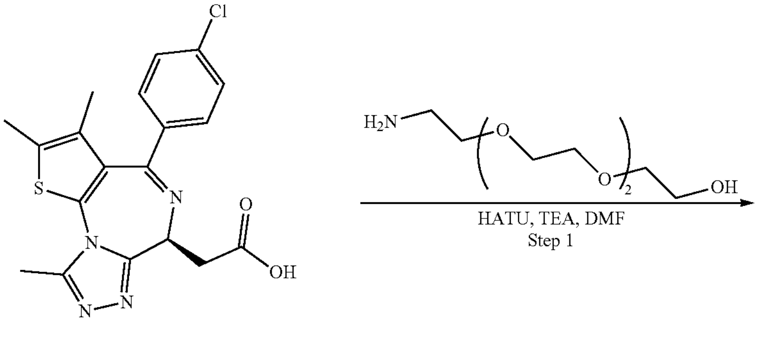

-continued

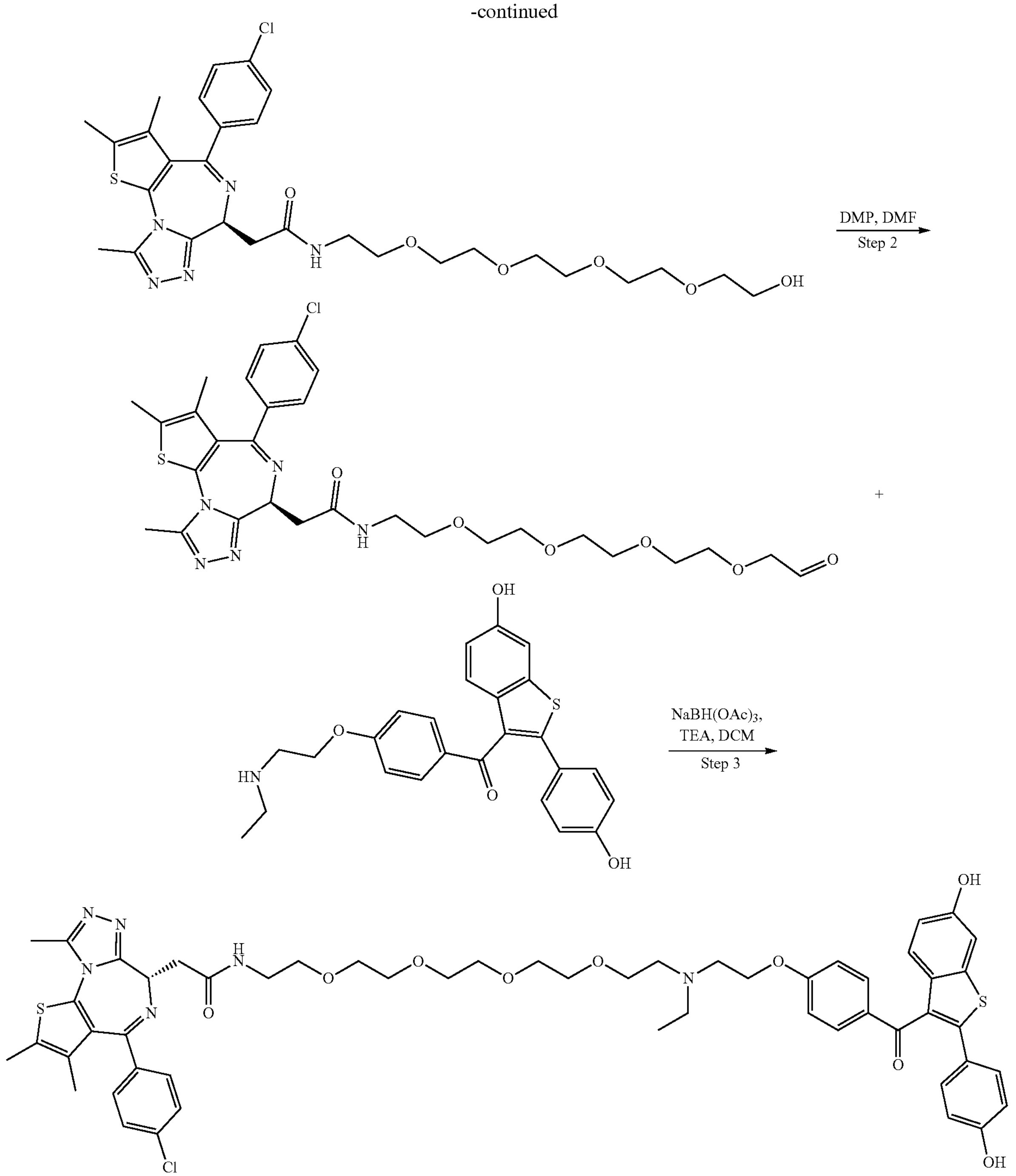

I-4

Step 1: Preparation of (S)-2-(4-(4-chlorophenyl)-2,3,9-trimethyl-6H-thieno[3,2-f][1,2,4]triazolo[4,3-a][1,4]diazepin-6-yl)-N-(14-hydroxy-3,6,9,12-tetraoxa-tetradecyl) acetamide. To a solution of 2-[2-[2-[2-(2-aminoethoxy) ethoxy]ethoxy]ethoxy]ethanol (200 mg, 569 μmol, 1.0 equiv, TFA salt) and 2-[(9S)-7-(4-chlorophenyl)-4,5,13-trimethyl-3-thia-1,8,11,12-tetrazatricyclo[8.3.0.$0^{2,6}$]trideca-2(6),4,7,10,12-pentaen-9-yl]acetic acid (293 mg, 569 μmol, 1.0 equiv, TFA salt) in DMF (2 mL) was added DIEA (368 mg, 2.85 mmol, 496 μL, 5.0 equiv) and HATU (238 mg, 626 μmol, 1.1 equiv). The mixture was stirred at 20° C. for 0.5 h. The reaction mixture was concentrated under reduced pressure to give a residue. The residue was purified by prep-HPLC (column: Phenomenex luna C18 150×25 mm×10 um; mobile phase: [water (0.225% FA)-ACN]; B %: 33%-63%, 10 min) to give compound (S)-2-(4-(4-chloro phenyl)-2,3,9-trimethyl-6H-thieno[3,2-f][1,2,4]triazolo[4,3-a][1,4]diazepin-6-yl)-N-(14-hydroxy-3,6,9,12-tetraoxatetra-decyl)acetamide (47.0 mg, 13% yield) as a yellow solid. LC-MS: MS ($ES^+$): RT=0.857 min, m/z=620.2 [$M+H^+$].

Step 2: Preparation of (S)-2-(4-(4-chlorophenyl)-2,3,9-trimethyl-6H-thieno[3,2-f][1,2,4]triazolo[4,3-a][1,4]diazepin-6-yl)-N-(14-oxo-3,6,9,12-tetraoxatetradecyl) acetamide. To a solution of 2-[(9S)-7-(4-chlorophenyl)-4,5,13-trimethyl-3-thia-1,8,11,12-tetrazatricyclo [8.3.0.0$^{2,6}$]trideca-2(6),4,7,10,12-pentaen-9-yl]-N-[2-[2-[2-[2-(2-hydroxy-ethoxy)ethoxy]ethoxy]ethoxy]ethyl]acetamide (47.0 mg, 75.8 µmol, 1.0 equiv) in DMF (1.5 mL) was added DMP (80.4 mg, 189 µmol, 58.7 µL, 2.5 equiv). The mixture was stirred at 20° C. for 1 h. The reaction mixture was concentrated to give (S)-2-(4-(4-chlorophenyl)-2,3,9-trimethyl-6H-thieno[3,2-f][1,2,4]triazolo[4,3-a][1,4]diazepin-6-yl)-N-(14-oxo-3,6,9,12-tetraoxatetradecyl) acetamide (46.5 mg) as a yellow oil. LC-MS: MS (ES$^+$): RT=0.824 min, m/z=620 [M+H$^+$].

Step 3: Preparation of (S)-2-(4-(4-chlorophenyl)-2,3,9-trimethyl-6H-thieno[3,2-f][1,2,4]triazolo[4,3-a][1,4]diazepin-6-yl)-N-(3-ethyl-1-(4-(6-hydroxy-2-(4-hydroxy phenyl)benzo[b]thiophene-3-carbonyl)phenoxy)-6,9,12,15-tetraoxa-3-azaheptadecan-17-yl)acetamide. To a solution of 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]-N-[2-[2-[2-[2-(2-oxoethoxy) ethoxy]ethoxy]ethoxy]ethyl]acetamide (46.0 mg, 74.4 µmol, 1.0 equiv) and [4-[2-(ethylamino) ethoxy]phenyl]-[6-hydroxy-2-(4-hydroxyphenyl)benzothiophen-3-yl]methanone (40.8 mg, 74.4 µmol, 1.0 equiv, TFA salt) in DCM (2 mL) was added $NaBH(OAc)_3$ (158 mg, 744 µmol, 10 equiv) and TEA (75.3 mg, 744 µmol, 104 µL, 10 equiv). The mixture was stirred at 20° C. for 12 h. The reaction mixture was concentrated under reduced pressure to remove solvent. The residue was purified by prep-HPLC (column: Phenomenex luna C18 150×25 mm×10 um; mobile phase: [water (0.225% FA)-ACN]; B %: 25%-55%, 10 min)) to give (S)-2-(4-(4-chlorophenyl)-2,3,9-trimethyl-6H-thieno[3,2-f][1,2,4]triazolo[4,3-a][1,4]diazepin-6-yl)-N-(3-ethyl-1-(4-(6-hydroxy-2-(4-hydroxyphenyl)benzo[b]thiophene-3-carbonyl)phenoxy)-6,9,12,15-tetraoxa-3-azaheptadecan-17-yl)acetamide (1-4, 15.4 mg, 20% yield) as a yellow solid. LC-MS: MS (ES$^+$): RT=1.077 min, m/z=1035.3 [M+H$^+$]; m/z=518.3 [M+2H$^+$]/2 LCMS Method: 40. $^1$H NMR (400 MHz, $CD_3OD$) δ 7.69-7.41 (m, 2H), 7.29-7.35 (m, 5H), 7.26-7.25 (m, 1H), 7.16-6.82 (m, 3H), 6.62-6.61 (m, 2H), 4.86-4.60 (m, 1H), 4.16 (s, 2H), 3.64-3.58 m, 2H), 3.58-3.55 (m, 14H), 3.43-3.32 (m, 3H), 3.31-3.30 (m, 1H), 3.15 (s, 2H), 2.65-2.42 (m, 4H), 2.65 (s, 3H), 2.42 (s, 3H), 1.67 (s, 3H), 1.15-1.12 (t, J=7 Hz, 3H).

Example 6—Synthesis of (S)-2-(4-(4-chlorophenyl)-2,3,9-trimethyl-6H-thieno[3,2-f][1,2,4]triazolo[4,3-a][1,4]diazepin-6-yl)-N-(3-ethyl-1-(4-(6-hydroxy-2-(4-hydroxyphenyl) benzo[b]thiophene-3-carbonyl)phenoxy)-6,9,12,15,18,21-hexaoxa-3-azatricosan-23-yl) acetamide (I-5)

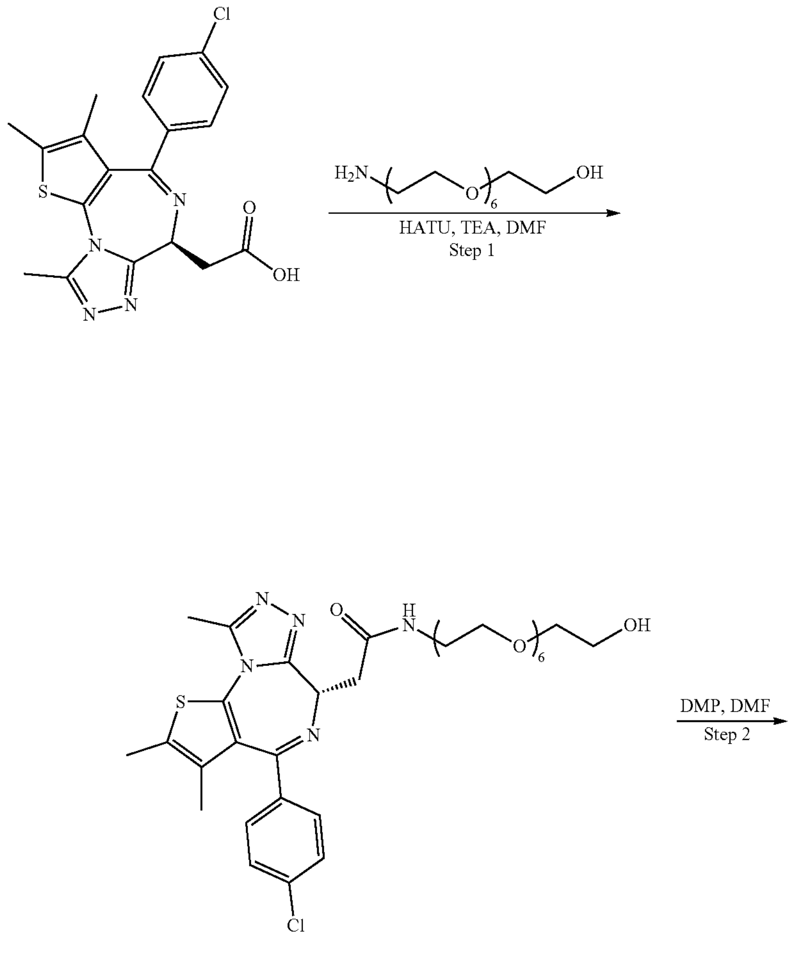

-continued

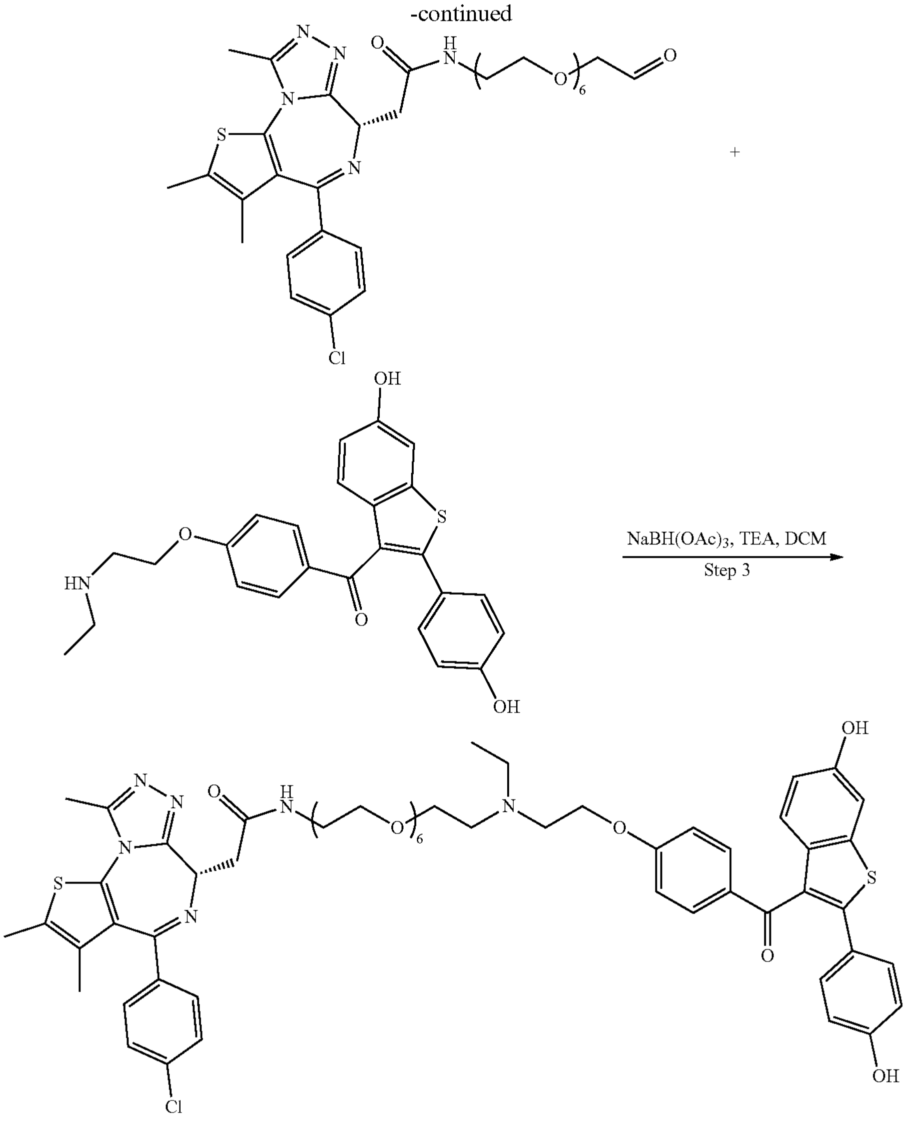

I-5

Step 1: Preparation of 2-[(9S)-7-(4-chlorophenyl)-4,5,13-trimethyl-3-thia-1,8,11, 12-tetrazatricyclo[8.3.0.0$^{2,6}$]trideca-2(6),4,7,10,12-pentaen-9-yl]-N-[2-[2-[2-[2-[2-[2-(2-hydroxyethoxy)ethoxy]ethoxy]ethoxy]ethoxy]ethoxy]ethyl] acetamide. To a solution of 2-[2-[2-[2-[2-[2-(2-aminoethoxy)ethoxy]ethoxy]ethoxy]ethoxy]ethoxy]ethanol (200 mg, 455 μmol, 1.0 equiv, TFA salt) and 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]acetic acid (234 mg, 455 μmol, 1.0 equiv, TFA salt) in DMF (4 mL) was added DIEA (176 mg, 1.37 mmol, 238 μL, 3.0 equiv) and HATU (190 mg, 501 μmol, 1.1 equiv). The mixture was stirred at 20° C. for 0.1 h. The reaction mixture was concentrated. It was purified by prep-HPLC (column: Phenomenex Gemini-NX C18 75*30 mm*3 um; mobile phase: [water (0.225% FA)-ACN]; B %: 20%-50%, 7 min) to give 2-[(9S)-7-(4-chlorophenyl)-4,5,13-trimethyl-3-thia-1,8,11, 12-tetrazatricyclo[8.3.0.0$^{2,6}$]trideca-2(6),4,7,10,12-pentaen-9-yl]-N-[2-[2-[2-[2-[2-[2-(2-hydroxyethoxy)ethoxy]ethoxy] ethoxy]ethoxy]ethoxy]ethyl]acetamide (50.0 mg, 70.6 μmol, 16% yield) as a yellow gum. LC-MS: MS (ES$^+$): RT=0.625 min, m/z=708.1 [M+H$^+$].

Step 2: Preparation of 2-[(9S)-7-(4-chlorophenyl)-4,5,13-trimethyl-3-thia-1,8,11, 12-tetrazatricyclo[8.3.0.0$^{2,6}$]trideca-2(6),4,7,10,12-pentaen-9-yl]-N-[2-[2-[2-[2-[2-[2-(2-oxoethoxy)ethoxy]ethoxy]ethoxy]ethoxy]ethoxy]ethyl] acetamide. To a solution of 2-[(9S)-7-(4-chlorophenyl)-4,5,13-trimethyl-3-thia-1,8,11,12-tetrazatricyclo[8.3.0.0$^{2,6}$] trideca-2(6),4,7,10,12-pentaen-9-yl]-N-[2-[2-[2-[2-[2-[2-(2-hydroxyethoxy) ethoxy]ethoxy]ethoxy]ethoxy]ethoxy] ethyl]acetamide (50.0 mg, 70.6 μmol, 1.0 equiv) in DMF (1 mL) was added DMP (74.9 mg, 176 μmol, 54.6 μL, 2.5 equiv). The mixture was stirred at 20° C. for 0.5 h. The reaction mixture was concentrated to give 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]-N-[2-[2-[2-[2-[2-[2-(2-oxoethoxy)ethoxy]ethoxy]ethoxy]ethoxy] ethoxy]ethyl]acetamide (49.0 mg, 69.4 μmol, 98% yield) as a yellow oil.

Step 3: Preparation of (S)-2-(4-(4-chlorophenyl)-2,3,9-trimethyl-6H-thieno[3,2-f][1,2,4]triazolo[4,3-a][1,4]diazepin-6-yl)-N-(3-ethyl-1-(4-(6-hydroxy-2-(4-hydroxyphenyl) benzo[b]thiophene-3-carbonyl)phenoxy)-6,9,12,15,18,21-hexaoxa-3-azatricosan-23-yl) acetamide. To a solution of [4-[2-(ethylamino)ethoxy]phenyl]-[6-hydroxy-2-(4-hydroxy phenyl)benzothiophen-3-yl]methanone (40.0 mg, 73.1 μmol, 1.0 equiv, TFA salt) in DCM (3 mL) was added TEA (73.9 mg, 731 μmol, 102 μL, 10 equiv) and NaBH(OAc)$_3$ (155 mg, 731 μmol, 10 equiv), then 2-[(9S)-7-(4-chlorophenyl)-4,5,13-trimethyl-3-thia-1,8,11,12-tetra zatricyclo[8.3.0.0$^{2,6}$]trideca-2(6),4,7,10,12-pentaen-9-yl]-N-[2-[2-[2-[2-[2-[2-(2-oxo ethoxy) ethoxy]ethoxy]ethoxy]ethoxy]ethoxy]ethyl]acetamide (49.0 mg, 69.4 μmol, 1.0 equiv) was added and the mixture was stirred at 20° C. for 1 h. The reaction mixture was concentrated under reduced pressure to remove solvent. The crude product was purified by prep-HPLC (column: Phenomenex luna C18 150*25 mm*10 um; mobile phase: [water (0.225% FA)-ACN]; B %: 25%-55%, 10 min and column: Phenomenex Gemini-NX C18 75*30 mm*3 um; mobile phase: [water (10 mM $NH_4HCO_3$)-ACN]; B %: 35%-65%, 8 min and column: Phenomenex Gemini-NX C18 75*30 mm*3 um; mobile phase: [water (10 mM $NH_4HCO_3$)-ACN]; B %: 35%-65%, 8 min) to give compound (S)-2-(4-(4-chlorophenyl)-2,3,9-trimethyl-6H-thieno[3,2-f][1,2,4]triazolo[4,3-a][1,4]diazepin-6-yl)-N-(3-ethyl-1-(4-(6-hydroxy-2-(4-hydroxy-phenyl)benzo[b]thiophene-3-carbonyl)phenoxy)-6,9,12,15,18,21-hexaoxa-3-azatricosan-23-yl)acetamide (I-5, 15.3 mg, 18% yield) as a yellow solid. LC-MS: MS (ES$^+$): RT=1.327 min, m/z=1123.4 [M+H$^+$]; m/z=562.3 [M+2H$^+$]/2; LCMS Method: 40. $^1$H NMR (400 MHz, $CD_3OD$) δ7.71 (d, J=9.0 Hz, 2H), 7.37-7.49 (m, 5H), 7.27 (d, J=2.3 Hz, 1H), 7.20 (d, J=8.8 Hz, 2H), 6.80-6.91 (m, 3H), 6.64 (d, J=8.8 Hz, 2H), 4.65 (d, J=5.3 Hz, 1H), 4.13 (s, 2H), 3.43-3.65 (m, 28H), 3.00 (s, 2H), 2.69 (s, 6H), 2.44 (s, 3H), 1.70 (s, 3H), 1.09 (t, J=7.6 Hz, 3H).

Example 7—Synthesis of (6S)-2,3,6,9-tetramethyl-4-(4-(3-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperidin-1-yl)pyrrolidin-1-yl)phenyl)-6H-thieno[3,2-f][1,2,4]triazolo[4,3-a][1,4]diazepine (I-6)

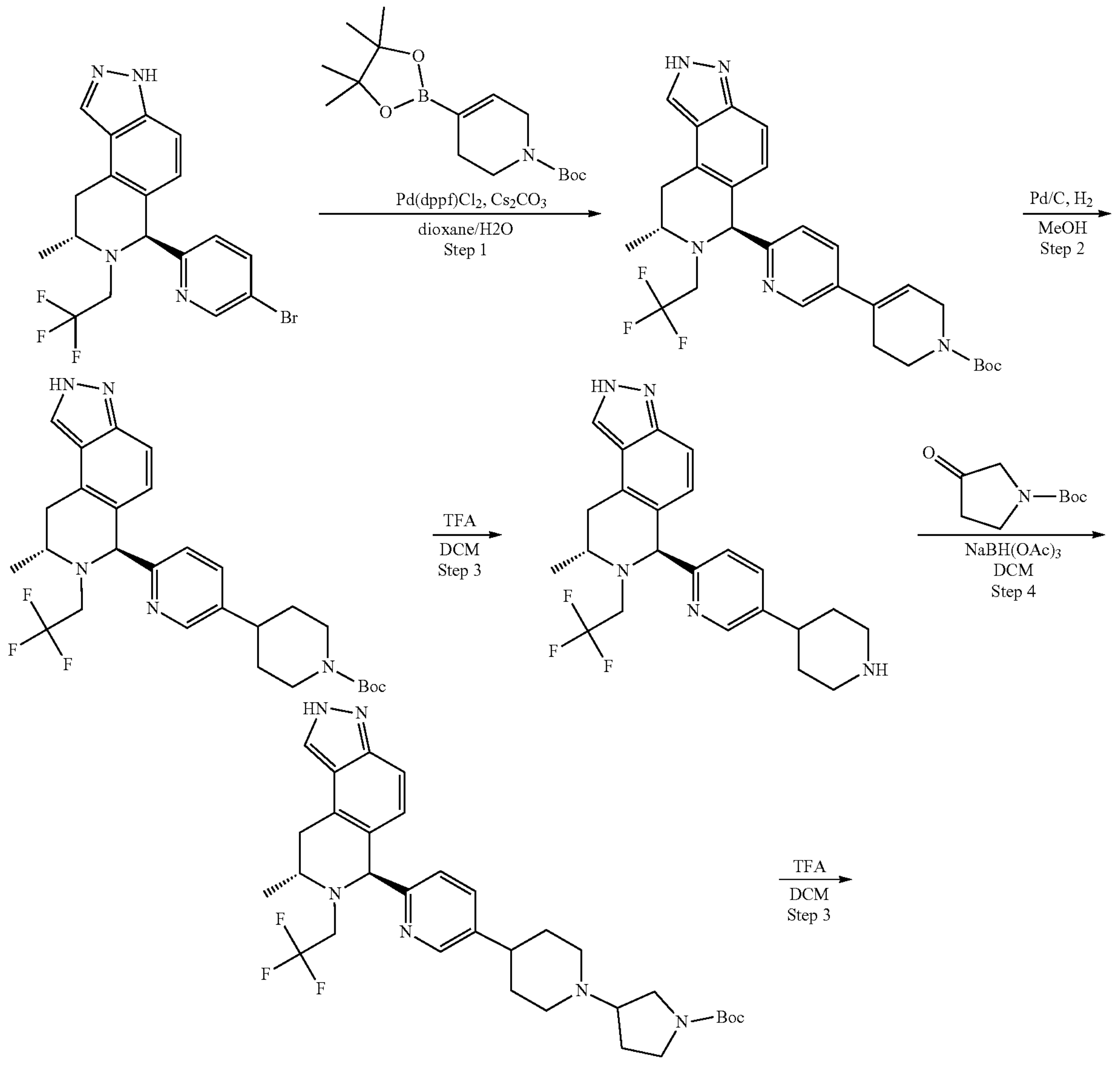

-continued

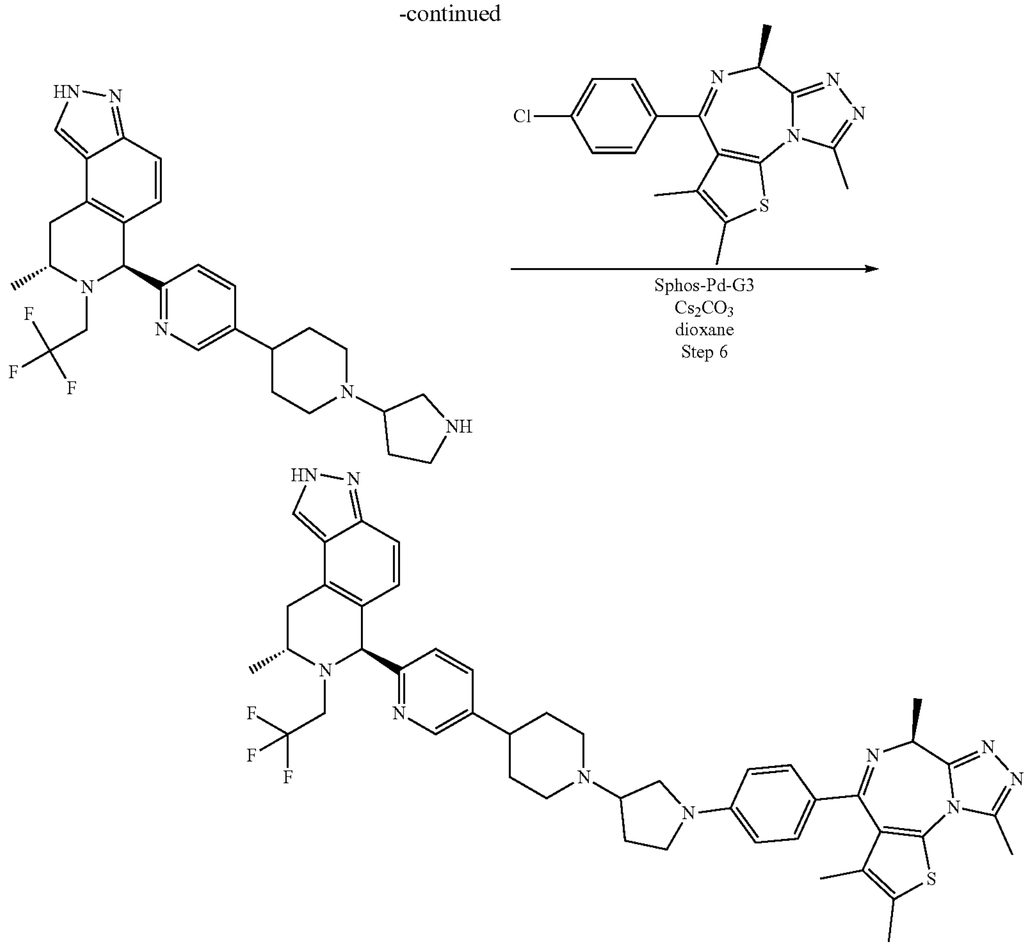

I-6

Step 1: Preparation of tert-butyl 6-((6S,8R)-8-methyl-7-(2,2,2-trifluoroethyl)-6,7,8,9-tetrahydro-2H-pyrazolo[4,3-f]isoquinolin-6-yl)-3',6'-dihydro-[3,4'-bipyridine]-1'(2'H)-carboxylate. To a solution of (6S,8R)-6-(5-bromopyridin-2-yl)-8-methyl-7-(2,2,2-trifluoroethyl)-6,7,8,9-tetrahydro-3H-pyrazolo[4,3-f]isoquinoline (700 mg, 1.65 mmol, 1.00 equiv), tert-butyl 4-(4,4,5,5-tetramethyl-1,3,2-dioxaborolan-2-yl)-3,6-dihydropyridine-1(2H)-carboxylate (610 mg, 1.98 mmol, 1.20 equiv), and cesium carbonate (1.61 g, 4.94 mmol, 3.00 equiv) in dioxane (12 mL) and water (3 mL) was added 1,1'-bis(diphenylphosphino)ferrocene-palladium(II) dichloride (240 mg, 0.32 mmol, 0.20 equiv) and the mixture was stirred at 90° C. for 2 h under a nitrogen atmosphere. The reaction mixture was quenched with water (60 mL), and then extracted with ethyl acetate (20 mL×3). The combined organic layers were washed with brine (80 mL), dried over anhydrous sodium sulfate, filtered and concentrated under reduced pressure to give a residue. The residue was purified by column chromatography (silica gel, petroleum ether/ethyl acetate=1/0 to 1/1) to afford tert-butyl 6-((6S,8R)-8-methyl-7-(2,2,2-trifluoroethyl)-6,7,8,9-tetrahydro-2H-pyrazolo[4,3-f]isoquinolin-6-yl)-3',6'-dihydro-[3,4'-bipyridine]-1'(2'H)-carboxylate (550 mg, 63% yield) as a yellow oil. LCMS: MS ($ES^+$): RT=0.530 min, m/z=528.3 $[M+H]^+$.

Step 2: Preparation of tert-butyl 4-(6-((6S,8R)-8-methyl-7-(2,2,2-trifluoro-ethyl)-6,7,8,9-tetrahydro-2H-pyrazolo[4,3-f]isoquinolin-6-yl)pyridin-3-yl)piperidine-1-carboxylate. To a solution of tert-butyl 6-((6S,8R)-8-methyl-7-(2,2,2-trifluoroethyl)-6,7,8,9-tetrahydro-2H-pyrazolo[4,3-f]isoquinolin-6-yl)-3',6'-dihydro-[3,4'-bipyridine]-1'(2'H)-carboxylate (550 mg, 1.04 mmol, 1.00 equiv) in methanol (15 mL) was added palladium on activated carbon (100 mg, 10% purity) and then the mixture was degassed and purged with hydrogen three times, and then the mixture was stirred at 25° C. for 5 h under a hydrogen (15 psi) atmosphere. The reaction mixture was filtered and concentrated under reduced pressure to afford tert-butyl 4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperidine-1-carboxylate (426 mg, 77% yield) as a yellow oil, which was used in the next step without further purification. LCMS: MS ($ES^+$): RT=0.544 min, m/z=530.3 $[M+H]^+$.

Step 3: Preparation of (6S,8R)-8-methyl-6-(5-(piperidin-4-yl)pyridin-2-yl)-7-(2,2,2-trifluoroethyl)-6,7,8,9-tetrahydro-2H-pyrazolo[4,3-f]isoquinoline. To a solution of tert-butyl 4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperidine-1-carboxylate (426 mg, 0.80 mmol, 1.00 equiv) in dichloromethane (4.5 mL) was added trifluoroacetic acid (2.30 g, 20.19 mmol, 25.10 equiv) dropwise and the mixture was stirred at 25° C. for 1 h. The reaction mixture was concentrated under reduced pressure to afford (6S,8R)-8-methyl-6-(5-(piperidin-4-yl)pyridin-2-yl)-7-(2,2,2-trifluoroethyl)-6,7,8,9-tetrahydro-2H-pyrazolo[4,3-f]isoquinoline (345 mg, 99% yield) as a white solid, which was used in the next step without further purification. LCMS: MS ($ES^+$): RT=0.432 min, m/z=430.3 $[M+H]^+$.

Step 4: Preparation of tert-butyl 3-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperidin-1-yl)pyrrolidine-1-carboxylate. To a solution of (6S,8R)-8-methyl-6-(5-(piperidin-4-yl)pyridin-2-yl)-7-(2,2,2-trifluoroethyl)-6,7,8,9-tetrahydro-2H-pyrazolo[4,3-f]isoquinoline (345 mg, 0.80 mmol, 1.00 equiv), tert-butyl 3-oxopyrrolidine-1-carboxylate (446 mg, 2.41 mmol, 3.00 equiv) in dichloromethane (8 mL) was added sodium triacetoxy borohydride (510 mg, 2.41 mmol, 3.00 equiv) and the mixture was stirred at 25° C. for 1 h. The reaction mixture was filtered and concentrated under reduced pressure to give a residue. The residue was purified by prep-TLC (dichloromethane:methanol=10:1) to afford tert-butyl 3-(4-(6-((6S,8R)-8-methyl-7-(2,2,2-trifluoroethyl)-6,7,8,9-tetrahydro-2H-pyrazolo[4,3-f] isoquinolin -6-yl)pyridin-3-yl)piperidin-1-yl)pyrrolidine-1-carboxylate (450 mg, 93% yield) as a white solid. LCMS: MS ($ES^+$): RT=0.440 min, m/z=599.3 $[M+H]^+$.

Step 5: Preparation of (6S,8R)-8-methyl-6-(5-(1-(pyrrolidin-3-yl)piperidin-4-yl)pyridin-2-yl)-7-(2,2,2-trifluoroethyl)-6,7,8,9-tetrahydro-2H-pyrazolo[4,3-f]isoquinoline. To a solution of tert-butyl 3-(4-(6-((6S,8R)-8-methyl-7-(2,2,2-trifluoroethyl)-6,7,8,9-tetrahydro-2H-pyrazolo[4,3-f] isoquinolin-6-yl)pyridin-3-yl)piperidin-1-yl)pyrrolidine-1-carboxylate (450 mg, 0.75 mmol, 1.00 equiv) in dichloromethane (4.5 mL) was added trifluoroacetic acid (2.30 g, 20.19 mmol, 26.87 equiv) dropwise and then the mixture was stirred at 25° C. for 1 h. The reaction mixture was concentrated under reduced pressure to give a residue. The residue was purified by prep-HPLC [column: Waters Xbridge Prep OBD C18 150*40 mm*10 um; mobile phase: [water($NH_4HCO_3$)-ACN]; gradient: 20%-50% B over 20 min] to afford (6S,8R)-8-methyl-6-(5-(1-(pyrrolidin-3-yl) piperidin-4-yl)pyridin-2-yl)-7-(2,2,2-trifluoroethyl)-6,7,8,9-tetrahydro-2H-pyrazolo[4,3-f]isoquinoline (230 mg, 61% yield) as a white solid. LCMS: MS ($ES^+$): RT=0.381 min, m/z=499.4 $[M+H]^+$.

Step 6: Preparation of (6S)-2,3,6,9-tetramethyl-4-(4-(3-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl) piperidin-1-yl)pyrrolidin-1-yl)phenyl)-6H-thieno[3,2-f][1, 2,4]triazolo[4,3-a][1,4]diazepine. To a solution of (6S,8R)-8-methyl-6-(5-(1-(pyrrolidin-3-yl)piperidin-4-yl)pyridin-2-yl)-7-(2,2,2-trifluoroethyl)-6,7,8,9-tetrahydro-2H-pyrazolo [4,3-f]isoquinoline (150 mg, 0.30 mmol, 1.00 equiv), (S)-4-(4-chlorophenyl)-2,3,6,9-tetramethyl-6H-thieno[3,2-f][1, 2,4]triazolo [4,3-a][1,4]diazepine (161 mg, 0.45 mmol, 1.50 equiv), cesium carbonate (294 mg, 0.90 mmol, 3.00 equiv) in dioxane (3 mL) was added (2-dicyclohexylphosphino-2',6'-dimethoxybiphenyl) [2-(2'-amino-1,1'-biphenyl)]palladium(II) methanesulfonate (46 mg, 0.060 mmol, 0.20 equiv) and the mixture was stirred at 90° C. for 4 h under nitrogen atmosphere. The reaction mixture was filtered and concentrated under reduced pressure to give a residue. The residue was purified by prep-HPLC [column: Phenomenex luna C18 150×25 mm×10 um; mobile phase: [water(FA)-ACN]; gradient: 8%-38% B over 1 min] to give the crude product. The product was purified by SFC [column: DAICEL CHIRALCEL OX (250 mm*30 mm, 10 um); mobile phase: [$CO_2$-ACN/MeOH (0.1% $NH_3H_2O$)]; B %: 70%, isocratic elution mode] to give the crude product (peak 1). The crude product was further purified by prep-HPLC [column: Phenomenex luna C18 150 mm×25 mm×10 um; mobile phase: [water (FA)-ACN]; gradient: 8%-38% B over 1 min] to afford (6S)-2,3,6,9-tetramethyl-4-(4-(3-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperidin-1-yl) pyrrolidin-1-yl)phenyl)-6H-thieno[3,2-f][1,2,4]triazolo[4,3-a][1,4] diazepine (I-6, 10.37 mg, 4.17% yield) as a yellow solid. LCMS: MS ($ES^+$): RT=0.981 min, m/z=819.6 $[M+H]^+$. $^1H$ NMR (400 MHz, $CDCl_3$) δ 8.38 (s, 1H), 8.06 (s, 1H), 7.50 (d, J=8.0 Hz, 1H), 7.42-7.35 (m, 3H), 7.23 (s, 1H), 6.98 (d, J=8.8 Hz, 1H), 6.47 (d, J=8.4 Hz, 2H), 5.13 (s, 1H), 4.16-4.08 (m, 1H), 3.63-3.54 (m, 2H), 3.52-3.45 (m, 1H), 3.40-3.25 (m, 4H), 3.23-3.15 (m, 1H), 3.12-2.95 (m, 3H), 2.93-2.86 (m, 1H), 2.67 (s, 3H), 2.61-2.53 (m, 1H), 2.41 (s, 3H), 2.34-2.14 (m, 4H), 2.07 (d, J=6.4 Hz, 3H), 1.92-1.85 (m, 4H), 1.78 (s, 3H), 1.17 (d, J=6.4 Hz, 3H).

Example 8—Synthesis of (S)-2,3,6,9-tetramethyl-4-(4-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl) piperazin-1-yl)phenyl)-6H-thieno[3,2-f][1,2,4]triazolo[4,3-a][1,4]diazepine (I-7)

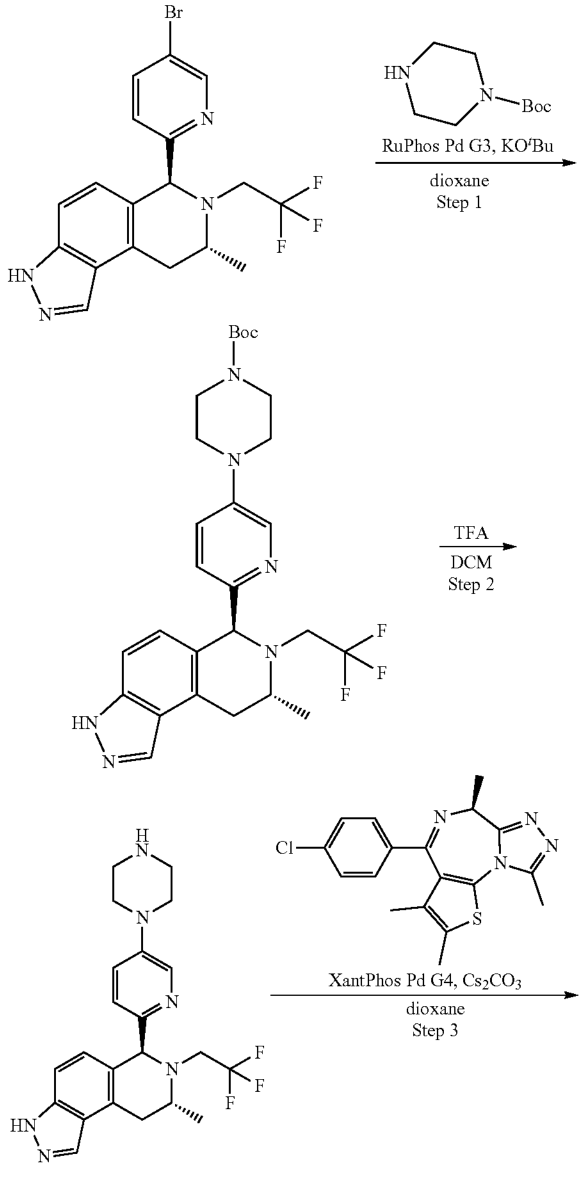

-continued

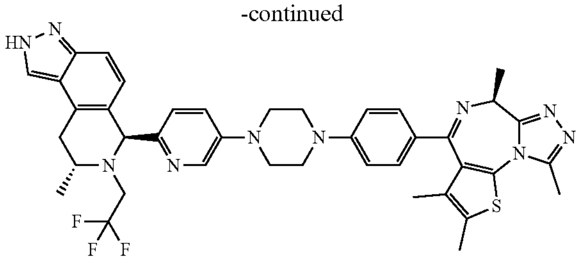

I-7

Step 1: Preparation of tert-butyl 4-(6-((6S,8R)-8-methyl-7-(2,2,2-trifluoroethyl)-6,7,8,9-tetrahydro-3H-pyrazolo[4,3-f]isoquinolin-6-yl)pyridin-3-yl)piperazine-1-carboxylate. To a solution of (6S,8R)-6-(5-bromopyridin-2-yl)-8-methyl-7-(2,2,2-trifluoroethyl)-6,7,8,9-tetrahydro-3H-pyrazolo[4,3-f]isoquinoline (1.00 g, 2.35 mmol, 1.00 equiv), tert-butyl piperazine-1-carboxylate (1.75 g, 9.41 mmol, 4.00 equiv), and potassium tert-butoxide (1.06 g, 9.41 mmol, 4.00 equiv) in dioxane (20 mL) was added methanesulfonato(2-dicyclo hexylphosphino-2,6-di-1-propoxy-1,1-biphenyl)(2-amino-1,1-biphenyl-2-yl)palladium(ii) (393 mg, 0.47 mmol, 0.20 equiv) and the mixture was stirred at 100° C. for 10 h under a nitrogen atmosphere. The reaction mixture was quenched with water (100 mL), and then extracted with ethyl acetate (30 mL×3). The combined organic layers were washed with brine (100 mL), dried over anhydrous sodium sulfate, filtered and concentrated under reduced pressure to give a residue. The residue was purified by column chromatography (silica gel, petroleum ether/ethyl acetate=1/0 to 1/1) to afford tert-butyl 4-(6-((6S,8R)-8-methyl-7-(2,2,2-trifluoroethyl)-6,7,8,9-tetrahydro-3H-pyrazolo[4,3-f]isoquinolin-6-yl)pyridin-3-yl)piperazine-1-carboxylate (400 mg, 32% yield) as a yellow solid. LCMS: MS ($ES^+$): RT=0.493 min, m/z=531.4 $[M+H]^+$.

Step 2: Preparation of (6S,8R)-8-methyl-6-(5-(piperazin-1-yl)pyridin-2-yl)-7-(2,2,2-trifluoroethyl)-6,7,8,9-tetrahydro-3H-pyrazolo[4,3-f]isoquinoline. To a solution of tert-butyl 4-(6-((6S,8R)-8-methyl-7-(2,2,2-trifluoroethyl)-6,7,8,9-tetrahydro-3H-pyrazolo[4,3-f]isoquinolin-6-yl)pyridin-3-yl)piperazine-1-carboxylate (400 mg, 0.75 mmol, 1.00 equiv) in dichloromethane (4.5 mL) was added dropwise trifluoroacetic acid (2.30 g, 20.19 mmol, 26.79 equiv) and the mixture was stirred at 25° C. for 1 h. The reaction mixture was concentrated under reduced pressure to give a residue. The residue was purified by prep-HPLC [column: Waters Xbridge 150×25 mm×5 um; mobile phase: [water (ammonia hydroxide v/v)-ACN]; gradient: 20%-500% B over 10 min] to afford (6S,8R)-8-methyl-6-(5-(piperazin-1-yl)pyridin-2-yl)-7-(2,2,2-trifluoroethyl)-6,7,8,9-tetrahydro-3H-pyrazolo[4,3-f]isoquinoline (130 mg, 40% yield) as a white solid. LCMS: MS ($ES^+$): RT=0.585 min, m/z=431.2 $[M+H]^+$.

Step 3: Preparation of (S)-2,3,6,9-tetramethyl-4-(4-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperazin-1-yl)phenyl)-6H-thieno[3,2-f][1,2,4]triazolo[4,3-a][1,4]diazepine. To a solution of (6S,8R)-8-methyl-6-(5-(piperazin-1-yl)pyridin-2-yl)-7-(2,2,2-trifluoroethyl)-6,7,8,9-tetrahydro-3H-pyrazolo[4,3-f]isoquinoline (35 mg, 0.08 mmol, 1.00 equiv), (S)-4-(4-chlorophenyl)-2,3,6,9-tetramethyl-6H-thieno[3,2-f][1,2,4]triazolo[4,3-a][1,4]diazepine (43 mg, 0.12 mmol, 1.50 equiv), and cesium carbonate (79 mg, 0.24 mmol, 3.00 equiv) in dioxane (1 mL) was added dicyclohexyl-[2-(2,4,6-triisopropylphenyl)phenyl]phosphane; methanesulfonate; [2-[2-(methylamino)phenyl]phenyl]palladium(1+) (13 mg, 0.01 mol, 0.20 equiv) and the mixture was stirred at 90° C. for 2 h under nitrogen atmosphere. The reaction mixture was filtered and concentrated under reduced pressure to give a residue. The residue was purified by prep-HPLC [column: Phenomenex luna C18 150×25 mm×10 um; mobile phase: [water(FA)-ACN]; gradient: 15%-45% B over 1 min] to give the crude product. The crude product was purified by SFC [column: DAICEL CHIRALCEL OD (250 mm*30 mm, 10 um); mobile phase: [$CO_2$-ACN/EtOH (0.1% NH3H2O)]; B %: 60%, isocratic elution mode] to give a product that was further purified by prep-HPLC [column: Phenomenex luna C18 150*25 mm*10 um; mobile phase: [water(FA)-ACN]; gradient: 15%-45% B over 1 min] to afford (S)-2,3,6,9-tetramethyl-4-(4-(4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperazin-1-yl)phenyl)-6H-thieno [3,2-f][1,2,4]triazolo [4,3-a][1,4]diazepine (I-7, 8.61 mg, 13.53% yield) as a yellow solid. LCMS: MS ($ES^+$): RT=1.483 min, m/z=751.6 $[M+H]^+$; LCMS Method: 10. $^1$H NMR (400 MHz, $CDCl_3$) δ 8.21 (d, J=2.8 Hz, 1H), 8.07 (s, 1H), 7.43 (d, J=8.4 Hz, 2H), 7.31 (d, J=9.2 Hz, 1H), 7.24-7.18 (m, 2H), 6.94 (d, J=8.8 Hz, 1H), 6.89 (d, J=8.8 Hz, 2H), 5.08 (s, 1H), 4.15 (q, J=6.8 Hz, 1H), 3.66-3.56 (m, 1H), 3.46-3.38 (m, 4H), 3.38-3.30 (m, 5H), 3.29-3.18 (m, 1H), 3.08-2.99 (m, 1H), 2.93-2.85 (m, 1H), 2.68 (s, 3H), 2.42 (s, 3H), 2.08 (d, J=6.8 Hz, 3H), 1.76 (s, 3H), 1.16 (d, J=6.4 Hz, 3H).

Example 9—Synthesis of 4-((3-(4-((ethyl(2-(6-hydroxy-1,2,3,4-tetrahydronaphthalen-2-yl)-5-methoxyphenyl)amino)methyl)phenyl)azetidin-1-yl)methyl)-1-(4-((S)-2,3,6,9-tetra methyl-6H-thieno[3,2-f][1,2,4]triazolo[4,3-a][1,4]diazepin-4-yl)phenyl)piperidin-4-ol (I-8)

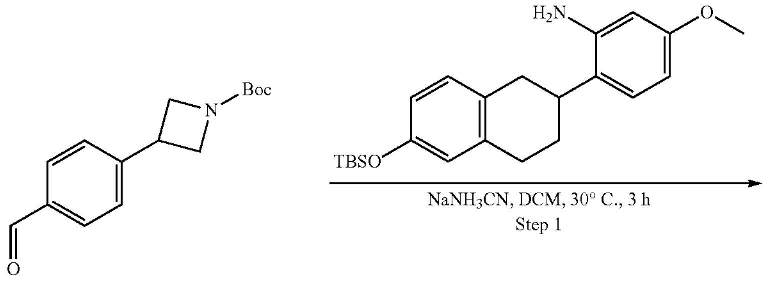

-continued
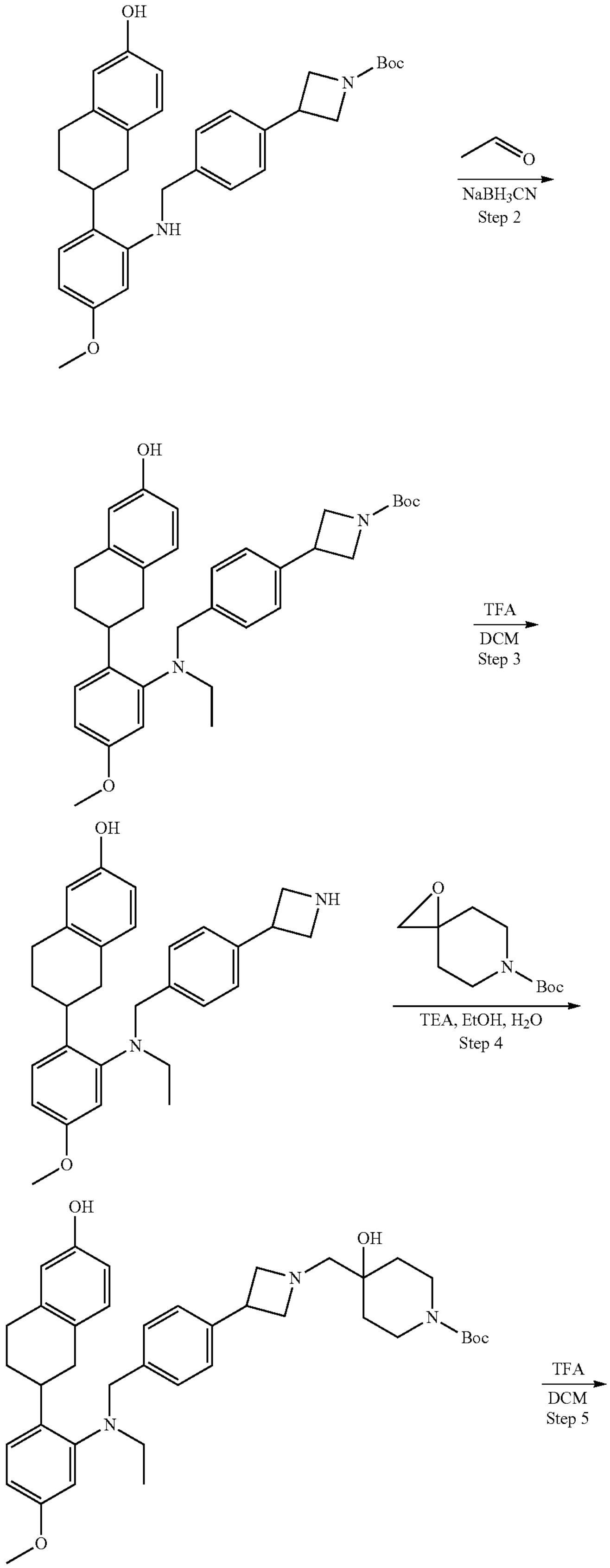

-continued

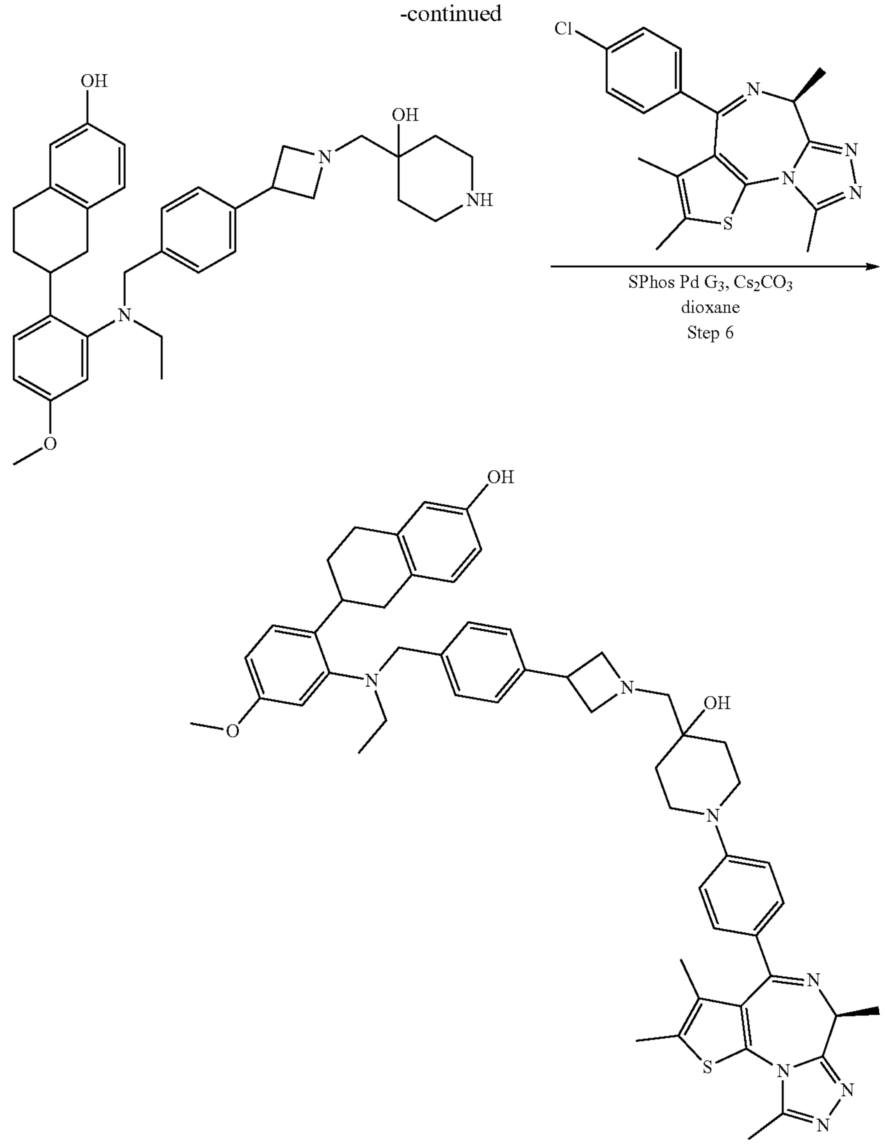

I-8

Step 1: Preparation of tert-butyl3-(4-(((2-(6-hydroxy-1,2,3,4-tetrahydro naphthalen-2-yl)-5-methoxyphenyl)amino)methyl)phenyl)azetidine-1-carboxylate. To a solution of tert-butyl 3-(4-formylphenyl)azetidine-1-carboxylate (900 mg, 2 mmol, 1 equiv) and 2-(6-((tert-butyldimethylsilyl)oxy)-1,2,3,4-tetrahydronaphthalen-2-yl)-5-methoxyaniline (603 mg, 2 mmol, 1 equiv) in DCM (5 mL) was added AcOH (201.65 mg, 3.36 mmol, 1.5 equiv). The mixture was stirred at 30° C. for 2 h, then $NaBH_3CN$ (281.36 mg, 4.48 mmol, 2 equiv) was added, and the mixture was stirred at 30° C. for 1 h. The reaction mixture was diluted with water (20 mL) and extracted with EA (20 mL×3). The combined organic layers were washed with brine (10 mL×3), dried over $Na_2SO_4$, filtered and concentrated under reduced pressure to give a residue. The residue was purified by prep-HPLC (column: Phenomenex luna C18 150*40 mm* 15 um; mobile phase: [water(FA)-ACN]; gradient: 55%-85% B over 15 min ) to afford tert-butyl3-(4-(((2-(6-hydroxy-1,2,3,4-tetrahydronaphthalen-2-yl)-5-methoxyphenyl)amino)methyl)phenyl)azetidine-1-carboxylate (610 mg, 52% yield) as a white solid. LC-MS: MS ($ES^+$): RT=0.608 min, m/z=515.3 [$M+H^+$].

Step 2: Preparation of tert-butyl 3-(4-((ethyl(2-(6-hydroxy-1,2,3,4-tetrahydro naphthalen-2-yl)-5-methoxyphenyl)amino)methyl)phenyl)azetidine-1-carboxylate. To a solution of tert-butyl3-(4-(((2-(6-hydroxy-1,2,3,4-tetrahydronaphthalen-2-yl)-5-methoxy phenyl)amino)methyl)phenyl)azetidine-1-carboxylate (380 mg, 0.74 mmol, 1 equiv) and acetaldehyde (5 M, 2.22 mL, 15 equiv) in MeOH (3 mL) was added $NaBH_3CN$ (92.80 mg, 1.48 mmol, 2 equiv). The mixture was stirred at 20° C. for 2 hr. The reaction mixture was diluted with water (20 mL) and extracted with EA (20 mL×3). The combined organic layers were washed with brine (10 mL×3), dried over $Na_2SO_4$, filtered and concentrated under reduced pressure to give a residue. The residue was purified by prep-TLC ($SiO_2$, petroleum ether/ethyl acetate=3/1) to afford tert-butyl 3-(4-((ethyl(2-(6-hydroxy-1,2,3,4-tetrahydro-naphthalen-2-yl)-5-methoxyphenyl)amino)methyl)phenyl)azetidine-1-carboxylate (362 mg, 84% yield) as a white solid. $^1$H NMR (400 MHz, $CDCl_3$) δ 7.26-7.21 (m, 2H), 7.16 (d, J=8.5 Hz, 3H), 6.90 (d, J=8.0 Hz, 1H), 6.80 (d, J=2.4 Hz, 1H), 6.71 (dd, J=2.4, 8.8 Hz, 1H), 6.66-6.59 (m, 2H), 4.31 (t, J=8.8 Hz, 2H), 4.01 (s, 2H), 3.94 (dd, J=6.4, 8.0 Hz, 2H), 3.81 (s, 3H), 3.74-3.56 (m, 2H), 3.03-2.90 (m, 2H), 2.85-2.75 (m, 2H), 2.75-2.64 (m, 2H), 1.84-1.69 (m, 2H), 1.62 (d, J=6.8 Hz, 2H), 1.48 (s, 9H), 0.96 (t, J=7.2 Hz, 3H). LC-MS: MS ($ES^+$): RT=0.530 min, m/z=543.4 [$M+H^+$].

Step 3: Preparation of 6-(2-((4-(azetidin-3-yl)benzyl)(ethyl)amino)-4-methoxyphenyl)-5,6,7,8-tetrahydronaphthalen-2-ol. To a solution of tert-butyl 3-(4-((ethyl(2-(6-hydroxy-1,2,3,4-tetrahydronaphthalen-2-yl)-5-methoxyphenyl)amino)methyl) phenyl)azetidine-1-carboxylate (380 mg, 0.7 mmol, 1 equiv) in DCM (3 mL) was added TFA (1.77 g, 15.48 mmol, 22 equiv). The mixture was stirred at 25° C. for 1 hr. The reaction mixture was concentrated under reduced pressure to remove solvent to afford 6-(2-((4-(azetidin-3-yl)benzyl)(ethyl)amino)-4-methoxyphenyl)-5,6,7,8-tetrahydronaphthalen-2-ol (310 mg, crude) as a yellow solid. LC-MS: MS ($ES^+$): RT=0.414 min, m/z=443.2 [$M+H^+$].

Step 4: Preparation of tert-butyl 4-((3-(4-((ethyl(2-(6-hydroxy-1,2,3,4-tetrahydronaphthalen-2-yl)-5-methoxyphenyl)amino)methyl)phenyl)azetidin-1-yl)methyl)-4-hydroxypiperidine-1-carboxylate. tert-Butyl 1-oxa-6-azaspiro[2.5]octane-6-carboxylate (223 mg, 1 mmol, 1.5 equiv), 6-(2-((4-(azetidin-3-yl)benzyl)(ethyl)amino)-4-methoxyphenyl)-5,6,7,8-tetrahydronaphthalen-2-ol (309 mg, 0.7 mmol, 1 equiv) and TEA (211 mg, 2.09 mmol, 3 equiv) were taken up into a microwave tube in ethyl alcohol (5 mL) and water (1 mL). The sealed tube was heated at 100° C. for 3 h under microwave irradiation. The reaction mixture was diluted with water (20 mL) and extracted with EA (20 mL×3). The combined organic layers were washed with brine (10 mL×3), dried over $Na_2SO_4$, filtered and concentrated under reduced pressure to give a residue. The residue was purified by prep-TLC ($SiO_2$, petroleum ether/ethyl acetate=0/1) to afford tert-butyl 4-((3-(4-((ethyl(2-(6-hydroxy-1,2,3,4-tetrahydronaphthalen-2-yl)-5-methoxyphenyl)amino)methyl)phenyl)azetidin-1-yl)methyl)-4-hydroxypiperidine-1-carboxylate (210 mg, 44% yield) as a white solid. LC-MS: MS ($ES^+$): RT=0.456 min, m/z=656.5 [$M+H^+$].

Step 5: Preparation of 4-((3-(4-((ethyl(2-(6-hydroxy-1,2,3,4-tetrahydro-naphthalen-2-yl)-5-methoxyphenyl)amino)methyl)phenyl)azetidin-1-yl)methyl)piperidin-4-ol. To a solution of tert-butyl 4-((3-(4-((ethyl(2-(6-hydroxy-1,2,3,4-tetrahydronaphthalen-2-yl)-5-methoxyphenyl)amino)methyl)phenyl)azetidin-1-yl)methyl)-4-hydroxypiperidine-1-carboxylate (110 mg, 0.16 mmol, 1 equiv) in DCM (2 mL) was added TFA (57.37 mg, 0.5 mmol, 3 equiv). The mixture was stirred at 20° C. for 0.5 hr. The reaction mixture was quenched by the addition of a saturated solution of aqueous sodium bicarbonate (10 mL) and then diluted with water (10 mL) and extracted with EA (10 mL×3). The combined organic layers were washed with brine (10 mL×3), dried over $Na_2SO_4$, filtered and concentrated under reduced pressure to afford 4-((3-(4-((ethyl(2-(6-hydroxy-1,2,3,4-tetrahydro naphthalen-2-yl)-5-methoxyphenyl)amino)methyl)phenyl)azetidin-1-yl)methyl)piperidin-4-ol (166 mg, crude) as a yellow solid. LC-MS: MS ($ES^+$): RT=0.398 min, m/z=556.4 [$M+H^+$].

Step 6: Preparation of 4-((3-(4-((ethyl(2-(6-hydroxy-1,2,3,4-tetrahydro-naphthalen-2-yl)-5-methoxyphenyl)amino)methyl)phenyl)azetidin-1-yl)methyl)-1-(4-((S)-2,3,6,9-tetramethyl-6H-thieno[3,2-f][1,2,4]triazolo[4,3-a][1,4]diazepin -4-yl)phenyl) piperidin-4-ol. A mixture of 4-((3-(4-((ethyl(2-(6-hydroxy-1,2,3,4-tetrahydro naphthalen-2-yl)-5-methoxyphenyl)amino)methyl)phenyl)azetidin-1-yl)methyl)piperidin-4-ol (160 mg, 0.28 mmol, 1 equiv), (S)-4-(4-chlorophenyl)-2,3,6,9-tetramethyl-6H-thieno[3,2-f][1,2,4]triazolo[4,3-a][1,4]diazepine (123.29 mg, 0.34 mmol, 1.2 equiv), $Cs_2CO_3$ (281.41 mg, 0.86 mmol, 3 equiv), and dicyclohexyl-[2-(2,6-dimethoxyphenyl)phenyl]phosphane; methanesulfonate; (2-phenylanilino)palladium(1+) (22.46 mg, 0.03 mmol, 0.1 equiv) in dioxane (3 mL) was degassed and purged with $N_2$ 3 times, and then the mixture was stirred at 90° C. for 3 hr under an $N_2$ atmosphere. The reaction mixture was diluted with water (20 mL) and extracted with EA (20 mL×3). The combined organic layers were washed with brine (10 mL×3), dried over $Na_2SO_4$, filtered and concentrated under reduced pressure to give a residue. The residue was purified by prep-TLC ($SiO_2$, DCM/MeOH=10/1) to afford 4-((3-(4-((ethyl(2-(6-hydroxy-1,2,3,4-tetrahydronaphthalen-2-yl)-5-methoxyphenyl)amino)methyl) phenyl)azetidin-1-yl)methyl)-1-(4-((S)-2,3,6,9-tetramethyl-6H-thieno[3,2-f][1,2,4]triazolo[4,3-a][1,4]diazepin-4-yl)phenyl)piperidin-4-ol as a white solid. The solid was purified by SFC (column: DAICEL CHIRALCEL OX (250 mm×30 mm, 10 um); mobile phase: [$CO_2$-ACN/EtOH (0.1% $NH_3H_2O$)]; B %: 70%, isocratic elution mode) to afford 4-((3-(4-((ethyl(2-(6-hydroxy-1,2,3,4-tetrahydro-naphthalen-2-yl)-5-methoxyphenyl)amino)methyl) phenyl)azetidin-1-yl)methyl)-1-(4-((S)-2,3,6,9-tetramethyl-6H-thieno[3,2-f][1,2,4]triazolo[4,3-a][1,4]diazepin-4-yl)phenyl) piperidin-4-ol (I-8, 40 mg, 46% yield) as a white solid. $^1$H NMR (400 MHz, DMSO-$d_6$) δ 9.01 (s, 1H), 7.27 (d, J=8.4 Hz, 2H), 7.21-7.12 (m, 5H), 6.90 (d, J=9.0 Hz, 2H), 6.83-6.77 (m, 2H), 6.66 (dd, J=2.8, 8.8 Hz, 1H), 6.55-6.45 (m, 2H), 4.17-4.07 (m, 2H), 3.98 (d, J=2.8 Hz, 2H), 3.71 (s, 3H), 3.65 (t, J=7.2 Hz, 2H), 3.56-3.46 (m, 5H), 3.14-3.07 (m, 4H), 2.87 (d, J=7.2 Hz, 2H), 2.73 (d, J=3.6 Hz, 2H), 2.57 (s, 3H), 2.40 (s, 5H), 1.84 (d, J=6.4 Hz, 3H), 1.70 (s, 3H), 1.62-1.41 (m, 6H), 1.27-1.19 (m, 1H), 0.87 (t, J=7.2 Hz, 3H). LC-MS: MS ($ES^+$): RT=1.513 min, m/z=876.5 [$M+H^+$]. LCMS Method: 5-95.

Example 10—Synthesis of (S)-(6-hydroxy-2-(4-hydroxyphenyl)benzo[b]thiophen-3-yl)(4-(2-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)ethoxy)phenyl)methanone (I-9)

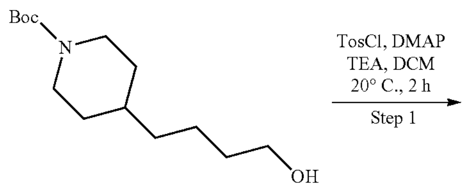

-continued
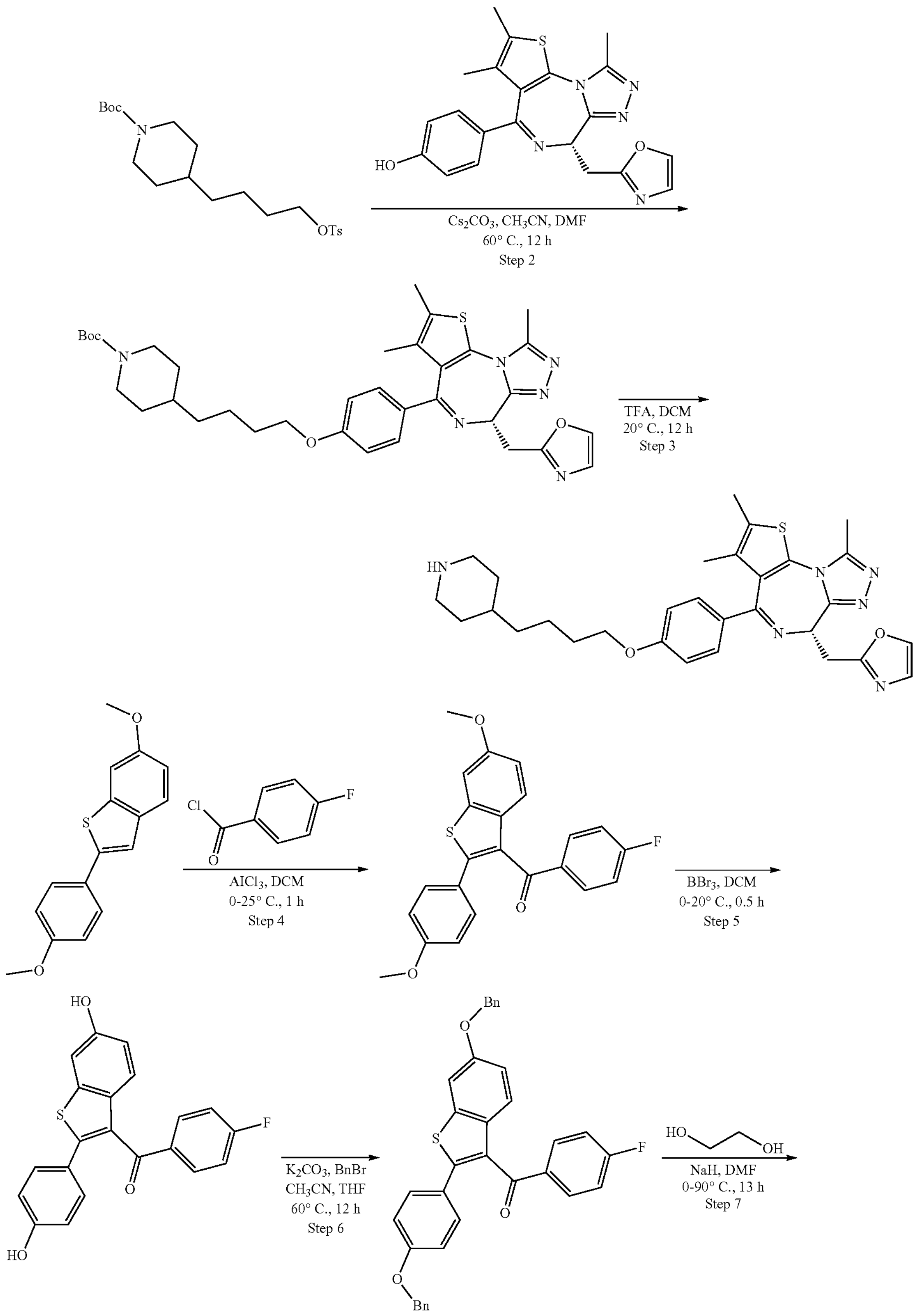

-continued

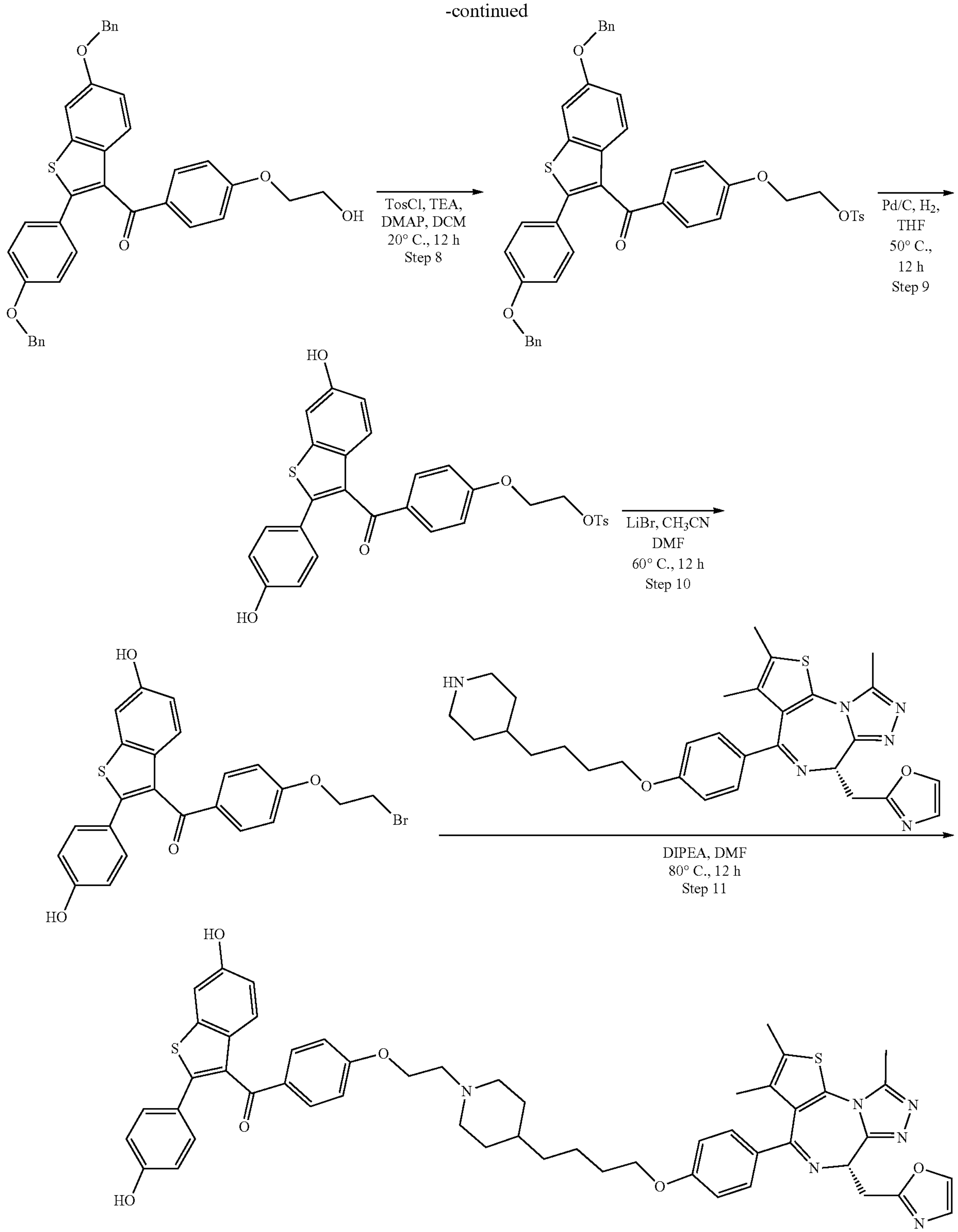

I-9

Step 1: Preparation of tert-butyl-4-[4-(p-tolylsulfonyloxy)butyl]piperidine-1-carboxylate. To a solution of tert-butyl 4-(4-hydroxybutyl)piperidine-1-carboxylate (1 g, 3.89 mmol, 1 eq) in DCM (10 mL) were added TosCl (1.1 g, 5.77 mmol, 1.48 eq) and TEA (1.16 g, 11.50 mmol, 1.60 mL, 2.96 eq), DMAP (48.00 mg, 392.90 mol, 1.01e-1 eq). The mixture was stirred at 20° C. for 2 hours. The mixture was concentrated in vacuum. The residue was purified by column chromatography (0~30% ethyl acetate/petroleum ether) to give tert-butyl-4-[4-(p-tolylsulfonyloxy)butyl]piperidine-1-carboxylate (1.5 g, 94% yield) as a colorless oil.

Step 2: Preparation of tert-butyl (S)-4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl) piperidine-1-carboxylate. To a solution of tert-butyl-4-[4-(p-tolylsulfonyloxy) butyl]piperidine-1-carboxylate (500 mg, 1.21 mmol, 1.64 eq) in MeCN (4 mL) and DMF (4 mL) were added $Cs_2CO_3$ (500 mg, 1.53 mmol, 2.07 eq) and 4-[(9S)-4,5,13-trimethyl-9-(oxazol-2-ylmethyl)-3-thia-1,8,11,12-tetrazatricyclo[8.3.0.02,6]trideca-2(6),4,7,10,12-pentaen-7-yl]phenol (300 mg, 739.88 mol, 1 eq). The mixture was stirred at 60° C. for 12 hours. The reaction mixture was poured into water (10 mL). The aqueous phase was extracted with EA (30 mL×2). The combined organic phase was washed with brine (20 mL×3), dried with anhydrous $Na_2SO_4$, filtered and concentrated in vacuum. The residue was purified by column chromatography (0-100% ethyl acetate/petroleum ether). tert-butyl-4-[4-[4-[(9S)-4,5,13-trimethyl-9-(oxazol-2-ylmethyl)-3-thia-1,8,11,12-tetrazatricyclo[8.3.0.02,6]trideca-2(6),4,7,10,12-pentaen-7-yl]phenoxy]butyl]piperidine-1-carboxylate (400 mg, 84% yield) was obtained as a yellow oil.

Step 3: Preparation of 2-[[(9S)-4,5,13-trimethyl-7-[4-[4-(4-piperidyl)butoxy]phenyl]-3-thia-1,8,11,12-tetrazatricyclo[8.3.0.02,6]trideca-2(6),4,7,10,12-pentaen-9-yl]methyl] oxazole. To a solution of tert-butyl-4-[4-[4-[(9S)-4,5,13-trimethyl-9-(oxazol-2-ylmethyl)-3-thia-1,8,11,12-tetrazatricyclo[8.3.0.02,6]trideca-2(6),4,7,10,12-pentaen-7-yl]phenoxy]butyl]piperidine-1-carboxylate (400 mg, 620.32 mol, 1 eq) in DCM (15 mL) was added TFA (7.68 g, 67.31 mmol, 5 mL, 108.51 eq). The mixture was stirred at 20° C. for 12 hours. The mixture was concentrated under vacuum. To the mixture was added $NaHCO_3$ to adjust the pH to 8-10. The mixture was poured into water (20 mL). The aqueous phase was extracted with DCM (20 mL×2). The combined organic phase was washed with brine (20 mL×2), dried with anhydrous $Na_2SO_4$, filtered and concentrated under vacuum. The residue was purified by prep-HPLC (column: Phenomenex Luna C18 150×25 mm×10 um; mobile phase: water (FA)-ACN; B %: 16%-46%, 10 min; Flow rate: 25 ml/min). 2-[[(9S)-4,5,13-trimethyl-7-[4-[4-(4-piperidyl)butoxy]phenyl]-3-thia-1,8,11,12-tetrazatricyclo[8.3.0.02,6]trideca-2(6),4,7,10,12-pentaen-9-yl]methyl]oxazole (200 mg, 59% yield) was obtained as a yellow solid.

Step 4: Preparation of (4-fluorophenyl)-[6-methoxy-2-(4-methoxyphenyl) benzothiophen-3-yl]methanone. To a solution of 6-methoxy-2-(4-methoxyphenyl)benzo thiophene (13 g, 48.09 mmol, 1 eq) and 4-fluorobenzoylchloride (10 g, 63.07 mmol, 7.56 mL, 1.31 eq) in DCM (150 mL) was added portion-wise $AlCl_3$ (7.80 g, 58.50 mmol, 3.20 mL, 1.22 eq) at 0° C. The mixture was stirred at 25° C. for 1 hour. The reaction mixture was quenched by the addition of $H_2O$ (150.0 mL) at 0° C., and then extracted with DCM (50.0 mL×3). The combined organic layers were dried over anhydrous $Na_2SO_4$, filtered and concentrated under reduced pressure to give a residue. The residue was purified by column chromatography ($SiO_2$, PE/EtOAc=1/0 to 8/1). Compound (4-fluorophenyl)-[6-methoxy-2-(4-methoxyphenyl) benzo thiophen-3-yl]methanone (12 g, 64% yield) was obtained as a yellow oil.

Step 5: Preparation of (4-fluorophenyl)-[6-hydroxy-2-(4-hydroxyphenyl)benzo thiophen-3-yl]methanone. To a solution of (4-fluorophenyl)-[6-methoxy-2-(4-methoxy phenyl) benzothiophen-3-yl]methanone (6 g, 15.29 mmol, 1 eq) in DCM (50 mL) was added dropwise $BBr_3$ (15.60 g, 62.27 mmol, 6 mL, 4.07 eq) at 0° C. and the mixture was stirred at 20° C. for 0.5 hour. The reaction mixture was quenched by the addition of sat. aq. $NaHCO_3$ (60.0 mL) at 0° C., and then diluted with $H_2O$ (10.0 mL) and extracted with DCM (40.0 mL×2). The combined organic layers were dried over anhydrous $Na_2SO_4$, filtered and concentrated under reduced pressure to give a residue. The residue was purified by column chromatography (0~30% ethyl acetate/petroleum ether). (4-fluorophenyl)-[6-hydroxy-2-(4-hydroxyphenyl) benzothiophen-3-yl]methanone (5 g, 90% yield) was obtained as a yellow solid.

Step 6: Preparation of [6-benzyloxy-2-(4-benzyloxyphenyl)benzothiophen-3-yl]-(4-fluorophenyl)methanone. To a solution of (4-fluorophenyl)-[6-hydroxy-2-(4-hydroxy phenyl)benzothiophen-3-yl]methanone (5 g, 13.72 mmol, 1 eq) in $CH_3CN$ (10 mL), THE (50 mL) were added $K_2CO_3$ (6 g, 43.41 mmol, 3.16 eq) and BnBr (10.08 g, 58.94 mmol, 7 mL, 4.30 eq). The mixture was stirred at 60° C. for 12 hours. The mixture was filtered and the filtrate was concentrated. The crude product was triturated with EA and PE to afford [6-benzyl oxy-2-(4-benzyloxyphenyl)benzothiophen-3-yl]-(4-fluorophenyl)methanone (5.9 g, 80% yield) as a yellow solid.

Step 7: Preparation of [6-benzyloxy-2-(4-benzyloxyphenyl)benzothiophen-3-yl]-[4-(2-hydroxyethoxy)phenyl] methanone. To a solution of ethylene glycol (700 mg, 11.28 mmol, 0.6 mL, 2.05 eq) in DMF (30 mL) was added NaH (550 mg, 13.75 mmol, 60% purity, 2.5 eq) at 0° C. After the addition, the mixture was stirred at 20° C. for 0.5 hours. Then [6-benzyloxy-2-(4-benzyloxyphenyl)benzothiophen-3-yl]-(4-fluorophenyl)methanone (3 g, 5.51 mmol, 1 eq) was added to the mixture and the resulting mixture was stirred at 20° C. for 0.5 hour. The mixture was then stirred at 90° C. for 12 hours. The reaction mixture was quenched by the addition of sat. aq. $NH_4Cl$ (60.0 mL), and then diluted with $H_2O$ (20.0 mL) and extracted with EtOAc (50.0 mL*2). The combined organic layers were dried over anhydrous $Na_2SO_4$, filtered and concentrated under reduced pressure to give a residue. The residue was purified by column chromatography (0~80% ethyl acetate/petroleum ether). [6-benzyloxy-2-(4-benzyloxy phenyl)benzothiophen-3-yl]-[4-(2-hydroxyethoxy)phenyl]methanone (1.4 g, 43% yield) was obtained as a yellow solid.

Step 8: Preparation of 2-[4-[6-benzyloxy-2-(4-benzyloxyphenyl) benzothiophene-3-carbonyl]phenoxy]ethyl-4-methylbenzenesulfonate. To a solution of [6-benzyloxy-2-(4-benzyloxyphenyl)benzothiophen-3-yl]-[4-(2-hydroxyethoxy)phenyl]methanone (1.4 g, 2.39 mmol, 1 eq) in DCM (15 mL) was added tosylchloride (700.00 mg, 3.67 mmol, 1.54 eq) and TEA (1.45 g, 14.37 mmol, 2 mL, 6.02 eq), DMAP (70.00 mg, 572.98 mol, 0.24 eq). The mixture was stirred at 20° C. for 12 hours. The mixture was concentrated in vacuum. The residue was purified by flash silica gel chromatography (0~50% Ethyl acetate/Petroleum ether). The residue was purified by a second time by column chromatography (gradient of 80-100% water (1% formic acid)/ACN). 2-(4-(6-(benzyloxy)-2-(4-(benzyloxy)phenyl) benzo[b]thiophene-3-carbonyl)phenoxy)ethyl 4-methylbenzenesulfonate (800 mg, 45% yield) was obtained as a yellow solid.

Step 9: Preparation of 2-(4-(6-hydroxy-2-(4-hydroxyphenyl)benzo[b]thiophene-3-carbonyl)phenoxy)ethyl 4-methylbenzenesulfonate. To a solution of 2-(4-(6-(benzyloxy)-2-(4-(benzyloxy)phenyl)benzo[b]thiophene-3-carbonyl) phenoxy)ethyl 4-methylbenzene sulfonate (500 mg, 674.87 mol, 1 eq) in THF (5 mL) was added Pd/C (100 mg, 10% w/w) under an $N_2$ atmosphere. The suspension was degassed and purged with $H_2$ 3 times. The mixture was stirred under $H_2$ (50 psi) at 50° C. for 12 hours. The reaction mixture was filtered and concentrated under reduced pressure to give a residue. The crude product was used into the next step without further purification. 2-(4-(6-hydroxy-2-(4-hydroxyphenyl) benzo[b]thiophene-3-carbonyl)phenoxy)ethyl 4-methylbenzenesulfonate (400 mg, crude) was obtained as a yellow oil.

Step 10: Preparation of [4-(2-bromoethoxy)phenyl]-[6-hydroxy-2-(4-hydroxyphenyl)benzothiophen-3-yl]methanone. To a solution of 2-(4-(6-hydroxy-2-(4-hydroxyphenyl) benzo[b]thiophene-3-carbonyl)phenoxy)ethyl 4-methylbenzenesulfonate (400 mg, 713.47 mol, 1 eq) in $CH_3CN$ (3 mL), and DMF (2 mL) was added LiBr (188.00 mg, 2.16 mmol, 54.34 L, 3.03 eq). The mixture was stirred at 60° C. for 12 hours. The mixture was concentrated in vacuum. The residue was purified by column chromatography (0~30% ethyl acetate/petroleum ether). [4-(2-bromoethoxy)phenyl]-[6-hydroxy-2-(4-hydroxyphenyl)benzo thiophen-3-yl]methanone (300 mg, 90% yield) was obtained as a yellow oil.

Step 11: Preparation of (S)-(6-hydroxy-2-(4-hydroxyphenyl)benzo[b]thiophen-3-yl)(4-(2-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)ethoxy) phenyl) methanone. To a solution of [4-(2-bromoethoxy) phenyl]-[6-hydroxy-2-(4-hydroxyphenyl)benzothiophen-3-yl]methanone (40 mg, 85.22 mol, 1 eq) in DMF (1 mL) were added DIEA (40 mg, 309.49 mol, 53.91 L, 3.63 eq) and 2-[[(9S)-4,5,13-trimethyl-7-[4-[4-(4-piperidyl)butoxy]phenyl]-3-thia-1,8,11,12-tetrazatricyclo[8.3.0.$0^{2,6}$]trideca-2(6),4,7,10,12-pentaen-9-yl]methyl]oxazole (20 mg, 36.7 mol, 0.4 eq). The mixture was stirred at 80° C. for 12 hours. The mixture was concentrated under vacuum. The residue was purified by prep-HPLC (column: Phenomenex Luna C18 150×25 mm×10 um; mobile phase: water (FA)-ACN; B %: 27%-57%, 10 min; Flow rate: 25 ml/min). (S)-(6-hydroxy-2-(4-hydroxyphenyl)benzo[b]thiophen-3-yl)(4-(2-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl) piperidin-1-yl)ethoxy)phenyl)methanone (I-9, 20.41 mg, 24% yield) was obtained as a yellow solid. $^{1}H$ NMR (400 MHz, DMSO-$d_6$) δ (ppm) 8.20 (s, 1H), 8.03 (s, 1H), 7.65 (d, J=8.8 Hz, 2H), 7.33 (d, J=2.4 Hz, 1H), 7.28 (d, J=8.8 Hz, 2H), 7.24 (d, J=8.8 Hz, 1H), 7.17 (d, J=8.8 Hz, 2H), 7.12 (s, 1H), 6.91 (dd, J=8.8, 2.4 Hz, 4H), 6.84 (dd, J=8.8, 2.4 Hz, 1H), 6.67 (d, J=8.4 Hz, 2H), 4.61 (t, J=7.2 Hz, 1H), 4.07 (br t, J=5.6 Hz, 2H) 3.97 (br t, J=6.4 Hz, 2H), 3.92-3.85 (m, 1H), 3.83-3.77 (m, 1H), 2.86 (br d, J=11.2 Hz, 2H), 2.67-2.62 (m, 1H), 2.59 (s, 3H), 2.45 (br d, J=2.0 Hz, 1H), 2.41 (s, 3H), 2.36-2.30 (m, 1H), 1.95 (br t, J=10.4 Hz, 2H), 1.68 (br d, J=7.2 Hz, 1H), 1.64 (s, 3H), 1.59 (br d, J=12.0 Hz, 2H), 1.38 (br d, J=6.0 Hz, 2H), 1.24-1.05 (m, 5H). LC-MS: MS ($ES^+$): RT=1.798 min, m/z=933.2[$M+H^+$]. LCMS Method: 25.

Example 11—Synthesis of (S)-(6-hydroxy-2-(4-hydroxyphenyl)benzo[b]thiophen-3-yl)(4-(2-(2-(4-(2,3,9-trimethyl-6-(oxazol-2-ylmethyl)-6H-thieno[3,2-f][1,2,4]triazolo[4,3-a][1,4]diazepin-4-yl) phenoxy)-7-azaspiro[3.5]nonan-7-yl)ethoxy)phenyl) methanone (I-10)

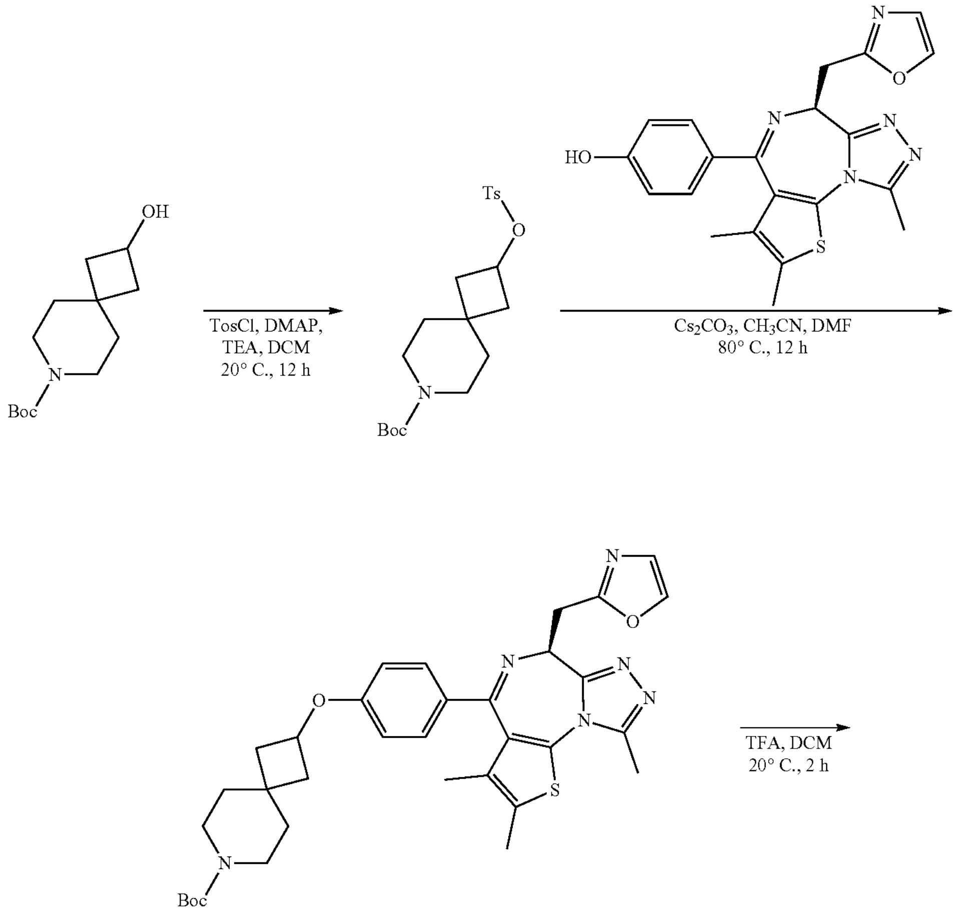

-continued

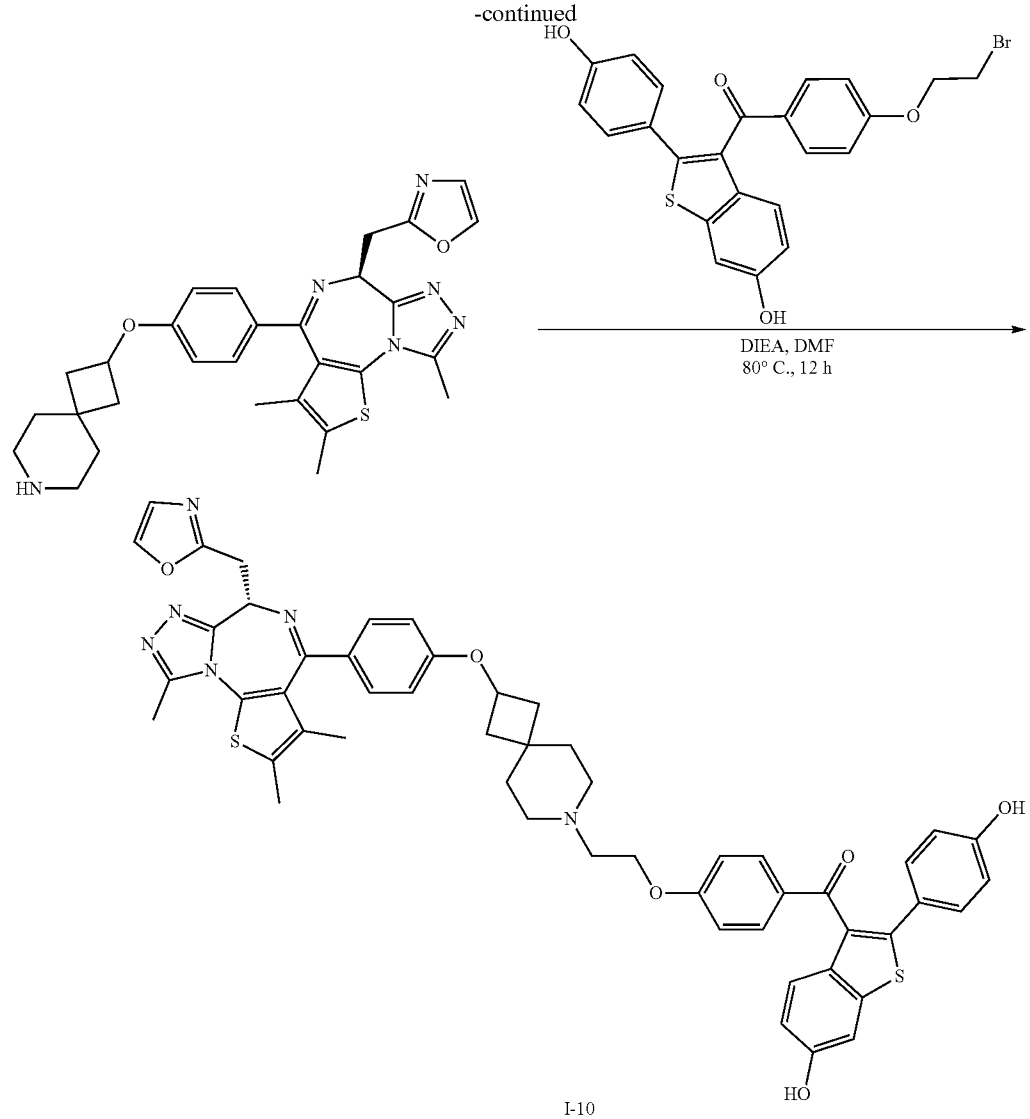

I-10

Step 1: Preparation of tert-butyl 2-(p-tolylsulfonyloxy)-7-azaspiro[3.5]nonane-7-carboxylate. To a solution of tert-butyl 2-hydroxy-7-azaspiro[3.5]nonane-7-carboxylate (1 g, 4.14 mmol, 1 eq) in DCM (10 mL) were added TosCl (1.2 g, 6.29 mmol, 1.52 eq), TEA (1.31 g, 12.93 mmol, 1.80 mL, 3.12 eq), DMAP (52.00 mg, 425.64 mol, 0.1 eq). The mixture was stirred at 20° C. for 12 hours. The mixture was concentrated in vacuum. The residue was purified by column chromatography (0~25% ethyl acetate/petroleum ether). Compound tert-butyl 2-(p-tolylsulfonyloxy)-7-azaspiro[3.5]nonane-7-carboxylate (1.3 g, 79% yield) was obtained as a black solid.

Step 2: Preparation of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]-7-azaspiro[3.5]nonane-7-carboxylate. To a solution of tert-butyl 2-(p-tolylsulfonyloxy)-7-azaspiro[3.5]nonane-7-carboxylate (600 mg, 1.52 mmol, 1.54 eq) in MeCN (2 mL), DMF (4 mL) were added $Cs_2CO_3$ (650 mg, 1.99 mmol, 2.02 eq) and 4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenol (400 mg, 986.50 mol, 1 eq). The mixture was stirred at 80° C. for 12 hours. The residue was poured into water (10 mL). The aqueous phase was extracted with EA (30 mL×2). The combined organic phase was washed with brine (20 mL×3), dried with anhydrous $Na_2SO_4$, filtered and concentrated in vacuum. The residue was purified by column chromatography (0~20% DCM/MeOH). Compound tert-butyl-2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]-7-azaspiro[3.5]nonane-7-carboxylate (450 mg, 73% yield) was obtained as a yellow solid.

Step 3: Preparation of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2(6),4,7,10,12-pentaen-9-yl]methyl]oxazole. To a solution of tert-butyl 2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]-7-azaspiro[3.5]nonane-7-carboxylate (450 mg, 715.67 mol, 1 eq) in DCM (5 mL) was added TFA (10.75 g, 94.24 mmol, 7 mL, 131.67 eq). The mixture was stirred at 20° C. for 2 hours. The mixture was concentrated in vacuum. The mixture was added $NaHCO_3$ adjust to pH 8-10. The residue was poured into water (20 mL). The aqueous phase was extracted with DCM (20 mL×2). The combined organic phase was washed with brine (20 mL×2), dried with anhydrous $Na_2SO_4$, filtered and concentrated in vacuum. The residue was purified by prep-HPLC (column: Phenomenex Luna C18 150×25 mm×10 um; mobile phase: water (FA)-ACN; B %: 19%-35%, 8 min; Flow rate: 25 ml/min). Compound 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2(6),4,7,10,12-pentaen-9-yl]methyl]oxazole (200 mg, 49% yield) was obtained as a white solid.

Step 4: Preparation of (S)-(6-hydroxy-2-(4-hydroxyphenyl)benzo[b]thiophen-3-yl)(4-(2-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)ethoxy)phenyl)methanone. To a solution of 2-[[(9S)-7-[4-(7-azaspiro[3.5]nonan-2-yloxy)phenyl]-4,5,13-trimethyl-3-thia-1,8,11,12-tetrazatricyclo[8.3.0.0$^{2,6}$]trideca-2(6),4,7,10,12-pentaen-9-yl]methyl]oxazole (70 mg, 132.41 mol, 1 eq), [4-(2-bromoethoxy)phenyl]-[6-hydroxy-2-(4-hydroxyphenyl)benzo thiophen-3-yl]methanone (77.00 mg, 164.06 mol, 1.24 eq) in DMF (1 mL) was added DIEA (74.20 mg, 574.13 mol, 0.1 mL, 4.34 eq). The mixture was stirred at 80° C. for 12 hours. The mixture was concentrated in vacuum. The residue was purified by prep-HPLC (FA condition: Instrument: ACS-WH-GX-E; column: Phenomenex Luna C18 150×25 mm×10 um; mobile phase: water (FA)-ACN; B %: 25%-55%, 10 min; Flow rate: 25 ml/min; Column temperature: R. T.; Wavelength: 220 nm). (S)-(6-hydroxy-2-(4-hydroxyphenyl)benzo[b]thiophen-3-yl)(4-(2-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)ethoxy)phenyl) methanone (I-10, 35.68 mg, 29% yield) was obtained as a yellow solid. $^1$H NMR (400 MHz, DMSO-$d_6$): δ (ppm) 8.27 (s, 1H), 8.03 (s, 1H), 7.65 (d, J=8.8 Hz, 2H), 7.33 (d, J=2.0 Hz, 1H), 7.25 (dd, J=11.2, 8.8 Hz, 3H), 7.17 (d, J=8.8 Hz, 2H), 7.12 (s, 1H), 6.91 (d, J=8.8 Hz, 2H), 6.86-6.80 (m, 3H), 6.67 (d, J=8.8 Hz, 2H), 4.73 (br t, J=6.8 Hz, 1H), 4.61 (t, J=7.2 Hz, 1H), 4.07 (br t, J=5.6 Hz, 2H), 3.93-3.73 (m, 3H), 2.62-2.61 (m, 1H), 2.59 (s, 3H), 2.41 (s, 3H), 2.40-2.23 (m, 6H), 1.73 (br dd, J=12.4, 6.0 Hz, 2H), 1.64 (s, 3H), 1.59-1.51 (m, 4H). LC-MS: MS (ES$^+$): RT=1.687 min, m/z=917.4 [M+H$^+$]. LCMS Method: 25.

Example 12—Synthesis of 4-(2-(4-(3-((1-(2-(4-(6-hydroxy-2-(4-hydroxyphenyl) benzo[b]thiophene-3-carbonyl)phenoxy)ethyl)piperidin-4-yl)methyl)azetidin-1-yl)phenoxy)-5-(2-hydroxypropan-2-yl)phenyl)-6-methyl-1,6-dihydro-7H-pyrrolo[2,3-c]pyridin-7-one (I-11)

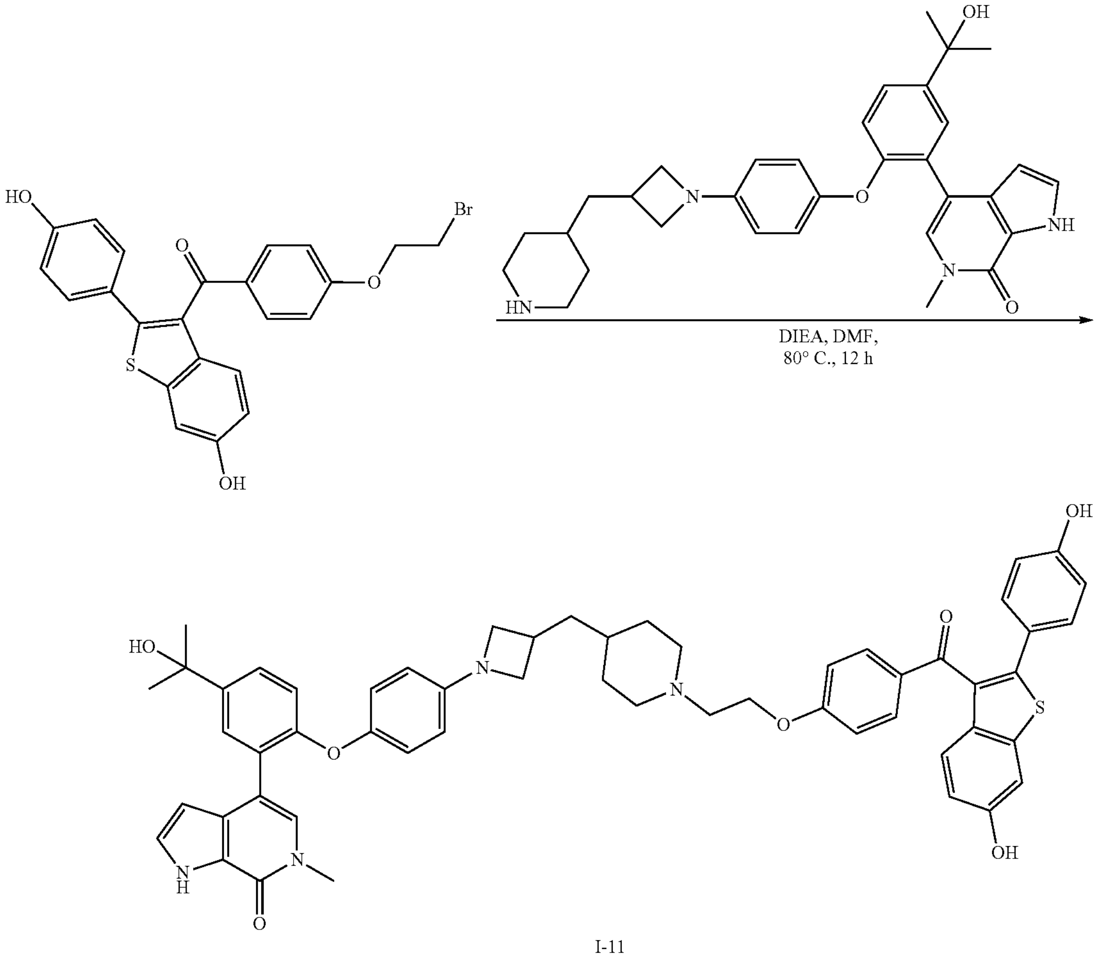

I-11

To a solution of 4-[5-(1-hydroxy-1-methyl-ethyl)-2-[4-[3-(4-piperidylmethyl) azetidin-1-yl]phenoxy]phenyl]-6-methyl-1H-pyrrolo[2,3-c]pyridin-7-one (50 mg, 94.94 mol, 1 eq), [4-(2-bromoethoxy)phenyl]-[6-hydroxy-2-(4-hydroxyphenyl)benzothiophen-3-yl]methanone (55.00 mg, 117.18 mol, 1.23 eq) in DMF (1 mL) was added DIEA (74.20 mg, 574.13 mol, 0.1 mL, 6.05 eq). The mixture was stirred at 80° C. for 12 hours. The mixture was concentrated under vacuum. The residue was purified by prep-HPLC (column: Phenomenex Luna C18 150×25 mm×10 um; mobile phase: water (FA)-ACN; B %: 23%-53%, 10 min; Flow rate: 25 ml/min). 4-(2-(4-(3-((1-(2-(4-(6-hydroxy-2-(4-hydroxyphenyl) benzo[b]thiophene-3-carbonyl)phenoxy)ethyl)piperidin-4-yl)methyl)azetidin-1-yl)phenoxy)-5-(2-hydroxypropan-2-yl)phenyl)-6-methyl-1,6-dihydro-7H-pyrrolo[2,3-c]pyridin-7-one (I-11, 17.07 mg, 19% yield) was obtained as a yellow solid. $^1$H NMR (400 MHz, DMSO-$d_6$) δ ppm 11.97 (br s, 1H), 9.88-9.69 (m, 1H), 7.65 (d, J=8.8 Hz, 2H), 7.52 (d, J=2.4 Hz, 1H), 7.36-7.32 (m, 2H), 7.27-7.22 (m, 3H), 7.19-7.14 (m, 2H), 6.91 (d, J=9.2 Hz, 2H), 6.85 (dd, J=8.8, 2.4 Hz, 1H), 6.79 (d, J=8.8 Hz, 2H), 6.72-6.66 (m, 3H), 6.34 (d, J=8.8 Hz, 2H), 6.23 (t, J=2.4 Hz, 1H), 5.04-4.89 (m, 1H), 4.08 (br t, J=5.6 Hz, 2H), 3.88 (br t, J=7.2 Hz, 2H), 3.54 (s, 3H), 2.86 (br d, J=11.2 Hz, 2H), 2.77-2.67 (m, 2H), 2.62 (br d, J=6.0 Hz, 2H), 1.96 (br t, J=10.8 Hz, 2H), 1.58-1.49 (m, 4H), 1.44 (s, 6H), 1.27-0.98 (m, 4H). LC-MS: MS (ES$^+$): RT=1.528 min, m/z=915.4 [M+H$^+$]. LCMS Method: 25.

Example 13—Synthesis of (5R,6S)-6-phenyl-5-(4-(4-((4-(4-((S)-2,3,9-trimethyl-6-(oxazol-2-ylmethyl)-6H-thieno[3,2-f][1,2,4]triazolo[4,3-a][1,4]diazepin-4-yl)phenyl) piperazin-1-yl)methyl)piperidin-1-yl) phenyl)-5,6,7,8-tetrahydronaphthalen-2-ol (I-12), (5R,6S)-6-phenyl-5-(4-(4-((4-(4-((R)-2,3,9-trimethyl-6-(oxazol-2-ylmethyl)-6H-thieno[3,2-f][1,2,4] triazolo[4,3-a][1,4]diazepin-4-yl)phenyl) piperazin-1-yl)methyl)piperidin-1-yl)phenyl)-5,6,7,8-tetrahydronaphthalen-2-ol (III-1), (5S,6R)-6-phenyl-5-(4-(4-((4-(4-((R)-2,3,9-trimethyl-6-(oxazol-2-ylmethyl)-6H-thieno[3,2-f][1,2,4]triazolo[4,3-a][1,4] diazepin-4-yl)phenyl) piperazin-1-yl)methyl) piperidin-1-yl)phenyl)-5,6,7,8-tetrahydronaphthalen-2-ol (11I-2), and (5S,6R)-6-phenyl-5-(4-(4-((4-(4-((S)-2,3,9-trimethyl-6-(oxazol-2-ylmethyl)-6H-thieno[3,2-f][1,2,4]triazolo[4,3-a][1,4]diazepin-4-yl) phenyl) piperazin-1-yl)methyl)piperidin-1-yl) phenyl)-5,6,7,8-tetrahydronaphthalen-2-ol (III-3)

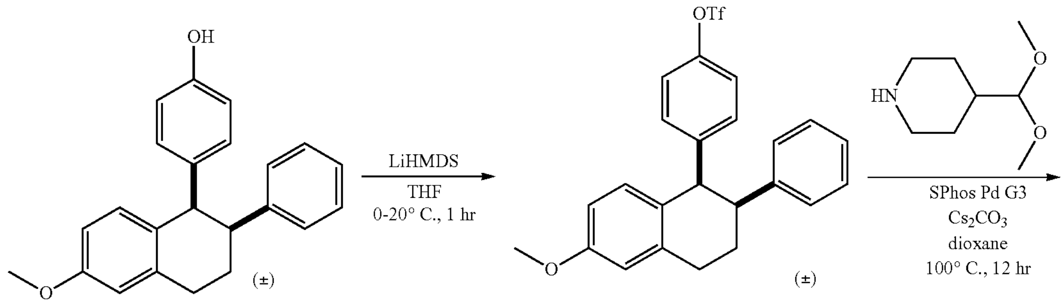

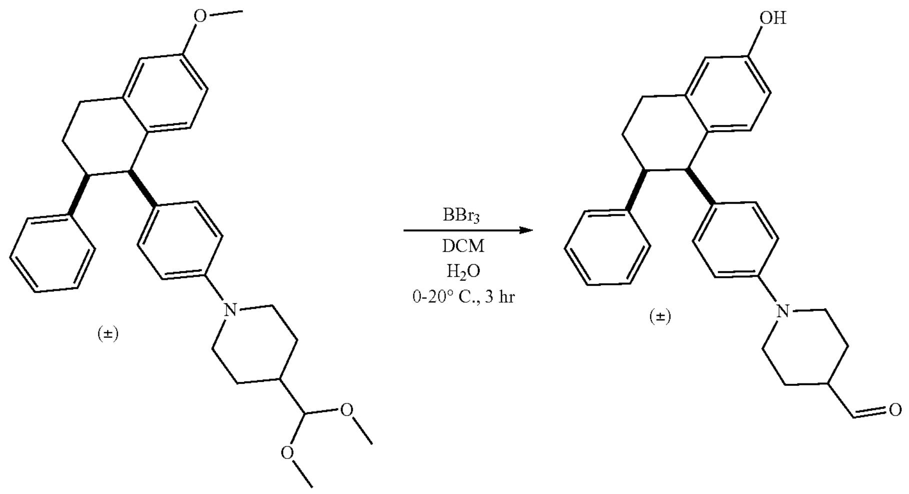

-continued
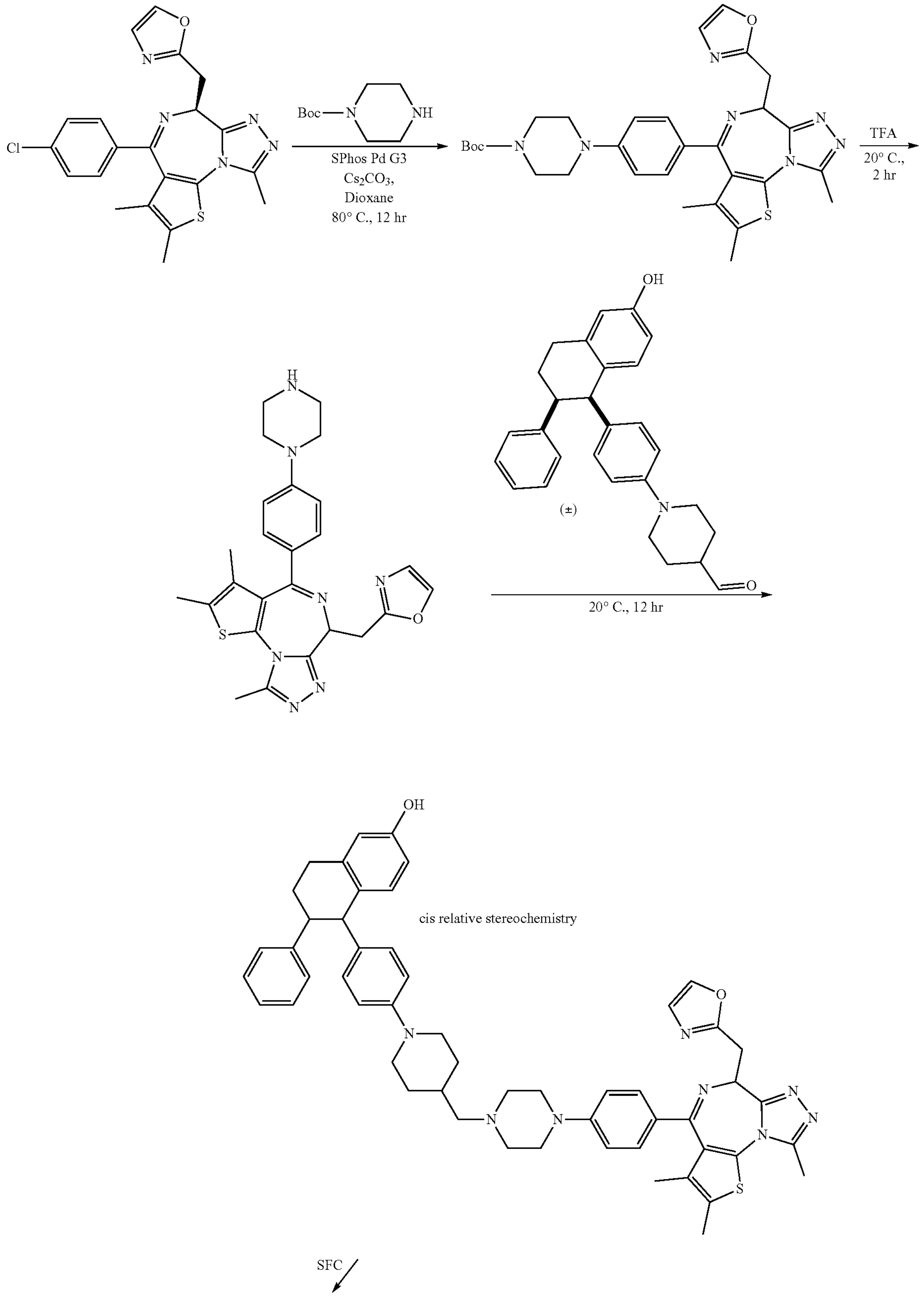

-continued

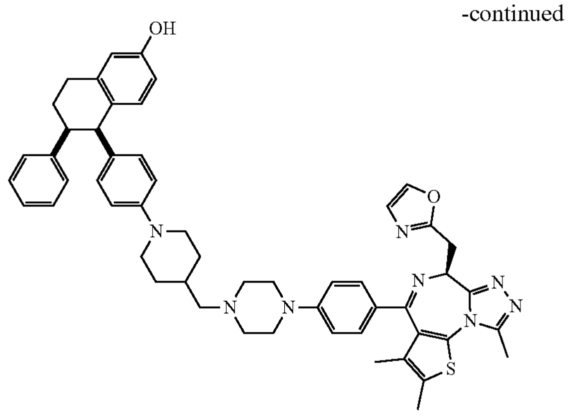

I-12

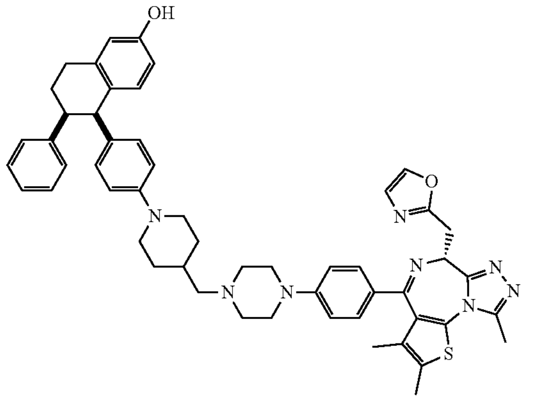

III-1

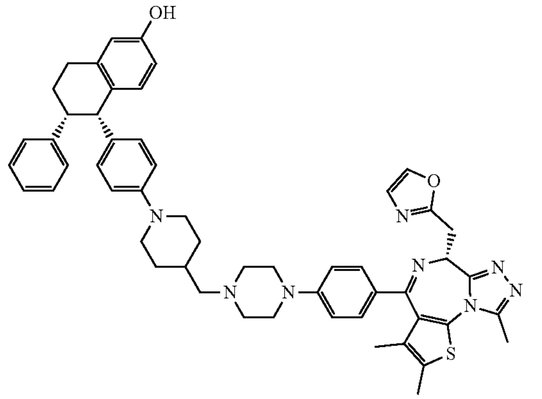

III-2

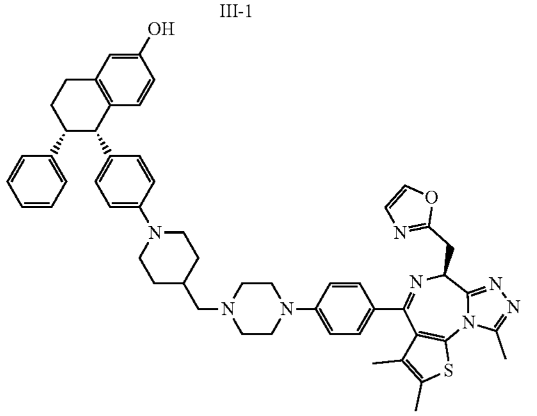

III-3

Step 1: Preparation of (+)-cis-[4-(6-methoxy-2-phenyl-tetralin-1-yl)phenyl]trifluoro-methanesulfonate. To a solution of (i)-cis-4-(6-methoxy-2-phenyl-tetralin-1-yl)phenol (500 mg, 1.51 mmol, 1 eq) in THE (20 mL) was added LiHMDS (1 M, 2.50 mL, 1.65 eq) and 1,1,1-trifluoro-N-phenyl-N-(trifluoromethylsulfonyl)methanesulfonamide (800.00 mg, 2.24 mmol, 1.48 eq) under $N_2$ at 0° C. The mixture was stirred at 20° C. for 1 hour. The reaction mixture was quenched by addition $H_2O$ 5 mL at 0° C., and then extracted with EA 8 mL (4 mL×2). The combined organic layers were washed with brine 5 mL, dried over $Na_2SO_4$, filtered and concentrated under reduced pressure to give a residue. The residue was purified by column chromatography (0-15% Ethyl acetate/Petroleum ether). Compound (±)-cis-[4-(6-methoxy-2-phenyl-tetralin-1-yl)phenyl] trifluoromethanesulfonate (650 mg, 93% yield) was obtained as a white solid.

Step 2: Preparation of (i)-cis-4-(dimethoxymethyl)-1-[4-(6-methoxy-2-phenyl-tetralin-1-yl)phenyl]piperidine. A mixture of (i)-cis-[4-(6-methoxy-2-phenyl-tetralin-1-yl)phenyl]trifluoromethanesulfonate (630.00 mg, 1.36 mmol, 1 eq), 4-(dimethoxymethyl) piperidine (315.00 mg, 1.98 mmol, 1.45 eq), SPhos Pd G3 (100.00 mg, 128.16 mol, 9.41e-2 eq), $Cs_2CO_3$ (1.10 g, 3.38 mmol, 2.48 eq) in dioxane (10 mL) was degassed and purged with $N_2$ for 3 times, and then the mixture was stirred at 100° C. for 12 hours under $N_2$ atmosphere. The reaction mixture was diluted with brine 5 mL and extracted with EA 15 mL (5 mL×3). The combined organic layers were washed with brine 10 mL, dried over $Na_2SO_4$, filtered and concentrated under reduced pressure to give a residue. The residue was purified by prep-TLC (5:1 Petroleum ether: Ethyl acetate). Compound (±)-cis-4-(dimethoxymethyl)-1-[4-(6-methoxy-2-phenyl-tetralin-1-yl)phenyl]piperidine (420 mg, 65% yield) was obtained as a brown gum.

Step 3: Preparation of (±)-cis-1-[4-(6-hydroxy-2-phenyl-tetralin-1-yl)phenyl]piperidine-4-carbaldehyde. To a solution of (i)-cis-4-(dimethoxymethyl)-1-[4-(6-methoxy-2-phenyl-tetralin-1-yl)phenyl]piperidine (400 mg, 848.12 mol, 1 eq) in DCM (4 mL) was added $BBr_3$ (2.60 g, 10.38 mmol, 1 mL, 12.24 eq) at 0° C. The mixture was stirred at 20° C. for 1 hours. And then $H_2O$ (4 mL) was added dropwise at 0° C. The resulting mixture was stirred at 20° C. for 2 hours. The reaction mixture was adjusted to pH 7-8 with aqueous $Na_2CO_3$ and extracted with EA 15 mL (5 mL×3). The combined organic layers were washed with brine 10 mL, dried over $Na_2SO_4$, filtered and concentrated under reduced pressure to give a residue. The residue was purified by prep-TLC ($SiO_2$, Petroleum ether: Ethyl acetate=1:1). Compound (±)-cis-1-[4-(6-hydroxy-2-phenyl-tetralin-1-yl)phenyl]piperidine-4-carbaldehyde (300 mg, 86% yield) was obtained as a brown solid.

Step 4: Preparation of tert-butyl-4-[4-[4,5,13-trimethyl-9-(oxazol-2-ylmethyl)-3-thia-1,8,11,12-tetrazatricyclo [8.3.0.0$^{2,6}$]trideca-2(6),4,7,10,12-pentaen-7-yl]phenyl]piperazine-1-carboxylate. A mixture of 2-[[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]methyl]oxazole (200 mg, 471.79 mol, 1 eq), tert-butyl piperazine-1-carboxylate (150.00 mg, 805.37 mol, 1.71 eq), SPhos Pd G3 (70.00 mg, 89.71 mol, 0.19 eq), $Cs_2CO_3$ (461.15 mg, 1.42 mmol, 3 eq) in dioxane (0.5 mL) was degassed and purged with $N_2$ three times, and then the mixture was stirred at 80° C. for 12 hours under $N_2$ atmosphere. The reaction mixture was diluted with $H_2O$ 5 mL and extracted with EA 15 mL (5 mL×3). The combined organic layers were washed with brine 10 mL (5 mL×2), dried over $Na_2SO_4$, filtered and concentrated under reduced pressure to give a residue. The residue was purified by prep-TLC (10:1 DCM:MeOH). Compound tert-butyl 4-[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]piperazine-1-carboxylate (210 mg, 78% yield) was obtained as a yellow solid.

Step 5: Preparation of 2-[[4,5,13-trimethyl-7-(4-piperazin-1-ylphenyl)-3-thia-1,8,11,12-tetrazatricyclo[8.3.0.0$^{2,6}$]trideca-2(6),4,7,10,12-pentaen-9-yl]methyl]oxazole. To a solution of tert-butyl 4-[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]piperazine-1-carboxylate (200 mg, 348.61 mol, 1 eq) in DCM (2 mL) was added TFA (1.23 g, 10.77 mmol, 800 L, 30.89 eq). The mixture was stirred at 20° C. for 2 hours. The reaction mixture was concentrated under reduced pressure to give a residue. The residue was purified by prep-HPLC (FA condition: column: Phenomenex luna C18 150*25 mm*10 um; mobile phase: [water(FA)-ACN]; gradient: 8%-38% B over 9 min). Compound 2-[[(9S)-4,5,13-trimethyl-7-(4-piperazin-1-ylphenyl)-3-thia-1,8,11,12-tetrazatricyclo[8.3.0.0$^{2,6}$]trideca-2(6),4,7,10,12-pentaen-9-yl]methyl]oxazole (200 mg, 98% yield, TFA) was obtained as a yellow solid.

Step 6: Preparation of Four cis-Tetraline Diastereomers of 6-phenyl-5-(4-(4-((4-(4-(2,3,9-trimethyl-6-(oxazol-2-ylmethyl)-6H-thieno[3,2-f][1,2,4]triazolo[4,3-a][1,4]diazepin-4-yl)phenyl) piperazin-1-yl)methyl)piperidin-1-yl)phenyl)-5,6,7,8-tetrahydronaphthalen-2-ol. To a solution of 2-[[4,5,13-trimethyl-7-(4-piperazin-1-ylphenyl)-3-thia-1,8,11,12-tetrazatricyclo[8.3.0.0$^{2,6}$]trideca-2(6),4,7,10,12-pentaen-9-yl]methyl]oxazole (190 mg, 323.34 mol, 1 eq, TFA) and (±)-cis-1-[4-(6-hydroxy-2-phenyl-tetralin-1-yl)phenyl]piperidine-4-carbaldehyde (150 mg, 364.49 mol, 1.13 eq) in MeOH (2 mL) was added AcOH (1.94 mg, 32.33 mol, 1.85 µL, 0.1 eq). After addition, the mixture was stirred at 20° C. for 0.5 hour, and then $NaBH(OAc)_3$ (137.06 mg, 646.68 mol, 2 eq), 1-[4-(6-hydroxy-2-phenyl-tetralin-1-yl)phenyl]piperidine-4-carbaldehyde (150 mg, 364.49 mol, 1.13 eq) was added. The resulting mixture was stirred at 20° C. for 12 hours. The reaction mixture was diluted with $H_2O$ 5 mL and extracted with EA15 mL (5 mL×3). The combined organic layers were washed with brine 10 mL, dried over $Na_2SO_4$, filtered and concentrated under reduced pressure to give a residue. The residue was purified by prep-HPLC (column: Phenomenex Luna C18 150×25 mm×10 um; mobile phase: [water(FA)-ACN]; gradient: 21%-51% B over 10 min). A mixture of the four cis-tetraline diastereomers of 2-phenyl-1-[4-[4-[[4-[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]piperazin-1-yl]methyl]-1-piperidyl]phenyl]tetralin-6-ol (100 mg, 115.06 mol, 35.58% yield) was obtained as a yellow solid.

Step 7: Preparation of Compounds I-12, III-1, III-2, and III-3. The yellow solid from the preceding step was separated by SFC (condition: column: (s,s) WHELK-01 (250 mm*30 mm, 10 um); mobile phase: [$CO_2$-ACN/MeOH (0.1% $NH_3H_2O$)]; B %: 60%, isocratic elution mode). The second fraction was further separated by SFC (condition: column: DAICEL CHIRALCEL OD (250 mm*30 mm, 10 um); mobile phase: [$CO_2$-ACN/MeOH (0.1% NH3H2O)]; B %: 55%, isocratic elution mode). The diastereomer that was found to be the most potent inhibitor of cell growth of T-Rex 293 cells having increased expression of estrogen receptor alpha protein (as described in the Example 56, below) was obtained as a yellow solid (13.58 mg, 16% yield). $^1$H NMR (400 MHz, $CDCl_3$) δ (ppm)=7.62 (s, 1H), 7.31 (br d, J=8.4 Hz, 2H), 7.19-7.09 (m, 3H), 7.04 (s, 1H), 6.85-6.75 (m, 5H), 6.70 (s, 1H), 6.61-6.50 (m, 3H), 6.29 (br d, J=8.4 Hz, 2H), 4.70 (t, J=7.2 Hz, 1H), 4.19 (br d, J=4.8 Hz, 1H), 4.15-3.99 (m, 2H), 3.54 (br d, J=8.8 Hz, 2H), 3.38-3.23 (m, 5H), 3.08-2.95 (m, 2H), 2.68-2.54 (m, 9H), 2.41 (s, 3H), 2.31 (br d, J=6.4 Hz, 2H), 2.19-2.14 (m, 1H), 1.84 (br d, J=13.6 Hz, 3H), 1.73 (s, 3H), 1.66 (br d, J=4.2 Hz, 1H), 1.40-1.27 (m, 2H). LC-MS: MS (ES$^+$): RT=1.438 min, m/z=869.4 [M+H]; LCMS Method: 25.

Example 14—Synthesis of (S)-(6-hydroxy-2-(4-hydroxyphenyl)benzo[b]thiophen-3-yl)(4-(2-(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)ethyl)piperidin-1-yl)ethoxy)phenyl)methanone (I-13)

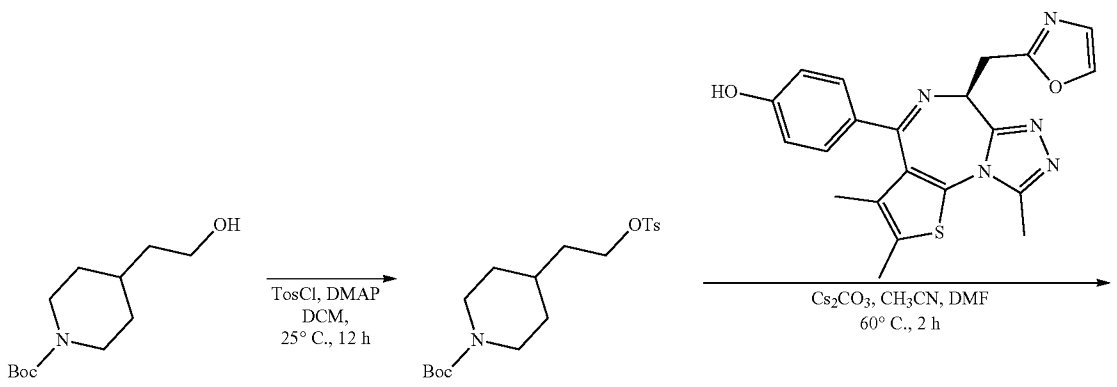

-continued

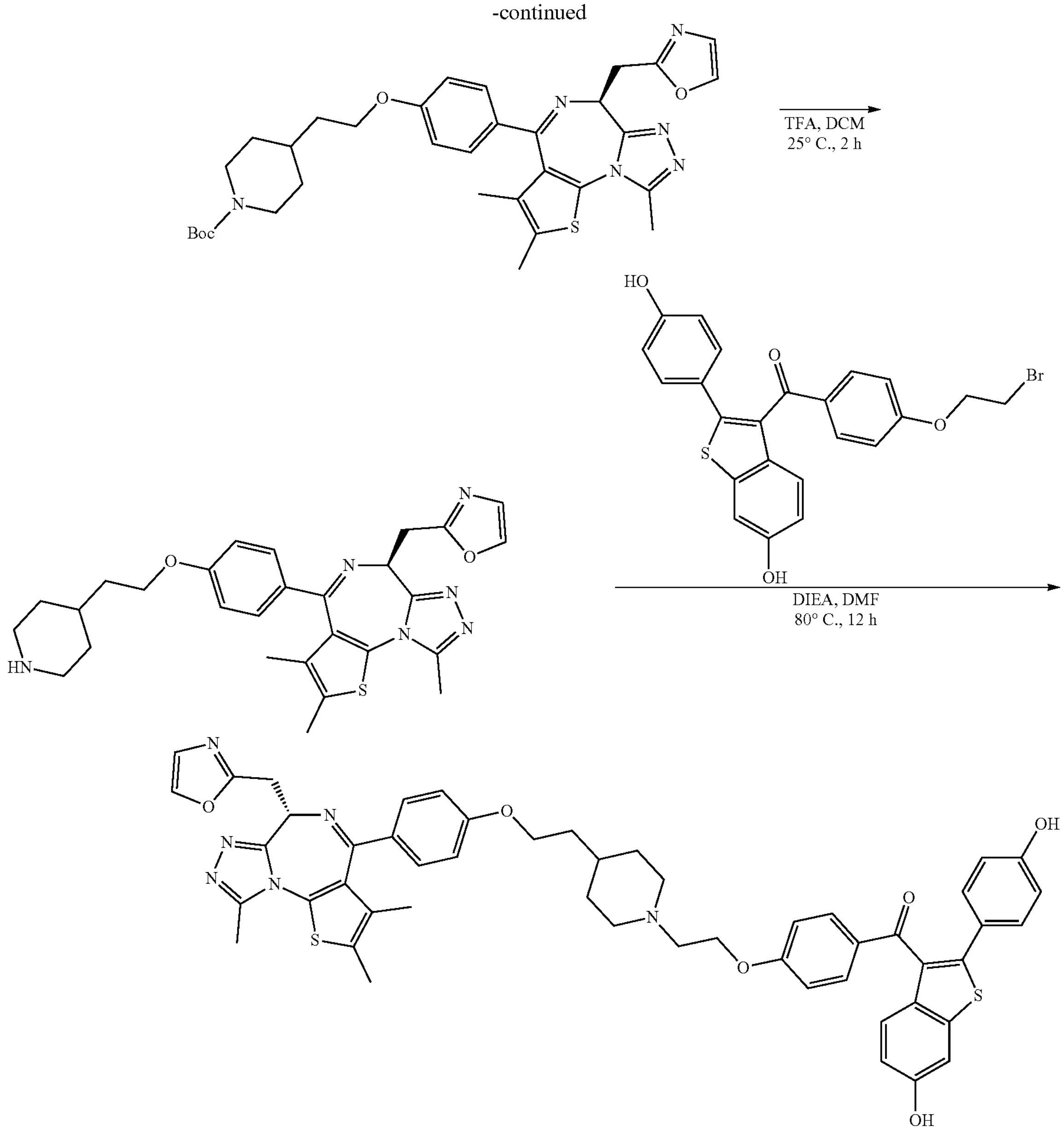

I-13

Step 1: Preparation of tert-butyl 4-[2-(p-tolylsulfonyloxy)ethyl]piperidine-1-carboxylate. To a solution of tert-butyl 4-(2-hydroxyethyl)piperidine-1-carboxylate (1 g, 4.36 mmol, 1 eq) in DCM (20 mL) were added DMAP (106.55 mg, 872.16 mol, 0.2 eq), TosCl (1.66 g, 8.72 mmol, 2 eq) and TEA (1.32 g, 13.08 mmol, 1.82 mL, 3 eq). The mixture was stirred at 25° C. for 12 hours. The reaction mixture was filtered and concentrated under reduced pressure to give a residue. The residue was purified by column chromatography (0~21% Ethyl acetate/Petroleum ether). Compound tert-butyl 4-[2-(p-tolylsulfonyloxy)ethyl]piperidine-1-carboxylate (1.5 g, 90% yield) was obtained as yellow oil.

Step 2: Preparation of tert-butyl 4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]ethyl]piperidine-1-carboxylate. To a solution of tert-butyl 4-[2-(p-tolylsulfonyl oxy)ethyl]piperidine-1-carboxylate (605.32 mg, 1.58 mmol, 1.6 eq) in $CH_3CN$ (4 mL) and DMF (4 mL) was added $Cs_2CO_3$ (964.27 mg, 2.96 mmol, 3 eq) and 4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenol (400 mg, 986.50 mol, 1 eq). The mixture was stirred at 60° C. for 2 hours. The reaction mixture was concentrated under reduced pressure to remove solvent. The residue was diluted with $H_2O$ 15 mL and extracted with EA 45 mL (15 mL×3). The combined organic layers were washed with brine 20 mL (10 mL×2), dried over $Na_2SO_4$, filtered and concentrated under reduced pressure to give a residue. The residue was purified by column chromatography (0-100% Ethyl acetate/Petroleum ether). tert-butyl 4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]ethyl]piperidine-1-carboxylate (468 mg, 77% yield) was obtained as yellow oil.

Step 3: Preparation of 2-[[(9S)-4,5,13-trimethyl-7-[4-[2-(4-piperidyl)ethoxy]phenyl]-3-thia-1,8,11,12-tetrazatricyclo[8.3.0.0$^{2,6}$]trideca-2(6),4,7,10,12-pentaen-9-yl]methyl]oxazole. To a solution of tert-butyl 4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]ethyl]piperidine-1-carboxylate (440 mg, 713.39 mol, 1 eq) in DCM (5 mL) was added TFA (1.54 g, 13.46 mmol, 1.00 mL, 18.87 eq). The mixture was stirred at 25° C. for 2 hours. The reaction mixture was concentrated under reduced pressure to remove solvent. The residue was diluted with $NaHCO_3$ 15 mL and extracted with DCM 45 mL (15 mL×3). The combined organic layers were dried over $Na_2SO_4$, filtered and concentrated under reduced pressure to give a residue. The residue was purified by prep-HPLC (column: Phenomenex Luna C18 150×25 mm×10 um; mobile phase: [water(FA)-ACN]; gradient: 12%-42% B over 10 min). Compound 2-[[(9S)-4,5,13-trimethyl-7-[4-[2-(4-piperidyl)ethoxy]phenyl]-3-thia-1,8,11,12-tetrazatricyclo[8.3.0.0$^{2,6}$]trideca-2(6),4,7,10,12-pentaen-9-yl]methyl]oxazole (368 mg, 99% yield) was obtained as a yellow solid.

Step 4: Preparation of (S)-(6-hydroxy-2-(4-hydroxyphenyl)benzo[b]thiophen-3-yl)(4-(2-(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)ethyl)piperidin-1-yl)ethoxy)phenyl)methanone. To a solution of 2-[[(9S)-4,5,13-trimethyl-7-[4-[2-(4-piperidyl)ethoxy]phenyl]-3-thia-1,8,11,12-tetrazatricyclo[8.3.0.0$^{2,6}$]trideca-2(6),4,7,10,12-pentaen-9-yl]methyl]oxazole (75 mg, 145.16 mol, 1 eq) in DMF (1 mL) was added DIEA (56.28 mg, 435.49 mol, 75.85 µL, 3 eq) and [4-(2-bromoethoxy)phenyl]-[6-hydroxy-2-(4-hydroxyphenyl)benzothiophen-3-yl]methanone (81.76 mg, 174.20 mol, 1.2 eq). The mixture was stirred at 80° C. for 12 hours. The reaction mixture was filtered and concentrated under reduced pressure to give a residue. The residue was purified by prep-HPLC (FA condition; column: Phenomenex Luna C18 150×25 mm×10 um; mobile phase: [water(FA)-ACN]; gradient: 25%-55% B over 10 min). (S)-(6-hydroxy-2-(4-hydroxyphenyl)benzo[b]thiophen-3-yl)(4-(2-(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)ethyl)piperidin-1-yl)ethoxy)phenyl)methanone (1-13, 27.6 mg, 21% yield) was obtained as a yellow gum. $^1H$ NMR (400 MHz, DMSO-$d_6$) δ (ppm) 9.95-9.54 (m, 1H), 8.04 (s, 1H), 7.65 (d, J=8.8 Hz, 2H), 7.34 (d, J=2.0 Hz, 1H), 7.29 (d, J=8.4 Hz, 2H), 7.25 (d, J=8.8 Hz, 1H), 7.20-7.16 (m, 2H), 7.13 (s, 1H), 6.93 (dd, J=8.8, 5.6 Hz, 4H), 6.85 (dd, J=8.8, 2.2 Hz, 1H), 6.68 (d, J=8.8 Hz, 2H), 4.62 (t, J=7.2 Hz, 1H), 4.12-3.99 (m, 4H), 3.92-3.85 (m, 1H), 3.84-3.77 (m, 1H), 2.87 (br d, J=10.8 Hz, 2H), 2.63 (br t, J=5.8 Hz, 2H), 2.60 (s, 3H), 2.42 (s, 3H), 1.97 (br t, J=10.8 Hz, 2H), 1.68-1.59 (m, 7H), 1.46-1.37 (m, 1H), 1.24-1.13 (m, 2H). LC-MS: MS (ES$^+$): RT=1.663 min, m/z=905.4 [M+H$^+$]. LCMS Method: 25.

Example 15—Synthesis of (S)-(2-(4-bromophenyl)-6-hydroxybenzo[b]thiophen-3-yl)(4-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)phenyl)methanone (I-14)

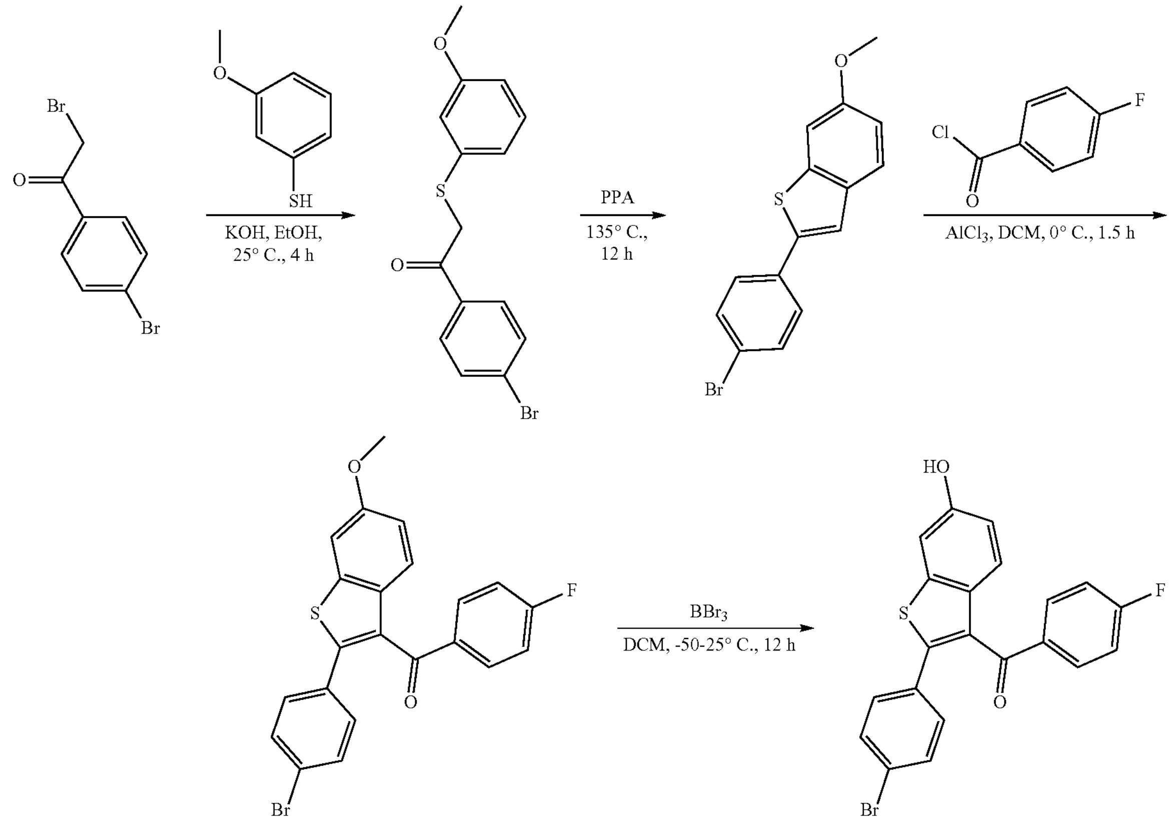

-continued

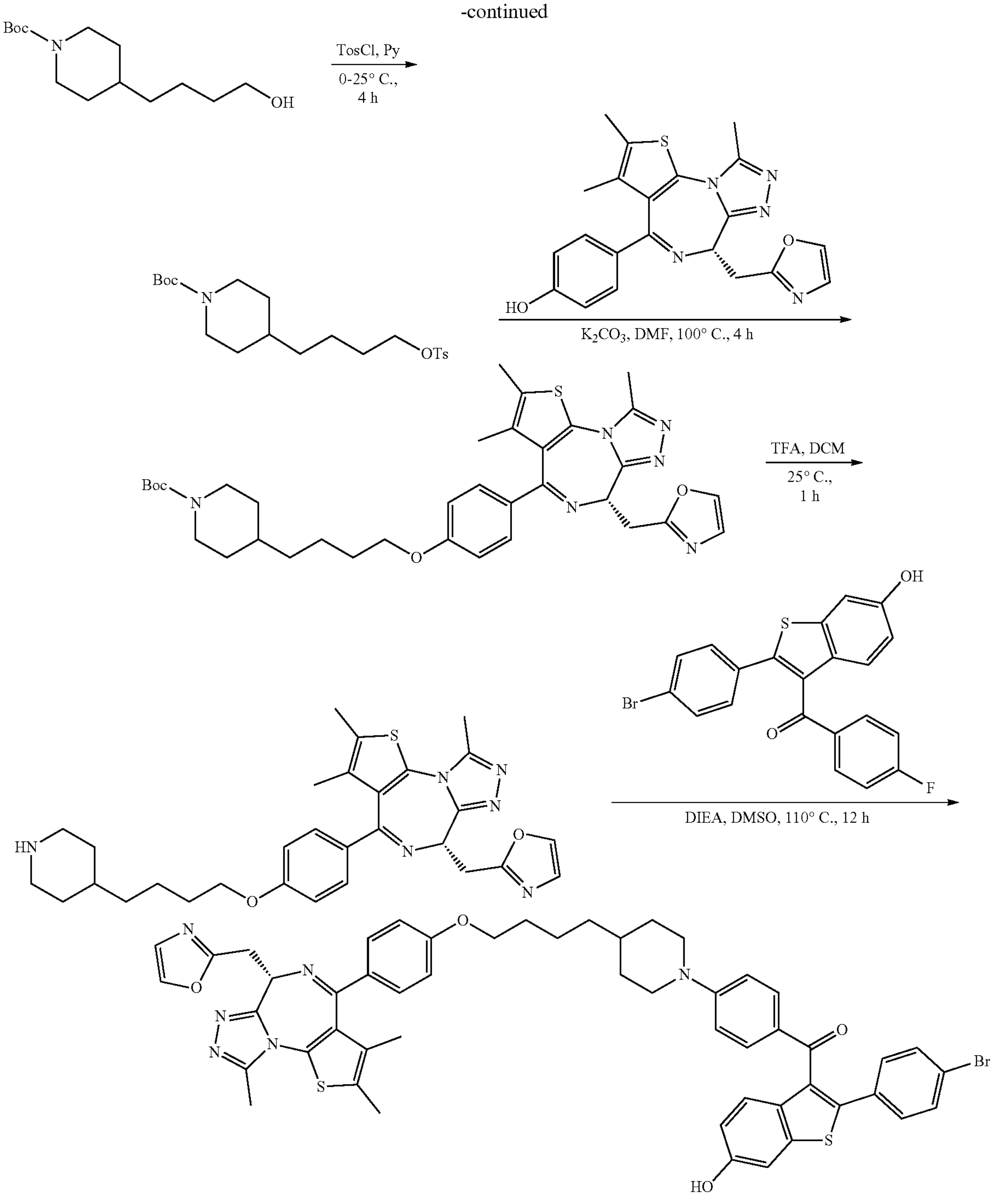

I-14

Step 1: Preparation of 1-(4-bromophenyl)-2-(3-methoxyphenyl)sulfanyl-ethanone. To a solution of KOH (88.82 g, 1.58 mol, 10 equiv) in EtOH (300 mL) was added 3-methoxybenzenethiol (24.41 g, 174.14 mmol, 21.40 mL, 1.1 equiv) at 25° C. The miture was stirred at 25° C. for 30 min. Then the mixture was cooled to 0° C. and 2-bromo-1-(4-bromophenyl)ethanone (44 g, 158.31 mmol, 1 equiv) in EtOAc (300 mL) were added subsequently at 0° C. The mixture was stirred at 0° C. for 30 min. The reaction mixture was warmed to 25° C. and stirred for 4 h. The solvent was removed under reduced pressure. The residue was extracted with ethyl acetate (500 mL×2), washed with brine (300 mL), and dried over anhydrous $Na_2SO_4$. The solvent was removed under reduced pressure. The residue was purified by column chromatography ($SiO_2$, Petroleum ether/Ethyl acetate, 1/0 to 10/1) to afford 1-(4-bromophenyl)-2-(3-methoxyphenyl)sulfanyl-ethanone (43 g, 80% yield) was obtained as a white solid.

Step 2: Preparation of 2-(4-bromophenyl)-6-methoxy-benzothiophene. To a stirring solution of PPA (30 mL) at 80°

C. was added 1-(4-bromophenyl)-2-(3-methoxy phenyl)sulfanyl-ethanone (3 g, 8.90 mmol, 1 equiv) in portions within 30 min. Then the reaction was heated to 90° C. and stirred for 1.5 h. The solution was stirred at 135° C., for another 10 h. The reaction mixture was poured into ice water. The crude product was collected by filtration and the solid was washed with water to afford 2-(4-bromophenyl)-6-methoxy-benzothiophene (2.3 g, 80% yield) as a white solid.

Step 3: Preparation of [2-(4-bromophenyl)-6-methoxy-benzothiophen-3-yl]-(4-fluorophenyl)methanone. To a solution of 2-(4-bromophenyl)-6-methoxy-benzothiophene (2.2 g, 6.89 mmol, 1 equiv) in DCM (20 mL) was added $AlCl_3$ (1.38 g, 10.34 mmol, 564.94 L, 1.5 equiv) and 4-fluorobenzoyl chloride (1.64 g, 10.34 mmol, 1.24 mL, 1.5 equiv) at 0° C. The mixture was stirred at 0° C. for 2 h. To a solution of $NaHCO_3$ (aq) (100 mL) was added the reaction mixture at 25° C., and then diluted with water 100 mL and extracted with EtOAc (100 mL×3). The combined organic layers were dried over $Na_2SO_4$, filtered and concentrated under reduced pressure to give a residue. The residue was purified by prep-HPLC (column: Phenomenex Luna C18 (250 mm×70 mm, 10 um); mobile phase: [water (FA)-ACN]; gradient 30%-95% B over 45 min) to give [2-(4-bromophenyl)-6-methoxy-benzothiophen-3-yl]-(4-fluorophenyl)methanone (140 mg, 4% yield) as a white solid.

Step 4: Preparation of [2-(4-bromophenyl)-6-hydroxy-benzothiophen-3-yl]-(4-fluorophenyl)methanone. To a solution of [2-(4-bromophenyl)-6-methoxy-benzothiophen-3-yl]-(4-fluorophenyl)methanone (140 mg, 317.24 mol, 1 equiv) in DCM (6 mL) was added $BBr_3$ (1 M, 317.24 µL, 1 equiv) at −50° C. under $N_2$. Then the mixture was stirred at 25° C. for 2 h. The reaction was poured into water (70 mL). The aqueous phase was extracted with ethyl acetate (15 mL×3). The reaction mixture was quenched by dropwise addition of $NaHCO_3$ (aq) 5 mL to pH 5 at 25° C. under $N_2$, and then diluted with $H_2O$ 20 mL and extracted with DCM (20 mL×3). The combined organic layers were dried over $Na_2SO_4$, filtered and concentrated under reduced pressure to give a residue. The residue was purified by prep-TLC (SiO2, PE:EtOAc=3:1) to afford [2-(4-bromophenyl)-6-hydroxy-benzothiophen-3-yl]-(4-fluorophenyl)methanone (120 mg, 88% yield) as a yellow solid.

Step 5: Preparation of tert-butyl 4-[4-(p-tolylsulfonyloxy)butyl]piperidine-1-carboxylate. To a solution of tert-butyl 4-(4-hydroxybutyl)piperidine-1-carboxylate (2.5 g, 9.71 mmol, 1 equiv) in pyridine (20 mL) was added TosCl (5.56 g, 29.14 mmol, 3.0 equiv) at 0° C. Then the mixture was stirred at 25° C. for 4 h. The reaction mixture was partitioned between $H_2O$ (100 mL) and EtOAc (100 mL×3). The organic phase was separated, dried over $Na_2SO_4$, filtered and concentrated under reduced pressure to give a residue. The residue was purified by column chromatography ($SiO_2$, Petroleum ether/Ethyl acetate, 1/0 to 10/1) to afford tert-butyl 4-[4-(p-tolylsulfonyloxy)butyl]piperidine-1-carboxylate (1.4 g, 35% yield) as a white oil.

Step 6: Preparation of tert-butyl 4-[4-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]butyl]piperidine-1-carboxylate. To a solution of tert-butyl 4-[4-(p-tolylsulfonyloxy)butyl]piperidine-1-carboxylate (203.00 mg, 493.25 mol, 2.0 equiv) and 4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenol (100 mg, 246.63 mol, 1 equiv) in DMF (3 mL) was added $K_2CO_3$ (68.17 mg, 493.25 mol, 2.0 equiv). The mixture was stirred at 100° C. for 3 h. The reaction mixture was partitioned between $H_2O$ 50 mL and EtOAc (50 mL×3). The organic phase was separated, dried over $Na_2SO_4$, filtered and concentrated under reduced pressure to give a residue. The residue was purified by prep-TLC ($SiO_2$, DCM:MeOH=10:1) to afford tert-butyl 4-[4-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]butyl]piperidine-1-carboxylate (150 mg, 94% yield) as a yellow oil.

Step 7: Preparation of 2-[[(9S)-4,5,13-trimethyl-7-[4-[4-(4-piperidyl)butoxy]phenyl]-3-thia-1,8,11,12-tetrazatricyclo[8.3.0.0$^{2,6}$]trideca-2(6),4,7,10,12-pentaen-9-yl]methyl]oxazole. To a solution of tert-butyl 4-[4-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]butyl]piperidine-1-carboxylate (130 mg, 201.61 mol, 1 equiv) in DCM (3 mL) was added TFA (1.54 g, 13.46 mmol, 1.00 mL, 66.78 equiv). The mixture was stirred at 25° C. for 1 h. The reaction mixture was quenched by addition $NaHCO_3$ (aq) 30 mL at 25° C., and then diluted with $H_2O$ (50 mL) and extracted with DCM (50 mL×3). The combined organic layers were dried over $Na_2SO_4$, filtered and concentrated under reduced pressure to give a residue to afford 2-[[(9S)-4,5,13-trimethyl-7-[4-[4-(4-piperidyl)butoxy]phenyl]-3-thia-1,8,11,12-tetrazatricyclo[8.3.0.0$^{2,6}$]trideca-2(6),4,7,10,12-pentaen-9-yl]methyl]oxazole (100 mg, 91% yield) as a yellow oil.

Step 8: Preparation of (S)-(2-(4-bromophenyl)-6-hydroxybenzo[b]thiophen-3-yl)(4-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)phenyl)methanone. To a solution of 2-[[(9S)-4,5,13-trimethyl-7-[4-[4-(4-piperidyl)butoxy]phenyl]-3-thia-1,8,11,12-tetraza tricyclo [8.3.0.0$^{2,6}$]trideca-2(6),4,7,10,12-pentaen-9-yl]methyl]oxazole (60 mg, 110.15 mol, 1 equiv) and [2-(4-bromophenyl)-6-hydroxy-benzothiophen-3-yl]-(4-fluorophenyl)methanone (51.77 mg, 121.17 mol, 1.1 equiv) in DMSO (2 mL) was added DIEA (42.71 mg, 330.45 mol, 57.56 L, 3.0 equiv). The mixture was stirred at 110° C. for 12 h. The reaction mixture was concentrated under reduced pressure to give a residue. The residue was purified by prep-HPLC (column: YMC-Actus Triart C18 150 mm×30 mm×7 um; mobile phase: [water (FA)-ACN]; gradient 80%-100% B over 10 min) to afford (S)-(2-(4-bromophenyl)-6-hydroxybenzo [b]thiophen-3-yl)(4-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)phenyl)methanone (I-14, 24.97 mg, 23% yield) as a yellow solid. $^1$H NMR (400 MHz, DMSO-$d_6$) δ 9.87 (s, 1H), 8.03 (s, 1H), 7.57-7.48 (m, 4H), 7.37 (d, J=2.0 Hz, 1H), 7.32 (d, J=8.8 Hz, 2H), 7.28 (d, J=8.8 Hz, 2H), 7.23 (d, J=8.8 Hz, 1H), 7.12 (s, 1H), 6.92 (d, J=8.8 Hz, 2H), 6.88-6.80 (m, 3H), 4.66-4.58 (m, 1H), 4.01-3.95 (m, 2H), 3.94-3.85 (m, 3H), 3.84-3.76 (m, 1H), 2.81 (t, J=12.0 Hz, 2H), 2.59 (s, 3H), 2.41 (s, 3H), 1.74-1.66 (m, 4H), 1.63 (s, 3H), 1.53-1.36 (m, 3H), 1.27-1.22 (m, 2H), 1.15-1.02 (m, 2H). LC-MS: MS ($ES^+$): RT=3.536 min, m/z=953.3 [$M+H^+$], LC-MS Method: 25.

Example 16—Synthesis of (S)-(6-hydroxy-2-(4-hydroxyphenyl)benzo[b]thiophen-3-yl)(4-(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)ethyl)piperidin-1-yl)phenyl)methanone (I-15)
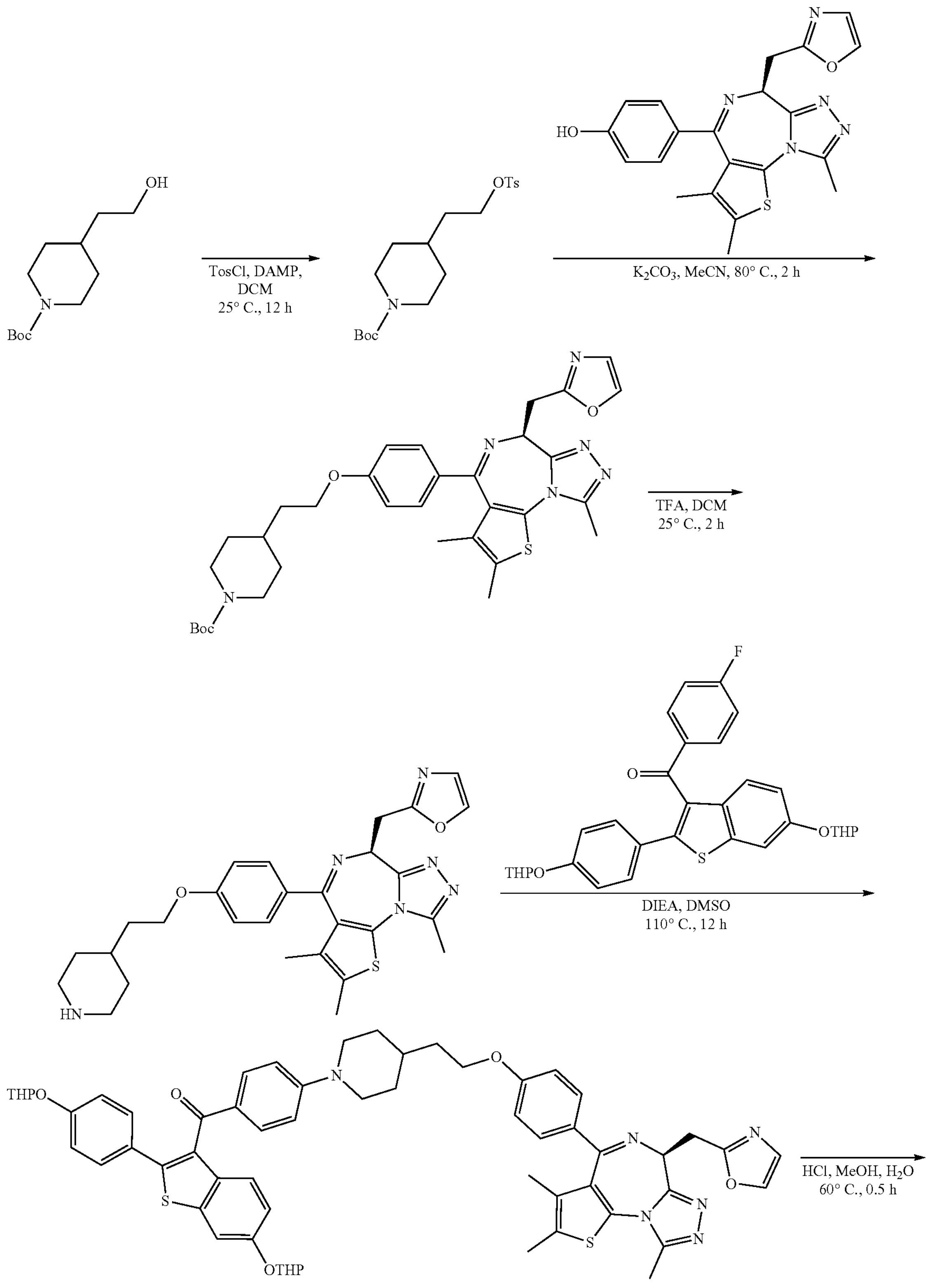

-continued

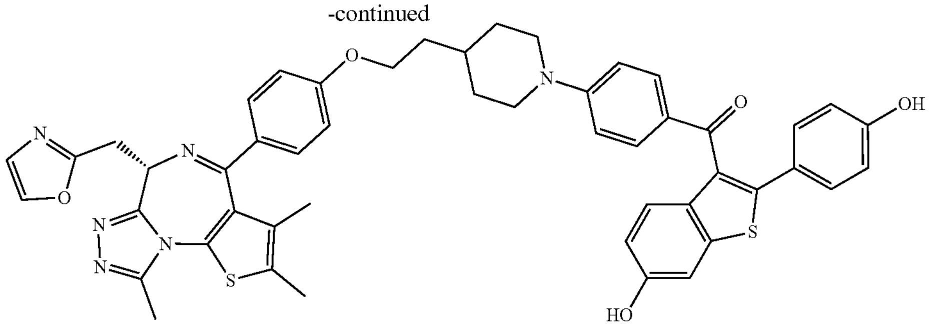

I-15

Step 1: Preparation of tert-butyl 4-[2-(p-tolylsulfonyloxy) ethyl]piperidine-1-carboxylate. To a solution of tert-butyl 4-(2-hydroxyethyl)piperidine-1-carboxylate (24 g, 104.66 mmol, 1 equiv) in DCM (240 mL) was added 4-methylbenzenesulfonyl chloride (29.93 g, 156.99 mmol, 1.5 equiv) and DMAP (12.79 g, 104.66 mmol, 1 equiv). The mixture was stirred at 25° C. for 12 h. The reaction mixture was partitioned between $H_2O$ 300 mL and DCM 300 mL. The organic phase was separated, dried over $Na_2SO_4$, filtered and concentrated under reduced pressure to give a residue. The residue was purified by column chromatography ($SiO_2$, Petroleum ether/Ethyl acetate=30/1 to 10/1) to afford tert-butyl 4-[2-(p-tolylsulfonyloxy)ethyl]piperidine-1-carboxylate (17 g, 42% yield) as a colorless oil.

Step 2: Preparation of afford tert-butyl 4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl] phenoxy]ethyl]piperidine-1-carboxylate. To a solution of tert-butyl 4-[2-(p-tolylsulfonyl oxy) ethyl]piperidine-1-carboxylate (141.87 mg, 369.94 mol, 1.5 equiv) in MeCN (10 mL) was added $K_2CO_3$ (68.17 mg, 493.25 mol, 2 equiv) and 4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenol (100 mg, 246.63 mol, 1 equiv). The mixture was stirred at 80° C. for 2 h. The reaction mixture was filtered and concentrated under reduced pressure to give a residue. The residue was purified by prep-TLC ($SiO_2$, DCM: MeOH=10:1) to afford tert-butyl 4-[2-[4-[(9S)-4,5,13-trimethyl-9-(oxazol-2-ylmethyl)-3-thia-1,8,11,12-tetrazatricyclo [8.3.0.0$^{2,6}$]trideca-2(6),4,7,10,12-pentaen-7-yl]phenoxy] ethyl]piperidine-1-carboxylate (130 mg, 85% yield) as a yellow oil.

Step 3: Preparation of 2-[[(9S)-4,5,13-trimethyl-7-[4-[2-(4-piperidyl)ethoxy]phenyl]-3-thia-1,8,11,12-tetrazatricyclo [8.3.0.0$^{2,6}$]trideca-2(6),4,7,10,12-pentaen-9-yl]methyl]oxazole. To a solution of tert-butyl 4-[2-[4-[(9S)-4,5,13-trimethyl-9-(oxazol-2-ylmethyl)-3-thia-1,8,11,12-tetrazatricyclo[8.3.0.02,6]trideca-2(6),4,7,10,12-pentaen-7-yl]phenoxy]ethyl]piperidine-1-carboxylate (170 mg, 275.63 mol, 1 equiv) in DCM (3 mL) was added TFA (1.54 g, 13.46 mmol, 1 mL, 49 equiv). The mixture was stirred at 25° C. for 2 h. The reaction mixture was quenched by addition $NaHCO_3$ (aq) 10 mL at 25° C., adjust PH to 8, and then diluted with $H_2O$ 20 mL and extracted with EA 40 mL (20 mL×2), dried over $Na_2SO_4$, filtered and concentrated under reduced pressure to afford 2-[[(9S)-4,5,13-trimethyl-7-[4-[2-(4-piperidyl)ethoxy]phenyl]-3-thia-1,8,11,12-tetrazatricyclo [8.3.0.0$^{2,6}$]trideca-2(6),4,7,10,12-pentaen-9-yl]methyl]oxazole (140 mg, 98% yield) as a white solid.

Step 4: Preparation of [6-tetrahydropyran-2-yloxy-2-(4-tetrahydropyran-2-yloxyphenyl) benzothiophen-3-yl]-[4-[4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]ethyl]-1-piperidyl]phenyl] methanone. To a solution of 2-[[(9S)-4,5,13-trimethyl-7-[4-[2-(4-piperidyl)ethoxy]phenyl]-3-thia-1,8,11,12-tetrazatricyclo[8.3.0.0$^{2,6}$]trideca-2(6),4,7,10,12-pentaen-9-yl]methyl]oxazole (60 mg, 116.13 mol, 1 equiv) in DMSO (2 mL) was added DIEA (45.03 mg, 348.39 mol, 60.68 µL, 3 equiv) and (4-fluorophenyl)-[6-tetrahydropyran-2-yloxy-2-(4-tetrahydropyran-2-yloxyphenyl)benzothiophen-3-yl] methanone (61.85 mg, 116.13 mol, 1 equiv). The mixture was stirred at 110° C. for 12 h. The reaction mixture was partitioned between EtOAc (20 mL) and $H_2O$ (20 mL). The organic phase was separated, washed with NaCl 20 mL (10 mL×2), filtered and concentrated under reduced pressure to give a residue. The residue was purified by prep-TLC ($SiO_2$, DCM:MeOH=10:1) to afford [6-tetrahydropyran-2-yloxy-2-(4-tetrahydropyran-2-yloxyphenyl) benzothiophen-3-yl]-[4-[4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]ethyl]-1-piperidyl]phenyl] methanone (40 mg, 33% yield) as a white solid.

Step 5: Preparation of (S)-(6-hydroxy-2-(4-hydroxyphenyl)benzo[b]thiophen-3-yl)(4-(4-(2-(4-(2,3,9-trimethyl-6-(oxazol-2-ylmethyl)-6H-thieno[3,2-f][1,2,4]triazolo[4,3-a] [1,4]diazepin-4-yl)phenoxy)ethyl)piperidin-1-yl)phenyl) methanone. To a solution of [6-tetrahydropyran-2-yloxy-2-(4-tetrahydropyran-2-yloxyphenyl)benzothiophen-3-yl]-[4-[4-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]ethyl]-1-piperidyl]phenyl] methanone (38 mg, 36.92 mol, 1 equiv) in MeOH (3 mL) and $H_2O$ (0.3 mL) was added HCl (306.00 mg, 8.39 mmol, 0.3 mL, 227 equiv). The mixture was stirred at 60° C. for 0.5 h. The reaction mixture was added HCl (4M) and adjust PH to 7, then partitioned between EA (10 mL) and $H_2O$ (10 mL). The organic phase was separated, filtered and concentrated under reduced pressure to give a residue. The residue was purified by prep-HPLC (column: C18 150×30 mm; mobile phase: [water(FA)-ACN]; gradient of 60%-90% over 7 min) to afford (S)-(6-hydroxy-2-(4-hydroxyphenyl)benzo [b]thiophen-3-yl)(4-(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)ethyl)piperidin-1-yl)phenyl) methanone (I-15, 16 mg, 49% yield) as a yellow solid. H NMR (400 MHz, DMSO-d6) δ 9.72 (br dd, J=6.4, 2.4 Hz, 2H) 8.03 (s, 1H) 7.48-7.54 (m, 2H) 7.26-7.32 (m, 3H) 7.20 (d, J=8.4 Hz, 2H) 7.11-7.18 (m, 2H) 6.90-6.96 (m, 2H) 6.82 (dd, J=8.8, 2.8 Hz, 3H) 6.69 (d, J=8.8 Hz, 2H) 4.58-4.65 (m, 1H) 4.01-4.06 (m, 2H) 3.78-3.93 (m, 4H) 2.78-2.86 (m, 2H) 2.59 (s, 3H) 2.41 (s, 3H) 1.72-1.77 (m, 2H) 1.64 (s, 3H) 1.23 (br s, 5H). LC-MS: MS ($ES^+$): RT=2.979 min, m/z=861.4 $[M+H^+]$. LCMS Method: 01.

Example 17—Synthesis of (S)-2-(4-(4-chlorophenyl)-2,3,9-trimethyl-6H-thieno[3,2-f][1,2,4]triazolo[4,3-a][1,4]diazepin-6-yl)-N-(7-(4-(6-hydroxy-2-(4-hydroxyphenyl) benzo[b]thiophene-3-carbonyl) phenoxy)heptyl)acetamide (I-16)
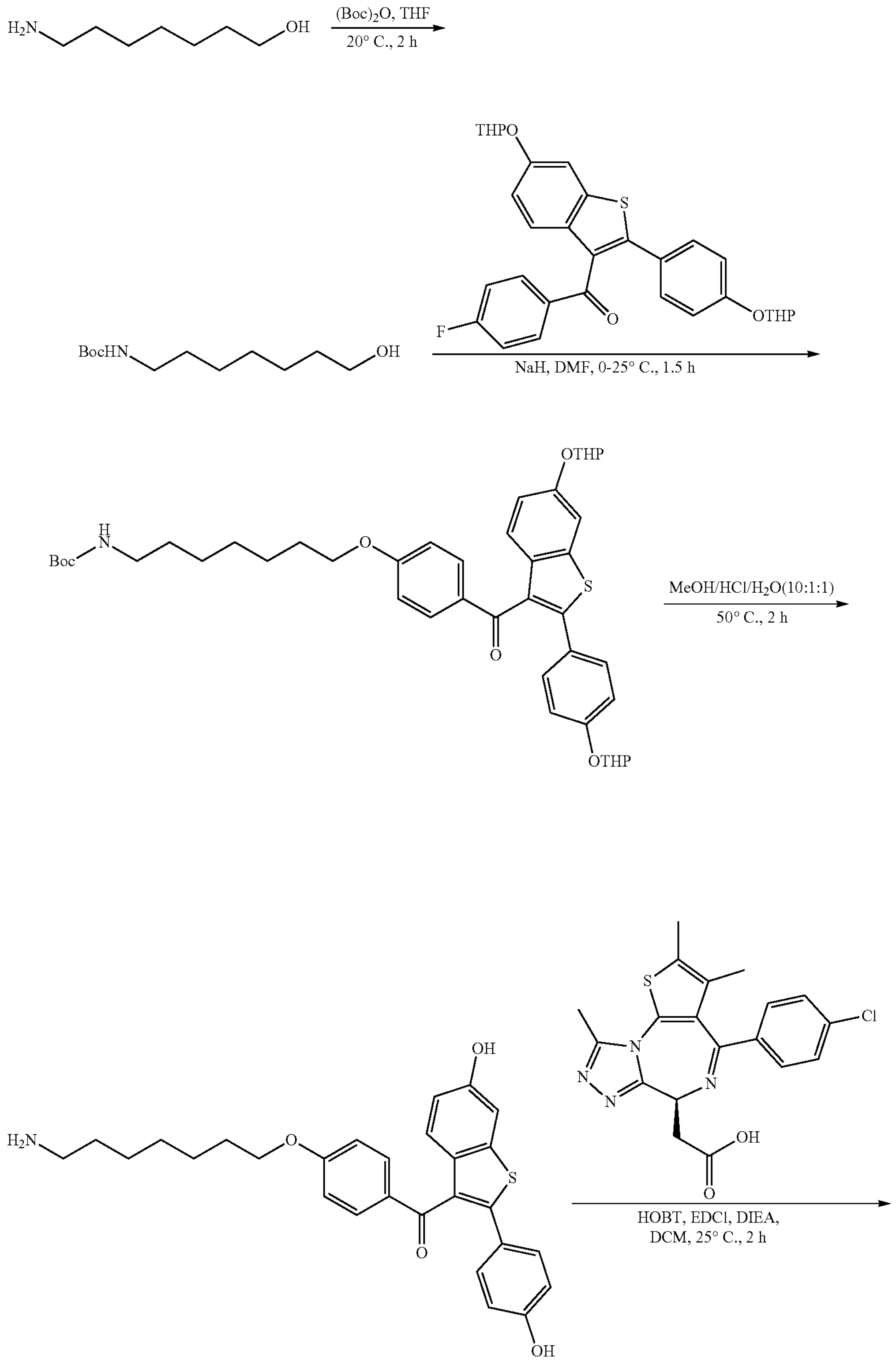

-continued

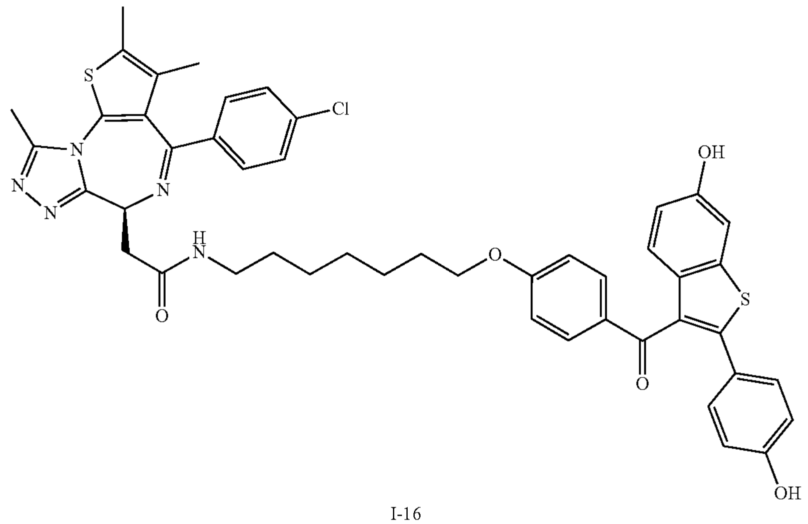

I-16

Step 1: Preparation of tert-butyl N-(7-hydroxyheptyl) carbamate. To a solution of 7-aminoheptan-1-ol (4 g, 30.48 mmol, 1 equiv) in THF (40 mL) was added $(Boc)_2O$ (7.98 g, 36.58 mmol, 8.40 mL, 1.2 equiv). The mixture was stirred at 20° C. for 2 h. The reaction mixture was concentrated under reduced pressure to give a residue. The residue was purified by column chromatography (Silica, Eluent of 0~30% Ethyl acetate/Petroleum ether) to afford tert-butyl N-(7-hydroxyheptyl)carbamate (6.3 g, 89% yield) as a colorless oil.

Step 2: Preparation of tert-butyl N-[7-[4-[6-tetrahydropyran-2-yloxy-2-(4-tetrahydropyran-2-yloxyphenyl)benzothiophene-3-carbonyl]phenoxy]heptyl]carbamate. To a solution of tert-butyl N-(7-hydroxyheptyl)carbamate (260.60 mg, 1.13 mmol, 2 equiv) in THE (4 mL) was added portion wise NaH (56.33 mg, 1.41 mmol, 60% purity, 2.5 equiv) at 0° C. under $N_2$, the mixture was stirred at 0° C. for 0.5 h under $N_2$, then (4-fluorophenyl)-[6-tetrahydropyran-2-yloxy-2-(4-tetrahydropyran-2-yloxyphenyl)benzothiophen-3-yl]methanone (300 mg, 563.25 mol, 1 equiv) was added. The mixture was stirred at 25° C. for 1 h under $N_2$. The reaction mixture was quenched by addition $NH_4Cl$ (10 mL) at 25° C., and then extracted with EA 27 mL (9 mL×3). The combined organic layers were dried over $Na_2SO_4$, filtered and concentrated under reduced pressure to give a residue. The residue was purified by column chromatography (silica, Eluent of $0\sim_{30}$% Ethyl acetate/Petroleum ether) to afford tert-butyl N-[7-[4-[6-tetrahydropyran-2-yloxy-2-(4-tetrahydropyran-2-yloxyphenyl) benzothiophene-3-carbonyl]phenoxy]heptyl]carbamate (300 mg, 71% yield) as a yellow solid.

Step 3: Preparation of [4-(7-aminoheptoxy)phenyl]-[6-hydroxy-2-(4-hydroxy phenyl) benzothiophen-3-yl]methanone. Tert-butyl N-[7-[4-[6-tetrahydropyran-2-yloxy-2-(4-tetrahydropyran-2-yloxyphenyl)benzothiophene-3-carbonyl]phenoxy]heptyl]carbamate (300 mg, 403.26 mol, 1 equiv) was added $H_2O$ (0.25 mL), MeOH (2.5 mL) and HCl (0.25 mL). The mixture was stirred at 50° C. for 2 h. The reaction mixture was quenched by addition $NaHCO_3$ (9 mL) at 25° C., and then extracted with EtOAc (12 mL×3). The combined organic layers were dried over $Na_2SO_4$, filtered and concentrated under reduced pressure to give a residue to afford [4-(7-aminoheptoxy)phenyl]-[6-hydroxy-2-(4-hydroxyphenyl) benzothiophen-3-yl]methanone (230 mg, crude) as a yellow solid.

Step 4: Preparation of (S)-2-(4-(4-chlorophenyl)-2,3,9-trimethyl-6H-thieno[3,2-f][1,2,4]triazolo[4,3-a][1,4]diazepin-6-yl)-N-(7-(4-(6-hydroxy-2-(4-hydroxyphenyl) benzo [b]thiophene-3-carbonyl)phenoxy)heptyl)acetamide. To a solution of (S)-2-(4-(4-chlorophenyl)-2,3,9-trimethyl-6H-thieno[3,2-f][1,2,4]triazolo[4,3-a][1,4]diazepin-6-yl)acetic acid (110 mg, 274.40 mol, 1 equiv) in DCM (2 mL) was added HOBT (55.61 mg, 411 mol, 1.5 equiv) and EDCI (78.90 mg, 411 mol, 1.5 equiv). Then the mixture was added the solution of [4-(7-aminoheptoxy)phenyl]-[6-hydroxy-2-(4-hydroxyphenyl)benzothiophen-3-yl]methanone (195.75 mg, 411 mol, 1.5 equiv) in DCM (1 mL) and DIEA (106.39 mg, 823.19 mol, 143 L, 3 equiv). The mixture was stirred at 25° C. for 2 h. The reaction mixture was concentrated under reduced pressure to give a residue. The residue was purified by prep-TLC ($SiO_2$, DCM:MeOH=9:1). Then the residue was purified by prep-HPLC (column: Phenomenex Luna C18 150 mm×25 mm×10 um; mobile phase: [water(FA)-ACN]; gradient: 55%-85% B over 10 min) to afford (S)-2-(4-(4-chlorophenyl)-2,3,9-trimethyl-6H-thieno[3,2-f][1,2,4]triazolo[4,3-a][1,4]diazepin-6-yl)-N-(7-(4-(6-hydroxy-2-(4-hydroxy-phenyl) benzo[b]thiophene-3-carbonyl)phenoxy)heptyl)acetamide (I-16, 81.64 mg, 34% yield) as a yellow solid. $^1H$ NMR (400 MHz, DMSO-$d_6$) δ 9.75 (d, J=17.2 Hz, 2H), 8.15 (t, J=5.6 Hz, 1H), 7.64 (d, J=8.8 Hz, 2H), 7.49-7.44 (m, 2H), 7.43-7.38 (m, 2H), 7.33 (d, J=2.4 Hz, 1H), 7.24 (d, J=8.8 Hz, 1H), 7.20-7.12 (m, 2H), 6.92-6.82 (m, 3H), 6.71-6.64 (m, 2H), 4.49 (dd, J=6.0, 8.0 Hz, 1H), 3.96 (t, J=6.4 Hz, 2H), 3.27-3.02 (m, 4H), 2.58 (s, 3H), 2.39 (s, 3H), 1.73-1.62 (m, 2H), 1.60 (s, 3H), 1.48-1.39 (m, 2H), 1.31 (d, J=3.6 Hz, 6H). LC-MS: MS ($ES^+$): RT=2.766 min, m/z=858.4 [$M+H^+$], LCMS Method: 25.

Example 18—Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(4-(6-hydroxy-2-(4-hydroxyphenyl) benzo[b]thiophene-3-carbonyl) phenoxy)ethoxy)butyl)acetamide (I-17)
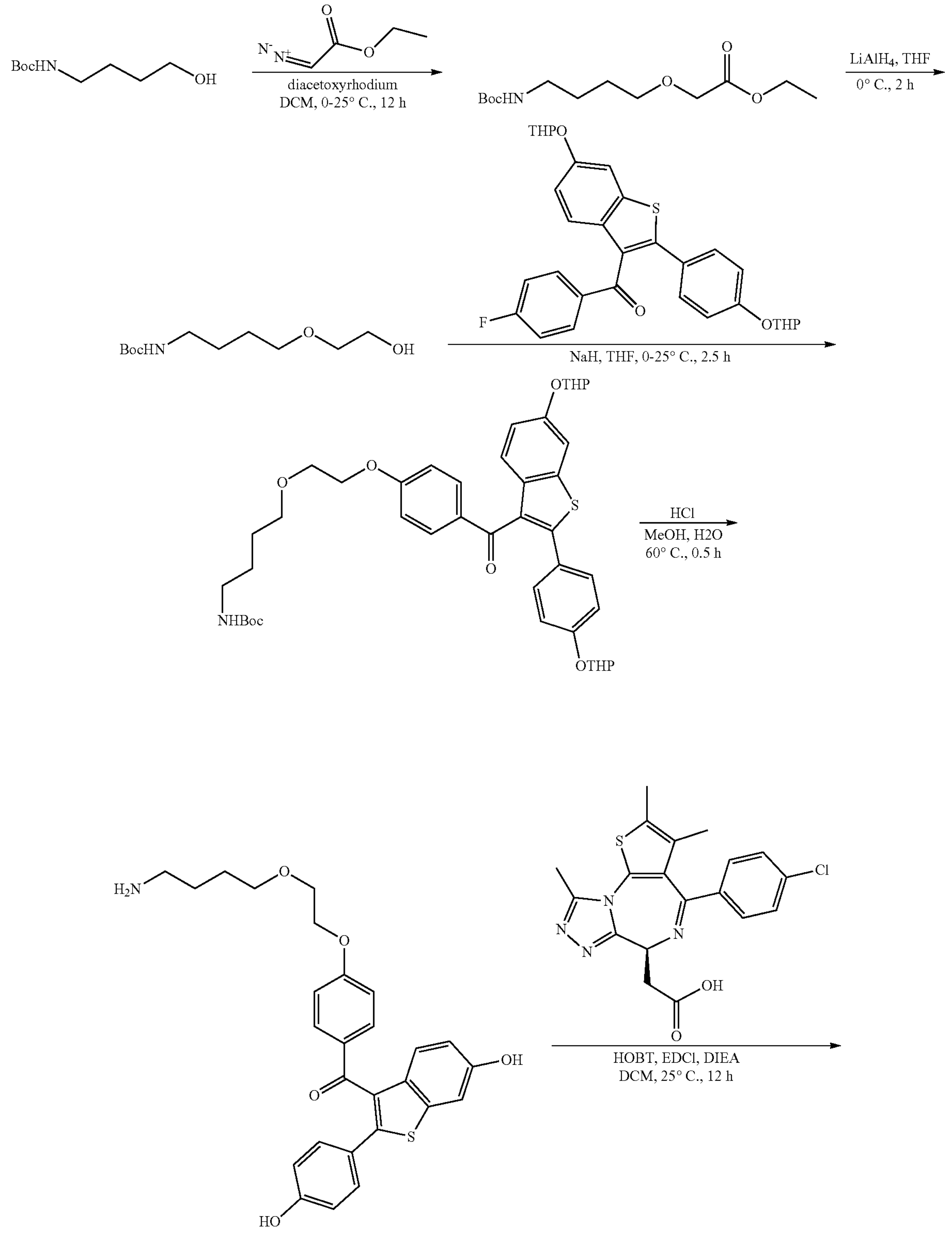

-continued

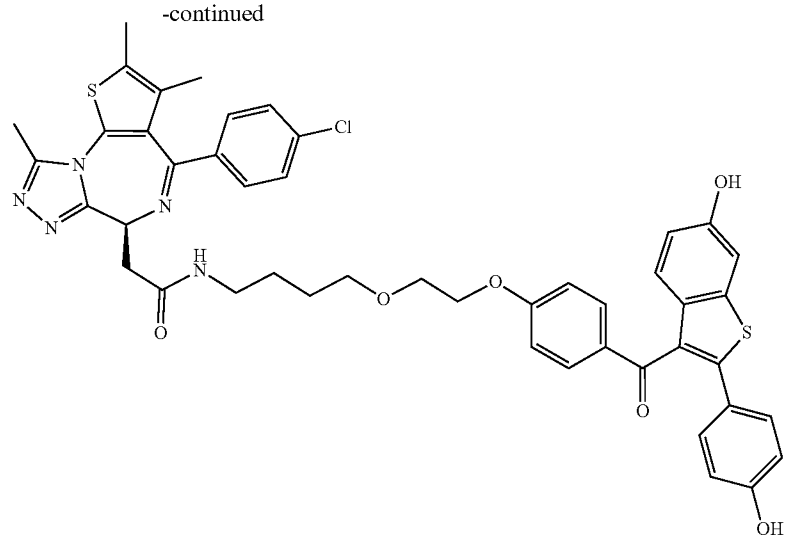

I-17

Step 1: Preparation of Ethyl 2-[4-(tert-butoxycarbonylamino)butoxy]acetate. To a solution of tert-butyl N-(4-hydroxybutyl) carbamate (8 g, 42.27 mmol, 1.0 equiv) in DCM (100 mL) was added diacetoxyrhodium (467.08 mg, 2.11 mmol, 0.05 equiv) and ethyl 2-diazoacetate (48.23 g, 422.72 mmol, 44.45 mL, 10.0 equiv) at 0° C. The mixture was stirred at 25° C. for 12 h. The reaction mixture was concentrated under reduced pressure to remove solvent. The residue was purified by column chromatography (silica, 0~50% Ethyl acetate/Petroleum ether) to afford ethyl 2-[4-(tert-butoxycarbonylamino)butoxy]acetate (12.3 g, crude) as a yellow oil.

Step 2: Preparation of Tert-butyl N-[4-(2-hydroxyethoxy) butyl]carbamate. To a solution of ethyl 2-[4-(tert-butoxycarbonylamino)butoxy]acetate (12.3 g, 44.67 mmol, 1 equiv) in THF (100 mL) was added portion-wise $LiAlH_4$ (2.5 M, 44.67 mL, 2.5 equiv) at 0° C. under $N_2$. The mixture was stirred at 0° C. for 2 hr under $N_2$. The reaction mixture was quenched with water (4.5 mL), 15% NaOH (4.5 mL) and water (13.5 mL) in turn at 0° C. under $N_2$. The reaction mixture was dried over $Na_2SO_4$, filtered and concentrated under reduced pressure to give a residue. The residue was purified by column chromatography (silica, 0-50% Ethyl acetate/Petroleum ether) to afford tert-butyl N-[4-(2-hydroxyethoxy) butyl]carbamate (2.9 g, 27% yield) as a light yellow oil.

Step 3: Preparation of tert-butyl N-[4-[2-[4-[6-tetrahydropyran-2-yloxy-2-(4-tetrahydropyran-2-yloxyphenyl)benzothiophene-3-carbonyl]phenoxy]ethoxy]butyl]carbamate. To a solution of tert-butyl N-[4-(2-hydroxyethoxy)butyl]carbamate (262.82 mg, 1.13 mmol, 2 equiv) in THE (5 mL) was added portion-wise NaH (67.58 mg, 1.69 mmol, 60% purity, 3 equiv) at 0° C. under $N_2$, the mixture was stirred at 0° C. for 0.5 h under $N_2$, then (4-fluorophenyl)-[6-tetrahydropyran-2-yloxy-2-(4-tetrahydropyran-2-yloxyphenyl) benzothiophen-3-yl]methanone (300 mg, 563.25 mol, 1 equiv) was added. The mixture was stirred at 25° C. for 2 h under $N_2$. The reaction mixture was quenched by addition saturated $NH_4Cl$ (50 ml) under $N_2$ at 25° C. and extracted with EtOAc (30 mL×3). The combined organic layers were dried over $Na_2SO_4$, filtered and concentrated under reduced pressure to give a residue. The residue was purified by column chromatography (silica, 0-50% Ethyl acetate/Petroleum ether) to afford tert-butyl N-[4-[2-[4-[6-tetrahydropyran-2-yloxy-2-(4-tetrahydropyran-2-yloxyphenyl) benzothiophene-3-carbonyl]phenoxy]ethoxy]butyl]carbamate (400 mg, 95% yield) as a yellow oil.

Step 4: Preparation of [4-[2-(4-aminobutoxy)ethoxy]phenyl]-[6-hydroxy-2-(4-hydroxyphenyl)benzothiophen-3-yl] methanone. To a solution of tert-butyl N-[4-[2-[4-[6-tetrahydropyran-2-yloxy-2-(4-tetrahydropyran-2-yloxyphenyl) benzothiophene-3-carbonyl]phenoxy]ethoxy]butyl] carbamate (250 mg, 335.16 mol, 1 equiv) in MeOH (3 mL), $H_2O$ (0.3 mL) and HCl (0.3 mL). The mixture was stirred at 60° C. for 0.5 h. The reaction mixture was concentrated under reduced pressure to afford [4-[2-(4-aminobutoxy) ethoxy]phenyl]-[6-hydroxy-2-(4-hydroxyphenyl)benzothiophen-3-yl]methanone (200 mg, crude, HCl) as a yellow oil.

Step 5: Preparation of (S)-2-(4-(4-chlorophenyl)-2,3,9-trimethyl-6H-thieno[3,2-f][1,2,4]triazolo[4,3-a][1,4]diazepin-6-yl)-N-(4-(2-(4-(6-hydroxy-2-(4-hydroxyphenyl) benzo[b]thiophene-3-carbonyl)phenoxy)ethoxy)butyl)acetamide. To a solution of [4-[2-(4-aminobutoxy)ethoxy]phenyl]-[6-hydroxy-2-(4-hydroxyphenyl) benzothiophen-3-yl] methanone (115.40 mg, 224 mol, 1.2 equiv, HCl) and 2-[(9S)-7-(4-chlorophenyl)-4,5,13-trimethyl-3-thia-1,8,11,12-tetrazatricyclo[$8.3.0.0^{2,6}$]trideca-2(6),4,7,10,12-pentaen-9-yl]acetic acid (75 mg, 187 mol, 1 equiv) in DCM (2 mL) was added HOBT (37.92 mg, 280 mol, 1.5 eq), EDCI (53.80 mg, 280 mol, 1.5 eq) and DIEA (120.90 mg, 935 mol, 162.94 μL, 5 eq). The mixture was stirred at 25° C. for 12 h. The reaction mixture was diluted with $H_2O$ (100 mL) and extracted with DCM (100 mL). The combined organic layers were washed with brine (15 mL×3), dried over $Na_2SO_4$, filtered and concentrated under reduced pressure to give a residue. The residue was purified by prep-HPLC (column: Welch Xtimate C18 150×25 mm×5 um; mobile phase: [water(FA)-ACN]; gradient: 53%-73% over 10 min) to afford (S)-2-(4-(4-chlorophenyl)-2,3,9-trimethyl-6H-thieno [3,2-f][1,2,4]triazolo[4,3-a][1,4]diazepin-6-yl)-N-(4-(2-(4-(6-hydroxy-2-(4-hydroxyphenyl)benzo[b]thiophene-3-carbonyl)phenoxy) ethoxy)butyl)acetamide (I-17, 36 mg, 22% yield) as a yellow solid. $^1$H NMR (400 MHz, DMSO-d6) δ 9.79 (br d, J=16.0 Hz, 2H), 8.18 (br t, J=5.6 Hz, 1H), 7.64 (d, J=8.8 Hz, 2H), 7.49-7.44 (m, 2H), 7.43-7.38 (m, 2H), 7.34 (d, J=2.0 Hz, 1H), 7.24 (d, J=8.8 Hz, 1H), 7.19-7.14 (m, 2H), 6.91 (d, J=8.8 Hz, 2H), 6.84 (dd, J=2.4, 8.8 Hz, 1H), 6.70-6.64 (m, 2H), 4.49 (dd, J=6.0, 8.0 Hz, 1H), 4.14-4.05 (m, 2H), 3.70-3.63 (m, 2H), 3.44 (t, J=6.4 Hz, 2H), 3.28-3.16 (m, 2H), 3.16-3.04 (m, 2H), 2.58 (s, 3H), 2.39 (s, 3H), 1.59 (s, 3H), 1.56-1.43 (m, 4H). LC-MS: MS (ES$^+$): RT=2.471 min, m/z=860.3 [M+H$^+$]; LC-MS Method: 25.

Example 19—Synthesis of 4-(2-(4-(4-((1-(4-((1R, 2S)-6-hydroxy-2-phenyl-1,2,3,4-tetrahydronaphthalen-1-yl)phenyl)piperidin-4-yl)methyl)piperazin-1-yl)phenoxy)-5-(2-hydroxypropan-2-yl)phenyl)-6-methyl-1,6-dihydro-7H-pyrrolo[2,3-c]pyridin-7-one (I-18)

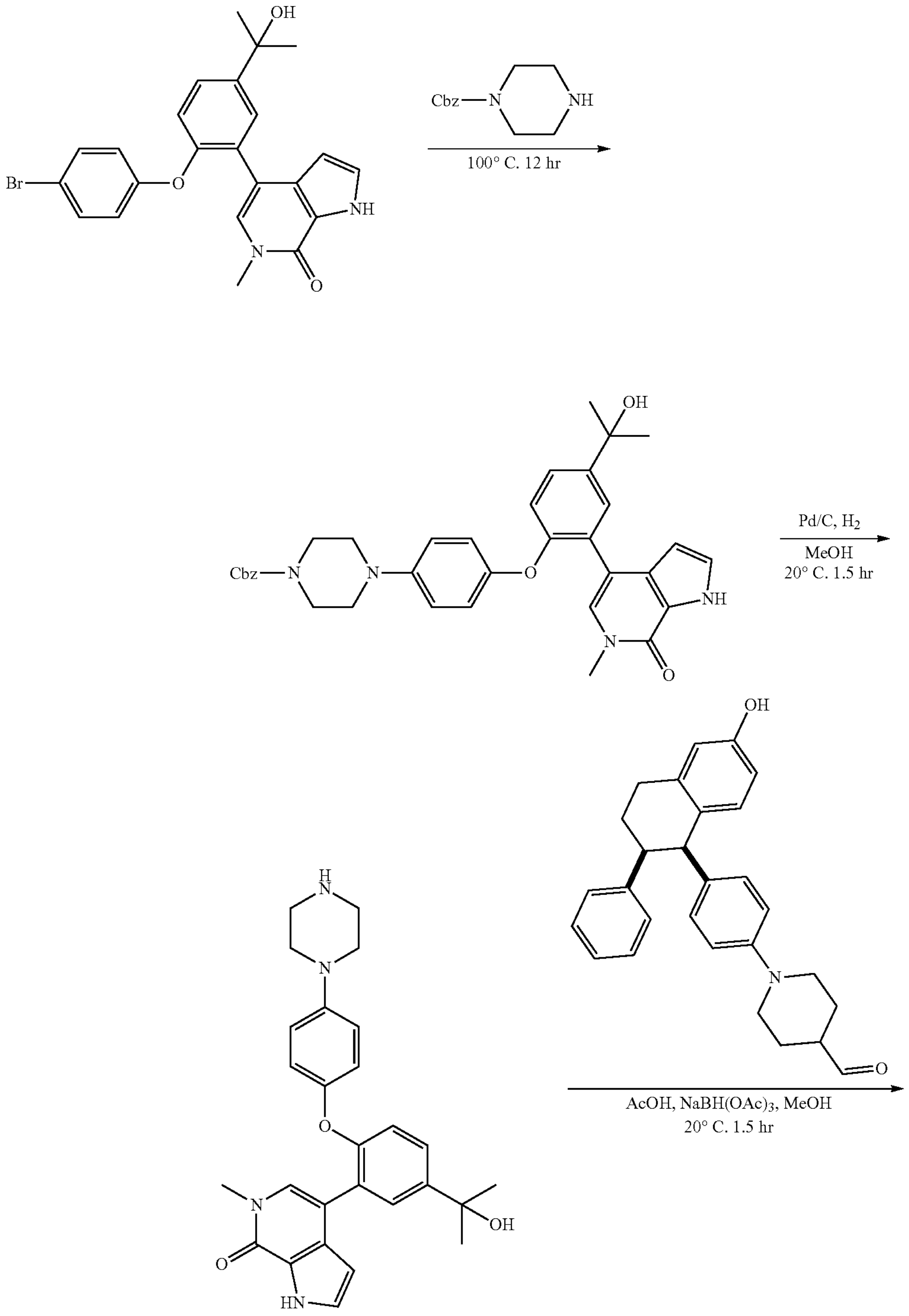

-continued

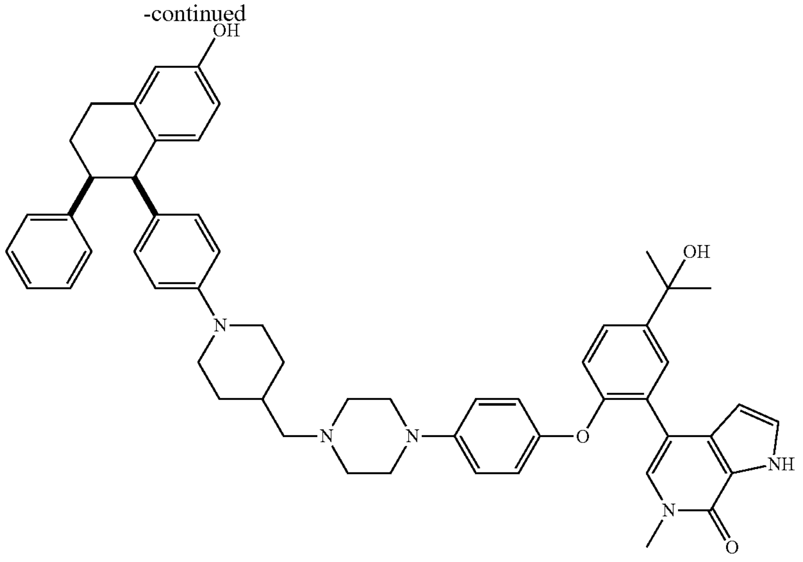

I-18

Step 1: Preparation of Benzyl 4-[4-[4-(1-hydroxy-1-methyl-ethyl)-2-(6-methyl-7-oxo-1H-pyrrolo[2,3-c]pyridin-4-yl)phenoxy]phenyl]piperazine-1-carboxylate. A mixture of 4-[2-(4-bromophenoxy)-5-(1-hydroxy-1-methyl-ethyl)phenyl]-6-methyl-1H-pyrrolo[2,3-c]pyridin-7-one (400 mg, 882 mol, 1 equiv), benzyl piperazine-1-carboxylate (600 mg, 2.72 mmol, 525.39 μL, 3.09 equiv), $K_3PO_4$ (561.90 mg, 2.65 mmol, 3 equiv), CuI (168.05 mg, 882 mol, 1 equiv) and 2-(2,6-dimethylanilino)-2-oxo-acetic acid (170.47 mg, 882 mol, 1 equiv) in DMSO (5 mL) was degassed and purged with $N_2$ three times, and then the mixture was stirred at 100° C. for 12 hours under a $N_2$ atmosphere. The reaction mixture was diluted with $H_2O$ (5 mL) and extracted with EA (5 mL×3). The combined organic layers were washed with brine (5 mL×2), dried over $Na_2SO_4$, filtered and concentrated under reduced pressure to give a residue. The residue was purified by prep-HPLC (Waters Xbridge C18 150×50 mm×10 um; mobile phase: [water ($NH_4HCO_3$)-ACN]; gradient: 35-65% over 10 min) to afford benzyl 4-[4-[4-(1-hydroxy-1-methyl-ethyl)-2-(6-methyl-7-oxo-1H-pyrrolo[2,3-c]pyridin-4-yl)phenoxy]phenyl]piperazine-1-carboxylate (240 mg, 46% yield) as a white solid.

Step 2: Preparation of 4-[5-(1-hydroxy-1-methyl-ethyl)-2-(4-piperazin-1-ylphenoxy) phenyl]-6-methyl-1H-pyrrolo[2,3-c]pyridin-7-one. To a solution of benzyl 4-[4-[4-(1-hydroxy-1-methyl-ethyl)-2-(6-methyl-7-oxo-1H-pyrrolo[2,3-c]pyridin-4-yl)phenoxy]phenyl]piperazine-1-carboxylate (240 mg, 404 mol, 1 equiv) in MeOH (5 mL) was added Pd/C (50 mg, 47 mol, 10% purity) under $N_2$ atmosphere. The suspension was degassed and purged with $H_2$ three times. The mixture was stirred under $H_2$ (50 Psi) at 50° C. for 12 hours. The reaction mixture was filtered and concentrated under reduced pressure to give 4-[5-(1-hydroxy-1-methyl-ethyl)-2-(4-piperazin-1-ylphenoxy)phenyl]-6-methyl-1H-pyrrolo[2,3-c]pyridin-7-one (180 mg, 97% yield) as a white solid.

Step 3: Preparation of 4-(2-(4-(4-((1-(4-((1R,2S)-6-hydroxy-2-phenyl-1,2,3,4-tetrahydronaphthalen-1-yl)phenyl) piperidin-4-yl)methyl)piperazin-1-yl)phenoxy)-5-(2-hydroxypropan-2-yl)phenyl)-6-methyl-1,6-dihydro-7H-pyrrolo[2,3-c]pyridin-7-one. To a solution of 4-[5-(1-hydroxy-1-methyl-ethyl)-2-(4-piperazin-1-ylphenoxy) phenyl]-6-methyl-1H-pyrrolo[2,3-c]pyridin-7-one (180.00 mg, 392 mol, 1.24 equiv) and 1-[4-(6-hydroxy-2-phenyl-tetralin-1-yl)phenyl]piperidine-4-carbaldehyde (130 mg, 315 mol, 1 equiv) in MeOH (1 mL) was added AcOH (18.97 mg, 315 mol, 18.08 μL, 1 equiv). After addition, the mixture was stirred at 20° C. for 0.5 hour, and then $NaBH(OAc)_3$ (66.95 mg, 315 mol, 1 equiv), 1-[4-(6-hydroxy-2-phenyl-tetralin-1-yl)phenyl]piperidine-4-carbaldehyde (130 mg, 315 mol, 1 equiv) was added. The resulting mixture was stirred at 20° C. for 1 hour. The reaction mixture was filtered and concentrated under reduced pressure to give a residue. The residue was purified by prep-HPLC (column: Phenomenex luna C18 150×25 mm×10 um; mobile phase: [water (FA)-ACN]; gradient: 21%-51% over 10 min). 4-(2-(4-(4-((1-(4-((1R,2S)-6-hydroxy-2-phenyl-1,2,3,4-tetrahydronaphthalen-1-yl)phenyl)piperidin-4-yl)methyl) piperazin-1-yl)phenoxy)-5-(2-hydroxypropan-2-yl)phenyl)-6-methyl-1,6-dihydro-7H-pyrrolo[2,3-c]pyridin-7-one (I-18, 100 mg, 37% yield) was obtained as a white solid. The white solid was further separated by SFC (column: DAICEL CHIRALPAK AS (250 mm×30 mm×10 um); mobile phase: [$CO_2$-ACN/i-PrOH (0.1% $NH_3$)]; 55% B, isocratic). 4-(2-(4-(4-((1-(4-((1R,2S)-6-hydroxy-2-phenyl-1,2,3,4-tetrahydronaphthalen-1-yl)phenyl)piperidin-4-yl)methyl)piperazin-1-yl)phenoxy)-5-(2-hydroxypropan-2-yl)phenyl)-6-methyl-1,6-dihydro-7H-pyrrolo[2,3-c]pyridin-7-one (I-18, 22.3 mg, 27% yield) was isolated as an off-white solid. $^1H$ NMR (400 MHz, $CDCl_3$) δ (ppm)=10.05 (br s, 1H), 7.62 (d, J 2.4 Hz, 1H), 7.43-7.38 (m, 1H), 7.23 (t, J 2.8 Hz, 1H), 7.19-7.13 (m, 3H), 7.09 (s, 1H), 6.92 (d, J 8.8 Hz, 1H), 6.87-6.79 (m, 7H), 6.72 (d, J 2.8 Hz, 1H), 6.63-6.54 (m, 3H), 6.40 (t, J 2.4 Hz, 1H), 6.29 (d, J 8.8 Hz, 2H), 4.20 (d, J 4.8 Hz, 1H), 3.65 (s, 3H), 3.60-3.48 (m, 2H), 3.39-3.29 (m, 1H), 3.16 (br s, 4H), 3.08-2.97 (m, 2H), 2.66 (br d, J=18.8 Hz, 4H), 2.60-2.53 (m, 2H), 2.36 (br d, J 6.4 Hz, 2H), 2.18 (br d, J 4.8 Hz, 1H), 1.90-1.75 (m, 4H), 1.64 (s, 6H), 1.40-1.29 (m, 2H). LC-MS: MS ($ES^+$): RT=1.510 min, m/z=854.4 [M+H]; LCMS Method: 25.

Example 20—Synthesis of (S)-(6-hydroxy-2-(4-hydroxyphenyl)benzo[b]thiophen-3-yl)(4-(2-(2-(4-(2,3,6,9-tetramethyl-6H-thieno[3,2-f][1,2,4]triazolo[4,3-a][1,4]diazepin-4-yl)benzyl)-7-azaspiro[3.5]nonan-7-yl)ethoxy)phenyl)methanone (I-19)
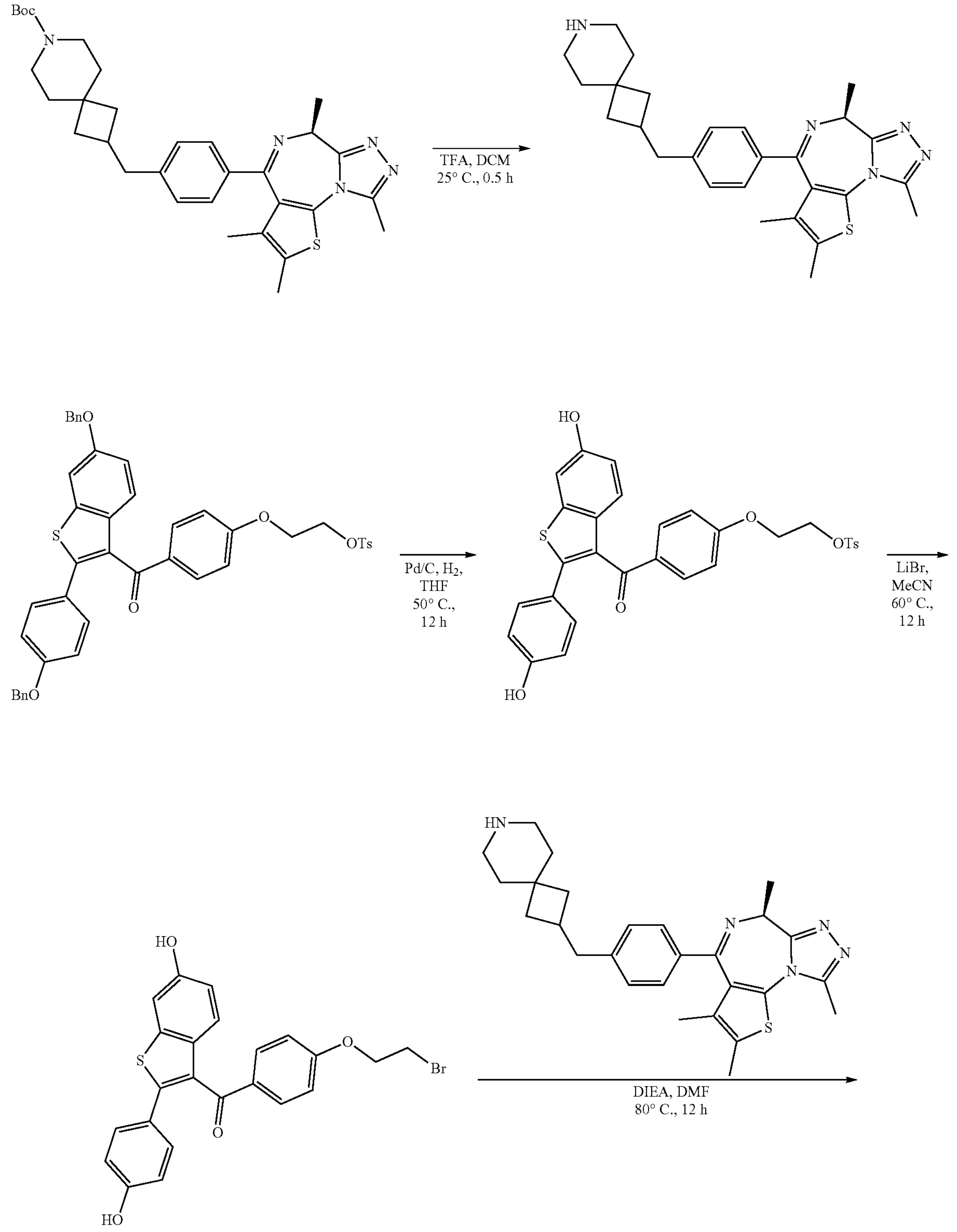

-continued

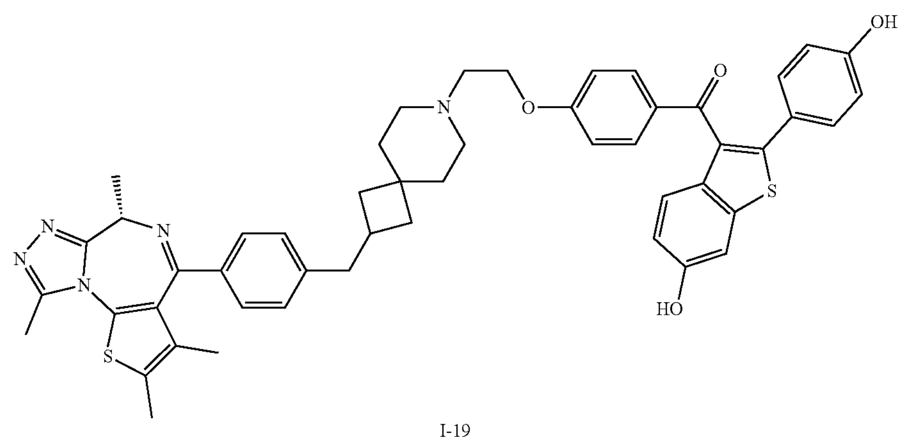

I-19

Step 1: Preparation of (9S)-7-[4-(7-azaspiro[3.5]nonan-2-ylmethyl)phenyl]-4,5,9,13-tetramethyl-3-thia-1,8,11,12-tetrazatricyclo[8.3.0.$0^{2,6}$]trideca-2(6),4,7,10,12-pentaene. To a solution of tert-butyl 2-[[4-[(9S)-4,5,9,13-tetramethyl-3-thia-1,8,11,12-tetrazatricyclo[8.3.0.$0^{2,6}$]trideca-2(6),4,7,10,12-pentaen-7-yl]phenyl]methyl]-7-azaspiro [3.5]nonane-7-carboxylate (200 mg, 357 mol, 1 equiv) in DCM (3 mL) was added TFA (3.07 g, 27 mmol, 2.00 mL, 75 equiv). The mixture was stirred at 25° C. for 0.5 h. The reaction mixture was adjusted to pH 8-9 by $NaHCO_3$ (aq) and then diluted with $H_2O$ (20 mL) and extracted with DCM (20 mL×2). The combined organic layers were washed with brine (20 mL×2), dried over $Na_2SO_4$, filtered and concentrated under reduced pressure to afford (9S)-7-[4-(7-azaspiro[3.5]nonan-2-ylmethyl)phenyl]-4,5,9,13-tetramethyl-3-thia-1,8,11,12-tetrazatricyclo[8.3.0.$0^{2,6}$]trideca-2(6),4,7,10,12-pentaene (160 mg, 97% yield) as a yellow solid.

Step 2: Preparation of 2-[4-[6-hydroxy-2-(4-hydroxyphenyl)benzothiophene-3-carbonyl]phenoxy]ethyl 4-methylbenzenesulfonate. The hydrogenation flask was filled with $N_2$, and $H_2$ was slowly added in the $N_2$ atmosphere, then 2-[4-[6-benzyloxy-2-(4-benzyloxyphenyl)benzothiophene-3-carbonyl]phenoxy]ethyl 4-methylbenzenesulfonate (430 mg, 580 mol, 1.0 equiv) and Pd/C (200 mg, 187 mol, 10% purity, 0.32 equiv) in THE (5 mL) was added under $N_2$ atmosphere. The suspension was degassed and purged with $H_2$ three times. The mixture was stirred under $H_2$ (50 Psi) at 50° C. for 12 h. The reaction mixture was filtered and concentrated under reduced pressure to give a residue. The residue was purified by prep-TLC ($SiO_2$, PE:EA=1:1) to afford 2-[4-[6-hydroxy-2-(4-hydroxyphenyl) benzothiophene-3-carbonyl]phenoxy]ethyl 4-methylbenzenesulfonate (300 mg, 92% yield) as a white solid.

Step 3: Preparation of [4-(2-bromoethoxy)phenyl]-[6-hydroxy-2-(4-hydroxyphenyl) benzothiophen-3-yl]methanone. To a solution of 2-[4-[6-hydroxy-2-(4-hydroxyphenyl) benzothiophene-3-carbonyl]phenoxy]ethyl 4-methylbenzenesulfonate (300 mg, 535 μmol, 1 equiv) in MeCN (5 mL) was added LiBr (140.81 mg, 1.62 mmol, 3.03 equiv). The mixture was stirred at 60° C. for 12 h. The reaction mixture was filtered and concentrated under reduced pressure to give a residue. The residue was purified by column chromatography ($SiO_2$, Petroleum ether/Ethyl acetate=10/1 to 1/1) to afford [4-(2-bromoethoxy)phenyl]-[6-hydroxy-2-(4-hydroxyphenyl)benzothiophen-3-yl]methanone (120 mg, 47% yield) as a white solid.

Step 4: Preparation of (S)-(6-hydroxy-2-(4-hydroxyphenyl)benzo[b]thiophen-3-yl)(4-(2-(2-(4-(2,3,6,9-tetramethyl-6H-thieno[3,2-f][1,2,4]triazolo[4,3-a][1,4]diazepin-4-yl) benzyl)-7-azaspiro[3.5]nonan-7-yl)ethoxy)phenyl) methanone. To a solution of [4-(2-bromoethoxy) phenyl]-[6-hydroxy-2-(4-hydroxyphenyl)benzothiophen-3-yl] methanone (40 mg, 85 mol, 1 equiv) in DMF (1 mL) was added DIEA (38.55 mg, 298 mol, 52 L, 3.5 equiv) and (9S)-7-[4-(7-azaspiro[3.5]nonan-2-ylmethyl)phenyl]-4,5,9,13-tetramethyl-3-thia-1,8,11,12-tetrazatricyclo[8.3.0.$0^{2,6}$] trideca-2(6),4,7,10,12-pentaene (58.76 mg, 127 mol, 1.5 equiv). The mixture was stirred at 80° C. for 12 h. The reaction mixture was filtered and concentrated under reduced pressure to give a residue. The residue was purified by prep-HPLC (column: Phenomenex Luna C18 150×25 mm×10 um; mobile phase: [water (FA)-I]; gradient: 28-58% over 9 min) to afford (S)-(6-hydroxy-2-(4-hydroxyphenyl) benzo[b]thiophen-3-yl)(4-(2-(2-(4-(2,3,6,9-tetramethyl-6H-thieno[3,2-f][1,2,4]triazolo[4,3-a][1,4]diazepin-4-yl)benzyl)-7-azaspiro[3.5]nonan-7-yl)ethoxy)phenyl)methanone (I-19, 29 mg, 38% yield) as a yellow solid. $^1H$ NMR (400 MHz, DMSO-d6) δ 9.80 (s, 1H) 9.75 (s, 1H) 7.70 (d, J=8.0 Hz, 2H) 7.31-7.36 (m, 3H) 7.25 (d, J=8.8 Hz, 1H) 7.18 (dd, J=8.0, 5.2 Hz, 4H) 6.96 (d, J=8.8 Hz, 2H) 6.85 (dd, J=8.8, 2.4 Hz, 1H) 6.64-6.70 (m, 2H) 4.34 (d, J=5.2 Hz, 2H) 4.20 (q, J=6.4 Hz, 1H) 3.43-3.46 (m, 2H) 3.37 (s, 4H) 2.66-2.74 (m, 3H) 2.59 (s, 3H) 2.39 (s, 3H) 1.86 (d, J=6.4 Hz, 3H) 1.74-1.80 (m, 1H) 1.68 (d, J=8.0 Hz, 3H) 1.61 (s, 3H) 1.44-1.56 (m, 2H) 1.22-1.29 (m, 2H). LC-MS: MS ($ES^+$): RT=1.868 min, m/z=848.5 [$M+H^+$], LCMS Method: 25.

Example 21—Synthesis of (S)-(6-hydroxy-2-(4-hydroxyphenyl)benzo[b]thiophen-3-yl)(4-(2-(2-((4-(2,3,9-trimethyl-6-(oxazol-2-ylmethyl)-6H-thieno[3,2-f][1,2,4]triazolo[4,3-a][1,4]diazepin-4-yl)phenyl)ethynyl)-7-azaspiro[3.5]nonan-7-yl)ethoxy)phenyl)methanone (I-20)

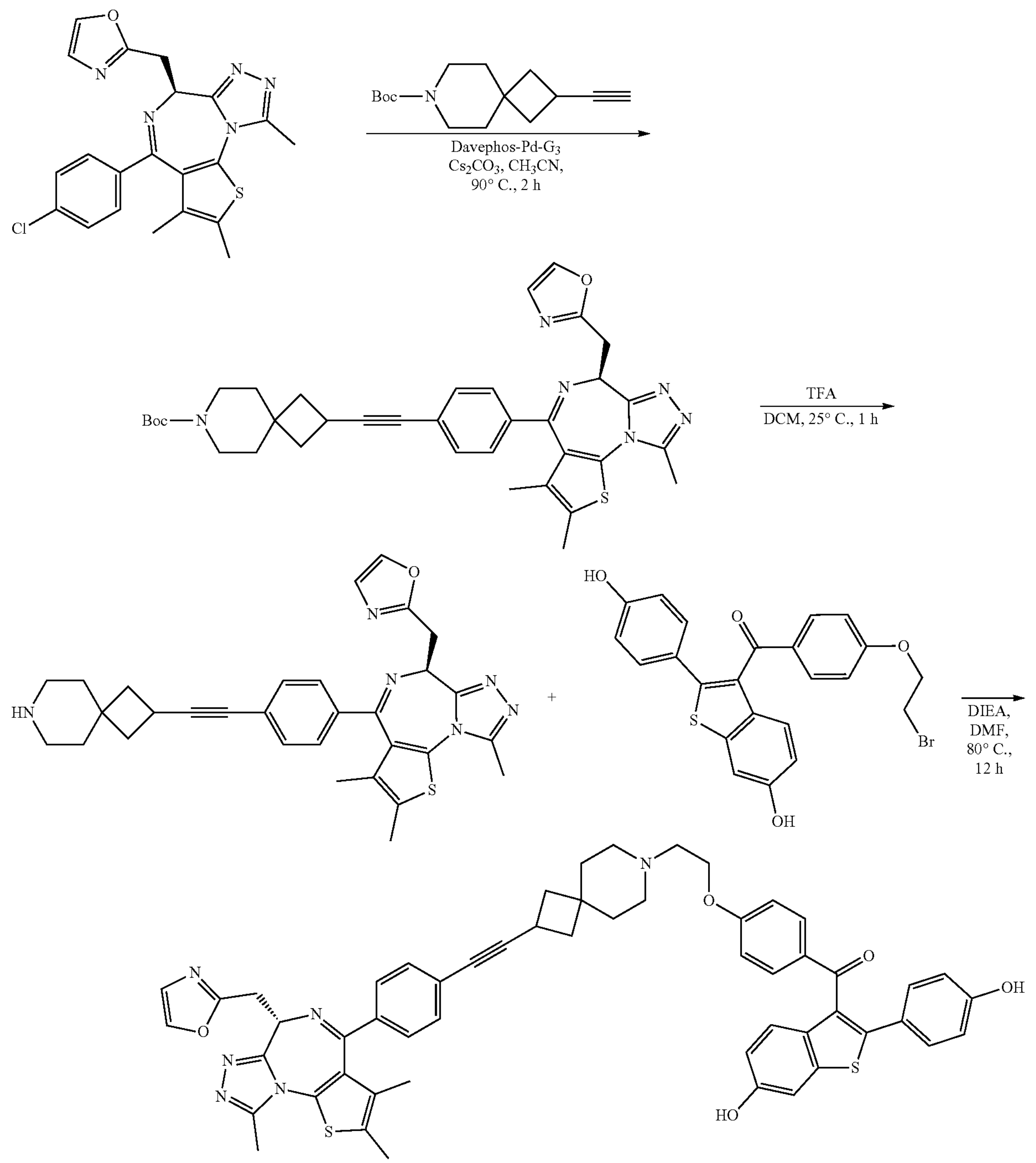

I-20

Step 1: Preparation of tert-butyl 2-[2-[4-[(9S)-4,5,13-trimethyl-9-(oxazol-2-ylmethyl)-3-thia-1,8,11,12-tetrazatricyclo[8.3.0.$0^{2,6}$]trideca-2(6),4,7,10,12-pentaen-7-yl]phenyl]ethynyl]-7-azaspiro[3.5]nonane-7-carboxylate. To a solution of 2-[[(9S)-7-(4-chlorophenyl)-4,5,13-trimethyl-3-thia-1,8,11,12-tetrazatricyclo[8.3.0.$0^{2,6}$]trideca-2(6),4,7,10,12-pentaen-9-yl]methyl]oxazole (500 mg, 1.18 mmol, 1 equiv) and tert-butyl 2-ethynyl-7-azaspiro[3.5]nonane-7-carboxylate (735.25 mg, 2.95 mmol, 2.5 equiv) in MeCN (15 mL) was added $Cs_2CO_3$ (768.59 mg, 2.36 mmol, 2.0 equiv) and DavePhos Pd $G_3$ (90.03 mg, 117.95 mol, 0.1 equiv) under $N_2$. The mixture was stirred at 90° C. for 2 h. The reaction mixture was concentrated under reduced pressure to give a residue. The residue was purified by column chromatography ($SiO_2$, Petroleum ether/Ethyl acetate 1/0 to 1/1) to afford tert-butyl 2-[2-[4-[(9S)-4,5,13-trimethyl-9-(oxazol-2-ylmethyl)-3-thia-1,8,11,12-tetrazatricyclo

[8.3.0.0$^{2,6}$]trideca-2(6),4,7,10,12-pentaen-7-yl]phenyl]ethynyl]-7-azaspiro[3.5]nonane-7-carboxylate (700 mg, 93% yield) as a white solid.

Step 2: Preparation of 2-[[(9S)-7-[4-[2-(7-azaspiro[3.5]nonan-2-yl)ethynyl]phenyl]-4,5,13-trimethyl-3-thia-1,8,11,12-tetrazatricyclo[8.3.0.0$^{2,6}$]trideca-2(6),4,7,10,12-pentaen-9-yl]methyl]oxazole. To a solution of tert-butyl 2-[2-[4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]ethynyl]-7-azaspiro[3.5]nonane-7-carboxylate (350 mg, 549 mol, 1 equiv) in DCM (3 mL) was added TFA (1.54 g, 13.46 mmol, 1 mL, 24 equiv). The mixture was stirred at 25° C. for 1 h. The reaction mixture was quenched by addition $NaHCO_3$ 25 mL at 25° C., and then diluted with $H_2O$ (20 mL) and extracted with EtOAc (20 mL×3). The combined organic layers were dried over $Na_2SO_4$, filtered and concentrated under reduced pressure to afford 2-[[(9S)-7-[4-[2-(7-azaspiro[3.5]nonan-2-yl)ethynyl]phenyl]-4,5,13-trimethyl-3-thia-1,8,11,12-tetrazatricyclo[8.3.0.0$^{2,6}$]trideca-2(6),4,7,10,12-pentaen-9-yl]methyl]oxazole (200 mg, 67% yield) as a brown solid.

Step 3: Preparation of (S)-(6-hydroxy-2-(4-hydroxyphenyl)benzo[b]thiophen-3-yl)(4-(2-(2-((4-(2,3,9-trimethyl-6-(oxazol-2-ylmethyl)-6H-thieno[3,2-f][1,2,4]triazolo[4,3-a][1,4]diazepin-4-yl)phenyl)ethynyl)-7-azaspiro[3.5]nonan-7-yl)ethoxy)phenyl) methanone. To a solution of [4-(2-bromoethoxy)phenyl]-[6-hydroxy-2-(4-hydroxyphenyl)benzothiophen-3-yl]methanone (40 mg, 85 mol, 1 equiv) and 2-[[(9S)-7-[4-[2-(7-azaspiro [3.5]nonan-2-yl) ethynyl]phenyl]-4,5,13-trimethyl-3-thia-1,8,11,12-tetrazatricyclo[8.3.0.0$^{2,6}$]trideca-2(6),4,7,10, 12-pentaen-9-yl]methyl]oxazole (45.74 mg, 85 mol, 1 equiv) in DMF (1 mL) was added DIEA (40.00 mg, 309 mol, 53.91 μL, 3.63 equiv). The mixture was stirred at 80° C. for 12 h. The reaction mixture was concentrated under reduced pressure to give a residue. The residue was purified by prep-HPLC (column: Phenomenex Luna C18 150×25 mm×10 um; mobile phase: [water (FA)-ACN]; gradient: 30-60% over 9 min) to afford (S)-(6-hydroxy-2-(4-hydroxyphenyl)benzo[b]thiophen-3-yl)(4-(2-(2-((4-(2,3,9-trimethyl-6-(oxazol-2-ylmethyl)-6H-thieno[3,2-f][1,2,4]triazolo[4,3-a][1,4]diazepin-4-yl)phenyl)ethynyl)-7-azaspiro[3.5]nonan-7-yl)ethoxy)phenyl)methanone (I-20, 10.41 mg, 12% yield) as a yellow solid. $^1H$ NMR (400 MHz, DMSO-$d_6$) δ 9.80 (s, 1H), 9.76 (s, 1H), 8.04 (s, 1H), 7.70 (d, J=8.8 Hz, 2H), 7.42-7.37 (m, 2H), 7.36-7.34 (m, 2H), 7.32 (s, 1H), 7.25 (d, J=8.8 Hz, 1H), 7.17 (d, J=8.8 Hz, 2H), 7.13 (s, 1H), 6.98 (d, J=8.8 Hz, 2H), 6.86 (J=2.4, 8.8 Hz, 1H), 6.71-6.65 (m, 2H), 4.68 (t, J=7.2 Hz, 1H), 4.39 (s, 2H), 3.98-3.77 (m, 2H), 3.54-3.39 (m, 3H), 3.06-2.89 (m, 2H), 2.60 (s, 3H), 2.41 (s, 3H), 2.38-2.32 (m, 1H), 2.18 (t, J=9.2 Hz, 1H), 2.00-1.92 (m, 3H), 1.88-1.72 (m, 3H), 1.60 (s, 3H), 1.32-1.17 (m, 2H). LC-MS: MS ($ES^+$): RT=1.260 min, m/z=925.3 [M+$H^+$]. LCMS Method: 5-95.

Example 22—Synthesis of (S)-(6-hydroxy-2-(4-hydroxyphenyl)benzo[b]thiophen-3-yl)(4-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)phenyl)methanone (I-21)

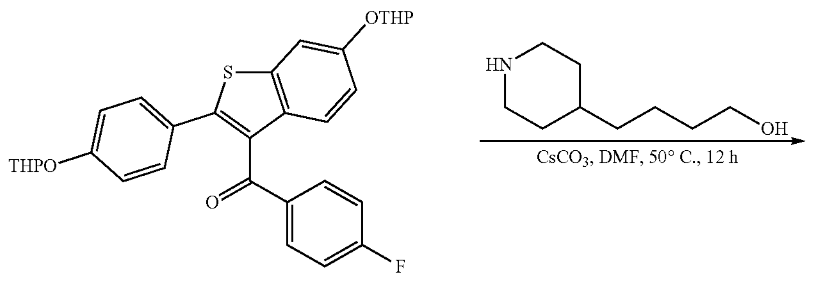

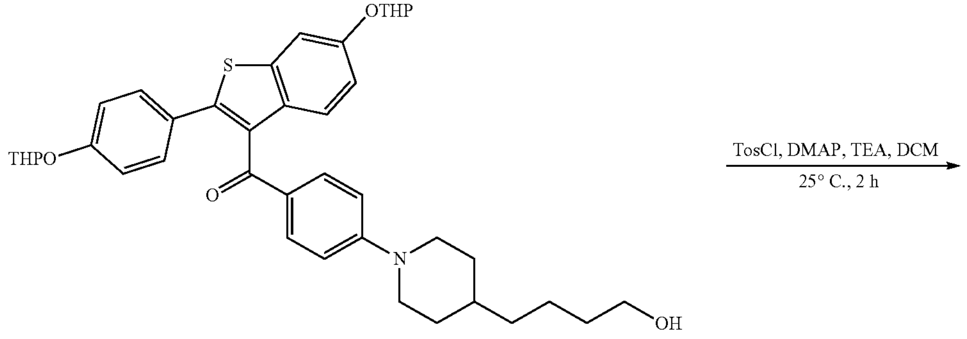

-continued
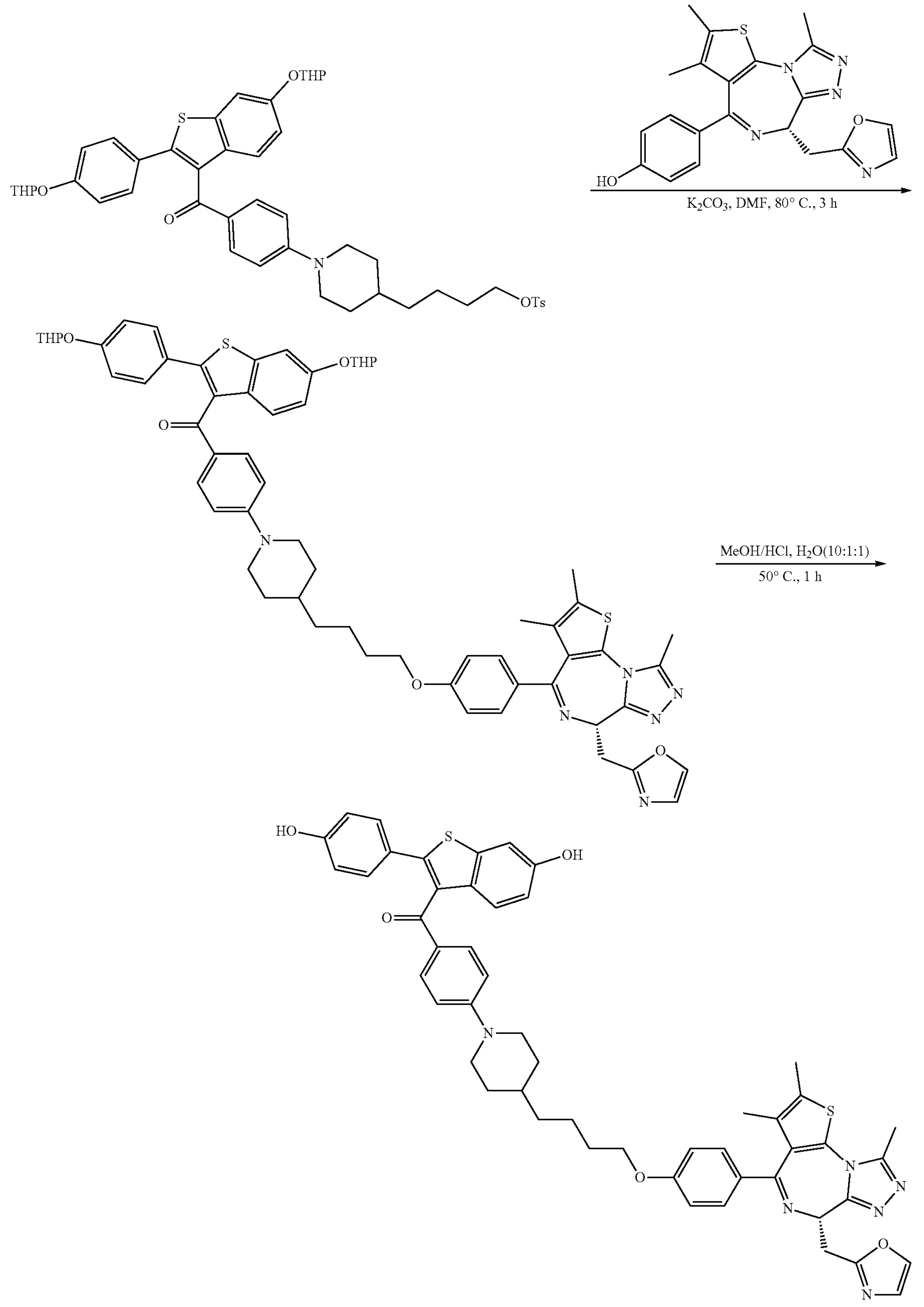
I-21

Step 1: Preparation of [4-[4-(4-hydroxybutyl)-1-piperidyl]phenyl]-[6-tetrahydropyran-2-yloxy-2-(4-tetrahydropyran-2-yloxyphenyl)benzothiophen-3-yl]methanone. To a solution of (4-fluorophenyl)-[6-tetrahydropyran-2-yloxy-2-(4-tetrahydropyran-2-yloxyphenyl) benzothiophen-3-yl] methanone (300 mg, 563 mol, 1 equiv) in DMF (3 mL) was added $Cs_2CO_3$ (550.56 mg, 1.69 mmol, 3 equiv) and 4-(4-piperidyl)butan-1-ol (177.15 mg, 1.13 mmol, 2 equiv). The mixture was stirred at 50° C. for 12 h. LCMS showed that the desired compound was detected. The reaction mixture was concentrated under reduced pressure to give a residue. The residue was purified by prep-TLC ($SiO_2$, DCM: MeOH=9:1) to afford [4-[4-(4-hydroxybutyl)-1-piperidyl] phenyl]-[6-tetrahydropyran-2-yloxy-2-(4-tetrahydropyran-2-yloxyphenyl)benzothiophen-3-yl]methanone (220 mg, 58% yield) as a brown solid.

Step 2: Preparation of 4-[1-[4-[6-tetrahydropyran-2-yloxy-2-(4-tetrahydropyran-2-yloxyphenyl)benzothiophene-3-carbonyl]phenyl]-4-piperidyl]butyl 4-methylbenzenesulfonate. To a solution of [4-[4-(4-hydroxybutyl)-1-piperidyl]phenyl]-[6-tetrahydropyran-2-yloxy-2-(4-tetrahydropyran-2-yloxyphenyl)benzothiophen-3-yl] methanone (200 mg, 298 mol, 1 equiv) in DCM (2 mL) was added DMAP (3.65 mg, 30 mol, 0.1 equiv) and TEA (75.53 mg, 746 mol, 103.89 µL, 2.5 equiv). Then the mixture was added TosCl (85.38 mg, 448 mol, 1.5 equiv). The mixture was stirred at 25° C. for 2 h. The reaction mixture was concentrated under reduced pressure to give a residue. The residue was purified by column chromatography (Silica, 0-50% Ethyl acetate/Petroleum ether) to afford 4-[1-[4-[6-tetrahydropyran-2-yloxy-2-(4-tetrahydropyran-2-yloxyphenyl)benzothiophene-3-carbonyl]phenyl]-4-piperidyl]butyl 4-methylbenzenesulfonate (230 mg, 93% yield) as a yellow solid.

Step 3: Preparation of (6-((tetrahydro-2H-pyran-2-yl) oxy)-2-(4-((tetrahydro-2H-pyran-2-yl)oxy)phenyl)benzo[b] thiophen-3-yl)(4-(4-(4-(4-((S)-2,3,9-trimethyl-6-(oxazol-2-ylmethyl)-6H-thieno[3,2-f][1,2,4]triazolo[4,3-a][1,4] diazepin-4-yl)phenoxy) butyl) piperidin-1-yl)phenyl) methanone. To a solution of 4-[1-[4-[6-tetrahydropyran-2-yloxy-2-(4-tetrahydropyran-2-yloxyphenyl) benzothiophene-3-carbonyl]phenyl]-4-piperidyl]butyl 4-methylbenzenesulfonate (101.62 mg, 123 mol, 1 equiv) in DMF (1.5 mL) was added $K_2CO_3$ (34.09 mg, 246 mol, 2 equiv) and 4-[(9S)-4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenol (50 mg, 123 mol, 1 equiv). The mixture was stirred at 80° C. for 3 h. The reaction mixture was quenched by addition $H_2O$ (3 mL) at 25° C., and then extracted with EA (5 mL×3). The combined organic layers were washed with aqueous NaCl 15 mL (5 mL×3), dried over $Na_2SO_4$, filtered and concentrated under reduced pressure to give a residue. The residue was purified by prep-TLC ($SiO_2$, DCM:MeOH=10:1) to afford (6-((tetrahydro-2H-pyran-2-yl)oxy)-2-(4-((tetrahydro-2H-pyran-2-yl)oxy)phenyl)benzo[b]thiophen-3-yl)(4-(4-(4-(4-((S)-2,3,9-trimethyl-6-(oxazol-2-ylmethyl)-6H-thieno[3,2-f][1,2,4]triazolo[4,3-a][1,4]diazepin-4-yl)phenoxy)butyl)piperidin-1-yl)phenyl) methanone (100 mg, 77% yield) as a brown solid.

Step 4: Preparation of (S)-(6-hydroxy-2-(4-hydroxyphenyl)benzo[b]thiophen-3-yl)(4-(4-(4-(4-(2,3,9-trimethyl-6-(oxazol-2-ylmethyl)-6H-thieno[3,2-f][1,2,4]triazolo[4,3-a] [1,4]diazepin-4-yl)phenoxy)butyl)piperidin-1-yl)phenyl) methanone. To a solution of (6-((tetrahydro-2H-pyran-2-yl) oxy)-2-(4-((tetrahydro-2H-pyran-2-yl)oxy)phenyl)benzo[b] thiophen-3-yl)(4-(4-(4-(4-((S)-2,3,9-trimethyl-6-(oxazol-2-ylmethyl)-6H-thieno[3,2-f][1,2,4]triazolo[4,3-a][1,4] diazepin-4-yl)phenoxy)butyl)piperidin-1-yl)phenyl) methanone (100 mg, 94 mol, 1 equiv) in MeOH (1 mL) was added HCl (0.1 mL) and $H_2O$ (0.1 mL). The mixture was stirred at 50° C. for 1 h. The reaction mixture was concentrated under reduced pressure to give a residue. The residue was purified by prep-HPLC (column: Welch Xtimate C18 150×25 mm×5 um; mobile phase: [water(FA)-ACN]; gradient: 65%-85% B over 10 min) to afford (S)-(6-hydroxy-2-(4-hydroxyphenyl)benzo[b]thiophen-3-yl)(4-(4-(4-(4-(2,3,9-trimethyl-6-(oxazol-2-ylmethyl)-6H-thieno[3,2-f][1,2,4]triazolo[4,3-a][1,4]diazepin-4-yl)phenoxy)butyl) piperidin-1-yl)phenyl)methanone (I-21, 32.74 mg, 39% yield) as a yellow solid. $^1$H NMR (400 MHz, DMSO-$d_6$) δ 9.86-9.56 (m, 2H), 8.04 (s, 1H), 7.52 (d, J=8.8 Hz, 2H), 7.33-7.26 (m, 3H), 7.22-7.16 (m, 3H), 7.13 (s, 1H), 6.93 (d, J=9.2 Hz, 2H), 6.82 (dd, J=2.0, 8.8 Hz, 3H), 6.72-6.66 (m, 2H), 4.63 (t, J=7.2 Hz, 1H), 3.98 (t, J=6.4 Hz, 2H), 3.93-3.84 (m, 3H), 3.84-3.77 (m, 1H), 2.79 (t, J=11.6 Hz, 2H), 2.60 (s, 3H), 2.41 (s, 3H), 1.70 (d, J=8.4 Hz, 4H), 1.64 (s, 3H), 1.49-1.37 (m, 3H), 1.28-1.22 (m, 2H), 1.15-1.03 (m, 2H). LC-MS: MS (ES$^+$): RT=2.815 min, m/z=889.4 [M+H$^+$]; LCMS Method: 25.

Example 23—Synthesis of 4-(2-(4-(3-((1-(4-(6-hydroxy-2-(4-hydroxyphenyl)benzo[b]thiophene-3-carbonyl)phenyl)piperidin-4-yl)methyl)azetidin-1-yl) phenoxy)-5-(2-hydroxy-propan-2-yl)phenyl)-6-methyl-1,6-dihydro-7H-pyrrolo[2,3-c]pyridin-7-one (I-22)

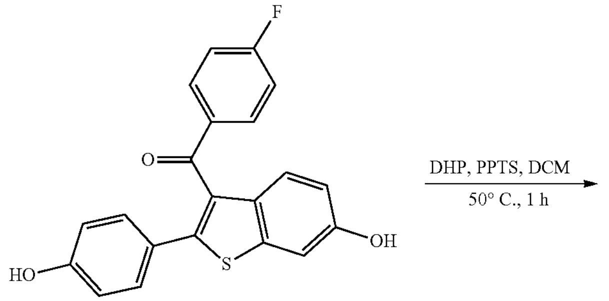

-continued
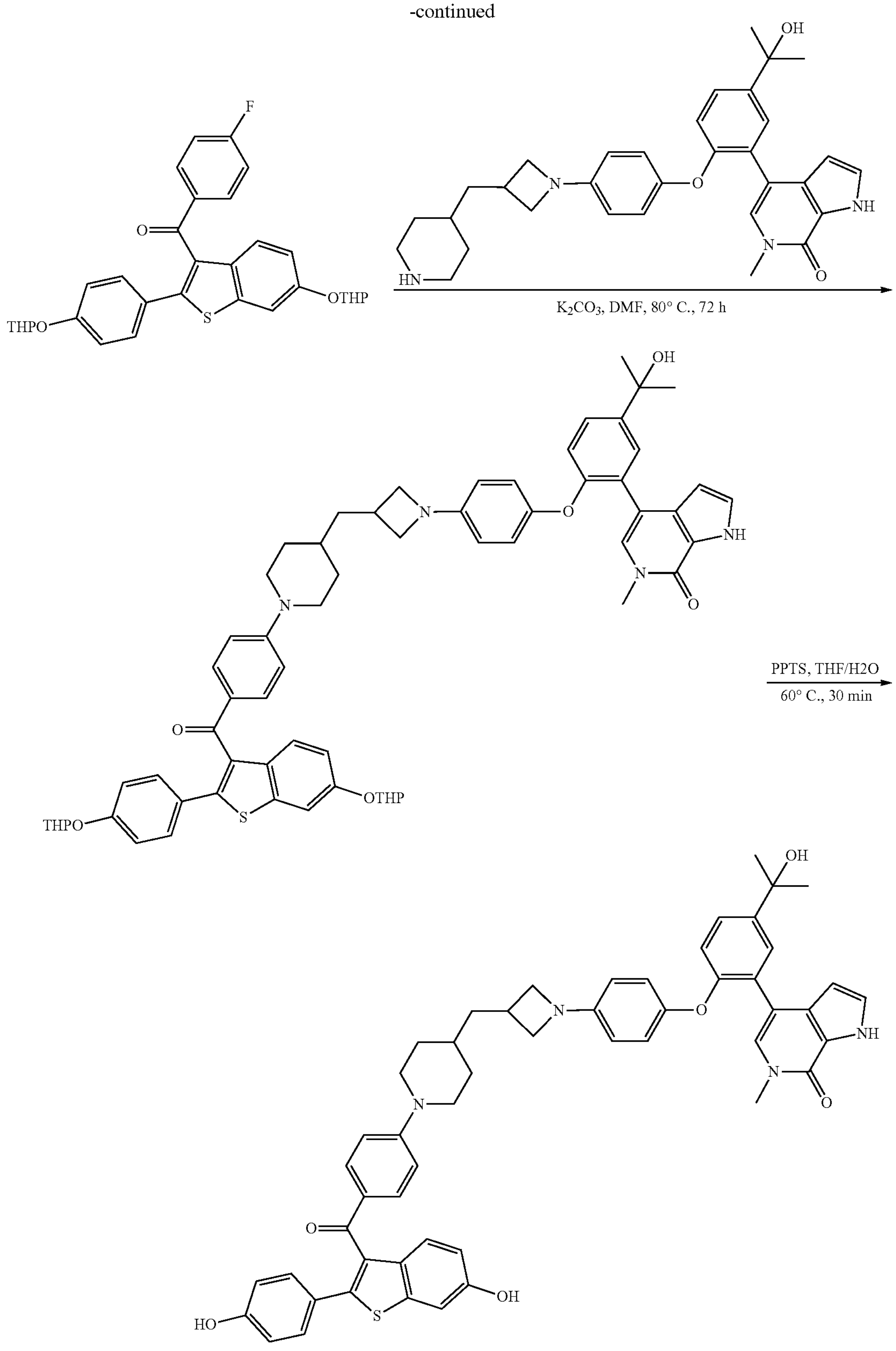
I-22
Step 1: Preparation of (4-fluorophenyl)-[6-tetrahydropyran-2-yloxy-2-(4-tetrahydropyran-2-yloxyphenyl)benzothiophen-3-yl]methanone. To a solution of (4-fluorophenyl)-[6-hydroxy-2-(4-hydroxyphenyl)benzothiophen-3-yl]methanone (1 g, 2.74 mmol, 1 equiv) in DCM (10 mL) was added 4-methylbenzenesulfonic acid-pyridine (206.90 mg, 823 mol, 0.3 equiv) and DHP (2.31 g, 27 mmol, 2.51 mL, 10 equiv). The mixture was stirred at 50° C. for 1 h. The mixture was concentrated under reduced pressure. The residue was purified by column chromatography (Silica, 0-20% Ethyl acetate/Petroleum ether) to afford (4-fluorophenyl)-[6-tetrahydropyran-2-yloxy-2-(4-tetrahydropyran-2-yloxy-phenyl) benzothiophen-3-yl]methanone (1.4 g, 91% yield) as a green oil.

Step 2: Preparation of 4-[5-(1-hydroxy-1-methyl-ethyl)-2-[4-[3-[[1-[4-[6-tetrahydropyran-2-yloxy-2-(4-tetrahydro-pyran-2-yloxyphenyl)benzothiophene-3-carbonyl]phenyl]-4-piperidyl]methyl]pyridine-1-yl]phenoxy]phenyl]-6-methyl-1H-pyrrolo[2,3-c]pyridine-7-one. To a solution of 4-[5-(1-hydroxy-1-methyl-ethyl)-2-[4-[3-(4-piperidylm-ethyl)pyridine-1-yl]phenoxy]phenyl]-6-methyl-1H-pyrrolo [2,3-c]pyridine-7-one (51.91 mg, 99 mol, 1.5 equiv) in DMF (1 mL) was added $K_2CO_3$ (27.25 mg, 197 mol, 3 equiv) and (4-fluorophenyl)-[6-tetrahydropyran-2-yloxy-2-(4-tetrahy-dropyran-2-yloxyphenyl) benzothiophen-3-yl]methanone (35 mg, 65 mol, 1 equiv). The mixture was stirred at 80° C. for 72 h. The reaction mixture was added to $H_2O$ (10 mL), and extracted with EtOAc (10 mL×3). The combined organic layers were washed with brine (10 mL), dried over $Na_2SO_4$, filtered and concentrated under reduced pressure. The residue was purified by prep-TLC ($SiO_2$, DCM: MeOH=10:1) to afford 4-[5-(1-hydroxy-1-methyl-ethyl)-2-[4-[3-[[1-[4-[6-tetrahydropyran-2-yloxy-2-(4-tetrahydropy-ran-2-yloxyphenyl)benzothiophene-3-carbonyl]phenyl]-4-piperidyl]methyl]pyridine-1-yl]phenoxy]phenyl]-6-methyl-1H-pyrrolo [2,3-c]pyridine-7-one (50 mg, 58% yield) as a green solid.

Step 3: Preparation of 4-(2-(4-(3-((1-(4-(6-hydroxy-2-(4-hydroxyphenyl) benzo[b]thiophene-3-carbonyl)phenyl)pip-eridin-4-yl)methyl)azetidin-1-yl)phenoxy)-5-(2-hydroxy-propan-2-yl)phenyl)-6-methyl-1,6-dihydro-7H-pyrrolo[2,3-c]pyridin-7-one. To a solution of 4-[5-(1-hydroxy-1-methyl-ethyl)-2-[4-[3-[[1-[4-[6-tetrahydropyran-2-yloxy-2-(4-tetrahydropyran-2-yloxyphenyl)benzothiophene-3-carbonyl]phenyl]-4-piperidyl]methyl]pyridine-1-yl] phenoxy]phenyl]-6-methyl-1H-pyrrolo[2,3-c]pyridine-7-one (35 mg, 34 mol, 1 equiv) in THE (0.5 mL) was added $H_2O$ (0.1 mL) and PPTS (11.00 mg, 44 mol, 1.3 equiv). The mixture was stirred at 60° C. for 0.5 h. The reaction mixture was added $H_2O$ (10 mL), pH was adjusted to 9-10 by adding saturated $NaHCO_3$ (aq) and extracted with DCM (10 mL×3). The combined organic layers were washed with brine (10 mL), dried over $Na_2SO_4$, filtered and concentrated under reduced pressure. The residue was purified by prep-HPLC (column: Welch Xtimate C18 150×25 mm×5 um; mobile phase: [water(FA)-ACN]; gradient: 50%-70% B over 10 min) to afford 4-(2-(4-(3-((1-(4-(6-hydroxy-2-(4-hydroxy-phenyl)benzo[b]thiophene-3-carbonyl)phenyl)piperidin-4-yl)methyl)azetidin-1-yl)phenoxy)-5-(2-hydroxy propan-2-yl)phenyl)-6-methyl-1,6-dihydro-7H-pyrrolo[2,3-c]pyridin-7-one (I-22, 15 mg, 50% yield) as a yellow solid. $^1H$ NMR (400 MHz, DMSO-$d_6$) δ 11.98 (s, 1H), 9.73 (d, 2H, J=9.2 Hz), 7.52 (dd, 3H, J=2.8, 5.2H), 7.38-7.30 (m, 2H), 7.28-7.15 (m, 5H), 6.86-6.76 (m, 5H), 6.74-6.65 (m, 3H), 6.34 (d, 2H, J=9.2H), 6.23 (t, 1H, J=2.4 Hz), 4.99 (s, 1H), 3.89 (t, 4H, J=7.2 Hz), 3.54 (s, 3H), 3.30 (s, 2H), 2.85-2.70 (m, 3H), 1.66 (d, 2H, J=11.6 Hz), 1.57-1.47 (m, 3H), 1.44 (s, 6H), 1.19-1.03 (m, 2H). LC-MS: MS ($ES^+$): RT=2.111 min, m/z=871.5 [$M+H^+$], LCMS Method: 10.

Example 24—Synthesis of (S)-4-(4-(2-(2-(3,5-difluoro-4-((1R,3R)-2-(2-fluoro-2-methyl propyl)-3-methyl-2,3,4,9-tetrahydro-1H-pyrido[3,4-b]indol-1-yl)phenoxy)ethoxy) ethoxy) phenyl)-2,3,6,9-tetramethyl-6H-thieno[3,2-f][1,2,4]triazolo[4,3-a][1,4]diazepine (I-23)

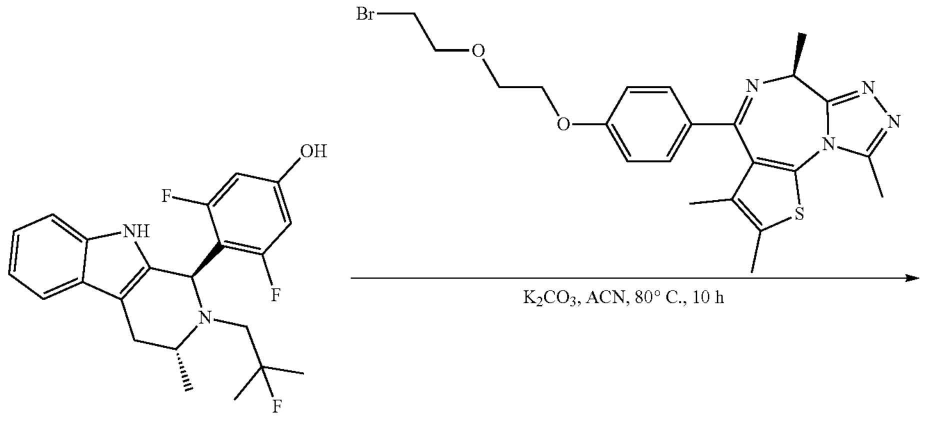

-continued

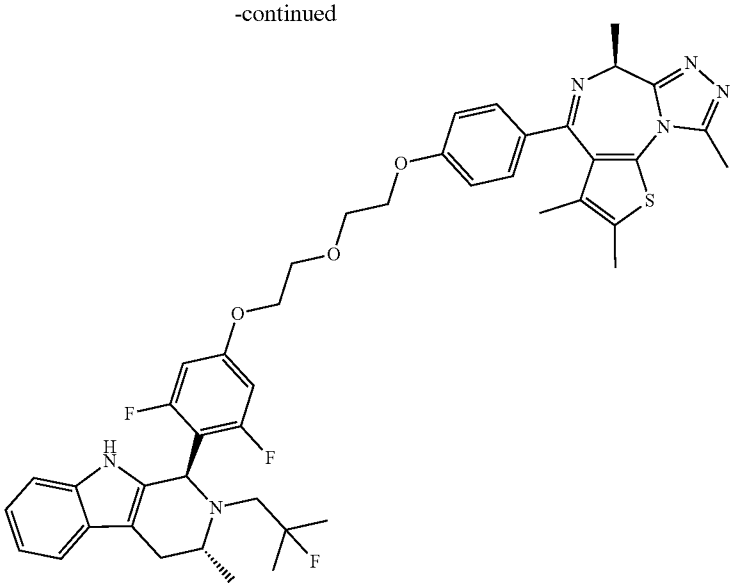

I-23

To a solution of 3,5-difluoro-4-[(1R,3R)-2-(2-fluoro-2-methyl-propyl)-3-methyl-1,3,4,9-tetrahydropyrido [3,4-b] indol-1-yl]phenol (70 mg, 0.18 mmol, 1 equiv) and (S)-4-(4-(2-(2-bromoethoxy)ethoxy) phenyl)-2,3,6,9-tetramethyl-6H-thieno[3,2-f][1,2,4]triazolo[4,3-a][1,4]diazepine (105.84 mg, 0.21 mmol, 1.2 equiv) in ACN (5 mL) was added $K_2CO_3$ (74.72 mg, 0.54 mmol, 3 equiv). The mixture was stirred at 80° C. for 10 h. The reaction mixture was diluted with water (20 mL) and extracted with ethyl acetate (20 mL×3). The combined organic layers were washed with brine (10 mL×3), dried over $Na_2SO_4$, filtered and concentrated under reduced pressure to give a residue. The residue was purified by prep-HPLC (column: YMC-Actus Triart C18 150×30 mm×7 um; mobile phase: [water(FA)-ACN]; gradient: 55%-85% B over 10 min) to afford (S)-4-(4-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy) ethoxy)ethoxy)phenyl)-2,3,6,9-tetramethyl-6H-thieno[3,2-f][1,2,4]triazolo[4,3-a][1,4]diazepine (I-23, 70.65 mg, 46% yield) as a yellow solid. $^1$H NMR (400 MHz, DMSO-$d_6$) δ 10.50 (s, 1H), 7.42-7.31 (m, 3H), 7.17 (d, J=7.6 Hz, 1H), 7.04-6.87 (m, 4H), 6.67 (d, J=11.2 Hz, 2H), 5.11 (s, 1H), 4.20-4.07 (m, 5H), 3.83-3.75 (m, 4H), 3.55-3.47 (m, 2H), 2.91-2.77 (m, 3H), 2.58 (s, 3H), 2.39 (s, 3H), 1.85 (d, J=6.4 Hz, 3H), 1.64 (s, 3H), 1.22-1.01 (m, 9H). LC-MS: MS (ES$^+$): RT=2.125 min, m/z=680.4 [M -116], m/z=796.6; LC-MS Method: 25.

Example 25—Synthesis of 4-(2-(4-((7-(2-(4-(6-hydroxy-2-(4-hydroxyphenyl) benzo[b]thiophene-3-carbonyl)phenoxy)ethyl)-7-azaspiro[3.5]nonan-2-yl) methyl) phenoxy) -5-(2-hydroxypropan-2-yl) phenyl)-6-methyl-1,6-dihydro-7H-pyrrolo[2,3-c] pyridin-7-one (I-24)

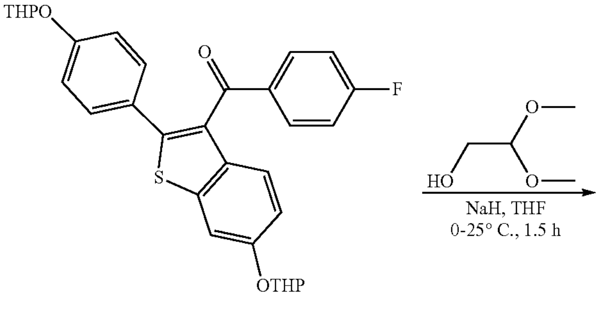

-continued
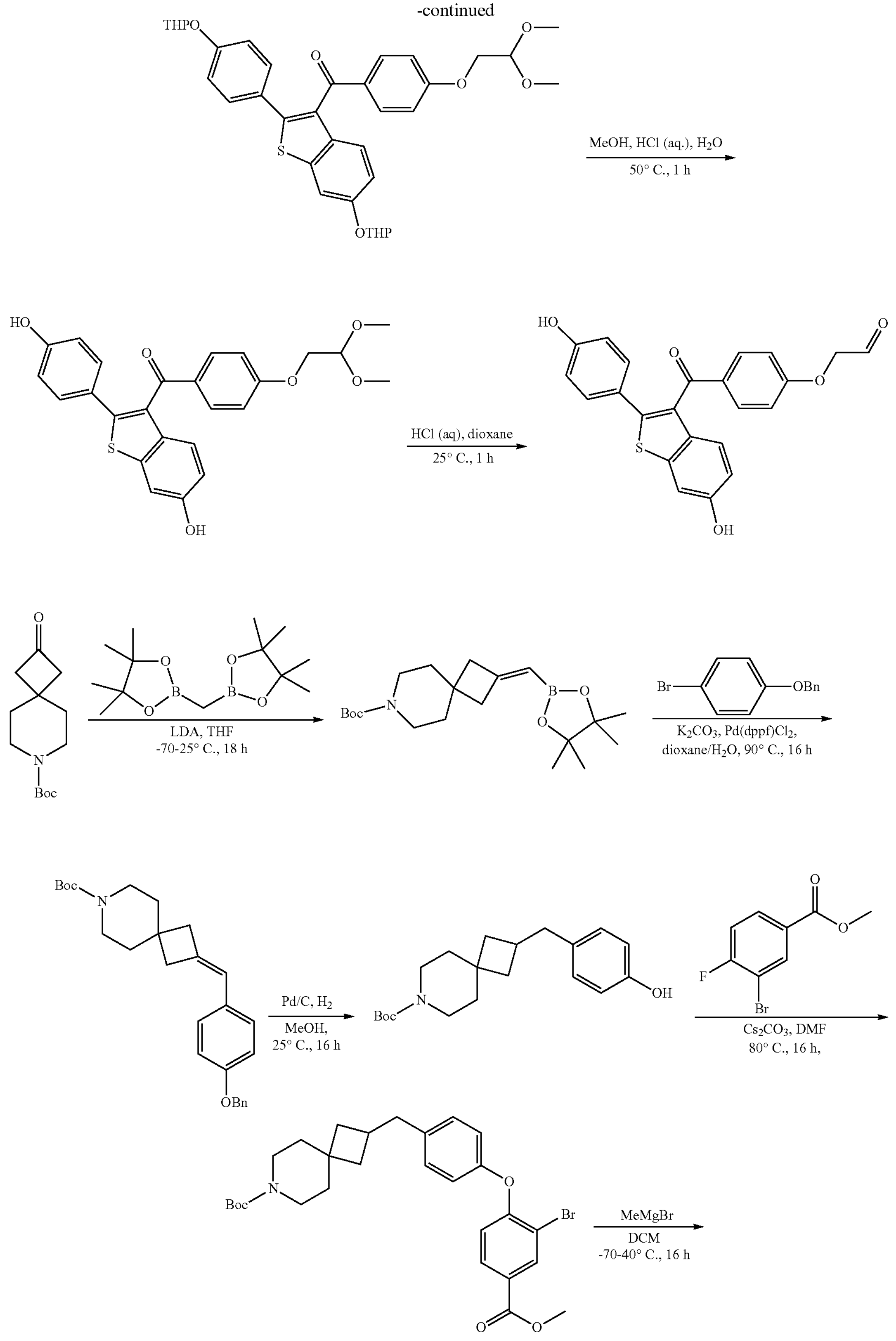

-continued
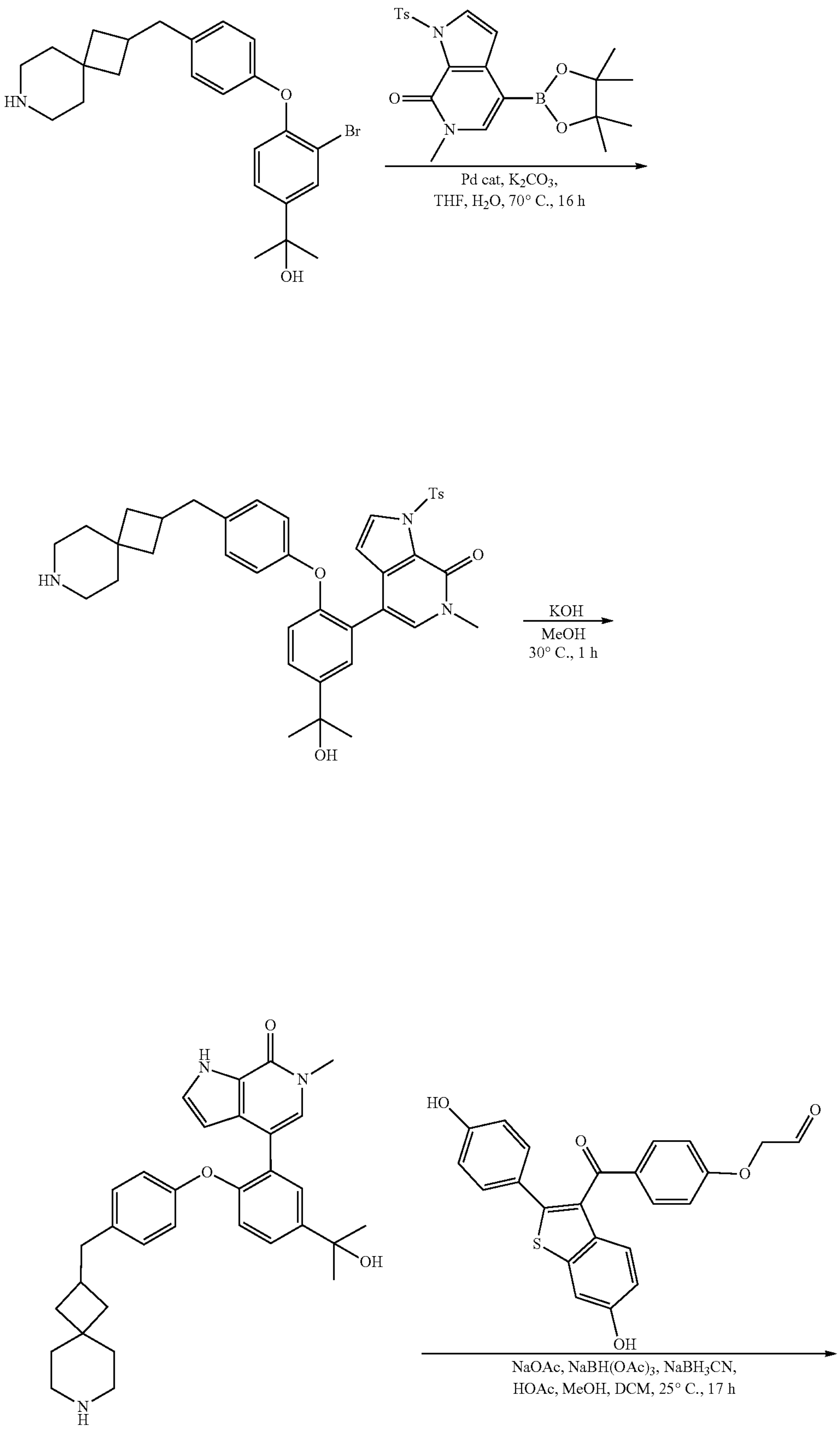

-continued

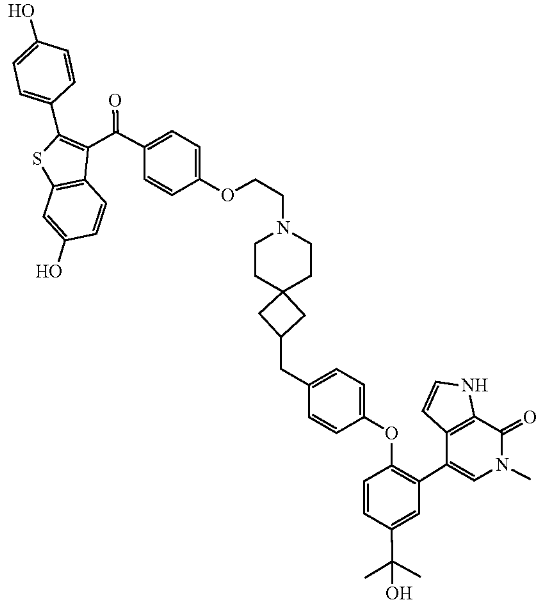

I-24

Step 1: Preparation of [4-(2, 2-dimethoxyethoxy)phenyl]-[6-tetrahydropyran-2-yloxy-2-(4-tetrahydropyran-2-yloxy-phenyl)benzothiophen-3-yl]methanone. To a solution of 2,2-dimethoxyethanol (398.48 mg, 3.76 mmol, 2 equiv) in THF (11 ml) was added portion wise NaH (187.75 mg, 4.69 mmol, 60% purity, 2.5 equiv) at 0° C. under $N_2$, the mixture was stirred at 0° C. for 0.5 h under $N_2$, then (4-fluorophenyl)-[6-tetrahydropyran-2-yloxy-2-(4-tetrahydropyran-2-yloxyphenyl)benzothiophen-3-yl]methanone (1 g, 1.88 mmol, 1 equiv) was added. The mixture was stirred at 25° C. for 1 h under $N_2$. The reaction mixture was quenched by addition saturated $NH_4Cl$ (10 ml) under $N_2$ at 25° C., and then extracted with EA (12 ml×3). The combined organic layers were dried over $Na_2SO_4$, filtered and concentrated under reduced pressure to give a residue. The residue was purified by flash silica gel chromatography (0-30% Ethyl acetate/Petroleum ether) to afford [4-(2, 2-dimethoxy-ethoxy) phenyl]-[6-tetrahydropyran-2-yloxy-2-(4-tetrahydropyran-2-yloxyphenyl)benzothiophen-3-yl]methanone (1 g, 86% yield) as a yellow oil.

Step 2: Preparation of [4-(2, 2-dimethoxyethoxy)phenyl]-[6-hydroxy-2-(4-hydroxyphenyl) benzothiophen-3-yl] methanone. To a solution of [4-(2,2-dimethoxy ethoxy) phenyl]-[6-tetrahydropyran-2-yloxy-2-(4-tetrahydropyran-2-yloxyphenyl)benzothio phen-3-yl]methanone (980 mg, 1.58 mmol, 1 equiv) in MeOH (10 ml) was added HCl (1 ml) and $H_2O$ (1 ml). The mixture was stirred at 50° C. for 1 h. The reaction mixture was concentrated under reduced pressure to afford [4-(2, 2-dimethoxyethoxy)phenyl]-[6-hydroxy-2-(4-hydroxyphenyl) benzothiophen-3-yl]methanone (710 mg, crude) as a yellow solid.

Step 3: Preparation of 2-[4-[6-hydroxy-2-(4-hydroxyphenyl)benzothiophene-3-carbonyl]phenoxy]acetaldehyde. To a solution of [4-(2,2-dimethoxyethoxy)phenyl]-[6-hydroxy-2-(4-hydroxyphenyl)benzothiophen-3-yl]methanone (710 mg, 1.58 mmol, 1 equiv) in dioxane (7.5 ml) was added HCl (12 M, 2.5 ml, 19 equiv). The mixture was stirred at 25° C. for 1 hr. The residue was purified by flash silica gel chromatography (0-50% Ethyl acetate/Petroleum ether) to afford 2-[4-[6-hydroxy-2-(4-hydroxyphenyl)benzothiophene-3-carbonyl]phenoxy]acetaldehyde (340 mg, 53% yield) as a yellow solid.

Step 4: Preparation of tert-butyl 2-[(4, 4, 5, 5-tetramethyl-1, 3, 2-dioxaborolan-2-yl) methylene]-7-azaspiro [3.5] nonane-7-carboxylate. To a solution of 4,4,5,5-tetramethyl -2-[(4,4,5,5-tetramethyl-1,3,2-dioxaborolan-2-yl)methyl]-1, 3,2-dioxaborolane (13.44 g, 50.14 mmol, 1.2 equiv) in THE (180 ml) was added LDA (2 M, 31.34 ml, 1.5 equiv) at −75° C. under $N_2$ atmosphere and the reaction mixture was stirred for 2 h. A solution of tert-butyl 2-oxo-7-azaspiro [3.5] nonane-7-carboxylate (10 g, 41.79 mmol, 1 equiv) in THE (20 ml) was added below −70° C. After 1 h, the mixture was stirred under $N_2$ at 25° C. for 15 h. The reaction mixture was quenched by addition $H_2O$ (80 ml), and then extracted with EA (100 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate 1/0 to 20/1) to afford tert-butyl 2-[(4, 4, 5, 5-tetramethyl-1, 3, 2-dioxaborolan-2-yl) methylene]-7-azaspiro [3.5]nonane-7-carboxylate (7.9 g, 52% yield) as a colorless oil.

Step 5: Preparation of tert-butyl 2-[(4-benzyloxyphenyl) methylene]-7-azaspiro [3.5]nonane-7-carboxylate. To a solution of tert-butyl 2-[(4,4,5,5-tetramethyl-1,3,2-dioxa borolan-2-yl)methylene]-7-azaspiro[3.5]nonane-7-carboxylate (2 g, 5.51 mmol, 1 equiv) and 1-benzyloxy-4-bromo-benzene (2.17 g, 8.26 mmol, 1.5 equiv) in dioxane (40 ml) and $H_2O$ (10 ml) was added $K_2CO_3$ (1.52 g, 11.01 mmol, 2 equiv) and Pd(dppf)Cl—(402.82 mg, 550 mol, 0.1 equiv) was degassed and purged with $N_2$ three times, and then the mixture was stirred at 90° C. for 16 h under $N_2$ atmosphere. The reaction mixture was quenched by addition $H_2O$ (20 ml), and then extracted with EA (30 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate, 1/0 to 20/1) to afford tert-butyl 2-[(4-benzyloxyphenyl) methylene]-7-azaspiro [3.5]nonane-7-carboxylate (1.51 g, 65% yield) as a yellow oil.

Step 6: Preparation of tert-butyl 2-[(4-hydroxyphenyl) methyl]-7-azaspiro [3.5]nonane-7-carboxylate. To a solution of tert-butyl 2-[(4-benzyloxyphenyl) methylene]-7-azaspiro [3.5]nonane-7-carboxylate (1.51 g, 3.60 mmol, 1 equiv) in MeOH (20 ml) was added Pd/C (10%, 0.5 g) under $N_2$ atmosphere. The suspension was degassed and purged with $H_2$ three times. The mixture was stirred under $H_2$ (50 Psi) at 25° C. for 16 hr. The reaction mixture was filtered and concentrated under reduced pressure to give a residue that was diluted with $H_2O$ (30 ml) and extracted with EA (30 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate, 1/0 to 10/1) to afford tert-butyl 2-[(4-hydroxyphenyl)methyl]-7-azaspiro [3.5]nonane-7-carboxylate (0.88 g, 73% yield) as a colorless oil.

Step 7: Preparation of tert-butyl 2-[[4-(2-bromo-4-methoxycarbonyl-phenoxy) phenyl]methyl]-7-azaspiro [3.5]nonane-7-carboxylate. To a solution of tert-butyl 2-[(4-hydroxyphenyl)methyl]-7-azaspiro [3.5]nonane-7-carboxylate (0.88 g, 2.66 mmol, 1 equiv) in DMF (50 ml) was added $Cs_2CO_3$ (2.60 g, 7.97 mmol, 3 equiv) and methyl 3-bromo-4-fluoro-benzoate (804.32 mg, 3.45 mmol, 1.3 equiv). The mixture was stirred at 80° C. for 16 hr. The reaction mixture was quenched by addition $H_2O$ (50 ml), and then extracted with EA (50 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate, 1/0 to 10/1) to afford tert-butyl 2-[[4-(2-bromo-4-methoxycarbonyl-phenoxy) phenyl]methyl]-7-azaspiro [3.5]nonane-7-carboxylate (0.97 g, 67% yield) as a colorless oil.

Step 8: Preparation of 2-[4-[4-(7-azaspiro [3.5]nonan-2-ylmethyl)phenoxy]-3-bromo-phenyl]propan-2-ol. A mixture of tert-butyl 2-[[4-(2-bromo-4-methoxycarbonyl-phenoxy) phenyl]methyl]-7-azaspiro[3.5]nonane-7-carboxylate (0.97 g, 1.78 mmol, 1 equiv) in DCM (50 ml) was degassed and purged with $N_2$ three times, and then to the mixture was added drop-wise MeMgBr (3 M, 8.91 ml, 15 equiv) at −70° C. under an $N_2$ atmosphere. The resulting mixture was stirred at 40° C. for 16 hours. The reaction mixture was quenched by adding to $NH_4Cl$·aq (100 ml) at 0-5° C. under $N_2$, and then mixture was extracted with DCM:MeOH (10:1, 150 ml×3). The organic layer was dried over $Na_2SO_4$, filtered and concentrated under reduced pressure to afford 2-[4-[4-(7-azaspiro [3.5]nonan-2-ylmethyl)phenoxy]-3-bromo-phenyl]propan-2-ol (700 mg, 88% yield) as a yellow gum.

Step 9: Preparation of 4-[2-[4-(7-azaspiro[3.5]nonan-2-ylmethyl)phenoxy]-5-(1-hydroxy-1-methyl-ethyl)phenyl]-6-methyl-1-(p-tolylsulfonyl)pyrrolo[2,3-c]pyridin-7-one. A mixture of 2-[4-[4-(7-azaspiro[3.5]nonan-2-ylmethyl)phenoxy]-3-bromo-phenyl]propan-2-ol (700 mg, 1.58 mmol, 1 equiv), 6-methyl-1-(p-tolylsulfonyl)-4-(4,4,5,5-tetramethyl-1,3,2-dioxaborolan-2-yl)pyrrolo[2,3-c]pyridin-7-one (674.65 mg, 1.58 mmol, 1 equiv), $K_2CO_3$ (478.93 mg, 3.47 mmol, 2.2 equiv), [2-(2-aminophenyl)phenyl]palladium (1+); bis(1-adamantyl)-butyl-phosphane; methanesulfonate (114.71 mg, 157.51 mol, 0.1 equiv) in THF (20 ml) and $H_2O$ (2 ml) was degassed and purged with $N_2$ for 3 times, and then the mixture was stirred at 70° C. for 16 hr under $N_2$ atmosphere. The mixture was concentrated to afford 4-[2-[4-(7-azaspiro[3.5]nonan-2-ylmethyl)phenoxy]-5-(1-hydroxy-1-methyl-ethyl) phenyl]-6-methyl-1-(p-tolylsulfonyl) pyrrolo[2,3-c]pyridin-7-one (900 mg, 1.35 mmol, 85% yield) as a yellow oil.

Step 10: Preparation of 4-[2-[4-(7-azaspiro[3.5]nonan-2-ylmethyl)phenoxy]-5-(1-hydroxy-1-methyl-ethyl)phenyl]-6-methyl-1H-pyrrolo[2,3-c]pyridin-7-one. To a solution of 4-[2-[4-(7-azaspiro[3.5]nonan-2-ylmethyl)phenoxy]-5-(1-hydroxy-1-methyl-ethyl)phenyl]-6-methyl-1-(p-tolylsulfonyl)pyrrolo[2,3-c]pyridin-7-one (900 mg, 1.35 mmol, 1 equiv) in MeOH (40 ml) was added KOH (1.67 g, 29.7 mmol, 22 equiv). The mixture was stirred at 30° C. for 1 hr. The reaction mixture was concentrated under reduced pressure to give a residue. The residue was purified by prep-HPLC (column: Phenomenex Luna C18 (250×70 mm×10 um); mobile phase: [water(FA)-ACN]; gradient: 15%-45% B over 20 min) to afford 4-[2-[4-(7-azaspiro[3.5]nonan-2-ylmethyl)phenoxy]-5-(1-hydroxy-1-methyl-ethyl)phenyl]-6-methyl-1H-pyrrolo[2,3-c]pyridin-7-one (290 mg, 41% yield) as a white solid.

Step 11: Preparation of 4-[2-[4-[[7-[2-[4-[6-hydroxy-2-(4-hydroxyphenyl) benzothiophene-3-carbonyl]phenoxy] ethyl]-7-azaspiro[3.5]nonan-2-yl]methyl]phenoxy]-5-(1-hydroxy-1-methyl-ethyl)phenyl]-6-methyl-1H-pyrrolo[2,3-c]pyridin-7-one. To a solution of 4-[2-[4-(7-azaspiro [3.5] nonan-2-ylmethyl)phenoxy]-5-(1-hydroxy-1-methyl-ethyl) phenyl]-6-methyl-1H-pyrrolo [2,3-c]pyridin-7-one (40 mg, 78.2 mol, 1 equiv) in MeOH (1 ml) and DCM (1 ml) was added NaOAc (12.83 mg, 156 mol, 2 equiv). The mixture was stirred at 25° C. for 1 h, then the mixture was added 2-[4-[6-hydroxy-2-(4-hydroxyphenyl)benzothiophene-3-carbonyl]phenoxy]acetaldehyde (79.04 mg, 195 mol, 2.5 equiv), the mixture was stirred at 25° C. for 1 h, then the mixture was added $NaBH(OAc)_3$ (49.71 mg, 234 mol, 3 equiv) and the mixture was stirred at 25° C. for 1 h, after the mixture was added $NaBH_3CN$ (9.83 mg, 156 mol, 2 equiv) and HOAc (104.90 mg, 1.75 mmol, 0.1 ml, 22.34 equiv), then the mixture was stirred at 25° C. for 14 h. The reaction mixture was concentrated under reduced pressure to give a residue. The residue was purified by prep-HPLC (column: Welch Xtimate C18 150×25 mm×5 um; mobile phase: [water(FA)-ACN]; gradient: 30%-50% B over 10 min) to afford 4-(2-(4-((7-(2-(4-(6-hydroxy-2-(4-hydroxyphenyl) benzo[b]thiophene-3-carbonyl)phenoxy)ethyl)-7-azaspiro [3.5]nonan-2-yl)methyl)phenoxy)-5-(2-hydroxypropan-2-yl)phenyl)-6-methyl-1,6-dihydro-7H-pyrrolo[2,3-c]pyridin-7-one (I-24, 14.6 mg, 19% yield) as a yellow solid. $^1$H NMR (400 MHz, methanol-$d_4$) δ=7.73 (d, J=8.8 Hz, 2H), 7.65 (d, J=2.4 Hz, 1H), 7.48 (dd, J=2.4, 8.6 Hz, 1H), 7.43 (d, J=8.8 Hz, 1H), 7.31 (d, J=2.8 Hz, 1H), 7.26 (d, J=2.0 Hz, 1H), 7.20-7.15 (m, 2H), 7.14 (s, 1H), 7.01 (d, J=8.4 Hz, 1H), 6.94 (d, J=8.4 Hz, 2H), 6.90-6.85 (m, 3H), 6.67-6.59 (m, 4H), 6.35 (d, J=2.8 Hz, 1H), 4.63-4.52 (m, 1H), 4.33-4.21 (m, 2H), 3.61-3.56 (m, 3H), 3.28-3.25 (m, 1H), 3.16-2.79 (m, 4H), 2.62-2.54 (m, 2H), 2.49-2.33 (m, 1H), 1.96-1.77 (m, 4H), 1.68 (br t, J=5.2 Hz, 2H), 1.59 (s, 6H), 1.49 (br dd, J=8.8, 11.6 Hz, 2H) LC-MS: MS (ES$^+$): RT=2.095 min, m/z=900.3 [M+H$^+$], LC-MS Method: 25.

Example 26—Synthesis of (S)-4-(4-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy) ethoxy)ethoxy)ethoxy)phenyl)-2,3,6,9-tetramethyl-6H-thieno[3,2-f][1,2,4]triazolo[4,3-a][1,4]diazepine (I-25)
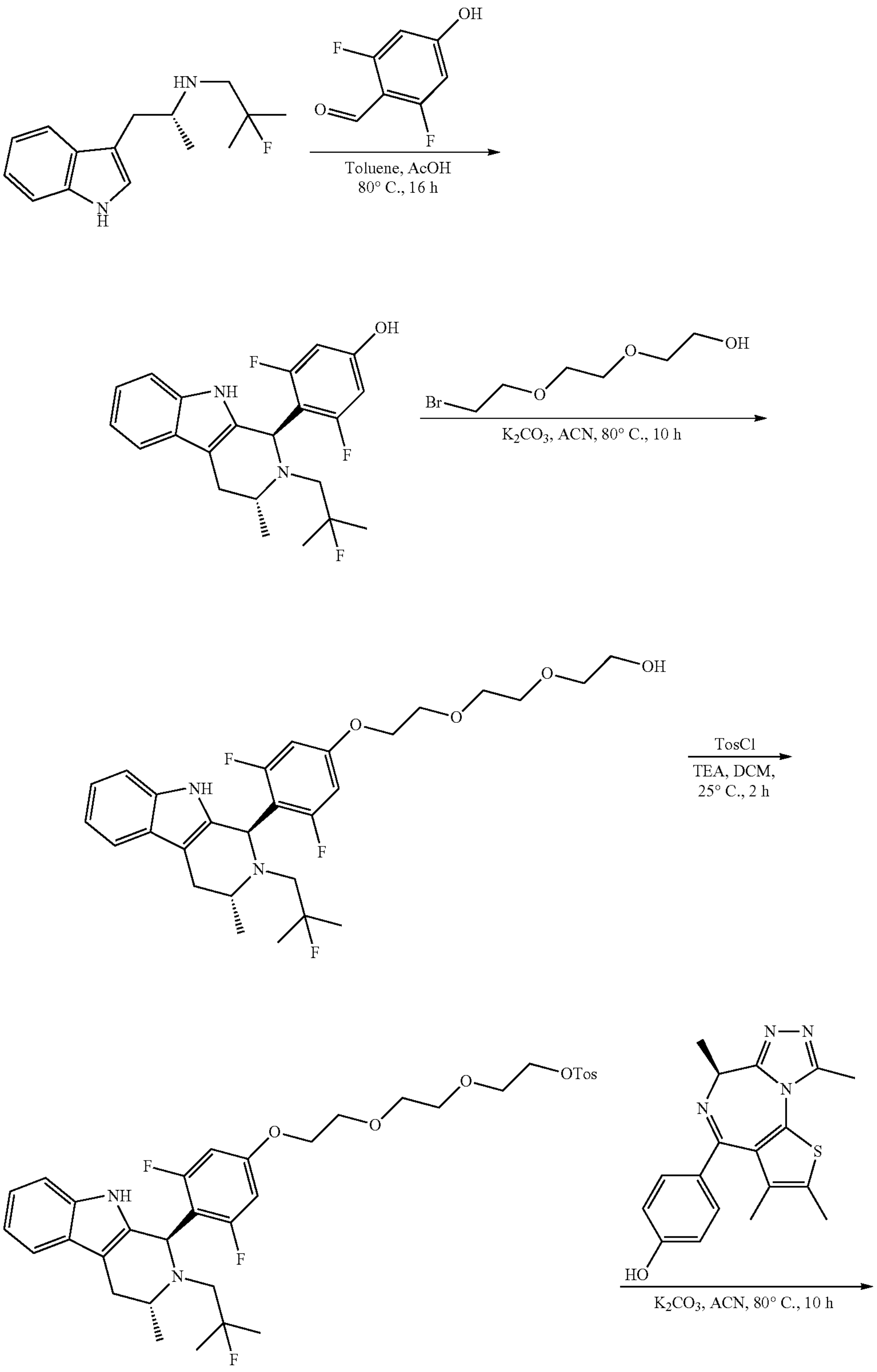

-continued

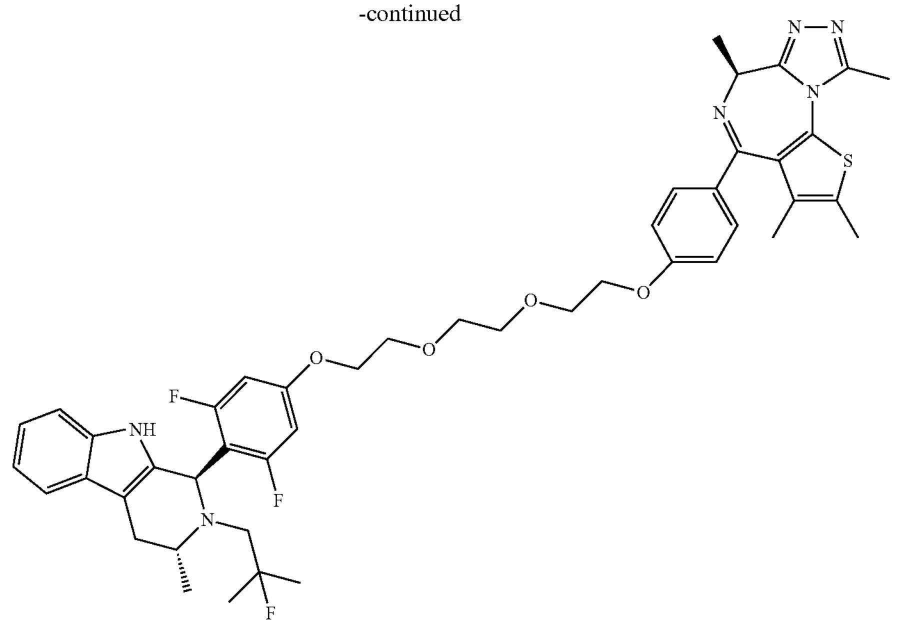

I-25

Step 1: Preparation of 3,5-difluoro-4-[(1R,3R)-2-(2-fluoro-2-methyl-propyl)-3-methyl-1,3,4,9-tetrahydro pyrido [3,4-b]indol-1-yl]phenol. To a solution of 2-fluoro-N-[(1R)-2-(1H-indol-3-yl)-1-methyl-ethyl]-2-methyl-propan-1-amine (113 mg, 0.45 mmol, 1 equiv) and 2,6-difluoro-4-hydroxy-benzaldehyde (71.94 mg, 0.45 mmol, 1 equiv) in toluene (2 mL) was added AcOH (54.65 mg, 0.90 mmol, 2 equiv). The mixture was stirred at 80° C. for 16 h. The reaction mixture was quenched by addition aqueous saturated sodium bicarbonate (10 mL) and then diluted with water (10 mL) and extracted with ethyl acetate (10 mL×3). The combined organic layers were washed with brine (10 mL×3), dried over $Na_2SO_4$, filtered and concentrated under reduced pressure to give a residue. The residue was purified by column chromatography (SiO2, Petroleum ether/Ethyl acetate, 3/1) to afford 3,5-difluoro-4-[(1R,3R)-2-(2-fluoro-2-methyl-propyl)-3-methyl-1,3,4,9-tetrahydro pyrido[3,4-b] indol-1-yl]phenol (136 mg, 71% yield) as a yellow solid.

Step 2: Preparation of 2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethanol. To a solution of 3,5-difluoro-4-[(1R,3R)-2-(2-fluoro-2-methyl-propyl)-3-methyl-1,3,4,9-tetrahydropyrido [3,4-b]indol-1-yl]phenol (136 mg, 0.35 mmol, 1 equiv) and 2-[2-(2-bromoethoxy)ethoxy]ethanol (82.06 mg, 0.38 mmol, 1.1 equiv) in ACN (3 mL) was added $K_2CO_3$ (48.39 mg, 0.35 mmol, 1 equiv). The mixture was stirred at 80° C. for 10 h. The reaction mixture was diluted with water (20 mL) and extracted with ethyl acetate (20 mL×3). The combined organic layers were washed with brine (10 mL×3), dried over $Na_2SO_4$, filtered and concentrated under reduced pressure to give a residue. The residue was purified by prep-TLC ($SiO_2$, Petroleum ether/Ethyl acetate, 1/1) to afford 2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy] ethoxy]ethoxy]ethanol (135 mg, 60% yield) as a yellow solid.

Step 3: Preparation of 2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethyl 4-methylbenzenesulfonate. To a solution of 2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy] ethoxy]ethoxy]ethanol (132 mg, 0.25 mmol, 1 equiv) in $CH_2Cl_2$ (3 mL) was added TosCl (62.84 mg, 0.30 mmol, 1.3 equiv), TEA (51.32 mg, 0.50 mmol, 2 equiv) and DMAP (3.10 mg, 25.36 mol, 0.1 eq). The mixture was stirred at 25° C. for 2 h. The reaction mixture was diluted with water (20 mL) and extracted with ethyl acetate (20 mL×3). The combined organic layers were washed with brine (10 mL×3), dried over $Na_2SO_4$, filtered and concentrated under reduced pressure to give a residue. The residue was purified by prep-TLC ($SiO_2$, dichloromethane/methanol, 3/1) to afford 2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethyl 4-methylbenzenesulfonate (98 mg, 51% yield) as a yellow oil.

Step 4: Preparation of (S)-4-(4-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy) ethoxy)ethoxy)phenyl)-2,3,6,9-tetramethyl-6H-thieno[3,2-f][1,2,4]triazolo[4,3-a][1,4]diazepine. To a solution of 2-[2-[2-[3,5-difluoro-4-[(1R,3R)-2-(2-fluoro-2-methyl-propyl)-3-methyl-1,3,4,9-tetrahydropyrido[3,4-b]indol-1-yl] phenoxy]ethoxy]ethoxy]ethyl 4-methylbenzenesulfonate (95 mg, 0.14 mmol, 1 equiv) and (S)-4-(2,3,6,9-tetramethyl-6H-thieno[3,2-f][1,2,4]triazolo[4,3-a][1,4]diazepin-4-yl) phenol (47.65 mg, 0.14 mmol, 1 equiv) in ACN (5 mL) was added $K_2CO_3$ (58.37 mg, 0.4 mmol, 3 equiv). The mixture was stirred at 80° C. for 10 h. The reaction mixture was diluted with water (20 mL) and extracted with ethyl acetate (20 mL×3). The combined organic layers were washed with brine (10 mL×3), dried over $Na_2SO_4$, filtered and concentrated under reduced pressure to give a residue. The residue was purified by prep-HPLC (column: YMC-Actus Triart C18 150×30 mm×7 um; mobile phase: [water (FA)-ACN]; gradient: 50%-80% B over 10 min) to afford (S)-4-(4-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)phenyl)-2,3,6,9-tetramethyl-6H-thieno[3,2-f][1,2,4]triazolo[4,3-a][1,4]diazepine (I-25, 13.52 mg, 11% yield) as a yellow solid. $^1H$ NMR (400 MHz, DMSO-$d_6$) 10.51 (s, 1H), 7.41-7.33 (m, 3H), 7.16 (d, J=7.6 Hz, 1H), 7.01-6.88 (m, 4H), 6.66 (d, J=10.8 Hz, 2H), 5.11 (d, J=0.8 Hz, 1H), 4.10 (d, J=3.2 Hz, 4H), 3.76-3.70 (m, 4H), 3.59 (s, 4H), 2.89-2.82 (m, 3H), 2.68-2.66 (m, 3H), 2.34-2.31 (m, 3H), 1.85 (d, J=6.4 Hz, 3H), 1.64 (s, 3H), 1.25-1.00 (m, 12H). LC-MS: MS ($ES^+$): RT=1.821 min, m/z=841.7 [$M+H^+$], LC-MS Method: 25.

Example 27—Synthesis of (6-hydroxy-2-(4-hydroxyphenyl)benzo[b]thiophen-3-yl)(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)phenyl)methanone (I-26)

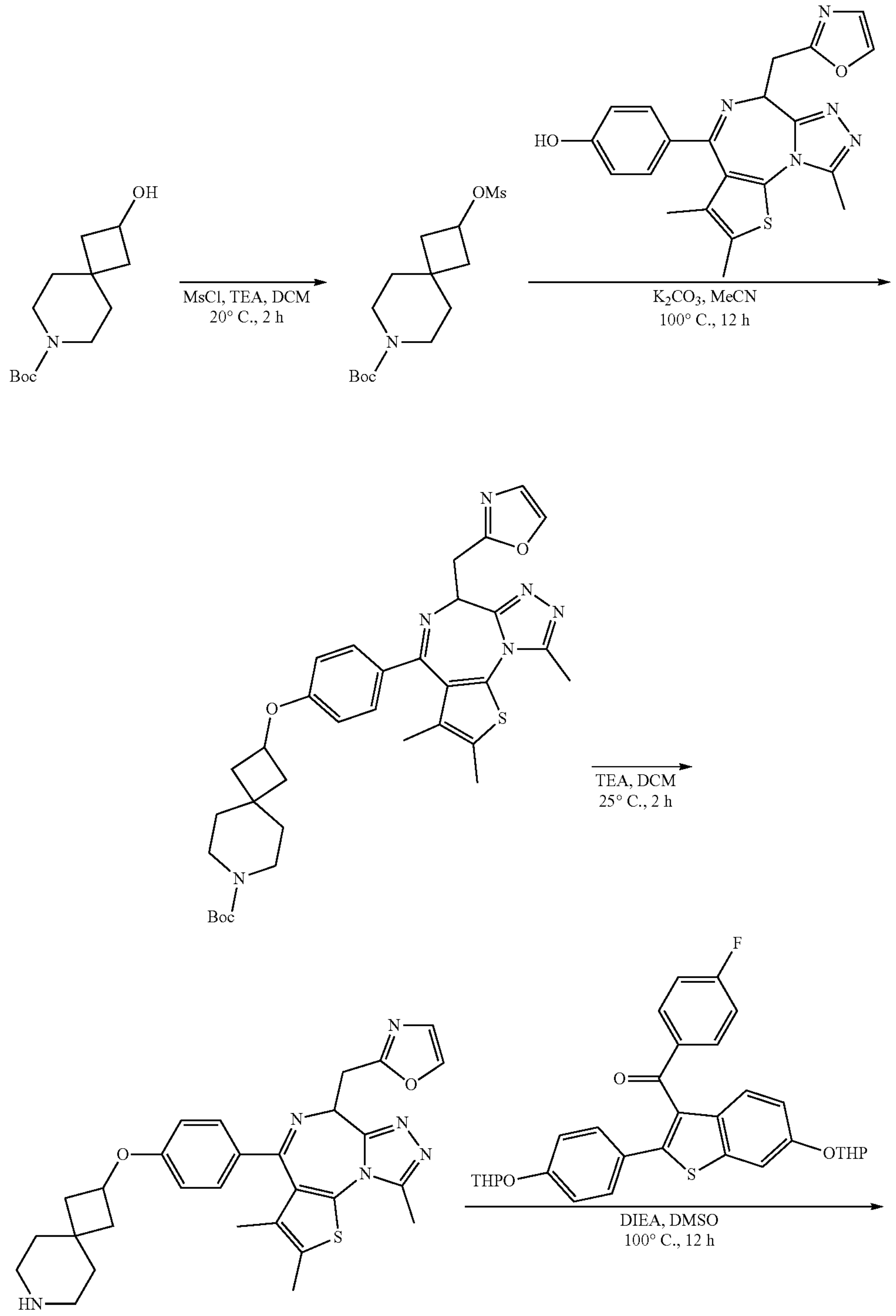

-continued

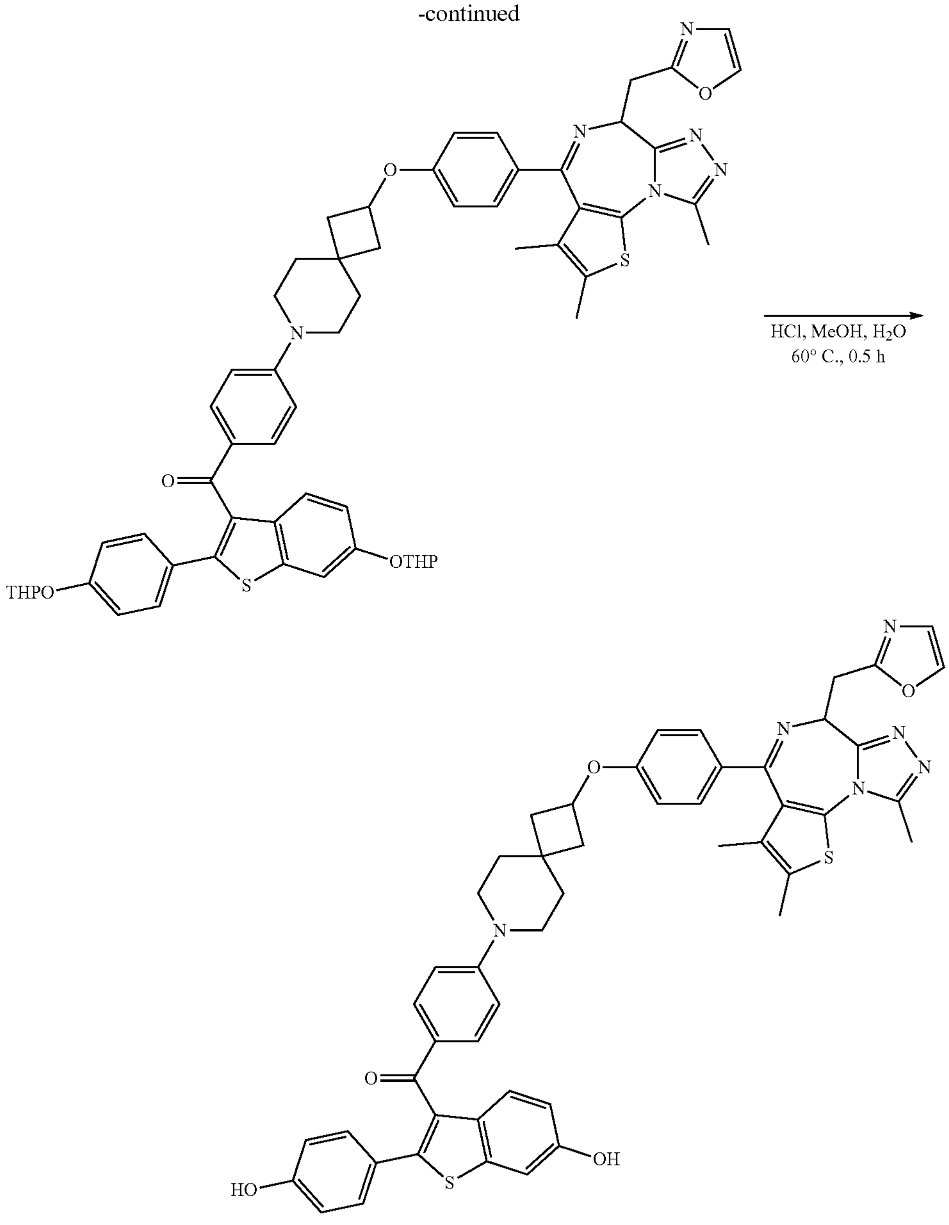

1-26

Step 1: Preparation of tert-butyl 2-methylsulfonyloxy-7-azaspiro[3.5]nonane-7-carboxylate. To a solution of tert-butyl 2-hydroxy-7-azaspiro[3.5]nonane-7-carboxylate (2 g, 8.29 mmol, 1 equiv) in DCM (30 mL) was added TEA (2.10 g, 20.72 mmol, 2.88 mL, 2.5 equiv) and MsCl (1.34 g, 11.70 mmol, 905 μL, 1.41 equiv) was added at 0° C. The mixture was stirred at 20° C. for 2 h. The reaction mixture was poured into ice water (50 mL) and then diluted with DCM (50 mL) and extracted with DCM (50 mL×2). The combined organic layers were washed with citric acid (100 mL) and brine (30 mL×2), dried over $Na_2SO_4$, filtered and concentrated under reduced pressure to afford tert-butyl 2-methylsulfonyloxy-7-azaspiro[3.5]nonane-7-carboxylate (2.6 g, 98% yield) as a white solid.

Step 2: Preparation of tert-butyl 2-[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenoxy]-7-azaspiro[3.5]nonane-7-carboxylate. To a solution of 4-(2,3,9-trimethyl-6-(oxazol-2-ylmethyl)-6H-thieno[3,2-f][1,2,4]triazolo[4,3-a][1,4]diazepin-4-yl)phenol (200 mg, 493 mol, 1 equiv) in DMF (7 mL) was added $K_2CO_3$ (136.34 mg, 986 mol, 2 equiv) and tert-butyl 2-methylsulfonyloxy-7-azaspiro[3.5]nonane-7-carboxylate (787.76 mg, 2.47 mmol, 5 equiv). The mixture was stirred at 100° C. for 12 h. The reaction mixture was filtered and concentrated under reduced pressure to give a residue. The residue was purified by prep-TLC ($SiO_2$, DCM:MeOH, 10:1) to afford tert-butyl 2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonane-7-carboxylate (240 mg, 77% yield) as a white solid.

Step 3: Preparation of 2-((4-(4-((7-azaspiro[3.5]nonan-2-yl)oxy)phenyl)-2,3,9-trimethyl-6H-thieno[3,2-f][1,2,4]triazolo[4,3-a][1,4]diazepin-6-yl)methyl)oxazole. To a solution of tert-butyl 2-(4-(2,3,9-trimethyl-6-(oxazol-2-ylmethyl)-6H-thieno[3,2-f][1,2,4]triazolo [4,3-a][1,4]diazepin-4-yl)phenoxy)-7-azaspiro[3.5]nonane-7-carboxylate (240 mg, 381 mol, 1 equiv) in DCM (3 mL) was added TFA (3.68 g, 32.31 mmol, 2.40 mL, 84.65 equiv). The mixture was stirred at 25° C. for 2 h. The reaction mixture was quenched by addition $NaHCO_3$ (aq) (10 mL) at 25° C., adjusted pH to 8, and then diluted with $H_2O$ (20 mL) and extracted with EA (20 mL×2). The combined organic fractions were dried over $Na_2SO_4$, filtered and concentrated under reduced pressure to afford 2-((4-(4-((7-azaspiro[3.5]nonan-2-yl)oxy)phenyl)-2,3,9-trimethyl-6H-thieno[3,2-f][1,2,4]triazolo[4,3-a][1,4]diazepin-6-yl)methyl)oxazole (200 mg, 99% yield) as a white solid.

Step 4: Preparation of (6-((tetrahydro-2H-pyran-2-yl)oxy)-2-(4-((tetrahydro-2H-pyran-2-yl)oxy)phenyl)benzo[b]thiophen-3-yl)(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro [3.5]nonan-7-yl)phenyl) methanone. To a solution of 2-((4-(4-((7-azaspiro[3.5]nonan-2-yl)oxy)phenyl)-2,3,9-trimethyl-6H-thieno[3,2-f][1,2,4]triazolo[4,3-a][1,4]diazepin-6-yl)methyl)oxazole (200 mg, 378 mol, 1 equiv) and (4-fluorophenyl)-[6-tetrahydropyran-2-yloxy-2-(4-tetrahydropyran-2-yloxyphenyl)benzothiophen-3-yl]methanone (201.50 mg, 378 mol, 1 equiv) in DMSO (2 mL) was added $Cs_2CO_3$ (246.52 mg, 756 mol, 2 equiv). The mixture was stirred at 100° C. for 12 h. The reaction mixture was partitioned between EA (50 mL) and $H_2O$ (50 mL). The organic phase was separated, washed with brine (30 mL), dried over $Na_2SO_4$, filtered and concentrated under reduced pressure to give a residue. The residue was purified by prep-TLC ($SiO_2$, DCM:MeOH, 10:1) to afford (6-((tetrahydro-2H-pyran-2-yl)oxy)-2-(4-((tetrahydro-2H-pyran-2-yl)oxy)phenyl)benzo[b]thiophen-3-yl)(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)phenyl)methanone (200 mg, 50% yield) as a white solid.

Step 5: Preparation of (6-hydroxy-2-(4-hydroxyphenyl)benzo[b]thiophen-3-yl)(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)phenyl) methanone (isomer 1 and isomer 2). To a solution of (6-((tetrahydro-2H-pyran-2-yl)oxy)-2-(4-((tetrahydro-2H-pyran-2-yl)oxy)phenyl) benzo[b]thiophen-3-yl)(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)phenyl) methanone (150 mg, 144 mol, 1 equiv) in MeOH (0.1 mL) was added HCl (102 mg, 2.80 mmol, 0.1 mL, 100% purity, 19.4 equiv) and $H_2O$ (1 mL). The mixture was stirred at 60° C. for 0.5 h. The reaction mixture was quenched by addition $NaHCO_3$ (aq) (10 mL) at 25° C., adjust pH to 8, and then diluted with $H_2O$ (20 mL) and extracted with EA (20 mL×2). The combined organic layers were dried over $Na_2SO_4$, filtered and concentrated under reduced pressure to give a residue. The residue was purified by prep-HPLC (column: Phenomenex Luna C18 150×25 mm×10 um; mobile phase: [water (FA)-ACN]; gradient: 58%-88% B over 9 min) to afford a white solid. The racemate was resolved by SFC ((s,s)-WHELK-O1 (250 mm×30 mm×10 um); mobile phase: [$CO_2$-ACN/EtOH (0.1% $NH_3H_2O$)]; 65% B, isocratic elution mode) to give isomer 1 as a white solid (peak 1, 18 mg, 44% yield) and isomer 2 of (6-hydroxy -2-(4-hydroxyphenyl)benzo[b]thiophen-3-yl)(4-(2-(4-(2,3,9-trimethyl-6-(oxazol-2-ylmethyl)-6H-thieno[3,2-f][1,2,4]triazolo[4,3-a][1,4]diazepin-4-yl)phenoxy)-7-azaspiro[3.5]nonan-7-yl)phenyl)methanone as a white solid (peak 2, 20 mg, 49% yield). $^1H$ NMR (400 MHz, DMSO-d6) δ 9.73 (br d, J=9.2 Hz, 2H) 8.03 (s, 1H) 7.52 (d, J=8.8 Hz, 2H) 7.31 (d, J=2.0 Hz, 1H) 7.27 (br d, J=8.8 Hz, 2H) 7.15-7.22 (m, 3H) 7.12 (s, 1H) 6.79-6.87 (m, 5H) 6.65-6.71 (m, 2H) 4.73-4.82 (m, 1H) 4.61 (t, J=7.6 Hz, 1H) 3.76-3.90 (m, 2H) 3.25 (br d, J=2.8 Hz, 2H) 2.59 (s, 3H) 2.52-2.54 (m, 2H) 2.41 (s, 5H) 1.77-1.84 (m, 2H) 1.53-1.65 (m, 7H). $^1H$ NMR (400 MHz, DMSO-d6) δ 9.68-9.79 (m, 2H) 8.03 (d, J=0.8 Hz, 1H) 7.52 (d, J=8.8 Hz, 2H) 7.31 (d, J=2.0 Hz, 1H) 7.27 (d, J=8.4 Hz, 2H) 7.15-7.22 (m, 3H) 7.12 (d, J=0.8 Hz, 1H) 6.79-6.87 (m, 5H) 6.68 (d, J=8.8 Hz, 2H) 4.78 (br t, J=6.8 Hz, 1H) 4.61 (t, J=7.6 Hz, 1H) 3.75-3.92 (m, 2H) 3.26 (dt, J=4.0, 2.2 Hz, 2H) 2.59 (s, 3H) 2.54 (s, 2H) 2.39-2.45 (m, 5H) 1.80 (br dd, J=12.8, 6.4 Hz, 2H) 1.64 (s, 7H).

Example 28—Synthesis of (S)-2,3,6,9-tetramethyl-4-(4-(4-((4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperazin-1-yl)methyl)piperidin-1-yl)phenyl)-6H-thieno[3,2-f][1,2,4]triazolo[4,3-a][1,4]diazepine (I-27)

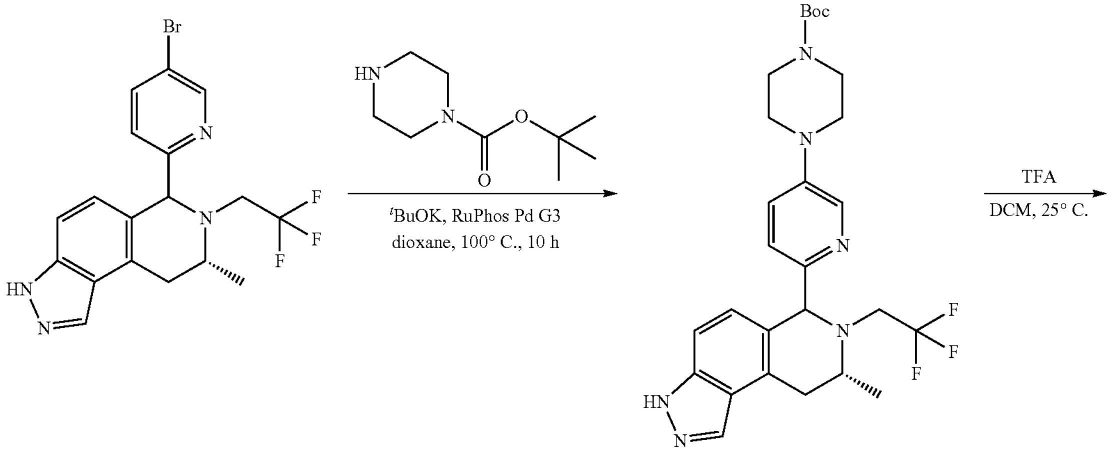

-continued
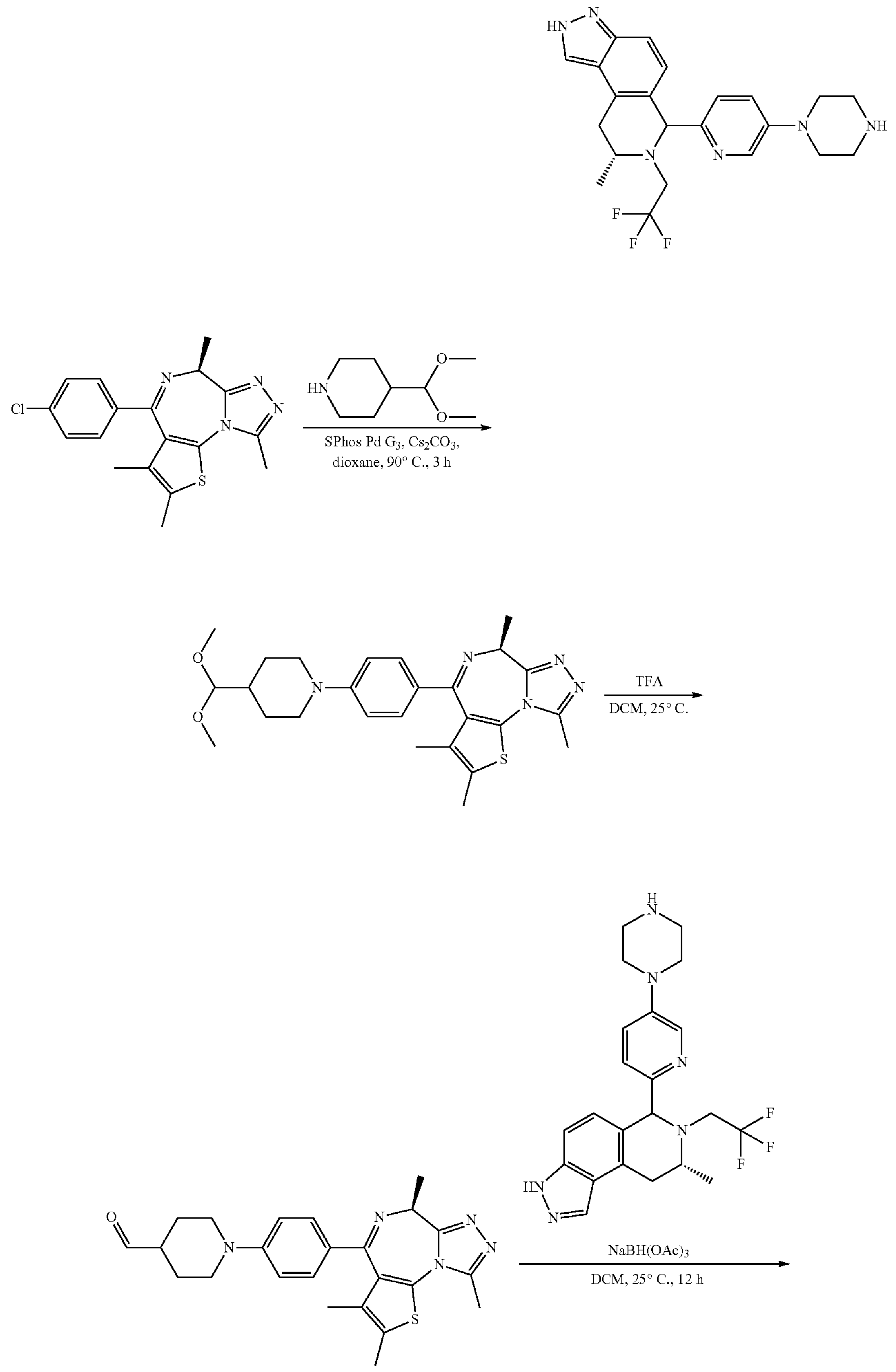

-continued

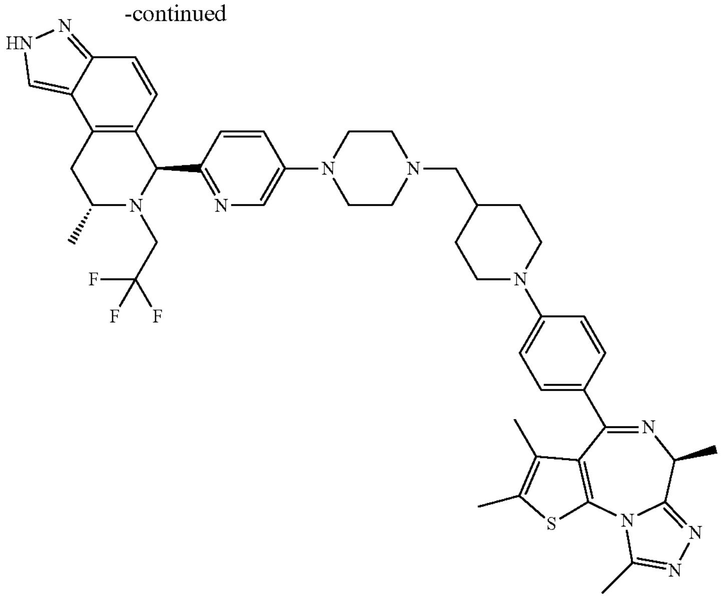

I-27

Step 1: Preparation of tert-butyl 4-(6-((8R)-8-methyl-7-(2,2,2-trifluoroethyl)-6,7,8,9-tetrahydro-3H-pyrazolo[4,3-f] isoquinolin-6-yl)pyridine-3-yl)piperazine-1-carboxylate. To a solution of (8R)-6-(5-bromopyridin-2-yl)-8-methyl-7-(2,2,2-trifluoroethyl)-6,7,8,9-tetrahydro-3H-pyrazolo[4,3-f] isoquinoline (1.00 g, 2.35 mmol, 1.00 equiv), tert-butyl piperazine-1-carboxylate (1.31 g, 7.05 mmol, 3.00 equiv), potassium tert-butoxide (1.32 g, 11.76 mmol, 5.00 equiv), [2-(2-aminophenyl)phenyl]-methylsulfonyloxy-palladium; dicyclohexyl-[2-(2,6-diisopropoxyphenyl)phenyl]phosphane (393 mg, 0.47 mmol, 0.20 equiv) in dioxane (20 mL) was stirred at 100° C. for 10 h under nitrogen atmosphere. The mixture was filtered and the filtrate was concentrated under reduced pressure to give a residue. The residue was purified by silica gel column chromatography (petroleum ether/ethyl acetate=6/1 to 1/1) to give tert-butyl 4-(6-((8R)-8-methyl-7-(2,2,2-trifluoroethyl)-6,7,8,9-tetrahydro-3H-pyrazolo[4,3-f]isoquinolin-6-yl)pyridine-3-yl)piperazine-1-carboxylate (450 mg, 36% yield) as a yellow solid.

Step 2: Preparation of (8R)-8-methyl-6-(5-(piperazin-1-yl)pyridine-2-yl)-7-(2,2,2-trifluoroethyl)-6,7,8,9-tetrahydro-2H-pyrazolo[4,3-f]isoquinoline. To a solution of tert-butyl 4-(6-((8R)-8-methyl-7-(2,2,2-trifluoroethyl)-6,7,8,9-tetrahydro-3H-pyrazolo[4,3-f]isoquinolin-6-yl)pyridine-3-yl)piperazine-1-carboxylate (150 mg, 0.28 mmol, 1.00 equiv) in dichloromethane (1 mL) was added trifluoroacetic acid (767 mg, 6.73 mmol, 23.81 equiv). The mixture was stirred at 25° C. for 10 min. Ethyl acetate (2 mL) and saturated sodium bicarbonate solution (2 mL) were added, then the mixture was extracted with ethyl acetate (2 mL×3). The organic layers was washed with brine (2 mL×3), dried over anhydrous sodium sulfate, filtered and concentrated under reduced pressure to give (8R)-8-methyl-6-(5-(piperazin-1-yl)pyridine-2-yl)-7-(2,2,2-trifluoroethyl)-6,7,8,9-tetrahydro-2H-pyrazolo[4,3-f]iso quinoline (120 mg, 98% yield) as a red oil, which was used into the next step without further purification.

Step 3: Preparation of (S)-4-(4-(4-(dimethoxymethyl)piperidin-1-yl)phenyl)-2,3,6,9-tetramethyl-6H-thieno[3,2-f][1,2,4]triazolo[4,3-a][1,4]diazepine. A mixture of (9S)-7-(4-chlorophenyl)-4,5,9,13-tetramethyl-3-thia-1,8,11,12-tetrazatricyclo[8.3.0.0$^{2,6}$]trideca-2(6),4,7,10,12-pentaene (100 mg, 0.28 mmol, 1.00 equiv), 4-(dimethoxymethyl)piperidine (223 mg, 1.40 mmol, 5.00 equiv), dicyclohexyl-[2-(2,6-dimethoxyphenyl)phenyl]phosphane; methanesulfonate; (2-phenylanilino)palladium(1+), (22 mg, 0.03 mmol, 0.10 equiv) and cesium carbonate (183 mg, 0.56 mmol, 2.00 equiv) in dioxane (1 mL) was degassed and purged with nitrogen for 3 times, and then the mixture was stirred at 90° C. for 3 h under nitrogen atmosphere. Ethyl acetate (5 mL) and water (5 mL) were added before the mixture was extracted with ethyl acetate (5 mL×3). The combined organic layers were washed with brine (5 mL×3), dried over anhydrous sodium sulfate, filtered and concentrated under reduced pressure to get the residue. The residue was purified by prep-TLC (dichloromethane/methanol=10/1) to afford (S)-4-(4-(4-(dimethoxymethyl)piperidin-1-yl)phenyl)-2,3,6,9-tetramethyl-6H-thieno[3,2-f][1,2,4]triazolo[4,3-a][1,4]diazepine (100 mg, 73% yield) as a yellow oil.

Step 4: Preparation of (S)-1-(4-(2,3,6,9-tetramethyl-6H-thieno[3,2-f][1,2,4]triazolo [4,3-a][1,4]diazepin-4-yl)phenyl)piperidine-4-carbaldehyde. To a solution of (S)-4-(4-(4-(dimethoxymethyl)piperidin-1-yl)phenyl)-2,3,6,9-tetramethyl-6H-thieno[3,2-f][1,2,4]triazolo[4,3-a][1,4] diazepine (100 mg, 0.21 mmol, 1.00 equiv) in dichloromethane (1 mL) was added trifluoroacetic acid (768 mg, 6.73 mmol, 32 equiv). The mixture was stirred at 25° C. for 10 min. The mixture was concentrated under reduced pressure to give (S)-1-(4-(2,3,6,9-tetramethyl-6H-thieno[3,2-f][1,2,4]triazolo[4,3-a][1,4]diazepin-4-yl)phenyl)piperidine-4-carbaldehyde (110 mg, 96% yield, trifluoroacetate) as a yellow oil, which was used into the next step without further purification.

Step 5: Preparation of (S)-2,3,6,9-tetramethyl-4-(4-(4-((4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperazin-1-yl)methyl)piperidin-1-yl)phenyl)-6H-thieno[3,2-f][1,2,4]triazolo[4,3-a][1,4]diazepine. To a solution of (S)-1-(4-(2,3,6,9-tetramethyl-6H-thieno[3,2-f][1,2,4]triazolo[4,3-a][1,4]diazepin-4-yl)phenyl)piperidine-4-carbaldehyde (110 mg, 0.20 mmol, 1.00 equiv, trifluoroacetate) in dichloromethane (2 mL) was added sodium triacetoxyborohydride (128 mg, 0.60 mmol, 3.00 equiv) and (8R)-8-methyl-6-(5-(piperazin-1-yl)pyridine-2-yl)-7-(2,2,2-trifluoroethyl)-6,7,8,9-tetrahydro-2H-pyrazolo[4,3-f]isoquinoline (86 mg, 0.20 mmol, 1.00 equiv). The mixture was stirred at 25° C. for 12 h. The mixture was concentrated under reduced pressure to get the residue. The residue was purified by prep-TLC (dichloromethane/methanol=10/1) to get the crude product. The crude product was purified by prep-SFC (column: DAICEL CHIRALCEL OD (250 mm×30 mm×10 um); mobile phase: [$CO_2$—I/EtOH (0.1% $NH_3H_2O$)]; 40/60 isocratic elution mode) give a crude product, and then the crude product was further purified by prep-HPLC (column: Phenomenex Luna C18 150×25 mm×10 um; mobile phase: [water(FIACN]; gradient: 10%-40% B over 8 min) to afford (S)-2,3,6,9-tetramethyl-4-(4-(4-((4-(6-((6S,8R)-8-methyl-7-(2,2,2-trifluoroethyl)-6,7,8,9-tetrahydro-2H-pyrazolo[4,3-f]isoquinolin-6-yl)pyridin-3-yl)piperazin-1-yl)methyl)piperidin-1-yl)phenyl)-6H-thieno[3,2-f][1,2,4]triazolo[4,3-a][1,4]diazepine (1-27, 38.7 mg, 22% yield) as a yellow solid. $^1H$ NMR (400 MHz, $CD_3OD$) δ 12.98 (s, 1H), 8.14-8.02 (m, 2H), 7.33-7.19 (m, 4H), 7.10 (d, J=8.8 Hz, 1H), 6.89 (d, J=8.8 Hz, 2H), 6.82 (d, J=8.8 Hz, 1H), 5.00 (s, 1H), 4.12 (q, J=6.2 Hz, 1H), 3.82-3.76 (m, 2H), 3.59-3.45 (m, 3H), 3.30-3.20 (m, 3H), 3.15 (s, 4H), 3.07-2.95 (m, 2H), 2.89-2.82 (m, 1H), 2.77-2.69 (m, 2H), 2.57 (s, 3H), 2.47-2.46 (m, 1H), 2.40 (s, 3H), 2.18 (d, J=6.4 Hz, 2H), 1.84 (d, J=6.4 Hz, 3H), 1.81-1.75 (m, 2H), 1.70 (s, 3H), 1.25-1.13 (m, 2H), 1.09 (d, J=6.4 Hz, 3H). LC-MS: MS ($ES^+$): RT=1.289 min, m/z=848.6 $[M+H]^+$, LC-MS Method: 10.

Example 29—Synthesis of (S)—N-(4-(2-(4-(2-(4-bromophenyl)-6-hydroxybenzo[b]thiophene-3-carbonyl)phenoxy)ethoxy)butyl)-2-(4-(4-chlorophenyl)-2,3,9-trimethyl-6H-thieno[3,2-f][1,2,4]triazolo[4,3-a][1,4]diazepin-6-yl)acetamide (I-28)

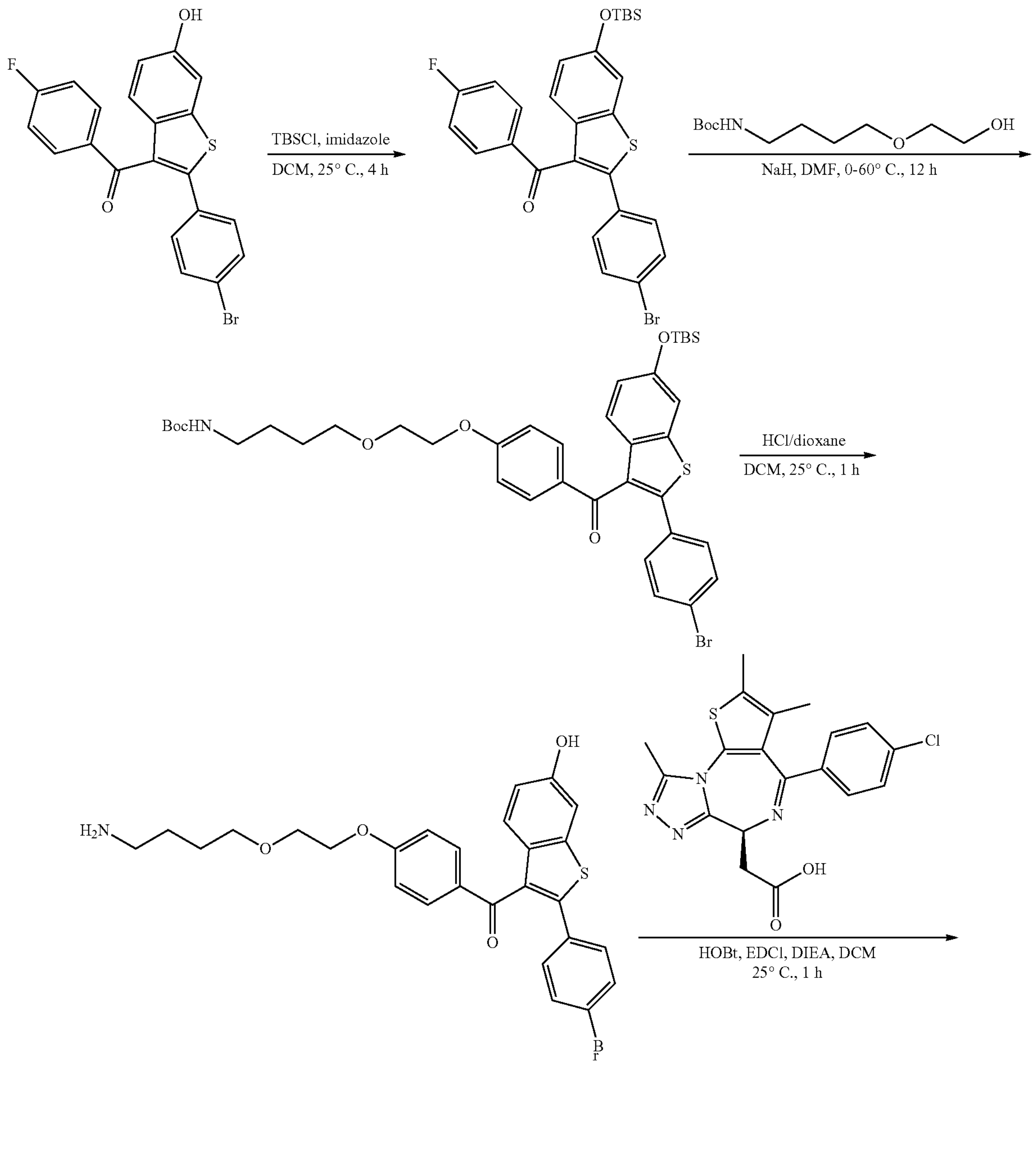

-continued

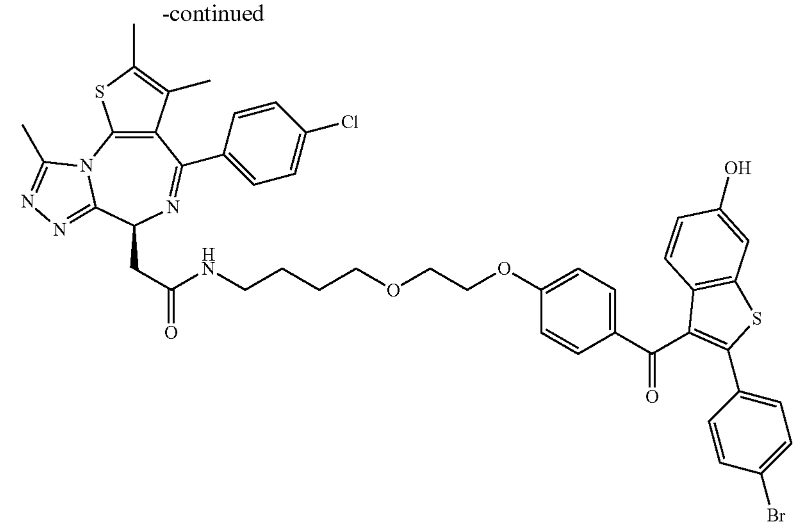

I-28

Step 1: Preparation of [2-(4-bromophenyl)-6-[tert-butyl (dimethyl)silyl]oxy-benzothiophen-3-yl]-(4-fluorophenyl) methanone. To a solution of [2-(4-bromophenyl)-6-hydroxy-benzothiophen-3-yl]-(4-fluorophenyl)methanone (350 mg, 819 mol, 1.0 equiv) in DCM (5 mL) was added TBSCl (185.19 mg, 1.23 mmol, 151 μL, 1.5 equiv) and IMIDAZOLE (66.92 mg, 983 mol, 1.2 equiv). The mixture was stirred at 25° C. for 4 h. The reaction mixture was partitioned between $H_2O$ 50 mL and EtOAc (50 mL×3). The organic phase was separated, dried over $Na_2SO_4$, filtered and concentrated under reduced pressure to give a residue. The residue was purified by column chromatography ($SiO_2$, Petroleum ether/Ethyl acetate=1/0 to 5/1) to afford [2-(4-bromophenyl)-6-[tert-butyl(dimethyl)silyl]oxy-benzothio phen-3-yl]-(4-fluorophenyl)methanone (300 mg, 67% yield) as a yellow solid.

Step 2: Preparation of tert-butyl N-[4-[2-[4-[2-(4-bromophenyl)-6-hydroxy-benzothiophene-3-carbonyl]phenoxy] ethoxy]butyl]carbamate. To a solution of tert-butyl N-[4-(2-hydroxyethoxy)butyl]carbamate (193.86 mg, 831 mol, 1.5 equiv) in THF (8 mL) was added NaH (44.32 mg, 1.11 mmol, 60% purity, 2 equiv) at 0° C. under $N_2$. The mixture was stirred at 0° C. for 1 h. Then added [2-(4-bromophenyl)-6-[tert-butyl(dimethyl)silyl]oxy-benzo thiophen-3-yl]-(4-fluorophenyl)methanone (300 mg, 554 mol, 1 equiv) to the mixture at 0° C. under $N_2$. The mixture was stirred at 60° C. for 11 h. The reaction mixture was quenched by addition $H_2O$ (2 mL) at 25° C., and then diluted with $H_2O$ (20 mL) and extracted with EtOAc (20 mL×3). The combined organic layers were dried over $Na_2SO_4$, filtered and concentrated under reduced pressure to give a residue. The residue was purified by column chromatography ($SiO_2$, Petroleum ether/Ethyl acetate=1/0 to 1/1) to afford tert-butyl N-[4-[2-[4-[2-(4-bromo phenyl)-6-hydroxy-benzothiophene-3-carbonyl]phenoxy]ethoxy]butyl]carbamate (210 mg, 59% yield) as a white solid.

Step 3: Preparation of [4-[2-(4-aminobutoxy)ethoxy]phenyl]-[2-(4-bromophenyl)-6-hydroxy-benzothiophen-3-yl] methanone. To a solution of tert-butyl N-[4-[2-[4-[2-(4-bromophenyl)-6-hydroxy-benzothiophene-3-carbonyl] phenoxy]ethoxy]butyl]carbamate (190 mg, 297 mol, 1 equiv) in DCM (6 mL) was added HCl/dioxane (4 M, 2 mL, 27 equiv). The mixture was stirred at 25° C. for 1 h. The reaction mixture was quenched by addition of $NaHCO_3$ (aq) (15 mL) at 25° C., and then diluted with $H_2O$ (50 mL) and extracted with EtOAc (50 mL×3). The combined organic layers were dried over $Na_2SO_4$, filtered and concentrated under reduced pressure to give a residue to afford [4-[2-(4-aminobutoxy) ethoxy]phenyl]-[2-(4-bromophenyl)-6-hydroxy-benzothiophen-3-yl]methanone (150 mg, 93% yield) as a yellow oil.

Step 4: Preparation of (S)—N-(4-(2-(4-(2-(4-bromophenyl)-6-hydroxybenzo [b]thiophene-3-carbonyl)phenoxy) ethoxy)butyl)-2-(4-(4-chlorophenyl)-2,3,9-trimethyl-6H-thieno[3,2-f][1,2,4]triazolo[4,3-a][1,4]diazepin-6-yl) acetamide. To a solution of [4-[2-(4-aminobutoxy)ethoxy] phenyl]-[2-(4-bromophenyl)-6-hydroxy-benzothiophen-3-yl]methanone (150 mg, 278 mol, 1 equiv) and (S)-2-(4-(4-chlorophenyl)-2,3,9-trimethyl-6H-thieno[3,2-f][1,2,4] triazolo[4,3-a][1,4]diazepin-6-yl)acetic acid (111.26 mg, 278 mol, 1 equiv) in DCM (5 mL) was added DIEA (143.48 mg, 1.11 mmol, 193 μL, 4.0 equiv), EDCI (159.61 mg, 832 mol, 3.0 equiv) and HOBt (56.25 mg, 416 mol, 1.5 equiv). The mixture was stirred at 25° C. for 1 h. The reaction mixture was partitioned between $H_2O$ 50 mL and EtOAc (50 mL×3). The organic phase was separated, dried over $Na_2SO_4$, filtered and concentrated under reduced pressure to give a residue. The residue was purified by prep-TLC ($SiO_2$, DCM:MeOH=10:1). The residue was purified by prep-HPLC (column: Phenomenex Luna C18 150×25 mm×10 um; mobile phase: [water(FA)-ACN]; gradient: 62%-92% B over 9 min) to afford (S)—N-(4-(2-(4-(2-(4-bromophenyl)-6-hydroxybenzo[b]thiophene-3-carbonyl)phenoxy) ethoxy) butyl)-2-(4-(4-chlorophenyl)-2,3,9-trimethyl-6H-thieno[3,2-f][1,2,4]triazolo[4,3-a][1,4]diazepin-6-yl)acetamide (I-28, 66.3 mg, 25% yield) as a yellow solid. $^1H$ NMR (400 MHz, DMSO-$d_6$) δ 10.13-9.69 (m, 1H), 8.17 (t, J=5.6 Hz, 1H), 7.66 (d, J=8.8 Hz, 2H), 7.54-7.49 (m, 2H), 7.47-7.43 (m, 2H), 7.42-7.37 (m, 3H), 7.32-7.26 (m, 3H), 6.93 (d, J=9.2 Hz, 2H), 6.88 (dd, J=2.4, 8.8 Hz, 1H), 4.49 (dd, J=6.0, 8.4 Hz, 1H), 4.16-4.05 (m, 2H), 3.71-3.62 (m, 2H), 3.44 (s, 2H), 3.27-3.17 (m, 2H), 3.15-3.04 (m, 2H), 2.58 (s, 3H), 2.38 (s, 3H), 1.59 (s, 3H), 1.55-1.43 (m, 4H). LC-MS: MS ($ES^+$): RT=1.494 min, m/z=924.4 [$M+H^+$]. LCMS Method: 50.

Example 30—Synthesis of (S)-(6-hydroxy-2-(4-hydroxyphenyl)benzo[b]thiophen-3-yl)(4-(2-(2-((4-(2,3,6,9-tetramethyl-6H-thieno[3,2-f][1,2,4]triazolo[4,3-a][1,4]diazepin-4-yl)phenyl)ethynyl)-7-azaspiro[3.5]nonan-7-yl)ethoxy)phenyl)methanone (I-29)

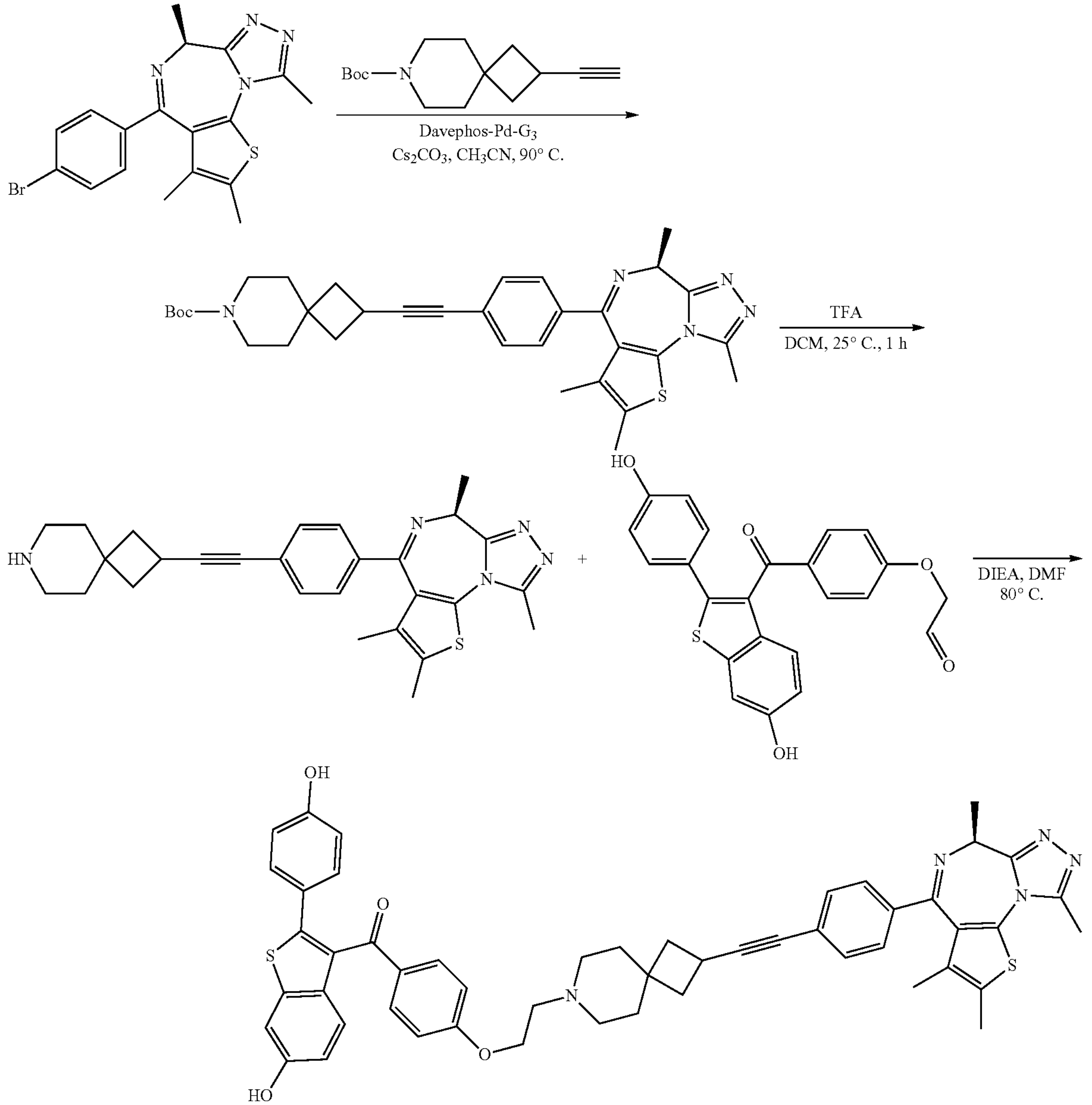

I-29

Step 1: Preparation of tert-butyl (S)-2-((4-(2,3,6,9-tetramethyl-6H-thieno[3,2-f][1,2,4]triazolo[4,3-a][1,4]diazepin-4-yl)phenyl)ethynyl)-7-azaspiro[3.5]nonane-7-carboxylate. To a solution of (S)-4-(4-bromophenyl)-2,3,6,9-tetramethyl-6H-thieno[3,2-f][1,2,4]triazolo[4,3-a][1,4]diazepine (500 mg, 1.25 mmol, 1 equiv) and tert-butyl 2-ethynyl-7-azaspiro[3.5]nonane-7-carboxylate (777 mg, 3.11 mmol, 2.5 equiv) in MeCN (15 mL) was added DavePhos Pd $G_3$ (95 mg, 125 mol, 0.1 equiv) and $Cs_2CO_3$ (812 mg, 2.49 mmol, 2.0 equiv) under $N_2$. The mixture was stirred at 90° C. for 2 h. The reaction mixture was concentrated under reduced pressure to give a residue. The residue was purified by column chromatography ($SiO_2$, Petroleum ether/Ethyl acetate=1/0 to 1/1) to afford tert-butyl (S)-2-((4-(2,3,6,9-tetramethyl-6H-thieno[3,2-f][1,2,4]triazolo[4,3-a][1,4]diazepin-4-yl)phenyl)ethynyl)-7-azaspiro[3.5]nonane-7-carboxylate (600 mg, 84% yield) as a white solid.

Step 2: Preparation of (S)-4-(4-((7-azaspiro[3.5]nonan-2-yl)ethynyl)phenyl)-2,3,6,9-tetramethyl-6H-thieno[3,2-f][1,2,4]triazolo[4,3-a][1,4]diazepine. To a solution of tert-butyl (S)-2-((4-(2,3,6,9-tetramethyl-6H-thieno[3,2-f][1,2,4]triazolo[4,3-a][1,4]diazepin-4-yl)phenyl)ethynyl)-7-azaspiro[3.5]nonane-7-carboxylate (300 mg, 526 mol, 1 equiv) in DCM (3 mL) was added TFA (1.54 g, 13.5 mmol, 1 mL, 26 equiv). The mixture was stirred at 25° C. for 1 h. The reaction mixture was quenched by addition $NaHCO_3$ (15 mL) at 25° C., and then diluted with $H_2O$ (20 mL) and extracted with DCM (20 mL×3). The combined organic layers were dried over $Na_2SO_4$, filtered and concentrated under reduced pressure to afford (S)-4-(4-((7-azaspiro[3.5]nonan-2-yl)ethynyl)phenyl)-2,3,6,9-tetramethyl-6H-thieno[3,2-f][1,2,4]tri azolo [4,3-a][1,4]diazepine (240 mg, 97% yield) as a yellow oil.

Step 3: Preparation of (S)-(6-hydroxy-2-(4-hydroxyphenyl)benzo[b]thiophen-3-yl)(4-(2-(2-((4-(2,3,6,9-tetramethyl-6H-thieno[3,2-f][1,2,4]triazolo[4,3-a][1,4]diazepin-4-yl)phenyl)ethynyl)-7-azaspiro[3.5]nonan-7-yl)ethoxy)phenyl)methanone. To a solution of [4-(2-bromoethoxy)phenyl]-[6-hydroxy-2-(4-hydroxyphenyl)benzothiophen-3-yl]methanone (60 mg, 127.84 mol, 1 equiv) and (S)-4-(4-((7-azaspiro[3.5]nonan-2-yl)ethynyl)phenyl)-2,3,6,9-tetramethyl-6H-thieno[3,2-f][1,2,4]triazolo[4,3-a][1,4]diazepine (60.04 mg, 127 mol, 1 equiv) in DMF (1.5 mL) was added DIEA (49.6 mg, 383 mol, 66.80 μL, 3.0 equiv). The mixture was stirred at 80° C. for 12 h. The reaction mixture was diluted with $H_2O$ (50 mL) and extracted with EtOAc (50 mL×3). The combined organic phases dried over $Na_2SO_4$, filtered and concentrated under reduced pressure to give a residue. The residue was purified by prep-TLC ($SiO_2$, DCM:MeOH=10:1) to give a residue. The residue was purified by prep-HPLC (column: Phenomenex Luna C18 150×25 mm×10 um; mobile phase: [water(FA)-ACN]; gradient: 30%-60% B over 9 min) to afford (S)-(6-hydroxy-2-(4-hydroxyphenyl) benzo[b]thiophen-3-yl)(4-(2-(2-((4-(2,3,6,9-tetramethyl-6H-thieno[3,2-f][1,2,4]triazolo[4,3-a][1,4]diazepin-4-yl)phenyl)ethynyl)-7-azaspiro[3.5]nonan-7-yl)ethoxy)phenyl)methanone (I-29, 33.6 mg, 29% yield) as a yellow solid. H NMR (400 MHz, DMSO-$d_6$) δ 9.87-9.62 (m, 2H), 8.14 (s, 1H), 7.65 (d, J=8.8 Hz, 2H), 7.40 (s, 3H), 7.33 (d, J=2.0 Hz, 1H), 7.24 (d, J=8.8 Hz, 1H), 7.17 (d, J=8.4 Hz, 2H), 6.92 (d, J=8.8 Hz, 2H), 6.84 (J=2.0, 8.8 Hz, 1H), 6.67 (d, J=8.4 Hz, 2H), 4.22 (q, J=6.8 Hz, 1H), 4.09 (t, J=5.6 Hz, 2H), 2.59 (s, 3H), 2.54 (s, 4H), 2.39 (s, 7H), 2.17 (t, J=10.0 Hz, 2H), 1.93-1.79 (m, 5H), 1.67-1.51 (m, 7H). LC-MS: MS ($ES^+$): RT=1.960 min, m/z=858.3 [$M+H^+$]. LCMS Method: 25.

Example 31—Synthesis of (S)-(6-hydroxy-2-(4-hydroxyphenyl)benzo[b]thiophen-3-yl)(4-(2-(2-(4-(2,3,9-trimethyl-6-(oxazol-2-ylmethyl)-6H-thieno[3,2-f][1,2,4]triazolo[4,3-a][1,4]diazepin-4-yl)benzyl)-7-azaspiro[3.5]nonan-7-yl)ethoxy)phenyl)methanone (I-30)

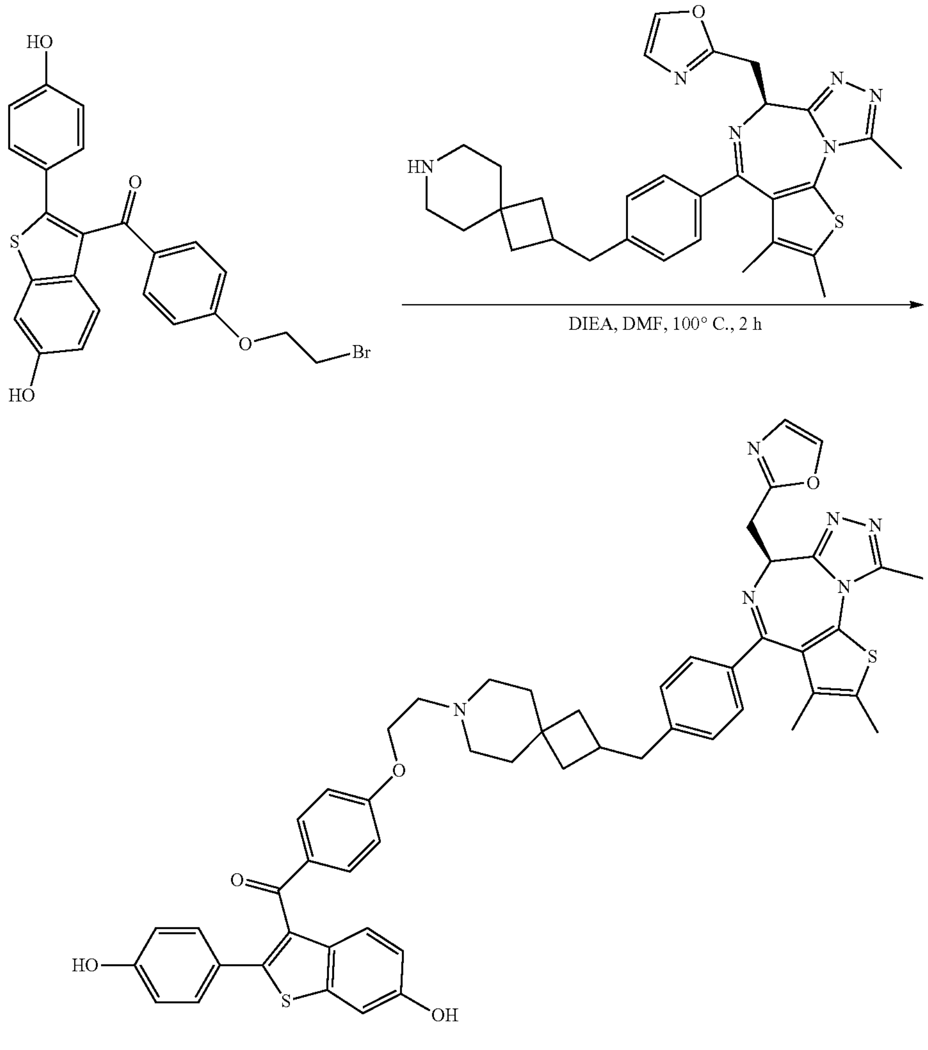

I-30

To a solution of [4-(2-bromoethoxy)phenyl]-[6-hydroxy-2-(4-hydroxyphenyl) benzothiophen-3-yl]methanone (40 mg, 85.22 μmol, 1 equiv) in DMF (1 mL) was added (S)-2-((4-(4-((7-azaspiro[3.5]nonan-2-yl)methyl)phenyl)-2,3,9-trimethyl-6H-thieno[3,2-f][1,2,4]triazolo[4,3-a][1,4]diazepin-6-yl)methyl)oxazole (44.89 mg, 85 mol, 1 equiv), DIEA (27.54 mg, 213 mol, 37 μL, 2.5 equiv). The mixture was stirred at 100° C. for 2 h. The reaction mixture was concentrated under reduced pressure to give a residue. The residue was purified by prep-HPLC (column: Welch Xtimate C18 150×25 mm×5 um; mobile phase: [water(FA)-ACN]; gradient: 23%-53% B over 10 min) to afford (S)-(6-hydroxy-2-(4-hydroxyphenyl) benzo[b]thiophen-3-yl)(4-(2-(2-(4-(2,3,9-trimethyl-6-(oxazol-2-ylmethyl)-6H-thieno[3,2-f][1,2,4]triazolo[4,3-a][1,4]diazepin-4-yl)benzyl)-7-azaspiro[3.5]nonan-7-yl)ethoxy)phenyl) methanone (I-30, 46.4 mg, 59% yield) as a yellow solid. $^1$H NMR (400 MHz, DMSO-$d_6$) δ 9.75 (d, J=18.4 Hz, 2H), 8.14 (s, 1H), 8.04 (s, 1H), 7.65 (d, J=8.8 Hz, 2H), 7.34 (d, J=2.4 Hz, 1H), 7.27-7.22 (m, 3H), 7.19-7.14 (m, 4H), 7.13 (s, 1H), 6.91 (d, J=8.8 Hz, 2H), 6.85 (dd, J=2.0, 8.8 Hz, 1H), 6.67 (d, J=8.8 Hz, 2H), 4.65 (t, J=7.6 Hz, 1H), 4.09 (d, J=5.2 Hz, 2H), 3.95-3.75 (m, 2H), 2.76-2.64 (m, 4H), 2.60 (s, 3H), 2.41 (s, 6H), 2.36-2.30 (m, 2H), 1.77 (t, J=9.6 Hz, 2H), 1.60 (s, 3H), 1.56-1.35 (m, 6H). LC-MS: MS (ES$^+$): RT=1.978 min, m/z=915.4 [M+H$^+$], LC-MS Method: 25.

Example 32—Synthesis of 4-(2-(4-((7-(2-(4-(6-hydroxy-2-(4-hydroxyphenyl)benzo [b]thiophene-3-carbonyl)phenoxy)ethyl)-7-azaspiro[3.5]nonan-2-yl) ethynyl)phenoxy)-5-(2-hydroxypropan-2-yl)phenyl)-6-methyl-1,6-dihydro-7H-pyrrolo[2,3-c]pyridin-7-one (I-31)

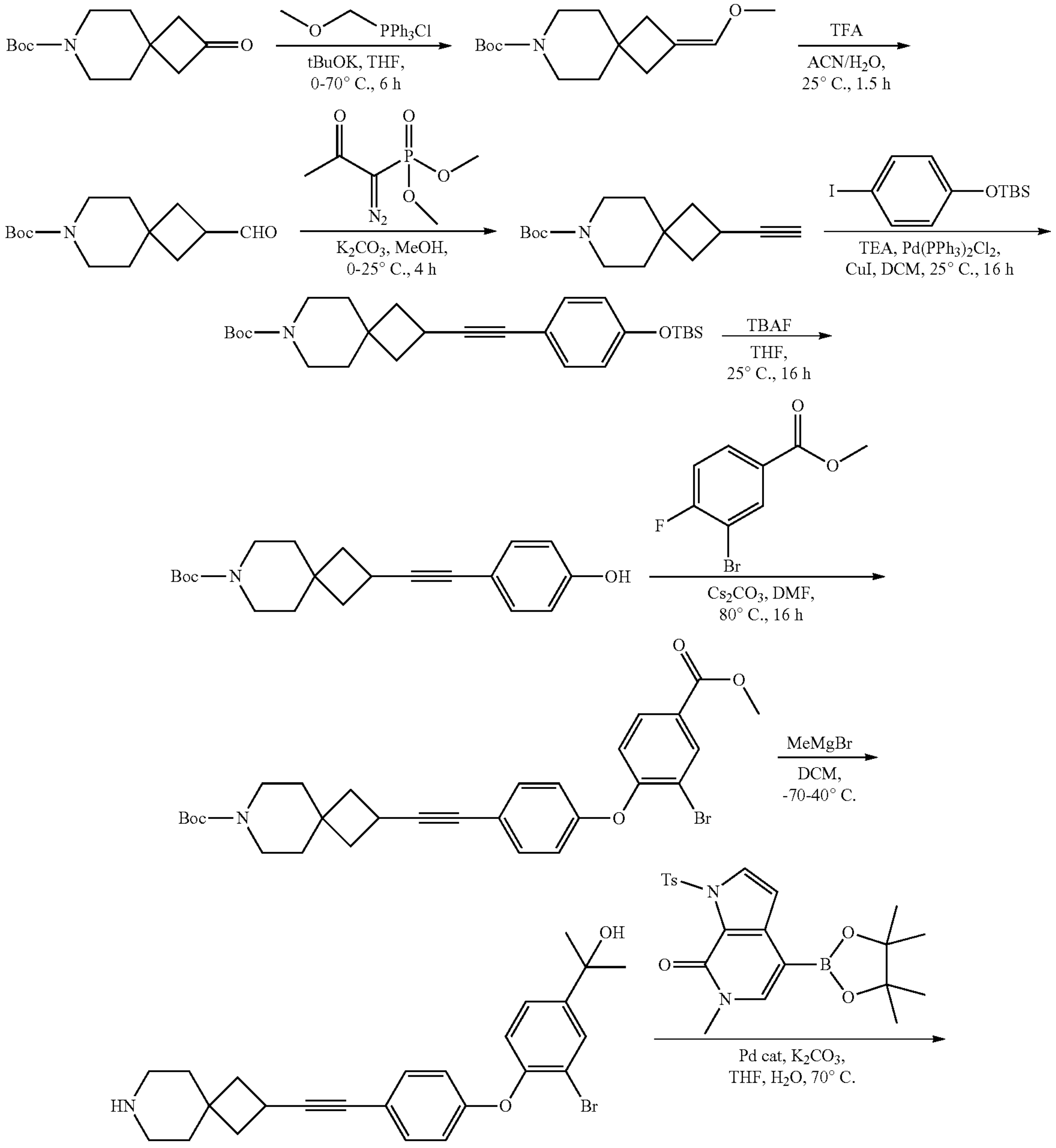

-continued

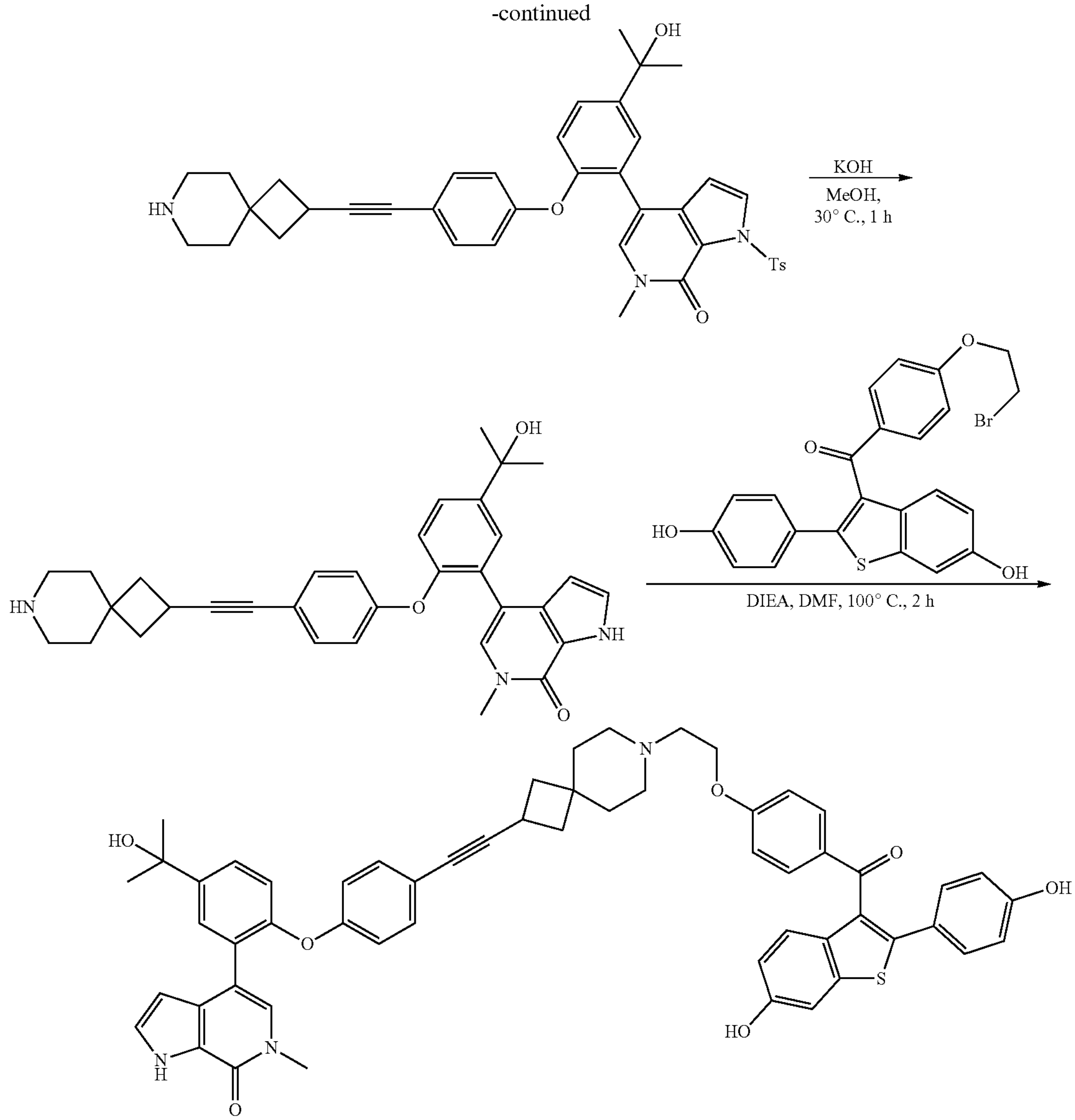

I-31

Step 1: Preparation of tert-butyl 2-(methoxymethylene)-7-azaspiro [3.5]nonane-7-carboxylate. A mixture of methoxymethyl(triphenyl)phosphonium chloride (35.81 g, 105 mmol, 2 equiv) in THE (400 ml) added tBuOK (9.38 g, 84 mmol, 1.6 equiv) in THF (70 ml) at 0° C. under $N_2$ atmosphere, and then the mixture was stirred at 20° C. for 3 h under $N_2$ atmosphere. Add tert-butyl 2-oxo-7-azaspiro [3.5]nonane-7-carboxylate (12.5 g, 52 mmol, 1 equiv) in THF (30 ml) to the reaction mixture, then the reaction was stirred at 70° C. for 3 hours. The reaction mixture was quenched by addition $H_2O$ (100 mL), and then extracted with EA (150 mLx3). The combined organic layers were washed with brine, dried over $Na_2SO_4$, filtered and concentrated under reduced pressure to give a residue. The residue was purified by column chromatography ($SiO_2$, Petroleum ether/Ethyl acetate=1/0 to 10/1). Compound tert-butyl 2-(methoxymethylene)-7-azaspiro [3.5]nonane-7-carboxylate (9.18 g, 65% yield) was obtained as a colorless oil.

Step 2: Preparation of tert-butyl 2-formyl-7-azaspiro [3.5] nonane-7-carboxylate. To a solution of tert-butyl 2-(methoxymethylene)-7-azaspiro [3.5]nonane-7-carboxylate (21.9 g, 81.9 mmol, 1 equiv) in ACN (520 ml) and $H_2O$ (130 ml) was added TFA (7.47 g, 65.5 mmol, 4.87 ml, 0.8 equiv). The mixture was stirred at 25° C. for 1.5 h. TLC (PE:EA=3:1) indicated Reactant 1 was consumed completely and one new spotformed. The mixture was adjusted to pH 9-10 with aqueous sodium bicarbonate solution, and then diluted extracted with EA (200 mLx3). The combined organic layers were washed with brine, dried over $Na_2SO_4$, filtered and concentrated under reduced pressure to give tert-butyl 2-formyl-7-azaspiro [3.5]nonane-7-carboxylate (20.4 g, 98% yield) as a yellow oil which was used in the next step without further purification.

Step 3: Preparation of tert-butyl 2-ethynyl-7-azaspiro [3.5]nonane-7-carboxylate. To a stirred mixture of tert-butyl 2-formyl-7-azaspiro[3.5]nonane-7-carboxylate (10 g, 39.5 mmol, 1 equiv) and $K_2CO_3$ (10.91 g, 78.9 mmol, 2 equiv) in MeOH (300 ml) was added 1-diazo-1-dimethoxyphosphoryl-propan-2-one (11.37 g, 59.2 mmol, 1.5 equiv) in portions at 0° C. The reaction mixture was stirred for 4 hours at 25°

C. TLC (PE:EA=5:1) indicated Reactant 1 was consumed completely and one new spot formed. The reaction mixture was concentrated under reduced pressure remove MeOH, and then diluted extracted with $H_2O$ (80 mL) and EA (80 mL×3). The combined organic layers were washed with brine, dried over $Na_2SO_4$, filtered and concentrated under reduced pressure to give a residue. The residue was purified by column chromatography ($SiO_2$, Petroleum ether/Ethyl acetate=1/0, 20/1) to afford tert-butyl 2-ethynyl-7-azaspiro [3.5]nonane-7-carboxylate (6.5 g, 66% yield) was obtained as a yellow oil.

Step 4: Preparation of tert-butyl 2-[2-[4-[tert-butyl (dimethyl) silyl]oxyphenyl]ethynyl]-7-azaspiro[3.5]nonane-7-carboxylate. To tert-butyl-(4-iodophenoxy)-dimethyl-silane (4.95 g, 14.81 mmol, 1 equiv) in DCM (60 ml) was added TEA (4.50 g, 44.42 mmol, 6.18 ml, 3 equiv) and $Pd(PPh_3)_2Cl_2$ (1.04 g, 1.48 mmol, 0.1 equiv) and CuI (423.02 mg, 2.22 mmol, 0.15 equiv), then, tert-butyl 2-ethynyl-7-azaspiro [3.5]nonane-7-carboxylate (4.8 g, 19.25 mmol, 1.3 equiv) in DCM (20 ml) was dropwise. The mixture was stirred at 25° C. for 16 h. The reaction mixture was quenched by addition $H_2O$ (30 mL), and then extracted with DCM (50 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate=1/0 to 20/1) to afford tert-butyl 2-[2-[4-[tert-butyl (dimethyl) silyl]oxyphenyl]ethynyl]-7-azaspiro [3.5]nonane-7-carboxylate (6.27 g, 92% yield) as a yellow oil.

Step 5: Preparation of tert-butyl 2-[2-(4-hydroxyphenyl) ethynyl]-7-azaspiro [3.5]nonane-7-carboxylate. To a solution of tert-butyl 2-[2-[4-[tert-butyl (dimethyl) silyl]oxyphenyl]ethynyl]-7-azaspiro[3.5]nonane-7-carboxylate (6.27 g, 13.76 mmol, 1 equiv) in THF (60 ml) was added TBAF (1 M, 20.64 ml, 1.5 equiv). The mixture was stirred at 25° C. for 16 h. The reaction mixture was quenched by addition $H_2O$ (20 mL) and extracted with EtOAc (30 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate=1/0 to 5/1) to afford tert-butyl 2-[2-(4-hydroxyphenyl) ethynyl]-7-azaspiro [3.5]nonane-7-carboxylate (4.38 g, 93% yield) as a colorless oil.

Step 6: Preparation of Compound tert-butyl 2-[2-[4-(2-bromo-4-methoxy carbonyl-phenoxy) phenyl]ethynyl]-7-azaspiro[3.5]nonane-7-carboxylate. To a solution of tert-butyl 2-[2-(4-hydroxyphenyl) ethynyl]-7-azaspiro [3.5] nonane-7-carboxylate (4.38 g, 12.83 mmol, 1 equiv) in DMF (100 ml) was added $Cs_2CO_3$ (12.54 g, 38.48 mmol, 3 equiv) and methyl 3-bromo-4-fluoro-benzoate (3.89 g, 16.7 mmol, 1.3 equiv). The mixture was stirred at 80° C. for 16 h. The reaction mixture was quenched by addition $H_2O$ (50 mL), and extracted with EA (100 ml×3). The combined organic layers were washed with brine, dried over $Na_2SO_4$, filtered and concentrated under reduced pressure to give a residue. The residue was purified by column chromatography ($SiO_2$, Petroleum ether/Ethyl acetate=1/0 to 5/1). Compound tert-butyl 2-[2-[4-(2-bromo-4-methoxycarbonyl-phenoxy) phenyl]ethynyl]-7-azaspiro[3.5]nonane-7-carboxylate (6.52 g, 91% yield) was obtained as a white solid.

Step 7: Preparation of 2-[4-[4-[2-(7-azaspiro [3.5]nonan-2-yl)ethynyl]phenoxy]-3-bromo-phenyl]propan-2-ol. A mixture of tert-butyl 2-[2-[4-(2-bromo-4-methoxycarbonyl-phenoxy)phenyl]ethynyl]-7-azaspiro[3.5]nonane-7-carboxylate (3 g, 5.41 mmol, 1 equiv) in DCM (100 ml) was degassed and purged with $N_2$ three times, and then the mixture was added MeMgBr (3 M, 9.02 ml, 5 equiv) at −70° C. dropwise under $N_2$ atmosphere. The resulting mixture was stirred at 40° C. for 16 hours. The reaction mixture was quenched by adding to $NH_4Cl$ (aq) (200 mL) at 0-5° C. under $N_2$, and then extracted with DCM/MeOH (10:1, 100 mL×3). The organic layer was dried over $Na_2SO_4$, filtered and concentrated under reduced pressure to afford 2-[4-[4-[2-(7-azaspiro [3.5]nonan-2-yl)ethynyl]phenoxy]-3-bromo-phenyl]propan-2-ol (2.1 g, 85% yield) as a yellow gum.

Step 8: Preparation of 4-[2-[4-[2-(7-azaspiro[3.5]nonan-2-yl)ethynyl]phenoxy]-5-(1-hydroxy-1-methyl-ethyl)phenyl]-6-methyl-1-(p-tolylsulfonyl)pyrrolo[2,3pyridinedin-7-one. A mixture of 2-[4-[4-[2-(7-azaspiro[3.5]nonan-2-yl) ethynyl]phenoxy]-3-bromo-phenyl]propan-2-ol (2.1 g, 4.62 mmol, 1 equiv), 6-methyl-1-(p-tolylsulfonyl)-4-(4,4,5,5-tetramethyl-1,3,2-dioxaborolan-2-yl)pyrrolo[2,3pyridinedin-7-one (1.98 g, 4.62 mmol, 1 equiv), $K_2CO_3$ (1.41 g, 10.17 mmol, 2.2 equiv), [2-(2-aminophenyl)phenyl]palladium[bis (1-adamantyl)-butyl-phosphane]methanesulfonate (336.57 mg, 462 mol, 0.1 equiv) in THE (50 ml) and $H_2O$ (5 ml) was degassed and purged with $N_2$ three times, and then the mixture was stirred at 70° C. for 16 hr under $N_2$ atmosphere. The mixture was concentrated to give crude 4-[2-[4-[2-(7-azaspiro[3.5]nonan-2-yl)ethynyl]phenoxy]-5-(1-hydroxy-1-methyl-ethyl)phenyl]-6-methyl-1-(p-tolylsulfonyl)pyrrolo [2,3pyridinedin-7-one (2.7 g, 4.00 mmol, 86% yield) as a yellow oil and was used without further purification.

Step 9: Preparation of 4-[2-[4-[2-(7-azaspiro [3.5]nonan-2-yl)ethynyl]phenoxy]-5-(1-hydroxy-1-methyl-ethyl) phenyl]-6-methyl-1H-pyrrolo[2,3pyridinedin-7-one. To a solution of 4-[2-[4-[2-(7-azaspiro[3.5]nonan-2-yl)ethynyl] phenoxy]-5-(1-hydroxy-1-methyl-ethyl)phenyl]-6-methyl-1-(p-tolylsulfonyl)pyrrolo[2,3pyridinedin-7-one (2.7 g, 4.00 mmol, 1 equiv) in MeOH (120 ml) was added KOH (4.93 g, 87.89 mmol, 22 equiv). The mixture was stirred at 30° C. for 1 h. The reaction mixture was concentrated under reduced pressure to give a residue. The residue was purified by prep-HPLC (column: Phenomenex Luna C18 (250×70 mm×10 um); mobile phase: [water(FIACN]; gradient: 20%-50% B over 20 min) to give 4-[2-[4-[2-(7-azaspiro [3.5] nonan-2-yl) ethynyl]phenoxy]-5-(1-hydroxy-1-methyl-ethyl) phenyl]-6-methyl-1H-pyrrolo[pyridineyridin-7-one (1 g, 47% yield) as a white solid.

Step 10: Preparation of 4-(2-(4-((7-(2-(4-(6-hydroxy-2-(4-hydroxyphenyl) benzo[b]thiophene-3-carbonyl)phenoxy)ethyl)-7-azaspiro[3.5]nonan-2-yl)ethynyl) phenoxy)-5-(2-hydroxypropan-2-yl)phenyl)-6-methyl-1,6-dihydro-7H-pyrrolo[2,3-c]pyridin-7-one. To a solution of [4-(2-bromoethoxy)phenyl]-[6-hydroxy-2-(4-hydroxy-phenyl) benzothiophen-3-yl]methanone (40 mg, 85.22 mol, 1 equiv) and 4-[2-[4-[2-(7-azaspiro[3.5]nonan-2-yl)ethynyl]phenoxy]-5-(1-hydroxy-1-methyl-ethyl)phenyl]-6-methyl-1H-pyrrolo[2,3-c]pyridin-7-one (44.46 mg, 85.2 mol, 1 equiv) in DMF (1 ml) was added DIEA (39.98 mg, 309 mol, 54 L, 3.63 equiv). The mixture was stirred at 100° C. for 2 h. The reaction mixture was concentrated under reduced pressure to give a residue. The residue was purified by prep-HPLC (column: Waters Xbridge 150×25 mm×5 um; mobile phase: [water ($NH_4HCO_3$)-ACN]; gradient: 48-78% B over 9 min) to provide 4-(2-(4-((7-(2-(4-(6-hydroxy-2-(4-hydroxyphenyl)benzo[b]thiophene-3-carbonyl)phenoxy)ethyl)-7-azaspiro[3.5]nonan-2-yl)ethynyl)phenoxy)-5-(2-hydroxypropan-2-yl)phenyl)-6-methyl-1,6-dihydro-7H-pyrrolo[2,3-c]pyridin-7-one (I-31, 19 mg, 24% yield) as a brown gum. $^1H$ NMR (400 MHz, DMSO-$d_6$) δ=12.03-11.94 (m, 1H), 9.85-9.62 (m, 2H), 7.67-7.59 (m, 3H), 7.47 (dd, J=2.4, 8.5 Hz, 1H), 7.33 (d, J=2.4 Hz, 1H), 7.27-7.14 (m, 7H), 7.02 (d, J=8.4 Hz, 1H), 6.94-6.88 (m, 2H), 6.86-6.81 (m, 1H), 6.77-6.71 (m, 2H), 6.70-6.64 (m, 2H), 6.22-6.16 (m, 1H), 5.08 (s, 1H), 4.06 (br t, J=6.0 Hz, 2H), 3.51-3.46 (m, 3H), 3.29-3.27 (m, 3H), 3.19-3.13 (m, 1H), 2.60-2.58 (m, 1H), 2.31-2.23 (m, 2H), 2.17-2.08 (m, 2H), 1.83-1.74 (m, 2H), 1.57-1.50 (m, 4H), 1.49-1.44 (m, 6H). LC-MS: MS ($ES^+$): RT=2.057 min, m/z=910.6 [$M+H^+$], LC-MS Method: 25.
Example 33—Synthesis of 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl) phenoxy)ethoxy) propyl)pyrrolidin-3-yl)oxy) phenyl)-6,7-dihydro-5H-benzo[7]annulene-3-carboxylic acid (I-32)
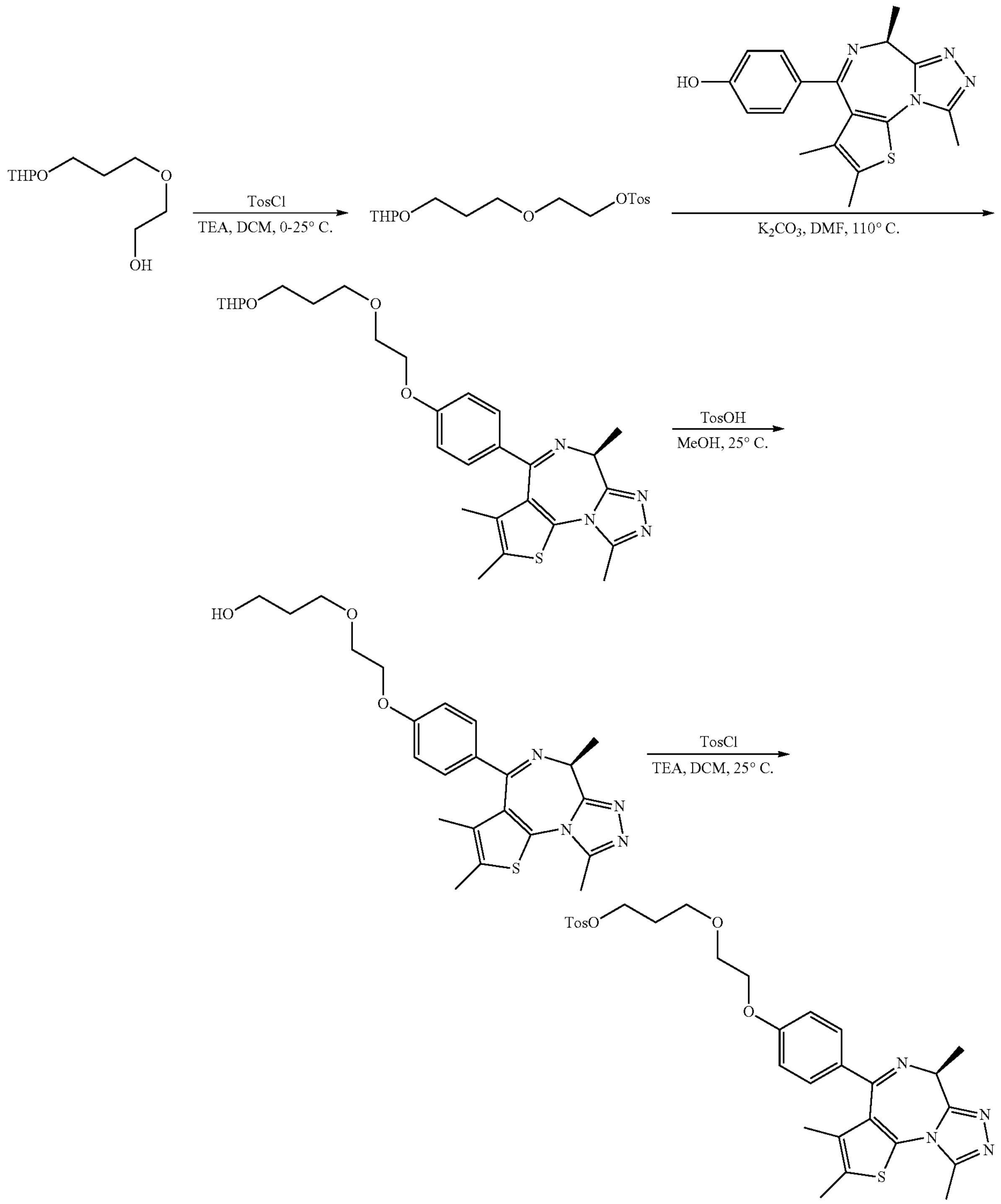

-continued

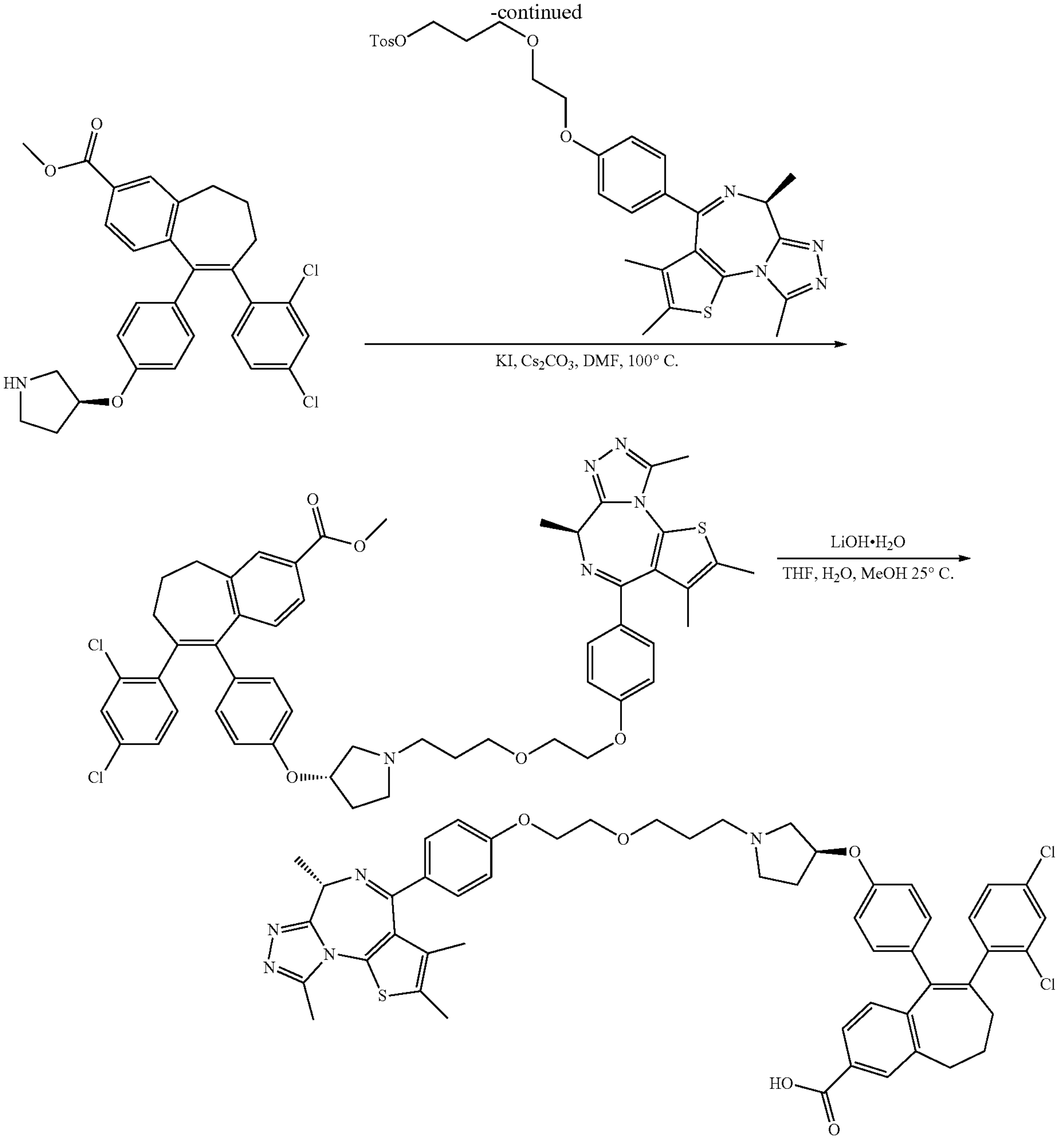

I-32

Step 1: Preparation of 2-(3-((tetrahydro-2H-pyran-2-yl)oxy)propoxy)ethyl 4-methylbenzenesulfonate. To a solution of 2-(3-((tetrahydro-2H-pyran-2-yl)oxy)propoxy) ethan-1-01 (2.70 g, 13.22 mmol, 1.00 equiv) in dichloromethane (30 mL) was added triethylamine (4.01 g, 39.65 mmol, 3.00 equiv). Then was added p-toluenesulfonyl chloride (2.52 g, 13.22 mmol, 1.00 equiv) at 0° C., and the mixture was stirred at 25° C. for 1 h. The reaction mixture was concentrated under reduced pressure to afford a residue. The residue was purified by column chromatography (Silica gel, Petroleum ether/Ethyl acetate=1/0 to 1/1) to afford 2-(3-((tetrahydro-2H-pyran-2-yl)oxy)propoxy)ethyl 4-methylbenzenesulfonate (500 mg, 10% yield) as a yellow oil.

Step 2: Preparation of (6S)-2,3,6,9-tetramethyl-4-(4-(2-(3-((tetrahydro-2H-pyran-2-yl)oxy)propoxy)ethoxy)phenyl)-6H-thieno[3,2-f][1,2,4]triazolo[4,3-a][1,4]diazepine. A mixture of 2-(3-((tetrahydro-2H-pyran-2-yl)oxy)propoxy) ethyl 4-methylbenzenesulfonate (444 mg, 1.24 mmol, 1.50 equiv), (S)-4-(2,3,6,9-tetramethyl-6H-thieno[3,2-f][1,2,4]triazolo[4,3-a][1,4]diazepin-4-yl)phenol (280 mg, 0.83 mmol, 1.00 equiv), potassium carbonate (343 mg, 2.48 mmol, 3.00 equiv) in N,N-dimethylformamide (5 mL) was stirred at 110° C. for 1 h. The reaction mixture was quenched by the addition of water (20 mL), and then extracted with ethyl acetate (10 mL×3). The combined organic layers were washed with brine (30 mL), dried over anhydrous sodium sulfate, filtered and concentrated under reduced pressure to give a residue. The residue was purified by prep-TLC (dichloromethane/methanol=10:1, $R_f$=0.45) to afford (6S)-2,3,6,9-tetramethyl-4-(4-(2-(3-((tetrahydro-2H-pyran-2-yl)

oxy)propoxy)ethoxy)phenyl)-6H-thieno[3,2-f][1,2,4]triazolo[4,3-a][1,4]diazepine (210 mg, 48% yield) as a yellow solid.

Step 3: Preparation of (S)-3-(2-(4-(2,3,6,9-tetramethyl-6H-thieno[3,2-f][1,2,4]triazolo[4,3-a][1,4]diazepin-4-yl)phenoxy)ethoxy)propan-1-ol. To a solution of (6S)-2,3,6,9-tetramethyl-4-(4-(2-(3-((tetrahydro-2H-pyran-2-yl)oxy)propoxy)ethoxy)phenyl)-6H-thieno[3,2-f][1,2,4]triazolo[4,3-a][1,4]diazepine (210 mg, 0.40 mmol, 1.00 equiv) in methanol (2 mL) was added tosyl chloride (6 mg, 0.04 mmol, 0.10 equiv) and the mixture was stirred at 25° C. for 0.5 h. The reaction mixture was filtered and concentrated under reduced pressure to give a residue. The residue was purified by prep-TLC (dichloromethane/methanol=10:1) to afford (S)-3-(2-(4-(2,3,6,9-tetramethyl-6H-thieno[3,2-f][1,2,4]triazolo[4,3-a][1,4]diazepin-4-yl)phenoxy)ethoxy)propan-1-ol (170 mg, 96% yield) as a yellow solid.

Step 4: Preparation of (S)-3-(2-(4-(2,3,6,9-tetramethyl-6H-thieno[3,2-f][1,2,4]triazolo[4,3-a][1,4]diazepin-4-yl)phenoxy)ethoxy)propyl 4-methylbenzene sulfonate. To a solution of (S)-3-(2-(4-(2,3,6,9-tetramethyl-6H-thieno[3,2-f][1,2,4]triazolo[4,3-a][1,4]diazepin-4-yl)phenoxy)ethoxy)propan-1-ol (160 mg, 0.36 mmol, 1.00 equiv), p-toluenesulfonyl chloride (138 mg, 0.73 mmol, 2.00 equiv) in dichloromethane (2 mL) was added triethylamine (147 mg, 1.45 mmol, 4.00 equiv) and the reaction mixture was stirred at 25° C. for 1 h. The reaction mixture was filtered and concentrated under reduced pressure to give a residue. The residue was purified by prep-TLC (dichloromethane/methanol=10:1) to afford (S)-3-(2-(4-(2,3,6,9-tetramethyl-6H-thieno[3,2-f][1,2,4]triazolo[4,3-a][1,4]diazepin-4-yl)phenoxy)ethoxy) propyl 4-methylbenzenesulfonate (145 mg, 67% yield) as a yellow oil.

Step 5: Preparation of methyl 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy) ethoxy) propyl)pyrrolidin-3-yl)oxy)phenyl)-6,7-dihydro-5H-benzo[7]annulene-3-carboxylate. A mixture of methyl (S)-8-(2,4-dichlorophenyl)-9-(4-(pyrrolidin-3-yloxy)phenyl)-6,7-dihydro-5H-benzo[7]annulene-3-carboxylate (51 mg, 0.10 mmol, 1.20 equiv), (S)-3-(2-(4-(2,3,6,9-tetramethyl-6H-thieno[3,2-f][1,2,4]triazolo[4,3-a][1,4]diazepin-4-yl)phenoxy)ethoxy)propyl 4-methylbenzenesulfonate (50 mg, 0.08 mmol, 1.00 equiv), potassium iodide (13 mg, 0.8 mmol, 1.00 equiv), cesium carbonate (82 mg, 0.25 mmol, 3.00 equiv) in N,N-dimethylformamide (1 mL) was stirred at 100° C. for 1 h. The reaction mixture was quenched by water (10 mL), and then extracted with ethyl acetate (5 mL×3). The combined organic layers were washed with brine (30 mL), dried over anhydrous sodium sulfate, filtered and concentrated under reduced pressure to give a residue. The residue was purified by prep-HPLC [column: Phenomenex Luna C18 150×25 mm×10 um; mobile phase: [water(FA)-ACN]; gradient: 35%-65% B over 10 min] to afford methyl 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy)ethoxy)propyl)pyrrolidin-3-yl)oxy)phenyl)-6,7-dihydro-5H-benzo[7]annulene-3-carboxylate (50 mg, 63% yield) as a yellow oil.

Step 6: Preparation of 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy)ethoxy) propyl)pyrrolidin-3-yl)oxy)phenyl)-6,7-dihydro-5H-benzo[7]annulene-3-carboxylic acid. To a solution of methyl 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy) ethoxy)propyl)pyrrolidin-3-yl)oxy)phenyl)-6,7-dihydro-5H-benzo[7]annulene-3-carboxylate (50 mg, 0.05 mmol, 1.00 equiv) in tetrahydrofuran (0.2 mL), methanol (0.2 mL) and water (0.2 mL) was added lithium hydroxide (6 mg, 0.16 mmol, 3.00 equiv) and the mixture was stirred at 25° C. for 1 h. The reaction mixture was quenched by aqueous hydrochloric acid (1 M, 5 mL), and then filtered and concentrated under reduced pressure to give a residue. The residue was purified by prep-HPLC [column: Welch Xtimate C18 150×25 mm×5 um; mobile phase: [water(FA)-ACN]; gradient: 28%-58% B over 10 min] to afford 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy) ethoxy)propyl)pyrrolidin-3-yl)oxy)phenyl)-6,7-dihydro-5H-benzo[7]annulene-3-carboxylic acid (I-32, 16.82 mg, 32% yield) as a white solid. $^1$H NMR (400 MHz, $CDCl_3$) δ 7.98 (s, 1H), 7.82 (d, J=8.4 Hz, 1H), 7.43 (d, J=8.4 Hz, 2H), 7.39-7.34 (m, 1H), 7.09-6.97 (m, 2H), 6.92 (d, J=8.4 Hz, 1H), 6.88 (d, J=8.8 Hz, 2H), 6.76 (d, J=8.8 Hz, 2H), 6.57-6.51 (m, 2H), 4.93-4.74 (m, 1H), 4.21-4.04 (m, 3H), 3.78 (t, J=4.4 Hz, 2H), 3.62 (t, J=5.6 Hz, 3H), 3.44-3.21 (m, 1H), 3.09-2.85 (m, 6H), 2.68 (s, 3H), 2.41 (s, 3H), 2.32-2.24 (m, 4H), 2.09 (s, 3H), 1.99-1.94 (m, 4H), 1.71 (s, 3H). LCMS: MS ($ES^+$): RT=2.014 min, m/z=916.6 $[M+H]^+$; LC-MS Method: 25.

Example 34—Synthesis of 6-((6S,8R)-8-methyl-7-(2,2,2-trifluoroethyl)-6,7,8,9-tetrahydro-2H-pyrazolo[4,3-f]isoquinolin-6-yl)-N-(1-(3-(2-(2-(4-((S)-2,3,6,9-tetramethyl-6H-thieno[3,2-f][1,2,4]triazolo[4,3-a][1,4]diazepin-4-yl)phenoxy)ethoxy)ethoxy)propyl)azetidin-3-yl)pyridin-3-amine (I-33)

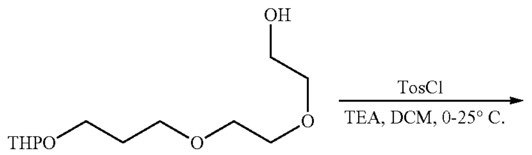

-continued

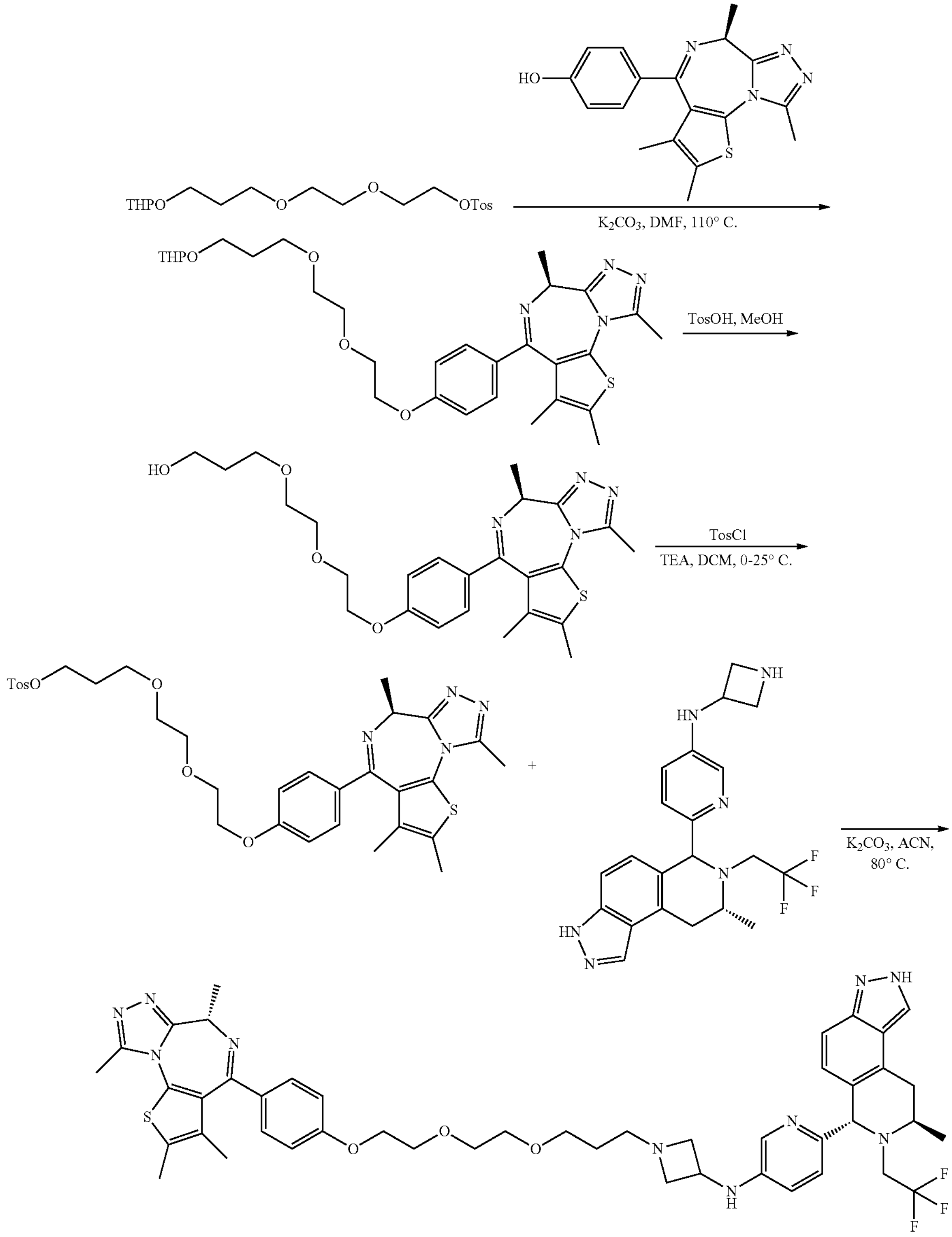

I-33

Step 1: Preparation of 2-[2-(3-tetrahydropyran-2-yloxypropoxy)ethoxy]ethyl 4-methylbenzenesulfonate. To a solution of 2-(2-(3-((tetrahydro-2H-pyran-2-yl)oxy)propoxy)ethoxy) ethan-1-ol (1.00 g, 4.03 mmol, 1.00 equiv) in dichloromethane (10 mL) was added triethylamine (1.22 g, 12.08 mmol, 3.00 equiv) and p-toluenesulfonyl chloride (1.54 g, 8.05 mmol, 2.00 equiv) at 0° C. The mixture was stirred at 25° C. for 1 h. The reaction mixture was concentrated under reduced pressure to give a residue. The residue was purified by silica gel column chromatography (petroleum ether/ethyl acetate=10:1 to 1:1) to afford 2-[2-(3-tetra hydropyran-2-yloxypropoxy)ethoxy]ethyl 4-methylbenzenesulfonate (1.50 g, 92% yield) as a yellow oil.

Step 2: Preparation of (6S)-2,3,6,9-tetramethyl-4-(4-(2-(2-(2-((tetrahydro-2H-pyran-2-yl)oxy)ethoxy)ethoxy) ethoxy)phenyl)-6H-thieno[3,2-f][1,2,4]triazolo[4,3-a][1,4] diazepine. To a solution of 2-[2-(3-tetrahydropyran-2-yloxypropoxy)ethoxy]ethyl 4-methylbenzenesulfonate (309 mg, 0.76 mmol, 2.00 equiv) and (S)-4-(2,3,6,9-tetramethyl-6H-thieno[3,2-f][1,2,4]triazolo[4,3-a][1,4]diazepin-4-yl) phenol (130 mg, 0.38 mmol, 1.00 equiv) in N,N-dimethylformamide (5 mL) was added potassium carbonate (159 mg, 1.15 mmol, 3.00 equiv). The mixture was stirred at 110° C. for 1 h. Ethyl acetate (20 mL) and water (30 mL) were added and the organic layer collected. The aqueous layer was extracted with ethyl acetate (30 mL×3). The combined organic layers were washed with brine (30 mL×3), dried over anhydrous sodium sulfate, filtered and concentrated under reduced pressure to get the residue. The residue was purified by silica gel column chromatography (DCM/methanol=100:1 to 10:1) to afford (6S)-2,3,6,9-tetramethyl-4-(4-(2-(2-(2-((tetrahydro-2H-pyran-2-yl)oxy)ethoxy) ethoxy) ethoxy)phenyl)-6H-thieno[3,2-f][1,2,4]triazolo[4,3-a][1,4] diazepine (216 mg, 98% yield) as a yellow oil.

Step 3: Preparation of (S)-3-(2-(2-(4-(2,3,6,9-tetramethyl-6H-thieno[3,2-f][1,2,4]triazolo[4,3-a][1,4]diazepin-4-yl) phenoxy)ethoxy)ethoxy)propan-1-ol. To a solution of (6S)-2,3,6,9-tetramethyl-4-(4-(2-(2-(2-((tetrahydro-2H-pyran-2-yl)oxy)ethoxy) ethoxy)ethoxy)phenyl)-6H-thieno[3,2-f][1,2,4]triazolo[4,3-a][1,4]diazepine (216 mg, 0.37 mmol, 1.00 equiv) in methanol (2 mL) was added p-toluenesulfonic acid (6 mg, 0.03 mmol, 0.10 equiv) and the mixture was stirred at 25° C. for 0.5 h. The reaction mixture was concentrated under reduced pressure to give a residue. The crude product was purified by prep-TLC (DCM:methanol=10:1) to afford (S)-3-(2-(2-(4-(2,3,6,9-tetramethyl-6H-thieno[3,2-f][1,2,4] triazolo[4,3-a][1,4]diazepin-4-yl)phenoxy)ethoxy)ethoxy) propan-1-ol (140 mg, 76% yield) as a yellow oil.

Step 4: Preparation of (S)-3-(2-(2-(4-(2,3,6,9-tetramethyl-6H-thieno[3,2-f][1,2,4]triazolo[4,3-a][1,4]diazepin-4-yl) phenoxy)ethoxy)ethoxy)propyl 4-methyl benzenesulfonate. To a solution of (S)-3-(2-(2-(4-(2,3,6,9-tetramethyl-6H-thieno[3,2-f][1,2,4]triazolo[4,3-a][1,4]diazepin-4-yl)phenoxy)ethoxy)ethoxy)propan-1-ol (140 mg, 0.28 mmol, 1.00 equiv) in dichloromethane (2 mL) was added triethylamine (87 mg, 0.86 mmol, 3.00 equiv). Then p-toluenesulfonyl chloride (82 mg, 0.43 mmol, 1.50 equiv) was added at 0° C. The mixture was stirred at 25° C. for 1 h. The reaction mixture was concentrated under reduced pressure to give a residue. The crude product was purified by prep-TLC (DCM/methanol=10:1) to afford (S)-3-(2-(2-(4-(2,3,6,9-tetramethyl-6H-thieno[3,2-f][1,2,4]triazolo[4,3-a][1,4]diazepin-4-yl)phenoxy)ethoxy)ethoxy)propyl 4-methylbenzenesulfonate (130 mg, 70% yield) as a yellow oil.

Step 5: Preparation of 6-((6S,8R)-8-methyl-7-(2,2,2-trifluoroethyl)-6,7,8,9-tetrahydro-2H-pyrazolo[4,3-f]isoquinolin-6-yl)-N-(1-(3-(2-(2-(4-((S)-2,3,6,9-tetramethyl-6H-thieno[3,2-f][1,2,4]triazolo[4,3-a][1,4]diazepin-4-yl) phenoxy)ethoxy)ethoxy) propyl)azetidin-3-yl)pyridin-3-amine. To a solution of (S)-3-(2-(2-(4-(2,3,6,9-tetramethyl-6H-thieno[3,2-f][1,2,4]triazolo[4,3-a][1,4]diazepin-4-yl) phenoxy)ethoxy)ethoxy)propyl 4-methyl-benzenesulfonate (118 mg, 0.18 mmol, 1.40 equiv) and N-(azetidin-3-yl)-6-[(6S,8R)-8-methyl-7-(2,2,2-trifluoroethyl)-3,6,8,9-tetrahydropyrazolo[4,3-f]isoquinolin-6-yl]pyridin-3-amine (70 mg, 0.13 mmol, 1.00 equiv, trifluoroacetate) in acetonitrile (2 mL) was added potassium carbonate (54 mg, 0.39 mmol, 3.00 equiv) and potassium iodide (43 mg, 0.26 mmol, 2.00 equiv). The mixture was stirred at 80° C. for 1 h. The mixture was concentrated under reduced pressure to give a residue. The residue was purified by prep-TLC (dichloromethane:methanol=10:1). The obtained residue was further purified by preparative SFC (Column: Chiralcel OD-3 50×4.6 mm×3 μm; Mobile phase: Phase A for $CO_2$, and Phase B for IPA/acetonitrile (0.05% DEA); Gradient elution: 40% IPA+ acetonitrile (0.05% DEA) in $CO_2$). The obtained residue was further purified by prep-HPLC (column: Phenomenex Luna C18 150×25 mm×10 um; mobile phase: [water (formic acid)-acetonitrile]; gradient: 10%-40% B over 10 min) to give 6-((6S,8R)-8-methyl-7-(2,2,2-trifluoroethyl)-6,7,8,9-tetrahydro-2H-pyrazolo [4,3-f]isoquinolin-6-yl)-N-(1-(3-(2-(2-(4-((S)-2,3,6,9-tetramethyl-6H-thieno [3,2-f][1,2,4]triazolo[4,3-a][1,4]diazepin-4-yl)phenoxy) ethoxy) ethoxy)propyl)azetidin-3-yl)pyridin-3-amine (I-33, 30 mg, 25% yield) as a white solid. $^1$H NMR (400 MHz, DMSO-$d_6$) δ 12.97 (s, 1H), 8.04 (s, 1H), 7.72 (d, J=2.4 Hz, 1H), 7.37 (d, J=8.8 Hz, 2H), 7.21 (d, J=8.8 Hz, 1H), 7.01-6.89 (m, 3H), 6.86-6.74 (m, 2H), 6.21 (d, J=6.8 Hz, 1H), 4.93 (s, 1H), 4.20-4.07 (m, 3H), 3.93-3.87 (m, 1H), 3.76-3.70 (m, 2H), 3.64-3.51 (m, 6H), 3.50-3.43 (m, 6H), 3.13-2.95 (m, 3H), 2.87-2.79 (m, 1H), 2.75-2.70 (m, 1H), 2.58 (s, 3H), 2.38 (s, 3H), 1.85 (d, J=6.8 Hz, 3H), 1.64 (s, 3H), 1.52-1.42 (m, 2H), 1.08 (d, J=6.8 Hz, 3H). LC-MS: MS ($ES^+$): RT=1.215 min, m/z=883.7 [M+$H^+$], LC-MS Method: 25.

Example 35—Synthesis of (R)-6-(2-(ethyl(4-(2-((R)-3-(2-(2-(4-((S)-2,3,6,9-tetramethyl-6H-thieno[3,2-f][1,2,4]triazolo[4,3-a][1,4]diazepin-4-yl)phenoxy) ethoxy)ethoxy) pyrrolidin-1-yl)ethyl)benzyl)amino)-4-methoxyphenyl)-5,6,7,8-tetrahydronaphthalen-2-ol and (S)-6-(2-(ethyl(4-(2-((R)-3-(2-(2-(4-((S)-2,3,6,9-tetramethyl-6H-thieno[3,2-f][1,2,4]triazolo[4,3-a][1,4]diazepin-4-yl)phenoxy)ethoxy)ethoxy)pyrrolidin-1-yl)ethyl)benzyl)amino)-4-methoxyphenyl)-5,6,7,8-tetrahydronaphthalen-2-ol (I-34a and I-34b)

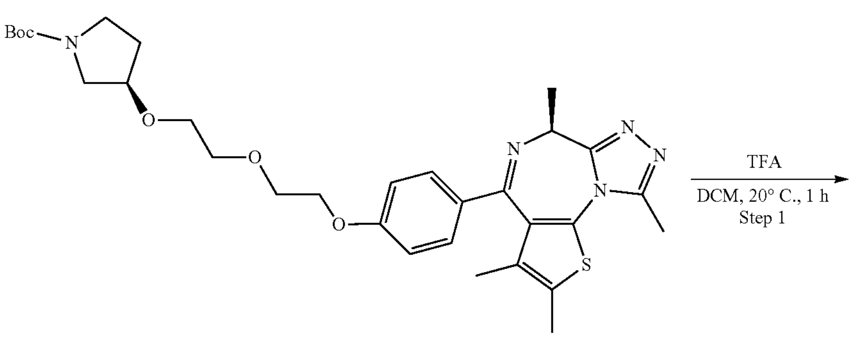

-continued

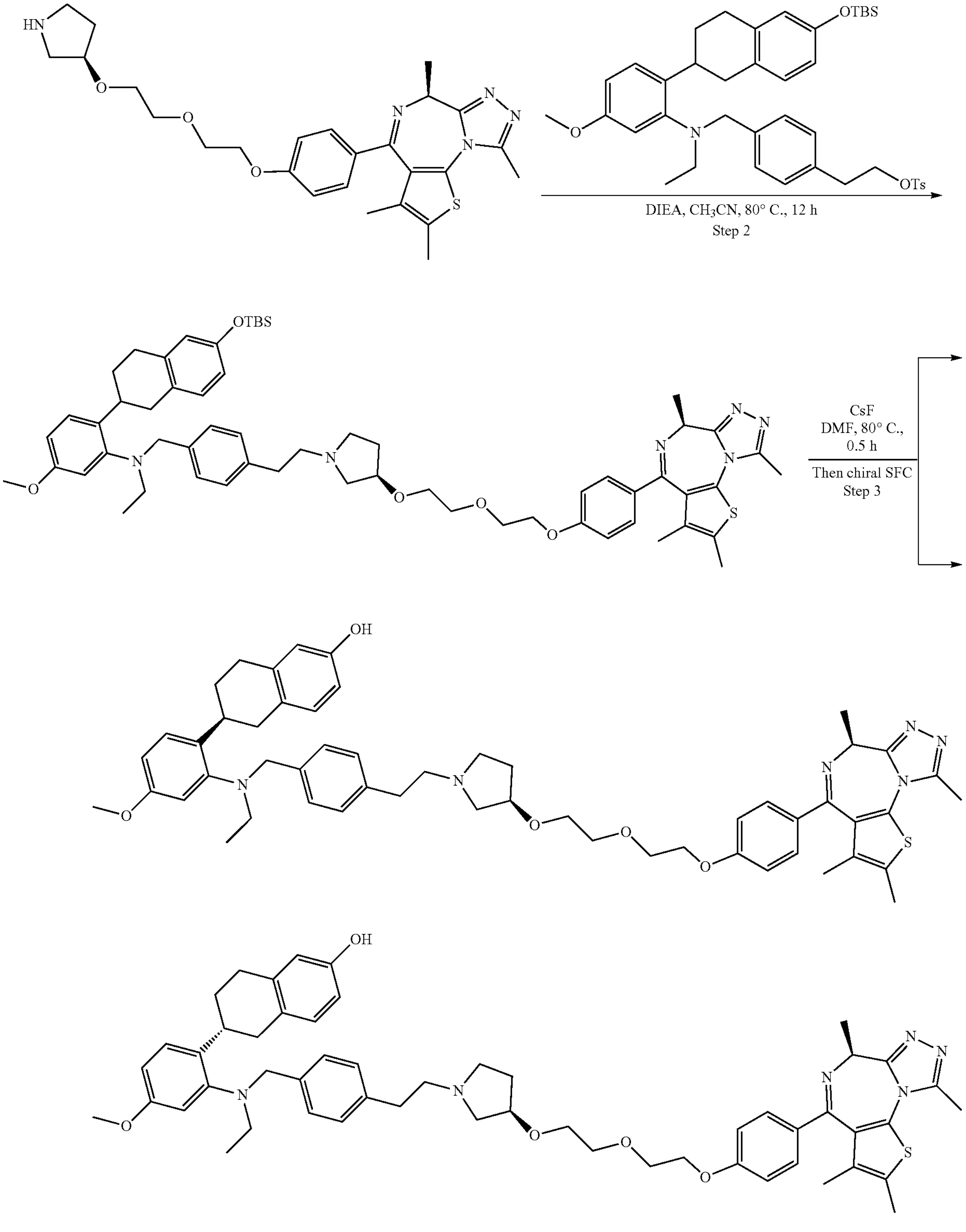

Step 1: Preparation of (S)-2,3,6,9-tetramethyl-4-(4-(2-(2-(((R)-pyrrolidin-3-yl)oxy)ethoxy)ethoxy)phenyl)-6H-thieno[3,2-f][1,2,4]triazolo[4,3-a][1,4]diazepine. To a solution of tert-butyl (R)-3-(2-(2-(4-((S)-2,3,6,9-tetramethyl-6H-thieno[3,2-f][1,2,4]triazolo[4,3-a][1,4]diazepin-4-yl)phenoxy)ethoxy)ethoxy)pyrrolidine-1-carboxylate (110 mg, 0.18 mmol, 1 equiv.) in DCM (3 mL) was added TFA (5.07 g, 44 mmol, 3.30 mL, 240 equiv.). The mixture was stirred at 20° C. for 1 hr. The reaction mixture was concentrated under reduced pressure to remove solvent to afford (S)-2,3,6,9-tetramethyl-4-(4-(2-(2-(((R)-pyrrolidin-3-yl)oxy)ethoxy)ethoxy)phenyl)-6H-thieno[3,2-f][1,2,4]triazolo[4,3-a][1,4]diazepine (92 mg, crude) as a yellow oil. LC-MS: MS ($ES^+$): RT=0.384 min, m/z=496.3 [$M+H^+$].

Step 2: Preparation of 2-(6-((tert-butyldimethylsilyl)oxy)-1,2,3,4-tetra hydronaphthalen-2-yl)-N-ethyl-5-methoxy-N-(4-(2-((R)-3-(2-(2-(4-((S)-2,3,6,9-tetramethyl-6H-thieno[3,2-f][1,2,4]triazolo[4,3-a][1,4]diazepin-4-yl)phenoxy)ethoxy) ethoxy)pyrrolidin-1-yl)ethyl)benzyl)aniline. To a solution of (S)-2,3,6,9-tetramethyl-4-(4-(2-(2-(((R)-pyrrolidin-3-yl)oxy)ethoxy)ethoxy)phenyl)-6H-thieno[3,2-f][1,2,4]triazolo[4,3-a][1,4]diazepine (92 mg, 0.18 mmol, 1 equiv) and 4-(((2-(6-((tert-butyldimethylsilyl)oxy)-1,2,3,4-tetrahydronaphthalen-2-yl)-5-methoxyphenyl)(ethyl)amino) methyl)phenethyl 4-methylbenzenesulfonate (129.94 mg, 0.18 mmol, 1 equiv) in ACN (5 mL) was added DIEA (72 mg, 0.5 mmol, 3 equiv). The mixture was stirred at 80° C. for 12 hr. The reaction mixture was diluted with water (20 mL) and extracted with EA (20 mL×3). The combined organic layers were washed with brine (10 mL×3), dried over $Na_2SO_4$, filtered and concentrated under reduced pressure to give a residue. The residue was purified by prep-TLC ($SiO_2$, DCM/MeOH=10/1) to afford 2-(6-((tert-butyldimethylsilyl)oxy)-1,2,3,4-tetrahydro-naphthalen-2-yl)-N-ethyl-5-methoxy-N-(4-(2-((R)-3-(2-(2-(4-((S)-2,3,6,9-tetramethyl-6H-thieno[3,2-f][1,2,4]triazolo[4,3-a][1,4]diazepin-4-yl) phenoxy)ethoxy) ethoxy)pyrrolidin-1-yl)ethyl) benzyl) aniline (103 mg, 49% yield) as a yellow solid. $^1$H NMR (400 MHz, $CDCl_3$) δ 7.44 (d, J=8.8 Hz, 2H), 7.19-7.12 (m, 3H), 7.07 (d, J=8.0 Hz, 2H), 6.92-6.85 (m, 3H), 6.78 (d, J=2.8 Hz, 1H), 6.69 (dd, J=2.8, 8.8 Hz, 1H), 6.64-6.58 (m, 2H), 4.19-4.08 (m, 4H), 3.98 (s, 2H), 3.86 (t, J=4.8 Hz, 2H), 3.79 (s, 3H), 3.74-3.66 (m, 3H), 3.60 (q, J=5.2 Hz, 2H), 2.94-2.87 (m, 3H), 2.86-2.76 (m, 5H), 2.76-2.69 (m, 4H), 2.67 (s, 3H), 2.41 (s, 3H), 2.17-2.06 (m, 4H), 1.96-1.85 (m, 1H), 1.82-1.70 (m, 6H), 1.26 (s, 1H), 1.00 (s, 9H), 0.93 (t, J=7.2 Hz, 3H), 0.24-0.19 (m, 6H). LC-MS: MS ($ES^+$): RT=0.493 min, m/z=289.2 [$M+H^+$].

Step 3: Preparation of (R)-6-(2-(ethyl(4-(2-((R)-3-(2-(2-(4-((S)-2,3,6,9-tetramethyl-6H-thieno[3,2-f][1,2,4]triazolo [4,3-a][1,4]diazepin-4-yl)phenoxy)ethoxy) ethoxy)pyrrolidin-1-yl)ethyl)benzyl)amino)-4-methoxyphenyl)-5,6,7,8-tetrahydro naphthalen-2-ol and (S)-6-(2-(ethyl(4-(2-((R)-3-(2-(2-(4-((S)-2,3,6,9-tetramethyl-6H-thieno[3,2-f][1,2,4] triazolo[4,3-a][1,4]diazepin-4-yl)phenoxy)ethoxy)ethoxy) pyrrolidin-1-yl)ethyl)benzyl)amino)-4-methoxyphenyl)-5,6,7,8-tetrahydronaphthalen-2-ol. To a solution of 2-(6-((tert-butyldimethylsilyl)oxy)-1,2,3,4-tetrahydronaphthalen-2-yl)-N-ethyl-5-methoxy-N-(4-(2-((R)-3-(2-(2-(4-((S)-2,3,6,9-tetramethyl-6H-thieno[3,2-f][1,2,4]triazolo[4,3-a][1,4] diazepin-4-yl)phenoxy)ethoxy)ethoxy)pyrrolidin-1-yl) ethyl)benzyl)aniline (80 mg, 0.07 mmol, 1 equiv) in DMF (3 mL) was added CsF (59.37 mg, 0.39 mmol, 5 equiv). The mixture was stirred at 80° C. for 0.5 hr. The reaction mixture was diluted with water (20 mL) and extracted with EA (20 mL×3). The combined organic layers were washed with brine (10 mL×3), dried over $Na_2SO_4$, filtered and concentrated under reduced pressure to give a residue. The residue was purified by prep-HPLC (column: Phenomenex luna C18 150*25 mm*10 um; mobile phase: [water(FA)-ACN]; gradient: 26%-56% B over min) to afford a mixture of I-34a and I-34b (50 mg, 66% yield) as a white solid. The mixture was separated by SFC (column: Phenomenex-Cellulose-2 (250 mm×30 mm, 01 um); mobile phase: [$CO_2$-ACN/MeOH (0.1% $NH_3H_2O$)]; B %: 70%, isocratic elution mode) to afford I-34a (16.14 mg, 31% yield) as a white solid and I-34b (19.8 mg, 38% yield) as a white solid. $^1$H NMR (I-34a) (400 MHz, DMSO-$d_6$) δ 7.75-7.64 (m, 1H), 7.37 (d, J=8.4 Hz, 2H), 7.15-7.03 (m, 5H), 6.95 (d, J=8.8 Hz, 2H), 6.84-6.75 (m, 2H), 6.66 (dd, J=2.4, 8.8 Hz, 1H), 6.52-6.46 (m, 2H), 4.18-4.08 (m, 5H), 3.96 (d, J=2.4 Hz, 3H), 3.75-3.71 (m, 4H), 3.70 (s, 3H), 3.55 (s, 3H), 2.89-2.83 (m, 4H), 2.72 (d, J=3.6 Hz, 4H), 2.69-2.65 (m, 4H), 2.64 (s, 2H), 2.33 (dd, J=1.6, 3.2 Hz, 2H), 1.94 (dd, J=6.0, 13.2 Hz, 2H), 1.85 (d, J=6.8 Hz, 3H), 1.64 (s, 3H), 1.29-1.20 (m, 2H), 0.87 (t, J=7.2 Hz, 5H). LC-MS: MS ($ES^+$): RT=1.395 min, m/z=909.7 [$M+H^+$], 25. $^1$H NMR (I-34b) (400 MHz, DMSO-$d_6$) δ 7.75-7.62 (m, 1H), 7.37 (d, J=8.8 Hz, 2H), 7.15-7.03 (m, 5H), 6.95 (d, J=8.8 Hz, 2H), 6.82-6.76 (m, 2H), 6.66 (dd, J=2.4, 8.4 Hz, 1H), 6.52-6.47 (m, 2H), 4.17-4.08 (m, 5H), 3.96 (d, J=2.4 Hz, 3H), 3.75-3.71 (m, 4H), 3.70 (s, 3H), 3.55 (s, 3H), 2.88-2.83 (m, 4H), 2.73 (d, J=5.2 Hz, 4H), 2.66 (d, J=3.6 Hz, 4H), 2.63 (s, 2H), 2.33 (d, J=1.6 Hz, 2H), 1.97-1.90 (m, 2H), 1.85 (d, J=6.4 Hz, 3H), 1.64 (s, 3H), 1.27-1.21 (m, 2H), 0.89-0.82 (m, 5H). LC-MS: MS ($ES^+$): RT=1.395 min, m/z=909.7 [$M+H^+$], Method 25.

Example 36—Synthesis of 4-(2-(4-(8-(2-(4-(6-hydroxy-2-(4-hydroxyphenyl) benzo[b]thiophene-3-carbonyl)phenoxy)ethyl)-2,8-diazaspiro[4.5]decan-2-yl)phenoxy)-5-(2-hydroxypropan-2-yl)phenyl)-6-methyl-1,6-dihydro-7H-pyrrolo[2,3-c]pyridin-7-one (I-35)

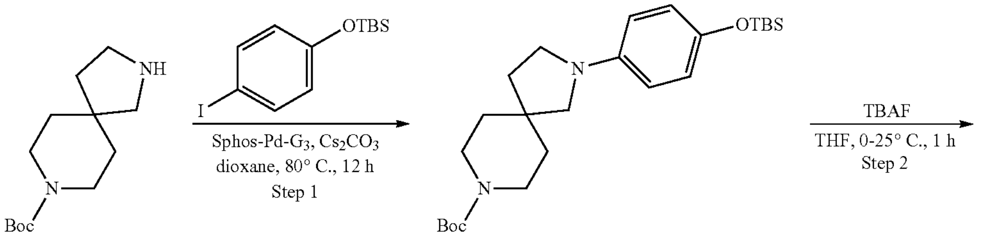

-continued
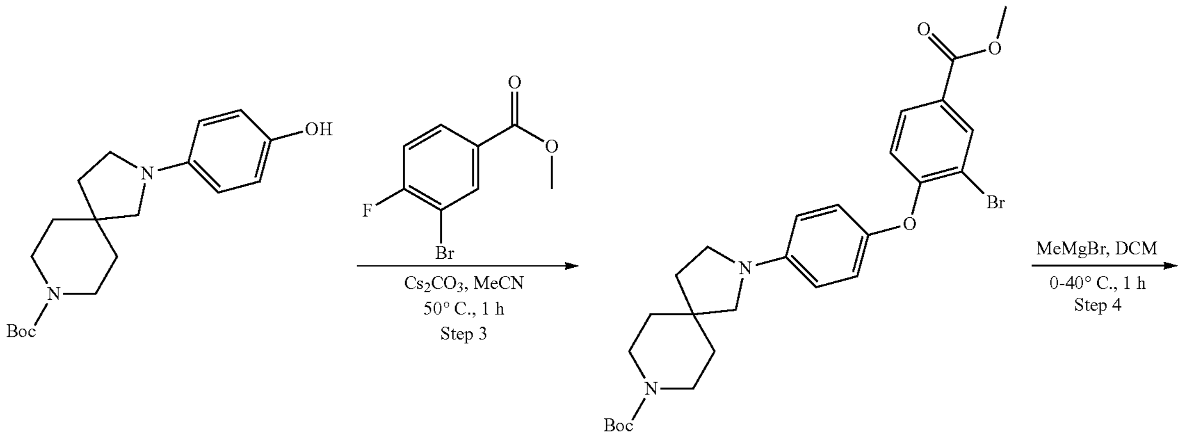
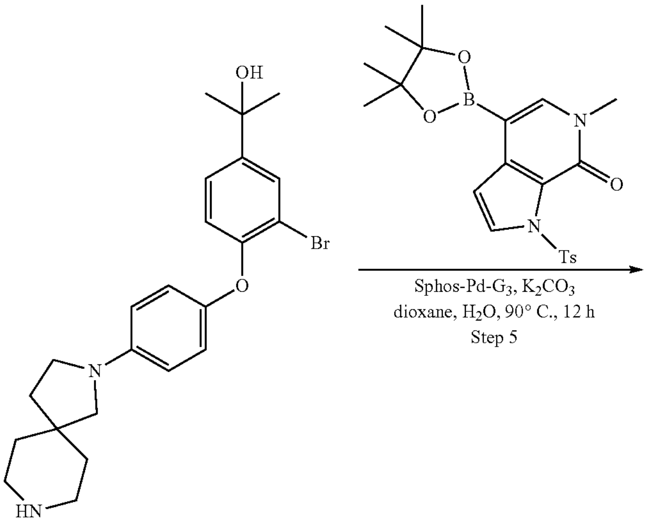
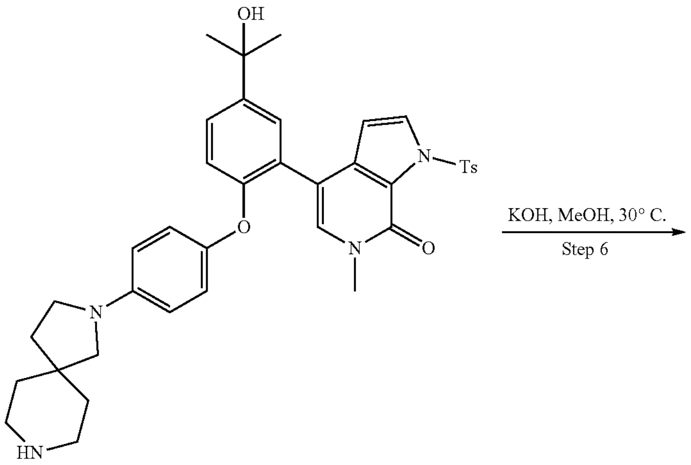

-continued

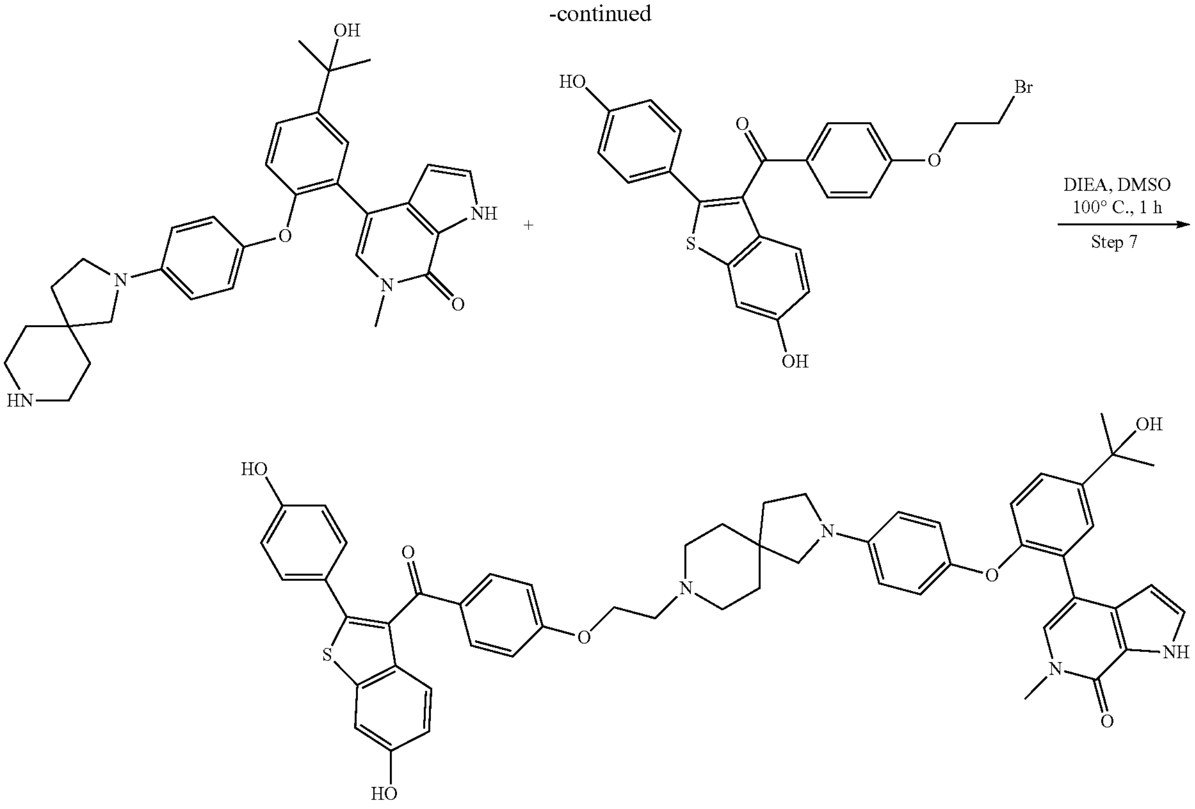

I-35

Step 1: Preparation of tert-butyl 2-[4-[tert-butyl(dimethyl)silyl]oxyphenyl]-2,8-diazaspiro[4.5]decane-8-carboxylate. A mixture of tert-butyl 2,8-diazaspiro[4.5]decane-8-carboxylate (1 g, 4.16 mmol, 1 equiv), tert-butyl-(4-iodophenoxy)-dimethyl-silane (1.39 g, 4.16 mmol, 1 equiv), SPhos Pd G3 (227.25 mg, 291.25 mol, 0.07 equiv), $Cs_2CO_3$ (3.39 g, 10.40 mmol, 2.5 equiv) in dioxane (20 mL) was degassed and purged with $N_2$ for 3 times, and then the mixture was stirred at 80° C. for 12 h under $N_2$ atmosphere. The mixture was filtered off, filter-cake was washed by EtOAc (20 mL *3), and the filtrate was concentrated under reduced pressure. The residue was purified by flash silica gel chromatography (20 g SepaFlash® Silica Flash Column, Eluent of 3-10% Ethyl acetate/Petroleum ether gradient 20 mL/min) to afford tert-butyl 2-[4-[tert-butyl(dimethyl)silyl]oxyphenyl]-2,8-diazaspiro[4.5]decane-8-carboxylate (1.2 g, 64% yield) as a colorless oil. $^1$H NMR (400 MHz, $CDCl_3$) δ 6.79-6.71 (m, 2H), 6.47-6.39 (m, 2H), 3.55-3.45 (m, 2H), 3.42-3.35 (m, 2H), 3.32 (t, 2H, J=6.8 Hz), 3.11 (s, 2H), 1.87 (t, 2H, J=7.2 Hz), 1.63 (s, 1H), 1.58 (s, 3H), 1.47 (s, 9H), 0.98 (s, 9H), 0.16 (s, 6H).

Step 2: Preparation of tert-butyl 2-(4-hydroxyphenyl)-2,8-diazaspiro [4.5]decane-8-carboxylate. To a solution of tert-butyl 2-[4-[tert-butyl(dimethyl)silyl]oxyphenyl]-2,8-diazaspiro[4.5]decane-8-carboxylate (1.2 g, 2.69 mmol, 1 equiv) in THE (20 mL) was added TBAF (1 M, 4.03 mL, 1.5 equiv) at 0° C. The mixture was stirred at 25° C. for 1 h. The mixture was concentrated under reduced pressure to afford tert-butyl 2-(4-hydroxy phenyl)-2,8-diazaspiro[4.5]decane-8-carboxylate (820 mg, crude) as brown solid.

Step 3: Preparation of tert-butyl 2-[4-(2-bromo-4-methoxycarbonyl-phenoxy)phenyl]-2,8-diazaspiro[4.5]decane-8-carboxylate. To a solution of tert-butyl 2-(4-hydroxyphenyl)-2,8-diazaspiro[4.5]decane-8-carboxylate (800 mg, 2.41 mmol, 1 equiv) in MeCN (3 mL) was added $Cs_2CO_3$ (1.96 g, 6.02 mmol, 2.5 equiv) and methyl 3-bromo-4-fluoro-benzoate (392.55 mg, 1.68 mmol, 0.7 equiv). The mixture was stirred at 50° C. for 1 h. The mixture was filtered, the filter-cake was washed by EtOAc (10 mL×3), and the filtrate was concentrated under reduced pressure. The residue was purified by flash silica gel chromatography (20 g SepaFlash Silica Flash Column, eluent: 15~30% ethyl acetate/petroleum ether gradient 30 mL/min) to afford tert-butyl 2-[4-(2-bromo-4-methoxycarbonyl-phenoxy) phenyl]-2,8-diazaspiro[4.5]decane-8-carboxylate (410 mg, 29% yield) as a yellow solid. $^1$H NMR (400 MHz, $CDCl_3$) δ 8.29 (d, 1H, J=2.4H), 7.82 (dd, 1H, J=2.0, 8.4 Hz), 7.02-6.94 (m, 2H), 6.71 (d, 1H, J=8.8 Hz), 6.60-6.50 (m, 2H), 3.90 (s, 3H), 3.57-3.47 (m, 2H), 3.45-3.36 (m, 4H), 3.18 (s, 2H), 1.92 (t, 2H, J=6.8 Hz), 1.65-1.59 (m, 4H), 1.48 (s, 9H). LC-MS: MS ($ES^+$): RT=0.730 min, m/z=545.1; 547.1 [$M+H^+$].

Step 4: Preparation of 2-[3-bromo-4-[4-(2,8-diazaspiro [4.5]decan-2-yl) phenoxy]phenyl]propan-2-ol. To a solution of tert-butyl 2-[4-(2-bromo-4-methoxycarbonyl -phenoxy) phenyl]-2,8-diazaspiro[4.5]decane-8-carboxylate (460 mg, 843.32 mol, 1 equiv) in THF (3 mL) was added MeMgBr (3 M, 5.62 mL, 20 equiv) at 0° C. under an $N_2$ atmosphere. The mixture was stirred at 40° C. for 1 h. The reaction mixture was quenched by adding saturated $NH_4Cl$ (10 mL), and extracted with DCM:MeOH (10:1, 20 mL *3). The combined organic layers were washed with brine (10 mL), dried over $Na_2SO_4$, filtered and concentrated under reduced pressure to afford 2-[3-bromo-4-[4-(2,8-diazaspiro[4.5]decan-2- yl)phenoxy]phenyl]propan-2-ol (220 mg, 54% yield) as a white solid. LC-MS: MS ($ES^+$): RT=0.730 min, m/z=445.1; 447.1 [$M+H^+$].

Step 5: Preparation of 4-(2-(4-(2,8-diazaspiro[4.5]decan-2-yl)phenoxy)-5-(2-hydroxypropan-2-yl)phenyl)-6-methyl-1-tosyl-1,6-dihydro-7H-pyrrolo[2,3-c]pyridin-7-one. A mixture of 2-[3-bromo-4-[4-(2,8-diazaspiro[4.5]decan-2-yl) phenoxy]phenyl]propan-2-ol (100 mg, 224.52 mol, 1 equiv), 6-methyl-1-(p-tolylsulfonyl)-4-(4,4,5,5-tetramethyl-1,3,2-dioxaborolan-2-yl)pyrrolo[2,3-c]pyridin-7-one (96.16 mg, 224.52 mol, 1 equiv), [2-(2-aminophenyl)phenyl]palladium (1+); bis(1-adamantyl)-butyl-phosphane; methanesulfonate (16.35 mg, 22.45 mol, 0.1 equiv) and $K_2CO_3$ (77.58 mg, 561.30 mol, 2.5 equiv) in dioxane (3 mL) and $H_2O$ (0.3 mL) was degassed and purged with $N_2$ 3 times, and then the mixture was stirred at 90° C. for 12 h under an $N_2$ atmosphere. To the reaction mixture was added $H_2O$ (10 mL) and the reaction mixture was extracted with DCM:MeOH=10:1 (10 mL *3). The combined organic layers were washed with brine (10 mL), dried over $Na_2SO_4$, filtered and concentrated under reduced pressure to afford the crude desired product (105 mg) as a yellow solid.

Step 6: Preparation of 4-[2-[4-(2,8-diazaspiro[4.5]decan-2-yl)phenoxy]-5-(1-hydroxy-1-methyl-ethyl)phenyl]-6-methyl-1H-pyrrolo[2,3-c]pyridin-7-one. To a solution of 4-[2-[4-(2,8-diazaspiro[4.5]decan-2-yl)phenoxy]-5-(1-hydroxy-1-methyl-ethyl)phenyl]-6-methyl-1-(p-tolylsulfonyl) pyrrolo[2,3-c]pyridin-7-one (100 mg, 149.96 mol, 1 equiv) in MeOH (3 mL) was added KOH (168.28 mg, 3.00 mmol, 20 equiv). The mixture was stirred at 30° C. for 1 h. The mixture was concentrated under reduced pressure. The residue was purified by prep-HPLC (column: Welch Xtimate C18 150×25 mm×5 um; mobile phase: [water(FA)-ACN]; gradient: 10%-40% B over 10 min) to afford 4-[2-[4-(2,8-diazaspiro[4.5]decan-2-yl)phenoxy]-5-(1-hydroxy-1-methyl-ethyl)phenyl]-6-methyl-1H-pyrrolo[2,3-c]pyridin-7-one (45 mg, 55% yield) as an off-white solid. LC-MS: MS ($ES^+$): RT=0.890 min, m/z=513.3 [$M+H^+$].

Step 7: Preparation of 4-(2-(4-(8-(2-(4-(6-hydroxy-2-(4-hydroxyphenyl) benzo[b]thiophene-3-carbonyl)phenoxy) ethyl)-2,8-diazaspiro[4.5]decan-2-yl)phenoxy)-5-(2-hydroxypropan-2-yl)phenyl)-6-methyl-1,6-dihydro-7H-pyrrolo[2,3-c]pyridin-7-one. To a solution of 4-[2-[4-(2,8-diazaspiro[4.5]decan-2-yl)phenoxy]-5-(1-hydroxy-1-methyl-ethyl)phenyl]-6-methyl-1H-pyrrolo[2,3-c]pyridin-7-one (40 mg, 78.03 mol, 1 equiv) in DMSO (0.5 mL) was added DIEA (30.25 mg, 234.08 mol, 40.77 μL, 3 equiv) and [4-(2-bromoethoxy)phenyl]-[6-hydroxy-2-(4-hydroxyphenyl)benzothiophen-3-yl]methanone (36.62 mg, 78.03 mol, 1 equiv). The mixture was stirred at 100° C. for 1 h. To the reaction mixture was added $H_2O$ (20 mL), and it was extracted with EtOAc (20 mL *3). The combined organic layers were washed with brine (10 mL), dried over $Na_2SO_4$, filtered and concentrated under reduced pressure. The residue was purified by prep-TLC ($SiO_2$, DCM:MeOH=10:1), and then purified by prep-HPLC (column: Welch Xtimate C18 150*25 mm*5 um; mobile phase: [water(FA)-ACN]; gradient: 20%-500% B over 10 min) to afford 4-(2-(4-(8-(2-(4-(6-hydroxy-2-(4-hydroxyphenyl)benzo[b]thiophene-3-carbonyl)phenoxy)ethyl)-2,8-diazaspiro[4.5]decan-2-yl) phenoxy)-5-(2-hydroxypropan-2-yl)phenyl)-6-methyl-1,6-dihydro-7H-pyrrolo[2,3-c]pyridin-7-one (1-35, 17 mg, 23% yield) as a yellow solid. $^1H$ NMR (400 MHz, DMSO-$d_6$) δ 11.98 (s, 1H), 10.03-9.51 (m, 2H), 8.20 (s, 1H), 7.65 (d, 2H, J=8.8 Hz), 7.51 (d, 1H, J=2.4 Hz), 7.35-7.30 (m, 2H), 7.28-7.22 (m, 3H), 7.19-7.14 (m, 2H), 6.92 (d, 2H, J=7.2 Hz), 6.88-6.80 (m, 3H), 6.71-6.64 (m, 3H), 6.47 (d, 2H, J=9.2 Hz), 6.24 (t, 1H, J=2.4 Hz), 4.98 (s, 1H), 4.10 (t, 2H, J=5.6 Hz), 3.55 (s, 3H), 3.23 (t, 4H, J=6.8 Hz), 3.03 (s, 2H), 2.67 (t, 2H, J=5.6 Hz), 2.44-2.38 (m, 2H), 1.79 (t, 2H, J=6.4 Hz), 1.58-1.48 (m, 4H), 1.44 (s, 6H). LC-MS: MS ($ES^+$): RT=1.917 min, m/z=901.7 [$M+H^+$], LCMS Method: 25.

Example 37—Synthesis of 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl) phenoxy)ethoxy) propyl) pyrrolidin-3-yl)oxy) phenyl)-6,7-dihydro-5H-benzo[7]annulen-3-ol (I-36)

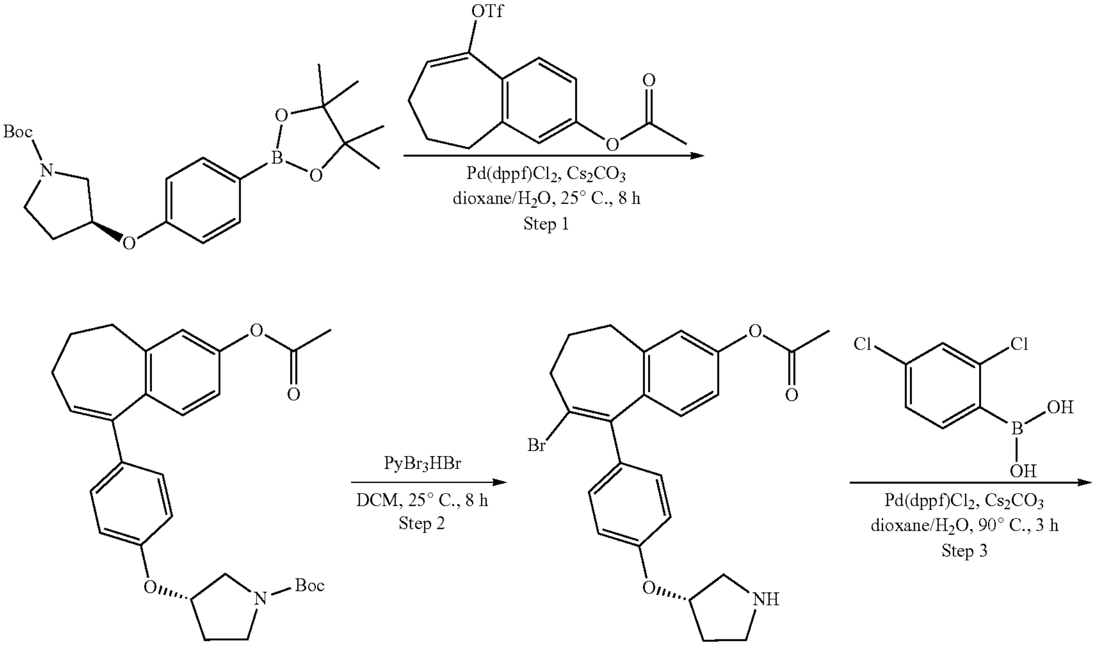

-continued
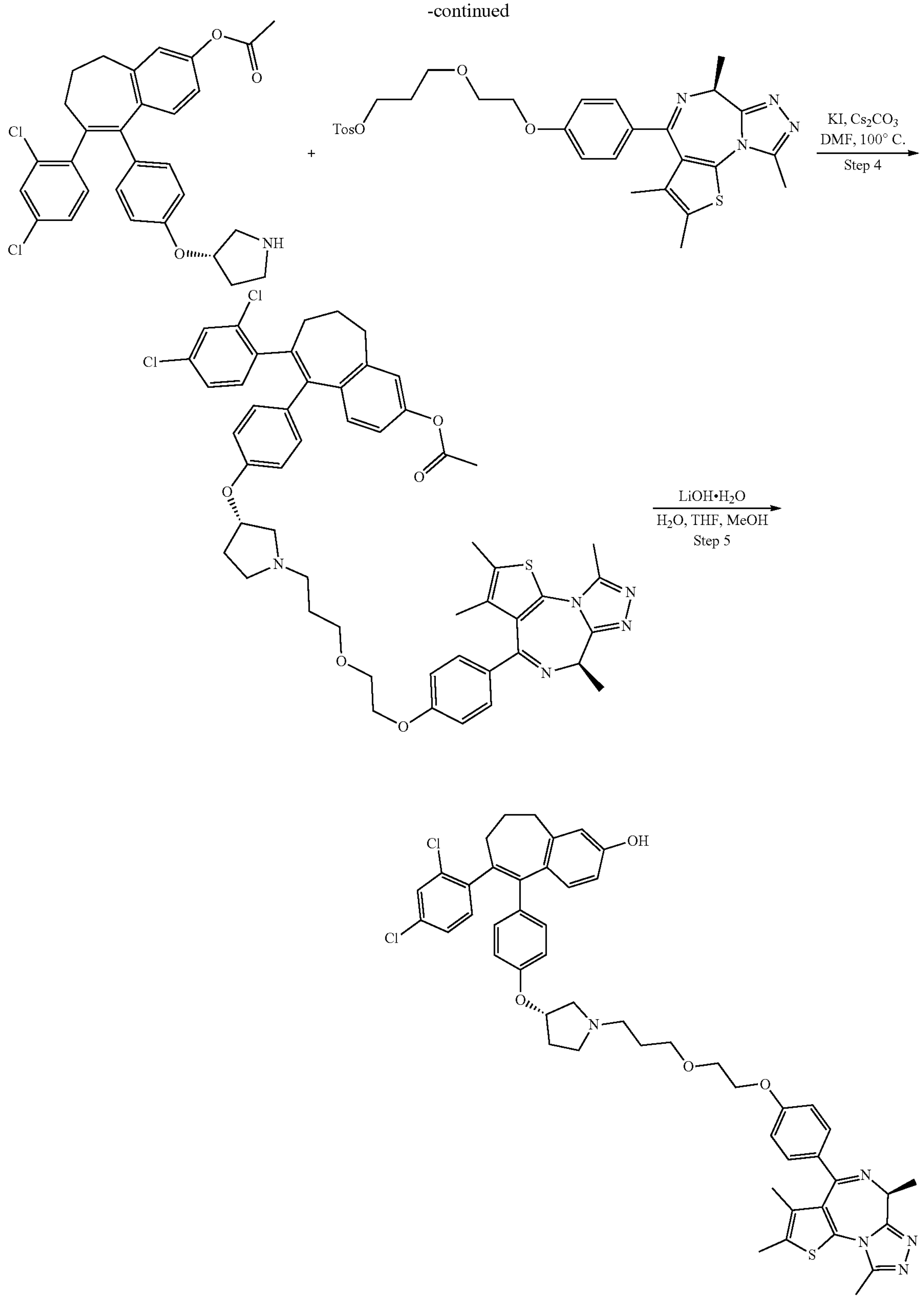
I-36
Step 1: Preparation of tert-butyl (S)-3-(4-(3-acetoxy-6,7-dihydro-5H-benzo[7]annulen-9-yl)phenoxy)pyrrolidine-1-carboxylate. To a solution of 9-(((trifluoro methyl)sulfonyl)oxy)-6,7-dihydro-5H-benzo[7]annulen-3-yl acetate (3.00 g, 8.56 mmol, 1.00 equiv), tert-butyl (S)-3-(4-(4,4,5,5-tetramethyl-1,3,2-dioxaborolan-2-yl)phenoxy) pyrrolidine-1-carboxylate (3.33 g, 8.56 mmol, 1.00 equiv), and cesium carbonate (5.58 g, 17.13 mmol, 2.00 equiv) in dioxane (24 mL) and water (6 mL) was added 1,1'-bis(diphenyl phosphino) ferrocene-palladium(II)dichloride (626 mg, 0.86 mmol, 0.10 equiv) and the mixture was stirred at 25° C. for 8 h under a nitrogen atmosphere. The reaction mixture was quenched with water (50 mL), and then extracted with ethyl acetate (30 mL×3). The combined organic layers were washed with brine (50 mL), dried over anhydrous sodium sulfate, filtered and concentrated under reduced pressure to give a residue. The residue was purified by column chromatography (silica gel, petroleum ether/ethyl acetate=1/0 to 3/1) to afford tert-butyl (S)-3-(4-(3-acetoxy-6,7-dihydro-5H-benzo[7]annulen-9-yl)phenoxy)pyrrolidine-1-carboxylate (3.50 g, 88% yield) as a white solid. LCMS: MS ($ES^+$): RT=0.758 min, m/z=486.4 $[M+Na]^+$.

Step 2: Preparation of (S)-8-bromo-9-(4-(pyrrolidin-3-yloxy)phenyl)-6,7-dihydro-5H-benzo[7]annulen-3-yl acetate. A mixture of monopyidinium tribromide (379 mg, 1.19 mmol, 1.10 equiv) and tert-butyl (S)-3-(4-(3-acetoxy-6,7-dihydro-5H-benzo[7]annulen-9-yl)phenoxy)pyrrolidine-1-carboxylate (500 mg, 1.08 mmol, 1.00 equiv) in dichloromethane (15 mL) was stirred at 25° C. for 8 h. The reaction mixture was concentrated under reduced pressure to give a residue. The residue was purified by column chromatography (silica gel, petroleum ether/ethyl acetate=1/0 to 10/1) to afford (S)-8-bromo-9-(4-(pyrrolidin-3-yloxy)phenyl)-6,7-dihydro-5H-benzo[7]annulen-3-yl acetate (330 mg, 69% yield) as a white solid. $^1$H NMR (400 MHz, $CDCl_3$) δ 7.21 (d, J=8.4 Hz, 2H), 6.99 (d, J=2.0 Hz, 1H), 6.94-6.78 (m, 4H), 5.09 (s, 1H), 3.70-3.53 (m, 4H), 2.77 (t, J=6.8 Hz, 2H), 2.64-2.57 (m, 2H), 2.44 (dd, J=6.0, 14.4 Hz, 1H), 2.38-2.22 (m, 7H).

Step 3: Preparation of (S)-8-(2,4-dichlorophenyl)-9-(4-(pyrrolidin-3-yloxy) phenyl)-6,7-dihydro-5H-benzo[7]annulen-3-yl acetate. To a solution of (S)-8-bromo-9-(4-(pyrrolidin-3-yloxy)phenyl)-6,7-dihydro-5H-benzo[7]annulen-3-yl acetate (330 mg, 0.74 mmol, 1.00 equiv), (2,4-dichlorophenyl)boronic acid (156 mg, 0.82 mmol, 1.10 equiv), and cesium carbonate (486 mg, 1.49 mmol, 2.00 equiv) in dioxane (4 mL) and water (1 mL) was added 1,1'-bis(diphenylphosphino)ferrocene-palladium(II)dichloride (54 mg, 0.07 mmol, 0.10 equiv) and the mixture was stirred at 90° C. for 3 h under a nitrogen atmosphere. The reaction mixture was quenched with water (20 mL), and then extracted with ethyl acetate (10 mL×3). The combined organic layers were washed with brine (30 mL), dried over anhydrous sodium sulfate, filtered and concentrated under reduced pressure to give a residue. The residue was purified by prep-TLC (dichloromethane:methanol=10:1) to afford (S)-8-(2,4-dichlorophenyl)-9-(4-(pyrrolidin-3-yloxy)phenyl)-6,7-dihydro-5H-benzo[7]annulen-3-yl acetate (320 mg, 84% yield) as a yellow solid. LCMS: MS ($ES^+$): RT=0.625 min, m/z=510.1 $[M+H]^+$.

Step 4: Preparation of 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy)ethoxy) propyl)pyrrolidin-3-yl)oxy)phenyl)-6,7-dihydro-5H-benzo[7]annulen-3-yl acetate. A mixture of (S)-8-(2,4-dichlorophenyl)-9-(4-(pyrrolidin-3-yloxy)phenyl)-6,7-dihydro-5H-benzo[7]annulen-3-yl acetate (51 mg, 0.10 mmol, 1.20 equiv), (S)-3-(2-(4-(2,3,6,9-tetramethyl-6H-thieno[3,2-f][1,2,4]triazolo[4,3-a][1,4]diazepin-4-yl)phenoxy)ethoxy)propyl 4-methyl benzenesulfonate (50 mg, 0.08 mmol, 1.00 equiv), potassium iodide (13 mg, 0.08 mmol, 1.00 equiv), and cesium carbonate (82 mg, 0.25 mmol, 3.00 equiv) in N,N-dimethylformamide (1 mL) was stirred at 100° C. for 1 h. The reaction mixture was quenched with water (10 mL), and then extracted with ethyl acetate (5 mL×3). The combined organic layers were washed with brine (30 mL), dried over anhydrous sodium sulfate, filtered and concentrated under reduced pressure to give a residue. The residue was purified by prep-HPLC [column: Phenomenex luna C18 150×25 mm×10 um; mobile phase: [water (FA)-ACN]; gradient: 80%-100% B over 10 min] to afford 8-(2,4-dichlorophenyl)-9-(4-(((S)-1-(3-(2-(4-((S)-2,3,6,9-tetramethyl-6H-thieno [3,2-f][1,2,4]triazolo[4,3-a][1,4]diazepin-4-yl)phenoxy)ethoxy)propyl) pyrrolidin-3-yl)oxy)phenyl)-6,7-dihydro-5H-benzo[7]annulen-3-yl acetate (50 mg, 63% yield) as a white solid. LCMS: MS ($ES^+$): RT=0.656 min, m/z=930.4 $[M+H]^+$.

Step 5: Preparation of 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy)ethoxy) propyl)pyrrolidin-3-yl)oxy)phenyl)-6,7-dihydro-5H-benzo[7]annulen-3-ol. To a solution of 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy)ethoxy)propyl)pyrrolidin-3-yl)oxy)phenyl)-6,7-dihydro-5H-benzo[7]annulen-3-yl acetate (50 mg, 0.05 mmol, 1.00 equiv) in water (0.2 mL), tetrahydrofuran (0.2 mL) and methanol (0.2 mL) was added lithium hydroxide (6 mg, 0.16 mmol, 3.00 equiv) and the mixture was stirred at 25° C. for 108 h. The reaction mixture was quenched with an aqueous hydrochloric acid solution (1M, 5 mL), and then filtered and concentrated under reduced pressure to give a residue. The residue was purified by prep-HPLC [column: Welch Xtimate C18 150×25 mm×5 um; mobile phase: [water(FA)-ACN]; gradient: 30%-60% B over 10 min] to afford 8-(2,4-dichlorophenyl)-9-(4-(((S)-1-(3-(2-(4-((S)-2,3,6,9-tetramethyl-6H-thieno[3,2-f][1,2,4]triazolo[4,3-a][1,4]diazepin-4-yl)phenoxy)ethoxy) propyl)pyrrolidin-3-yl)oxy)phenyl)-6,7-dihydro-5H-benzo[7]annulen-3-ol (I-36, 22.78 mg, 42.09% yield) as a white solid. LCMS: MS ($ES^+$): RT=2.604 min, m/z=888.4 $[M+H]^+$; 5-95. $^1$H NMR (400 MHz, DMSO-$d_6$) δ 8.38 (s, 2H), 7.57 (d, J=2.0 Hz, 1H), 7.36 (d, J=8.4 Hz, 2H), 7.27-7.22 (m, 1H), 7.15 (d, J=8.4 Hz, 1H), 6.94 (d, J=8.4 Hz, 2H), 6.89 (d, J=2.4 Hz, 1H), 6.75-6.69 (m, 3H), 6.67-6.62 (m, 3H), 4.75 (t, J=7.6 Hz, 1H), 4.17-4.10 (m, 3H), 4.04 (t, J=6.0 Hz, 2H), 3.75-3.72 (m, 2H), 3.62 (s, 2H), 3.43 (s, 1H), 3.07-3.03 (m, 1H), 2.85-2.76 (m, 4H), 2.58 (s, 3H), 2.38 (s, 3H), 2.19-2.12 (m, 2H), 2.10-2.03 (m, 2H), 2.00-1.93 (m, 3H), 1.87-1.82 (m, 3H), 1.76-1.69 (m, 1H), 1.63 (s, 3H).

Example 38—Synthesis of (5S,6R)-6-phenyl-5-(4-(4-((4-(4-((S)-2,3,6,9-tetramethyl-6H-thieno[3,2-f][1,2,4]triazolo[4,3-a][1,4]diazepin-4-yl)phenyl)piperazin-1-yl)methyl) piperidin-1-yl)phenyl)-5,6,7,8-tetrahydronaphthalen-2-ol and (5R,6S)-6-phenyl-5-(4-(4-((4-(4-((S)-2,3,6,9-tetramethyl-6H-thieno[3,2-f][1,2,4]triazolo[4,3-a][1,4]diazepin-4-yl) phenyl) piperazin-1-yl)methyl)piperidin-1-yl)phenyl)-5,6,7,8-tetrahydronaphthalen-2-ol (I-37a and I-37b)
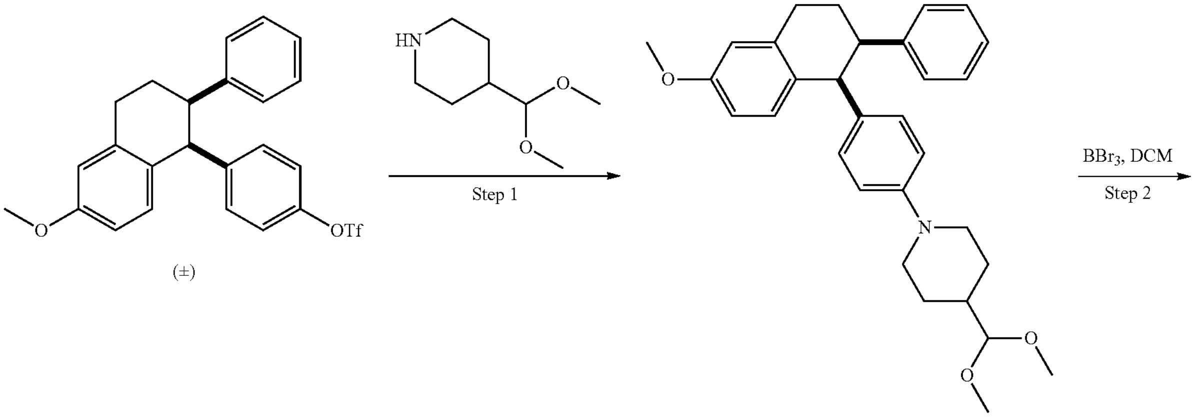
(±)
(±)
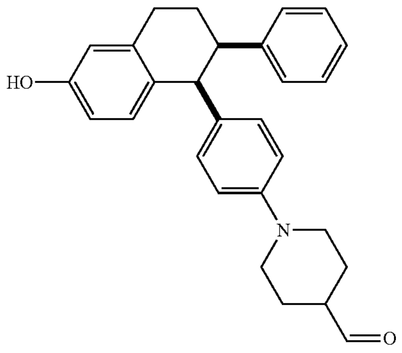
(±)
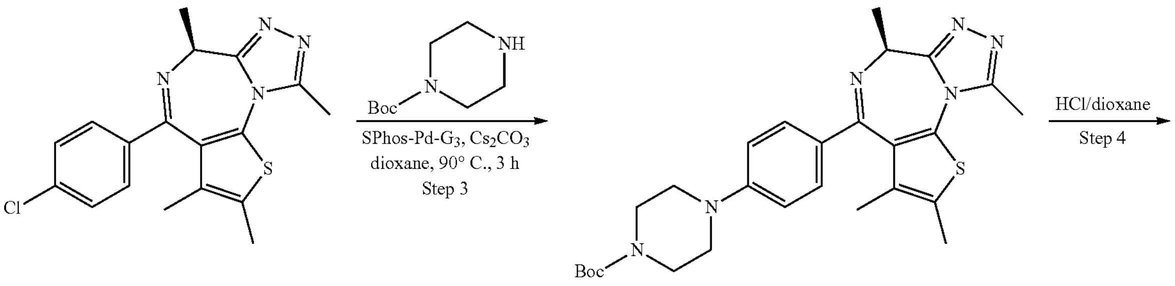

-continued

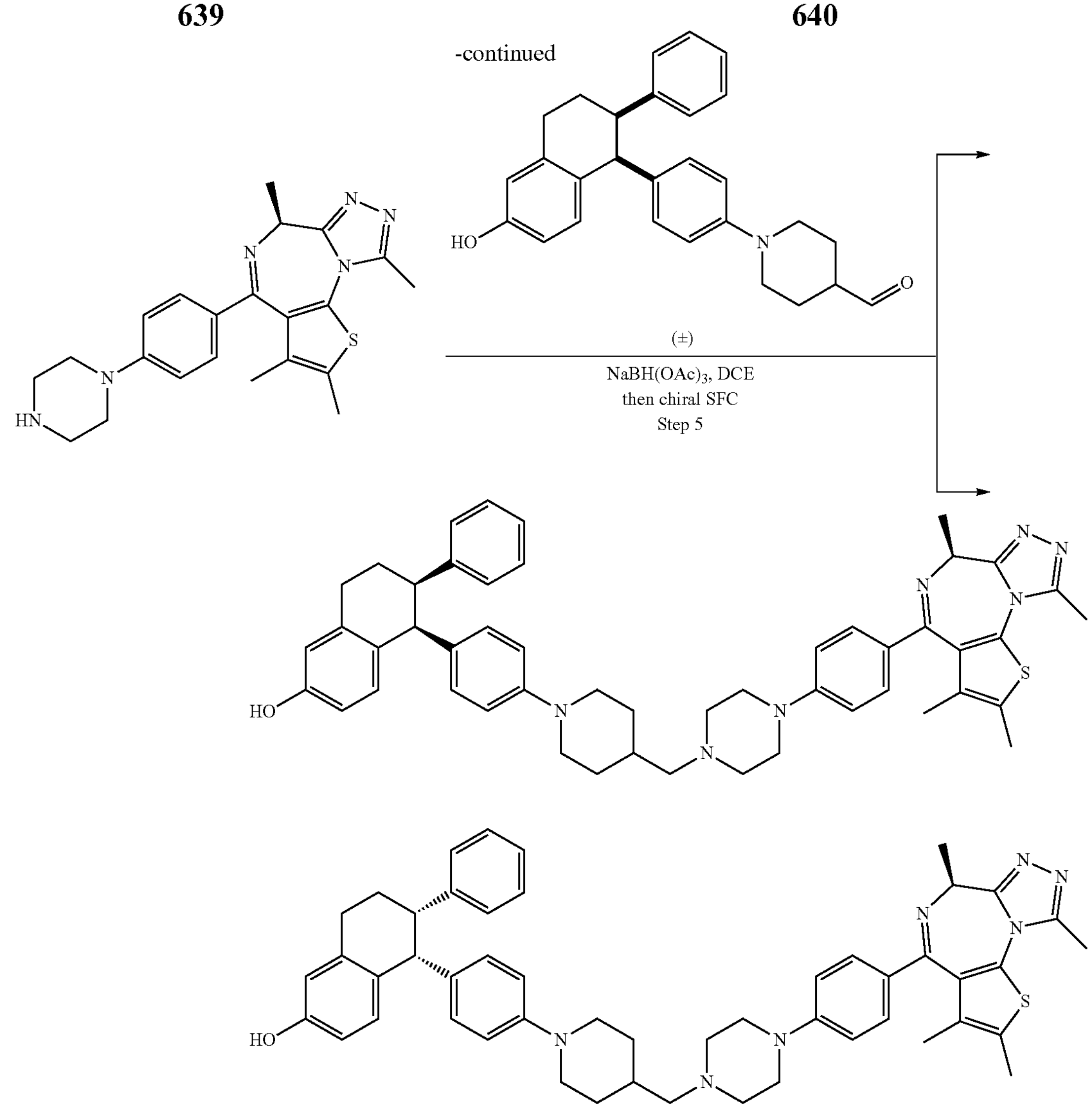

Step 1: Preparation of (+)-cis-4-(dimethoxymethyl)-1-[4-(6-methoxy-2-phenyl-tetralin-1-yl)phenyl]piperidine. A mixture of (i)-cis-[4-(6-methoxy-2-phenyl-tetralin-1-yl)phenyl]trifluoromethanesulfonate (200 mg, 0.43 mmol, 1 equiv), 4-(dimethoxymethyl)piperidine (103 mg, 0.64 mmol, 1.5 equiv), CPHOS PD $G_3$ (69 mg, 0.08 mmol, 0.2 equiv), Xantphos (75 mg, 0.12 mmol, 0.3 equiv) and $Cs_2CO_3$ (281 mg, 0.86 mol, 2 equiv) in dioxane (5 mL) was degassed and purged with $N_2$ 3 times, and then the mixture was stirred at 95° C. for 12 h under an $N_2$ atmosphere. The reaction mixture was quenched by addition $H_2O$ (50 mL), and then extracted with ethyl acetate (200 mL). The combined organic layers were dried over $Na_2SO_4$, filtered and concentrated under reduced pressure to give a residue. The residue was purified by prep-TLC ($SiO_2$, petroleum ether/ethyl acetate=5:1). (+)-cis-4-(dimethoxymethyl)-1-[4-(6-methoxy-2-phenyl-tetralin-1-yl)phenyl]piperidine (150 mg, 0.31 mmol, 73% yield) was obtained as a yellow oil. LC-MS: MS ($ES^+$): RT=0.537 min, m/z=472.3 $[M+H^+]$.

Step 2: Preparation of (±)-cis-1-[4-(6-hydroxy-2-phenyl-tetralin-1-yl)phenyl]piperidine -4-carbaldehyde. To a solution of (i)-cis-4-(dimethoxymethyl)-1-[4-(6-methoxy-2-phenyl-tetralin-1-yl)phenyl]piperidine (150.00 mg, 0.31 mmol, 1 equiv) in DCM (2 mL) was added $BBr_3$ (1.30 g, 5.19 mmol, 0.5 mL, 16.32 equiv) at 0° C. . The mixture was stirred at 20° C. for 3 h. And then $H_2O$ (2 mL) was added dropwise at 0° C. The resulting mixture was stirred at 20° C. for 2 hours. The reaction mixture was adjusted to pH=7-8 with aqueous $NaHCO_3$ and extracted with EA 15 mL (5 mL*3). The combined organic layers were washed with brine (10 mL), dried over $Na_2SO_4$, filtered and concentrated under reduced pressure to afford (±)-cis-1-[4-(6-hydroxy-2-phenyl-tetralin-1-yl)phenyl]piperidine-4-carbaldehyde (120 mg, 0.29 mmol, 91% yield) as a white solid. LC-MS: MS (ES+): RT=0.471 min, m/z=412.2 $[M+H^+]$.

Step 3: Preparation of tert-butyl (S)-4-(4-(2,3,6,9-tetramethyl-6H-thieno[3,2-f][1,2,4]triazolo[4,3-a][1,4]diazepin-4-yl)phenyl)piperazine-1-carboxylate. A mixture of (S)-4-(4-chlorophenyl)-2,3,6,9-tetramethyl-6H-thieno[3,2-f][1,2,4]triazolo[4,3-a][1,4]diazepine (100 mg, 0.28 mmol, 1 equiv), tert-butyl piperazine-1-carboxylate (78 mg, 0.42 mmol, 1.5 equiv), SPhos Pd $G_3$ (21 mg, 0.02 mmol, 0.1 equiv), and $Cs_2CO_3$ (182 mg, 0.56 mmol, 2 equiv) in dioxane (10 mL) was degassed and purged with $N_2$ 3 times, and then the mixture was stirred at 100° C. for 12 h under an $N_2$ atmosphere. The reaction mixture was partitioned between EtOAc (20 mL) and $H_2O$ (20 mL). The organic phase was separated, filtered and concentrated under reduced pressure to give a residue. The residue was purified by prep-TLC ($SiO_2$, DCM:MeOH=10:1) to afford tert-butyl (S)-4-(4-(2,3,6,9-tetramethyl-6H-thieno[3,2-f][1,2,4]triazolo[4,3-a][1,4]diazepin-4-yl)phenyl)piperazine-1-carboxylate (140 mg, 98% yield) as a white solid. LC-MS: MS ($ES^+$): RT=0.478 min, m/z=507.3 [$M+H^+$].

Step 4: Preparation of (S)-2,3,6,9-tetramethyl-4-(4-(piperazin-1-yl)phenyl)-6H-thieno[3,2-f][1,2,4]triazolo[4,3-a][1,4]diazepine. To a solution of tert-butyl 4-[4-[(9S)-4,5,9,13-tetramethyl-3-thia-1,8,11,12-tetrazatricyclo[8.3.0.$0^{2,6}$]trideca-2(6),4,7,10,12-pentaen-7-yl]phenyl]piperazine-1-carboxylate (140 mg, 0.27 mmol, 1 equiv) in DCM (2 mL) was added HCl/dioxane (2 M, 3.50 mL, 25.33 equiv). The mixture was stirred at 25° C. for 12 h. The reaction mixture was concentrated under reduced pressure to remove solvent to afford (S)-2,3,6,9-tetramethyl-4-(4-(piperazin-1-yl)phenyl)-6H-thieno[3,2-f][1,2,4]triazolo[4,3-a][1,4]diazepine (120 mg, 98% yield, HCl) as a yellow solid. LC-MS: MS ($ES^+$): RT=0.352 min, m/z=407.2 [$M+H^+$].

Step 5: Preparation of (5S,6R)-6-phenyl-5-(4-(4-((4-(4-((S)-2,3,6,9-tetramethyl-6H-thieno[3,2-f][1,2,4]triazolo[4,3-a][1,4]diazepin-4-yl)phenyl)piperazin-1-yl)methyl) piperidin -1-yl)phenyl)-5,6,7,8-tetrahydronaphthalen-2-ol and (5R,6S)-6-phenyl-5-(4-(4-((4-(4-((S)-2,3,6,9-tetramethyl-6H-thieno[3,2-f][1,2,4]triazolo[4,3-a][1,4]diazepin-4-yl)phenyl)piperazin-1-yl)methyl)piperidin-1-yl)phenyl)-5,6,7,8-tetrahydronaphthalen-2-ol (I-37a and I-37b). To a solution of (S)-2,3,6,9-tetramethyl-4-(4-(piperazin-1-yl)phenyl)-6H-thieno[3,2-f][1,2,4]triazolo [4,3-a][1,4]diazepine (80 mg, 0.18 mmol, 1 equiv, HCl) in DCM (3 mL) was added NaOAc (148 mg, 1.81 mmol, 10 equiv) at 25° C. The mixture was stirred at 25° C. for 0.5 h. Then (+)-cis-1-[4-(6-hydroxy-2-phenyl-tetralin-1-yl)phenyl]piperidine-4-carbaldehyde (81 mg, 0.19 mmol, 1.1 equiv) and $NaBH(OAc)_3$ (57 mg, 0.27 mmol, 1.5 equiv) were added. The mixture was stirred at 25° C. for 12 hr. The reaction mixture was concentrated under reduced pressure to remove solvent. The residue was purified by prep-TLC ($SiO_2$, DCM:MeOH=10:1) to afford 2-phenyl-1-[4-[4-[[4-[4-[(9S)-4,5,9,13-tetramethyl-3-thia-1,8,11,12-tetrazatricyclo[8.3.0.$0^{2,6}$]trideca-2(6),4,7,10,12-pentaen-7-yl]phenyl]piperazin-1-yl]methyl]-1-piperidyl]phenyl]tetralin-6-ol (40 mg, 0.04 mmol, 27% yield) as a white solid. The stereoisomeric mixture was purified by prep-HPLC (column: DAICEL CHIRALPAK AD (250 mm×30 mm, 10 um); mobile phase: [$CO_2$-ACN/i-PrOH (0.1% $NH_3H_2O$)]; B %: 70%, isocratic elution mode) to give I-37a (about 22% yield) as a white solid and I-37b (about 22% yield) as a white solid. $^1H$ NMR (peak 1): (400 MHz, CHLOROFORM-d) δ ppm 1.29-1.38 (m, 3H) 1.56-1.68 (m, 2H) 1.76 (s, 3H) 1.83 (br d, J=13.6 Hz, 3H) 2.05-2.09 (m, 3H) 2.22-2.28 (m, 2H) 2.41 (s, 3H) 2.52-2.61 (m, 6H) 2.66-2.68 (m, 3H) 2.95-3.07 (m, 2H) 3.25 (br d, J=2.8 Hz, 4H) 3.50-3.59 (m, 2H) 4.11-4.21 (m, 2H) 6.29 (d, J=8.8 Hz, 2H) 6.55-6.62 (m, 3H) 6.72 (d, J=2.4 Hz, 1H) 6.79-6.86 (m, 5H) 7.11-7.18 (m, 3H) 7.38-7.44 (m, 2H) LC-MS (peak 1): MS ($ES^+$): RT=1.035 min, m/z=802.5 [$M+H^+$], LCMS Method 10. $^1H$ NMR (peak 2): (400 MHz, CHLOROFORM-d) δ ppm 1.28-1.38 (m, 3H) 1.56-1.69 (m, 2H) 1.76 (s, 3H) 1.83 (br d, J=14.4 Hz, 3H) 2.08 (d, J=6.8 Hz, 3H) 2.22-2.29 (m, 2H) 2.41 (s, 3H) 2.52-2.62 (m, 6H) 2.67 (s, 3H) 2.93-3.06 (m, 2H) 3.25 (br d, J=2.0 Hz, 4H) 3.55 (br dd, J=8.8, 3.2 Hz, 2H) 4.11-4.21 (m, 2H) 6.29 (d, J=8.8 Hz, 2H) 6.54-6.60 (m, 3H) 6.72 (d, J=2.4 Hz, 1H) 6.78-6.87 (m, 5H) 7.12-7.18 (m, 3H) 7.39 (d, J=8.8 Hz, 2H). LC-MS (peak 2): MS ($ES^+$): RT=1.035 min, m/z=802.5 [$M+H^+$], LCMS Method 10.

Example 39—Synthesis of (5R,6S)-6-phenyl-5-(4-(2-(4-((S)-2,3,9-trimethyl-6-(oxazol-2-ylmethyl)-6H-thieno[3,2-f][1,2,4]triazolo[4,3-a][1,4]diazepin-4-yl)benzyl)-7-azaspiro[3.5]nonan-7-yl)phenyl)-5,6,7,8-tetrahydronaphthalen-2-ol (I-62) and (5R,6S)-6-phenyl-5-(4-(2-(4-((R)-2,3,9-trimethyl-6-(oxazol-2-ylmethyl)-6H-thieno[3,2-f][1,2,4]triazolo[4,3-a][1,4]diazepin-4-yl)benzyl)-7-azaspiro[3.5]nonan-7-yl)phenyl)-5,6,7,8-tetrahydronaphthalen-2-ol (III-4)

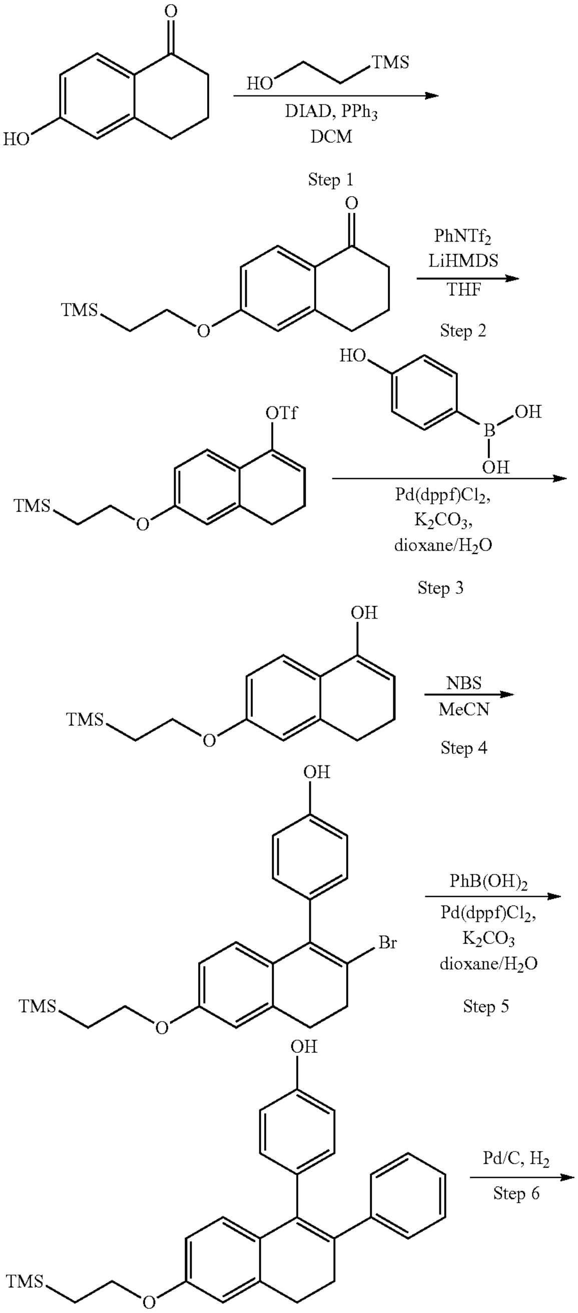

-continued

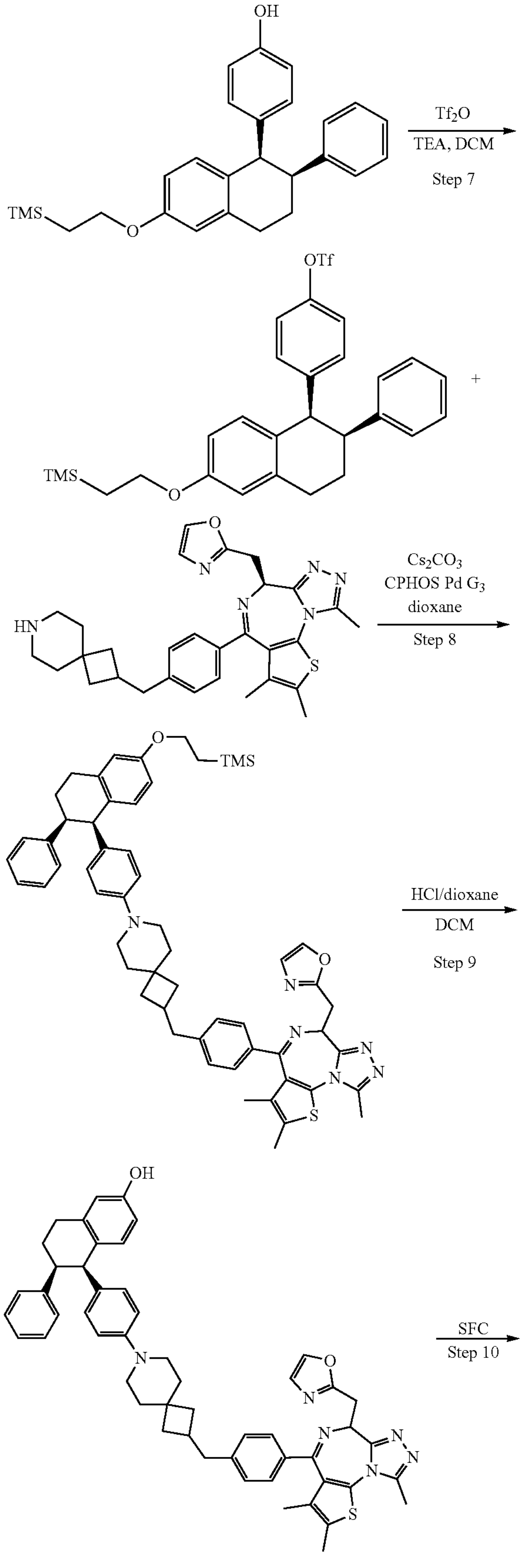

-continued

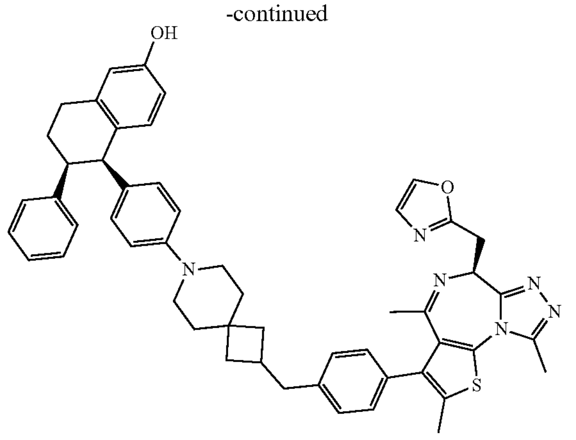

I-62

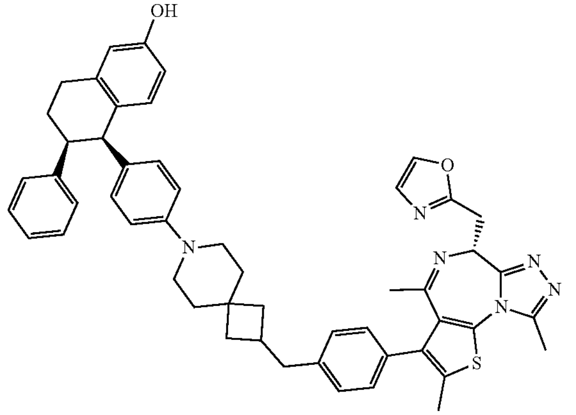

III-4

Step 1: Preparation of 6-(2-trimethylsilylethoxy)tetralin-1-one. To a solution of 6-hydroxytetralin-1-one (21 g, 129.48 mmol, 1 equiv), 2-trimethylsilylethanol (19.14 g, 161.85 mmol, 23.20 mL, 1.25 equiv) and $PPh_3$ (42.45 g, 161.85 mmol, 1.25 equiv) in DCM (210 mL) was added DIAD (32.73 g, 161.85 mmol, 31.38 mL, 1.25 equiv) at −78° C. The mixture was stirred at 40° C. for 12 h. The reaction mixture was partitioned between DCM (100 mL) and $H_2O$ (100 mL). The organic phase was separated, dried over $Na_2SO_4$, filtered and concentrated under reduced pressure to give a residue. The residue was purified by column chromatography ($SiO_2$, petroleum ether/ethyl acetate=10/1 to 3/1). 6-(2-trimethylsilylethoxy) tetralin-1-one (8.4 g, 32.01 mmol, 24% yield) was obtained as a yellow oil. LC-MS: MS ($ES^+$): RT=0.460 min, m/z=265.2 [$M+H^+$].

Step 2: Preparation of [6-(2-trimethylsilylethoxy)-3,4-dihydronaphthalen-1-yl]trifluoromethanesulfonate. To a mixture of 6-(2-trimethylsilylethoxy)tetralin-1-one (10.6 g, 40.39 mmol, 1 equiv) in THF (100 mL) was added LiHMDS (1 M, 60.59 mL, 1.5 equiv) dropwise at −78° C. and the mixture was stirred at −78° C. for 1 h under an $N_2$ atmosphere. Then 1,1,1-trifluoro-N-phenyl-N-(trifluoromethylsulfonyl)methanesulfonamide (15.87 g, 44.43 mmol, 1.1 equiv) in THE (30 mL) was added dropwise to the mixture. The mixture was stirred at 25° C. for 12 h under an $N_2$ atmosphere. The reaction mixture was quenched by the addition of $H_2O$ (100 mL) at 0° C. under an $N_2$ atmosphere, stirred at 0° C. for 20 min and then stirred at 25° C. for 20 min. The reaction mixture was then diluted with $H_2O$ (500 mL) and extracted with EtOAc (500 mL×2). The combined organic layers were washed with brine (300 mL×2), dried over $Na_2SO_4$, filtered and concentrated under reduced pressure to give a residue. The residue was purified by column chromatography ($SiO_2$, petroleum ether/ethyl acetate=20/1 to 3/1) to afford [6-(2-trimethylsilylethoxy)-3,4-dihydronaphthalen-1-yl]trifluoromethanesulfonate (10.5 g, 26.62 mmol, 65% yield) as a white solid. LC-MS: MS ($ES^+$): RT=0.718 min.

Step 3: Preparation of 4-[6-(2-trimethylsilylethoxy)-3,4-dihydronaphthalen-1-yl]phenol. A mixture of [6-(2-trimethylsilylethoxy)-3,4-dihydronaphthalen-1-yl]trifluoromethane sulfonate (6.5 g, 16.48 mmol, 1 equiv), (4-hydroxyphenyl) boronic acid (2.73 g, 19.77 mmol, 1.2 equiv), $K_2CO_3$ (4.55 g, 32.95 mmol, 2 equiv), and Pd(dppf)$Cl_2$ (1.21 g, 1.65 mmol, 0.1 equiv) in dioxane (65 mL) and $H_2O$ (13 mL) was degassed and purged with $N_2$ 3 times, and then the mixture was stirred at 100° C. for 2 hr under an $N_2$ atmosphere. The reaction mixture was filtered and concentrated under reduced pressure to give a residue. The residue was purified by prep-HPLC (column: Phenomenex luna C18 (250×70 mm, 10 um); mobile phase: [water (FA)-ACN]; gradient: 66%-96% B over 21 min) to afford 4-[6-(2-trimethylsilylethoxy)-3,4-dihydronaphthalen-1-yl]phenol (4.1 g, 73% yield) as a white solid. LC-MS: MS ($ES^+$): RT=0.686 min, m/z=339.2 [M+$H^+$].

Step 4: Preparation of 4-[2-bromo-6-(2-trimethylsilylethoxy)-3,4-dihydro naphthalen-1-yl]phenol. To a solution of 4-[6-(2-trimethylsilylethoxy)-3,4-dihydro naphthalen-1-yl]phenol (4.1 g, 12.11 mmol, 1 equiv) in MeCN (40 mL) was added NBS (2.05 g, 11.51 mmol, 0.95 equiv). The mixture was stirred at 20° C. for 2 h. The reaction mixture was partitioned between EA (50 mL) and $H_2O$ (50 mL). The organic phase was separated, filtered and concentrated under reduced pressure to give a residue. The residue was purified by column chromatography ($SiO_2$, petroleum ether/ethyl acetate=10/1 to 3/1) to afford 4-[2-bromo-6-(2-trimethylsilylethoxy)-3,4-dihydronaphthalen-1-yl]phenol (4.3 g, 85% yield) as a white solid. LC-MS: MS ($ES^+$): RT=0.720 min.

Step 5: Preparation of 4-[2-phenyl-6-(2-trimethylsilylethoxy)-3,4-dihydronaphthalen-1-yl]phenol. A mixture of 4-[2-bromo-6-(2-trimethylsilylethoxy)-3,4-dihydronaphthalen-1-yl]phenol (4.3 g, 10.30 mmol, 1 equiv), phenylboronic acid (1.51 g, 12.36 mmol, 1.2 equiv), $K_2CO_3$ (2.85 g, 20.60 mmol, 2 equiv), and Pd(dppf)$Cl_2$ (753.78 mg, 1.03 mmol, 0.1 equiv) in dioxane (50 mL) and $H_2O$ (10 mL) was degassed and purged with $N_2$ 3 times, and then the mixture was stirred at 90° C. for 3 hr under an $N_2$ atmosphere. The reaction mixture was filtered and concentrated under reduced pressure to give a residue. The residue was purified by column chromatography ($SiO_2$, petroleum ether/ethyl acetate=30/1 to 3/1) to afford 4-[2-phenyl-6-(2-trimethylsilylethoxy)-3,4-dihydronaphthalen-1-yl]phenol (4.2 g, 98% yield) as a white solid. LC-MS: MS ($ES^+$): RT=0.793 min, m/z=415.2 [M+$H^+$].

Step 6: Preparation of 4-[(1R,2S)-2-phenyl-6-(2-trimethylsilylethoxy)tetralin-1-yl]phenol. To a hydrogenation vessel filled with $N_2$ was added Pd/C (500 mg, 469.84 mol, 10% purity, 4.64e-2 equiv), followed by 4-[2-phenyl-6-(2-trimethylsilylethoxy)-3,4-dihydronaphthalen-1-yl]phenol (4.2 g, 10.13 mmol, 1 equiv) in MeOH (40 mL). The suspension was degassed and purged with $H_2$ 3 times. The mixture was stirred under $H_2$ (45 psi) at 25° C. for 12 h. The reaction mixture was filtered and concentrated under reduced pressure to give a residue. The residue was purified by prep-HPLC (column: Phenomenex luna C18 150×40 mm×15 um; mobile phase: [water (FA)-ACN]; gradient: 70%-100% B over 15 min) and SFC (column: DAICEL CHIRALPAKAD (250 mm×30 mm×10 um); mobile phase: [$CO_2$-i-PrOH (0.1% $NH_3H_2O$)]; B %: 40%, isocratic elution mode) to afford 4-[(1R,2S)-2-phenyl-6-(2-trimethylsilylethoxy)tetralin-1-yl]phenol (280 mg, 672.07 mol, 6% yield, $[a]_D$: −287.21) as a white solid and 4-[(1S,2R)-2-phenyl-6-(2-trimethylsilylethoxy)tetralin-1-yl]phenol (280 mg, 672.07 μmol, 6% yield, $[a]_D$: +356.42) as a white solid. LC-MS: MS ($ES^+$): RT=0.729 min.

Step 7: Preparation of [4-[(1R,2S)-2-phenyl-6-(2-trimethylsilylethoxy)tetralin-1-yl]phenyl]trifluoromethanesulfonate. To a solution of 4-[(1R,2S)-2-phenyl-6-(2-trimethyl silylethoxy)tetralin-1-yl]phenol (250 mg, 600.06 mol, 1 equiv) in DCM (5 mL) was added $Tf_2O$ (338.60 mg, 1.20 mmol, 198.01 L, 2 equiv) and TEA (182.16 mg, 1.80 mmol, 250.56 μL, 3 equiv). The mixture was stirred at 25° C. for 1 h. The reaction mixture was partitioned between EtOAc (30 mL) and $H_2O$ (30 mL). The organic phase was separated, filtered and concentrated under reduced pressure to give a residue. The residue was purified by prep-TLC ($SiO_2$, PE:EA=5:1) to afford [4-[(1R,2S)-2-phenyl-6-(2-trimethylsilylethoxy) tetralin-1-yl]phenyl]trifluoromethanesulfonate (280 mg, 510.31 mol, 85% yield) as a white solid.

Step 8: Preparation of trimethyl-[2-[(1R,2S)-2-phenyl-1-[4-[2-[[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]methyl]-7-azaspiro[3.5]nonan-7-yl]phenyl]tetralin-6-yl]oxyethyl]silane. To a mixture of 2-[[(9S)-7-[4-(7-azaspiro[3.5]nonan-2-ylmethyl)phenyl]-4,5,13-trimethyl-3-thia-1,8,11,12-tetrazatricyclo[8.3.0.0$^{2,6}$]trideca-2(6),4,7,10,12-pentaen-9-yl]methyl]oxazole (100 mg, 189.86 mol, 1 equiv), [4-[(1R,2S)-2-phenyl-6-(2-trimethylsilyl ethoxy)tetralin-1-yl]phenyl]trifluoromethanesulfonate (125.01 mg, 227.84 mol, 1.2 equiv), $Cs_2CO_3$ (185.58 mg, 569.59 mol, 3 equiv), and CPHOS PD $G_3$ (15.31 mg, 18.99 mol, 0.1 equiv) in dioxane (5 mL) was degassed and purged with $N_2$ 3 times, and then the mixture was stirred at 90° C. for 12 h under an $N_2$ atmosphere. The reaction mixture was partitioned between EA (20 mL) and $H_2O$ (20 mL). The organic phase was separated, filtered and concentrated under reduced pressure to give a residue. The residue was purified by prep-TLC ($SiO_2$, DCM:MeOH=10:1) to afford trimethyl-[2-[(1R,2S)-2-phenyl-1-[4-[2-[[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]methyl]-7-azaspiro[3.5]nonan-7-yl]phenyl]tetralin-6-yl]oxyethyl]silane (80 mg, 45% yield) as a white solid. LC-MS: MS ($ES^+$): RT=0.702 min, m/z=925.6 [M+$H^+$].

Step 9: Preparation of (1R,2S)-2-phenyl-1-[4-[2-[[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]methyl]-7-azaspiro[3.5]nonan-7-yl]phenyl]tetralin-6-ol. To a solution of trimethyl-[2-[(1R,2S)-2-phenyl-1-[4-[2-[[4-[4,5,13-trimethyl-9-(oxazol-2-ylmethyl)-3-thia-1,8,11,12-tetrazatricyclo[8.3.0.0$^{2,6}$]trideca-2(6),4,7,10,12-pentaen-7-yl]phenyl]methyl]-7-azaspiro[3.5]nonan-7-yl]phenyl]tetralin-6-yl]oxyethyl]silane (30 mg, 32.42 mol, 1 equiv) in DCM (3 mL) was added HCl/dioxane (4 M, 3.60 mL, 444.15 equiv). The mixture was stirred at 25° C. for 3 h. The reaction mixture was filtered and concentrated under reduced pressure to give a residue. The residue was purified by prep-HPLC (column: Phenomenex luna C18 150×25 mm×10 um; mobile phase: [water (FA)-ACN]; gradient: 48%-78% B over 9 min) to afford (5R,6S)-6-phenyl-5-(4-(2-(4-(2,3,9-trimethyl-6-(oxazol-2-ylmethyl)-6H-thieno[3,2-f][1,2,4]triazolo[4,3-a][1,4]diazepin-4-yl)benzyl)-7-azaspiro[3.5]nonan-7-yl)phenyl)-5,6,7,8- tetrahydronaphthalen-2-ol (6.76 mg, 25% yield) as a white solid. LC-MS: MS ($ES^+$): RT=0.785 min, m/z=825.5 [$M+H^+$].

Step 10: Preparation of I-62 and III-4. The residue from the prior step was purified by SFC (column: DAICEL CHIRALPAK IC (250 mm×30 mm×10 um); mobile phase: [$CO_2$-ACN/EtOH (0.1% $NH_3H_2O$)]; B %: 75%, isocratic elution mode) to afford compounds I-62 and III-4, each of the two diastereomers of (1R,2S)-2-phenyl-1-[4-[2-[[4-[4,5,13-trimethyl-9-(oxazol-2-ylmethyl)-3-thia-1,8,11,12-tetrazatricyclo[8.3.0.$0^{2,6}$]trideca-2(6),4,7,10,12-pentaen-7-yl]phenyl]methyl]-7-azaspiro[3.5]nonan-7-yl]phenyl]tetralin-6-ol. The diastereomer that was found to be the more potent inhibitor of cell growth of T-Rex 293 cells having increased expression of estrogen receptor alpha protein (as described in the Example 56, below), was obtained as a white solid (6.76 mg, 8.19 mol, 25% yield, 100% purity). $^1$H NMR (400 MHz, $CDCl_3$) δ 7.64 (s, 1H), 7.30 (d, J=8.0 Hz, 2H), 7.17-7.12 (m, 3H), 7.09 (d, J=8.4 Hz, 2H), 7.06 (br s, 1H), 6.84-6.77 (m, 3H), 6.70 (d, J=2.4 Hz, 1H), 6.58 (br dd, J=2.8, 8.1 Hz, 3H), 6.28 (br d, J=8.4 Hz, 2H), 4.75-4.70 (m, 1H), 4.20 (br d, J=4.4 Hz, 1H), 4.14-4.03 (m, 2H), 3.41-3.26 (m, 1H), 3.10-2.87 (m, 6H), 2.71 (br d, J=7.6 Hz, 2H), 2.68 (s, 3H), 2.50-2.44 (m, 1H), 2.41 (s, 3H), 2.26-2.08 (m, 1H), 1.92-1.86 (m, 2H), 1.83-1.78 (m, 1H), 1.67 (s, 3H), 1.50-1.39 (m, 4H), 1.27 (s, 2H). LCMS ($ES^+$): RT=2.165 min, m/z=825.3 [$M+H^+$]; LCMS Method: 10.

Example 40—Synthesis of 3-(2,6-difluoro-4-(2-(2-(4-((S)-2,3,6,9-tetramethyl-6H-thieno[3,2-f][1,2,4]triazolo[4,3-a][1,4]diazepin-4-yl)phenoxy)ethoxy)ethoxy)phenyl)-4-methyl-2-phenyl-2H-chromen-6-ol (I-39) As a Mixture of Stereoisomer I and II

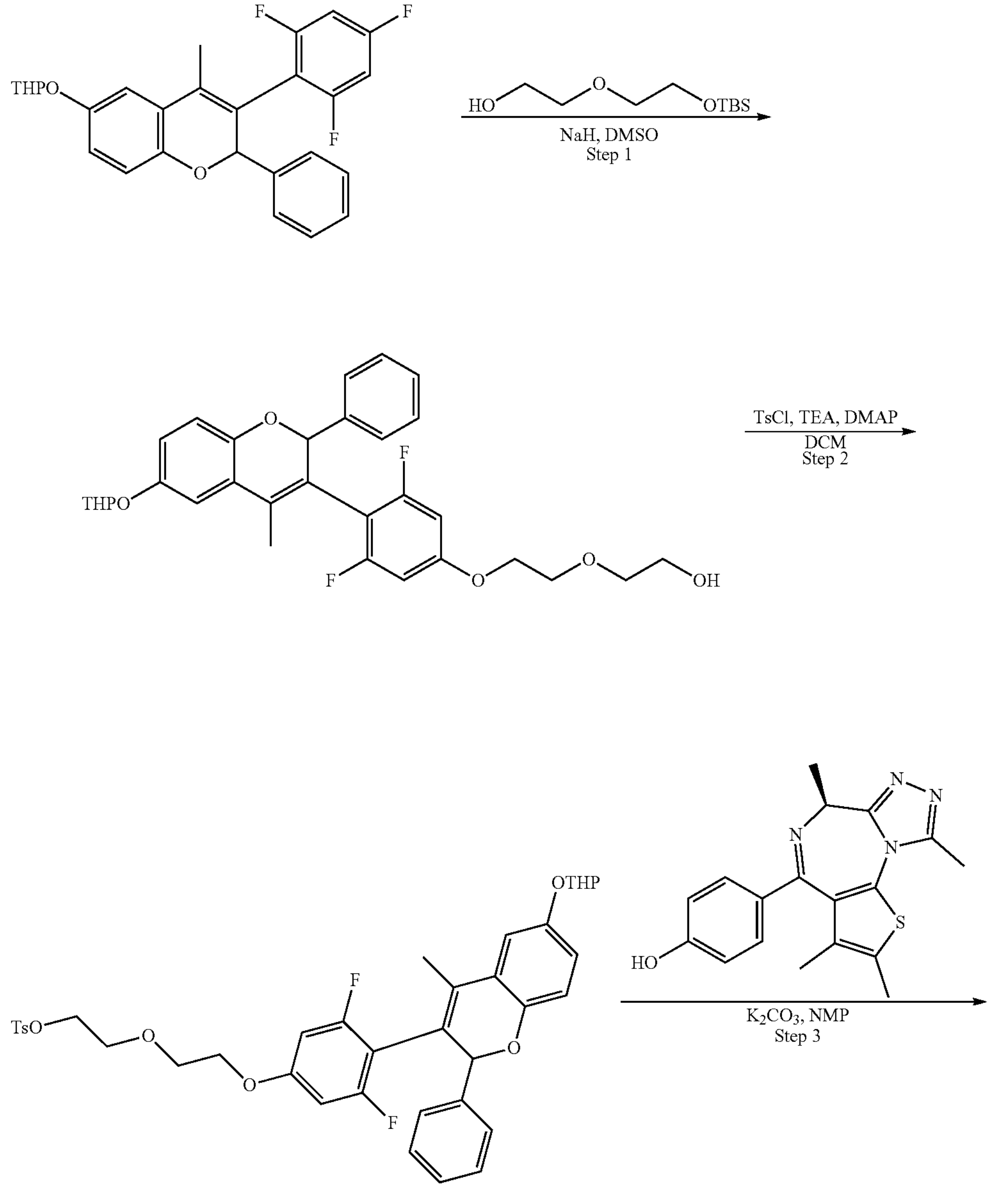

-continued

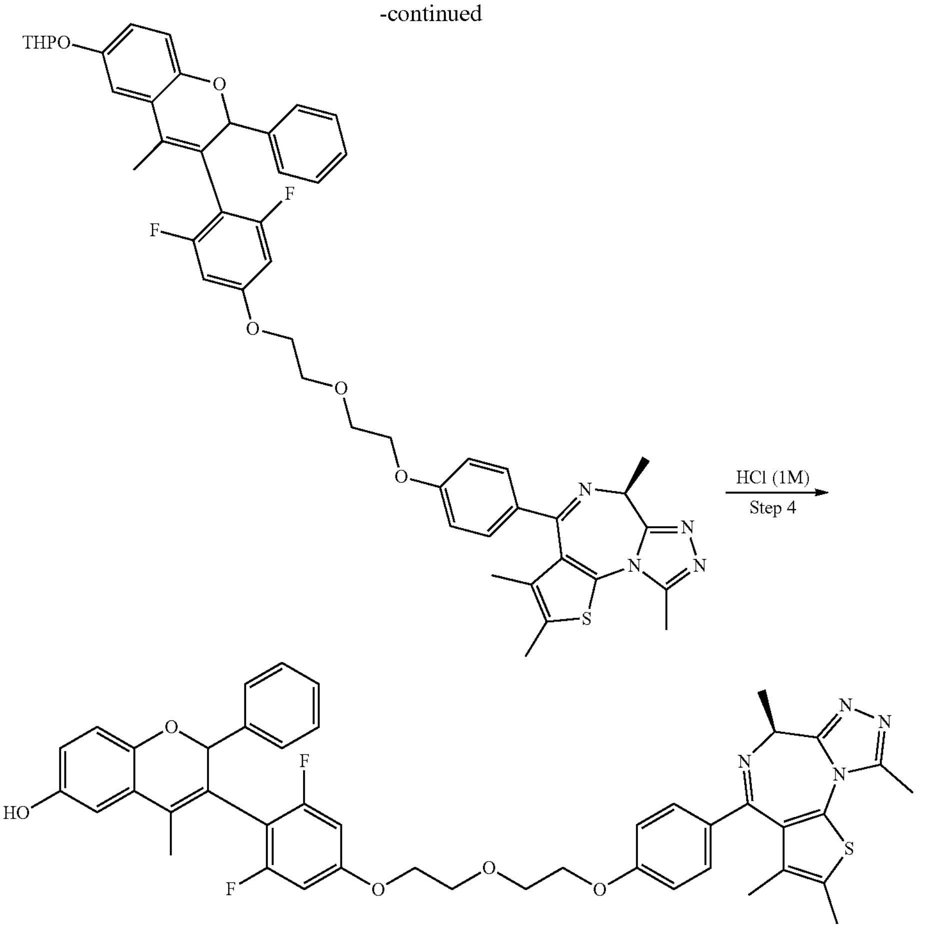

I-39

Step 1: Preparation of 2-[2-[3,5-difluoro-4-(4-methyl-2-phenyl-6-tetrahydro pyran-2-yloxy-2H-chromen-3-yl)phenoxy]ethoxy]ethanol. To a solution of 2-[2-[tert-butyl(dimethyl)silyl]oxyethoxy]ethanol (97.41 mg, 0.44 mmol, 2 equiv) in DMSO (3 mL) was added NaH (17.68 mg, 0.4 mmol, 60% purity, 2 equiv) at 20° C. and the reaction mixture was stirred for 0.5 h. Then 4-methyl-2-phenyl-6-tetrahydropyran-2-yloxy-3-(2,4,6-trifluoro phenyl)-2H-chromene (100 mg, 0.2 mmol, 1 equiv) was added and the mixture was stirred at 60° C. for 2.5 h. The reaction mixture was quenched by the addition of water (50 mL) and then the reaction mixture was diluted with water (20 mL) and extracted with ethyl acetate (20 mL×3). The combined organic layers were washed with brine (20 mL×3), dried over anhydrous $Na_2SO_4$, filtered and concentrated under reduced pressure to give a residue. The residue was purified by column chromatography ($SiO_2$, petroleum ether/ethyl acetate=1/1) to afford 2-[2-[3,5-difluoro-4-(4-methyl-2-phenyl-6-tetrahydropyran-2-yloxy-2H-chromen-3-yl)phenoxy]ethoxy]ethanol (52 mg, 42% yield) as a yellow solid. LC-MS: MS ($ES^+$): RT=0.645 min, m/z=561.2 [$M+Na^+$].

Step 2: Preparation of 2-(2-(3,5-difluoro-4-(4-methyl-2-phenyl-6-((tetrahydro-2H-pyran-2-yl)oxy)-2H-chromen-3-yl)phenoxy)ethoxy)ethyl 4-methylbenzenesulfonate. To a solution of 2-[2-[3,5-difluoro-4-(4-methyl-2-phenyl-6-tetrahydropyran-2-yloxy-2H-chromen-3-yl)phenoxy]ethoxy]ethanol (140 mg, 0.26 mmol, 1 equiv) in DCM (3 mL) was added TosCl (99.12 mg, 0.5 mmol, 2 equiv), DMAP (3.18 mg, 0.025 mmol, 0.1 equiv) and TEA (78.91 mg, 0.78 mmol, 3 equiv). The mixture was stirred at 20° C. for 12 hr. The reaction mixture was diluted with water (20 mL) and extracted with ethyl acetate (20 mL×3). The combined organic layers were washed with brine (10 mL×3), dried over anhydrous $Na_2SO_4$, filtered and concentrated under reduced pressure to give a residue. The residue was purified by prep-TLC ($SiO_2$, petroleum ether/ethyl acetate=1/1) to afford 2-(2-(3,5-difluoro-4-(4-methyl-2-phenyl-6-((tetrahydro-2H-pyran-2-yl)oxy)-2H-chromen-3-yl)phenoxy)ethoxy)ethyl 4-methylbenzenesulfonate (135 mg, 60% yield) as a yellow solid. LC-MS: MS ($ES^+$): RT=0.703 min, m/z=691.3 [$M-H^+$].

Step 3: Preparation of (6S)-4-(4-(2-(2-(3,5-difluoro-4-(4-methyl-2-phenyl-6-((tetrahydro-2H-pyran-2-yl)oxy)-2H-chromen-3-yl)phenoxy)ethoxy)ethoxy)phenyl)-2,3,6,9-tetramethyl-6H-thieno[3,2-f][1,2,4]triazolo[4,3-a][1,4]diazepine. To a solution of 2-[2-[3,5-difluoro-4-(4-methyl-2-phenyl-6-tetrahydropyran-2-yloxy-2H-chromen-3-yl)phenoxy]ethoxy]ethyl 4-methylbenzenesulfonate (150 mg, 0.21 mmol, 1 equiv) and 4-[(9S)-4,5,9,13-tetramethyl-3-thia-1,8,11,12-tetrazatricyclo[8.3.0.$0^{2,6}$]trideca-2(6),4,7,10,12-pentaen-7-yl]phenol (73.28 mg, 0.21 mmol, 1 equiv) in DMF (3 mL) was added $K_2CO_3$ (89.77 mg, 0.64 mmol, 3 equiv). The mixture was stirred at 120° C. for 12 hr. The reaction mixture was diluted with water (20 mL) and extracted with ethyl acetate (20 mL×3). The combined organic layers were washed with brine (10 mL×3), dried over anhydrous $Na_2SO_4$, filtered and concentrated under reduced pressure to give a residue. The residue was purified by prep-TLC ($SiO_2$, DCM/MeOH=10/1) to afford (6S)-4-(4-(2-(2-(3,5-difluoro-4-(4-methyl-2-phenyl-6-((tetrahydro-2H-pyran-2-yl)oxy)-2H-chromen-3-yl)phenoxy)ethoxy) ethoxy)phenyl)-2,3,6,9-tetramethyl-6H-thieno[3,2-f][1,2,4] triazolo[4,3-a][1,4]diazepine (110 mg, 57% yield) as a white solid. LC-MS: MS ($ES^+$): RT=0.643 min, m/z=859.3 $[M+H^+]$ Step 4: Preparation of 3-(2,6-difluoro-4-(2-(2-(4-((S)-2,3, 6,9-tetramethyl-6H-thieno[3,2-f][1,2,4]triazolo[4,3-a][1,4] diazepin-4-yl)phenoxy)ethoxy)ethoxy)phenyl)-4-methyl-2-phenyl-2H-chromen-6-ol. To a solution of (9S)-7-[4-[2-[2-[3,5-difluoro-4-(4-methyl-2-phenyl-6-tetrahydropyran-2-yloxy-2H-chromen-3-yl)phenoxy]ethoxy]ethoxy]phenyl]-4, 5,9,13-tetramethyl-3-thia-1,8,11,12-tetrazatricyclo[8.3.0.02, 6]trideca-2(6),4,7,10,12-pentaene (100 mg, 0.11 mmol, 1 equiv) in dioxane (3 mL) was added HCl (1 M, 2 mL, 17.18 equiv). The mixture was stirred at 20° C. for 1 hr. The reaction mixture was concentrated under reduced pressure to remove solvent. The residue was purified by prep-HPLC (column: YMC-Actus Triart C18 150 mm×30 mm×7 um; mobile phase: [water (FA)-ACN]; gradient: 53%-83% B over 10 min) to afford 3-(2,6-difluoro-4-(2-(2-(4-((S)-2,3,6, 9-tetramethyl-6H-thieno [3,2-f][1,2,4]triazolo[4,3-a][1,4]diazepin-4-yl)phenoxy)ethoxy)ethoxy) phenyl)-4-methyl-2-phenyl-2H-chromen-6-ol (I-39, 42.73 mg, 44% yield) as a mixture of stereoisomers, which were a white solid. $^1H$ NMR (400 MHz, DMSO-d6) 7.50-7.39 (m, 2H), 7.31 (t, J=6.0 Hz, 2H), 7.24-7.07 (m, 4H), 7.05-6.98 (m, 1H), 6.92-6.81 (m, 3H), 6.75-6.66 (m, 1H), 6.49-6.26 (m, 2H), 6.06-5.86 (m, 1H), 5.35-5.25 (m, 1H), 4.22-4.11 (m, 3H), 4.10-3.93 (m, 4H), 3.93-3.80 (m, 3H), 3.75-3.53 (m, 2H), 2.69 (s, 3H), 2.41 (s, 3H), 2.11 (d, J=6.4 Hz, 3H), 2.01-1.93 (m, 3H), 1.91-1.79 (m, 3H), 1.72-1.70 (m, 2H), 1.68 (d, J=7.6 Hz, 2H). LC-MS: MS ($ES^+$): RT=2.121 min, m/z=775.5 $[M+H^+]$; LCMS Method: 25.

Example 41—Synthesis of 4-((4-(3,5-difluoro-4-((1S,2S)-2-(4-fluorophenyl)-6-hydroxy-1,2,3,4-tetrahydronaphthalen-1-yl)phenyl)piperidin-1-yl) methyl)-1-(4-((6S)-2,3,6,9-tetramethyl-6H-thieno[3, 2-f][1,2,4]triazolo[4,3-a][1,4]diazepin-4-yl)phenyl) piperidin-4-ol (III-245) and 4-((4-(3,5-difluoro-4-((1R,2R)-2-(4-fluorophenyl)-6-hydroxy-1,2,3,4-tetrahydronaphthalen-1-yl)phenyl)piperidin-1-yl) methyl)-1-(4-((6S)-2,3,6,9-tetramethyl-6H-thieno[3, 2-f][1,2,4]triazolo[4,3-a][1,4]diazepin-4-yl)phenyl) piperidin-4-ol (III-244)

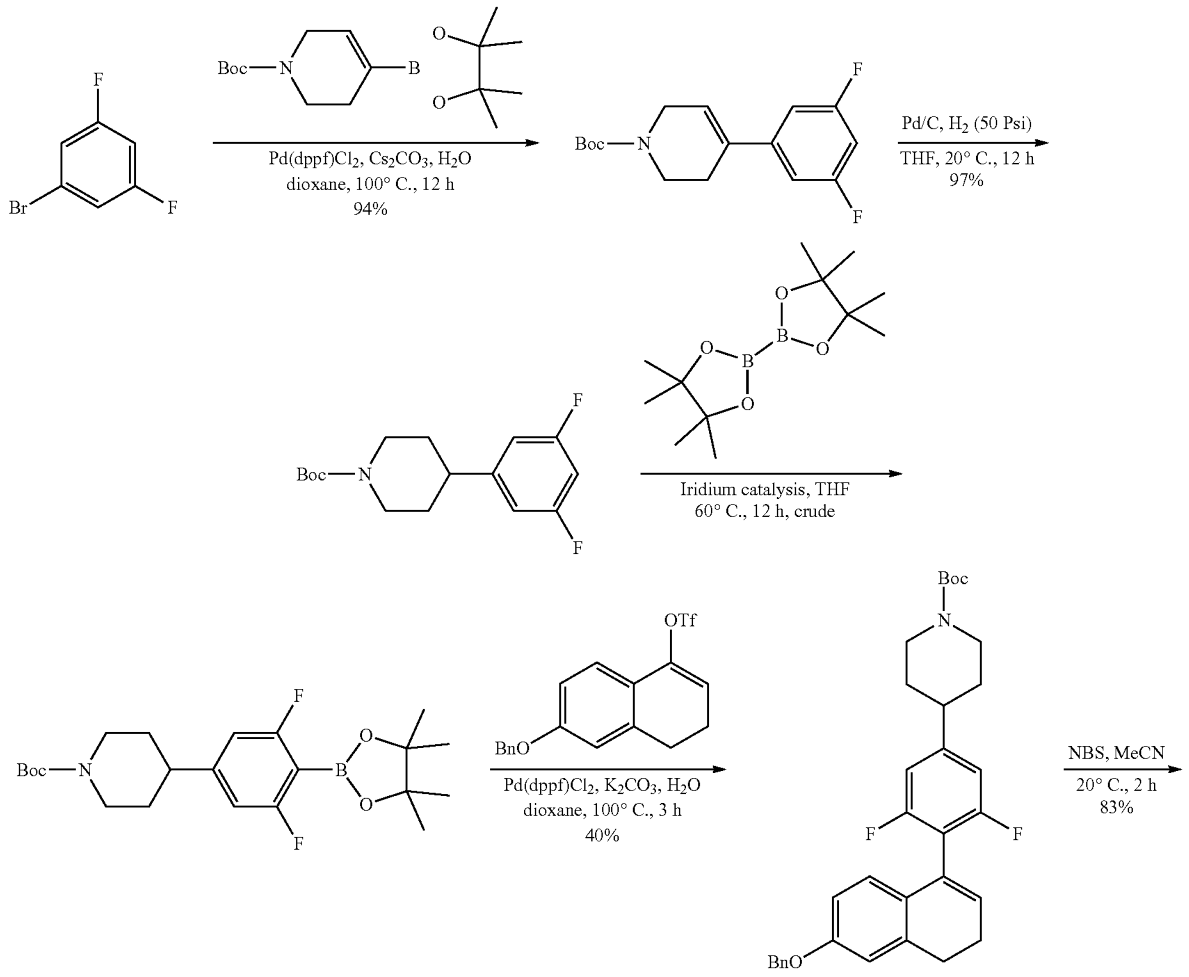

-continued
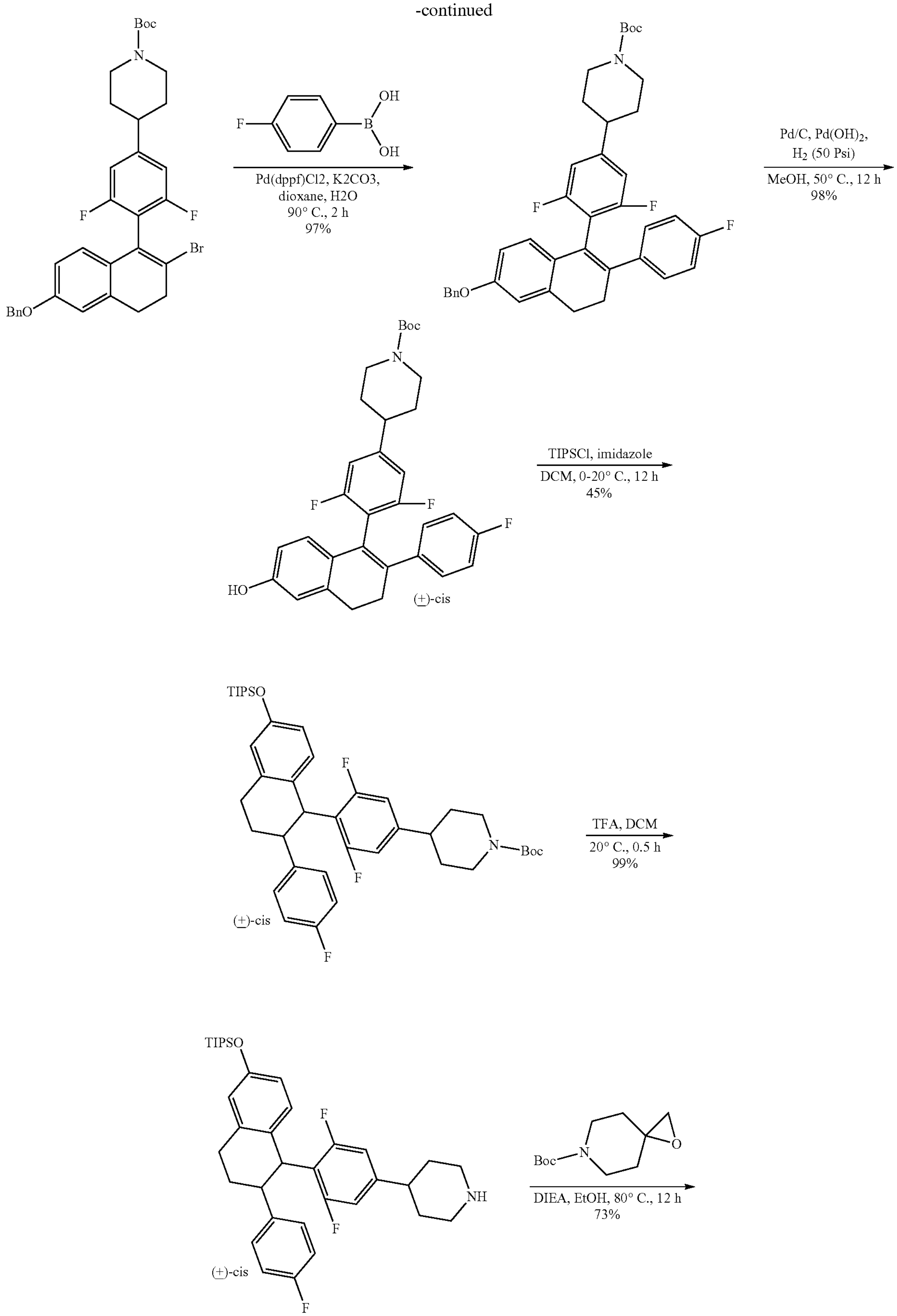

-continued
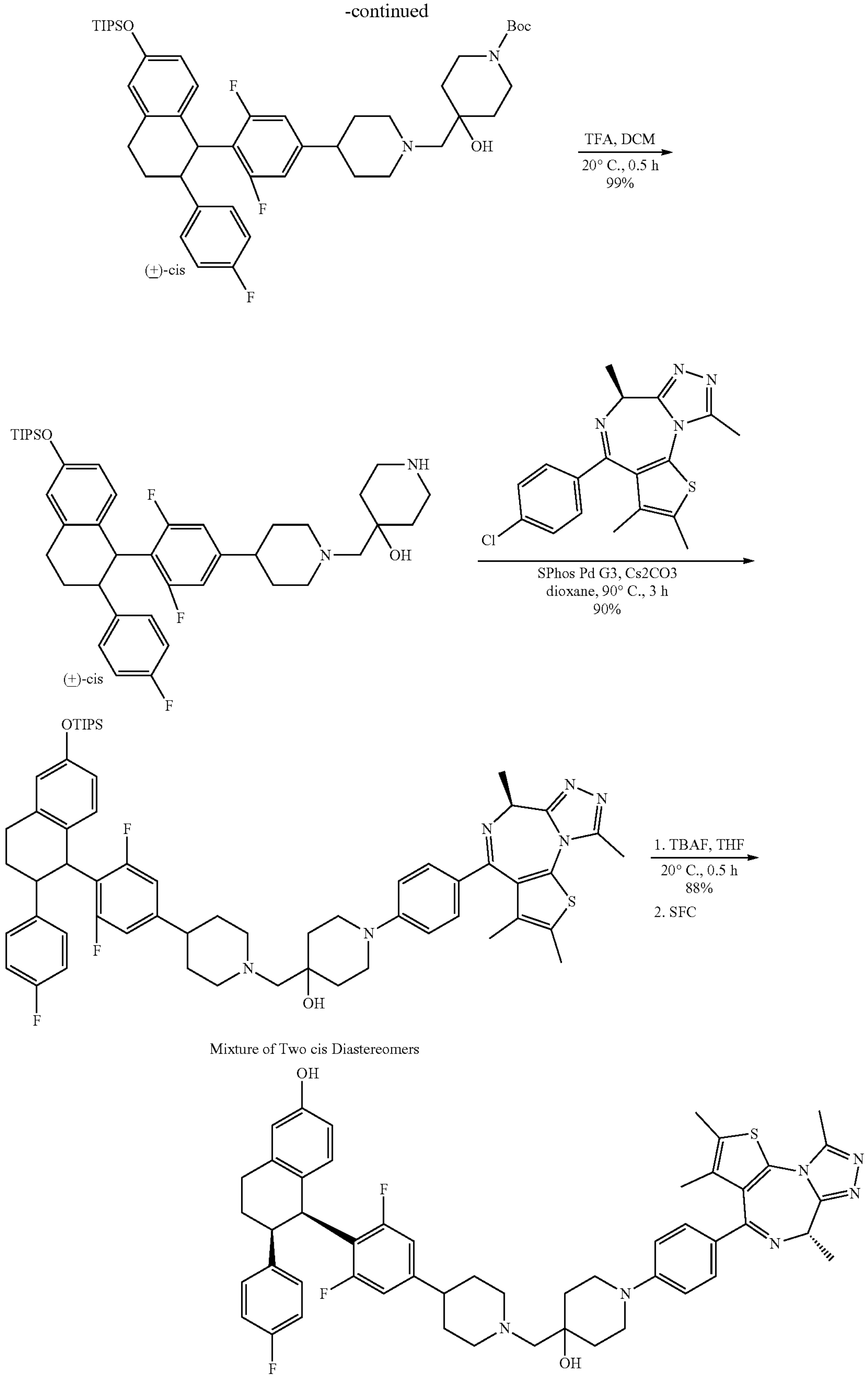
III-245

-continued

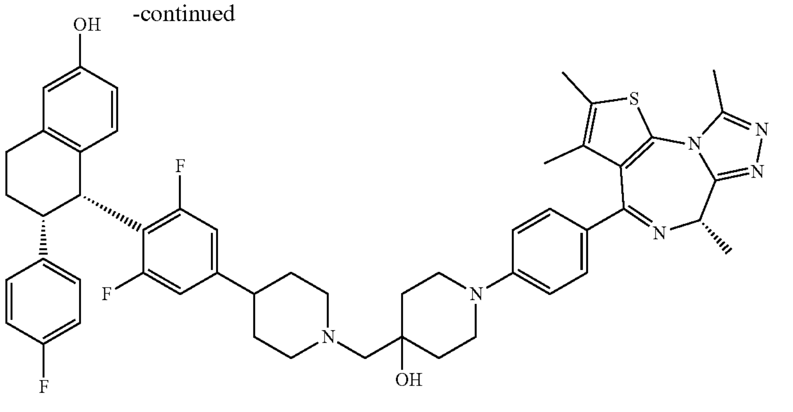

III-244

Step 1: A mixture of 1-bromo-3,5-difluoro-benzene (9 g, 46.63 mmol, 5.37 mL, 1 equiv), tert-butyl 4-(4,4,5,5-tetramethyl-1,3,2-dioxaborolan-2-yl)-3,6-dihydro-2H-pyridine-1-carboxylate (17.30 g, 55.96 mmol, 1.2 equiv), $Cs_2CO_3$ (45.58 g, 139.90 mmol, 3 equiv), and Pd(dppf)$Cl_2$ (3.41 g, 4.66 mmol, 0.1 equiv) in dioxane (200 mL) and $H_2O$ (40 mL) was degassed and purged with $N_2$ for 3 times, and then the mixture was stirred at 100° C. for 12 h under $N_2$ atmosphere. The reaction mixture was filtered and concentrated under reduced pressure to give a residue. The residue was purified by prep-TLC ($SiO_2$, PE:EA=3:1) to afford tert-butyl 4-(3,5-difluorophenyl)-3,6-dihydro-2H-pyridine-1-carboxylate (13 g, 94% yield) as a yellow oil. LC-MS: MS (ES): RT=0.903 min, m/z=240.4 [M−55]; LCMS method 5-95.

Step 2: A mixture of tert-butyl 4-(3,5-difluorophenyl)-3,6-dihydro-2H-pyridine-1-carboxylate (13 g, 44. mmol, 1 equiv) and Pd/C (4.68 g, 4.40 mmol, 10% purity, 0.1 equiv) in THF (130 mL) was degassed and purged with $H_2$ for 3 times, and then the mixture was stirred at 20° C. for 12 h under $H_2$ atmosphere. The reaction mixture was filtered and concentrated under reduced pressure to afford tert-butyl 4-(3,5-difluorophenyl)piperidine-1-carboxylate (12.7 g, 97% yield) as a yellow oil. LC-MS: MS ($ES^+$): RT=0.922 min, m/z=242.2 [M−55]; LCMS method 5-95.

Step 3: A mixture of tert-butyl 4-(3,5-difluorophenyl) piperidine-1-carboxylate (4 g, 13.45 mmol, 1 equiv), 4,4,5,5-tetramethyl-2-(4,4,5,5-tetramethyl-1,3,2-dioxaborolan-2-yl)-1,3,2-dioxaborolane (5.12 g, 20.18 mmol, 1.5 equiv), 3,4,7,8-tetramethyl-1,10-phenanthroline (317 mg, 1.35 mmol, 0.1 equiv), and (1Z,5Z)-cycloocta-1,5-diene; 2,4-dimethyl-BLAHbicyclo[1.1.0]butane (445 mg, 672 mol, 0.05 equiv) in THF (45 mL) was degassed and purged with $N_2$ for 3 times, and then the mixture was stirred at 60° C. for 12 h under $N_2$ atmosphere. The reaction mixture was filtered, and the filtrate was concentrated to give crude compound as a yellow solid. The crude product tert-butyl 4-[3,5-difluoro-4-(4,4,5,5-tetramethyl-1,3,2-dioxaborolan-2-yl)phenyl]piperidine-1-carboxylate (5.6 g, crude) was used in the next step without further purification. LC-MS: MS ($ES^+$): RT=0.993 min, m/z=368.1 [M−55]; LCMS method 5-95.

Step 4: A mixture of (6-benzyloxy-3,4-dihydronaphthalen-1-yl) trifluoromethanesulfonate (4.24 g, 11.02 mmol, 1 equiv), tert-butyl 4-[3,5-difluoro-4-(4,4,5,5-tetramethyl-1,3,2-dioxaborolan-2-yl)phenyl]piperidine-1-carboxylate (5.6 g, 13.23 mmol, 1.2 equiv), Pd(dppf)$Cl_2$ (806 mg, 1.10 mmol, 0.1 equiv), and $K_2CO_3$ (4.57 g, 33.07 mmol, 3 equiv) in dioxane (50 mL) and $H_2O$ (12 mL) was degassed and purged with $N_2$ for 3 times, and then the mixture was stirred at 100° C. for 3 h under $N_2$ atmosphere. The reaction mixture was filtered and concentrated in vacuum. The residue was purified by prep-TLC (SiO2, PE:EA=3:1) to afford tert-butyl 4-[4-(6-benzyloxy-3,4-dihydronaphthalen-1-yl)-3,5-difluoro-phenyl]piperidine-1-carboxylate (2.3 g, 39% yield) as a yellow solid. LC-MS: MS ($ES^+$): RT=1.090 min, m/z=476.1 [M−55]; LCMS method 5-95.

Step 5: To a solution of tert-butyl 4-[4-(6-benzyloxy-3,4-dihydronaphthalen-1-yl)-3,5-difluoro-phenyl]piperidine-1-carboxylate (2.3 g, 4.33 mmol, 1 equiv) in MeCN (20 mL) was added NBS (770 mg, 4.33 mmol, 1 equiv). The mixture was stirred at 20° C. for 2 h. The reaction mixture was partitioned between ethyl acetate 100 mL and water 50 mL. The organic phase was separated, filtered and concentrated under reduced pressure to give a residue. The residue was purified by silica column chromatography on silica gel (Petroleum ether: Ethyl acetate from 1/0 to 3/1) to afford tert-butyl 4-[4-(6-benzyloxy-2-bromo-3,4-dihydronaphthalen-1-yl)-3,5-difluoro-phenyl]piperidine-1-carboxylate (2.2 g, 83% yield) as a yellow oil. LC-MS: MS ($ES^+$): RT=1.223 min, m/z=554.2 [M−55]; LCMS method 5-95.

Step 6: A mixture of (4-fluorophenyl)boronic acid (504 mg, 3.60 mmol, 1.1 equiv), tert-butyl 4-[4-(6-benzyloxy-2-bromo-3,4-dihydronaphthalen-1-yl)-3, 5-difluoro-phenyl] piperidine-1-carboxylate (2 g, 3.28 mmol, 1 equiv), Pd(dppf)$Cl_2$ (239 mg, 327 mol, 0.1 equiv), and $K_2CO_3$ (1.13 g, 8.19 mmol, 2.5 equiv) in dioxane (30 mL) and $H_2O$ (3 mL) was degassed and purged with $N_2$ for 3 times, and then the mixture was stirred at 90° C. for 2 h under $N_2$ atmosphere. The reaction mixture was filtered and concentrated under reduced pressure to give a residue. The residue was purified by silica gel column chromatography (Petroleum ether: Ethyl acetate from 1/0 to 3/1) to afford tert-butyl 4-[4-[6-benzyloxy-2-(4-fluorophenyl)-3,4-dihydronaphthalen-1-yl]-3,5-difluoro-phenyl]piperidine-1-carboxylate (2 g, 97% yield) as a yellow solid. $^1H$ NMR (400 MHz, CDCl3) δ=7.47-7.34 (m, 5H), 7.10-7.01 (m, 2H), 6.94-6.79 (m, 3H), 6.79-6.55 (m, 4H), 5.08 (s, 2H), 4.38-4.13 (m, 2H), 3.03 (t, J=7.8 Hz, 2H), 2.92-2.70 (m, 4H), 2.69-2.53 (m, 1H), 1.90-1.75 (m, 2H), 1.68-1.58 (m, 2H), 1.50 (s, 9H). LC-MS: MS ($ES^+$): RT=1.238 min, m/z=526.3 [M−100]; LCMS method 5-95.

Step 7: To a solution of tert-butyl 4-[4-[6-benzyloxy-2-(4-fluorophenyl)-3,4-dihydronaphthalen-1-yl]-3,5-difluoro-phenyl]piperidine-1-carboxylate (2 g, 3.20 mmol, 1 equiv)

in MeOH (30 mL) was added Pd/C (680 mg, 639 mol, 10% purity, 0.2 equiv) and $Pd(OH)_2$ (448 mg, 639 mol, 20% purity, 0.2 equiv) under $H_2$ atmosphere. The suspension was degassed and purged with $H_2$ for 3 times. The mixture was stirred under $H_2$ (50 Psi.) at 50° C. for 12 h. The reaction mixture was filtered, and the filtrate was concentrated. The residue was purified by silica gel column chromatography (Petroleum ether: Ethyl acetate from 1/0 to 3/1) to afford (±)-cis-tert-butyl 4-[3,5-difluoro-4-[2-(4-fluorophenyl)-6-hydroxy-tetralin-1-yl]phenyl]piperidine-1-carboxylate (1.7 g, 98% yield) as a yellow oil. LC-MS: MS ($ES^+$): RT=1.098 min, m/z=482.3 [M−55]; LCMS method 5-95.

Step 8: To a solution of (i)-cis-tert-butyl 4-[3,5-difluoro-4-[2-(4-fluorophenyl)-6-hydroxy-tetralin-1-yl]phenyl]piperidine-1-carboxylate (1.7 g, 3.16 mmol, 1 equiv) in DCM (20 mL) was added TIPSCl (1.22 g, 6.32 mmol, 1.35 mL, 2 equiv) and imidazole (645.81 mg, 9.49 mmol, 3 equiv) at 0° C. The mixture was stirred at 20° C. for 12 h. The reaction mixture was partitioned between DCM 200 mL and water 100 mL. The organic phase was separated, filtered and concentrated under reduced pressure to give a residue. The residue was purified by silica gel column chromatography (Petroleum ether: Ethyl acetate from 1/0 to 3/1) to afford (±)-cis-tert-butyl 4-[3,5-difluoro-4-[2-(4-fluorophenyl)-6-triisopropylsilyloxy-tetralin-1-yl]phenyl]piperidine-1-carboxylate (1 g, 45% yield) as a yellow oil. LC-MS: MS ($ES^+$): RT=1.280 min, m/z=594.4 [M−100]; LCMS method 5-95.

Step 9: To a solution of (i)-cis-tert-butyl 4-[3,5-difluoro-4-[2-(4-fluorophenyl)-6-triisopropylsilyloxy-tetralin-1-yl] phenyl]piperidine-1-carboxylate (1 g, 1.44 mmol, 1 equiv) in DCM (6 mL) was added TFA (2.30 g, 20.19 mmol, 1.50 mL, 14.01 equiv). The mixture was stirred at 20° C. for 0.5 h. The reaction mixture was partitioned between DCM 100 mL and water 50 mL. The organic phase was separated, filtered and concentrated under reduced pressure to afford (±)-cis-[1-[2,6-difluoro-4-(4-piperidyl)phenyl]-2-(4-fluorophenyl)tetralin-6-yl]oxy-triisopropyl-silane (855 mg, 99% yield) as a yellow oil. LC-MS: MS ($ES^+$): RT=0.954 min, m/z=594.4 [$M+H^+$]; LCMS method 5-95.

Step 10: To a solution of (i)-cis-[1-[2,6-difluoro-4-(4-piperidyl)phenyl]-2-(4-fluorophenyl)tetralin-6-yl]oxy-triisopropyl-silane (1.7 g, 2.86 mmol, 1 equiv) in EtOH (20 mL) was added DIEA (1.11 g, 8.59 mmol, 1.50 mL, 3 equiv) and tert-butyl 1-oxa-6-azaspiro[2.5]octane-6-carboxylate (915 mg, 4.29 mmol, 1.5 equiv. The mixture was stirred at 80° C. for 12 h. The reaction mixture was filtered and concentrated under reduced pressure to give a residue. The residue was purified by silica gel column chromatography (Petroleum ether: Ethyl acetate from 1/0 to 3/1) to afford (±)-cis-tert-butyl 4-[[4-[3,5-difluoro-4-[2-(4-fluorophenyl) -6-triisopropylsilyloxy-tetralin-1-yl]phenyl]-1-piperidyl] methyl]-4-hydroxy-piperidine-1-carboxylate (1.7 g, 73% yield) as a yellow oil. $^1H$ NMR (400 MHz, $CDCl_3$) δ=7.10-7.01 (m, 1H), 6.93-6.72 (m, 5H), 6.69-6.65 (m, 1H), 6.63-6.57 (m, 1H), 6.51-6.41 (m, 1H), 4.03-3.60 (m, 4H), 3.50-3.40 (m, 2H), 3.23-3.13 (m, 2H), 3.01-2.91 (m, 3H), 2.62-2.22 (m, 6H), 1.85-1.78 (m, 2H), 1.51-1.46 (m, 18H), 1.15-1.09 (m, 18H). LC-MS: MS ($ES^+$): RT=1.012 min, m/z=807.5 [$M+H^+$]; LCMS method 5-95.

Step 11: To a solution of (i)-cis-tert-butyl 4-[[4-[3,5-difluoro-4-[2-(4-fluorophenyl)-6-triisopropylsilyloxy-tetralin-1-yl]phenyl]-1-piperidyl]methyl]-4-hydroxy-piperidine-1-carboxylate (1 g, 1.24 mmol, 1 equiv) in DCM (5 mL) was added TFA (3.84 g, 33.66 mmol, 2.5 mL, 27.16 equiv). The mixture was stirred at 20° C. for 0.5 h. The reaction mixture was partitioned between DCM 100 mL and $NaHCO_3$ 50 mL. The organic phase was separated, filtered and concentrated under reduced pressure to afford (±)-cis-4-[[4-[3,5-difluoro-4-[2-(4-fluorophenyl)-6-triisopropylsilyloxy-tetralin-1-yl] phenyl]-1-piperidyl]methyl]piperidin-4-ol (875 mg, 99% yield) as a yellow oil. LC-MS: MS ($ES^+$): RT=0.876 min, m/z=707.2 [$M+H^+$]; LCMS method: 5-95.

Step 12: A mixture of (9S)-7-(4-chlorophenyl)-4,5,9,13-tetramethyl-3-thia-1,8,11,12-tetrazatricyclo[8.3.0.0$^{2,6}$]trideca-2(6),4,7,10,12-pentaene (326 mg, 913.49 mol, 1 equiv), (±)-cis-4-[[4-[3,5-difluoro-4-[2-(4-fluorophenyl)-6-triisopropylsilyloxy-tetralin-1-yl]phenyl]-1-piperidyl] methyl]piperidin-4-ol (775 mg, 1.10 mmol, 1.2 equiv), $Cs_2CO_3$ (892 mg, 2.74 mmol, 3 equiv) and SPhos Pd $G_3$ (71 mg, 91 mol, 0.1 equiv) in dioxane (10 mL) was degassed and purged with $N_2$ for 3 times, and then the mixture was stirred at 90° C. for 3 h under $N_2$ atmosphere. The reaction mixture was filtered and concentrated under reduced pressure to give a residue. The residue was purified by silica gel column chromatography (Petroleum ether: Ethyl acetate from 1/0 to 3/1) to afford a mixture of the two cis-tetraline diastereomers of 4-[[4-[3,5-difluoro-4-[2-(4-fluorophenyl)-6-triisopropylsilyloxy-tetralin-1-yl]phenyl]-1-piperidyl]methyl]-1-[4-[(9S)-4,5,9,13-tetramethyl-3-thia-1,8,11,12-tetrazatricyclo [8.3.0.0$^{2,6}$]trideca-2(6),4,7,10,12-pentaen-7-yl]phenyl] piperidin-4-ol (850 mg, 90% yield) as a yellow solid. LC-MS: MS ($ES^+$): RT=0.927 min, m/z=1026.9 [$M+H^+$]; LCMS method 5-95.

Step 13: To a solution of the two cis-tetraline diastereomers of 4-[[4-[3,5-difluoro-4-[2-(4-fluorophenyl)-6-triisopropylsilyloxy-tetralin-1-yl]phenyl]-1-piperidyl]methyl]-1-[4-[(9S)-4,5,9,13-tetramethyl-3-thia-1,8,11,12-tetrazatricyclo [8.3.0.0$^{2,6}$]trideca-2(6),4,7,10,12-pentaen-7-yl]phenyl] piperidin-4-ol (400 mg, 389 mol, 1 equiv) in THF (5 mL) was added TBAF (1 M, 1.00 mL, 2.57 equiv). The mixture was stirred at 20° C. for 0.5 h. The reaction mixture was partitioned between EA 100 mL and water 50 mL. The organic phase was separated, filtered and concentrated under reduced pressure to give a residue. The residue was purified by prep-TLC ($SiO_2$, DCM:MeOH=10:1) to afford a mixture of the two cis-tetraline diastereomers of 4-[[4-[3,5-difluoro-4-[2-(4-fluorophenyl)-6-hydroxy-tetralin-1-yl]phenyl]-1-piperidyl]methyl]-1-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]piperidin-4-ol (300 mg, 88% yield) as a yellow solid. LC-MS: MS ($ES^+$): RT=0.761 min, m/z=871.3 [$M+H^+$]; LCMS method: 5-95.

Step 14: A mixture of the two cis-tetraline diastereomers of 4-[[4-[3,5-difluoro-4-[2-(4-fluorophenyl)-6-hydroxy-tetralin-1-yl]phenyl]-1-piperidyl]methyl]-1-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]piperidin-4-ol (300 mg, 344 mol) was purified by prep-SFC (column: DAICEL CHIRALPAK AD (250 mm*30 mm, 10 um); mobile phase: [CO2-ACN/i-PrOH (0.1% NH3H2O)]; B %: 65%, isocratic elution mode) and (column: DAICEL CHIRALPAK IG (250 mm*30 mm, 10 um); mobile phase: [CO2-ACN/EtOH (0.1% NH3H2O)]; B %: 65%, isocratic elution mode) to afford compounds III-245 and III-244. The second-eluting diastereomer, which was found to be the more potent inhibitor of cell growth of T-Rex 293 cells having increased expression of estrogen receptor alpha protein (as described in the Example 56, below), was obtained as a yellow solid (45 mg, 16% yield). $^1H$ NMR (400 MHz, CDCl3) δ=7.30 (d, J=8.8 Hz, 2H), 6.83-6.75 (m, 4H), 6.74-6.69 (m, 3H), 6.62 (d, J=2.4 Hz, 1H), 6.55-6.47 (m, 1H), 6.45-6.27 (m, 2H), 4.57 (d, J=5.6 Hz, 1H), 4.07 (d, J=6.8 Hz, 1H), 3.57-3.45 (m, 2H), 3.37-3.27 (m, 1H), 3.26-3.14 (m, 2H), 2.99-2.91 (m, 3H), 2.59 (s, 3H), 2.47-2.37 (m, 2H), 2.34 (s, 3H), 2.29-2.20 (m, 2H), 2.00 (d, J=6.8 Hz, 3H), 1.84-1.76 (m, 2H), 1.69 (s, 3H), 1.65-1.45 (m, 10H). LC-MS: MS ($ES^+$): RT=1.530 min, m/z=871.3 [$M+H^+$]; LCMS method 25.

Example 42—Synthesis of 4-((4-(2-fluoro-4-((1R,2S)-2-(4-fluorophenyl)-6-hydroxy-1,2,3,4-tetrahydronaphthalen-1-yl)phenyl)piperazin-1-yl)methyl)-1-(4-((S)-2,3,6,9-tetramethyl-6H-thieno[3,2-f][1,2,4]triazolo[4,3-a][1,4]diazepin-4-yl)phenyl)piperidin-4-ol (III-251) and 4-((4-(2-fluoro-4-((1S,2R)-2-(4-fluorophenyl)-6-hydroxy-1,2,3,4-tetrahydronaphthalen-1-yl)phenyl)piperazin-1-yl)methyl)-1-(4-((S)-2,3,6,9-tetramethyl-6H-thieno[3,2-f][1,2,4]triazolo[4,3-a][1,4]diazepin-4-yl)phenyl)piperidin-4-ol (III-250)
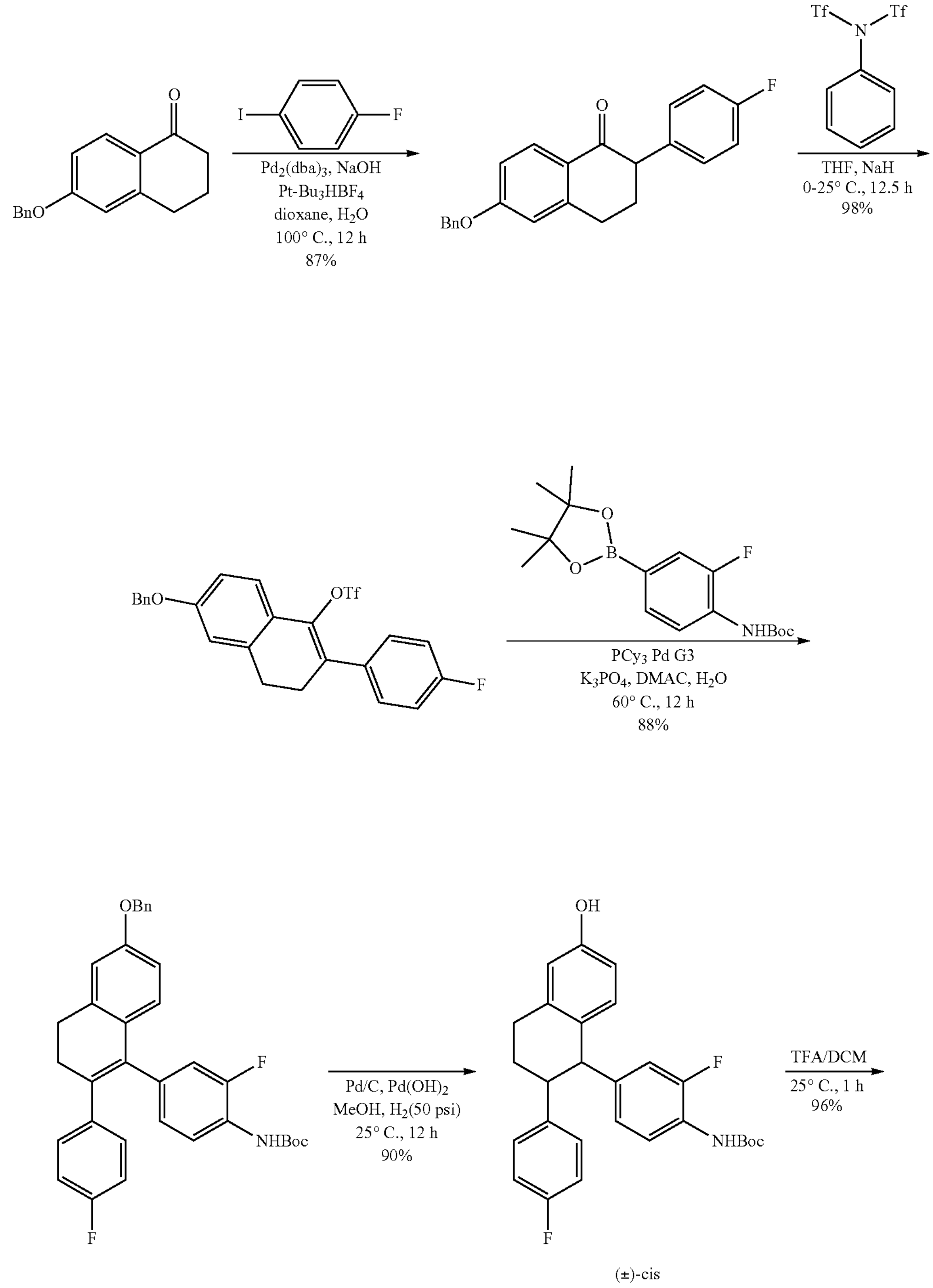

-continued
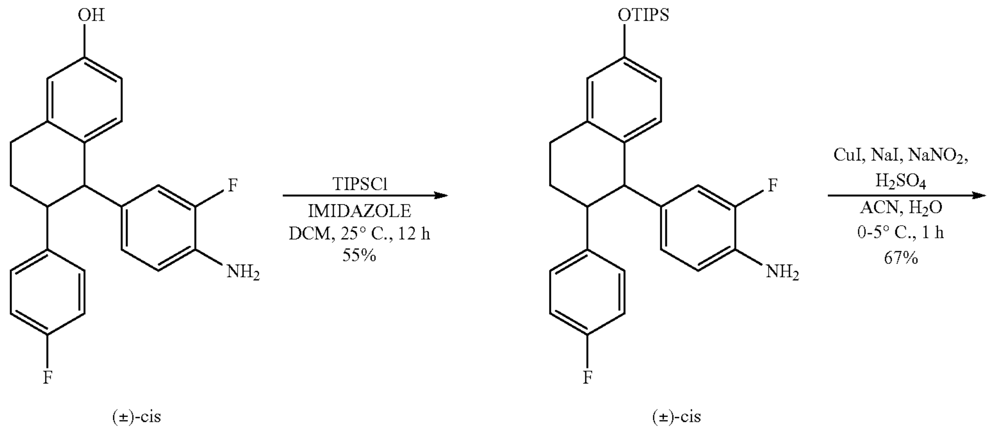
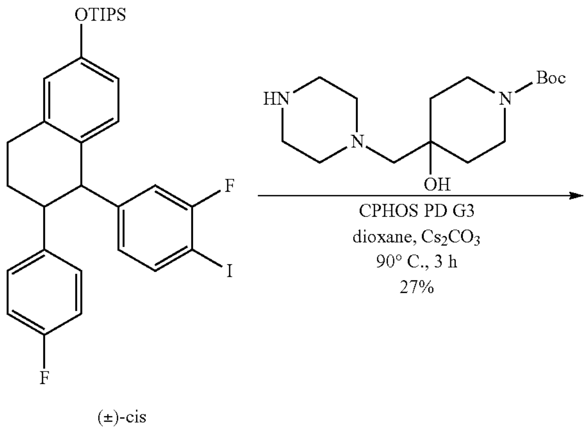
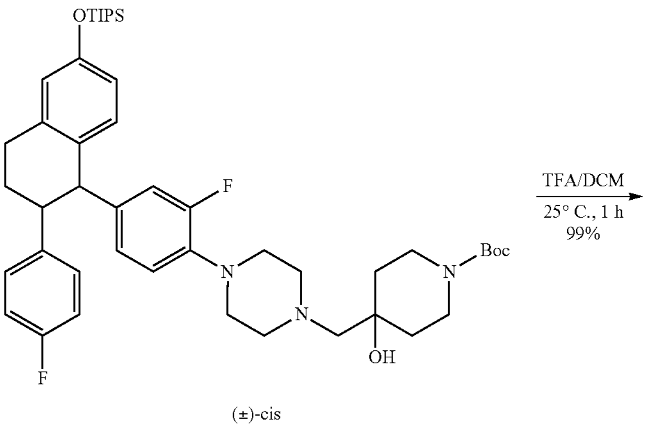

-continued
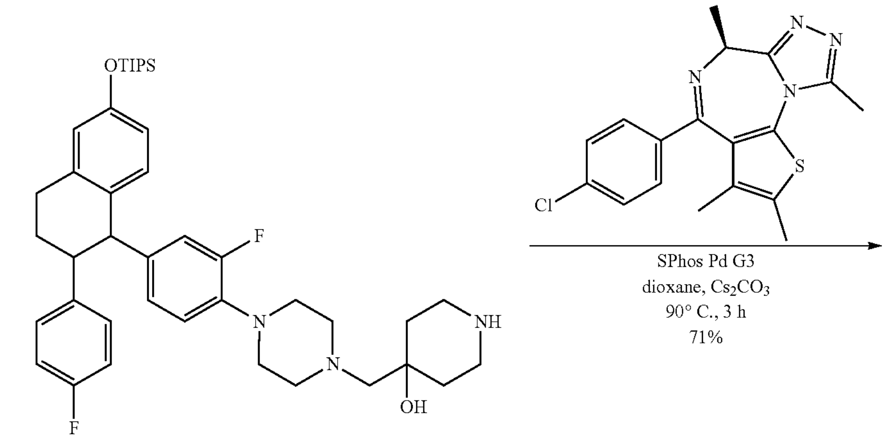
(±)-cis
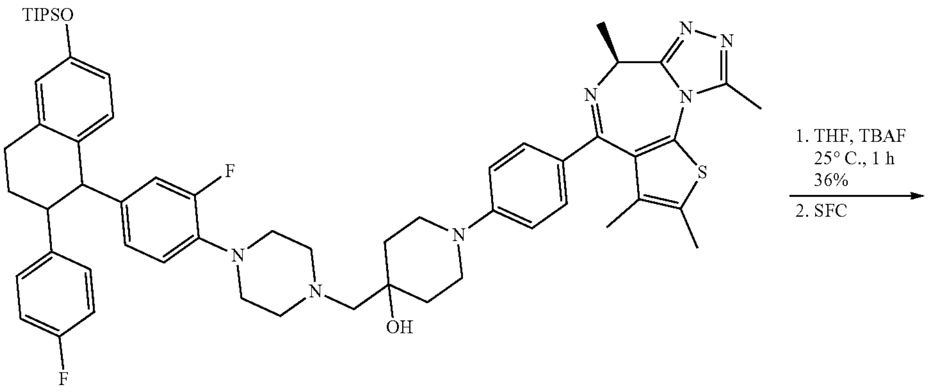
Mixture of Two cis Diastereomers
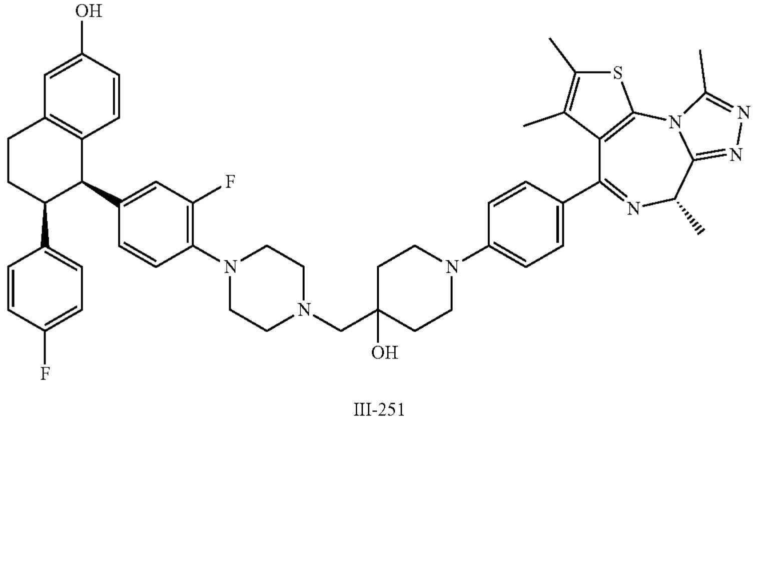
III-251

-continued

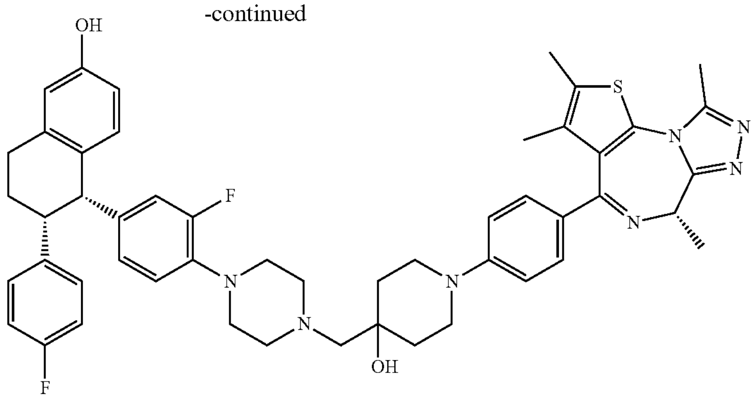

III-250

Step 1: To a solution of 6-benzyloxytetralin-1-one (10 g, 39.63 mmol, 1.0 equiv) in dioxane (200 mL) and $H_2O$ (50 mL) was added 1-fluoro-4-iodo-benzene (10.56 g, 47.56 mmol, 5.48 mL, 1.2 equiv), tritert-butylphosphonium tetrafluoroborate (2.30 g, 7.93 mmol, 0.2 equiv), $Pd_2(dba)_3$ (3.63 g, 3.96 mmol, 0.1 equiv) and NaOH (3.17 g, 79.27 mmol, 2.0 equiv). The mixture was stirred at 100° C. for 12 h. The reaction mixture was diluted with $H_2O$ 100 mL and extracted with EA 150 mL (50 mL*3). The combined organic layers were washed with saturated NaCl aqueous (20 mL*2), dried over $Na_2SO_4$, filtered and concentrated under reduced pressure to give a residue. The residue was purified by column chromatography ($SiO_2$, Petroleum ether/Ethyl acetate=1/0 to 1/1) to give 6-benzyloxy-2-(4-fluorophenyl)tetralin-1-one (12 g, 87% yield) as a brown solid. $^1H$ NMR (400 MHz, CDCl3) δ 8.12-8.05 (m, 1H), 7.49-7.34 (m, 5H), 7.21-7.12 (m, 2H), 7.08-6.99 (m, 2H), 6.97-6.92 (m, 1H), 6.85-6.80 (m, 1H), 5.15 (s, 2H), 3.88-3.65 (m, 1H), 3.20-2.91 (m, 2H), 2.49-2.30 (m, 2H). LC-MS: MS ($ES^+$): RT=0.667 min, m/z=347.1 [$M+H^+$]; LCMS Method: 5-95.

Step 2: To a mixture of 6-benzyloxy-2-(4-fluorophenyl) tetralin-1-one (4.6 g, 13.28 mmol, 1.0 equiv) in THE (50 mL) was added NaH (1.06 g, 26.56 mmol, 60% purity, 2.0 equiv) at 0° C. for 0.5 h under $N_2$ atmosphere. Then 1,1,1-trifluoro-N-phenyl-N-(trifluoromethylsulfonyl) methanesulfonamide (13.05 g, 36.52 mmol, 2.75 equiv) was added to the mixture. The mixture was stirred at 25° C. for 12.5 h under $N_2$ atmosphere. The reaction mixture was quenched by addition saturated $NH_4Cl$ (20 mL) under $N_2$ atmosphere, and then extracted with EA (30 mLx3). The combined organic layers were dried over $Na_2SO_4$ and concentrated under reduced pressure to give a residue. The residue was purified by column chromatography ($SiO_2$, PE/EA=100/1 to 1/1) to give [6-benzyloxy-2-(4-fluorophenyl)-3,4-dihydronaphthalen-1-yl]trifluoromethanesulfonate (10 g, 98% yield, 62% purity) as a yellow solid. $^1H$ NMR (400 MHz, $CDCl_3$) δ 7.64-7.51 (m, 3H), 7.44-7.41 (m, 5H), 7.15-7.08 (m, 2H), 6.95-6.86 (m, 2H), 5.11 (s, 2H), 3.09-2.93 (m, 2H), 2.82-2.74 (m, 2H).

Step 3: To a solution of [6-benzyloxy-2-(4-fluorophenyl)-3,4-dihydronaphthalen-1-yl]trifluoromethanesulfonate (8.70 g, 11.27 mmol, 1.0 equiv) in DMAC (225 mL) and $H_2O$ (45 mL) was added tert-butyl N-[2-fluoro-4-(4,4,5,5-tetramethyl1,3,2-dioxaborolan-2-yl)phenyl]carbamate (3.8 g, 11.27 mmol, 1.0 equiv), [2-(2-aminophenyl)phenyl]-methylsulfonyloxypalladium; dichloromethane; tricyclohexylphosphane (828.41 mg, 1.13 mmol, 0.1 equiv) and $K_3PO_4$ (7.18 g, 33.81 mmol, 3.0 equiv). The mixture was stirred at 60° C. for 12 h. The reaction mixture was diluted with $H_2O$ 150 mL and extracted with EA (50 mL*3). The combined organic layers were washed with saturated NaCl aqueous (50 mL*2), dried over $Na_2SO_4$, filtered and concentrated under reduced pressure to give a residue. The residue was purified by column chromatography ($SiO_2$, Petroleum ether/Ethyl acetate=1/0 to 1/1) to give tert-butyl N-[4-[6-benzyloxy-2-(4-fluorophenyl)-3,4-dihydronaphthalen-1-yl]-2-fluoro-phenyl]carbamate (5.33 g, 88% yield) as a yellow solid. LC-MS: MS ($ES^+$): RT=1.227 min, m/z=562.3 [$M+Na^+$]; LCMS Method: 5-95.

Step 4: To a solution of tert-butyl N-[4-[6-benzyloxy-2-(4-fluorophenyl)-3,4-dihydronaphthalen-1-yl]-2-fluorophenyl]carbamate (5.3 g, 9.82 mmol, 1.0 equiv) in MeOH (60 mL) was added Pd/C (500 mg, 470 mol, 10% purity, 0.1 equiv) and $Pd(OH)_2$ (500 mg, 712 mol, 20% purity, 0.1 equiv) under $N_2$ atmosphere. The suspension was degassed and purged with $H_2$ for 3 times. The mixture was stirred under $H_2$ (50 psi) at 25° C. for 12 h. The reaction mixture was filtered and concentrated under reduced pressure to give (±)-cis-tert-butyl 3-[(4-methoxycarbonylcyclohexyl) methyl]azetidine-1-carboxylate (4 g, 90% yield) as a white solid. LC-MS: MS ($ES^+$): RT=0.670 min, m/z=474.2 [$M+Na^+$]; LCMS Method: 5-95.

Step 5: To a solution of (i)-cis-tert-butyl N-[2-fluoro-4-[2-(4-fluorophenyl)-6-hydroxy-tetralin-1-yl]phenyl]carbamate (2 g, 4.43 mmol, 1.0 equiv) in DCM (20 mL) was added TFA (3.07 g, 26.92 mmol, 2 mL, 6.08 equiv). The mixture was stirred at 25° C. for 1 h. The reaction mixture was added $NaHCO_3$ to adjust pH>7. To the reaction mixture was added water (2 mL) and the mixture was extracted with DCM (30 mL). The combined organic phase was washed with brine (3 mLx3), dried over anhydrous $Na_2SO_4$, filtered and concentrated in vacuum give (i)-cis-1-(4-amino-3-fluoro-phenyl)-2-(4-fluorophenyl)tetralin-6-ol (1.5 g, 96% yield) as a white oil. LC-MS: MS ($ES^+$): RT=0.813 min, m/z=352.3 [$M+H^+$]; LCMS Method: 5-95.

Step 6: To a solution of (i)-cis-1-(4-amino-3-fluoro-phenyl)-2-(4-fluorophenyl)tetralin-6-ol (1.5 g, 4.27 mmol, 1.0 equiv) in DCM (15 mL) was added TIPSCl (2.47 g, 12.81 mmol, 2.74 mL, 3.0 equiv) and imidazole (1.45 g, 21.34 mmol, 5.0 equiv). The mixture was stirred at 25° C. for 12 h. The reaction mixture was quenched by addition $Na_2SO_3$ (5 mL) at 0° C., and then diluted with $H_2O$ 10 mL and extracted with EA 30 mL (10 mL*3). The combined organic layers were washed with saturated NaCl aqueous 30 mL (10 mL*3), dried over $Na_2SO_4$, filtered and concentrated under reduced pressure to give a residue. The residue was purified by column chromatography ($SiO_2$, Petroleum ether/Ethyl acetate=1/0 to 1/1) to give (±)-cis-2-fluoro-4-[2-(4-fluorophenyl)-6-triisopropylsilyloxy-tetralin-1-yl]aniline (1.2 g, 2.36 mmol, 55% yield) as a white oil. $^1H$ NMR (400 MHz, $CDCl_3$) δ 6.93-6.84 (m, 2H), 6.81-6.74 (m, 4H), 6.67-6.61 (m, 1H), 6.45-6.38 (m, 1H), 6.11-6.03 (m, 1H), 5.98-5.92

(m, 1H), 4.17-4.10 (m, 1H), 3.39-3.29 (m, 1H), 3.06-2.95 (m, 2H), 2.20-2.05 (m, 1H), 1.86-1.72 (m, 1H), 1.33-1.23 (m, 3H), 1.20-1.05 (m, 18H). LC-MS: MS ($ES^+$): RT=0.916 min, m/z=508.3 [$M+H^+$]; LCMS Method: 5-95.

Step 7: To a solution of (i)-cis-2-fluoro-4-[2-(4-fluorophenyl)-6-triisopropylsilyloxy-tetralin-1-yl]aniline (1 g, 1.97 mmol, 1.0 equiv) in THE (20 mL) was added $NaNO_2$ (271.78 mg, 3.94 mmol, 2.0 equiv) in $H_2O$ (1 mL). Then was added $H_2SO_4$ (2 M, 2.95 mL, 3.0 equiv) at 0-5° C., the mixture was stirred at this temperature for 0.5 h. Then NaI (1.48 g, 9.85 mmol, 5.0 equiv) in $H_2O$ (2.5 mL) was added into the mixture. Then mixture was stirred at 0-5° C. for 0.5 hr. Then the reaction mixture was added $NaHCO_3$ to adjust pH>7. Then the reaction mixture was added water (2 mL) and was extracted with DCM (5 mL). The combined organic phase was washed with brine (3 mL×3), dried over anhydrous $Na_2SO_4$, filtered and concentrated in vacuum to give a residue. The residue was purified by column chromatography ($SiO_2$, Petroleum ether/Ethyl acetate=1/0 to 1/1) to give (±)-cis-[1-(3-fluoro-4-iodo-phenyl)-2-(4-fluorophenyl) tetralin-6-yl]oxy-triisopropyl-silane (820 mg, 67% yield) as a white solid. LC-MS: MS ($ES^+$): RT=1.280 min, m/z=619.2 [$M+H^+$]; LCMS Method: 5-95.

Step 8: To a solution of (i)-cis-[1-(3-fluoro-4-iodo-phenyl)-2-(4-fluorophenyl)tetralin-6-yl]oxy-triisopropyl-silane (700 mg, 1.13 mmol, 1.0 equiv) in dioxane (15 mL) was added tert-butyl 4-hydroxy-4-(piperazin-1-ylmethyl)piperidine-1-carboxylate (677.60 mg, 2.26 mmol, 2.0 equiv), CPhos Pd G3 (182.49 mg, 226 mol, 0.2 equiv) and $Cs_2CO_3$ (1.11 g, 3.39 mmol, 3.0 equiv). The mixture was stirred at 90° C. for 3 h. The reaction mixture was filtered and concentrated under reduced pressure to give a residue. The residue was purified by column chromatography (SiO2, Petroleum ether/Ethyl acetate=100/1 to 0/1) to give (±)-cis-tert-butyl 4-[[4-[2-fluoro-4-[2-(4-fluorophenyl)-6-triisopropylsilyloxytetralin-1-yl]phenyl]piperazin-1-yl]methyl]-4-hydroxy-piperidine-1-carboxylate (240 mg, 27% yield) as a white solid. LC-MS: MS ($ES^+$): RT=1.073 min, m/z=790.6 [$M+H^+$]; LCMS Method: 5-95.

Step 9: To a solution of (i)-cis-tert-butyl 4-[[4-[2-fluoro-4-[2-(4-fluorophenyl)-6-triisopropylsilyloxy-tetralin-1-yl] phenyl]piperazin1-yl]methyl]-4-hydroxy-piperidine-1-carboxylate (240 mg, 304 mol, 1.0 equiv) in DCM (2 mL) was added TFA (307.00 mg, 2.69 mmol, 0.2 mL, 8.86 equiv). The mixture was stirred at 25° C. for 1 h. The reaction mixture was added $NaHCO_3$ to adjust pH>7. To the reaction mixture was added water (2 mL) and the mixture was extracted with DCM (5 mL). The combined organic phase was washed with brine (3 mL×3), dried over anhydrous $Na_2SO_4$, filtered and concentrated in vacuum to give (±)-cis-4-[[4-[2-fluoro-4-[2-(4-fluorophenyl)-6-triisopropylsilyloxy-tetralin-1-yl]phenyl]piperazin-1-yl]methyl]piperidin-4-ol (209 mg, 99% yield) as a white solid. LC-MS: MS ($ES^+$): RT=0.711 min, m/z=690.4 [$M+H^+$]; LCMS Method: 5-95.

Step 10: To a solution of (i)-cis-4-[[4-[2-fluoro-4-[2-(4-fluorophenyl)-6-triisopropylsilyloxy-tetralin-1-yl]phenyl] piperazin-1-yl]methyl]piperidin-4-ol (209 mg, 308 mol, 1.0 equiv) in dioxane (8 mL) was added (9S)-7-(4-chlorophenyl)-4,5,9,13-tetramethyl-3-thia-1,8,11,12-tetrazatricyclo [$8.3.0.0^{2,6}$]trideca-2(6),4,7,10,12-pentaene (110 mg, 308 mol, 1.0 equiv), SPhos Pd G3 (48 mg, 63 mol, 0.2 equiv) and $Cs_2CO_3$ (301 mg, 925 mol, 3.0 equiv). The mixture was stirred at 90° C. for 3 h. The reaction mixture was filtered and concentrated under reduced pressure to give a residue. The residue was purified by prep-TLC ($SiO_2$, DCM: MeOH=10:1) to give a mixture of the two cis-tetraline diastereomers of 4-[[4-[2-fluoro-4-[2-(4-fluorophenyl)-6-triisopropylsilyloxytetralin-1-yl]phenyl]piperazin-1-yl] methyl]-1-[4-[(9S)-4,5,9,13-tetramethyl-3-thia1,8,11,12-tetrazatricyclo[$8.3.0.0^{2,6}$]trideca-2(6),4,7,10,12-pentaen-7-yl]phenyl]piperidin-4-ol (210 mg, 71% yield) as a yellow solid. LC-MS: MS ($ES^+$): RT=0.703 min, m/z=1010.3 [$M+H^+$]; LCMS Method: 5-95.

Step 11: To a solution of the two cis-tetraline diastereomers of 4-[[4-[2-fluoro-4-[2-(4-fluorophenyl)-6-triisopropylsilyloxy-tetralin-1-yl]phenyl]piperazin-1-yl]methyl]-1-[4-[(9S)-4,5,9,13-tetramethyl-3-thia-1,8,11,12-tetrazatricyclo [$8.3.0.0^{2,6}$]trideca-2(6),4,7,10,12-pentaen-7-yl]phenyl] piperidin-4-ol (210 mg, 208 mol, 1.0 equiv) in THE (1 mL) was added TBAF (1 M, 208 L, 1.0 equiv). The mixture was stirred at 25° C. for 2 h. The reaction mixture was filtered and concentrated under reduced pressure to give a residue. The residue was purified by prep-TLC (SiO2, DCM: MeOH=10:1) and SFC (Column: Chiralcel OD-350×4.6 mm I.D., 3 um Mobile phase: Phase A for CO2, and Phase B for IPA+ACN (0.05% DEA); Gradient elution: 40% IPA+ACN (0.05% DEA) in CO2 Flow rate: 3 mL/min; Detector: PDA; Column Temp: 35C; Back Pressure: 100 Bar) to give III-251 and III-250. The second-eluting diastereomer, which was found to be the more potent inhibitor of cell growth of T-Rex 293 cells having increased expression of estrogen receptor alpha protein (as described in the Example 56, below), was obtained as a white solid (65.43 mg, 36% yield, 98.86% purity). $^1H$ NMR (400 MHz, $CDCl_3$) δ 7.42-7.35 (m, 2H), 6.95-6.82 (m, 4H), 6.81-6.70 (m, 4H), 6.65-6.49 (m, 2H), 6.17-6.06 (m, 2H), 4.19-4.10 (m, 2H), 3.3.63-3.52 (m, 2H), 3.39-3.31 (m, 1H), 3.30-3.19 (m, 2H), 3.09-2.93 (m, 6H), 2.86-2.75 (m, 4H), 2.67 (s, 3H), 2.41 (s, 5H), 2.14-2.05 (m, 4H), 1.77 (s, 6H), 1.70-1.66 m, 2H). LCMS: MS ($ES^+$): RT=1.493 min, m/z=854.3 [$M+H^+$]. LCMS Method: 25.

Example 43—Synthesis of 4-((4-(4-((1S,2S)-2-(4-fluorophenyl)-6-hydroxy-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-276) and 4-((4-(4-((1R,2R)-2-(4-fluorophenyl)-6-hydroxy-1,2,3,4-tetrahydronaphthalen-1-yl)-3-methoxyphenyl) piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-275)

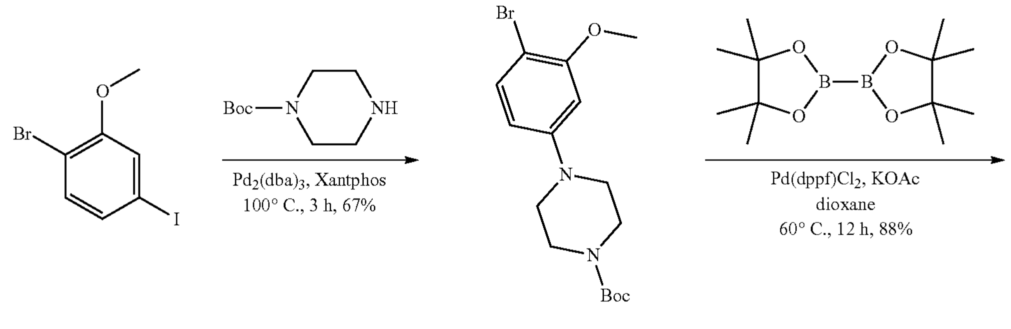

-continued
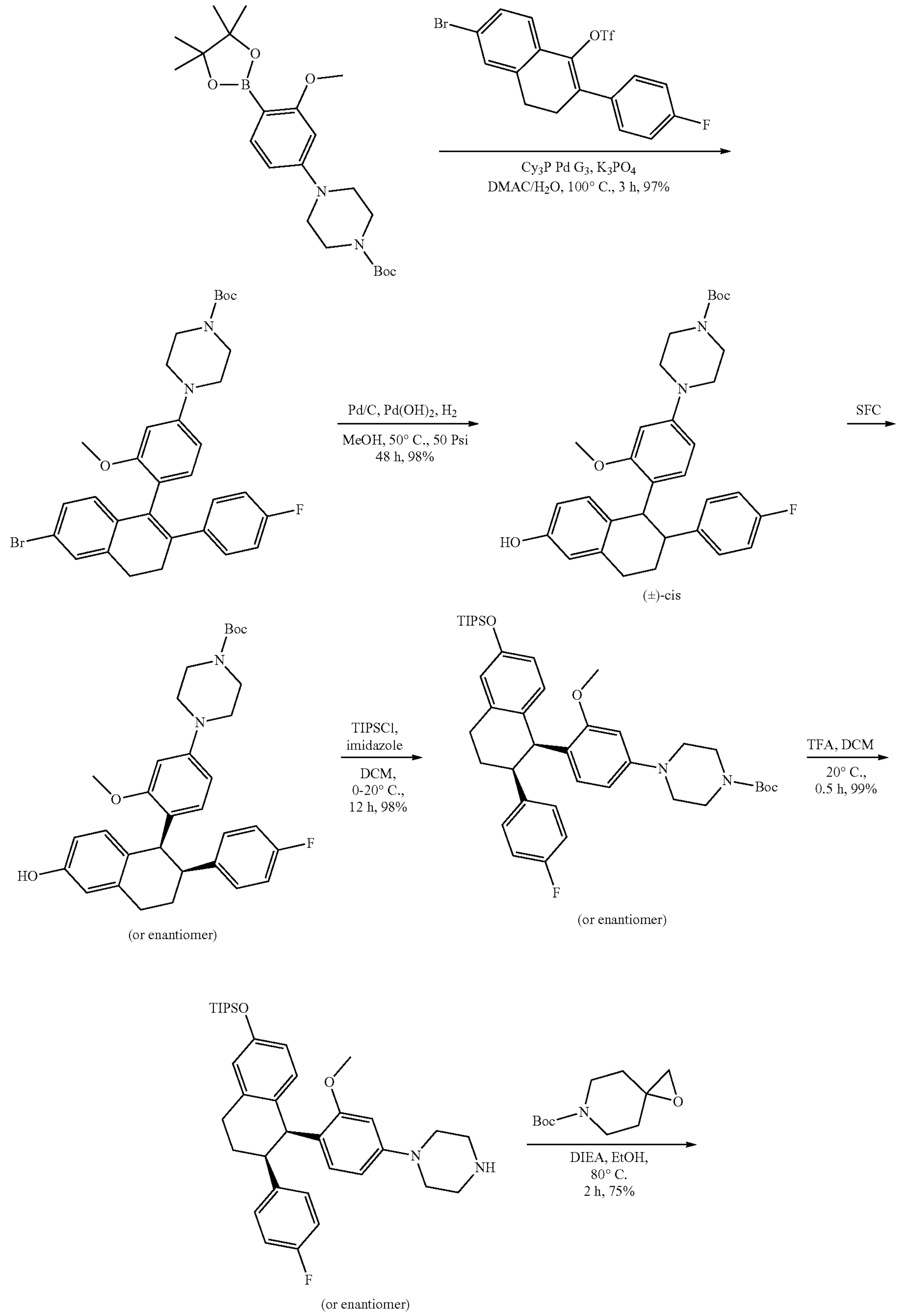

-continued
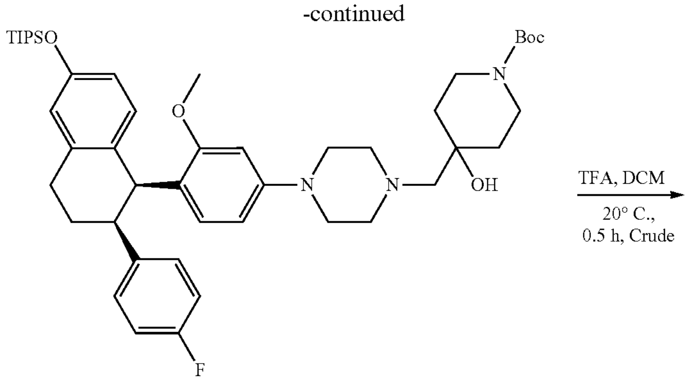
(or enantiomer)
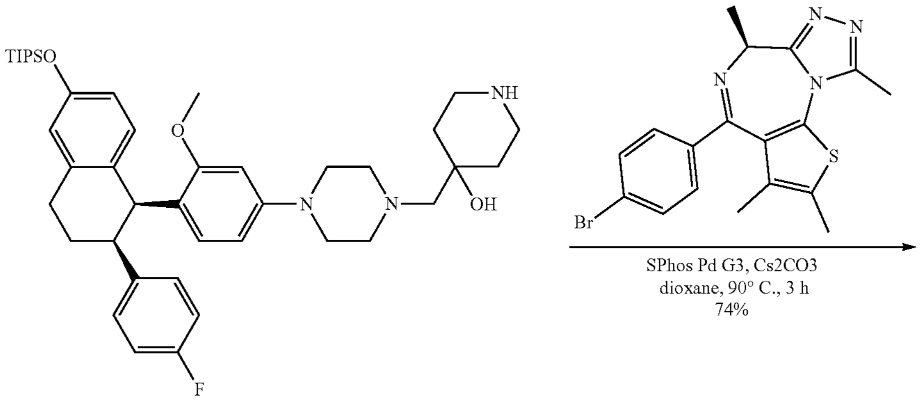
(or enantiomer)
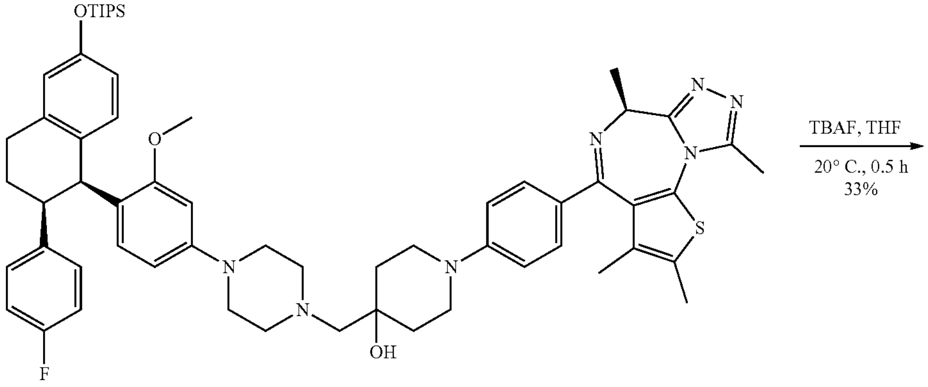
(or cis tetraline diasteromer)
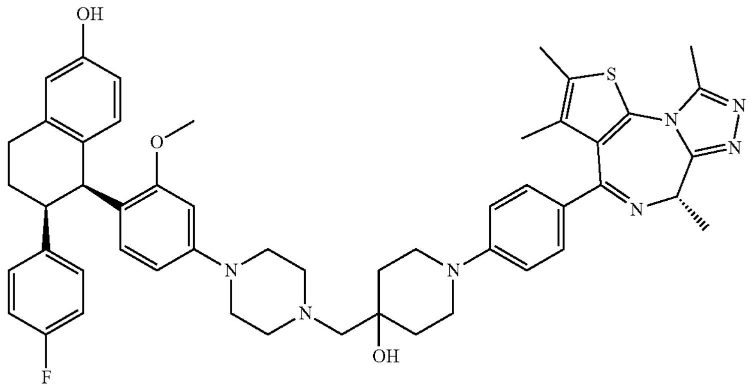
or
III-276

-continued

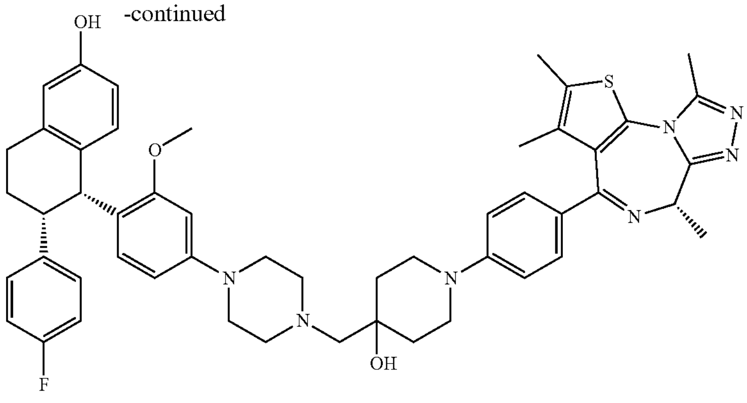

III-275

Step 1: A mixture of tert-butyl piperazine-1-carboxylate (2.98 g, 15 mmol, 1 equiv), 1-bromo-4-iodo-2-methoxy-benzene (5 g, 15 mmol, 1 equiv), $Pd_2(dba)_3$ (1 g, 1 mmol, 0.1 equiv), Xantphos (924 mg, 1 mmol, 0.1 equiv) and $Cs_2CO_3$ (15 g, 47 mmol, 3 equiv) in DMF (50 mL) was degassed and purged with $N_2$ for 3 times, and then the mixture was stirred at 100° C. for 12 h under $N_2$ atmosphere. The reaction mixture was diluted with water (20 mL) and then extracted with ethyl acetate (120 mL). The combined organic layer was washed with brine (30 mL), dried over anhydrous $Na_2SO_4$, filtered and concentrated under reduced pressure. The residue was purified by column chromatography ($SiO_2$, Petroleum ether: Ethyl acetate=10/1) to give compound tert-butyl 4-(4-bromo-3-methoxy-phenyl)piperazine-1-carboxylate (4 g, 10.8 mmol, 67% yield) as a red solid, and used for next step directly. LC-MS: MS ($ES^+$): RT=0.906 min, m/z=371.0 [M−100]; LCMS Method: 5-95.

Step 2: A mixture of tert-butyl 4-(4-bromo-3-methoxy-phenyl)piperazine-1-carboxylate (4 g, 10 mmol, 1 equiv), 4,4,5,5-tetramethyl-2-(4,4,5,5-tetramethyl-1,3,2-dioxaborolan-2-yl)-1,3,2-dioxaborolane (8 g, 32 mmol, 3 equiv), $Pd(dppf)Cl_2$ (788 mg, 1 mmol, 0.1 equiv), and potassium acetate (3 g, 32 mmol, 3 equiv) in dioxane (80 mL) was degassed and purged with $N_2$ for 3 times, and then the mixture was stirred at 60° C. for 12 h under $N_2$ atmosphere. The reaction mixture was diluted with water (20 mL) and then extracted with ethyl acetate (60 mL×3). The combined organic layer was washed with brine (30 mL), dried over anhydrous $Na_2SO_4$, filtered and concentrated under reduced pressure. The residue was purified by column chromatography ($SiO_2$, Petroleum ether: Ethyl acetate=3/1) to give compound tert-butyl 4-[3-methoxy-4-(4,4,5,5-tetramethyl-1,3,2-dioxaborolan-2-yl)phenyl]piperazine-1-carboxylate (4 g, 9 mmol, 88% yield) as a yellow solid. LC-MS: MS ($ES^+$): RT=0.883 min, m/z=419.4 [M+1]; LCMS Method: 5-95.

Step 3: A mixture of tert-butyl 4-[3-methoxy-4-(4,4,5,5-tetramethyl-1,3,2-dioxaborolan-2-yl)phenyl]piperazine-1-carboxylate (2 g, 6 mmol, 1 equiv), [6-benzyloxy-2-(4-fluorophenyl)-3,4-dihydronaphthalen-1-yl] trifluoromethanesulfonate (3 g, 6 mmol, 1 equiv), tricyclohexylphosphane Pd G3 (460 mg, 627 mol, 0.1 equiv), $K_3PO_4$ (3 g, 18 mmol, 3 equiv) in $H_2O$ (15 mL) and DMAC (75 mL) was degassed and purged with $N_2$ for 3 times, and then the mixture was stirred at 60° C. for 12 h under $N_2$ atmosphere. The reaction mixture was diluted with water (20 mL) and then extracted with ethyl acetate (60 mL×3). The combined organic layer was washed with brine (30 mL), dried over anhydrous $Na_2SO_4$, filtered and concentrated under reduced pressure. The residue was purified by column chromatography ($SiO_2$, Petroleum ether: Ethyl acetate=5/1) to give compound tert-butyl 4-[4-[6-benzyloxy-2-(4-fluorophenyl)-3,4-dihydronaphthalen-1-yl]-3-methoxy-phenyl]piperazine-1-carboxylate (3.8 g, 6 mmol, 97% yield) as a yellow solid. LC-MS: MS ($ES^+$): RT=1.058 min, m/z=621.4 [M+1]; LCMS Method: 5-95.

Step 4: Palladium on carbon (1.5 g, 1 mmol, 10% purity, 0.2 equiv) and $Pd(OH)_2$ (1.5 g, 2 mmol, 20% purity, 0.4 equiv) were added into a 250 mL single-necked round bottom flask under $N_2$, and then MeOH (80 mL) was added at 25° C. under $N_2$. After addition, tert-butyl 4-[4-[6-benzyloxy-2-(4-fluorophenyl)-3,4-dihydronaphthalen-1-yl]-3-methoxy-phenyl]piperazine-1-carboxylate (3.8 g, 6 mmol, 1 equiv) was added under $N_2$. The suspension was degassed under vacuum and purged with $H_2$ several times. The mixture was stirred under $H_2$ (50 psi) at 50° C. for 48 h. The residue was filtered and concentrated under reduced pressure to give (±)-cis-tert-butyl 4-[4-[2-(4-fluorophenyl)-6-hydroxy-tetralin-1-yl]-3-methoxy-phenyl]piperazine-1-carboxylate (3.2 g, 98% yield) as a white solid. LC-MS: MS ($ES^+$): RT=0.948 min, m/z=533.3 [M+1]; LCMS Method: 5-95.

Step 5: Racemic cis-tert-butyl 4-[4-[2-(4-fluorophenyl)-6-hydroxy-tetralin-1-yl]-3-methoxy-phenyl]piperazine-1-carboxylate (500 mg, 0.938 mmol) was purified by prep-SFC (column: DAICEL CHIRALPAK AD (250 mm*30 mm, 10 um); mobile phase: [$CO_2$-EtOH (0.1% $NH_3H_2O$)]; B %: 40%, isocratic elution mode) to afford (1S,2S)- and (1R,2R)-tert-butyl 4-[4-[2-(4-fluorophenyl)-6-hydroxy-tetralin-1-yl]-3-methoxy-phenyl]piperazine-1-carboxylate. The faster-eluting enantiomer (146 mg, 274.10 mol, 29.20% yield, 99% ee) was obtained as a yellow oil, and the slower-eluting enantiomer (188 mg, 37% yield, 99% ee) was obtained as a yellow solid. LC-MS: MS ($ES^+$): RT=1.025 min, m/z=533.3 [$M+H^+$]; LCMS Method: 5-95.

The following Steps 6 through 11 describe further synthetic procedures conducted on the slower-eluting enantiomer of cis-tert-butyl 4-[4-[2-(4-fluorophenyl)-6-hydroxy-tetralin-1-yl]-3-methoxy-phenyl]piperazine-1-carboxylate. This slower-eluting enantiomer produced the diastereomer of compounds III-276 and III-275 that was found to be the more potent inhibitor of cell growth of T-Rex 293 cells having increased expression of estrogen receptor alpha protein (as described in the Example 56, below). The faster-eluting enantiomer of cis-tert-butyl 4-[4-[2-(4-fluorophenyl)-6-hydroxy-tetralin-1-yl]-3-methoxy-phenyl]piperazine-1-carboxylate was carried through the same steps to afford the other one of compounds III-276 and III-275.

Step 6: To a solution of tert-butyl 4-[4-(1S,2S)-[2-(4-fluorophenyl)-6-hydroxy-tetralin-1-yl]-3-methoxy-phenyl] piperazine-1-carboxylate or its enantiomer (188 mg, 352 mol, 1 equiv) in DCM (2 mL) was added TIPSCl (136 mg, 705 mol, 151 µL, 2 equiv) and imidazole (72 mg, 1.06 mmol, 3 equiv) at 0° C. The mixture was stirred at 20° C. for 12 h. The reaction mixture was partitioned between dichloromethane (100 mL) and water (50 mL). The organic phase was separated, filtered and concentrated under reduced pressure to give a residue. The residue was purified by prep-TLC ($SiO_2$, Petroleum ether: Ethyl acetate=3:1) to afford tert-butyl 4-[4-(1S,2S)-[2-(4-fluorophenyl)-6-triisopropylsilyloxy-tetralin-1-yl]-3-methoxy-phenyl]piperazine-1-carboxylate or its enantiomer (240 mg, 98% yield) as a yellow oil. LC-MS: MS ($ES^+$): RT=1.338 min, m/z=689.5 [M+1]; LCMS Method: 5-95.

Step 7: To a solution of tert-butyl 4-[4-(1S,2S)-[2-(4-fluorophenyl)-6-triisopropylsilyloxy-tetralin-1-yl]-3-methoxy-phenyl]piperazine-1-carboxylate or its enantiomer (240 mg, 348 mol, 1 equiv) in DCM (2 mL) was added TFA (1.54 g, 13.46 mmol, 1 mL, 38 equiv). The mixture was stirred at 20° C. for 0.5 h. The reaction mixture was partitioned between dichloromethane (100 mL) and water (50 mL). The organic phase was separated, filtered and concentrated under reduced pressure to afford [2-(1S,2S)-(4-fluorophenyl)-1-(2-methoxy-4-piperazin-1-yl-phenyl)tetralin-6-yl]oxy-triisopropyl-silane or its enantiomer (205 mg, 99% yield) as a yellow oil. LC-MS: MS ($ES^+$): RT=1.046 min, m/z=589.5 [M+1]; LCMS Method: 5-95.

Step 8: To a solution of [2-(1S,2S)-(4-fluorophenyl)-1-(2-methoxy-4-piperazin-1-yl-phenyl)tetralin-6-yl]oxy-triisopropyl-silane or its enantiomer (180 mg, 305 mol, 1 equiv) in EtOH (3 mL) was added DIEA (118 mg, 917 mol, 159 µL, 3 equiv) and tert-butyl 1-oxa-6-azaspiro[2.5]octane-6-carboxylate (97 mg, 458 µmol, 1.5 equiv). The mixture was stirred at 80° C. for 2 h. The reaction mixture was filtered and concentrated under reduced pressure to give a residue. The residue was purified by prep-TLC ($SiO_2$, Petroleum ether: Ethyl acetate=3:1) to afford tert-butyl 4-[[4-[4-(1S,2S)-[2-(4-fluorophenyl)-6-triisopropylsilyloxy-tetralin-1-yl]-3-methoxy-phenyl]piperazin-1-yl]methyl]-4-hydroxy-piperidine-1-carboxylate or its enantiomer (186 mg, 75% yield) as a yellow oil. LC-MS: MS ($ES^+$): RT=0.986 min, m/z=802.2 [M+1]; LCMS Method: 5-95.

Step 9: To a solution of tert-butyl 4-[[4-(1S,2S)-[4-[2-(4-fluorophenyl)-6-triisopropylsilyloxy-tetralin-1-yl]-3-methoxy-phenyl]piperazin-1-yl]methyl]-4-hydroxy-piperidine-1-carboxylate or its enantiomer (140 mg, 174 mol, 1 equiv) in DCM (1 mL) was added TFA (2.15 g, 18.85 mmol, 1.40 mL, 107 equiv). The mixture was stirred at 20° C. for 0.5 h. The reaction mixture was partitioned between aqueous $NaHCO_3$ (30 mL) and dichloromethane (50 mL). The organic phase was separated, filtered and concentrated under reduced pressure to afford 4-[[4-[4-(1S,2S)-[2-(4-fluorophenyl)-6-triisopropylsilyloxy-tetralin-1-yl]-3-methoxy-phenyl]piperazin-1-yl]methyl]piperidin-4-ol or its enantiomer (122 mg, 99% yield) as a yellow oil. LC-MS: MS ($ES^+$): RT=0.858 min, m/z=702.3 [M+1]; LCMS Method: 5-95.

Step 10: A mixture of (9S)-7-(4-bromophenyl)-4,5,9,13-tetramethyl-3-thia-1,8,11,12-tetrazatricyclo[8.3.0.0$^{2,6}$]trideca-2(6),4,7,10,12-pentaene (58 mg, 144 mol, 1 equiv), 4-[[4-[4-(1S,2S)-[2-(4-fluorophenyl)-6-triisopropylsilyloxy-tetralin-1-yl]-3-methoxy-phenyl]piperazin-1-yl]methyl]piperidin-4-ol or its enantiomer (122 mg, 173 mol, 1.2 equiv), SPhos Pd $G_3$ (16 mg, 21 mol, 0.15 equiv) and $Cs_2CO_3$ (141 mg, 434 mol, 3 equiv) in dioxane (3 mL) was degassed and purged with $N_2$ for 3 times, and then the mixture was stirred at 90° C. for 3 h under $N_2$ atmosphere. The reaction mixture was filtered and concentrated under reduced pressure to give a residue. The residue was purified by prep-TLC ($SiO_2$, Dichloromethane:Methanol=10:1) to afford 4-[[4-[4-[(1S,2S)- or (1R,2R)-2-(4-fluorophenyl)-6-triisopropylsilyloxy-tetralin-1-yl]-3-methoxy-phenyl]piperazin-1-yl]methyl]-1-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]piperidin-4-ol (110 mg, 74% yield) as a yellow oil. LC-MS: MS (ES): RT=1.033 min, m/z=1022.6 [M+1]; LCMS Method: 5-95.

Step 11: To a solution of 4-[[4-[4-[(1S,2S)- or (1R,2R)-2-(4-fluorophenyl)-6-triisopropylsilyloxy-tetralin-1-yl]-3-methoxy-phenyl]piperazin-1-yl]methyl]-1-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]piperidin-4-ol (110 mg, 107 mol, 1 equiv) in THF (3 mL) was added TBAF (28 mg, 107 mol, 0.6 mL, 1 equiv). The mixture was stirred at 20° C. for 0.5 h. The reaction mixture was partitioned between ethyl acetate (50 mL) and water (30 mL). The organic phase was separated, filtered and concentrated under reduced pressure to give a residue. The residue was purified by prep-HPLC (column: Phenomenex luna C18 150*25 mm*10 um; mobile phase: [water(FA)-ACN]; gradient: 20%-50% B over 10 min) to afford compound III-276 or III-275 (32 mg, 33% yield) as a yellow solid. $^1H$ NMR (400 MHz, $CDCl_3$) δ=7.40 (d, J=8.8 Hz, 2H), 6.87 (d, J=9.0 Hz, 2H), 6.82-6.76 (m, 3H), 6.76-6.69 (m, 3H), 6.59 (dd, J=2.4, 8.0 Hz, 1H), 6.51 (d, J=8.4 Hz, 1H), 6.32 (dd, J=2.0, 8.4 Hz, 1H), 6.09 (d, J=2.0 Hz, 1H), 4.77 (d, J=5.6 Hz, 1H), 4.20-4.12 (m, 1H), 3.65-3.51 (m, 2H), 3.32-3.22 (m, 3H), 3.17-3.10 (m, 7H), 3.05-2.95 (m, 2H), 2.85-2.77 (m, 4H), 2.68 (s, 3H), 2.43 (s, 5H), 2.31-2.15 (m, 2H), 2.11-2.07 (m, 3H), 1.78 (s, 3H), 1.67-1.63 (m, 4H). LC-MS: MS ($ES^+$): RT=2.612 min, m/z=866.6 [M+1]; LCMS Method: 01.

Example 44—Synthesis of 4-((4-(4-((1S,2S)-2-(2-fluorophenyl)-6-hydroxy-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-307) and 4-((4-(4-((1R,2R)-2-(2-fluorophenyl)-6-hydroxy-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-308)

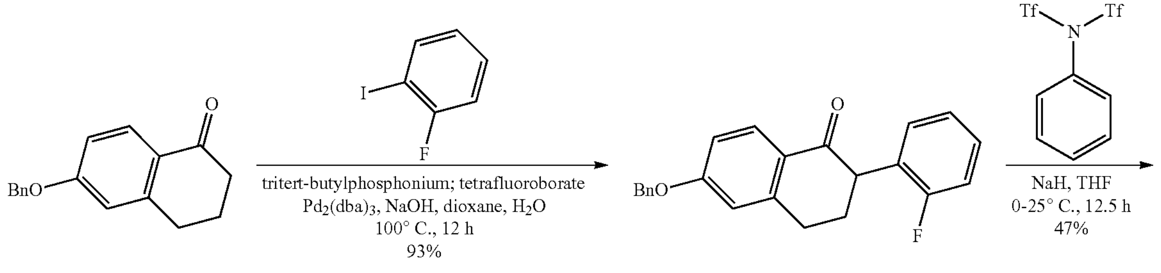

-continued
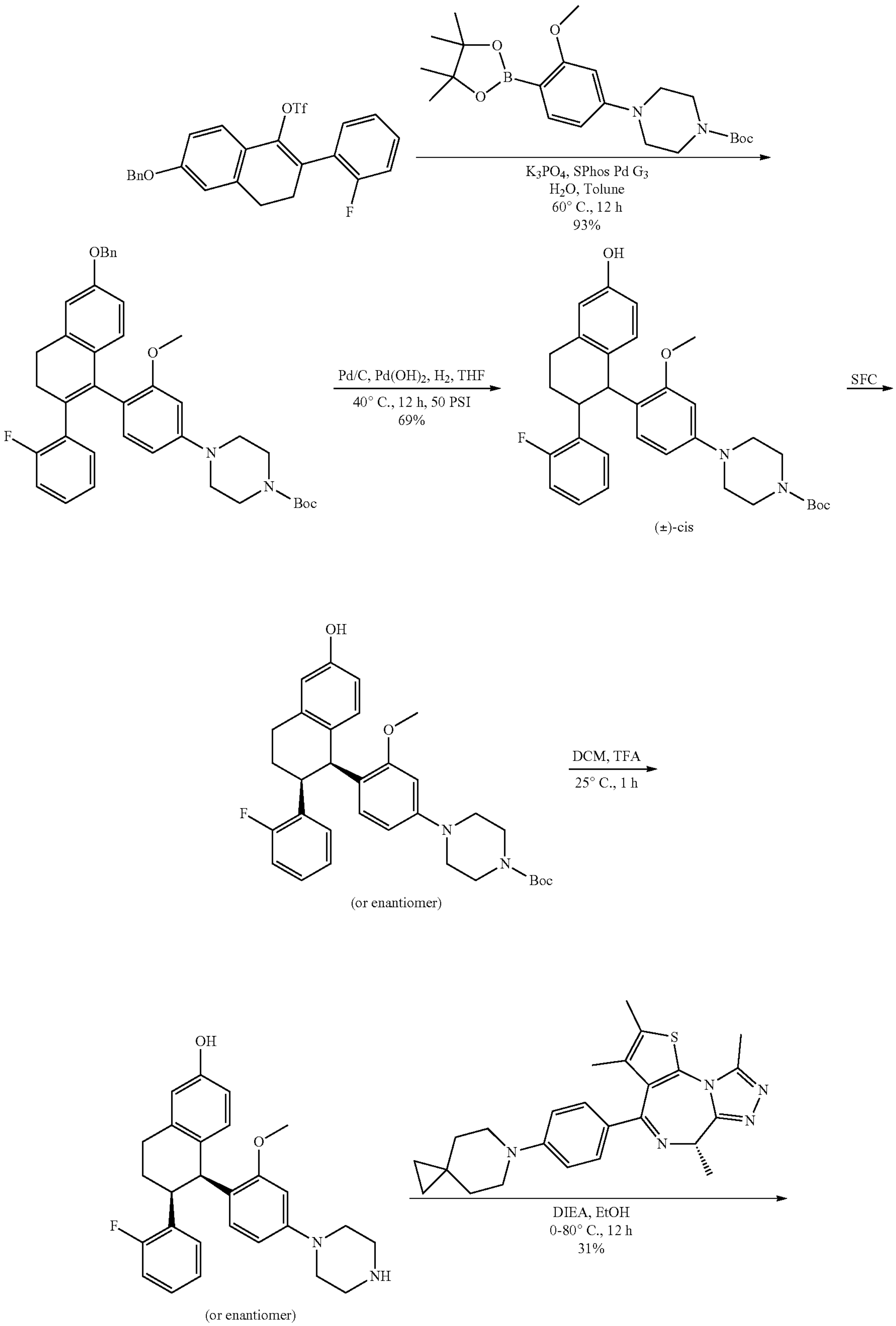

-continued

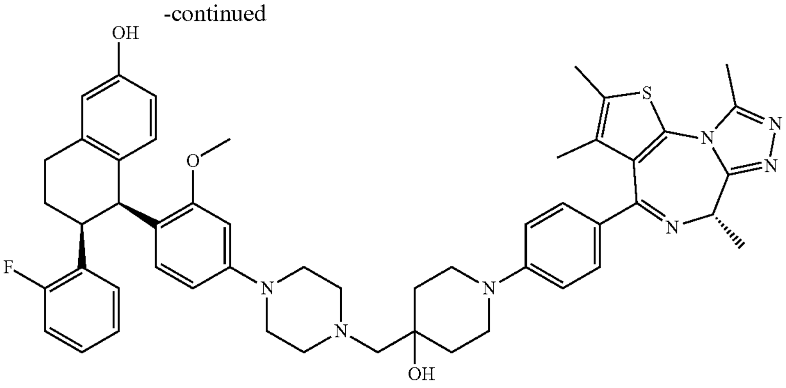

III-307 or

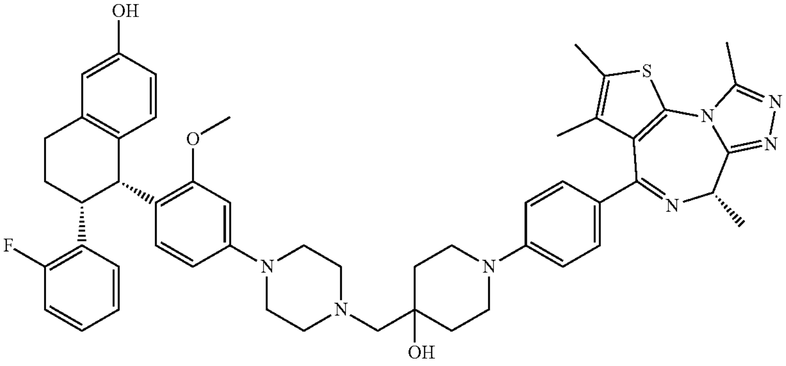

III-308

Step 1: To a solution of 6-benzyloxytetralin-1-one (5 g, 19 mmol, 1.0 equiv) and 1-fluoro-2-iodo-benzene (6.6 g, 29 mmol, 3.4 mL, 1.5 equiv) in dioxane (40.0 mL) and $H_2O$ (10.0 mL) was added $Pd_2(dba)_3$ (1.8 g, 1 mmol, 0.1 equiv), NaOH (1.5 g, 39 mmol, 2.0 equiv) and tritert-butylphosphonium tetrafluoroborate (1.1 g, 3 mmol, 0.2 equiv) in one portion at 25° C. Then the resulting mixture was heated to 100° C. and stirred under $N_2$ atmosphere for 12 h. The residue was diluted with water (10.0 mL) and extracted with ethyl acetate (20.0 mL*3). The combined organic layers were washed with saturated aqueous NaCl solution (10.0 mL), dried over $Na_2SO_4$, filtered and concentrated under reduced pressure to give a residue. The residue was purified by column chromatography ($SiO_2$, Petroleum ether/Ethyl acetate=20/1 to 1/1) to give 6-benzyloxy-2-(2-fluorophenyl) tetralin-1-one (6.4 g, 93% yield) as yellow solid. LC-MS: MS ($ES^+$): RT=0.653 min, m/z=347.1 [$M+H^+$]. LCMS Method: 5-95.

Step 2: To a mixture of 6-benzyloxy-2-(2-fluorophenyl) tetralin-1-one (6 g, 17 mmol, 1.0 equiv) in THE (60.0 mL) was added NaH (1.3 g, 34 mmol, 60% purity, 2.0 equiv) at 0° C. for 0.5 h under $N_2$ atmosphere. Then 1,1,1-trifluoro-N-phenyl-N-(trifluoromethylsulfonyl) methanesulfonamide (18.5 g, 51 mmol, 3.0 equiv) was added to the mixture. The mixture was stirred at 25° C. for 12 h under $N_2$ atmosphere. The reaction mixture was quenched with saturated aqueous $NH_4Cl$ (50.0 mL) solution at 0° C. dropwise. And the resulting mixture was extracted with ethyl acetate (30.0 mL*3). The combined organic layers were dried over anhydrous $Na_2SO_4$, filtered and concentrated in vacuum. The residue was purified by column chromatography ($SiO_2$, Petroleum ether/Ethyl acetate=1/0 to 5/1) to give [6-benzyloxy-2-(2-fluorophenyl)-3,4-dihydronaphthalen-1-yl]trifluoromethanesulfonate (3.9 g, 47% yield) as white solid. $^1H$ NMR (400 MHz, DMSO-$d_6$): δ 7.52-7.45 (m, 4H), 7.43-7.34 (m, 3H), 7.33-7.24 (m, 3H), 7.09-6.98 (m, 2H), 5.16 (s, 2H), 2.96 (s, 2H), 2.76-2.66 (m, 2H).

Step 3: To a solution of [6-benzyloxy-2-(2-fluorophenyl)-3,4-dihydronaphthalen-1-yl]trifluoromethanesulfonate (2.9 g, 6 mmol, 1.0 equiv) and tert-butyl 4-[3-methoxy-4-(4,4,5,5-tetramethyl-1,3,2-dioxaborolan-2-yl)phenyl]piperazine-1-carboxylate (2.5 g, 6 mmol, 1.0 equiv) in $H_2O$ (8.0 mL) and toluene (32.0 mL) was added $K_3PO_4$ (3.8 g, 18 mmol, 3.0 equiv), SPhos Pd $G_3$ (472 mg, 606 mol, 0.1 equiv) in one portion at 25° C. Then the resulting mixture was heated to 60° C. and stirred under $N_2$ atmosphere for 12 h. The residue was diluted with water (30.0 mL) and extracted with ethyl acetate (30.0 mL*3). The combined organic layers were washed with saturated aqueous NaCl solution (30.0 mL), dried over $Na_2SO_4$, filtered and concentrated under reduced pressure to give a residue. The residue was purified by column chromatography ($SiO_2$, Petroleum ether/Ethyl acetate=5/1 to 3/1) to give tert-butyl 4-[4-[6-benzyloxy-2-(2-fluorophenyl)-3,4-dihydronaphthalen-1-yl]-3-methoxy-phenyl]piperazine-1-carboxylate (3.5 g, 93% yield) as white solid. LC-MS: MS ($ES^+$): RT=0.795 min, m/z=621.5 [$M+H^+$]. LCMS Method: 5-95.

Step 4: To a solution of tert-butyl 4-[4-[6-benzyloxy-2-(2-fluorophenyl)-3,4-dihydronaphthalen-1-yl]-3-methoxy-phenyl]piperazine-1-carboxylate (3.5 g, 5 mmol, 1.0 equiv) in THE (35.0 mL) was added Pd/C (6.0 g, 5 mmol, 10% purity, 1.0 equiv) and $Pd(OH)_2$ (3.9 g, 5 mmol, 20% purity, 1.0 equiv) under $N_2$ atmosphere. The suspension was degassed and purged with $H_2$ for 3 times. The mixture was stirred under $H_2$ (50 Psi) at 40° C. for 12 h. The reaction mixture was filtered and concentrated under reduced pressure to give a residue. The crude product was triturated with MeOH at 25° C. for 30 min to give (±)-cis-tert-butyl 4-[4-[2-(2-fluorophenyl)-6-hydroxy-tetralin-1-yl]-3-methoxy-phenyl]piperazine-1-carboxylate (2.1 g, 69% yield) as white solid. LC-MS: MS ($ES^+$): RT=3.038 min, m/z=533.4 [$M+H^+$]. LCMS Method: 5-95.

Step 5: Racemic cis-tert-butyl 4-[4-[2-(2-fluorophenyl)-6-hydroxy-tetralin-1-yl]-3-methoxy-phenyl]piperazine-1-carboxylate (700 mg, 1 mmol, 1.0 equiv) was purified by preparative SFC (column: DAICEL CHIRALPAK AD (250 mm*30 mm, 10 um); mobile phase: [$CO_2$—IPA (0.1% $NH_3H_2O$)]; B %: 25%, isocratic elution mode) to give (1S,2S)- and (1R,2R)-tert-butyl 4-[4-[2-(2-fluorophenyl)-6-hydroxy-tetralin-1-yl]-3-methoxy-phenyl]piperazine-1-carboxylate. The slower-eluting enantiomer (340 mg) was obtained as a white solid. LC-MS: MS ($ES^+$): RT=0.655 min, m/z=533.2 [$M+H^+$]; LCMS Method: 5-95.

The following Steps 6 and 7 describe further synthetic procedures conducted on the slower-eluting enantiomer of cis-tert-butyl 4-[4-[2-(2-fluorophenyl)-6-hydroxy-tetralin-1-yl]-3-methoxy-phenyl]piperazine-1-carboxylate. This slower-eluting enantiomer produced the diastereomer of compounds III-307 and III-308 that was found to be the more potent inhibitor of cell growth of T-Rex 293 cells having increased expression of estrogen receptor alpha protein (as described in the Example 56, below). The faster-eluting enantiomer of cis-tert-butyl 4-[4-[2-(2-fluorophenyl)-6-hydroxy-tetralin-1-yl]-3-methoxy-phenyl]piperazine-1-carboxylate was carried through the same steps to afford the other one of compounds III-307 and III-308.

Step 6: To a solution of tert-butyl 4-[4-[(1S,2S)-2-(2-fluorophenyl)-6-hydroxy-tetralin-1-yl]-3-methoxy-phenyl] piperazine-1-carboxylate or its enantiomer (150 mg, 281 mol, 1.0 equiv) in DCM (1.0 mL) was added TFA (307 mg, 2 mmol, 0.2 mL, 9.5 equiv). The mixture was stirred at 25° C. for 1 h. The mixture was concentrated to give a residue. The crude (1S,2S)-2-(2-fluorophenyl)-1-(2-methoxy-4-piperazin-1-yl-phenyl)tetralin-6-ol or its enantiomer (121 mg, crude) as white solid was used into the next step without further purification. LC-MS: MS ($ES^+$): RT=0.536 min, m/z=433.2[$M+H^+$]. LCMS Method: 5-95.

Step 7: To a solution of (1S,2S)-2-(2-fluorophenyl)-1-(2-methoxy-4-piperazin-1-yl-phenyl)tetralin-6-ol or its enantiomer (121 mg, 279 mol, 1.0 equiv) in EtOH (4.0 mL) was added DIEA (180 mg, 1 mmol, 243 L, 5.0 equiv) and 6-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro[2.5]octane (303 mg, 699 mol, 2.5 equiv) at 0° C. The mixture was stirred at 80° C. for 12 h. The mixture was concentrated to give a residue. The residue was purified by preparative HPLC (column: Waters Xbridge C18 150*50 mm*10 um; mobile phase: [$H_2O$ (10 mM $NH_4HCO_3$)-ACN]; gradient: 58%-88% B over 11.0 min) to give compound III-307 or III-308 (118 mg, 47% yield, 97% purity) as white solid. $^1H$ NMR (400 MHz, DMSO-$d_6$): δ 9.29-8.86 (m, 1H), 7.26 (s, 2H), 7.16-7.04 (m, 2H), 6.89 (s, 2H), 6.80-6.73 (m, 1H), 6.59-6.51 (m, 2H), 6.46-6.40 (m, 1H), 6.36-6.21 (m, 3H), 6.06 (s, 1H), 4.72 (s, 1H), 4.23 (s, 1H), 4.10 (s, 1H), 3.54-3.42 (m, 6H), 3.30 (s, 3H), 3.14 (s, 2H), 3.00 (s, 3H), 2.95 (s, 5H), 2.60 (s, 3H), 2.57 (s, 2H), 2.47 (s, 1H), 2.38 (s, 3H), 2.28 (s, 1H), 1.83 (s, 3H), 1.64 (s, 3H), 1.52 (s, 3H). LC-MS: MS ($ES^+$): RT=1.779 min, m/z=866.7[$M+H^+$]. LCMS method: 25.

Example 45—Synthesis of 4-((4-(2-fluoro-4-((1S, 2S)-6-hydroxy-2-phenyl-1,2,3,4-tetrahydronaphthalen-1-yl)-5-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-311) and 4-((4-(2-fluoro-4-((1R,2R)-6-hydroxy-2-phenyl-1,2,3,4-tetrahydronaphthalen-1-yl)-5-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-312)

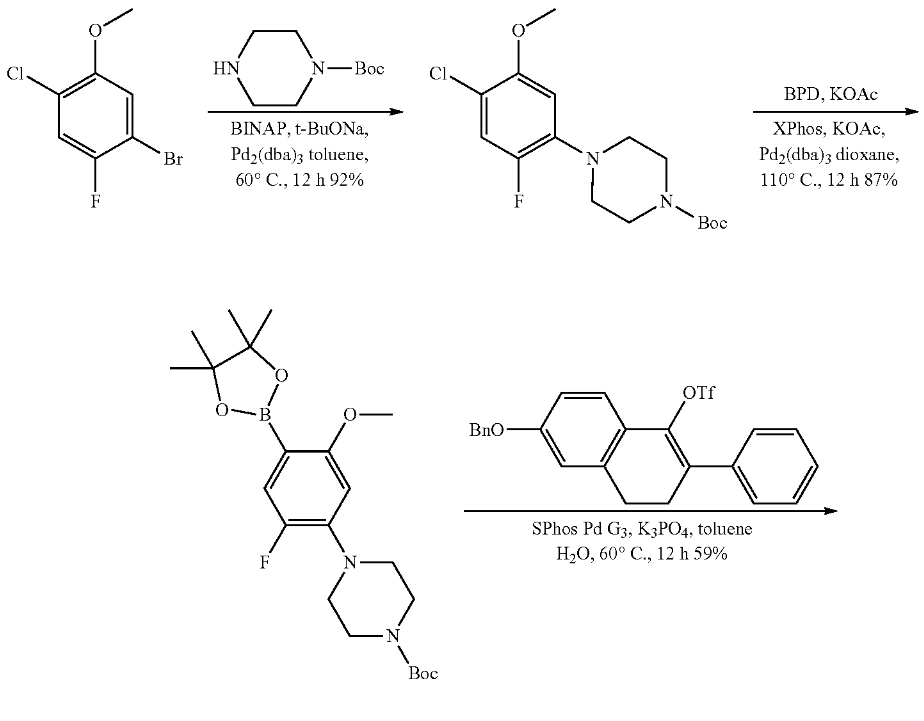

-continued
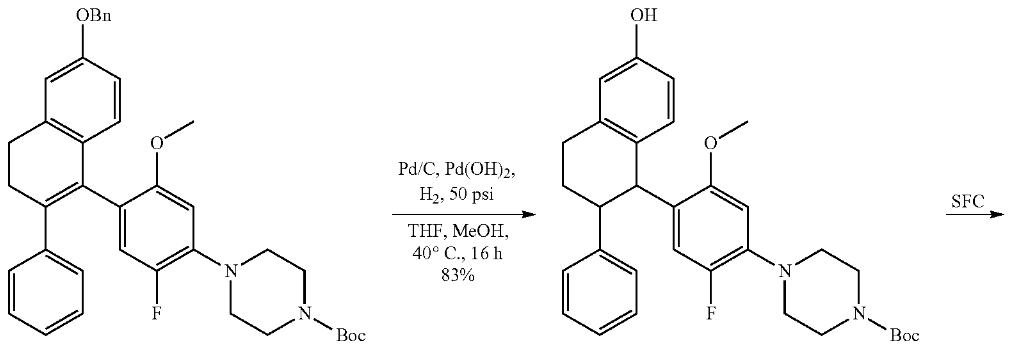
(±)-cis
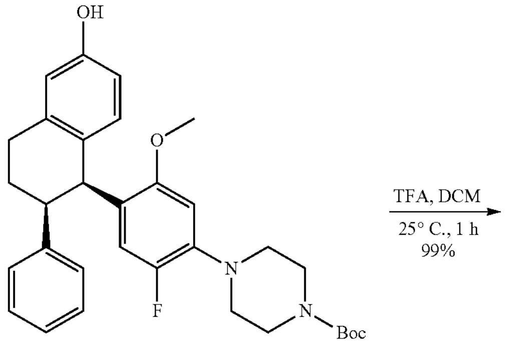
(or enantiomer)
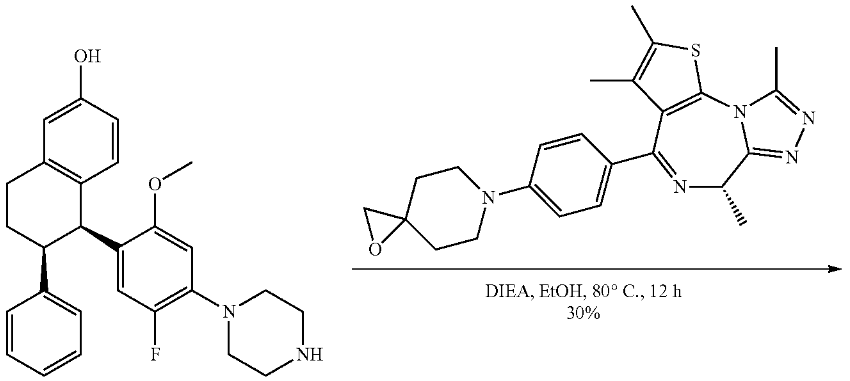
(or enantiomer)
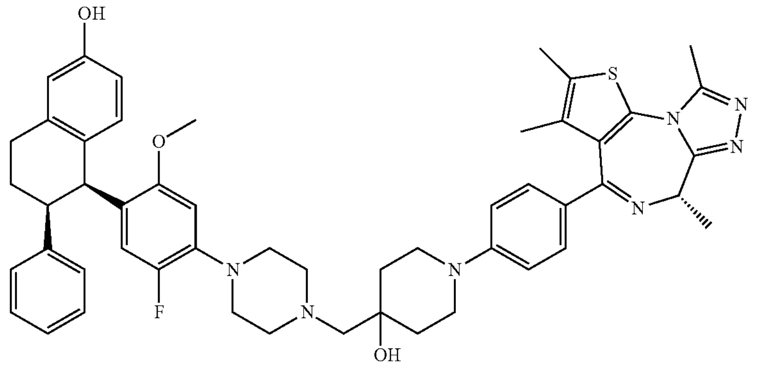
III-311
or -continued

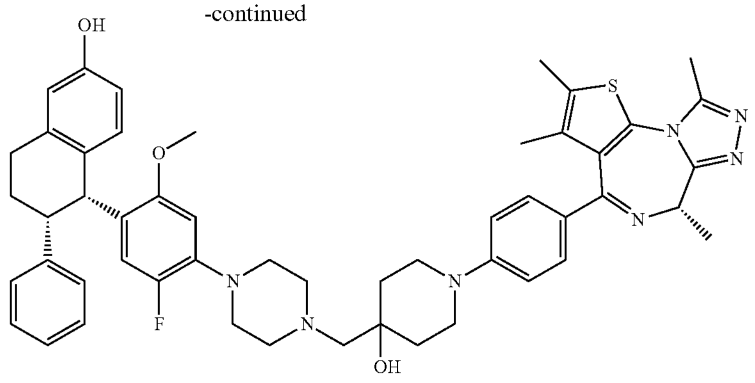

III-312

Step 1: A mixture of 1-bromo-4-chloro-2-fluoro-5-methoxy-benzene (5 g, 20.8 mmol, 1.0 equiv), tert-butyl piperazine-1-carboxylate (3.89 g, 20.9 mmol, 1.0 equiv), [1-(2-diphenylphosphanyl-1-naphthyl)-2-naphthyl]-diphenyl-phosphane (2.60 g, 4.18 mmol, 0.2 equiv), $Pd_2(dba)_3$ (1.91 g, 2.09 mmol, 0.1 equiv) and t-BuONa (4.01 g, 41.8 mmol, 2.0 equiv) in toluene (50 mL) was degassed and purged with $N_2$ for 3 times, and then the mixture was stirred at 60° C. for 12 h under $N_2$ atmosphere. The mixture was filtered and concentrated to give a residue. The residue was purified by silica column chromatography on silica gel (Petroleum ether: Ethyl acetate from 50/1 to 5/1) to give tert-butyl 4-(4-chloro-2-fluoro-5-methoxy-phenyl)piperazine-1-carboxylate (6.6 g, 92% yield) as a yellow solid. $^1H$ NMR (400 MHz, $CDCl_3$): δ 7.08 (d, J=11.6 Hz, 1H), 6.50 (d, J=7.6 Hz, 1H), 3.86 (s, 3H), 3.65-3.55 (m, 4H), 3.08-2.96 (m, 4H), 1.49 (s, 9H). LC-MS: MS ($ES^+$): RT=0.684 min, m/z=345.1 [M+H$^+$]. LCMS Method: 5-95.

Step 2: A mixture of tert-butyl 4-(4-chloro-2-fluoro-5-methoxy-phenyl)piperazine-1-carboxylate (8.5 g, 24.7 mmol, 1.0 equiv), BPD (12.5 g, 49.3 mmol, 2.0 equiv), XPhos (1.76 g, 3.70 mmol, 0.15 equiv), $Pd_2(dba)_3$ (1.13 g, 1.23 mmol, 0.05 equiv) and KOAc (7.26 g, 74.0 mmol, 3.0 equiv) in dioxane (100 mL) was degassed and purged with $N_2$ for 3 times, and then the mixture was stirred at 110° C. for 12 h under $N_2$ atmosphere. The mixture was filtered and concentrated to give a residue. The residue was purified by silica column chromatography on silica gel (Petroleum ether: Ethyl acetate from 50/1 to 3/1) to give tert-butyl 4-[2-fluoro-5-methoxy-4-(4,4,5,5-tetramethyl-1,3,2-dioxaborolan-2-yl)phenyl]piperazine-1-carboxylate (9.4 g, 87% yield) as a yellow solid. $^1H$ NMR (400 MHz, $CDCl_3$): δ 7.34 (d, J=13.2 Hz, 1H), 6.39 (d, J=6.8 Hz, 1H), 3.80 (s, 3H), 3.66-3.54 (m, 4H), 3.14-3.02 (m, 4H), 1.48 (s, 9H), 1.33 (s, 12H). LC-MS: MS ($ES^+$): RT=0.713 min, m/z=437.3 [M+H$^+$]. LCMS Method: 5-95.

Step 3: To a solution of tert-butyl 4-[2-fluoro-5-methoxy-4-(4,4,5,5-tetramethyl-1,3,2-dioxaborolan-2-yl)phenyl]piperazine-1-carboxylate (3.41 g, 7.82 mmol, 1.2 equiv) in toluene (40 mL) and $H_2O$ (10 mL) and was added $K_3PO_4$ (4.15 g, 19.6 mmol, 3.0 equiv), (6-benzyloxy-2-phenyl-3,4-dihydronaphthalen-1-yl) trifluoromethanesulfonate (3 g, 6.52 mmol, 1.0 equiv) and SPhos Pd $G_3$ (508 mg, 652 mol, 0.1 equiv). The mixture was stirred at 60° C. for 12 h under $N_2$ atmosphere. The mixture was filtered and concentrated to give a residue. The residue was purified by silica column chromatography on silica gel (Petroleum ether: Ethyl acetate from 50/1 to 5/1) to give tert-butyl 4-[4-(6-benzyloxy-2-phenyl-3,4-dihydronaphthalen-1-yl)-2-fluoro-5-methoxy-phenyl]piperazine-1-carboxylate (2.4 g, 59% yield) as a yellow solid. $^1H$ NMR (400 MHz, $CDCl_3$): δ 7.47-7.42 (m, 2H), 7.39 (t, J=7.6 Hz, 2H), 7.36-7.30 (m, 1H), 7.15-7.08 (m, 2H), 7.08-7.01 (m, 3H), 6.85 (d, J=1.6 Hz, 1H), 6.72-6.59 (m, 3H), 6.37 (d, J=7.2 Hz, 1H), 5.07 (s, 2H), 3.60 (t, J=4.8 Hz, 4H), 3.48 (s, 3H), 3.11-2.94 (m, 6H), 2.79 (m, J=3.6, 7.6 Hz, 2H), 1.50 (s, 9H). LC-MS: MS ($ES^+$): RT=0.727 min, m/z=621.3 [M+H$^+$]. LCMS Method: 5-95.

Step 4: To a solution of tert-butyl 4-[4-(6-benzyloxy-2-phenyl-3,4-dihydronaphthalen-1-yl)-2-fluoro-5-methoxy-phenyl]piperazine-1-carboxylate (2.4 g, 3.87 mmol, 1.0 equiv) in THE (24 mL) and MeOH (12 mL) was added Pd/C (1 g, 10% purity) and $Pd(OH)_2$ (1 g) under $N_2$. The suspension was degassed under vacuum and purged with $H_2$ several times. The mixture was stirred under $H_2$ (50 psi) at 40° C. for 16 h. The mixture was filtered and concentrated to give a residue. The crude product was triturated with PE:EA=5/1 (36 mL) at 25° C. for 1 h. The mixture was filtered to give (±)-cis-tert-butyl 4-[2-fluoro-4-(6-hydroxy-2-phenyl-tetralin-1-yl)-5-methoxy-phenyl]piperazine-1-carboxylate (1.7 g, 83% yield) as a white solid. $^1H$ NMR (400 MHz, $CDCl_3$): δ 7.15-7.02 (m, 3H), 6.70-6.82 (m, 3H), 6.69 (d, J=2.0 Hz, 1H), 6.55-6.63 (m, 1H), 6.37 (d, J=13.6 Hz, 1H), 6.06 (d, J=7.2 Hz, 1H), 5.34-5.14 (m, 1H), 4.81 (d, J=5.2 Hz, 1H), 3.57 (s, 4H), 3.31 (m, J=5.2, 11.6 Hz, 1H), 3.09-2.88 (m, 9H), 2.24 (m, J=6.4, 12.8 Hz, 1H), 1.80-1.63 (m, 2H), 1.49 (s, 9H). LC-MS: MS ($ES^+$): RT=3.255 min, m/z=533.4 [M+H$^+$]. LCMS Method: 5-95.

Step 5: Racemic cis-tert-butyl 4-[2-fluoro-4-(6-hydroxy-2-phenyl-tetralin-1-yl)-5-methoxy-phenyl]piperazine-1-carboxylate (700 mg, 1.31 mmol, 1.0 equiv) was purified by preparative SFC (column: DAICEL CHIRALCEL OD (250 mm*30 mm, 10 um); mobile phase: [$CO_2$—IPA (0.1% $NH_3H_2O$)]; B %: 55%, isocratic elution mode) to give (1S,2S)- and (1R,2R)-tert-butyl 4-[2-fluoro-4-[6-hydroxy-2-phenyl-tetralin-1-yl]-5-methoxy-phenyl]piperazine-1-carboxylate. The faster-eluting enantiomer was isolated (340 mg, 49% yield) as a white solid. LC-MS: MS ($ES^+$): RT=0.651 min, m/z=533.3 [M+H$^+$]; LCMS Method: 5-95.

The following Steps 6 and 7 describe further synthetic procedures conducted on the faster-eluting enantiomer of cis-tert-butyl 4-[2-fluoro-4-(6-hydroxy-2-phenyl-tetralin-1-yl)-5-methoxy-phenyl]piperazine-1-carboxylate. This faster-eluting enantiomer produced the diastereomer of compounds III-311 and III-312 that was found to be the more potent inhibitor of cell growth of T-Rex 293 cells having increased expression of estrogen receptor alpha protein (as described in the Example 56, below). The slower-eluting enantiomer of cis-tert-butyl 4-[2-fluoro-4-(6-hydroxy-2-phenyl-tetralin-1-yl)-5-methoxy-phenyl]piperazine-1-carboxylate was carried through the same steps to afford the other one of compounds III-311 and III-312.

Step 6: To a solution of tert-butyl 4-[2-fluoro-4-[(1S,2S)-6-hydroxy-2-phenyl-tetralin-1-yl]-5-methoxy-phenyl]piperazine-1-carboxylate or its enantiomer (150 mg, 281 mol, 1.0 equiv) in DCM (1.5 mL) was added TFA (461 mg, 4.04 mmol, 0.3 mL, 14.3 equiv). The mixture was stirred at 25° C. for 1 h. The mixture was concentrated to give (1S,2S)-1-(5-fluoro-2-methoxy-4-piperazin-1-yl-phenyl)-2-phenyl-tetralin-6-ol or its enantiomer (120 mg, 99% yield) as a colorless oil. LC-MS: MS (ES$^+$): RT=0.489 min, m/z=433.2 [M+H$^+$]. LCMS Method: 5-95.

Step 7: To a solution of 6-[4-[(9S)-4,5,9,13-tetramethyl-3-thia-1,8,11,12-tetrazatricyclo[8.3.0.$0^{2,6}$]trideca-2(6),4,7,10,12-pentaen-7-yl]phenyl]-1-oxa-6-azaspiro[2.5]octane (241 mg, 555 mol, 2.0 equiv) in EtOH (3 mL) was added DIEA (179 mg, 1.39 mmol, 0.2 mL, 5.0 equiv) and (1S,2S)-1-(5-fluoro-2-methoxy-4-piperazin-1-yl-phenyl)-2-phenyltetralin-6-ol or its enantiomer (120 mg, 277 mol, 1.0 equiv). The mixture was stirred at 80° C. for 12 h. The mixture was concentrated to give a residue. The residue was purified by preparative HPLC (column: Waters Xbridge C18 150*25 mm*5 um; mobile phase: [$H_2O$ (10 mM $NH_4HCO_3$)-ACN]; gradient: 64%-94% B over 9.0 min) to give compound III-311 or III-312 (74 mg, 30% yield, 98% purity) as an off-white solid. $^1$H NMR (400 MHz, $CDCl_3$): δ 7.38 (d, J=8.8 Hz, 2H), 7.12-7.04 (m, 3H), 6.86 (d, J=9.2 Hz, 2H), 6.81-6.74 (m, 3H), 6.69 (d, J=2.4 Hz, 1H), 6.65-6.55 (m, 1H), 6.35 (d, J=13.6 Hz, 1H), 6.06 (d, J=7.6 Hz, 1H), 5.56-5.11 (m, 1H), 4.80 (d, J=5.2 Hz, 1H), 4.15 (q, J=6.8 Hz, 1H), 3.70-3.50 (m, 2H), 3.34-3.20 (m, 3H), 3.12-2.95 (m, 9H), 2.80 (d, J=4.0 Hz, 4H), 2.67 (s, 3H), 2.46-2.35 (m, 5H), 2.30-2.19 (m, 1H), 2.08 (d, J=6.8 Hz, 3H), 1.82-1.65 (m, 8H). LC-MS: MS (ES$^+$): RT=1.796 min, m/z=866.7 [M+H$^+$]. LCMS method: 25.

Example 46—Synthesis of 4-((4-(4-((1S,2S)-6-hydroxy-2-phenyl-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-321) and 4-((4-(4-((1R,2R)-6-hydroxy-2-phenyl-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-322)

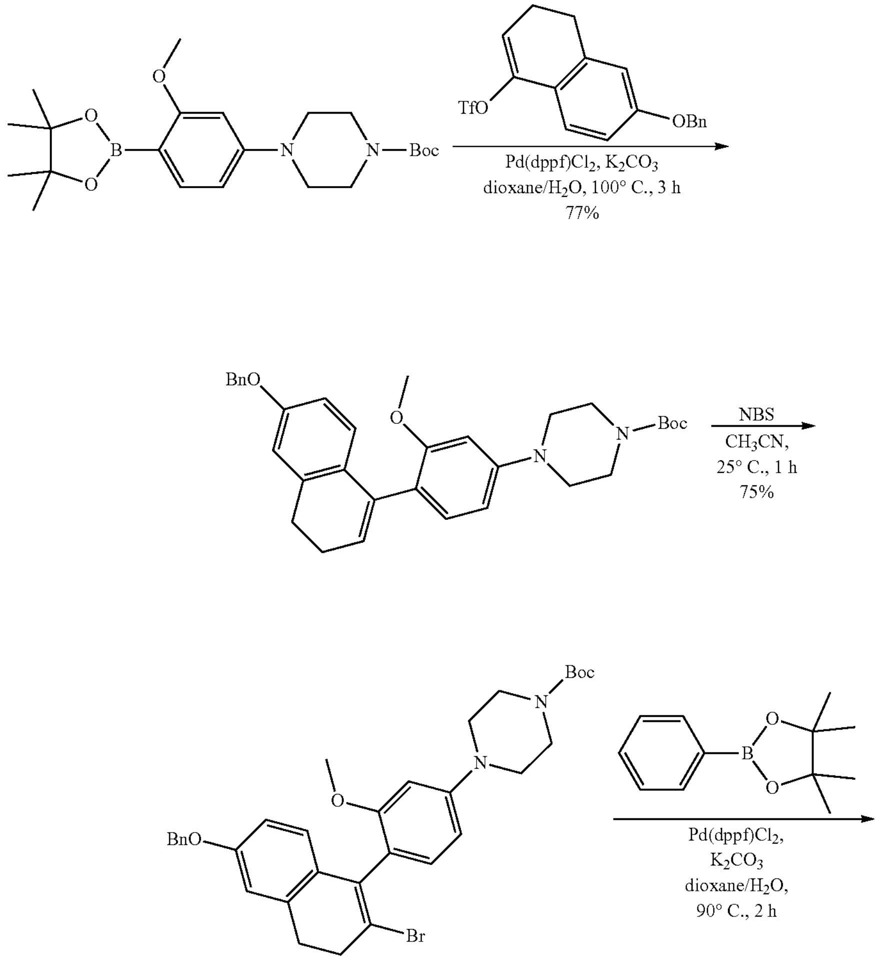

-continued
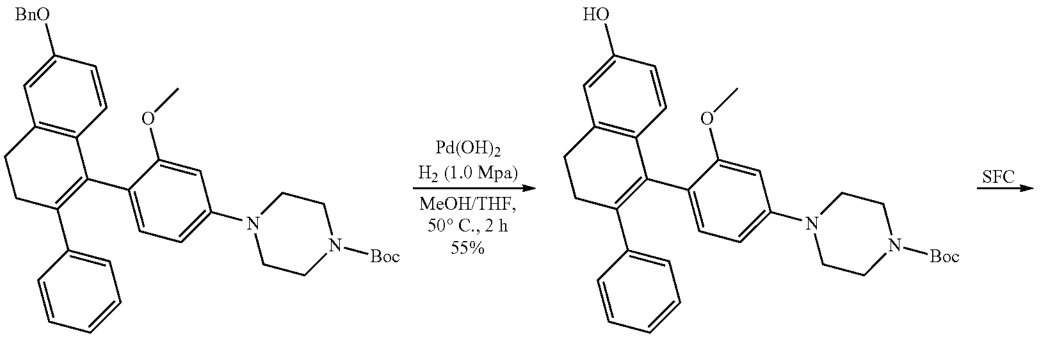
(±)-cis
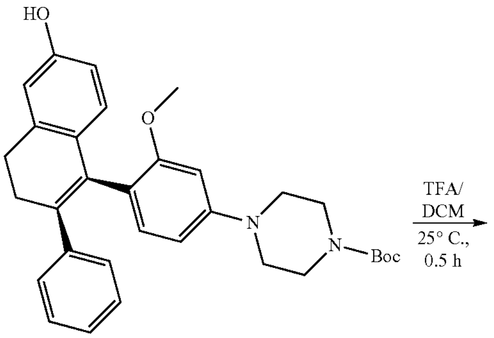
(or enantiomer)
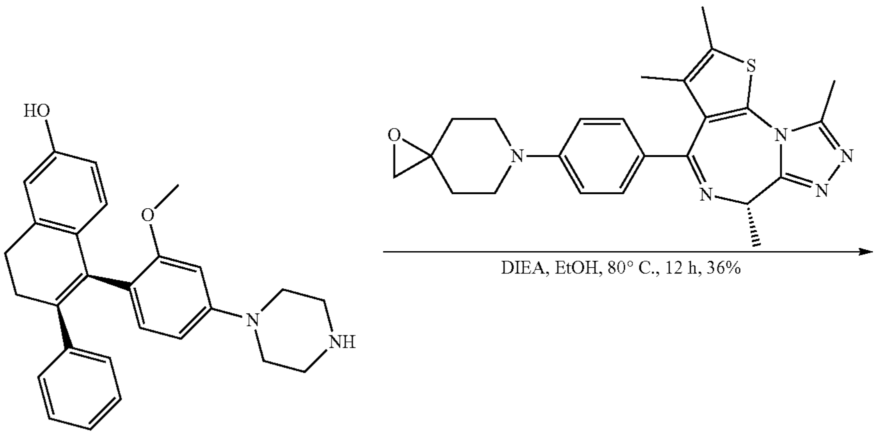
(or enantiomer)
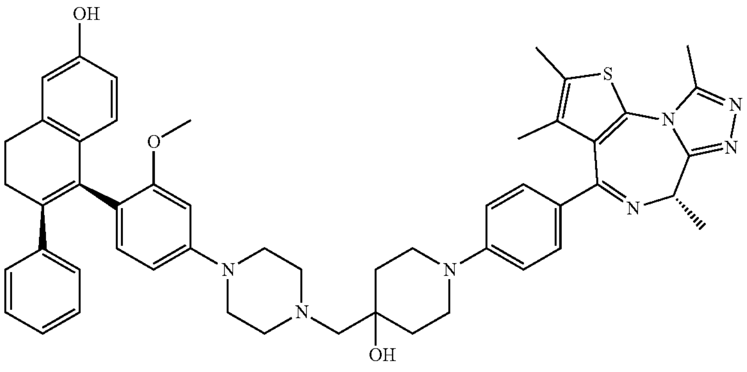
or
III-321

-continued

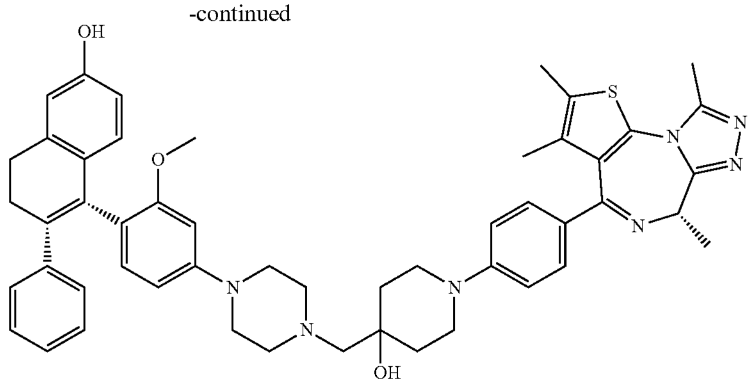

III-322

Step 1: A mixture of tert-butyl 4-[3-methoxy-4-(4,4,5,5-tetramethyl-1,3,2-dioxaborolan-2-yl)phenyl]piperazine-1-carboxylate (4.80 g, 11.4 mmol, 1.0 equiv), (6-benzyloxy-3,4-dihydronaphthalen-1-yl) trifluoromethanesulfonate (5.29 g, 13.7 mmol, 1.2 equiv), $K_2CO_3$ (4.76 g, 34.4 mmol, 3.0 equiv) and Pd(dppf)$Cl_2$ (834 mg, 1.15 mmol, 0.1 equiv) in dioxane (80.0 mL) and $H_2O$ (20.0 mL) was degassed and purged with $N_2$ for 3 times, and then the mixture was stirred at 100° C. for 3 h under $N_2$ atmosphere. The mixture was filtered, and the filtrate was concentrated under reduced pressure to remove solvent and give a residue. The residue was purified by column chromatography ($SiO_2$, Petroleum ether/Ethyl acetate=20/1 to 3/1) to obtain compound tert-butyl 4-[4-(6-benzyloxy-3,4-dihydronaphthalen-1-yl)-3-methoxy-phenyl]piperazine-1-carboxylate (4.88 g, 8.80 mmol, 77% yield) as a pale yellow solid. LC-MS: MS ($ES^+$): RT=0.763 min, m/z=527.3 $[M+H]^+$.

Step 2: To a solution of tert-butyl 4-[4-(6-benzyloxy-3,4-dihydronaphthalen-1-yl)-3-methoxy-phenyl]piperazine-1-carboxylate (4.88 g, 8.80 mmol, 1.0 equiv) in MeCN (50.0 mL) was added NBS (1.48 g, 8.33 mmol, 0.9 equiv) solution in MeCN (50.0 mL) dropwise. The mixture was stirred at 25° C. for 1 h. The reaction mixture was quenched by addition of saturated $NH_4Cl$ (aq, 100 mL) at 0° C., and then extracted with EtOAc (100 mL×3). The combined organic layers were dried over $Na_2SO_4$, filtered and concentrated under reduced pressure to give a residue. The residue was purified by column chromatography ($SiO_2$, Petroleum ether/Ethyl acetate=10/1) to obtain compound tert-butyl 4-[4-(6-benzyloxy-2-bromo-3,4-dihydronaphthalen-1-yl)-3-methoxy-phenyl]piperazine-1-carboxylate (4.20 g, 6.94 mmol, 75% yield) as a colorless oil. LC-MS: MS ($ES^+$): RT=0.783 min, m/z=607.2 $[M+H]^+$.

Step 3: A mixture of tert-butyl 4-[4-(6-benzyloxy-2-bromo-3,4-dihydronaphthalen-1-yl)-3-methoxy-phenyl]piperazine-1-carboxylate (1.40 g, 2.31 mmol, 1.0 equiv), 4,4,5,5-tetramethyl-2-phenyl-1,3,2-dioxaborolane (708 mg, 3.47 mmol, 1.5 equiv), $K_2CO_3$ (799 mg, 5.78 mmol, 2.5 equiv) and Pd(dppf)$Cl_2$ (169 mg, 231 mol, 0.1 equiv) in dioxane (10.0 mL) and $H_2O$ (1.0 mL) was degassed and purged with $N_2$ for 3 times, and then the mixture was stirred at 90° C. for 2 h under $N_2$ atmosphere. The reaction mixture was treated under reduced pressure to remove solvent and give a residue. The residue was purified by column chromatography ($SiO_2$, Petroleum ether/Ethyl acetate=10/1) to obtain compound tert-butyl 4-[4-(6-benzyloxy-2-phenyl-3,4-dihydronaphthalen-1-yl)-3-methoxy-phenyl]piperazine-1-carboxylate (1.41 g, crude) as a pale yellow solid. LC-MS: MS ($ES^+$): RT=0.800 min, m/z=603.4 [M+H]f; LCMS Method: 5-95.

Step 4: A solution of tert-butyl 4-[4-(6-benzyloxy-2-phenyl-3,4-dihydronaphthalen-1-yl)-3-methoxy-phenyl]piperazine-1-carboxylate (1.4 g) in MeOH (14.0 mL) and THE (14.0 mL) was prepared. To a fixed bed flow reactor was added 5% $Pd(OH)_2/Al_2O_3$. The $H_2$ back pressure regulator was adjusted to 1.0 MPa, and the flow rate of $H_2$ was 30 mL/min. Then the solution was pumped (0.3 mL/min) through fixed bed reactor (set at 50° C.). The flow process continued for 2 h. The resultant reaction solution was concentrated under reduced pressure to give a residue. The residue was purified by prep-HPLC (column: Phenomenex luna C18 150×40 mm×15 um; mobile phase: [$H_2O$ (0.225% FA)-ACN]; gradient: 60%-90% B over 15.0 min) to obtain compound (±)-cis-tert-butyl 4-[4-(6-hydroxy-2-phenyl-tetralin-1-yl)-3-methoxy-phenyl]piperazine-1-carboxylate (765 mg, 1.47 mmol, 55% yield) as a pale yellow solid. LC-MS: MS ($ES^+$): RT=0.690 min, m/z=515.3 $[M+H]^+$; LCMS Method: 5-95.

Step 5: The compound (±)-cis-tert-butyl 4-[4-(6-hydroxy-2-phenyl-tetralin-1-yl)-3-methoxy-phenyl]piperazine-1-carboxylate (765 mg, 1.47 mmol, 1.0 equiv) was separated by Chiral SFC (column: DAICEL CHIRALCEL OD (250 mm*30 mm, 10 um); mobile phase: [$CO_2$-IPA (0.1% $NH_3H_2O$)]; B %: 50%, isocratic elution mode; RT=1.785 and 1.994 min.) to obtain (1S,2S)- and (1R,2R)-tert-butyl 4-[4-[6-hydroxy-2-phenyl-tetralin-1-yl]-3-methoxy-phenyl]piperazine-1-carboxylate. The faster-eluting enantiomer was isolated (282 mg, 510 mol) as a pale yellow solid; and the slower-eluting enantiomer was isolated (301 mg, 550 mol) as a pale yellow solid. LC-MS: MS ($ES^+$): RT=0.691 min, m/z=515.3 $[M+H]^+$ (isomer-1); 0.690 min, m/z=515.3 $[M+H]^+$ (isomer-2); LCMS Method: 5-95.

The following Steps 6 and 7 describe further synthetic procedures conducted on the faster-eluting enantiomer of cis-tert-butyl 4-[4-[6-hydroxy-2-phenyl-tetralin-1-yl]-3-methoxy-phenyl]piperazine-1-carboxylate. This faster-eluting enantiomer produced the diastereomer of compounds III-321 and III-322 that was found to be the more potent inhibitor of cell growth of T-Rex 293 cells having increased expression of estrogen receptor alpha protein (as described in the Example 56, below). The slower-eluting enantiomer of cis-tert-butyl 4-[4-[6-hydroxy-2-phenyl-tetralin-1-yl]-3-methoxy-phenyl]piperazine-1-carboxylate was carried through the same steps to afford the other one of compounds III-321 and III-322.

Step 6: To a solution of tert-butyl 4-[4-[(1S,2S)-6-hydroxy-2-phenyl-tetralin-1-yl]-3-methoxy-phenyl]piperazine-1-carboxylate or its enantiomer (100 mg, 194 mol, 1.0 equiv) in DCM (1.0 mL) was added TFA (0.5 mL). The mixture was stirred at 25° C. for 0.5 h. The reaction mixture was concentrated under reduced pressure to obtain compound (1S,2S)-1-(2-methoxy-4-piperazin-1-yl-phenyl)-2-phenyl-tetralin-6-ol or its enantiomer (110 mg, crude, TFA salt) as a green oil. LC-MS: MS ($ES^+$): RT=0.563 min, m/z=415.2 $[M+H]^+$; LCMS Method: 5-95.

Step 7: To a solution of (1S,2S)-1-(2-methoxy-4-piperazin-1-yl-phenyl)-2-phenyl-tetralin-6-ol or its enantiomer (110 mg, 208 mol, 1.0 equiv, TFA salt) and 6-[4-[(9S)-4,5,9,13-tetramethyl-3-thia-1,8,11,12-tetrazatricyclo[8.3.0.$0^{2,6}$]trideca-2(6),4,7,10,12-pentaen-7-yl]phenyl]-1-oxa-6-azaspiro[2.5]octane (246 mg, 250 mol, 1.2 equiv) in EtOH (5.0 mL) was added DIEA (80.7 mg, 624 mol, 109 μL, 3.0 equiv). The mixture was stirred at 80° C. for 12 h. The reaction mixture was treated under reduced pressure to remove solvent and give a residue. The residue was purified by prep-HPLC (column: Waters Xbridge C18 150×25 mm×5 um; mobile phase: [$H_2O$ (10 mM $NH_4HCO_3$)-ACN]; gradient: 53%-83% B over 15.0 min) to obtain compound III-321 or III-322 (65.4 mg, 74.3 mol, 36% yield) as a yellow solid. LC-MS: MS ($ES^+$): RT=2.592 min, m/z=848.8 $[M+H]^+$; LCMS Method: 01. $^1H$ NMR (400 MHz, $CD_3OD$) δ=7.31 (br d, J=8.4 Hz, 2H), 7.05-7.00 (m, 3H), 6.94 (br d, J=8.9 Hz, 2H), 6.75-6.69 (m, 2H), 6.64-6.57 (m, 2H), 6.54-6.41 (m, 2H), 6.35 (dd, J=1.7 Hz, 1H), 6.15 (d, J=1.7 Hz, 1H), 4.75 (br d, J=5.1 Hz, 1H), 4.24-4.14 (m, 1H), 3.60 (br dd, J=4.1 Hz, 2H), 3.28-3.18 (m, 3H), 3.09-2.92 (m, 9H), 2.77-2.66 (m, 7H), 2.46-2.35 (m, 5H), 2.34-2.22 (m, 1H), 1.96 (d, J=6.7 Hz, 3H), 1.78 (dt, J=3.9 Hz, 2H).

Example 47—Synthesis of 1-(3-fluoro-4-((6S)-2,3,6,9-tetramethyl-6H-thieno[3,2-f][1,2,4]triazolo[4,3-a][1,4]diazepin-4-yl)phenyl)-4-((4-(4-((1S,2S)-2-(4-fluorophenyl)-6-hydroxy-1,2,3,4-tetrahydronaphthalen-1-yl)-3-methoxyphenyl)piperazin-1-yl)methyl)piperidin-4-ol (111-328) and 1-(3-fluoro-4-((6S)-2,3,6,9-tetramethyl-6H-thieno[3,2-f][1,2,4]triazolo[4,3-a][1,4]diazepin-4-yl)phenyl)-4-((4-(4-((1R,2R)-2-(4-fluorophenyl)-6-hydroxy-1,2,3,4-tetrahydronaphthalen-1-yl)-3-methoxyphenyl)piperazin-1-yl)methyl)piperidin-4-ol (III-327)

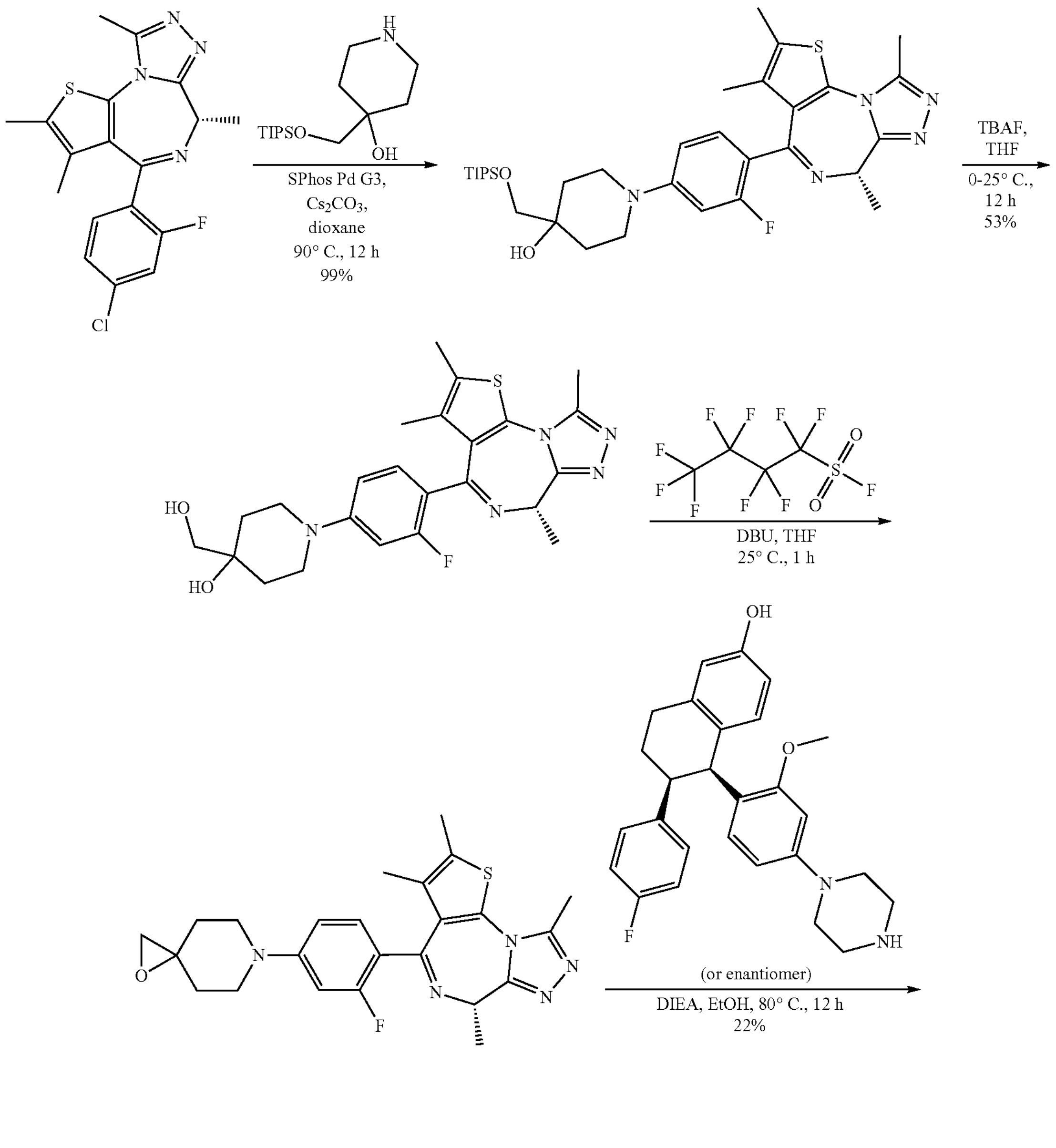

-continued

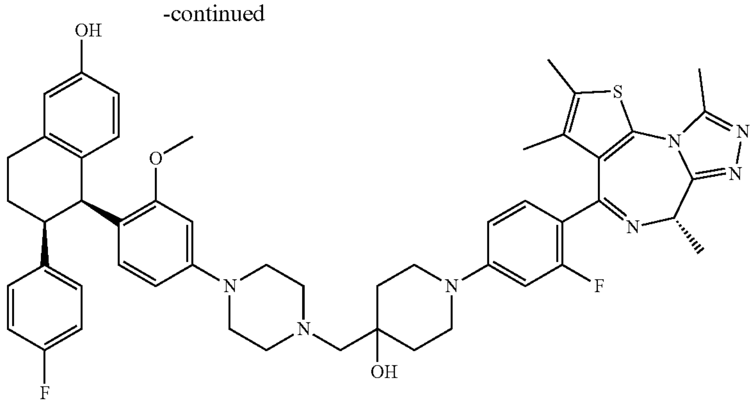

III-328 or

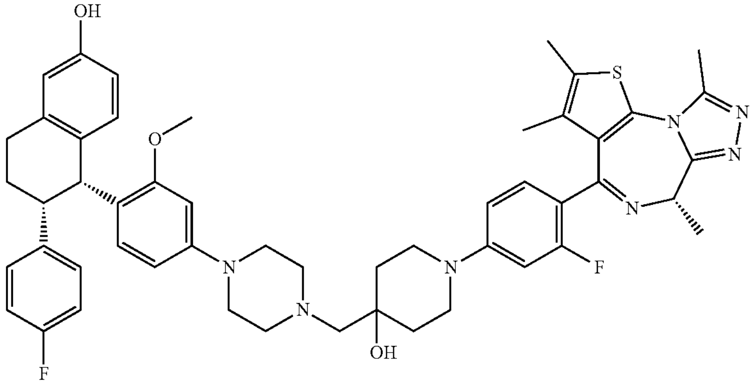

III-327

Step 1: A mixture of (9S)-7-(4-chloro-2-fluoro-phenyl)-4,5,9,13-tetramethyl-3-thia-1,8,11,12-tetrazatricyclo [8.3.0.0$^{2,6}$]trideca-2(6),4,7,10,12-pentaene (2.1 g, 5.6 mmol, 1.0 equiv), 4-(triisopropylsilyloxymethyl)piperidin-4-ol (1.9 g, 6.7 mmol, 1.2 equiv), SPhos Pd G3 (874 mg, 1.1 mmol, 0.2 equiv), $Cs_2CO_3$ (5.5 g, 16.8 mmol, 3.0 equiv) in dioxane (20.0 mL) was degassed and purged with $N_2$ for 3 times, and then the mixture was stirred at 90° C. for 12 h under $N_2$ atmosphere. The reaction mixture was partitioned between Ethyl acetate 200 mL and $H_2O$ 50 mL. The organic phase was separated, washed with NaCl 50 mL, dried over $Na_2SO_4$, filtered and concentrated under reduced pressure to give a residue. The reaction mixture was filtered and concentrated under reduced pressure to give compound 1-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl] phenyl]-4-(triisopropylsilyloxymethyl)piperidin-4-ol (3.5 g, 5.6 mmol, 99% yield) as a brown solid. LC-MS: MS (ES$^+$): RT=0.623 min, m/z=626.4 [M+1]$^+$. LCMS Method: 5-95.

Step 2: To a solution of 1-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-4-(triisopropylsilyloxymethyl)piperidin-4-ol (3.5 g, 5.6 mmol, 1.0 equiv) in THE (35 mL) was added TBAF (1.00 M, 5.6 mL, 1.0 equiv) at 0-25° C. The mixture was stirred at 0-25° C. for 12 h. The reaction mixture was partitioned between Ethyl acetate 200 mL and $H_2O$ 50 mL. The organic phase was separated, washed with NaCl 50 mL, dried over $Na_2SO_4$, filtered and concentrated under reduced pressure to give a residue. The residue was purified by column chromatography ($SiO_2$, Petroleum ether/Ethyl acetate=0/1 to Ethylacetate: MeOH=10:1) to give compound 1-[3-fluoro-4-[(9S)-4,5,9,13-tetramethyl-3-thia-1,8,11,12-tetrazatricyclo[8.3.0.0$^{2,6}$] trideca-2(6),4,7,10,12-pentaen-7-yl]phenyl]-4-(hydroxymethyl)piperidin-4-01 (1.4 g, 3.0 mmol, 53% yield) as a yellow solid. LC-MS: MS (ES$^+$): RT=0.478 min, m/z=470.2 [M+1]$^+$. LCMS Method: 5-95.

Step 3: To a solution of 1-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-4-(hydroxymethyl)piperidin-4-01 (200 mg, 426 mol, 1.0 equiv) and 1,1,2,2,3,3,4,4,4-nonafluorobutane-1-sulfonyl fluoride (386 mg, 1.3 mmol, 225 μL, 3.0 equiv) in THE (3.0 mL) was added DBU (324 mg, 2.1 mmol, 321 L, 5.0 equiv). The mixture was stirred at 25° C. for 1 h. The mixture was quenched with $H_2O$ (10 mL) and extracted with DCM 20 mL (10 mL×2). The combined organic layers were dried over anhydrous sodium sulfate, filtered and concentrated under reduced pressure to give a residue. The crude product was used into the next step without purification. Compound 6-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro[2.5]octane (200 mg, crude) was obtained as a brown oil. LC-MS: MS (ES$^+$): RT=0.467 min, m/z=452.2 [M+1]$^+$. LCMS Method: 5-95.

Step 4: To a solution of 6-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro [2.5]octane (80.0 mg, 177 mol, 1.0 equiv) and the slower-eluting enantiomer of (5S,6S)- or (5R,6R)-6-(4-fluorophenyl)-5-(2-methoxy-4-(piperazin-1-yl)phenyl)-5,6,7,8-tetrahydronaphthalen-2-ol (76.6 mg, 177 mol, 1.0 equiv;

prepared as described in Example 43) in EtOH (2 mL) was added DIEA (22.9 mg, 177 mol, 30.8 μL, 1.0 equiv). The mixture was stirred at 80° C. for 12 h. It was filtered. The residue was purified by prep-HPLC (column: Waters xbridge 150*25 mm 10 um; mobile phase: [$H_2O$ (10 mM $NH_4HCO_3$)-ACN]; gradient: 68-88% B over 8.0 min) (column: Phenomenex Luna C18 150*25 mm*10 um; mobile phase: [$H_2O$ (0.225% FA)-ACN]; gradient: 3%-33% B over 10.0 min) to afford compound III-328 or III-327 (34.92 mg, 39.50 mol, 22% yield) as a yellow solid. $^1H$ NMR (400 MHz, $CD_3OD$) δ 7.33 (br t, J=8.9 Hz, 1H), 6.82-6.69 (m, 5H), 6.64-6.57 (m, 3H), 6.51-6.43 (m, 2H), 6.36 (dd, J=2.1, 8.5 Hz, 1H), 6.18 (d, J=2.0 Hz, 1H), 4.72 (br d, J=5.4 Hz, 1H), 4.22 (q, J=6.7 Hz, 1H), 3.67-3.57 (m, 2H), 3.25 (br d, J=11.8 Hz, 3H), 3.11 (s, 3H), 3.06 (br s, 4H), 3.00-2.93 (m, 2H), 2.73 (br d, J=4.5 Hz, 4H), 2.67 (s, 3H), 2.43-2.36 (m, 5H), 2.31-2.17 (m, 1H), 1.97 (d, J=6.9 Hz, 3H), 1.81-1.73 (m, 2H), 1.71-1.60 (m, 6H). LC-MS: MS ($ES^+$): RT=2.674 min, m/z=884.7 [$M+H^+$]; LCMS Method: 01. This diastereomer of compounds III-328 and III-327 was found to be the more potent inhibitor of cell growth of T-Rex 293 cells having increased expression of estrogen receptor alpha protein (as described in the Example 56, below).

The faster-eluting enantiomer of cis-6-(4-fluorophenyl)-5-(2-methoxy-4-(piperazin-1-yl)phenyl)-5,6,7,8-tetrahydronaphthalen-2-ol was used in a similar reaction to afford the other one of compounds III-327 and III-328.

Example 48—Synthesis of 4-((4-(4-((1S,2S)-2-(2,4-difluorophenyl)-6-hydroxy-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-334) and 4-((4-(4-((1R,2R)-2-(2,4-difluorophenyl)-6-hydroxy-1,2,3,4-tetrahydronaphthalen-1-yl)-3-methoxyphenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-333)

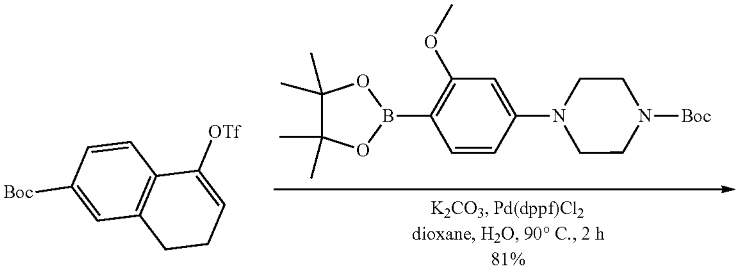

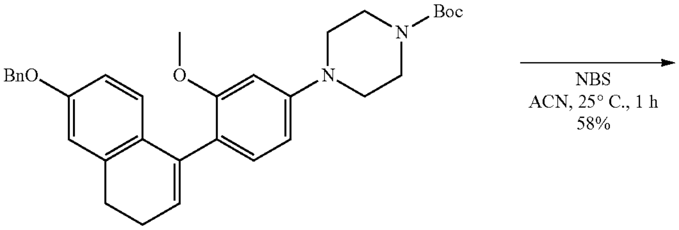

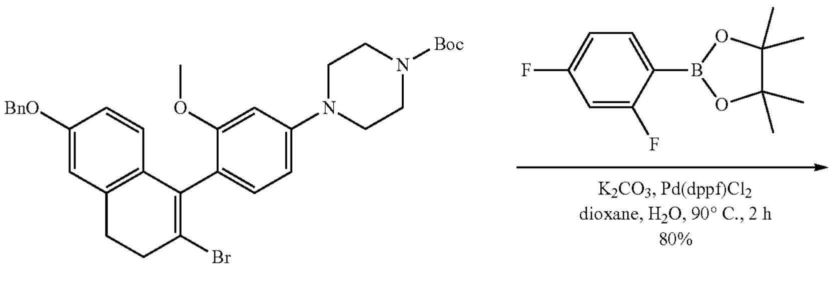

-continued
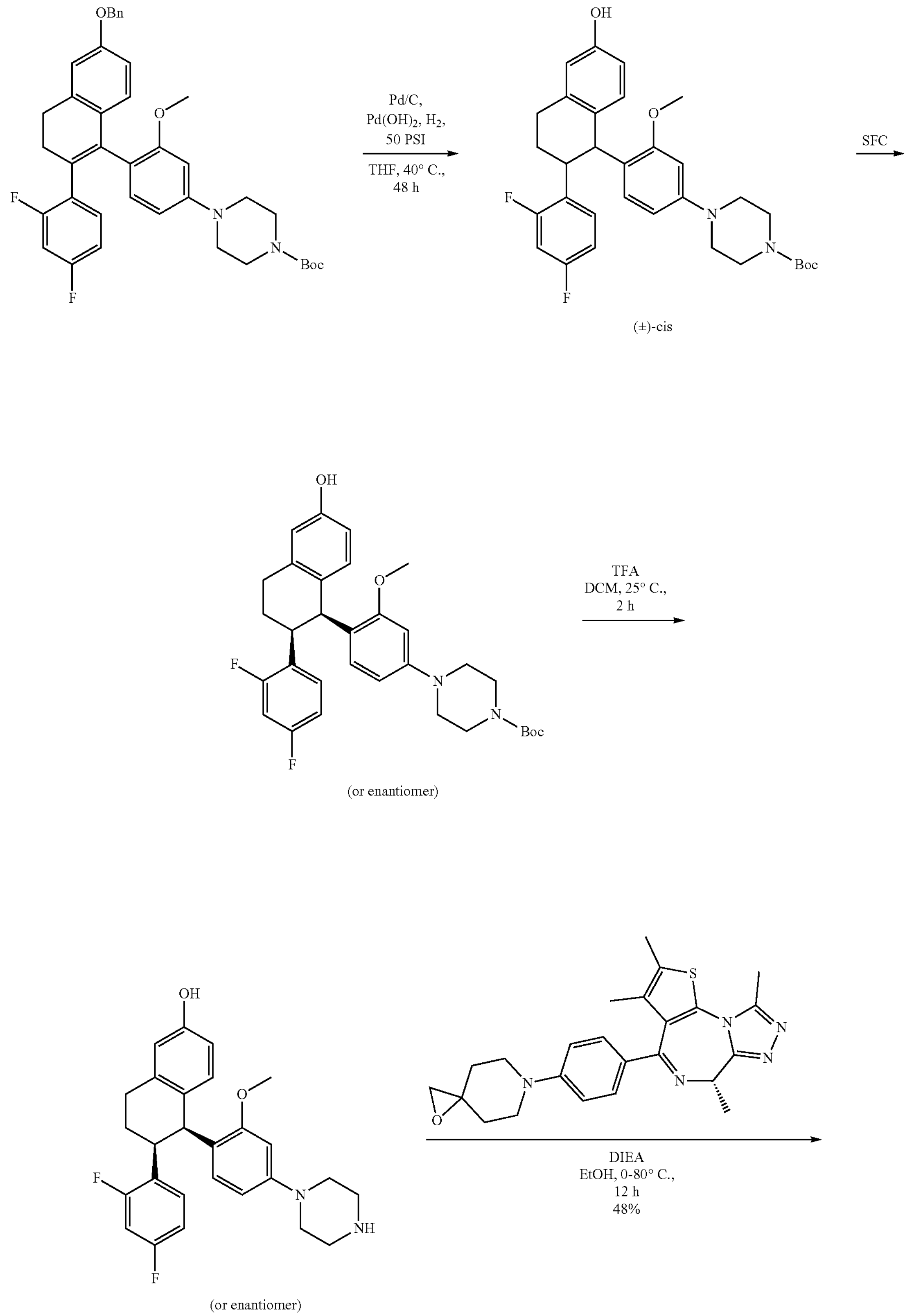

-continued

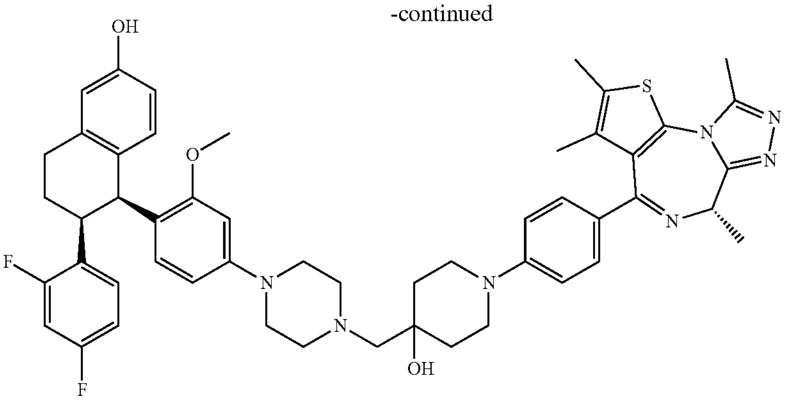

or

III-334

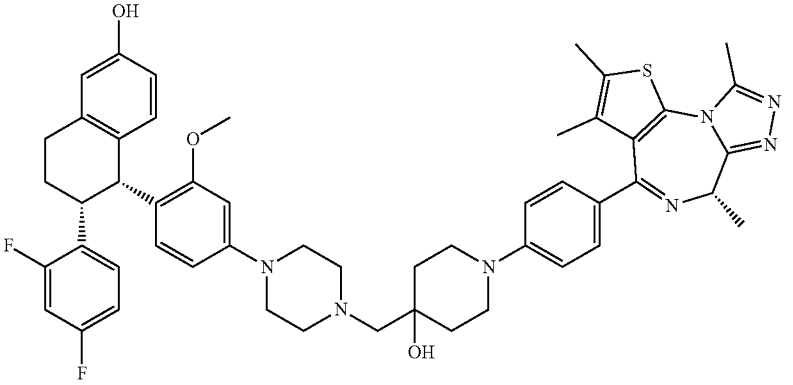

III-333

Step 1: A mixture of (6-benzyloxy-3,4-dihydronaphthalen-1-yl) trifluoromethanesulfonate (1.8 g, 4.68 mmol, 1.0 equiv), tert-butyl 4-[3-methoxy-4-(4,4,5,5-tetramethyl-1,3,2-dioxaborolan-2-yl)phenyl]piperazine-1-carboxylate (2.55 g, 6 mmol, 1.3 equiv), $K_2CO_3$ (1.62 g, 12 mmol, 2.5 equiv), and Pd(dppf)$Cl_2$ (171 mg, 234 mol, 0.05 equiv) in dioxane (20 mL) and $H_2O$ (4 mL) in one portion at 25° C. Then the resulting mixture was degassed and purged with $N_2$ for 3 times, and then the mixture was stirred at 90° C. for 2 h under $N_2$ atmosphere. The residue was filtered and concentrated under reduced pressure to give a residue. The residue was purified by column chromatography ($SiO_2$, Petroleum ether/Ethyl acetate=1/0 to 20/1) to give tert-butyl 4-[4-(6-benzyloxy-3,4-dihydronaphthalen-1-yl)-3-methoxy-phenyl]piperazine-1-carboxylate (2.0 g, 81% yield) as a white solid. $^1$H NMR (400 MHz, $CDCl_3$): δ 7.53-7.30 (m, 7H), 7.15-7.07 (m, 1H), 6.84 (s, 1H), 6.67 (s, 2H), 6.63-6.51 (m, 1H), 5.93-5.95 (m, 1H), 5.06 (s, 2H), 3.77-3.56 (m, 6H), 3.30-3.15 (m, 4H), 2.92-2.80 (m, 2H), 2.47-2.36 (m, 2H), 1.52 (s, 9H). LC-MS: MS ($ES^+$): RT=0.767 min, m/z=527.3 [$M+H^+$]. LCMS method: 5-95.

Step 2: To a solution of tert-butyl 4-[4-(6-benzyloxy-3,4-dihydronaphthalen-1-yl)-3-methoxy-phenyl]piperazine-1-carboxylate (1.80 g, 3 mmol, 1.0 equiv) in ACN (20 mL) was added NBS (547 mg, 3 mmol, 0.9 equiv). The mixture was stirred at 25° C. for 1 h. The reaction mixture was filtered and concentrated under reduced pressure to give a residue. The residue was purified by column chromatography ($SiO_2$, Petroleum ether/Ethyl acetate=1/0 to 20/1) to give tert-butyl 4-[4-(6-benzyloxy-2-bromo-3,4-dihydronaphthalen-1-yl)-3-methoxy-phenyl]piperazine-1-carboxylate (1.20 g, 58% yield) as a white solid. LC-MS: MS ($ES^+$): RT=0.777 min, m/z=605.2 [$M+H^+$]. LCMS method: 5-95.

Step 3: A mixture of tert-butyl 4-[4-(6-benzyloxy-2-bromo-3,4-dihydronaphthalen-1-yl)-3-methoxy-phenyl]piperazine-1-carboxylate (500 mg, 826 mol, 1.0 equiv), 2-(2,4-difluorophenyl)-4,4,5,5-tetramethyl-1,3,2-dioxaborolane (208 mg, 867 mol, 1.05 equiv), $K_2CO_3$ (285 mg, 2 mmol, 2.5 equiv), and Pd(dppf)$Cl_2$ (30 mg, 41 mol, 0.05 equiv) in dioxane (5 mL) and $H_2O$ (0.5 mL) in one portion at 25° C. Then the resulting mixture was degassed and purged with $N_2$ for 3 times, and then the mixture was stirred at 90° C. for 2 h under $N_2$ atmosphere. The residue was filtered and concentrated under reduced pressure to give a residue. The residue was purified by prep-HPLC (column: Phenomenex luna C18 150*40 mm* 15 um; mobile phase: [$H_2O$ (0.225% FA)-ACN]; gradient: 90%-100% B over 15.0 min) to give tert-butyl 4-[4-[6-benzyloxy-2-(2,4-difluorophenyl)-3,4-dihydronaphthalen-1-yl]-3-methoxy-phenyl]piperazine-1-carboxylate (420 mg, 80% yield) as a white solid. LC-MS: MS ($ES^+$): RT=0.797 min, m/z=639.3[$M+H^+$]. LCMS method: 5-95.

Step 4: Pd/C (200 mg, 10% purity), $Pd(OH)_2$ (200 mg, 10% purity) was added into a flask under $N_2$, tert-butyl 4-[4-[6-benzyloxy-2-(2,4-difluorophenyl)-3,4-dihydronaphthalen-1-yl]-3-methoxy-phenyl]piperazine-1-carboxylate (420 mg, 657 mol, 1.0 equiv) in THF (4 mL) and MeOH (2 mL) was added into the mixture. The suspension was degassed and purged with $H_2$ for 3 times. The mixture was stirred under $H_2$ (50 Psi) at 40° C. for 48 h. The reaction mixture was filtered and concentrated under reduced pressure to give a residue. The crude (±)-cis-tert-butyl 4-[4-[2-(2,4-difluorophenyl)-6-hydroxy-tetralin-1-yl]-3-methoxy-phenyl]piperazine-1-carboxylate (360 mg, crude) as a white solid was used into the next step without further purification. LC-MS: MS ($ES^+$): RT=0.682 min, m/z=551.4[$M+H^+$]. LCMS method: 5-95.

Step 5: The (±)-cis-tert-butyl 4-[4-[2-(2,4-difluorophenyl)-6-hydroxy-tetralin-1-yl]-3-methoxy-phenyl]piperazine-1-carboxylate (360 mg, crude) was purified by preparative SFC (column: DAICEL CHIRALPAK AD (250 mm*30 mm, 10 um); mobile phase: [$CO_2$-IPA (0.1% $NH_3H_2O$)]; B %: 35%, isocratic elution mode) to give (1S,2S)- and (1R,2R)-tert-butyl 4-[4-[2-(2,4-difluorophenyl)-6-hydroxy-tetralin-1-yl]-3-methoxy-phenyl]piperazine-1-carboxylate. The slower-eluting enantiomer (150 mg, 42% yield) was obtained as a white solid. LC-MS: MS ($ES^+$): RT=0.689 min, m/z=551.2 [$M+H^+$]. LCMS method: 5-95.

The following Steps 6 and 7 describe further synthetic procedures conducted on the slower-eluting enantiomer of cis-tert-butyl 4-[4-[2-(2,4-difluorophenyl)-6-hydroxy-tetralin-1-yl]-3-methoxy-phenyl]piperazine-1-carboxylate. This slower-eluting enantiomer produced the diastereomer of compounds III-333 and III-334 that was found to be the more potent inhibitor of cell growth of T-Rex 293 cells having increased expression of estrogen receptor alpha protein (as described in the Example 56, below). The faster-eluting enantiomer of cis-tert-butyl 4-[4-[2-(2,4-difluorophenyl)-6-hydroxy-tetralin-1-yl]-3-methoxy-phenyl]piperazine-1-carboxylate was carried through the same steps to afford the other one of compounds III-333 and III-334.

Step 6: To a solution of tert-butyl 4-[4-[(1S,2S)-2-(2,4-difluorophenyl)-6-hydroxy-tetralin-1-yl]-3-methoxy-phenyl]piperazine-1-carboxylate or its enantiomer (150 mg, 272 mol, 1.0 equiv) in DCM (1.5 mL) was added TFA (767 mg, 7 mmol, 0.5 mL, 25.0 equiv). The mixture was stirred at 25° C. for 2 h. The mixture was diluted with $NaHCO_3$ (10 mL), then extracted with DCM (10 mL *3). The combined organic layers were washed with $H_2O$ (10 mL *2), dried over $Na_2SO_4$, filtered and concentrated under reduced pressure to give a residue. The crude (1S,2S)-2-(2,4-difluorophenyl)-1-(2-methoxy-4-piperazin-1-yl-phenyl)tetralin-6-ol or its enantiomer (122 mg, crude) as a yellow solid was used into the next step without further purification. LC-MS: MS ($ES^+$): RT=0.548 min, m/z=451.1 [$M+H^+$]. LCMS method: 5-95.

Step 7: To a solution of (1S,2S)-2-(2,4-difluorophenyl)-1-(2-methoxy-4-piperazin-1-yl-phenyl)tetralin-6-ol or its enantiomer (122 mg, 271 mol, 1.0 equiv) in EtOH (4 mL) was added DIEA (105 mg, 812 mol, 141 L, 3.0 equiv) and 6-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro[2.5]octane (141 mg, 325 mol, 1.2 equiv) at 0° C. The mixture was stirred at 80° C. for 12 h. The mixture was concentrated to give a residue. The residue was purified by preparative HPLC (column: Waters Xbridge C18 150*50 mm*10 um; mobile phase: [$H_2O$ (10 mM $NH_4HCO_3$)-ACN]; gradient: 60%-90% B over 11.0 min) to give compound III-334 or III-333 (114 mg, 48% yield) as a yellow solid. $^1H$ NMR (400 MHz, $CDCl_3$): δ 7.43-7.35 (m, 2H), 6.93-6.84 (m, 2H), 6.81-6.72 (m, 2H), 6.70 (s, 1H), 6.63-6.57 (m, 1H), 6.53-6.43 (m, 2H), 6.34-6.24 (m, 2H), 6.07 (s, 1H), 5.35 (s, 1H), 4.88 (s, 1H), 4.24-4.07 (m, 1H), 3.73-3.51 (m, 3H), 3.33-3.23 (m, 2H), 3.20 (s, 3H), 3.17-3.06 (m, 4H), 3.05-2.98 (m, 2H), 2.78 (br s, 4H), 2.68 (s, 3H), 2.47-2.33 (m, 5H), 2.31-2.16 (m, 1H), 2.13-2.05 (m, 3H), 1.78 (s, 3H), 1.62 (s, 6H). LC-MS: MS ($ES^+$): RT=1.84 min, m/z=884.8 [$M+H^+$]. LCMS method: 25.

Example 49—Synthesis of 4-((4-(3-chloro-4-((1S,2S)-6-hydroxy-2-(4-methoxyphenyl)-1,2,3,4-tetrahydronaphthalen-1-yl)phenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-336) and 4-((4-(3-chloro-4-((1R,2R)-6-hydroxy-2-(4-methoxyphenyl)-1,2,3,4-tetrahydronaphthalen-1-yl)phenyl)piperazin-1-yl)methyl)-1-(4-((6S)-2,3,6,9-tetramethyl-6H-thieno[3,2-f][1,2,4]triazolo[4,3-a][1,4]diazepin-4-yl)phenyl)piperidin-4-ol (III-335)

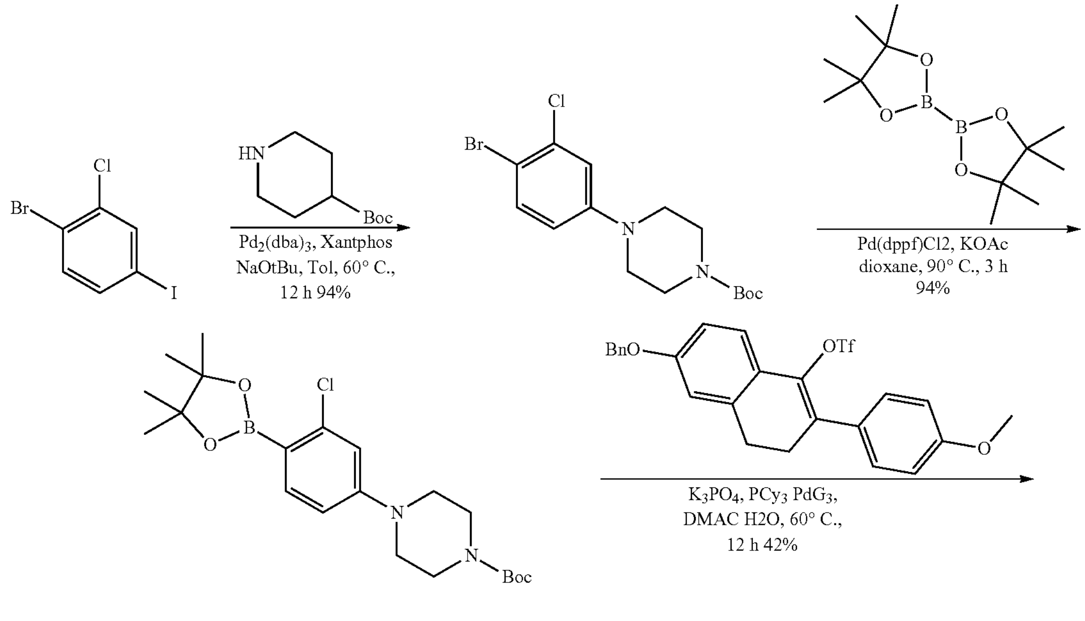

-continued
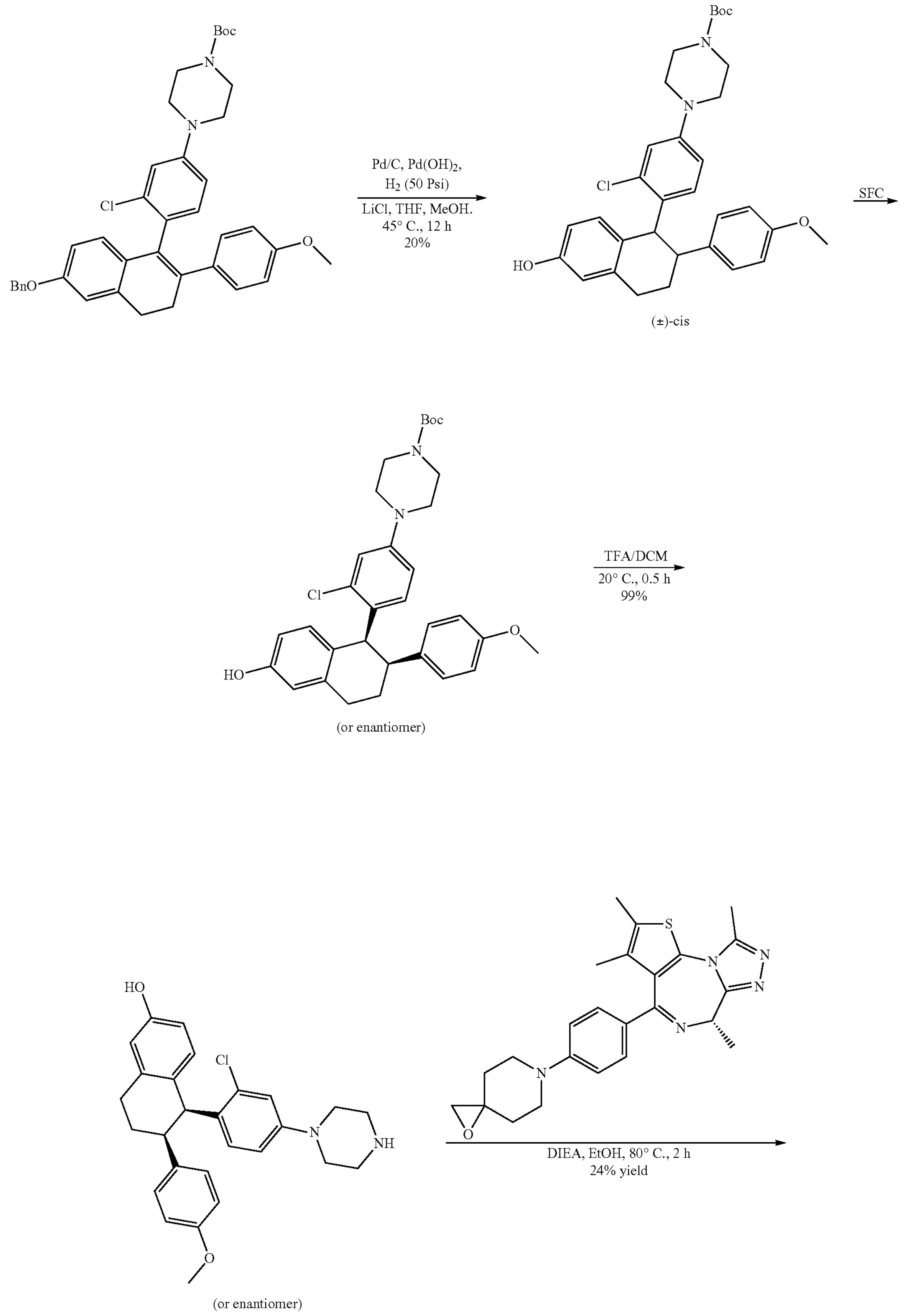

-continued

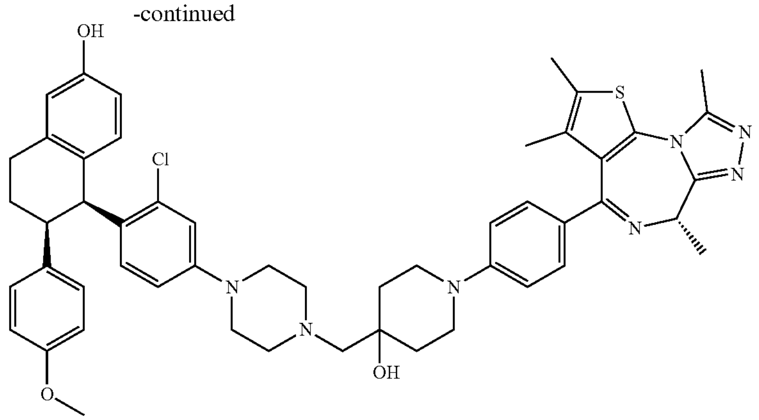

III-336 or

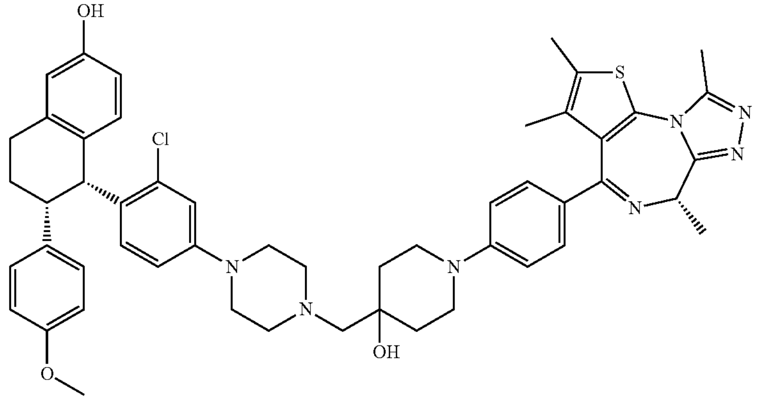

III-335

Step 1: A mixture of tert-butyl piperazine-1-carboxylate (10 g, 53 mmol, 1 equiv), 1-bromo-2-chloro-4-iodo-benzene (20.45 g, 64 mmol, 1.2 equiv), $Pd_2(dba)_3$ (4.92 g, 5.37 mmol, 0.1 equiv), Xantphos (9.32 g, 16.11 mmol, 0.3 equiv) and NaOtBu (15.48 g, 161.07 mmol, 3 equiv) in Tol. (180 mL) was degassed and purged with $N_2$ for 3 times, and then the mixture was stirred at 60° C. for 12 h under $N_2$ atmosphere. The reaction mixture was filtered and concentrated under reduced pressure to give a residue. The residue was purified by silica column chromatography on silica gel (Petroleum ether: Ethyl acetate from 1/0 to 3/1) to afford desired producd tert-butyl 4-(4-bromo-3-chloro-phenyl) piperazine-1-carboxylate (19 g, 94% yield) as a yellow oil. LC-MS: MS ($ES^+$): RT=0.643 min, m/z=320.9 [M−55]. LCMS method: 5-95.

Step 2: A mixture of tert-butyl 4-(4-bromo-3-chloro-phenyl)piperazine-1-carboxylate (15 g, 39.93 mmol, 1 equiv), 4,4,5,5-tetramethyl-2-(4,4,5,5-tetramethyl-1,3,2-dioxaborolan-2-yl)-1,3,2-dioxaborolane (20.28 g, 79.85 mmol, 2 equiv), KOAc (7.84 g, 79.85 mmol, 2 equiv), $Pd(dppf)Cl_2$ (5.84 g, 7.99 mmol, 0.2 eq) and 4,4,5,5-tetramethyl-2-(4,4,5,5-tetramethyl-1,3,2-dioxaborolan-2-yl)-1,3,2-dioxaborolane (20.28 g, 79.85 mmol, 2 equiv) in dioxane (200 mL) was degassed and purged with $N_2$ for 3 times, and then the mixture was stirred at 90° C. for 3 h under $N_2$ atmosphere. The reaction mixture was filtered and concentrated under reduced pressure to give a residue. The residue was purified by silica column chromatography on silica gel (Petroleum ether: Ethyl acetate from 1/0 to 10/1) to afford tert-butyl 4-[3-chloro-4-(4,4,5,5-tetramethyl-1,3,2-dioxaborolan-2-yl)phenyl]piperazine-1-carboxylate (16 g, 94% yield) as yellow oil. $^1H$ NMR (400 MHz, $CDCL_3$): δ=7.63 (d, J=8.4 Hz, 1H), 6.86 (d, J=2.4 Hz, 1H), 6.75 (dd, J=2.4, 8.4 Hz, 1H), 3.60-3.57 (m, 4H), 3.24-3.21 (m, 4H), 1.50 (s, 9H), 1.36 (s, 12H). LC-MS: MS ($ES^+$): RT=0.711 min, m/z=423.1 [$M+H^+$]. LCMS method: 5-95.

Step 3: A mixture of [6-benzyloxy-2-(4-methoxyphenyl)-3,4-dihydronaphthalen-1-yl]trifluoromethanesulfonate (6.54 g, 13.33 mmol, 1 equiv), tert-butyl 4-[3-chloro-4-(4,4,5,5-tetramethyl-1,3,2-dioxaborolan-2-yl)phenyl]piperazine-1-carboxylate (6.2 g, 14.67 mmol, 1.1 equiv), tricyclohexylphosphane Pd G3 (980 mg, 1.33 mmol, 0.1 equiv) and $K_3PO_4$ (8.49 g, 40.00 mmol, 3 equiv) in $H_2O$ (20 mL) and DMAC (100 mL) was degassed and purged with $N_2$ for 3 times, and then the mixture was stirred at 60° C. for 12 h under $N_2$ atmosphere. The reaction mixture was filtered and concentrated in vacuum. The residue was purified by prep-TLC ($SiO_2$, PE:EA=3:1) to afford tert-butyl 4-[4-[6-benzyloxy-2-(4-methoxyphenyl)-3,4-dihydronaphthalen-1-yl]-3-chloro-phenyl]piperazine-1-carboxylate (3.6 g, 42% yield) as a yellow solid. LC-MS: MS ($ES^+$): RT=0.806 min, m/z=637.1 [$M+H^+$]. LCMS method: 5-95.

Step 4: To a solution of tert-butyl 4-[4-[6-benzyloxy-2-(4-methoxyphenyl)-3,4-dihydronaphthalen-1-yl]-3-chloro-phenyl]piperazine-1-carboxylate (3.45 g, 5.41 mmol, 1 equiv) in MeOH (15 mL) and THE (15 mL) was added LiCl (229 mg, 5.41 mmol, 110 μL, 1 equiv) and Pd/C (1.15 g, 1.08 mmol, 10% purity, 0.2 equiv) under $N_2$ atmosphere. The suspension was degassed and purged with $H_2$ for 3 times. The mixture was stirred under $H_2$ (50 Psi) at 45° C. for 12 h. The reaction mixture was filtered and concentrated under reduced pressure to afford (±)-cis-tert-butyl 4-[3-chloro-4-[6-hydroxy-2-(4-methoxyphenyl)tetralin-1-yl]phenyl]piperazine-1-carboxylate (600 mg, 20% yield) as a yellow oil. $^1$H NMR (400 MHz, $CDCl_3$): δ=7.11 (s, 2H), 6.98-6.85 (m, 3H), 6.80-6.74 (m, 2H), 6.64-6.58 (m, 3H), 4.13-4.06 (m, 1H), 3.67 (s, 3H), 3.54-3.46 (m, 5H), 3.06-3.01 (m, 4H), 2.86-2.80 (m, 1H), 2.58-2.51 (m, 1H), 2.33-2.25 (m, 1H), 1.94-1.89 (m, 1H), 1.41 (s, 9H). LC-MS: MS ($ES^+$): RT=0.684 min, m/z=549.2 [$M+H^+$]. LCMS method: 5-95.

Step 5: Racemic cis-tert-butyl 4-[3-chloro-4-[6-hydroxy-2-(4-methoxyphenyl)tetralin-1-yl]phenyl]piperazine-1-carboxylate (600 mg, 1.09 mmol) was purified by prep-SFC (column: DAICEL CHIRALPAK AD (250 mm*30 mm, 10 um); mobile phase: [$CO_2$-EtOH (0.1% NH3H2O)]; B %: 45%, isocratic elution mode) to afford (1S,2S)- and (1R, 2R)-tert-butyl 4-[3-chloro-4-[6-hydroxy-2-(4-methoxyphenyl)tetralin-1-yl]phenyl]piperazine-1-carboxylate. The slower-eluting enantiomer (238 mg, 39% yield) was obtained as a yellow solid. LC-MS: MS ($ES^+$): RT=0.682 min, m/z=549.3 [$M+H^+$]. LCMS method: 5-95.

The following Steps 6 and 7 describe further synthetic procedures conducted on the slower-eluting enantiomer of cis-tert-butyl 4-[3-chloro-4-[6-hydroxy-2-(4-methoxyphenyl) tetralin-1-yl]phenyl]piperazine-1-carboxylate. This slower-eluting enantiomer produced the diastereomer of compounds III-335 and III-336 that was found to be the more potent inhibitor of cell growth of T-Rex 293 cells having increased expression of estrogen receptor alpha protein (as described in the Example 56, below). The faster-eluting enantiomer of cis-tert-butyl 4-[3-chloro-4-[6-hydroxy-2-(4-methoxyphenyl) tetralin-1-yl]phenyl]piperazine-1-carboxylate was carried through the same steps to afford the other one of compounds III-335 and III-336.

Step 6: To a solution of tert-butyl 4-[3-chloro-4-[(1S,2S)-6-hydroxy-2-(4-methoxyphenyl)tetralin-1-yl]phenyl]piperazine-1-carboxylate or its enantiomer (119 mg, 216 mol, 1 equiv) in DCM (1 mL) was added TFA (767 mg, 6.73 mmol, 0.5 mL, 31.06 equiv). The mixture was stirred at 20° C. for 0.5 h. The reaction mixture was partitioned between $NaHCO_3$ 30 mL and DCM 50 mL. The organic phase was separated, filtered and concentrated under reduced pressure to afford desired product (1S,2S)-1-(2-chloro-4-piperazin-1-yl-phenyl)-2-(4-methoxyphenyl)tetralin-6-ol or its enantiomer (97 mg, 99% yield) as a white solid. LC-MS: MS ($ES^+$): RT=0.480 min, m/z=449.1 [$M+H^+$]. LCMS method: 5-95.

Step 7: To a solution of 6-[4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro[2.5]octane (281 mg, 648 mol, 3 equiv) in EtOH (3 mL) was added DIEA (83 mg, 648 mol, 112 μL, 3 equiv) and (1S,2S)-1-(2-chloro-4-piperazin-1-yl-phenyl)-2-(4-methoxyphenyl)tetralin-6-ol or its enantiomer (97 mg, 216 mol, 1 equiv). The mixture was stirred at 80° C. for 2 h. The mixture was filtered and concentrated under reduced pressure to give a residue. The residue was purified by prep-HPLC (column: Waters xbridge 150*25 mm 10 um; mobile phase: [$H_2O$ (10 mM $NH_4HCO_3$)-ACN]; gradient: 55%-85% B over 15.0 min) to afford compound III-336 or III-335 (46 mg, 23% yield) as a yellow solid. $^1$H NMR (400 MHz, MeOD): δ=7.32 (d, J=6.0 Hz, 2H), 6.96 (d, J=7.6 Hz, 2H), 6.71 (s, 2H), 6.67-6.57 (m, 7H), 6.51-6.41 (m, 1H), 4.80-4.75 (m, 1H), 4.29-4.15 (m, 1H), 3.72 (s, 3H), 3.65-3.55 (m, 2H), 3.29-3.21 (m, 3H), 3.10-3.05 (m, 4H), 3.04-2.94 (m, 2H), 2.76-2.66 (m, 7H), 2.45-2.36 (m, 5H), 2.00-1.974 (m, 3H), 1.87-1.74 (m, 3H), 1.70-1.5 (m, 6H). LC-MS: MS ($ES^+$): RT=2.625 min, m/z=882.7 [$M+H^+$]. LCMS Method: 01.

Example 50—Synthesis of 4-((4-(3,5-difluoro-4-((1S,2S)-2-(4-fluorophenyl)-6-hydroxy-1,2,3,4-tetrahydronaphthalen-1-yl)phenyl)piperidin-1-yl) methyl)-1-(3-fluoro-4-((6S)-2,3,6,9-tetramethyl-6H-thieno[3,2-f][1,2,4]triazolo[4,3-a][1,4]diazepin-4-yl) phenyl)piperidin-4-ol (III-338) and 4-((4-(3,5-difluoro-4-((1R,2R)-2-(4-fluorophenyl)-6-hydroxy-1,2,3,4-tetrahydronaphthalen-1-yl)phenyl)piperidin-1-yl)methyl)-1-(3-fluoro-4-((6S)-2,3,6,9-tetramethyl-6H-thieno[3,2-f][1,2,4]triazolo[4,3-a][1,4]diazepin-4-yl)phenyl)piperidin-4-ol (II-337)

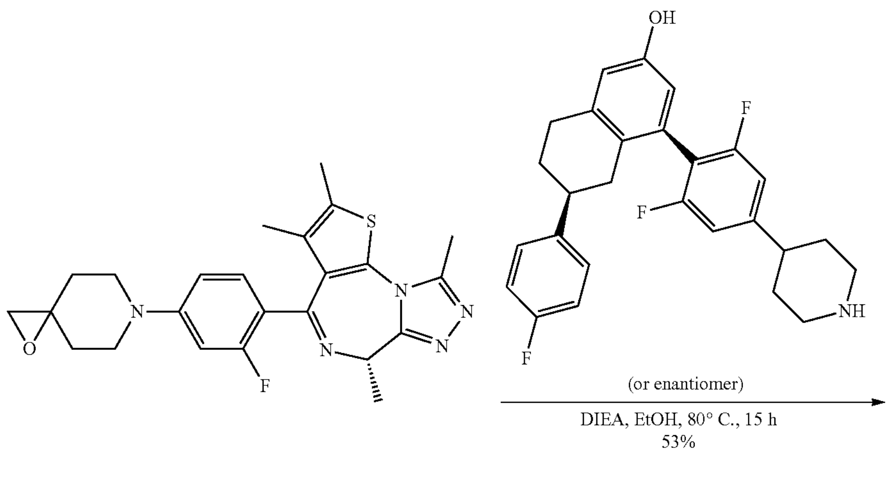

-continued

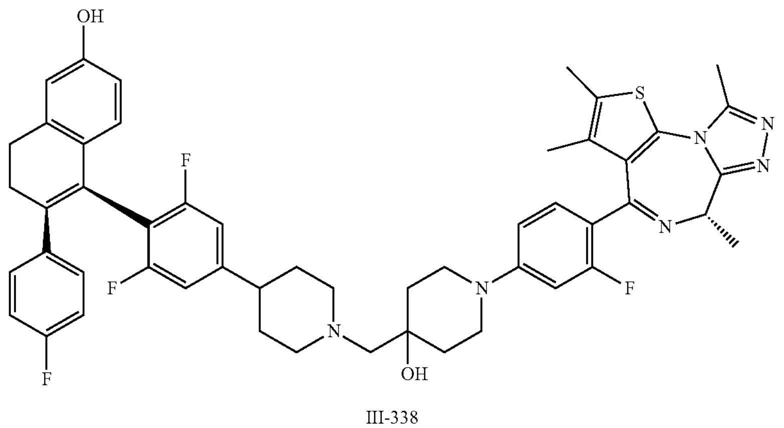

III-338 or

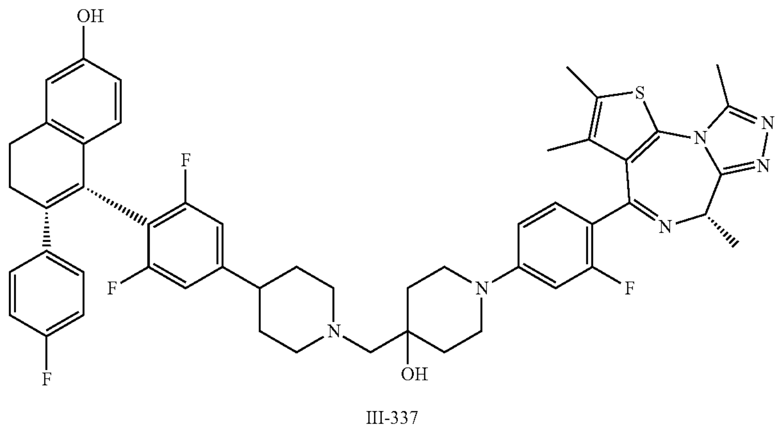

III-337

Step 1: To a mixture of (1S,2S)-1-[2,6-difluoro-4-(4-piperidyl)phenyl]-2-(4-fluorophenyl)tetralin-6-ol or its enantiomer (106 mg, 0.24 mmol, 1.0 equiv) in EtOH (5 mL) was added DIEA (156 mg, 1.21 mmol, 0.21 mL, 5.0 equiv) and 6-[3-fluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro[2.5]octane (144 mg, 0.32 mmol, 1.3 equiv) under $N_2$. The mixture was stirred at 80° C. for 15 h under $N_2$. The reaction mixture was concentrated in vacuum to give a residue. The residue was purified by Prep-HPLC (column: Waters xbridge 150*25 mm 10 um; mobile phase: [$H_2O$ (10 mM $NH_4HCO_3$)-ACN]; gradient: 65%-95% B over 9.0 min) to give compound III-338 or 11I-337 (114.21 mg, 127.81 mol, 53% yield, 99.5% purity) as a white solid. LCMS: MS (ES$^+$): RT=2.701 min, m/z=889.7 [M+H$^+$]. LCMS method: 01. $^1$H NMR (400 MHz, DMSO-$d_6$): δ 9.11 (s, 1H), 7.28 (t, J=8.4 Hz, 1H), 6.98-6.86 (m, 4H), 6.77 (dd, $J_1$=1.6 Hz, $J_2$=8.8 Hz, 1H), 6.69-6.52 (m, 5H), 6.42 (dd, J=2.0, $J_2$=8.0 Hz, 1H), 4.54 (d, J=6.0 Hz, 1H), 4.19 (s, 1H), 4.16-4.09 (m, 1H), 3.57-3.39 (m, 3H), 3.14 (t, J=11.2 Hz, 2H), 2.95-2.93 (m, 4H), 2.57 (s, 3H), 2.39-2.29 (m, 4H), 2.25 (s, 2H), 2.22-2.11 (m, 3H), 1.84 (d, J=6.8 Hz, 3H), 1.76-1.73 (m, 1H), 1.64 (s, 3H), 1.62-1.58 (m, 4H), 1.53-1.41 (m, 4H). This diastereomer of compounds III-337 and III-338 was found to be the more potent inhibitor of cell growth of T-Rex 293 cells having increased expression of estrogen receptor alpha protein (as described in the Example 56, below).

The other enantiomer of cis-1-[2,6-difluoro-4-(4-piperidyl)phenyl]-2-(4-fluorophenyl)tetralin-6-ol was used in a similar reaction to afford the other one of compounds III-337 and III-338.

Example 51—Synthesis of 1-(3-fluoro-4-((6S)-2,3,6,9-tetramethyl-6H-thieno[3,2-f][1,2,4]triazolo[4,3-a][1,4]diazepin-4-yl)phenyl)-4-((4-(4-((1S,2S)-2-(3-fluorophenyl)-6-hydroxy-1,2,3,4-tetrahydronaphthalen-1-yl)-3-methoxyphenyl) piperazin-1-yl)methyl)piperidin-4-ol (III-344) and 1-(3-fluoro-4-((6S)-2,3,6,9-tetramethyl-6H1-thieno [3,2-f][1,2,4]triazolo[4,3-a][1,4]diazepin-4-yl)phenyl)-4-((4-(4-((1R,2R)-2-(3-fluorophenyl)-6-hydroxy-1,2,3,4-tetrahydronaphthalen-1-yl)-3-methoxyphenyl)piperazin-1-yl)methyl)piperidin-4-ol (III-343)
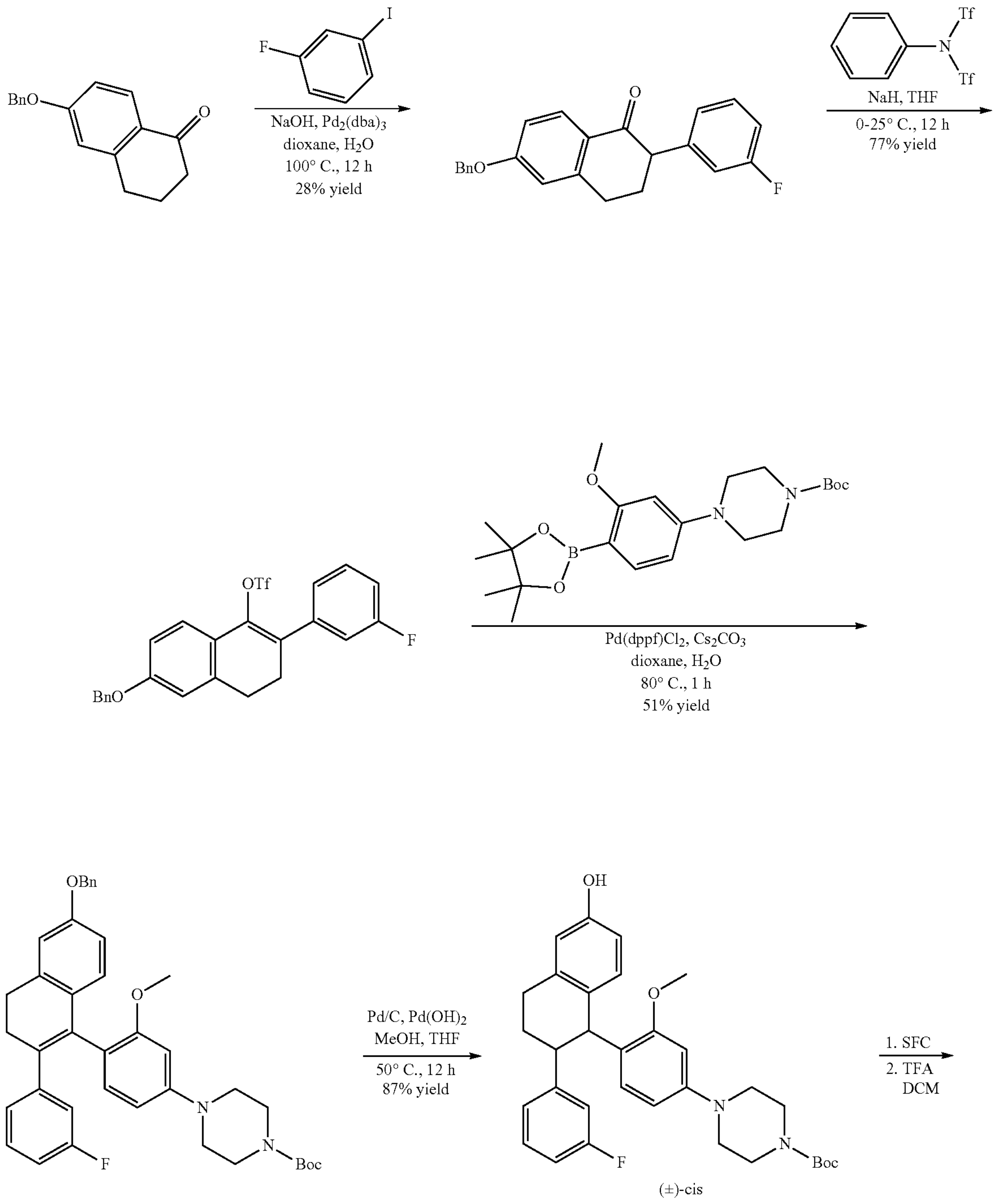

-continued

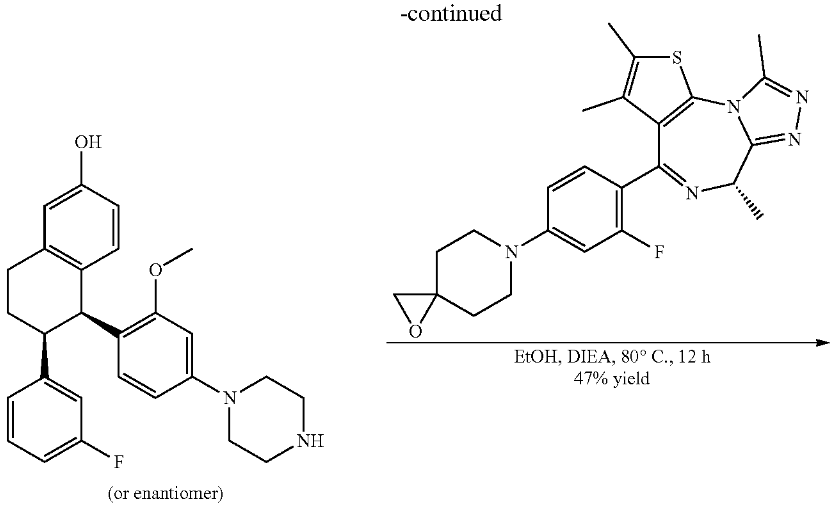

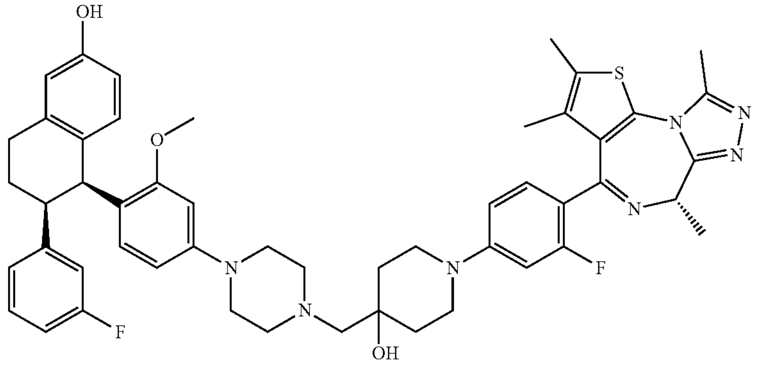

or

III-344

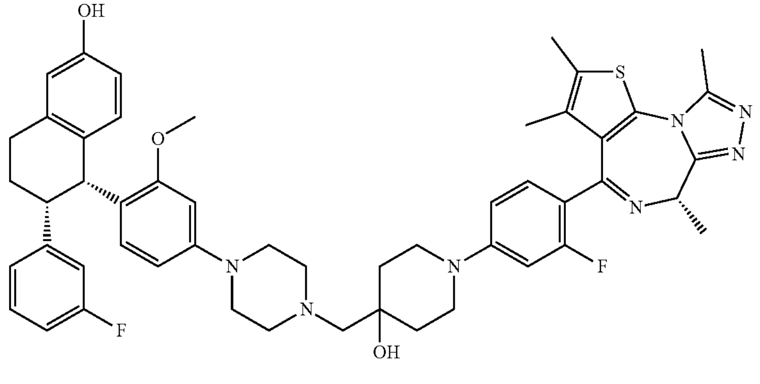

III-343

Step 1: A mixture of 6-benzyloxytetralin-1-one (8.0 g, 31.7 mmol, 1.0 equiv), 1-fluoro-3-iodo-benzene (8.5 g, 38.1 mmol, 4.5 mL, 1.2 equiv), NaOH (1.3 g, 31.7 mmol, 1.0 equiv), $Pd_2(dba)_3$ (2.9 g, 3.2 mmol, 0.1 equiv) and tritert-butylphosphonium tetrafluoroborate (1.8 g, 6.3 mmol, 0.2 equiv) in dioxane (80.0 mL) and $H_2O$ (20.0 mL) was degassed and purged with $N_2$ for 3 times, and then the mixture was stirred at 100° C. for 12 h under $N_2$ atmosphere. The reaction mixture was partitioned between Ethyl acetate (300 mL) and $H_2O$ (300 mL×2). The organic phase was separated, washed with brine (300 mL), dried over $Na_2SO_4$, filtered and concentrated under reduced pressure to give a residue. The residue was purified by prep-HPLC (column: Welch Ultimate XB—$NH_2$ 250*50 mm*10 um; mobile phase: [Heptane-EtOH (0.1% $NH_3H_2O$)]; gradient: 1%-30% B over 15.0 min) to give the 6-benzyloxy-2-(3-fluorophenyl)tetralin-1-one (3.1 g, 9.0 mmol, 28% yield) as a yellow solid. LC-MS: MS ($ES^+$): RT=0.703 min, m/z=347.1 [$M+H^+$]. LCMS Method: 5-95.

Step 2: To a solution of 6-benzyloxy-2-(3-fluorophenyl) tetralin-1-one (3.1 g, 9.0 mmol, 1.0 equiv) in THE (31.0 mL) was added NaH (716 mg, 17.9 mmol, 60% purity, 2.0 equiv) at 0° C. under $N_2$, the mixture was stirred at 25° C. for 30 min, then the 1,1,1-trifluoro-N-phenyl-N-(trifluoromethylsulfonyl)methanesulfonamide (6.4 g, 17.9 mmol, 2.0 equiv) was added to the mixture at 0° C. The mixture was stirred at 25° C. for 12 h under $N_2$. The reaction mixture was quenched with saturated aqueous $NH_4Cl$ (10 mL) solution at 0° C. dropwise. And the resulting mixture was extracted with Ethyl acetate (70 mL×3). The organic phase was separated, washed with brine (100 mL), dried over $Na_2SO_4$, filtered and concentrated under reduced pressure to give a residue. The residue was purified by column chromatography ($SiO_2$, Petroleum ether/Ethyl acetate=1/0 to 20/1) to give the [6-benzyloxy-2-(3-fluorophenyl)-3,4-dihydronaphthalen-1-yl]trifluoromethanesulfonate (3.3 g, 6.9 mmol, 77% yield) as a white solid. LC-MS: MS ($ES^+$): RT=0.736 min, m/z=501.2 $[M+Na]^+$. LCMS Method: 5-95.

Step 3: A mixture of [6-benzyloxy-2-(3-fluorophenyl)-3,4-dihydronaphthalen-1-yl]trifluoromethanesulfonate (3.0 g, 6.3 mmol, 1.0 equiv), tert-butyl 4-[3-methoxy-4-(4,4,5,5-tetramethyl-1,3,2-dioxaborolan-2-yl)phenyl]piperazine-1-carboxylate (3.2 g, 7.5 mmol, 1.2 equiv), Pd(dppf)$Cl_2$ (459 mg, 627 mol, 0.1 equiv), $Cs_2CO_3$ (4.1 g, 12.5 mmol, 2.0 equiv) in dioxane (30.0 mL) and $H_2O$ (3.0 mL) was degassed and purged with $N_2$ for 3 times, and then the mixture was stirred at 80° C. for 1 h under $N_2$ atmosphere. The reaction mixture was partitioned between Ethyl acetate (100 mL) and $H_2O$ (100 mL×2). The organic phase was separated, washed with brine (100 mL), dried over $Na_2SO_4$, filtered and concentrated under reduced pressure to give a residue. The residue was purified by prep-HPLC (column: Phenomenex luna C18 250*50 mm*10 um; mobile phase: [$H_2O$ (0.225% FA)-ACN]; gradient: 70%-100% B over 22.0 min) to give the tert-butyl 4-[4-[6-benzyloxy-2-(3-fluorophenyl)-3,4-dihydronaphthalen-1-yl]-3-methoxy-phenyl] piperazine-1-carboxylate (2.0 g, 3.2 mmol, 51% yield, 99% purity) as a yellow solid. LC-MS: MS ($ES^+$): RT=0.731 min, m/z=621.3 [$M+H^+$]. LCMS Method: 5-95.

Step 4: Pd/C (1.0 g, 940 mol, 10% purity, 2.92e-1 equiv) and $Pd(OH)_2$ (1.0 g, 1.4 mmol, 20% purity, 4.42e-1 equiv) was added into a 75 mL single-necked round bottom flask under $N_2$, and then MeOH (10.0 mL) was added at 25° C. under $N_2$. After addition, tert-butyl 4-[4-[6-benzyloxy-2-(3-fluorophenyl)-3,4-dihydronaphthalen-1-yl]-3-methoxy-phenyl]piperazine-1-carboxylate (2.0 g, 3.2 mmol, 1.0 equiv) in THF (10.0 mL) was added under $N_2$. The suspension was degassed under vacuum and purged with $H_2$ several times. The mixture was stirred under $H_2$ (50 PSI) at 50° C. for 12 h. The reaction mixture was filtered and concentrated under reduced pressure to give a residue. The residue was purified by column chromatography ($SiO_2$, Petroleum ether/Ethyl acetate=20/1 to 10/1) to give the (±)-cis-tert-butyl 4-[4-[2-(3-fluorophenyl)-6-hydroxy-tetralin-1-yl]-3-methoxy-phenyl]piperazine-1-carboxylate (1.5 g, 2.8 mmol, 87% yield) as a yellow solid. LC-MS: MS ($ES^+$): RT=0.653 min, m/z=533.2 [$M+H^+$]. LCMS Method: 5-95.

Step 5: The residue was purified by SFC (column: DAICEL CHIRALPAK AD (250 mm*30 mm, 10 um); mobile phase: [$CO_2$-EtOH (0.1% $NH_3H_2O$)]; B %: 45%, isocratic elution mode) to give the (1S,2S)- and (1R,2R)-tert-butyl 4-[4-[2-(3-fluorophenyl)-6-hydroxy-tetralin-1-yl]-3-methoxy-phenyl]piperazine-1-carboxylate. The faster-eluting enantiomer (Rt=1.195 min) was isolated (730 mg, 1.4 mmol, 49% yield) as a yellow solid, and the slower-eluting enantiomer (Rt=1.437 min) was isolated (720 mg, 1.4 mmol, 48% yield) as a yellow solid.

The following Steps 6 and 7 describe further synthetic procedures conducted on the slower-eluting enantiomer of cis-tert-butyl 4-[4-[2-(3-fluorophenyl)-6-hydroxy-tetralin-1-yl]-3-methoxy-phenyl]piperazine-1-carboxylate. This slower-eluting enantiomer produced the diastereomer of compounds III-343 and III-344 that was found to be the more potent inhibitor of cell growth of T-Rex 293 cells having increased expression of estrogen receptor alpha protein (as described in the Example 56, below). The faster-eluting enantiomer of cis-tert-butyl 4-[4-[2-(3-fluorophenyl)-6-hydroxy-tetralin-1-yl]-3-methoxy-phenyl]piperazine-1-carboxylate was carried through the same steps to afford the other one of compounds III-343 and III-344.

Step 6: To a solution of tert-butyl 4-[4-[(1S,2S)-2-(3-fluorophenyl)-6-hydroxy-tetralin-1-yl]-3-methoxy-phenyl] piperazine-1-carboxylate or its enantiomer (720 mg, 1.4 mmol, 1.0 equiv) in DCM (6.0 mL) was added TFA (2.0 mL). The mixture was stirred at 25° C. for 1 h. The reaction was added saturated aqueous $NaHCO_3$ solution to adjust the PH>7 and the reaction mixture was partitioned between DCM (80 mL) and $H_2O$ (80 mL×2). The organic phase was separated, washed with brine (80 mL), dried over $Na_2SO_4$, filtered and concentrated under reduced pressure to give a residue to give the (1S,2S)-2-(3-fluorophenyl)-1-(2-methoxy-4-piperazin-1-yl-phenyl)tetralin-6-ol or its enantiomer (crude) as a white solid.

Step 7: A mixture of (1S,2S)-2-(3-fluorophenyl)-1-(2-methoxy-4-piperazin-1-yl-phenyl)tetralin-6-ol or its enantiomer (109 mg, 252 mol, 1.2 equiv), 6-[3-fluoro-4-[(9S)-4,5,9,13-tetramethyl-3-thia-1,8,11,12-tetrazatricyclo [$8.3.0.0^{2,6}$]trideca-2(6),4,7,10,12-pentaen-7-yl]phenyl]-1-oxa-6-azaspiro[2.5]octane (95 mg, 210 mol, 1.0 equiv) and DIEA (136 mg, 1.1 mmol, 183 L, 5.0 equiv) in EtOH (2.0 mL) was degassed and purged with $N_2$ for 3 times, and then the mixture was stirred at 80° C. for 12 h under $N_2$ atmosphere. The reaction mixture was concentrated under reduced pressure to give a residue. The residue was purified by prep-HPLC (column: Waters xbridge 150*25 mm 10 um; mobile phase: [$H_2O$ (10 mM $NH_4HCO_3$)-ACN]; gradient: 62%-82% B over 8.0 min) to give compound III-344 or III-343 (90 mg, 99 mol, 47% yield, 97% purity) as a yellow solid. LC-MS: MS ($ES^+$): RT=2.655 min, m/z=884.7 [$M+H^+$]. LCMS Method: 01. $^1H$ NMR: (400 MHz, $CD_3OD$) δ=7.40-7.28 (m, 1H), 7.11-7.00 (m, 1H), 6.84-6.71 (m, 2H), 6.68-6.55 (m, 4H), 6.53-6.41 (m, 2H), 6.41-6.30 (m, 2H), 6.19 (d, J=2.0 Hz, 1H), 4.76 (d, J=5.2 Hz, 1H), 4.28-4.16 (m, 1H), 3.70-3.53 (m, 2H), 3.29-3.22 (m, 3H), 3.10 (s, 3H), 3.06 (s, 4H), 3.00-2.90 (m, 2H), 2.73 (d, J=4.4 Hz, 4H), 2.68 (s, 3H), 2.41-2.34 (m, 5H), 2.30-2.19 (m, 1H), 1.97 (d, J=6.8 Hz, 3H), 1.84-1.71 (m, 2H), 1.70-1.58 (m, 6H).

Example 52—Synthesis of 1-(2-fluoro-4-((6S)-2,3,6,9-tetramethyl-6H-thieno[3,2-f][1,2,4]triazolo[4,3-a][1,4]diazepin-4-yl)phenyl)-4-((4-(4-((1S,2S)-2-(2-fluorophenyl)-6-hydroxy-1,2,3,4-tetrahydronaphthalen-1-yl)-3-methoxyphenyl)piperazin-1-yl)methyl)piperidin-4-ol (III-346) and 1-(2-fluoro-4-((6S)-2,3,6,9-tetramethyl-6H-thieno[3,2-f][1,2,4]triazolo[4,3-a][1,4]diazepin-4-yl)phenyl)-4-((4-(4-((1R,2R)-2-(2-fluorophenyl)-6-hydroxy-1,2,3,4-tetrahydronaphthalen-1-yl)-3-methoxyphenyl)piperazin-1-yl)methyl)piperidin-4-ol (III-345)

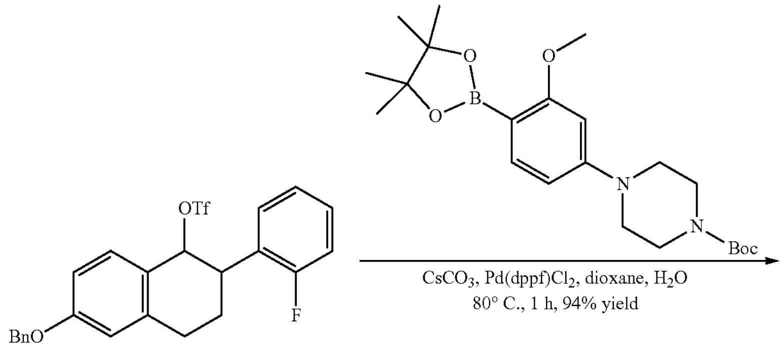

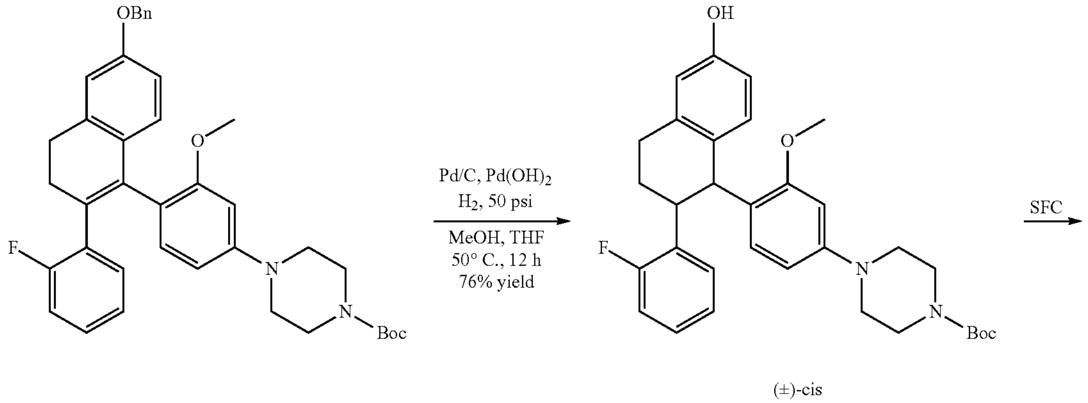

(±)-cis

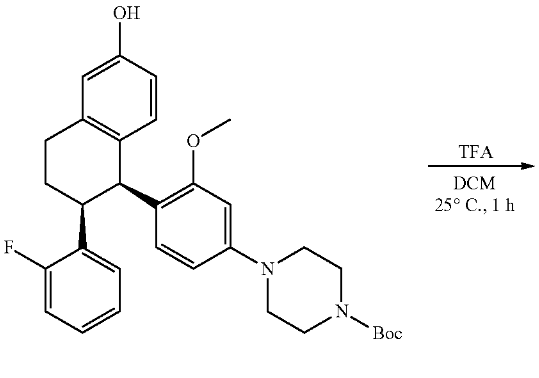

(or enantiomer)

-continued

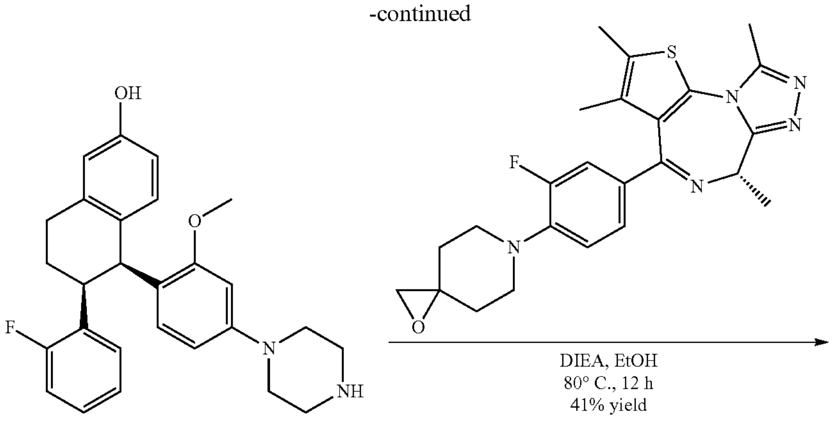

(or enantiomer)

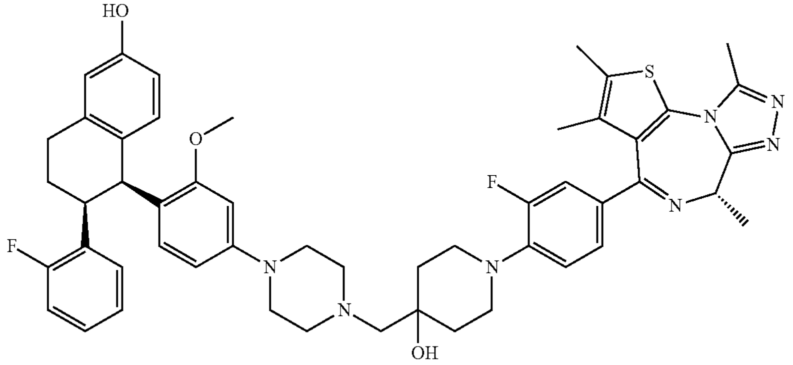

III-346 or

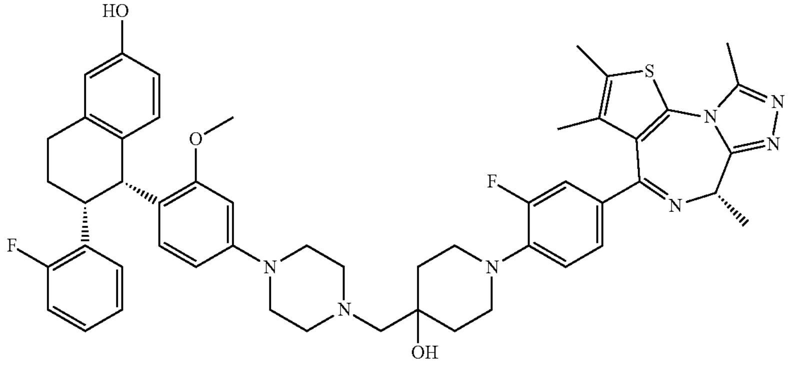

III-345

Step 1: To a solution of [6-benzyloxy-2-(2-fluorophenyl)-3,4-dihydronaphthalen-1-yl]trifluoromethanesulfonate (3.0 g, 6.3 mmol, 1.0 equiv) and tert-butyl 4-[3-methoxy-4-(4,4,5,5-tetramethyl-1,3,2-dioxaborolan-2-yl)phenyl]piperazine-1-carboxylate (3.7 g, 8.8 mmol, 1.4 equiv) in dioxane (30.0 mL) and $H_2O$ (3.0 mL) was added $Cs_2CO_3$ (4.1 g, 12.5 mmol, 2.0 equiv) and Pd(dppf)$Cl_2$ (459 mg, 627 mol, 0.1 equiv). The mixture was stirred at 80° C. for 1 h under $N_2$. The resulting mixture was partitioned between EtOAc (50 mL) and $H_2O$ (50 mL), the $H_2O$ phase was separated, washed twice with EtOAc (50 mL), then the organic phase was separated, dried over $Na_2SO_4$, filtered and concentrated under reduced pressure to give a residue. The residue was purified by column chromatography ($SiO_2$, Petroleum ether/Ethyl acetate=20/1 to 8/1). Compound tert-butyl 4-[4-[6-benzyloxy-2-(2-fluorophenyl)-3,4-dihydronaphthalen-1-yl]-3-methoxy-phenyl]piperazine-1-carboxylate (3.7 g, 5.9 mmol, 94% yield, 99% purity) was obtained as a white solid. LC-MS: MS ($ES^+$): RT=0.733 min, m/z=621.3 $[M+H]^+$. LCMS method: 5-95.

Step 2: Pd/C (1.8 g, 1.7 mmol, 10% purity, 0.3 equiv) and $Pd(OH)_2$ (1.8 g, 2.6 mmol, 20% purity, 0.4 equiv) was added into a 250 mL single-necked round bottom flask under $N_2$, and then THF (30.0 mL) and MeOH (30.0 mL) was added at 25° C. under $N_2$. After addition, tert-butyl 4-[4-[6-benzyloxy-2-(2-fluorophenyl)-3,4-dihydronaphthalen-1-yl]-3- methoxy-phenyl]piperazine-1-carboxylate (3.7 g, 6.0 mmol, 1.0 equiv) was added under $N_2$. The suspension was degassed under vacuum and purged with $H_2$ several times. The mixture was stirred under $H_2$ (50 psi) at 50° C. for 12 h. The reaction mixture was filtered and the filtrate was concentrated and then triturated with MeOH at 25° C. for 8 h. Compound (1)-cis-tert-butyl 4-[4-[2-(2-fluorophenyl)-6-hydroxy-tetralin-1-yl]-3-methoxy-phenyl]piperazine-1-carboxylate (2.4 g, 4.5 mmol, 76% yield, 99% purity) was obtained as a white solid. LC-MS: MS ($ES^+$): RT=0.643 min, m/z=533.3 $[M+H]^+$. LCMS Method: 5-95.

Step 3: Compound (±)-cis-tert-butyl 4-[4-[2-(2-fluorophenyl)-6-hydroxy-tetralin-1-yl]-3-methoxy-phenyl]piperazine-1-carboxylate (2.4 g, 4.5 mmol) was separated by SFC (column: DAICEL CHIRALPAK AD (250 mm*30 mm, 10 um); mobile phase: [$CO_2$-EtOH (0.1% $NH_3H_2O$)]; B %: 30%, isocratic elution mode) to afford (1S,2S)- and (1R, 2R)-tert-butyl 4-[4-[2-(2-fluorophenyl)-6-hydroxy-tetralin-1-yl]-3-methoxy-phenyl]piperazine-1-carboxylate. Each of the faster-eluting and slower-eluting enantiomers were isolated as white solids (710 mg, 1.3 mmol, 47% yield, 99% purity). LC-MS: MS ($ES^+$): RT=0.641 min, m/z=533.3 $[M+H]^+$; LCMS Method: 5-95.

The following Steps 4 and 5 were conducted on the slower-eluting enantiomer of cis-tert-butyl 4-[4-[2-(2-fluorophenyl)-6-hydroxy-tetralin-1-yl]-3-methoxy-phenyl]piperazine-1-carboxylate. This slower-eluting enantiomer produced the diastereomer of compounds III-345 and III-346 that was found to be the more potent inhibitor of cell growth of T-Rex 293 cells having increased expression of estrogen receptor alpha protein (as described in the Example 56, below). The faster-eluting enantiomer of cis-tert-butyl 4-[4-[2-(2-fluorophenyl)-6-hydroxy-tetralin-1-yl]-3-methoxy-phenyl]piperazine-1-carboxylate was carried through the same step to afford the other one of compounds III-345 and III-346.

Step 4: To a solution of tert-butyl 4-[4-[(1S,2S)-2-(2-fluorophenyl)-6-hydroxy-tetralin-1-yl]-3-methoxy-phenyl] piperazine-1-carboxylate or its enantiomer (710 mg, 1.3 mmol, 1.0 equiv) in DCM (9.0 mL) was added TFA (3.0 mL). The mixture was stirred at 25° C. for 1 h. The reaction mixture was concentrated under reduced pressure to remove solvent. The resulting mixture was basified with saturated aqueous $NaHCO_3$ solution to adjust pH=8, and then diluted with DCM (30 mL) and extracted with DCM (30 mL×2). The combined organic layers were washed with DCM (20 mL), dried over anhydrous $Na_2SO_4$, filtered and concentrated under reduced pressure to give a residue. Compound (1S,2S)-2-(2-fluorophenyl)-1-(2-methoxy-4-piperazin-1-yl-phenyl)tetralin-6-ol or its enantiomer (560 mg, 1.3 mmol, 97% yield) was obtained as a yellow solid and used in the next step without further purification. LC-MS: MS ($ES^+$): RT=0.843 min, m/z=433.2 $[M+H^+]$; LCMS method: 5-95.

Step 5: To a solution of (1S,2S)-2-(2-fluorophenyl)-1-(2-methoxy-4-piperazin-1-yl-phenyl)tetralin-6-ol or its enantiomer (120 mg, 277 mol, 1.3 equiv) and 6-[3-fluoro-4-[(9S)-4,5,9,13-tetramethyl-3-thia-1,8,11,12-tetrazatricyclo [8.3.0.$0^{2,6}$]trideca-2(6),4,7,10,12-pentaen-7-yl]phenyl]-1-oxa-6-azaspiro[2.5]octane (95 mg, 210 mol, 1.0 equiv) in EtOH (3.0 mL) was added DIEA (82 mg, 631 mol, 110 μL, 3.0 equiv). The mixture was stirred at 80° C. for 12 h. The reaction mixture was concentrated under reduced pressure to remove solvent and purified by prep-HPLC (column: Waters xbridge 150*25 mm 10 um; mobile phase: [$H_2O$ (10 mM $NH_4HCO_3$)-ACN]; gradient: 63%-83% B over 8.0 min). Compound III-346 or III-345 (80 mg, 87 mol, 41% yield, 96% purity) was obtained as an off-white solid. LC-MS: MS ($ES^+$): RT=2.626 min, m/z=884.6 $[M+H]^+$; LCMS method: 01. $^1H$ NMR (400 MHz, $CD_3OD$) δ=7.37-7.29 (m, 1H), 7.11-7.03 (m, 1H), 7.02-6.95 (m, 1H), 6.82-6.77 (m, 1H), 6.72-6.66 (m, 1H), 6.62-6.56 (m, 3H), 6.50-6.43 (m, 2H), 6.37-6.25 (m, 2H), 6.12 (d, J=2.0 Hz, 1H), 4.26-4.18 (m, 1H), 3.66-3.56 (m, 3H), 3.29-3.21 (m, 2H), 3.16-2.88 (m, 10H), 2.74-2.65 (m, 7H), 2.40-2.26 (m, 5H), 1.97 (d, J=6.8 Hz, 3H), 1.81-1.73 (m, 2H), 1.69-1.57 (m, 6H).

Example 53—Synthesis of 1-(2,5-difluoro-4-((S)-2,3,6,9-tetramethyl-6H-thieno[3,2-f][1,2,4]triazolo[4,3-a][1,4]diazepin-4-yl)phenyl)-4-((4-(4-((1S,2S)-6-hydroxy-2-phenyl-1,2,3,4-tetrahydronaphthalen-1-yl)-3-methoxyphenyl)piperazin-1-yl)methyl)piperidin-4-ol (III-339) and 1-(2,5-difluoro-4-((S)-2,3,6,9-tetramethyl-6H-thieno[3,2-f][1,2,4]triazolo[4,3-a][1,4]diazepin-4-yl)phenyl)-4-((4-(4-((1R,2R)-6-hydroxy-2-phenyl-1,2,3,4-tetrahydronaphthalen-1-yl)-3-methoxyphenyl)piperazin-1-yl)methyl)piperidin-4-ol (III-340)

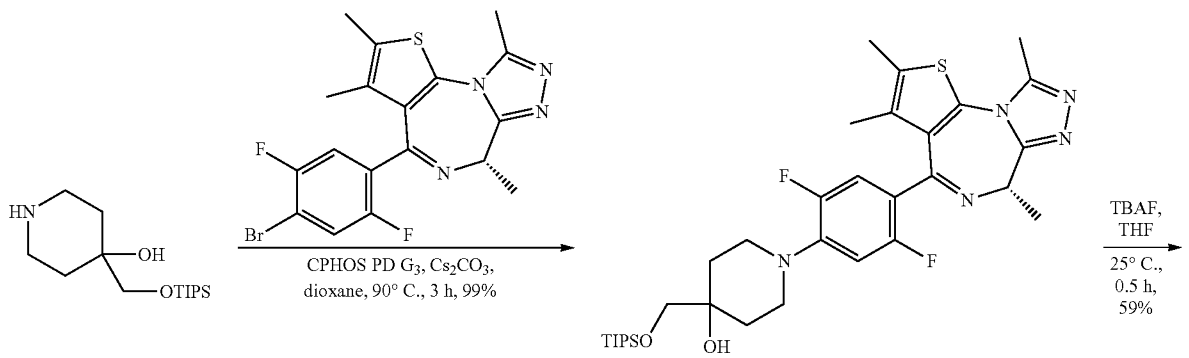

-continued
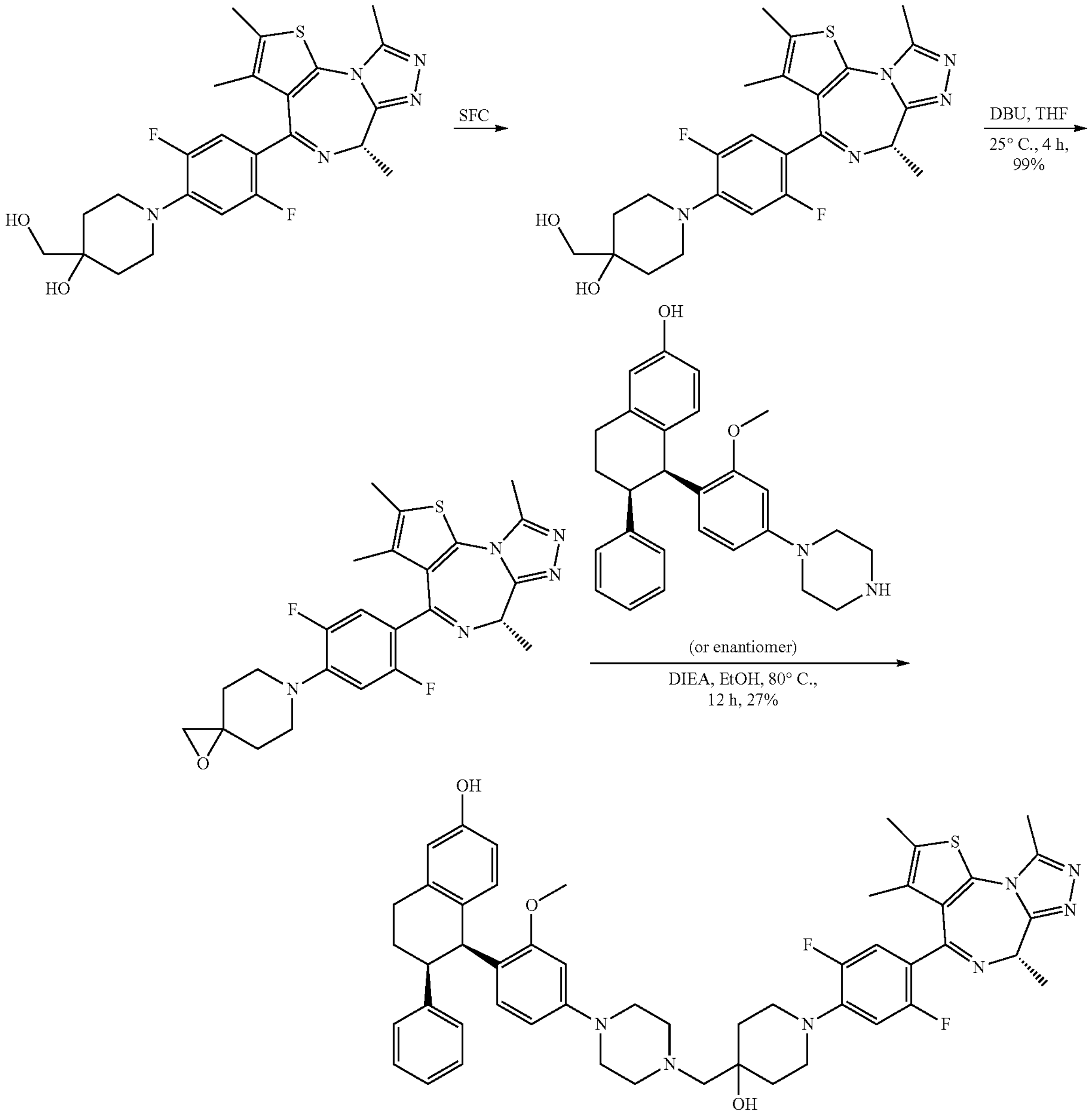
III-339
or
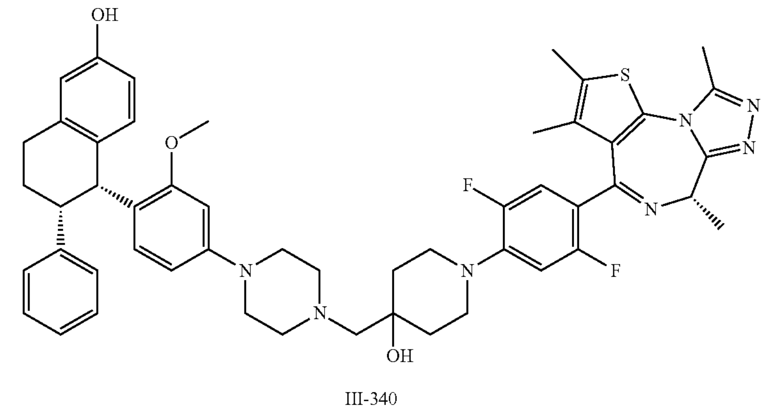
III-340

Step 1: To a solution of 4-(triisopropylsilyloxymethyl) piperidin-4-ol (2 g, 10 mmol, 1 equiv), (9S)-7-(4-bromo-2, 5-difluoro-phenyl)-4,5,9,13-tetramethyl-3-thia-1,8,11,12-tetrazatricyclo[8.3.0.0$^{2,6}$]trideca-2(6),4,7,10,12-pentaene (3 g, 6 mmol, 1 equiv) in dioxane (50 mL) was added $Cs_2CO_3$ (6 g, 20 mmol, 3 equiv) and Cphos Pd $G_3$ (553 mg, 686 mol, 0.1 equiv). The mixture was stirred at 90° C. for 3 h. The combined organic phase was filtered and concentrated under vacuum to give a residue. The residue was purified by column chromatography ($SiO_2$, Petroleum ether/Ethyl acetate=0/1) to give compound 1-[2,5-difluoro-4-[(9S)-4,5, 9,13-tetramethyl-3-thia-1,8,11,12-tetrazatricyclo[8.3.0.0$^{2,6}$] trideca-2(6),4,7,10,12-pentaen-7-yl]phenyl]-4-(triisopropyl-silyloxymethyl)piperidin-4-ol (3 g, crude) as a white solid. LC-MS: MS ($ES^+$): RT=0.733 min, m/z=644.4 [M−55]. LCMS Method: 5-95.

Step 2: To a solution of 1-[2,5-difluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-4-(triisopropylsilyloxymethyl)piperidin-4-ol (2 g, 4 mmol, 1 equiv) in THE (30 mL) was added TBAF (1 M, 6 mL, 1.5 equiv). The mixture was stirred at 25° C. for 0.5 h. The combined organic phase was filtered and concentrated under vacuum to give a residue. The residue was purified by column chromatography ($SiO_2$, Dichloromethane:Methanol=10/1) to give compound 1-[2,5-difluoro-4-[(9S)-4,5,9,13-tetramethyl-3-thia-1,8,11,12-tetrazatricyclo[8.3.0.0$^{2,6}$]trideca-2 (6),4,7,10,12-pentaen-7-yl]phenyl]-4-(hydroxymethyl)piperidin-4-ol (1 g, 2 mmol, 59% yield) as a white solid. LC-MS: MS ($ES^+$): RT=0.464 min, m/z=488.2 [M−100]. LCMS Method: 5-95.

Step 3: 1-[2,5-difluoro-4-[(9S)-4,5,9,13-tetramethyl-3-thia-1,8,11,12-tetrazatricyclo [8.3.0.0$^{2,6}$]trideca-2(6),4,7,10, 12-pentaen-7-yl]phenyl]-4-(hydroxymethyl)piperidin-4-ol (1.3 g) was purified by prep-SFC to remove impurities, including any minor amounts of enantiomeric material (column: DAICEL CHIRALPAK AD (250 mm*30 mm, 10 um); mobile phase: [$CO_2$-IPA:ACN=4:1 (0.1% $NH_3H_2O$)]; B %: 45%, isocratic elution mode) to give compound 1-[2,5-difluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl] phenyl]-4-(hydroxymethyl)piperidin-4-ol (950 mg, 1 mmol, 73% yield) as a white solid. LC-MS: MS ($ES^+$): RT=0.481 min, m/z=488.1 [M+1]. LCMS Method: 5-95.

Step 4: To a solution of 1-[2,5-difluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-4-(hydroxymethyl)piperidin-4-ol (400 mg, 820 mol, 1 equiv), 1,1,2,2,3, 3,4,4,4-nonafluorobutane-1-sulfonyl fluoride (371 mg, 1 mmol, 216 L, 1 equiv) in THE (4 mL) was added DBU (249 mg, 1 mmol, 247 µL, 2 equiv). The mixture was stirred at 25° C. for 1 h. The combined organic layers were filtered and concentrated in vacuum and used directly. LC-MS: MS ($ES^+$): RT=0.501 min, m/z=470.1 [M+1]. LCMS Method: 5-95.

Step 5: To a solution of 6-[2,5-difluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro [2.5]octane (95 mg, 202 mol, 1 equiv) and the enantiomer of cis-1-(2-methoxy-4-piperazin-1-yl-phenyl)-2-phenyl-tetralin-6-ol prepared in Step 6 of Example 46 (83 mg, 202 mol, 1 equiv) in EtOH (2 mL) was added DIEA (78 mg, 606 mol, 105 µL, 3 equiv). The mixture was stirred at 80° C. for 12 h. The combined organic layers were filtered and concentrated under reduced pressure to give a residue. The residue was purified by prep-HPLC (column: Waters xbridge 150*25 mm 10 um; mobile phase: [$H_2O$ (10 mM $NH_4HCO_3$)-ACN]; gradient: 55%-85% B over 15.0 min) to give compound III-339 or III-340 (49 mg, 27% yield, 99% purity) as a white solid. $^1H$ NMR (400 MHz, MeOD)$^1H$ NMR (400 MHz, METHANOL-$d_4$) δ=7.30-7.16 (m, 1H), 7.12-7.00 (m, 3H), 6.82-6.70 (m, 3H), 6.68-6.60 (m, 2H), 6.58-6.44 (m, 2H), 6.42-6.32 (m, 1H), 6.18 (d, J=2.1 Hz, 1H), 4.76 (d, J=5.4 Hz, 1H), 4.32-4.20 (m, 1H), 3.42-3.34 (m, 2H), 3.28-3.12 (m, 3H), 3.11 (d, J=4.2 Hz, 4H), 3.02 (s, 5H), 2.82-2.72 (m, 4H), 2.68 (s, 3H), 2.48-2.36 (m, 5H), 2.36-2.24 (m, 1H), 2.00 (d, J=6.8 Hz, 3H), 1.92-1.80 (m, 2H), 1.78-1.64 (m, 6H). LC-MS: MS ($ES^+$): RT=2.927 min, m/z=884.1 [M+1]. LCMS Method: 25. This diastereomer of compounds III-339 and III-340 was found to be the more potent inhibitor of cell growth of T-Rex 293 cells having increased expression of estrogen receptor alpha protein (as described in the Example 56, below). The other diastereomer of compounds III-339 and III-340 was prepared from the other enantiomer of cis-1-(2-methoxy-4-piperazin-1-yl-phenyl)-2-phenyl-tetralin-6-ol.

Example 54—Synthesis of 1-(2,5-difluoro-4-((6S)-2,3,6,9-tetramethyl-6H-thieno[3,2-f][1,2,4]triazolo [4,3-a][1,4]diazepin-4-yl)phenyl)-4-((4-(2-fluoro-4-((1S,2S)-6-hydroxy-2-phenyl-1,2,3,4-tetrahydronaphthalen-1-yl)-5-methoxyphenyl) piperazin-1-yl)methyl)piperidin-4-ol (111-341) and 1-(2,5-difluoro-4-((6S)-2,3,6,9-tetramethyl-6H-thieno[3,2-f][1,2,4]triazolo[4,3-a][1,4]diazepin-4-yl) phenyl)-4-((4-(2-fluoro-4-((1R,2R)-6-hydroxy-2-phenyl-1,2,3,4-tetrahydronaphthalen-1-yl)-5-methoxyphenyl)piperazin-1-yl)methyl)piperidin-4-ol (III-342)

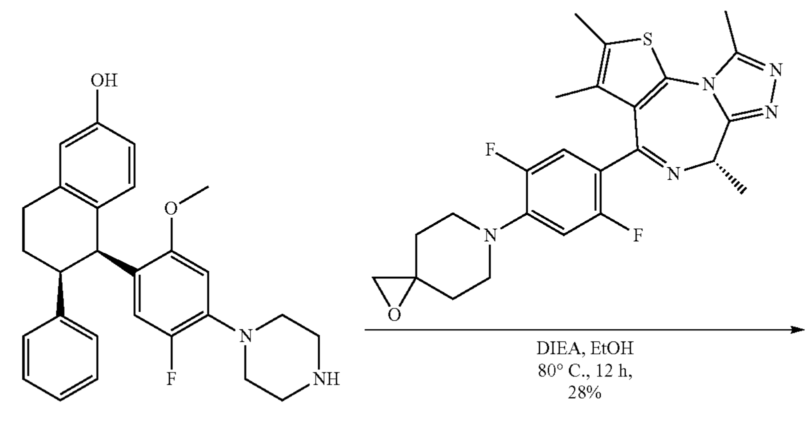

(or enantiomer)

-continued

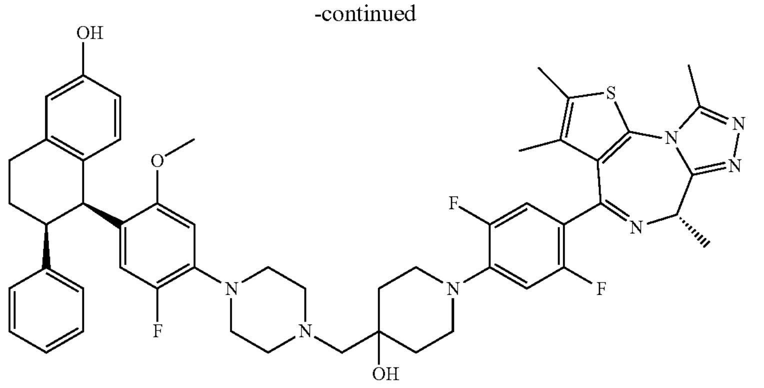

III-341 or

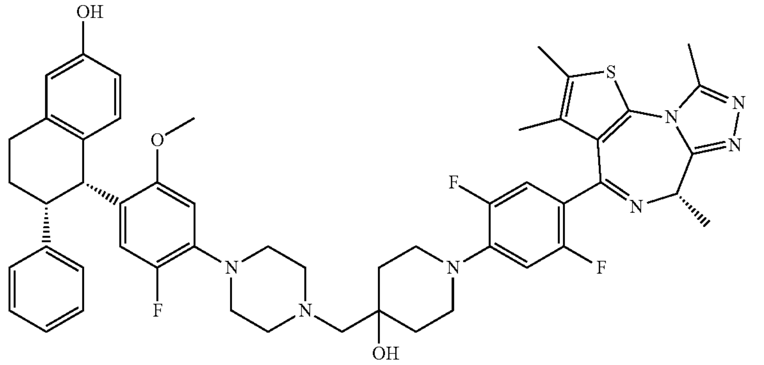

III-342

Step 1: To a solution of the enantiomer of cis-1-(5-fluoro-2-methoxy-4-piperazin-1-yl-phenyl)-2-phenyl-tetralin-6-ol prepared in Step 6 of Example 45 (87 mg, 201 mol, 1 equiv) in EtOH (2 mL) was added DIEA (129 mg, 1.01 mmol, 175 μL, 5 equiv) and 6-[2,5-difluoro-4-[(9S)-4,5,9,13-tetramethyl-3-thia-1,8,11,12-tetrazatricyclo[8.3.0.0$^{2,6}$]trideca-2(6),4,7,10,12-pentaen-7-yl]phenyl]-1-oxa-6-azaspiro[2.5]octane (94 mg, 201 μmol, 1 equiv). The mixture was stirred at 80° C. for 12 h. The reaction mixture was filtered. The residue was purified by prep-HPLC (neutral condition; column: Waters Xbridge C18 150*25 mm*5 um; mobile phase: [$H_2O$ (10 mM $NH_4HCO_3$)-ACN]; gradient: 50%-80% B over 15.0 min) to give compound III-341 or III-342 (51 mg, 28% yield). $^1$H NMR (400 MHz, $CDCl_3$): δ 7.34-7.27 (m, 1H), 7.16-7.03 (m, 3H), 6.85-6.73 (m, 3H), 6.70 (d, J=2.4 Hz, 1H), 6.62-6.48 (m, 2H), 6.36 (d, J=13.2 Hz, 1H), 6.05 (d, J=7.2 Hz, 1H), 5.70-5.18 (m, 1H), 4.80 (d, J=5.2 Hz, 1H), 4.17 (q, J=6.6 Hz, 1H), 3.41-3.23 (m, 4H), 3.22-3.05 (m, 5H), 3.04-2.99 (m, 2H), 2.97 (s, 3H), 2.89-2.75 (m, 2H), 2.68 (s, 3H), 2.54-2.41 (m, 1H), 2.39 (s, 3H), 2.30-2.20 (m, 1H), 2.09 (d, J=6.8 Hz, 3H), 1.77 (s, 3H), 1.75-1.56 (m, 8H). LC-MS: MS ($ES^+$): RT=2.962 min, m/z=902.6 [$M+H^+$]. LCMS method: 01. This diastereomer of compounds III-341 and III-342 was found to be the more potent inhibitor of cell growth of T-Rex 293 cells having increased expression of estrogen receptor alpha protein (as described in the Example 56, below). The other diastereomer of compounds III-339 and III-340 was prepared from the other enantiomer of cis-1-(5-fluoro-2-methoxy-4-piperazin-1-yl-phenyl)-2-phenyl-tetralin-6-ol.

Example 55—Synthesis of Additional Compounds in Tables 2, 3, 4, and 5

All compounds in Tables 2, 3, 4, and 5 that do not have a synthetic procedure described in the preceding examples were synthesized by analogy to the procedures described above. Observed mass data (m/z values) obtained from LC/MS of the compounds is provided in Table 6, below.

TABLE 6

| Compound No. | Observed Mass (m/z) |
|---|---|
| I-34a | 909.7 |
| I-34b | 909.7 |
| I-37a or | 802.5 |
| I-37b | 802.7 |
| I-57 | 839.5 |
| I-59 | 862.6 |
| I-60 | 868.7 |
| II-1 | 1234.6 |
| II-2 | 1318.7 |
| II-3 | 970.4 |
| II-4 | 1230.7 |
| II-5 | 1146.4 |
| I-12, | 869.7 |
| III-1, | 869.4 |
| III-2, or | 869.4 |
| III-3 | 869.6 |
| I-62 or | 825.6 |
| III-4 | 825.6 |
| III-5 or | 802.7 |
| III-6 | 802.6 |
| III-7 or | 775.6 |
| III-8 | 775.6 |

TABLE 6-continued

| Compound No. | Observed Mass (m/z) |
|---|---|
| III-9 or | 803.7 |
| III-10 | 803.7 |
| III-11 or | 842.7 |
| III-12 | 842.7 |
| I-44 or | 758.4 |
| III-13 | 758.4 |
| III-14 or | 758.4 |
| III-15 | 758.4 |
| III-16 or | 749.6 |
| III-17 | 749.6 |
| I-47 or | 768.8 |
| III-18 | 768.7 |
| I-46, | 835.6 |
| III-19, | 835.6 |
| III-20, or | 835.6 |
| III-21 | 835.6 |
| III-22 or | 800.4 |
| III-23 | 800.4 |
| III-24 or | 817.7 |
| III-25 | 817.7 |
| III-26 or | 817.4 |
| III-27 | 817.6 |
| III-28 | 816.3 |
| III-29 | 859.3 |
| III-30 | 862.3 |
| III-31 | 842.3 |
| III-32 | 858.4 |
| III-33 | 844.3 |
| III-34 | 844.4 |
| III-35 | 899.3 |
| III-36 | 870.4 |
| III-37 | 873.3 |
| III-38 | 884.4 |
| III-39 | 846.4 |
| III-40 | 828.3 |
| III-41 | 871.3 |
| III-42 | 887.4 |
| III-43 | 858.4 |
| III-44 | 858.4 |
| III-45 | 858.4 |
| III-46 | 848.3 |
| III-47 | 844.3 |
| III-48 | 872.3 |
| III-49 | 872.3 |
| III-50 | 885.4 |
| III-51 | 856.3 |
| III-52 | 844.3 |
| III-53 | 844.3 |
| III-54 | 844.3 |
| III-55 | 884.3 |
| III-56 | 844.4 |
| III-57 | 830.4 |
| III-58 | 844.3 |
| III-59 | 856.3 |
| III-60 | 886.4 |
| III-61 | 830.3 |
| III-62 | 858.4 |
| III-63 | 899.4 |
| III-64 | 870.3 |
| III-65 | 870.4 |
| III-66 | 846.4 |
| III-67 or | 774.4 |
| III-68 | 774.4 |
| III-69 or | 803.4 |
| III-70 | 803.4 |
| III-71, | 869.4 |
| III-72, | 869.4 |
| III-73, or | 869.4 |
| III-74 | 869.4 |
| III-75 or | 816.4 |
| III-76 | 816.7 |
| III-77a or b | 843.4 |
| III-78 or | 789.7 |
| III-79 | 789.7 |
| III-80 | 788.7 |
| III-81 | 846.7 |
| III-82 or | 801.7 |
| III-83 | 801.7 |

TABLE 6-continued

| Compound No. | Observed Mass (m/z) |
|---|---|
| III-84 or | 789.6 |
| III-85 | 789.6 |
| III-86 | 817.8 |
| III-87 | 842.6 |
| III-88 | 842.7 |
| III-89 | 774.6 |
| III-90 | 760.5 |
| III-91 or | 870.7 |
| III-92 | 870.7 |
| III-93a or b | 899.7 |
| III-94a or b | 803.5 |
| III-95 or | 789.7 |
| III-96 | 789.7 |
| III-97 | 408 |
| III-98 | 773.5 |
| III-99 or | 761.5 |
| III-100 | 381.3 |
| III-101 or | 775.6 |
| III-102 | 775.6 |
| III-103 or | 859.7 |
| III-104 | 859.6 |
| III-105 | 899.7 |
| III-106 | 803.7 |
| III-107 | 759.7 |
| III-108 | 407.9 |
| III-109 or | 860.6 |
| III-110 | 860.7 |
| III-111 or | 845.7 |
| III-112 | 845.7 |
| III-113 or | 871.7 |
| III-114 | 871.6 |
| III-115 | 787.7 |
| III-116 | 773.6 |
| III-117 | 759.5 |
| III-118 | 818.6 |
| III-119 | 816.5 |
| III-120 | 759.5 |
| III-121 | 832.7 |
| III-122 or | 804.5 |
| III-123 | 804.5 |
| III-124 | 841.6 |
| III-125 or | 870.8 |
| III-126 | 870.7 |
| III-127 or | 871.6 |
| III-128 | 871.6 |
| III-129 | 787.6 |
| III-130 | 831.6 |
| III-131 | 842.8 |
| III-132 | 801.7 |
| III-133 | 843.7 |
| III-134 | 857.6 |
| III-135 | 857.7 |
| III-136 | 844.8 |
| III-137 | 801.6 |
| III-138 | 774.6 |
| III-139 | 788.6 |
| III-140 | 885.6 |
| III-141 | 774.3 |
| III-142 | 788.6 |
| III-143 | 886.6 |
| III-144 | 819.6 |
| III-145 | 816.6 |
| III-146 | 844.6 |
| III-147 | 844.7 |
| III-148 | 773.4 |
| III-149 | 884.6 |
| III-150 | 827.6 |
| III-151 | 860.6 |
| III-152 | 817.6 |
| III-153 | 817.6 |
| III-154 or | 884.6 |
| III-155 | 884.6 |
| III-156 | 855.6 |
| III-157 | 861.4 |
| III-158 | 790.4 |
| III-159 | 790.3 |
| III-160 | 858.6 |
| III-161 | 909.6 |

TABLE 6-continued

| Compound No. | Observed Mass (m/z) |
| --- | --- |
| III-162 | 910.6 |
| III-163 or | 885.4 |
| III-164 | 885.4 |
| III-165 | 858.4 |
| III-166 | 859.4 |
| III-167 | 857.4 |
| III-168 | 925.7 |
| III-169 | 925.6 |
| III-170 | 788.4 |
| III-171 | 858.6 |
| III-172 | 857.4 |
| III-173 | 857.4 |
| III-174 | 855.4 |
| III-175 | 924.5 |
| III-176 | 924.5 |
| III-177 | 859.6 |
| III-178 | 857.4 |
| III-179 | 925.5 |
| III-180 | 926.5 |
| III-181 | 927.7 |
| III-182 or | 854.6 |
| III-183 | 854.6 |
| III-184 or | 837.6 |
| III-185 | 836.6 |
| III-186 or | 854.6 |
| III-187 | 854.6 |
| III-188 or | 846.6 |
| III-189 | 846.6 |
| III-190 | 857.7 |
| III-191 | 856.6 |
| III-192 | 921.3 |
| III-193 | 921.6 |
| III-194, | 922.6 |
| III-195, | 922.7 |
| III-196, or | 922.7 |
| III-197 | 922.6 |
| III-198, | 914.6 |
| III-199, | 914.7 |
| III-200, or | 914.6 |
| III-201 | 914.6 |
| III-202 | 924.8 |
| III-203 | 861.7 |
| III-204 or | 883.6 |
| III-205 | 883.6 |
| III-206 | 858.7 |
| III-207, | 904.7 |
| III-208, | 904.6 |
| III-209, or | 904.7 |
| III-210 | 904.7 |
| III-211 | 925.7 |
| III-212 | 861.7 |
| III-213 or | 950.6 |
| III-214 | 949.7 |
| III-215 | 869.6 |
| III-216 | 869.6 |
| III-217 or | 821.6 |
| III-218 | 821.6 |
| III-219 | 815.5 |
| III-220 | 815.6 |
| III-221 | 815.7 |
| III-222 | 859.4 |
| III-223, | 888.7 |
| III-224, | 888.7 |
| III-225, or | 888.7 |
| III-226 | 888.7 |
| III-227 | 927.7 |
| III-228 | 829.7 |
| III-229 | 842.6 |
| III-230 | 843.8 |
| III-231 or | 886.6 |
| III-232 | 886.6 |
| III-233 | 842.7 |
| III-234 | 841.6 |
| III-235 | 859.6 |
| III-236 or | 873.6 |
| III-237 | 873.6 |
| III-238 or | 877.5 |
| III-239 | 877.4 |

TABLE 6-continued

| Compound No. | Observed Mass (m/z) |
| --- | --- |
| III-240 | 831.6 |
| III-241 | 831.6 |
| III-242 | 814.4 |
| III-243 | 814.4 |
| III-244 or | 871.4 |
| III-245 | 871.5 |
| III-246 or | 855.7 |
| III-247 | 854.3 |
| III-248 or | 854.3 |
| III-249 | 855.3 |
| III-250 or | 855.3 |
| III-251 | 854.5 |
| III-252 or | 861.1 |
| III-253 | 861.1 |
| III-254 or | 867.5 |
| III-255 | 867.2 |
| III-256 or | 873.3 |
| III-257 | 873.3 |
| III-258 or | 922.4 |
| III-259 | 922.3 |
| III-260 or | 814.5 |
| III-261 | 813.6 |
| III-262 or | 833.6 |
| III-263 | 833.6 |
| III-264 | 847.6 |
| III-265 | 878.4 |
| III-266 or | 911.7 |
| III-267 | 911.6 |
| III-268 | 831.5 |
| III-269 or | 873.6 |
| III-270 | 873.6 |
| III-271 or | 873.6 |
| III-272 | 873.6 |
| III-273 or | 873.5 |
| III-274 | 873.6 |
| III-275 or | 866.4 |
| III-276 | 866.4 |
| III-277 or | 851.5 |
| III-278 | 851.6 |
| III-279 or | 885.6 |
| III-280 | 885.6 |
| III-281 or | 851.5 |
| III-282 | 851.6 |
| III-283 or | 851.6 |
| III-284 | 851.6 |
| III-285 or | 851.6 |
| III-286 | 851.7 |
| III-287 or | 851.7 |
| III-288 | 851.6 |
| III-289 or | 855.7 |
| III-290 | 855.6 |
| III-291 or | 855.8 |
| III-292 | 855.6 |
| III-293 or | 872.7 |
| III-294 | 873.5 |
| III-295 or | 869.6 |
| III-296 | 869.5 |
| III-297 or | 851.6 |
| III-298 | 851.5 |
| III-299 or | 922.6 |
| III-300 | 922.6 |
| III-301 or | 871.6 |
| III-302 | 872.4 |
| III-303 or | 873.5 |
| III-304 | 873.4 |
| III-305 or | 870.8 |
| III-306 | 870.8 |
| III-307 or | 867.7 |
| III-308 | 867.7 |
| III-309 or | 867.9 |
| III-310 | 867.7 |
| III-311 or | 867.8 |
| III-312 | 867.8 |
| III-313 or | 868.7 |
| III-314 | 869.7 |
| III-315 or | 851.8 |
| III-316 | 851.7 |
| III-317 or | 839.7 |

TABLE 6-continued

| Compound No. | Observed Mass (m/z) |
|---|---|
| III-318 | 839.7 |
| III-319 or | 885.6 |
| III-320 | 885.7 |
| III-321 or | 848.5 |
| III-322 | 849.5 |
| III-323 or | 839.7 |
| III-324 | 839.8 |
| III-325 or | 839.7 |
| III-326 | 839.7 |
| III-327 or | 885.8 |
| III-328 | 884.7 |
| III-329 or | 846.9 |
| III-330 | 846.8 |
| III-331 or | 864.5 |
| III-332 | 865.8 |
| III-333 or | 885.7 |
| III-334 | 885.8 |
| III-335 or | 882.8 |
| III-336 | 883.7 |
| III-337 or | 890.7 |
| III-338 | 890.7 |
| III-339 or | 885.6 |
| III-340 | 885.7 |
| III-341 or | 903.7 |
| III-342 | 903.7 |
| III-343 or | 885.7 |
| III-344 | 885.7 |
| III-345 or | 885.7 |
| III-346 | 885.7 |
| III-347 | 828.3 |
| III-348 | 917.7 |
| III-349 | 917.8 |
| III-350 | 919.8 |
| III-351 | 919.7 |
| III-352 | 885.6 |
| III-353 | 885.6 |
| III-354 | 935.7 |
| III-355 | 935.7 |
| III-356 | 885.8 |
| III-357 | 885.7 |
| III-358 | 902.7 |
| III-359 | 902.7 |
| IV-1 | 912.6 |
| IV-2 | 928.6 |
| IV-3 | 912.6 |
| IV-4 | 977.6 |
| IV-5 | 927.6 |
| IV-6 | 911.6 |
| IV-7 | 926.6 |
| IV-8 | 951.6 |
| IV-9 | 928.6 |
| IV-10 | 884.6 |
| IV-11 | 912.6 |
| IV-12 | 911.5 |
| IV-13 | 951.3 |
| IV-14 | 979.4 |
| IV-15 | 928.6 |
| IV-16 | 859.6 |
| IV-17 | 830.6 |
| IV-18 | 893.6 |
| IV-19 | 900.6 |
| IV-20 | 865.6 |
| IV-21 | 929.6 |
| IV-22 | 855.6 |
| IV-23 | 855.6 |
| IV-24 | 882.6 |
| IV-25 | 920.7 |
| IV-26 | 894.5 |
| IV-27 | 930.6 |
| IV-28 | 877.6 |
| IV-29 | 899.6 |
| IV-30 or | 995.4 |
| IV-31 | 995.6 |
| IV-32 | 882.6 |
| IV-33 | 877.6 |
| IV-34 | 912.5 |
| IV-35 | 910.6 |
| IV-36 | 855.6 |

TABLE 6-continued

| Compound No. | Observed Mass (m/z) |
|---|---|
| IV-37 | 877.4 |
| IV-38 | 902.4 |
| IV-39 | 814.3 |
| IV-40 | 850.2 |
| IV-41 | 854.3 |
| IV-42 | 870.3 |
| IV-43 | 870.3 |
| IV-44 | 882.3 |
| IV-45 | 900.4 |
| IV-46 | 899.2 |
| IV-47 | 855.1 |
| IV-48 | 896.3 |
| IV-49 | 963.3 |
| IV-50 | 826.6 |
| IV-51 | 893.5 |
| IV-52 | 928.5 |
| IV-53 | 928.5 |
| IV-54 | 917.6 |
| IV-55 | 843.6 |
| IV-56 | 916.5 |
| IV-57 | 892.6 |
| IV-58 | 906.6 |
| IV-59 | 890.5 |
| IV-60 | 978.5 |
| IV-61 | 928.6 |
| IV-62 | 853.6 |
| IV-63 | 859.6 |
| IV-64 | 932.6 |
| IV-65 | 922.7 |
| IV-66 | 888.4 |
| IV-67 | 895.7 |
| IV-68 | 925.7 |
| IV-69 | 894.4 |
| IV-70 | 920.6 |
| IV-71 | 947.5 |
| IV-72 | 909.5 |
| V-1 | 961.4 |
| V-2 | 945.4 |
| V-3 | 933.4 |
| V-4 or | 885.6 |
| V-5 | 885.6 |
| V-6 | 831.6 |
| V-7, | 871.5 |
| V-8, | 871.5 |
| V-9, or | 871.6 |
| V-10 | 871.6 |
| V-11 | 871.4 |
| V-12 or | 869.4 |
| V-13 | 869.4 |
| V-14 or | 885.6 |
| V-15 | 885.6 |
| V-16 | 872.6 |
| V-17 | 872.6 |
| V-18 | 870.6 |
| V-19 or | 911.6 |
| V-20 | 911.7 |
| V-21 | 843.6 |
| V-22 or | 870.4 |
| V-23 | 870.4 |
| V-24 or | 871.4 |
| V-25 | 871.4 |
| V-26 or | 886.4 |
| V-27 | 886.4 |
| V-28 | 887.4 |
| V-29 or | 886.4 |
| V-30 | 886.3 |
| V-31 or | 886.5 |
| V-32 | 886.6 |
| V-33 or | 953.4 |
| V-34 | 953.4 |
| V-35 or | 911.6 |
| V-36 | 911.6 |
| V-37 or | 921.7 |
| V-38 | 921.7 |
| V-39 or | 921.8 |
| V-40 | 921.7 |

Example 56—Cellular Growth Inhibition Assay Using T-Rex 293 Cells

Exemplary compounds were tested for the ability to inhibit the proliferation of the following types of cells: (i) a T-Rex 293 cell line having increased expression of estrogen receptor alpha protein from exposure to doxycycline and (ii) a T-Rex 293 cell line lacking increased expression of estrogen receptor alpha protein. Experimental procedures and results are provided below.

Part I—Experimental Procedure

The following types of cells were prepared for this experiment: (i) a T-Rex 293 cell line having increased expression of estrogen receptor alpha protein from exposure to doxycycline and (ii) a T-Rex 293 cell line lacking increased expression of estrogen receptor alpha protein. The ability of the test compounds to inhibit proliferation of the foregoing cell types was evaluated according to the procedures set forth below.

The doxycycline-inducible estrogen receptor alpha protein expressing cell line was established using the following protocol: T-Rex 293 cells were purchased from Invitrogen (Cat #R71007) and transfected using Lipofectamine 2000 with the wild-type estrogen receptor alpha protein sequence cloned into the pcDNA4/TO vector. Transfected cells were selected using 400 μg/mL Zeocin (Invitrogen Cat #R25001). Following selection, single clones were raised and maintained in Dulbecco's Modified Eagle Medium (DMEM) supplemented with 10% w/w Tetracycline-free fetal bovine serum (FBS) and 250 μg/mL Zeocin. Clones were analyzed for expression of estrogen receptor alpha protein in the presence and absence of 3 ng/mL doxycycline (Sigma Cat #D9891), and a single doxycycline-inducible clone (hereinafter "SC") was selected for use in downstream assays.

The SC cells were seeded on poly-D-lysine coated, black clear-bottom 384-well plates at 2500/well, in 25 μL Phenol Red Free Dulbecco's Modified Eagle Medium (DMEM) supplemented with 10% w/w charcoal-dextran treated fetal bovine serum (FBS) and 1% w/w pen-strep, with or without 3 ng/mL doxycycline. Pen-Strep is a commercially available mixture of penicillin G and streptomycin, which is used in mammalian cell culture media to prevent bacterial contamination. Phenol Red Free Dulbecco's Modified Eagle Medium (DMEM) supplemented with 10% w/w charcoal-dextran treated fetal bovine serum (FBS) and 1% w/w pen-strep, with or without 3 ng/mL doxycycline is herein referred to as Treatment Medium. Following seeding of cells in the plates, the plates were spun at 300×g for 30 seconds, then equilibrated to room temperature for 30 minutes, and then deposited in a humidified tissue culture incubator maintained at 37° C. with 5% $CO_2$.

At 24 hours after seeding of the cells, dilutions of test compound were prepared in DMSO and dissolved in Treatment Medium, to achieve a final DMSO concentration of 0.5% w/w, thereby providing the Test Compound Solution. A 25 μL aliquot of the Test Compound Solution was added to cells in the well plates. An equal volume of a solution containing DMSO and Treatment Medium was used as a negative control. Following treatment of cells with Test Compound Solution or said equal volume of a solution containing DMSO and Treatment Medium, the plates were spun at 300×g for 30 seconds, and then left in an incubator for 72 hours.

At the end of the treatment duration, cell viability was quantified with CellTiter-Glo 2.0 reagent (Promega Cat #G9243). For this purpose, plates were equilibrated to room temperature for 30 minutes, and then 25 μL of CellTiter-Glo 2.0 reagent was added to cells in the plate wells. Plates were then agitated on a shaker for two minutes at 500 rpm and subsequently incubated at room temperature for 10 minutes. Following incubation, the plates were spun at 3000×g for 30 seconds, then sealed with an optical adhesive cover, and luminescence readings were measured with an EnVision Plate Reader (Perkin Elmer).

Data was normalized using zero luminescence for baseline. A four-parameter non-linear regression curve fit was applied to dose-response data in GraphPad Prism data analysis software to determine the half-maximal growth inhibitory concentration ($GI_{50}$) for each test compound.

Part II—Results

Results showing ability of exemplary compounds to inhibit the proliferation of T-Rex 293 cells having, or lacking, increased expression of estrogen receptor alpha protein are provided in Tables 7, 7-A, and 7-B, below, where columns labeled "(+) Dox TRex ERα" or "(+) Dox" refer to results in the experiment where compound was exposed to T-Rex 293 cells having increased expression of estrogen receptor alpha protein due to exposing the cells to doxycycline. Columns labeled "(−) Dox TRex ERα" or "(−) Dox" refer to results in the experiment where compound was exposed to T-Rex 293 cells lacking increased expression of estrogen receptor alpha protein. The symbol "++++" indicates a $GI_{50}$ less than 0.05 μM. The symbol "+++" indicates a $GI_{50}$ in the range of 0.05 μM to 0.5 μM. The symbol "++" indicates a $GI_{50}$ in the range of greater than 0.5 μM to 2.5 μM. The symbol "+" indicates a $GI_{50}$ greater than 2.5 μM. The symbol "N/A" indicates that no data was available.

Unless indicated otherwise, for compounds depicted in Tables 2-5 above having one or more stereogenic center(s) where stereochemistry is not defined using a dashed or wedged bond, the results reported in Tables 7, 7-A, and 7-B below are for a mixture of compounds that are diastereomers.

TABLE 7

| Compound No. | (+) Dox TRex ERa | (−) Dox TRex ERa |
|---|---|---|
| I-1 | +++ | +++ |
| I-2 | +++ | +++ |
| I-3 | +++ | ++ |
| I-4 | ++++ | ++ |
| I-5 | ++++ | ++ |
| I-6 | +++ | +++ |
| I-7 | +++ | +++ |
| I-8 | +++ | +++ |
| I-9 | ++++ | +++ |
| I-10 | ++++ | ++++ |
| I-11 | ++++ | ++++ |
| I-13 | ++++ | +++ |
| I-14 | +++ | + |
| I-15 | ++++ | ++++ |
| I-16 | + | + |
| I-17 | ++ | ++ |
| I-18 | ++++ | +++ |
| I-19 | ++++ | +++ |
| I-20 | ++++ | ++++ |
| I-21 | ++++ | +++ |
| I-22 | ++++ | +++ |
| I-23 | ++ | ++ |
| I-24 | +++ | +++ |
| I-25 | +++ | +++ |
| I-26 | ++++ | +++ |
| I-27 | ++++ | ++ |
| I-28 | +++ | ++ |
| I-29 | ++++ | ++++ |
| I-30 | ++++ | ++++ |
| I-31 | ++++ | +++ |
| I-32 | ++++ | ++ |
| I-33 | ++++ | + |

TABLE 7-continued

| Compound No. | (+) Dox TRex ERa | (−) Dox TRex ERa |
|---|---|---|
| I-35 | ++++ | ++++ |
| I-36 | ++ | ++ |
| I-39 | +++ | ++ |

TABLE 7-A

| Compound No. | (+) Dox | (−) Dox |
|---|---|---|
| I-34a | +++ | ++ |
| I-34b | ++++ | ++ |
| I-37a or | +++ | ++ |
| I-37b | ++ | ++ |
| I-57 | ++++ | ++ |
| I-59 | +++ | ++ |
| I-60 | +++ | ++ |
| I-12, | ++++ | ++ |
| III-1, | + | + |
| III-2, or | + | + |
| III-3 | +++ | ++ |
| I-62 or | +++ | ++ |
| III-4 | ++ | + |
| III-5 or | ++++ | ++ |
| III-6 | +++ | ++ |
| III-7 or | +++ | ++ |
| III-8 | ++ | ++ |
| III-9 or | ++++ | +++ |
| III-10 | ++++ | +++ |
| III-11 or | ++++ | +++ |
| III-12 | ++++ | ++ |
| I-44 or | +++ | ++ |
| III-13 | ++ | + |
| III-14 or | +++ | ++ |
| III-15 | ++ | ++ |
| III-16 or | +++ | +++ |
| III-17 | ++ | ++ |
| I-47 or | +++ | + |
| III-18 | + | + |
| I-46, | ++++ | + |
| III-19, | + | + |
| III-20, or | + | + |
| III-21 | ++ | + |
| III-22 or | ++++ | ++ |
| III-23 | ++++ | + |
| III-24 or | ++++ | +++ |
| III-25 | ++++ | ++ |
| III-26 or | ++++ | +++ |
| III-27 | ++++ | +++ |
| III-28 | +++ | +++ |
| III-29 | ++++ | +++ |
| III-30 | ++++ | +++ |
| III-31 | + | +++ |
| III-32 | ++++ | +++ |
| III-33 | ++++ | +++ |
| III-34 | ++++ | +++ |
| III-35 | ++++ | +++ |
| III-36 | ++++ | +++ |
| III-37 | ++++ | +++ |
| III-38 | ++++ | +++ |
| III-39 | ++++ | +++ |
| III-40 | +++ | +++ |
| III-41 | ++++ | +++ |
| III-42 | ++++ | +++ |
| III-43 | ++++ | +++ |
| III-44 | +++ | ++ |
| III-45 | ++++ | +++ |
| III-46 | ++++ | ++++ |
| III-47 | +++ | +++ |
| III-48 | ++++ | +++ |
| III-49 | ++++ | +++ |
| III-50 | ++++ | +++ |
| III-51 | ++++ | +++ |
| III-52 | +++ | +++ |
| III-53 | +++ | +++ |
| III-54 | +++ | +++ |
| III-55 | +++ | ++ |

TABLE 7-A-continued

| Compound No. | (+) Dox | (−) Dox |
|---|---|---|
| III-56 | +++ | +++ |
| III-57 | +++ | +++ |
| III-58 | ++++ | +++ |
| III-59 | ++++ | +++ |
| III-60 | +++ | +++ |
| III-61 | ++++ | +++ |
| III-62 | ++++ | +++ |
| III-63 | ++++ | +++ |
| III-64 | +++ | +++ |
| III-65 | ++++ | +++ |
| III-66 | +++ | +++ |
| III-67 or | ++++ | ++++ |
| III-68 | +++ | ++ |
| III-69 or | +++ | +++ |
| III-70 | ++++ | +++ |
| III-71, | + | + |
| III-72, | ++ | ++ |
| III-73, or | ++++ | ++ |
| III-74 | ++++ | +++ |
| III-75 or | +++ | +++ |
| III-76 | +++ | +++ |
| III-77a or b | ++++ | +++ |
| III-78 or | +++ | +++ |
| III-79 | +++ | +++ |
| III-80 | +++ | ++ |
| III-81 | +++ | + |
| III-82 or | +++ | ++ |
| III-83 | +++ | ++ |
| III-84 or | ++++ | ++ |
| III-85 | +++ | ++ |
| III-86 | +++ | ++ |
| III-87 | ++++ | +++ |
| III-88 | ++++ | +++ |
| III-89 | ++++ | ++ |
| III-90 | ++ | + |
| III-91 or | +++ | ++ |
| III-92 | +++ | +++ |
| III-93a or b | +++ | +++ |
| III-94a or b | ++++ | +++ |
| III-95 or | ++++ | +++ |
| III-96 | +++ | +++ |
| III-97 | ++++ | ++ |
| III-98 | ++++ | ++ |
| III-99 or | +++ | +++ |
| III-100 | +++ | +++ |
| III-101 or | ++++ | +++ |
| III-102 | +++ | +++ |
| III-103 or | ++++ | +++ |
| III-104 | ++++ | +++ |
| III-105 | ++++ | +++ |
| III-106 | ++++ | ++ |
| III-107 | +++ | ++ |
| III-108 | ++++ | +++ |
| III-109 or | ++++ | +++ |
| III-110 | ++++ | ++++ |
| III-111 or | ++++ | +++ |
| III-112 | +++ | +++ |
| III-113 or | ++++ | +++ |
| III-114 | ++++ | +++ |
| III-115 | +++ | ++ |
| III-116 | + | + |
| III-117 | ++ | ++ |
| III-118 | ++++ | ++ |
| III-119 | +++ | ++ |
| III-120 | + | ++ |
| III-121 | ++ | + |
| III-122 or | ++ | + |
| III-123 | ++++ | ++ |
| III-124 | +++ | ++ |
| III-125 or | ++++ | +++ |
| III-126 | ++++ | +++ |
| III-127 or | +++ | ++ |
| III-128 | ++++ | +++ |
| III-129 | +++ | ++ |
| III-130 | +++ | ++ |
| III-131 | ++++ | ++ |
| III-132 | +++ | ++ |
| III-133 | ++++ | +++ |

TABLE 7-A-continued

| Compound No. | (+) Dox | (−) Dox |
|---|---|---|
| III-134 | ++++ | +++ |
| III-135 | ++++ | ++ |
| III-136 | + | + |
| III-137 | ++ | ++ |
| III-138 | ++ | + |
| III-139 | ++ | ++ |
| III-140 | +++ | ++ |
| III-141 | +++ | ++ |
| III-142 | +++ | +++ |
| III-143 | + | + |
| III-144 | +++ | + |
| III-145 | ++ | ++ |
| III-146 | ++ | ++ |
| III-147 | +++ | +++ |
| III-148 | ++++ | ++ |
| III-149 | ++++ | +++ |
| III-150 | ++++ | ++ |
| III-151 | ++++ | + |
| III-152 | ++++ | ++ |
| III-153 | ++++ | ++ |
| III-154 or | + | + |
| III-155 | ++++ | +++ |
| III-156 | ++++ | ++++ |
| III-157 | ++++ | ++ |
| III-158 | ++++ | +++ |
| III-159 | ++++ | ++++ |
| III-160 | ++++ | +++ |
| III-161 | ++++ | +++ |
| III-162 | ++++ | +++ |
| III-163 or | + | + |
| III-164 | ++++ | +++ |
| III-165 | ++++ | +++ |
| III-166 | ++++ | +++ |
| III-167 | ++++ | +++ |
| III-168 | ++++ | +++ |
| III-169 | ++++ | +++ |
| III-170 | ++++ | +++ |
| III-171 | ++++ | +++ |
| III-172 | ++++ | +++ |
| III-173 | ++++ | +++ |
| III-174 | ++++ | +++ |
| III-175 | ++++ | +++ |
| III-176 | ++++ | +++ |
| III-177 | ++++ | +++ |
| III-178 | ++++ | +++ |
| III-179 | ++++ | ++++ |
| III-180 | ++++ | +++ |
| III-181 | ++++ | +++ |
| III-182 or | ++++ | ++ |
| III-183 | ++++ | ++ |
| III-184 or | ++++ | +++ |
| III-185 | ++++ | ++ |
| III-186 or | ++++ | ++ |
| III-187 | ++++ | +++ |
| III-188 or | ++++ | +++ |
| III-189 | + | + |
| III-190 | ++++ | ++ |
| III-191 | ++++ | +++ |
| III-192 | + | + |
| III-193 | +++ | ++ |
| III-194, | + | + |
| III-195, | + | + |
| III-196, or | ++++ | +++ |
| III-197 | ++++ | +++ |
| III-198, | + | + |
| III-199, | + | + |
| III-200, or | ++++ | +++ |
| III-201 | +++ | +++ |
| III-202 | ++++ | +++ |
| III-203 | ++++ | ++ |
| III-204 or | ++++ | ++ |
| III-205 | +++ | ++ |
| III-206 | ++++ | ++ |
| III-207, | + | + |
| III-208, | + | + |
| III-209, or | ++++ | +++ |
| III-210 | ++++ | +++ |
| III-211 | ++++ | +++ |

TABLE 7-A-continued

| Compound No. | (+) Dox | (−) Dox |
|---|---|---|
| III-212 | ++++ | +++ |
| III-213 or | + | + |
| III-214 | ++++ | +++ |
| III-215 | ++++ | + |
| III-216 | + | + |
| III-217 or | ++++ | +++ |
| III-218 | ++++ | +++ |
| III-219 | ++++ | +++ |
| III-220 | ++++ | +++ |
| III-221 | ++++ | +++ |
| III-222 | ++++ | + |
| III-223, | ++ | ++ |
| III-224, | + | + |
| III-225, or | ++++ | +++ |
| III-226 | ++++ | +++ |
| III-227 | ++++ | + |
| III-228 | ++++ | ++ |
| III-229 | ++++ | ++ |
| III-230 | ++++ | + |
| III-231 or | + | + |
| III-232 | ++++ | + |
| III-233 | ++++ | ++ |
| III-234 | ++++ | ++ |
| III-235 | ++++ | ++ |
| III-236 or | ++++ | ++ |
| III-237 | +++ | ++ |
| III-238 or | +++ | ++ |
| III-239 | ++++ | +++ |
| III-240 | ++++ | +++ |
| III-241 | ++++ | +++ |
| III-242 | ++++ | ++ |
| III-243 | ++++ | ++ |
| III-244 or | + | + |
| III-245 | ++++ | ++ |
| III-246 or | ++++ | ++ |
| III-247 | ++++ | +++ |
| III-248 or | ++++ | ++ |
| III-249 | +++ | ++ |
| III-250 or | +++ | +++ |
| III-251 | ++++ | ++ |
| III-252 or | +++ | ++ |
| III-253 | ++++ | ++ |
| III-254 or | ++++ | ++ |
| III-255 | ++++ | ++ |
| III-256 or | ++++ | ++ |
| III-257 | +++ | ++ |
| III-258 or | +++ | +++ |
| III-259 | ++++ | ++ |
| III-260 or | ++++ | ++ |
| III-261 | ++++ | ++ |
| III-262 or | +++ | ++ |
| III-263 | ++++ | ++ |
| III-264 | ++++ | ++ |
| III-265 | +++ | + |
| III-266 or | ++++ | ++ |
| III-267 | +++ | + |
| III-268 | ++++ | ++ |
| III-269 or | +++ | +++ |
| III-270 | ++++ | ++ |
| III-271 or | +++ | +++ |
| III-272 | ++++ | ++ |
| III-273 or | +++ | +++ |
| III-274 | ++++ | ++ |
| III-275 or | +++ | +++ |
| III-276 | ++++ | ++ |
| III-277 or | ++++ | ++ |
| III-278 | +++ | ++ |
| III-279 or | ++++ | ++ |
| III-280 | +++ | ++ |
| III-281 or | +++ | ++ |
| III-282 | ++++ | +++ |
| III-283 or | +++ | ++ |
| III-284 | +++ | ++ |
| III-285 or | +++ | +++ |
| III-286 | ++++ | ++ |
| III-287 or | ++++ | ++ |
| III-288 | +++ | ++ |
| III-289 or | ++++ | ++ |

TABLE 7-A-continued

| Compound No. | (+) Dox | (−) Dox |
|---|---|---|
| III-290 | ++++ | +++ |
| III-291 or | ++++ | ++ |
| III-292 | +++ | +++ |
| III-293 or | ++++ | ++ |
| III-294 | +++ | +++ |
| III-295 or | ++ | ++ |
| III-296 | +++ | ++ |
| III-297 or | +++ | +++ |
| III-298 | +++ | +++ |
| III-299 or | ++++ | +++ |
| III-300 | ++++ | +++ |
| III-301 or | ++ | ++ |
| III-302 | +++ | ++ |
| III-303 or | +++ | +++ |
| III-304 | ++++ | ++ |
| III-305 or | ++++ | ++ |
| III-306 | +++ | ++ |
| III-307 or | ++++ | ++ |
| III-308 | +++ | +++ |
| III-309 or | +++ | +++ |
| III-310 | ++++ | ++ |
| III-311 or | ++++ | ++ |
| III-312 | +++ | +++ |
| III-313 or | ++++ | ++ |
| III-314 | +++ | ++ |
| III-315 or | ++ | ++ |
| III-316 | ++++ | ++ |
| III-317 or | ++++ | +++ |
| III-318 | +++ | +++ |
| III-319 or | ++++ | +++ |
| III-320 | ++++ | ++ |
| III-321 or | ++++ | ++ |
| III-322 | +++ | +++ |
| III-323 or | ++++ | ++ |
| III-324 | +++ | +++ |
| III-325 or | +++ | ++ |
| III-326 | ++ | ++ |
| III-327 or | +++ | +++ |
| III-328 | ++++ | ++ |
| III-329 or | +++ | +++ |
| III-330 | ++++ | +++ |
| III-331 or | ++ | ++ |
| III-332 | ++++ | +++ |
| III-333 or | +++ | ++ |
| III-334 | ++++ | ++ |
| III-335 or | +++ | ++ |
| III-336 | ++++ | ++ |
| III-337 or | +++ | ++ |
| III-338 | ++++ | ++ |
| III-339 or | ++++ | + |
| III-340 | +++ | +++ |
| III-341 or | ++++ | + |
| III-342 | +++ | +++ |
| III-343 or | +++ | +++ |
| III-344 | ++++ | ++ |
| III-345 or | ++++ | +++ |
| III-346 | ++++ | ++ |
| IV-1 | ++++ | + |
| IV-2 | +++ | ++ |
| IV-3 | ++++ | ++ |
| IV-4 | +++ | ++ |
| IV-5 | ++++ | + |
| IV-6 | +++ | ++ |
| IV-7 | +++ | ++ |
| IV-8 | ++++ | ++ |
| IV-9 | ++++ | ++ |
| IV-10 | +++ | ++ |
| IV-11 | ++++ | ++ |
| IV-12 | +++ | ++ |
| IV-13 | ++++ | +++ |
| IV-14 | ++++ | ++ |
| IV-15 | + | + |
| IV-16 | ++++ | ++ |
| IV-17 | ++++ | ++ |
| IV-18 | ++++ | ++ |
| IV-19 | ++++ | ++ |
| IV-20 | ++++ | ++ |
| IV-21 | ++++ | ++ |

TABLE 7-A-continued

| Compound No. | (+) Dox | (−) Dox |
|---|---|---|
| IV-22 | ++++ | +++ |
| IV-23 | ++++ | +++ |
| IV-24 | ++++ | ++ |
| IV-25 | ++++ | +++ |
| IV-26 | ++++ | ++ |
| IV-27 | +++ | ++ |
| IV-28 | ++++ | ++ |
| IV-29 | ++++ | +++ |
| IV-30 or | ++ | ++ |
| IV-31 | ++++ | +++ |
| IV-32 | ++++ | +++ |
| IV-33 | ++++ | ++ |
| IV-34 | ++++ | +++ |
| IV-35 | ++++ | ++ |
| IV-36 | ++++ | +++ |
| IV-37 | ++++ | ++ |
| IV-38 | ++++ | ++ |
| IV-39 | ++++ | + |
| IV-40 | ++++ | + |
| IV-41 | ++++ | +++ |
| IV-42 | ++++ | +++ |
| IV-43 | ++++ | +++ |
| IV-44 | ++++ | ++ |
| IV-45 | ++++ | ++++ |
| IV-46 | ++++ | ++ |
| IV-47 | ++++ | ++ |
| IV-48 | ++++ | ++ |
| IV-49 | ++++ | ++ |
| IV-50 | ++++ | ++ |
| IV-51 | ++++ | ++ |
| IV-52 | +++ | ++ |
| IV-53 | ++++ | ++ |
| IV-54 | ++++ | +++ |
| IV-55 | ++++ | ++ |
| IV-56 | ++++ | +++ |
| IV-57 | ++++ | ++ |
| IV-58 | ++++ | ++ |
| IV-59 | ++++ | ++ |
| IV-60 | ++++ | +++ |
| IV-61 | ++++ | ++ |
| IV-62 | ++++ | ++ |
| IV-63 | ++++ | ++ |
| IV-64 | +++ | ++ |
| V-1 | +++ | +++ |
| V-2 | +++ | ++ |
| V-3 | +++ | +++ |
| V-4 or | ++ | ++ |
| V-5 | +++ | ++ |
| V-6 | +++ | ++ |
| V-7, | ++++ | +++ |
| V-8, | ++++ | ++ |
| V-9, or | + | ++ |
| V-10 | ++ | ++ |
| V-11 | +++ | ++ |
| V-12 or | ++++ | +++ |
| V-13 | +++ | +++ |
| V-14 or | +++ | ++ |
| V-15 | ++++ | +++ |
| V-16 | ++ | ++ |
| V-17 | +++ | +++ |
| V-18 | +++ | +++ |
| V-19 or | ++++ | ++ |
| V-20 | ++++ | ++ |
| V-21 | ++++ | +++ |
| V-22 or | ++++ | ++ |
| V-23 | ++++ | ++ |
| V-24 or | + | + |
| V-25 | + | + |
| V-26 or | ++++ | +++ |
| V-27 | ++++ | ++ |
| V-28 | ++++ | +++ |
| V-29 or | +++ | +++ |
| V-30 | +++ | +++ |
| V-31 or | ++++ | +++ |
| V-32 | ++++ | ++ |
| V-33 or | ++++ | +++ |

TABLE 7-A-continued

| Compound No. | (+) Dox | (−) Dox |
|---|---|---|
| V-34 | +++ | +++ |
| V-35 or | ++++ | +++ |
| V-36 | ++++ | ++ |

TABLE 7-B

| Compound No. | (+) Dox | (−) Dox |
|---|---|---|
| III-347 | ++++ | ++++ |
| III-348 | ++ | ++ |
| III-349 | ++++ | ++ |
| III-350 | + | + |
| III-351 | ++++ | + |
| III-352 | ++++ | ++ |
| III-353 | +++ | ++ |
| III-354 | +++ | ++ |
| III-355 | ++++ | ++ |
| III-356 | ++++ | ++ |
| III-357 | +++ | ++ |
| III-358 | ++++ | ++ |
| III-359 | +++ | ++ |
| IV-65 | ++++ | ++ |
| IV-66 | ++++ | ++ |
| IV-67 | ++++ | ++ |
| IV-68 | ++++ | ++ |
| IV-69 | ++++ | ++ |
| IV-70 | ++++ | ++ |
| IV-71 | ++++ | ++ |
| IV-72 | ++++ | ++ |
| V-37 or | ++++ | ++ |
| V-38 | +++ | +++ |
| V-39 or | +++ | +++ |
| V-40 | ++++ | ++ |

Example 57—Cellular Growth Inhibition Assay Using MCF7 Cells

Exemplary compounds were tested for the ability to inhibit the proliferation of MCF7 cells. Experimental procedures and results are provided below.

Part I—Experimental Procedure

MCF7 cells (ATCC #HTB-22 or ECACC #86012803) were cultured in RPMI 1640 medium supplemented with 10% heat-inactivated fetal bovine serum, 1% pen-strep, and 0.2 U/ml insulin. Cells were seeded in 25 μL of RPMI 1640 medium supplemented with 10% heat-inactivated fetal bovine serum, 1% pen-strep, 0.2 U/ml insulin in poly-D-lysine treated, black clear-bottom 384-well plates at 225 cells/well for MCF7 cells purchased from ECACC or 1,500 cells/well for MCF7 cells purchased from ATCC. Following seeding, plates were spun at 300×g for 30 seconds and cultured at 37° C. with 5% $CO_2$ in a humidified tissue culture incubator.

At 24 hours after seeding, compounds were titrated in 100% DMSO and diluted in RPMI 1640 medium supplemented with 10% heat-inactivate fetal bovine serum, 1% pen-strep, and 0.2 U/ml insulin. A 25 μL aliquot of the compound/media mixture was added to cells, bringing the total volume in each well to 50 μL. An equal volume of DMSO without compound was used as a negative control. After treatment, plates were spun at 300×g for 30 seconds, then cultured at 37° C. with 5% $CO_2$ for six days in a humidified tissue culture incubator.

On Day 6 of treatment, cell viability was quantified with CellTiter-Glo 2.0 reagent (Promega). Plates were equilibrated to room temperature for 30 minutes, then 25 μL of CellTiter-Glo 2.0 reagent was added to cells, bringing the total volume in each well to 75 μL. After reagent was added, plates were mixed on a shaker for two minutes at 500 rpm and then incubated at room temperature for 10 minutes. Following incubation, plates were spun at 3,000×g for 30 seconds, sealed with an optical adhesive cover, and luminescence readings were measured with an EnVision Plate Reader.

Data was normalized to 0 luminescence for baseline. A four-parameter, non-linear regression curve fit was applied to dose-response data in GraphPad Prism data analysis software to determine the half maximal growth inhibitory concentration ($GI_{50}$) for each compound.

Part II—Results

Results showing ability of exemplary compounds to inhibit the proliferation of MCF7 cells purchased from ATCC are provided in Table 8-A, below. Results showing ability of exemplary compounds to inhibit the proliferation of MCF7 cells purchased from ECACC are provided in Table 8-B, below. The symbol "++++" indicates a $GI_{50}$ less than 0.05 μM. The symbol "+++" indicates a $GI_{50}$ in the range of 0.05 μM to 0.5 μM. The symbol "++" indicates a $GI_{50}$ in the range of greater than 0.5 μM to 2.5 μM. The symbol "+" indicates a $GI_{50}$ greater than 2.5 M.

Unless indicated otherwise, for compounds depicted in Tables 2-5 above having one or more stereogenic center(s) where stereochemistry is not defined using a dashed or wedged bond, the results reported in Tables 8-A and 8-B below are for a mixture of compounds that are diastereomers.

TABLE 8-A

| Compound No. | $GI_{50}$ |
|---|---|
| I-1 | +++ |
| I-2 | +++ |
| I-3 | +++ |
| I-4 | +++ |
| I-5 | +++ |
| I-6 | +++ |
| I-7 | +++ |
| I-8 | ++++ |
| I-9 | ++++ |
| I-10 | ++++ |
| I-11 | ++++ |
| I-13 | ++++ |
| I-14 | ++ |
| I-15 | ++++ |
| I-16 | +++ |
| I-17 | +++ |
| I-19 | ++++ |
| I-20 | ++++ |
| I-21 | ++++ |
| I-22 | ++++ |
| I-23 | +++ |
| I-24 | ++++ |
| I-25 | ++++ |
| I-26 | ++++ |
| I-27 | +++ |
| I-28 | +++ |
| I-29 | ++++ |
| I-30 | ++++ |
| I-31 | ++++ |
| I-32 | +++ |
| I-33 | ++++ |
| I-34a | +++ |
| I-34b | +++ |
| I-35 | ++++ |
| I-36 | ++ |
| I-37a or | +++ |
| I-37b | ++ |
| I-39 | +++ |
| I-57 | ++++ |
| I-59 | +++ |

TABLE 8-A-continued

| Compound No. | $GI_{50}$ |
|---|---|
| I-60 | +++ |
| II-1 | ++++ |
| II-2 | ++++ |
| II-3 | ++++ |
| II-4 | ++++ |
| II-5 | ++++ |
| I-12, | ++++ |
| III-1, | ++ |
| III-2, or | ++ |
| III-3 | +++ |
| I-62 or | + |
| III-4 | + |
| III-5 or | ++++ |
| III-6 | +++ |
| III-7 or | +++ |
| III-8 | +++ |
| III-9 or | +++ |
| III-10 | +++ |
| III-11 or | +++ |
| III-12 | +++ |
| I-44 or | ++ |
| III-13 | ++ |
| III-14 or | ++ |
| III-15 | ++ |
| III-16 or | +++ |
| III-17 | ++ |
| I-47 or | ++ |
| III-18 | ++ |
| I-46, | +++ |
| III-19, | + |
| III-20, or | + |
| III-21 | ++ |
| III-22 or | +++ |
| III-23 | +++ |
| III-24 or | +++ |
| III-25 | ++++ |
| III-26 or | +++ |
| III-27 | +++ |
| III-28 | +++ |
| III-29 | +++ |
| III-30 | +++ |
| III-31 | +++ |
| III-32 | +++ |
| III-33 | +++ |
| III-34 | +++ |
| III-35 | ++++ |
| III-36 | ++++ |
| III-37 | ++++ |
| III-38 | ++++ |
| III-39 | ++++ |
| III-40 | ++++ |
| III-42 | +++ |
| III-43 | +++ |
| III-44 | +++ |
| III-45 | +++ |
| III-46 | ++++ |
| III-47 | +++ |
| III-48 | ++++ |
| III-49 | ++++ |
| III-50 | ++++ |
| III-51 | ++++ |
| III-52 | +++ |
| III-53 | +++ |
| III-54 | +++ |
| III-55 | +++ |
| III-56 | +++ |
| III-57 | +++ |
| III-58 | +++ |
| III-59 | +++ |
| III-60 | +++ |
| III-61 | ++++ |
| III-62 | +++ |
| III-63 | +++ |
| III-64 | +++ |
| III-65 | +++ |
| III-66 | +++ |
| III-67 or | ++++ |
| III-68 | +++ |

TABLE 8-A-continued

| Compound No. | $GI_{50}$ |
|---|---|
| III-69 or | +++ |
| III-70 | ++++ |
| III-71, | + |
| III-72, | ++ |
| III-73, or | ++++ |
| III-74 | +++ |
| III-75 or | +++ |
| III-76 | +++ |
| III-77a or b | ++++ |
| III-78 or | +++ |
| III-79 | +++ |
| III-80 | + |
| III-81 | +++ |
| III-82 or | +++ |
| III-83 | +++ |
| III-84 or | +++ |
| III-85 | +++ |
| III-86 | +++ |
| III-87 | ++++ |
| III-88 | ++++ |
| III-89 | +++ |
| III-90 | +++ |
| III-91 or | ++++ |
| III-92 | +++ |
| III-93a or b | ++++ |
| III-94a or b | +++ |
| III-95 or | ++++ |
| III-96 | +++ |
| III-97 | ++++ |
| III-98 | +++ |
| III-99 or | +++ |
| III-100 | +++ |
| III-101 or | +++ |
| III-102 | +++ |
| III-103 or | ++++ |
| III-104 | ++++ |
| III-105 | ++++ |
| III-106 | +++ |
| III-107 | +++ |
| III-108 | ++++ |
| III-109 or | +++ |
| III-110 | ++++ |
| III-111 or | +++ |
| III-112 | +++ |
| III-113 or | ++++ |
| III-114 | +++ |
| III-115 | +++ |
| III-116 | ++ |
| III-117 | +++ |
| III-118 | +++ |
| III-119 | +++ |
| III-120 | +++ |
| III-121 | ++ |
| III-122 or | ++ |
| III-123 | +++ |
| III-124 | +++ |
| III-125 or | +++ |
| III-126 | +++ |
| III-127 or | +++ |
| III-128 | +++ |
| III-129 | +++ |
| III-130 | +++ |
| III-131 | +++ |
| III-132 | +++ |
| III-133 | +++ |
| III-134 | ++++ |
| III-135 | ++++ |
| III-136 | + |
| III-137 | +++ |
| III-138 | ++ |
| III-139 | +++ |
| III-140 | ++++ |
| III-141 | +++ |
| III-142 | +++ |
| III-143 | + |
| III-144 | ++ |
| III-145 | +++ |
| III-146 | ++++ |

TABLE 8-A-continued

| Compound No. | $GI_{50}$ |
|---|---|
| III-147 | +++ |
| III-148 | ++++ |
| III-149 | ++++ |
| III-150 | +++ |
| III-151 | ++++ |
| III-152 | +++ |
| III-153 | +++ |
| III-154 or | +++ |
| III-155 | ++++ |
| III-156 | ++++ |
| III-157 | +++ |
| III-158 | ++++ |
| III-159 | ++++ |
| III-160 | ++++ |
| III-161 | ++++ |
| III-162 | ++++ |
| III-163 or | +++ |
| III-164 | ++++ |
| III-165 | ++++ |
| III-166 | +++ |
| III-167 | ++++ |
| III-168 | ++++ |
| III-169 | +++ |
| III-170 | +++ |
| III-171 | +++ |
| III-172 | +++ |
| III-173 | ++++ |
| III-174 | ++++ |
| III-175 | ++++ |
| III-176 | ++++ |
| III-177 | +++ |
| III-178 | ++++ |
| III-179 | ++++ |
| III-180 | ++++ |
| III-181 | ++++ |
| III-182 or | +++ |
| III-183 | +++ |
| III-184 or | +++ |
| III-185 | ++++ |
| III-186 or | ++++ |
| III-187 | +++ |
| III-188 or | +++ |
| III-189 | +++ |
| III-190 | +++ |
| III-191 | +++ |
| III-192 | + |
| III-193 | +++ |
| III-194, | + |
| III-195, | ++ |
| III-196, or | ++++ |
| III-197 | +++ |
| III-198, | + |
| III-199, | + |
| III-200, or | ++++ |
| III-201 | +++ |
| III-202 | ++++ |
| III-203 | ++++ |
| III-204 or | +++ |
| III-205 | +++ |
| III-206 | ++++ |
| III-207, | ++ |
| III-208, | ++ |
| III-209, or | +++ |
| III-210 | ++++ |
| III-211 | ++++ |
| III-212 | ++++ |
| III-213 or | + |
| III-214 | ++++ |
| III-215 | ++++ |
| III-216 | +++ |
| III-217 or | +++ |
| III-218 | +++ |
| III-219 | +++ |
| III-220 | +++ |
| III-221 | ++++ |
| III-222 | +++ |
| III-223, | ++ |
| III-224, | +++ |

TABLE 8-A-continued

| Compound No. | $GI_{50}$ |
|---|---|
| III-225, or | +++ |
| III-226 | ++++ |
| III-227 | +++ |
| III-228 | +++ |
| III-229 | +++ |
| III-230 | +++ |
| III-231 or | ++ |
| III-232 | ++++ |
| III-233 | +++ |
| III-234 | +++ |
| III-235 | ++++ |
| III-236 or | ++++ |
| III-237 | +++ |
| III-238 or | +++ |
| III-239 | ++++ |
| III-240 | ++++ |
| III-241 | ++++ |
| III-242 | ++++ |
| III-243 | ++++ |
| III-244 or | +++ |
| III-245 | ++++ |
| III-246 or | ++++ |
| III-247 | +++ |
| III-248 or | ++++ |
| III-249 | +++ |
| III-250 or | +++ |
| III-251 | ++++ |
| III-252 or | ++ |
| III-253 | ++++ |
| III-254 or | +++ |
| III-255 | +++ |
| III-256 or | ++++ |
| III-257 | +++ |
| III-258 or | +++ |
| III-259 | ++++ |
| III-260 or | +++ |
| III-261 | +++ |
| III-262 or | +++ |
| III-263 | ++++ |
| III-264 | ++++ |
| III-265 | +++ |
| III-266 or | ++++ |
| III-267 | +++ |
| III-268 | ++++ |
| III-269 or | +++ |
| III-270 | +++ |
| III-271 or | +++ |
| III-272 | ++++ |
| III-273 or | +++ |
| III-274 | ++++ |
| III-275 or | +++ |
| III-276 | ++++ |
| III-277 or | ++++ |
| III-278 | +++ |
| III-279 or | ++++ |
| III-280 | +++ |
| III-281 or | ++ |
| III-282 | ++++ |
| III-283 or | +++ |
| III-284 | +++ |
| III-285 or | +++ |
| III-286 | ++++ |
| III-287 or | +++ |
| III-288 | +++ |
| III-289 or | ++++ |
| III-290 | +++ |
| III-291 or | ++++ |
| III-292 | +++ |
| III-293 or | ++++ |
| III-294 | +++ |
| III-295 or | +++ |
| III-296 | +++ |
| III-297 or | +++ |
| III-298 | +++ |
| III-299 or | ++++ |
| III-300 | +++ |
| III-301 or | +++ |
| III-302 | +++ |

TABLE 8-A-continued

| Compound No. | GI$_{50}$ |
|---|---|
| III-303 or | +++ |
| III-304 | ++++ |
| III-305 or | ++++ |
| III-306 | +++ |
| III-307 or | ++++ |
| III-308 | +++ |
| III-309 or | +++ |
| III-310 | ++++ |
| III-311 or | ++++ |
| III-312 | +++ |
| III-317 or | +++ |
| III-318 | +++ |
| III-339 or | ++++ |
| III-340 | +++ |
| III-341 or | ++++ |
| III-342 | +++ |
| III-343 or | ++++ |
| III-344 | ++++ |
| III-345 or | ++++ |
| III-346 | ++++ |
| III-347 | ++++ |
| IV-1 | +++ |
| IV-2 | +++ |
| IV-3 | +++ |
| IV-4 | ++++ |
| IV-5 | +++ |
| IV-6 | +++ |
| IV-7 | +++ |
| IV-8 | ++++ |
| IV-9 | ++++ |
| IV-10 | +++ |
| IV-11 | +++ |
| IV-12 | +++ |
| IV-13 | ++++ |
| IV-14 | ++++ |
| IV-15 | ++ |
| IV-16 | ++++ |
| IV-17 | ++++ |
| IV-18 | ++++ |
| IV-19 | +++ |
| IV-20 | ++++ |
| IV-21 | +++ |
| IV-22 | ++++ |
| IV-23 | ++++ |
| IV-24 | ++++ |
| IV-25 | ++++ |
| IV-26 | ++++ |
| IV-27 | +++ |
| IV-28 | ++++ |
| IV-29 | ++++ |
| IV-30 or | +++ |
| IV-31 | ++++ |
| IV-32 | +++ |
| IV-33 | ++++ |
| IV-34 | ++++ |
| IV-35 | ++++ |
| IV-36 | ++++ |
| IV-37 | ++++ |
| IV-38 | ++++ |
| IV-39 | +++ |
| IV-40 | ++++ |
| IV-41 | ++++ |
| IV-42 | ++++ |
| IV-43 | ++++ |
| IV-44 | ++++ |
| IV-45 | ++++ |
| IV-46 | +++ |
| IV-47 | ++++ |
| IV-48 | ++++ |
| IV-49 | ++++ |
| IV-50 | ++++ |
| IV-51 | ++++ |
| IV-52 | +++ |
| IV-53 | ++++ |
| IV-54 | ++++ |
| IV-55 | ++++ |
| IV-56 | ++++ |
| IV-57 | ++++ |
| IV-58 | ++++ |
| IV-59 | ++++ |
| IV-60 | ++++ |
| IV-61 | ++++ |
| IV-62 | ++++ |
| IV-63 | ++++ |
| IV-64 | ++++ |
| IV-65 | +++ |
| V-1 | +++ |
| V-2 | +++ |
| V-3 | +++ |
| V-4 or | +++ |
| V-5 | +++ |
| V-6 | +++ |
| V-7, | +++ |
| V-8, | +++ |
| V-9, or | +++ |
| V-10 | ++ |
| V-11 | +++ |
| V-12 or | +++ |
| V-13 | +++ |
| V-14 or | +++ |
| V-15 | +++ |
| V-16 | +++ |
| V-17 | +++ |
| V-18 | +++ |
| V-19 or | ++++ |
| V-20 | +++ |
| V-21 | ++++ |
| V-22 or | +++ |
| V-23 | +++ |
| V-24 or | + |
| V-25 | + |
| V-26 or | +++ |
| V-27 | +++ |
| V-28 | ++++ |
| V-29 or | +++ |
| V-30 | +++ |
| V-31 or | +++ |
| V-32 | +++ |
| V-33 or | +++ |
| V-34 | +++ |
| V-35 or | ++++ |
| V-36 | +++ |
| V-37 or | ++++ |
| V-38 | +++ |
| V-39 or | +++ |
| V-40 | ++++ |

TABLE 8-B

| Compound No. | GI$_{50}$ |
|---|---|
| III-244 or | +++ |
| III-245 | ++++ |
| III-250 or | +++ |
| III-251 | ++++ |
| III-275 or | ++++ |
| III-276 | ++++ |
| III-307 or | ++++ |
| III-308 | +++ |
| III-311 or | ++++ |
| III-312 | ++++ |
| III-313 or | +++ |
| III-314 | +++ |
| III-315 or | +++ |
| III-316 | ++++ |
| III-317 or | ++++ |
| III-318 | +++ |
| III-319 or | +++ |
| III-320 | ++++ |
| III-321 or | ++++ |
| III-322 | +++ |
| III-323 or | ++++ |
| III-324 | +++ |

TABLE 8-B-continued

| Compound No. | $GI_{50}$ |
|---|---|
| III-325 or | +++ |
| III-326 | ++ |
| III-327 or | +++ |
| III-328 | ++++ |
| III-329 or | +++ |
| III-330 | ++++ |
| III-331 or | ++ |
| III-332 | ++++ |
| III-333 or | +++ |
| III-334 | ++++ |
| III-335 or | +++ |
| III-336 | ++++ |
| III-337 or | +++ |
| III-338 | ++++ |
| III-339 or | ++++ |
| III-340 | +++ |
| III-341 or | ++++ |
| III-342 | +++ |
| III-343 or | +++ |
| III-344 | ++++ |
| III-345 or | +++ |
| III-346 | ++++ |
| III-348 | ++ |
| III-349 | ++++ |
| III-350 | +++ |
| III-351 | ++++ |
| III-352 | ++++ |
| III-353 | +++ |
| III-354 | +++ |
| III-355 | ++++ |
| III-356 | +++ |
| III-357 | +++ |
| III-358 | ++++ |
| III-359 | +++ |
| IV-66 | ++++ |
| IV-67 | ++++ |
| IV-68 | ++++ |
| IV-69 | ++++ |
| IV-70 | ++++ |
| IV-71 | ++++ |
| IV-72 | ++++ |

Example 58—Assay for Binding Affinity to BRD4-BD1

Exemplary compounds were tested for ability to bind to BRD4-BD 1. Experimental procedures and results are provided below.

Part I—Experimental Procedure

Compounds were tested using a bromoKdELECT assay. T7 phage strains displaying bromodomains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 m) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds were prepared as 1000× stocks in 100% DMSO. Kds were determined using an 11-point 3-fold compound dilution series with one DMSO control point. All compounds for Kd measurements are distributed by acoustic transfer (non-contact dispensing) in 100% DMSO. The compounds were then diluted directly into the assays such that the final concentration of DMSO was 0.09%. All reactions performed in polypropylene 384-well plates. Each was a final volume of 0.02 ml. The assay plates were incubated at room temperature with shaking for 1 hour and the affinity beads were washed with wash buffer (1×PBS, 0.05% Tween 20). The beads were then resuspended in elution buffer (1×PBS, 0.05% Tween 20, 2 μM non-biotinylated affinity ligand) and incubated at room temperature with shaking for 30 minutes. The bromodomain concentration in the eluates was measured by qPCR.

Part II—Results

Results showing ability of exemplary compounds to bind to BRD4-BD1 are provided in Table 9 below. The symbol "++++" indicates a $K_d$ less than 0.05 μM. The symbol "+++" indicates a $K_d$ in the range of 0.05 μM to 0.5 μM. The symbol "++" indicates a $K_d$ in the range of greater than 0.5 μM to 2.5 μM. The symbol "+" indicates a $K_d$ greater than 2.5 μM. The symbol "N/A" indicates that no data was available.

TABLE 9

| Compound No. | $K_d$ |
|---|---|
| I-2 | +++ |
| I-3 | ++++ |
| I-5 | ++++ |

Example 59—Assay for Binding Affinity to BRD4-BD2

Exemplary compounds were tested for ability to bind to BRD4-BD2. Experimental procedures and results are provided below.

Part I—Experimental Procedure

Compounds were tested using a bromoKdELECT assay. T7 phage strains displaying bromodomains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 m) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds were prepared as 1000× stocks in 100% DMSO. Kds were determined using an 11-point 3-fold compound dilution series with one DMSO control point. All compounds for Kd measurements are distributed by acoustic transfer (non-contact dispensing) in 100% DMSO. The compounds were then diluted directly into the assays such that the final concentration of DMSO was 0.09%. All reactions performed in polypropylene 384-well plates. Each was a final volume of 0.02 ml. The assay plates were incubated at room temperature with shaking for 1 hour and the affinity beads were washed with wash buffer (1×PBS, 0.05% Tween 20). The beads were then resuspended in elution buffer (1×PBS, 0.05% Tween 20, 2 μM non-biotinylated affinity ligand) and incubated at room temperature with shaking for 30 minutes. The bromodomain concentration in the eluates was measured by qPCR.

Part II—Results

Results showing ability of exemplary compounds to bind to BRD4-BD2 are provided in Table 10 below. The symbol "++++" indicates a $K_d$ less than 0.05 μM. The symbol "+++" indicates a $K_d$ in the range of 0.05 μM to 0.5 μM. The symbol "++" indicates a $K_d$ in the range of greater than 0.5 μM to 2.5 μM. The symbol "+" indicates a $K_d$ greater than 2.5 μM. The symbol "N/A" indicates that no data was available.

TABLE 10

| Compound No. | $K_d$ |
|---|---|
| I-2 | ++++ |
| I-3 | ++++ |

Example 60—Assay for Binding Affinity to CDK1

Exemplary compounds were tested for ability to bind to CDK1. Experimental procedures and results are provided below.

Part I—Experimental Procedure

Compounds were tested using a KdELECT assay. Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 11 IX stocks in 100% DMSO. Kd values were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM nonbiotinylated affinity ligand) and incubated at room temperature with shaking for 30 minutes. The kinase concentration in the eluates was measured by qPCR.

Part II—Results

Results showing ability of exemplary compounds to bind to CDK1 are provided in Table 11 below. The symbol "++++" indicates a $K_d$ less than 0.05 μM. The symbol "+++" indicates a $K_d$ in the range of 0.05 μM to 0.5 μM. The symbol "++" indicates a $K_d$ in the range of greater than 0.5 μM to 2.5 μM. The symbol "+" indicates a $K_d$ greater than 2.5 μM. The symbol "N/A" indicates that no data was available.

TABLE 11

| Compound No. | $K_d$ |
|---|---|
| I-40 | +++ |
| I-42 | +++ |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A compound represented by Formula I-A:

(I-A)

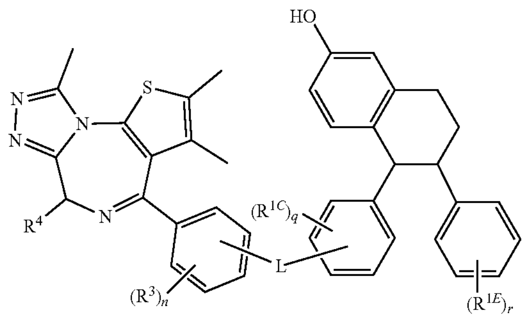

or a pharmaceutically acceptable salt thereof, wherein:

$R^3$, $R^{1C}$, and $R^{1E}$ are each independently for each occurrence hydrogen, fluoro, chloro, methoxy, or methyl;

$R^4$ is methyl, —$CH_2$-(oxazolyl), or —$CH_2$-(thiazolyl);

L is one of the following, wherein *** is the point of attachment to the phenyl ring bearing $R^{1C}$:

(i) -(4-6 membered saturated monocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-* or (ii) -(7-11 membered saturated spirocyclic heterocyclyl containing 1 or 2 nitrogen atoms, wherein the heterocyclyl is substituted with 0 or 1 occurrence of hydroxyl or fluoro)-($C_{1-4}$ alkylene)-(4-6 membered saturated monocyclic heterocyclyl containing 1 or 2 nitrogen atoms)-*; and n, q, and r are independently 0, 1, or 2.

2. The compound of claim 1, wherein L is one of the following:

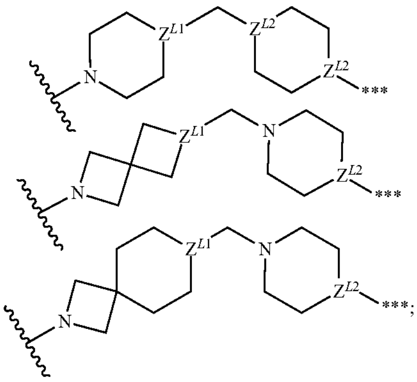

wherein: $Z^{L1}$ is C(OH), C(H), C(F), or N;

$Z^{L2}$ is independently for each occurrence N or C(H); and

*** is the point of attachment to the phenyl ring bearing $R^{1C}$.

3. The compound of claim 2, wherein $R^4$ is methyl, and L is

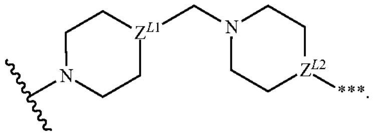

4. A compound represented by Formula I-A-6, or a pharmaceutically acceptable salt thereof:

(I-A-6)

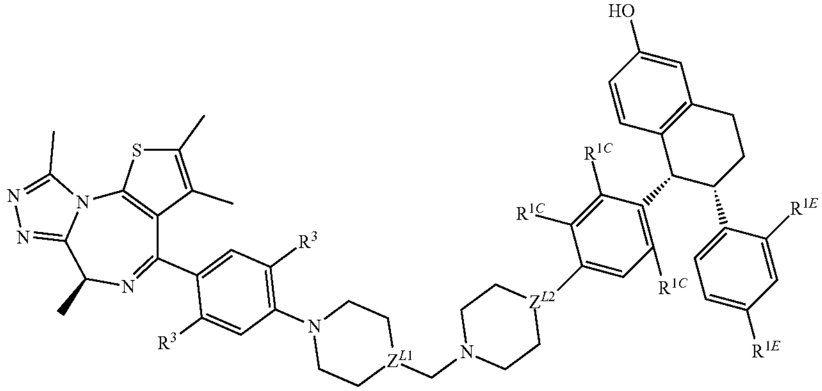

wherein $Z^{L1}$ is C(OH) or C(H), and $Z^{L2}$ is N or C(H); and $R^3$, $R^{1C}$, and $R^{1E}$ are each independently for each occurrence hydrogen, fluoro, chloro, methoxy, or methyl.

5. The compound of claim 4, wherein the compound is a compound of Formula I-A-6.

6. The compound of claim 5, wherein $R^{1C}$ and $R^{1E}$ are each independently for each occurrence hydrogen, fluoro, or methoxy.

7. The compound of claim 6, wherein $R^3$ represents independently for each occurrence hydrogen or fluoro.

8. A compound selected from the following, or a pharmaceutically acceptable salt thereof:

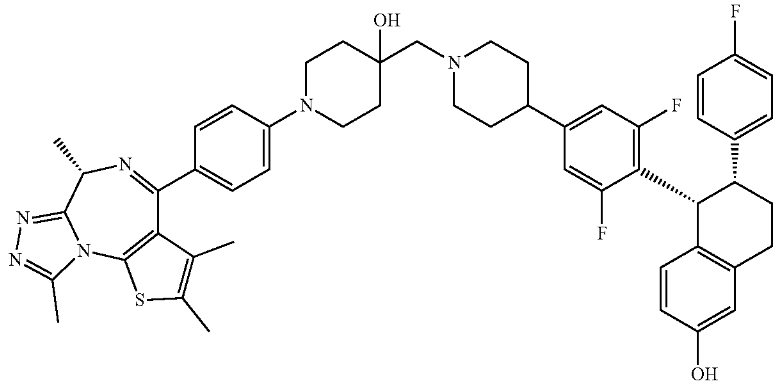 [SMILES: Cc1sc2c(c1C)C(c1ccc(N3CCC(O)(CN4CCC(c5cc(F)c([C@H]6c7ccc(O)cc7CC[C@H]6c6ccc(F)cc6)c(F)c5)CC4)CC3)cc1)=N[C@@H](C)c1nnc(C)n1-2]

-continued
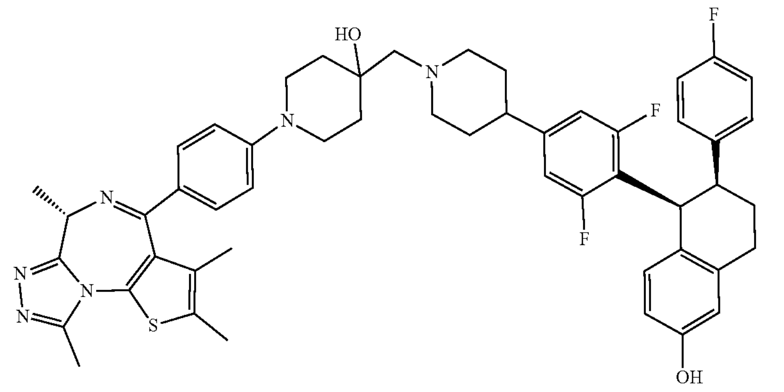
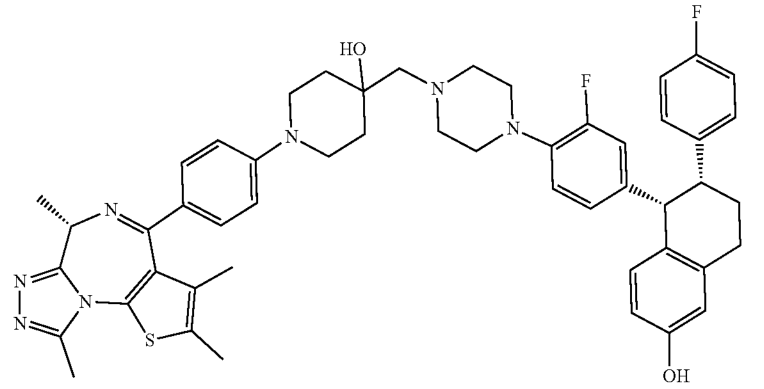
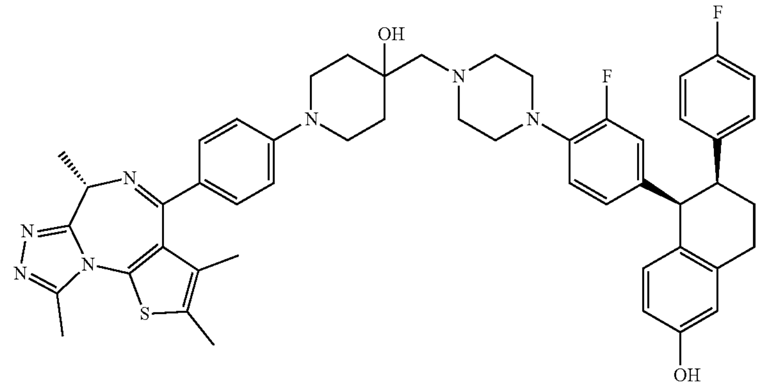
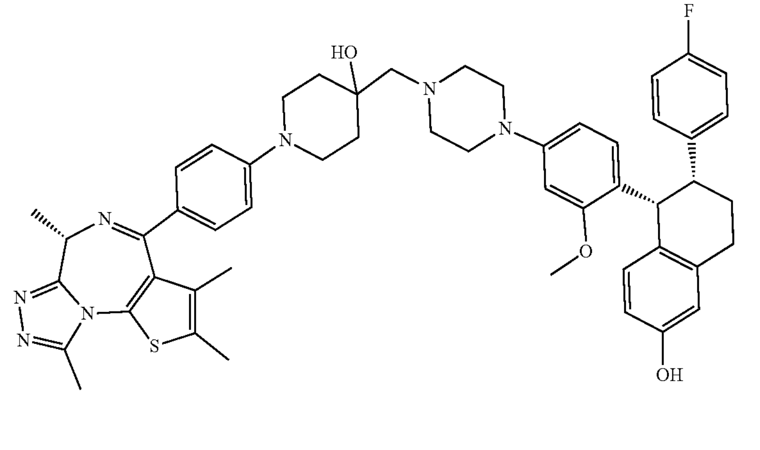

-continued
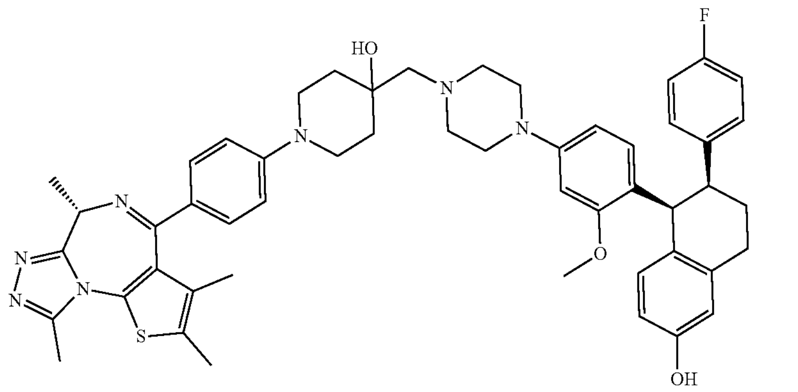
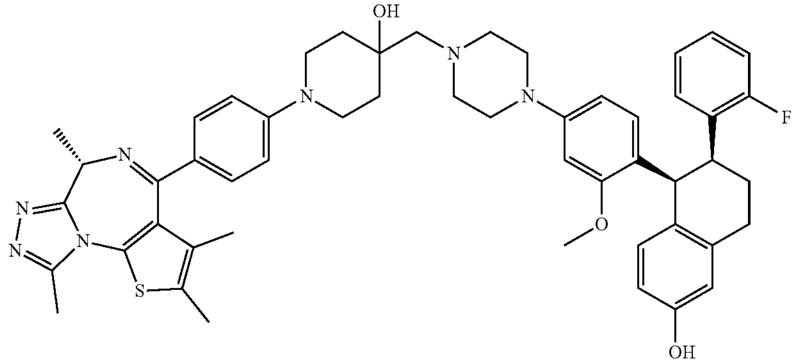
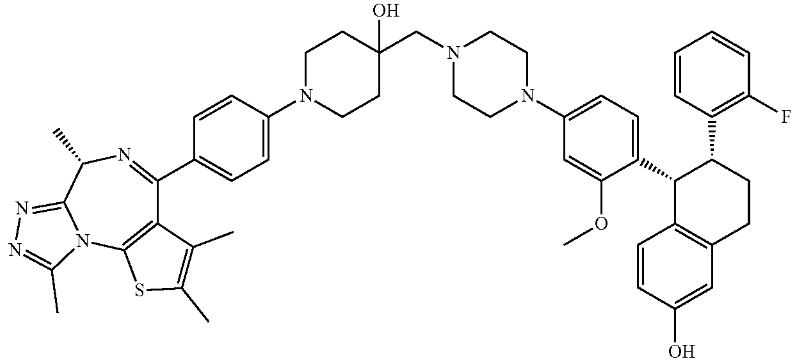
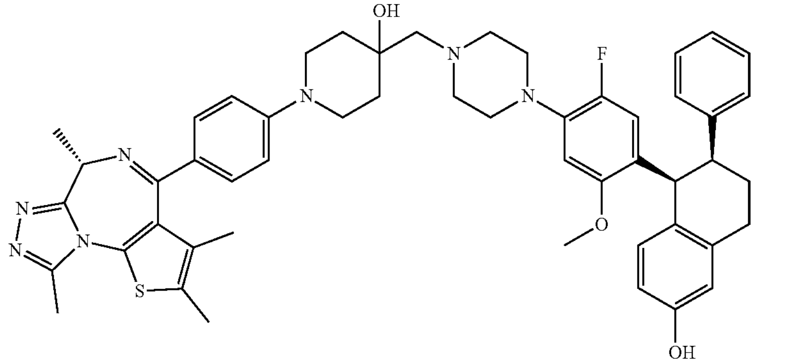

-continued
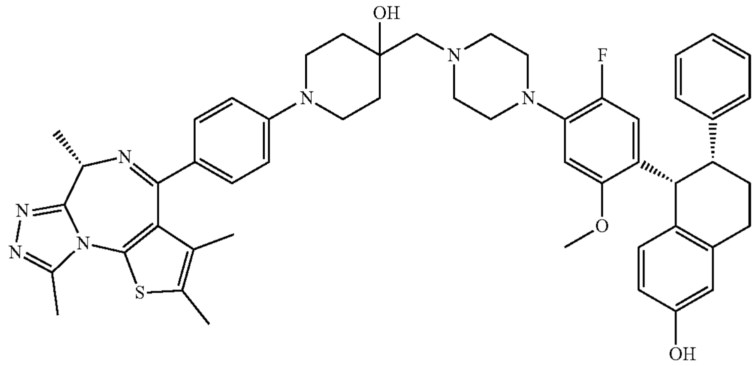
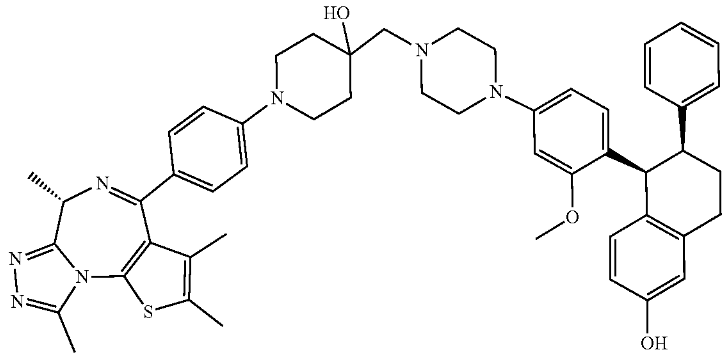
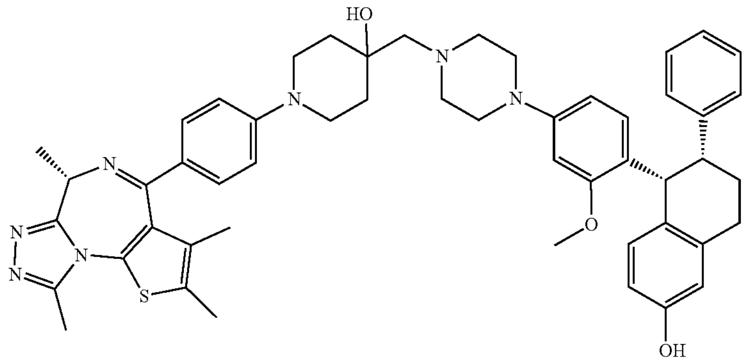
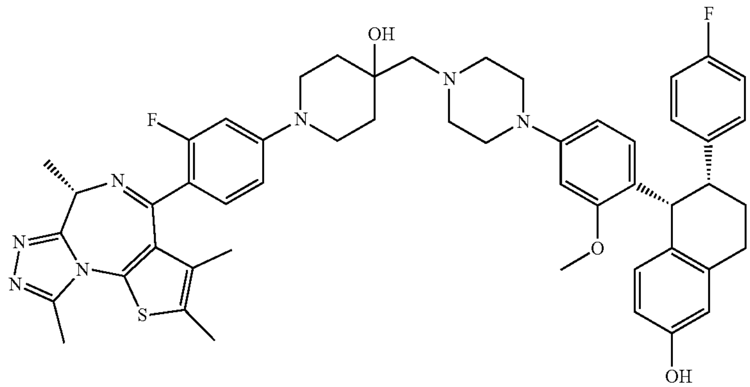

-continued
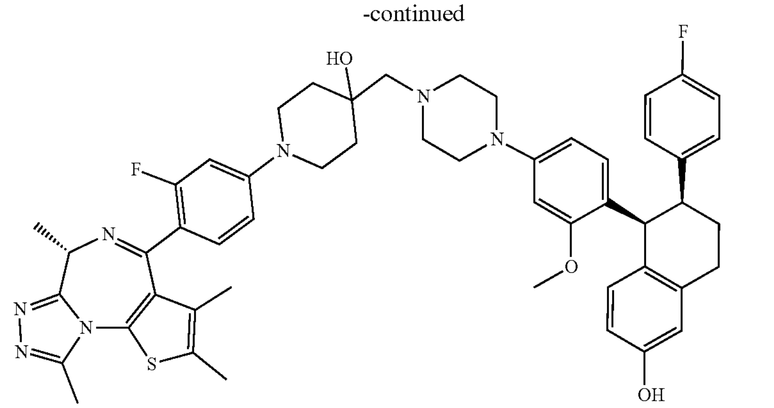
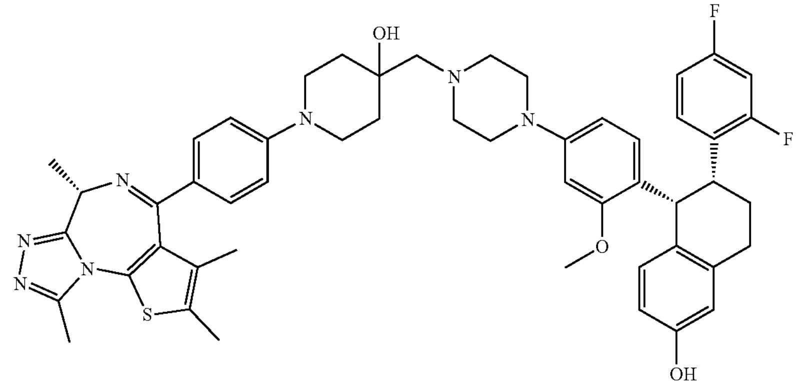
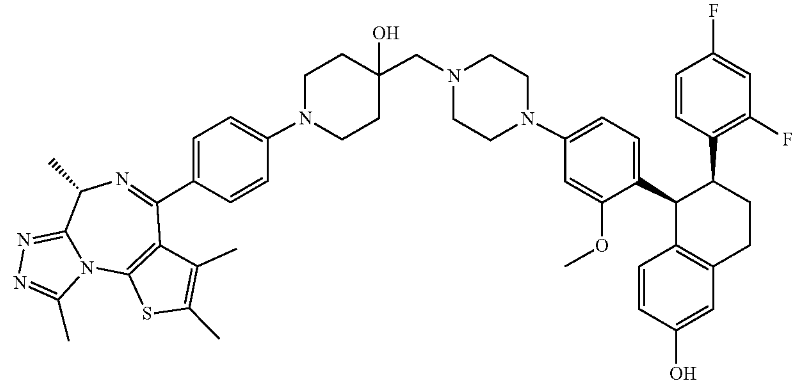
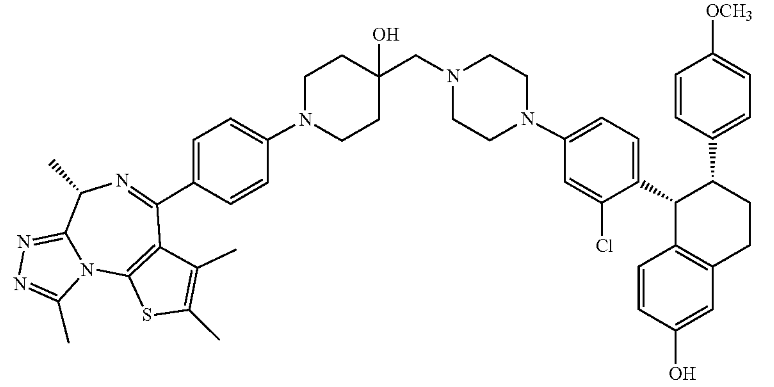

-continued
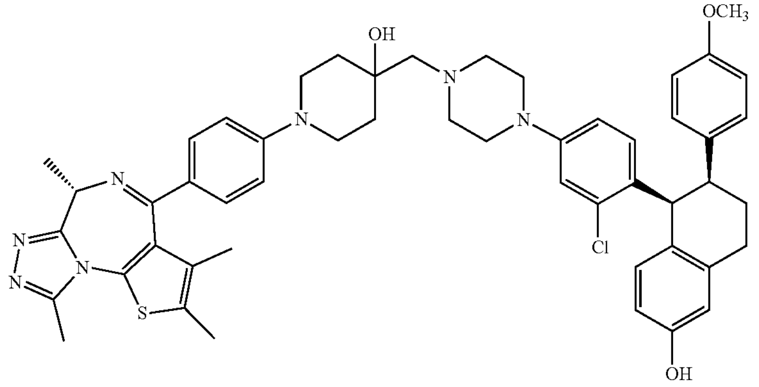
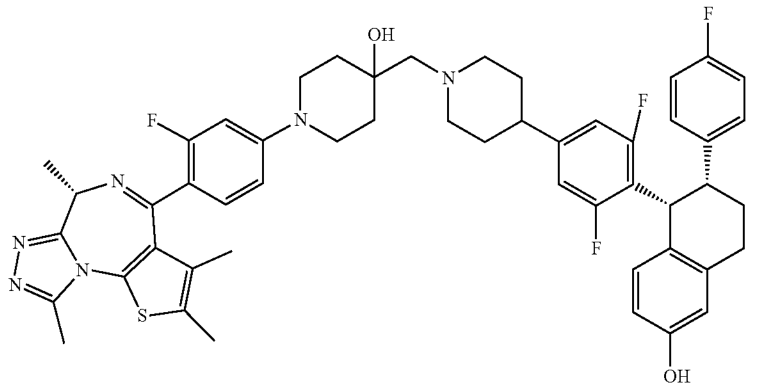
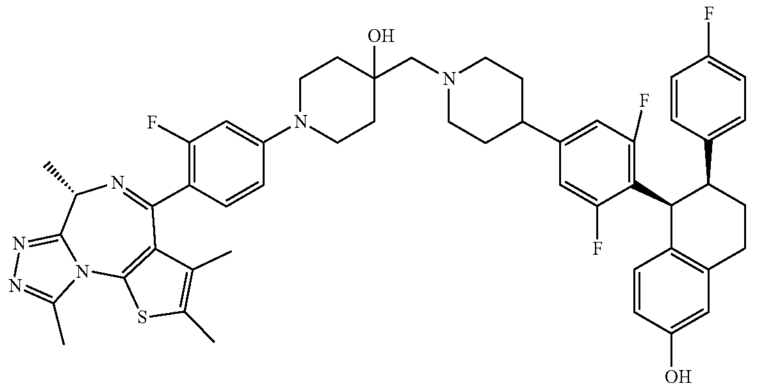
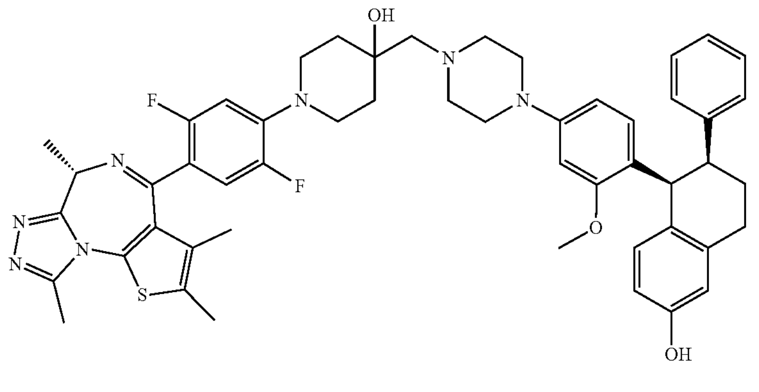

-continued
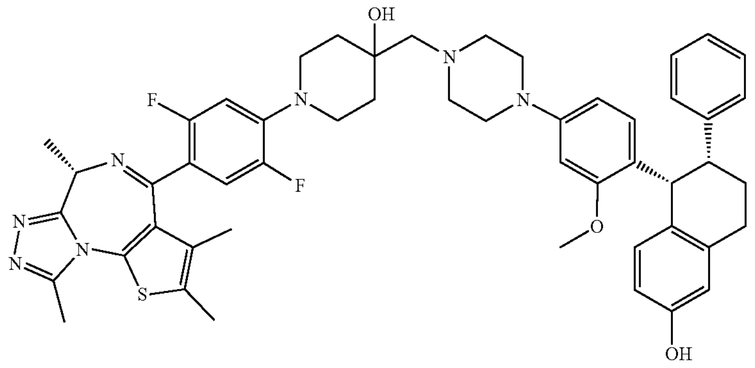
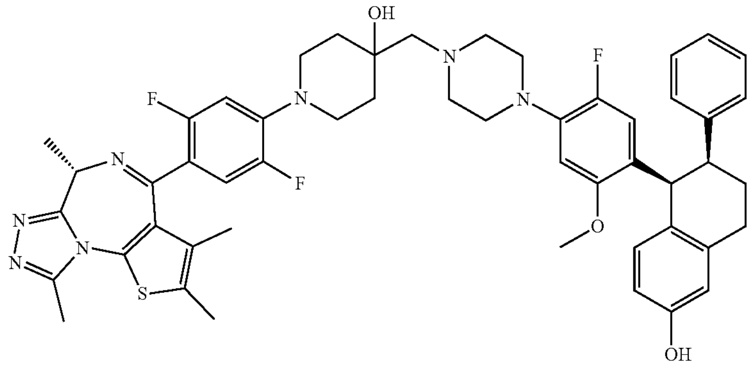
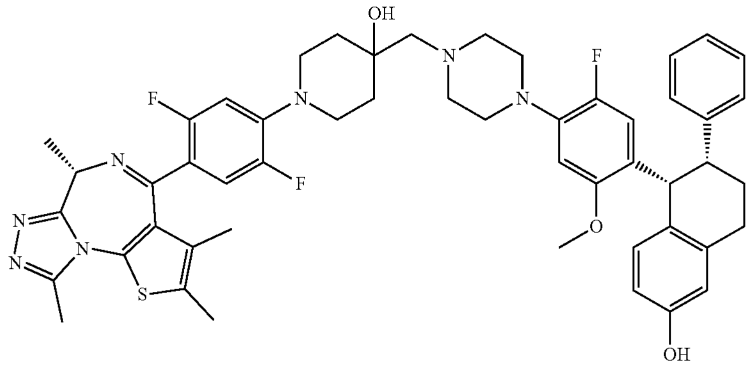
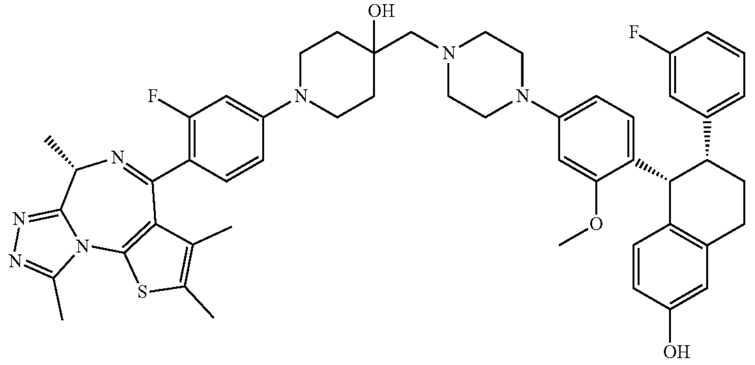

-continued
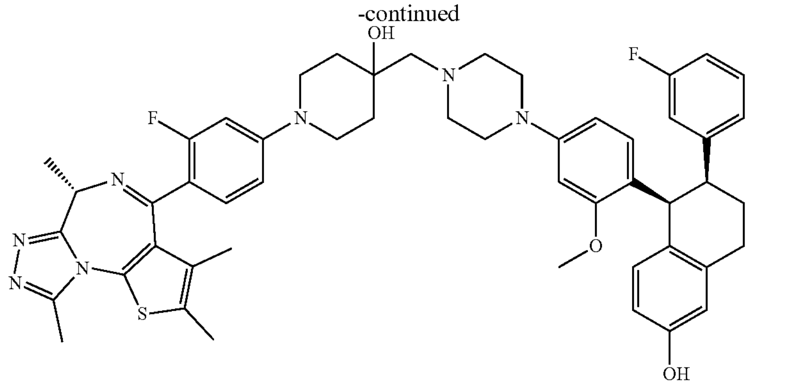
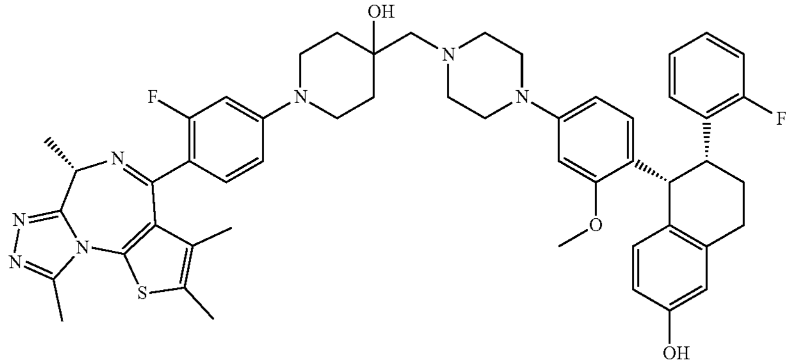
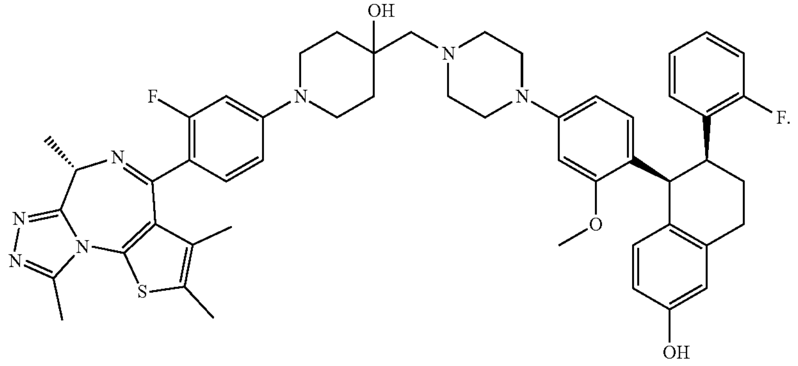 [SMILES: COc1cc(N2CCN(CC3(O)CCN(c4ccc(C5=N[C@@H](C)c6nnc(C)n6-c6sc(C)c(C)c65)c(F)c4)CC3)CC2)ccc1[C@@H]1c2ccc(O)cc2CC[C@@H]1c1ccccc1F]
9. The compound of claim 8, wherein the compound is
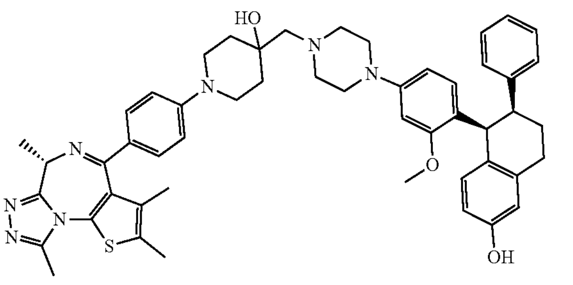 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccccc1]
or a pharmaceutically acceptable salt thereof.
10. The compound of claim 8, wherein the compound is
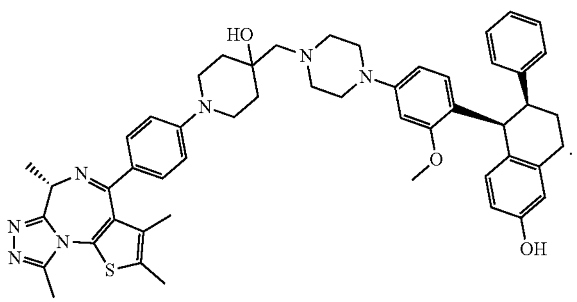 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccccc1]

11. The compound of claim 8, wherein the compound is

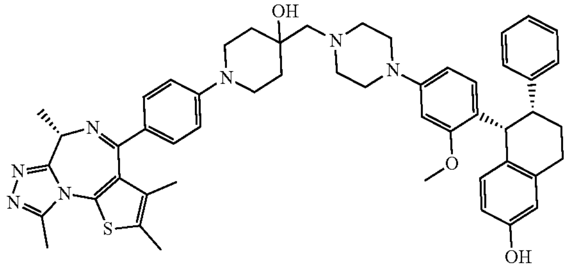 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccccc1]

or a pharmaceutically acceptable salt thereof.

12. The compound of claim 8, wherein the compound is

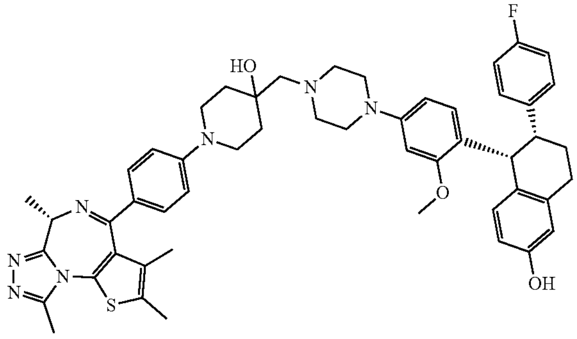 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@H]1c2ccc(O)cc2CC[C@H]1c1ccc(F)cc1]

or a pharmaceutically acceptable salt thereof.

13. A compound represented by

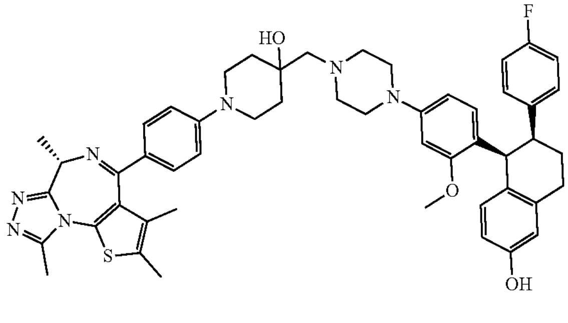 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(F)cc1]

or a pharmaceutically acceptable salt thereof.

14. The compound of claim 13, wherein the compound is

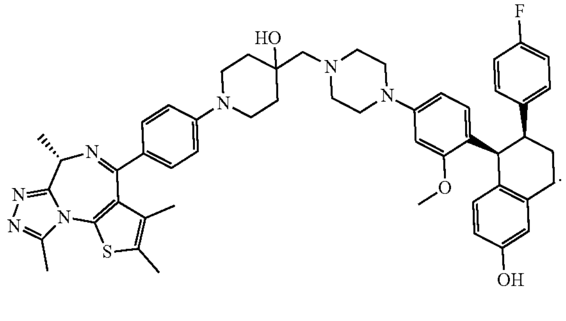 [SMILES: COc1cc(N2CCN(CC3(O)CCN(c4ccc(C5=N[C@@H](C)c6nnc(C)n6-c6sc(C)c(C)c65)cc4)CC3)CC2)ccc1[C@@H]1c2ccc(O)cc2CC[C@@H]1c1ccc(F)cc1]

15. A pharmaceutical composition comprising a compound of claim 1 and a pharmaceutically acceptable carrier.

16. A pharmaceutical composition comprising a compound of claim 9 and a pharmaceutically acceptable carrier.

17. A pharmaceutical composition comprising a compound of claim 10 and a pharmaceutically acceptable carrier.

18. A pharmaceutical composition comprising a compound of claim 13 and a pharmaceutically acceptable carrier.

19. A pharmaceutical composition comprising a compound of claim 14 and a pharmaceutically acceptable carrier.

20. A method of treating cancer, comprising administering to a patient in need thereof a therapeutically effective amount of a compound of claim 1 to treat the cancer, wherein the cancer is ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct cancer, gallbladder cancer, liver cancer, pancreatic cancer, bladder cancer, urinary tract cancer, kidney cancer, eye cancer, thyroid cancer, lymphoma, or leukemia.

21. A method of treating cancer, comprising administering to a patient in need thereof a therapeutically effective amount of a compound of claim 9 to treat the cancer, wherein the cancer is ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct cancer, gallbladder cancer, liver cancer, pancreatic cancer, bladder cancer, urinary tract cancer, kidney cancer, eye cancer, thyroid cancer, lymphoma, or leukemia.

22. A method of treating cancer, comprising administering to a patient in need thereof a therapeutically effective amount of a compound of claim 13 to treat the cancer, wherein the cancer is ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct cancer, gallbladder cancer, liver cancer, pancreatic cancer, bladder cancer, urinary tract cancer, kidney cancer, eye cancer, thyroid cancer, lymphoma, or leukemia.

23. A method of treating breast cancer, comprising administering to a patient in need thereof a therapeutically effective amount of a compound of claim 1 to treat the breast cancer.

24. A method of treating breast cancer, comprising administering to a patient in need thereof a therapeutically effective amount of a compound of claim 9 to treat the breast cancer.

25. A method of treating breast cancer, comprising administering to a patient in need thereof a therapeutically effective amount of a compound of claim 13 to treat the breast cancer.

26. The method of claim 24, wherein the patient is a human.

27. The method of claim 25, wherein the patient is a human.

28. A method of causing death of a cancer cell, comprising contacting a cancer cell with an effective amount of a compound of claim 1 to cause death of the cancer cell, wherein the cancer cell is selected from an ovarian cancer, uterine cancer, endometrial cancer, cervical cancer, prostate cancer, testicular cancer, breast cancer, brain cancer, lung cancer, oral cancer, esophageal cancer, head and neck cancer, stomach cancer, colon cancer, rectal cancer, skin cancer, sebaceous gland carcinoma, bile duct cancer, gallbladder cancer, liver cancer, pancreatic cancer, bladder cancer, urinary tract cancer, kidney cancer, eye cancer, thyroid cancer, lymphoma, or leukemia cell.

29. A method of causing death of a breast cancer cell, comprising contacting a breast cancer cell with an effective amount of a compound of claim 9 to cause death of the breast cancer cell.

30. A method of causing death of a breast cancer cell, comprising contacting a breast cancer cell with an effective amount of a compound of claim 13 to cause death of the breast cancer cell.

* * * * *